US012673961B2

(12) United States Patent
De Pascalis et al.

(10) Patent No.: US 12,673,961 B2

(45) Date of Patent: Jul. 7, 2026

(54) COMPOUNDS AND METHODS USEFUL FOR STABILIZING PHENYLALANINE HYDROXYLASE MUTATIONS

(71) Applicant: Agios Pharmaceuticals, Inc., Cambridge, MA (US)

(72) Inventors: Lucrezia De Pascalis, Cambridge, MA (US); Heather Jane Finlay, Skillman, NJ (US); Sandra King, Jamaica Plain, MA (US); Zenon D. Konteatis, Chatham Township, NJ (US); Brian C. Shook, Holliston, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 544 days.

(21) Appl. No.: 18/114,635

(22) Filed: Feb. 27, 2023

(65) Prior Publication Data

US 2023/0365592 A1 Nov. 16, 2023

Related U.S. Application Data

(60) Provisional application No. 63/314,580, filed on Feb. 28, 2022.

(51) Int. Cl.

| | |
|---|---|
| ***C07D 519/00*** | (2006.01) |
| ***A61K 31/437*** | (2006.01) |
| ***A61K 31/4709*** | (2006.01) |
| ***A61K 31/4725*** | (2006.01) |
| ***A61K 31/496*** | (2006.01) |
| ***A61K 31/502*** | (2006.01) |
| ***A61K 31/506*** | (2006.01) |
| ***A61K 31/517*** | (2006.01) |
| ***C07D 471/04*** | (2006.01) |

(52) U.S. Cl.

CPC .......... *C07D 519/00* (2013.01); *A61K 31/437* (2013.01); *A61K 31/4709* (2013.01); *A61K 31/4725* (2013.01); *A61K 31/496* (2013.01); *A61K 31/502* (2013.01); *A61K 31/506* (2013.01); *A61K 31/517* (2013.01); *C07D 471/04* (2013.01)

(58) Field of Classification Search

CPC ............................ C07D 519/00; A61K 31/437

USPC ..................................................... 514/255.05

See application file for complete search history.

(56) References Cited

U.S. PATENT DOCUMENTS

| | | | |
|---|---|---|---|
| 11,919,915 B2 * | 3/2024 | De Pascalis | ......... C07D 519/00 |
| 2025/0074922 A1 | 3/2025 | De Pascalis et al. | |
| 2025/0171437 A1 | 5/2025 | De Pascalis et al. | |
| 2025/0171438 A1 | 5/2025 | King et al. | |
| 2025/0262201 A1 | 8/2025 | King et al. | |
| 2025/0320201 A1 | 10/2025 | King et al. | |

FOREIGN PATENT DOCUMENTS

| | | |
|---|---|---|
| WO | 2009/000552 A2 | 12/2008 |
| WO | 2017/029202 A1 | 2/2017 |
| WO | 2019/105886 A1 | 6/2019 |
| WO | 2020/165318 A1 | 8/2020 |
| WO | 2022/192370 A1 | 9/2022 |
| WO | 2023/164235 A1 | 8/2023 |

OTHER PUBLICATIONS

Pey et al., Identification of pharmacological chaperones as potential therapeutic agents to treat phenylketonuria. J Clin Invest. Aug. 2008;118(8):2858-67.

Santos-Sierra et al., Novel pharmacological chaperones that correct phenylketonuria in mice. Hum Mol Genet. Apr. 15, 2012;21(8):1877-87.

STN, Imidazopyridine derivatives. Retrieved online at: www.stn.org. 3 pages, Jun. 13, 2021.

International Search Report and Written Opinion for Application No. PCT/US2023/013992, dated May 19, 2023, 14 pages.

(Continued)

*Primary Examiner* — Kahsay Habte

(74) *Attorney, Agent, or Firm* — McCarter & English, LLP; Michael J. DeGrazia; James M. Alburger

(57) ABSTRACT

The disclosure relates to compounds of Formula I or a pharmaceutically acceptable salt thereof, wherein, m, $R^1$-$R^5$, $R^{5A}$, and L are defined herein.

I

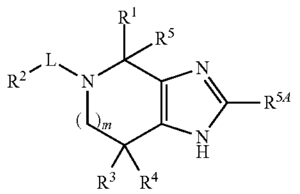

These compounds are useful in methods for stabilizing a mutant PAH protein or reducing blood phenylalanine concentration in a subject suffering from phenylketonuria. In some embodiments, the mutant PAH protein contains at least one R408W, R261Q, R243Q, Y414C, L48S, A403V, I65T, R241C, L348V, R408Q, or V388M mutation. In other embodiments, the mutant PAH protein contains at least one R408W, Y414C, I65T, F39L, R408Q, L348V, R261Q, A300S, or L48S mutation.

39 Claims, No Drawings

(56) References Cited

OTHER PUBLICATIONS

International Search Report and Written Opinion for Application No. PCT/US2023/013988, dated Jun. 9, 2023, 12 pages.
International Search Report and Written Opinion for Application No. PCT/US2023/013989, dated May 24, 2023, 14 pages.
International Search Report and Written Opinion for Application No. PCT/US2023/013986, dated Jun. 20, 2023, 11 pages.
International Search Report and Written Opinion for Application No. PCT/US2023/013990, dated May 24, 2023, 14 bages.
Meanwell, Synopsis of some recent tactical application of bioisosteres in drug design. J Med Chem. Apr. 28, 2011;54 (8):2529-91.
International Search Report and Written Opinion for Application No. PCT/US2024/044303, dated Dec. 5, 2024, 10 pages.
International Search Report and Written Opinion for Application No. PCT/US2024/044308, dated Dec. 5, 2024, 10 pages.

* cited by examiner

COMPOUNDS AND METHODS USEFUL FOR STABILIZING PHENYLALANINE HYDROXYLASE MUTATIONS

RELATED APPLICATIONS

This application claims the benefit of priority to U.S. provisional application No. 63/314,580, filed Feb. 28, 2022, the entire contents of which are incorporated herein by reference.

TECHNICAL FIELD

This application pertains to compounds that stabilize phenylalanine hydroxylase (PAH) mutations, pharmaceutical compositions comprising those compounds, and methods of using those compounds for treating phenylketonuria.

BACKGROUND

Phenylketonuria (PKU) is an autosomal recessive disorder affecting approximately 1:10,000 people worldwide (approx. 1:15,000-1:20,000 in the U.S.). The number of patients varies globally depending on region. PKU arises in patients who have mutations in the gene encoding the phenylalanine hydroxylase (PAH) enzyme responsible for converting phenylalanine to tyrosine. PAH is a tetrameric enzyme expressed in the liver requiring BH4 cofactor for activity. Reduction or loss of PAH activity results in toxic accumulation of phenylalanine (Phe) in the blood and brain. High levels of Phe damage brain white matter and interfere with neurotransmitter production. If untreated, high levels of Phe can result in mental retardation and decreased IQ in children and neurocognitive and psychiatric issues in adults, such as executive function deficits (for example, difficulty with attention, memory, flexible thinking, and organization/time management), psychological issues (for example, depression, anxiety, and mood swings), psychiatric and/or behavioral issues (for example, attention deficit hyperactivity disorder, self-harm, schizophrenia, agoraphobia, and agitation) and neurological abnormalities (for example, spasticity, tremor, gait disturbances, and seizures).

PKU phenotypes can vary from mild hyperphenylalaninemia (HPA) to more severe phenotypes that result in untreated blood Phe concentrations exceeding 1200 μM. American medical guidelines currently recommend maintaining blood Phe concentration in the range of 120 to 360 μM in both adults and children under the age of 12 years. European medical guidelines currently recommend maintaining blood Phe concentration below 360 μM in children under the age of 12 years and in pregnant women and below 600 μM in non-pregnant patients older than 12 years.

A standard of care for treating PKU is a Phe-restricted diet that severely limits the intake of natural protein. Such diets are very strict diets and challenging to adhere to. Two medications are currently approved for treating PKU, each having its own challenges. Kuvan (sapropterin dihydrochloride) is a synthetic BH4 cofactor approved in 2007 for use in infants to adults. Kuvan is not effective for all PKU patients, and the current guidelines suggest response testing in patients unless the patient is known to have two null mutations. Pegvaliase is an enzyme substitution therapy approved in 2018 for adults with a blood Phe concentration greater than 600 μM, despite prior management with available treatment options. Pegvaliase typically involves injection of a purified PEGylated form of phenylalanine ammonia lyase that reduces Phe by converting it to ammonia and trans-cinnamic acid instead of tyrosine. One of the main complications with enzyme substitution therapy is the attainment and maintenance of therapeutically effective amounts of protein in vivo due to rapid degradation or inactivation of the infused protein. A current approach to overcome this problem is to perform numerous costly high dose injections.

Pharmaceutical agents that enable patients to increase their intake of natural protein are desired.

SUMMARY

In some aspects, the disclosure provides compounds of Formula I:

I

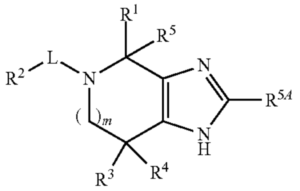

or a pharmaceutically acceptable salt thereof, wherein:

m is 1 or 2;

$R^1$ is

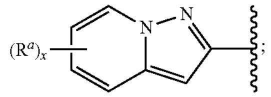

x is 0 to 5;

each $R^a$ independently is halo, $C_{1-6}$alkyl, $C_{3-6}$cycloalkyl, $C_{1-6}$haloalkyl, $C_{1-6}$alkoxy or $C_{1-6}$haloalkoxy;

$R^2$ is $C_{1-4}$alkyl, optionally substituted $C_{3-8}$cycloalkyl, optionally substituted heterocyclyl, optionally substituted aryl, or optionally substituted heteroaryl;

$R^3$ is H or $C_{1-6}$alkyl;

$R^4$ is H or $C_{1-6}$alkyl;

or $R^3$ and $R^4$, together with the atom to which they are attached, form a $C_{3-6}$cycloalkyl;

$R^5$ is H or D;

$R^{5A}$ is H or D; and

L is a bond, carbonyl, optionally substituted $C_{1-6}$alkylene, optionally substituted $C_{1-6}$alkylenecarbonyl, optionally substituted $C_{2-6}$alkenylenecarbonyl, optionally substituted $C_{1-6}$haloalkylenecarbonyl, or optionally substituted —C(O)NR$^b$($C_{1-6}$alkylene)-, wherein the carbon atom of the carbonyl group is connected to N in Formula I; and $R^b$ is H or $C_{1-6}$alkyl.

In other aspects, the disclosure provides compounds of Formula I-A, I-B, I-C, I-D, I-E, I-F, I-G, I-H, I-I, I-J, I-K, I-L, or I-M, or a pharmaceutically acceptable salt thereof:

I-A

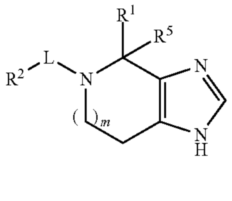

-continued

I-B

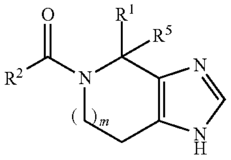

I-C

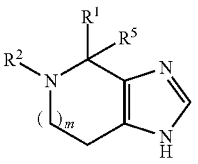

I-D

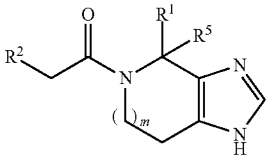

I-E

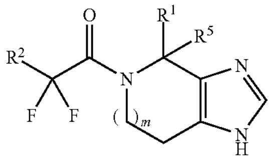

I-F

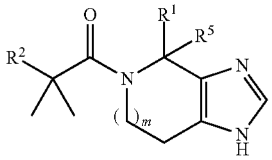

I-G

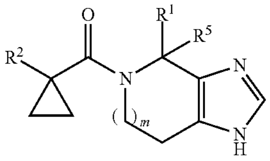

I-H

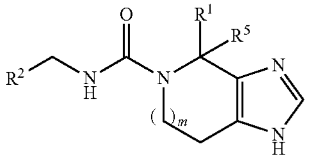

I-I

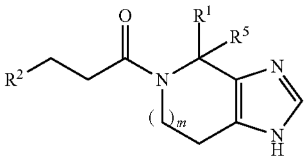

I-J

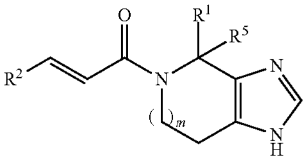

-continued

I-K

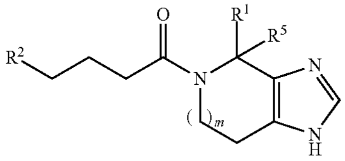

I-L

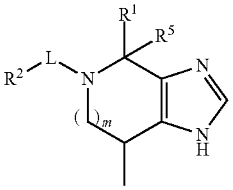

I-M

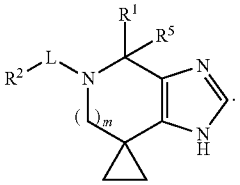

Stereoisomers and mixtures of stereoisomers of the compounds of Formula I, I-A, I-B, I-C, I-D, I-E, I-F, I-G, I-H, I-I, I-J, I-K, I-L, and I-M, and the pharmaceutical salts thereof, are also described.

In further aspects, the disclosure provides pharmaceutical compositions comprising one or more compound described herein or a pharmaceutically acceptable salt thereof, and a pharmaceutically acceptable excipient.

In yet other aspects, the disclosure provides methods for stabilizing a mutant PAH protein, comprising contacting the protein with one or more compound as described herein or a pharmaceutically acceptable salt thereof. In some embodiments, the mutant PAH protein contains at least one R408W, R261Q, R243Q, Y414C, L48S, A403V, I65T, R241C, L348V, R408Q, or V388M mutation. In other embodiments, the mutant PAH protein contains at least one R408W, Y414C, I65T, F39L, R408Q, L348V, R261Q, A300S, or L48S mutation.

In still further aspects, the disclosure provides methods for reducing phenylalanine levels in a subject suffering from phenylketonuria comprising administering a therapeutically effective amount of one or more compound as described herein or a pharmaceutically acceptable salt thereof.

DETAILED DESCRIPTION OF ILLUSTRATIVE EMBODIMENTS

Definitions

Unless otherwise defined, all technical and scientific terms used herein have the same meaning as commonly understood by one of ordinary skill in the art to which this disclosure pertains. The terminology used in the description is for describing particular embodiments only and is not intended to be limiting of the disclosure.

As used in structures herein, "⊢" indicates the point of attachment of the particular depicted structure or substituent group to the appropriate atom(s) in the remainder of the molecule.

The articles "a" and "an" as used herein and in the appended claims are used herein to refer to one or to more than one (e.g., to at least one) of the grammatical object of the article unless the context clearly indicates otherwise. By way of example, "an element" means one element or more than one element.

"Pharmaceutically acceptable" means approved or approvable by a regulatory agency of the Federal or a state government or the corresponding agency in a country other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic and may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, fumarate, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith.

The term "alkyl," when used alone or as part of a substituent group, refers to a straight- or branched-chain hydrocarbon group having from 1 to 12 carbon atoms ("$C_{1-12}$"), for example 1 to 6 carbons atoms ("$C_{1-6}$"), in the group. Examples of alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentyl, amyl, neopentyl, 3-methyl-2-butanyl, tertiary amyl), hexyl ($C_6$) (e.g., n-hexyl), heptyl ($C_7$) (e.g., n-heptyl), octyl ($C_8$) (e.g., n-octyl), and the like. In some embodiments, the alkyl group is a $C_{1-6}$alkyl; in other embodiments, it is a $C_{1-4}$alkyl; and in other embodiments, it is a $C_{1-3}$alkyl.

The term "alkylene," when used alone or as part of a substituent group, refers to an alkyl diradical, i.e., a straight- or branched-chain hydrocarbon group that is attached to two other groups. For example, one embodiment of a $C_2$alkylene is the diradical $—CH_2CH_2—$. In some embodiments, the alkylene group is $C_{1-6}$alkylene; in other embodiments, it is $C_{1-4}$alkylene.

When a range of carbon atoms is used herein, for example, $C_{1-6}$, all ranges, as well as individual numbers of carbon atoms are encompassed. For example, "$C_{1-3}$" includes $C_{1-3}$, $C_{1-12}$, $C_{2-3}$, $C_1$, $C_2$, and $C_3$.

The term "cycloalkyl" when used alone or as part of a substituent group refers to cyclic-containing, non-aromatic hydrocarbon groups having from 3 to 10 carbon atoms ("$C_{3-10}$"), for example from 3 to 7 carbon atoms ("$C_{3-7}$"). Examples of cycloalkyl groups include cyclopropyl ($C_3$), cyclobutyl ($C_4$), cyclopentyl ($C_5$), cyclohexyl ($C_6$), cycloheptyl ($C_7$), and the like. In some embodiments, the cycloalkyl group is a $C_{3-4}$cycloalkyl; in other embodiments, it is a $C_{3-6}$cycloalkyl; and in other embodiments, it is $C_{3-8}$ cycloalkyl. The cycloalkyl may be unsubstituted or substituted. In some embodiments, the cycloalkyl is substituted with two substituents. In further embodiments, the cycloalkyl is substituted with one substituent. In yet other embodiments, the cycloalkyl is substituted with three substituents. In still further embodiments, the cycloalkyl is unsubstituted.

The term "aryl" when used alone or as part of a substituent group also refers to a mono- or bicyclic-aromatic hydrocarbon ring structure having 6 or 10 carbon atoms in the ring, wherein one or more of the carbon atoms in the ring is optionally substituted. The term "aryl" also includes a mono- or bicyclic-aromatic hydrocarbon ring structure having 6 or 10 carbon atoms in the ring, wherein two adjacent carbon atoms in the ring are optionally substituted such that said two adjacent carbon atoms and their respective substituents form a cycloalkyl or heterocyclyl ring. Examples of aryl groups include phenyl, indenyl, naphthyl, 1,2,3,4-tetrahydronaphthyl, and the like. The aryl may be unsubstituted or substituted. In other embodiments, the optionally substituted phenyl has four substituents. In further embodiments, the optionally substituted phenyl has three substituents. In yet other embodiments, the optionally substituted phenyl has two substituents. In still further embodiments, the optionally substituted phenyl has one substituent. In other embodiments, the optionally substituted phenyl is unsubstituted.

As used herein, the term "alkenyl" refers to a straight- or branched-chain group having from 2 to 12 carbon atoms ("$C_{2-12}$") in the group, wherein the group includes at least one carbon-carbon double bond. Examples of alkenyl groups include vinyl ($—CH=CH_2$; $C_2$alkenyl), allyl ($—CH_2—CH=CH_2$; $C_3$alkenyl), propenyl ($—CH=CHCH_3$; $C_3$alkenyl), isopropenyl ($—C(CH_3)=CH_2$; $C_3$alkenyl), butenyl ($—CH=CHCH_2CH_3$; $C_4$alkenyl), sec-butenyl ($—C(CH_3)=CHCH_3$; $C_4$alkenyl), iso-butenyl ($—CH=C(CH_3)_2$; $C_4$alkenyl), 2-butenyl ($—CH_2CH=CHCH_3$; $C_4$alkyl), pentenyl ($—CH=CHCH_2CH_2CH_3$; $C_5$alkenyl), and the like. In some embodiments, the alkenyl group is a $C_{2-6}$ alkenyl group; in other embodiments, it is $C_{2-4}$alkenyl.

As used herein, the term "alkynyl" refers to a straight- or branched-chain group having from 2 to 12 carbon atoms ("$C_{2-12}$") in the group, and wherein the group includes at least one carbon-carbon triple bond. Examples of alkynyl groups include ethynyl ($—C≡CH$; $C_2$alkynyl), propargyl ($—CH_2—C≡CH$; $C_3$alkynyl), propynyl ($—C≡CCH_3$; $C_3$alkynyl), butynyl ($—C≡CCH_2CH_3$; $C_4$alkynyl), pentynyl ($—C≡CCH_2CH_2CH_3$; $C_5$alkynyl), and the like. In some embodiments, the alkynyl group is a $C_{2-6}$alkynyl group; in other embodiments, it is $C_{2-4}$alkynyl.

The term "carbonyl" as used by itself or as part of another group refers to C(O) or C(═O).

The term "alkylcarbonyl" as used by itself or as part of another group refers to an alkyl group as defined above wherein at least one carbon is bonded to an oxo group. For example, one embodiment of an $C_3$alkylcarbonyl is —$CH_2C(O)CH_3$. In some embodiments, the alkylcarbonyl group is a $C_{1-6}$alkylcarbonyl group.

The term "alkenylenecarbonyl" as used by itself or as part of another group refers to an —C(O)-(alkenylene) group, where alkenylene refers to an alkylene diradical, i.e., a straight- or branched-chain hydrocarbon group containing at least one carbon-carbon double bond that is attached to two other groups. For example, one embodiment of a —C(O)—$C_2$alkenylene is —C(O)—CH═CH—. In some embodiments, the alkenylene group of the alkenylenecarbonyl is a $C_{2-6}$alkenylene group; in other embodiments, the alkenylene group is $C_{2-4}$alkenylene.

The term "halo" or "halogen," as used by itself or as part of another group refers to a fluorine, chlorine, bromine, or iodine atom.

As used herein, the term "haloalkyl" refers to an alkyl group wherein one or more of the hydrogen atoms has been replaced with one or more halogen atoms which may be the same or different. In some embodiments, the alkyl is substituted by at least one halogen. In other embodiments, the alkyl is substituted by one, two, or three F and/or Cl. Examples of haloalkyl groups include fluoromethyl ($CH_2F$), 1-fluoroethyl ($CH(CH_3)F$), 2-fluoroethyl, difluoromethyl ($CHF_2$), trifluoromethyl (CF), pentafluoroethyl, 1,1-difluoroethyl ($C(CH_3)F_2$), 2,2-difluoroethyl ($CH_2CHF_2$), 2,2,2-trifluoroethyl ($CH_2CF_3$), 2-fluoropropan-2-yl ($C(CH_3)_2F$), 3,3,3-trifluoropropyl, 4,4,4-trifluorobutyl, trichloromethyl and the like. In some embodiments, the haloalkyl group is a $C_{1-6}$haloalkyl; in other embodiments, it is a $C_{1-4}$haloalkyl; and in other embodiments, it is a $C_{1-3}$haloalkyl.

The term "haloalkylenecarbonyl" as used by itself or as part of another group refers to a —C(O)-(haloalkylene) group, where the haloalkylene refers to a haloalkyl diradical. For example, one embodiment of a —C(O)—$C_1$haloalkylene is —C(O)—$CF_2$—. In some embodiments, the haloalkylene group is a $C_{1-6}$haloalkylene; in other embodiments, it is a $C_{1-4}$haloalkylene; and in other embodiments, it is a $C_{1-3}$haloalkylene.

The term "cyanoalkyl" as used by itself or as part of another group refers to an alkyl as defined herein that is substituted by one or more CN. In some embodiments, the alkyl is substituted by at least one CN. In other embodiments, the alkyl is substituted by one, two, or three CN. In further embodiments, the cyanoalkyl group is a $C_{1-6}$cyanoalkyl. In yet other embodiments, the cyanoalkyl is a $C_{1-4}$cyanoalkyl. Examples of cyanoalkyl groups include $CH_2CN$, $CH_2CH_2CN$, $CH(CN)CH_3$, $CH_2CH_2CH_2CN$, $C(CH_3)_2CN$, $CH_2CH(CN)CH_3$, $CH(CN)CH_2CH_3$, and the like.

The term "hydroxyalkyl" as used by itself or as part of another group refers to an alkyl group as defined herein wherein one or more of the hydrogen atoms has been replaced with one or more hydroxyl (i.e., —OH). In some embodiments, the hydroxyalkyl contains one OH. In other embodiments, the hydroxyalkyl contains two OH. In further embodiments, the hydroxyalkyl contains three OH. Examples of hydroxyalkyl groups include hydroxymethyl, hydroxyethyl (e.g., 1-hydroxyethyl, 2-hydroxyethyl), 1,2-dihydroxyethyl, hydroxypropyl (e.g., 2-hydroxypropyl, 3-hydroxypropyl), hydroxybutyl (e.g., 3-hydroxybutyl, 4-hydroxybutyl), 2-hydroxy-1-methylpropyl, 1,3-dihydroxyprop-2-yl, and the like. In some embodiments, the hydroxyalkyl group is $C_{1-6}$hydroxyalkyl; in other embodiments, it is $C_{1-4}$hydroxyalkyl; and in other embodiments, it is $C_{1-3}$hydroxyalkyl.

The term "cycloalkylsulfonyl" as used by itself or as part of another group refers to a cycloalkyl as defined herein that is bound to a sulfonyl, i.e., —$SO_2$—, and the sulfonyl group forms the point of attachment to the remainder of the molecule. In some embodiments, the cycloalkylsulfonyl is a $C_{3-8}$cycloalkylsulfonyl; in other embodiments, it is a $C_{3-6}$cycloalkylsulfonyl. Examples of cycloalkylsulfonyl groups include —$SO_2$-cyclopropyl, —$SO_2$— cyclobutyl, —$SO_2$-cyclopentyl, and the like.

The term "alkylsulfonyl" as used by itself or as part of another group refers to an alkyl as defined herein that is bound to a sulfonyl, i.e., —$SO_2$—, and the sulfonyl group forms the point of attachment to the remainder of the molecule. In some embodiments, the alkylsulfonyl is $C_{1-6}$alkylsulfonyl; in other embodiments, it is a $C_{1-4}$alkylsulfonyl. Examples of alkylsulfonyl groups include —$SO_2CH_3$, —$SO_2CH_2CH_3$, and the like.

The term "alkylsulfonyl(alkylene)" as used by itself or as part of another group refers to an alkylene group as defined herein that is bound to the sulfonyl of an alkylsulfonyl group as defined herein. Examples of alkylsulfonyl(alkylene) groups include —$C(CH_3)_2SO_2CH_3$, —$CH_2SO_2CH_3$, —$CH(CH_3)SO_2CH_3$, and the like.

The term "alkoxy" as used by itself or as part of another group refers to an oxygen radical attached to an alkyl group by a single bond. Examples of alkoxyl groups include methoxy (OCH), ethoxy ($OCH_2CH_3$), propoxy (e.g., —$O^n$Pr, —$O^i$Pr), or butoxy (e.g., —$O^n$Bu, —$O^i$Bu, —$O^s$Bu, —$O^t$Bu), and the like. In other embodiments, the alkoxy group is a $C_{1-6}$ alkoxy. In further embodiments, the alkoxy group is a $C_{1-4}$alkoxy.

The term "alkoxy(alkylene)" as used by itself or as part of another group refers to an alkylene group as defined herein that is bound to an alkoxy group as defined herein. Examples of alkoxy(alkylene) groups include —$CH_2OCH_3$, —$CH_2CH_2OCH_3$, and the like.

The term "haloalkoxy" as used by itself or as part of another group refers an oxygen radical attached to a haloalkyl group by a single bond, wherein haloalkyl is defined above. Examples of haloalkoxy groups include fluoromethoxy ($OCH_2F$), 2-fluoroethoxy, difluoromethoxy ($OCHF_2$), trifluoromethoxy ($OCF_3$), pentafluoroethoxy, 1,1-difluoroethoxy ($OC(CH_3)F_2$), 2,2-difluoroethoxy, 2,2,2-trifluoroethoxy ($OCH_2CFA$) 3,3,3-trifluoropropoxy, 4,4,4-trifluorobutoxy, trichloromethoxy groups, and the like. In some embodiments, the haloalkoxy group is a $C_{1-6}$haloalkoxy; in other embodiments, it is $C_{1-4}$haloalkoxy; and in other embodiments, it is $C_{1-3}$haloalkoxy.

The term "haloalkoxy(alkylene)" as used by itself or as part of another group refers to an alkylene group as defined herein that is bound to an haloalkoxy group as defined herein. Examples of haloalkoxy(alkylene) groups include —$CH_2OCF_3$, and the like.

The term "heteroaryl" when used alone or as part of a substituent group refers to a mono- or bicyclic-aromatic ring structure including carbon atoms as well as up to four heteroatoms that are each independently nitrogen, oxygen, or sulfur. Heteroaryl rings can include a total of 5, 6, 9, or 10 ring atoms. In some embodiments, heteroaryl rings are characterized by the number of ring atoms in the heteroaryl group. For example, a 6-membered heteroaryl group refers to a heteroaryl group having 6 ring atoms in the group. Similarly, a 5-membered heteroaryl group refers to a heteroaryl group having 5 ring atoms in the group. The heteroaryl moiety can be unsubstituted, or one or more of the carbon atoms or nitrogen atoms in the ring can be substituted. Examples of heteroaryl groups include thienyl, benzo[b]thienyl, furanyl, benzofuryl, pyranyl, thiophenyl, isobenzofuranyl, benzoxazinyl, chromenyl, xanthenyl, 2H pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, quinoxalyl, phthalazinyl, naphthyridinyl, cinnolinyl, triazolyl, tetrazolyl, thiadiazolyl, oxadiazolyl, quinazolinyl, pteridinyl, pyrimidinyl, thiazolyl, isothiazolyl, oxazolyl, isoxazolyl, furazanyl, pyrazolo[1,5-a]pyridinyl, benzoisothiazolyl, imidazol[1,5-a]pyridinyl, pyrrolo[1,2]pyridazinyl, benzo[d]thiazolyl, benzo[d]imidazolyl, benzo[d]oxazolyl, benzoisoxazolyl, isothiazolyl, tetrahydropyrazolo[1,5-a]pyridinyl and the like. In some embodiments, the heteroaryl is thienyl (e.g., thien-2-yl and thien-3-yl), furyl (e.g., 2-furanyl, 3-furanyl, 4-furanyl), pyrrolyl (e.g., pyrrol-2-yl, pyrrol-3-yl), imidazolyl (e.g., imidazol-2-yl, imidazol-4-yl), pyrazolyl (e.g., pyrazol-1-yl, pyrazol-3-yl, pyrazol-4-yl, pyrazol-5-yl), pyridyl (e.g., pyridin-1-yl, pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), pyrazinyl (e.g., pyrazin-2-yl, pyrazin-3-yl, pyrazin-5-yl, pyrazin-6-yl), triazolyl (e.g., 1,2,4-triazol-1-yl, 1,2,4-triazol-3-yl, 1,2,4-triazol-5-yl), thiadiazolyl (e.g., 1,2,3-thiadiazolyl, 1,2,4-thiadiazolyl, 1,2,5-thiadiazolyl, 1,3,4-thiadiazolyl), oxadiazolyl (e.g., 1,2,3-oxadiazolyl, 1,2,4-oxadiazolyl, 1,2,5-oxadiazolyl, 1,3,4-oxadiazolyl), indazolyl (e.g., indazol-3-yl), pyrazolo[1,5-a]pyridinyl (e.g., pyrazolo[1,5-a]pyridin-3-yl), imidazol[1,5-a]pyridinyl (e.g., imidazol[1,5-a]pyridin-1-yl), pyrrolo[1,2]pyridazinyl (e.g., pyrrolo[1,2]pyridazin-5-yl, pyrrolo[1,2]pyridazin-6-yl), benzo[d]thiazolyl (e.g., benzo[d]thiazol-3-yl, benzo[d]thiazol-2-yl), benzo[d]imidazolyl (e.g., benzo[d]imidazol-2-yl), benzo[d]oxazolyl (e.g., benzo[d]oxazol-2-yl), benzo[d]isoxazolyl (e.g., benzo[d]isoxazol-3-yl), benzo[d]isothiazolyl (e.g., benzo[d]isothiazol-3-yl), benzo[c]isoxazolyl (e.g., benzo[c]isoxazol-3-yl), quinolinyl (e.g., quinolin-3-yl), and pyridazinyl (e.g., pyridazin-3-yl, pyridazin-4-yl). The term "heteroaryl" also includes N-oxides. The heteroaryl may be unsubstituted or substituted. In some embodiments, the heteroaryl is substituted with two substituents. In further embodiments, the heteroaryl is substituted with one substituent. In yet other embodiments, the heteroaryl is substituted with three substituents. In still further embodiments, the heteroaryl is unsubstituted. Substitution may occur on any available carbon or heteroatom (e.g., nitrogen), or both, as permitted by substituent valency.

In some embodiments, the heteroaryl is a 5- or 6-membered heteroaryl. In some embodiments, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Examples of 5-membered heteroaryl groups include thienyl, furyl, pyrrolyl, oxazolyl, pyrazolyl, imidazolyl, thiazolyl, isothiazolyl, and isoxazolyl and the like. In other embodiments, the heteroaryl is a 6-membered heteroaryl, e.g., the heteroaryl is a monocyclic aromatic ring system having 6 ring atoms wherein at least one carbon atom of the ring is replaced with a nitrogen atom. Examples of 6-membered heteroaryl groups include pyridyl, pyrazinyl, pyrimidinyl, pyridazinyl and the like.

The term "heterocyclyl" as used by itself or as part of another group refers to non-aromatic, saturated or partially unsaturated, e.g., containing one or two double bonds, cyclic groups containing one, two, or three rings having from three to fourteen ring members, i.e., a 3-14-membered heterocyclyl, wherein at least one carbon atom of one of the rings is replaced with a heteroatom. Each heteroatom is independently selected from oxygen, sulfur, including sulfoxide and sulfone, and/or nitrogen atoms, which can be oxidized or quaternized. The term "heterocyclyl" also includes groups wherein a ring —$CH_2$— is replaced with a —C(O)—. The term "heterocyclyl" also includes groups having fused optionally substituted aryl groups, e.g., indolinyl or chroman-4-yl and groups having fused optionally substituted cycloalkyl groups, e.g., 6-azaspiro[2,5]octanyl. In some embodiments, the heterocyclyl group is a $C_{4-6}$heterocyclyl, i.e., a 4-, 5- or 6-membered cyclic group, containing one ring and one or two oxygen and/or nitrogen atoms. In other embodiments, the heterocyclyl is a $C_{4-6}$heterocyclyl containing one ring and one nitrogen atom. The heterocyclyl can be optionally linked to the rest of the molecule through any available carbon or heteroatom that results in a stable structure. Examples of heterocyclyl groups include azetidinyl, dioxanyl, tetrahydropyranyl, pyrrolidinyl, piperidinyl, morpholinyl, piperazinyl, pyrrolidinyl, indolinyl, oxetanyl, tetrahydrofuranyl, tetrahydrothiophenyl, azepanyl, aziridinyl, dioxolanyl, imidazolidinyl, pyrazolidinyl, thianyl, dithianyl, thiomorpholinyl, oxazepanyl, oxiranyl, tetrahydropyranyl, and the like. In some embodiments, the heterocyclyl group includes azetidinyl, pyrrolidinyl, piperidinyl, piperazinyl, morpholinyl, and 6-azaspiro[2,5]octanyl. The heterocyclyl may be unsubstituted or substituted. In some embodiments, the heterocyclyl is substituted with two substituents. In further embodiments, the heterocyclyl is substituted with one substituent. In yet other embodiments, the heterocyclyl is substituted with three substituents. In still further embodiments, the heterocyclyl is unsubstituted.

The term "(heterocyclyl)alkylene" as used by itself or part of another group refers to an alkylene group as defined herein that is bound to a heterocyclyl group as defined herein.

The term "optionally substituted," as used herein to describe a chemical moiety defined herein, means that the moiety may, but is not required to be, substituted with one or more suitable functional groups or other substituents as provided herein. For example, a substituent may be optionally substituted with one or more of: halo, cyano, —$NO_2$, —$N_3$, —OH, —SH, $C_{1-6}$alkyl, $C_{3-8}$cycloalkyl, $C_{3-8}$cycloalkenyl, $C_{2-6}$alkenyl, $C_{2-6}$alkynyl, $C_{1-6}$haloalkyl, $C_{1-6}$alkoxy, $C_{1-6}$alkoxy(alkylene), $C_{1-6}$haloalkoxy, $C_{1-6}$haloalkoxy(alkylene), $C_{1-6}$ alkylcarbonyl, $C_{1-6}$cyanoalkyl, $C_{1-6}$hydroxyalkyl, $C_{1-6}$alkylenethio, $(CR^vR^x)_pNR^yR^z$ (wherein $R^v$ and $R^x$ are, independently, H or $C_{1-6}$alkyl; $R^y$ and $R^z$, are independently, H, $C_{1-6}$alkyl, $C_{3-6}$cycloalkyl, $C_{1-6}$hydroxyalkyl, $C_{1-6}$haloalkyl, $C_{1-6}$alkoxy(alkylene), or C(O)O$C_{1-6}$alkyl, and p is 0, 1, 2, or 3), —C(O)$NH_2$, —C(O)NH$C_{1-6}$alkyl, —C(O)N($C_{1-6}$alkyl)$_2$, —C(O)NH$C_{3-6}$cycloalkyl, —C(O)N($C_{3-6}$cycloalkyl)$_2$, —COOH, —$C_{1-6}$alkyleneCOOH, —$C_{3-6}$cycloalkylCOOH, —$C_{1-6}$ alkyleneCON$H_2$, $C_{3-6}$cycloalkylCON$H_2$, —$C_{1-6}$alkyleneCONH$C_{1-6}$alkyl, —$C_{1-6}$alkyleneCON($C_{1-6}$ alkyl)$_2$, —C(O)O$C_{1-6}$alkyl, —NHCO($C_{1-6}$alkyl), —N($C_{1-6}$alkyl)C(O)($C_{1-6}$alkyl), —S(O)$C_{1-6}$alkyl, —S(O)$C_{3-6}$cycloalkyl, $C_{1-6}$alkylsulfonyl, $C_{3-6}$cycloalkylsulfonyl, $C_{1-6}$alkylsulfonyl(alkylene), oxo (=O), 3-7-membered heterocyclyl, heterocyclyl(alkylene), aryl, aryl(alkylene), or heteroaryl groups. In some embodiments, the $C_{1-6}$alkyl group in any of the substituent groups in this paragraph is a $C_{1-4}$alkyl; in other embodiments it is $C_{1-3}$alkyl. In some embodiments, the $C_{1-6}$alkylene group in any of the substituent groups in this paragraph is a $C_{1-4}$alkylene. In some embodiments, the $C_{1-6}$haloalkyl substituent is a $C_{1-4}$haloalkyl; in other embodiments, it is $C_{1-3}$haloalkyl. In some embodiments, the $C_{3-6}$cycloalkyl substituent is a $C_{3-4}$cycloalkyl substituent. In some embodiments, the $C_{1-6}$alkoxy substituent is a $C_{1-3}$alkoxy; in other embodiments, it is $C_{1-4}$alkoxy. In some embodiments, the $C_{1-6}$haloalkoxy substituent is a $C_{1-3}$haloalkoxy; in other embodiments, it is $C_{1-4}$haloalkoxy.

In some embodiments, a substituent may be optionally substituted with one or more of $C_{1-6}$alkyl, optionally substituted $C_{2-6}$alkenyl, halo, CN, $C_{1-6}$-cyanoalkyl, $C_{1-6}$ haloalkyl, OH, optionally substituted $C_{3-6}$cycloalkyl, optionally substituted $C_{3-8}$cycloalkenyl, optionally substituted aryl, optionally substituted aryl(alkylene), optionally substituted heteroaryl, optionally substituted heterocyclyl, optionally substituted heterocyclyl(alkylene), $C_{1-6}$hydroxyalkyl, $C_{1-6}$haloalkoxy, $C_{1-6}$haloalkoxy(alkylene), $C_{1-6}$alkoxy, $C_{1-6}$ alkoxy(alkylene), $C_{1-6}$deuterated alkoxy(alkylene), $C_{1-6}$alkylcarbonyl, $C_{3-8}$cycloalkylsulfonyl, $C_{1-6}$alkylsulfonyl(alkylene), $(CR^vR^x)_pNR^yR^z$ (wherein $R^v$ and $R^x$ are, independently, H or $C_{1-6}$alkyl; $R^y$ and $R^z$, are independently, H, $C_{1-6}$alkyl, $C_{3-6}$cycloalkyl, $C_{1-6}$hydroxyalkyl, $C_{1-6}$ haloalkyl, $C_{1-6}$alkoxy(alkylene), or C(O)O$C_{1-6}$alkyl, and p is 0, 1, 2, or 3), and C(O)$NR^{y2}R^{z2}$ (wherein $R^{y2}$ and $R^{z2}$, are independently, H, $C_{1-6}$alkyl, or $C_{3-6}$cycloalkyl).

The term "nitrogen protecting group" refers to a moiety that is attached to a nitrogen atom to prevent reaction at that nitrogen atom. Nitrogen protecting groups will be known by those skilled in the art and include those described in Wuts, P. G., *Greene's Protective Groups in Organic Synthesis*. Wiley; 5th edition (Oct. 27, 2014), which is incorporated by reference herein.

Recitation of ranges of values herein are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about" when used in combination with a numeric value or range of values means the value or range of values may deviate to an extent deemed reasonable to one of ordinary skill in the art.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including supercritical fluid chromatography (SFC), chiral high-pressure liquid chromatography (HPLC) and the formation and crystallization of chiral salts; or preferred isomers can be prepared by asymmetric syntheses. See, for example, Jacques et al., Enantiomers. Racemates and Resolutions (Wiley Interscience, New York, 1981); Wilen et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, IN 1972).

Exemplary compounds of the disclosure including a chiral center may be depicted herein as having particular stereochemistries, but for which absolute stereochemistry has not been obtained. Absolute configurations can be obtained using methods known in the art.

As used herein, the term "stereoisomers" refers to compounds which have identical chemical constitution and connectivity but differ with regard to the arrangement of the atoms or groups in space, e.g., enantiomers or diastereomers.

When the stereochemical configuration at a chiral center in a compound having one or more chiral centers is depicted by its chemical name (e.g., where the configuration is indicated in the chemical name by "R" or "S") or structure (e.g., the configuration is indicated by dashed or wedge bonds), the enrichment of the indicated configuration relative to the opposite configuration is greater than 50%, 60%, 70%, 80%, 90%, 99% or 99.9%. "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When a disclosed compound is named or depicted by structure without indicating stereochemistry, it is understood that the name or the structure encompasses one of the possible stereoisomers or geometric isomers free of the others, or a mixture of the encompassed stereoisomers or geometric isomers.

It will be understood that certain compounds disclosed herein may exist in tautomeric forms. Such forms are included as part of the present disclosure. Thus, when a compound herein is represented by a structural formula or designated by a chemical name herein, all tautomeric forms which may exist for the compound are encompassed by the structural formula.

When the compounds described herein contain olefinic double bonds or other centers of geometric asymmetry, and unless specified otherwise, it is intended that they include both E and Z geometric isomers.

In some embodiments, the compounds described herein are isotopically enriched compound, e.g., an isotopologue. The term "isotopically enriched" refers to an atom having an isotopic composition other than the naturally abundant isotopic composition of that atom. "Isotopically enriched" may also refer to a compound containing at least one atom having an isotopic composition other than the natural isotopic composition of that atom. In an isotopologue, "isotopic enrichment" refers to the percentage of incorporation of an amount of a specific isotope of a given atom in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. In one embodiment, one or more hydrogen atoms on a described compound may be replaced by deuterium.

Thus, as used herein, and unless otherwise indicated, the term "isotopic enrichment factor" refers to the ratio between the isotopic composition and the natural isotopic composition of a specified isotope.

With regard to the compounds provided herein, when a particular atom's position is designated as having deuterium or "D" or "$^2$H", it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium atom. The isotopic enrichment and isotopic enrichment factor of the compounds provided herein can be determined using conventional analytical methods known to one of ordinary skill in the art, including mass spectrometry and nuclear magnetic resonance spectroscopy.

The term "patient" or "subject" is used throughout the specification to describe an animal, preferably a human or a domesticated animal, to whom treatment, including prophylactic treatment, with the compounds or compositions according to the present disclosure is provided. For treatment of those conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The terms "therapeutically effective amount" or "effective amount" means an amount or dose of a compound of the disclosure (or a pharmaceutically acceptable salt thereof) sufficient to generally bring about the desired therapeutic benefit in subjects in need of such treatment for the designated disease or disorder. Further, a therapeutically effective amount with respect to a compound of the disclosure means that amount of therapeutic agent alone, or in combination with other therapies, that provides a therapeutic benefit in the treatment or prevention of a disease.

"Treating" or "treatment" of any disease or disorder refers, in one embodiment, to ameliorating the disease or disorder (e.g., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

The terms "prevent," "preventing," and "prevention" refer to the prevention of the onset, recurrence, or spread of the disease in a subject resulting from the administration of a prophylactic or therapeutic agent.

Compounds

The present disclosure provides compounds of Formula I or pharmaceutically acceptable salts thereof:

I

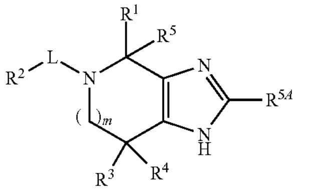

In Formula I, m is 1 or 2. In some embodiments, m is 1. In other embodiments, m is 2.

In formula I, $R^1$ is

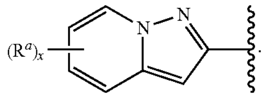

In the structures for $R^1$, x is 0 to 5. In some embodiments, x is 0. In other embodiments, x is 1. In further embodiments, x is 2. In yet other embodiments, x is 3. In still further embodiments, x is 4. In other embodiments, x is 5.

In further embodiments, $R^1$ is

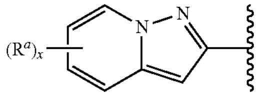

and x is 0 or 1, such as

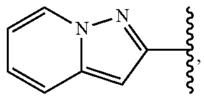,

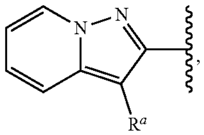,

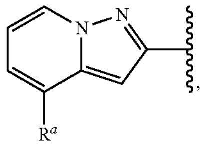,

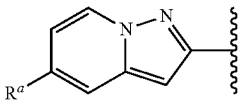,

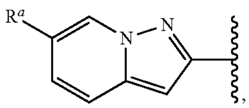, or

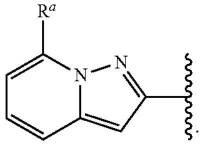.

In other embodiments, $R^1$ is

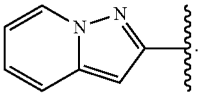 [SMILES: *c1cc2ccccn2n1].

In yet other embodiments, $R^1$ is

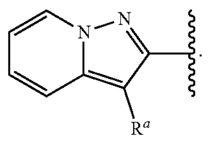

In still other embodiments, $R^1$ is

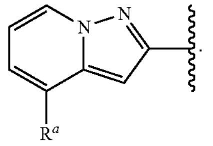

In yet other embodiment, $R^1$ is

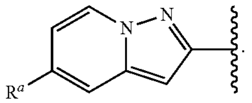

In still further embodiments, $R^1$ is

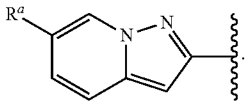

In other embodiments, $R^1$ is

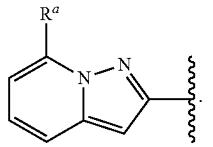

In some embodiments, the compound is a single enantiomer and the $R^1$ moiety is in an alpha (α) configuration. In some embodiments, the compound is a single enantiomer and the $R^1$ moiety is in an beta (β) configuration.

In the structures for $R^1$, each $R^a$ is independently halo, $C_{1-6}$alkyl, $C_{3-6}$ cycloalkyl, $C_{1-6}$haloalkyl, $C_{1-6}$alkoxy or $C_{1-6}$haloalkoxy. In some embodiments, R is halo such as F, Cl, Br, or I. In other embodiments, $R^a$ is F, Br, or Cl. In still other embodiments, $R^a$ is F. In further embodiments, R is Br. In yet other embodiments, $R^a$ is Cl. In still further embodiments, $R^a$ is I. In other embodiments, $R^a$ is $C_{1-6}$alkyl such as methyl, ethyl, propyl, butyl, pentyl, or hexyl. In further embodiments, $R^a$ is methyl, ethyl, or isopropyl. In yet other embodiments, $R^a$ is methyl. In further embodiments, $R^a$ is $C_{3-6}$cycloalkyl such as cyclopropyl, cyclobutyl, cyclopentyl, or cyclohexyl. In still further embodiments, $R^a$ is cyclopropyl. In yet other embodiments, $R^a$ is $C_{1-6}$haloalkyl such as $CF_3$, $CHF_2$, $CH_2F$, $CH_2CF_3$, $C(CH_3)_2F$, or $C(CH_3)F_2$. In still other embodiments, $R^a$ is $CF_3$ or $CHF_2$. In further embodiments, $R^a$ is $C_{1-6}$ alkoxy such as methoxy, ethoxy, propoxy, butoxy, pentoxy, or hexoxy. In yet other embodiments, $R^8$ is methoxy or ethoxy. In other embodiments, $R^a$ is $C_{1-6}$haloalkoxy such as $OCF_3$ or $OCH_2CF_3$. In still other embodiments, one $R^a$ is halo and the second $R^a$ is $C_{1-6}$ alkoxy or $C_{1-6}$alkyl.

In Formula I, $R^2$ is $C_{1-4}$alkyl, optionally substituted $C_{3-8}$cycloalkyl, optionally substituted heterocyclyl, optionally substituted aryl, or optionally substituted heteroaryl. In some embodiments, $R^2$ is optionally substituted $C_{3-8}$cycloalkyl, optionally substituted heterocyclyl, optionally substituted aryl, or optionally substituted heteroaryl. In further embodiments, $R^2$ is unsubstituted $C_{3-8}$cycloalkyl, unsubstituted heterocyclyl, unsubstituted aryl, or unsubstituted heteroaryl. In other embodiments, $R^2$ is substituted $C_{3-8}$ cycloalkyl, substituted heterocyclyl, substituted aryl, or substituted heteroaryl. In some embodiments, $R^2$ is $C_{1-4}$alkyl such as methyl, ethyl, propyl, butyl, or tert-butyl. In other embodiments, $R^2$ is optionally substituted $C_{3-8}$cycloalkyl such as cyclopropyl, cyclobutyl, cyclopentyl, cyclohexyl, cycloheptyl, or cyclooctyl. In further embodiments, $R^2$ is optionally substituted heterocyclyl such as azetidinyl. In still other embodiments, $R^2$ is optionally substituted aryl such as phenyl. In yet further embodiments, $R^2$ is optionally substituted heteroaryl such as pyridinyl, pyrazolyl, oxazolyl, isoxazolyl, thiazolyl, isothiazolyl, triazolyl, oxadiazolyl, thiadiazolyl, furanyl, thiophenyl, pyrimidinyl, pyrazinyl, indazolyl, pyrazolo[1,5-a]pyridinyl, imidazol[1,5-a]pyridinyl, pyrrolo[1,2-b]pyridazinyl, benzo[d]thiazolyl, benzo[d]isothiazolyl, benzo[d]imidazolyl, benzo[d]oxazolyl, benzo[d]isoxazolyl, or benzo[d]isothiazolyl.

In Formula I, $R^3$ is H or $C_{1-6}$alkyl. In some embodiments, $R^3$ is H. In other embodiments, $R^3$ is $C_{1-6}$alkyl such as methyl, ethyl, propyl, butyl, pentyl, or hexyl. In further embodiments, $R^3$ is methyl. In yet other embodiments, $R^3$ is ethyl. In still further embodiments, $R^3$ is propyl. In other embodiments, $R^3$ is butyl. In further embodiments, $R^3$ is pentyl. In yet other embodiments, $R^3$ is hexyl.

In Formula I, $R^4$ is H or $C_{1-6}$alkyl. In some embodiments, $R^4$ is H. In other embodiments, $R^4$ is $C_{1-6}$alkyl such as methyl, ethyl, propyl, butyl, pentyl, or hexyl. In further embodiments, $R^4$ is methyl. In yet other embodiments, $R^4$ is ethyl. In still further embodiments, $R^4$ is propyl. In other embodiments, $R^4$ is butyl. In further embodiments, $R^4$ is pentyl. In yet other embodiments, $R^4$ is hexyl.

Alternatively, $R^3$ and $R^4$, together with the atom to which they are attached, form a $C_{3-6}$cycloalkyl. In some embodiments, $R^3$ and $R^4$ together form a cyclopropyl. In other embodiments, $R^3$ and $R^4$ together form a cyclobutyl. In further embodiments, $R^3$ and $R^4$ together form a cyclopentyl. In yet other embodiments, $R^3$ and $R^4$ together form a cyclohexyl.

In some embodiments, both $R^3$ and $R^4$ are H. In other embodiments, $R^3$ is methyl and $R^4$ is H. In still other embodiments, both $R^3$ and $R^4$ are methyl.

In Formula I, $R^5$ is H or D. In some embodiments, $R^5$ is H. In further embodiments, $R^5$ is D.

In Formula I, $R^{5A}$ is H or D. In some embodiments, $R^{5A}$ is H. In further embodiments, $R^{5A}$ is D.

In Formula I, L is a bond, carbonyl, optionally substituted $C_{1-6}$alkylene, optionally substituted $C_{1-6}$alkylenecarbonyl, optionally substituted $C_{2-6}$alkenylenecarbonyl, optionally substituted $C_{1-6}$haloalkylenecarbonyl, or optionally substituted —C(O)$NR^b$($C_{1-6}$alkylene)-, wherein the carbon atom of the carbonyl group is connected to N in Formula I. In some embodiments, L is a bond. In other embodiments, L is carbonyl (wherein the carbon atom of the carbonyl group is connected to N in Formula I). In further embodiments, L is optionally substituted $C_{1-6}$alkylene such as methylene, ethylene, propylene, butylene, pentylene, or hexylene. In other embodiments, L is $C_1$alkylene. In still other embodiments, L is $C_2$alkylene. In further embodiments, L is $C_3$alkylene. In yet other embodiments, L is $C_4$alkylene. In still further embodiments, L is $C_5$alkylene. In other embodiments, L is $C_6$alkylene. In yet other embodiments, L is optionally substituted $C_{1-6}$alkylenecarbonyl (wherein the carbon atom of the carbonyl group is connected to N in Formula I). In further embodiments, L is —$C_1$alkylene-C(O)—. In other embodiments, L is —$C_2$alkylene-C(O)—. In further embodiments, L is —$C_3$alkylene-C(O)—. In yet other embodiments, L is —$C_4$alkylene-C(O)—. In still further embodiments, L is —$C_5$alkylene-C(O)—. In other embodiments, L is —$C_6$alkylene-C(O)—. In still further embodiments, L is optionally substituted $C_{2-6}$alkenylenecarbonyl (wherein the carbon atom of the carbonyl group is connected to N in Formula I). In other embodiments, L is —$C_2$alkenylene-C(O)—. In further embodiments, L is —$C_3$alkenylene-C(O)—. In yet other embodiments, L is —$C_4$alkenylene-C(O)—. In still further embodiments, L is —$C_5$alkenylene-C(O)—. In other embodiments, L is —$C_6$alkenylene-C(O)—. In other embodiments, L is optionally substituted $C_{1-6}$haloalkylenecarbonyl (wherein the carbon atom of the carbonyl group is connected to N in Formula I). In yet other embodiments, L is —$C_1$haloalkylene-C(O)—. In other embodiments, L is —$C_2$haloalkylene-C(O)—. In further embodiments, L is —$C_3$haloalkylene-C(O)—. In yet other embodiments, L is —$C_4$haloalkylene-C(O)—. In still further embodiments, L is —$C_5$haloalkylene-C(O)—. In other embodiments, L is —$C_6$haloalkylene-C(O)—. In further embodiments, L is —C(O)$NR^b$($C_{1-6}$alkylene)- (wherein the carbon atom of the carbonyl group is connected to N in Formula I). In yet other embodiments, L is —C(O)$NR^bC_3$alkylene-. In other embodiments, L is —C(O)$NR^bC_2$alkylene-. In further embodiments, L is —C(O)$NR^bC_3$alkylene-. In yet other embodiments, L is —C(O)$NR^bC_4$alkylene-. In still further embodiments, L is —C(O)$NR^bC_5$alkylene-. In other embodiments, L is —C(O)$NR^bC_6$alkylene-.

In the structures for L, $R^b$ is H or $C_{1-6}$alkyl. In some embodiments, $R^b$ is H. In other embodiments, $R^b$ is $C_{1-6}$alkyl, such as methyl, ethyl, propyl, butyl, pentyl, or hexyl. In further embodiments, $R^b$ is methyl. In yet other embodiments, $R^b$ is ethyl. In still further embodiments, $R^b$ is propyl. In other embodiments, $R^b$ is butyl. In further embodiments, $R^b$ is pentyl. In yet other embodiments, $R^b$ is hexyl.

In some embodiments, L is a bond, —C(O)—, —C(O)$CH_2$—, —C(O)$CH_2CH_2$—, —C(O)$CH_2CH_2CH_2$—, —C(O)$CF_2$—, —C(O)CHF—, —C(O)$C(CH_3)_2$—, —C(O)CH═CH—,

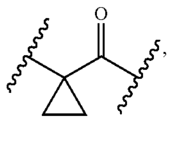 [SMILES: *C(=O)C1(*)CC1]

—C(O)NH$CH_2$—, —$CH_2$—, or —$CH_2CH_2$—. In yet other embodiments, L is a bond, —C(O)—, —C(O)$CH_2$—, or —C(O)$CF_2$.

In some embodiments, $R^2$ is cyclopentyl, cyclobutyl, cyclopropyl, azetidinyl, phenyl, pyrazolyl, oxazolyl, thiazolyl, triazolyl, oxadiazolyl, pyridinyl, pyrimidinyl, pyrazolo[1,5-a]pyridinyl, indazolyl, thiadiazolyl, imidazol[1,5-a]pyridinyl, pyrrolo[1,2]pyridazinyl, thiophenyl, isoxazolyl, isothiazolyl, benzo[d]thiazolyl, benzo[d]imidazolyl, benzo[d]oxazolyl, benzo[d]isoxazolyl, benzo[d]isothiazolyl, furanyl, or pyrazinyl, each of which is optionally substituted.

In further embodiments, $R^2$ is cyclopentyl, cyclobutyl, cyclopropyl, cyclohexyl, azetidinyl, phenyl, pyrazolyl, oxazolyl, thiazolyl, triazolyl, oxadiazolyl, pyridinyl, pyrimidinyl, pyrazolo[1,5-a]pyridinyl, indazolyl, thiadiazolyl, imidazol[1,5-a]pyridinyl, pyrrolo[1,2]pyridazinyl, thiophenyl, isoxazolyl, isothiazolyl, benzo[d]thiazolyl, benzo[d]imidazolyl, benzo[d]oxazolyl, benzo[d]isoxazolyl, benzo[c]isoxazolyl, benzo[d]isothiazolyl, furanyl, pyrazinyl or quinolinyl, each of which is optionally substituted.

In other embodiments, $R^2$ is cyclopentyl, cyclobutyl, cyclopropyl, azetidinyl, phenyl, pyrazolyl, oxazolyl, thiazolyl, triazolyl, oxadiazolyl, pyridinyl, pyrimidinyl, pyrazolo[1,5-a]pyridinyl, indazolyl, thiadiazolyl, imidazol[1,5-a]pyridinyl, pyrrolo[1,2]pyridazinyl, thiophenyl, isoxazolyl, isothiazolyl, benzo[d]thiazolyl, benzo[d]imidazolyl, benzo[d]oxazolyl, benzo[d]isoxazolyl, benzo[d]isothiazolyl, furanyl, or pyrazinyl, each of which is unsubstituted.

In yet other embodiments, $R^2$ is cyclopentyl, cyclobutyl, cyclopropyl, cyclohexyl, azetidinyl, phenyl, pyrazolyl, oxazolyl, thiazolyl, triazolyl, oxadiazolyl, pyridinyl, pyrimidinyl, pyrazolo[1,5-a]pyridinyl, indazolyl, thiadiazolyl, imidazol[1,5-a]pyridinyl, pyrrolo[1,2]pyridazinyl, thiophenyl, isoxazolyl, isothiazolyl, benzo[d]thiazolyl, benzo[d]imidazolyl, benzo[d]oxazolyl, benzo[d]isoxazolyl, benzo[c]isoxazolyl, benzo[d]isothiazolyl, furanyl, pyrazinyl or quinolinyl, each of which is unsubstituted.

In further embodiments, $R^2$ is optionally substituted cyclopentyl. In further embodiments, $R^2$ is optionally substituted cyclobutyl. In still other embodiments, $R^2$ is optionally substituted cyclopropyl. In yet other embodiments, $R^2$ is optionally substituted cyclohexyl. In yet further embodiments, $R^2$ is optionally substituted azetidinyl. In other embodiments, $R^2$ is optionally substituted phenyl. In further embodiments, $R^2$ is optionally substituted pyrazolyl. In still other embodiments, $R^2$ is optionally substituted oxazolyl. In yet further embodiments, $R^2$ is optionally substituted thiazolyl. In other embodiments, $R^2$ is optionally substituted triazolyl. In further embodiments, $R^2$ is optionally substituted oxadiazolyl. In still other embodiments, $R^2$ is optionally substituted pyridinyl. In yet further embodiments, $R^2$ is optionally substituted pyrimidinyl. In other embodiments, $R^2$ is optionally substituted pyrazolo[1,5-a]pyridinyl. In further embodiments, $R^2$ is optionally substituted indazolyl. In yet other embodiments, $R^2$ is optionally substituted thiadiazolyl. In other embodiments, $R^2$ is optionally substituted imidazol[1,5-a]pyridinyl. In further embodiments, $R^2$ is optionally substituted pyrrolo[1,2]pyridazinyl. In still other embodiments, $R^2$ is optionally substituted thiophenyl. In yet further embodiments, $R^2$ is optionally substituted isoxazolyl. In further embodiments, $R^2$ is optionally substituted isothiazolyl. In other embodiments, $R^2$ is optionally substituted benzo[d]thiazolyl. In further embodiments, $R^2$ is optionally substituted benzo[d]imidazolyl. In still other embodiments, $R^2$ is optionally substituted benzo[d]oxazolyl. In yet further embodiments, $R^2$ is benzo[d]isoxazolyl. In yet other embodiments, $R^2$ is optionally substituted benzo[c]isoxazolyl. In still further embodiments, $R^2$ is optionally substituted benzo[d]isothiazolyl. In other embodiments, $R^2$ is optionally substituted furanyl. In yet other embodiments, $R^2$ is optionally substituted pyrazinyl. In still further embodiments, $R^2$ is optionally substituted quinolinyl.

In other embodiments, $R^2$ is azetidin-1-yl, azetidin-3-yl, pyrazol-1-yl, pyrazol-3-yl, pyrazol-4-yl, pyrazol-5-yl, 1,2,4-triazol-1-yl, 1,2,4-triazol-3-yl, 1,2,4-triazol-5-yl, 1,2,3-triazol-5-yl, 1,3,4-oxadiazol-2-yl, 1,2,4-oxadiazol-3-yl, 1,2,4- oxadiazol-5-yl, pyrazolo[1,5-a]pyridin-3-yl, indazol-3-yl, thiazol-2-yl, thiazol-4-yl, thiazol-5-yl, oxazol-2-yl, oxazol-4-yl, oxazol-5-yl, 1,3,4-thiadiazol-2-yl, pyridin-1-yl, pyridin-2-yl, pyridin-3-yl, pyridin-4-yl, pyrimidin-2-yl, imidazol[1,5-a]pyridin-1-yl, pyrrolo[1,2]pyridazin-5-yl, pyrrolo[1,2]pyridazin-6-yl, thiophen-2-yl, isoxazol-3-yl, isoxazol-4-yl, isoxazol-5-yl, benzo[d]thiazol-2-yl, benzo[d]thiazol-3-yl, benzo[d]imidazol-2-yl, benzo[d]oxazol-2-yl, benzo[d]isoxazol-3-yl, benzo[d]isothiazol-3-yl, furan-3-yl, isothiazol-3-yl, isothiazol-4-yl, isothiazol-5-yl, or pyrazin-2-yl, each of which is optionally substituted.

In yet other embodiments, $R^2$ is azetidin-1-yl, azetidin-3-yl, pyrazol-1-yl, pyrazol-3-yl, pyrazol-4-yl, pyrazol-5-yl, 1,2,4-triazol-1-yl, 1,2,4-triazol-3-yl, 1,2,4-triazol-5-yl, 1,2,3-triazol-5-yl, 1,3,4-oxadiazol-2-yl, 1,2,4-oxadiazol-3-yl, 1,2,4-oxadiazol-5-yl, pyrazolo[1,5-a]pyridin-3-yl, indazol-3-yl, thiazol-2-yl, thiazol-4-yl, thiazol-5-yl, oxazol-2-yl, oxazol-4-yl, oxazol-5-yl, 1,3,4-thiadiazol-2-yl, pyridin-1-yl, pyridin-2-yl, pyridin-3-yl, pyridin-4-yl, pyrimidin-2-yl, imidazol[1,5-a]pyridin-1-yl, pyrrolo[1,2]pyridazin-5-yl, pyrrolo[1,2]pyridazin-6-yl, thiophen-2-yl, isoxazol-3-yl, isoxazol-4-yl, isoxazol-5-yl, benzo[d]thiazol-2-yl, benzo[d]thiazol-3-yl, benzo[d]imidazol-2-yl, benzo[d]oxazol-2-yl, benzo[d]isoxazol-3-yl, benzo[d]isothiazol-3-yl, furan-3-yl, isothiazol-3-yl, isothiazol-4-yl, isothiazol-5-yl, pyrazin-2-yl, benzo[c]isoxazole-3-yl, or quinolin-3-yl, each of which is optionally substituted.

In further embodiments, $R^2$ is $C_{3-8}$cycloalkyl, heterocyclyl, aryl, or heteroaryl, each of which is substituted with one or more of $C_{1-6}$alkyl, optionally substituted $C_{2-6}$alkenyl, halo, CN, $C_{1-6}$cyanoalkyl, $C_{1-6}$haloalkyl, OH, optionally substituted $C_{3-8}$ cycloalkyl, optionally substituted $C_{3-8}$cycloalkyl(alkylene), optionally substituted $C_{3-8}$cycloalkenyl, optionally substituted aryl, optionally substituted aryl(alkylene), optionally substituted heteroaryl, optionally substituted heterocyclyl, optionally substituted heterocyclyl(alkylene), $C_{1-6}$hydroxyalkyl, $C_{1-6}$haloalkoxy, $C_{1-6}$haloalkoxy (alkylene), $C_{1-6}$ alkoxy, $C_{1-6}$alkoxy(alkylene), $C_{1-6}$deuterated alkoxy(alkylene), $C_{1-6}$alkylcarbonyl, $C_{3-8}$cycloalkylsulfonyl, $C_{1-6}$alkylsulfonyl, $C_{1-6}$alkylsulfonyl(alkylene), $(CR^vR^x)_pNR^yR^z$ (wherein $R^v$ and $R^x$ are, independently, H or $C_{1-6}$alkyl; $R^y$ and $R^z$, are independently, H, $C_{1-6}$alkyl, $C_{3-6}$cycloalkyl, $C_{1-4}$hydroxyalkyl, $C_{1-6}$haloalkyl, $C_{1-6}$alkoxy(alkylene), or C(O)O$C_{1-6}$alkyl and p is 0, 1, 2, or 3), or C(O)$NR^{y2}R^{z2}$ (wherein $R^{y2}$ and $R^{z2}$, are independently, H, $C_{1-6}$alkyl, or $C_{3-6}$cycloalkyl). In other embodiments, $R^2$ is optionally substituted with $C_{1-6}$alkyl, such as methyl, ethyl, propyl, isopropyl, or tert-butyl. In yet further embodiments, $R^2$ is optionally substituted with $C_{2-6}$alkenyl such as $CH{=}CH_2$, CH=CHC(CH)?OH, or CH=CH-cyclopropyl. In further embodiments, $R^2$ is optionally substituted with halo such as Br, Cl, or F. In yet other embodiments, $R^2$ is optionally substituted with CN. In still further embodiments, $R^2$ is optionally substituted with $C_{1-6}$cyanoalkyl such as $C(CH_3)_2CN$. In other embodiments, $R^2$ is optionally substituted with $C_{1-6}$haloalkyl, such as $CF_3$, $CHF_2$, $CH_2F$, $CH(CH_3)F$, $CH_2CF_3$, $C(CH_3)_2F$, $C(CH)F_2$, or $CH_2CHF_2$. In further embodiments, $R^2$ is optionally substituted with OH. In still other embodiments, $R^2$ is optionally substituted with optionally substituted $C_{3-8}$cycloalkyl, such as optionally substituted cyclopropyl, optionally substituted cyclobutyl, optionally substituted cyclopentyl, or optionally substituted cyclohexyl. In further embodiments, $R^2$ is optionally substituted with optionally substituted $C_{3-8}$cycloalkyl(alkylene) such as optionally substituted cyclopropyl(alkylene) or optionally substituted cyclobutyl(alkylene). In other embodiments, $R^2$ is optionally substituted with optionally substituted $C_{3-8}$cycloalkenyl, such as optionally substituted cyclohexenyl. In yet further embodiments, $R^2$ is optionally substituted with optionally substituted aryl such as optionally substituted phenyl. In further embodiments, $R^2$ optionally substituted with optionally substituted aryl(alkylene) such as optionally substituted benzyl. In other embodiments, $R^2$ is optionally substituted with optionally substituted heteroaryl, such optionally substituted pyrazolyl, optionally substituted imidazolyl, optionally substituted pyridinyl, optionally substituted pyrimidinyl, or optionally substituted pyrazinyl. In yet other embodiments, $R^2$ is optionally substituted with optionally substituted heteroaryl, such optionally substituted pyrazolyl, optionally substituted imidazolyl, optionally substituted pyridinyl, optionally substituted pyrimidinyl, optionally substituted pyrazinyl, or optionally substituted pyridazinyl. In further embodiments, $R^2$ is optionally substituted with optionally substituted heterocyclyl such as optionally substituted azetidinyl, optionally substituted piperidinyl, optionally substituted piperazinyl, optionally substituted pyrrolidinyl, optionally substituted morpholinyl, or optionally substituted 6-azaspiro[2,5]octan-6-yl. In yet further embodiments, $R^2$ is optionally substituted with optionally substituted morpholinyl(alkylene), optionally substituted piperidinyl(alkylene), optionally substituted piperazinyl(alkylene), or optionally substituted azetidinyl(alkylene). In still other embodiments, $R^2$ is optionally substituted with $C_{1-6}$hydroxyalkyl such as $C(CH_3)_2OH$, $CH(CH_3)OH$, $C(CH_3)_2CH_2OH$, $CH_2C(CH_3)_2OH$, or $CH(CH_2CH_3)OH$. In yet further embodiments, $R^2$ is optionally substituted with $C_{1-6}$haloalkoxy such as $OCF_3$, $OCH_2CF_3$, or $OCH_2CH_2CF_3$. In still further embodiments, $R^2$ is optionally substituted with $C_{1-6}$haloalkoxy(alkylene) such as $CH_2OCF_3$. In other embodiments, $R^2$ is optionally substituted with $C_{1-6}$alkoxy, such as methoxy or ethoxy. In yet other embodiments, $R^2$ is optionally substituted with $C_{1-6}$alkoxy(alkylene), such as $C(CH_3)_2OCH_3$, $CH_2OCH_3$, or $(CH_2)_2OCH_3$. In further embodiments, $R^2$ is optionally substituted with $C_{1-6}$deuterated alkoxy(alkylene) such as $CH_2OCH_3$. In further embodiments, $R^2$ is optionally substituted with $C_{1-6}$alkylcarbonyl, such as $C(=O)CH_3$ or $CH_2C(=O)CH_3$. In yet other embodiments, $R^2$ is optionally substituted with $C_{3-6}$cycloalkylsulfonyl such as cyclopropylsulfonyl, cyclobutylsulfonyl, or cyclopentylsulfonyl. In other embodiments, $R^2$ is optionally substituted with $C_{1-6}$alkylsulfonyl such as methylsulfonyl, ethylsulfonyl, or propylsulfonyl. In yet other embodiments, $R^2$ is optionally substituted with $C_{1-6}$alkylsulfonyl(alkylene), such as $C(CH_3)_2SO_2CH_3$. In still further embodiments, $R^2$ is optionally substituted with $(CR^vR^x)_pNR^yR^z$, wherein $R^v$, $R^x$, $R^y$, $R^z$, and p are defined above, such as $NH_2$, NHcyclopropyl, $NHCH_3$, $N(CH_3)_2$, $CH_2N(CH_3)_2$, $(CH_2)_2N(CH_3)_2$, $CH_2N(CH_3)(CH_2CH_3)$, $C(CH_3)_2NH(CH_3)$, $C(CH_3)_2N(CH_3)_2$, $CH_2N(CH_3)$cyclobutyl, or $CH_2N(CH_3)$(C(O)Otert-butyl). In some embodiments, p is 0. In other embodiments, p is 1. In further embodiments, p is 2. In still other embodiments, p is 3. In some embodiments, $R^v$ and $R^x$ are, independently, hydrogen or methyl. In other embodiments, $R^y$ and $R^z$ are, independently, hydrogen, methyl, ethyl, cyclopropyl, cyclobutyl, C(O)Omethyl, C(O)Oethyl, C(O)Opropyl, or C(O)Otert-butyl. In other embodiments, $R^2$ is C(O)$NR^{y2}R^{z2}$, wherein $R^{y2}$ and $R^{z2}$ are defined above, such as $C(O)N(CH_3)_2$ or C(O)NHcyclopropyl. In yet other embodiments, $R^{y2}$ and $R^{z2}$ are, independently, hydrogen, methyl, or cyclopropyl. In further embodiments, $R^2$ is substituted with one or more of methyl, ethyl, propyl, isopropyl, tert-butyl, $CH{=}CH_2$, $CH{=}CHC(CH_3)_2OH$, CH=CH-cyclopropyl, Br, Cl, F, CN, $C(CH_3)_2CN$, $CF_3$, $CHF_2$, $CH_2F$, $CH(CH_3)F$, $CH_2CF_3$, $C(CH_3)_2F$, $C(CH_3)F_2$, $CH_2CHF_2$, OH, optionally substituted cyclopropyl, optionally substituted cyclobutyl, optionally substituted cyclopentyl, optionally substituted cyclohexyl, optionally substituted cyclohexenyl, optionally substituted cyclopropyl(alkylene), optionally substituted cyclobutyl(alkylene), optionally substituted phenyl, optionally substituted benzyl, optionally substituted pyrazolyl, optionally substituted imidazolyl, optionally substituted pyridinyl, optionally substituted pyrimidinyl, optionally substituted pyrazinyl, optionally substituted azetidinyl, optionally substituted piperidinyl, optionally substituted piperazinyl, optionally substituted pyrrolidinyl, optionally substituted morpholinyl, optionally substituted 6-azaspiro[2,5]octan-6-yl, optionally substituted morpholinyl(alkylene), optionally substituted piperidinyl(alkylene), optionally substituted piperazinyl(alkylene), or optionally substituted azetidinyl(alkylene), $C(CH_3)_2OH$, $CH(CH_3)OH$, $C(CH_3)_2CH_2OH$, $CH_2C(CH_3)_2OH$, $CH(CH_2CH_3)OH$, $OCH_2CH_2CF_3$, $OCF_3$, $OCH_2CF_3$, $CH_2OCF_3$, methoxy, ethoxy, $C(CH_3)_2OCH_3$, $CH_2OCH_3$, $(CH_2)_2OCH_3$, $CH_2OCD_3$, $C(=O)CH_3$, $CH_2C(=O)CH_3$, cyclopropylsulfonyl, cyclobutylsulfonyl, cyclopentylsulfonyl, $C(CH_3)_2SO_2CH_3$, $NH_2$, NHcyclopropyl, $NHCH_3$, $N(CH_3)_2$, $CH_2N(CH_3)_2$, $(CH_2)_2N(CH_3)_2$, $CH_2N(CH_3)(CH_2CH_3)$, $C(CH_3)_2NH(CH_3)$, $C(CH_3)_2N(CH_3)_2$, $CH_2N(CH_3)$cyclobutyl, $CH_2N(CH_3)(C(O)$Otert-butyl), $C(O)N(CH_3)_2$, or C(O)NHcyclopropyl.

In yet further embodiments, $R^2$ is

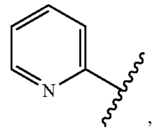 , 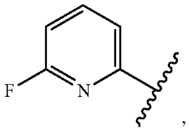 , 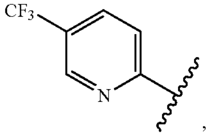 ,

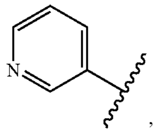 , 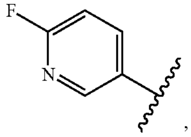 , 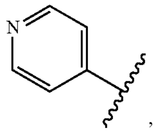 ,

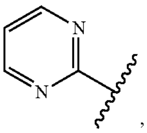 , 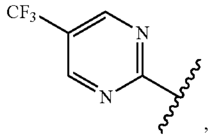 , 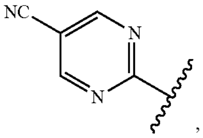 ,

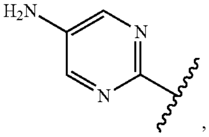 , 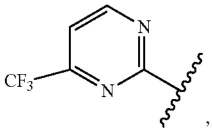 ,

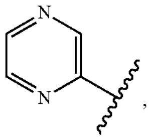 , 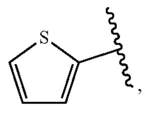 , 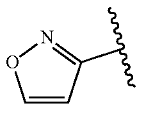 ,

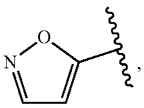 , 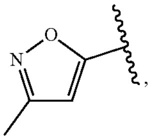 , 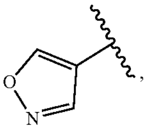 ,

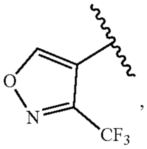 , 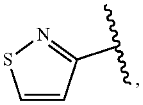 , 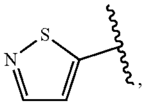 ,

-continued

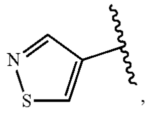 , 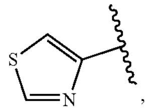 , or 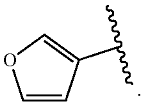 .

In other embodiments, $R^2$ is

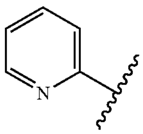 or 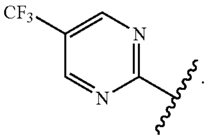 .

In yet other embodiments, $R^2$ is

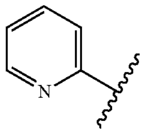 , 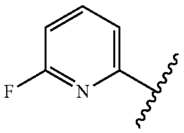 ,

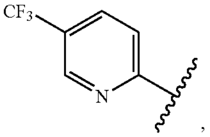 , 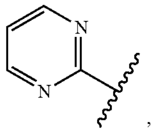 ,

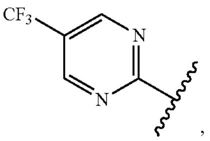 , 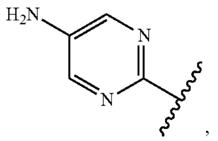 ,

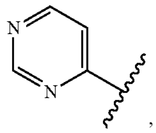 , or 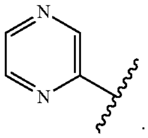 .

In some embodiments, $R^2$ is heterocyclyl, optionally substituted with one or more of halo, $C_{1-6}$haloalkyl, or optionally substituted heteroaryl. In still other embodiments, $R^2$ is In yet other embodiments, $R^2$ is heterocyclyl, substituted with one or more of halo, $C_{1-6}$haloalkyl, or optionally substituted heteroaryl. In further embodiments, $R^2$ is

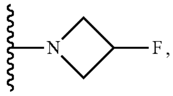 , 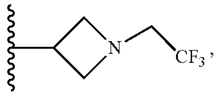 ,

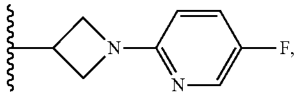 , or

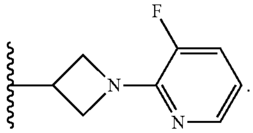 .

In still further embodiments, $R^2$ is

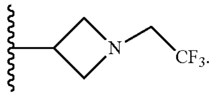 [SMILES: *C1CN(CC(F)(F)F)C1]

In some embodiments, $R^2$ is $C_{3-8}$cycloalkyl, optionally substituted with one or more of halo, $C_{1-6}$alkyl, $C_{1-6}$haloalkyl, or OH In other embodiments, $R^2$ is $C_{3-8}$cycloalkyl, optionally substituted with one or more of halo or OH. In yet other embodiments, $R^2$ is unsubstituted cyclopropyl, unsubstituted cyclobutyl, unsubstituted cyclopentyl, unsubstituted cyclohexyl,

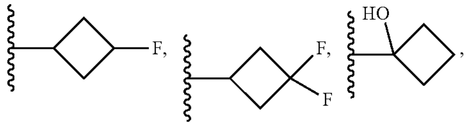

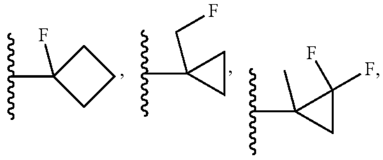

or

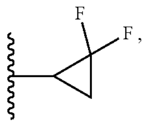 [SMILES: *C1CC1(F)F]

In further embodiments, $R^2$ is $C_{3-8}$cycloalkyl, substituted with one or more of halo, $C_{1-6}$alkyl, $C_{1-6}$haloalkyl, or OH. In still further embodiments, $R^2$ is

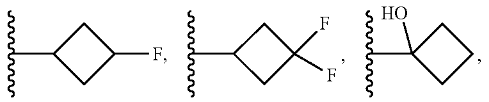

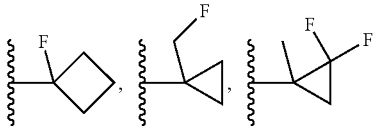

, or

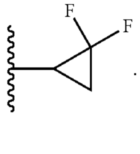

.

In other embodiments, $R^2$ is

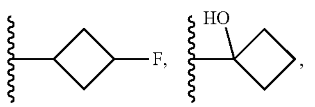

or

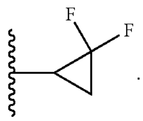

.

In some embodiments, $R^2$ is aryl, optionally substituted with one or more of halo or $C_{1-6}$alkoxy. In other embodiments, $R^2$ is unsubstituted phenyl,

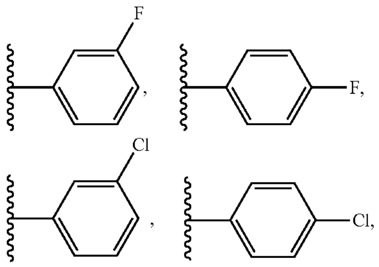

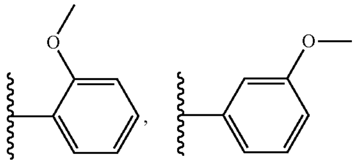

, or

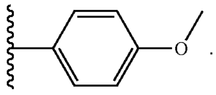

.

In yet other embodiments, $R^2$ is aryl, substituted with one or more of halo or $C_{1-6}$alkoxy. In further embodiments, $R^2$ is

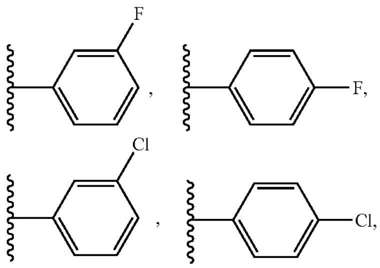

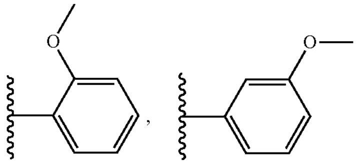

, or

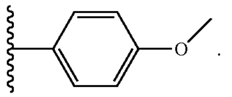

.

In some embodiments, $R^2$ is optionally substituted pyridinyl, optionally substituted pyrimidinyl, or optionally substituted pyrazinyl. In other embodiments, the pyridinyl, pyrimidinyl, or pyrazinyl group is substituted with one or more of halo, $C_{1-6}$ haloalkyl, cyano, or $NR^yR^z$, wherein $R^y$ and $R^z$ are independently H or $C_{1-6}$alkyl.

In still further embodiments, $R^2$ is heteroaryl, substituted with one or more of $C_{1-6}$alkyl, $C_{1-6}$cyanoalkyl, $C_{1-6}$haloalkyl, or $C_{1-6}$hydroxyalkyl. In other embodiments, $R^2$ is heteroaryl substituted with one or more of $C_{1-6}$alkyl. In yet other embodiments, $R^2$ is heteroaryl substituted with one or more of $C_{1-6}$cyanoalkyl. In further embodiments, $R^2$ is heteroaryl substituted with one or more of $C_{1-6}$haloalkyl. In still further embodiments, $R^2$ is heteroaryl substituted with one or more of $C_{1-6}$fluoroalkyl. In yet other embodiments, $R^2$ is heteroaryl substituted with one or more of $C_{1-6}$hydroxyalkyl. In other embodiments, $R^2$ is heteroaryl, substituted with one or more of methyl, ethyl, isopropyl, tert-butyl, $C(CH_3)_2CN$, $CH(CH_3)OH$, $C(CH_3)_2OH$, $C(CH_3)CH_2OH$, $CH(CH_2CH_3)OH$, $CH_2C(CH_3)_2OH$, $CH_2F$, $CHF_2$, $CF_3$, $CH_2CF_3$, $CH_2CHF_2$, $CH(CH_3)F$, $C(CH_3)F_2$, or $C(CH_3)_2F$. In yet other embodiments, $R^2$ is heteroaryl, substituted with one or more of methyl, isopropyl, tert-butyl, $C(CH_3)_2CN$, $CH(CH_3)OH$, $C(CH_3)_2OH$, $CHF_2$, $CF_3$, $CH_2CF_3$, $CH(CH_3)F$, or $C(CH_3)_2F$. In other embodiments, $R^2$ is heteroaryl, substituted with methyl. In yet other embodiments, $R^2$ is heteroaryl, substituted with isopropyl. In other embodiments, $R^2$ is heteroaryl, substituted with tert-butyl. In yet other embodiments, $R^2$ is heteroaryl, substituted with $C(CH_3)_2CN$. In still further embodiments, $R^2$ is heteroaryl, substituted with $CH(CH_3)OH$. In other embodiments, $R^2$ is heteroaryl, substituted with $C(CH_3)_2OH$. In further embodiments, $R^2$ is heteroaryl, substituted with $CHF_2$. In still other embodiments, $R^2$ is heteroaryl, substituted with $CF_3$. In further embodiments, $R^2$ is heteroaryl, substituted with $CH_2CF_3$. In still other embodiments, $R^2$ is heteroaryl, substituted with $CH(CH_3)F$. In other embodiments, $R^2$ is heteroaryl, substituted with $C(CH_3)_2F$.

In other embodiments, $R^2$ is heteroaryl, substituted with $C_{3-8}$cycloalkyl, wherein the $C_{3-8}$cycloalkyl itself is optionally substituted with one or more of halo, OH, $C_{1-6}$haloalkyl, $C_{1-6}$alkyl or $C_{1-6}$alkoxy. In yet other embodiments, $R^2$ is heteroaryl, substituted with an unsubstituted $C_{3-8}$cycloalkyl, such as cyclopropyl, cyclobutyl, cyclopentyl, or cyclohexyl. In further embodiments, $R^2$ is heteroaryl, substituted with cyclopropyl or cyclobutyl. In yet other embodiments, $R^2$ is heteroaryl, substituted with $C_{3-8}$cycloalkyl, such as cyclopropyl, cyclobutyl, cyclopentyl, or cyclohexyl, wherein the $C_{3-8}$cycloalkyl itself is substituted with one or more of halo, OH, $C_{1-6}$haloalkyl, $C_{1-6}$alkyl or $C_{1-6}$alkoxy. In some embodiments, the substituted $C_{3-8}$cycloalkyl is substituted with OH. In still further embodiments, the substituted $C_{3-8}$cycloalkyl is substituted with one or more of halo, such as F, Cl, or Br. In other embodiments, the substituted $C_{3-8}$cycloalkyl is substituted with $C_{1-6}$alkyl, such as methyl, ethyl, or propyl. In further embodiments, the substituted $C_{3-8}$cycloalkyl is substituted with $C_{1-6}$haloalkyl, such as $CF_3$, $CH_2CF_3$, or $CHF_2$. In still other embodiments, the substituted $C_{3-8}$cycloalkyl is substituted with $C_{1-6}$alkoxy, such as methoxy, ethoxy, or propoxy. In further embodiments, the substituted $C_{3-8}$cycloalkyl is cyclopropyl or cyclobutyl, each of which is substituted with one or more of F, OH, or methyl. In other embodiments, $R^2$ is heteroaryl, substituted with

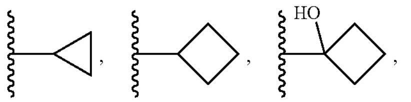
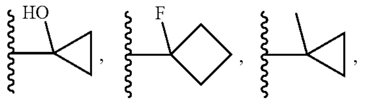
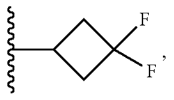
or
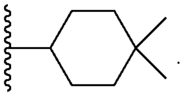

In still other embodiments, $R^2$ is heteroaryl, substituted with

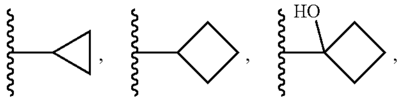
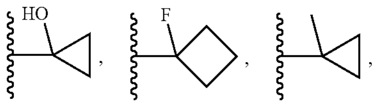
or
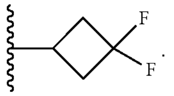

In other embodiments, $R^2$ is heteroaryl, substituted with aryl, wherein the aryl itself is optionally substituted with one or more of halo, $C_{1-6}$haloalkyl, $C_{1-6}$alkyl, or $C_{3-8}$cycloalkyl. In yet other embodiments, $R^2$ is heteroaryl, substituted with an unsubstituted phenyl. In further embodiments, $R^2$ is heteroaryl, substituted with aryl, such as phenyl, wherein the aryl itself is substituted with one or more of halo, $C_{1-6}$haloalkyl, $C_{1-6}$alkyl, or $C_{3-8}$cycloalkyl. In some embodiments, the substituted aryl is substituted with one or more of halo, such as F, Cl, or Br. In yet other embodiments, the substituted aryl is substituted with $C_{1-6}$haloalkyl, such as $CF_3$, $CH_2CF_3$, or $CHF_2$. In still further embodiments, the substituted aryl is substituted with $C_{1-6}$alkyl, such as methyl, ethyl, or propyl. In other embodiments, the substituted aryl is substituted with $C_{3-8}$cycloalkyl, such as cyclopropyl, cyclobutyl, or cyclopentyl. In yet other embodiments, the substituted aryl is phenyl that is substituted with one or more of F, methyl, or $CF_3$. In further embodiments, $R^2$ is heteroaryl, substituted with

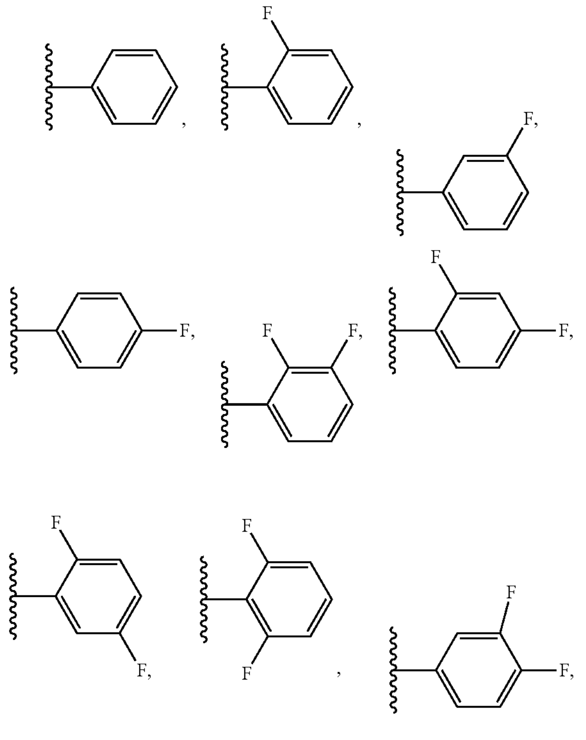

-continued

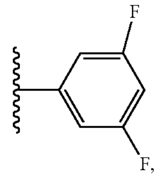, 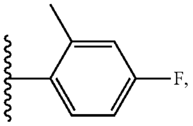, 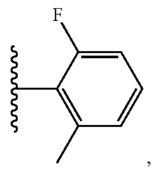, or 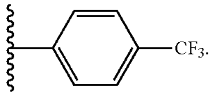.

In still further embodiments, $R^2$ is heteroaryl, substituted with

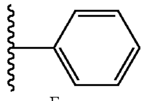, 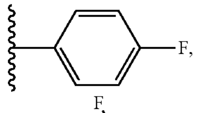, 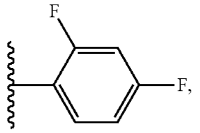, 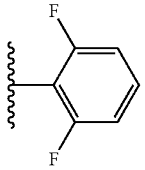, 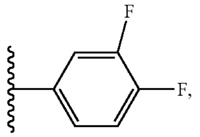, 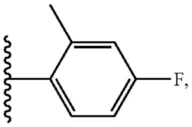, or 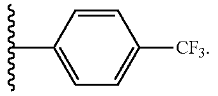.

In still further embodiments, $R^2$ is heteroaryl, substituted with an optionally substituted heteroaryl. In some embodiments, the optionally substituted heteroaryl is optionally substituted pyridinyl, optionally substituted pyrazinyl, optionally substituted pyrazolyl, optionally substituted imidazolyl, or optionally substituted pyrimidinyl. In yet other embodiments, the optional substitution on the heteroaryl is one or more of halo, $C_{1-6}$ haloalkyl, $C_{1-6}$alkyl, $C_{1-6}$alkoxy, $C_{1-6}$haloalkoxy, $C_{3-8}$cycloalkyl or $C_{3-8}$cycloalkylsulfonyl. In other embodiments, the optionally substituted heteroaryl is substituted with one or more of halo, such as F, Cl, or Br. In still other embodiments, the optionally substituted heteroaryl is substituted with one or more of $C_{1-6}$haloalkyl, such as $CF_3$, $CH_2CF_3$, $CH_2CHF_2$, or $CHF_2$. In other embodiments, the optionally substituted heteroaryl is substituted with one or more of $C_{1-6}$alkyl, such as methyl, ethyl, propyl, or isopropyl. In still other embodiments, the optionally substituted heteroaryl is substituted with one or more of $C_{1-6}$alkoxy, such as methoxy, ethoxy, or propoxy. In other embodiments, the optionally substituted heteroaryl is substituted with one or more of $C_{1-6}$haloalkoxy, such as $OCF_3$. In yet other embodiments, the optionally substituted heteroaryl is substituted with one or more of $C_{3-8}$cycloalkyl, such as cyclopropyl, cyclobutyl, or cyclopentyl. In other embodiments, the optionally substituted heteroaryl is substituted with one or more of $C_{3-8}$cycloalkylsulfonyl, such as cyclopropylsulfonyl, cyclobutylsulfonyl, or cyclopentylsulfonyl. In still other embodiments, the optionally substituted heteroaryl is substituted with one or more of F, $CF_3$, $CH_2CHF_2$, $CHF_2$, methyl, methoxy, cyclobutyl, or cyclopropylsulfonyl.

In yet other embodiments, $R^2$ is heteroaryl, substituted with pyrazol-1-yl, pyrazol-3-yl, pyrazol-4-yl, pyrazol-5-yl, pyridin-2-yl, pyridin-3-yl, pyridin-4-yl, pyrimidin-2-yl, pyrimidin-4-yl, pyrimidin-5-yl, pyrazin-2-yl, pyrazin-3-yl, pyrazin-4-yl, pyrazin-5-yl, imidazol-4-yl, or imidazol-5-yl, each of which can be optionally substituted. In further embodiments, $R^2$ is substituted with pyrazol-1-yl, pyrazol-3-yl, pyrazol-4-yl, pyrazol-5-yl, pyridin-2-yl, pyridin-3-yl, pyridin-4-yl, pyrimidin-2-yl, pyrimidin-4-yl, pyrimidin-5-yl, pyrazin-2-yl, pyrazin-3-yl, pyrazin-4-yl, pyrazin-5-yl, imidazol-4-yl, imidazol-5-yl, pyridazin-3-yl, pyridazin-4-yl, each of which is optionally substituted. In still further embodiments, $R^2$ is substituted with optionally substituted pyrazol-1-yl. In other embodiments, $R^2$ is substituted with optionally substituted pyrazol-3-yl. In further embodiments, $R^2$ is substituted with optionally substituted pyrazol-4-yl. In yet further embodiments, $R^2$ is substituted with optionally substituted pyridin-2-yl. In other embodiments, $R^2$ is substituted with optionally substituted pyridin-3-yl. In further embodiments, $R^2$ is substituted with optionally substituted pyridin-4-yl. In further embodiments, $R^2$ is substituted with optionally substituted imidazol-4-yl. In yet other embodiments, $R^2$ is substituted with optionally substituted imidazol-5-yl. In further embodiments, $R^2$ is substituted with optionally substituted pyrimidin-2-yl. In other embodiments, $R^2$ is substituted with optionally substituted pyrimidin-4-yl. In still further embodiments, $R^2$ is substituted with optionally substituted pyrimidin-5-yl. In yet other embodiments, $R^2$ is substituted with optionally substituted pyrazin-2-yl. In other embodiments, $R^2$ is substituted with optionally substituted pyridazin-3-yl. In further embodiments, $R^2$ is substituted with optionally substituted pyridazin-4-yl.

In some embodiments, $R^2$ is heteroaryl, substituted with

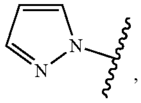, 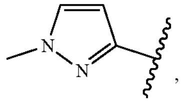, 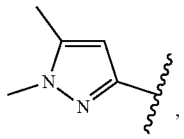,

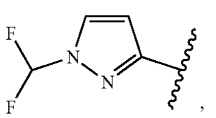, 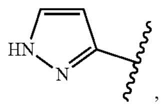, 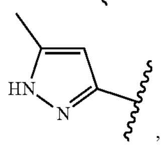,

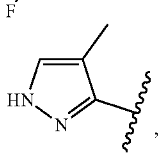, 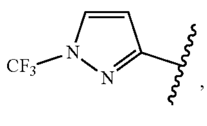, 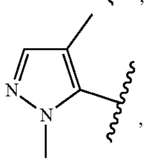,

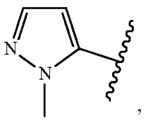, 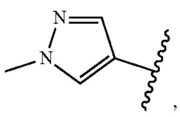, 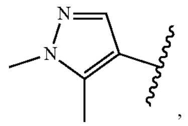,

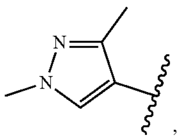, 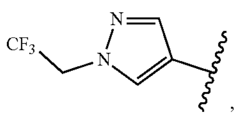,

-continued
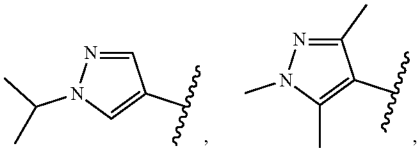
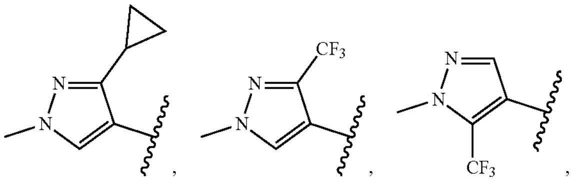
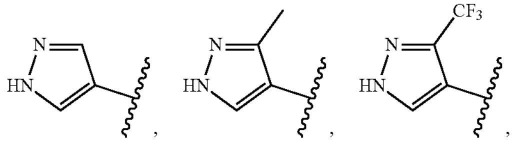
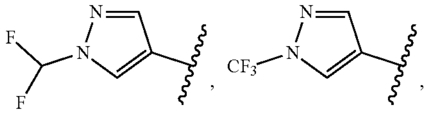
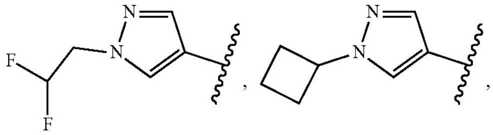
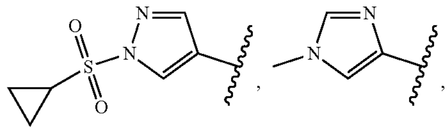, or
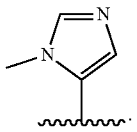.
In still further embodiments, $R^2$ is heteroaryl, substituted with
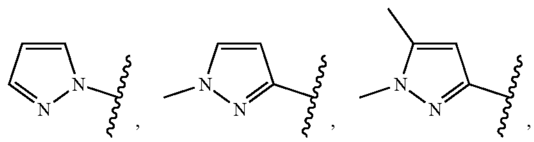
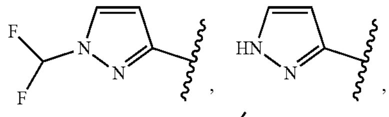
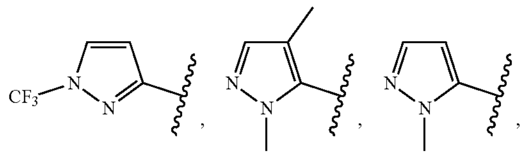
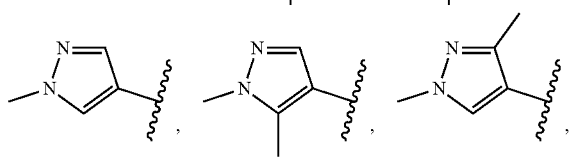
-continued
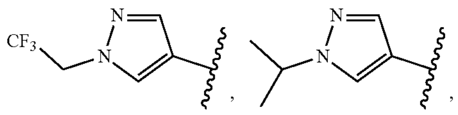
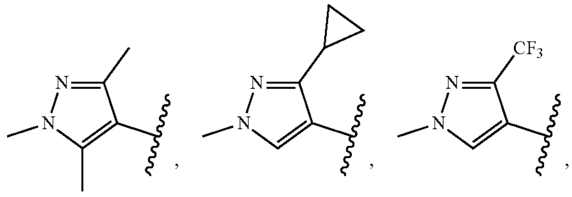
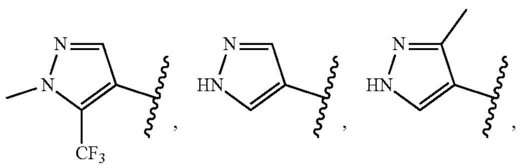
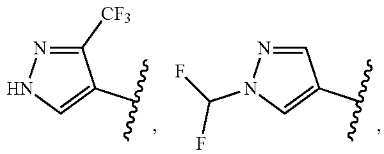
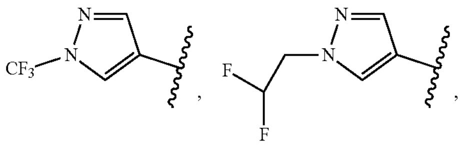
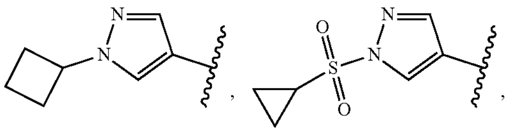
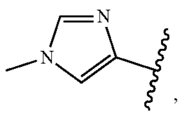, or 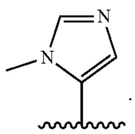.
In still further embodiments, $R^2$ is heteroaryl, substituted with
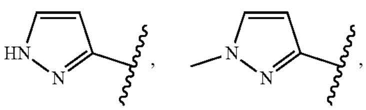
In some embodiments, $R^2$ is heteroaryl, substituted with
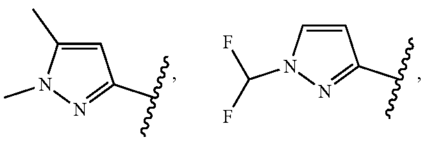
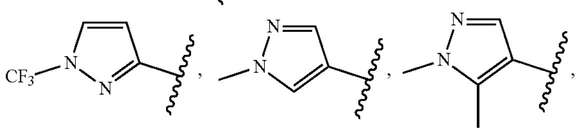

-continued
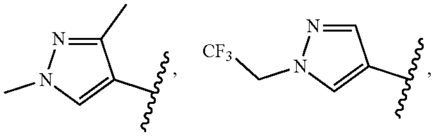
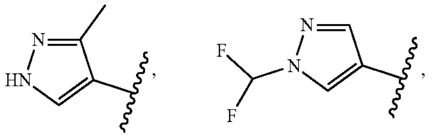
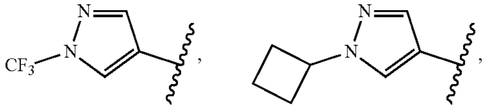
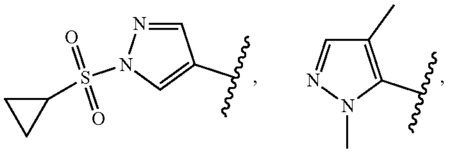
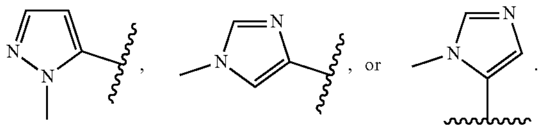
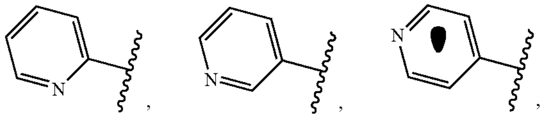
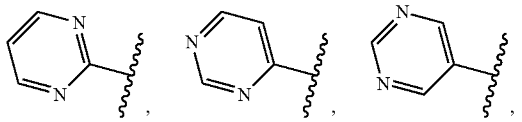
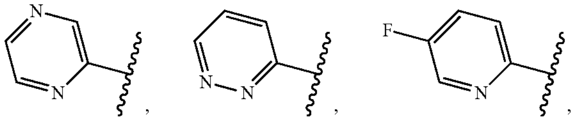
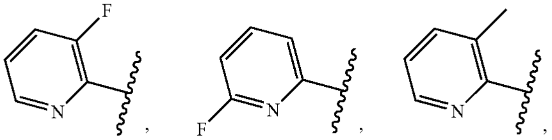
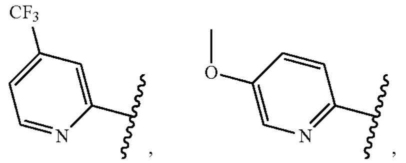
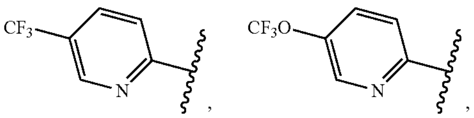
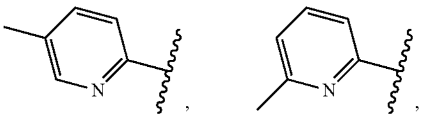
-continued
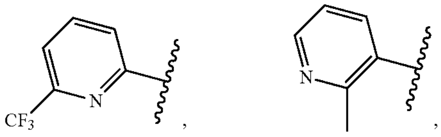
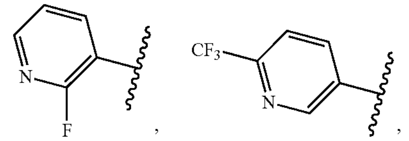
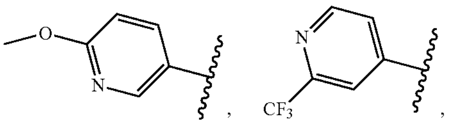
or
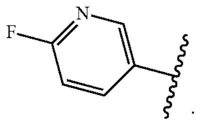
In other embodiments, $R^2$ is heteroaryl, substituted with
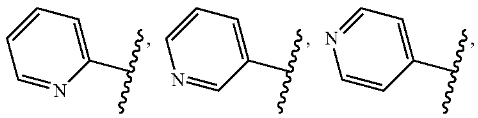
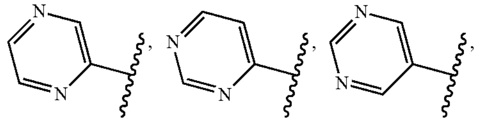
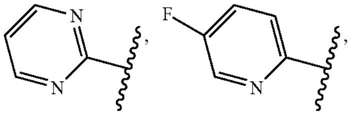
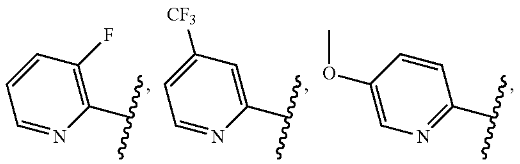
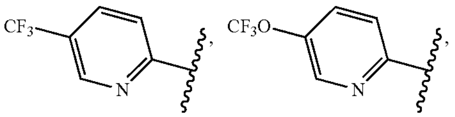
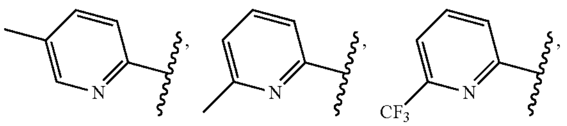
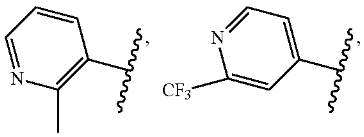
or
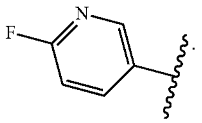

In still other embodiments, $R^2$ is heteroaryl, substituted with

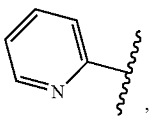, 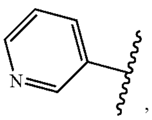, 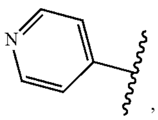, 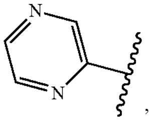, 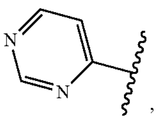, 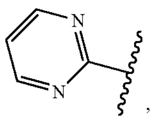, 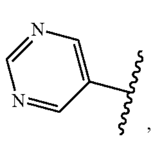, 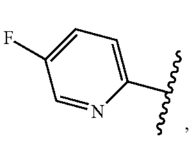, 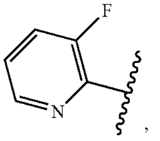, 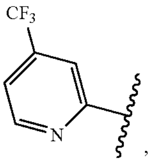, 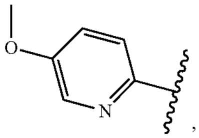, 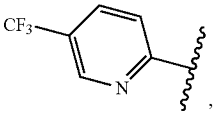, 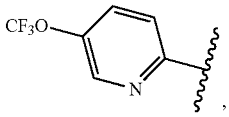, 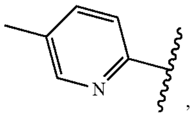, 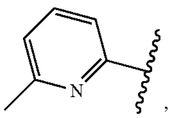, or 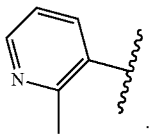.

In other embodiments, $R^2$ is heteroaryl, substituted with heterocyclyl or heterocyclyl(alkylene), wherein the heterocyclyl and heterocyclyl(alkylene) groups themselves are each optionally substituted with one or more of halo, OH, $C_{1-6}$haloalkyl, $C_{1-6}$alkyl, $C_{1-6}$hydroxyalkyl, $C_{1-6}$alkoxy, C(O)O($C_{1-6}$alkyl), or $C_{3-8}$cycloalkyl. In yet other embodiments, $R^2$ is heteroaryl, substituted with an unsubstituted heterocyclyl group such as azetidinyl, pyrrolidinyl, piperidinyl, piperazinyl, morpholinyl, or 6-azaspiro[2,5]octan-6-yl, or unsubstituted heterocyclyl(alkylene) group, such as azetidinyl(alkylene), pyrrolidinyl(alkylene), piperidinyl(alkylene), piperazinyl(alkylene), or morpholinyl(alkylene). In further embodiments, $R^2$ is heteroaryl, substituted with heterocyclyl, such as azetidinyl, pyrrolidinyl, piperidinyl, piperazinyl, or morpholinyl, or heterocyclyl(alkylene), such as azetidinyl(alkylene), pyrrolidinyl(alkylene), piperidinyl(alkylene), piperazinyl(alkylene), or morpholinyl(alkylene), wherein the heterocyclyl and heterocyclyl(alkylene) groups themselves are each substituted with one or more of halo, OH, $C_{1-6}$haloalkyl, $C_{1-6}$alkyl, $C_{1-6}$hydroxyalkyl, $C_{1-6}$alkoxy, C(O)O($C_{1-6}$alkyl), or $C_{3-8}$cycloalkyl. In further embodiments, the substituted heterocyclyl or substituted heterocyclyl(alkylene) is substituted with one or more of halo, such as F, Cl, or Br. In yet further embodiments, the substituted heterocyclyl or substituted heterocyclyl(alkylene) is substituted with one or more of OH. In yet other embodiments, the substituted heterocyclyl or substituted heterocyclyl(alkylene) is substituted with one or more of $C_{1-6}$haloalkyl, such as $CF_3$, $CH_2CF_3$, or $CHF_2$. In still further embodiments, the substituted heterocyclyl or substituted heterocyclyl(alkylene) is substituted with one or more of $C_{1-6}$alkyl, such as methyl, ethyl, or propyl. In yet further embodiments, the substituted heterocyclyl or substituted heterocyclyl(alkylene) is substituted with one or more of $C_{1-6}$hydroxyalkyl such as $C(CH_3)_2OH$, or $CH(CH_3)OH$. In other embodiments, the substituted heterocyclyl or substituted heterocyclyl(alkylene) is substituted with one or more of $C_{1-6}$alkoxy, such as methoxy, ethoxy, or propoxy. In yet other embodiments, the substituted heterocyclyl or substituted heterocyclyl(alkylene) is substituted with one or more of C(O)O($C_{1-6}$alkyl), such as C(O)Omethyl, C(O)Oethyl, C(O)Opropyl, or C(O)Otert-butyl. In further embodiments, the substituted heterocyclyl or substituted heterocyclyl(alkylene) is substituted with one or more of $C_{3-8}$cycloalkyl, such as cyclopropyl, cyclobutyl, or cyclopentyl. In yet other embodiments, the substituted heterocyclyl or substituted heterocyclyl(alkylene) is substituted with one or more of F, OH or methyl. In yet other embodiments where $R^2$ is heteroaryl, the $R^2$ is substituted with

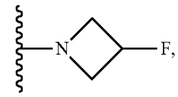, 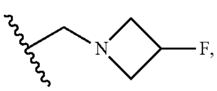, 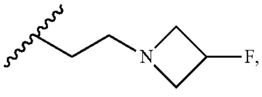, 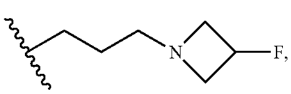, 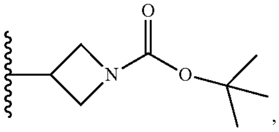, 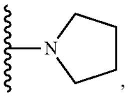, 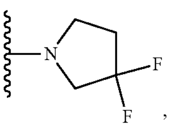, 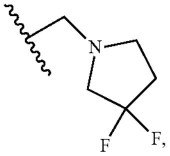, 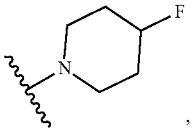, 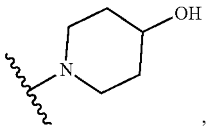, 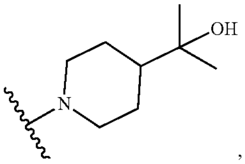, 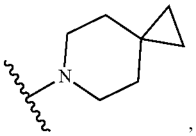, 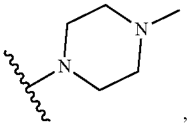, 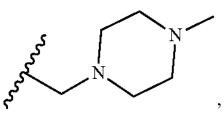, 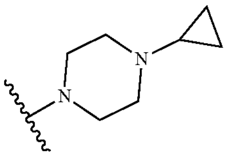, 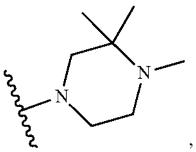, 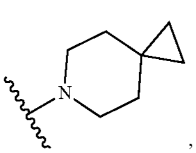, 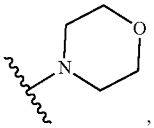, 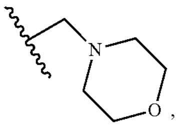, 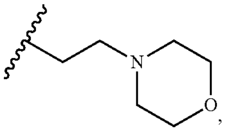, or -continued
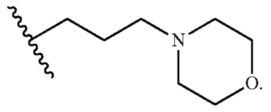
In still further embodiments where $R^2$ is heteroaryl, the $R^2$ is substituted with
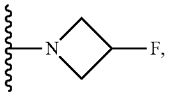
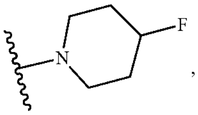
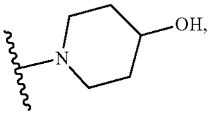
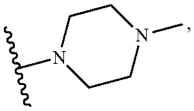
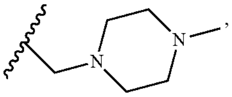
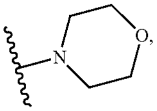
or
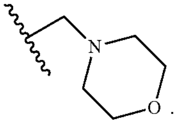
In further embodiments, $R^2$ is
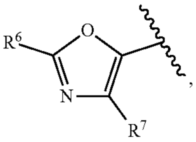
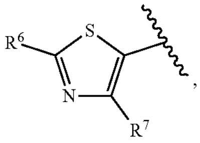
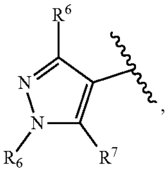
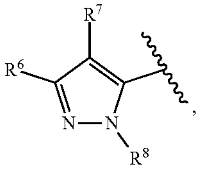
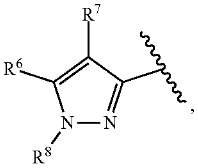
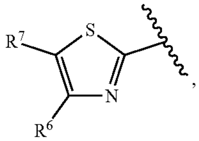
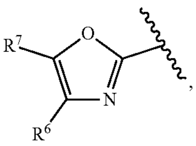
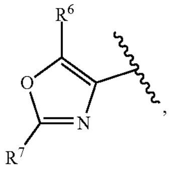
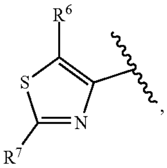
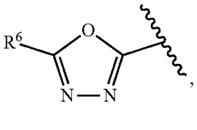
-continued
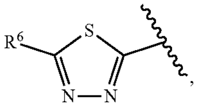
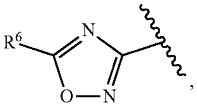
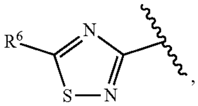
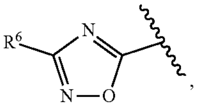
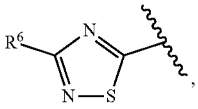
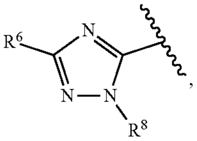
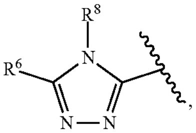
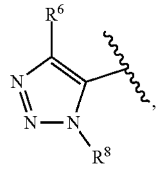
or
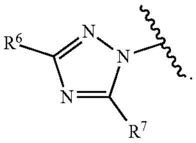
In yet further embodiments, $R^2$ is
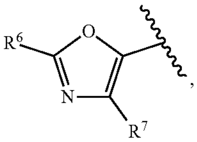
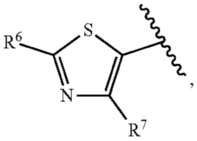
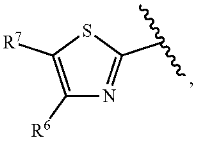
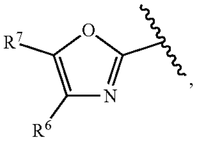
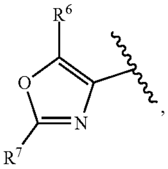
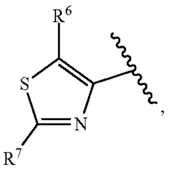
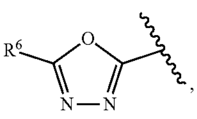
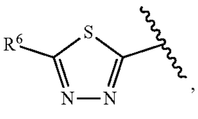
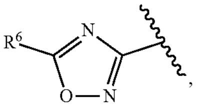
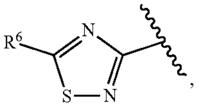
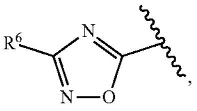
or
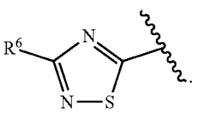

In still further embodiments, $R^2$ is,
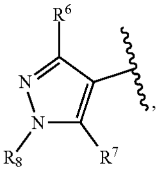
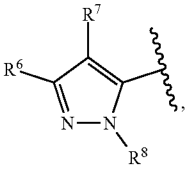
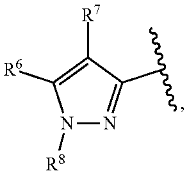
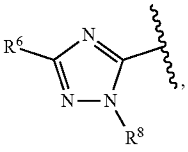
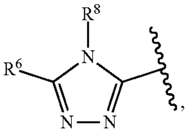
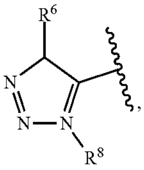
or
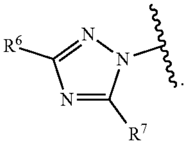
In other embodiments, $R^2$ is
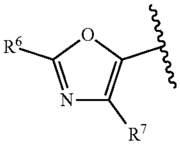
or
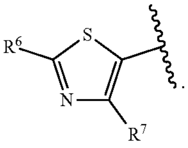
In further embodiments, $R^2$ is
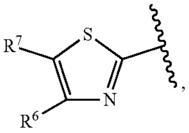
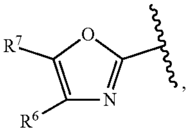
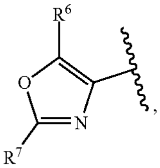
or
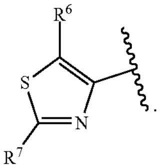
In yet further embodiments, $R^2$ is
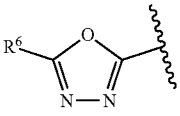
or
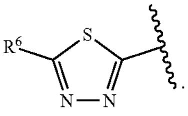
In still further embodiments, $R^2$ is
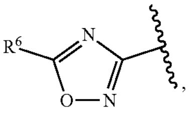
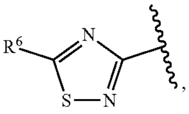
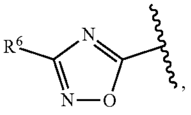
or
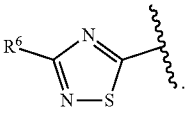
In yet other embodiments, $R^2$ is
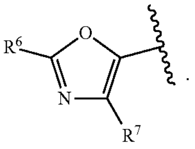
In other embodiments, $R^2$ is
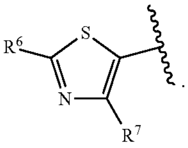
In further embodiments, $R^2$ is
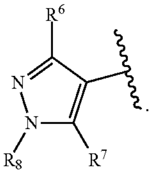
In yet other embodiments, $R^2$ is
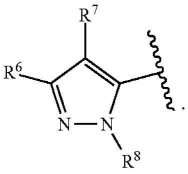
In still further embodiments, $R^2$ is
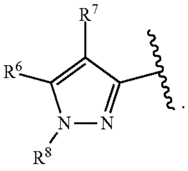

In other embodiments, $R^2$ is

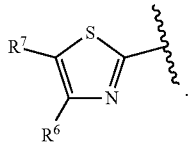

In further embodiments, $R^2$ is

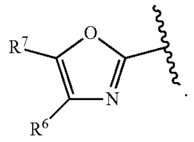

In still other embodiments, $R^2$ is

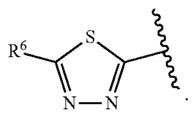

In yet further embodiments, $R^2$ is

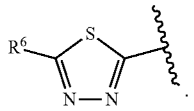

In other embodiments, $R^2$ is

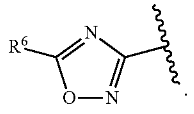

In further embodiments, $R^2$ is

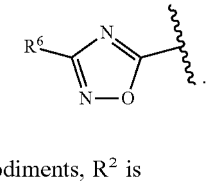

In yet other embodiments, $R^2$ is

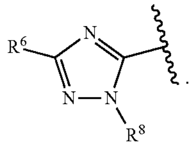

In still further embodiments, $R^2$ is

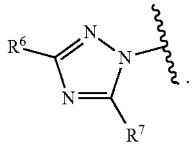

In other embodiments, $R^2$ is

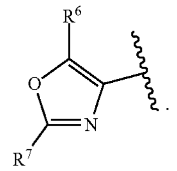

In other embodiments, $R^2$ is

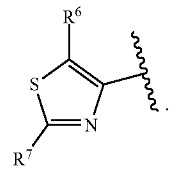

In further embodiments, $R^2$ is

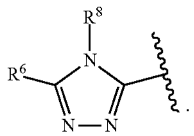

In yet other embodiments, $R^2$ is

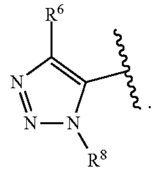

In these structures for $R^2$, $R^6$ and $R^7$ are each independently, H, CN, $C_{1-6}$alkyl, $C_{1-6}$haloalkyl, $C_{1-6}$cyanoalkyl, $C_{1-6}$hydroxyalkyl, $C_{1-6}$alkoxy, $C_{1-6}$alkoxy(alkylene), $C_{1-6}$haloalkoxy, $C_{1-6}$haloalkoxy(alkylene), $C_{1-6}$deuterated alkoxy(alkylene), halo, $(CR^vR^x)_pNR^yR^z$, $C(O)NR^{y2}R^{z2}$, $C_{1-6}$alkylcarbonyl, optionally substituted $C_{1-6}$cycloalkyl, optionally substituted heterocyclyl, optionally substituted aryl, optionally substituted heteroaryl, optionally substituted $C_{2-6}$alkenyl, optionally substituted $C_{3-8}$cycloalkenyl, optionally substituted ($C_{3-8}$cycloalkyl)alkylene, optionally substituted (aryl)alkylene, optionally substituted (heterocyclyl)alkylene, or $C_{1-6}$alkylsulfonyl; $R^8$ is H, $C_{1-6}$alkyl, $C_{1-6}$haloalkyl, $C_{1-4}$alkoxy(alkylene), $C_{1-4}$alkylcarbonyl, $C_{1-6}$hydroxyalkyl, $(CR^vR^x)_pNR^yR^z$, optionally substituted $C_{3-8}$cycloalkyl, optionally substituted aryl, optionally substituted heteroaryl, or optionally substituted ($C_{3-8}$cycloalkyl) alkylene; $R^v$ and $R^x$ are, independently, H or $C_{1-6}$alkyl; $R^y$ and $R^z$ are, independently, H, $C_{1-6}$alkyl, $C_{1-6}$alkoxy(alkylene), or $C_{3-6}$cycloalkyl; $R^{y2}$ and $R^{z2}$ are, independently, H, $C_{1-6}$alkyl, or $C_{3-6}$cycloalkyl; and p is 0, 1, 2, or 3. In some embodiments, $R^6$, $R^7$, and $R^8$ are H.

In other embodiments, $R^6$ is $C_{1-6}$alkyl, $C_{1-6}$haloalkyl, $C_{1-6}$cyanoalkyl, or $C_{1-6}$hydroxyalkyl. In further embodiments, $R^6$ is $C_{1-6}$alkyl such as methyl, ethyl, isopropyl or tert-butyl. In still further embodiments, $R^6$ is $C_{1-4}$haloalkyl such as $CF_3$, $CHF_2$, $CH_2F$, $CH_2CF_3$, $CH(CH_3)F$, $C(CH_3)F_2$, or $C(CH_3)_2F$. In further embodiments, $R^6$ is $C_{1-6}$cyanoalkyl such as $C(CH_3)_2CN$. In other embodiments, $R^6$ is $C_{1-6}$hydroxyalkyl such as $C(CH_3)_2OH$, $CH(CH_3)OH$, $CH(CH_2CH_3)OH$, $CH_2C(CH_3)_2OH$, or $C(CH_3)_2CH_2OH$. In further embodiments, $R^6$ is methyl, isopropyl, tert-butyl, $CF_3$, $CHF_2$, $C(CH_3)F_2$, $C(CH_3)_2F$, $C(CH_3)_2OH$, or $CH(CH_3)OH$.

In other embodiments, $R^6$ is $C_{3-6}$cycloalkyl optionally substituted with one or more of halo, OH, $C_{1-6}$haloalkyl, $C_{1-6}$alkyl, or $C_{1-6}$alkoxy. In further embodiments, $R^6$ is cyclopropyl, cyclobutyl, cyclopentyl or cyclohexyl, optionally substituted with one or more of halo, OH, $C_{1-6}$haloalkyl, $C_{1-6}$alkyl, or $C_{1-6}$alkoxy. In still further embodiments, $R^6$ is unsubstituted cyclopropyl, cyclobutyl, cyclopentyl or cyclohexyl. In other embodiments, $R^6$ is $C_{3-6}$cycloalkyl substituted with one or more halo such as F, Cl, or Br. In yet other embodiments, $R^6$ is $C_{3-6}$cycloalkyl substituted with one or more OH. In still further embodiments, $R^6$ is $C_{3-6}$cycloalkyl substituted with one or more $C_{1-6}$haloalkyl such as $CF_3$, $CH_2CF_3$, or $CHF_2$. In further embodiments, $R^6$ is $C_{3-6}$cycloalkyl substituted with one or more $C_{1-6}$alkyl such as methyl, ethyl, or propyl. In still further embodiments, $R^6$ is $C_{3-6}$cycloalkyl substituted with $C_{1-6}$alkoxy, such as one or more methoxy, ethoxy, or propoxy. In other embodiments, $R^6$ is cyclopropyl, cyclobutyl, or cyclohexyl, each of which is optionally substituted with one or more of F, OH, or methyl. In other embodiments, $R^6$ is

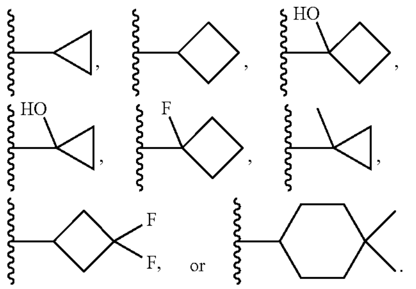

In other embodiments, $R^6$ is

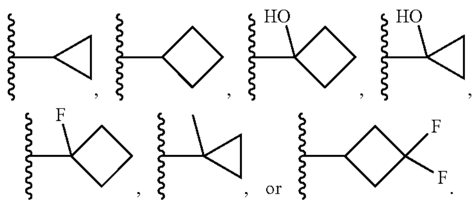

In further embodiments, $R^6$ is aryl optionally substituted with one or more of halo, $C_{1-6}$haloalkyl, $C_{1-6}$alkyl or $C_{3-6}$cycloalkyl. In other embodiments, $R^6$ is phenyl optionally substituted with one or more of halo, $C_{1-6}$haloalkyl, $C_{1-6}$alkyl or $C_{3-6}$cycloalkyl. In still other embodiments, $R^6$ is aryl optionally substituted with one or more of halo such as F, Cl, or Br. In yet other embodiments, $R^6$ is aryl optionally substituted with one or more of $C_{1-6}$haloalkyl such as $CF_3$, $CH_2CF_3$, or $CHF_2$. In other embodiments, $R^6$ is aryl optionally substituted with one or more of $C_{1-6}$alkyl such as methyl, ethyl, or propyl. In yet other embodiments, $R^6$ is aryl optionally substituted with one or more of $C_{3-6}$cycloalkyl such as cyclopropyl, cyclobutyl, or cyclopentyl. In other embodiments, $R^6$ is aryl (e.g., phenyl) optionally substituted with F, methyl, or $CF_3$. In other embodiments, $R^6$ is

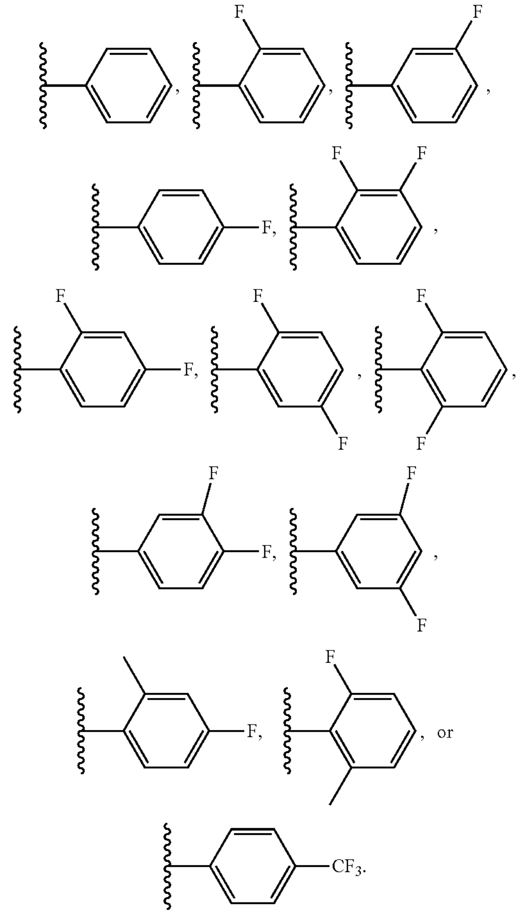

In yet other embodiments, $R^6$ is

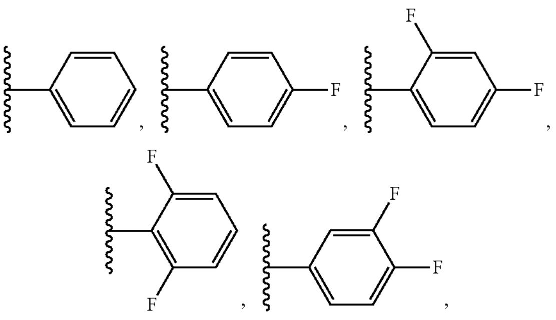

-continued

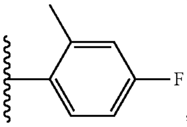

, or

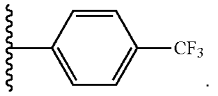

.

In yet other embodiments, $R^6$ is heteroaryl, optionally substituted with one or more of halo, $C_{1-6}$haloalkyl, $C_{1-6}$alkyl, $C_{1-6}$alkoxy, $C_{1-6}$haloalkoxy, $C_{3-6}$cycloalkyl, or $C_{3-6}$cycloalkylsulfonyl. In still other embodiments, $R^6$ is pyridinyl, pyrazolyl, pyrazinyl, imidazolyl, or pyrimidinyl, each of which is optionally substituted. In still other embodiments, $R^6$ is pyridinyl, pyrazolyl, pyrazinyl, pyridazinyl, imidazolyl, or pyrimidinyl, each of which is optionally substituted. In further embodiments, $R^6$ is optionally substituted pyrazinyl such as pyrazin-2-yl, pyrazin-3-yl, pyrazin-4-yl, or pyrazin-5-yl. In other embodiments, $R^6$ is optionally substituted pyrazolyl such as pyrazol-1-yl, pyrazol-3-yl, pyrazol-4-yl, or pyrazol-5-yl. In still further embodiments, $R^6$ is optionally substituted pyridinyl such as pyridin-2-yl, pyridin-3-yl, or pyridin-4-yl. In other embodiments, $R^6$ is optionally substituted pyridazinyl such as pyridazin-3-yl or pyridazin-4-yl. In yet other embodiments, $R^6$ is optionally substituted imidazolyl such as imidazol-4-yl or imidazol-5-yl. In further embodiments, $R^6$ is optionally substituted pyrimidinyl such as pyridimin-2-yl, pyrimidin-4-yl, or pyrimidin-5-yl. In other embodiments, $R^6$ is pyrazin-2-yl, pyrazin-3-yl, pyrazin-4-yl, pyrazin-5-yl, pyrazol-1-yl, pyrazol-3-yl, pyrazol-4-yl, pyrazol-5-yl, pyridin-2-yl, pyridin-3-yl, pyridin-4-yl, imidazol-4-yl, imidazol-5-yl, pyrimidin-2-yl, pyrimidin-4-yl, or pyrimidin-5-yl, each of which is optionally substituted. In yet other embodiments, $R^6$ is pyrazin-2-yl, pyrazin-3-yl, pyrazin-4-yl, pyrazin-5-yl, pyrazol-1-yl, pyrazol-3-yl, pyrazol-4-yl, pyrazol-5-yl, pyridin-2-yl, pyridin-3-yl, pyridin-4-yl, imidazol-4-yl, imidazol-5-yl, pyrimidin-2-yl, pyrimidin-4-yl, pyrimidin-5-yl, pyridazin-3-yl or pyridazin-4-yl, each of which is optionally substituted. In further embodiments, $R^6$ is unsubstituted pyridin-2-yl, unsubstituted pyridin-3-yl, unsubstituted pyridin-4-yl, unsubstituted pyrimidin-2-yl, unsubstituted pyrimidin-4-yl, unsubstituted pyrimidin-5-yl, or unsubstituted pyrazin-2-yl. In further embodiments, $R^6$ is unsubstituted pyridin-2-yl, unsubstituted pyridin-3-yl, unsubstituted pyridin-4-yl, unsubstituted pyrimidin-2-yl, unsubstituted pyrimidin-4-yl, unsubstituted pyrimidin-5-yl, unsubstituted pyrazin-2-yl, or pyridazin-3-yl. In other embodiments, $R^6$ is optionally substituted with one or more halo such as F, Cl, or Br. In yet other embodiments, $R^6$ is optionally substituted with one or more $C_{1-6}$haloalkyl such as $CF_3$, $CH_2CF_3$, or $CHF_2$. In other embodiments, $R^6$ is optionally substituted with one or more $C_{1-6}$alkyl such as methyl, ethyl, propyl, or isopropyl. In still other embodiments, $R^6$ is optionally substituted with one or more $C_{1-6}$alkoxy such as methoxy, ethoxy, or propoxy. In yet further embodiments, $R^6$ is optionally substituted with one or more $C_{1-6}$haloalkoxy such as $OCF_3$. In further embodiments, $R^6$ is optionally substituted with one or more $C_{3-6}$cycloalkyl such as cyclopropyl, cyclobutyl, or cyclopentyl. In yet further embodiments, $R^6$ is optionally substituted with one or more $C_{3-6}$cycloalkylsulfonyl such as cyclopropylsulfonyl, cyclobutylsulfonyl, or cyclopentylsulfonyl. In yet other embodiments, $R^6$ is heteroaryl optionally substituted with one or more of F, $CF_3$, $CH_2CF_3$, $CHF_2$, methyl, methoxy, $OCF_3$, cyclobutyl, or cyclopropylsulfonyl.

In other embodiments, $R^6$ is a five-membered heteroaryl, optionally substituted with one or more of $CF_3$, $CH_2CF_3$, $CHF_2$, methyl, cyclobutyl, or cyclopropylsulfonyl. In further embodiments, $R^6$ is

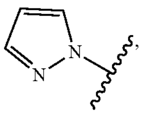,
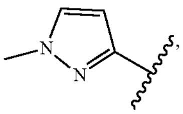,
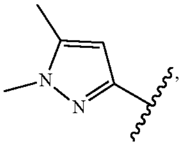,
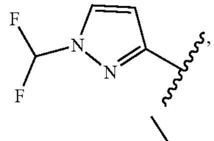,
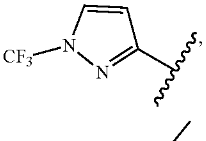,
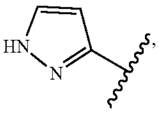,
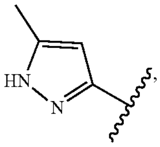,
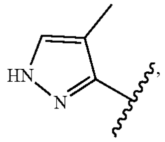,
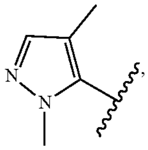,
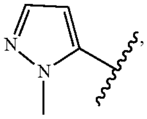,
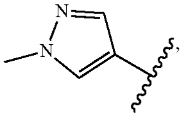,
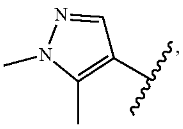,
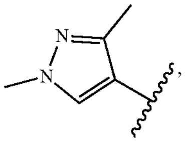,
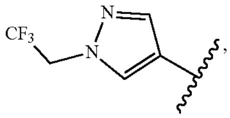,
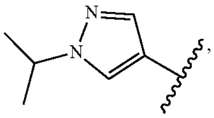,
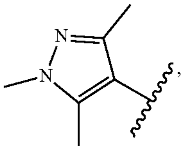,
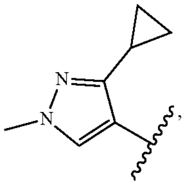,
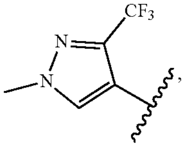,
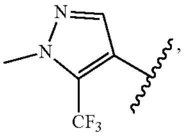,
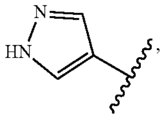,
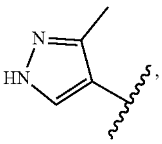,
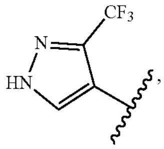,
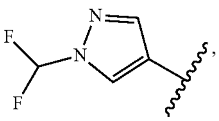,
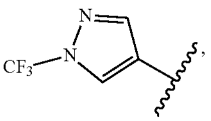,
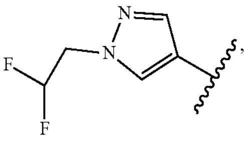,
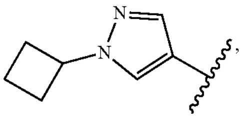, -continued
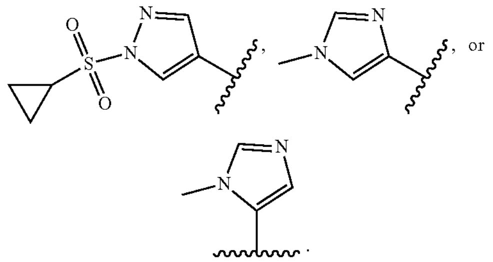
In still further embodiments, $R^6$ is F
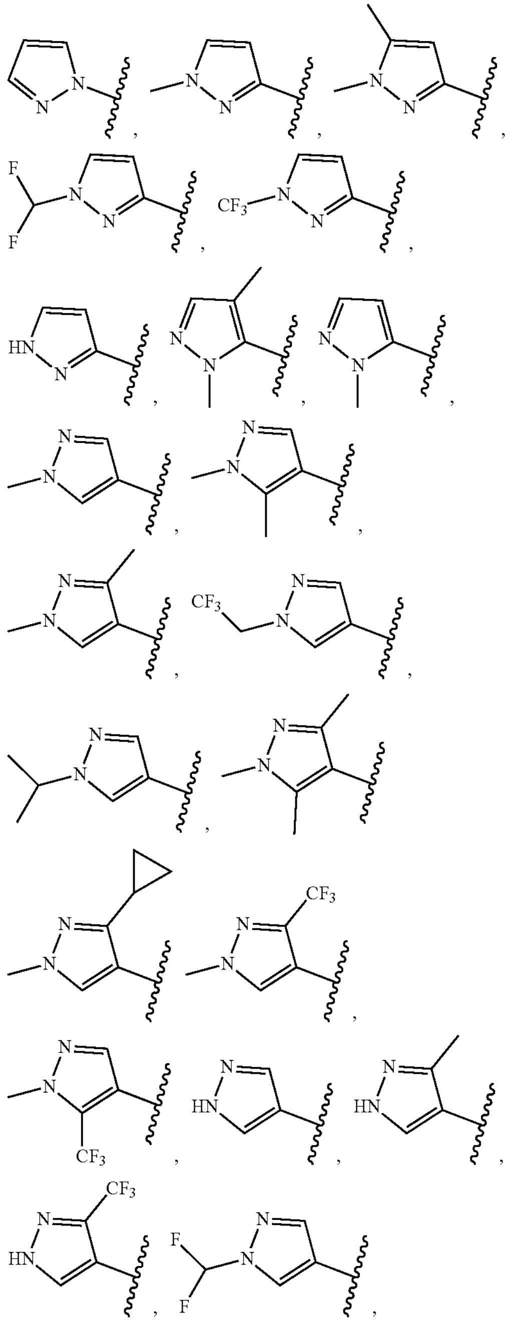
-continued
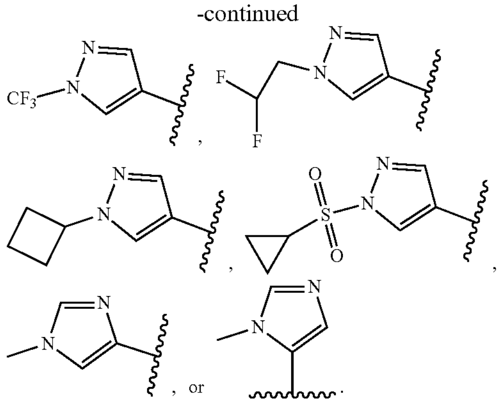
In other embodiments, $R^6$ is
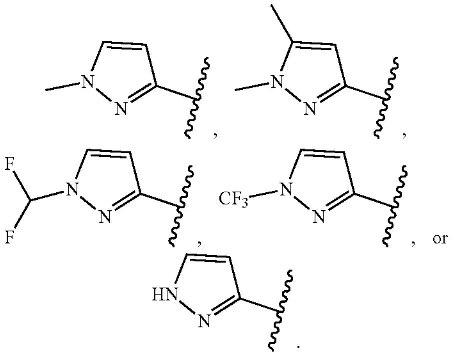
In still further embodiments, $R^6$ is
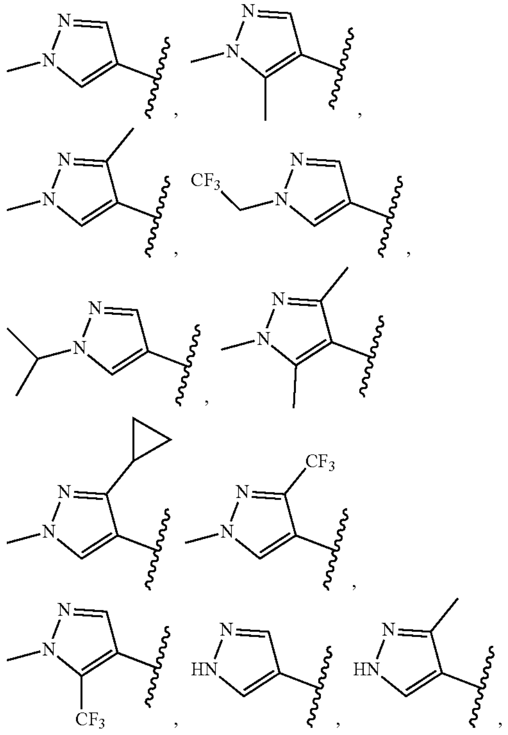

-continued
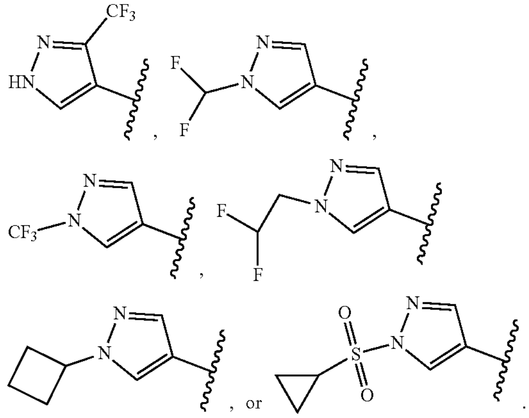
, or
In yet further embodiments, $R^6$ is
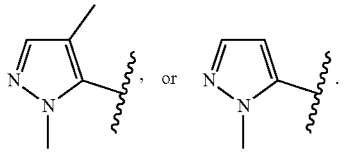
, or
In further embodiments, $R^6$ is or
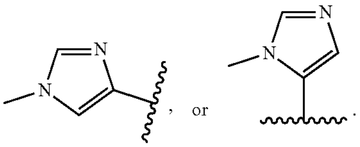
, or
In yet further embodiments, $R^6$ is
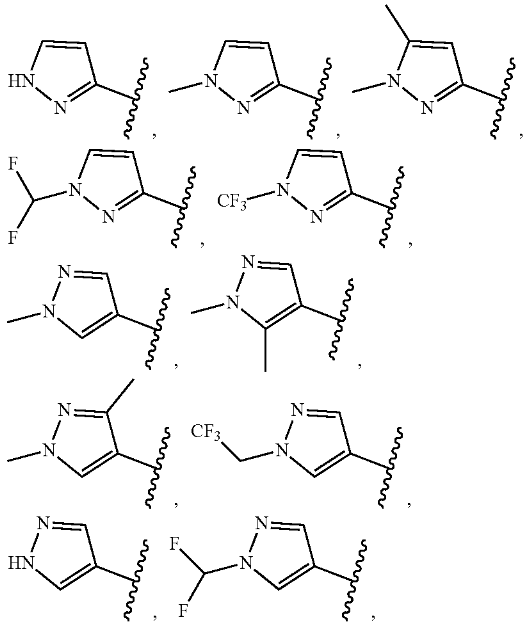
-continued
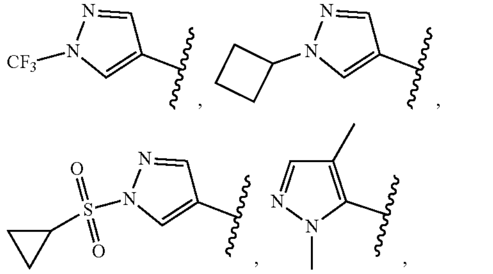
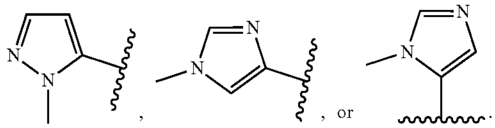
, or
In other embodiments, $R^6$ is a six-membered heteroaryl, optionally substituted with one or more of F, $CF_3$, methoxy, $OCF_3$, or methyl. In still other embodiments, $R^6$ is
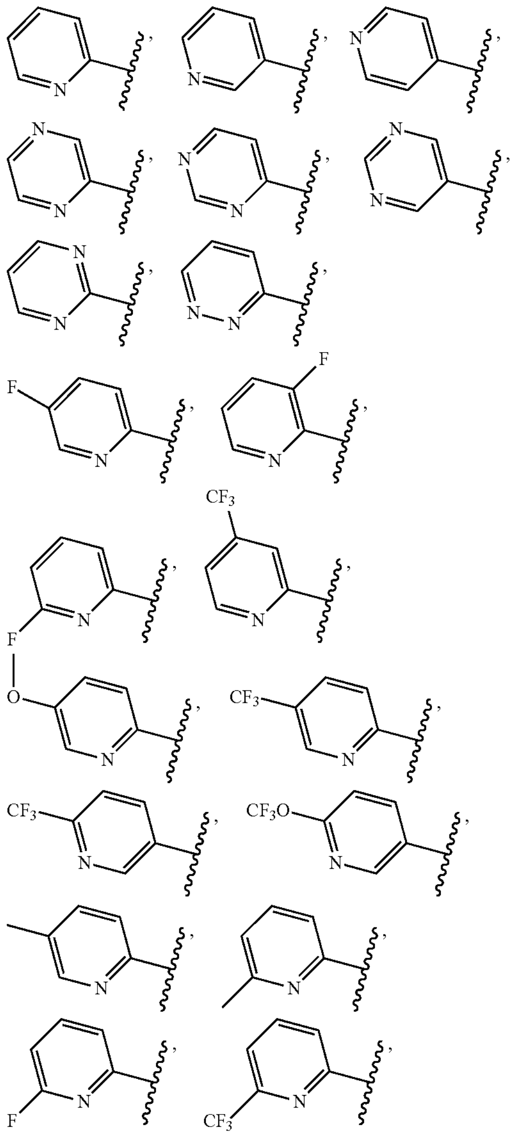

-continued

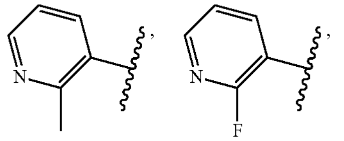

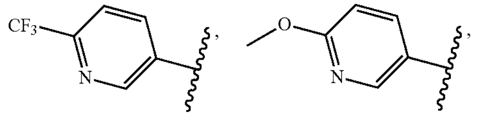

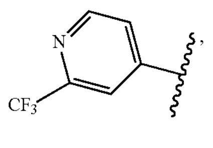 or 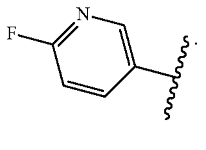

In still further embodiments, $R^6$ is

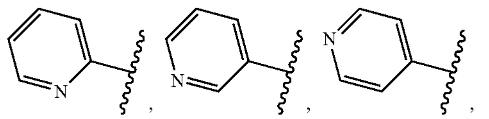

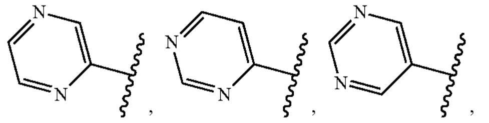

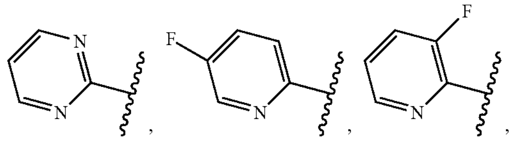

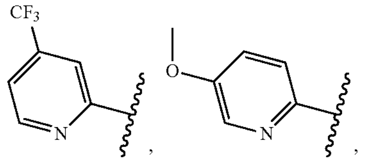

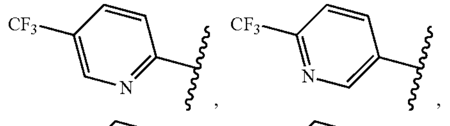

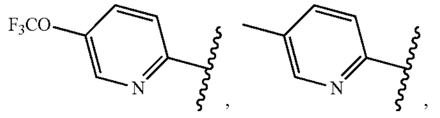

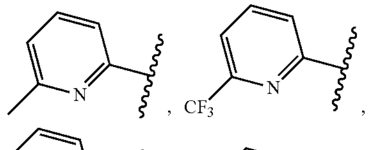

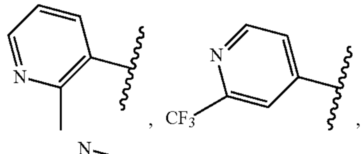 or

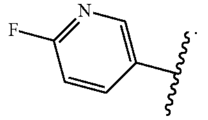

In yet other embodiments, $R^6$ is

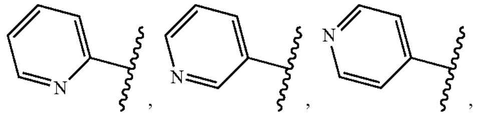

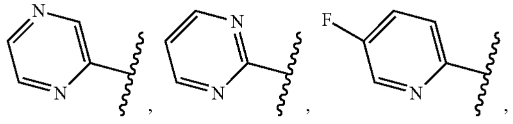

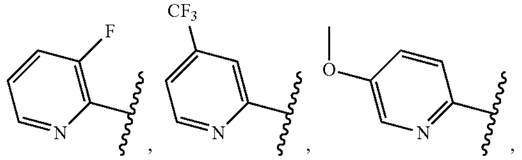

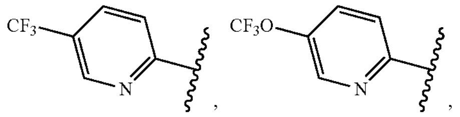

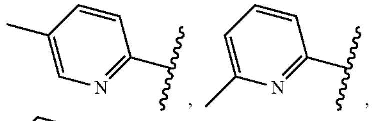 , or

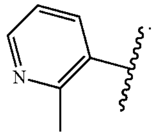

In yet other embodiments, $R^6$ is heterocyclyl or heterocyclyl(alkylene), each optionally substituted with one or more of halo, OH, $C_{1-6}$haloalkyl, $C_{1-6}$alkyl, $C_{1-6}$hydroxyalkyl, $C_{1-6}$-alkoxy, $C(O)O(C_{1-6}alkyl)$, or $C_{3-6}$cycloalkyl. In further embodiments, $R^6$ is optionally substituted azetidinyl, optionally substituted pyrrolidinyl, optionally substituted piperidinyl, optionally substituted piperazinyl, or optionally substituted morpholinyl. In other embodiments, $R^6$ is optionally substituted azetidinyl. In yet other embodiments, $R^6$ is optionally substituted pyrrolidinyl. In further embodiments, $R^6$ is optionally substituted piperidinyl. In yet other embodiments, $R^6$ is optionally substituted piperazinyl. In still further embodiments, $R^6$ is optionally substituted morpholinyl. In other embodiments, $R^6$ is optionally substituted morpholinyl(alkylene), optionally substituted piperidinyl (alkylene), optionally substituted piperazinyl(alkylene), or optionally substituted azetidinyl(alkylene). In further embodiments, $R^6$ is unsubstituted azetidinyl, pyrrolidinyl, piperidinyl, piperazinyl, or morpholinyl. In other embodiments, $R^6$ is unsubstituted morpholinyl(alkylene), piperidinyl(alkylene), piperazinyl(alkylene), or azetidinyl(alkylene). In yet other embodiments, $R^6$ is unsubstituted morpholinyl or morpholinyl(alkylene). In other embodiments, the heterocyclyl and heterocyclyl(alkylene) groups are optionally substituted with one or more halo such as F, Cl, or Br. In yet other embodiments, the heterocyclyl and heterocyclyl(alkylene) groups are optionally substituted with one or more OH. In further embodiments, the heterocyclyl and heterocyclyl(alkylene) groups are optionally substituted with one or more $C_{1-6}$haloalkyl such as $CF_3$, $CH_2CF_3$, or $CHF_2$. In still further embodiments, the heterocyclyl and heterocyclyl(alkylene) groups are optionally substituted with one or more $C_{1-6}$alkyl such as methyl, ethyl, or propyl. In further embodiments, the heterocyclyl and heterocyclyl(alkylene) groups are optionally substituted with one or more $C_{1-6}$hydroxyalkyl such as $C(CH_3)_2OH$. In yet further embodiments, the heterocyclyl and heterocyclyl(alkylene) groups are optionally substituted with one or more $C_{1-6}$alkoxy, such as methoxy, ethoxy, or propoxy. In other embodiments, the heterocyclyl and heterocyclyl(alkylene) groups are optionally substituted with one or more C(O)O ($C_{1-6}$alkyl), such as C(O)Omethyl, C(O)Oethyl, C(O)Opropyl, or C(O)Otert-butyl. In still further embodiments, the heterocyclyl and heterocyclyl(alkylene) groups are optionally substituted with one or more $C_{3-6}$cycloalkyl such as one or more cyclopropyl, cyclobutyl, or cyclopentyl. In yet other embodiments, $R^6$ is heterocyclyl and heterocyclyl(alkylene), each optionally substituted with one or more of F, OH, $C(CH_3)_2(OH)$, methyl, C(O)O(tert-butyl), or cyclopropyl.

In further embodiments, $R^6$ is

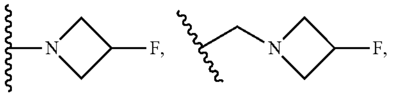
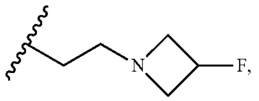
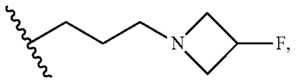
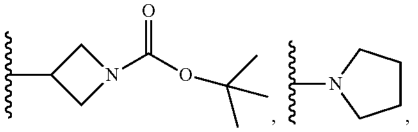
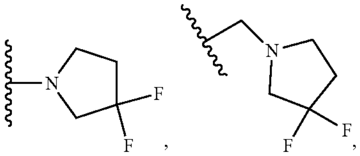
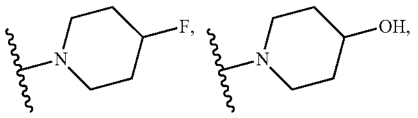
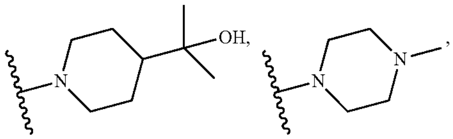
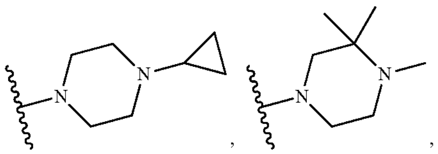
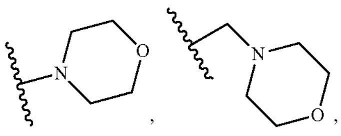
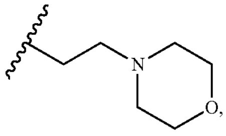
or
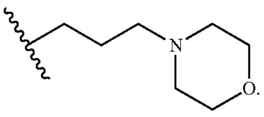

In yet other embodiments, $R^6$ is

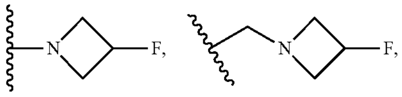
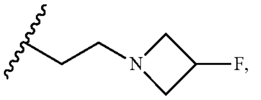
or
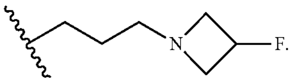

In further embodiments, $R^6$ is

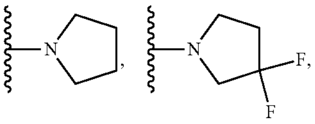
or
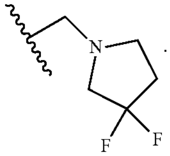

In still further embodiments, $R^6$ is

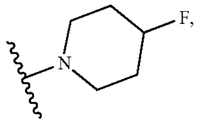
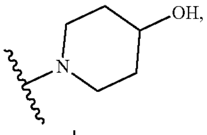
or
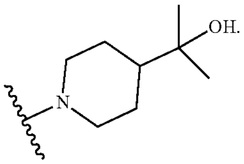

In yet other embodiments, $R^6$ is

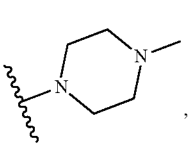
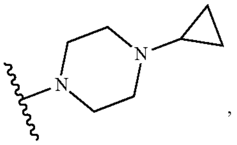
or
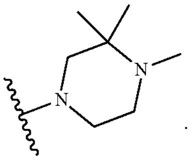

In other embodiments $R^6$ is

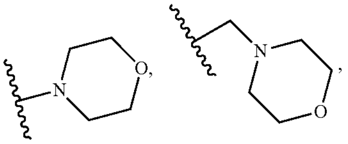

-continued

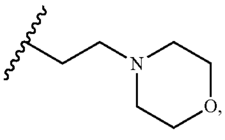, or 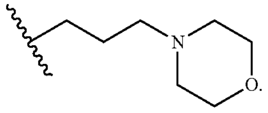.

In yet further embodiments, $R^6$ is

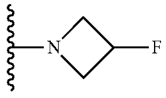 or 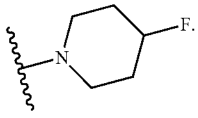.

In further embodiments, $R^6$ is H, CN, $C_{1-6}$alkoxy, $C_{1-6}$alkoxy(alkylene), $C_{1-6}$haloalkoxy, $C_{1-6}$haloalkoxy(alkylene), $C_{1-6}$deuterated alkoxy(alkylene), halo, $(CR^vR^x)_pNR^vR^x$, $C(O)NR^{y2}R^{z2}$, $C_{1-6}$alkylcarbonyl, optionally substituted $C_{2-6}$alkenyl, optionally substituted $C_{3-6}$cycloalkenyl, optionally substituted ($C_{3-6}$cycloalkyl)alkylene, optionally substituted (aryl)alkylene, or $C_{1-6}$alkylsulfonyl. In other embodiments, $R^6$ is H. In further embodiments, $R^6$ is CN. In still other embodiments, $R^6$ is $C_{1-6}$alkoxy such as methoxy. In yet other embodiments, $R^6$ is $C_{1-6}$alkoxy(alkylene) such as $CH_2OCH_3$, $C(CH_3)_2OCH_3$, or $(CH_2)_2OCH_3$. In still other embodiments, $R^6$ is $C_{1-6}$haloalkoxy such as $OCF_3$, $OCHF_2$, $OCH_2F$, or $O(CH_2)_2CF_3$. In other embodiments, $R^6$ is $C_{1-6}$haloalkoxy(alkylene) such as $CH_2OCF_3$. In yet other embodiments, $R^6$ is $C_{1-6}$deuterated alkoxy(alkylene) such as $CH_2OCD_3$. In further embodiments, $R^6$ is halo such as F, Br, or Cl. In yet further embodiments, $R^6$ is $(CR^vR^x)_pNR^yR^z$ such as $NH_2$, $N(CH_3)_2$, $NHCH_2CF_3$, $NHCH_2CH_2OCH_3$, NH(cyclopropyl), $CH_2N(CH_3)_2$, $(CH_2)_2N(CH_3)_2$, $C(CH_3)_2NHCH_3$, $C(CH_3)_2N(CH_3)_2$, $CH_2$NH(cyclopropyl), or $CH_2CH_2$NH(cyclopropyl). In other embodiments, $R^6$ is $C(O)NR^{y2}R^{z2}$ such as $C(O)N(CH_3)_2$ or C(O)NH(cyclopropyl). In yet other embodiments, $R^6$ is $C_{1-6}$alkylcarbonyl such as $C(O)CH_3$. In further embodiments, $R^6$ is optionally substituted $C_{2-6}$alkenyl such as $CH{=}CH_2$, CH=CH-cyclopropyl, or $CH{=}CHC(CH_3)_2OH$. In yet other embodiments, $R^6$ is optionally substituted $C_{3-6}$cycloalkenyl such as

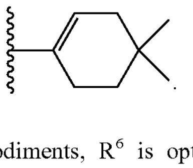.

In still other embodiments, $R^6$ is optionally substituted ($C_{3-6}$cycloalkyl)alkylene such as $CH_2$-cyclopropyl, $CH_2CH_2$-cyclopropyl or $C(CH_3)$OH-cyclopropyl. In further embodiments, $R^6$ is optionally substituted (aryl)alkylene such as benzyl. In other embodiments, $C_{1-6}$alkylsulfonyl (alkylene) such as $C(CH_3)_2SO_2CH_3$. In yet other embodiments, $R^6$ is H, $CH_2OCH_3$, Cl, NH(cyclopropyl), or $C(O)N(CH_3)_2$.

In some embodiments, $R^7$ is H, CN, $C_{1-6}$alkyl, $C_{1-6}$haloalkyl, halo, $C_{3-8}$cycloalkyl, aryl, or heteroaryl. In yet other embodiments, $R^7$ is H. In still further embodiments, $R^7$ is CN. In other embodiments, $R^7$ is $C_{1-6}$alkyl, such as methyl, ethyl, or propyl. In further embodiments, $R^7$ is methyl. In yet other embodiments, $R^7$ is $C_{1-6}$haloalkyl, such as $CHF_2$, $CH_2F$, $C(CH_3)F_2$, $CH_2CHF_2$, or $CF_3$. In still further embodiments, $R^7$ is $CHF_2$ or $CF_3$. In further embodiments, $R^7$ is halo, such as F, Br, or Cl. In yet other embodiments, $R^7$ is Br or Cl. In still further embodiments, $R^7$ is $C_{3-6}$cycloalkyl, such as cyclopropyl, cyclobutyl, or cyclopentyl. In other embodiments, $R^7$ is cyclopropyl. In further embodiments, $R^7$ is aryl. In yet other embodiments, $R^7$ is phenyl. In still further embodiments, $R^7$ is heteroaryl. In other embodiments, $R^7$ is pyridinyl. In further embodiments, $R^7$ is H, CN, methyl, $CF_3$, $CH_2F$, $CHF_2$, $CF_2(CH_3)$, $CH_2CHF_2$, Br, Cl, cyclopropyl, phenyl, or pyridinyl. In yet other embodiments, $R^7$ is H, CN, methyl, $CHF_2$, $CF_3$, Br, Cl, cyclopropyl, phenyl, or pyridinyl.

In some embodiments of $R^2$, $R^8$ is H. In other embodiments, $R^8$ is $C_{1-6}$alkyl such as methyl, ethyl, isopropyl, or tert-butyl. In further embodiments, $R^8$ is $C_{1-6}$haloalkyl such as $CF_3$, $CHF_2$, $CH_2F$, $CH_2CF_3$, $CH_2CHF_2$, $C(CH_3)_2F$, or $C(CH_3)F_2$. In still further embodiments, $R^a$ is $C_{1-6}$alkoxy (alkylene) such as $CH_2CH_2OCH_3$. In other embodiments, $R^8$ is $C_{1-6}$alkylcarbonyl such as $CH_2C({=}O)CH_3$. In still other embodiments, $R^8$ is $C_{1-6}$hydroxyalkyl such as $CH_2C(CH_3)_2OH$. In further embodiments, $R^8$ is $(CR^vR^x)_pNR^vR^x$ such as $(CH_2)_2N(CH_3)_2$. In yet other embodiments, $R^8$ is optionally substituted $C_{3-8}$cycloalkyl such as optionally substituted cyclopropyl, optionally substituted cyclobutyl, optionally substituted cyclopentyl, or optionally substituted cyclohexyl. In other embodiments, $R^8$ is optionally substituted aryl such as optionally substituted phenyl. In further embodiments, $R^8$ is optionally substituted heteroaryl, such as optionally substituted pyridinyl. In still further embodiments, $R^8$ is optionally substituted heteroaryl such as optionally substituted pyridinyl. In yet other embodiments, $R^8$ is optionally substituted ($C_{3-8}$cycloalkyl)alkylene such as

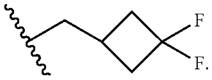 [SMILES: *CC1CC(F)(F)C1].

In still further embodiments, $R^8$ is H, methyl, isopropyl, $CHF_2$, $CH_2CF_3$, $CF_3$, cyclopropyl, or

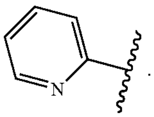.

In some embodiments, one or both of $R^v$ and $R^x$ are H. In other embodiments, one or both of $R^v$ and $R^x$ are $C_{1-6}$alkyl such as methyl, ethyl, propyl, or butyl. In yet other embodiments, one or both of $R^v$ and $R^x$ are methyl. In some embodiments, one or both of $R^y$ and $R^z$ are H. In other embodiments, one or both of $R^y$ and $R^z$ are $C_{1-6}$alkyl such as methyl, ethyl, propyl, or butyl. In yet other embodiments, one or both of $R^y$ and $R^z$ are $C_{1-6}$alkoxy(alkylene) such as $CH_2OCH_3$. In further embodiments, one or both of $R^v$ and $R^x$ are $C_{3-6}$cycloalkyl such as cyclopropyl, cyclobutyl, cyclopentyl, or cyclohexyl. In some embodiments, one or both of $R^{y2}$ and $R^{z2}$ are H. In other embodiments, one or both of $R^{y2}$ and $R^{z2}$ are $C_{1-6}$alkyl such as methyl, ethyl, propyl, or butyl. In further embodiments, one or both of $R^{y2}$ and $R^{z2}$ are $C_{3-6}$cycloalkyl such as cyclopropyl, cyclobutyl, cyclopentyl, or cyclohexyl. In further embodiments, p is 0. In other embodiments, p is 1. In still further embodiments, p is 2. In yet other embodiments, p is 3.

In some embodiments, $R^2$ is

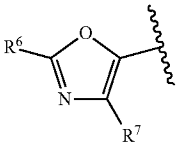

wherein: $R^6$ is H, $C_{1-6}$alkyl, $C_{1-6}$haloalkyl, $C_{1-6}$cyanoalkyl, $C_{1-6}$hydroxyalkyl, $C_{1-6}$alkoxy, $C_{1-6}$alkoxy(alkylene), optionally substituted $C_{3-6}$cycloalkyl, or optionally substituted heteroaryl; and $R^6$ is H, CN, $C_{1-6}$alkyl, $C_{1-6}$haloalkyl, halo, $C_{3-6}$cycloalkyl, aryl, or heteroaryl. In further embodiments, $R^6$ is H, $C_{1-6}$alkyl, $C_{1-6}$haloalkyl, $C_{1-6}$cyanoalkyl, $C_{1-6}$hydroxyalkyl, optionally substituted $C_{3-6}$cycloalkyl, or optionally substituted heteroaryl; and $R^7$ is H, CN, $C_{1-6}$alkyl, $C_{1-6}$haloalkyl, halo, or $C_{3-6}$ cycloalkyl. In other embodiments, $R^6$ is H. In further embodiments, $R^6$ is $C_{1-6}$alkyl. In still further embodiments, $R^6$ is methyl, isopropyl, or tert-butyl. In yet other embodiments, $R^6$ is $C_{1-6}$haloalkyl. In still further embodiments, $R^6$ is $CF_2H$, $C(CH_3)_2F$, $CH(CH_3)F$, or $CF_3$. In other embodiments, $R^6$ is $C_{1-6}$cyanoalkyl. In further embodiments, $R^6$ is $C(CH_3)_2CN$. In yet other embodiments, $R^6$ is $C_{1-6}$hydroxyalkyl. In still further embodiments, $R^6$ is $C(CH_3)_2OH$, $CH_2C(CH_3)_2OH$, $CH(CH_2CH_3)OH$, $C(CH_3)_2(CH_2OH)$, or $CH(CH_3)OH$. In other embodiments, $R^6$ is $C_{1-6}$alkoxy. In still other embodiments, $R^6$ is methoxy or ethoxy. In yet other embodiments, $R^6$ is $C_{1-6}$alkoxy(alkylene). In further embodiments, $R^6$ is $CH_2OCH_3$ or $(CH_2)_2OCH_3$. In other embodiments, $R^6$ is optionally substituted $C_{3-6}$cycloalkyl. In yet other embodiments, the optionally substituted C cycloalkyl is substituted with one or more OH. In further embodiments, $R^6$ is

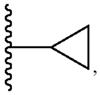, 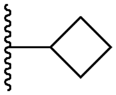, 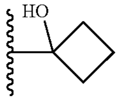, 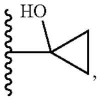, 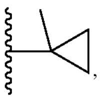, or 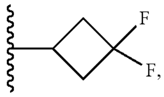

In yet other embodiments, $R^6$ is

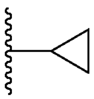 or 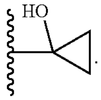.

In other embodiments, $R^6$ is optionally substituted heteroaryl. In yet other embodiments, $R^6$ is optionally substituted pyridinyl, optionally substituted pyrazolyl, optionally substituted pyrazinyl, optionally substituted pyrimidinyl, or optionally substituted imidazolyl. In still other embodiments, the optionally substituted heteroaryl is substituted with one or more $C_{1-6}$alkyl such as methyl, ethyl, or isopropyl. In further embodiments, $R^6$ is

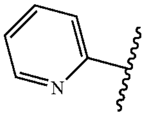, 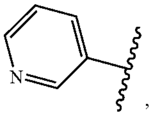, 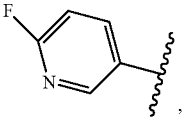, 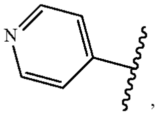, 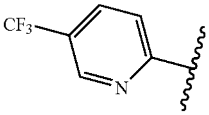, 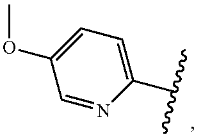, 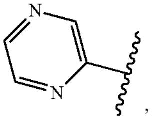, 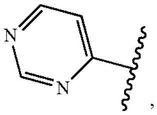, 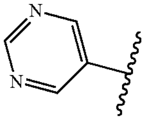, 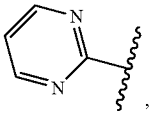, 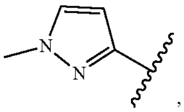, 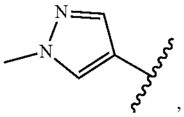, 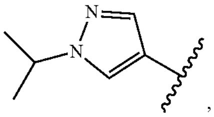, 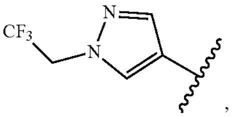, 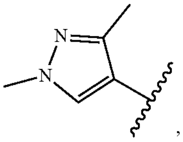, 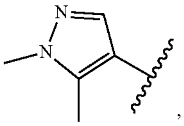, 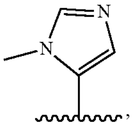, or 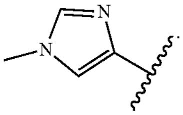.

In still further embodiments, $R^6$ is

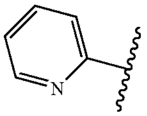, 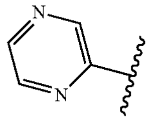, 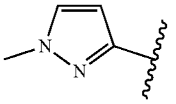, 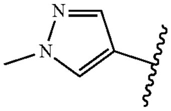, 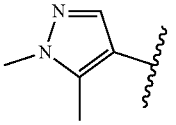, 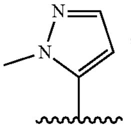, or 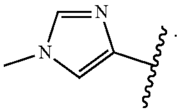.

In other embodiments, $R^6$ is H, methyl, tert-butyl, $C(CH_3)_2F$, $C(CH_3)_2CN$, $C(CH_3)OH$, $CH(CH_3)OH$, $CH_2OCH_3$, cyclopropyl,

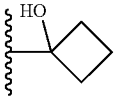, 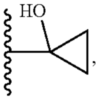, 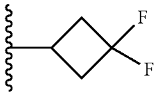,

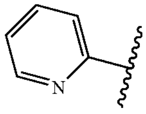, 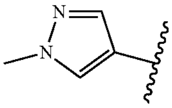,

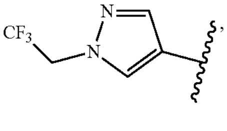, 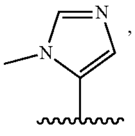, or

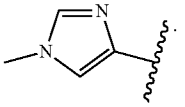.

In further embodiments, $R^6$ is H, tert-butyl, $C(CH_3)_2F$, $C(CH_3)_2CN$, $C(CH_3)_2OH$, $CH(CH_3)OH$,

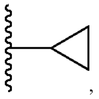, 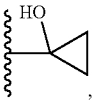,

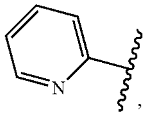, 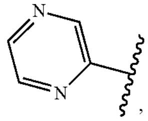,

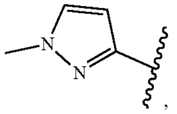, 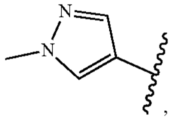,

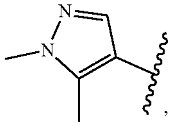, 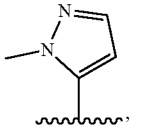, or

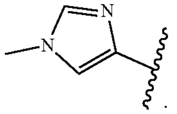.

In yet other embodiments, $R^7$ is H. In still further embodiments, $R^7$ is CN. In other embodiments, $R^7$ is $C_{1-6}$alkyl. In further embodiments, $R^7$ is methyl. In yet other embodiments, $R^7$ is $C_{1-6}$haloalkyl. In still further embodiments, $R^7$ is $CF_2H$, $CHF_2$, $CH_2F$, $C(CH_3)F_2$, or $CF_3$. In other embodiments, $R^7$ is $CHF_2$ or $CF_3$. In further embodiments, $R^7$ is halo. In yet other embodiments, $R^7$ is Br or Cl. In still further embodiments, $R^7$ is $C_{3-6}$cycloalkyl. In other embodiments, $R^7$ is cyclopropyl. In further embodiments, $R^7$ is aryl. In yet other embodiments, $R^7$ is phenyl. In still further embodiments, $R^7$ is heteroaryl. In other embodiments, $R^7$ is pyridinyl. In yet other embodiments, $R^7$ is H, CN, methyl, $CHF_2$, $CF_3$, Br, Cl, cyclopropyl, phenyl, or pyridinyl. In still other embodiments, $R^7$ is H, CN, methyl, $CHF_2$, $CF_3$, Br, Cl, or cyclopropyl.

In other embodiments, $R^2$ is

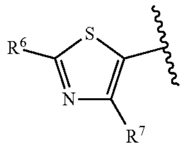

wherein: $R^6$ is H, CN, $C_{1-6}$alkyl, $C_{1-6}$haloalkyl, $C_{1-6}$hydroxyalkyl, $C_{1-6}$alkoxy, $C_{1-6}$alkoxy(alkylene), optionally substituted $C_{3-6}$cycloalkyl, optionally substituted heteroaryl; and $R^7$ is H, $C_{1-6}$alkyl, $C_{1-6}$haloalkyl, halo, or $C_{3-6}$cycloalkyl. In yet other embodiments, $R^6$ is H, $C_{1-6}$alkyl, $C_{1-6}$haloalkyl, or $C_{1-6}$ hydroxyalkyl; and $R^7$ is H. In further embodiments, $R^6$ is H. In other embodiments, $R^6$ is CN. In further embodiments, $R^6$ is $C_{1-6}$alkyl. In still further embodiments, $R^6$ is methyl, isopropyl, or tert-butyl. In yet other embodiments, $R^6$ is $C_{1-6}$haloalkyl. In still further embodiments, $R^6$ is $CHF_2$, $C(CH_3)_2F$, $C(CH_3)F_2$, or $CF_3$. In yet other embodiments, $R^6$ is $C_{1-6}$ hydroxyalkyl. In still further embodiments, $R^6$ is $C(CH_3)_2OH$. In other embodiments, $R^6$ is $C_{1-6}$alkoxy. In still further embodiments, $R^6$ is methoxy or ethoxy. In yet other embodiments, $R^6$ is $C_{1-6}$alkoxy(alkylene). In further embodiments, $R^6$ is $CH_2OCH_3$. In other embodiments, $R^6$ is optionally substituted $C_{3-6}$cycloalkyl. In yet further embodiments, $R^6$ is

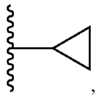, 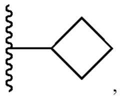,

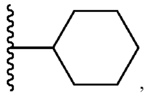, 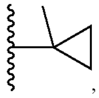,

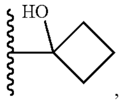, 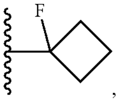, or

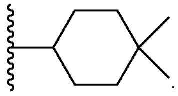.

In other embodiments, $R^6$ is optionally substituted heteroaryl. In yet other embodiments, $R^6$ is optionally substituted pyridinyl or optionally substituted pyrazolyl. In further embodiments, $R^6$ is 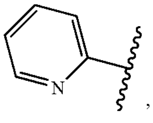, 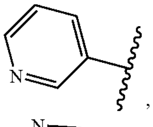, 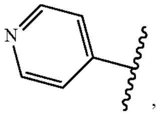,

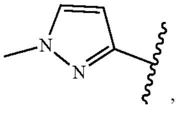, 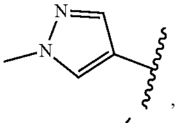,

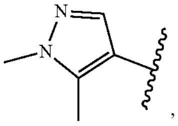, 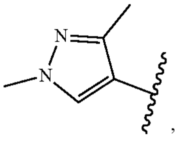,

-continued

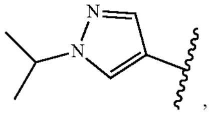,
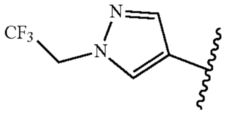,
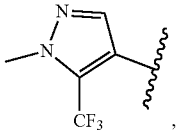,
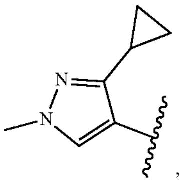,
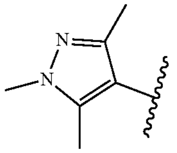
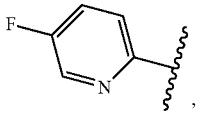,
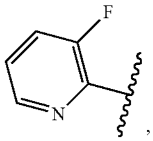,
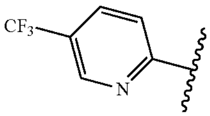,
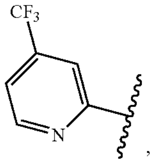, or
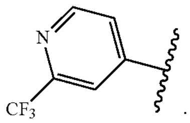.

In other embodiments, $R^6$ is H, tert-butyl, $C(CH_3)_2F$, $C(CH_3)F_2$, $C(CH_3)_2OH$, $CH_2OCH_3$,

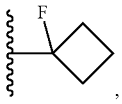,
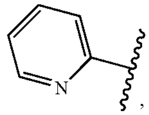,
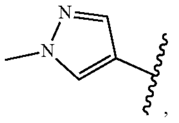,
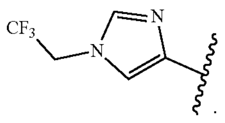. or
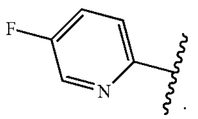.

In further embodiments, $R^6$ is H or $C(CH_3)_2F$. In yet other embodiments, $R^7$ is H. In other embodiments, $R^7$ is $C_{1-6}$alkyl. In further embodiments, $R^7$ is methyl. In yet other embodiments, $R^7$ is $C_{1-6}$haloalkyl. In still further embodiments, $R^7$ is $CF_2H$ or $CF_3$. In further embodiments, $R^7$ is halo. In yet other embodiments, $R^7$ is Br or Cl. In still further embodiments, $R^7$ is $C_{3-6}$cycloalkyl. In other embodiments, $R^7$ is cyclopropyl. In still further embodiments, $R^7$ is H, methyl, $CF_2H$ $CF_3$, Br, Cl, or cyclopropyl.

In further embodiments, $R^2$ is

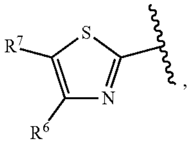, wherein $R^6$ and $R^7$ are independently H, $C_{1-6}$alkyl, $C_{1-6}$haloalkyl, halo, optionally substituted $C_{3-6}$cycloalkyl, or optionally substituted aryl. In other embodiments, $R^6$ and $R^7$ are each H. In further embodiments, one of $R^6$ or $R^7$ is $C_{1-6}$alkyl such as methyl. In yet other embodiments, one of $R^6$ or $R^7$ is $C_{1-6}$haloalkyl such as $CF_3$. In still other embodiments, one of $R^6$ or $R^7$ is halo such as Br or Cl. In yet further embodiments, one of $R^6$ or $R^7$ is optionally substituted $C_{3-6}$cycloalkyl such as unsubstituted cyclopropyl. In other embodiments, one of $R^6$ or $R^7$ is optionally substituted aryl such as unsubstituted phenyl. In yet other embodiments, $R^6$ is methyl, $CF_3$, Cl, cyclopropyl, or phenyl and $R^7$ is H. In still other embodiments, $R^7$ is methyl, $CF_3$, Cl, cyclopropyl, or phenyl and $R^6$ is H.

In yet further embodiments, $R^2$ is

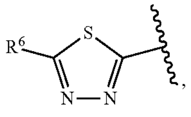, wherein $R^6$ is H, $C_{1-6}$ alkyl, halo, or optionally substituted aryl. In other embodiments, $R^6$ is H. In further embodiments, $R^6$ is $C_{1-6}$alkyl, such as methyl, ethyl, isopropyl, or tert-butyl. In other embodiments, $R^6$ is methyl or ethyl. In other embodiments, $R^6$ is halo, such as F, Br, or Cl. In further embodiments, $R^6$ is Br. In other embodiments, $R^6$ is optionally substituted aryl. In further embodiments, $R^6$ is phenyl. In yet other embodiments, $R^6$ is H, methyl, ethyl, Br, or phenyl. In still other embodiments, $R^6$ is H, methyl, or phenyl.

In yet other embodiments, $R^2$ is

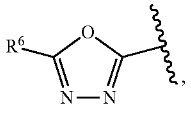, wherein $R^6$ is H, $C_{1-6}$alkyl, $C_{1-6}$haloalkyl, $C_{1-6}$hydroxyalkyl, $C(O)NR^{y2}R^{z2}$, $(CR^vR^x)_pNR^yR^z$, optionally substituted $C_{3-6}$cycloalkyl, optionally substituted aryl, optionally substituted heterocyclyl, or optionally substituted heteroaryl; $R^v$ and $R^x$ are, independently, H or $C_{1-6}$alkyl; $R^y$ and $R^z$ are, independently, H, $C_{1-6}$alkyl, $C_{1-6}$alkoxy(alkylene), or $C_{3-6}$cycloalkyl; $R^{y2}$ and $R^{z2}$ are, independently, H, $C_{1-6}$alkyl, or $C_{1-6}$cycloalkyl; and p is 0, 1, 2, or 3. In further embodiments, $R^6$ is H, $C_{1-6}$alkyl, $C_{1-6}$haloalkyl, $C_{1-6}$hydroxyalkyl, optionally substituted $C_{3-6}$cycloalkyl, optionally substituted aryl, optionally substituted heterocyclyl, or optionally substituted heteroaryl. In some embodiments, $R^6$ is H. In further embodiments, $R^6$ is $C_{1-6}$alkyl. In other embodiments, $R^6$ is methyl, ethyl, isopropyl, or tert-butyl. In further embodiments, $R^6$ is methyl, isopropyl, or tert-butyl. In other embodiments, $R^6$ is $C_{1-6}$haloalkyl. In further embodiments, $R^6$ is $CHF_2$, $CF_3$, or $C(CH_3)_2F$. In still further embodiments, $R^6$ is $CF_3$, $CHF_2$, $C(CH_3)F_2$, or $C(CH_3)_2F$. In yet other embodiments, $R^6$ is $C_{1-6}$hydroxyalkyl. In still further embodiments, $R^6$ is $C(CH_3)_2OH$ or $CH(CH_3)OH$. In still other embodiments, $R^6$ is $C(O)NR^{y2}R^{z2}$. In yet further embodiments, $R^6$ is $C(O)N(CH_3)_2$ or C(O)NH(cyclopropyl). In other embodiments, $R^6$ is $(CR^wR^x)_pNR^yR^z$. In further embodiments, $R^6$ is $NH_2$, $N(CH_3)_2$, $NHCH_2CF_3$, $NHCH_2CH_2OCH_3$, NH(cyclopropyl), $CH_2N(CH_3)_2$, $CH_2$NH(cyclopropyl), or $CH_2CH_2$NH(cyclopropyl). In yet other embodiments, $R^6$ is optionally substituted $C_{3-6}$cycloalkyl. In still other embodiments, the optionally substituted $C_{3-6}$cycloalkyl is substituted with one or more of halo such as F or $C_{1-6}$alkyl such as methyl. In still further embodiments, $R^6$ is

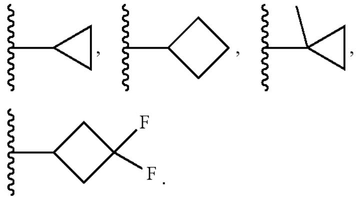

, or

In other embodiments, $R^6$ is optionally substituted aryl. In yet other embodiments, the optionally substituted aryl is substituted with one or more of halo such as F, $C_{1-6}$alkyl such as methyl, or $C_{1-6}$haloalkyl such as $CF_3$. In further embodiments, $R^6$ is

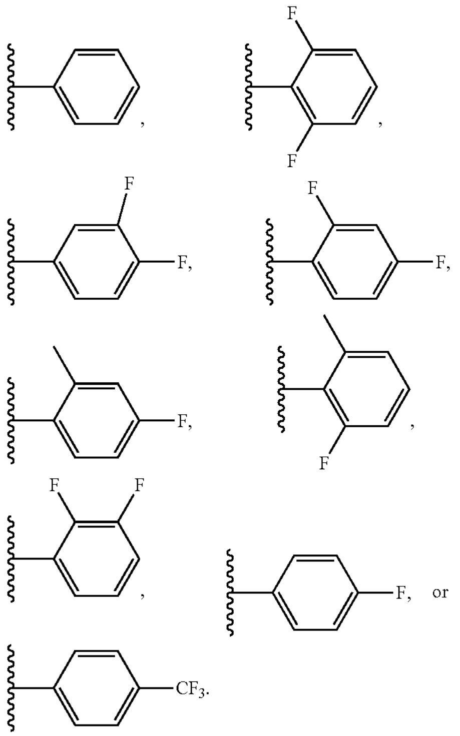

, or

In still other embodiments, $R^6$ is optionally substituted heterocyclyl. In further embodiments, the optionally substituted heterocyclyl is substituted with one or more of halo such as F or $C_{1-6}$alkyl such as methyl. In yet further embodiments, $R^6$ is

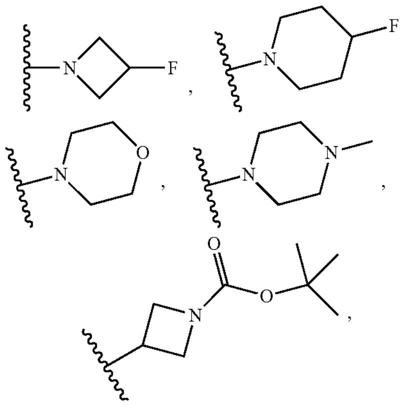

, or

In yet other embodiments, $R^6$ is

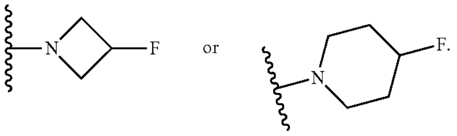 [SMILES: *N1CC(F)C1 ; *N1CCC(F)CC1]

or

In other embodiments, $R^6$ is optionally substituted heteroaryl such as optionally substituted pyrazolyl, optionally substituted imidazolyl, optionally substituted pyridinyl, or optionally substituted pyrazinyl. In further embodiments, the optionally substituted heteroaryl is substituted with one or more of $C_{1-6}$alkyl such as methyl, ethyl, or isopropyl, $C_{1-6}$haloalkyl such as $CF_3$, $CH_2CF_3$, or $CHF_2$, halo such as F, $C_{1-6}$alkoxy such as methoxy, ethoxy, or propoxy, $C_{3-6}$cycloalkyl such as cyclopropyl or cyclobutyl; or $C_{3-6}$cycloalkylsulfonyl such as cyclopropylsulfonyl, cyclobutylsulfonyl, or cyclopentylsulfonyl. In yet other embodiments, $R^6$ is

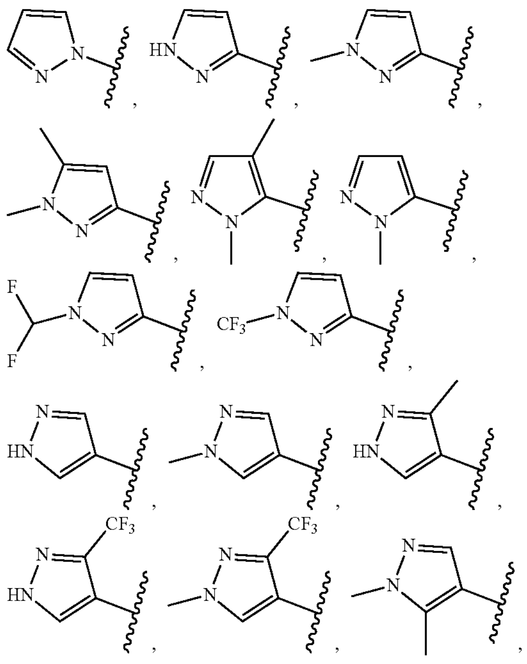

-continued
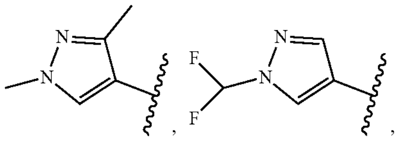
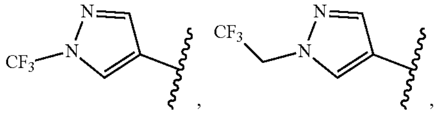
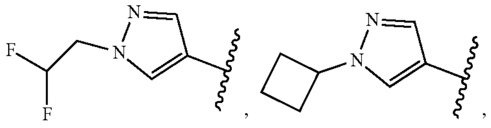
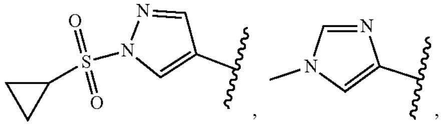
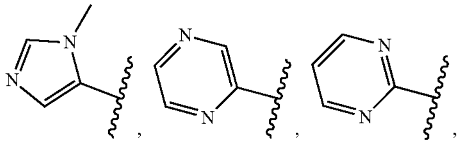
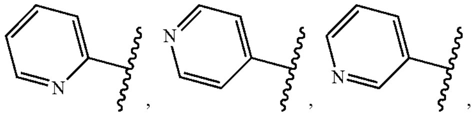
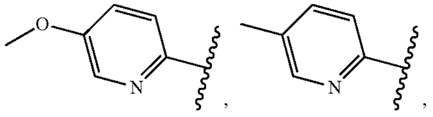
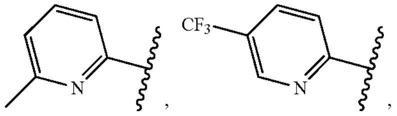
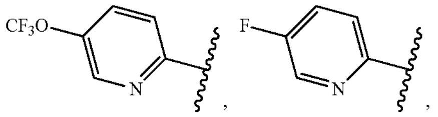
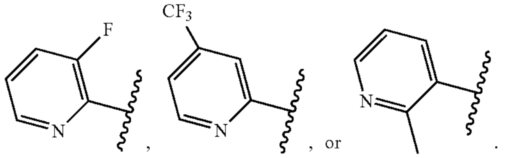
In still other embodiments, $R^6$ is
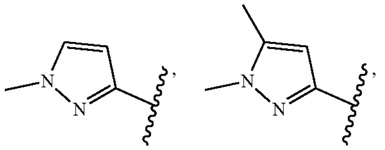
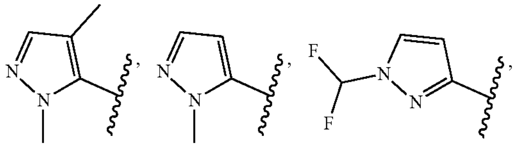
-continued
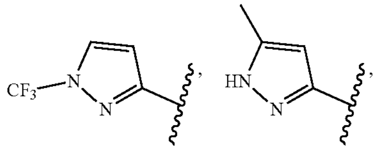
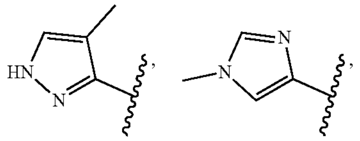
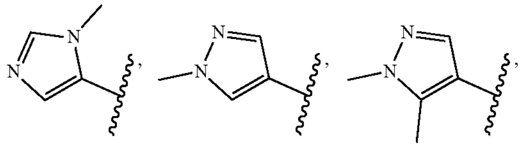
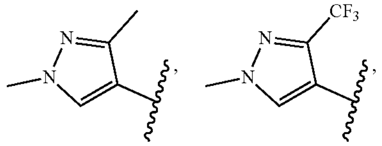
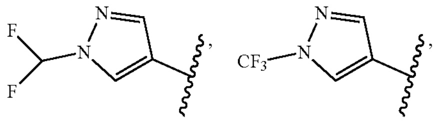
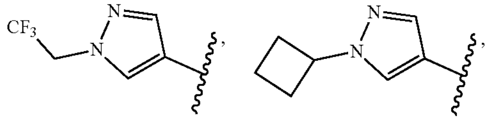
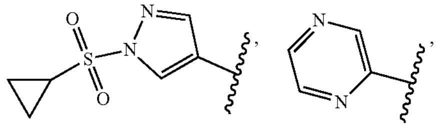
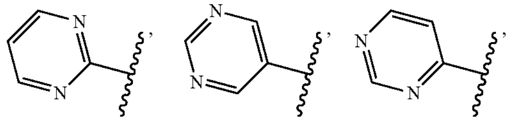
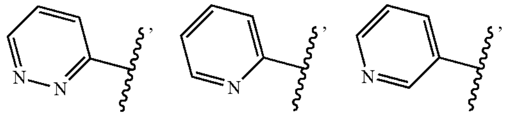
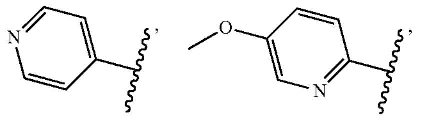
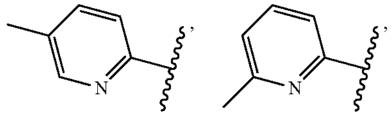
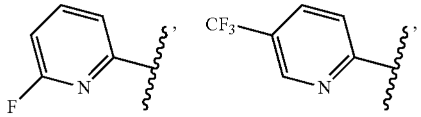
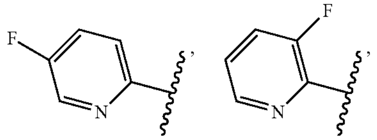

-continued
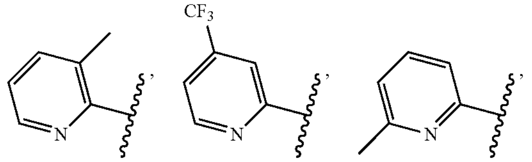
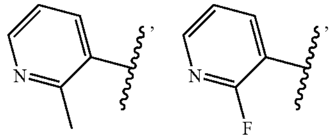
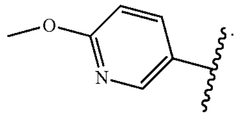
In further embodiments, $R^6$ is methyl, isopropyl, tert-butyl, $CHF_2$, $C(CH_3)_2F$, $C(CH_3)_2OH$, $CH(CH)OH$, $C(O)N(CH_3)$, NH(cyclopropyl),
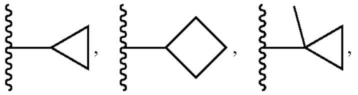
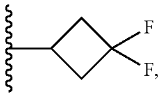
phenyl,
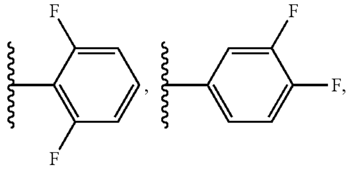
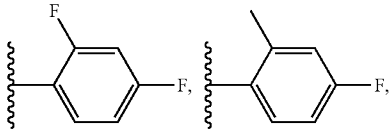
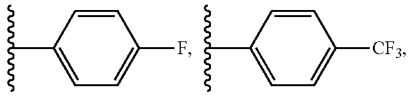
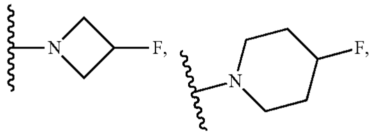
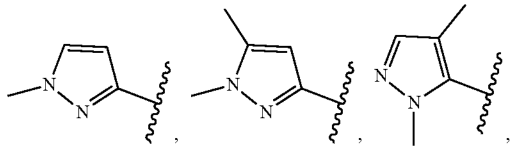
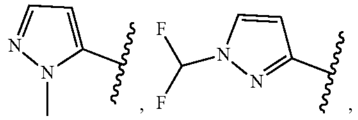
-continued
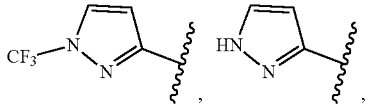
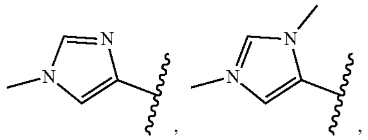
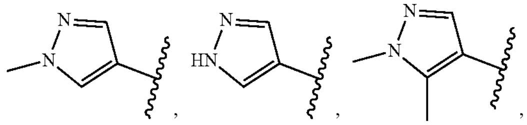
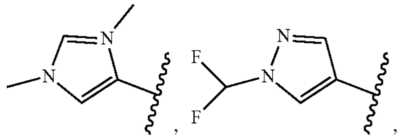
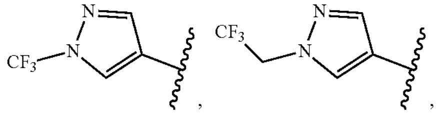
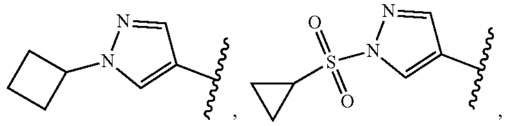
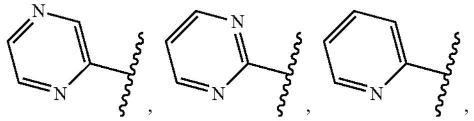
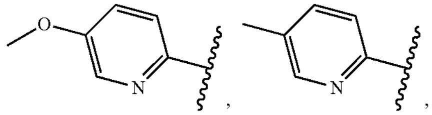
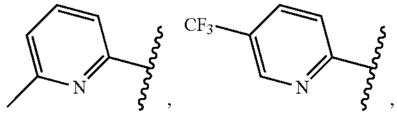
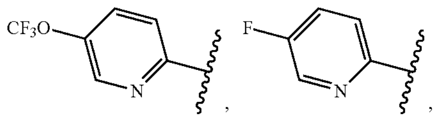
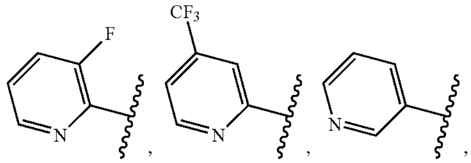
or
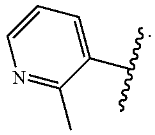
In still further embodiments, $R^6$ is methyl, isopropyl, tert-butyl, $CF_3$, $CHF_2$, $C(CH_3)F_2$, $C(CH_3)_2F$, $C(CH_3)_2OH$,

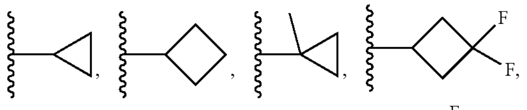
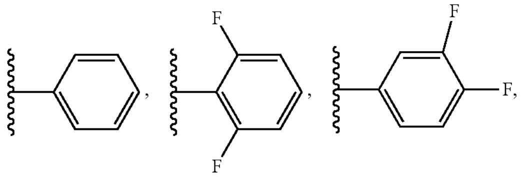
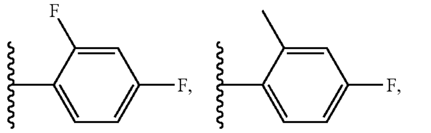
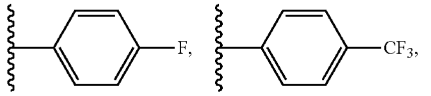
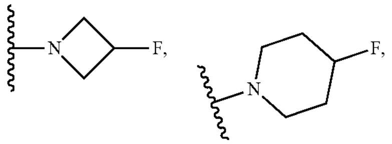
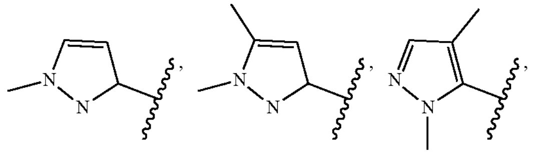
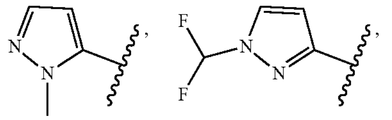
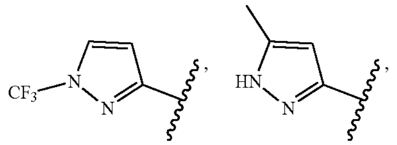
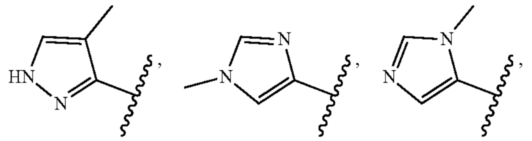
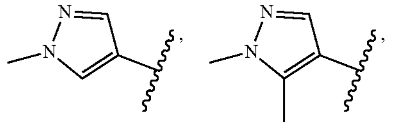
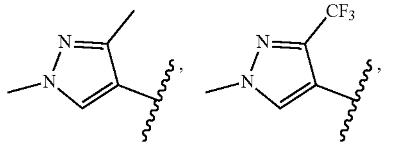
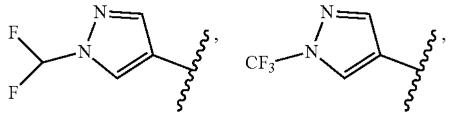
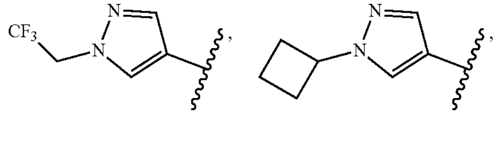
-continued
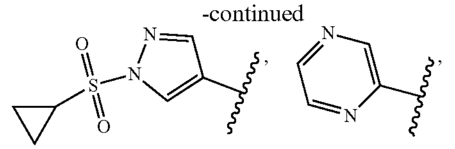
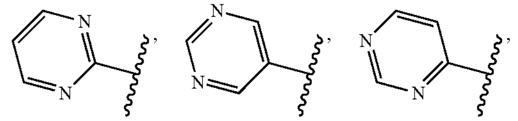
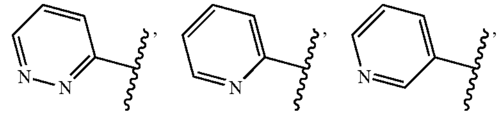
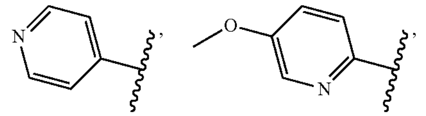
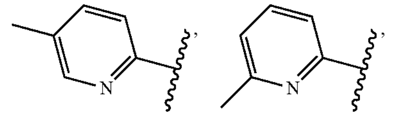
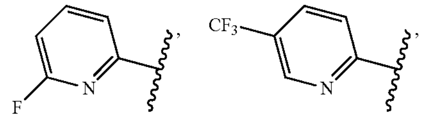
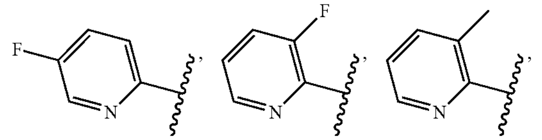
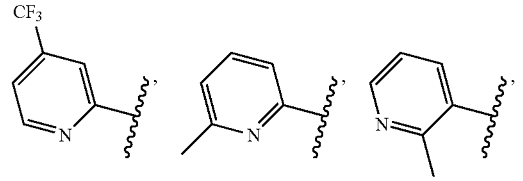
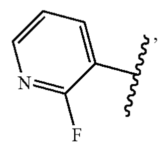
or
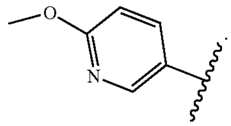
In still further embodiments, $R^2$ is
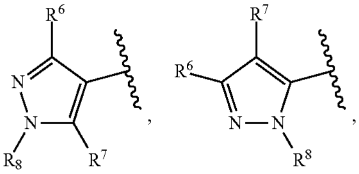
or
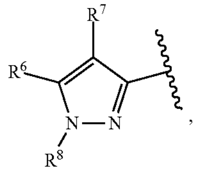
wherein $R^6$ and $R^7$ are independently H, halo, $C_{1-6}$alkyl, or $C_{1-6}$haloalkyl; and $R^8$ is H, $C_{1-6}$alkyl, $C_{1-6}$haloalkyl, $C_{3-6}$cycloalkyl, optionally substituted aryl, or heteroaryl. In yet other embodiments, $R^6$ and $R^7$ are independently H, halo, $C_{1-6}$alkyl, $C_{1-4}$haloalkyl, or $NR^yR^z$ wherein $R^y$ and $R^z$ are, independently, H or $C_{1-6}$alkyl; $R^3$ is H, $C_{1-4}$alkyl, $C_{1-6}$alkyl, $C_{3-6}$cycloalkyl, or heteroaryl. In other embodiments, one or both of $R^6$ and $R^7$ are H. In still other embodiments, one of $R^6$ or $R^7$ is halo. In further embodiments, one of $R^6$ or $R^7$ is Cl or Br. In still further embodiments, one of $R^6$ or $R^7$ is Cl. In yet other embodiments, one of $R^6$ or $R^7$ is $C_{1-6}$alkyl. In still further embodiments, one of $R^6$ or $R^7$ is methyl. In other embodiments, one of $R^6$ or $R^7$ is $C_{1-6}$haloalkyl. In further embodiments, one of $R^6$ or $R^7$ is $CHF_2$, $CH_2CF_3$, $CF_2H$, or $CF_3$. In other embodiments, one of $R^6$ or $R^7$ is $CHF_2$. In further embodiments, one of $R^6$ or $R^7$ is $NR^yR^z$ wherein $R^y$ and $R^z$ are, independently, H or $C_{1-6}$alkyl, such as $NH_2$. In yet other embodiments, one of $R^6$ or $R^7$ is Cl, Br, methyl, $CHF_2$, or $CF_3$. In further embodiments, one of $R^6$ or $R^7$ is Cl, methyl, $CHF_2$, or $NH_2$. In other embodiments, one of $R^6$ or $R^7$ is methyl, Cl, $CHF_2$, or CF. In some embodiments, $R^7$ is H. In other embodiments, $R^8$ is $C_{1-6}$alkyl. In further embodiments, $R^8$ is methyl, ethyl, isopropyl, or tert-butyl. In yet other embodiments, $R^8$ is methyl or isopropyl. In still other embodiments, $R^8$ is $C_{1-6}$haloalkyl. In yet further embodiments, $R^8$ is $CHF_2$, $CH_2CF_3$, $CF_2H$, $CH_2CHF_2$, or $CF_3$. In yet further embodiments, $R^8$ is $CHF_2$, $CH_2CF_3$, or $CF_3$. In other embodiments, $R^8$ is $C_{3-6}$ cycloalkyl. In further embodiments, $R^8$ is cyclopropyl. In yet other embodiments, $R^8$ is optionally substituted aryl. In still further embodiments, $R^8$ is phenyl or fluorophenyl. In other embodiments, $R^8$ is heteroaryl. In further embodiments, $R^8$ is pyridinyl. In still other embodiments, $R^8$ is H, methyl, isopropyl, tert-butyl, $CHF_2$, $CH_2CF_3$, $CH_2CHF_2$, $CH_2C(=O)CH_3$, $CH_2C(CH_3)_2OH$, $(CH_2)_2N(CH_3)_2$, cyclopropyl, fluorophenyl, pyridinyl, $CH_2$-cyclopropyl or $CH_2$-cyclobutyl. In yet other embodiments, $R^8$ is methyl, isopropyl, $CHF_2$, $CH_2CF_3$, $CF_3$, cyclopropyl, and pyridinyl.

In further embodiments, $R^2$ is

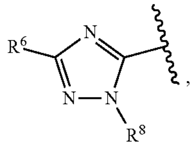, wherein $R^6$ is H, $C_{1-6}$alkyl, halo, $C_{1-6}$haloalkyl, or $C_{3-6}$cycloalkyl; and $R^8$ is H, $C_{1-6}$alkyl, or $C_{1-6}$haloalkyl. In still further embodiments, $R^6$ is H, $C_{1-6}$alkyl, halo, $C_{1-6}$haloalkyl, or $C_{3-6}$cycloalkyl; and $R^8$ is H or $C_{1-6}$ alkyl. In other embodiments, $R^6$ is H. In still other embodiments, $R^6$ is $C_{3-6}$alkyl, such as methyl. In yet other embodiments, $R^6$ is halo such as Cl or Br. In further embodiments, $R^6$ is Cl. In other embodiments, $R^6$ is $C_{1-6}$haloalkyl such as $CHF_2$ or $CF_3$. In yet other embodiments, $R^6$ is $C_{3-6}$cycloalkyl such as cyclopropyl. In still further embodiments, $R^6$ is H, methyl, Cl, $CHF_2$, $CF_3$, or cyclopropyl. In some embodiments, $R^8$ is H. In other embodiments, $R^8$ is $C_{1-6}$alkyl such as methyl, ethyl, or isopropyl. In yet other embodiments, $R^8$ is $C_{1-6}$haloalkyl, such as $CF_3$ or $CHF_2$. In other embodiments, $R^8$ is methyl.

In yet other embodiments, $R^2$ is

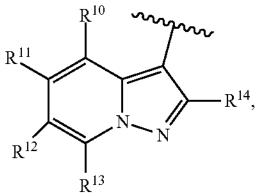,

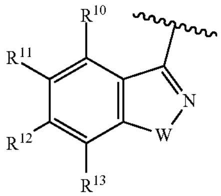,

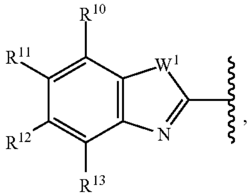,

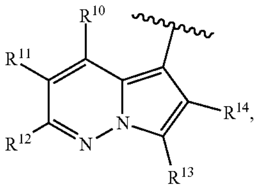,

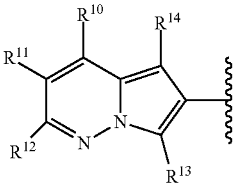, or

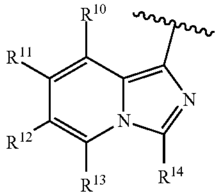.

In these structures, W is S or $NR^{15}$; $W^1$ is S, O, or $NR^{15}$; $R^{10}$, $R^{11}$, $R^{12}$, $R^{13}$, and $R^{14}$ are each independently, H, $C_{1-6}$alkyl, $C_{1-6}$haloalkyl, $C_{1-4}$alkoxy, $C_{1-6}$alkoxy(alkylene), $C_{1-6}$ hydroxyalkyl, $C_{1-6}$haloalkoxy, $C_{1-6}$haloalkoxy(alkylene), $C_{2-6}$alkenyl, CN, halo, $(CR^vR^x)_pNR^yR^z$, $C(O)NR^{y2}R^{z2}$, optionally substituted $C_{3-8}$cycloalkyl, optionally substituted heterocyclyl, optionally substituted heterocyclyl(alkylene), optionally substituted aryl, or optionally substituted heteroaryl; $R^v$ and $R^x$ are, independently, H or $C_{1-6}$alkyl; $R^y$ and $R^z$ are, independently, H, $C_{1-6}$alkyl, $C_{3-6}$cycloalkyl, $C_{1-6}$hydroxyalkyl, $C_{1-6}$haloalkyl, $C_{1-6}$ alkoxy(alkylene), or $C(O)OC_{1-6}$alkyl; $R^{y2}$ and $R^{z2}$, are independently, H, $C_{1-6}$alkyl, or $C_{3-6}$ cycloalkyl; p is 0, 1, 2, or 3; and $R^5$ is H or $C_{1-6}$alkyl.

In some embodiments, W is S. In other embodiments, W is $NR^{15}$. In some embodiments, $W^1$ is S. In other embodiments, $W^1$ is O. In further embodiments, $W^1$ is $NR^{15}$. In some embodiments, $R^{10}$, $R^{11}$, $R^{12}$, $R^{13}$, and $R^{14}$ are H. In further embodiments, $R^{10}$, $R^{11}$, $R^{12}$, and $R^v$ are H. In other embodiments, at least one of $R^{10}$, $R^{11}$, $R^{12}$, $R^{13}$, and $R^{14}$ is $C_{1-6}$ alkyl. In further embodiments, at least one of $R^{10}$, $R^{11}$, $R^{12}$, $R^{13}$, and $R^4$ is $C_{1-6}$haloalkyl. In yet other embodiments, at least one of $R^{10}$, $R^{11}$, $R^{12}$, $R^{13}$, and $R^{14}$ is $C_{1-6}$alkoxy. In still other embodiments, at least one of $R^{10}$, $R^{11}$, $R^{12}$, $R^{13}$, and $R^{14}$ is $C_{1-6}$alkoxy(alkylene). In further embodiments, at least one of $R^{10}$, $R^{11}$, $R^{12}$, $R^{13}$, and $R^{14}$ is $C_{1-6}$hydroxyalkyl. In other embodiments, at least one of $R^{10}$, $R^{11}$, $R^{12}$, $R^{13}$, and $R^{14}$ is $C_{1-6}$haloalkoxy. In still other embodiments, at least one of $R^{10}$, $R^{11}$, $R^{12}$, $R^{13}$, and $R^{14}$ is $C_{1-6}$haloalkoxy(alkylene). In yet other embodiments, at least one of $R^{10}$, $R^{11}$, $R^{12}$, $R^{13}$, and $R^{14}$ is $C_{2-6}$alkenyl. In further embodiments, at least one of $R^{10}$, $R^{11}$, $R^{12}$, $R^{13}$, and $R^{14}$ is CN. In yet other embodiments, at least one of $R^{10}$, $R^{11}$, $R^{12}$, $R^{13}$, and $R^{14}$ is halo. In still further embodiments, at least one of $R^{10}$, $R^{11}$, $R^{12}$, $R^{13}$, and $R^{14}$ is $(CR^vR^x)_pNR^yR^z$. In other embodiments, at least one of $R^{10}$, $R^{11}$, $R^{12}$, $R^{13}$, and $R^{14}$ is $C(O)NR^{y2}R^{z2}$. In further embodiments, at least one of $R^{10}$, $R^{11}$, $R^{12}$, $R^{13}$, and $R^4$ is optionally substituted $C_{3-8}$cycloalkyl. In yet other embodiments, at least one of $R^{10}$, $R^{11}$, $R^{12}$, $R^{13}$, and $R^{14}$ is optionally substituted heterocyclyl. In still other embodiments, at least one of $R^{10}$, $R^{11}$, $R^{12}$, $R^{13}$, and $R^{14}$ is optionally substituted heterocyclyl(alkylene). In still further embodiments, at least one of $R^{10}$, $R^{11}$, $R^{12}$, $R^{13}$, and $R^{14}$ is optionally substituted aryl. In other embodiments, at least one of $R^{10}$, $R^{11}$, $R^{12}$, $R^{13}$, and $R^{14}$ is optionally substituted heteroaryl. In some embodiments, one or both of $R^v$ and $R^x$ are H. In other embodiments, one or both of $R^v$ and $R^x$ is $C_{1-6}$alkyl. In some embodiments, one or both of $R^y$ and $R^z$ is H. In other embodiments, one or both of $R^y$ and $R^z$ is $C_{1-6}$alkyl. In further embodiments, one or both of $R^y$ and $R^z$ is $C_{1-6}$cycloalkyl. In yet other embodiments, one or both of $R^y$ and $R^z$ is $C_{1-6}$ hydroxyalkyl. In still further embodiments, one or both of $R^y$ and $R^z$ is $C_{1-6}$haloalkyl. In further embodiments, one or both of $R^y$ and $R^z$ is $C(O)OC_{1-6}$alkyl. In some embodiments, one or both of $R^{y2}$ and $R^{z2}$ is H. In other embodiments, one or both of $R^{y2}$ and $R^{z2}$ is $C_{1-6}$alkyl. In further embodiments, one or both of $R^{y2}$ and $R^{z2}$ is $C_{3-6}$cycloalkyl. In some embodiments, p is 0. In other embodiments, p is 1. In further embodiments, p is 2. In yet other embodiments, p is 3. In some embodiments, $R^{15}$ is H. In other embodiments, $R^5$ is $C_{1-6}$alkyl.

In still further embodiments, $R^2$ is

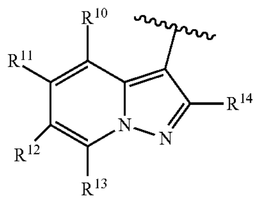

wherein $R^{10}$, $R^{11}$, $R^{12}$, $R^{13}$, and $R^{14}$ are each independently H, $C_{1-6}$alkyl, $C_{1-6}$haloalkyl, $C_{3-6}$cycloalkyl, $C_{1-6}$alkoxy, $C_{1-6}$alkoxy(alkylene), halo, optionally substituted aryl, optionally substituted heterocyclyl, optionally substituted heterocyclyl(alkylene), optionally substituted heteroaryl, or $(CR^vR^x)_pNR^yR^z$. In other embodiments, $R^{10}$, $R^{11}$, $R^{12}$, $R^{13}$, and $R^{14}$ are each independently H, $C_{1-6}$alkyl, $C_{3-6}$cycloalkyl, $C_{1-6}$alkoxy, $C_{1-6}$alkoxy(alkylene), optionally substituted heterocyclyl, optionally substituted heterocyclyl(alkylene), optionally substituted heteroaryl, or $(CR^vR^x)_pNR^yR^z$. In some embodiments, $R^{10}$, $R^{11}$, $R^{12}$, $R^{13}$, and $R^{14}$ are H. In other embodiments, at least one of $R^{10}$, $R^{11}$, $R^{12}$, $R^{13}$, and $R^{14}$ is $C_{1-4}$alkyl such as methyl or ethyl. In yet other embodiments, at least one of $R^{10}$, $R^{11}$, $R^{12}$, $R^{13}$, and $R^{14}$ is $C_{1-6}$alkyl such as methyl. In further embodiments, at least one of $R^{10}$, $R^{11}$, $R^{12}$, $R^{13}$, and $R^{14}$ is $C_{1-6}$haloalkyl such as $CF_3$, or $C(CH_3)_2F$. In yet further embodiments, at least one of $R^{10}$, $R^{11}$, $R^{12}$, $R^{13}$, and/or $R^4$ is $C_{3-6}$cycloalkyl such as cyclopropyl. In yet other embodiments, at least one of $R^{10}$, $R^{11}$, $R^{12}$, $R^{13}$, and $R^{14}$ is $C_{1-6}$alkoxy such as methoxy. In other embodiments, at least one of $R^{10}$, $R^{11}$, $R^{12}$, $R^{13}$, and $R^{14}$ is $C_{1-6}$alkoxy(alkylene) such as $CH_2OCH_3$ or $(CH_2)_2OCH_3$. In yet other embodiments, at least one of $R^{10}$, $R^{11}$, $R^{12}$, $R^{13}$, and $R^{14}$ is halo such as F, Br, or Cl. In still further embodiments, at least one of $R^{10}$, $R^{11}$, $R^{12}$, $R^{13}$, and $R^{14}$ is optionally substituted aryl such as unsubstituted phenyl. In yet other embodiments, at least one of $R^{10}$, $R^{11}$, $R^{12}$, $R^{13}$, and $R^{14}$ is optionally substituted heterocyclyl such as

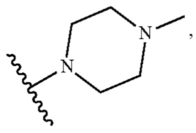,
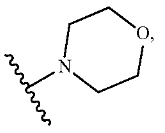
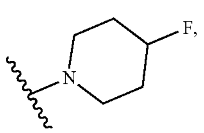

-continued

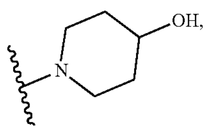
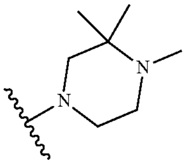,
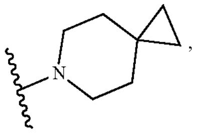,
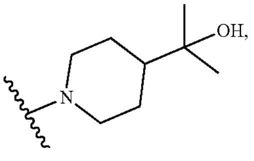 or
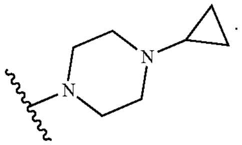.

In still other embodiments, at least one of $R^{10}$, $R^{11}$, $R^{12}$, $R^{13}$, and $R^{14}$ is optionally substituted heterocyclyl such as

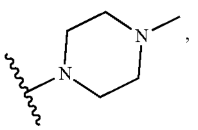,
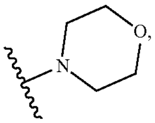
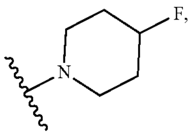 or
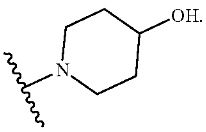

In other embodiments, the optionally substituted heterocyclyl is

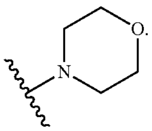 [SMILES: *N1CCOCC1]

In further embodiments, at least one of $R^{10}$, $R^{11}$, $R^{12}$, $R^{13}$, and $R^{14}$ is optionally substituted heterocyclyl(alkylene). In still further embodiments, at least one of $R^{10}$, $R^{11}$, $R^{12}$, $R^{13}$, and $R^{14}$ is

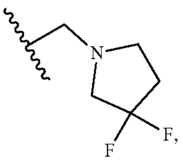
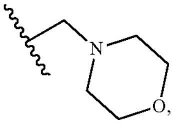 or
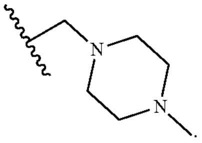

In yet other embodiments, at least one of $R^{10}$, $R^{11}$, $R^{12}$, $R^{13}$, and $R^{14}$ is

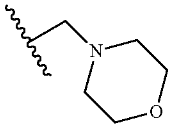 or 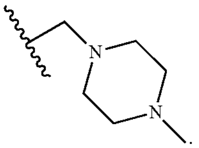.

In other embodiments, at least one of $R^{10}$, $R^{11}$, $R^{12}$, $R^{13}$, and $R^{14}$ is optionally substituted heteroaryl such as optionally substituted pyridinyl, optionally substituted pyrazinyl, optionally substituted pyrimidinyl, or optionally substituted pyrazolyl. In yet other embodiments, at least one of $R^{10}$, $R^{11}$, $R^{12}$, $R^{13}$, and $R^{14}$ is

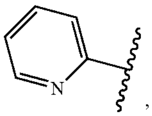, 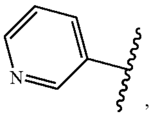, 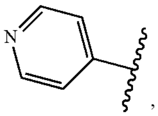,

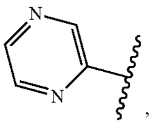, 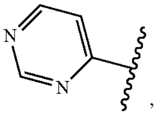, 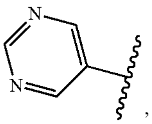,

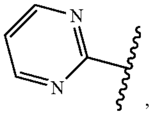, 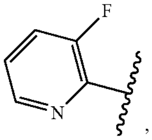, 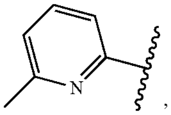,

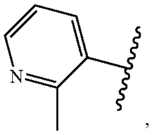, 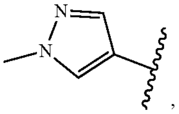,

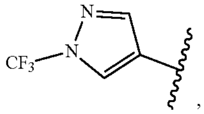, 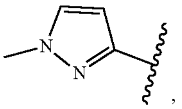, or

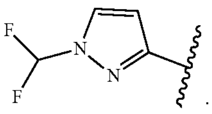.

In still further embodiments, at least one of $R^{10}$, $R^{11}$, $R^{12}$, $R^{13}$, and $R^{14}$ is $(CR^yR^x)_pNR^yR^z$ such as $NH_2$, $NH(CH_3)$, $N(CH_3)_2$, $CH_2N(CH_3)_2$, or $CH_2CH_2N(CH_3)_2$. In other embodiments, at least one of $R^{10}$, $R^{11}$, $R^{12}$, $R^{13}$, and $R^{14}$ is $(CR^yR^x)_pNR^yR^z$ such as $N(CH_3)_2$, $CH_2N(CH_3)_2$, or $CH_2CH_2N(CH_3)_2$. In further embodiments, $R^{10}$, $R^{11}$, $R^{12}$, $R^{13}$, and $R^{14}$ are each independently H, methyl, $C(CH_3)_2F$, cyclopropyl, methoxy, $CH_2OCH_3$, $(CH_2)_2OCH_3$, Br, F, Cl, phenyl,

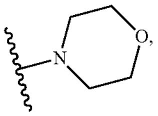, 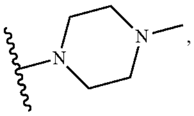,

-continued

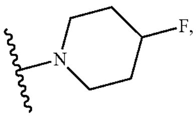, 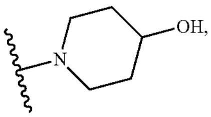,

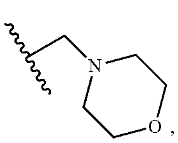, 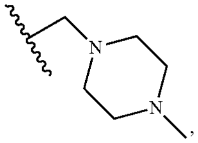,

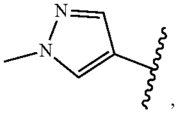, 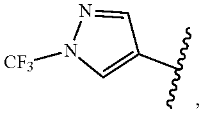,

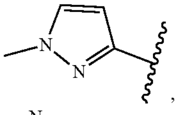, 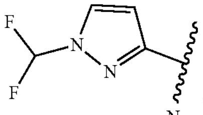,

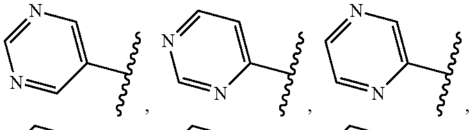

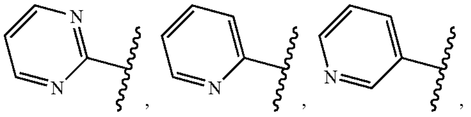

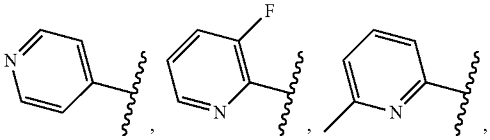

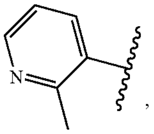, $N(CH_3)_2$, $CH_2N(CH_3)_2$, or $CH_2CH_2N(CH_3)_2$. In yet other embodiments, $R^{10}$, $R^{11}$, $R^{12}$, $R^{13}$, and $R^{14}$ are each independently H, methyl, cyclopropyl, methoxy, $CH_2OCH_3$, $(CH_2)_2OCH_3$,

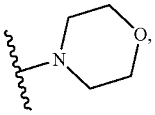, 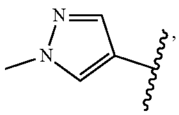, 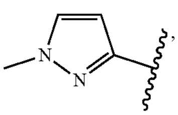,

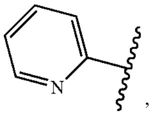, $N(CH_3)_2$, $CH_2N(CH_3)_2$, or $CH_2CH_2N(CH_3)_2$. In other embodiments, $R^{10}$, $R^{13}$, and $R^{14}$ are each hydrogen. In further embodiments, $R^{10}$, $R^{13}$, and $R^{14}$ are each hydrogen; and $R^{11}$ is halo.

In further embodiments, at least one of $R^{10}$, $R^{11}$, $R^{12}$, $R^{13}$, and $R^{14}$ is substituted heterocyclyl or substituted heterocyclyl(alkylene), substituted with one or more of halo such as F, Cl, or Br; $C_{1-6}$haloalkyl such as $CF_3$, $CH_2CF_3$, or $CHF_2$; $C_{1-6}$alkyl such as methyl, ethyl, or propyl; OH; $C_{1-6}$hydroxyalkyl such as $C(CH_3)_2OH$; $C_{1-6}$alkoxy such as methoxy, ethoxy, or propoxy; or $C_{3-6}$cycloalkyl such as cyclopropyl, cyclobutyl, or cyclopentyl. In other embodiments, the substituted heterocyclyl or substituted heterocyclyl(alkylene) is substituted with one or more methyl, OH, or F.

In further embodiments, at least one of $R^{10}$, $R^{11}$, $R^{12}$, $R^{13}$, and $R^{14}$ is substituted heteroaryl, substituted with one or more of halo such as F, Cl, or Br; $C_{1-6}$haloalkyl such as $CF_3$, $CH_2CF_3$, or $CHF_2$; $C_{1-6}$alkyl such as methyl, ethyl, propyl, or isopropyl; $C_{1-6}$ alkoxy such as methoxy, ethoxy, or propoxy; $C_{1-6}$haloalkoxy such as $OCF_3$; $C_{3-6}$cycloalkyl such as cyclopropyl, cyclobutyl, or cyclopentyl; or $C_{3-6}$cycloalkylsulfonyl such as cyclopropylsulfonyl, cyclobutylsulfonyl, or cyclopentylsulfonyl. In yet other embodiments, the substituted heteroaryl is substituted with one or more of F, $CF_3$, $CHF_2$, or methyl. In further embodiments, the optionally substituted heteroaryl is pyrazolyl, substituted with one methyl.

In other embodiments, $R^2$ is

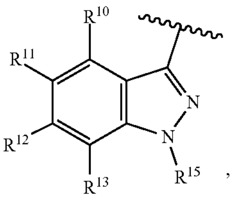

, wherein $R^{10}$, $R^{11}$, $R^{12}$, and $R^{13}$ are each independently H, $C_{1-6}$alkyl, or halo and $R^{15}$ is H or $C_{1-6}$alkyl. In further embodiments, $R^{10}$, $R^{11}$, $R^{12}$, and $R^{13}$ are H. In other embodiments, at least one of $R^{10}$, $R^{11}$, $R^{12}$, and $R^{13}$ is $C_{1-6}$alkyl. In further embodiments, at least one of $R^{10}$, $R^{11}$, $R^{12}$, and $R^{13}$ is halo. In yet other embodiments, at least one of $R^{10}$, $R^{11}$, $R^{12}$, and $R^{13}$ is Br. In some embodiments, $R^{15}$ is H. In other embodiments, $R^{15}$ is $C_{1-6}$alkyl. In further embodiments, $R^{15}$ is methyl. In yet other embodiments, $R^{15}$ is H or methyl.

In further embodiments, $R^2$ is

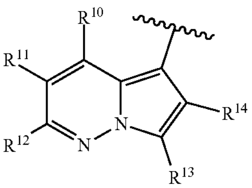

or

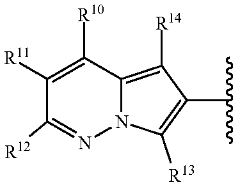

, wherein $R^{10}$, $R^{11}$, $R^{12}$, $R^{13}$, and $R^{14}$ are each independently H, halo, or $C_{1-6}$alkyl. In some embodiments, $R^2$ is

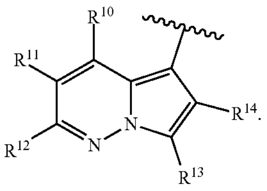

In other embodiments, $R^2$ is

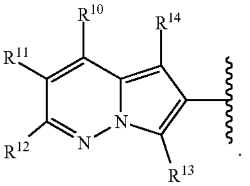

In some embodiments, $R^{10}$, $R^{11}$, $R^{12}$, $R^{13}$, and $R^{14}$ are H. In other embodiments, at least one of $R^{10}$, $R^{11}$, $R^{12}$, $R^{13}$, and $R^{14}$ is halo. In further embodiments, at least one of $R^{10}$, $R^{11}$, $R^{12}$, $R^{13}$, and $R^{14}$ is $C_{1-6}$alkyl.

In yet other embodiments, $R^2$ is

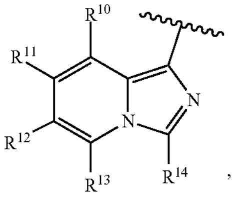

, wherein $R^{10}$, $R^{11}$, $R^{12}$, $R^{13}$ and $R^{14}$ are each independently H, halo, or $C_{1-6}$alkyl. In some embodiments, $R^{10}$, $R^{11}$, $R^{12}$, $R^{13}$, and $R^{14}$ are H. In other embodiments, at least one of $R^{10}$, $R^{11}$, $R^{12}$, $R^{13}$, and $R^{14}$ is halo. In further embodiments, at least one of $R^{10}$, $R^{11}$, $R^{12}$, $R^{13}$, and $R^{14}$ is Br. In yet other embodiments, at least one of $R^{10}$, $R^{11}$, $R^{12}$, $R^{13}$, and $R^{14}$ is $C_{1-6}$alkyl.

In still further embodiments, $R^2$ is

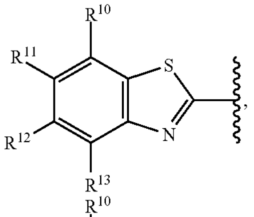

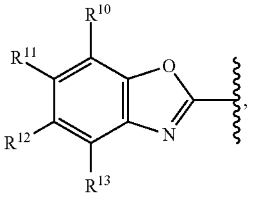

or

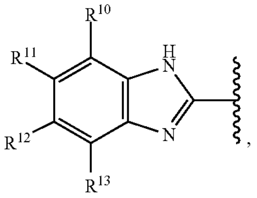

wherein $R^{10}$, $R^{11}$, $R^{12}$, and $R^{13}$ are each independently, H, $C_{1-6}$alkyl, or halo. In some embodiments, $R^2$ is

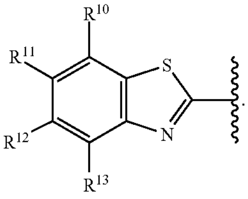.

In other embodiments, $R^2$ is

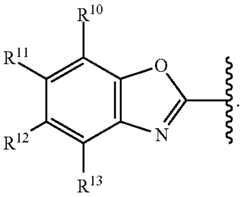.

In further embodiments, $R^2$ is

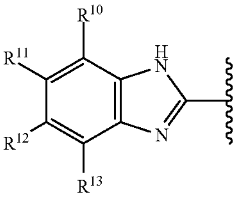.

In some embodiments, $R^{10}$, $R^{11}$, $R^{12}$, and $R^{13}$ are H. In other embodiments, at least one of $R^{10}$, $R^{11}$, $R^{12}$, and $R^{13}$ is halo. In further embodiments, at least one of $R^{10}$, $R^{11}$, $R^{12}$, and $R^{13}$ is F. In yet other embodiments, at least one of $R^{10}$, $R^{11}$, $R^{12}$, and $R^{13}$ is $C_{1-6}$alkyl. In still further embodiments, at least one of $R^{10}$, $R^{11}$, $R^{12}$, and $R^{13}$ is methyl. In yet other embodiments, $R^{10}$, $R^{11}$, $R^{12}$, and $R^{13}$ are each independently H, methyl, or F.

In other embodiments, $R^2$ is

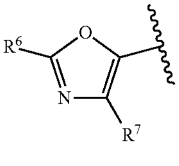

wherein $R^6$ is defined herein and $R^7$ is H. In yet other embodiments, $R^2$ is

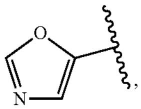, 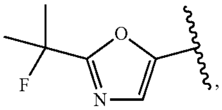, 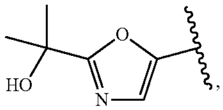, 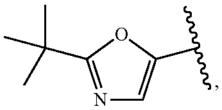,

-continued

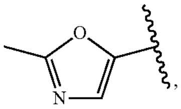, 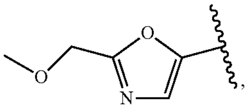, 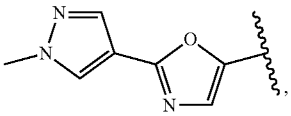, 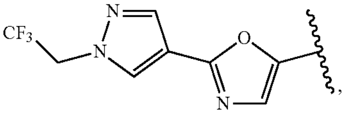, or 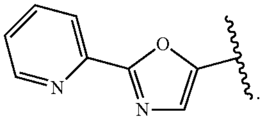.

In still other embodiments, $R^2$ is

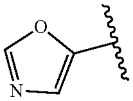, 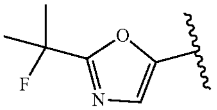, 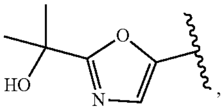, 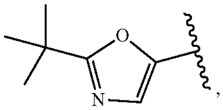, 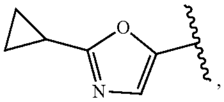, 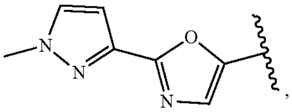, 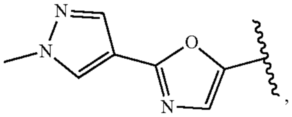, 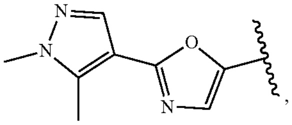, 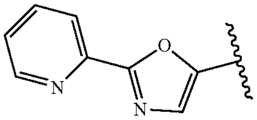, or 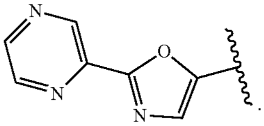.

In further embodiments, $R^2$ is

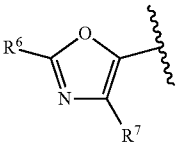

wherein $R^6$ is defined herein and $R^7$ is $CH_3$. In other embodiments, $R^2$ is
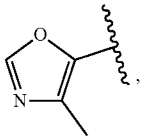,
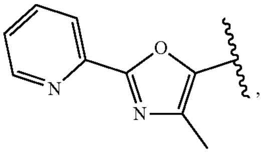,
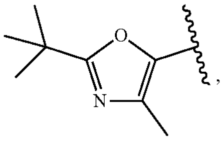,
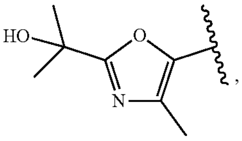,
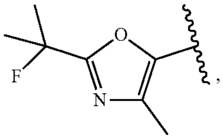,
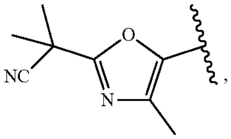,
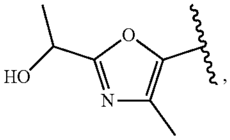,
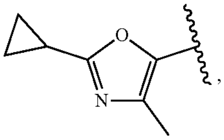,
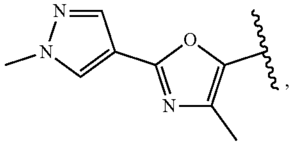,
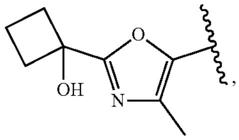, or
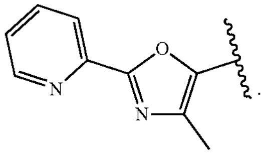.
In yet other embodiments, $R^2$ is
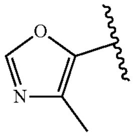,
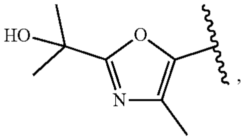,
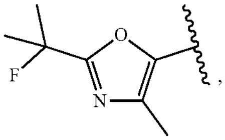,
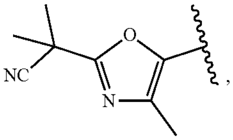, or
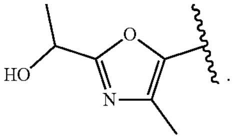.
In yet other embodiments, $R^2$ is
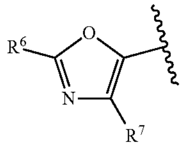
wherein $R^6$ is defined herein and $R^7$ is cyclopropyl. In further embodiments, $R^2$ is
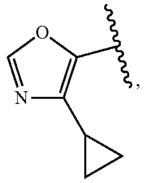,
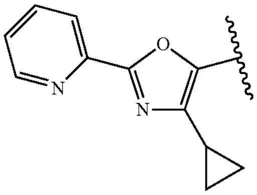, or
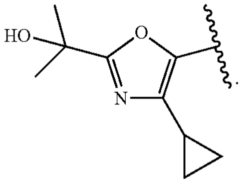.
In still further embodiments, $R^2$ is
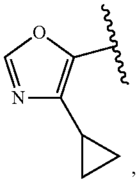,
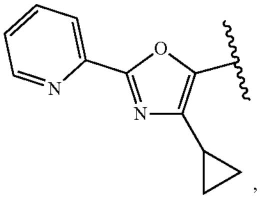,
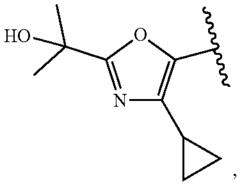, or
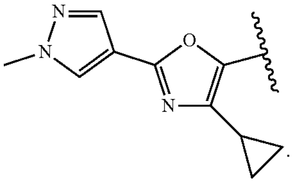.
In still further embodiments, $R^2$ is
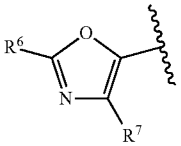

wherein $R^6$ is defined herein and $R^7$ is $CHF_2$. In other embodiments, $R^2$ is
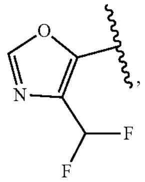
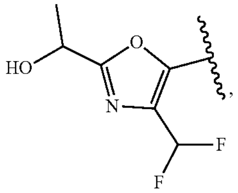
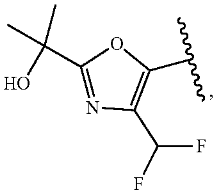
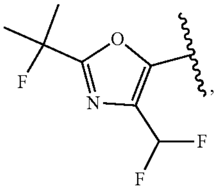
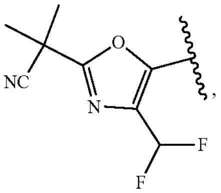
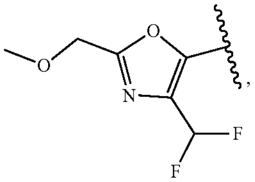
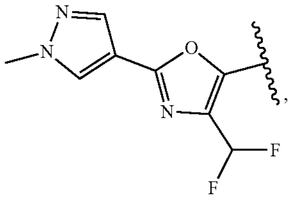
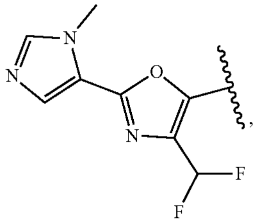
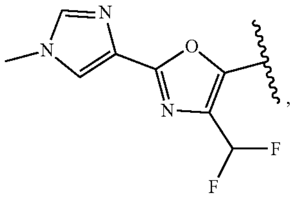
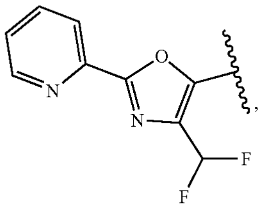
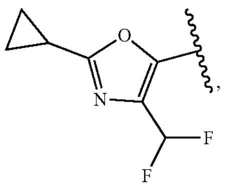
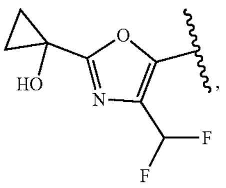
or
-continued
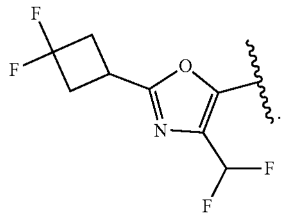
In yet other embodiments, $R^2$ is
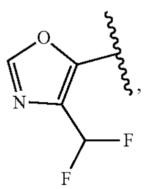
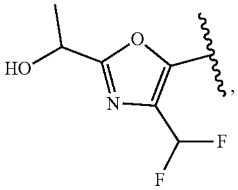
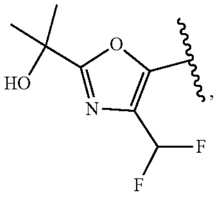
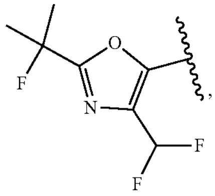
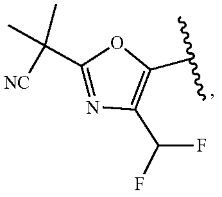
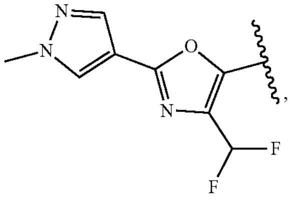
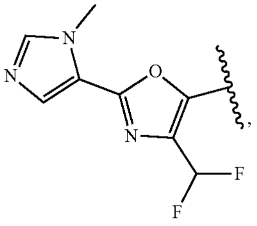
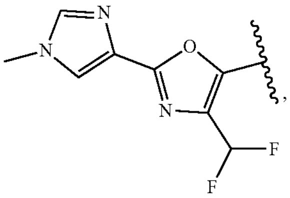
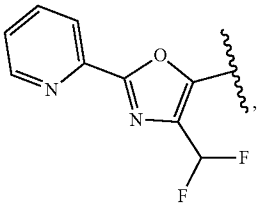

-continued

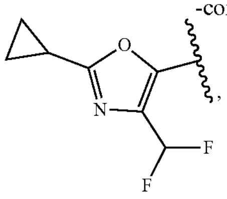
or
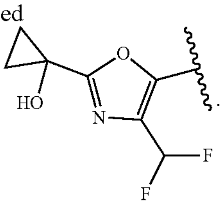

In other embodiments, $R^2$ is

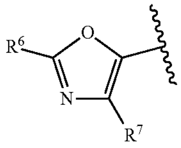

wherein $R^6$ is defined herein and $R^7$ is $CF_3$. In still other embodiments, $R^2$ is

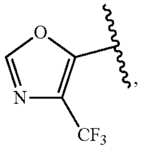
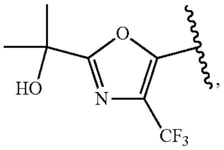
or
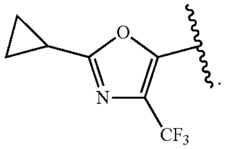

In yet other embodiments, $R^2$ is

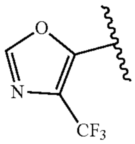
or
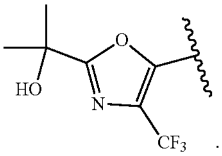
.

In further embodiments, $R^2$ is

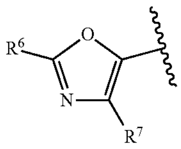

wherein $R^6$ is defined herein and $R^7$ is CN. In still further embodiments, $R^2$ is

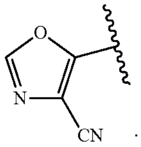 [SMILES: *c1ocnc1C#N]
.

In yet other embodiments, $R^2$ is

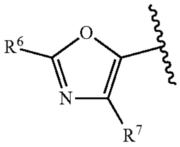

wherein $R^6$ is defined herein and $R^7$ is Br or Cl. In further embodiments, $R^2$ is

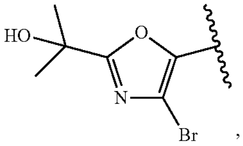
,
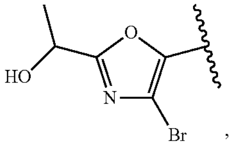
,
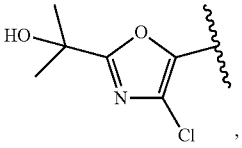
, or
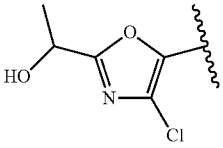
.

In still further embodiments, $R^2$ is

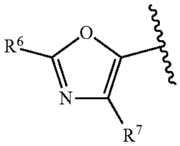

wherein $R^6$ is defined herein and $R^7$ is phenyl or pyridinyl. In other embodiments, $R^2$ is

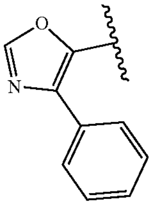
or
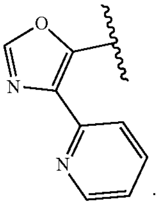
.

In further embodiments, $R^2$ is

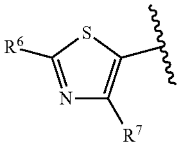

wherein $R^6$ is defined herein and $R^7$ is H. In yet other embodiments, $R^2$ is
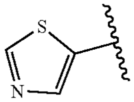, 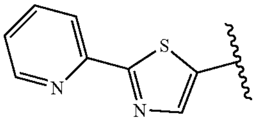,
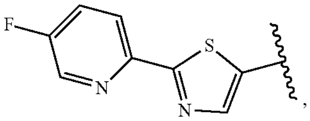,
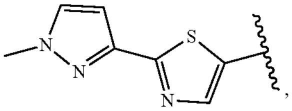,
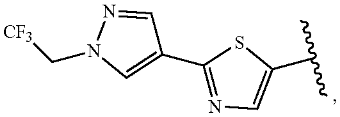,
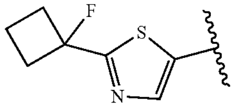, 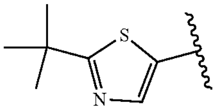,
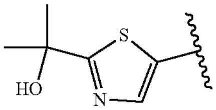, 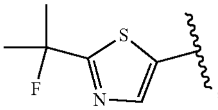,
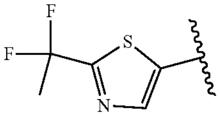, 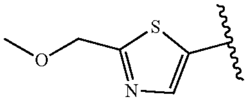.
In still other embodiments, $R^2$ is
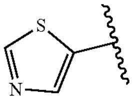 or 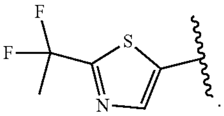.
In other embodiments, $R^2$ is
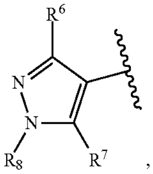,
wherein $R^6$-$R^8$ are defined herein. In still other embodiments, $R^2$ is
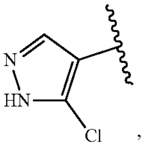, 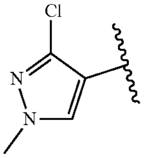
-continued
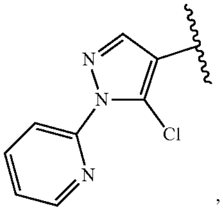, 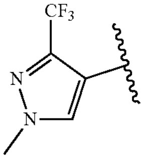,
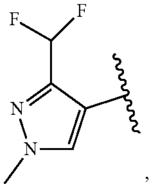, 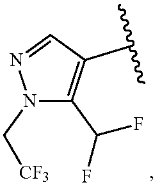, or
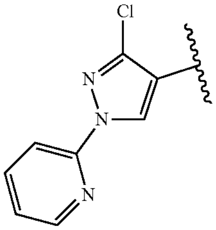.
In yet other embodiments, $R^2$ is
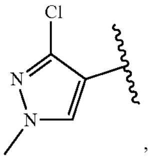, 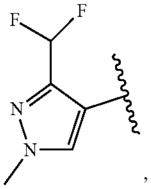,
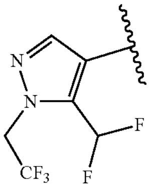, 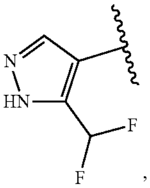, or
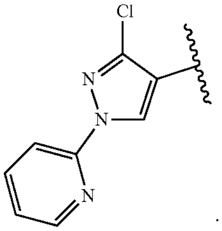.
In further embodiments, $R^2$ is
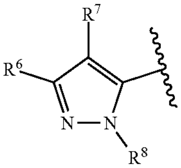 or 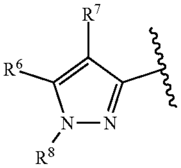

wherein $R^6$-$R^8$ are defined herein. In still further embodiments, $R^2$ is

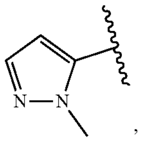,
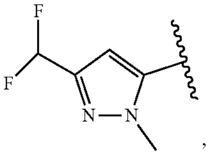,
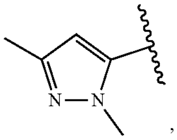,
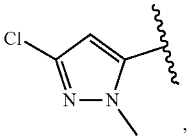,
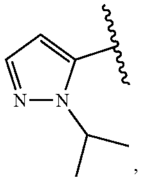,
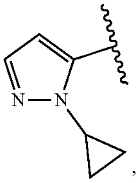,
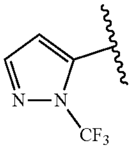,
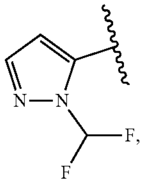 or
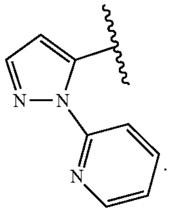.

In yet other embodiments, $R^2$ is

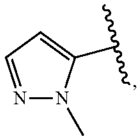,
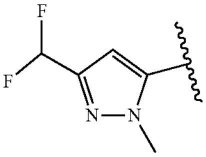,
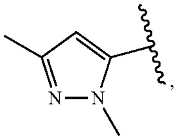,
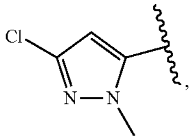,
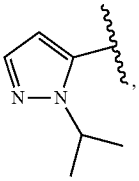,
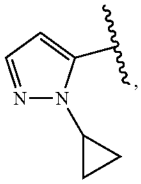,
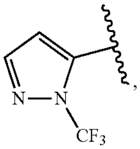,
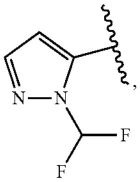,
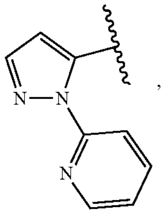, or
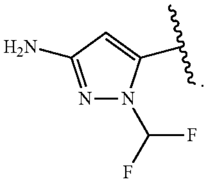.

In other embodiments, $R^2$ is

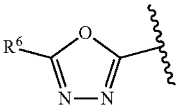

wherein $R^6$ is optionally substituted heterocyclyl. In yet other embodiments, $R^2$ is

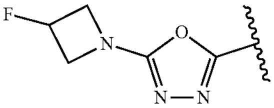
or
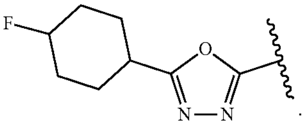 [SMILES: *c1nnc(C2CCC(F)CC2)o1].

In still other embodiments, $R^2$ is

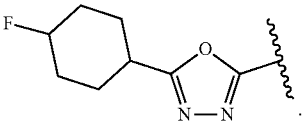.

In further embodiments, $R^2$ is

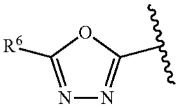

wherein $R^6$ is optionally substituted heteroaryl. In still further embodiments, $R^2$ is

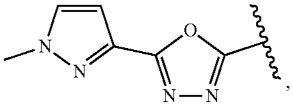,
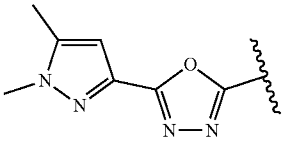,
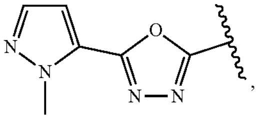,
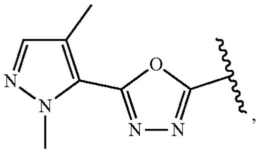,

-continued
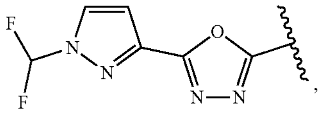
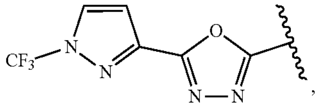
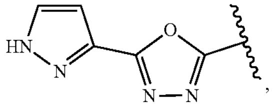
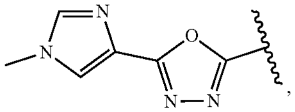
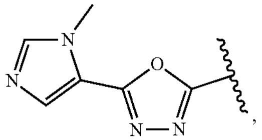
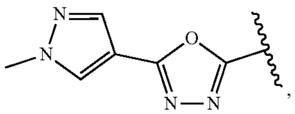
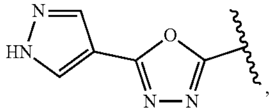
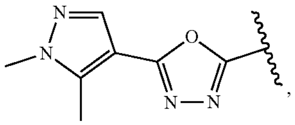
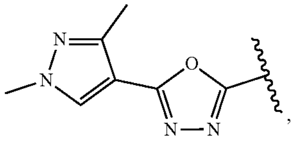
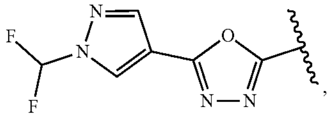
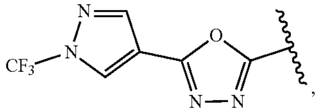
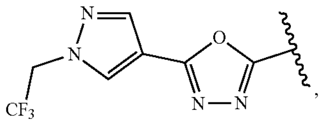
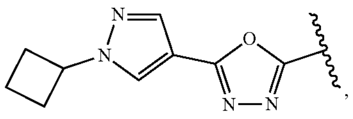
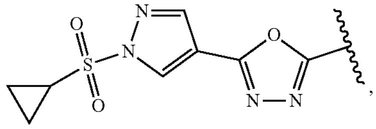
-continued
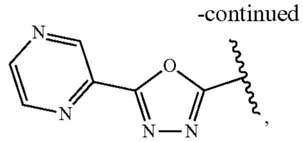
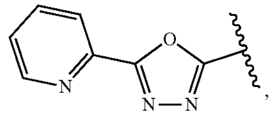
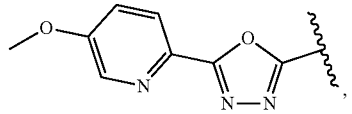
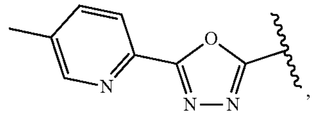
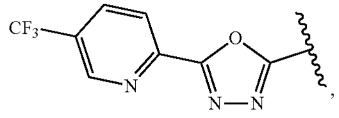
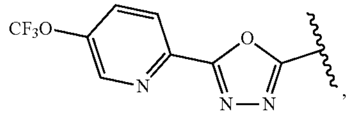
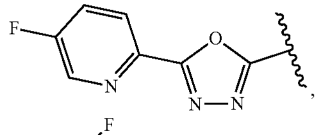
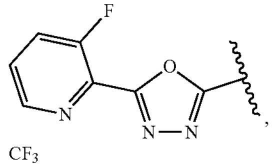
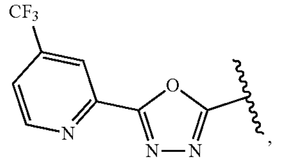
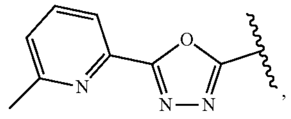
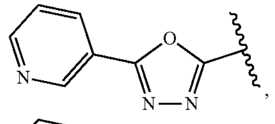
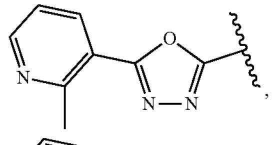
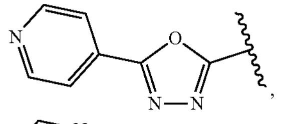
or
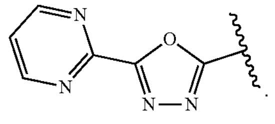

In yet other embodiments, $R^2$ is
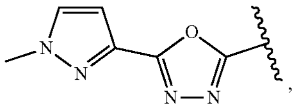
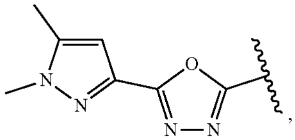
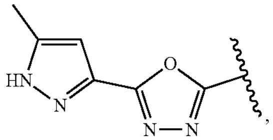
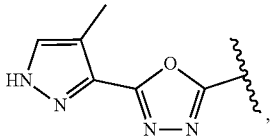
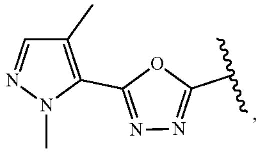
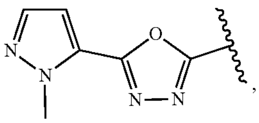
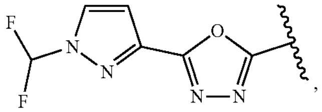
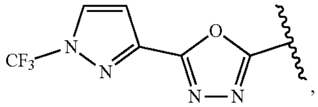
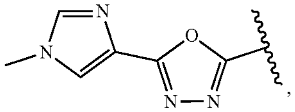
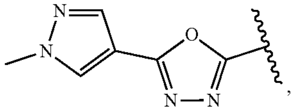
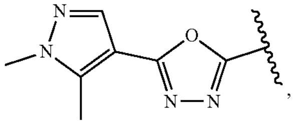
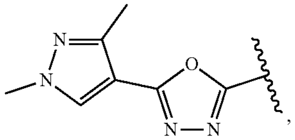
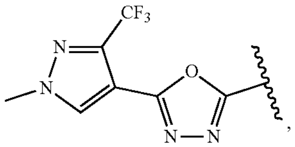
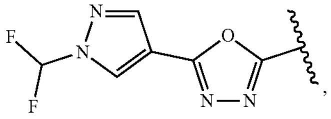
-continued
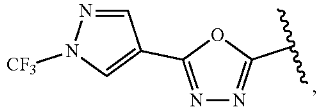
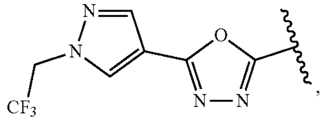
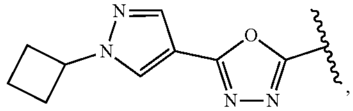
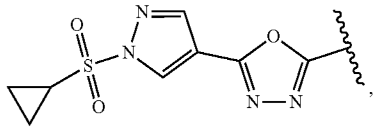
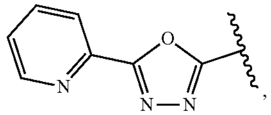
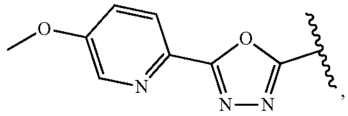
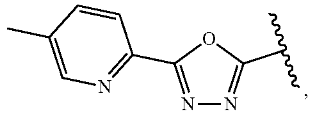
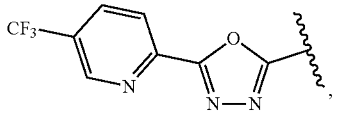
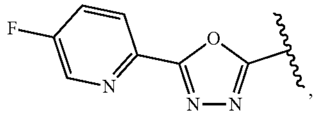
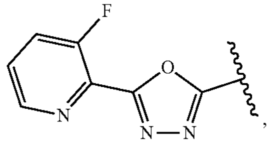
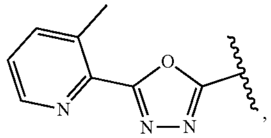
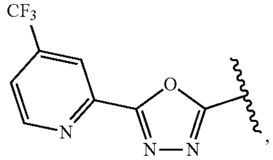
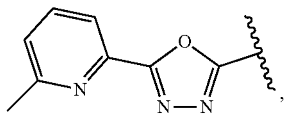
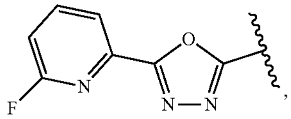

-continued
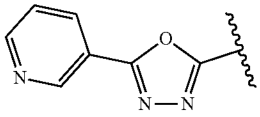
,
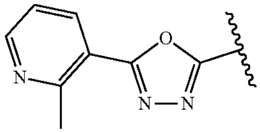
,
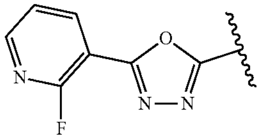
,
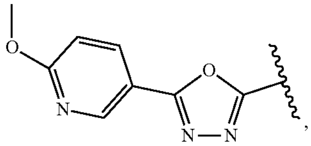
,
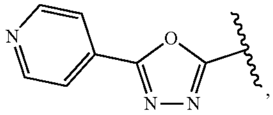
,
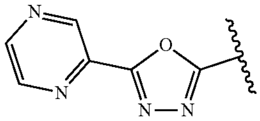
,
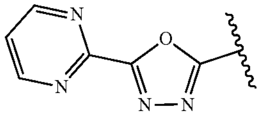
,
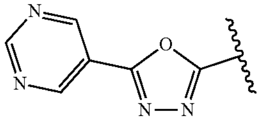
,
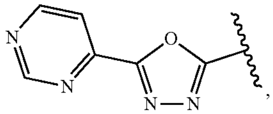
, or
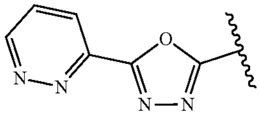
.
In other embodiments, $R^2$ is
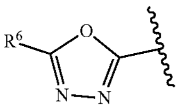
wherein $R^6$ is optionally substituted aryl. In still other embodiments, $R^2$ is
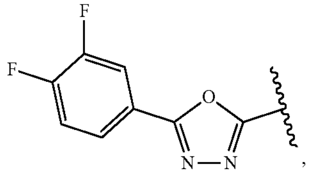
,
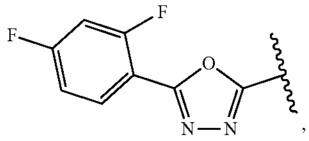
,
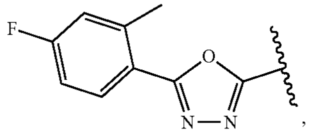
,
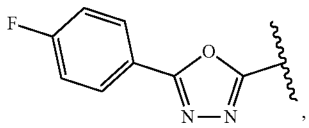
, or
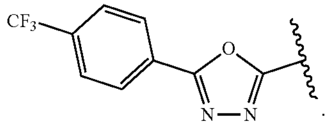
.
In further embodiments, $R^2$ is
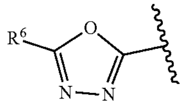
wherein $R^6$ is $C_{1-6}$alkyl, $C_{1-6}$ haloalkyl, or $C_{1-6}$hydroxyalkyl. In still further embodiments, $R^2$ is
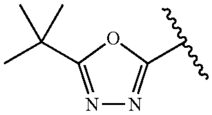
,
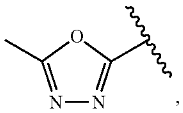
,
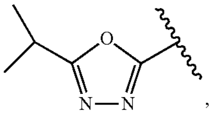
,
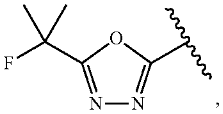
,
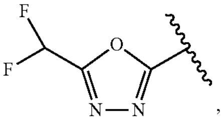
,
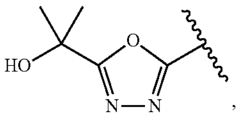
, or
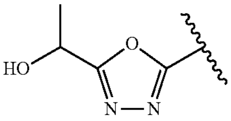
.

In yet other embodiments, $R^2$ is

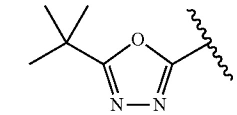, 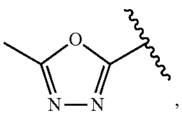, 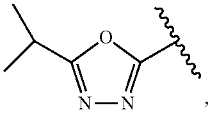, 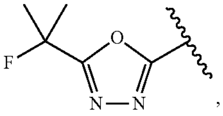, 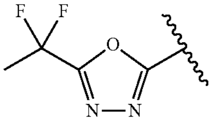, 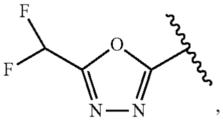, 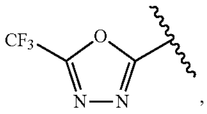, or 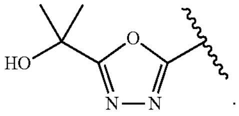.

In other embodiments, $R^2$ is

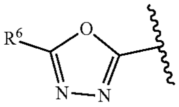

wherein $R^6$ is optionally substituted $C_{3-8}$cycloalkyl. In yet other embodiments, $R^2$ is

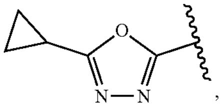, 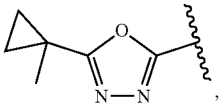, 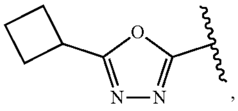, or 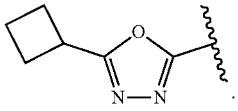.

In yet other embodiments, $R^2$ is

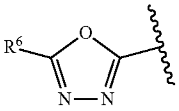

wherein $R^4$ is $C(O)NR^{y2}R^{z2}$ or $(CR^vR^x)_pNR^yR^z$ and $R^{y2}$, $R^{z2}$, p, $R^v$, $R^x$, $R^y$, and $R^z$ are defined herein. In other embodiments, $R^2$ is

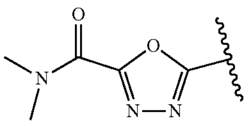 or

-continued

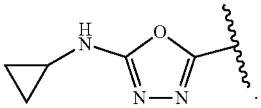.

In other embodiments, $R^2$ is

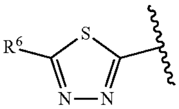

wherein $R^6$ is H, $C_{1-6}$alkyl, or optionally substituted aryl. In still other embodiments, $R^2$ is

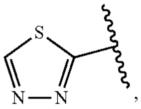, 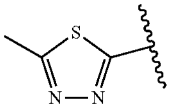, or 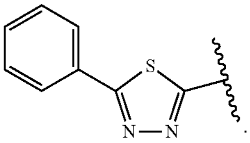.

In yet other embodiments, $R^2$ is

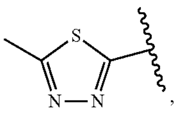, 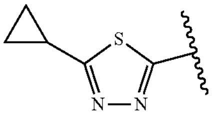, 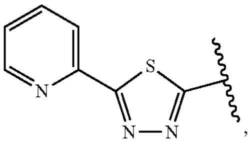, 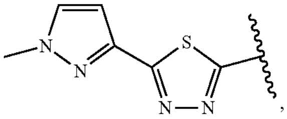, or 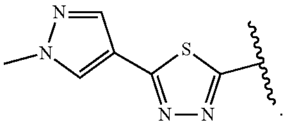.

In further embodiments, $R^2$ is

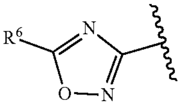 or 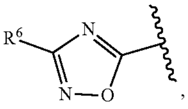, wherein $R^6$ is $C_{1-6}$hydroxyalkyl. In yet further embodiments, $R^2$ is
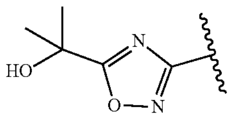
or
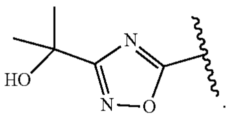
In other embodiments, $R^2$ is
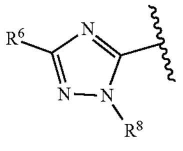
wherein $R^6$ is $C_{1-6}$alkyl and $R^6$ is defined herein. In still other embodiments, $R^2$ is
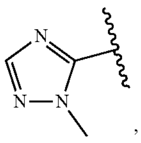
,
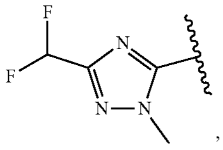
,
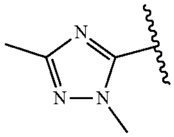
,
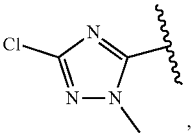
,
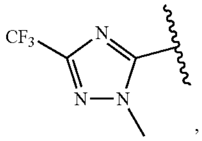
, or
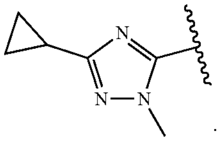
In further embodiments, $R^2$ is
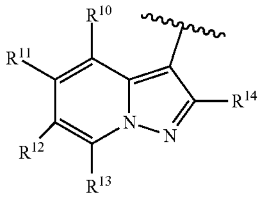
wherein $R^{10}$-$R^{14}$ are defined herein. In still further embodiments, $R^2$ is
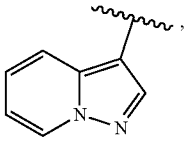
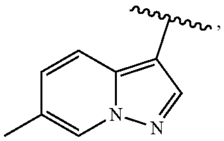
-continued
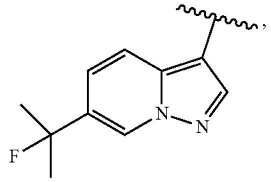
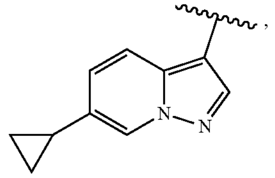
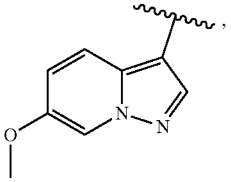
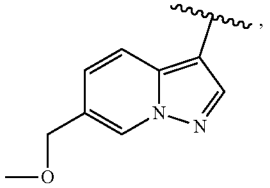
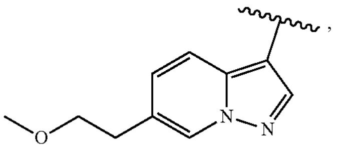
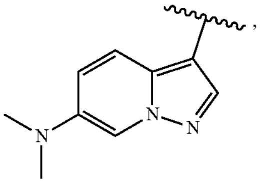
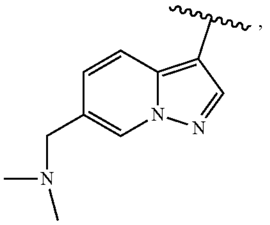
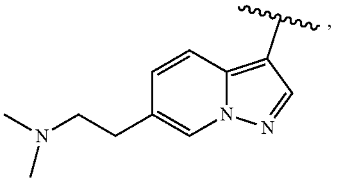
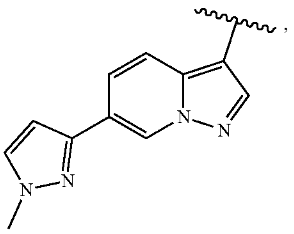

-continued
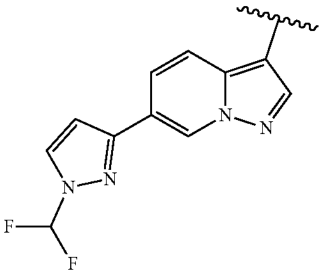
,
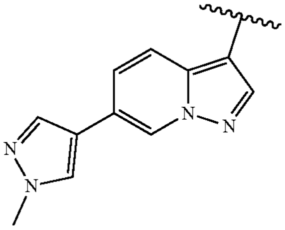
,
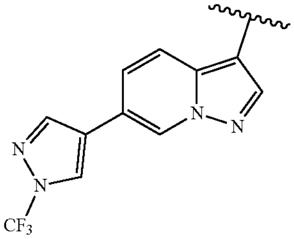
,
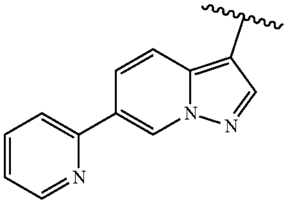
,
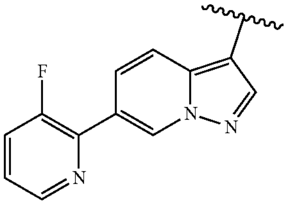
,
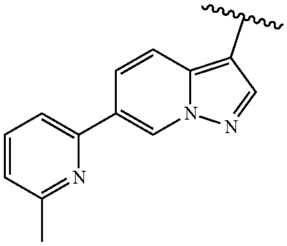
,
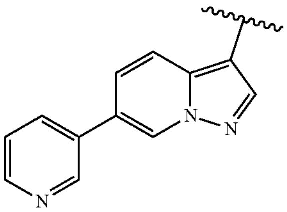
,
-continued
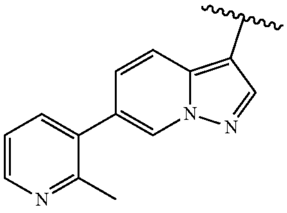
,
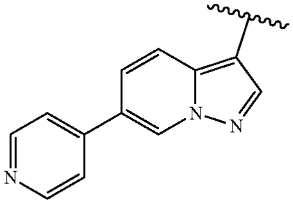
,
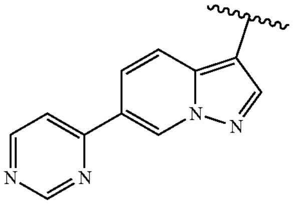
,
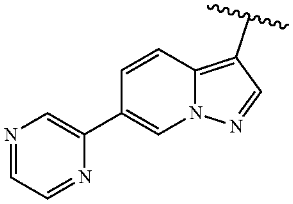
,
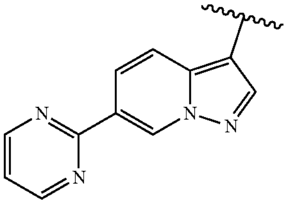
,
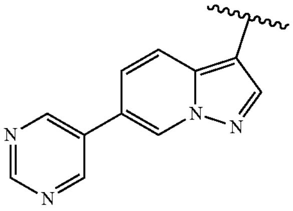
,
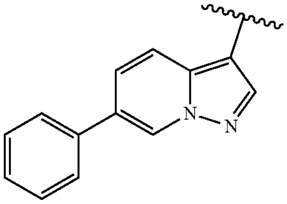
,
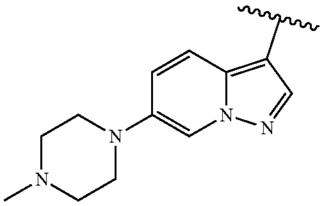
, -continued
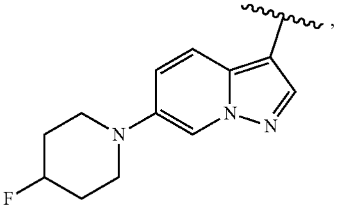
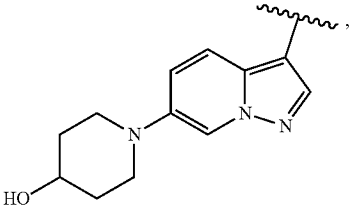
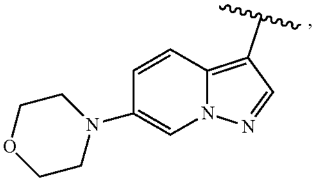
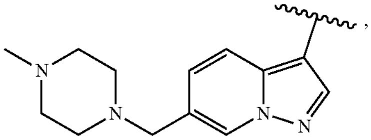
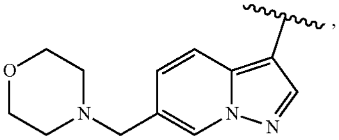
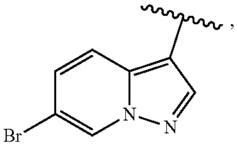
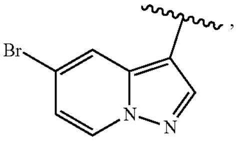
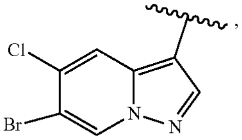
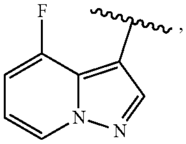
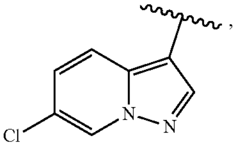
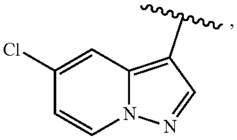
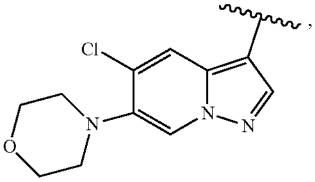
or
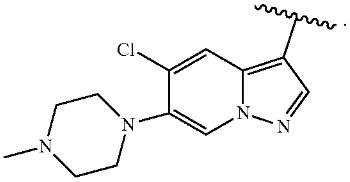
In yet other embodiments, $R^2$ is
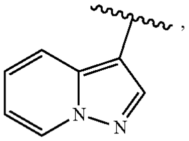
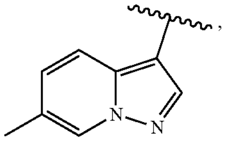
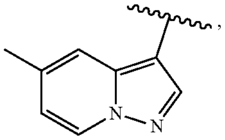
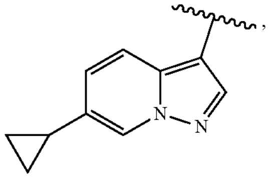
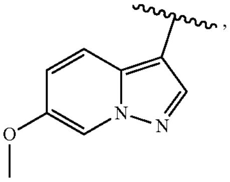
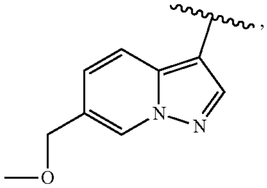
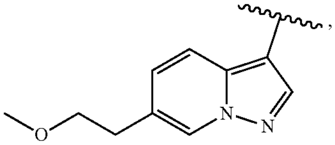
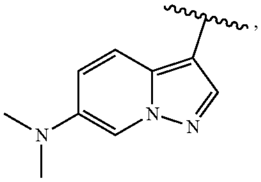
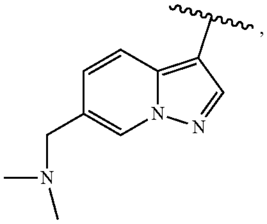
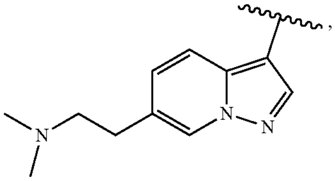
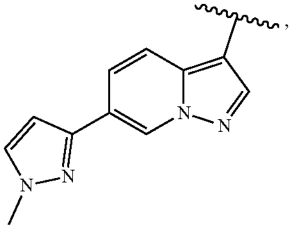
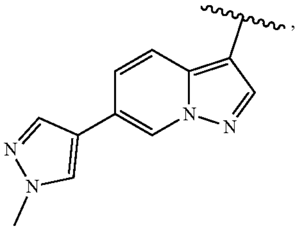

-continued

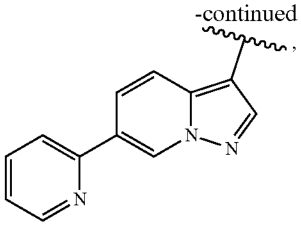

, or

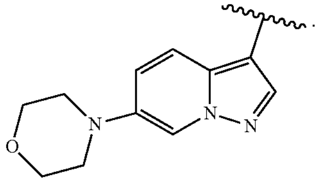

.

In other embodiments, $R^2$ is

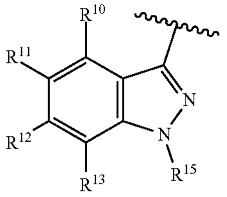

wherein $R^{13}$ is H and $R^{10}$, $R^{11}$, $R^{12}$, $R^{13}$, and $R^{14}$ are defined herein. In yet other embodiments, $R^2$ is

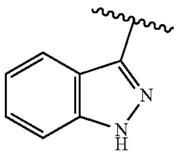

or

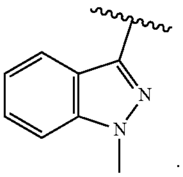

.

In some embodiments, the compound of Formula I is of Formula I-A or a pharmaceutically acceptable salt thereof:

I-A

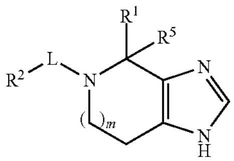

such as

I-A-1

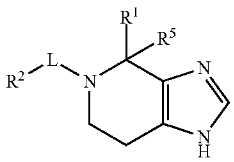

or

I-A-2

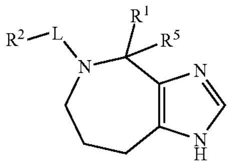

wherein $R^1$, $R^2$, $R^5$, L, and m are defined herein. In other embodiments, the compound is

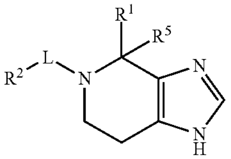

I-A-1 or a pharmaceutically acceptable salt thereof. In other embodiments, the compound is

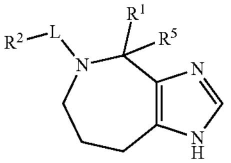

I-A-2 or a pharmaceutically acceptable salt thereof.

In other embodiments, the compound of Formula I is of Formula I-B or a pharmaceutically acceptable salt thereof:

I-B

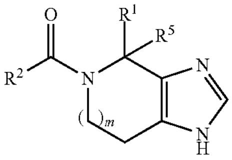

such as

I-B-1

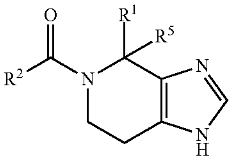

or

I-B-2

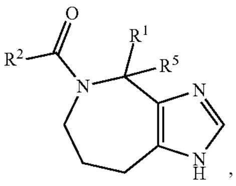

, wherein $R^1$, $R^2$, $R^5$, and m are defined herein. In further embodiments, the compound is

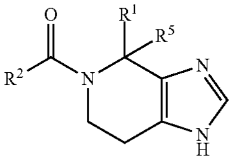

B-1 or a pharmaceutically acceptable salt thereof. In other embodiments, the compound is

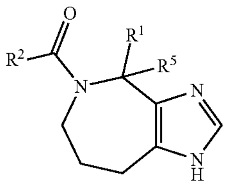

I-B-2 or a pharmaceutically acceptable salt thereof.

In further embodiments, the compound of Formula I is of Formula I-C or a pharmaceutically acceptable salt thereof:

I-C

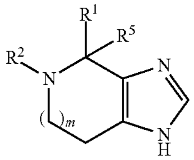

such as

I-C-1

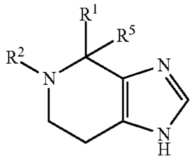

or

I-C-2

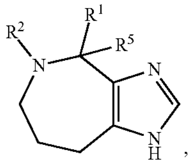

, wherein $R^1$, $R^2$, $R^5$, and m are defined herein. In other embodiments, the compound is

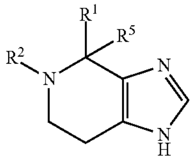

I-C-1 or a pharmaceutically acceptable salt thereof. In other embodiments, the compound is

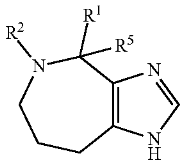

I-C-2 or a pharmaceutically acceptable salt thereof.

In still other embodiments, the compound of Formula I is of Formula I-D or a pharmaceutically acceptable salt thereof:

I-D

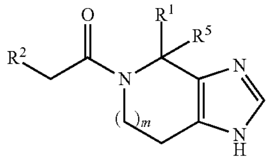

such as

I-D-1

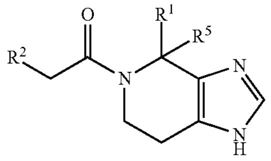

or

I-D-2

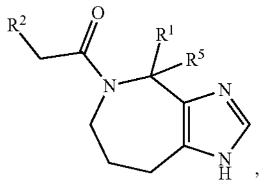

, wherein $R^1$, $R^2$, $R^5$, and m are defined herein. In some embodiments, the compound is

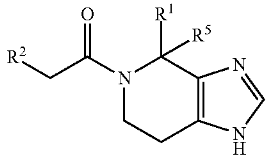

I-D-1 or a pharmaceutically acceptable salt thereof. In other embodiments, the compound is

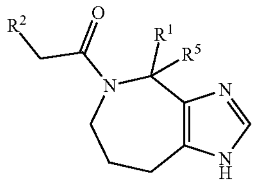

I-D-2 or a pharmaceutically acceptable salt thereof.

In still further embodiments, the compound of Formula I is of Formula I-E or a pharmaceutically acceptable salt thereof:

I-E

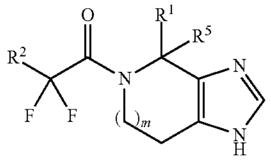

such as

-continued

I-E-1

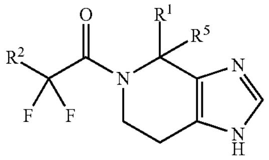

or

I-E-2

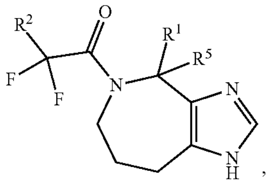

, wherein $R^1$, $R^2$, $R^5$, and m are defined herein. In other embodiments, the compound is

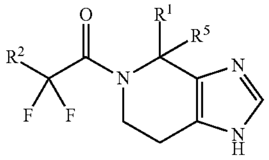

I-E-1 or a pharmaceutically acceptable salt thereof. In other embodiments, the compound is

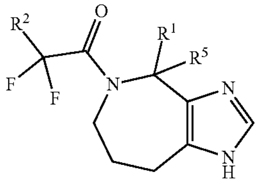

I-E-2 or a pharmaceutically acceptable salt thereof.

In other embodiments, the compound of Formula I is of Formula I-F or a pharmaceutically acceptable salt thereof:

I-F

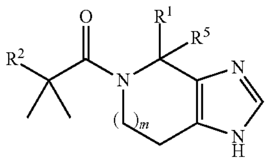

such as

I-F-1

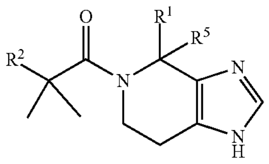

or

-continued

I-F-2

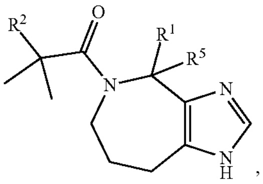

, wherein $R^1$, $R^2$, $R^5$, and m are defined herein. In yet other embodiments, the compound is

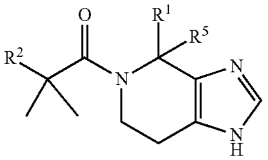

I-F-1 or a pharmaceutically acceptable salt thereof. In other embodiments, the compound is

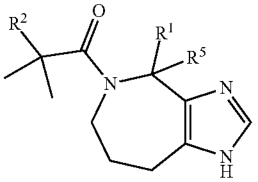

I-F-2 or a pharmaceutically acceptable salt thereof.

In further embodiments, the compound of Formula I is of Formula I-G or a pharmaceutically acceptable salt thereof:

I-G

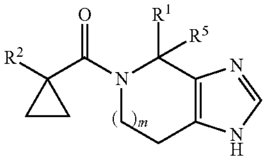

such as

I-G-1

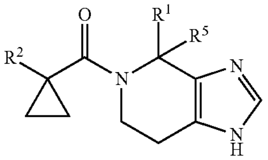

or

I-G-2

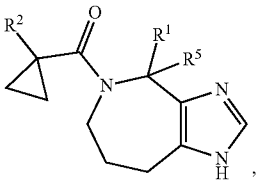

, wherein $R^1$, $R^2$, $R^5$, and m are defined herein. In still further embodiments, the compound is

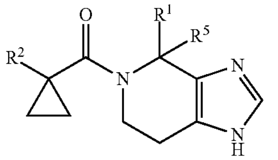

I-G-1 or a pharmaceutically acceptable salt thereof. In other embodiments, the compound is

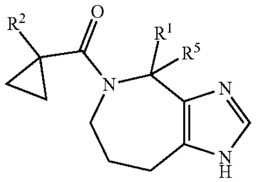

I-G-2 or a pharmaceutically acceptable salt thereof.

In yet other embodiments, the compound of Formula I is of Formula I-H or a pharmaceutically acceptable salt thereof:

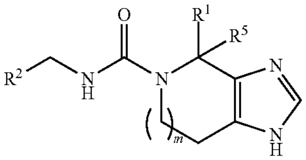

I-H such as

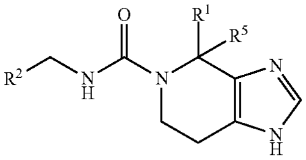

I-H-1 or

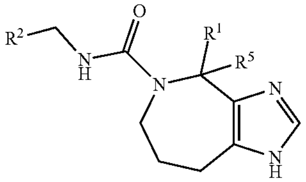

I-H-2, wherein $R^1$, $R^2$, $R^5$, and m are defined herein. In other embodiments, the compound is

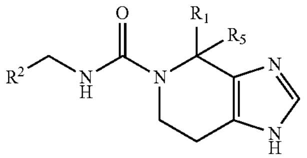

I-H-1 or a pharmaceutically acceptable salt thereof. In other embodiments, the compound is

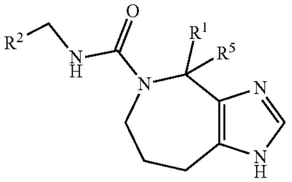

I-H-2 or a pharmaceutically acceptable salt thereof.

In still further embodiments, the compound of Formula I is of Formula I-I or a pharmaceutically acceptable salt thereof:

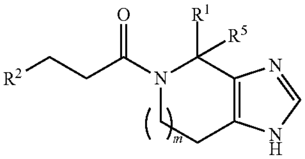

I-I such as

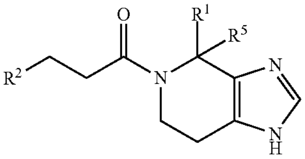

I-I-1 or

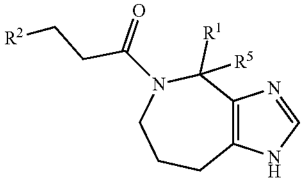

I-1-2, wherein $R^1$, $R^2$, $R^5$, and m are defined herein. In other embodiments, the compound is

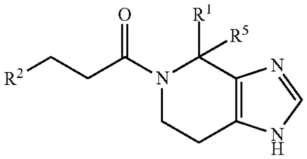

I-1-1 or a pharmaceutically acceptable salt thereof. In other embodiments, the compound is

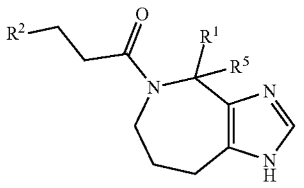

I-I-2

I-I-2or a pharmaceutically acceptable salt thereof.

In other embodiments, the compound of Formula I is of Formula I-J or a pharmaceutically acceptable salt thereof:

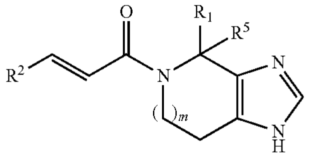

I-J such as

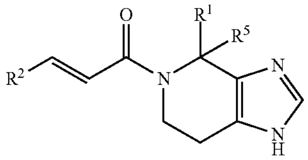

I-J-1 or

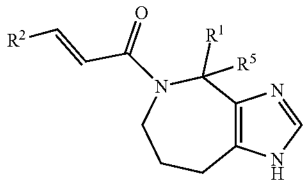

I-J-2, wherein $R^1$, $R^2$, $R^5$, and m are defined herein. In yet other embodiments, the compound is

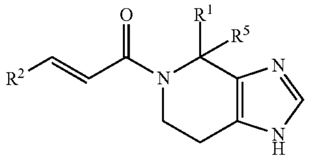

I-J-1 or a pharmaceutically acceptable salt thereof. In other embodiments, the compound is

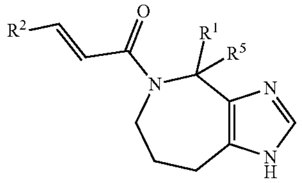

I-J-2 or a pharmaceutically acceptable salt thereof.

In further embodiments, the compound of Formula I is of Formula I-K or a pharmaceutically acceptable salt thereof:

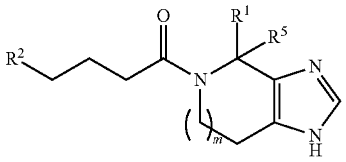

I-K such as

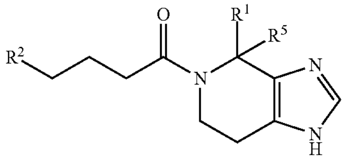

I-K-1 or

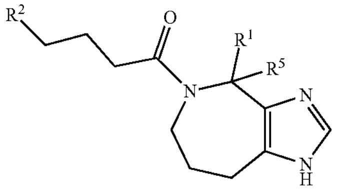

I-K-2, wherein $R^1$, $R^2$, $R^5$, and m are defined herein. In other embodiments, the compound is

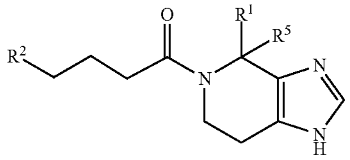

I-K-1 or a pharmaceutically acceptable salt thereof. In other embodiments, the compound is

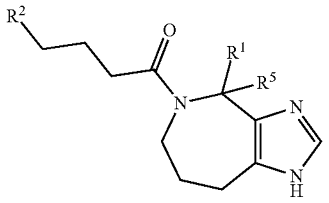

I-K-2 or a pharmaceutically acceptable salt thereof.

In still other embodiments, the compound of Formula I is of Formula I-L or a pharmaceutically acceptable salt thereof:

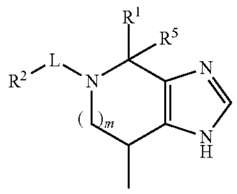

I-L, wherein $R^1$, $R^2$, $R^5$, L, and m are defined herein. In further embodiments, the compound is

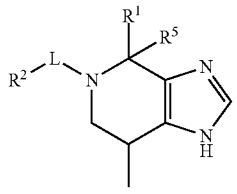

I-L-1, or a pharmaceutically acceptable salt thereof.

In yet further embodiments, the compound of Formula I is of Formula I-M or a pharmaceutically acceptable salt thereof:

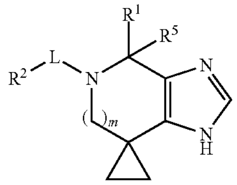

I-M, wherein $R^1$, $R^2$, $R^5$, L, and m are defined herein. In other embodiments, the compound is

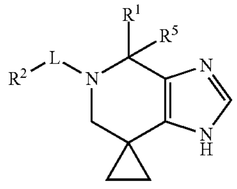

I-M-1 or a pharmaceutically acceptable salt thereof.

In some embodiments, compounds of the disclosure are any one or more of the compounds of Table 1, and their pharmaceutically acceptable salts and/or isotopologues. Compounds having the Formula I are further disclosed in the Exemplification and are included in the present disclosure. Pharmaceutically acceptable salts thereof as well as the neutral forms are included.

The disclosure further provides R-enantiomers, S-enantiomers, or racemic mixtures of any of the compounds described herein. In some embodiments, the compound is an S-enantiomer. In other embodiments, the compound is the R-enantiomer. In further embodiments, the compound is racemic.

In another embodiment, the compounds of the disclosure may be enantiomerically enriched, e.g., the enantiomeric excess or "ee" of the compound is greater than about 5% as measured by chiral HPLC. In some embodiments, the ee is greater than about 10%. In other embodiments, the ee is greater than about 20%. In further embodiments, the ee is greater than about 30%. In yet other embodiments, the ee is greater than about 40%. In still further embodiments, the ee is greater than about 50%. In other embodiments, the ee is greater than about 60%. In further embodiments, the ee is greater than about 70%. In still other embodiments, the ee is greater than about 80%. In yet further embodiments, the ee is greater than about 85%. In other embodiments, the ee is greater than about 90%. In further embodiments, the ee is greater than about 91%. In yet other embodiments, the ee is greater than about 92%. In still further embodiments, the ee is greater than about 93%. In other embodiments, the ee is greater than about 94%. In further embodiments, the ee is greater than about 95%. In still other embodiments, the ee is greater than about 96%. In yet further embodiments, the ee is greater than about 97%. In other embodiments, the ee is greater than about 98%. In further embodiments, the ee is greater than about 99%.

The present disclosure encompasses the preparation and use of salts of compounds of the disclosure. Salts of compounds of the disclosure can be prepared during the final isolation and purification of the compounds or separately by reacting the compound with an acid or base as appropriate.

Treatment Methods

Compounds of the disclosure have several uses as described herein. In some embodiments, compounds of the disclosure are useful in methods for stabilizing mutant PAH proteins. These methods comprise contacting the protein with one or more compounds described herein or a pharmaceutically acceptable salt thereof. The compounds of the disclosure can provide for better Phe control for patients whose disease is not well-managed on diet alone and lessen the severity of a patient's phenylketonuria. Thus, patients administered a compound of the disclosure will have a better quality of life, e.g., a more normal lifestyle and/or none or fewer dietary restrictions, as compared with phenylketonuria patients who have not been administered a compound of the disclosure. In some embodiments, patients administered a compound of the disclosure may experience increases in executive function, decreases in anxiety symptoms, and/or decreases in attention deficit hyperactivity disorder symptoms.

The term "mutant PAH gene" as used herein refers to the full DNA sequence of PAH that differs in one or more ways from the canonically accepted sequence ("the basis gene") that is published in any one of a variety of curated databases. As one example, the sequence described by GenBank Accession number NG_008690.2 describes the basis gene.

The term "mutant PAH protein" as used herein refers to a PAH protein that contains at least one mutation in the amino acid sequence relative to that encoded by the reference. The reference human PAH protein is described by Genbank Accession number NP_000268 and contains 452 amino acids. PAH protein mutations can be identified using methods known in the art. In some embodiments, the mutant PAH protein contains at least one R408W, R261Q, R243Q, Y414C, L48S, A403V, I65T, R241C, L348V, R408Q, or V388M mutation. In other embodiments, the mutant PAH protein contains at least one R408W, Y414C, I65T, F39L, R408Q, L348V, R261Q, A300S, or L48S mutation. In still other embodiments, the mutant PAH protein contains at least one R408W, R243Q, R408Q, V388M, or L348V mutation. In yet other embodiments, the mutant PAH protein contains at least one R408W mutation. In further embodiments, the mutant PAH protein contains at least two R408W mutations. In further embodiments, the mutant PAH protein contains at least one R261Q mutation. In yet other embodiments, the mutant PAH protein contains at least one R243Q mutation. In yet other embodiments, the mutant PAH protein contains at least one Y414C mutation. In still further embodiments, the mutant PAH protein contains at least one L48S mutation. In other embodiments, the mutant PAH protein contains at least one A403V mutation. In further embodiments, the mutant PAH protein contains at least one I65T mutation. In yet further embodiments, the mutant PAH protein contains at least one R241C mutation. In yet other embodiments, the mutant PAH protein contains at least one L348V mutation. In further embodiments, the mutant PAH protein contains at least one R408Q mutation. In other embodiments, the mutant PAH protein contains at least one V388M mutation. In other embodiments, the mutant PAH protein contains at least one F39L mutation. In still further embodiments, the mutant PAH protein contains at least one A300S mutation. In yet further embodiments, the mutant PAH protein contains at least one L48S mutation.

In other embodiments, the disclosure provides methods for stabilizing the activity of mutant phenylalanine hydroxylase (PAH) proteins as compared to wild type PAH. Such methods include contacting phenylalanine hydroxylase with one or more compounds described herein, or a pharmaceutically acceptable salt thereof. The term "stabilizing" as used herein refers to modulating the activity or quantity of a PAH enzyme so that it catalyzes hydroxylation of the aromatic side-chain of phenylalanine at a rate that is more similar to the PAH catalysis rate of a control population having wild type PAH, i.e., without a mutant PAH gene mutation, as compared to the baseline PAH catalysis rate. In some aspects, the term "stabilizing" refers to modulating the activity of a subject's PAH so that it catalyzes hydroxylation of the aromatic side-chain of phenylalanine at a flux more similar to the PAH catalytic flux of a control subject population without a mutant PAH gene mutation. In some embodiments, "stabilizing" activity of PAH includes increasing levels of the enzyme PAH as compared to baseline. By increasing the buildup of stabilized active PAH protein, a subject's toxic Phe levels can be reduced as compared to the subject's baseline levels of dietary Phe prior to administration of a compound of the disclosure or a pharmaceutical composition comprising compounds of the disclosure.

In some embodiments, the disclosure provides methods for reducing blood phenylalanine concentrations in a subject suffering from phenylketonuria to a concentration less than or equal to about 600 μM. In other embodiments, the blood Phe concentration is reduced to a concentration less than or equal to about 360 μM. In other embodiments, the disclosure provides methods for reducing blood Phe concentrations as compared to untreated baseline. In some embodiments, a subject's blood Phe concentration as compared to untreated baseline is reduced by a percentage including but not limited at least about 10%, at least about 20%, at least about 30%, at least about 40%, at least about 50%, at least about 60%, at least about 70%, at least about 80%, or at least about 90%. In other embodiments, a subject's blood Phe concentration as compared to untreated baseline is reduced by at least about 10%. In further embodiments, a subject's blood Phe concentration as compared to untreated baseline is reduced by at least about 20%. In yet other embodiments, a subject's blood Phe concentration as compared to untreated baseline is reduced by at least about 30%. In still further embodiments, a subject's blood Phe concentration as compared to untreated baseline is reduced by at least about 40%. In other embodiments, a subject's blood Phe concentration as compared to untreated baseline is reduced by at least about 50%. In further embodiments, a subject's blood Phe concentration as compared to untreated baseline is reduced by at least about 60%. In yet other embodiments, a subject's blood Phe concentration as compared to untreated baseline is reduced by at least about 70%. In still further embodiments, a subject's blood Phe concentration as compared to untreated baseline is reduced by at least about 80%. In other embodiments, a subject's blood Phe concentration as compared to untreated baseline is reduced by at least about 90%. A subject's Phe concentration can be determined by blood tests and methods for measuring such levels are known in the art. In some embodiments, the reduction in Phe concentration achieved using compounds of the disclosure is obtained in conjunction with the subject actively managing their dietary Phe intake. In other embodiments, the reduction in Phe concentration is obtained in conjunction with the subject maintaining a Phe-restricted diet.

In some embodiments, a subject is treated with compounds of the disclosure, or a pharmaceutical composition comprising compounds of the disclosure. The compound is administered in an amount sufficient for stabilizing the PAH protein, or for reducing blood phenylalanine concentration in a subject, or combinations thereof in the subject.

In further embodiments, the subject is a human patient, such as a human adult over 18 years old in need of treatment. In yet further embodiments, the human patient is a human child less than 18 years old. In still further embodiments, the human patient is a human child between 12 years and 18 years old. In yet other embodiments, the human patient is a human child less than 12 years old. In any of the embodiments, the subject has phenylketonuria (PKU), optionally classic PKU or severe PKU. In some embodiments, the subject has a blood Phe concentration greater than about 600 μM prior to administration of a compound of the disclosure or a pharmaceutical composition comprising compounds of the disclosure. In other embodiments, the subject's blood Phe concentration prior to administration is greater than about 700 μM. In further embodiments, the subject's blood Phe concentration prior to administration is greater than about 800 μM. In still further embodiments, the subject's blood Phe concentration prior to administration is greater than about 900 μM. In yet other embodiments, the subject's blood Phe concentration prior to administration is greater than about 1000 μM. In further embodiments, the subject's blood Phe concentration prior to administration is greater than about 1100 μM. In other embodiments, the subject's blood Phe concentration prior to administration is greater than about 1200 μM.

The present methods also encompass administering an additional therapeutic agent to the subject in addition to the compounds of the disclosure. In some embodiments, the additional therapeutic agent is selected from drugs known as useful in a stabilizing mutant PAH protein and/or reducing blood Phe concentrations. The additional therapeutic agent is different from the compounds of the disclosure. In some embodiments, the additional therapeutic agent is sapropterin or sepiapterin. In other embodiments, the additional therapeutic agent is a nutritional supplement. Nutritional supplements that may be used include those that contain amino acids and other nutrients. In further embodiments, the nutritional supplement contains large neutral amino acids such as leucine, tyrosine, tryptophan, methionine, histidine, isoleucine, valine, threonine. In other embodiments, the nutritional supplement contains tyrosine. In further embodiments, the nutritional supplement contains casein glycomacropeptide, i.e., a milk peptide naturally free of Phe in its pure form. In other embodiments, the additional therapeutic agent is an enzyme substrate or enzyme co-factor. In yet other embodiments, the enzyme substrate or co-factor is tetrahydrobiopterin. In other embodiments, the additional therapeutic agent is a biopterin analogue. In further embodiments, the additional therapeutic agent is a biotherapeutic, synthetic biotic, microbiota or probiotic. In yet other embodiments, the biotherapeutic, synthetic biotic, microbiota or probiotic contains a genetically modified phenylalanine ammonia lyase (PAL) gene, such as, for example, *E. coli* Nissle PAL. Examples of genetically modified *E. coli* Nissle PAL biotherapeutics include SYNB1934 and SYNB1618, and the like. In still further embodiments, the additional therapeutic agent is an inhibitor of an amino acid transporter. In some embodiments, the amino acid transporter is $B^0$ AT1 (also referred to as SLC6A19), and the additional therapeutic agent is a SLC6A19 inhibitor. Examples of SLC6A19 inhibitors include nimesulide, benztropine, NSC63912, NSC22789, cinromide, CB3, E62, JNT-517, and the like.

Compounds of the disclosure and the additional therapeutic agents can be administered simultaneously or sequentially to achieve the desired effect. In addition, the compounds of the disclosure and additional therapeutic agent can be administered in a single composition or two separate compositions.

The additional therapeutic agent is administered in an amount to provide its desired therapeutic effect. The effective dosage range for each additional therapeutic agent is known in the art, and the additional therapeutic agent is administered to an individual in need thereof within such established ranges.

Compounds of the disclosure and the additional therapeutic agents can be administered together as a single-unit dose or separately as multi-unit doses, wherein the compounds of the disclosure are administered before the additional therapeutic agent or vice versa. One or more doses of the compounds of the disclosure and/or one or more dose of the additional therapeutic agents can be administered.

The compounds of the disclosure may also be administered sequentially or concurrently with non-pharmacological techniques. In some embodiments, the patient uses non-pharmacological techniques to maintain lower Phe levels. In other embodiments, the non-pharmacological technique is administering a diet that is low in Phe. One skilled in the art would be able to determine what type of diet to maintain appropriate levels of Phe. In some embodiments, a phenylamine diet containing about 200 to about 500 mg/day (patients 10 years or younger) of Phe or less than about 600 mg/day (patients over 10 years of age). In other embodiments, the diet may include restricting or eliminating one or more foods that are high in Phe, such as soybeans, egg whites, shrimp, chicken breast, spirulina, watercress, fish, nuts, crayfish, lobster, tuna, turkey, legumes, and low-fat cottage cheese.

An example of a dose is in the range of from about 0.001 to about 100 mg of compound per kg of subject's body weight per day, in single or divided dosage units (e.g., BID, TID, QID). For a 70-kg human, a suitable dosage amount is from about 0.05 to about 7 g/day.

In some embodiments, the therapeutically effective amount of one or more compounds described herein is an amount that is effective in stabilizing a mutant PAH protein described herein. In other embodiments, the therapeutically effective amount of one or more compounds described herein is an amount that is effective in reducing blood phenylalanine concentrations.

Unless otherwise noted, the amounts of the compounds described herein are set forth on a free base basis. That is, the amounts indicate that amount of the compound administered, exclusive of, for example, solvent or counterions (such as in pharmaceutically acceptable salts).

Pharmaceutical Compostions

The disclosure also provides pharmaceutical compositions comprising compounds of the disclosure and a pharmaceutically acceptable carrier or excipient.

The methods of the present disclosure can be accomplished by administering compounds of the disclosure as the neat compound or as a pharmaceutical composition. Administration of a pharmaceutical composition, or neat compound of the disclosure, can be performed at any time period as determined by the attending physician. Typically, the pharmaceutical compositions contain no toxic, carcinogenic, or mutagenic compounds that would cause an adverse reaction when administered.

Pharmaceutical compositions include those wherein compounds of the disclosure are administered in an effective amount to achieve its intended purpose. The exact formulation, route of administration, and dosage is determined by an individual physician.

Compounds of the disclosure can be administered by any suitable route. e.g., by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high-pressure technique.

The above-mentioned additional therapeutically active agents, one or more of which can be used in combination with compounds of the disclosure, are prepared and administered as described in the art.

Compounds of the disclosure may be administered in admixture with pharmaceutical carriers selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of compounds of the disclosure.

Administration of the compounds or pharmaceutical compositions of the disclosure can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. The desired dose can be administered in a single dose, or as multiple doses administered at appropriate intervals, e.g., as one, two, three, four or more subdoses per day. In some embodiments, the compounds disclosed herein are effective over a wide dosage range. For example, in the treatment of adult humans, dosage forms containing from about 0.01 to 2000 mg of a compound disclosed herein per day are examples of dosage forms that may be used. The exact dosage will depend upon the route of administration, the form in which the compound is administered, the subject to be treated, the body weight of the subject to be treated, and the preference and experience of the attending physician. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, a compound of the disclosure is administered in a single dose.

Typically, such administration will be by a solid oral dosage form such as tablet or capsule. However, other routes may be used as appropriate. A single dose of a compound may also be used for treatment of an acute condition.

In some embodiments, a compound of the disclosure may be administered in multiple doses. Dosing may be about once, twice, three times, four times, five times, six times, or more than six times per day. In another embodiment, a compound described herein and another therapeutic agent are administered together about once per day to about 6 times per day. Administration of the compounds disclosed herein may continue as long as necessary. In some embodiments, a compound is administered chronically on an ongoing basis, e.g., for the treatment of chronic effects.

An effective amount of a compound of the disclosure may be administered in either single or multiple doses by any of the accepted modes of administration of therapeutic agents having similar utilities, including rectal, buccal, intranasal and transdermal routes, by intra-arterial injection, intravenously, intraperitoneally, parenterally, intramuscularly, subcutaneously, orally, topically, or as an inhalant.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include one or more conventional pharmaceutical carriers or excipients and a compound disclosed herein as an active ingredient. In addition, it may include other medicinal or pharmaceutical agents, carriers, adjuvants, etc.

Exemplary parenteral administration forms include solutions or suspensions of the compound of the disclosure in sterile aqueous solutions, for example, aqueous propylene glycol or dextrose solutions. Such dosage forms can be suitably buffered, if desired.

Pharmaceutical Compostions for Oral Administration

In some embodiments, the disclosure provides a pharmaceutical composition for oral administration containing a compound of the disclosure and pharmaceutical excipients suitable for oral administration.

In some embodiments, the disclosure provides a solid pharmaceutical composition for oral administration containing: (i) an effective amount of a compound of the disclosure; optionally (ii) an effective amount of a second therapeutic agent; and (iii) a pharmaceutical excipient suitable for oral administration. In some embodiments, the composition further contains: (iv) an effective amount of a third therapeutic agent.

In some embodiments, the pharmaceutical composition may be a pharmaceutical composition suitable for oral consumption. Pharmaceutical compositions containing a compound of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the compound of the disclosure into association with the carrier, which constitutes one or more necessary ingredients. In general, the compositions are prepared by uniformly and intimately admixing the compound of the disclosure with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This disclosure further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms containing a compound of the disclosure can be prepared using anhydrous or low moisture containing ingredients and low moisture or low humidity conditions. Pharmaceutical compositions and dosage forms containing a compound of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits.

Examples of suitable packaging include, but are not limited to, hermetically sealed foils, plastic or the like, unit dose containers, blister packs, and strip packs.

The compound of the disclosure can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, colloidal silicon dioxide, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the disclosure to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the disclosure include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 2 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical, and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof: polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-1000 succinate, PEG-24 cholesterol, polyglyceryl-10-oleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the disclosure and to minimize precipitation of the compound of the disclosure. This can be important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol (PEG), polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; polyethylene glycol 660 12-hydroxystearate; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, glycofurol, transcutol, propylene glycol, and dimethyl isosorbide. Particularly preferred solubilizers include sorbitol, glycerol, triacetin, ethyl alcohol, PEG having an average molecular weight of about 100 to about 8000 g/mole, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of less than about 10%, less than about 25%, less than about 50%, about 100%, or up to less than about 200% by weight, based on the combined weight of the drug, and other excipients. If desired, very small amounts of solubilizer may also be used, such as less than about 5%, less than about 2%, less than about 1% or even less. Typically, the solubilizer may be present in an amount of less than about 1% to about 100%, more typically less than about 5% to less than about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

Pharmaceutical Compositions for Injection

In some embodiments, the disclosure provides a pharmaceutical composition for injection containing a compound described herein and pharmaceutical excipients suitable for injection. Components and amounts of agents in the compositions are as described herein.

The forms in which the compositions of the disclosure may be incorporated for administration by injection include aqueous or oil suspensions or emulsions. Such compositions may comprise sesame oil, corn oil, cottonseed oil, peanut oil, elixirs containing mannitol or dextrose, sterile water, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Other Pharmaceutical Compositions

Pharmaceutical compositions may also be prepared from compositions described herein and one or more pharmaceutically acceptable excipients suitable for topical, sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2004; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Synthesis of Compounds of the Disclosure

Compounds of the disclosure can be prepared by methods described in the General Schemes, procedures, and Examples set forth within, and by related methods known in the art. For example, Compounds of Formula I can be prepared by the general methods shown in General Schemes 1-11.

General Scheme 1: Preparation of Compounds of Formula I

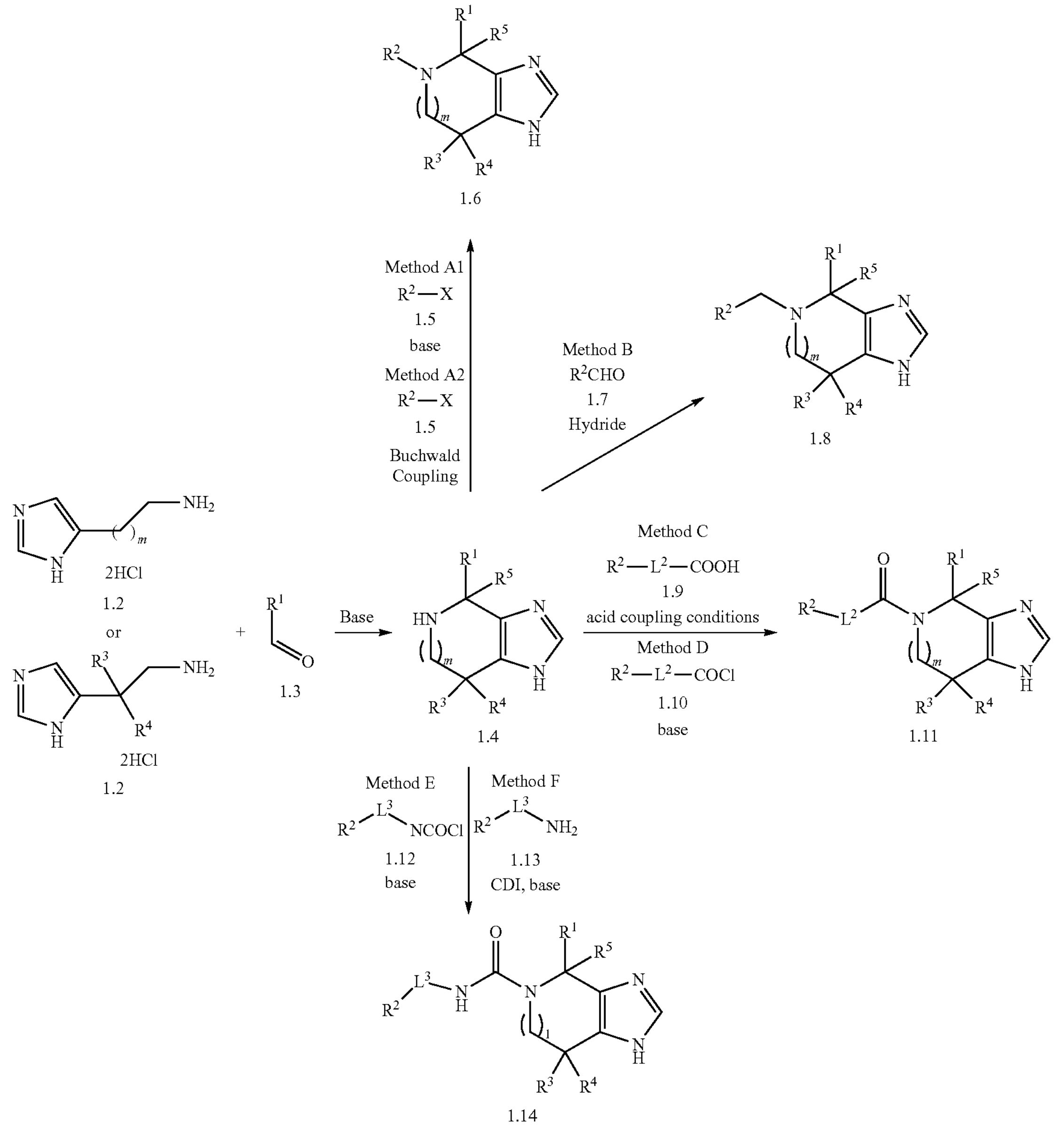

Compounds of Formula I were obtained through the reactions depicted in General Scheme 1. An amine of formulas 1.1 or 1.2 and an aldehyde of formula 1.3 were first reacted under Pictet-Spengler reaction conditions to afford the core amine of formula 1.4. To the extent that an imine by-product is formed during the Pictet-Spengler reaction, the imine by-product can be converted to the core amine of formula 1.4 by reaction with sodium borohydride in an alcoholic solvent (for example, methanol or ethanol). Various L and $R^2$ groups were then installed by using either a nucleophilic substitution reaction (Method A1), a Buchwald or other similar cross-coupling reaction (Method A2), a reductive animation reaction (Method B), or amide coupling reactions (Methods C, D, E, and F). Under Method A1, a $R^2$ aryl or heteroaryl halide of formula 1.5 (wherein X is Br, Cl, or F) is coupled to the core amine of formula 1.4 using a nucleophilic substitution reaction under basic conditions, such as DIPEA, to afford compounds of formula 1.6. Under Method A2, a $R^2$ aryl or heteroaryl halide of formula 1.5 (wherein X is Br, Cl, or I) is coupled to the core amine of formula 1.4 using Buchwald coupling or cross-coupling conditions known in the art, such as using a palladium catalyst (for example, CPhos-Pd-G3, $Pd(OAc)_2$, Pd(dppf) $Cl_2$), and a base such as $Cs_2CO_3$ to afford compounds of formula 1.6. Under Method B, a $R^2$ aryl or heteroaryl aldehyde of formula 1.7 is coupled to the core amine of formula 1.4 under reductive animation reaction conditions using a hydride such as sodium triacetoxyborohydride to afford compounds of formula 1.8. Under Method C, a $R^2$ carboxylic acid of formula 1.9 or a basic salt (i.e., Li, K, or Na) thereof is coupled to core amine of formula 1.4 using acid coupling conditions known in the art, such as using one of the following reagents—HOBt, EDCI, HATU, T3P—along with a base, such as DIPEA (Hunig's base), pyridine, or TEA, to afford compounds of formula 1.11, wherein $L^2$ is a bond, optionally substituted $C_{1-6}$alkylene, optionally substituted $C_{2-6}$alkenylene, or optionally substituted $C_{1-6}$haloalkylene. Alternatively, under Method D, a $R^2$ acid chloride of formula 1.10 is coupled to the core amine of formula 1.4 under basic conditions to afford compounds of formula 1.11, wherein $L^2$ is a bond, optionally $C_{1-6}$alkylene, optionally substituted $C_{2-6}$alkenylene, or optionally substituted $C_{1-6}$haloalkylene. Under Method E, a $R^2$ acid chloride of formula 1.12 is coupled to the core amine of formula 1.4 under basic conditions to afford compounds of formula 1.14, wherein $L^3$ is a bond or optionally substituted $C_{1-6}$alkylene. Under Method F, an $R^2$ amine of formula 1.13 is coupled to the core amine of formula 1.4 and carbonyldiimidazole under basic conditions to afford compounds of formula 1.14, wherein $L^3$ is a bond or optionally substituted $C_{1-6}$alkylene.

General Scheme 2: Preparation of Deuterated Core Amine Intermediates of Formula 2.2

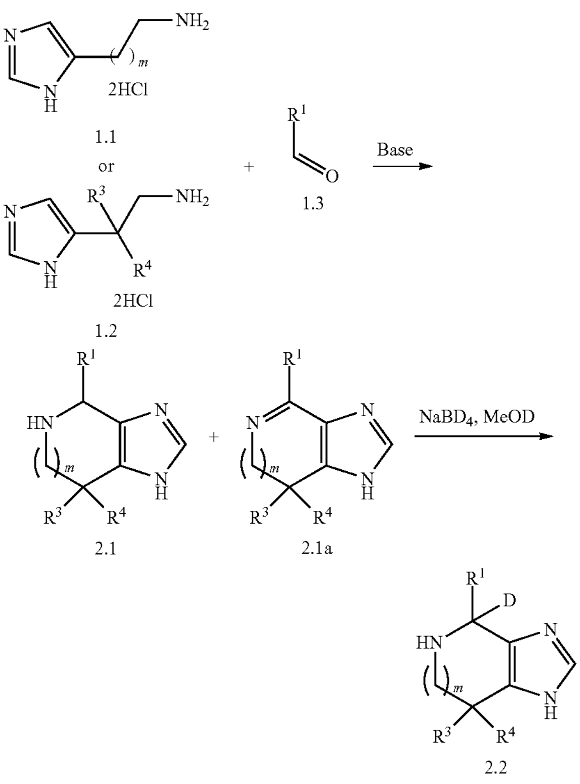

1.1
or
1.2
1.3
2.1
2.1a
2.2

Compounds of Formula I wherein $R^5$ is D are prepared in accordance with General Scheme 2. An amine of formula 1.1 or 1.2 and an aldehyde of formula 1.3 are reacted under Pictet-Spengler reaction conditions to afford compounds of formula 2.1 or mixtures of compounds of formula 2.1 and the imine by-product of formula 2.1a. Compounds of formula 2.1 or mixtures of compounds of formulas 2.1 and 2.1a are then reacted with sodium borodeuteride in deuterated methanol to afford deuterated core amine of formula 2.2. Deuterated core amine intermediates of formula 2.2 can then be further coupled to various L and $R^2$ groups via methods A, B, C, D, E, and F as described in General Scheme 1 to afford Compounds of Formula I, wherein $R^5$ is D.

General Scheme 3: Preparation of Oxazolyl $R^2$ Acid Intermediates

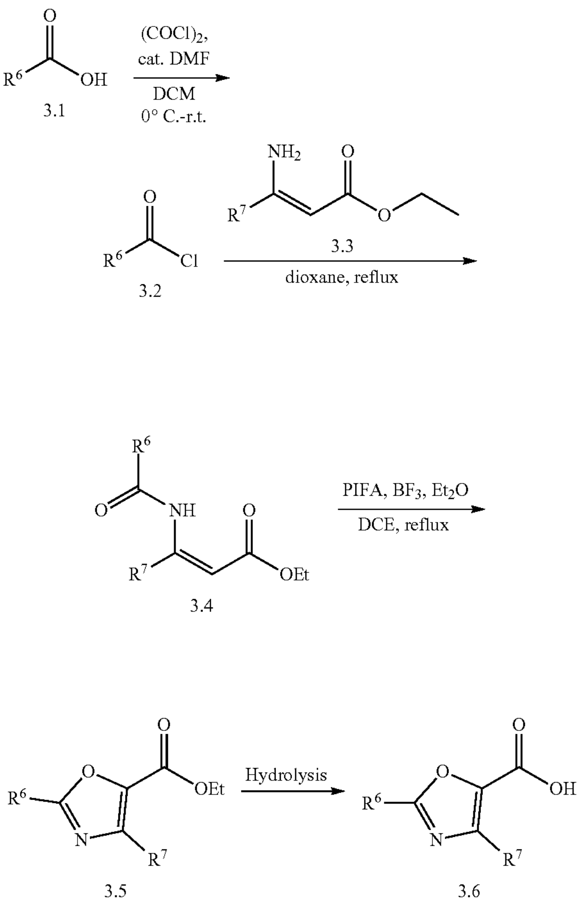

3.1
3.2
3.3
3.4
3.5
3.6

Oxazolyl $R^2$ carboxylic acid intermediates containing substitutions at the $R^6$ and/or $R^7$ positions were prepared in accordance with General Scheme 3. A carboxylic acid of formula 3.1 was reacted with oxalyl chloride and catalytic N,N-dimethylformamide to afford acid chloride of formula 3.2. Acid chloride of formula 3.2 was then reacted with an enamine of formula 3.3 to afford an enamide of formula 3.4. An enamide of formula 3.4 then underwent hypervalent iodine-mediated cyclization after reaction with [bis(trifluoroacetoxy)iodo]benzene and boron trifluoride diethyl etherate to afford oxazole of formula 3.5. Hydrolysis of the ester of the oxazole formula 3.5 with a base such as LiOH, KOH, or NaOH in THF/water afforded compounds of formula 3.6. Alternatively, the basic salt (i.e., Li, K, or Na) of the carboxylic acid of formula 3.6 may be obtained after the hydrolysis reaction by isolating the product at a basic pH. The carboxylic acid or basic salt thereof can then be used without further purification in the coupling reactions described in General Scheme 1, Method C.

General Scheme 4: Preparation of Oxazolyl $R^2$ Acid Intermediates

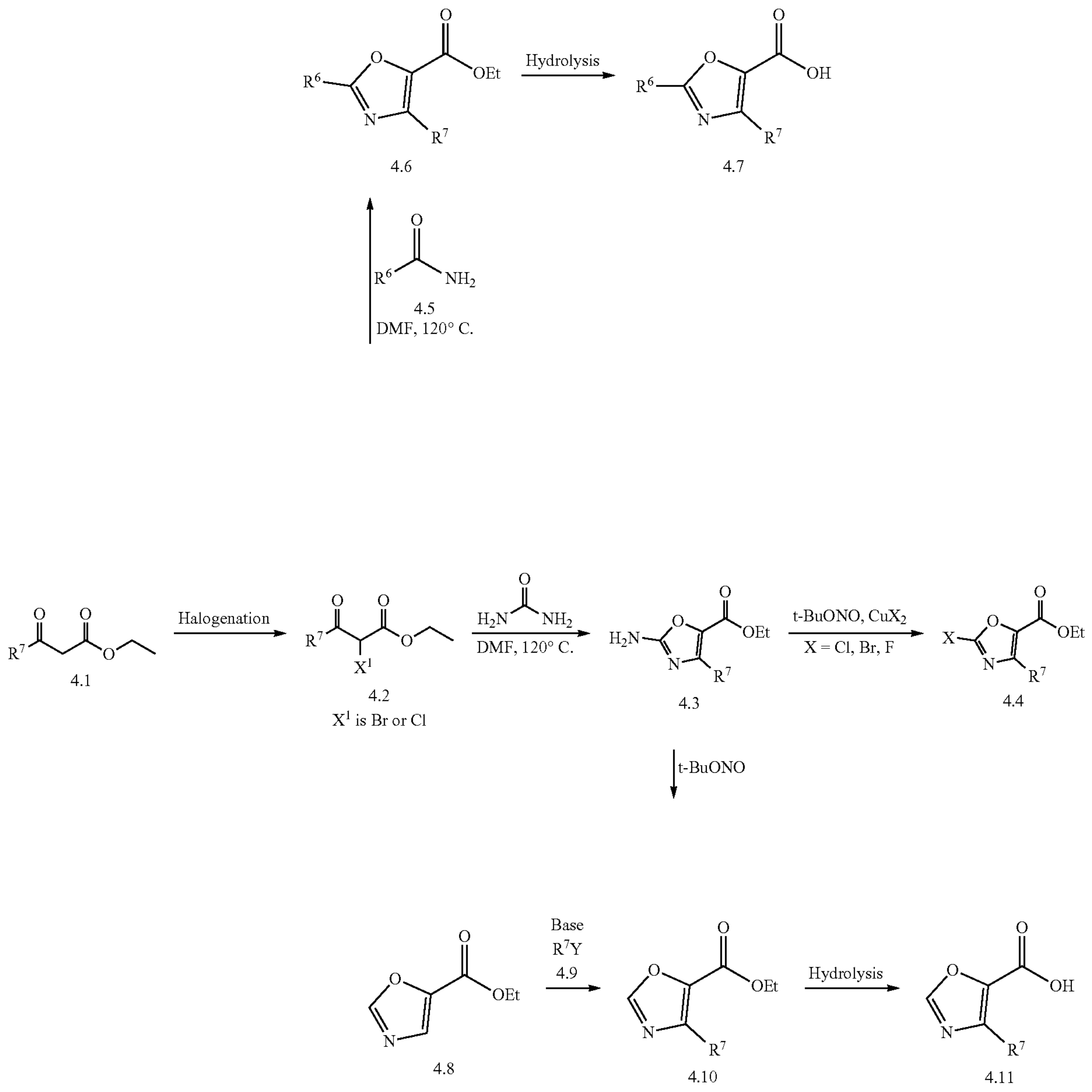

Oxazolyl $R^2$ carboxylic acid intermediates containing substitutions at the $R^6$ and/or $R^7$ positions were prepared in accordance with General Scheme 4. A β-keto ester of formula 4.1 was halogenated with a chlorinating agent such as $SOCl_2$ or brominating agent such as NBS to yield compounds of formula 4.2 (wherein $X^1$ is Br or Cl). Compounds of formula 4.2 were reacted with urea to afford amine oxazole compounds of formula 4.3. In addition, compounds of formula 4.2 were reacted with amides of formula 4.5 to afford oxazole compounds of formula 4.6. The amine in compounds of formula 4.3 was subjected to Sandmeyer reaction conditions to afford compounds of formula 4.4 (wherein X is Cl, Br, or F) and compounds of formula 4.10. Alternatively, compounds of formula 4.10 may be obtained by deprotonating a compound of formula 4.8 with a base such as LiHMDS followed by reaction in a nucleophilic substitution reaction with reagents of formula 4.9 (wherein Y is a suitable leaving group such as Br, Cl, mesylate, or tosylate) to afford compounds of formula 4.10. Hydrolysis of the ester of compounds of formulas 4.6 and 4.10 with abase such as LiOH, KOH, or NaOH in THF/water affords compounds of formulas 4.7 and 4.11. Alternatively, the basic salt (i.e., Li, K, or Na) of the carboxylic acid of formulas 4.7 and 4.11 may be obtained after the hydrolysis reaction by isolating the product at a basic pH. The carboxylic acid or basic salt thereof can then be used without further purification in the coupling reactions described in General Scheme 1, Method C.

General Scheme 5: Synthesis of Thiazolyl and Oxazolyl $R^2$ Acid Intermediates

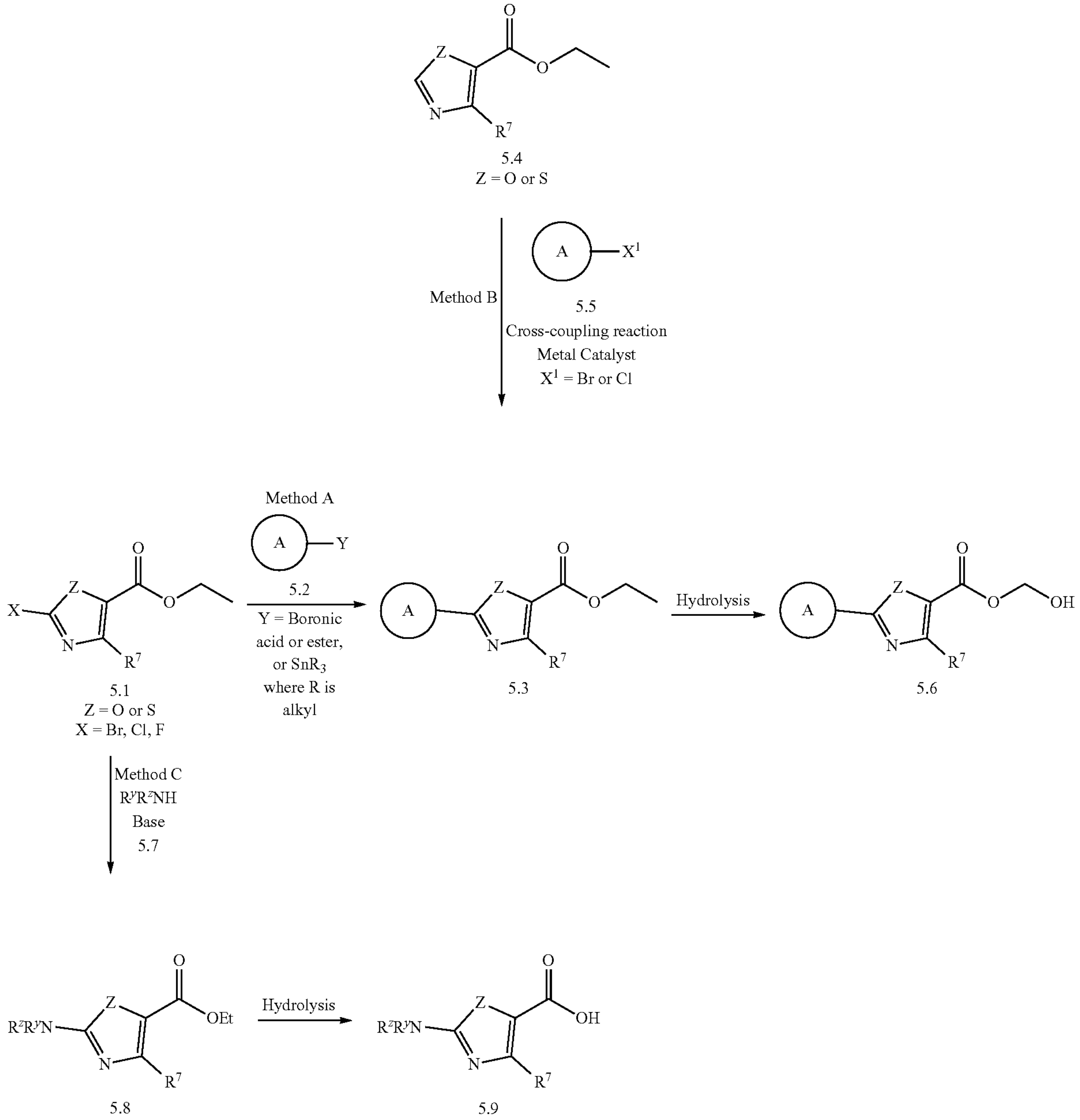

Oxazolyl and thiazolyl $R^2$ carboxylic acid intermediates containing substitutions at the $R^6$ and/or $R^7$ positions were prepared in accordance with General Scheme 5. Under Method A, a halide of formula 5.1 was reacted with a heteroaryl or aryl of formula 5.2 in either a Suzuki coupling (where Y is a boronic acid or ester) or a Stille coupling (where Y is $SnR_3$) to afford compounds of formula 5.3. Under Method B, compounds of formula 5.3 were obtained by reaction of a compound of formula 5.4 with a heteroaryl or aryl halide compound of formula 5.5 in a cross-coupling reaction using a metal catalyst such as a Buchwald catalyst or Ullman catalyst. Under Method C, a halide of formula 5.1 may also be reacted with an amine of formula 5.7 or a heterocyclic amine such as piperidine, morpholine, piperazine, azetidine, and pyrrolidine, and a base such as TEA in a displacement reaction to afford compounds of formula 5.8. Hydrolysis of the ester of compounds of formulas 5.3 and 5.8 with a base such as LiOH, KOH, or NaOH in THF/water affords compounds of formulas 5.6 and 5.9. Alternatively, the basic salt (i.e., Li, K, or Na) of the carboxylic acid of formulas 5.6 and 5.9 may be obtained after the hydrolysis reaction by isolating the product at a basic pH. The carboxylic acid or basic salt thereof can then be used without further purification in the coupling reactions described in General Scheme 1, Method C.

General Scheme 6: Synthesis of Thiazoyl and Oxazolyl $R^2$ Acid Intermediates

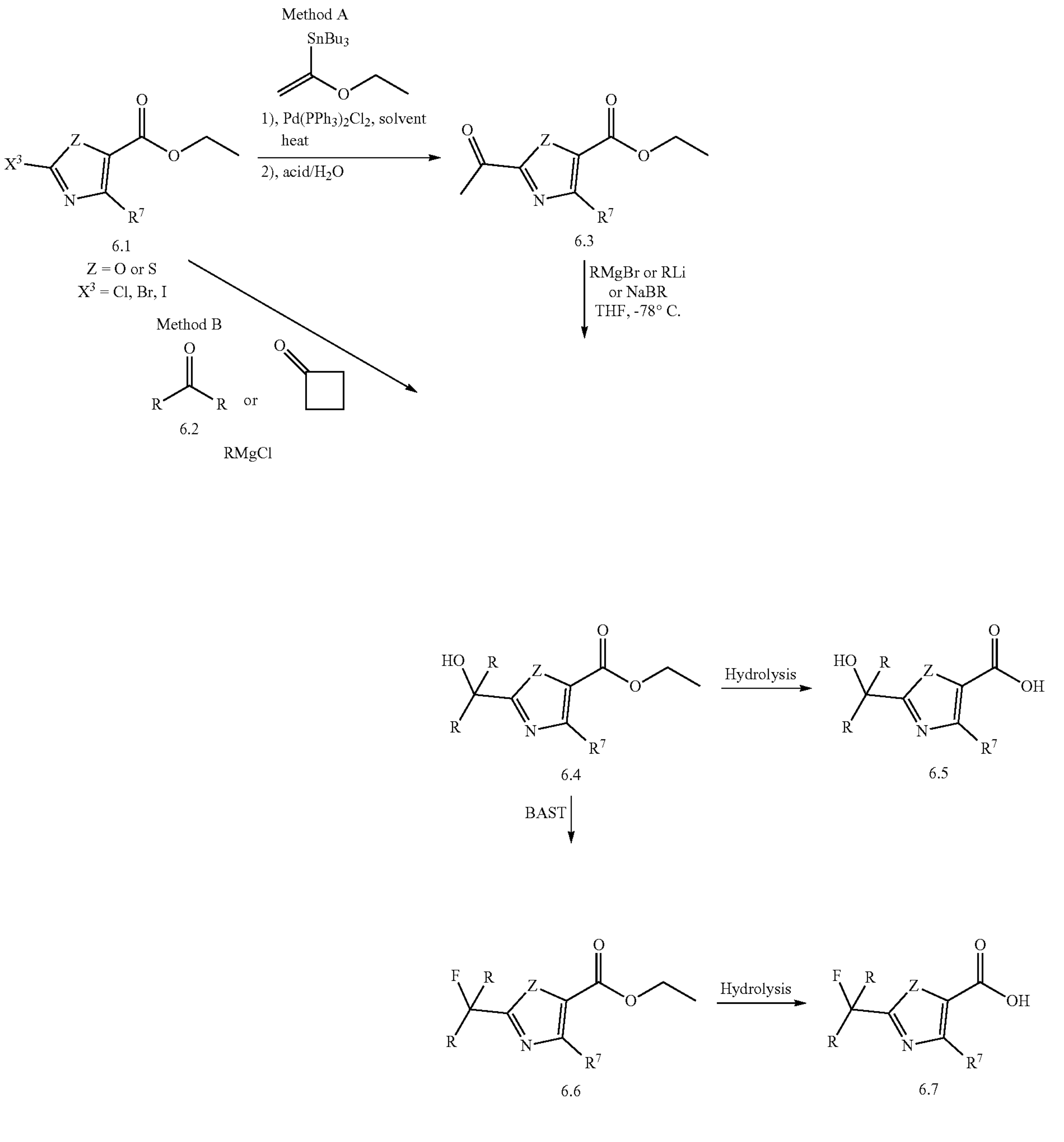

6.1
6.2
6.3
6.4
6.5
6.6
6.7

Oxazolyl and thiazolyl $R^2$ carboxylic acid intermediates containing hydroxyalkyl and haloalkyl substitutions were prepared in accordance with General Scheme 6. Under Method A, a halide of formula 6.1 was reacted with tributyl (1-ethoxyvinyl)stannane in a Stille coupling, followed by hydrolysis with acid/water such as TFA to afford compounds of formula 6.3. An alkyl group ("R") is then added to the ketone in compounds of formula 6.3 using RMgBr or RLi or through reduction of the ketone with NaBR to afford compounds of formula 6.4. Under Method B, compounds of formula 6.4 may also be obtained starting with a compound of formula 6.1 through a Grignard addition reaction with a ketone of formula 6.2 (wherein R is an alkyl) or cyclobutanone and RMgCl such as iPrMgCl. The hydroxyl substituent in compounds of formula 6.4 was converted to a fluorine substituent using a fluorinating agent such as BAST to afford compounds of formula 6.6. Hydrolysis of the ester of compounds of formulas 6.4 and 6.6 with a base such as LiOH, KOH, or NaOH in THF/water affords compounds of formulas 6.5 and 6.7. Alternatively, the basic salt (i.e., Li, K, or Na) of the carboxylic acid of formulas 6.5 and 6.7 may be obtained after the hydrolysis reaction by isolating the product at a basic pH. The carboxylic acid or basic salt thereof can then be used without further purification in the coupling reactions described in General Scheme 1, Method C.

General Scheme 7: Synthesis of Pyrazolo[1,5-a]pyridinyl $R^2$ Acid Intermediates

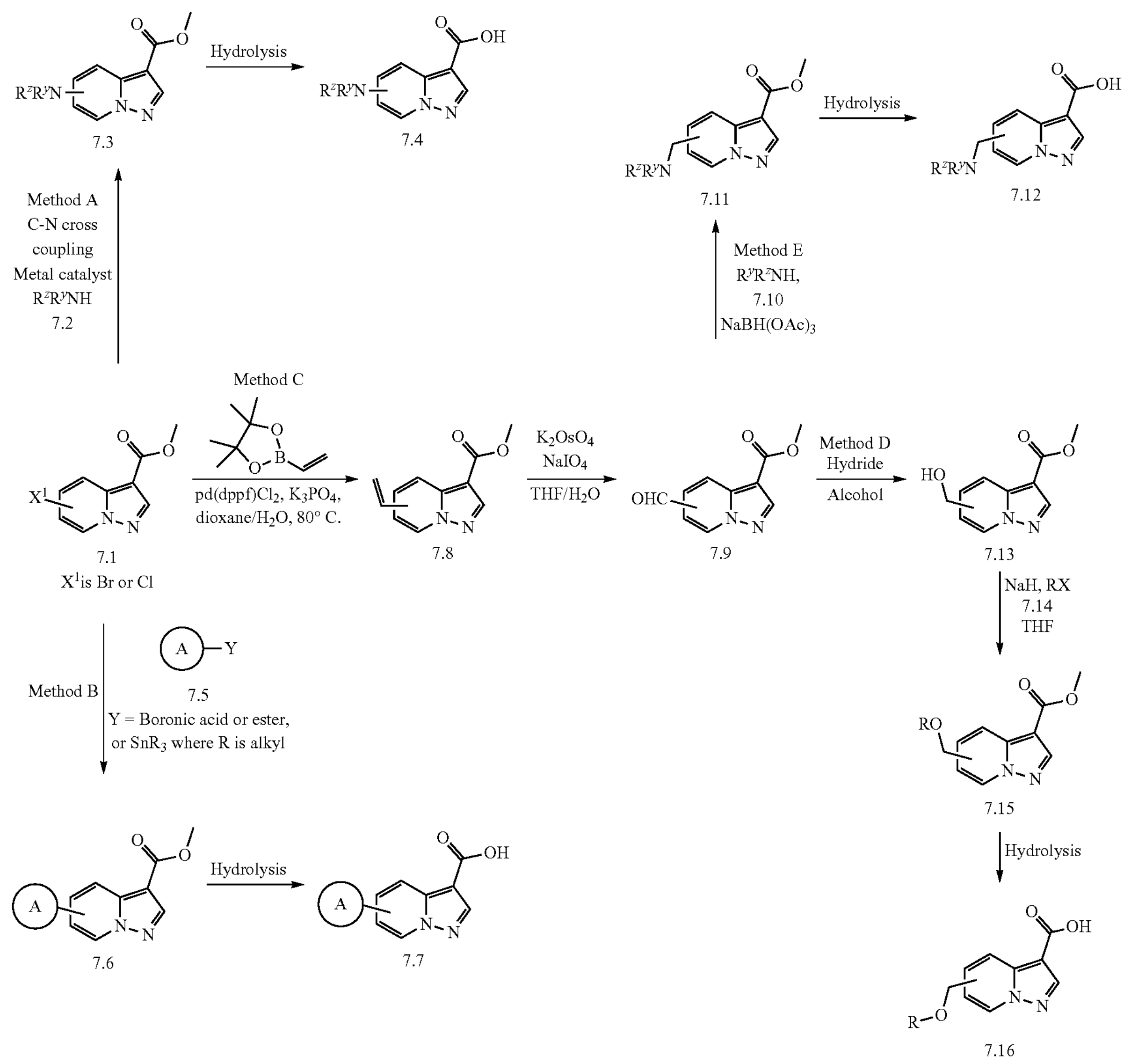

Substituted pyrazolo[1,5-a]pyridinyl $R^2$ caboxylic acid intermediates were prepared in accordance with General Scheme 7. Under Method A, a halide of formula 7.1 (wherein $X^1$ is Br or Cl) was reacted in a C—N cross-coupling reaction using a metal catalyst such as a Buchwald catalyst or Ullman catalyst with an amine of formula 7.2 or a heterocyclic amine such as piperidine, morpholine, piperazine, azetidine, and pyrrolidine to afford compounds of formula 7.3. Under Method B, a halide of formula 7.1 (wherein $X^1$ is Br or Cl) may also be reacted with a heteroaryl or aryl compound of formula 7.5 in either a Suzuki coupling (where Y is a boronic acid or ester) or a Stille coupling (where Y is $SnR_3$) to afford compounds of formula 7.6. Under Method C, a halide of formula 7.1 (wherein $X^1$ is Br or Cl) was reacted with 4,4,5,5-tetramethyl-2-vinyl-1,3,2-dioxaborolane in a Suzuki coupling to afford compounds of formula 7.8. The olefin in compounds of formula 7.8 then underwent oxidative cleavage to an aldehyde to afford compounds of formula 7.9. Under Method D, the aldehyde in compounds of formula 7.9 was reduced to an alcohol with a hydride such as $NaBH_4$ in an alcoholic solvent such as methanol or ethanol to afford formula 7.13. The alcohol in compounds of formula 7.13 was alkylated with sodium hydride and an alkyl ("R") halide of formula 7.14 (wherein X is Cl, Br, or F) to afford compounds of formula 7.15. Under Method E, a compound of formula 7.9 was reacted with an amine of formula 7.10 under reductive animation conditions to afford compounds of formula 7.11. Hydrolysis of the ester of compounds of formulas 7.3, 7.6, 7.11, and 7.15 with a base such as LiOH, KOH, or NaOH in THF/water affords compounds of formulas 7.4, 7.7, 7.12, and 7.16. Alternatively, the basic salt (i.e., Li, K, or Na) of the carboxylic acid of formulas 7.4, 7.7, 7.12, and 7.16 may be obtained after the hydrolysis reaction by isolating the product at a basic pH. The carboxylic acid or basic salt thereof can then be used without further purification in the coupling reactions described in General Scheme 1, Method C.

General Scheme 8: Synthesis of Pyrazolo[1,5-a]pyridinyls $R^2$ Acid Intermediates

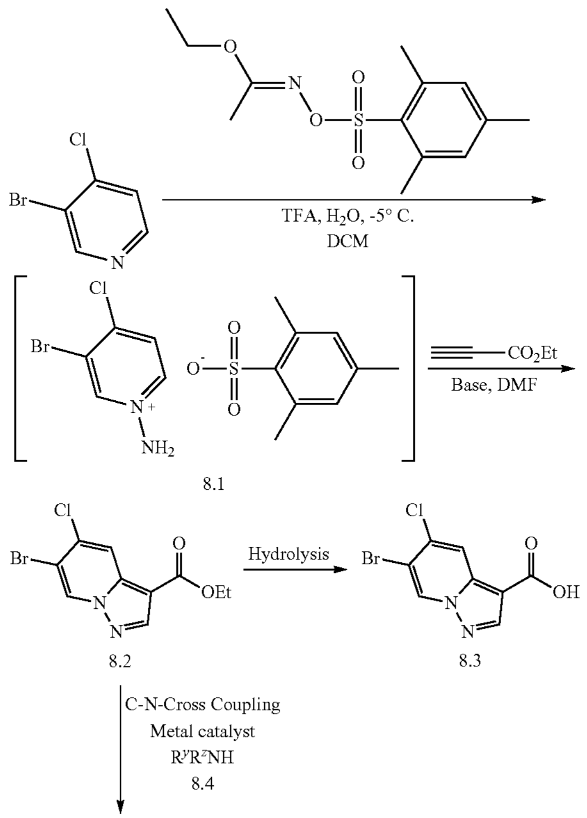

8.1

8.2

8.3

8.4

-continued

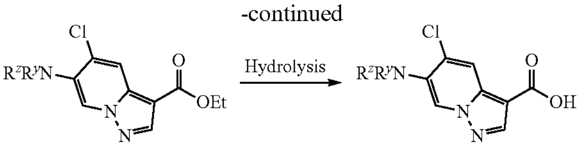

8.5

8.6

Di-substituted pyrazolo[1,5-a]pyridinyl $R^2$ carboxylic acid intermediates were prepared in accordance with General Scheme 8. Starting reagent 3-bromo-4-chloropyridine was reacted with ethyl (E)-N-((mesitylsulfonyl)oxy)acetimidate to afford the N-aminopyridinium salt 8.1. A cycloaddition reaction of the N-aminopyridinium salt 8.1 with ethyl propiolate and base such as $K_2CO_3$ afforded ethyl 6-bromo-5-chloropyrazolo[1,5-a]pyridine-3-carboxylate 8.2. Compound 8.2 was reacted in a C—N cross-coupling reaction using a metal catalyst such as a Buchwald catalyst or Ullman catalyst with an amine of formula 8.4 or a heterocyclic amine such as piperidine, morpholine, piperazine, azetidine, and pyrrolidine to afford compounds of formula 8.5. Hydrolysis of the ester of compounds of formulas 8.2 and 8.5 with a base such as LiOH, KOH, or NaOH in THF/water affords compounds of formulas 8.3 and 8.6. Alternatively, the basic salt (i.e., Li, K, or Na) of the carboxylic acid of formulas 8.3 and 8.6 may be obtained after the hydrolysis reaction by isolating the product at a basic pH. The carboxylic acid or basic salt thereof can then be used without further purification in the coupling reactions described in General Scheme 1, Method C.

General Scheme 9: Synthesis of 1,3,4-Oxadiazolyl $R^2$ Acid Intermediates

Method A

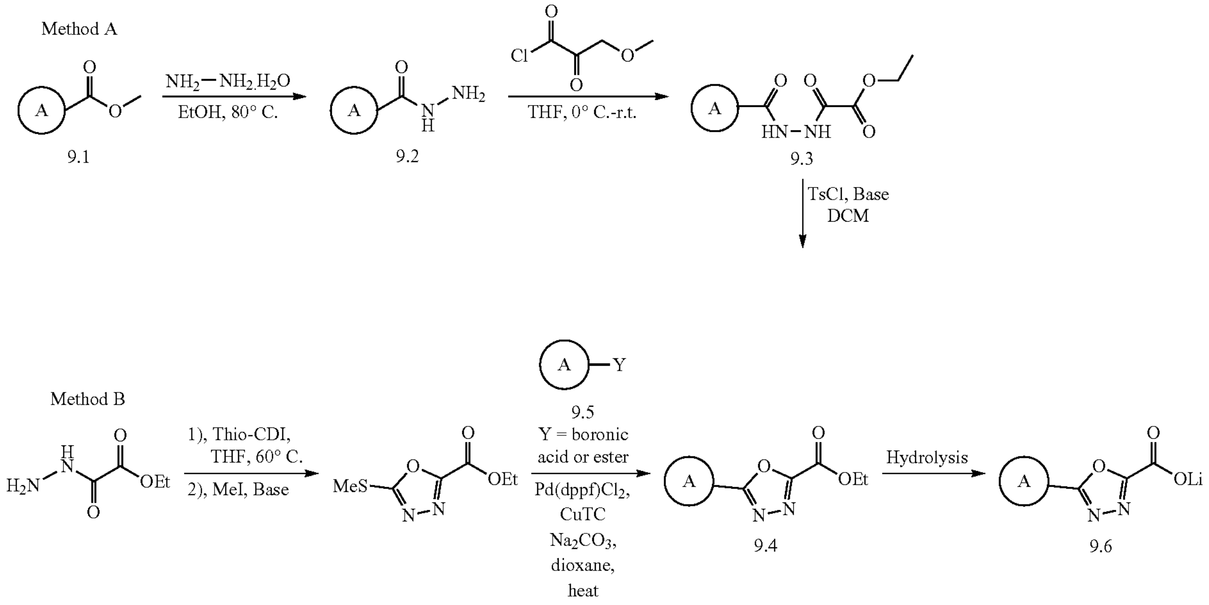

Method B 9.1

9.2

9.3

9.5

9.4

9.6

Heteroaryl and aryl-substituted oxadiazolyl $R^2$ carboxylic acid intermediates were prepared in accordance with General Scheme 9. Under Method A, heteroaryl and aryl esters of formula 9.1 were reacted with hydrazine hydrate to afford hydrazines of formula 9.2. Compounds of formula 9.2 were then reacted with ethyl-2-chloro-2-oxoacetate to afford compounds of formula 9.3, which subsequently underwent intramolecular cyclization with p-toluenesulfonyl chloride and a base such as TEA to afford the 1,3,4-oxadiazole of formula 9.4. Alternatively, compounds of formula 9.4 can be made using Method B. Under Method B, ethyl 2-hydrazineyl-2-oxoacetate was reacted with 1,1'-thiocarbonyldiimidazole to form the 1,3,4-oxadiazole, which was then alkylated with methyl iodide and base such as TEA to afford ethyl 5-(methylthio)-1,3,4-oxadiazole-2-carboxylate. Ethyl 5-(methylthio)-1,3,4-oxadiazole-2-carboxylate was reacted with a heteroaryl or aryl boronic acid or ester of formula 9.5 in a desulfitative C—C cross coupling reaction (also known as Liebeskind-Srogl cross-coupling) to afford compounds of formula 9.4. Hydrolysis of the ester of compounds of formula 9.4 with a base such as LiOH, KOH, or NaOH in THF/water affords compounds of formula 9.6. Alternatively, the basic salt (i.e., Li, K, or Na) of the carboxylic acid of formula 9.6 may be obtained after the hydrolysis reaction by isolating the product at a basic pH. The carboxylic acid or basic salt thereof can then be used without further purification in the coupling reactions described in General Scheme 1, Method C.

General Scheme 10: Synthesis of 1,3,4-Oxadiazolyl $R^2$ Acid Intermediates

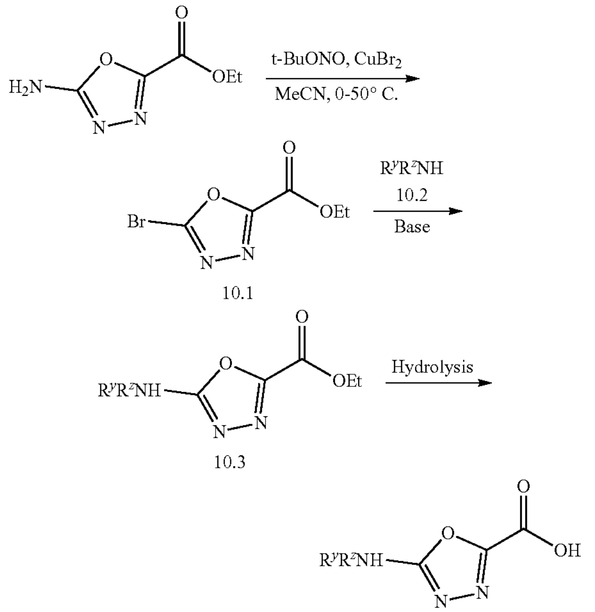

10.1

10.3

10.4

Substituted 1,3,4-oxadiazolyl $R^2$ carboxylic acid intermediates were prepared in accordance with General Scheme 10. Starting reagent ethyl 5-amino-1,3,4-oxadiazole-2-carboxylate was subjected to Sandmeyer reaction conditions to afford ethyl 5-bromo-1,3,4-oxadiazole-2-carboxylate (Compound 10.1). The bromo in compound 10.1 was reacted with an amine of formula 10.2 or a heterocyclic amine such as piperidine, morpholine, piperazine, azetidine, and pyrrolidine, and a base such as TEA to afford compounds of formula 10.3. Hydrolysis of the ester of compounds of formula 10.3 with a base such as LiOH, KOH, or NaOH in THF/water afforded compounds of formula 10.4. Alternatively, the basic salt (i.e., Li, K, or Na) of the carboxylic acid of formula 10.4 may be obtained after the hydrolysis reaction by isolating the product at a basic pH. The carboxylic acid or basic salt thereof can then be used without further purification in the coupling reactions described in General Scheme 1, Method C.

General Scheme 11: Preparation of Deuterated Core Amine Intermediates of Formulas 11.6 and 11.7

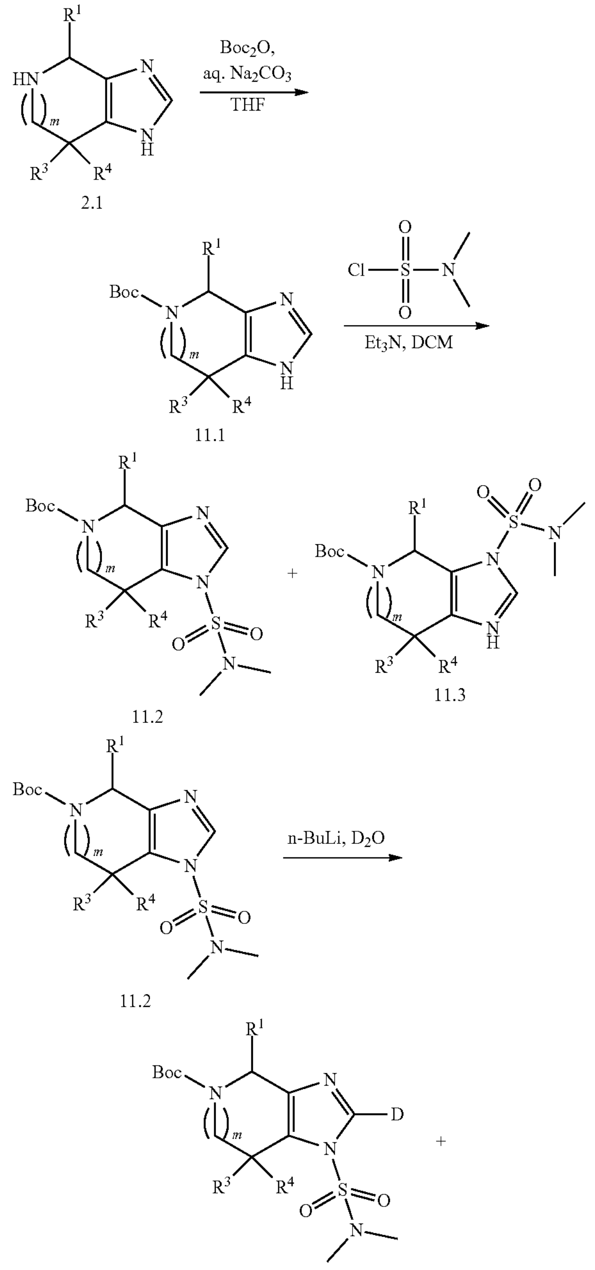

2.1

11.1

11.2

11.3

11.2

11.4

-continued

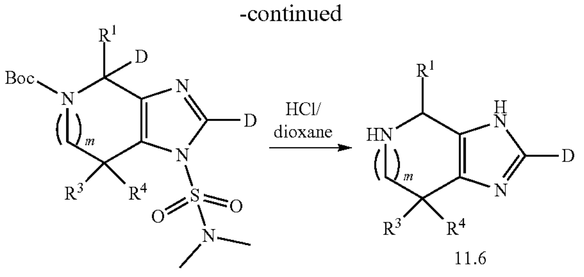

11.5

11.6

Compounds of Formula I wherein $R^{5A}$ is D are prepared in accordance with General Scheme 11. An amine of formula 2.1, prepared according to General Scheme 2, is protected with a BOC protecting group or other suitable nitrogen protecting group to afford compounds of formula 11.1. The amine in formula 11.1 is then protected with a dimethylsulfamoyl protecting group to afford a mixture of compounds of formula 11.2 and 11.3, which are separated during purification. Deuterium is then incorporated at the $R^{5A}$ position by deprotonating compounds of formula 11.2 with butyllithium and then adding $D_2O$ to afford compounds of formulas 11.4 and 11.5. Deprotection of the nitrogen protecting groups with acid afforded deuterated core amine intermediates of formulas 11.6. Deuterated core amine intermediates of formulas 11.6 can be further coupled to various L and $R^2$ groups via methods A, B, C, D, E, and F as described in General Scheme 1 to afford Compounds of Formula I, wherein $R^{5A}$ is D.

The present disclosure will be more fully understood by reference to the following examples. The examples provided herein are illustrative and should not, however, be construed as limiting the scope of the present disclosure.

EXAMPLES

In some embodiments, the disclosure provides specific examples of Formula I, and their pharmaceutically acceptable salts and/or isotopologues, as set forth in Table 1 below.

TABLE 1

| Pyrazolo[1,5-a]pyridines | | |
|---|---|---|
| Ex. # | Structure | Name |
| 600 | 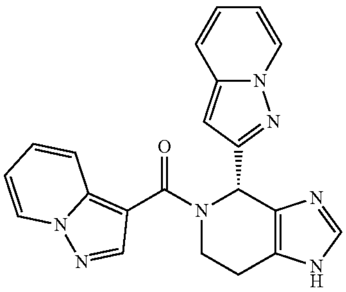 [SMILES: O=C(c1cnn2ccccc12)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 601 | 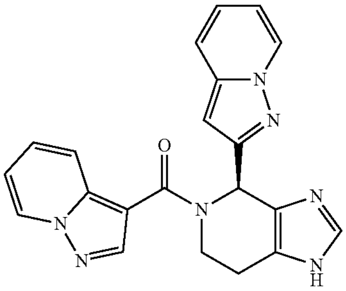 [SMILES: O=C(c1cnn2ccccc12)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 602 | 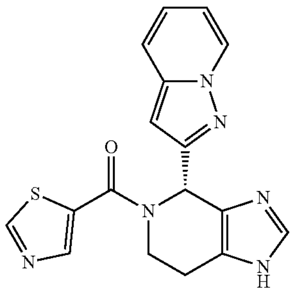 [SMILES: O=C(c1cncs1)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(thiazol-5-yl)methanone |

TABLE 1-continued

| Pyrazolo[1,5-a]pyridines | | |
|---|---|---|
| Ex. # | Structure | Name |
| 603 | 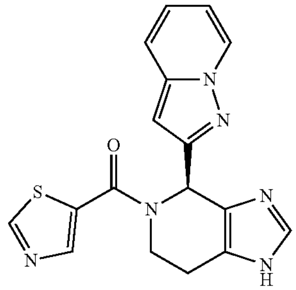 [SMILES: O=C(c1cncs1)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(thiazol-5-yl)methanone |
| 604 | 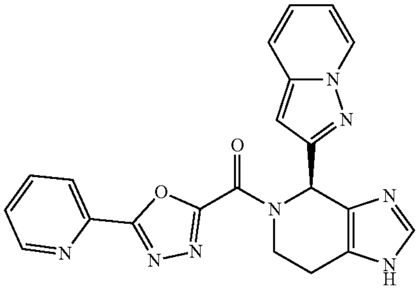 [SMILES: O=C(c1nnc(-c2ccccn2)o1)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 605 | 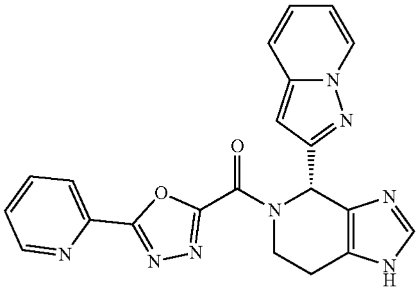 | (S)-(4-(pyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 606 | 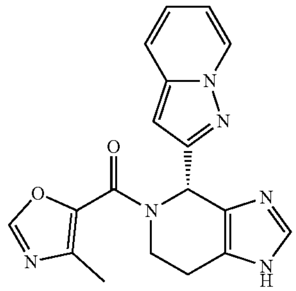 [SMILES: Cc1ncoc1C(=O)N1CCc2[nH]cnc2[C@H]1c1cc2ccccn2n1] | (S)-(4-methyloxazol-5-yl)(4-(pyrazolo[1,5-a]pyridin-2-yl)-6,7-dihydro-1H-imidazo[4,5-c]pyridin-5(4H)-yl)methanone |
| 607 | 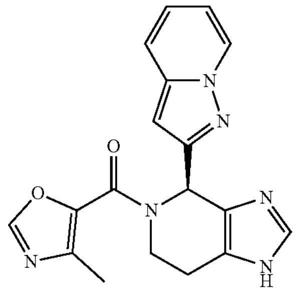 [SMILES: Cc1ncoc1C(=O)N1CCc2[nH]cnc2[C@@H]1c1cc2ccccn2n1] | (R)-(4-methyloxazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
| --- | --- | --- |
| | Pyrazolo[1,5-a]pyridines | |
| 608 | 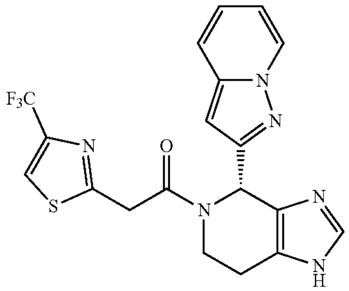 [SMILES: O=C(Cc1nc(C(F)(F)F)cs1)N1CCc2[nH]cnc2[C@H]1c1cc2ccccn2n1] | (S)-1-(4-(pyrazolo[1,5-a]pyridin-2-yl)-6,7-dihydro-1H-imidazo[4,5-c]pyridin-5(4H)-yl)-2-(4-(trifluoromethyl)thiazol-2-yl)ethanone |
| 609 | 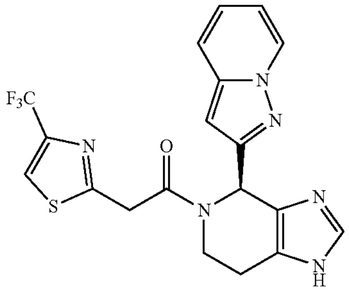 [SMILES: O=C(Cc1nc(C(F)(F)F)cs1)N1CCc2[nH]cnc2[C@@H]1c1cc2ccccn2n1] | (R)-1-(4-(pyrazolo[1,5-a]pyridin-2-yl)-6,7-dihydro-1H-imidazo[4,5-c]pyridin-5(4H)-yl)-2-(4-(trifluoromethyl)thiazol-2-yl)ethanone |
| 610 | 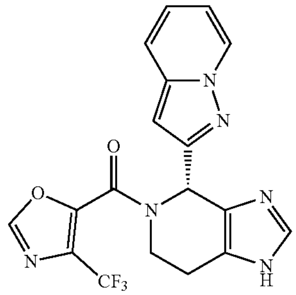 [SMILES: O=C(c1ocnc1C(F)(F)F)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(4-(trifluoromethyl)oxazol-5-yl)methanone |
| 611 | 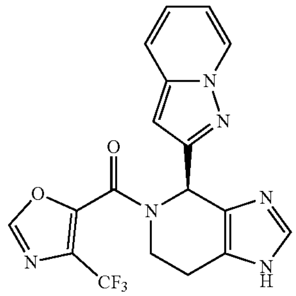 [SMILES: O=C(c1ocnc1C(F)(F)F)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(4-(trifluoromethyl)oxazol-5-yl)methanone |
| 612 | 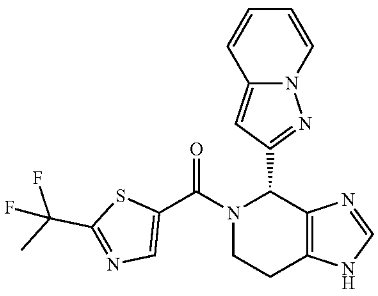 [SMILES: CC(F)(F)c1ncc(C(=O)N2CCc3[nH]cnc3[C@H]2c2cc3ccccn3n2)s1] | (S)-(2-(1,1-difluoroethyl)thiazol-5-yl)(4-(pyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 613 | 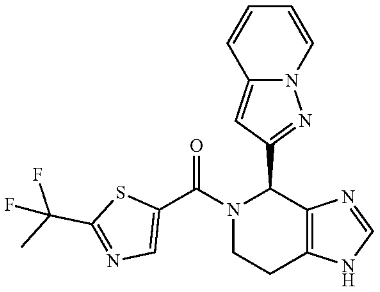 [SMILES: CC(F)(F)c1ncc(C(=O)N2CCc3[nH]cnc3[C@@H]2c2cc3ccccn3n2)s1] | (R)-(2-(1,1-difluoroethyl) thiazol-5-yl)(4-(pyrazolo [1,5-a]pyridin-2-yl)-6,7-dihydro-1H-imidazo[4,5-c] pyridin-5(4H)-yl)methanone |
| 614 | 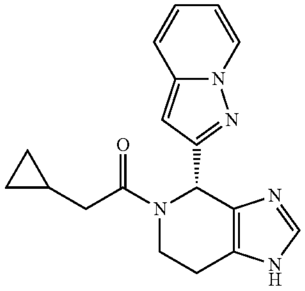 [SMILES: O=C(CC1CC1)N1CCc2[nH]cnc2[C@H]1c1cc2ccccn2n1] | (S)-2-cyclopropyl-1-(4-(pyrazolo[1,5-a]pyridin-2-yl)-6,7-dihydro-1H-imidazo[4,5-c]pyridin-5(4H)-yl)ethanone |
| 615 | 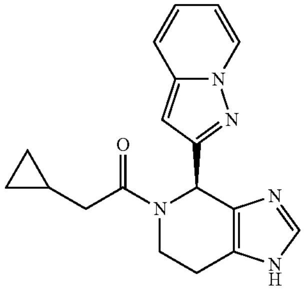 [SMILES: O=C(CC1CC1)N1CCc2[nH]cnc2[C@@H]1c1cc2ccccn2n1] | (R)-2-cyclopropyl-1-(4-(pyrazolo[1,5-a]pyridin-2-yl)-6,7-dihydro-1H-imidazo[4,5-c]pyridin-5(4H)-yl)ethanone |
| 616 | 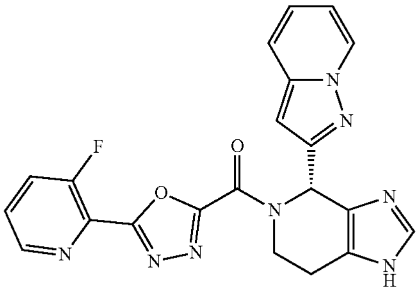 [SMILES: O=C(c1nnc(-c2ncccc2F)o1)N1CCc2[nH]cnc2[C@H]1c1cc2ccccn2n1] | (S)-(5-(3-fluoropyridin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 617 | 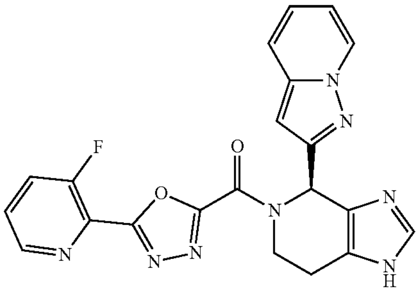 [SMILES: O=C(c1nnc(-c2ncccc2F)o1)N1CCc2[nH]cnc2[C@@H]1c1cc2ccccn2n1] | (R)-(5-(3-fluoropyridin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 618 | 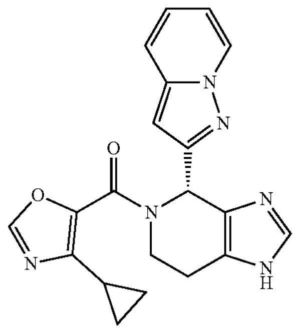 [SMILES: O=C(c1ocnc1C1CC1)N1CCc2[nH]cnc2[C@H]1c1cc2ccccn2n1] | (S)-(4-cyclopropyloxazol-5-yl)(4-(pyrazolo[1,5-a]pyridin-2-yl)-6,7-dihydro-1H-imidazo[4,5-c]pyridin-5(4H)-yl)methanone |
| 619 | 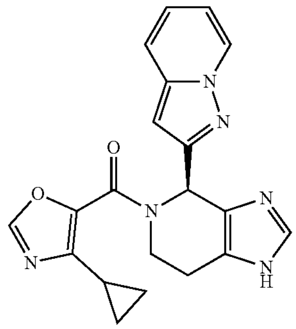 [SMILES: O=C(c1ocnc1C1CC1)N1CCc2[nH]cnc2[C@@H]1c1cc2ccccn2n1] | (R)-(4-cyclopropyloxazol-5-yl)(4-(pyrazolo[1,5-a]pyridin-2-yl)-6,7-dihydro-1H-imidazo[4,5-c]pyridin-5(4H)-yl)methanone |
| 620 | 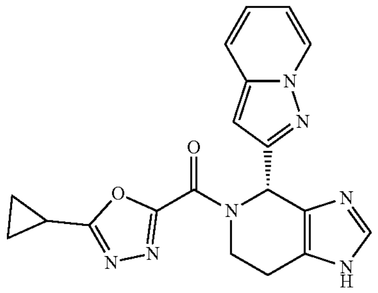 | (S)-(5-cyclopropyl-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 621 | 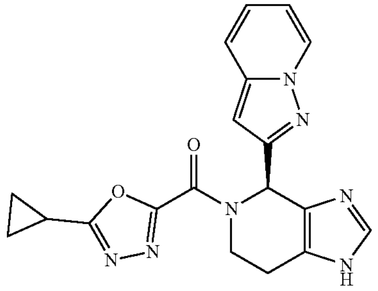 | (R)-(5-cyclopropyl-1,3,4-oxadiazol-2-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 622 | 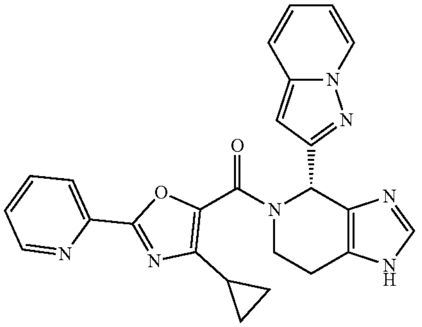 [SMILES: O=C(c1oc(-c2ccccn2)nc1C1CC1)N1CCc2[nH]cnc2[C@H]1c1cc2ccccn2n1] | (S)-(4-cyclopropyl-2-(pyridin-2-yl)oxazol-5-yl)(4-(pyrazolo[1,5-a]pyridin-2-yl)-6,7-dihydro-1H-imidazo[4,5-c]pyridin-5(4H)-yl)methanone |
| 623 | 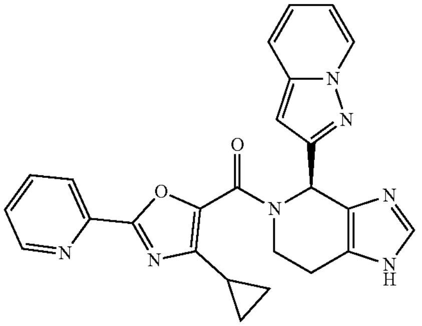 [SMILES: O=C(c1oc(-c2ccccn2)nc1C1CC1)N1CCc2[nH]cnc2[C@@H]1c1cc2ccccn2n1] | (R)-(4-cyclopropyl-2-(pyridin-2-yl)oxazol-5-yl)(4-(pyrazolo[1,5-a]pyridin-2-yl)-6,7-dihydro-1H-imidazo[4,5-c]pyridin-5(4H)-yl)methanone |
| 624 | 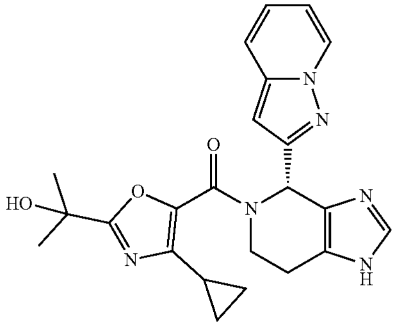 [SMILES: CC(C)(O)c1nc(C2CC2)c(C(=O)N2CCc3[nH]cnc3[C@H]2c2cc3ccccn3n2)o1] | (S)-(4-cyclopropyl-2-(2-hydroxypropan-2-yl)oxazol-5-yl)(4-(pyrazolo[1,5-a]pyridin-2-yl)-6,7-dihydro-1H-imidazo[4,5-c]pyridin-5(4H)-yl)methanone |
| 625 | 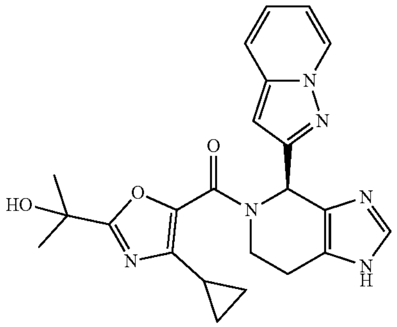 [SMILES: CC(C)(O)c1nc(C2CC2)c(C(=O)N2CCc3[nH]cnc3[C@@H]2c2cc3ccccn3n2)o1] | (R)-(4-cyclopropyl-2-(2-hydroxypropan-2-yl)oxazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 626 | 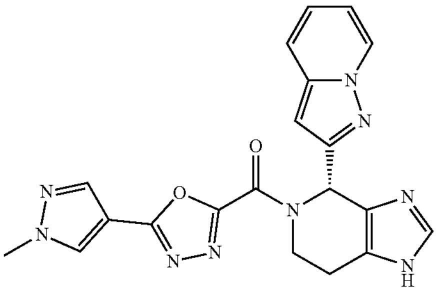 [SMILES: Cn1cc(-c2nnc(C(=O)N3CCc4[nH]cnc4[C@H]3c3cc4ccccn4n3)o2)cn1] | (S)-(5-(1-methyl-1H-pyrazol-4-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 627 | 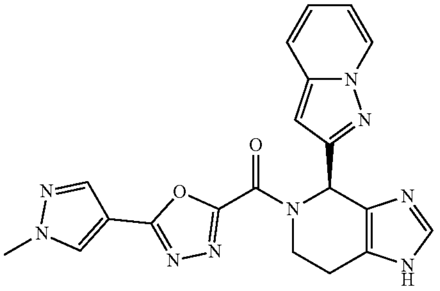 [SMILES: Cn1cc(-c2nnc(C(=O)N3CCc4[nH]cnc4[C@@H]3c3cc4ccccn4n3)o2)cn1] | (R)-(5-(1-methyl-1H-pyrazol-4-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 628 | 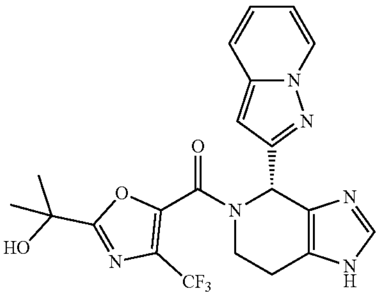 [SMILES: CC(C)(O)c1nc(C(F)(F)F)c(C(=O)N2CCc3[nH]cnc3[C@H]2c2cc3ccccn3n2)o1] | (S)-(2-(2-hydroxypropan-2-yl)-4-(trifluoromethyl)oxazol-5-yl)(4-(pyrazolo[1,5-a]pyridin-2-yl)-6,7-dihydro-1H-imidazo[4,5-c]pyridin-5(4H)-yl)methanone |
| 629 | 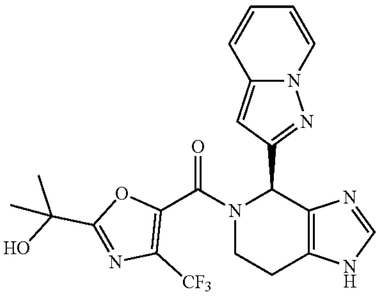 [SMILES: CC(C)(O)c1nc(C(F)(F)F)c(C(=O)N2CCc3[nH]cnc3[C@@H]2c2cc3ccccn3n2)o1] | (R)-(2-(2-hydroxypropan-2-yl)-4-(trifluoromethyl)oxazol-5-yl)(4-(pyrazolo[1,5-a]pyridin-2-yl)-6,7-dihydro-1H-imidazo[4,5-c]pyridin-5(4H)-yl)methanone |
| 630 | 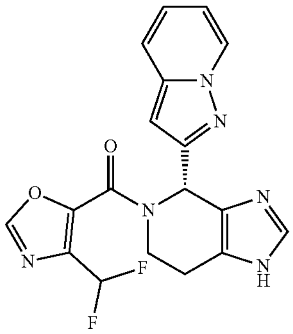 [SMILES: O=C(c1ocnc1C(F)F)N1CCc2[nH]cnc2[C@H]1c1cc2ccccn2n1] | (S)-(4-(difluoromethyl)oxazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 631 | 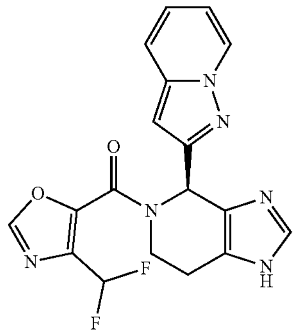 [SMILES: O=C(c1ocnc1C(F)F)N1CCc2[nH]cnc2[C@@H]1c1cc2ccccn2n1] | (R)-(4-(difluoromethyl) oxazol-5-yl)(4-(pyrazolo[1,5-a]pyridin-2-yl)-6,7-dihydro-1H-imidazo[4,5-c]pyridin-5(4H)-yl)methanone |
| 632 | 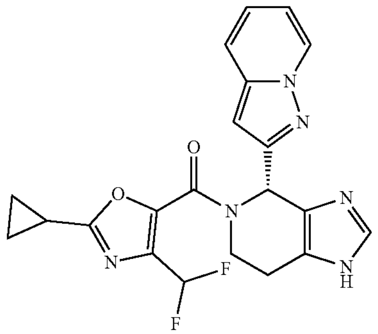 [SMILES: O=C(c1oc(C2CC2)nc1C(F)F)N1CCc2[nH]cnc2[C@H]1c1cc2ccccn2n1] | (S)-(2-cyclopropyl-4-(difluoromethyl)oxazol-5-yl)(4-(pyrazolo[1,5-a] pyridin-2-yl)-6,7-dihydro-1H-imidazo[4,5-c]pyridin-5(4H)-yl)methanone |
| 633 | 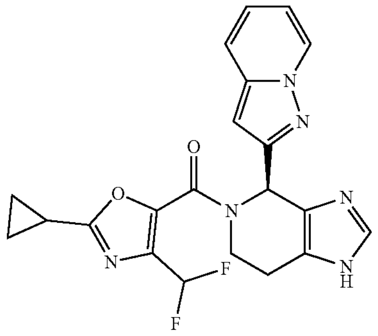 [SMILES: O=C(c1oc(C2CC2)nc1C(F)F)N1CCc2[nH]cnc2[C@@H]1c1cc2ccccn2n1] | (R)-(2-cyclopropyl-4-(difluoromethyl)oxazol-5-yl)(4-(pyrazolo[1,5-a] pyridin-2-yl)-6,7-dihydro-1H-imidazo[4,5-c]pyridin-5(4H)-yl)methanone |
| 634 | 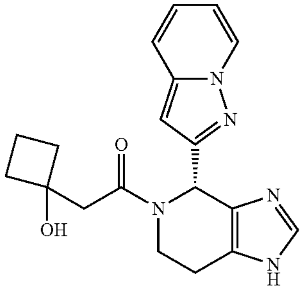 [SMILES: O=C(CC1(O)CCC1)N1CCc2[nH]cnc2[C@H]1c1cc2ccccn2n1] | (S)-2-(1-hydroxycyclobutyl)-1-(4-(pyrazolo[1,5-a]pyridin-2-yl)-6,7-dihydro-1H-imidazo [4,5-c]pyridin-5(4H)-yl)ethanone |

TABLE 1-continued

| Ex. # | Structure | Name |
|---|---|---|
| | Pyrazolo[1,5-a]pyridines | |
| 635 | 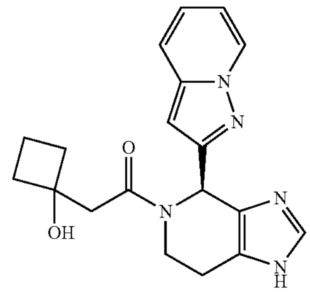 [SMILES: O=C(CC1(O)CCC1)N1CCc2[nH]cnc2[C@@H]1c1cc2ccccn2n1] | (R)-2-(1-hydroxycyclobutyl)-1-(4-(pyrazolo[1,5-a]pyridin-2-yl)-6,7-dihydro-1H-imidazo[4,5-c]pyridin-5(4H)-yl)ethanone |
| 636 | 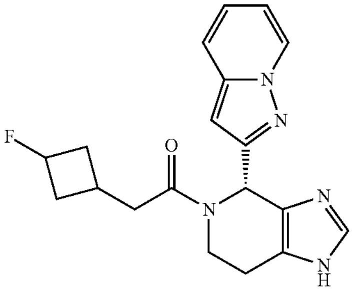 [SMILES: O=C(CC1CC(F)C1)N1CCc2[nH]cnc2[C@H]1c1cc2ccccn2n1] | (S)-2-(3-fluorocyclobutyl)-1-(4-(pyrazolo[1,5-a]pyridin-2-yl)-6,7-dihydro-1H-imidazo[4,5-c]pyridin-5(4H)-yl)ethenone |
| 637 | 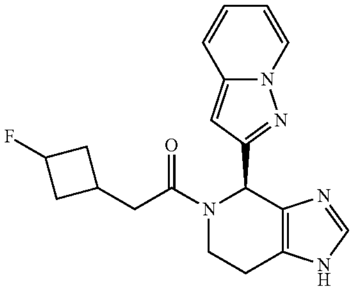 [SMILES: O=C(CC1CC(F)C1)N1CCc2[nH]cnc2[C@@H]1c1cc2ccccn2n1] | (R)-2-(3-fluorocyclobutyl)-1-(4-(pyrazolo[1,5-a]pyridin-2-yl)-6,7-dihydro-1H-imidazo[4,5-c]pyridin-5(4H)-yl)ethanone |
| 638 | 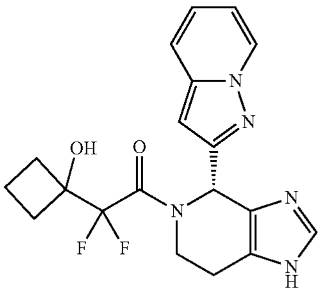 [SMILES: O=C(N1CCc2[nH]cnc2[C@H]1c1cc2ccccn2n1)C(F)(F)C1(O)CCC1] | (S)-2,2-difluoro-2-(1-hydroxycyclobutyl)-1-(4-(pyrazolo[1,5-a]pyridin-2-yl)-6,7-dihydro-1H-imidazo[4,5-c]pyridin-5(4H)-yl)ethanone |
| 639 | 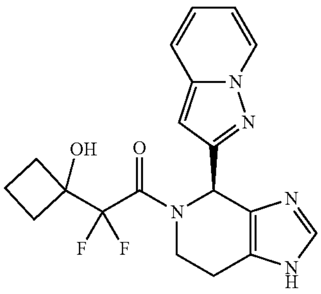 [SMILES: O=C(N1CCc2[nH]cnc2[C@@H]1c1cc2ccccn2n1)C(F)(F)C1(O)CCC1] | (R)-2,2-difluoro-2-(1-hydroxycyclobutyl)-1-(4-(pyrazolo[1,5-a]pyridin-2-yl)-6,7-dihydro-1H-imidazo[4,5-c]pyridin-5(4H)-yl)ethanone |

TABLE 1-continued

| Ex. # | Structure | Name |
|---|---|---|
| | Pyrazolo[1,5-a]pyridines | |
| 640 | 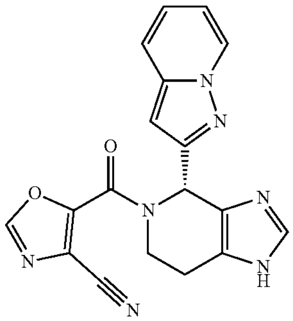 [SMILES: N#Cc1ncoc1C(=O)N1CCc2[nH]cnc2[C@H]1c1cc2ccccn2n1] | (S)-5-(4-(pyrazolo[1,5-a]pyridin-2-yl)-4,5,6,7-tetrahydro-1H-imidazo[4,5-c]pyridine-5-carbonyl)oxazole-4-carbonitrile |
| 641 | 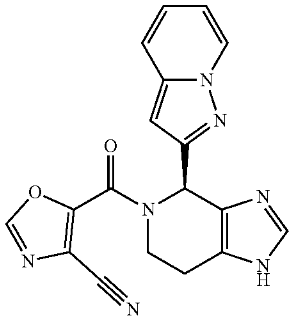 [SMILES: N#Cc1ncoc1C(=O)N1CCc2[nH]cnc2[C@@H]1c1cc2ccccn2n1] | (R)-5-(4-(pyrazolo[1,5-a]pyridin-2-yl)-4,5,6,7-tetrahydro-1H-imidazo[4,5-c]pyridine-5-carbonyl)oxazole-4-carbonitrile |
| 642 | 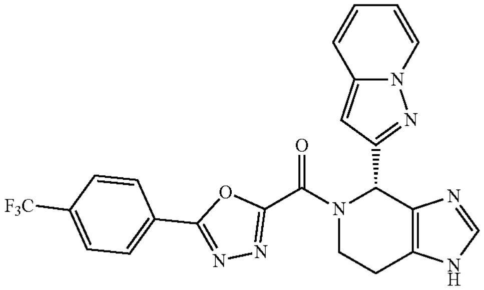 [SMILES: O=C(c1nnc(-c2ccc(C(F)(F)F)cc2)o1)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(5-(4-(trifluoromethyl)phenyl)-1,3,4-oxadiazol-2-yl)methanone |
| 643 | 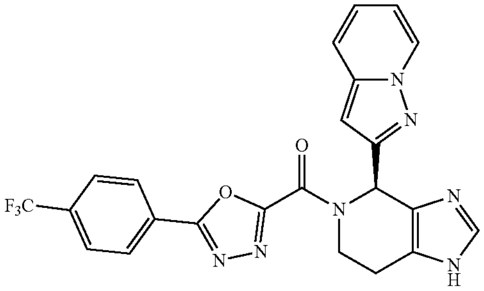 [SMILES: O=C(c1nnc(-c2ccc(C(F)(F)F)cc2)o1)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(5-(4-(trifluoromethyl)phenyl)-1,3,4-oxadiazol-2-yl)methanone |

TABLE 1-continued

| Ex. # | Structure | Name |
|---|---|---|
| | Pyrazolo[1,5-a]pyridines | |
| 644 | 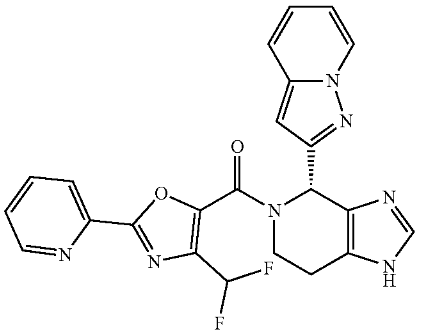 [SMILES: O=C(c1oc(-c2ccccn2)nc1C(F)F)N1CCc2[nH]cnc2[C@H]1c1cc2ccccn2n1] | (S)-(4-(difluoromethyl)-2-(pyridin-2-yl)oxazol-5-yl)(4-(pyrazolo[1,5-a]pyridin-2-yl)-6,7-dihydro-1H-imidazo[4,5-c]pyridin-5(4H)-yl)methanone |
| 645 | 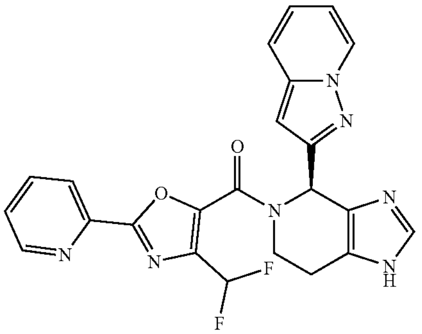 [SMILES: O=C(c1oc(-c2ccccn2)nc1C(F)F)N1CCc2[nH]cnc2[C@@H]1c1cc2ccccn2n1] | (R)-(4-(difluoromethyl)-2-(pyridin-2-yl)oxazol-5-yl)(4-(pyrazolo[1,5-a]pyridin-2-yl)-6,7-dihydro-1H-imidazo[4,5-c]pyridin-5(4H)-yl)methanone |
| 646 | 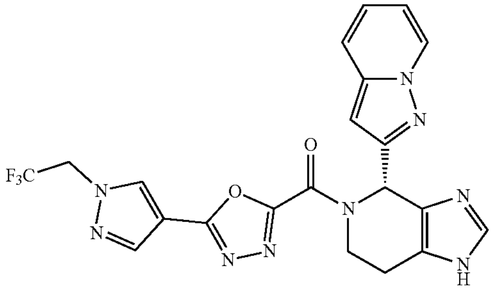 [SMILES: O=C(c1nnc(-c2cnn(CC(F)(F)F)c2)o1)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(5-(1-(2,2,2-trifluoroethyl)-1H-pyrazol-4-yl)-1,3,4-oxadiazol-2-yl)methanone |
| 647 | 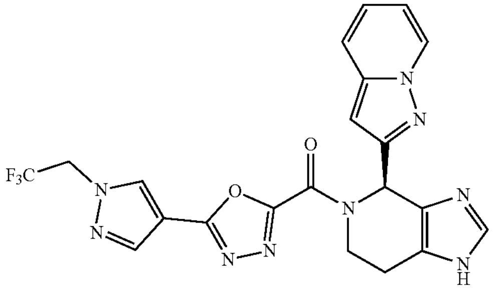 [SMILES: O=C(c1nnc(-c2cnn(CC(F)(F)F)c2)o1)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(5-(1-(2,2,2-trifluoroethyl)-1H-pyrazol-4-yl)-1,3,4-oxadiazol-2-yl)methanone |

TABLE 1-continued

| Pyrazolo[1,5-a]pyridines | | |
|---|---|---|
| Ex. # | Structure | Name |
| 648 | 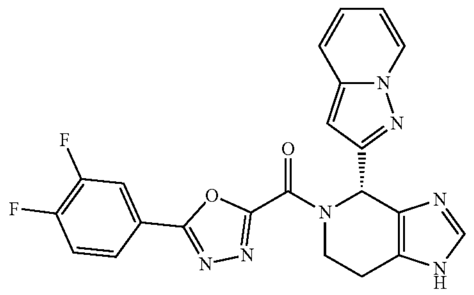 [SMILES: O=C(c1nnc(-c2ccc(F)c(F)c2)o1)N1CCc2[nH]cnc2[C@H]1c1cc2ccccn2n1] | (S)-(5-(3,4-difluorophenyl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 649 | 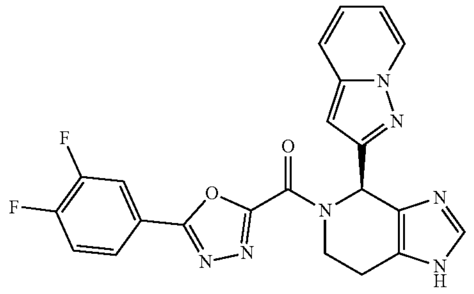 [SMILES: O=C(c1nnc(-c2ccc(F)c(F)c2)o1)N1CCc2[nH]cnc2[C@@H]1c1cc2ccccn2n1] | (R)-(5-(3,4-difluorophenyl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 650 | 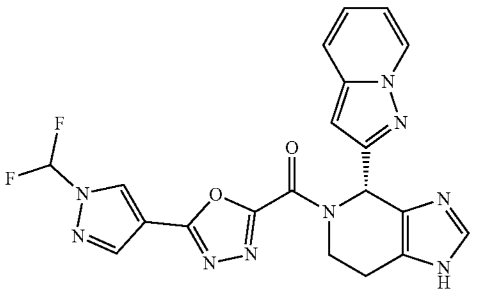 [SMILES: O=C(c1nnc(-c2cnn(C(F)F)c2)o1)N1CCc2[nH]cnc2[C@H]1c1cc2ccccn2n1] | (S)-(5-(1-(difluoromethyl)-1H-pyrazol-4-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 651 | 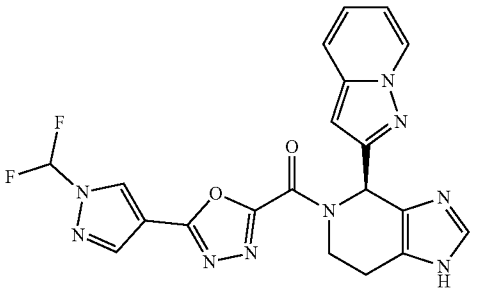 [SMILES: O=C(c1nnc(-c2cnn(C(F)F)c2)o1)N1CCc2[nH]cnc2[C@@H]1c1cc2ccccn2n1] | (R)-(5-(1-(difluoromethyl)-1H-pyrazol-4-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 652 | 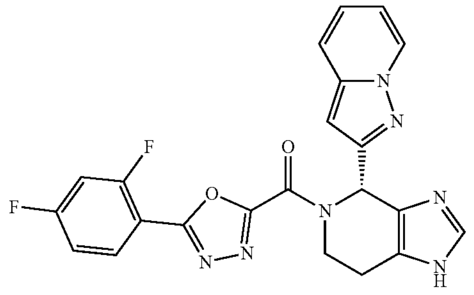 [SMILES: O=C(c1nnc(-c2ccc(F)cc2F)o1)N1CCc2[nH]cnc2[C@H]1c1cc2ccccn2n1] | (S)-(5-(2,4-difluorophenyl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 653 | 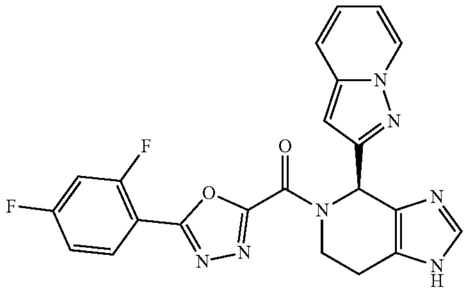 [SMILES: O=C(c1nnc(-c2ccc(F)cc2F)o1)N1CCc2[nH]cnc2[C@@H]1c1cc2ccccn2n1] | (R)-(5-(2,4-difluorophenyl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 654 | 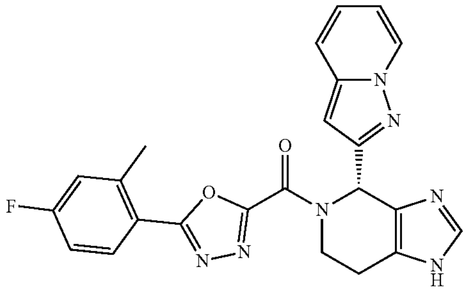 [SMILES: Cc1cc(F)ccc1-c1nnc(C(=O)N2CCc3[nH]cnc3[C@H]2c2cc3ccccn3n2)o1] | (S)-(5-(4-fluoro-2-methylphenyl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 655 | 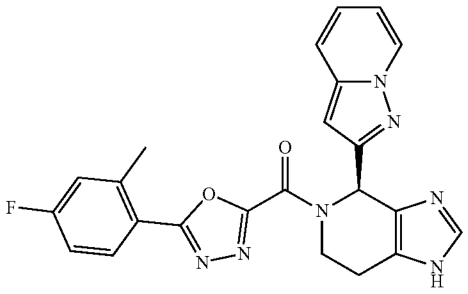 [SMILES: Cc1cc(F)ccc1-c1nnc(C(=O)N2CCc3[nH]cnc3[C@@H]2c2cc3ccccn3n2)o1] | (R)-(5-(4-fluoro-2-methylphenyl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 656 | 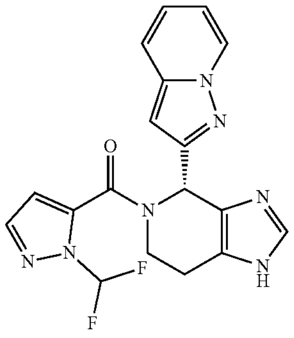 [SMILES: O=C(c1ccnn1C(F)F)N1CCc2[nH]cnc2[C@H]1c1cc2ccccn2n1] | (S)-(1-(difluoromethyl)-1H-pyrazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 657 | 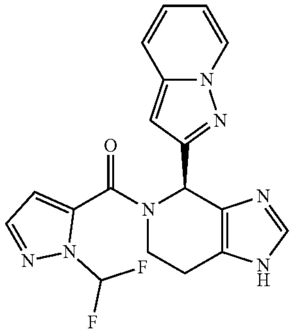 [SMILES: O=C(c1ccnn1C(F)F)N1CCc2[nH]cnc2[C@@H]1c1cc2ccccn2n1] | (R)-(1-(difluoromethyl)-1H-pyrazol-5-yl)(4-(pyrazolo[1,5-a]pyridin-2-yl)-6,7-dihydro-1H-imidazo[4,5-c]pyridin-5(4H)-yl)methanone |
| 658 | 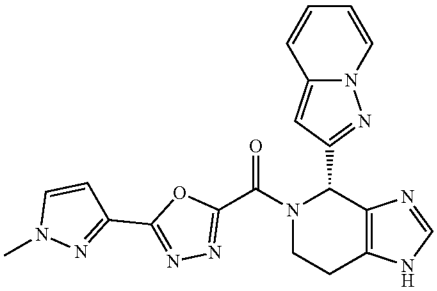 [SMILES: Cn1ccc(-c2nnc(C(=O)N3CCc4[nH]cnc4[C@H]3c3cc4ccccn4n3)o2)n1] | (S)-(5-(1-methyl-1H-pyrazol-3-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 659 | 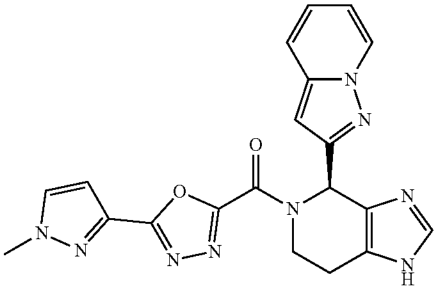 [SMILES: Cn1ccc(-c2nnc(C(=O)N3CCc4[nH]cnc4[C@@H]3c3cc4ccccn4n3)o2)n1] | (R)-(5-(1-methyl-1H-pyrazol-3-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 660 | 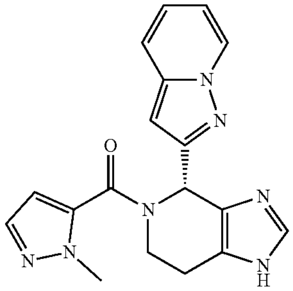 [SMILES: Cn1nccc1C(=O)N1CCc2[nH]cnc2[C@H]1c1cc2ccccn2n1] | (S)-(1-methyl-1H-pyrazol-5-yl)(4-(pyrazolo[1,5-a]pyridin-2-yl)-6,7-dihydro-1H-imidazo[4,5-c]pyridin-5(4H)-yl)methanone |
| 661 | 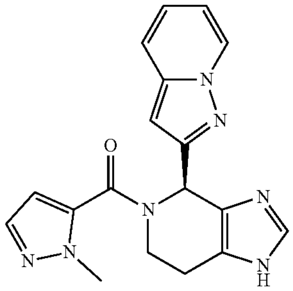 [SMILES: Cn1nccc1C(=O)N1CCc2[nH]cnc2[C@@H]1c1cc2ccccn2n1] | (R)-(1-methyl-1H-pyrazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 662 | 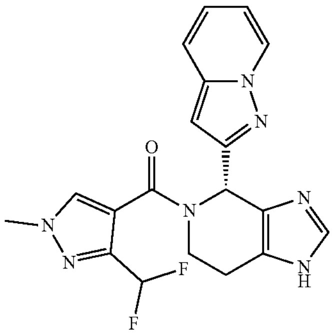 [SMILES: Cn1cc(C(=O)N2CCc3[nH]cnc3[C@H]2c2cc3ccccn3n2)c(C(F)F)n1] | (S)-(3-(difluoromethyl)-1-methyl-1H-pyrazol-4-yl)(4-(pyrazolo[1,5-a]pyridin-2-yl)-6,7-dihydro-1H-imidazo[4,5-c]pyridin-5(4H)-yl)methanone |
| 663 | 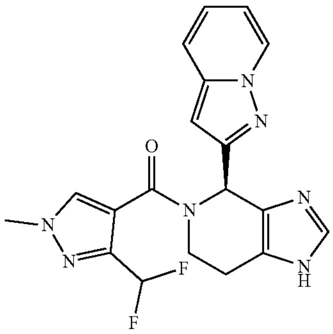 [SMILES: Cn1cc(C(=O)N2CCc3[nH]cnc3[C@@H]2c2cc3ccccn3n2)c(C(F)F)n1] | (R)-(3-(difluoromethyl)-1-methyl-1H-pyrazol-4-yl)(4-(pyrazolo[1,5-a]pyridin-2-yl)-6,7-dihydro-1H-imidazo[4,5-c]pyridin-5(4H)-yl)methanone |
| 664 | 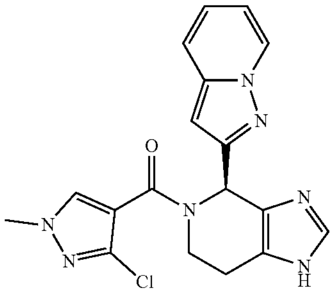 [SMILES: Cn1cc(C(=O)N2CCc3[nH]cnc3[C@@H]2c2cc3ccccn3n2)c(Cl)n1] | (R)-(3-chloro-1-methyl-1H-pyrazol-4-yl)(4-(pyrazolo[1,5-a]pyridin-2-yl)-6,7-dihydro-1H-imidazo[4,5-c]pyridin-5(4H)-yl)methanone |
| 665 | 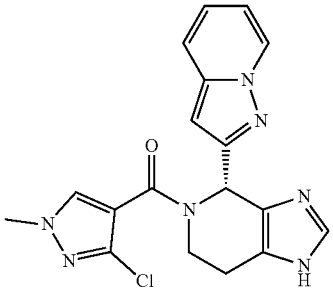 [SMILES: Cn1cc(C(=O)N2CCc3[nH]cnc3[C@H]2c2cc3ccccn3n2)c(Cl)n1] | (S)-(3-chloro-1-methyl-1H-pyrazol-4-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 666 | 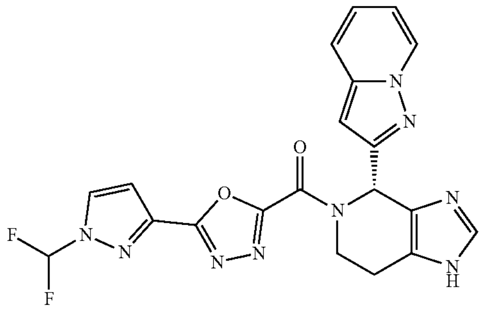 | (S)-(5-(1-(difluoromethyl)-1H-pyrazol-3-yl)-1,3,4-oxadiazol-2-yl)(4-(pyrazolo[1,5-a]pyridin-2-yl)-6,7-dihydro-1H-imidazo [4,5-c]pyridin-5(4H)-yl)methanone |
| 667 | 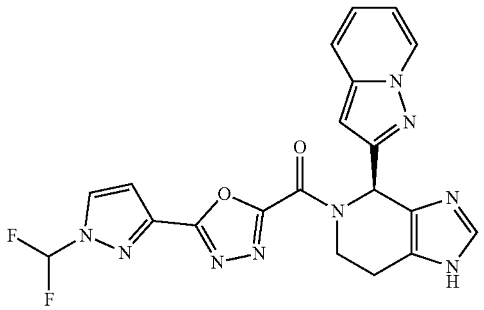 [SMILES: O=C(c1nnc(-c2ccn(C(F)F)n2)o1)N1CCc2[nH]cnc2[C@@H]1c1cc2ccccn2n1] | (R)-(5-(1-(difluoromethyl)-1H-pyrazol-3-yl)-1,3,4-oxadiazol-2-yl)(4-(pyrazolo[1,5-a]pyridin-2-yl)-6,7-dihydro-1H-imidazo [4,5-c]pyridin-5(4H)-yl)methanone |
| 668 | 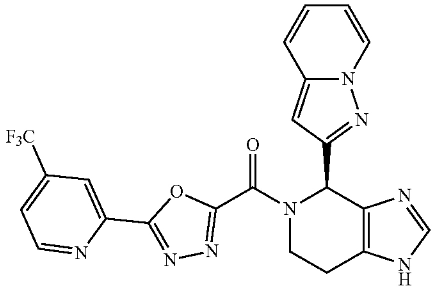 [SMILES: O=C(c1nnc(-c2cc(C(F)(F)F)ccn2)o1)N1CCc2[nH]cnc2[C@@H]1c1cc2ccccn2n1] | (R)-(4-(pyrazolo[1,5-a]pyridin-2-yl)-6,7-dihydro-1H-imidazo [4,5-c]pyridin-5(4H)-yl)(5-(4-(trifluoromethyl)pyridin-2-yl)-1,3,4-oxadiazol-2-yl)methanone |
| 669 | 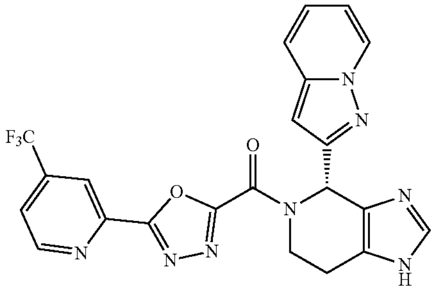 [SMILES: O=C(c1nnc(-c2cc(C(F)(F)F)ccn2)o1)N1CCc2[nH]cnc2[C@H]1c1cc2ccccn2n1] | (S)-(4-(pyrazolo[1,5-a]pyridin-2-yl)-6,7-dihydro-1H-imidazo [4,5-c]pyridin-5(4H)-yl)(5-(4-(trifluoromethyl)pyridin-2-yl)-1,3,4-oxadiazol-2-yl)methanone |

TABLE 1-continued

| Ex. # | Structure | Name |
|---|---|---|
| | Pyrazolo[1,5-a]pyridines | |
| 670 | 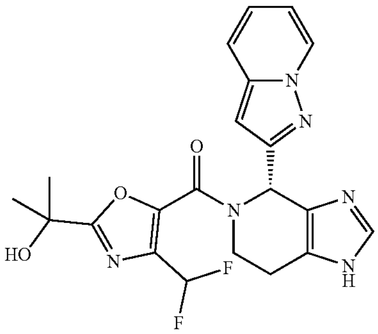 [SMILES: CC(C)(O)c1nc(C(F)F)c(C(=O)N2CCc3[nH]cnc3[C@H]2c2cc3ccccn3n2)o1] | (S)-(4-(difluoromethyl)-2-(2-hydroxypropan-2-yl)oxazol-5-yl)(4-(pyrazolo[1,5-a]pyridin-2-yl)-6,7-dihydro-1H-imidazo[4,5-c]pyridin-5(4H)-yl)methanone |
| 671 | 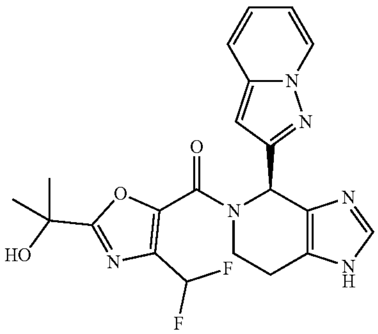 [SMILES: CC(C)(O)c1nc(C(F)F)c(C(=O)N2CCc3[nH]cnc3[C@@H]2c2cc3ccccn3n2)o1] | (R)-(4-(difluoromethyl)-2-(2-hydroxypropan-2-yl)oxazol-5-yl)(4-(pyrazolo[1,5-a]pyridin-2-yl)-6,7-dihydro-1H-imidazo[4,5-c]pyridin-5(4H)-yl)methanone |
| 672 | 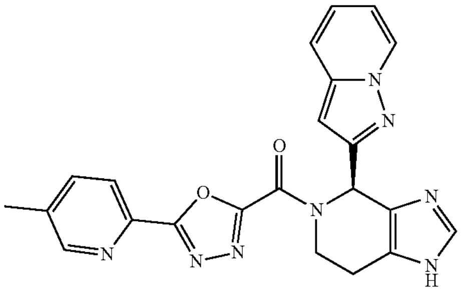 [SMILES: Cc1ccc(-c2nnc(C(=O)N3CCc4[nH]cnc4[C@@H]3c3cc4ccccn4n3)o2)nc1] | (R)-(5-(5-methylpyridin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 673 | 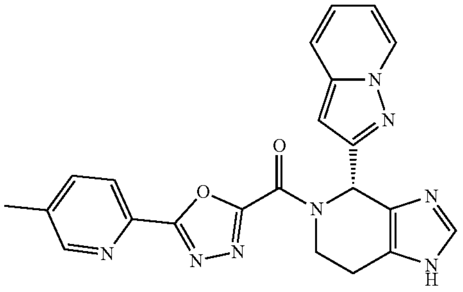 [SMILES: Cc1ccc(-c2nnc(C(=O)N3CCc4[nH]cnc4[C@H]3c3cc4ccccn4n3)o2)nc1] | (S)-(5-(5-methylpyridin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 674 | 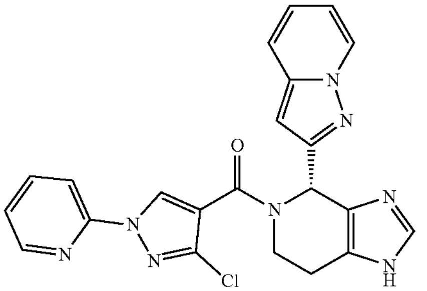 [SMILES: O=C(c1cn(-c2ccccn2)nc1Cl)N1CCc2[nH]cnc2[C@H]1c1cc2ccccn2n1] | (S)-(3-chloro-1-(pyridin-2-yl)-1H-pyrazol-4-yl)(4-(pyrazolo[1,5-a]pyridin-2-yl)-6,7-dihydro-1H-imidazo[4,5-c]pyridin-5(4H)-yl)methanone |
| 675 | 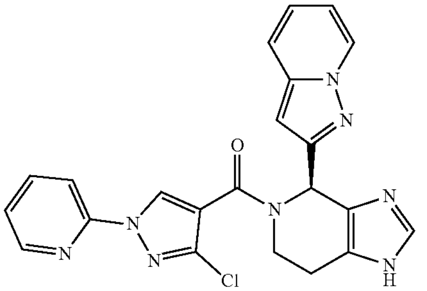 [SMILES: O=C(c1cn(-c2ccccn2)nc1Cl)N1CCc2[nH]cnc2[C@@H]1c1cc2ccccn2n1] | (R)-(3-chloro-1-(pyridin-2-yl)-1H-pyrazol-4-yl)(4-(pyrazolo[1,5-a]pyridin-2-yl)-6,7-dihydro-1H-imidazo[4,5-c]pyridin-5(4H)-yl)methanone |
| 676 | 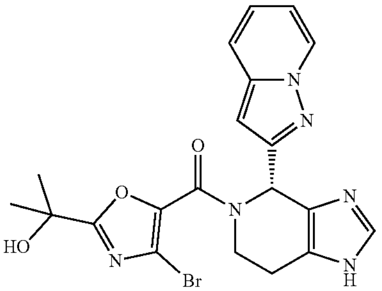 [SMILES: CC(C)(O)c1nc(Br)c(C(=O)N2CCc3[nH]cnc3[C@H]2c2cc3ccccn3n2)o1] | (S)-(4-bromo-2-(2-hydroxypropan-2-yl)oxazol-5-yl)(4-(pyrazolo[1,5-a]pyridin-2-yl)-6,7-dihydro-1H-imidazo[4,5-c]pyridin-5(4H)-yl)methanone |
| 677 | 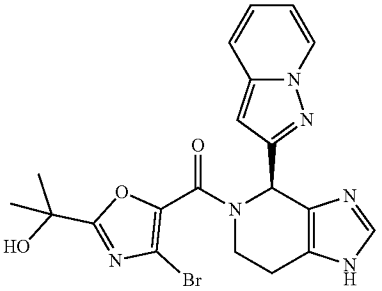 [SMILES: CC(C)(O)c1nc(Br)c(C(=O)N2CCc3[nH]cnc3[C@@H]2c2cc3ccccn3n2)o1] | (R)-(4-bromo-2-(2-hydroxypropan-2-yl)oxazol-5-yl)(4-(pyrazolo[1,5-a]pyridin-2-yl)-6,7-dihydro-1H-imidazo[4,5-c]pyridin-5(4H)-yl)methanone |
| 678 | 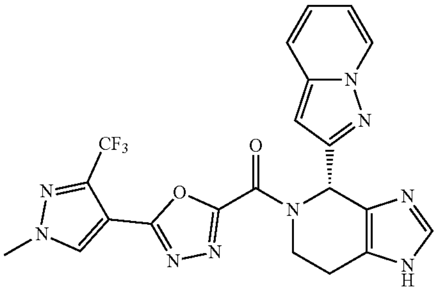 [SMILES: Cn1cc(-c2nnc(C(=O)N3CCc4[nH]cnc4[C@H]3c3cc4ccccn4n3)o2)c(C(F)(F)F)n1] | (S)-(5-(1-methyl-3-(trifluoromethyl)-1H-pyrazol-4-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 679 | 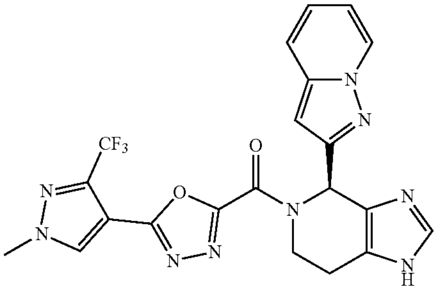 [SMILES: Cn1cc(-c2nnc(C(=O)N3CCc4[nH]cnc4[C@@H]3c3cc4ccccn4n3)o2)c(C(F)(F)F)n1] | (R)-(5-(1-methyl-3-(trifluoromethyl)-1H-pyrazol-4-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 680 | 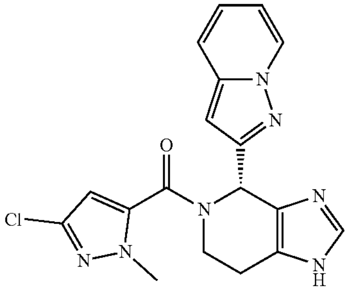 [SMILES: Cn1nc(Cl)cc1C(=O)N1CCc2[nH]cnc2[C@H]1c1cc2ccccn2n1] | (S)-(3-chloro-1-methyl-1H-pyrazol-5-yl)(4-(pyrazolo[1,5-a]pyridin-2-yl)-6,7-dihydro-1H-imidazo[4,5-c]pyridin-5(4H)-yl)methanone |
| 681 | 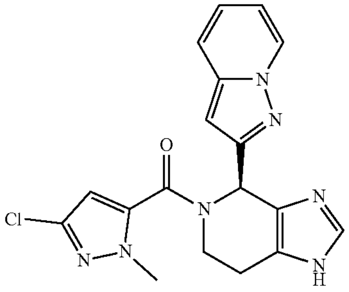 [SMILES: Cn1nc(Cl)cc1C(=O)N1CCc2[nH]cnc2[C@@H]1c1cc2ccccn2n1] | (R)-(3-chloro-1-methyl-1H-pyrazol-5-yl)(4-(pyrazolo[1,5-a]pyridin-2-yl)-6,7-dihydro-1H-imidazo[4,5-c]pyridin-5(4H)-yl)methanone |
| 682 | 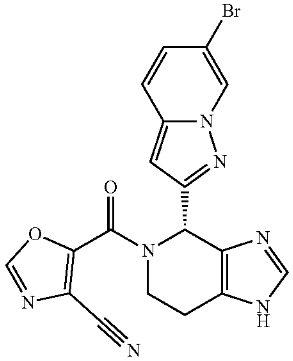 [SMILES: N#Cc1ncoc1C(=O)N1CCc2[nH]cnc2[C@H]1c1cc2ccc(Br)cn2n1] | (S)-5-(4-(6-bromopyrazolo[1,5-a]pyridin-2-yl)-4,5,6,7-tetrahydro-1H-imidazo[4,5-c]pyridine-5-carbonyl)oxazole-4-carbonitrile |

TABLE 1-continued

| Pyrazolo[1,5-a]pyridines | | |
|---|---|---|
| Ex. # | Structure | Name |
| 683 | 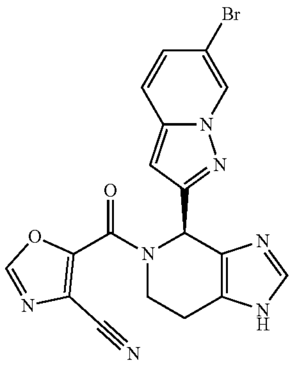 [SMILES: N#Cc1ncoc1C(=O)N1CCc2[nH]cnc2[C@@H]1c1cc2ccc(Br)cn2n1] | (R)-5-(4-(6-bromopyrazolo [1,5-a]pyridin-2-yl)-4,5,6,7-tetrahydro-1H-imidazo [4,5-c]pyridine-5-carbonyl) oxazole-4-carbonitrile |
| 684 | 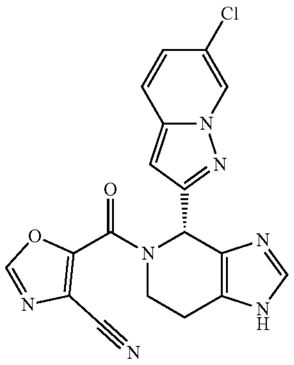 [SMILES: N#Cc1ncoc1C(=O)N1CCc2[nH]cnc2[C@H]1c1cc2ccc(Cl)cn2n1] | (S)-5-(4-(6-chloropyrazolo [1,5-a]pyridin-2-yl)-4,5,6,7-tetrahydro-1H-imidazo[4,5-c] pyridine-5-carbonyl) oxazole-4-carbonitrile |
| 685 | 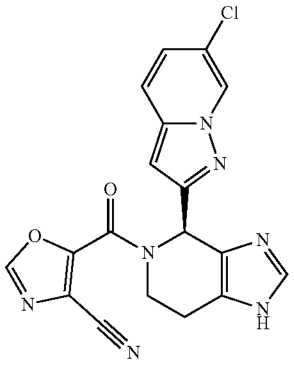 [SMILES: N#Cc1ncoc1C(=O)N1CCc2[nH]cnc2[C@@H]1c1cc2ccc(Cl)cn2n1] | (R)-5-(4-(6-chloropyrazolo [1,5-a]pyridin-2-yl)-4,5,6,7-tetrahydro-1H-imidazo[4,5-c] pyridine-5-carbonyl) oxazole-4-carbonitrile |
| 686 | 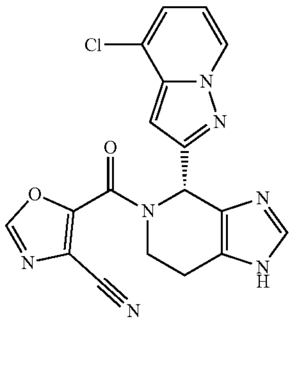 [SMILES: N#Cc1ncoc1C(=O)N1CCc2[nH]cnc2[C@H]1c1cc2c(Cl)cccn2n1] | (S)-5-(4-(4-chloropyrazolo [1,5-a]pyridin-2-yl)-4,5,6,7-tetrahydro-1H-imidazo[4,5-c] pyridine-5-carbonyl) oxazole-4-carbonitrile |

TABLE 1-continued

| Pyrazolo[1,5-a]pyridines | | |
|---|---|---|
| Ex. # | Structure | Name |
| 687 | 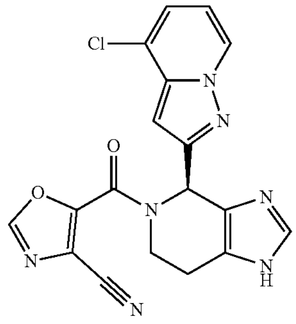 [SMILES: N#Cc1ncoc1C(=O)N1CCc2[nH]cnc2[C@@H]1c1cc2c(Cl)cccn2n1] | (R)-5-(4-(4-chloropyrazolo[1,5-a]pyridin-2-yl)-4,5,6,7-tetrahydro-1H-imidazo[4,5-c]pyridine-5-carbonyl)oxazole-4-carbonitrile |
| 688 | 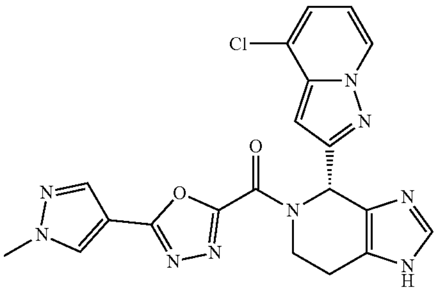 [SMILES: Cn1cc(-c2nnc(C(=O)N3CCc4[nH]cnc4[C@H]3c3cc4c(Cl)cccn4n3)o2)cn1] | (S)-(4-(4-chloropyrazolo[1,5-a]pyridin-2-yl)-6,7-dihydro-1H-imidazo[4,5-c]pyridin-5(4H)-yl)(5-(1-methyl-1H-pyrazol-4-yl)-1,3,4-oxadiazol-2-yl)methanone |
| 689 | 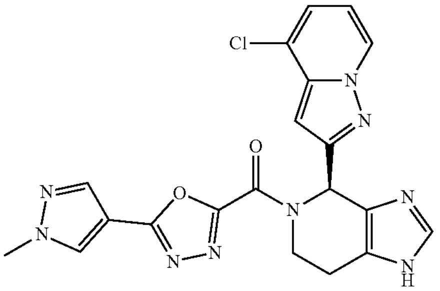 [SMILES: Cn1cc(-c2nnc(C(=O)N3CCc4[nH]cnc4[C@@H]3c3cc4c(Cl)cccn4n3)o2)cn1] | (R)-(4-(4-chloropyrazolo[1,5-a]pyridin-2-yl)-6,7-dihydro-1H-imidazo[4,5-c]pyridin-5(4H)-yl)(5-(1-methyl-1H-pyrazol-4-yl)-1,3,4-oxadiazol-2-yl)methanone |
| 690 | 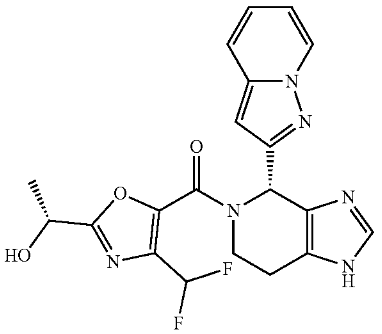 [SMILES: C[C@@H](O)c1nc(C(F)F)c(C(=O)N2CCc3[nH]cnc3[C@H]2c2cc3ccccn3n2)o1] | (4-(difluoromethyl)-2-((R)-1-hydroxyethyl)oxazol-5-yl)((S)-4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 691 | 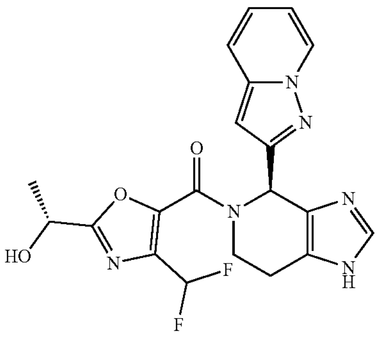 [SMILES: C[C@@H](O)c1nc(C(F)F)c(C(=O)N2CCc3[nH]cnc3[C@@H]2c2cc3ccccn3n2)o1] | (4-(difluoromethyl)-2-((R)-1-hydroxyethyl)oxazol-5-yl)((R)-4-(pyrazolo[1,5-a]pyridin-2-yl)-6,7-dihydro-1H-imidazo[4,5-c]pyridin-5(4H)-yl)methanone |
| 692 | 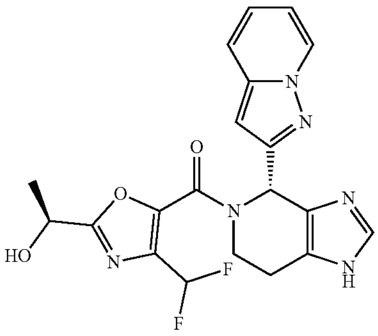 [SMILES: C[C@H](O)c1nc(C(F)F)c(C(=O)N2CCc3[nH]cnc3[C@H]2c2cc3ccccn3n2)o1] | (4-(difluoromethyl)-2-((S)-1-hydroxyethyl)oxazol-5-yl)((S)-4-(pyrazolo[1,5-a]pyridin-2-yl)-6,7-dihydro-1H-imidazo[4,5-c]pyridin-5(4H)-yl)methanone |
| 693 | 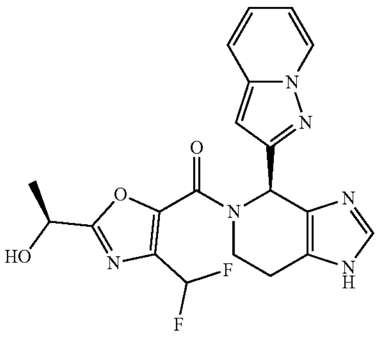 [SMILES: C[C@H](O)c1nc(C(F)F)c(C(=O)N2CCc3[nH]cnc3[C@@H]2c2cc3ccccn3n2)o1] | (4-(difluoromethyl)-2-((S)-1-hydroxyethyl)oxazol-5-yl)((R)-4-(pyrazolo[1,5-a]pyridin-2-yl)-6,7-dihydro-1H-imidazo[4,5-c]pyridin-5(4H)-yl)methanone |
| 694 | 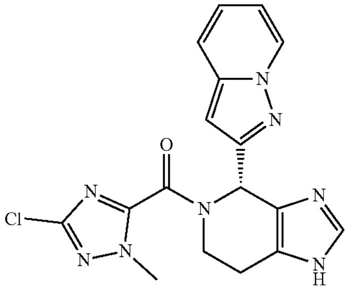 [SMILES: Cn1nc(Cl)nc1C(=O)N1CCc2[nH]cnc2[C@H]1c1cc2ccccn2n1] | (S)-(3-chloro-1-methyl-1H-1,2,4-triazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 695 | 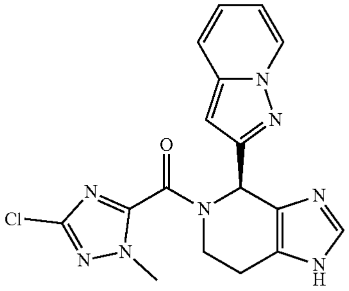 [SMILES: Cn1nc(Cl)nc1C(=O)N1CCc2[nH]cnc2[C@@H]1c1cc2ccccn2n1] | (R)-(3-chloro-1-methyl-1H-1,2,4-triazol-5-yl)(4-(pyrazolo[1,5-a]pyridin-2-yl)-6,7-dihydro-1H-imidazo[4,5-c]pyridin-5(4H)-yl)methanone |
| 696 | 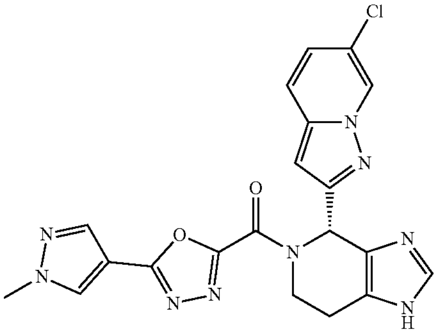 [SMILES: Cn1cc(-c2nnc(C(=O)N3CCc4[nH]cnc4[C@H]3c3cc4ccc(Cl)cn4n3)o2)cn1] | (S)-(4-(6-chloropyrazolo[1,5-a]pyridin-2-yl)-6,7-dihydro-1H-imidazo[4,5-c]pyridin-5(4H)-yl)(5-(1-methyl-1H-pyrazol-4-yl)-1,3,4-oxadiazol-2-yl)methanone |
| 697 | 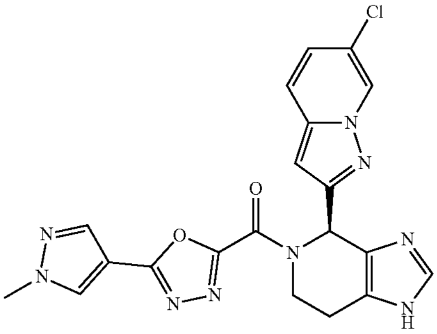 | (R)-(4-(6-chloropyrazolo[1,5-a]pyridin-2-yl)-6,7-dihydro-1H-imidazo[4,5-c]pyridin-5(4H)-yl)(5-(1-methyl-1H-pyrazol-4-yl)-1,3,4-oxadiazol-2-yl)methanone |
| 698 | 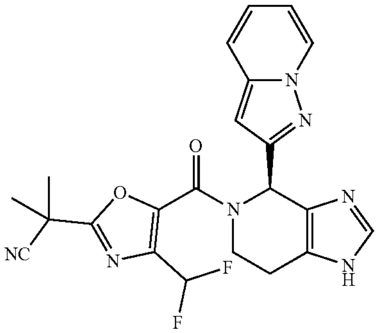 [SMILES: CC(C)(C#N)c1nc(C(F)F)c(C(=O)N2CCc3[nH]cnc3[C@@H]2c2cc3ccccn3n2)o1] | (R)-2-(4-(difluoromethyl)-5-(4-(pyrazolo[1,5-a]pyridin-2-yl)-4,5,6,7-tetrahydro-1H-imidazo[4,5-c]pyridine-5-carbonyl)oxazol-2-yl)-2-methylpropanenitrile |

TABLE 1-continued

| Ex. # | Structure | Name |
|---|---|---|
| | Pyrazolo[1,5-a]pyridines | |
| 699 | 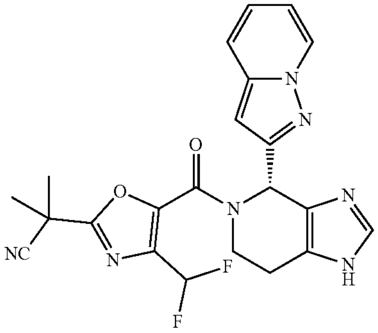 | (S)-2-(4-(difluoromethyl)-5-(4-(pyrazolo[1,5-a]pyridin-2-yl)-4,5,6,7-tetrahydro-1H-imidazo[4,5-c]pyridine-5-carbonyl)oxazol-2-yl)-2-methylpropanenitrile |
| 700 | 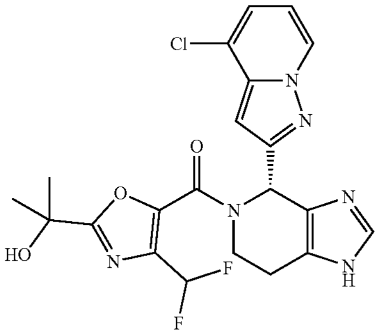 [SMILES: CC(C)(O)c1nc(C(F)F)c(C(=O)N2CCc3[nH]cnc3[C@H]2c2cc3c(Cl)cccn3n2)o1] | (S)-(4-(4-chloropyrazolo[1,5-a]pyridin-2-yl)-6,7-dihydro-1H-imidazo[4,5-c]pyridin-5(4H)-yl)(4-(difluoromethyl)-2-(2-hydroxypropan-2-yl)oxazol-5-yl)methanone |
| 701 | 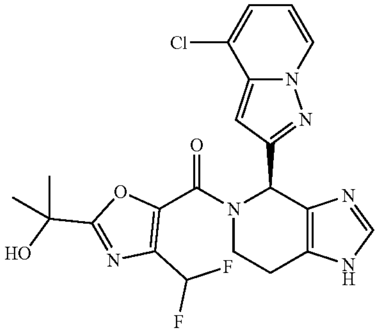 [SMILES: CC(C)(O)c1nc(C(F)F)c(C(=O)N2CCc3[nH]cnc3[C@@H]2c2cc3c(Cl)cccn3n2)o1] | (R)-(4-(4-chloropyrazolo[1,5-a]pyridin-2-yl)-6,7-dihydro-1H-imidazo[4,5-c]pyridin-5(4H)-yl)(4-(difluoromethyl)-2-(2-hydroxypropan-2-yl)oxazol-5-yl)methanone |
| 702 | 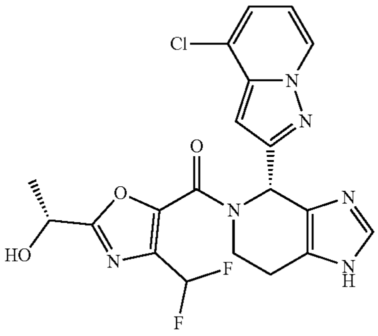 [SMILES: C[C@@H](O)c1nc(C(F)F)c(C(=O)N2CCc3[nH]cnc3[C@H]2c2cc3c(Cl)cccn3n2)o1] | ((S)-4-(4-chloropyrazolo[1,5-a]pyridin-2-yl)-6,7-dihydro-1H-imidazo[4,5-c]pyridin-5(4H)-yl)(4-(difluoromethyl)-2-((R)-1-hydroxyethyl)oxazol-5-yl)methanone |

TABLE 1-continued

| Pyrazolo[1,5-a]pyridines | | |
|---|---|---|
| Ex. # | Structure | Name |
| 703 | 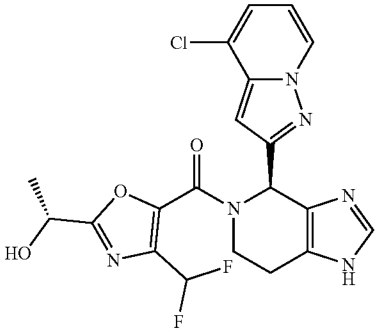 [SMILES: C[C@@H](O)c1nc(C(F)F)c(C(=O)N2CCc3[nH]cnc3[C@@H]2c2cc3c(Cl)cccn3n2)o1] | ((R)-4-(4-chloropyrazolo[1,5-a]pyridin-2-yl)-6,7-dihydro-1H-imidazo[4,5-c]pyridin-5(4H)-yl)(4-(difluoromethyl)-2-((R)-1-hydroxyethyl)oxazol-5-yl)methanone |
| 704 | 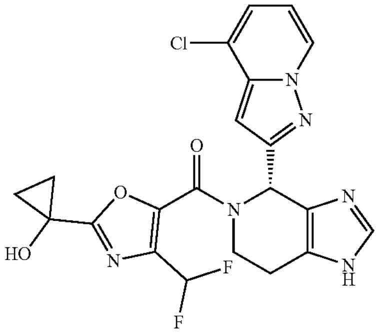 [SMILES: O=C(c1oc(C2(O)CC2)nc1C(F)F)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(4-(difluoromethyl)-2-(1-hydroxycyclopropyl)oxazol-5-yl)methanone |
| 705 | 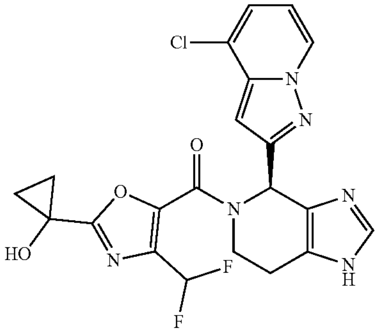 [SMILES: O=C(c1oc(C2(O)CC2)nc1C(F)F)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(4-(difluoromethyl)-2-(1-hydroxycyclopropyl)oxazol-5-yl)methanone |
| 706 | 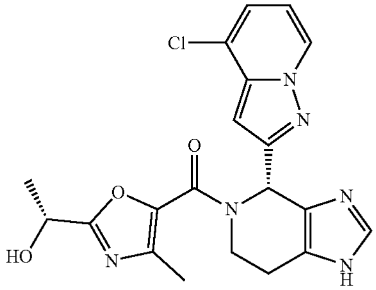 [SMILES: Cc1nc([C@@H](C)O)oc1C(=O)N1CCc2[nH]cnc2[C@H]1c1cc2c(Cl)cccn2n1] | ((S)-4-(4-chloropyrazolo[1,5-a]pyridin-2-yl)-6,7-dihydro-1H-imidazo[4,5-c]pyridin-5(4H)-yl)(2-((R)-1-hydroxyethyl)-4-methyloxazol-5-yl)methanone |

TABLE 1-continued

Pyrazolo[1,5-a]pyridines

| Ex. # | Structure | Name |
|---|---|---|
| 707 | 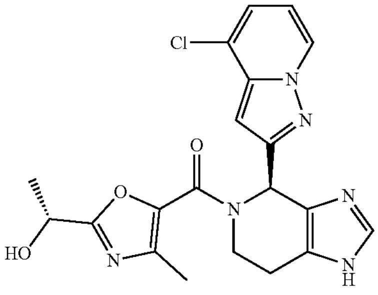 [SMILES: Cc1nc([C@@H](C)O)oc1C(=O)N1CCc2[nH]cnc2[C@@H]1c1cc2c(Cl)cccn2n1] | ((R)-4-(4-chloropyrazolo [1,5-a]pyridin-2-yl)-6,7-dihydro-1H-imidazo[4,5-c] pyridin-5(4H)-yl)(2-((R)-1-hydroxyethyl)-4-methyloxazol-5-yl)methanone |
| 708 | 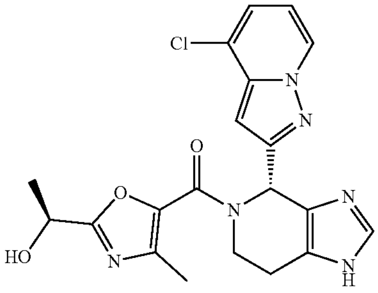 [SMILES: Cc1nc([C@H](C)O)oc1C(=O)N1CCc2[nH]cnc2[C@H]1c1cc2c(Cl)cccn2n1] | ((S)-4-(4-chloropyrazolo [1,5-a]pyridin-2-yl)-6,7-dihydro-1H-imidazo[4,5-c] pyridin-5(4H)-yl)(2-((S)-1-hydroxyethyl)-4-methyloxazol-5-yl)methanone |
| 709 | 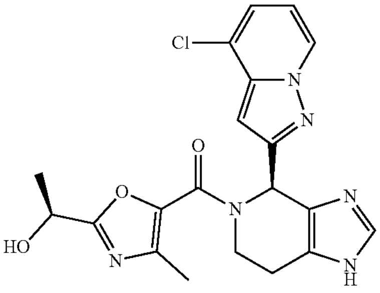 [SMILES: Cc1nc([C@H](C)O)oc1C(=O)N1CCc2[nH]cnc2[C@@H]1c1cc2c(Cl)cccn2n1] | ((R)-4-(4-chloropyrazolo [1,5-a]pyridin-2-yl)-6,7-dihydro-1H-imidazo[4,5-c] pyridin-5(4H)-yl)(2-((S)-1-hydroxyethyl)-4-methyloxazol-5-yl)methanone |
| 710 | 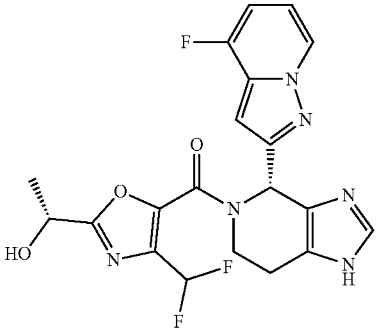 [SMILES: C[C@@H](O)c1nc(C(F)F)c(C(=O)N2CCc3[nH]cnc3[C@H]2c2cc3c(F)cccn3n2)o1] | (4-(difluoromethyl)-2-((R)-1-hydroxyethyl)oxazol-5-yl)((S)-4-(4-fluoropyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 711 | 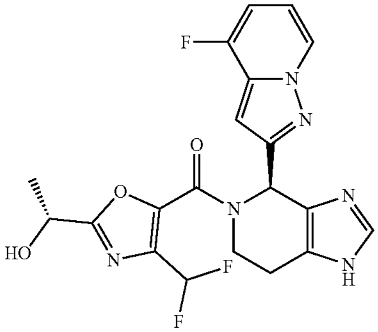 | (4-(difluoromethyl)-2-((R)-1-hydroxyethyl)oxazol-5-yl)((R)-4-(4-fluoropyrazolo[1,5-a]pyridin-2-yl)-6,7-dihydro-1H-imidazo[4,5-c]pyridin-5(4H)-yl)methanone |
| 712 | 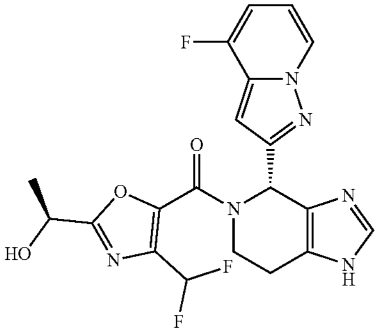 [SMILES: C[C@H](O)c1nc(C(F)F)c(C(=O)N2CCc3[nH]cnc3[C@H]2c2cc3c(F)cccn3n2)o1] | (4-(difluoromethyl)-2-((S)-1-hydroxyethyl)oxazol-5-yl)((S)-4-(4-fluoropyrazolo[1,5-a]pyridin-2-yl)-6,7-dihydro-1H-imidazo[4,5-c]pyridin-5(4H)-yl)methanone |
| 713 | 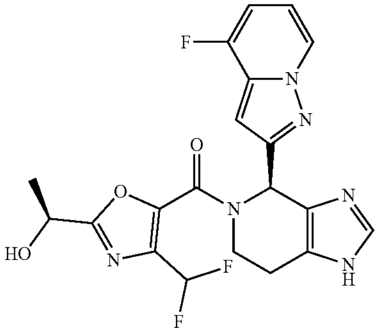 [SMILES: C[C@H](O)c1nc(C(F)F)c(C(=O)N2CCc3[nH]cnc3[C@@H]2c2cc3c(F)cccn3n2)o1] | (4-(difluoromethyl)-2-((S)-1-hydroxyethyl)oxazol-5-yl)((R)-4-(4-fluoropyrazolo[1,5-a]pyridin-2-yl)-6,7-dihydro-1H-imidazo[4,5-c]pyridin-5(4H)-yl)methanone |
| 714 | 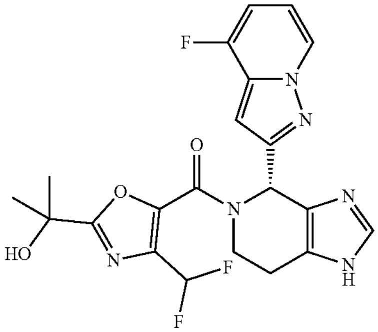 [SMILES: CC(C)(O)c1nc(C(F)F)c(C(=O)N2CCc3[nH]cnc3[C@H]2c2cc3c(F)cccn3n2)o1] | (S)-(4-(difluoromethyl)-2-(2-hydroxypropan-2-yl)oxazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 715 | 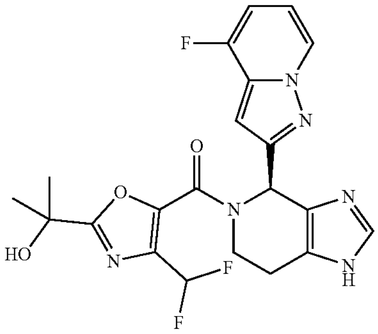 | (R)-(4-(difluoromethyl)-2-(2-hydroxypropan-2-yl)oxazol-5-yl)(4-(4-fluoropyrazolo[1,5-a]pyridin-2-yl)-6,7-dihydro-1H-imidazo[4,5-c]pyridin-5(4H)-yl)methanone |
| 716 | 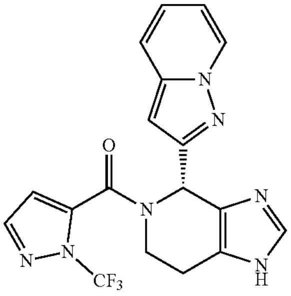 [SMILES: O=C(c1ccnn1C(F)(F)F)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(1-(trifluoromethyl)-1H-pyrazol-5-yl)methanone |
| 717 | 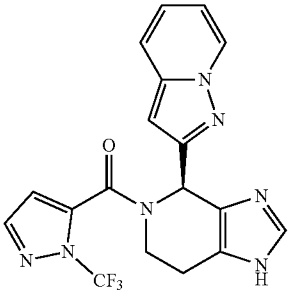 [SMILES: O=C(c1ccnn1C(F)(F)F)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(1-(trifluoromethyl)-1H-pyrazol-5-yl)methanone |
| 718 | 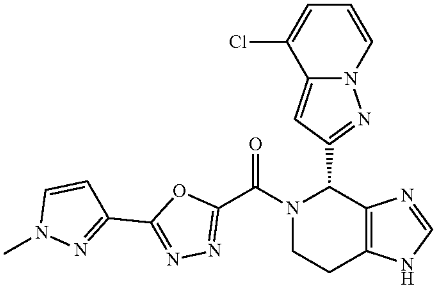 [SMILES: Cn1ccc(-c2nnc(C(=O)N3CCc4[nH]cnc4[C@H]3c3cc4c(Cl)cccn4n3)o2)n1] | (S)-(4-(4-chloropyrazolo[1,5-a]pyridin-2-y]l)-6,7-dihydro-1H-imidazo[4,5-c]pyridin-5(4H)-yl)(5-(1-methyl-1H-pyrazol-3-yl)-1,3,4-oxadiazol-2-yl)methanone |
| 719 | 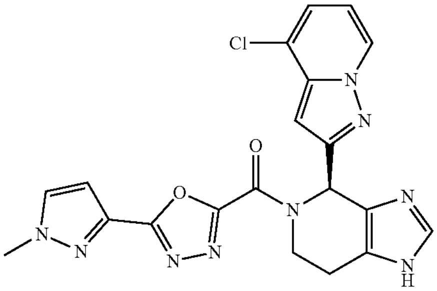 [SMILES: Cn1ccc(-c2nnc(C(=O)N3CCc4[nH]cnc4[C@@H]3c3cc4c(Cl)cccn4n3)o2)n1] | (R)-(4-(4-chloropyrazolo[1,5-a]pyridin-2-yl)-6,7-dihydro-1H-imidazo[4,5-c]pyridin-5(4H)-yl)(5-(1-methyl-1H-pyrazol-3-yl)-1,3,4-oxadiazol-2-yl)methanone |

TABLE 1-continued

| Ex. # | Structure | Name |
|---|---|---|
| | Pyrazolo[1,5-a]pyridines | |
| 720 | 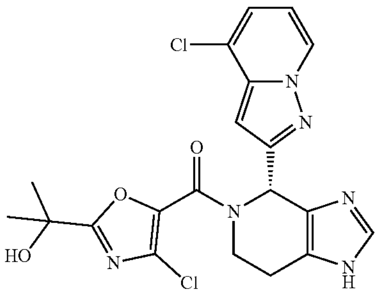 | (S)-(4-chloro-2-(2-hydroxypropan-2-yl)oxazol-5-yl)(4-(4-chloropyrazolo[1,5-a]pyridin-2-yl)-6,7-dihydro-1H-imidazo[4,5-c]pyridin-5(4H)-yl)methanone |
| 721 | 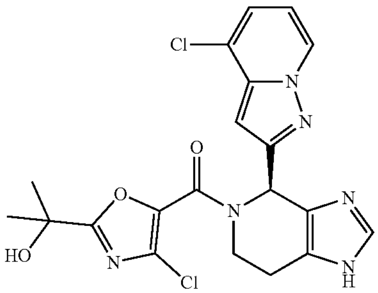 [SMILES: CC(C)(O)c1nc(Cl)c(C(=O)N2CCc3[nH]cnc3[C@@H]2c2cc3c(Cl)cccn3n2)o1] | (R)-(4-chloro-2-(2-hydroxypropan-2-yl)oxazol-5-yl)(4-(4-chloropyrazolo[1,5-a]pyridin-2-yl)-6,7-dihydro-1H-imidazo[4,5-c]pyridin-5(4H)-yl)methanone |
| 722 | 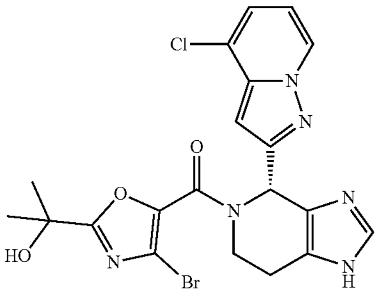 [SMILES: CC(C)(O)c1nc(Br)c(C(=O)N2CCc3[nH]cnc3[C@H]2c2cc3c(Cl)cccn3n2)o1] | (S)-(4-bromo-2-(2-hydroxypropan-2-yl)oxazol-5-yl)(4-(4-chloropyrazolo[1,5-a]pyridin-2-yl)-6,7-dihydro-1H-imidazo[4,5-c]pyridin-5(4H)-yl)methanone |
| 723 | 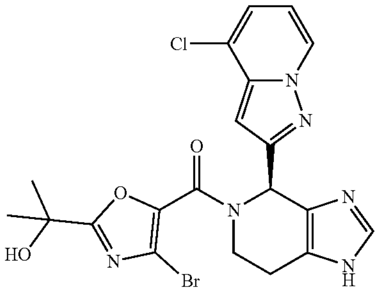 [SMILES: CC(C)(O)c1nc(Br)c(C(=O)N2CCc3[nH]cnc3[C@@H]2c2cc3c(Cl)cccn3n2)o1] | (R)-(4-bromo-2-(2-hydroxypropan-2-yl)oxazol-5-yl)(4-(4-chloropyrazolo[1,5-a]pyridin-2-yl)-6,7-dihydro-1H-imidazo[4,5-c]pyridin-5(4H)-yl)methanone |
| 724 | 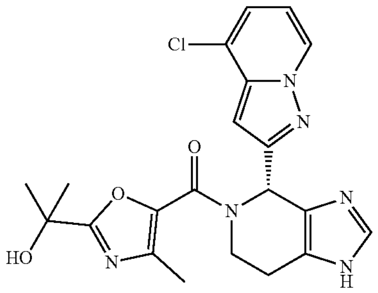 [SMILES: Cc1nc(C(C)(C)O)oc1C(=O)N1CCc2[nH]cnc2[C@H]1c1cc2c(Cl)cccn2n1] | (S)-(4-(4-chloropyrazolo[1,5-a]pyridin-2-y]l)-6,7-dihydro-1H-imidazo[4,5-c]pyridin-5(4H)-yl)(2-(2-hydroxypropan-2-yl)-4-methyloxazol-5-yl)methanone |

TABLE 1-continued

| Pyrazolo[1,5-a]pyridines | | |
|---|---|---|
| Ex. # | Structure | Name |
| 725 | 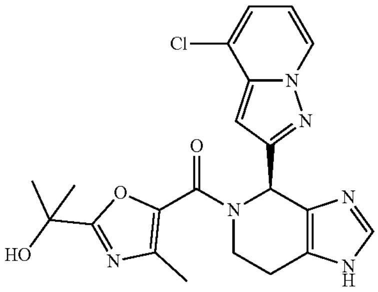 [SMILES: Cc1nc(C(C)(C)O)oc1C(=O)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(2-(2-hydroxypropan-2-yl)-4-methyloxazol-5-yl)methanone |
| 726 | 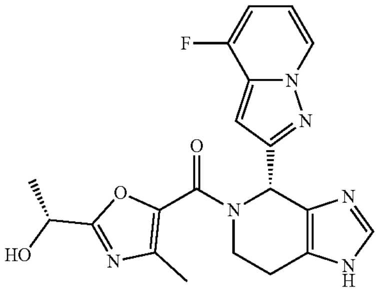 [SMILES: Cc1nc([C@@H](C)O)oc1C(=O)N1CCc2[nH]cnc2[C@H]1c1cc2c(F)cccn2n1] | ((S)-4-(4-fluoropyrazolo[1,5-a]pyridin-2-yl)-6,7-dihydro-1H-imidazo[4,5-c]pyridin-5(4H)-yl)(2-((R)-1-hydroxyethyl)-4-methyloxazol-5-yl)methanone |
| 727 | 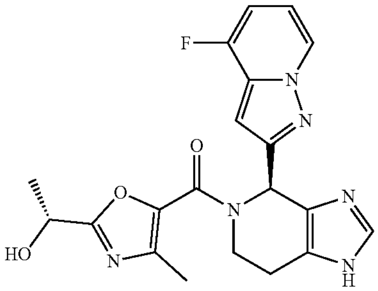 | ((R)-4-(4-fluoropyrazolo[1,5-a]pyridin-2-yl)-6,7-dihydro-1H-imidazo[4,5-c]pyridin-5(4H)-yl)(2-((R)-1-hydroxyethyl)-4-methyloxazol-5-yl)methanone |
| 728 | 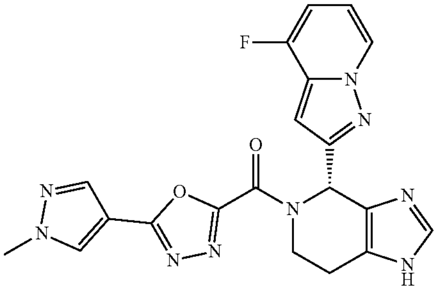 [SMILES: Cn1cc(-c2nnc(C(=O)N3CCc4[nH]cnc4[C@H]3c3cc4c(F)cccn4n3)o2)cn1] | (S)-(4-(4-fluoropyrazolo[1,5-a]pyridin-2-yl)-6,7-dihydro-1H-imidazo[4,5-c]pyridin-5(4H)-yl)(5-(1-methyl-1H-pyrazol-4-yl)-1,3,4-oxadiazol-2-yl)methanone |
| 729 | 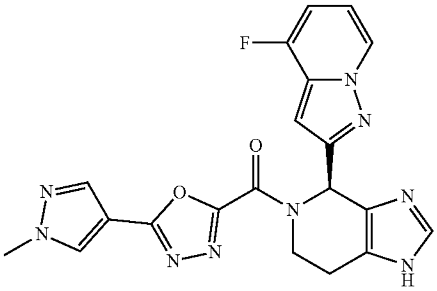 [SMILES: Cn1cc(-c2nnc(C(=O)N3CCc4[nH]cnc4[C@@H]3c3cc4c(F)cccn4n3)o2)cn1] | (R)-(4-(4-fluoropyrazolo[1,5-a]pyridin-2-yl)-6,7-dihydro-1H-imidazo[4,5-c]pyridin-5(4H)-yl)(5-(1-methyl-1H-pyrazol-4-yl)-1,3,4-oxadiazol-2-yl)methanone |

TABLE 1-continued

Pyrazolo[1,5-a]pyridines

| Ex. # | Structure | Name |
|---|---|---|
| 730 | 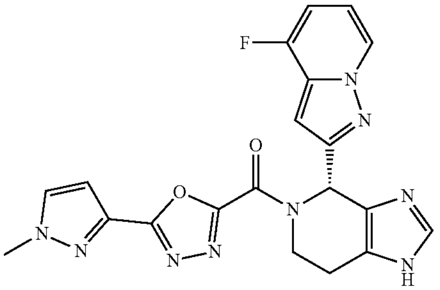 [SMILES: Cn1ccc(-c2nnc(C(=O)N3CCc4[nH]cnc4[C@H]3c3cc4c(F)cccn4n3)o2)n1] | (S)-(4-(4-fluoropyrazolo [1,5-a]pyridin-2-yl)-6,7-dihydro-1H-imidazo[4,5-c]pyridin-5(4H)-yl)(5-(1-methyl-1H-pyrazol-3-yl)-1,3,4-oxadiazol-2-yl)methanone |
| 731 | 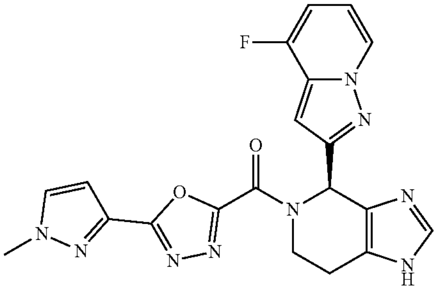 [SMILES: Cn1ccc(-c2nnc(C(=O)N3CCc4[nH]cnc4[C@@H]3c3cc4c(F)cccn4n3)o2)n1] | (R)-(4-(4-fluoropyrazolo [1,5-a]pyridin-2-yl)-6,7-dihydro-1H-imidazo[4,5-c]pyridin-5(4H)-yl)(5-(1-methyl-1H-pyrazol-3-yl)-1,3,4-oxadiazol-2-yl)methanone |
| 732 | 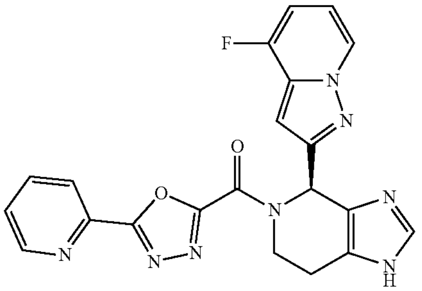 [SMILES: O=C(c1nnc(-c2ccccn2)o1)N1CCc2[nH]cnc2[C@@H]1c1cc2c(F)cccn2n1] | (R)-(4-(4-fluoropyrazolo [1,5-a]pyridin-2-yl)-6,7-dihydro-1H-imidazo[4,5-c] pyridin-5(4H)-yl)(5-(pyridin-2-yl)-1,3,4-oxadiazol-2-yl)methanone |
| 733 | 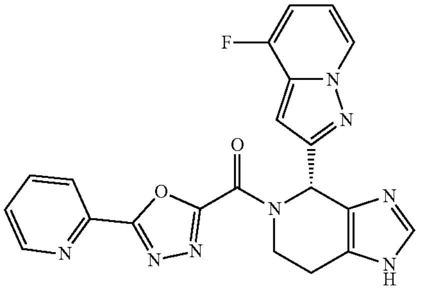 [SMILES: O=C(c1nnc(-c2ccccn2)o1)N1CCc2[nH]cnc2[C@H]1c1cc2c(F)cccn2n1] | (S)-(4-(4-fluoropyrazolo [1,5-a]pyridin-2-yl)-6,7-dihydro-1H-imidazo[4,5-c] pyridin-5(4H)-yl)(5-(pyridin-2-yl)-1,3,4-oxadiazol-2-yl)methanone |
| 734 | 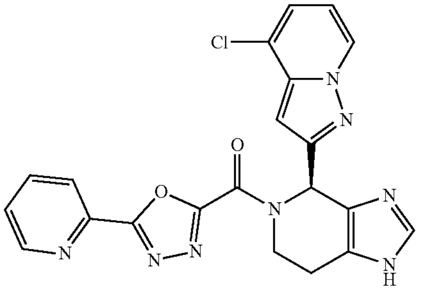 [SMILES: O=C(c1nnc(-c2ccccn2)o1)N1CCc2[nH]cnc2[C@@H]1c1cc2c(Cl)cccn2n1] | (R)-(4-(4-chloropyrazolo[1,5-a] pyridin-2-yl)-6,7-dihydro-1H-imidazo[4,5-c]pyridin-5(4H)-yl) (5-(pyridin-2-yl)-1,3,4-oxadiazol-2-yl)methanone |

TABLE 1-continued

| Pyrazolo[1,5-a]pyridines | | |
|---|---|---|
| Ex. # | Structure | Name |
| 735 | 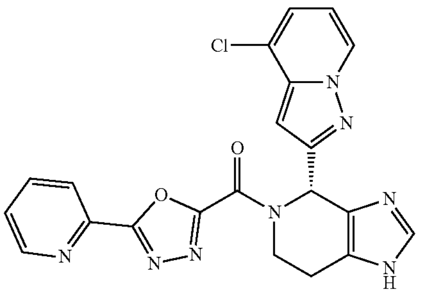 [SMILES: O=C(c1nnc(-c2ccccn2)o1)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 736 | 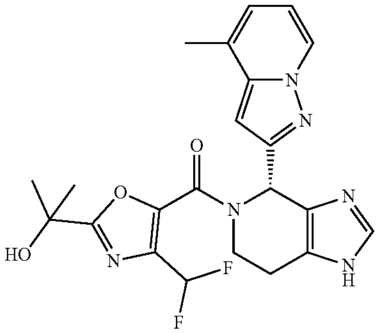 [SMILES: Cc1cccn2nc([C@@H]3c4nc[nH]c4CCN3C(=O)c3oc(C(C)(C)O)nc3C(F)F)cc12] | (S)-(4-(difluoromethyl)-2-(2-hydroxypropan-2-yl)oxazol-5-yl)(4-(4-methylpyrazolo[1,5-a]pyridin-2-yl)-6,7-dihydro-1H-imidazo[4,5-c]pyridin-5(4H)-yl)methanone |
| 737 | 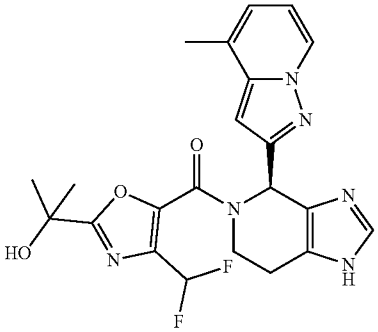 [SMILES: Cc1cccn2nc([C@H]3c4nc[nH]c4CCN3C(=O)c3oc(C(C)(C)O)nc3C(F)F)cc12] | (R)-(4-(difluoromethyl)-2-(2-hydroxypropan-2-yl)oxazol-5-yl)(4-(4-methylpyrazolo[1,5-a]pyridin-2-yl)-6,7-dihydro-1H-imidazo[4,5-c]pyridin-5(4H)-yl)methanone |
| 738 | 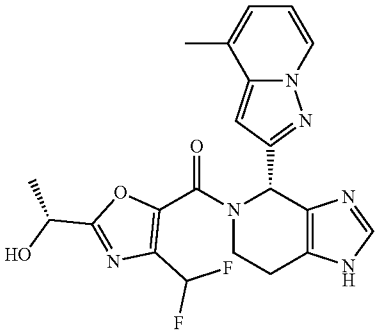 [SMILES: Cc1cccn2nc([C@@H]3c4nc[nH]c4CCN3C(=O)c3oc([C@@H](C)O)nc3C(F)F)cc12] | (4-(difluoromethyl)-2-((R)-1-hydroxyethyl)oxazol-5-yl)((S)-4-(4-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 739 | 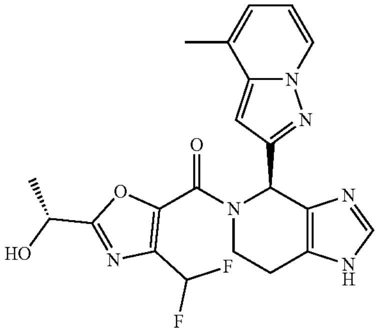 | (4-(difluoromethyl)-2-((R)-1-hydroxyethyl)oxazol-5-yl)((R)-4-(4-methylpyrazolo[1,5-a]pyridin-2-yl)-6,7-dihydro-1H-imidazo[4,5-c]pyridin-5(4H)-yl)methanone |
| 740 | 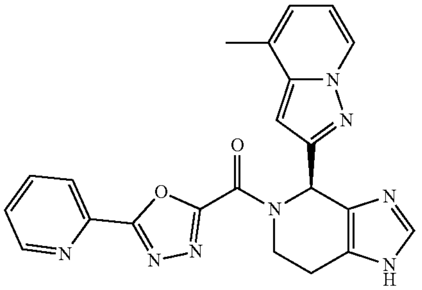 | (R)-(4-(4-methylpyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 741 | 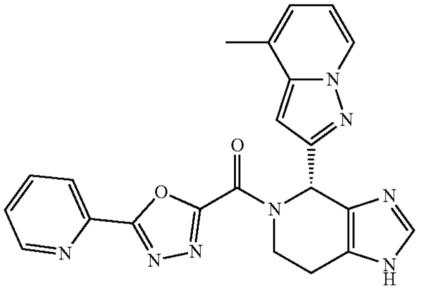 [SMILES: Cc1cccn2nc([C@@H]3c4nc[nH]c4CCN3C(=O)c3nnc(-c4ccccn4)o3)cc12] | (S)-(4-(4-methylpyrazolo[1,5-a]pyridin-2-y])-6,7-dihydro-1H-imidazo[4,5-c]pyridin-5(4H)-yl)(5-(pyridin-2-yl)-1,3,4-oxadiazol-2-yl)methanone |
| 742 | 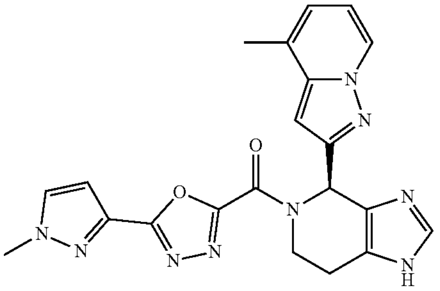 [SMILES: Cc1cccn2nc([C@H]3c4nc[nH]c4CCN3C(=O)c3nnc(-c4ccn(C)n4)o3)cc12] | (R)-(5-(1-methyl-1H-pyrazol-3-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 743 | 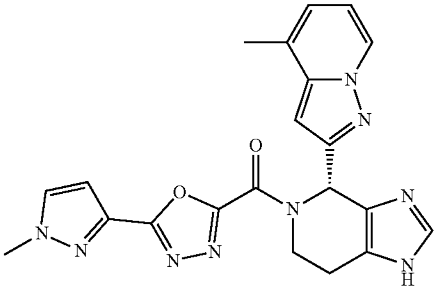 | (S)-(5-(1-methyl-1H-pyrazol-3-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 744 | 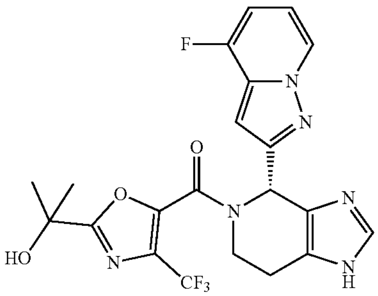 [SMILES: CC(C)(O)c1nc(C(F)(F)F)c(C(=O)N2CCc3[nH]cnc3[C@H]2c2cc3c(F)cccn3n2)o1] | (S)-(4-(4-fluoropyrazolo[1,5-a]pyridin-2-yl)-6,7-dihydro-1H-imidazo[4,5-c]pyridin-5(4H)-yl)(2-(2-hydroxypropan-2-yl)-4-(trifluoromethyl)oxazol-5-yl)methanone |
| 745 | 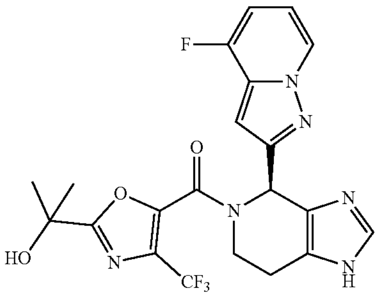 | (R)-(4-(4-fluoropyrazolo[1,5-a]pyridin-2-y])-6,7-dihydro-1H-imidazo[4,5-c]pyridin-5(4H)-yl)(2-(2-hydroxypropan-2-yl)-4-(trifluoromethyl)oxazol-5-yl)methanone |
| 746 | 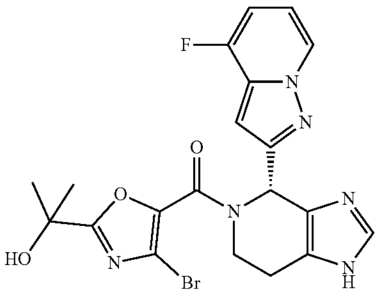 [SMILES: CC(C)(O)c1nc(Br)c(C(=O)N2CCc3[nH]cnc3[C@H]2c2cc3c(F)cccn3n2)o1] | (S)-(4-bromo-2-(2-hydroxypropan-2-yl)oxazol-5-yl)(4-(4-fluoropyrazolo[1,5-a]pyridin-2-yl)-6,7-dihydro-1H-imidazo[4,5-c]pyridin-5(4H)-yl)methanone |
| 747 | 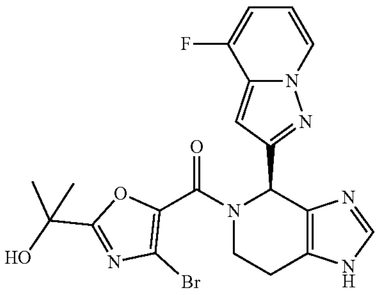 [SMILES: CC(C)(O)c1nc(Br)c(C(=O)N2CCc3[nH]cnc3[C@@H]2c2cc3c(F)cccn3n2)o1] | (R)-(4-bromo-2-(2-hydroxypropan-2-yl)oxazol-5-yl)(4-(4-fluoropyrazolo[1,5-a]pyridin-2-yl)-6,7-dihydro-1H-imidazo[4,5-c]pyridin-5(4H)-yl)methanone |
| 748 | 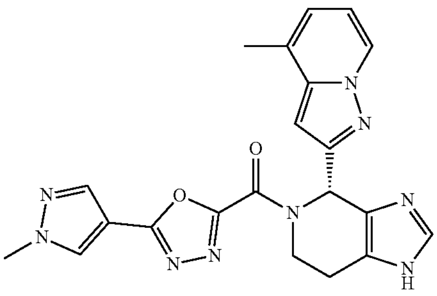 [SMILES: Cc1cccn2nc([C@@H]3c4nc[nH]c4CCN3C(=O)c3nnc(-c4cnn(C)c4)o3)cc12] | (S)-(5-(1-methyl-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 749 | 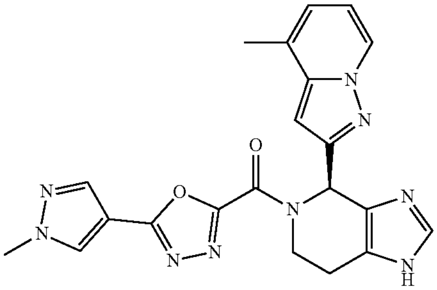 [SMILES: Cc1cccn2nc([C@H]3c4nc[nH]c4CCN3C(=O)c3nnc(-c4cnn(C)c4)o3)cc12] | (R)-(5-(1-methyl-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 750 | 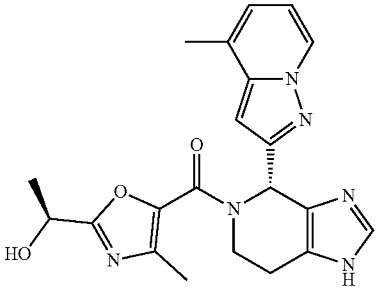 [SMILES: Cc1nc([C@H](C)O)oc1C(=O)N1CCc2[nH]cnc2[C@H]1c1cc2c(C)cccn2n1] | (2-((S)-1-hydroxyethyl)-4-methyloxazol-5-yl)((S)-4-(4-methylpyrazolo[1,5-a]pyridin-2-yl)-6,7-dihydro-1H-imidazo[4,5-c]pyridin-5(4H)-yl)methanone |
| 751 | 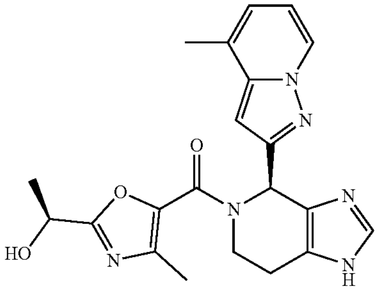 [SMILES: Cc1nc([C@H](C)O)oc1C(=O)N1CCc2[nH]cnc2[C@@H]1c1cc2c(C)cccn2n1] | (2-((S)-1-hydroxyethyl)-4-methyloxazol-5-yl)((R)-4-(4-methylpyrazolo[1,5-a]pyridin-2-yl)-6,7-dihydro-1H-imidazo[4,5-c]pyridin-5(4H)-yl)methanone |
| 752 | 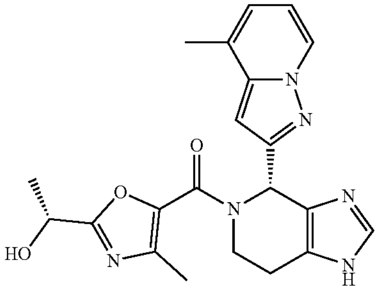 [SMILES: Cc1nc([C@@H](C)O)oc1C(=O)N1CCc2[nH]cnc2[C@H]1c1cc2c(C)cccn2n1] | (2-((R)-1-hydroxyethyl)-4-methyloxazol-5-yl)((S)-4-(4-methylpyrazolo[1,5-a]pyridin-2-yl)-6,7-dihydro-1H-imidazo[4,5-c]pyridin-5(4H)-yl)methanone |
| 753 | 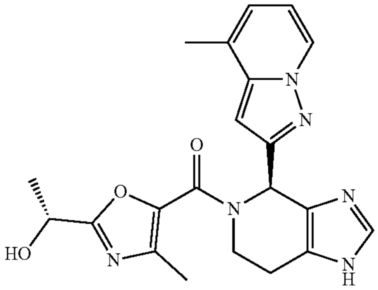 | (2-((R)-1-hydroxyethyl)-4-methyloxazol-5-yl)((R)-4-(4-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 754 | 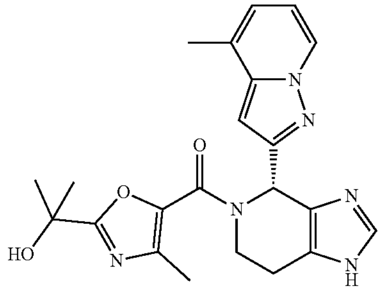 [SMILES: Cc1nc(C(C)(C)O)oc1C(=O)N1CCc2[nH]cnc2[C@H]1c1cc2c(C)cccn2n1] | (S)-(2-(2-hydroxypropan-2-yl)-4-methyloxazol-5-yl)(4-(4-methylpyrazolo[1,5-a]pyridin-2-yl)-6,7-dihydro-1H-imidazo[4,5-c]pyridin-5(4H)-yl)methanone |
| 755 | 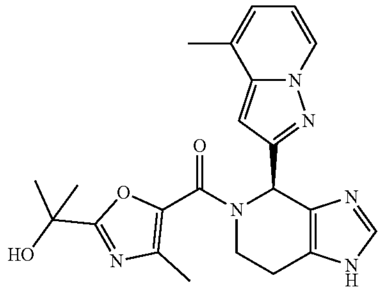 [SMILES: Cc1nc(C(C)(C)O)oc1C(=O)N1CCc2[nH]cnc2[C@@H]1c1cc2c(C)cccn2n1] | (R)-(2-(2-hydroxypropan-2-yl)-4-methyloxazol-5-yl)(4-(4-methylpyrazolo[1,5-a]pyridin-2-yl)-6,7-dihydro-1H-imidazo[4,5-c]pyridin-5(4H)-yl)methanone |
| 756 | 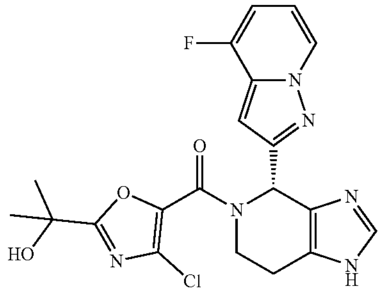 [SMILES: CC(C)(O)c1nc(Cl)c(C(=O)N2CCc3[nH]cnc3[C@H]2c2cc3c(F)cccn3n2)o1] | (S)-(4-chloro-2-(2-hydroxypropan-2-yl)oxazol-5-yl)(4-(4-fluoropyrazolo[1,5-a]pyridin-2-yl)-6,7-dihydro-1H-imidazo[4,5-c]pyridin-5(4H)-yl)methanone |
| 757 | 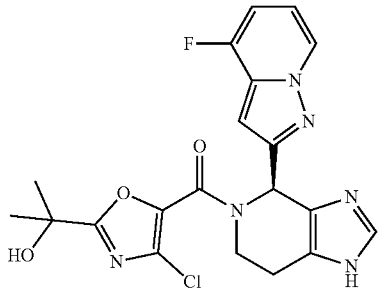 [SMILES: CC(C)(O)c1nc(Cl)c(C(=O)N2CCc3[nH]cnc3[C@@H]2c2cc3c(F)cccn3n2)o1] | (R)-(4-chloro-2-(2-hydroxypropan-2-yl)oxazol-5-yl)(4-(4-fluoropyrazolo[1,5-a]pyridin-2-yl)-6,7-dihydro-1H-imidazo[4,5-c]pyridin-5(4H)-yl)methanone |
| 758 | 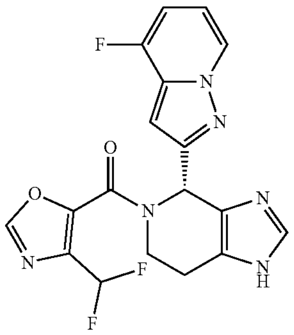 [SMILES: O=C(c1ocnc1C(F)F)N1CCc2[nH]cnc2[C@H]1c1cc2c(F)cccn2n1] | (S)-(4-(difluoromethyl)oxazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 759 | 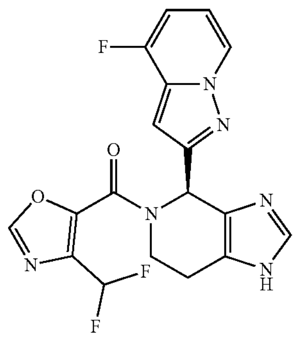 [SMILES: O=C(c1ocnc1C(F)F)N1CCc2[nH]cnc2[C@@H]1c1cc2c(F)cccn2n1] | (R)-(4-(difluoromethyl) oxazol-5-yl)(4-(4-fluoropyrazolo[1,5-a]pyridin-2-yl)-6,7-dihydro-1H-imidazo[4,5-c]pyridin-5(4H)-yl)methanone |
| 760 | 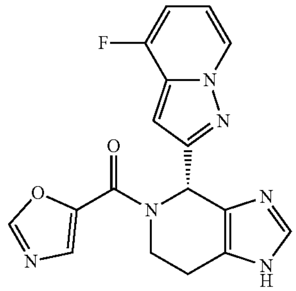 [SMILES: O=C(c1cnco1)N1CCc2[nH]cnc2[C@H]1c1cc2c(F)cccn2n1] | (S)-(4-(4-fluoropyrazolo[1,5-a] pyridin-2-yl)-6,7-dihydro-1H-imidazo[4,5-c]pyridin-5(4H)-yl)(oxazol-5-yl)methanone |
| 761 | 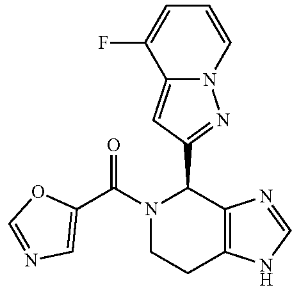 [SMILES: O=C(c1cnco1)N1CCc2[nH]cnc2[C@@H]1c1cc2c(F)cccn2n1] | (R)-(4-(4-fluoropyrazolo[1,5-a] pyridin-2-yl)-6,7-dihydro-1H-imidazo[4,5-c] pyridin-5(4H)-yl)(oxazol-5-yl)methanone |
| 762 | 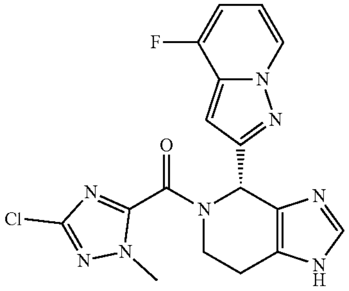 [SMILES: Cn1nc(Cl)nc1C(=O)N1CCc2[nH]cnc2[C@H]1c1cc2c(F)cccn2n1] | (S)-(3-chloro-1-methyl-1H-1,2,4-triazol-5-yl)(4-(4-fluoropyrazolo[1,5-a]pyridin-2-yl)-6,7-dihydro-1H-imidazo[4,5-c]pyridin-5(4H)-yl)methanone |
| 763 | 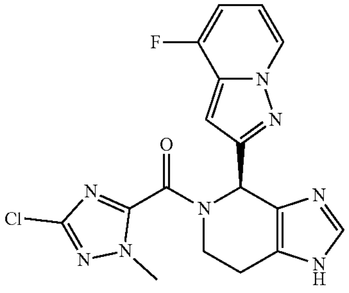 | (R)-(3-chloro-1-methyl-1H-1,2,4-triazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 764 | 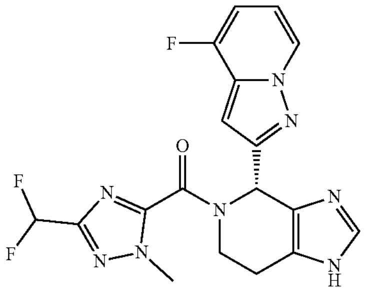 [SMILES: Cn1nc(C(F)F)nc1C(=O)N1CCc2[nH]cnc2[C@H]1c1cc2c(F)cccn2n1] | (S)-(3-(difluoromethyl)-1-methyl-1H-1,2,4-triazol-5-yl)(4-(4-fluoropyrazolo[1,5-a]pyridin-2-yl)-6,7-dihydro-1H-imidazo[4,5-c]pyridin-5(4H)-yl)methanone |
| 765 | 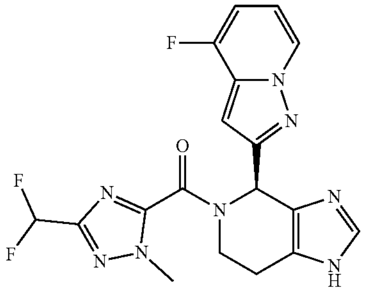 [SMILES: Cn1nc(C(F)F)nc1C(=O)N1CCc2[nH]cnc2[C@@H]1c1cc2c(F)cccn2n1] | (R)-(3-(difluoromethyl)-1-methyl-1H-1,2,4-triazol-5-yl)(4-(4-fluoropyrazolo[1,5-a]pyridin-2-yl)-6,7-dihydro-1H-imidazo[4,5-c]pyridin-5(4H)-yl)methanone |
| 766 | 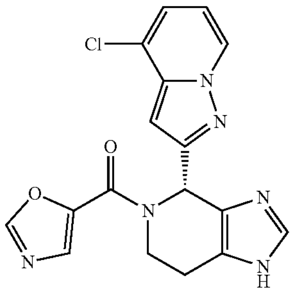 [SMILES: O=C(c1cnco1)N1CCc2[nH]cnc2[C@H]1c1cc2c(Cl)cccn2n1] | (S)-(4-(4-chloropyrazolo[1,5-a]pyridin-2-y])-6,7-dihydro-1H-imidazo[4,5-c]pyridin-5(4H)-yl)(oxazol-5-yl)methanone |
| 767 | 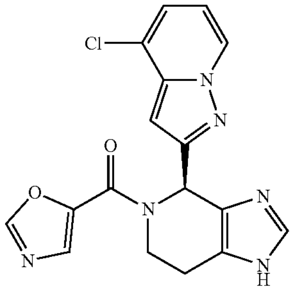 [SMILES: O=C(c1cnco1)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(oxazol-5-yl)methanone |
| 768 | 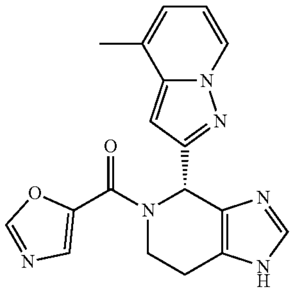 [SMILES: Cc1cccn2nc([C@@H]3c4nc[nH]c4CCN3C(=O)c3cnco3)cc12] | (S)-(4-(4-methylpyrazolo[1,5-a]pyridin-2-yl)-6,7-dihydro-1H-imidazo[4,5-c]pyridin-5(4H)-yl)(oxazol-5-yl)methanone |

TABLE 1-continued

| Pyrazolo[1,5-a]pyridines | | |
|---|---|---|
| Ex. # | Structure | Name |
| 769 | 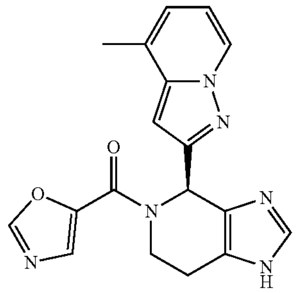 [SMILES: Cc1cccn2nc([C@H]3c4nc[nH]c4CCN3C(=O)c3cnco3)cc12] | (R)-(4-(4-methylpyrazolo[1,5-a]pyridin-2-yl)-6,7-dihydro-1H-imidazo[4,5-c]pyridin-5(4H)-yl)(oxazol-5-yl)methanone |
| 770 | 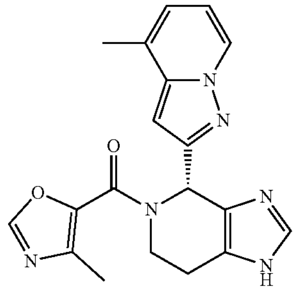 [SMILES: Cc1ncoc1C(=O)N1CCc2[nH]cnc2[C@H]1c1cc2c(C)cccn2n1] | (S)-(4-methyloxazol-5-yl)(4-(4-methylpyrazolo[1,5-a]pyridin-2-yl)-6,7-dihydro-1H-imidazo[4,5-c]pyridin-5(4H)-yl)methanone |
| 771 | 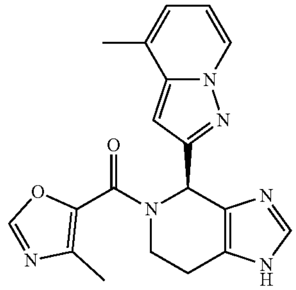 [SMILES: Cc1ncoc1C(=O)N1CCc2[nH]cnc2[C@@H]1c1cc2c(C)cccn2n1] | (R)-(4-methyloxazol-5-yl)(4-(4-methylpyrazolo[1,5-a]pyridin-2-yl)-6,7-dihydro-1H-imidazo[4,5-c]pyridin-5(4H)-yl)methanone |
| 772 | 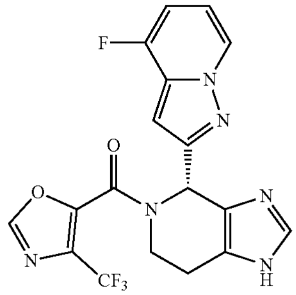 [SMILES: O=C(c1ocnc1C(F)(F)F)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(4-(trifluoromethyl)oxazol-5-yl)methanone |
| 773 | 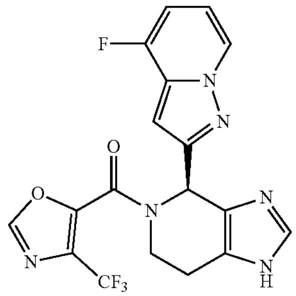 [SMILES: O=C(c1ocnc1C(F)(F)F)N1CCc2[nH]cnc2[C@@H]1c1cc2c(F)cccn2n1] | (R)-(4-(4-fluoropyrazolo[1,5-a]pyridin-2-yl)-6,7-dihydro-1H-imidazo[4,5-c]pyridin-5(4H)-yl)(4-(trifluoromethyl)oxazol-5-yl)methanone |

TABLE 1-continued

| Pyrazolo[1,5-a]pyridines | | |
|---|---|---|
| Ex. # | Structure | Name |
| 774 | 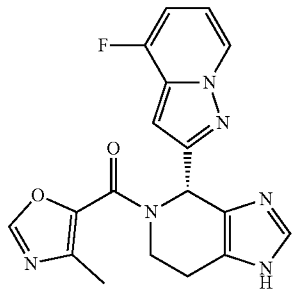 [SMILES: Cc1ncoc1C(=O)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(4-methyloxazol-5-yl)methanone |
| 775 | 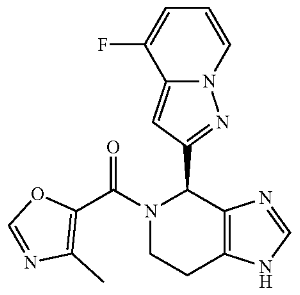 [SMILES: Cc1ncoc1C(=O)N1CCc2[nH]cnc2[C@@H]1c1cc2c(F)cccn2n1] | (R)-(4-(4-fluoropyrazolo[1,5-a]pyridin-2-y])-6,7-dihydro-1H-imidazo[4,5-c]pyridin-5(4H)-yl)(4-methyloxazol-5-yl)methanone |
| 776 | 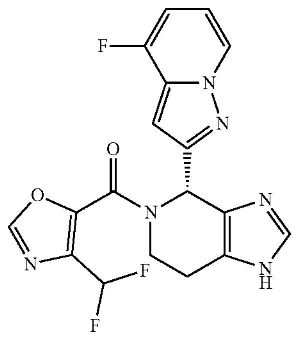 [SMILES: O=C(c1ocnc1C(F)F)N1CCc2[nH]cnc2[C@H]1c1cc2c(F)cccn2n1] | (S)-(1-(difluoromethyl)-1H-pyrazol-5-yl)(4-(4-fluoropyrazolo[1,5-a]pyridin-2-yl)-6,7-dihydro-1H-imidazo[4,5-c]pyridin-5(4H)-yl)methanone |
| 777 | 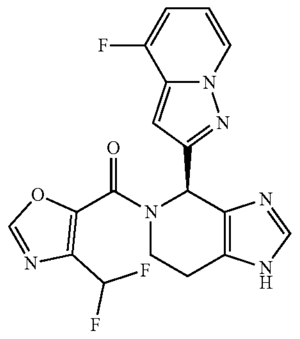 [SMILES: O=C(c1ocnc1C(F)F)N1CCc2[nH]cnc2[C@@H]1c1cc2c(F)cccn2n1] | (R)-(1-(difluoromethyl)-1H-pyrazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 778 | 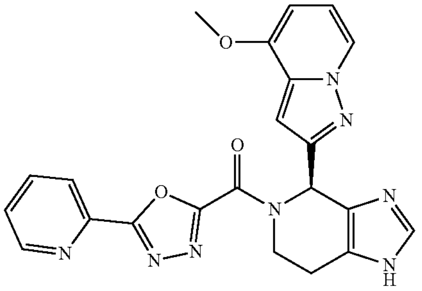 [SMILES: COc1cccn2nc([C@H]3c4nc[nH]c4CCN3C(=O)c3nnc(-c4ccccn4)o3)cc12] | (R)-(4-(4-methoxypyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 779 | 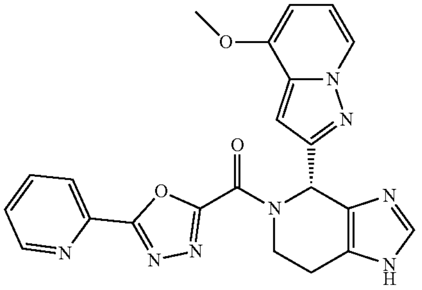 [SMILES: COc1cccn2nc([C@@H]3c4nc[nH]c4CCN3C(=O)c3nnc(-c4ccccn4)o3)cc12] | (S)-(4-(4-methoxypyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 780 | 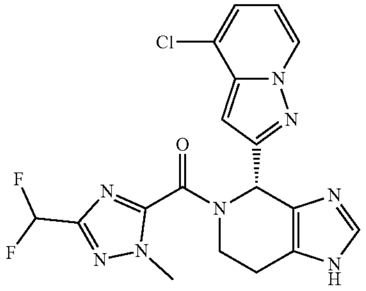 | (S)-(4-(4-chloropyrazolo[1,5-a]pyridin-2-yl)-6,7-dihydro-1H-imidazo[4,5-c]pyridin-5(4H)-yl)(3-(difluoromethyl)-1-methyl-1H-1,2,4-triazol-5-yl)methanone |
| 781 | 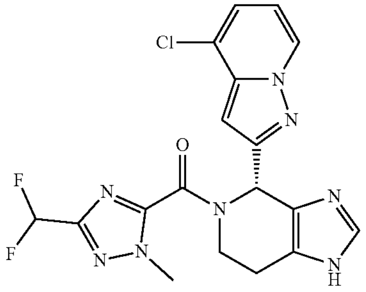 | (R)-(4-(4-chloropyrazolo[1,5-a]pyridin-2-yl)-6,7-dihydro-1H-imidazo[4,5-c]pyridin-5(4H)-yl)(3-(difluoromethyl)-1-methyl-1H-1,2,4-triazol-5-yl)methanone |
| 782 | 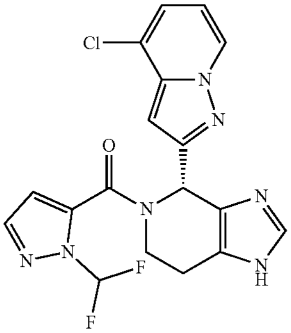 [SMILES: O=C(c1ccnn1C(F)F)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(1-(difluoromethyl)-1H-pyrazol-5-yl)methanone |

TABLE 1-continued

| Ex. # | Structure | Name |
|---|---|---|
| | Pyrazolo[1,5-a]pyridines | |
| 783 | 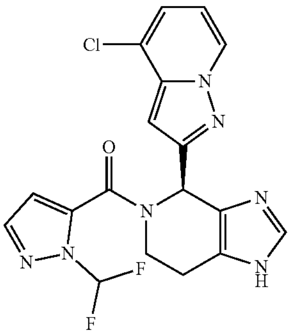 [SMILES: O=C(c1ccnn1C(F)F)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(1-(difluoromethyl)-1H-pyrazol-5-yl)methanone |
| 784 | 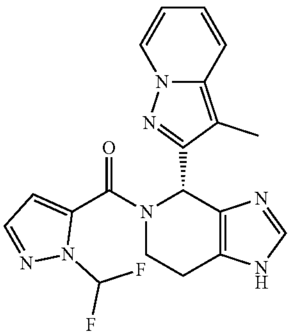 [SMILES: Cc1c([C@@H]2c3nc[nH]c3CCN2C(=O)c2ccnn2C(F)F)nn2ccccc12] | (S)-(4-(difluoromethyl)oxazol-5-yl)(4-(3-methylpyrazolo[1,5-a]pyridin-2-yl)-6,7-dihydro-1H-imidazo[4,5-c]pyridin-5(4H)-yl)methanone |
| 785 | 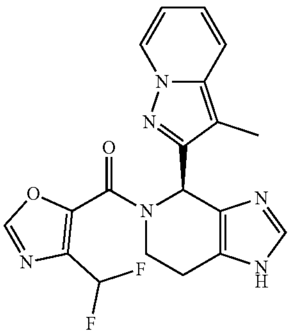 [SMILES: Cc1c([C@H]2c3nc[nH]c3CCN2C(=O)c2ocnc2C(F)F)nn2ccccc12] | (R)-(4-(difluoromethyl)oxazol-5-yl)(4-(3-methylpyrazolo[1,5-a]pyridin-2-yl)-6,7-dihydro-1H-imidazo[4,5-c]pyridin-5(4H)-yl)methanone |
| 786 | 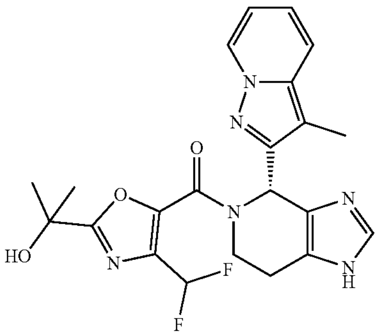 [SMILES: Cc1c([C@@H]2c3nc[nH]c3CCN2C(=O)c2oc(C(C)(C)O)nc2C(F)F)nn2ccccc12] | (S)-(4-(difluoromethyl)-2-(2-hydroxypropan-2-yl)oxazol-5-yl)(4-(3-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 787 | 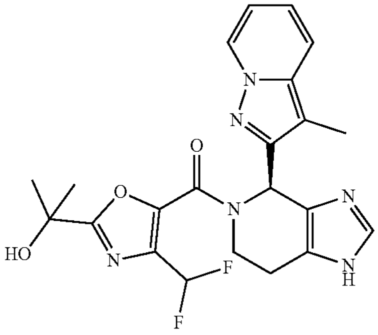 [SMILES: Cc1c([C@H]2c3nc[nH]c3CCN2C(=O)c2oc(C(C)(C)O)nc2C(F)F)nn2ccccc12] | (R)-(4-(difluoromethyl)-2-(2-hydroxypropan-2-yl) oxazol-5-yl)(4-(3-methylpyrazolo[1,5-a]pyridin-2-yl)-6,7-dihydro-1H-imidazo [4,5-c]pyridin-5(4H)-yl)methanone |
| 788 | 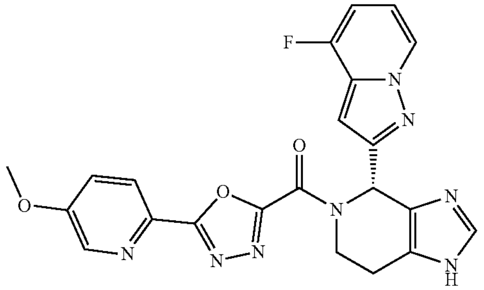 [SMILES: COc1ccc(-c2nnc(C(=O)N3CCc4[nH]cnc4[C@H]3c3cc4c(F)cccn4n3)o2)nc1] | (S)-(4-(4-fluoropyrazolo[1,5-a] pyridin-2-yl)-6,7-dihydro-1H-imidazo[4,5-c]pyridin-5(4H)-yl)(5-(5-methoxypyridin-2-yl)-1,3,4-oxadiazol-2-yl)methanone |
| 789 | 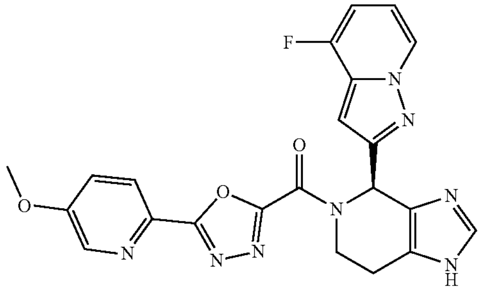 [SMILES: COc1ccc(-c2nnc(C(=O)N3CCc4[nH]cnc4[C@@H]3c3cc4c(F)cccn4n3)o2)nc1] | (R)-(4-(4-fluoropyrazolo[1,5-a] pyridin-2-y]l)-6,7-dihydro-1H-imidazo[4,5-c] pyridin-5(4H)-yl)(5-(5-methoxypyridin-2-yl)-1,3,4-oxadiazol-2-yl)methanone |
| 790 | 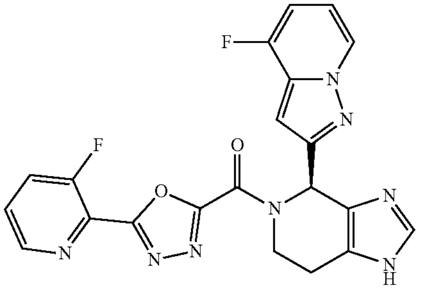 [SMILES: O=C(c1nnc(-c2ncccc2F)o1)N1CCc2[nH]cnc2[C@@H]1c1cc2c(F)cccn2n1] | (R)-(4-(4-fluoropyrazolo[1,5-a] pyridin-2-yl)-6,7-dihydro-1H-imidazo[4,5-c] pyridin-5(4H)-yl)(5-(3-fluoropyridin-2-yl)-1,3,4-oxadiazol-2-yl)methanone |
| 791 | 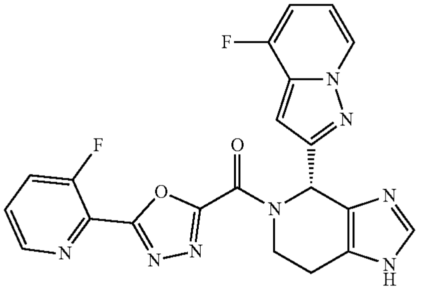 [SMILES: O=C(c1nnc(-c2ncccc2F)o1)N1CCc2[nH]cnc2[C@H]1c1cc2c(F)cccn2n1] | (S)-(4-(4-fluoropyrazolo[1,5-a] pyridin-2-yl)-6,7-dihydro-1H-imidazo[4,5-c]pyridin-5(4H)-yl)(5-(3-fluoropyridin-2-yl)-1,3,4-oxadiazol-2-yl) methanone |

TABLE 1-continued

| Pyrazolo[1,5-a]pyridines | | |
|---|---|---|
| Ex. # | Structure | Name |
| 792 | 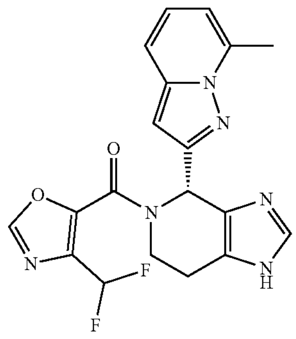 [SMILES: Cc1cccc2cc([C@@H]3c4nc[nH]c4CCN3C(=O)c3ocnc3C(F)F)nn12] | (S)-(4-(difluoromethyl)oxazol-5-yl)(4-(7-methylpyrazolo[1,5-a]pyridin-2-yl)-6,7-dihydro-1H-imidazo[4,5-c]pyridin-5(4H)-yl)methanone |
| 793 | 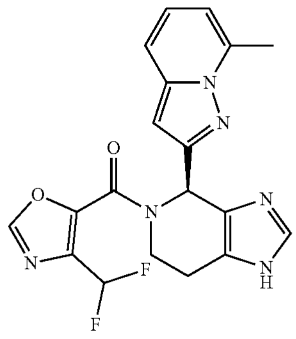 [SMILES: Cc1cccc2cc([C@H]3c4nc[nH]c4CCN3C(=O)c3ocnc3C(F)F)nn12] | (R)-(4-(difluoromethyl)oxazol-5-yl)(4-(7-methylpyrazolo[1,5-a]pyridin-2-yl)-6,7-dihydro-1H-imidazo[4,5-c]pyridin-5(4H)-yl)methanone |
| 794 | 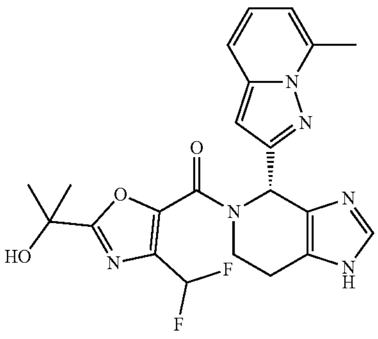 [SMILES: Cc1cccc2cc([C@@H]3c4nc[nH]c4CCN3C(=O)c3oc(C(C)(C)O)nc3C(F)F)nn12] | (S)-(4-(difluoromethyl)-2-(2-hydroxypropan-2-yl)oxazol-5-yl)(4-(7-methylpyrazolo[1,5-a]pyridin-2-yl)-6,7-dihydro-1H-imidazo[4,5-c]pyridin-5(4H)-yl)methanone |
| 795 | 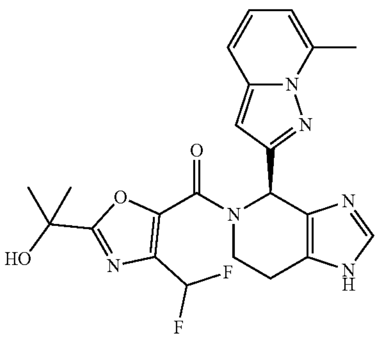 [SMILES: Cc1cccc2cc([C@H]3c4nc[nH]c4CCN3C(=O)c3oc(C(C)(C)O)nc3C(F)F)nn12] | (R)-(4-(difluoromethyl)-2-(2-hydroxypropan-2-yl)oxazol-5-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 796 | 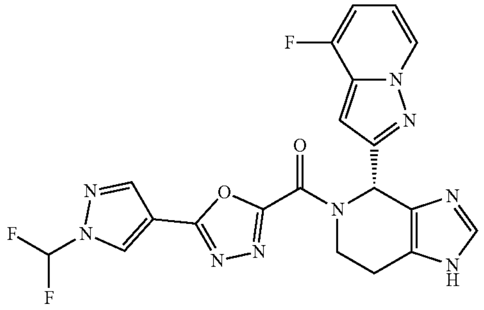 [SMILES: O=C(c1nnc(-c2cnn(C(F)F)c2)o1)N1CCc2[nH]cnc2[C@H]1c1cc2c(F)cccn2n1] | (S)-(5-(1-(difluoromethyl)-1H-pyrazol-4-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 797 | 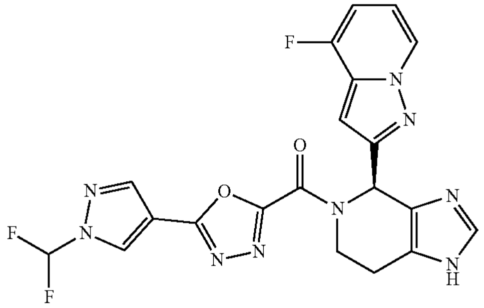 | (R)-(5-(1-(difluoromethyl)-1H-pyrazol-4-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 798 | 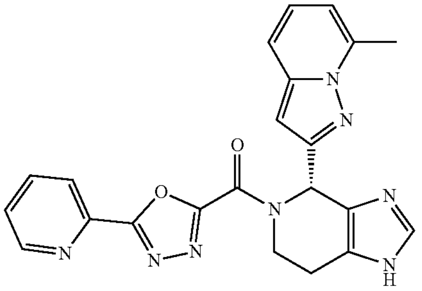 [SMILES: Cc1cccc2cc([C@@H]3c4nc[nH]c4CCN3C(=O)c3nnc(-c4ccccn4)o3)nn12] | (S)-(4-(7-methylpyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 799 | 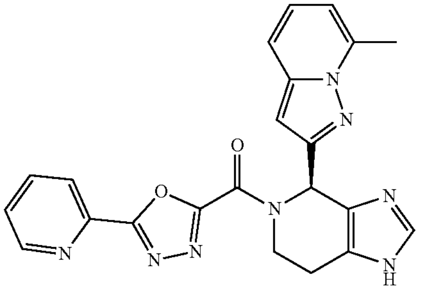 [SMILES: Cc1cccc2cc([C@H]3c4nc[nH]c4CCN3C(=O)c3nnc(-c4ccccn4)o3)nn12] | (R)-(4-(7-methylpyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 800 | 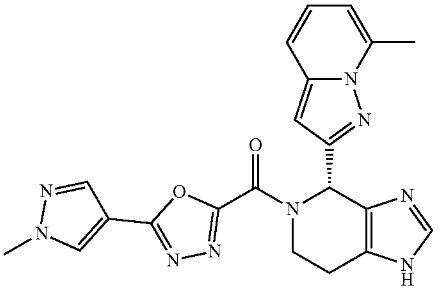 [SMILES: Cc1cccc2cc([C@@H]3c4nc[nH]c4CCN3C(=O)c3nnc(-c4cnn(C)c4)o3)nn12] | (S)-(5-(1-methyl-1H-pyrazol-4-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 801 | 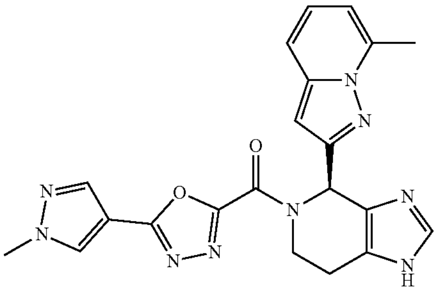 [SMILES: Cc1cccc2cc([C@H]3c4nc[nH]c4CCN3C(=O)c3nnc(-c4cnn(C)c4)o3)nn12] | (R)-(5-(1-methyl-1H-pyrazol-4-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 802 | 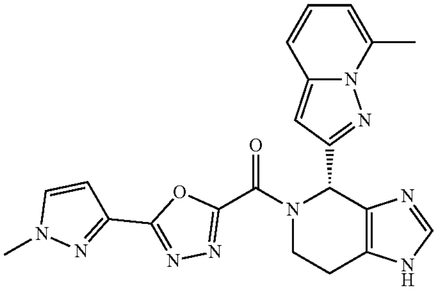 [SMILES: Cc1cccc2cc([C@@H]3c4nc[nH]c4CCN3C(=O)c3nnc(-c4ccn(C)n4)o3)nn12] | (S)-(5-(1-methyl-1H-pyrazol-3-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 803 | 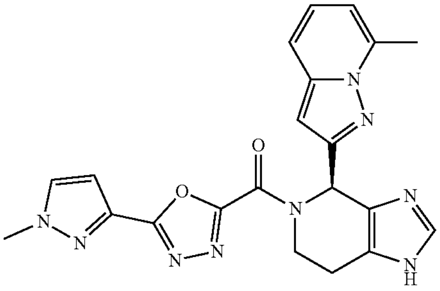 [SMILES: Cc1cccc2cc([C@H]3c4nc[nH]c4CCN3C(=O)c3nnc(-c4ccn(C)n4)o3)nn12] | (R)-(5-(1-methyl-1H-pyrazol-3-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 804 | 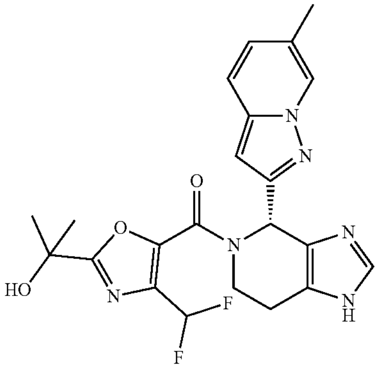 [SMILES: Cc1ccc2cc([C@@H]3c4nc[nH]c4CCN3C(=O)c3oc(C(C)(C)O)nc3C(F)F)nn2c1] | (S)-(2-(2-hydroxypropan-2-yl)-4-(trifluoromethyl)oxazol-5-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 805 | 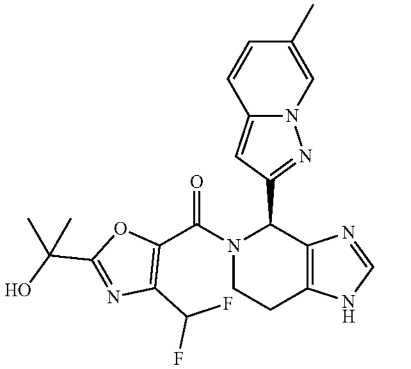 [SMILES: Cc1ccc2cc([C@H]3c4nc[nH]c4CCN3C(=O)c3oc(C(C)(C)O)nc3C(F)F)nn2c1] | (R)-(4-(difluoromethyl)-2-(2-hydroxypropan-2-yl)oxazol-5-yl)(4-(6-methylpyrazolo[1,5-a]pyridin-2-yl)-6,7-dihydro-1H-imidazo[4,5-c]pyridin-5(4H)-yl)methanone |
| 806 | 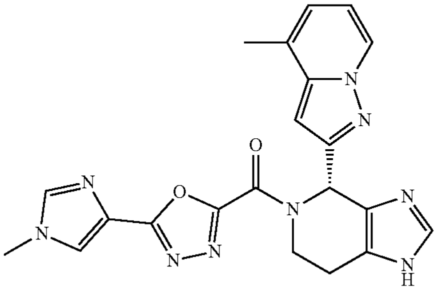 [SMILES: Cc1cccn2nc([C@@H]3c4nc[nH]c4CCN3C(=O)c3nnc(-c4cn(C)cn4)o3)cc12] | (S)-(5-(1-methyl-1H-imidazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 807 | 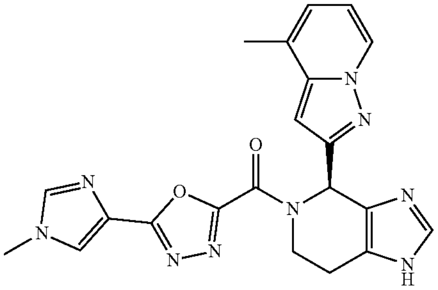 [SMILES: Cc1cccn2nc([C@H]3c4nc[nH]c4CCN3C(=O)c3nnc(-c4cn(C)cn4)o3)cc12] | (R)-(5-(1-methyl-1H-imidazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 808 | 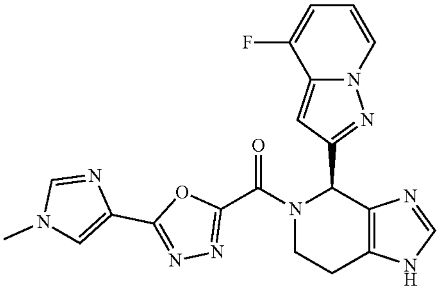 [SMILES: Cn1cnc(-c2nnc(C(=O)N3CCc4[nH]cnc4[C@@H]3c3cc4c(F)cccn4n3)o2)c1] | (R)-(4-(4-fluoropyrazolo[1,5-a]pyridin-2-yl)-6,7-dihydro-1H-imidazo[4,5-c]pyridin-5(4H)-yl)(5-(1-methyl-1H-imidazol-4-yl)-1,3,4-oxadiazol-2-yl)methanone |

TABLE 1-continued

| Pyrazolo[1,5-a]pyridines | | |
|---|---|---|
| Ex. # | Structure | Name |
| 809 | 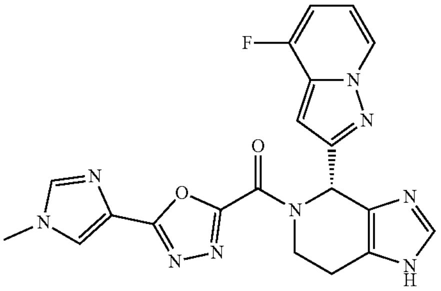 [SMILES: Cn1cnc(-c2nnc(C(=O)N3CCc4[nH]cnc4[C@H]3c3cc4c(F)cccn4n3)o2)c1] | (S)-(4-(4-fluoropyrazolo[1,5-a]pyridin-2-yl)-6,7-dihydro-1H-imidazo[4,5-c]pyridin-5(4H)-yl)(5-(1-methyl-1H-imidazol-4-yl)-1,3,4-oxadiazol-2-yl)methanone |
| 810 | 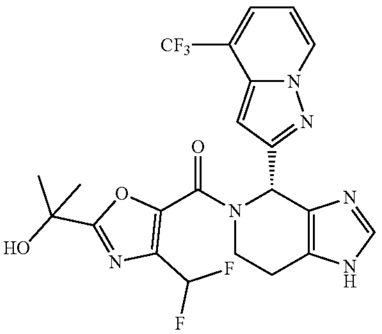 [SMILES: CC(C)(O)c1nc(C(F)F)c(C(=O)N2CCc3[nH]cnc3[C@H]2c2cc3c(C(F)(F)F)cccn3n2)o1] | (S)-(4-(difluoromethyl)-2-(2-hydroxypropan-2-yl)oxazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 811 | 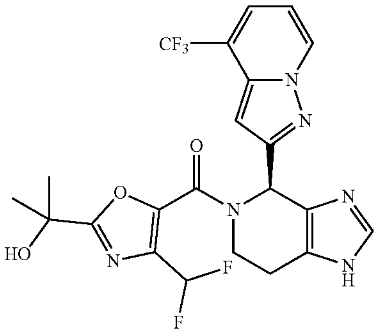 [SMILES: CC(C)(O)c1nc(C(F)F)c(C(=O)N2CCc3[nH]cnc3[C@@H]2c2cc3c(C(F)(F)F)cccn3n2)o1] | (R)-(4-(difluoromethyl)-2-(2-hydroxypropan-2-yl)oxazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 812 | 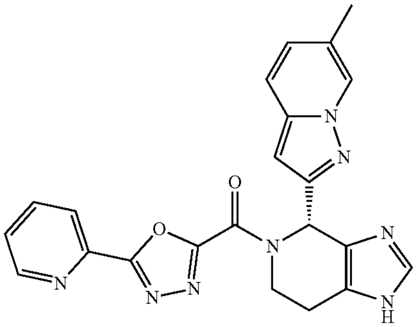 [SMILES: Cc1ccc2cc([C@@H]3c4nc[nH]c4CCN3C(=O)c3nnc(-c4ccccn4)o3)nn2c1] | (S)-(4-(6-methylpyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |

TABLE 1-continued

| Ex. # | Structure | Name |
|---|---|---|
| | Pyrazolo[1,5-a]pyridines | |
| 813 | 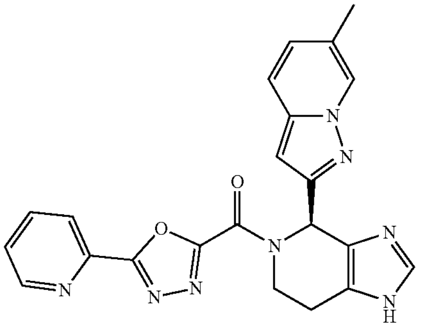 [SMILES: Cc1ccc2cc([C@H]3c4nc[nH]c4CCN3C(=O)c3nnc(-c4ccccn4)o3)nn2c1] | (R)-(4-(6-methylpyrazolo [1,5-a]pyridin-2-yl)-6,7-dihydro-1H-imidazo[4,5-c] pyridin-5(4H)-yl)(5-(pyridin-2-yl)-1,3,4-oxadiazol-2-yl) methanone |
| 814 | 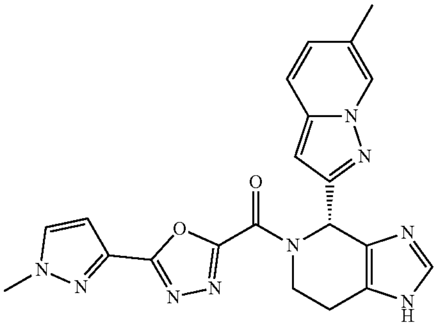 [SMILES: Cc1ccc2cc([C@@H]3c4nc[nH]c4CCN3C(=O)c3nnc(-c4ccn(C)n4)o3)nn2c1] | (S)-(5-(1-methyl-1H-pyrazol-3-yl)-1,3,4-oxadiazol-2-yl)(4-(6-methylpyrazolo[1,5-a] pyridin-2-yl)-6,7-dihydro-1H-imidazo[4,5-c]pyridin-5(4H)-yl)methanone |
| 815 | 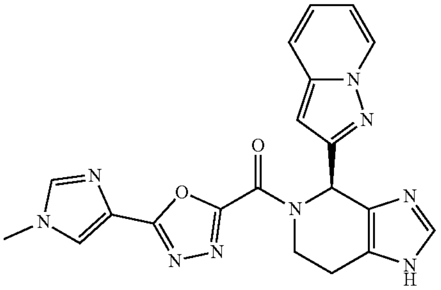 [SMILES: Cn1cnc(-c2nnc(C(=O)N3CCc4[nH]cnc4[C@@H]3c3cc4ccccn4n3)o2)c1] | (R)-(5-(1-methyl-1H-pyrazol-3-yl)-1,3,4-oxadiazol-2-yl)(4-(6-methylpyrazolo[1,5-a] pyridin-2-yl)-6,7-dihydro-1H-imidazo[4,5-c]pyridin-5(4H)-yl)methanone |
| 816 | 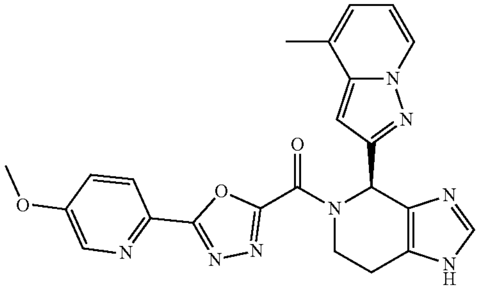 | (R)-(5-(5-methoxypyridin-2-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 817 | 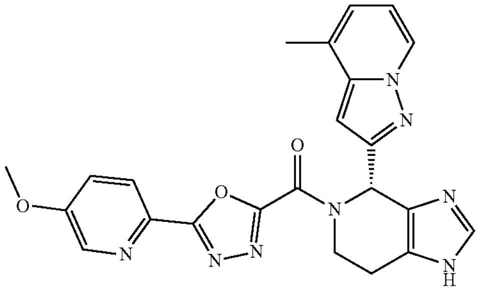 | (S)-(5-(5-methoxypyridin-2-yl)-1,3,4-oxadiazol-2-yl)(4-(4-methylpyrazolo[1,5-a] pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 818 | 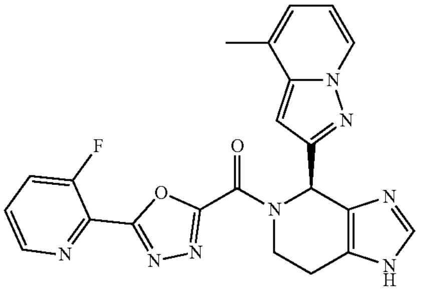 [SMILES: Cc1cccn2nc([C@H]3c4nc[nH]c4CCN3C(=O)c3nnc(-c4ncccc4F)o3)cc12] | (R)-(5-(3-fluoropyridin-2-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 819 | 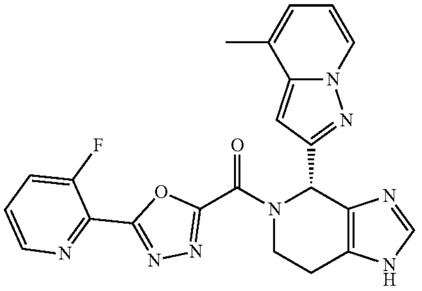 [SMILES: Cc1cccn2nc([C@@H]3c4nc[nH]c4CCN3C(=O)c3nnc(-c4ncccc4F)o3)cc12] | (S)-(5-(3-fluoropyridin-2-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 820 | 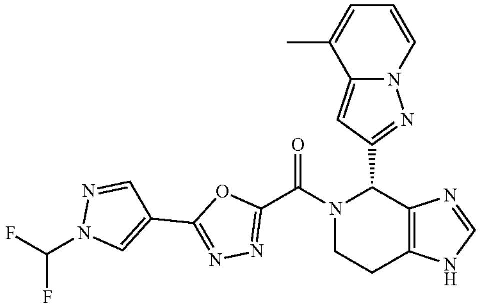 [SMILES: Cc1cccn2nc([C@@H]3c4nc[nH]c4CCN3C(=O)c3nnc(-c4cnn(C(F)F)c4)o3)cc12] | (S)-(5-(1-(difluoromethyl)-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 821 | 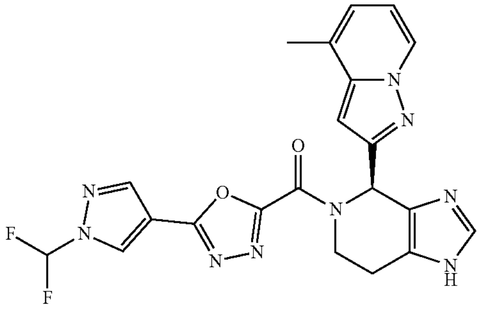 | (R)-(5-(1-(difluoromethyl)-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 822 | 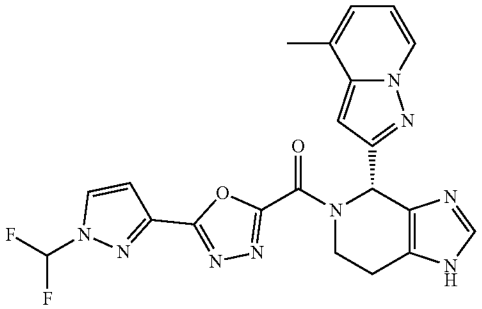 | (S)-(5-(1-(difluoromethyl)-1H-pyrazol-3-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 823 | 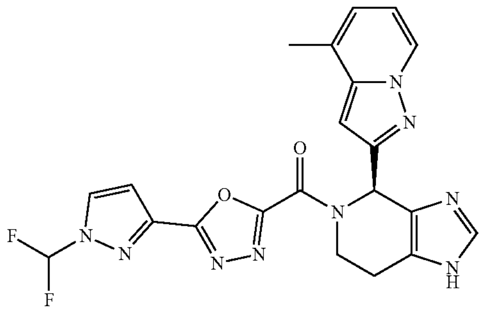 | (R)-(5-(1-(difluoromethyl)-1H-pyrazol-3-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 824 | 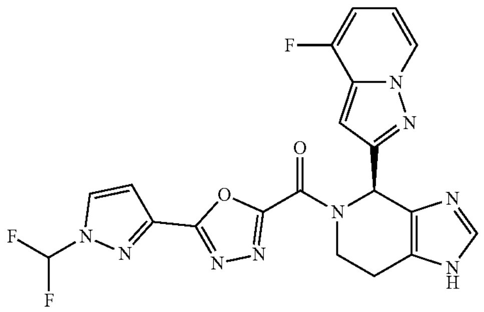 [SMILES: Cc1cccn2nc([C@H]3c4nc[nH]c4CCN3C(=O)c3nnc(-c4ccn(C(F)F)n4)o3)cc12] | (R)-(5-(1-(difluoromethyl)-1H-pyrazol-3-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 825 | 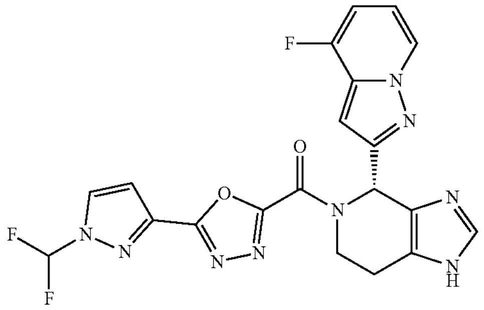 [SMILES: O=C(c1nnc(-c2ccn(C(F)F)n2)o1)N1CCc2[nH]cnc2[C@H]1c1cc2c(F)cccn2n1] | (S)-(5-(1-(difluoromethyl)-1H-pyrazol-3-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 826 | 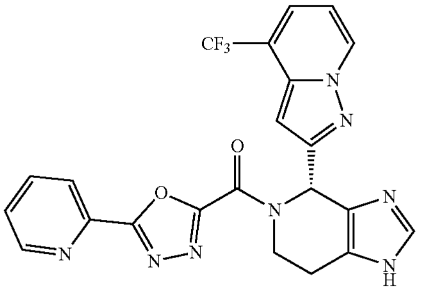 [SMILES: O=C(c1nnc(-c2ccccn2)o1)N1CCc2[nH]cnc2[C@H]1c1cc2c(C(F)(F)F)cccn2n1] | (S)-(5-(pyridin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 827 | 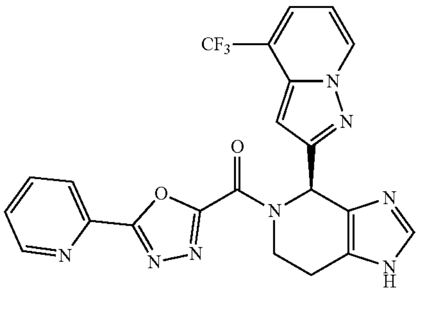 [SMILES: O=C(c1nnc(-c2ccccn2)o1)N1CCc2[nH]cnc2[C@@H]1c1cc2c(C(F)(F)F)cccn2n1] | (R)-(5-(pyridin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 828 | 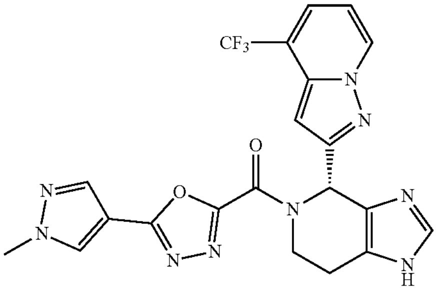 | (S)-(5-(1-methyl-1H-pyrazol-4-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 829 | 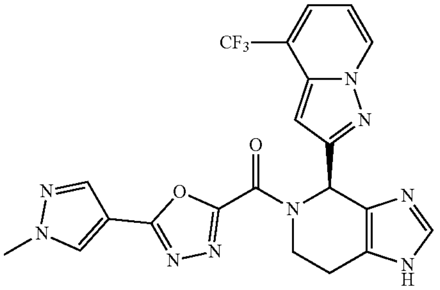 [SMILES: Cn1cc(-c2nnc(C(=O)N3CCc4[nH]cnc4[C@@H]3c3cc4c(C(F)(F)F)cccn4n3)o2)cn1] | (R)-(5-(1-methyl-1H-pyrazol-4-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 830 | 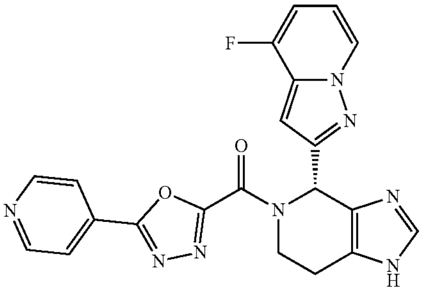 [SMILES: O=C(c1nnc(-c2ccncc2)o1)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(5-(pyridin-4-yl)-1,3,4-oxadiazol-2-yl)methanone |
| 831 | 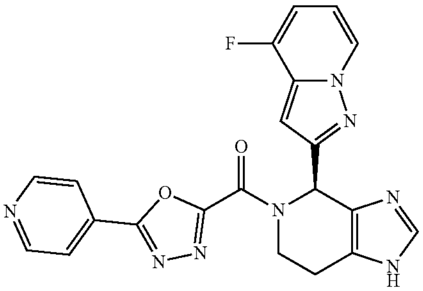 [SMILES: O=C(c1nnc(-c2ccncc2)o1)N1CCc2[nH]cnc2[C@@H]1c1cc2c(F)cccn2n1] | (R)-(4-(4-fluoropyrazolo[1,5-a]pyridin-2-yl)-6,7-dihydro-1H-imidazo[4,5-c]pyridin-5(4H)-yl)(5-(pyridin-4-yl)-1,3,4-oxadiazol-2-yl)methanone |
| 832 | 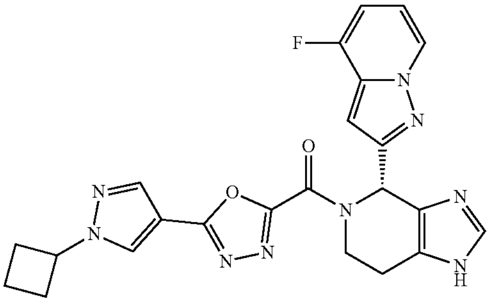 [SMILES: O=C(c1nnc(-c2cnn(C3CCC3)c2)o1)N1CCc2[nH]cnc2[C@H]1c1cc2c(F)cccn2n1] | (S)-(5-(1-cyclobutyl-1H-pyrazol-4-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 833 | 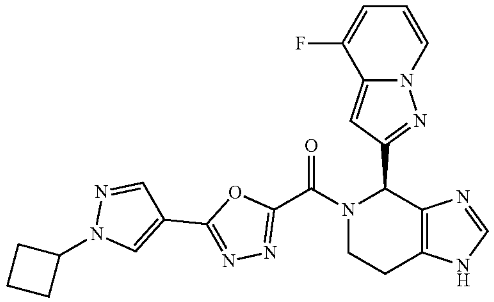 [SMILES: O=C(c1nnc(-c2cnn(C3CCC3)c2)o1)N1CCc2[nH]cnc2[C@@H]1c1cc2c(F)cccn2n1] | (R)-(5-(1-cyclobutyl-1H-pyrazol-4-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl) methanone |
| 834 | 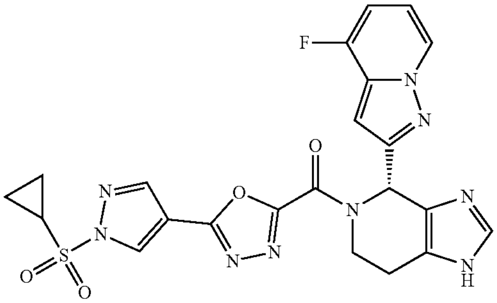 [SMILES: O=C(c1nnc(-c2cnn(S(=O)(=O)C3CC3)c2)o1)N1CCc2[nH]cnc2[C@H]1c1cc2c(F)cccn2n1] | (S)-(5-(1-(cyclopropylsulfonyl)-1H-pyrazol-4-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 835 | 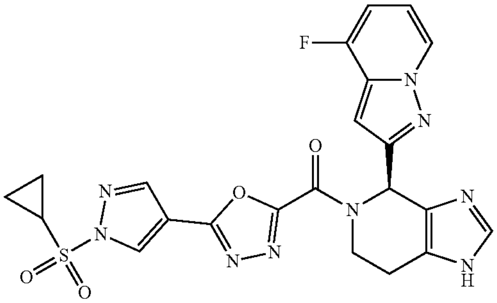 [SMILES: O=C(c1nnc(-c2cnn(S(=O)(=O)C3CC3)c2)o1)N1CCc2[nH]cnc2[C@@H]1c1cc2c(F)cccn2n1] | (R)-(5-(1-(cyclopropylsulfonyl)-1H-pyrazol-4-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 836 | 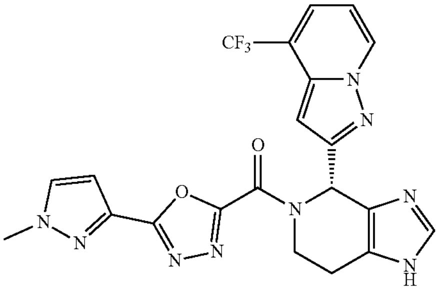 | (S)-(5-(1-methyl-1H-pyrazol-3-yl)-1,3,4-oxadiazol-2-yl)(4-(4-(trifluoromethyl) pyrazolo[1,5-a]pyridin-2-yl)-6,7-dihydro-1H-imidazo[4,5-c]pyridin-5(4H)-yl)methanone |
| 837 | 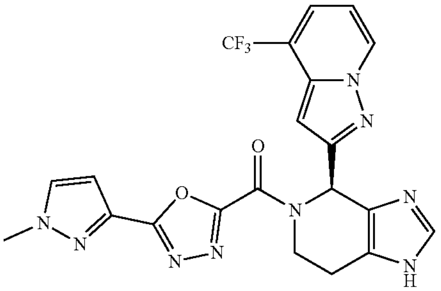 [SMILES: Cn1ccc(-c2nnc(C(=O)N3CCc4[nH]cnc4[C@@H]3c3cc4c(C(F)(F)F)cccn4n3)o2)n1] | (R)-(5-(1-methyl-1H-pyrazol-3-yl)-1,3,4-oxadiazol-2-yl)(4-(4-(trifluoromethyl) pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 838 | 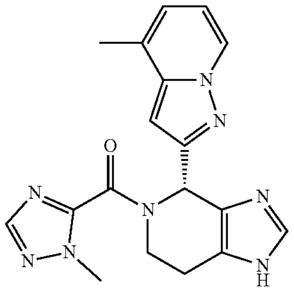 [SMILES: Cc1cccn2nc([C@@H]3c4nc[nH]c4CCN3C(=O)c3ncnn3C)cc12] | (S)-(1-methyl-1H-1,2,4-triazol-5-yl)(4-(4-methylpyrazolo[1,5-a]pyridin-2-yl)-6,7-dihydro-1H-imidazo[4,5-c]pyridin-5(4H)-yl)methanone |
| 839 | 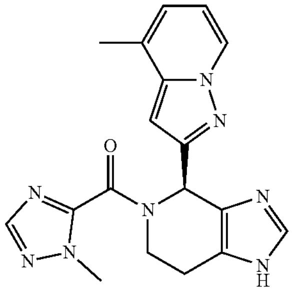 [SMILES: Cc1cccn2nc([C@H]3c4nc[nH]c4CCN3C(=O)c3ncnn3C)cc12] | (R)-(1-methyl-1H-1,2,4-triazol-5-yl)(4-(4-methylpyrazolo[1,5-a]pyridin-2-yl)-6,7-dihydro-1H-imidazo[4,5-c]pyridin-5(4H)-yl)methanone |
| 840 | 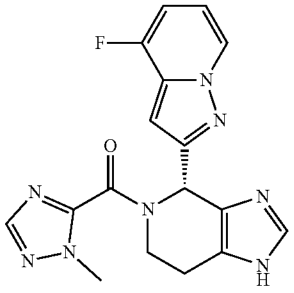 | (S)-(4-(4-fluoropyrazolo[1,5-a]pyridin-2-yl)-6,7-dihydro-1H-imidazo[4,5-c]pyridin-5(4H)-yl)(1-methyl-1H-1,2,4-triazol-5-yl)methanone |
| 841 | 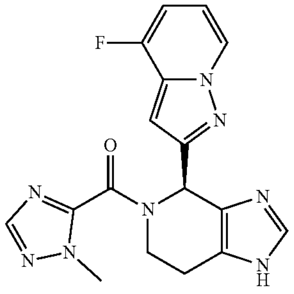 [SMILES: Cn1ncnc1C(=O)N1CCc2[nH]cnc2[C@@H]1c1cc2c(F)cccn2n1] | (R)-(4-(4-fluoropyrazolo[1,5-a]pyridin-2-yl)-6,7-dihydro-1H-imidazo[4,5-c]pyridin-5(4H)-yl)(1-methyl-1H-1,2,4-triazol-5-yl)methanone |
| 842 | 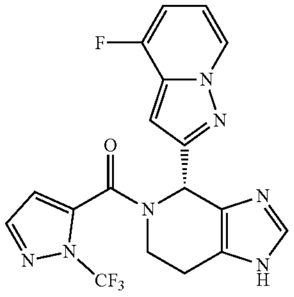 [SMILES: O=C(c1ccnn1C(F)(F)F)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(1-(trifluoromethyl)-1H-pyrazol-5-yl)methanone |

TABLE 1-continued

Pyrazolo[1,5-a]pyridines

| Ex. # | Structure | Name |
|---|---|---|
| 843 | 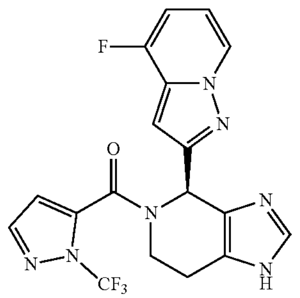 [SMILES: O=C(c1ccnn1C(F)(F)F)N1CCc2[nH]cnc2[C@@H]1c1cc2c(F)cccn2n1] | (R)-(4-(4-fluoropyrazolo[1,5-a] pyridin-2-yl)-6,7-dihydro-1H-imidazo[4,5-c] pyridin-5(4H)-yl)(1-(trifluoromethyl)-1H-pyrazol-5-yl)methanone |
| 844 | 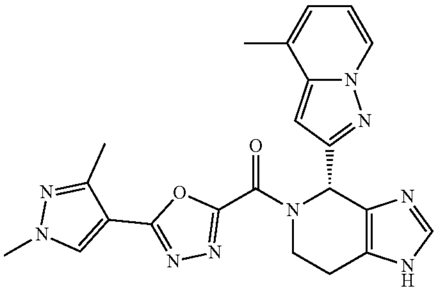 [SMILES: Cc1nn(C)cc1-c1nnc(C(=O)N2CCc3[nH]cnc3[C@H]2c2cc3c(C)cccn3n2)o1] | (S)-(5-(1,3-dimethyl-1H-pyrazol-4-yl)-1,3,4-oxadiazol-2-yl)(4-(4-methylpyrazolo[1,5-a] pyridin-2-yl)-6,7-dihydro-1H-imidazo[4,5-c]pyridin-5(4H)-yl)methanone |
| 845 | 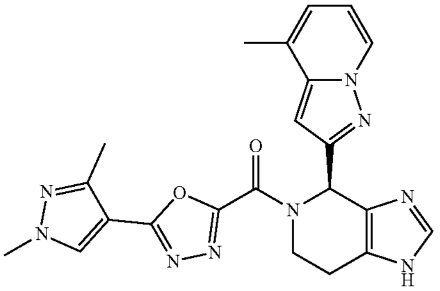 [SMILES: Cc1nn(C)cc1-c1nnc(C(=O)N2CCc3[nH]cnc3[C@@H]2c2cc3c(C)cccn3n2)o1] | (R)-(5-(1,3-dimethyl-1H-pyrazol-4-y]l)-1,3,4-oxadiazol-2-yl)(4-(4-methylpyrazolo [1,5-a]pyridin-2-yl)-6,7-dihydro-1H-imidazo[4,5-c] pyridin-5(4H)-yl)methanone |
| 846 | 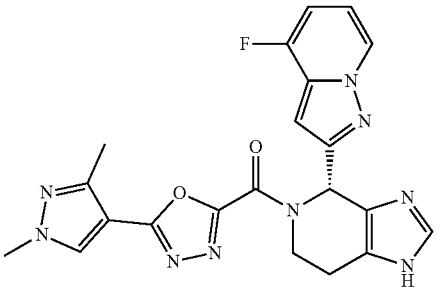 [SMILES: Cc1nn(C)cc1-c1nnc(C(=O)N2CCc3[nH]cnc3[C@H]2c2cc3c(F)cccn3n2)o1] | (S)-(5-(1,3-dimethyl-1H-pyrazol-4-yl)-1,3,4-oxadiazol-2-yl)(4-(4-fluoropyrazolo [1,5-a]pyridin-2-yl)-6,7-dihydro-1H-imidazo[4,5-c]pyridin-5(4H)-yl)methanone |
| 847 | 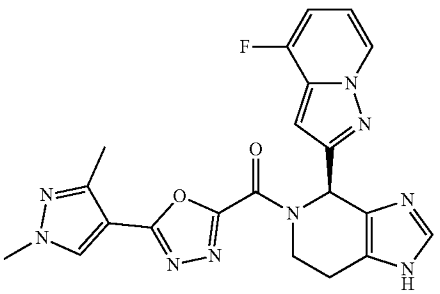 [SMILES: Cc1nn(C)cc1-c1nnc(C(=O)N2CCc3[nH]cnc3[C@@H]2c2cc3c(F)cccn3n2)o1] | (R)-(5-(1,3-dimethyl-1H-pyrazol-4-yl)-1,3,4-oxadiazol-2-yl)(4-(4-fluoropyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 848 | 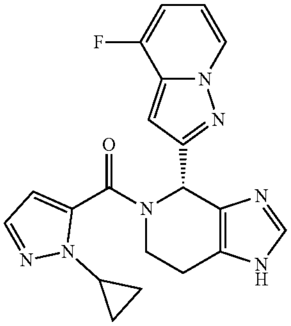 | (S)-(1-cyclopropyl-1H-pyrazol-5-yl)(4-(4-fluoropyrazolo[1,5-a]pyridin-2-yl)-6,7-dihydro-1H-imidazo[4,5-c]pyridin-5(4H)-yl)methanone |
| 849 | 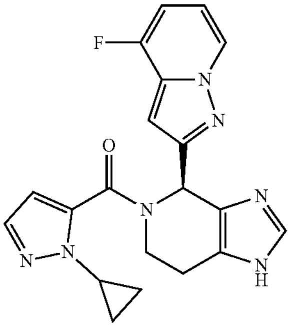 [SMILES: O=C(c1ccnn1C1CC1)N1CCc2[nH]cnc2[C@@H]1c1cc2c(F)cccn2n1] | (R)-(1-cyclopropyl-1H-pyrazol-5-yl)(4-(4-fluoropyrazolo[1,5-a]pyridin-2-yl)-6,7-dihydro-1H-imidazo[4,5-c]pyridin-5(4H)-yl)methanone |
| 850 | 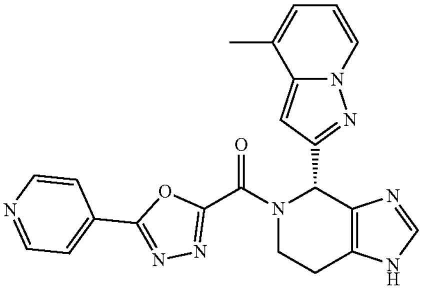 [SMILES: Cc1cccn2nc([C@@H]3c4nc[nH]c4CCN3C(=O)c3nnc(-c4ccncc4)o3)cc12] | (S)-(4-(4-methylpyrazolo[1,5-a]pyridin-2-yl)-6,7-dihydro-1H-imidazo[4,5-c]pyridin-5(4H)-yl)(5-(pyridin-4-yl)-1,3,4-oxadiazol-2-yl)methanone |
| 851 | 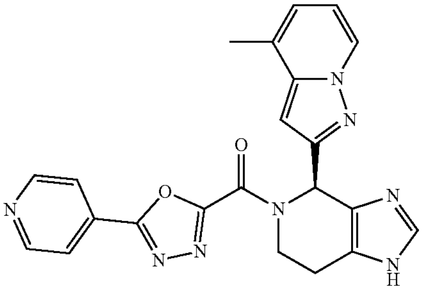 [SMILES: Cc1cccn2nc([C@H]3c4nc[nH]c4CCN3C(=O)c3nnc(-c4ccncc4)o3)cc12] | (R)-(4-(4-methylpyrazolo[1,5-a]pyridin-2-yl)-6,7-dihydro-1H-imidazo[4,5-c]pyridin-5(4H)-yl)(5-(pyridin-4-yl)-1,3,4-oxadiazol-2-yl)methanone |

TABLE 1-continued

| Ex. # | Structure | Name |
|---|---|---|
| | Pyrazolo[1,5-a]pyridines | |
| 852 | 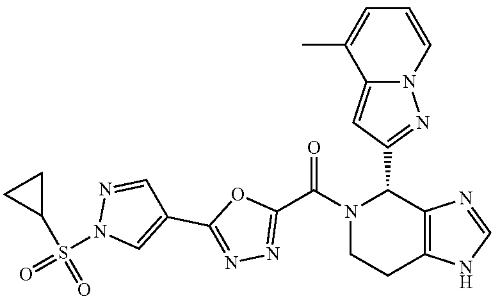 [SMILES: Cc1cccn2nc([C@@H]3c4nc[nH]c4CCN3C(=O)c3nnc(-c4cnn(S(=O)(=O)C5CC5)c4)o3)cc12] | (S)-(5-(1-(cyclopropylsulfonyl)-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 853 | 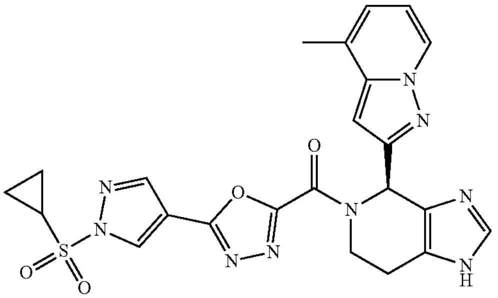 [SMILES: Cc1cccn2nc([C@H]3c4nc[nH]c4CCN3C(=O)c3nnc(-c4cnn(S(=O)(=O)C5CC5)c4)o3)cc12] | (R)-(5-(1-(cyclopropylsulfonyl)-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 854 | 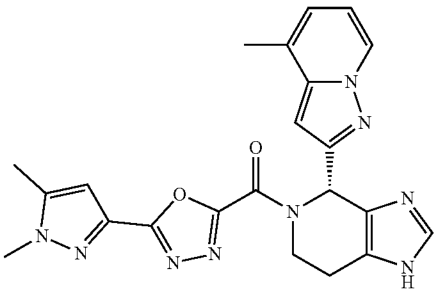 [SMILES: Cc1cccn2nc([C@@H]3c4nc[nH]c4CCN3C(=O)c3nnc(-c4cc(C)n(C)n4)o3)cc12] | (S)-(5-(1,5-dimethyl-1H-pyrazol-3-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 855 | 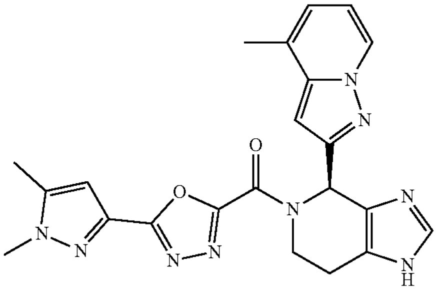 [SMILES: Cc1cccn2nc([C@H]3c4nc[nH]c4CCN3C(=O)c3nnc(-c4cc(C)n(C)n4)o3)cc12] | (R)-(5-(1,5-dimethyl-1H-pyrazol-3-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 856 | 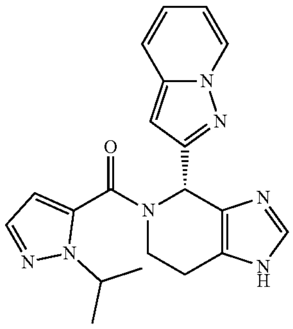 [SMILES: CC(C)n1nccc1C(=O)N1CCc2[nH]cnc2[C@H]1c1cc2ccccn2n1] | (S)-(1-isopropyl-1H-pyrazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| Pyrazolo[1,5-a]pyridines | | |
| 857 | 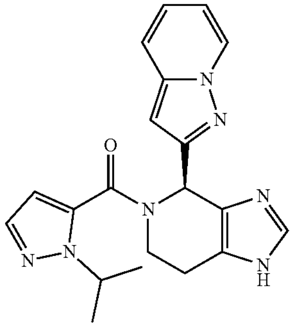 [SMILES: CC(C)n1nccc1C(=O)N1CCc2[nH]cnc2[C@@H]1c1cc2ccccn2n1] | (R)-(1-isopropyl-1H-pyrazol-5-yl)(4-(pyrazolo[1,5-a]pyridin-2-yl)-6,7-dihydro-1H-imidazo[4,5-c]pyridin-5(4H)-yl)methanone |
| 858 | 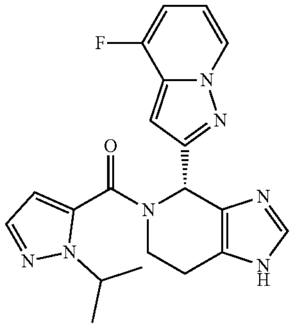 [SMILES: CC(C)n1nccc1C(=O)N1CCc2[nH]cnc2[C@H]1c1cc2c(F)cccn2n1] | (S)-(4-(4-fluoropyrazolo[1,5-a] pyridin-2-y]l)-6,7-dihydro-1H-imidazo[4,5-c]pyridin-5(4H)-yl)(1-isopropyl-1H-pyrazol-5-yl)methanone |
| 859 | 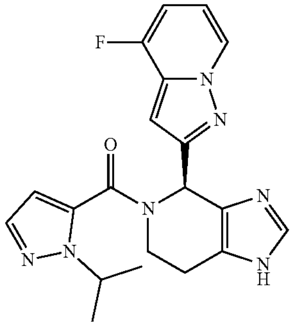 [SMILES: CC(C)n1nccc1C(=O)N1CCc2[nH]cnc2[C@@H]1c1cc2c(F)cccn2n1] | (R)-(4-(4-fluoropyrazolo [1,5-a]pyridin-2-yl)-6,7-dihydro-1H-imidazo[4,5-c] pyridin-5(4H)-yl)(1-isopropyl-1H-pyrazol-5-yl)methanone |
| 860 | 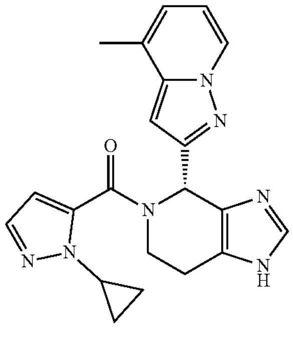 [SMILES: Cc1cccn2nc([C@@H]3c4nc[nH]c4CCN3C(=O)c3ccnn3C3CC3)cc12] | (S)-(1-cyclopropyl-1H-pyrazol-5-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 861 | 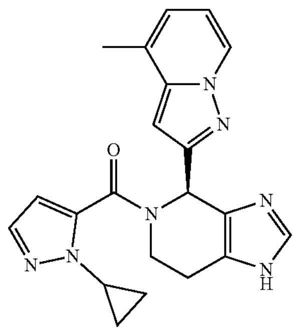 [SMILES: Cc1cccn2nc([C@H]3c4nc[nH]c4CCN3C(=O)c3ccnn3C3CC3)cc12] | (R)-(1-cyclopropyl-1H-pyrazol-5-yl)(4-(4-methylpyrazolo[1,5-a]pyridin-2-yl)-6,7-dihydro-1H-imidazo[4,5-c]pyridin-5(4H)-yl)methanone |
| 862 | 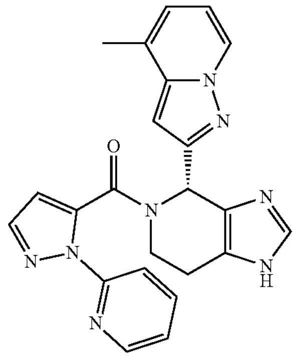 | (S)-(4-(4-methylpyrazolo [1,5-a]pyridin-2-y]l)-6,7-dihydro-1H-imidazo[4,5-c] pyridin-5(4H)-yl)(1-(pyridin-2-yl)-1H-pyrazol-5-yl)methanone |
| 863 | 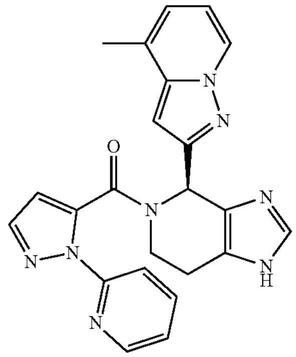 [SMILES: Cc1cccn2nc([C@H]3c4nc[nH]c4CCN3C(=O)c3ccnn3-c3ccccn3)cc12] | (R)-(4-(4-methylpyrazolo [1,5-a]pyridin-2-yl)-6,7-dihydro-1H-imidazo[4,5-c] pyridin-5(4H)-yl)(1-(pyridin-2-yl)-1H-pyrazol-5-yl) methanone |
| 864 | 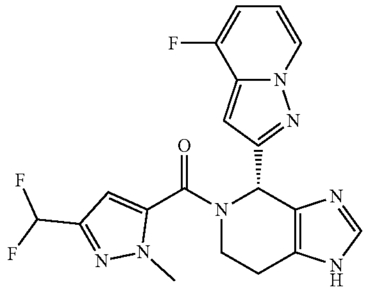 [SMILES: Cn1nc(C(F)F)cc1C(=O)N1CCc2[nH]cnc2[C@H]1c1cc2c(F)cccn2n1] | (S)-(3-(difluoromethyl)-1-methyl-1H-pyrazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 865 | 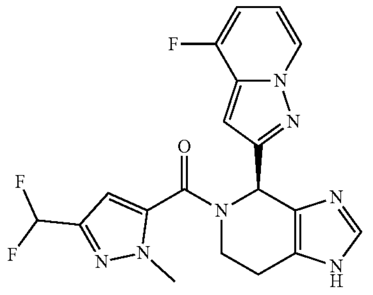 | (R)-(3-(difluoromethyl)-1-methyl-1H-pyrazol-5-yl)(4-(4-fluoropyrazolo[1,5-a]pyridin-2-yl)-6,7-dihydro-1H-imidazo[4,5-c]pyridin-5(4H)-yl)methanone |
| 866 | 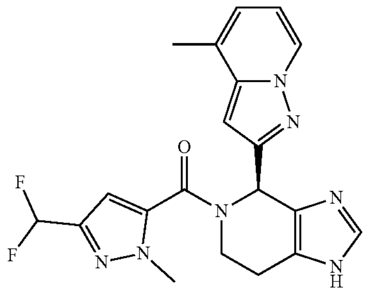 [SMILES: Cc1cccn2nc([C@H]3c4nc[nH]c4CCN3C(=O)c3cc(C(F)F)nn3C)cc12] | (R)-(3-(difluoromethyl)-1-methyl-1H-pyrazol-5-yl)(4-(4-methylpyrazolo[1,5-a]pyridin-2-yl)-6,7-dihydro-1H-imidazo[4,5-c]pyridin-5(4H)-yl)methanone |
| 867 | 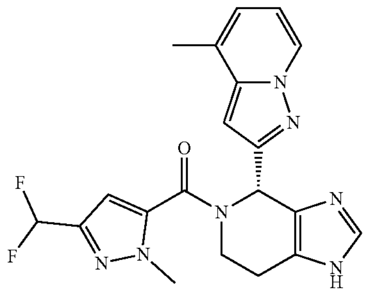 [SMILES: Cc1cccn2nc([C@@H]3c4nc[nH]c4CCN3C(=O)c3cc(C(F)F)nn3C)cc12] | (S)-(3-(difluoromethyl)-1-methyl-1H-pyrazol-5-yl)(4-(4-methylpyrazolo[1,5-a]pyridin-2-yl)-6,7-dihydro-1H-imidazo[4,5-c]pyridin-5(4H)-yl)methanone |
| 868 | 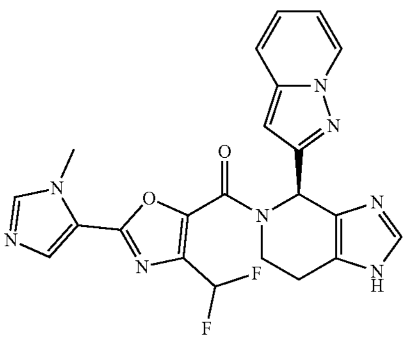 [SMILES: Cn1cncc1-c1nc(C(F)F)c(C(=O)N2CCc3[nH]cnc3[C@@H]2c2cc3ccccn3n2)o1] | (R)-(4-(difluoromethyl)-2-(1-methyl-1H-imidazol-5-yl)oxazol-5-yl)(4-(pyrazolo [1,5-a]pyridin-2-yl)-6,7-dihydro-1H-imidazo[4,5-c] pyridin-5(4H)-yl)methanone |

TABLE 1-continued

| Ex. # | Structure | Name |
|---|---|---|
| Pyrazolo[1,5-a]pyridines | | |
| 869 | 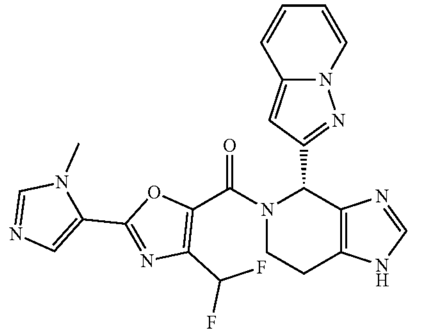 [SMILES: Cn1cncc1-c1nc(C(F)F)c(C(=O)N2CCc3[nH]cnc3[C@H]2c2cc3ccccn3n2)o1] | (S)-(4-(difluoromethyl)-2-(1-methyl-1H-imidazol-5-yl)oxazol-5-yl)(4-(pyrazolo[1,5-a]pyridin-2-yl)-6,7-dihydro-1H-imidazo[4,5-c]pyridin-5(4H)-yl)methanone |
| 870 | 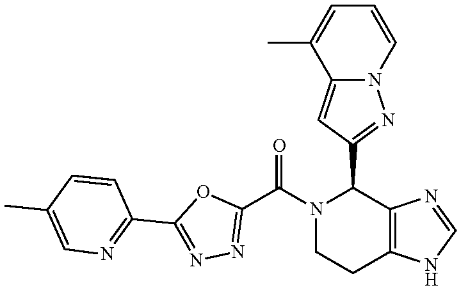 [SMILES: Cc1ccc(-c2nnc(C(=O)N3CCc4[nH]cnc4[C@@H]3c3cc4c(C)cccn4n3)o2)nc1] | (R)-(4-(4-methylpyrazolo[1,5-a]pyridin-2-yl)-6,7-dihydro-1H-imidazo[4,5-c]pyridin-5(4H)-yl)(5-(5-methylpyridin-2-yl)-1,3,4-oxadiazol-2-yl)methanone |
| 871 | 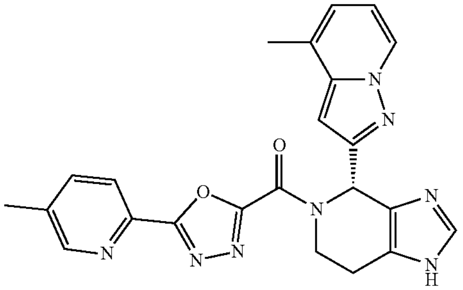 | (S)-(4-(4-methylpyrazolo[1,5-a]pyridin-2-yl)-6,7-dihydro-1H-imidazo[4,5-c]pyridin-5(4H)-yl)(5-(5-methylpyridin-2-yl)-1,3,4-oxadiazol-2-yl)methanone |
| 872 | 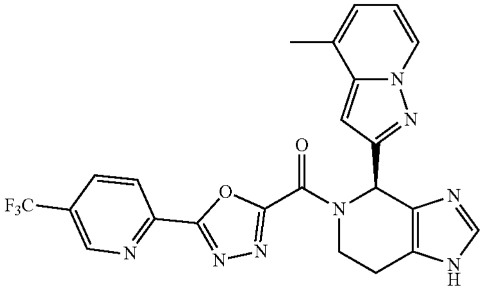 [SMILES: Cc1cccn2nc([C@H]3c4nc[nH]c4CCN3C(=O)c3nnc(-c4ccc(C(F)(F)F)cn4)o3)cc12] | (R)-(4-(4-methylpyrazolo[1,5-a]pyridin-2-yl)-6,7-dihydro-1H-imidazo[4,5-c]pyridin-5(4H)-yl)(5-(5-(trifluoromethyl)pyridin-2-yl)-1,3,4-oxadiazol-2-yl)methanone |
| 873 | 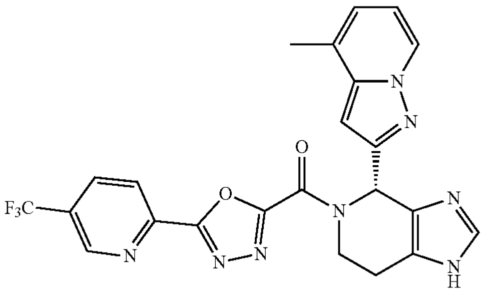 [SMILES: Cc1cccn2nc([C@@H]3c4nc[nH]c4CCN3C(=O)c3nnc(-c4ccc(C(F)(F)F)cn4)o3)cc12] | (S)-(4-(4-methylpyrazolo[1,5-a]pyridin-2-yl)-6,7-dihydro-1H-imidazo[4,5-c]pyridin-5(4H)-yl)(5-(5-(trifluoromethyl)pyridin-2-yl)-1,3,4-oxadiazol-2-yl)methanone |

TABLE 1-continued

| Ex. # | Structure | Name |
|---|---|---|
| | Pyrazolo[1,5-a]pyridines | |
| 874 | 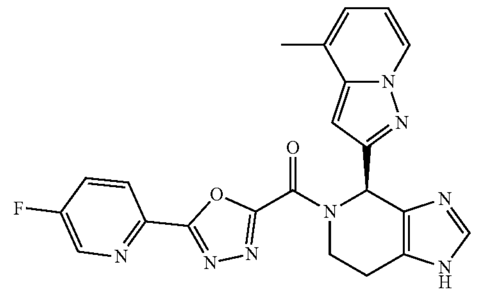 [SMILES: Cc1cccn2nc([C@H]3c4nc[nH]c4CCN3C(=O)c3nnc(-c4ccc(F)cn4)o3)cc12] | (R)-(5-(5-fluoropyridin-2-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 875 | 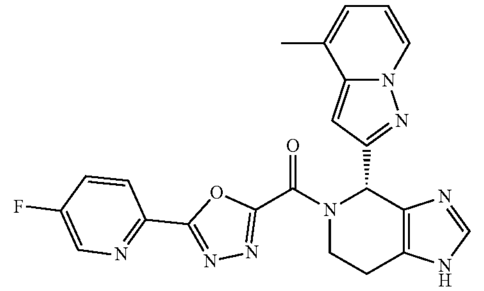 [SMILES: Cc1cccn2nc([C@@H]3c4nc[nH]c4CCN3C(=O)c3nnc(-c4ccc(F)cn4)o3)cc12] | (S)-(5-(5-fluoropyridin-2-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 876 | 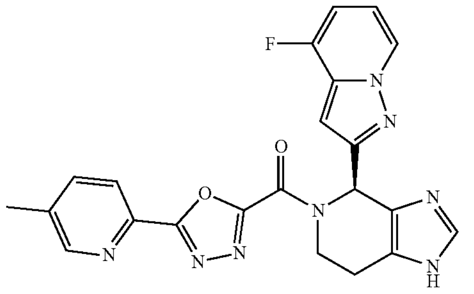 | (R)-(4-(4-fluoropyrazolo[1,5-a]pyridin-2-yl)-6,7-dihydro-1H-imidazo[4,5-c]pyridin-5(4H)-yl)(5-(5-methylpyridin-2-yl)-1,3,4-oxadiazol-2-yl)methanone |
| 877 | 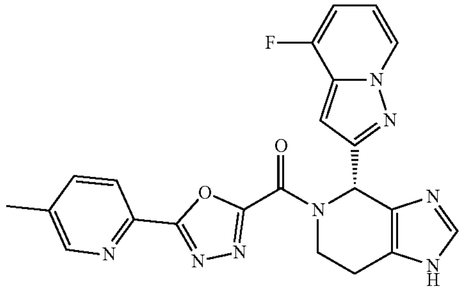 [SMILES: Cc1ccc(-c2nnc(C(=O)N3CCc4[nH]cnc4[C@H]3c3cc4c(F)cccn4n3)o2)nc1] | (S)-(4-(4-fluoropyrazolo[1,5-a]pyridin-2-yl)-6,7-dihydro-1H-imidazo[4,5-c]pyridin-5(4H)-yl)(5-(5-methylpyridin-2-yl)-1,3,4-oxadiazol-2-yl)methanone |
| 878 | 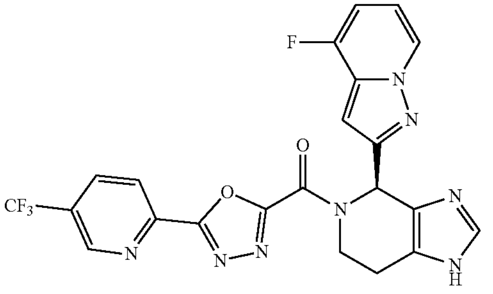 [SMILES: O=C(c1nnc(-c2ccc(C(F)(F)F)cn2)o1)N1CCc2[nH]cnc2[C@@H]1c1cc2c(F)cccn2n1] | (R)-(4-(4-fluoropyrazolo[1,5-a]pyridin-2-yl)-6,7-dihydro-1H-imidazo[4,5-c]pyridin-5(4H)-yl)(5-(5-(trifluoromethyl)pyridin-2-yl)-1,3,4-oxadiazol-2-yl)methanone |

TABLE 1-continued

| Ex. # | Structure | Name |
| --- | --- | --- |
| | Pyrazolo[1,5-a]pyridines | |
| 879 | 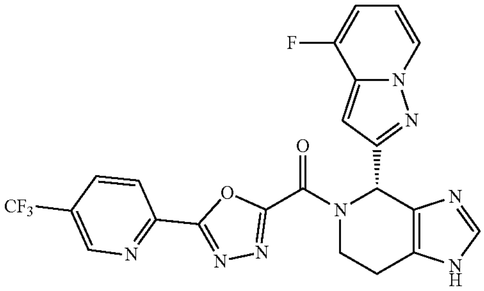 | (S)-(4-(4-fluoropyrazolo[1,5-a]pyridin-2-yl)-6,7-dihydro-1H-imidazo[4,5-c]pyridin-5(4H)-yl)(5-(5-(trifluoromethyl)pyridin-2-yl)-1,3,4-oxadiazol-2-yl)methanone |
| 880 | 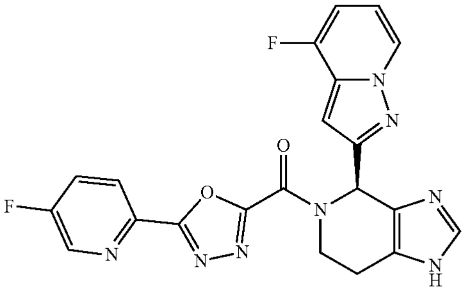 [SMILES: O=C(c1nnc(-c2ccc(F)cn2)o1)N1CCc2[nH]cnc2[C@@H]1c1cc2c(F)cccn2n1] | (R)-(4-(4-fluoropyrazolo[1,5-a]pyridin-2-yl)-6,7-dihydro-1H-imidazo[4,5-c]pyridin-5(4H)-yl)(5-(5-fluoropyridin-2-yl)-1,3,4-oxadiazol-2-yl)methanone |
| 881 | 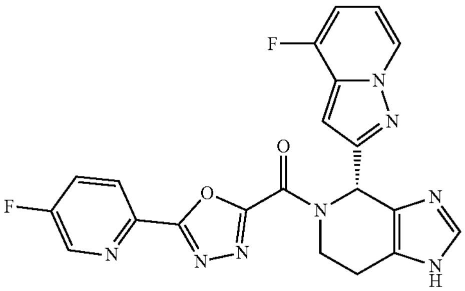 [SMILES: O=C(c1nnc(-c2ccc(F)cn2)o1)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(5-(5-fluoropyridin-2-yl)-1,3,4-oxadiazol-2-yl)methanone |
| 882 | 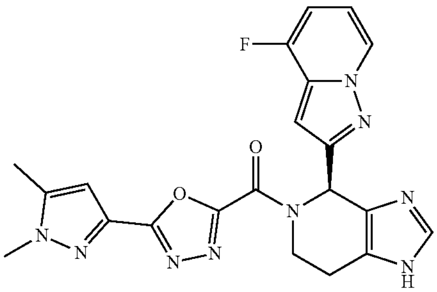 | (R)-(5-(1,5-dimethyl-1H-pyrazol-3-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 883 | 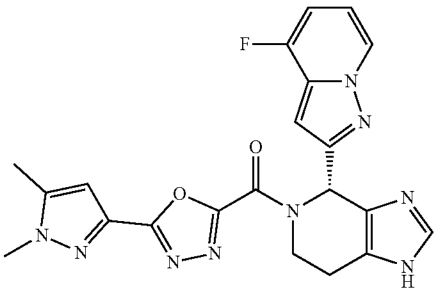 [SMILES: Cc1cc(-c2nnc(C(=O)N3CCc4[nH]cnc4[C@H]3c3cc4c(F)cccn4n3)o2)nn1C] | (S)-(5-(1,5-dimethyl-1H-pyrazol-3-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 884 | 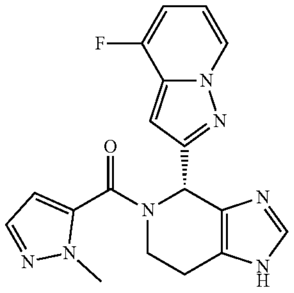 [SMILES: Cn1nccc1C(=O)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(1-methyl-1H-pyrazol-5-yl)methanone |
| 885 | 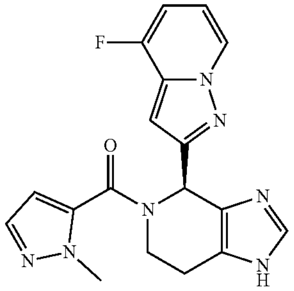 [SMILES: Cn1nccc1C(=O)N1CCc2[nH]cnc2[C@@H]1c1cc2c(F)cccn2n1] | (R)-(4-(4-fluoropyrazolo[1,5-a]pyridin-2-y]l)-6,7-dihydro-1H-imidazo[4,5-c]pyridin-5(4H)-yl)(1-methyl-1H-pyrazol-5-yl)methanone |
| 886 | 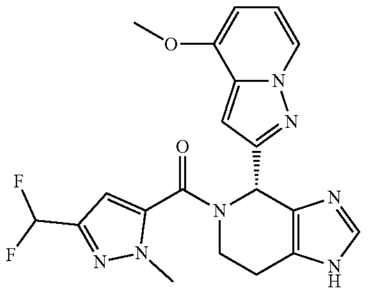 [SMILES: COc1cccn2nc([C@@H]3c4nc[nH]c4CCN3C(=O)c3cc(C(F)F)nn3C)cc12] | (S)-(3-(difluoromethyl)-1-methyl-1H-pyrazol-5-yl)(4-(4-methoxypyrazolo[1,5-a]pyridin-2-yl)-6,7-dihydro-1H-imidazo[4,5-c]pyridin-5(4H)-yl)methanone |
| 887 | 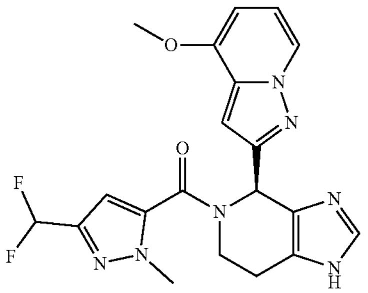 [SMILES: COc1cccn2nc([C@H]3c4nc[nH]c4CCN3C(=O)c3cc(C(F)F)nn3C)cc12] | (R)-(3-(difluoromethyl)-1-methyl-1H-pyrazol-5-yl)(4-(4-methoxypyrazolo[1,5-a]pyridin-2-yl)-6,7-dihydro-1H-imidazo[4,5-c]pyridin-5(4H)-yl)methanone |
| 888 | 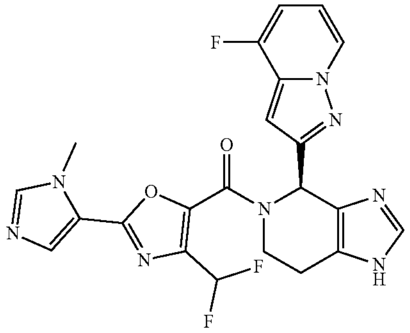 [SMILES: Cn1cncc1-c1nc(C(F)F)c(C(=O)N2CCc3[nH]cnc3[C@@H]2c2cc3c(F)cccn3n2)o1] | (R)-(4-(difluoromethyl)-2-(1-methyl-1H-imidazol-5-yl)oxazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 889 | 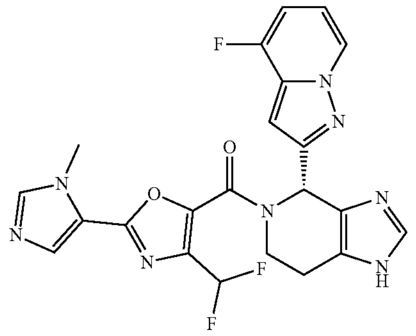 [SMILES: Cn1cncc1-c1nc(C(F)F)c(C(=O)N2CCc3[nH]cnc3[C@H]2c2cc3c(F)cccn3n2)o1] | (S)-(4-(difluoromethyl)-2-(1-methyl-1H-imidazol-5-yl)oxazol-5-yl)(4-(4-fluoropyrazolo[1,5-a]pyridin-2-yl)-6,7-dihydro-1H-imidazo[4,5-c]pyridin-5(4H)-yl)methanone |
| 890 | 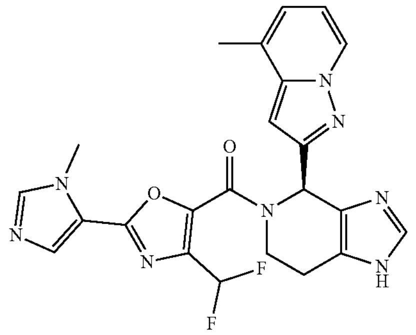 [SMILES: Cc1cccn2nc([C@H]3c4nc[nH]c4CCN3C(=O)c3oc(-c4cncn4C)nc3C(F)F)cc12] | (R)-(4-(difluoromethyl)-2-(1-methyl-1H-imidazol-5-yl)oxazol-5-yl)(4-(4-methylpyrazolo[1,5-a]pyridin-2-yl)-6,7-dihydro-1H-imidazo[4,5-c]pyridin-5(4H)-yl)methanone |
| 891 | 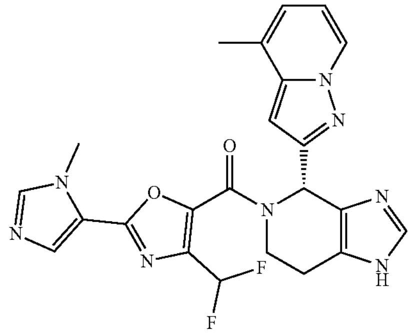 [SMILES: Cc1cccn2nc([C@@H]3c4nc[nH]c4CCN3C(=O)c3oc(-c4cncn4C)nc3C(F)F)cc12] | (S)-(4-(difluoromethyl)-2-(1-methyl-1H-imidazol-5-yl)oxazol-5-yl)(4-(4-methylpyrazolo[1,5-a]pyridin-2-yl)-6,7-dihydro-1H-imidazo[4,5-c]pyridin-5(4H)-yl)methanone |
| 892 | 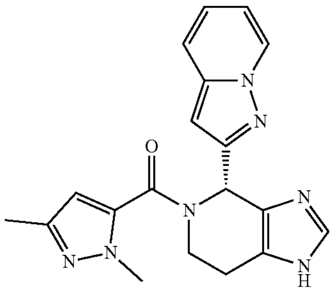 [SMILES: Cc1cc(C(=O)N2CCc3[nH]cnc3[C@H]2c2cc3ccccn3n2)n(C)n1] | (S)-(1,3-dimethyl-1H-pyrazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 893 | 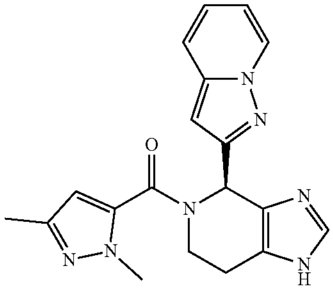 [SMILES: Cc1cc(C(=O)N2CCc3[nH]cnc3[C@@H]2c2cc3ccccn3n2)n(C)n1] | (R)-(1,3-dimethyl-1H-pyrazol-5-yl)(4-(pyrazolo[1,5-a]pyridin-2-yl)-6,7-dihydro-1H-imidazo[4,5-c]pyridin-5(4H)-yl)methanone |
| 894 | 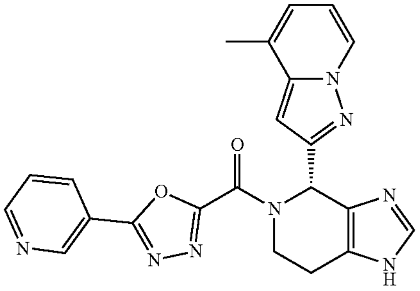 [SMILES: Cc1cccn2nc([C@@H]3c4nc[nH]c4CCN3C(=O)c3nnc(-c4cccnc4)o3)cc12] | (S)-(4-(4-methylpyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 895 | 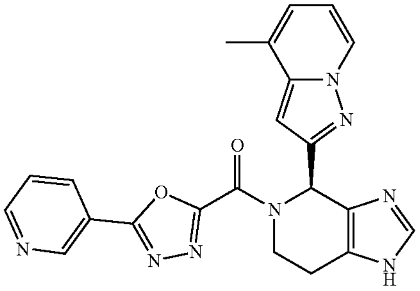 [SMILES: Cc1cccn2nc([C@H]3c4nc[nH]c4CCN3C(=O)c3nnc(-c4cccnc4)o3)cc12] | (R)-(4-(4-methylpyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 896 | 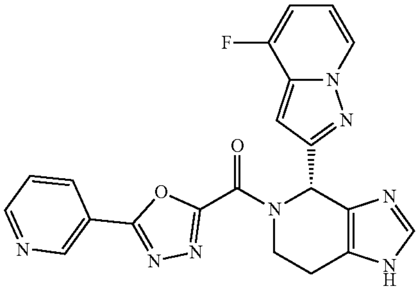 [SMILES: O=C(c1nnc(-c2cccnc2)o1)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 897 | 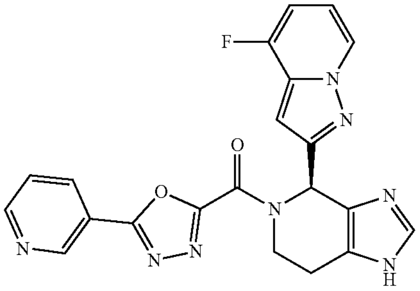 [SMILES: O=C(c1nnc(-c2cccnc2)o1)N1CCc2[nH]cnc2[C@@H]1c1cc2c(F)cccn2n1] | (R)-(4-(4-fluoropyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |

TABLE 1-continued

| Pyrazolo[1,5-a]pyridines | | |
|---|---|---|
| Ex. # | Structure | Name |
| 898 | 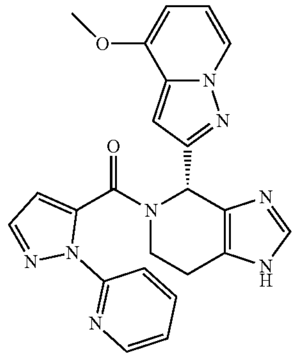 [SMILES: COc1cccn2nc([C@@H]3c4nc[nH]c4CCN3C(=O)c3ccnn3-c3ccccn3)cc12] | (S)-(4-(4-methoxypyrazolo[1,5-a]pyridin-2-yl)-6,7-dihydro-1H-imidazo[4,5-c]pyridin-5(4H)-yl)(1-(pyridin-2-yl)-1H-pyrazol-5-yl)methanone |
| 899 | 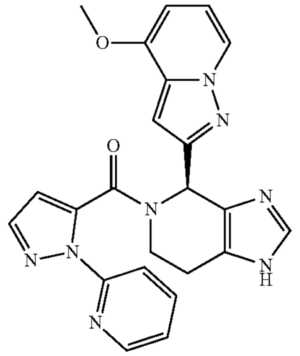 [SMILES: COc1cccn2nc([C@H]3c4nc[nH]c4CCN3C(=O)c3ccnn3-c3ccccn3)cc12] | (R)-(4-(4-methoxypyrazolo[1,5-a]pyridin-2-yl)-6,7-dihydro-1H-imidazo[4,5-c]pyridin-5(4H)-yl)(1-(pyridin-2-yl)-1H-pyrazol-5-yl)methanone |
| 900 | 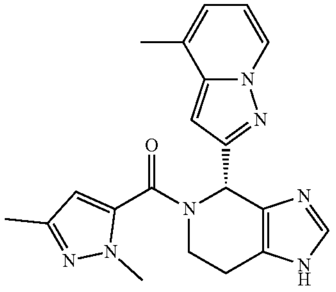 | (S)-(1,3-dimethyl-1H-pyrazol-5-yl)(4-(4-methylpyrazolo[1,5-a]pyridin-2-yl)-6,7-dihydro-1H-imidazo[4,5-c]pyridin-5(4H)-yl)methanone |
| 901 | 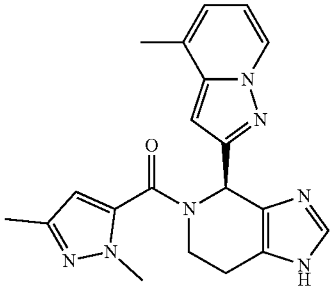 [SMILES: Cc1cc(C(=O)N2CCc3[nH]cnc3[C@@H]2c2cc3c(C)cccn3n2)n(C)n1] | (R)-(1,3-dimethyl-1H-pyrazol-5-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 902 | 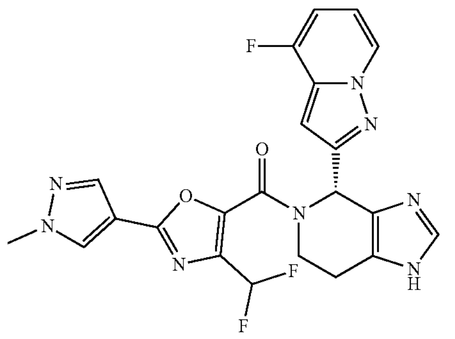 [SMILES: Cn1cc(-c2nc(C(F)F)c(C(=O)N3CCc4[nH]cnc4[C@H]3c3cc4c(F)cccn4n3)o2)cn1] | (S)-(4-(difluoromethyl)-2-(1-methyl-1H-pyrazol-4-yl)oxazol-5-yl)(4-(4-fluoropyrazolo[1,5-a]pyridin-2-yl)-6,7-dihydro-1H-imidazo[4,5-c]pyridin-5(4H)-yl)methanone |
| 903 | 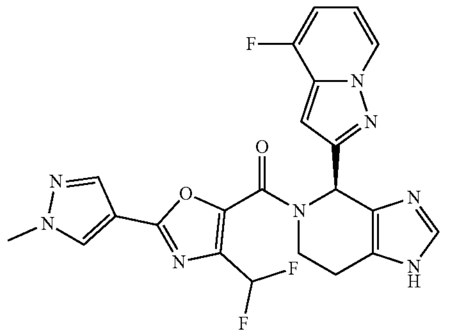 [SMILES: Cn1cc(-c2nc(C(F)F)c(C(=O)N3CCc4[nH]cnc4[C@@H]3c3cc4c(F)cccn4n3)o2)cn1] | (R)-(4-(difluoromethyl)-2-(1-methyl-1H-pyrazol-4-yl)oxazol-5-yl)(4-(4-fluoropyrazolo[1,5-a]pyridin-2-yl)-6,7-dihydro-1H-imidazo[4,5-c]pyridin-5(4H)-yl)methanone |
| 904 | 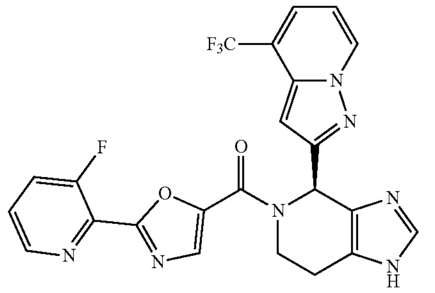 [SMILES: O=C(c1cnc(-c2ncccc2F)o1)N1CCc2[nH]cnc2[C@@H]1c1cc2c(C(F)(F)F)cccn2n1] | (R)-(5-(3-fluoropyridin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 905 | 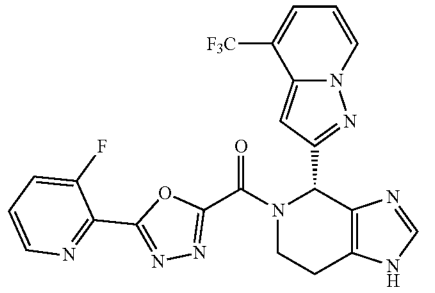 [SMILES: O=C(c1nnc(-c2ncccc2F)o1)N1CCc2[nH]cnc2[C@H]1c1cc2c(C(F)(F)F)cccn2n1] | (S)-(5-(3-fluoropyridin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 906 | 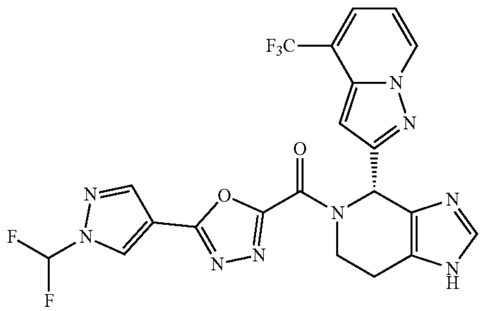 [SMILES: O=C(c1nnc(-c2cnn(C(F)F)c2)o1)N1CCc2[nH]cnc2[C@H]1c1cc2c(C(F)(F)F)cccn2n1] | (S)-(5-(1-(difluoromethyl)-1H-pyrazol-4-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 907 | 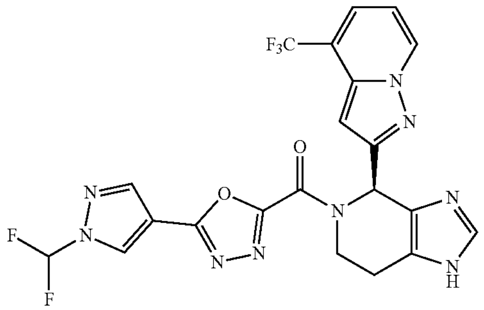 [SMILES: O=C(c1nnc(-c2cnn(C(F)F)c2)o1)N1CCc2[nH]cnc2[C@@H]1c1cc2c(C(F)(F)F)cccn2n1] | (R)-(5-(1-(difluoromethyl)-1H-pyrazol-4-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 908 | 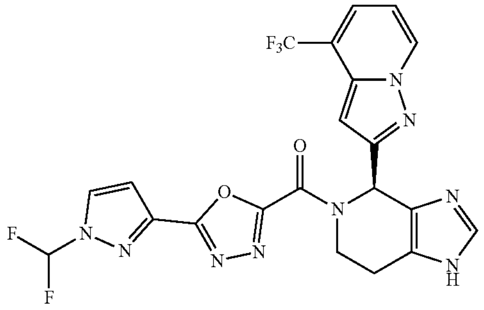 [SMILES: O=C(c1nnc(-c2ccn(C(F)F)n2)o1)N1CCc2[nH]cnc2[C@@H]1c1cc2c(C(F)(F)F)cccn2n1] | (R)-(5-(1-(difluoromethyl)-1H-pyrazol-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 909 | 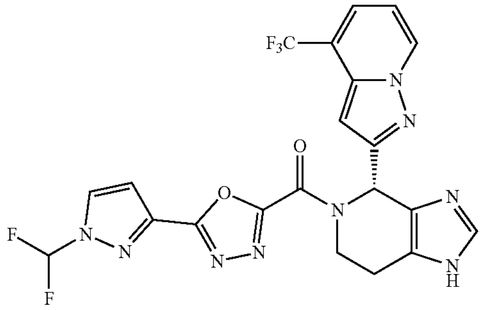 [SMILES: O=C(c1nnc(-c2ccn(C(F)F)n2)o1)N1CCc2[nH]cnc2[C@H]1c1cc2c(C(F)(F)F)cccn2n1] | (S)-(5-(1-(difluoromethyl)-1H-pyrazol-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 910 | 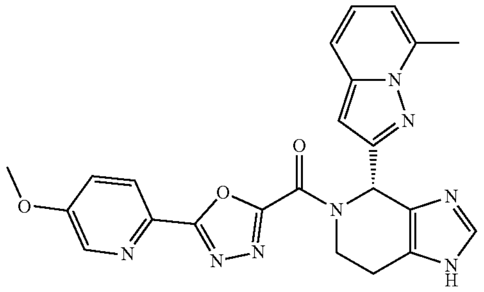 [SMILES: COc1ccc(-c2nnc(C(=O)N3CCc4[nH]cnc4[C@H]3c3cc4cccc(C)n4n3)o2)nc1] | (S)-(5-(5-methoxypyridin-2-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 911 | 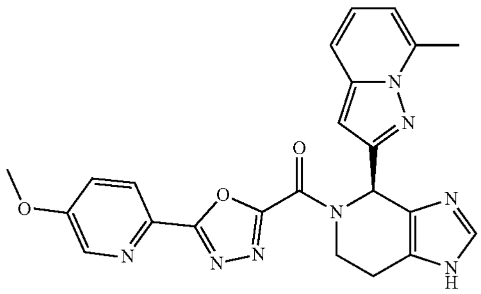 | (R)-(5-(5-methoxypyridin-2-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 912 | 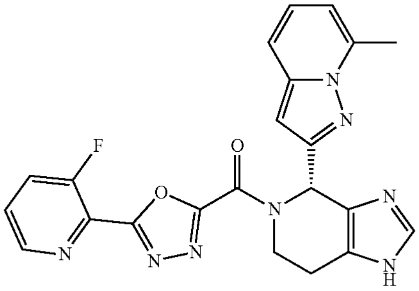 [SMILES: Cc1cccc2cc([C@@H]3c4nc[nH]c4CCN3C(=O)c3nnc(-c4ncccc4F)o3)nn12] | (S)-(5-(3-fluoropyridin-2-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 913 | 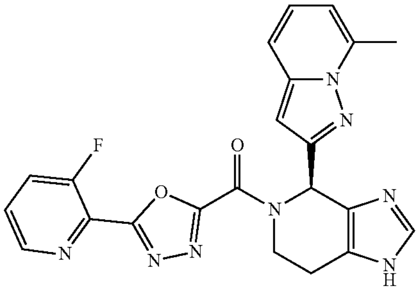 [SMILES: Cc1cccc2cc([C@H]3c4nc[nH]c4CCN3C(=O)c3nnc(-c4ncccc4F)o3)nn12] | (R)-(5-(3-fluoropyridin-2-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 914 | 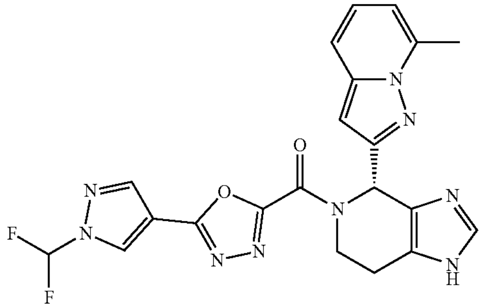 [SMILES: Cc1cccc2cc([C@@H]3c4nc[nH]c4CCN3C(=O)c3nnc(-c4cnn(C(F)F)c4)o3)nn12] | (S)-(5-(1-(difluoromethyl)-1H-pyrazol-4-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 915 | 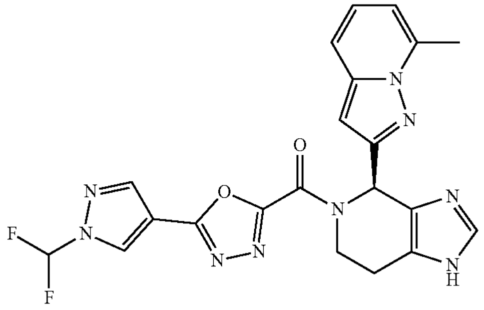 [SMILES: Cc1cccc2cc([C@H]3c4nc[nH]c4CCN3C(=O)c3nnc(-c4cnn(C(F)F)c4)o3)nn12] | (R)-(5-(1-(difluoromethyl)-1H-pyrazol-4-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 916 | 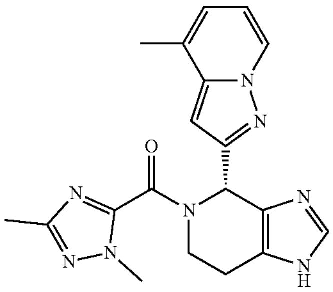 [SMILES: Cc1nc(C(=O)N2CCc3[nH]cnc3[C@H]2c2cc3c(C)cccn3n2)n(C)n1] | (S)-(1,3-dimethyl-1H-1,2,4-triazol-5-yl)(4-(4-methylpyrazolo[1,5-a]pyridin-2-yl)-6,7-dihydro-1H-imidazo[4,5-c]pyridin-5(4H)-yl)methanone |
| 917 | 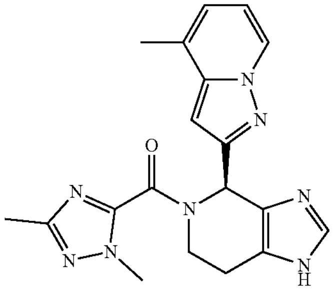 [SMILES: Cc1nc(C(=O)N2CCc3[nH]cnc3[C@@H]2c2cc3c(C)cccn3n2)n(C)n1] | (R)-(1,3-dimethyl-1H-1,2,4-triazol-5-yl)(4-(4-methylpyrazolo[1,5-a]pyridin-2-yl)-6,7-dihydro-1H-imidazo[4,5-c]pyridin-5(4H)-yl)methanone |
| 918 | 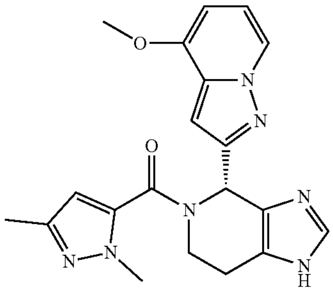 [SMILES: COc1cccn2nc([C@@H]3c4nc[nH]c4CCN3C(=O)c3cc(C)nn3C)cc12] | (S)-(1,3-dimethyl-1H-pyrazol-5-yl)(4-(4-methoxypyrazolo[1,5-a]pyridin-2-yl)-6,7-dihydro-1H-imidazo[4,5-c]pyridin-5(4H)-yl)methanone |
| 919 | 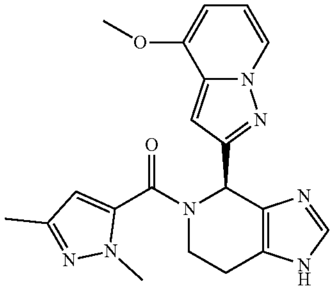 [SMILES: COc1cccn2nc([C@H]3c4nc[nH]c4CCN3C(=O)c3cc(C)nn3C)cc12] | (R)-(1,3-dimethyl-1H-pyrazol-5-yl)(4-(4-methoxypyrazolo[1,5-a]pyridin-2-yl)-6,7-dihydro-1H-imidazo[4,5-c]pyridin-5(4H)-yl)methanone |
| 920 | 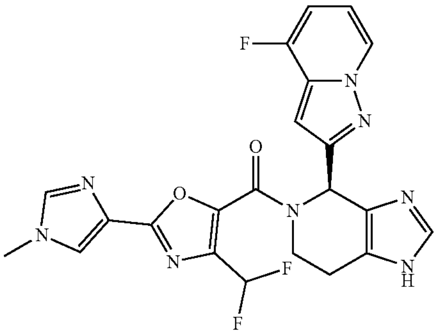 [SMILES: Cn1cnc(-c2nc(C(F)F)c(C(=O)N3CCc4[nH]cnc4[C@@H]3c3cc4c(F)cccn4n3)o2)c1] | (R)-(4-(difluoromethyl)-2-(1-methyl-1H-imidazol-4-yl)oxazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| Pyrazolo[1,5-a]pyridines | | |
| 921 | 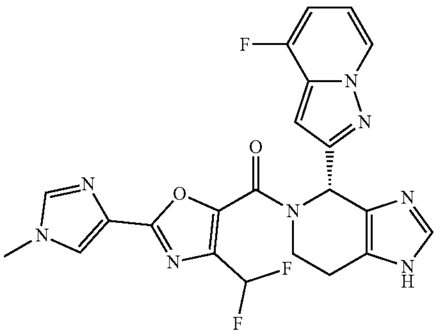 [SMILES: Cn1cnc(-c2nc(C(F)F)c(C(=O)N3CCc4[nH]cnc4[C@H]3c3cc4c(F)cccn4n3)o2)c1] | (S)-(4-(difluoromethyl)-2-(1-methyl-1H-imidazol-4-yl)oxazol-5-yl)(4-(4-fluoropyrazolo[1,5-a]pyridin-2-yl)-6,7-dihydro-1H-imidazo[4,5-c]pyridin-5(4H)-yl)methanone |
| 922 | 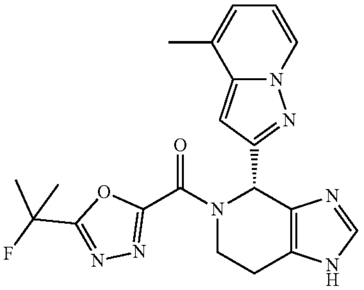 | (S)-(5-(2-fluoropropan-2-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 923 | 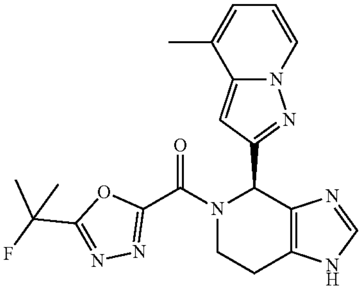 | (R)-(5-(2-fluoropropan-2-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 924 | 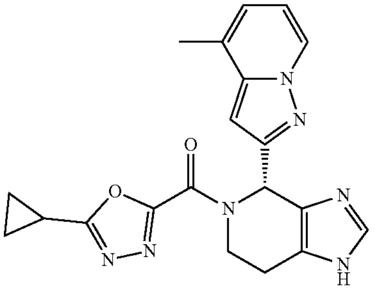 [SMILES: Cc1cccn2nc([C@@H]3c4nc[nH]c4CCN3C(=O)c3nnc(C4CC4)o3)cc12] | (S)-(5-cyclopropyl-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 925 | 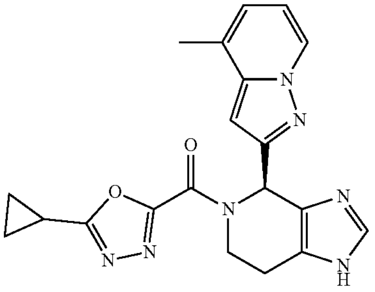 [SMILES: Cc1cccn2nc([C@H]3c4nc[nH]c4CCN3C(=O)c3nnc(C4CC4)o3)cc12] | (R)-(5-cyclopropyl-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 926 | 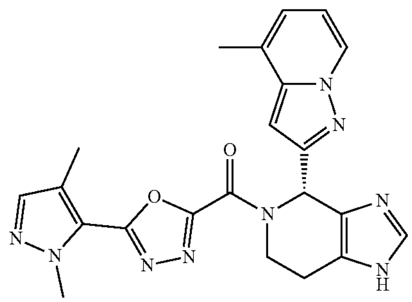 [SMILES: Cc1cnn(C)c1-c1nnc(C(=O)N2CCc3[nH]cnc3[C@H]2c2cc3c(C)cccn3n2)o1] | (S)-(5-(1,4-dimethyl-1H-pyrazol-5-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 927 | 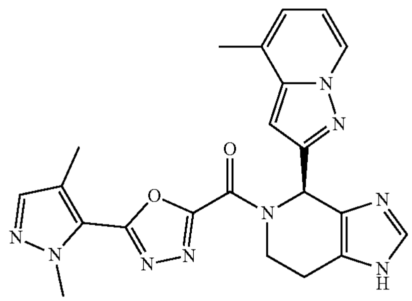 [SMILES: Cc1cnn(C)c1-c1nnc(C(=O)N2CCc3[nH]cnc3[C@@H]2c2cc3c(C)cccn3n2)o1] | (R)-(5-(1,4-dimethyl-1H-pyrazol-5-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 928 | 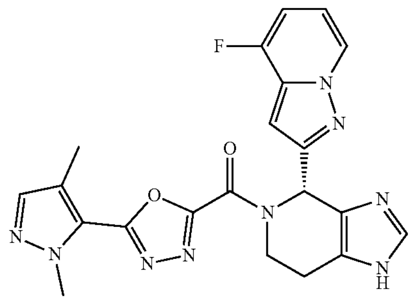 [SMILES: Cc1cnn(C)c1-c1nnc(C(=O)N2CCc3[nH]cnc3[C@H]2c2cc3c(F)cccn3n2)o1] | (S)-(5-(1,4-dimethyl-1H-pyrazol-5-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 929 | 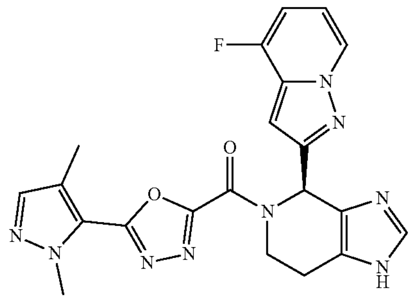 [SMILES: Cc1cnn(C)c1-c1nnc(C(=O)N2CCc3[nH]cnc3[C@@H]2c2cc3c(F)cccn3n2)o1] | (R)-(5-(1,4-dimethyl-1H-pyrazol-5-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 930 | 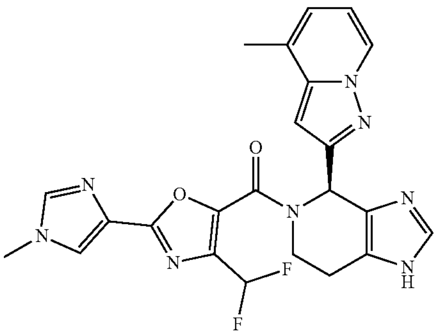 [SMILES: Cc1cccn2nc([C@H]3c4nc[nH]c4CCN3C(=O)c3oc(-c4cn(C)cn4)nc3C(F)F)cc12] | (R)-(4-(difluoromethyl)-2-(1-methyl-1H-imidazol-4-yl)oxazol-5-yl)(4-(4-methylpyrazolo[1,5-a]pyridin-2-yl)-6,7-dihydro-1H-imidazo[4,5-c]pyridin-5(4H)-yl)methanone |
| 931 | 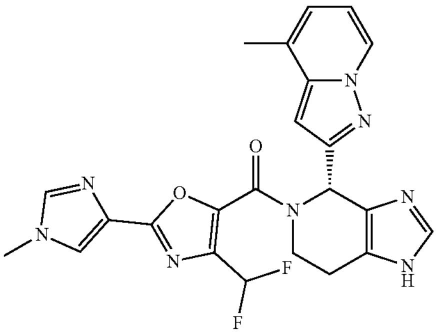 [SMILES: Cc1cccn2nc([C@@H]3c4nc[nH]c4CCN3C(=O)c3oc(-c4cn(C)cn4)nc3C(F)F)cc12] | (S)-(4-(difluoromethyl)-2-(1-methyl-1H-imidazol-4-yl)oxazol-5-yl)(4-(4-methylpyrazolo[1,5-a]pyridin-2-yl)-6,7-dihydro-1H-imidazo[4,5-c]pyridin-5(4H)-yl)methanone |
| 932 | 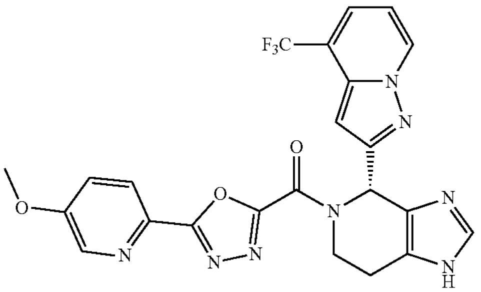 [SMILES: COc1ccc(-c2nnc(C(=O)N3CCc4[nH]cnc4[C@H]3c3cc4c(C(F)(F)F)cccn4n3)o2)nc1] | (S)-(5-(5-methoxypyridin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 933 | 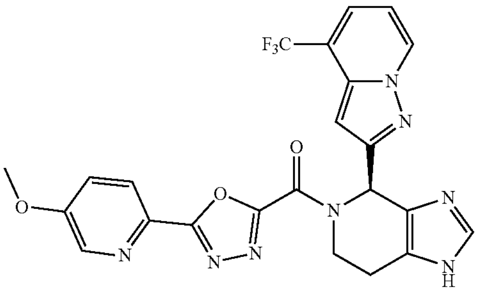 [SMILES: COc1ccc(-c2nnc(C(=O)N3CCc4[nH]cnc4[C@@H]3c3cc4c(C(F)(F)F)cccn4n3)o2)nc1] | (R)-(5-(5-methoxypyridin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 934 | 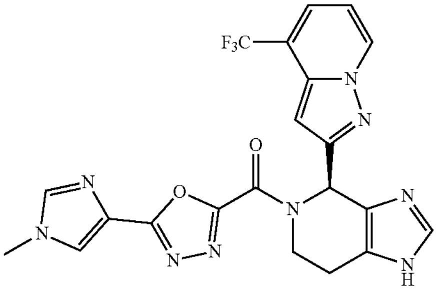 [SMILES: Cn1cnc(-c2nnc(C(=O)N3CCc4[nH]cnc4[C@@H]3c3cc4c(C(F)(F)F)cccn4n3)o2)c1] | (S)-(5-(1-methyl-1H-imidazol-4-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 935 | 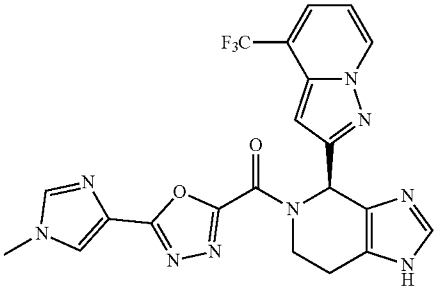 [SMILES: Cn1cnc(-c2nnc(C(=O)N3CCc4[nH]cnc4[C@@H]3c3cc4c(C(F)(F)F)cccn4n3)o2)c1] | (R)-(5-(1-methyl-1H-imidazol-4-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 936 | 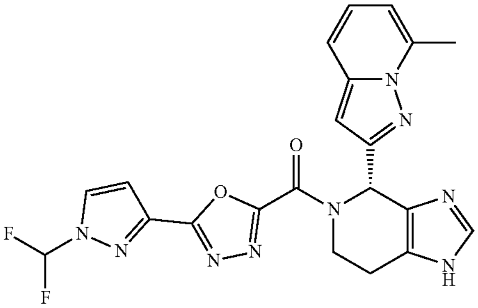 [SMILES: Cc1cccc2cc([C@@H]3c4nc[nH]c4CCN3C(=O)c3nnc(-c4ccn(C(F)F)n4)o3)nn12] | (S)-(5-(1-(difluoromethyl)-1H-pyrazol-3-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 937 | 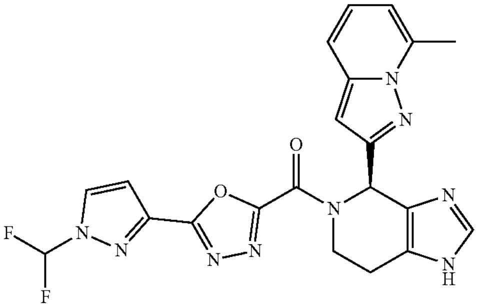 [SMILES: Cc1cccc2cc([C@H]3c4nc[nH]c4CCN3C(=O)c3nnc(-c4ccn(C(F)F)n4)o3)nn12] | (R)-(5-(1-(difluoromethyl)-1H-pyrazol-3-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 938 | 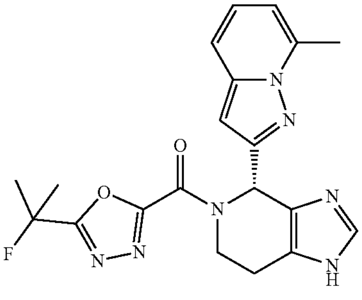 [SMILES: Cc1cccc2cc([C@@H]3c4nc[nH]c4CCN3C(=O)c3nnc(C(C)(C)F)o3)nn12] | (S)-(5-(2-fluoropropan-2-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 939 | 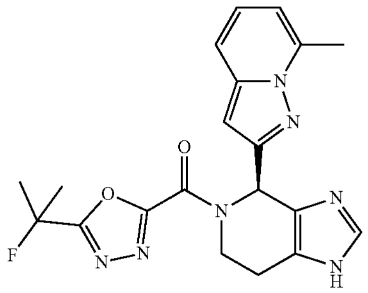 [SMILES: Cc1cccc2cc([C@H]3c4nc[nH]c4CCN3C(=O)c3nnc(C(C)(C)F)o3)nn12] | (R)-(5-(2-fluoropropan-2-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 940 | 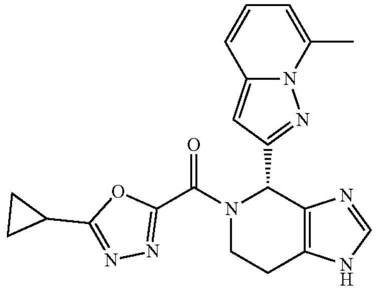 [SMILES: Cc1cccc2cc([C@@H]3c4nc[nH]c4CCN3C(=O)c3nnc(C4CC4)o3)nn12] | (S)-(5-cyclopropyl-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 941 | 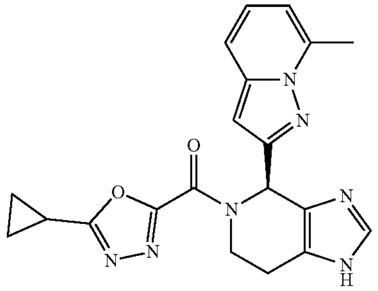 [SMILES: Cc1cccc2cc([C@H]3c4nc[nH]c4CCN3C(=O)c3nnc(C4CC4)o3)nn12] | (R)-(5-cyclopropyl-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 942 | 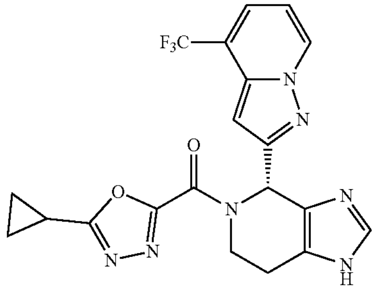 | (S)-(5-cyclopropyl-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 943 | 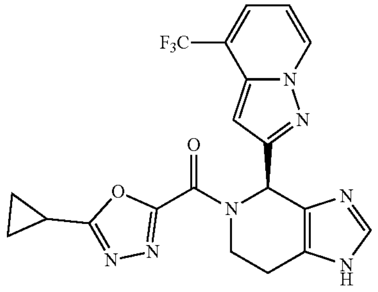 | (R)-(5-cyclopropyl-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 944 | 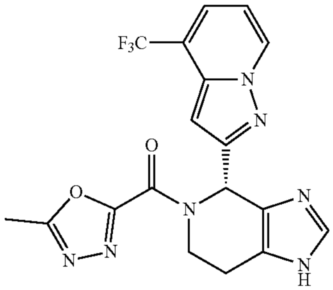 [SMILES: Cc1nnc(C(=O)N2CCc3[nH]cnc3[C@H]2c2cc3c(C(F)(F)F)cccn3n2)o1] | (S)-(5-methyl-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 945 | 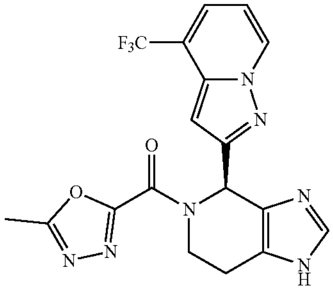 | (R)-(5-methyl-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 946 | 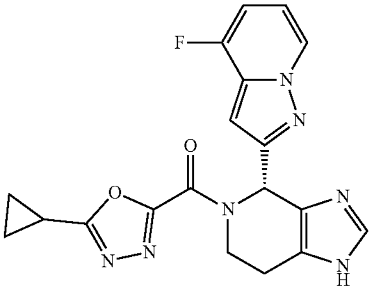 | (S)-(5-cyclopropyl-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 947 | 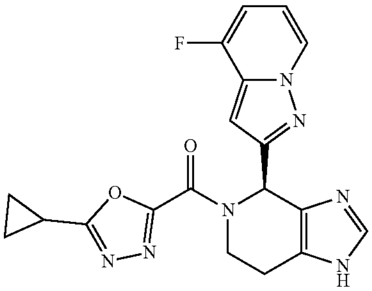 | (R)-(5-cyclopropyl-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 948 | 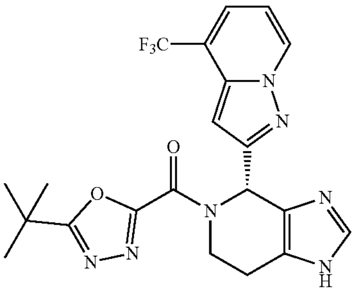 [SMILES: CC(C)(C)c1nnc(C(=O)N2CCc3[nH]cnc3[C@H]2c2cc3c(C(F)(F)F)cccn3n2)o1] | (S)-(5-(tert-butyl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 949 | 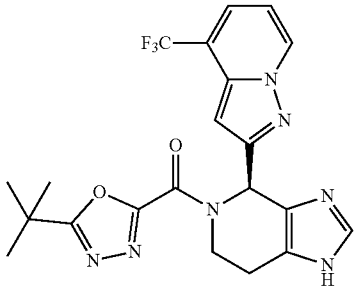 [SMILES: CC(C)(C)c1nnc(C(=O)N2CCc3[nH]cnc3[C@@H]2c2cc3c(C(F)(F)F)cccn3n2)o1] | (R)-(5-(tert-butyl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 950 | 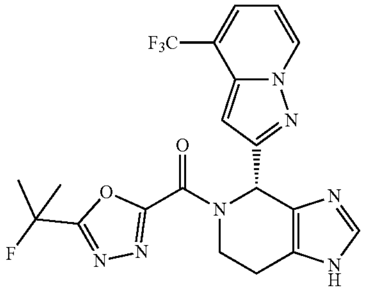 [SMILES: CC(C)(F)c1nnc(C(=O)N2CCc3[nH]cnc3[C@H]2c2cc3c(C(F)(F)F)cccn3n2)o1] | (S)-(5-(2-fluoropropan-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 951 | 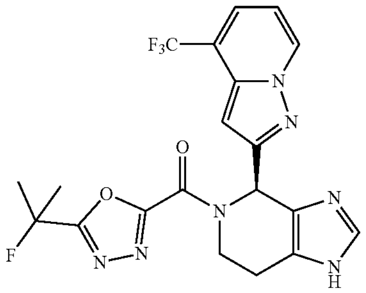 [SMILES: CC(C)(F)c1nnc(C(=O)N2CCc3[nH]cnc3[C@@H]2c2cc3c(C(F)(F)F)cccn3n2)o1] | (R)-(5-(2-fluoropropan-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 952 | 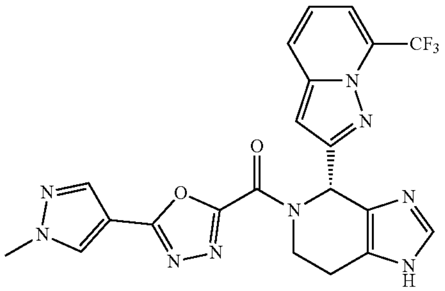 [SMILES: Cn1cc(-c2nnc(C(=O)N3CCc4[nH]cnc4[C@H]3c3cc4cccc(C(F)(F)F)n4n3)o2)cn1] | (S)-(5-(1-methyl-1H-pyrazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 953 | 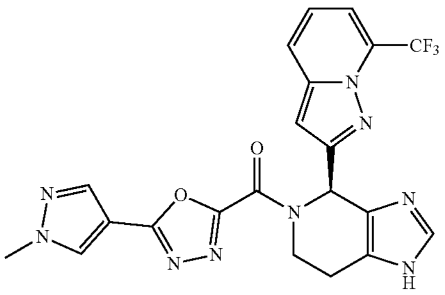 [SMILES: Cn1cc(-c2nnc(C(=O)N3CCc4[nH]cnc4[C@@H]3c3cc4cccc(C(F)(F)F)n4n3)o2)cn1] | (R)-(5-(1-methyl-1H-pyrazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 954 | 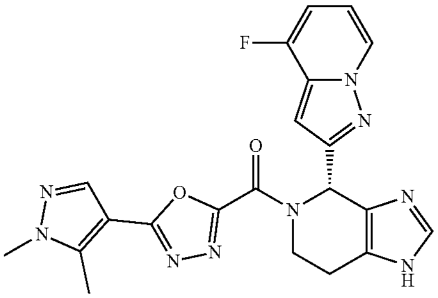 [SMILES: Cc1c(-c2nnc(C(=O)N3CCc4[nH]cnc4[C@H]3c3cc4c(F)cccn4n3)o2)cnn1C] | (S)-(5-(1,5-dimethyl-1H-pyrazol-4-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 955 | 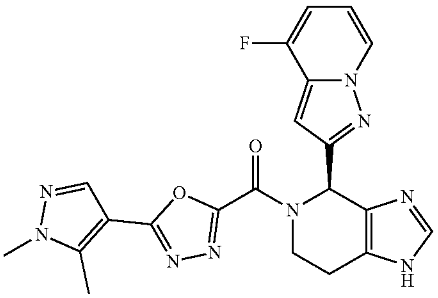 | (R)-(5-(1,5-dimethyl-1H-pyrazol-4-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 956 | 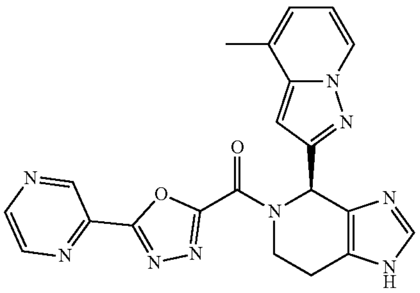 [SMILES: Cc1cccn2nc([C@H]3c4nc[nH]c4CCN3C(=O)c3nnc(-c4cnccn4)o3)cc12] | (R)-(4-(4-methylpyrazolo[1,5-a]pyridin-2-yl)-6,7-dihydro-1H-imidazo[4,5-c]pyridin-5(4H)-yl)(5-(pyrazin-2-yl)-1,3,4-oxadiazol-2-yl)methanone |
| 957 | 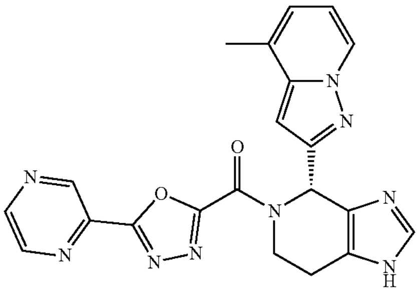 [SMILES: Cc1cccn2nc([C@@H]3c4nc[nH]c4CCN3C(=O)c3nnc(-c4cnccn4)o3)cc12] | (S)-(4-(4-methylpyrazolo[1,5-a]pyridin-2-yl)-6,7-dihydro-1H-imidazo[4,5-c]pyridin-5(4H)-yl)(5-(pyrazin-2-yl)-1,3,4-oxadiazol-2-yl)methanone |
| 958 | 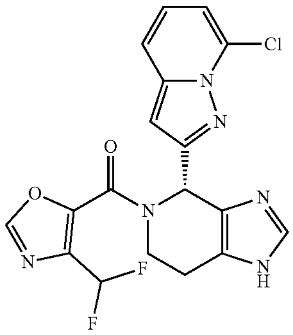 | (S)-(4-(7-chloropyrazolo[1,5-a]pyridin-2-yl)-6,7-dihydro-1H-imidazo[4,5-c]pyridin-5(4H)-yl)(4-(difluoromethyl)oxazol-5-yl)methanone |

TABLE 1-continued

Pyrazolo[1,5-a]pyridines

| Ex. # | Structure | Name |
| --- | --- | --- |
| 959 | 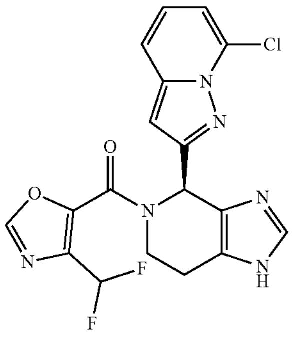 | (R)-(4-(7-chloropyrazolo[1,5-a]pyridin-2-yl)-6,7-dihydro-1H-imidazo[4,5-c]pyridin-5(4H)-yl)(4-(difluoromethyl)oxazol-5-yl)methanone |
| 960 | 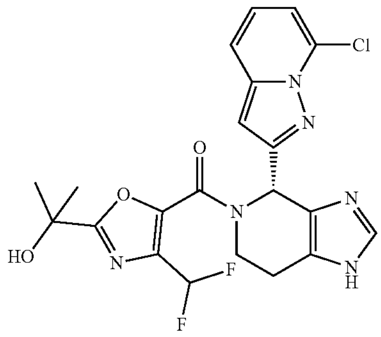 [SMILES: CC(C)(O)c1nc(C(F)F)c(C(=O)N2CCc3[nH]cnc3[C@H]2c2cc3cccc(Cl)n3n2)o1] | (S)-(4-(7-chloropyrazolo[1,5-a]pyridin-2-yl)-6,7-dihydro-1H-imidazo[4,5-c]pyridin-5(4H)-yl)(4-(difluoromethyl)-2-(2-hydroxypropan-2-yl)oxazol-5-yl)methanone |
| 961 | 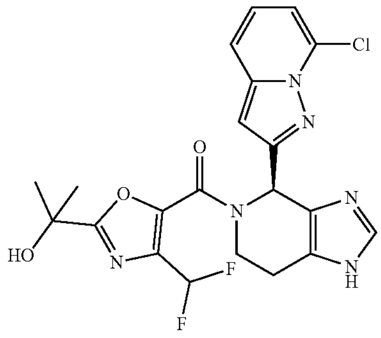 [SMILES: CC(C)(O)c1nc(C(F)F)c(C(=O)N2CCc3[nH]cnc3[C@@H]2c2cc3cccc(Cl)n3n2)o1] | (R)-(4-(7-chloropyrazolo[1,5-a]pyridin-2-yl)-6,7-dihydro-1H-imidazo[4,5-c]pyridin-5(4H)-yl)(4-(difluoromethyl)-2-(2-hydroxypropan-2-yl)oxazol-5-yl)methanone |
| 962 | 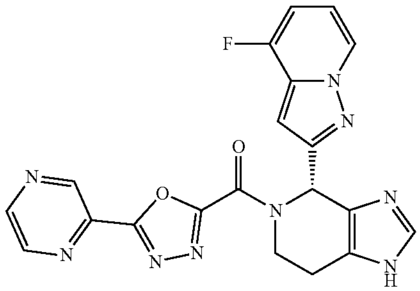 [SMILES: O=C(c1nnc(-c2cnccn2)o1)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(5-(pyrazin-2-yl)-1,3,4-oxadiazol-2-yl)methanone |

TABLE 1-continued

| Ex. # | Structure | Name |
|---|---|---|
| | Pyrazolo[1,5-a]pyridines | |
| 963 | 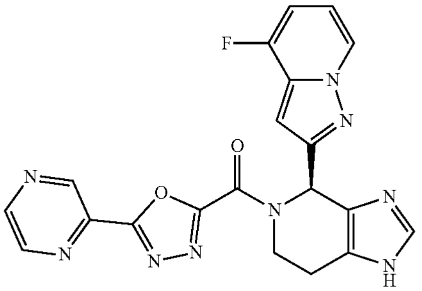 | (R)-(4-(4-fluoropyrazolo[1,5-a]pyridin-2-y]l)-6,7-dihydro-1H-imidazo[4,5-c]pyridin-5(4H)-yl)(5-(pyrazin-2-yl)-1,3,4-oxadiazol-2-yl)methanone |
| 964 | 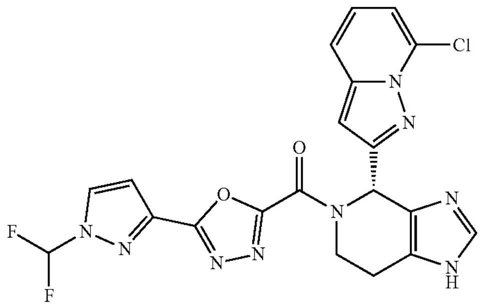 [SMILES: O=C(c1nnc(-c2ccn(C(F)F)n2)o1)N1CCc2[nH]cnc2[C@H]1c1cc2cccc(Cl)n2n1] | (S)-(4-(7-chloropyrazolo[1,5-a]pyridin-2-y])-6,7-dihydro-1H-imidazo[4,5-c]pyridin-5(4H)-yl)(5-(1-(difluoromethyl)-1H-pyrazol-3-yl)-1,3,4-oxadiazol-2-yl)methanone |
| 965 | 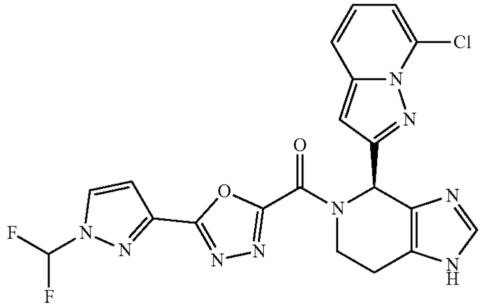 | (R)-(4-(7-chloropyrazolo[1,5-a]pyridin-2-yl)-6,7-dihydro-1H-imidazo[4,5-c]pyridin-5(4H)-yl)(5-(1-(difluoromethyl)-1H-pyrazol-3-yl)-1,3,4-oxadiazol-2-yl)methanone |
| 966 | 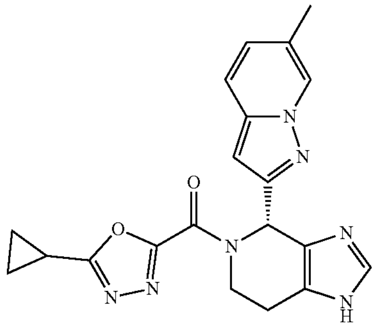 [SMILES: Cc1ccc2cc([C@@H]3c4nc[nH]c4CCN3C(=O)c3nnc(C4CC4)o3)nn2c1] | (S)-(5-cyclopropyl-1,3,4-oxadiazol-2-yl)(4-(6-methylpyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 967 | 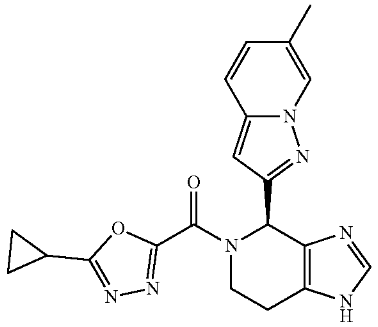 [SMILES: Cc1ccc2cc([C@H]3c4nc[nH]c4CCN3C(=O)c3nnc(C4CC4)o3)nn2c1] | (R)-(5-cyclopropyl-1,3,4-oxadiazol-2-yl)(4-(6-methylpyrazolo[1,5-a]pyridin-2-yl)-6,7-dihydro-1H-imidazo[4,5-c]pyridin-5(4H)-yl)methanone |
| 968 | 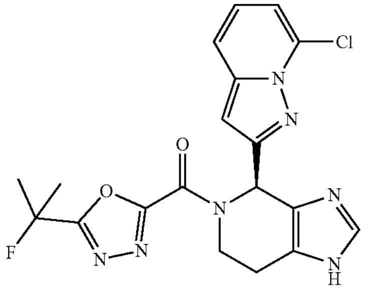 | (R)-(4-(7-chloropyrazolo[1,5-a]pyridin-2-yl)-6,7-dihydro-1H-imidazo[4,5-c]pyridin-5(4H)-yl)(5-(2-fluoropropan-2-yl)-1,3,4-oxadiazol-2-yl)methanone |
| 969 | 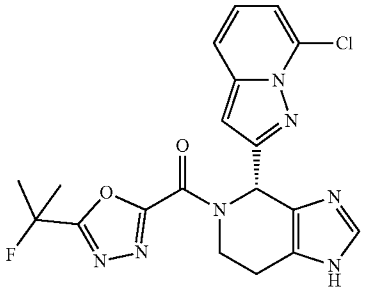 [SMILES: CC(C)(F)c1nnc(C(=O)N2CCc3[nH]cnc3[C@H]2c2cc3cccc(Cl)n3n2)o1] | (S)-(4-(7-chloropyrazolo[1,5-a]pyridin-2-yl)-6,7-dihydro-1H-imidazo[4,5-c]pyridin-5(4H)-yl)(5-(2-fluoropropan-2-yl)-1,3,4-oxadiazol-2-yl)methanone |
| 970 | 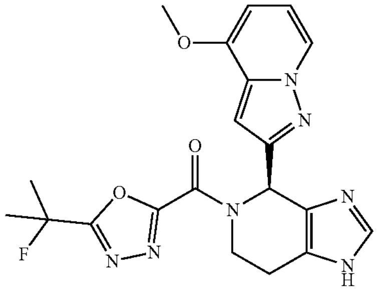 [SMILES: COc1cccn2nc([C@H]3c4nc[nH]c4CCN3C(=O)c3nnc(C(C)(C)F)o3)cc12] | (R)-(5-(2-fluoropropan-2-yl)-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 971 | 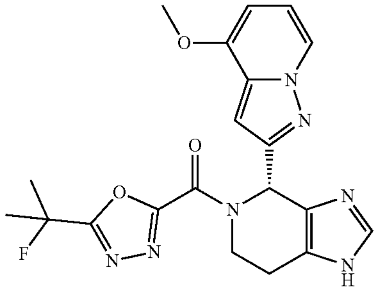 [SMILES: COc1cccn2nc([C@@H]3c4nc[nH]c4CCN3C(=O)c3nnc(C(C)(C)F)o3)cc12] | (S)-(5-(2-fluoropropan-2-yl)-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 972 | 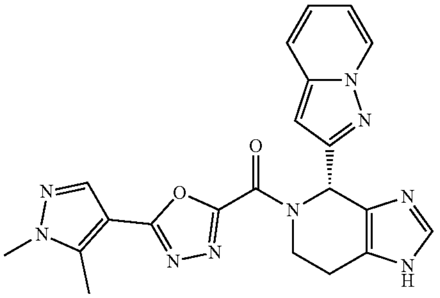 [SMILES: Cc1c(-c2nnc(C(=O)N3CCc4[nH]cnc4[C@H]3c3cc4ccccn4n3)o2)cnn1C] | (S)-(5-(1,5-dimethyl-1H-pyrazol-4-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 973 | 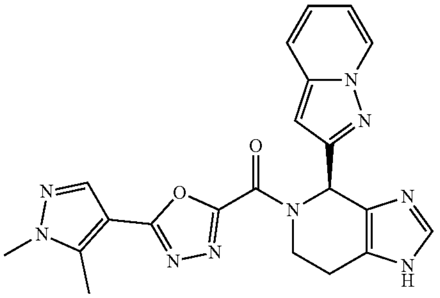 [SMILES: Cc1c(-c2nnc(C(=O)N3CCc4[nH]cnc4[C@@H]3c3cc4ccccn4n3)o2)cnn1C] | (R)-(5-(1,5-dimethyl-1H-pyrazol-4-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 974 | 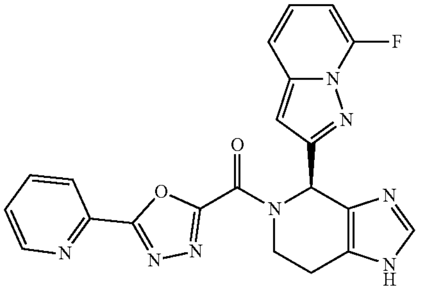 [SMILES: O=C(c1nnc(-c2ccccn2)o1)N1CCc2[nH]cnc2[C@@H]1c1cc2cccc(F)n2n1] | (R)-(4-(7-fluoropyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 975 | 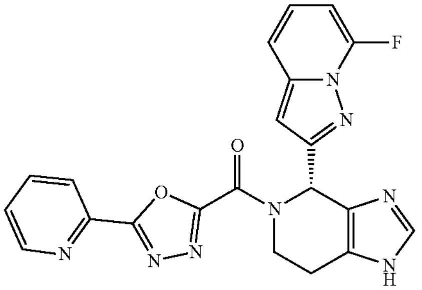 [SMILES: O=C(c1nnc(-c2ccccn2)o1)N1CCc2[nH]cnc2[C@H]1c1cc2cccc(F)n2n1] | (S)-(4-(7-fluoropyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 976 | 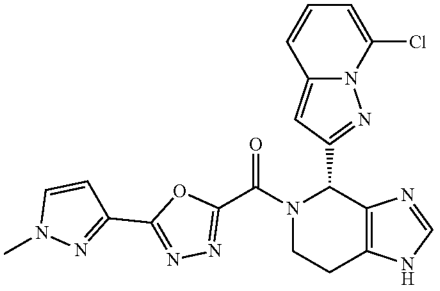 [SMILES: Cn1ccc(-c2nnc(C(=O)N3CCc4[nH]cnc4[C@H]3c3cc4cccc(Cl)n4n3)o2)n1] | (S)-(4-(7-chloropyrazolo[1,5-a]pyridin-2-yl)-6,7-dihydro-1H-imidazo[4,5-c]pyridin-5(4H)-yl)(5-(1-methyl-1H-pyrazol-3-yl)-1,3,4-oxadiazol-2-yl)methanone |

TABLE 1-continued

Pyrazolo[1,5-a]pyridines

| Ex. # | Structure | Name |
|---|---|---|
| 977 | 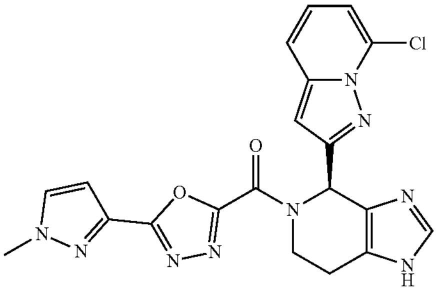 [SMILES: Cn1ccc(-c2nnc(C(=O)N3CCc4[nH]cnc4[C@@H]3c3cc4cccc(Cl)n4n3)o2)n1] | (R)-(4-(7-chloropyrazolo[1,5-a]pyridin-2-yl)-6,7-dihydro-1H-imidazo[4,5-c]pyridin-5(4H)-yl)(5-(1-methyl-1H-pyrazol-3-yl)-1,3,4-oxadiazol-2-yl)methanone |
| 978 | 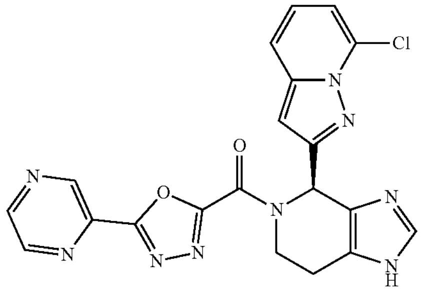 [SMILES: O=C(c1nnc(-c2cnccn2)o1)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(5-(pyrazin-2-yl)-1,3,4-oxadiazol-2-yl)methanone |
| 979 | 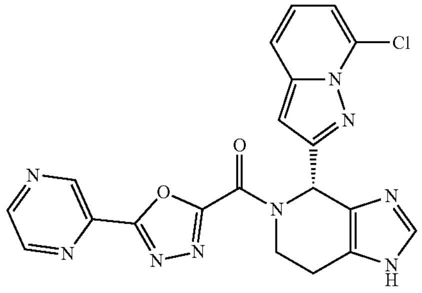 [SMILES: O=C(c1nnc(-c2cnccn2)o1)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(5-(pyrazin-2-yl)-1,3,4-oxadiazol-2-yl)methanone |
| 980 | 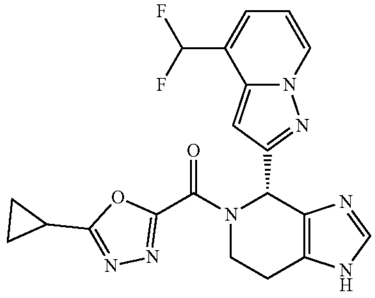 | (S)-(5-cyclopropyl-1,3,4-oxadiazol-2-yl)(4-(4-(difluoromethyl)pyrazolo[1,5-a]pyridin-2-yl)-6,7-dihydro-1H-imidazo[4,5-c]pyridin-5(4H)-yl)methanone |
| 981 | 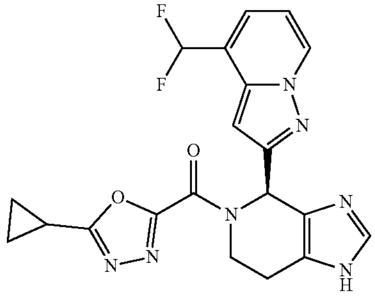 | (R)-(5-cyclopropyl-1,3,4-oxadiazol-2-yl)(4-(4-(difluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 982 | 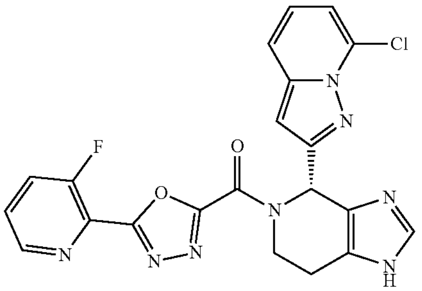 [SMILES: O=C(c1nnc(-c2ncccc2F)o1)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(5-(3-fluoropyridin-2-yl)-1,3,4-oxadiazol-2-yl)methanone |
| 983 | 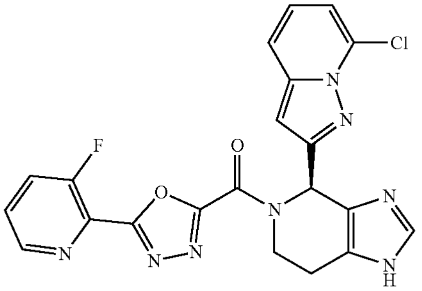 [SMILES: O=C(c1nnc(-c2ncccc2F)o1)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(5-(3-fluoropyridin-2-yl)-1,3,4-oxadiazol-2-yl)methanone |
| 984 | 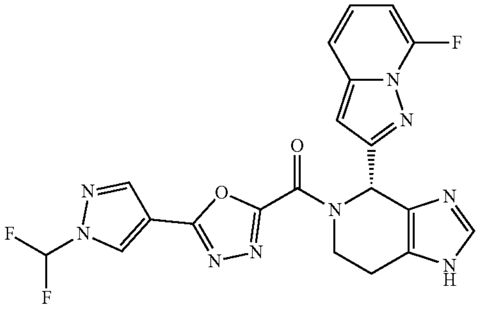 | (S)-(5-(1-(difluoromethyl)-1H-pyrazol-4-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 985 | 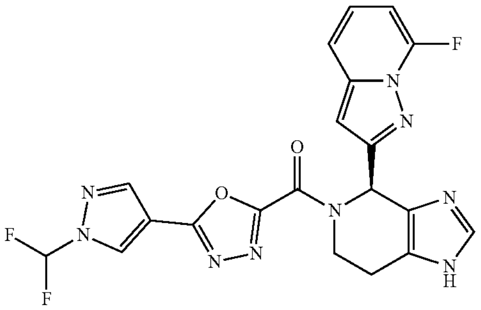 | (R)-(5-(1-(difluoromethyl)-1H-pyrazol-4-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 986 | 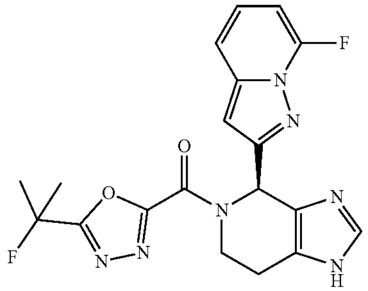 | (R)-(5-(2-fluoropropan-2-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| Pyrazolo[1,5-a]pyridines | | |
| 987 | 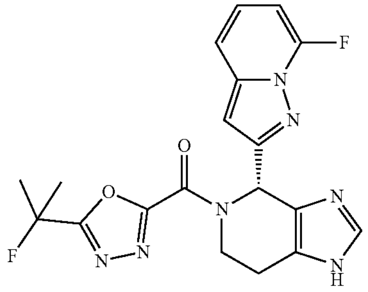 [SMILES: CC(C)(F)c1nnc(C(=O)N2CCc3[nH]cnc3[C@H]2c2cc3cccc(F)n3n2)o1] | (S)-(5-(2-fluoropropan-2-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 988 | 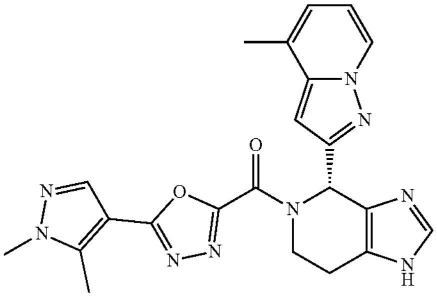 [SMILES: Cc1cccn2nc([C@@H]3c4nc[nH]c4CCN3C(=O)c3nnc(-c4cnn(C)c4C)o3)cc12] | (S)-(5-(1,5-dimethyl-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 989 | 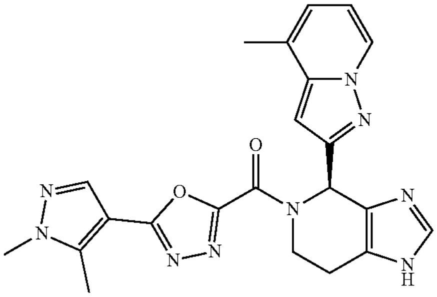 [SMILES: Cc1cccn2nc([C@H]3c4nc[nH]c4CCN3C(=O)c3nnc(-c4cnn(C)c4C)o3)cc12] | (R)-(5-(1,5-dimethyl-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 990 | 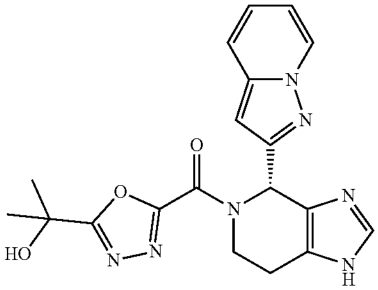 [SMILES: CC(C)(O)c1nnc(C(=O)N2CCc3[nH]cnc3[C@H]2c2cc3ccccn3n2)o1] | (S)-(4-chloro-2-(2-hydroxypropan-2-yl)oxazol-5-yl)(4-(pyrazolo[1,5-a]pyridin-2-yl)-6,7-dihydro-1H-imidazo[4,5-c]pyridin-5(4H)-yl)methanone |
| 991 | 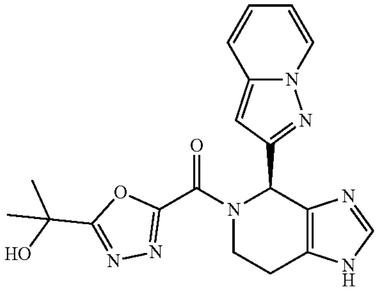 [SMILES: CC(C)(O)c1nnc(C(=O)N2CCc3[nH]cnc3[C@@H]2c2cc3ccccn3n2)o1] | (R)-(4-chloro-2-(2-hydroxypropan-2-yl)oxazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 992 | 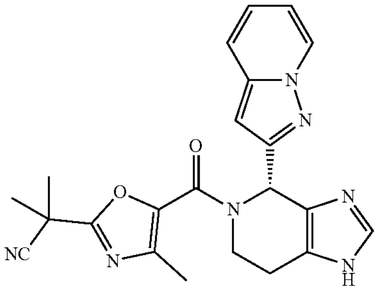 [SMILES: Cc1nc(C(C)(C)C#N)oc1C(=O)N1CCc2[nH]cnc2[C@H]1c1cc2ccccn2n1] | (S)-2-methyl-2-(4-methyl-5-(4-(pyrazolo[1,5-a]pyridin-2-yl)-4,5,6,7-tetrahydro-1H-imidazo[4,5-c]pyridine-5-carbonyl)oxazol-2-yl)propanenitrile |
| 993 | 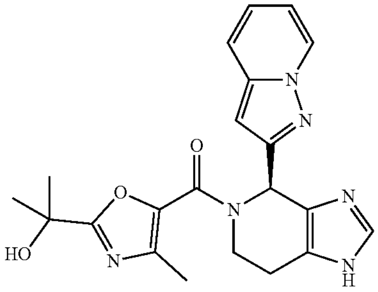 | (R)-2-methyl-2-(4-methyl-5-(4-(pyrazolo[1,5-a]pyridin-2-yl)-4,5,6,7-tetrahydro-1H-imidazo[4,5-c]pyridine-5-carbonyl)oxazol-2-yl)propanenitrile |
| 994 | 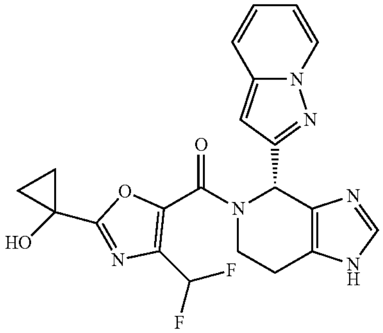 [SMILES: O=C(c1oc(C2(O)CC2)nc1C(F)F)N1CCc2[nH]cnc2[C@H]1c1cc2ccccn2n1] | (S)-(4-(difluoromethyl)-2-(1-hydroxycyclopropyl) oxazol-5-yl)(4-(pyrazolo[1,5-a]pyridin-2-yl)-6,7-dihydro-1H-imidazo[4,5-c]pyridin-5(4H)-yl)methanone |
| 995 | 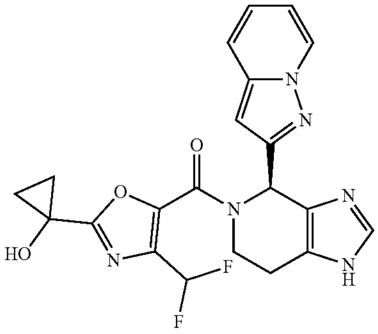 [SMILES: O=C(c1oc(C2(O)CC2)nc1C(F)F)N1CCc2[nH]cnc2[C@@H]1c1cc2ccccn2n1] | (R)-(4-(difluoromethyl)-2-(1-hydroxycyclopropyl) oxazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 996 | 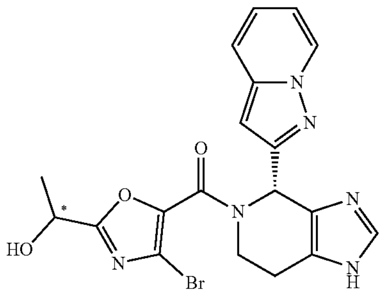 | (4-bromo-2-(1-hydroxyethyl) oxazol-5-yl)((S)-4-(pyrazolo[1,5-a]pyridin-2-yl)-6,7-dihydro-1H-imidazo[4,5-c]pyridin-5(4H)-yl)methanone Diastereomer #1 (Rt = 5.586 min) |
| 997 | 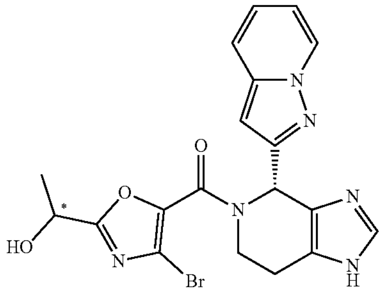 | (4-bromo-2-(1-hydroxyethyl) oxazol-5-yl)((S)-4-(pyrazolo[1,5-a]pyridin-2-yl)-6,7-dihydro-1H-imidazo[4,5-c]pyridin-5(4H)-yl)methanone Diastereomer #2 (Rt = 5.796 min) |
| 998 | 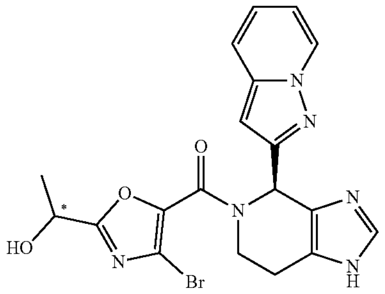 | (4-bromo-2-(1-hydroxyethyl) oxazol-5-yl)((R)-4-(pyrazolo[1,5-a]pyridin-2-yl)-6,7-dihydro-1H-imidazo[4,5-c]pyridin-5(4H)-yl)methanone Diastereomer #1 (Rt = 4.830 min) |
| 999 | 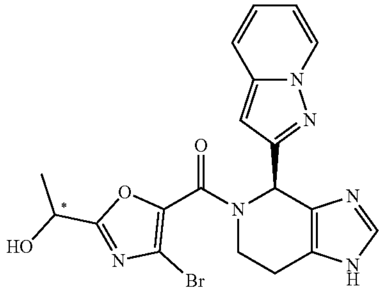 | (4-bromo-2-(1-hydroxyethyl) oxazol-5-yl)((R)-4-(pyrazolo[1,5-a]pyridin-2-yl)-6,7-dihydro-1H-imidazo[4,5-c]pyridin-5(4H)-yl)methanone Diastereomer #2 (Rt = 5.133 min) |
| 1000 | 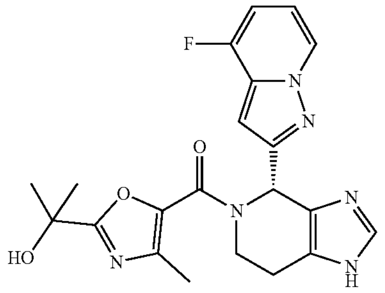 [SMILES: Cc1nc(C(C)(C)O)oc1C(=O)N1CCc2[nH]cnc2[C@H]1c1cc2c(F)cccn2n1] | (S)-(4-(4-fluoropyrazolo[1,5-a] pyridin-2-yl)-6,7-dihydro-1H-imidazo[4,5-c] pyridin-5(4H)-yl)(2-(2-hydroxypropan-2-yl)-4-methyloxazol-5-yl)methanone |

TABLE 1-continued

| Pyrazolo[1,5-a]pyridines | | |
|---|---|---|
| Ex. # | Structure | Name |
| 1001 | 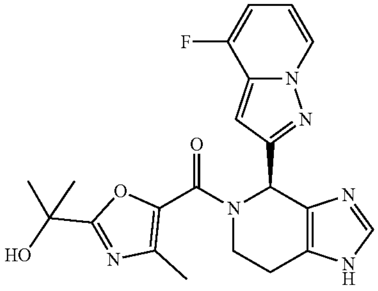 [SMILES: Cc1nc(C(C)(C)O)oc1C(=O)N1CCc2[nH]cnc2[C@@H]1c1cc2c(F)cccn2n1] | (R)-(4-(4-fluoropyrazolo [1,5-a]pyridin-2-y]l)-6,7-dihydro-1H-imidazo[4,5-c] pyridin-5(4H)-yl)(2-(2-hydroxypropan-2-yl)-4-methyloxazol-5-yl)methanone |
| 1002 | 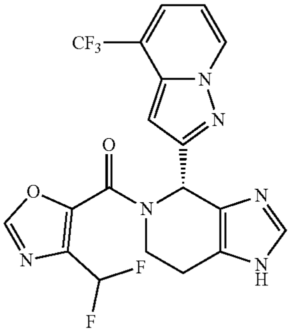 [SMILES: O=C(c1ocnc1C(F)F)N1CCc2[nH]cnc2[C@H]1c1cc2c(C(F)(F)F)cccn2n1] | (S)-(4-(difluoromethyl) oxazol-5-yl)(4-(4-(trifluoromethyl)pyrazolo [1,5-a]pyridin-2-yl)-6,7-dihydro-1H-imidazo[4,5-c] pyridin-5(4H)-yl)methanone |
| 1003 | 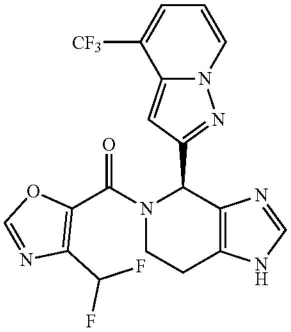 [SMILES: O=C(c1ocnc1C(F)F)N1CCc2[nH]cnc2[C@@H]1c1cc2c(C(F)(F)F)cccn2n1] | (R)-(4-(difluoromethyl) oxazol-5-yl)(4-(4-(trifluoromethyl)pyrazolo [1,5-a]pyridin-2-yl)-6,7-dihydro-1H-imidazo[4,5-c] pyridin-5(4H)-yl)methanone |
| 1004 | 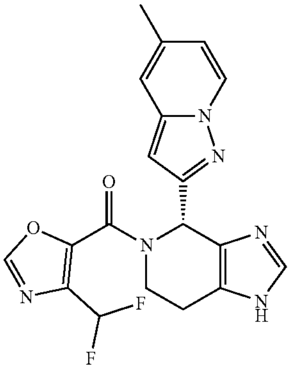 [SMILES: Cc1ccn2nc([C@@H]3c4nc[nH]c4CCN3C(=O)c3ocnc3C(F)F)cc2c1] | (S)-(4-(difluoromethyl) oxazol-5-yl)(4-(5-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1005 | 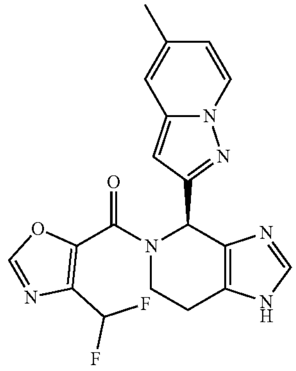 [SMILES: Cc1ccn2nc([C@H]3c4nc[nH]c4CCN3C(=O)c3ocnc3C(F)F)cc2c1] | (R)-(4-(difluoromethyl) oxazol-5-yl)(4-(5-methylpyrazolo[1,5-a]pyridin-2-yl)-6,7-dihydro-1H-imidazo[4,5-c]pyridin-5(4H)-yl)methanone |
| 1006 | 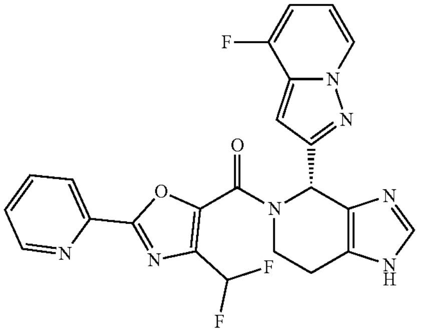 [SMILES: O=C(c1oc(-c2ccccn2)nc1C(F)F)N1CCc2[nH]cnc2[C@H]1c1cc2c(F)cccn2n1] | (S)-(4-(difluoromethyl)-2-(pyridin-2-yl)oxazol-5-yl)(4-(4-fluoropyrazolo[1,5-a] pyridin-2-yl)-6,7-dihydro-1H-imidazo[4,5-c]pyridin-5(4H)-yl)methanone |
| 1007 | 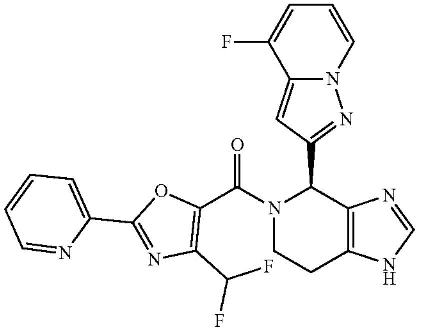 [SMILES: O=C(c1oc(-c2ccccn2)nc1C(F)F)N1CCc2[nH]cnc2[C@@H]1c1cc2c(F)cccn2n1] | (R)-(4-(difluoromethyl)-2-(pyridin-2-yl)oxazol-5-yl)(4-(4-fluoropyrazolo[1,5-a] pyridin-2-yl)-6,7-dihydro-1H-imidazo[4,5-c]pyridin-5(4H)-yl)methanone |
| 1008 | 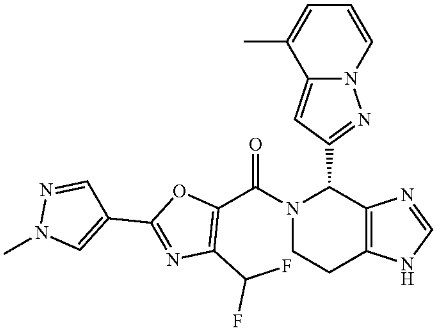 [SMILES: Cc1cccn2nc([C@@H]3c4nc[nH]c4CCN3C(=O)c3oc(-c4cnn(C)c4)nc3C(F)F)cc12] | (S)-(4-(difluoromethyl)-2-(1-methyl-1H-pyrazol-4-yl)oxazol-5-yl)(4-(4-methylpyrazolo[1,5-a] pyridin-2-yl)-6,7-dihydro-1H-imidazo [4,5-c]pyridin-5(4H)-yl)methanone |

TABLE 1-continued

| Ex. # | Structure | Name |
|---|---|---|
| | Pyrazolo[1,5-a]pyridines | |
| 1009 | 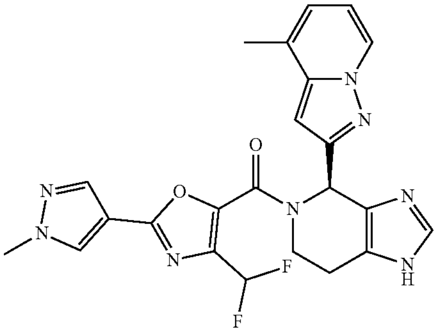 [SMILES: Cc1cccn2nc([C@H]3c4nc[nH]c4CCN3C(=O)c3oc(-c4cnn(C)c4)nc3C(F)F)cc12] | (R)-(4-(difluoromethyl)-2-(1-methyl-1H-pyrazol-4-yl)oxazol-5-yl)(4-(4-methylpyrazolo[1,5-a]pyridin-2-yl)-6,7-dihydro-1H-imidazo[4,5-c]pyridin-5(4H)-yl)methanone |
| 1010 | 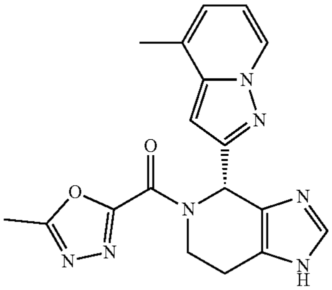 [SMILES: Cc1nnc(C(=O)N2CCc3[nH]cnc3[C@H]2c2cc3c(C)cccn3n2)o1] | (S)-(5-methyl-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1011 | 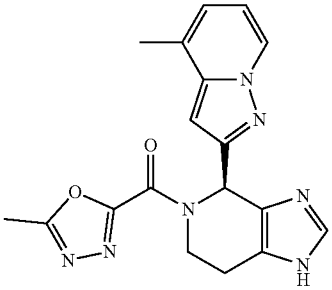 [SMILES: Cc1nnc(C(=O)N2CCc3[nH]cnc3[C@@H]2c2cc3c(C)cccn3n2)o1] | (R)-(5-methyl-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1012 | 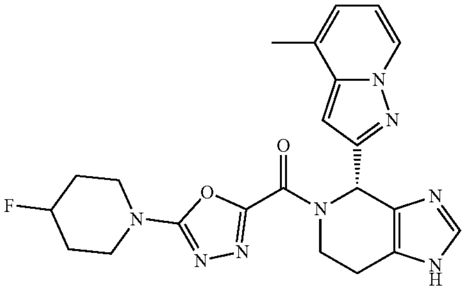 [SMILES: Cc1cccn2nc([C@@H]3c4nc[nH]c4CCN3C(=O)c3nnc(N4CCC(F)CC4)o3)cc12] | (S)-(5-(4-fluoropiperidin-1-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1013 | 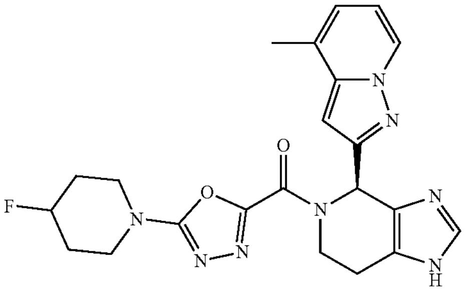 [SMILES: Cc1cccn2nc([C@H]3c4nc[nH]c4CCN3C(=O)c3nnc(N4CCC(F)CC4)o3)cc12] | (R)-(5-(4-fluoropiperidin-1-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1014 | 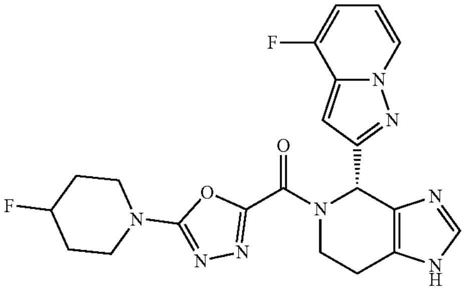 [SMILES: O=C(c1nnc(N2CCC(F)CC2)o1)N1CCc2[nH]cnc2[C@H]1c1cc2c(F)cccn2n1] | (S)-(5-(4-fluoropiperidin-1-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 1015 | 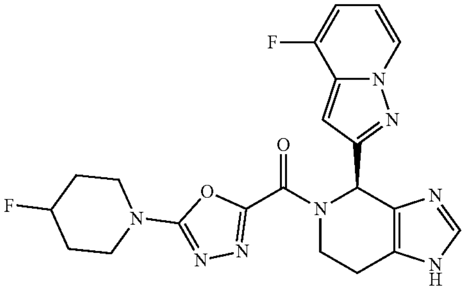 [SMILES: O=C(c1nnc(N2CCC(F)CC2)o1)N1CCc2[nH]cnc2[C@@H]1c1cc2c(F)cccn2n1] | (R)-(5-(4-fluoropiperidin-1-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 1016 | 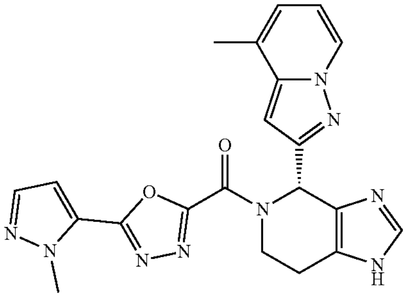 | (S)-(5-(1-methyl-1H-pyrazol-5-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1017 | 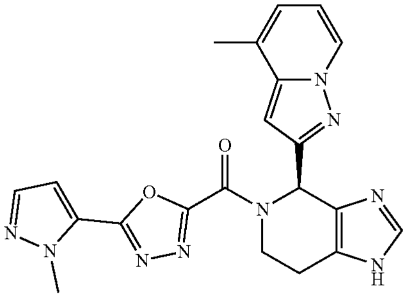 [SMILES: Cc1cccn2nc([C@H]3c4nc[nH]c4CCN3C(=O)c3nnc(-c4ccnn4C)o3)cc12] | (R)-(5-(1-methyl-1H-pyrazol-5-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1018 | 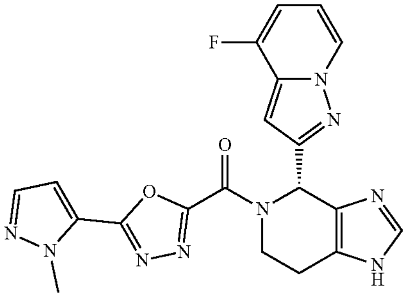 [SMILES: Cn1nccc1-c1nnc(C(=O)N2CCc3[nH]cnc3[C@H]2c2cc3c(F)cccn3n2)o1] | (S)-(4-(4-fluoropyrazolo[1,5-a]pyridin-2-yl)-6,7-dihydro-1H-imidazo[4,5-c]pyridin-5(4H)-yl)(5-(1-methyl-1H-pyrazol-5-yl)-1,3,4-oxadiazol-2-yl)methanone |

TABLE 1-continued

| Ex. # | Structure | Name |
|---|---|---|
| | Pyrazolo[1,5-a]pyridines | |
| 1019 | 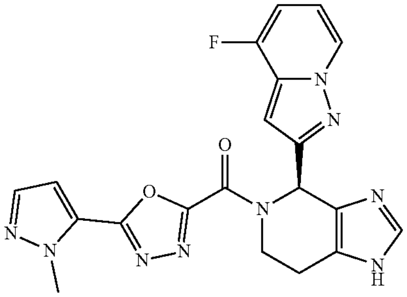 [SMILES: Cn1nccc1-c1nnc(C(=O)N2CCc3[nH]cnc3[C@@H]2c2cc3c(F)cccn3n2)o1] | (R)-(4-(4-fluoropyrazolo[1,5-a]pyridin-2-yl)-6,7-dihydro-1H-imidazo[4,5-c]pyridin-5(4H)-yl)(5-(1-methyl-1H-pyrazol-5-yl)-1,3,4-oxadiazol-2-yl)methanone |
| 1020 | 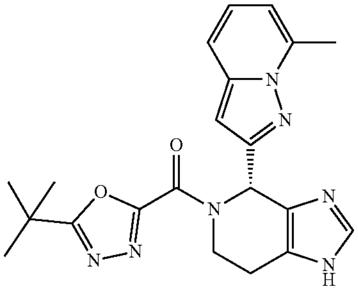 [SMILES: Cc1cccc2cc([C@@H]3c4nc[nH]c4CCN3C(=O)c3nnc(C(C)(C)C)o3)nn12] | (S)-(5-(tert-butyl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 1021 | 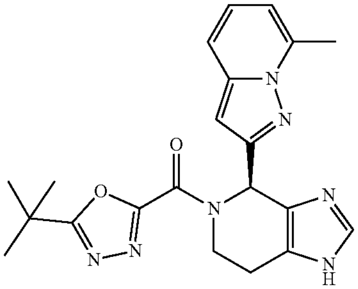 [SMILES: Cc1cccc2cc([C@H]3c4nc[nH]c4CCN3C(=O)c3nnc(C(C)(C)C)o3)nn12] | (R)-(5-(tert-butyl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 1022 | 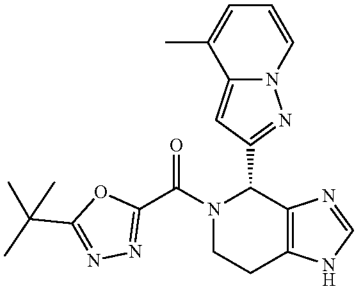 [SMILES: Cc1cccn2nc([C@@H]3c4nc[nH]c4CCN3C(=O)c3nnc(C(C)(C)C)o3)cc12] | (S)-(5-(tert-butyl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1023 | 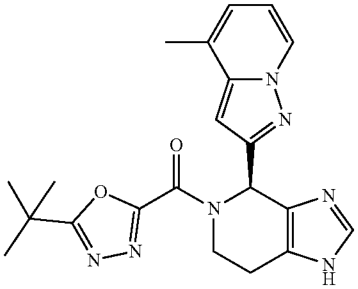 [SMILES: Cc1cccn2nc([C@H]3c4nc[nH]c4CCN3C(=O)c3nnc(C(C)(C)C)o3)cc12] | (R)-(5-(tert-butyl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 1024 | 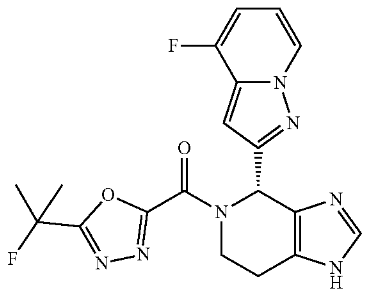 [SMILES: CC(C)(F)c1nnc(C(=O)N2CCc3[nH]cnc3[C@H]2c2cc3c(F)cccn3n2)o1] | (S)-(5-(2-fluoropropan-2-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 1025 | 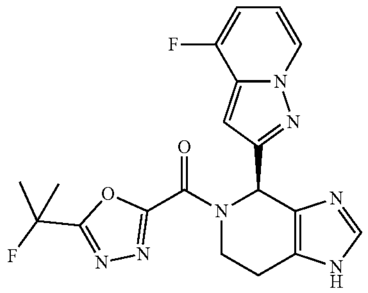 [SMILES: CC(C)(F)c1nnc(C(=O)N2CCc3[nH]cnc3[C@@H]2c2cc3c(F)cccn3n2)o1] | (R)-(5-(2-fluoropropan-2-yl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 1026 | 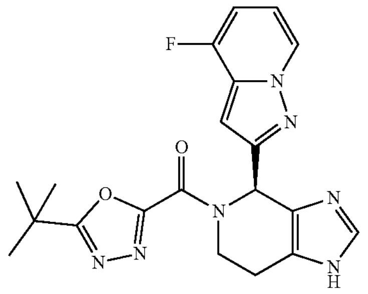 [SMILES: CC(C)(C)c1nnc(C(=O)N2CCc3[nH]cnc3[C@@H]2c2cc3c(F)cccn3n2)o1] | (R)-(5-(tert-butyl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 1027 | 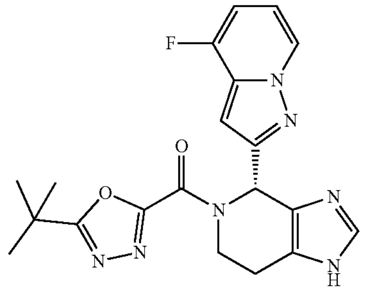 [SMILES: CC(C)(C)c1nnc(C(=O)N2CCc3[nH]cnc3[C@H]2c2cc3c(F)cccn3n2)o1] | (S)-(5-(tert-butyl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 1028 | 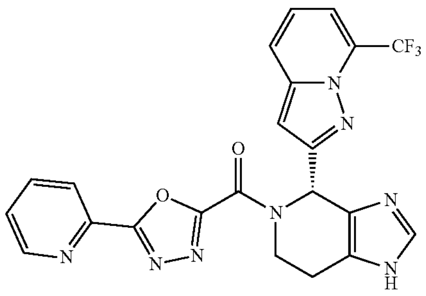 [SMILES: O=C(c1nnc(-c2ccccn2)o1)N1CCc2[nH]cnc2[C@H]1c1cc2cccc(C(F)(F)F)n2n1] | (S)-(5-(pyridin-2-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1029 | 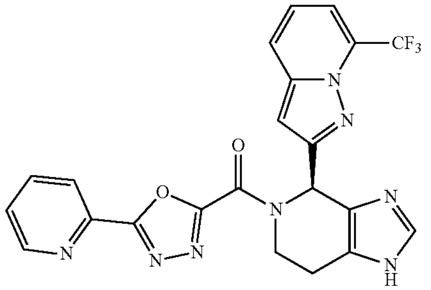 [SMILES: O=C(c1nnc(-c2ccccn2)o1)N1CCc2[nH]cnc2[C@@H]1c1cc2cccc(C(F)(F)F)n2n1] | (R)-(5-(pyridin-2-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1030 | 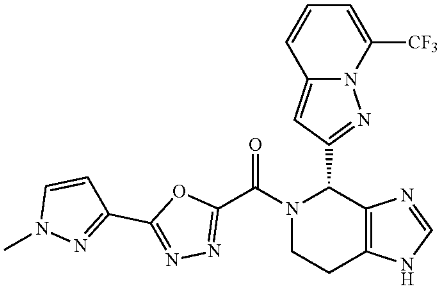 [SMILES: Cn1ccc(-c2nnc(C(=O)N3CCc4[nH]cnc4[C@H]3c3cc4cccc(C(F)(F)F)n4n3)o2)n1] | (S)-(5-(1-methyl-1H-pyrazol-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1031 | 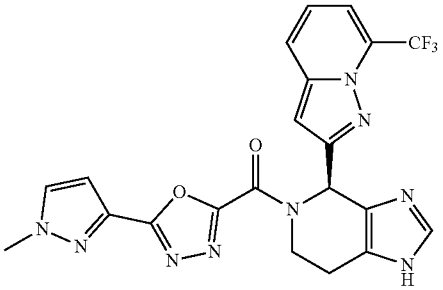 [SMILES: Cn1ccc(-c2nnc(C(=O)N3CCc4[nH]cnc4[C@@H]3c3cc4cccc(C(F)(F)F)n4n3)o2)n1] | (R)-(5-(1-methyl-1H-pyrazol-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1032 | 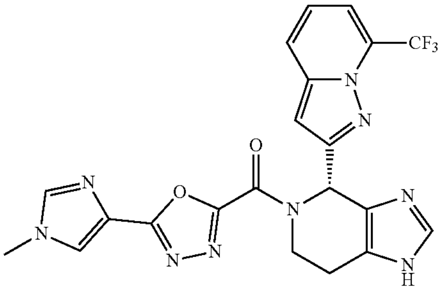 [SMILES: Cn1cnc(-c2nnc(C(=O)N3CCc4[nH]cnc4[C@H]3c3cc4cccc(C(F)(F)F)n4n3)o2)c1] | (S)-(5-(1-methyl-1H-imidazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1033 | 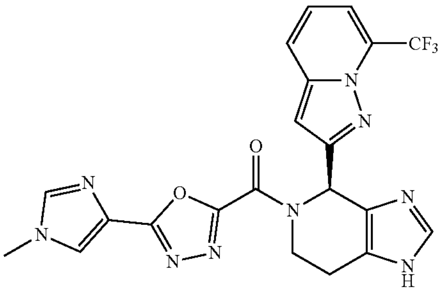 [SMILES: Cn1cnc(-c2nnc(C(=O)N3CCc4[nH]cnc4[C@@H]3c3cc4cccc(C(F)(F)F)n4n3)o2)c1] | (R)-(5-(1-methyl-1H-imidazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1034 | 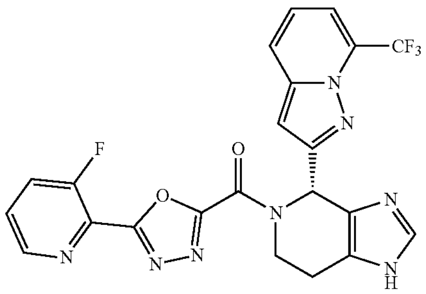 [SMILES: O=C(c1nnc(-c2ncccc2F)o1)N1CCc2[nH]cnc2[C@H]1c1cc2cccc(C(F)(F)F)n2n1] | (S)-(5-(3-fluoropyridin-2-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1035 | 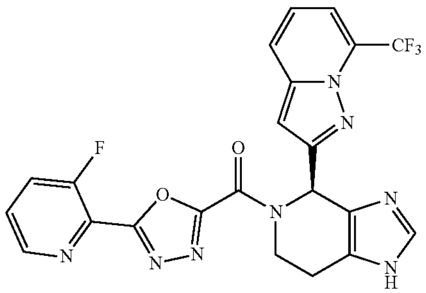 [SMILES: O=C(c1nnc(-c2ncccc2F)o1)N1CCc2[nH]cnc2[C@@H]1c1cc2cccc(C(F)(F)F)n2n1] | (R)-(5-(3-fluoropyridin-2-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1036 | 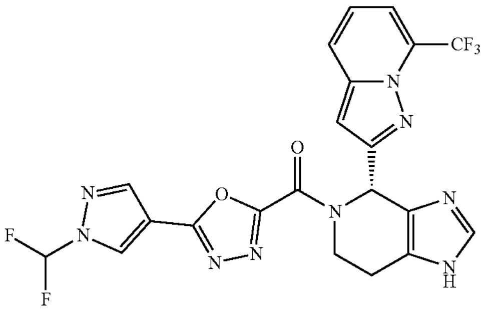 [SMILES: O=C(c1nnc(-c2cnn(C(F)F)c2)o1)N1CCc2[nH]cnc2[C@H]1c1cc2cccc(C(F)(F)F)n2n1] | (S)-(5-(1-(difluoromethyl)-1H-pyrazol-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1037 | 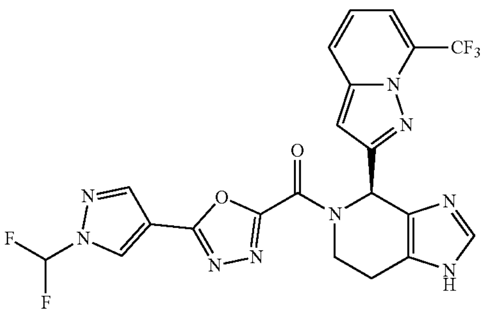 [SMILES: O=C(c1nnc(-c2cnn(C(F)F)c2)o1)N1CCc2[nH]cnc2[C@@H]1c1cc2cccc(C(F)(F)F)n2n1] | (R)-(5-(1-(difluoromethyl)-1H-pyrazol-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1038 | 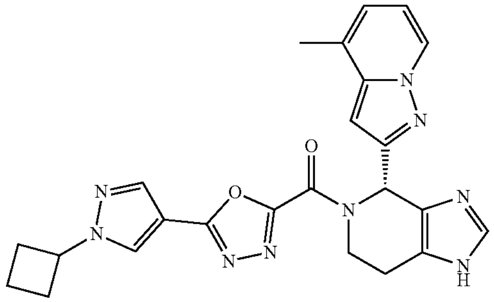 [SMILES: Cc1cccn2nc([C@@H]3c4nc[nH]c4CCN3C(=O)c3nnc(-c4cnn(C5CCC5)c4)o3)cc12] | (S)-(5-(1-cyclobutyl-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1039 | 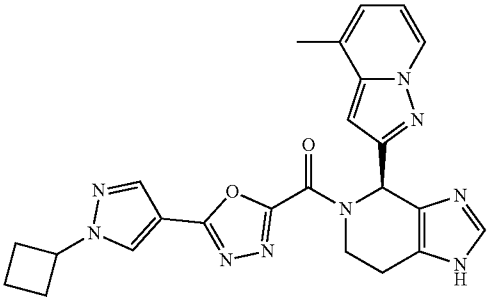 | (R)-(5-(1-cyclobutyl-1H-pyrazol-4-yl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1040 | 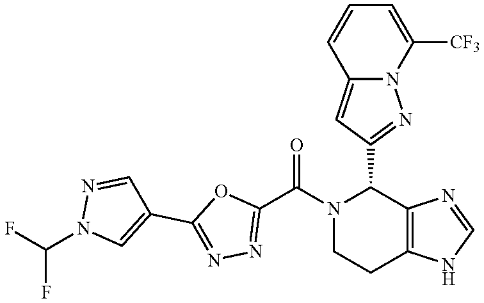 [SMILES: O=C(c1nnc(-c2cnn(C(F)F)c2)o1)N1CCc2[nH]cnc2[C@H]1c1cc2cccc(C(F)(F)F)n2n1] | (S)-(5-(1-(difluoromethyl)-1H-pyrazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1041 | 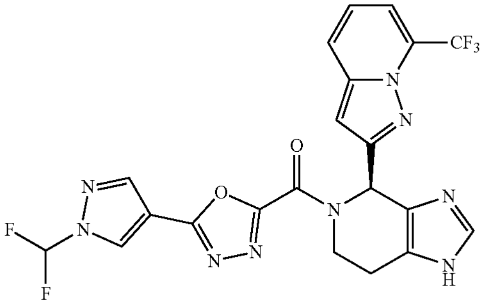 [SMILES: O=C(c1nnc(-c2cnn(C(F)F)c2)o1)N1CCc2[nH]cnc2[C@@H]1c1cc2cccc(C(F)(F)F)n2n1] | (R)-(5-(1-(difluoromethyl)-1H-pyrazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1042 | 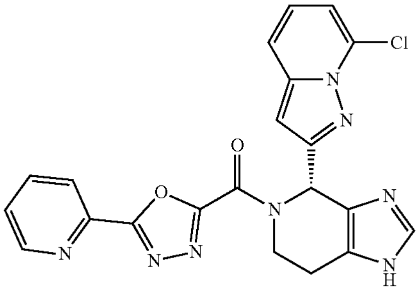 [SMILES: O=C(c1nnc(-c2ccccn2)o1)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 1043 | 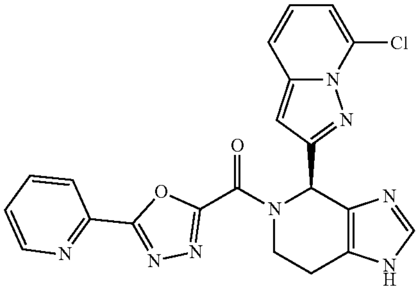 [SMILES: O=C(c1nnc(-c2ccccn2)o1)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |

TABLE 1-continued

Pyrazolo[1,5-a]pyridines

| Ex. # | Structure | Name |
|---|---|---|
| 1044 | 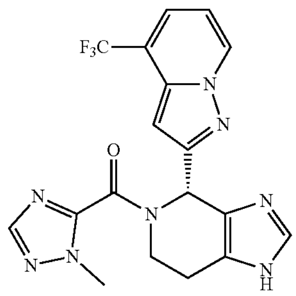 | (S)-(1-methyl-1H-1,2,4-triazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1045 | 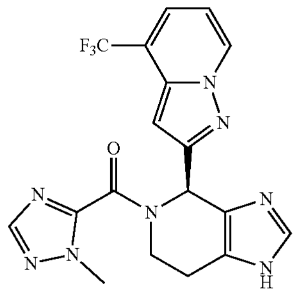 [SMILES: Cn1ncnc1C(=O)N1CCc2[nH]cnc2[C@@H]1c1cc2c(C(F)(F)F)cccn2n1] | (R)-(1-methyl-1H-1,2,4-triazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1046 | 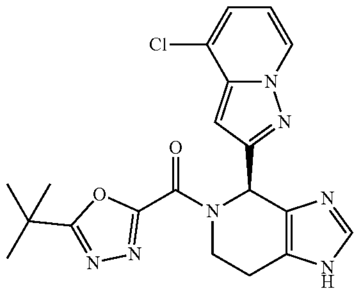 [SMILES: CC(C)(C)c1nnc(C(=O)N2CCc3[nH]cnc3[C@@H]2c2cc3c(Cl)cccn3n2)o1] | (R)-(5-(tert-butyl)-1,3,4-oxadiazol-2-yl)(4-(4-chloropyrazolo[1,5-a]pyridin-2-yl)-6,7-dihydro-1H-imidazo[4,5-c]pyridin-5(4H)-yl)methanone |
| 1047 | 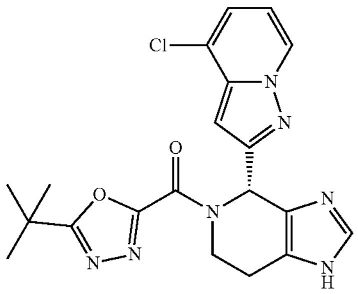 [SMILES: CC(C)(C)c1nnc(C(=O)N2CCc3[nH]cnc3[C@H]2c2cc3c(Cl)cccn3n2)o1] | (S)-(5-(tert-butyl)-1,3,4-oxadiazol-2-yl)(4-(4-chloropyrazolo[1,5-a]pyridin-2-yl)-6,7-dihydro-1H-imidazo[4,5-c]pyridin-5(4H)-yl)methanone |
| 1048 | 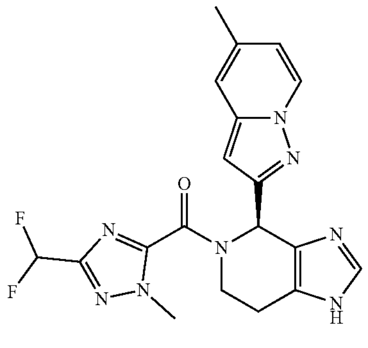 [SMILES: Cc1ccn2nc([C@H]3c4nc[nH]c4CCN3C(=O)c3nc(C(F)F)nn3C)cc2c1] | (R)-(3-(difluoromethyl)-1-methyl-1H-1,2,4-triazol-5-yl)(4-(5-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1049 | 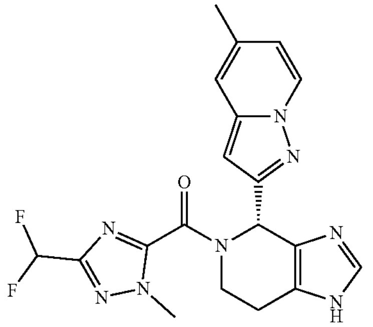 [SMILES: Cc1ccn2nc([C@@H]3c4nc[nH]c4CCN3C(=O)c3nc(C(F)F)nn3C)cc2c1] | (S)-(3-(difluoromethyl)-1-methyl-1H-1,2,4-triazol-5-yl)(4-(5-methylpyrazolo[1,5-a]pyridin-2-yl)-6,7-dihydro-1H-imidazo[4,5-c]pyridin-5(4H)-yl)methanone |
| 1050 | 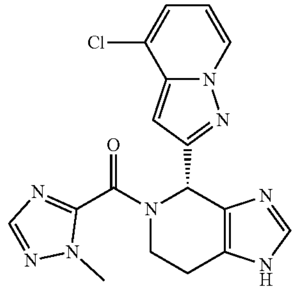 [SMILES: Cn1ncnc1C(=O)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(1-methyl-1H-1,2,4-triazol-5-yl)methanone |
| 1051 | 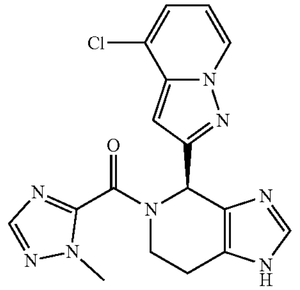 [SMILES: Cn1ncnc1C(=O)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(1-methyl-1H-1,2,4-triazol-5-yl)methanone |
| 1052 | 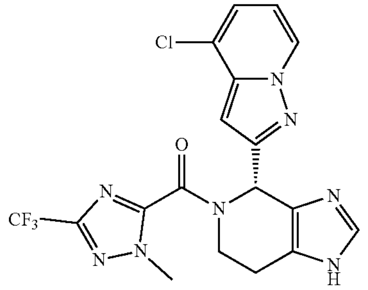 | (S)-(4-(4-chloropyrazolo[1,5-a]pyridin-2-yl)-6,7-dihydro-1H-imidazo[4,5-c]pyridin-5(4H)-yl)(1-methyl-3-(trifluoromethyl)-1H-1,2,4-triazol-5-yl)methanone |
| 1053 | 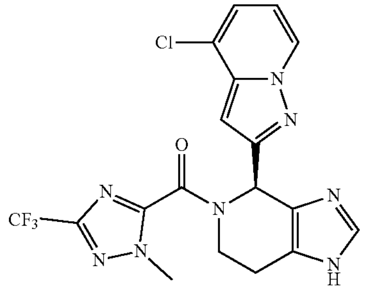 [SMILES: Cn1nc(C(F)(F)F)nc1C(=O)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(1-methyl-3-(trifluoromethyl)-1H-1,2,4-triazol-5-yl)methanone |

TABLE 1-continued

| Pyrazolo[1,5-a]pyridines | | |
|---|---|---|
| Ex. # | Structure | Name |
| 1054 | 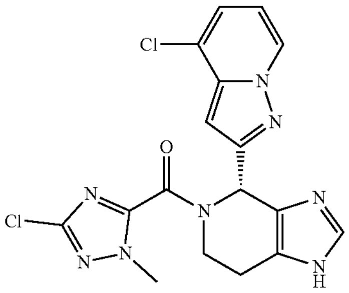 [SMILES: Cn1nc(Cl)nc1C(=O)N1CCc2[nH]cnc2[C@H]1c1cc2c(Cl)cccn2n1] | (S)-(3-chloro-1-methyl-1H-1,2,4-triazol-5-yl)(4-(4-chloropyrazolo[1,5-a]pyridin-2-yl)-6,7-dihydro-1H-imidazo[4,5-c]pyridin-5(4H)-yl)methanone |
| 1055 | 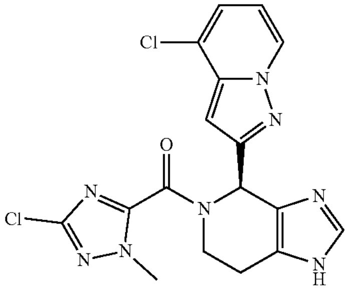 [SMILES: Cn1nc(Cl)nc1C(=O)N1CCc2[nH]cnc2[C@@H]1c1cc2c(Cl)cccn2n1] | (R)-(3-chloro-1-methyl-1H-1,2,4-triazol-5-yl)(4-(4-chloropyrazolo[1,5-a]pyridin-2-yl)-6,7-dihydro-1H-imidazo[4,5-c]pyridin-5(4H)-yl)methanone |
| 1056 | 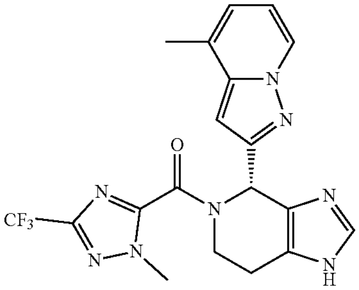 [SMILES: Cc1cccn2nc([C@@H]3c4nc[nH]c4CCN3C(=O)c3nc(C(F)(F)F)nn3C)cc12] | (S)-(1-methyl-3-(trifluoromethyl)-1H-1,2,4-triazol-5-yl)(4-(4-methylpyrazolo[1,5-a]pyridin-2-yl)-6,7-dihydro-1H-imidazo[4,5-c]pyridin-5(4H)-yl)methanone |
| 1057 | 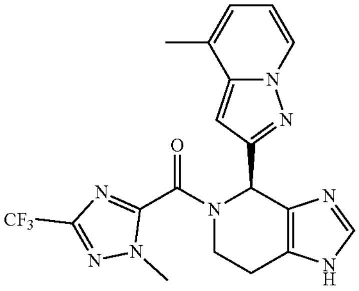 [SMILES: Cc1cccn2nc([C@H]3c4nc[nH]c4CCN3C(=O)c3nc(C(F)(F)F)nn3C)cc12] | (R)-(1-methyl-3-(trifluoromethyl)-1H-1,2,4-triazol-5-yl)(4-(4-methylpyrazolo[1,5-a]pyridin-2-yl)-6,7-dihydro-1H-imidazo[4,5-c]pyridin-5(4H)-yl)methanone |
| 1058 | 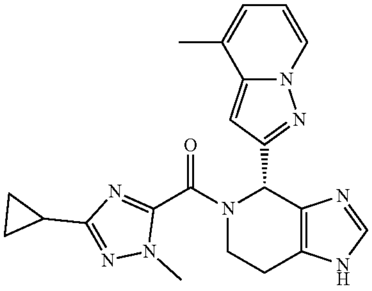 [SMILES: Cc1cccn2nc([C@@H]3c4nc[nH]c4CCN3C(=O)c3nc(C4CC4)nn3C)cc12] | (S)-(3-cyclopropyl-1-methyl-1H-1,2,4-triazol-5-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1059 | 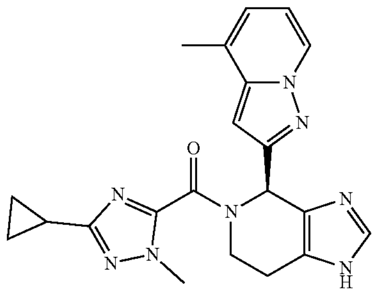 [SMILES: Cc1cccn2nc([C@H]3c4nc[nH]c4CCN3C(=O)c3nc(C4CC4)nn3C)cc12] | (R)-(3-cyclopropyl-1-methyl-1H-1,2,4-triazol-5-y]l)(4-(4-methylpyrazolo[1,5-a]pyridin-2-yl)-6,7-dihydro-1H-imidazo[4,5-c]pyridin-5(4H)-yl)methanone |
| 1060 | 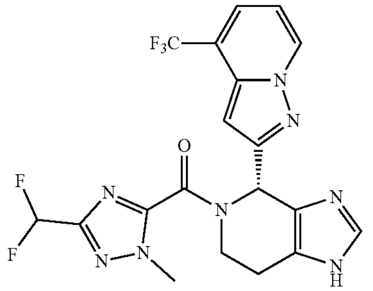 [SMILES: Cn1nc(C(F)F)nc1C(=O)N1CCc2[nH]cnc2[C@H]1c1cc2c(C(F)(F)F)cccn2n1] | (S)-(3-(difluoromethyl)-1-methyl-1H-1,2,4-triazol-5-yl)(4-(4-(trifluoromethyl) pyrazolo[1,5-a]pyridin-2-yl)-6,7-dihydro-1H-imidazo [4,5-c]pyridin-5(4H)-yl)methanone |
| 1061 | 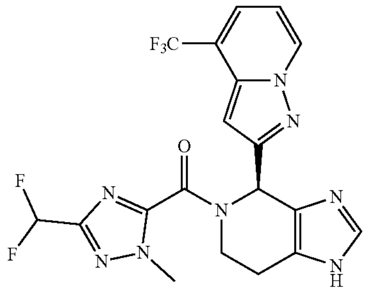 [SMILES: Cn1nc(C(F)F)nc1C(=O)N1CCc2[nH]cnc2[C@@H]1c1cc2c(C(F)(F)F)cccn2n1] | (R)-(3-(difluoromethyl)-1-methyl-1H-1,2,4-triazol-5-yl)(4-(4-(trifluoromethyl) pyrazolo[1,5-a]pyridin-2-yl)-6,7-dihydro-1H-imidazo [4,5-c]pyridin-5(4H)-yl)methanone |
| 1062 | 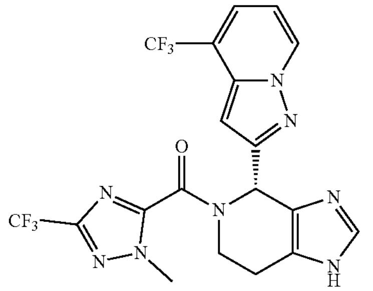 [SMILES: Cn1nc(C(F)(F)F)nc1C(=O)N1CCc2[nH]cnc2[C@H]1c1cc2c(C(F)(F)F)cccn2n1] | (S)-(1-methyl-3-(trifluoromethyl)-1H-1,2,4-triazol-5-yl)(4-(4-(trifluoromethyl) pyrazolo[1,5-a]pyridin-2-yl)-6,7-dihydro-1H-imidazo [4,5-c]pyridin-5(4H)-yl)methanone |
| 1063 | 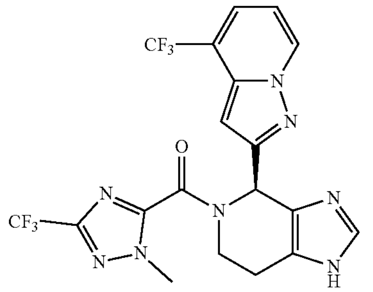 [SMILES: Cn1nc(C(F)(F)F)nc1C(=O)N1CCc2[nH]cnc2[C@@H]1c1cc2c(C(F)(F)F)cccn2n1] | (R)-(1-methyl-3-(trifluoromethyl)-1H-1,2,4-triazol-5-yl)(4-(4-(trifluoromethyl) pyrazolo[1,5-a]pyridin-2-yl)-6,7-dihydro-1H-imidazo [4,5-c]pyridin-5(4H)-yl)methanone |

TABLE 1-continued

| Ex. # | Structure | Name |
| --- | --- | --- |
| Pyrazolo[1,5-a]pyridines | | |
| 1064 | 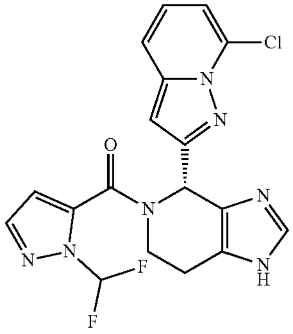 [SMILES: O=C(c1ccnn1C(F)F)N1CCc2[nH]cnc2[C@H]1c1cc2cccc(Cl)n2n1] | (S)-(4-(7-chloropyrazolo [1,5-a]pyridin-2-yl)-6,7-dihydro-1H-imidazo [4,5-c]pyridin-5(4H)-yl)(1-(difluoromethyl)-1H-pyrazol-5-yl)methanone |
| 1065 | 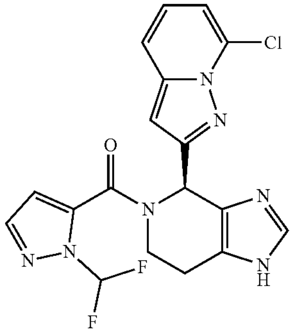 [SMILES: O=C(c1ccnn1C(F)F)N1CCc2[nH]cnc2[C@@H]1c1cc2cccc(Cl)n2n1] | (R)-(4-(7-chloropyrazolo [1,5-a]pyridin-2-yl)-6,7-dihydro-1H-imidazo[4,5-c] pyridin-5(4H)-yl)(1-(difluoromethyl)-1H-pyrazol-5-yl)methanone |
| 1066 | 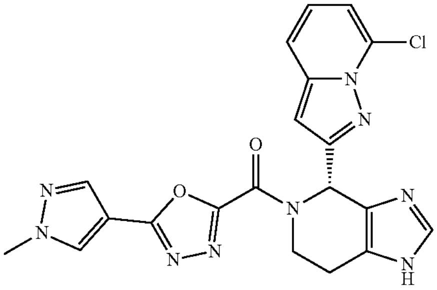 [SMILES: Cn1cc(-c2nnc(C(=O)N3CCc4[nH]cnc4[C@H]3c3cc4cccc(Cl)n4n3)o2)cn1] | (S)-(4-(7-chloropyrazolo [1,5-a]pyridin-2-y]l)-6,7-dihydro-1H-imidazo[4,5-c] pyridin-5(4H)-yl)(5-(1-methyl-1H-pyrazol-4-yl)-1,3,4-oxadiazol-2-yl)methanone |
| 1067 | 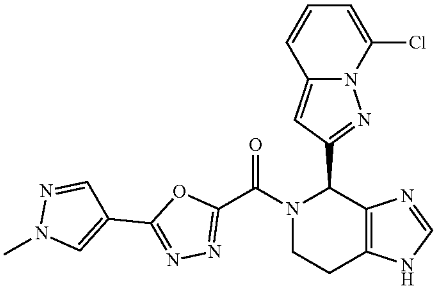 [SMILES: Cn1cc(-c2nnc(C(=O)N3CCc4[nH]cnc4[C@@H]3c3cc4cccc(Cl)n4n3)o2)cn1] | (R)-(4-(7-chloropyrazolo [1,5-a]pyridin-2-yl)-6,7-dihydro-1H-imidazo[4,5-c] pyridin-5(4H)-yl)(5-(1-methyl-1H-pyrazol-4-yl)-1,3,4-oxadiazol-2-yl)methanone |

TABLE 1-continued

| Pyrazolo[1,5-a]pyridines | | |
|---|---|---|
| Ex. # | Structure | Name |
| 1068 | 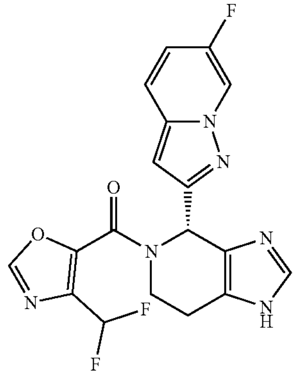 [SMILES: O=C(c1ocnc1C(F)F)N1CCc2[nH]cnc2[C@H]1c1cc2ccc(F)cn2n1] | (S)-(4-(difluoromethyl) oxazol-5-yl)(4-(6-fluoropyrazolo[1,5-a]pyridin-2-yl)-6,7-dihydro-1H-imidazo[4,5-c]pyridin-5(4H)-yl)methanone |
| 1069 | 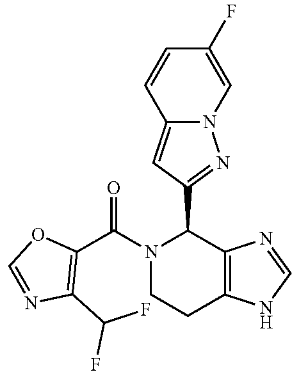 [SMILES: O=C(c1ocnc1C(F)F)N1CCc2[nH]cnc2[C@@H]1c1cc2ccc(F)cn2n1] | (R)-(4-(difluoromethyl) oxazol-5-yl)(4-(6-fluoropyrazolo[1,5-a]pyridin-2-yl)-6,7-dihydro-1H-imidazo[4,5-c]pyridin-5(4H)-yl)methanone |
| 1070 | 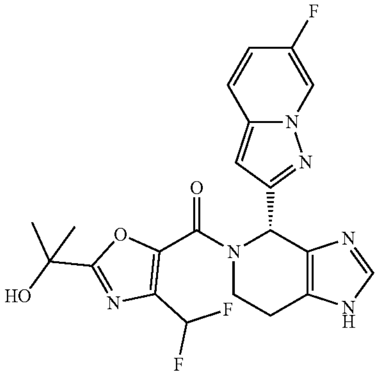 [SMILES: CC(C)(O)c1nc(C(F)F)c(C(=O)N2CCc3[nH]cnc3[C@H]2c2cc3ccc(F)cn3n2)o1] | (S)-(4-(difluoromethyl)-2-(2-hydroxypropan-2-yl)oxazol-5-yl)(4-(6-fluoropyrazolo [1,5-a]pyridin-2-yl)-6,7-dihydro-1H-imidazo[4,5-c] pyridin-5(4H)-yl)methanone |
| 1071 | 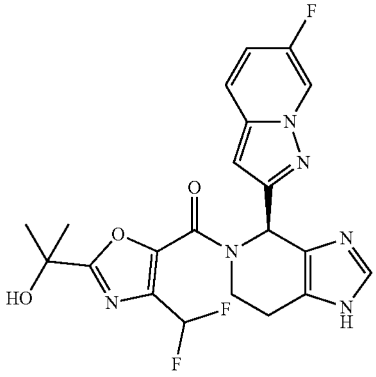 [SMILES: CC(C)(O)c1nc(C(F)F)c(C(=O)N2CCc3[nH]cnc3[C@@H]2c2cc3ccc(F)cn3n2)o1] | (R)-(4-(difluoromethyl)-2-(2-hydroxypropan-2-yl)oxazol-5-yl)(4-(6-fluoropyrazolo[1,5-a] pyridin-2-yl)-6,7-dihydro-1H-imidazo [4,5-c]pyridin-5(4H)-yl)methanone |

TABLE 1-continued

| Ex. # | Structure | Name |
|---|---|---|
| | Pyrazolo[1,5-a]pyridines | |
| 1072 | 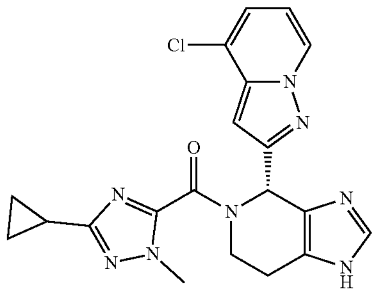 | (S)-(4-(4-chloropyrazolo[1,5-a]pyridin-2-yl)-6,7-dihydro-1H-imidazo[4,5-c]pyridin-5(4H)-yl)(3-cyclopropyl-1-methyl-1H-1,2,4-triazol-5-yl)methanone |
| 1073 | 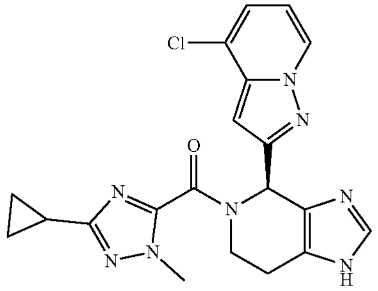 | (R)-(4-(4-chloropyrazolo[1,5-a]pyridin-2-yl)-6,7-dihydro-1H-imidazo[4,5-c]pyridin-5(4H)-yl)(3-cyclopropyl-1-methyl-1H-1,2,4-triazol-5-yl)methanone |
| 1074 | 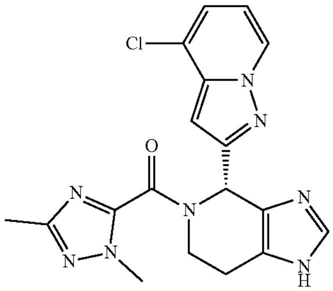 | (S)-(4-(4-chloropyrazolo[1,5-a]pyridin-2-yl)-6,7-dihydro-1H-imidazo[4,5-c]pyridin-5(4H)-yl)(1,3-dimethyl-1H-1,2,4-triazol-5-yl)methanone |
| 1075 | 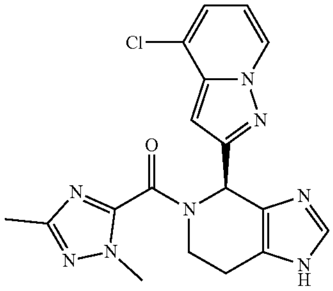 [SMILES: Cc1nc(C(=O)N2CCc3[nH]cnc3[C@@H]2c2cc3c(Cl)cccn3n2)n(C)n1] | (R)-(4-(4-chloropyrazolo[1,5-a]pyridin-2-yl)-6,7-dihydro-1H-imidazo[4,5-c]pyridin-5(4H)-yl)(1,3-dimethyl-1H-1,2,4-triazol-5-yl)methanone |
| 1076 | 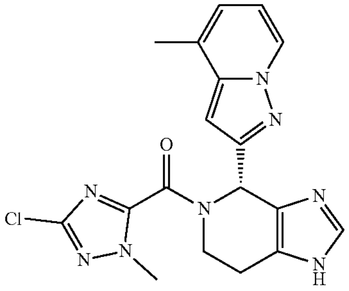 | (S)-(3-chloro-1-methyl-1H-1,2,4-triazol-5-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
| --- | --- | --- |
| Pyrazolo[1,5-a]pyridines | | |
| 1077 | 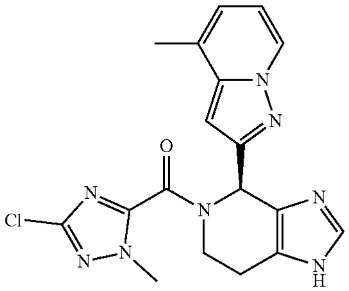 [SMILES: Cc1cccn2nc([C@H]3c4nc[nH]c4CCN3C(=O)c3nc(Cl)nn3C)cc12] | (R)-(3-chloro-1-methyl-1H-1,2,4-triazol-5-yl)(4-(4-methylpyrazolo[1,5-a]pyridin-2-yl)-6,7-dihydro-1H-imidazo[4,5-c]pyridin-5(4H)-yl)methanone |
| 1078 | 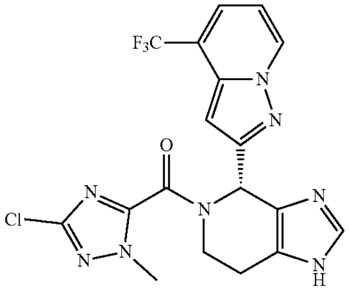 [SMILES: Cn1nc(Cl)nc1C(=O)N1CCc2[nH]cnc2[C@H]1c1cc2c(C(F)(F)F)cccn2n1] | (S)-(3-chloro-1-methyl-1H-1,2,4-triazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1079 | 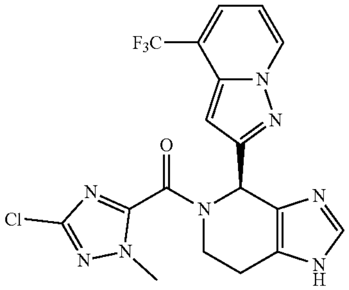 [SMILES: Cn1nc(Cl)nc1C(=O)N1CCc2[nH]cnc2[C@@H]1c1cc2c(C(F)(F)F)cccn2n1] | (R)-(3-chloro-1-methyl-1H-1,2,4-triazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1080 | 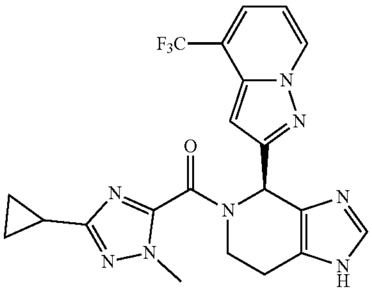 | (R)-(3-cyclopropyl-1-methyl-1H-1,2,4-triazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1081 | 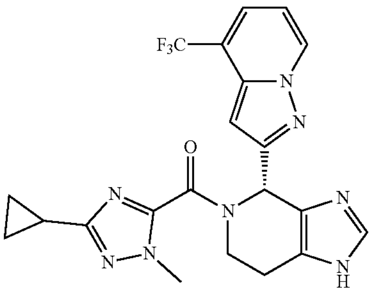 | (S)-(3-cyclopropyl-1-methyl-1H-1,2,4-triazol-5-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1082 | 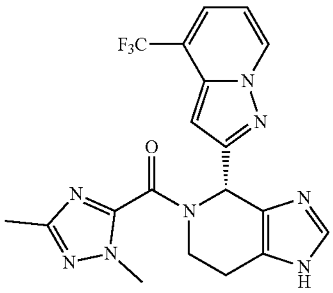 | (S)-(1,3-dimethyl-1H-1,2,4-triazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1083 | 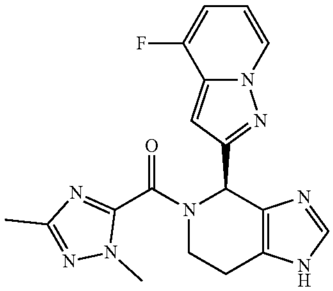 [SMILES: Cc1nc(C(=O)N2CCc3[nH]cnc3[C@@H]2c2cc3c(F)cccn3n2)n(C)n1] | (R)-(1,3-dimethyl-1H-1,2,4-triazol-5-y]l)(4-(4-(trifluoromethyl)pyrazolo[1,5-a]pyridin-2-yl)-6,7-dihydro-1H-imidazo[4,5-c]pyridin-5(4H)-yl)methanone |
| 1084 | 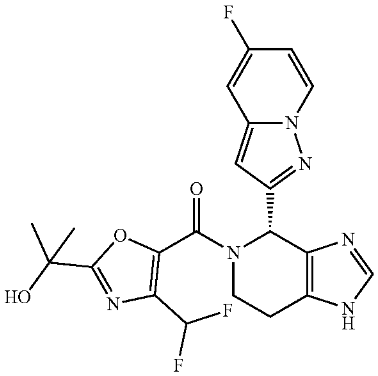 [SMILES: CC(C)(O)c1nc(C(F)F)c(C(=O)N2CCc3[nH]cnc3[C@H]2c2cc3cc(F)ccn3n2)o1] | (S)-(4-(difluoromethyl)-2-(2-hydroxypropan-2-yl)oxazol-5-yl)(4-(5-fluoropyrazolo[1,5-a]pyridin-2-yl)-6,7-dihydro-1H-imidazo[4,5-c]pyridin-5(4H)-yl)methanone |
| 1085 | 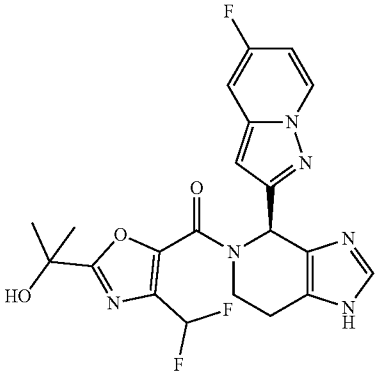 [SMILES: CC(C)(O)c1nc(C(F)F)c(C(=O)N2CCc3[nH]cnc3[C@@H]2c2cc3cc(F)ccn3n2)o1] | (R)-(4-(difluoromethyl)-2-(2-hydroxypropan-2-yl)oxazol-5-yl)(4-(5-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1086 | 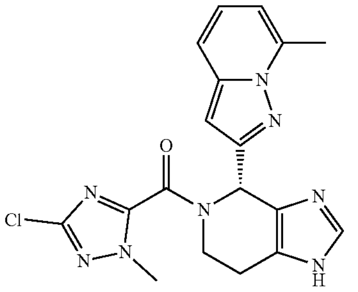 [SMILES: Cc1cccc2cc([C@@H]3c4nc[nH]c4CCN3C(=O)c3nc(Cl)nn3C)nn12] | (S)-(3-chloro-1-methyl-1H-1,2,4-triazol-5-yl)(4-(7-methylpyrazolo[1,5-a]pyridin-2-yl)-6,7-dihydro-1H-imidazo[4,5-c]pyridin-5(4H)-yl)methanone |
| 1087 | 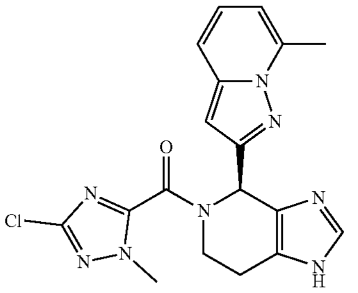 | (R)-(3-chloro-1-methyl-1H-1,2,4-triazol-5-yl)(4-(7-methylpyrazolo[1,5-a]pyridin-2-yl)-6,7-dihydro-1H-imidazo[4,5-c]pyridin-5(4H)-yl)methanone |
| 1088 | 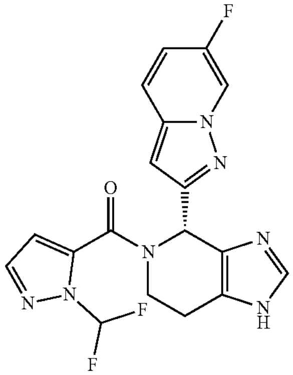 [SMILES: O=C(c1ccnn1C(F)F)N1CCc2[nH]cnc2[C@H]1c1cc2ccc(F)cn2n1] | (S)-(1-(difluoromethyl)-1H-pyrazol-5-yl)(4-(6-fluoropyrazolo[1,5-a]pyridin-2-yl)-6,7-dihydro-1H-imidazo[4,5-c]pyridin-5(4H)-yl)methanone |
| 1089 | 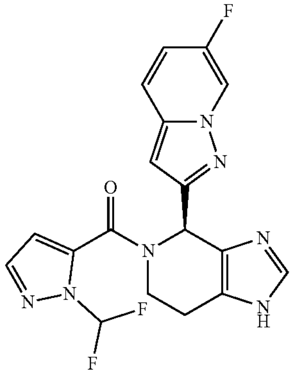 [SMILES: O=C(c1ccnn1C(F)F)N1CCc2[nH]cnc2[C@@H]1c1cc2ccc(F)cn2n1] | (R)-(1-(difluoromethyl)-1H-pyrazol-5-yl)(4-(6-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1090 | 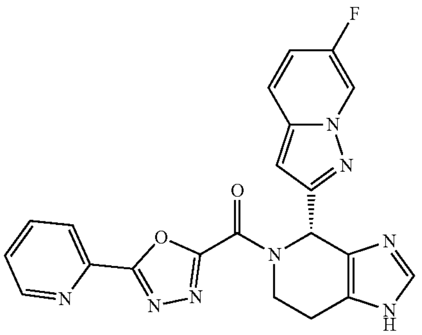 [SMILES: O=C(c1nnc(-c2ccccn2)o1)N1CCc2[nH]cnc2[C@H]1c1cc2ccc(F)cn2n1] | (S)-(4-(6-fluoropyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 1091 | 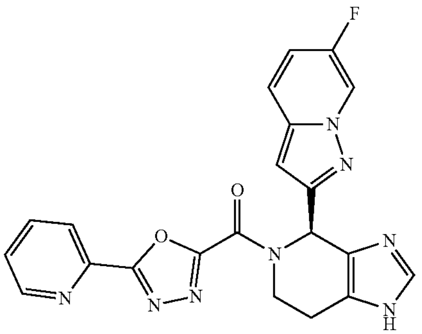 [SMILES: O=C(c1nnc(-c2ccccn2)o1)N1CCc2[nH]cnc2[C@@H]1c1cc2ccc(F)cn2n1] | (R)-(4-(6-fluoropyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 1092 | 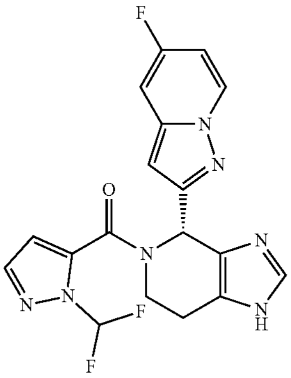 [SMILES: O=C(c1ccnn1C(F)F)N1CCc2[nH]cnc2[C@H]1c1cc2cc(F)ccn2n1] | (S)-(1-(difluoromethyl)-1H-pyrazol-5-yl)(4-(5-fluoropyrazolo[1,5-a]pyridin-2-yl)-6,7-dihydro-1H-imidazo[4,5-c]pyridin-5(4H)-yl)methanone |
| 1093 | 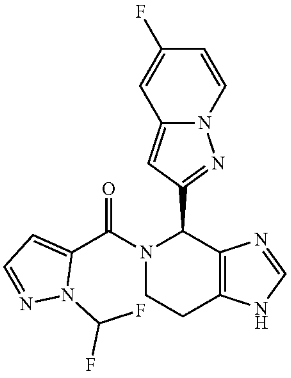 [SMILES: O=C(c1ccnn1C(F)F)N1CCc2[nH]cnc2[C@@H]1c1cc2cc(F)ccn2n1] | (R)-(1-(difluoromethyl)-1H-pyrazol-5-yl)(4-(5-fluoropyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 1094 | 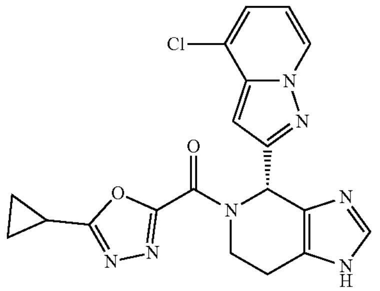 [SMILES: O=C(c1nnc(C2CC2)o1)N1CCc2[nH]cnc2[C@H]1c1cc2c(Cl)cccn2n1] | (S)-(4-(4-chloropyrazolo [1,5-a]pyridin-2-yl)-6,7-dihydro-1H-imidazo[4,5-c] pyridin-5(4H)-yl)(5-cyclopropyl-1,3,4-oxadiazol-2-yl)methanone |
| 1095 | 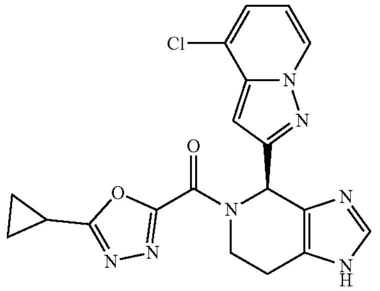 | (R)-(4-(4-chloropyrazolo [1,5-a]pyridin-2-yl)-6,7-dihydro-1H-imidazo [4,5-c]pyridin-5(4H)-yl)(5-cyclopropyl-1,3,4-oxadiazol-2-yl)methanone |
| 1096 | 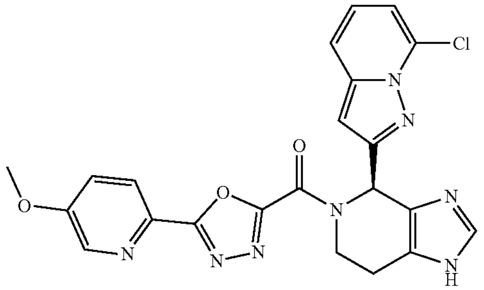 | (R)-(4-(7-chloropyrazolo [1,5-a]pyridin-2-yl)-6,7-dihydro-1H-imidazo [4,5-c]pyridin-5(4H)-yl)(5-(5-methoxypyridin-2-yl)-1,3,4-oxadiazol-2-yl)methanone |
| 1097 | 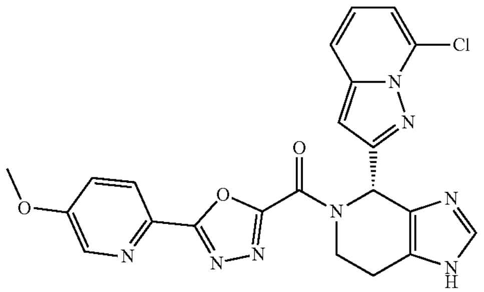 [SMILES: COc1ccc(-c2nnc(C(=O)N3CCc4[nH]cnc4[C@H]3c3cc4cccc(Cl)n4n3)o2)nc1] | (S)-(4-(7-chloropyrazolo [1,5-a]pyridin-2-yl)-6,7-dihydro-1H-imidazo[4,5-c] pyridin-5(4H)-yl)(5-(5-methoxypyridin-2-yl)-1,3,4-oxadiazol-2-yl)methanone |
| 1098 | 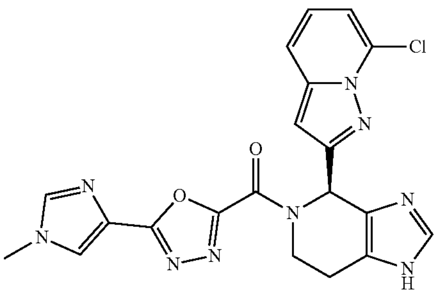 [SMILES: Cn1cnc(-c2nnc(C(=O)N3CCc4[nH]cnc4[C@@H]3c3cc4cccc(Cl)n4n3)o2)c1] | (R)-(4-(7-chloropyrazolo [1,5-a]pyridin-2-yl)-6,7-dihydro-1H-imidazo[4,5-c] pyridin-5(4H)-yl)(5-(1-methyl-1H-imidazol-4-yl)-1,3,4-oxadiazol-2-yl)methanone |

TABLE 1-continued

| Pyrazolo[1,5-a]pyridines | | |
|---|---|---|
| Ex. # | Structure | Name |
| 1099 | 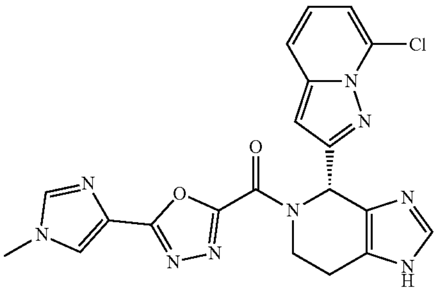 [SMILES: Cn1cnc(-c2nnc(C(=O)N3CCc4[nH]cnc4[C@H]3c3cc4cccc(Cl)n4n3)o2)c1] | (S)-(4-(7-chloropyrazolo[1,5-a]pyridin-2-yl)-6,7-dihydro-1H-imidazo[4,5-c]pyridin-5(4H)-yl)(5-(1-methyl-1H-imidazol-4-yl)-1,3,4-oxadiazol-2-yl)methanone |
| 1100 | 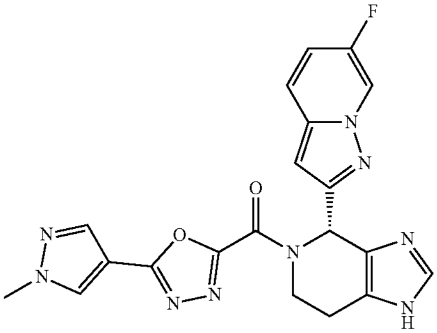 [SMILES: Cn1cc(-c2nnc(C(=O)N3CCc4[nH]cnc4[C@H]3c3cc4ccc(F)cn4n3)o2)cn1] | (S)-(4-(6-fluoropyrazolo[1,5-a]pyridin-2-yl)-6,7-dihydro-1H-imidazo[4,5-c]pyridin-5(4H)-yl)(5-(1-methyl-1H-pyrazol-4-yl)-1,3,4-oxadiazol-2-yl)methanone |
| 1101 | 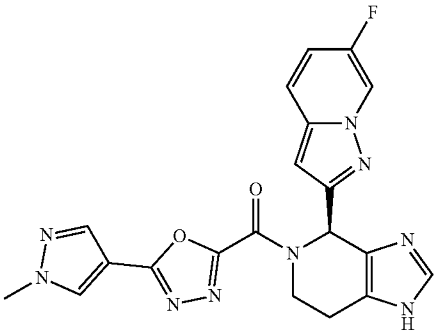 [SMILES: Cn1cc(-c2nnc(C(=O)N3CCc4[nH]cnc4[C@@H]3c3cc4ccc(F)cn4n3)o2)cn1] | (R)-(4-(6-fluoropyrazolo[1,5-a]pyridin-2-yl)-6,7-dihydro-1H-imidazo[4,5-c]pyridin-5(4H)-yl)(5-(1-methyl-1H-pyrazol-4-yl)-1,3,4-oxadiazol-2-yl)methanone |
| 1102 | 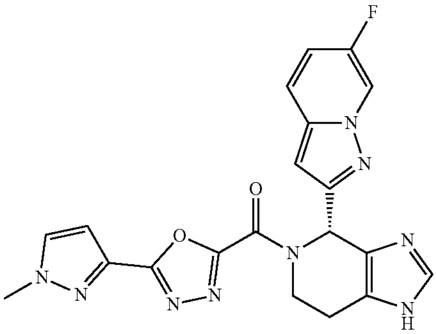 [SMILES: Cn1ccc(-c2nnc(C(=O)N3CCc4[nH]cnc4[C@H]3c3cc4ccc(F)cn4n3)o2)n1] | (S)-(4-(6-fluoropyrazolo[1,5-a]pyridin-2-yl)-6,7-dihydro-1H-imidazo[4,5-c]pyridin-5(4H)-yl)(5-(1-methyl-1H-pyrazol-3-yl)-1,3,4-oxadiazol-2-yl)methanone |

TABLE 1-continued

| Pyrazolo[1,5-a]pyridines | | |
|---|---|---|
| Ex. # | Structure | Name |
| 1103 | 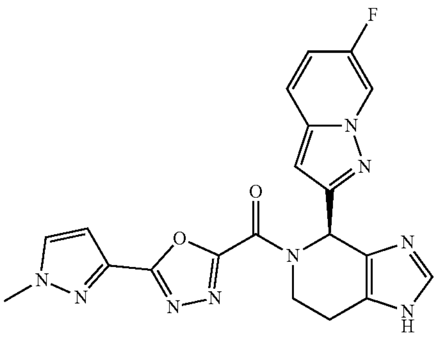 [SMILES: Cn1ccc(-c2nnc(C(=O)N3CCc4[nH]cnc4[C@@H]3c3cc4ccc(F)cn4n3)o2)n1] | (R)-(4-(6-fluoropyrazolo[1,5-a]pyridin-2-yl)-6,7-dihydro-1H-imidazo[4,5-c]pyridin-5(4H)-yl)(5-(1-methyl-1H-pyrazol-3-yl)-1,3,4-oxadiazol-2-yl)methanone |
| 1104 | 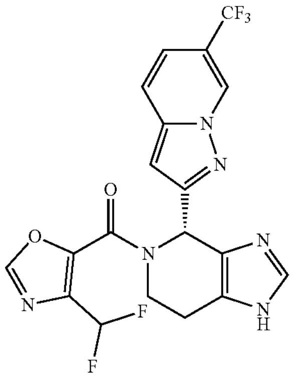 [SMILES: O=C(c1ocnc1C(F)F)N1CCc2[nH]cnc2[C@H]1c1cc2ccc(C(F)(F)F)cn2n1] | (S)-(4-(difluoromethyl)oxazol-5-yl)(4-(6-(trifluoromethyl)pyrazolo[1,5-a]pyridin-2-yl)-6,7-dihydro-1H-imidazo[4,5-c]pyridin-5(4H)-yl)methanone |
| 1105 | 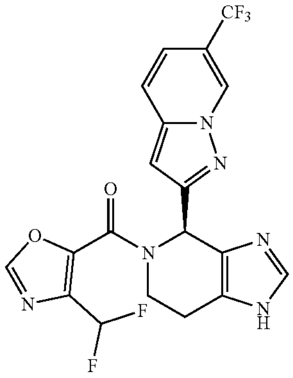 [SMILES: O=C(c1ocnc1C(F)F)N1CCc2[nH]cnc2[C@@H]1c1cc2ccc(C(F)(F)F)cn2n1] | (R)-(4-(difluoromethyl)oxazol-5-yl)(4-(6-(trifluoromethyl)pyrazolo[1,5-a]pyridin-2-yl)-6,7-dihydro-1H-imidazo[4,5-c]pyridin-5(4H)-yl)methanone |
| 1106 | 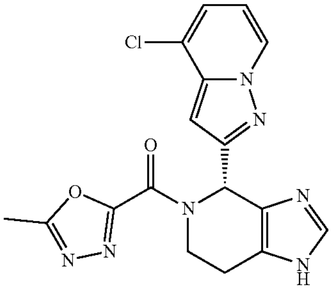 | (S)-(4-(4-chloropyrazolo[1,5-a]pyridin-2-yl)-6,7-dihydro-1H-imidazo[4,5-c]pyridin-5(4H)-yl)(5-methyl-1,3,4-oxadiazol-2-yl)methanone |

TABLE 1-continued

| Ex. # | Structure | Name |
|---|---|---|
| Pyrazolo[1,5-a]pyridines | | |
| 1107 | 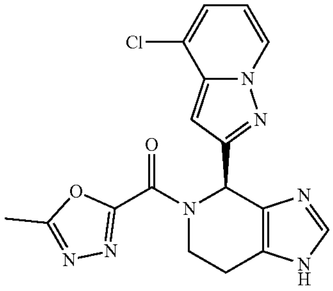 [SMILES: Cc1nnc(C(=O)N2CCc3[nH]cnc3[C@@H]2c2cc3c(Cl)cccn3n2)o1] | (R)-(4-(4-chloropyrazolo [1,5-a]pyridin-2-yl)-6,7-dihydro-1H-imidazo[4,5-c] pyridin-5(4H)-yl)(5-methyl-1,3,4-oxadiazol-2-yl)methanone |
| 1108 | 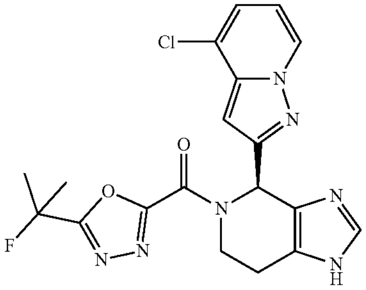 [SMILES: CC(C)(F)c1nnc(C(=O)N2CCc3[nH]cnc3[C@@H]2c2cc3c(Cl)cccn3n2)o1] | (R)-(4-(4-chloropyrazolo [1,5-a]pyridin-2-yl)-6,7-dihydro-1H-imidazo[4,5-c] pyridin-5(4H)-yl)(5-(2-fluoropropan-2-yl)-1,3,4-oxadiazol-2-yl)methanone |
| 1109 | 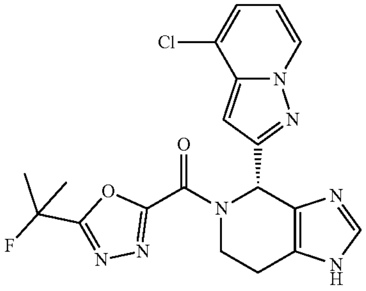 [SMILES: CC(C)(F)c1nnc(C(=O)N2CCc3[nH]cnc3[C@H]2c2cc3c(Cl)cccn3n2)o1] | (S)-(4-(4-chloropyrazolo [1,5-a]pyridin-2-yl)-6,7-dihydro-1H-imidazo[4,5-c] pyridin-5(4H)-yl)(5-(2-fluoropropan-2-yl)-1,3,4-oxadiazol-2-yl)methanone |
| 1110 | 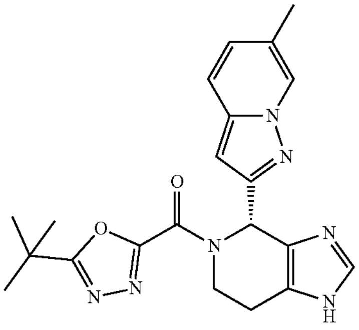 [SMILES: Cc1ccc2cc([C@@H]3c4nc[nH]c4CCN3C(=O)c3nnc(C(C)(C)C)o3)nn2c1] | (S)-(5-(tert-butyl)-1,3,4-oxadiazol-2-yl)(4-(6-methylpyrazolo[1,5-a]pyridin-2-yl)-6,7-dihydro-1H-imidazo[4,5-c]pyridin-5(4H)-yl)methanone |
| 1111 | 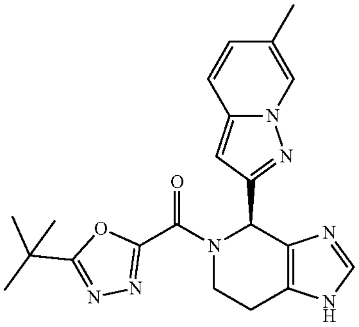 [SMILES: Cc1ccc2cc([C@H]3c4nc[nH]c4CCN3C(=O)c3nnc(C(C)(C)C)o3)nn2c1] | (R)-(5-(tert-butyl)-1,3,4-oxadiazol-2-yl)(4-(6-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1112 | 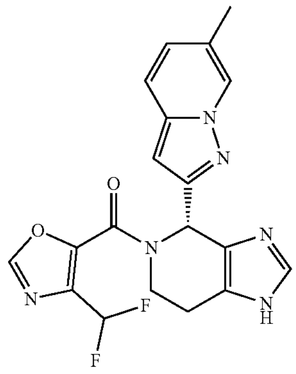 [SMILES: Cc1ccc2cc([C@@H]3c4nc[nH]c4CCN3C(=O)c3ocnc3C(F)F)nn2c1] | (S)-(1-(difluoromethyl)-1H-pyrazol-5-yl)(4-(6-methylpyrazolo[1,5-a]pyridin-2-yl)-6,7-dihydro-1H-imidazo[4,5-c]pyridin-5(4H)-yl)methanone |
| 1113 | 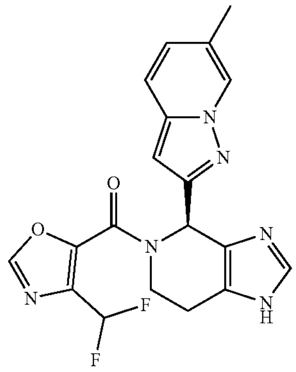 [SMILES: Cc1ccc2cc([C@H]3c4nc[nH]c4CCN3C(=O)c3ocnc3C(F)F)nn2c1] | (R)-(1-(difluoromethyl)-1H-pyrazol-5-yl)(4-(6-methylpyrazolo[1,5-a]pyridin-2-yl)-6,7-dihydro-1H-imidazo[4,5-c]pyridin-5(4H)-yl)methanone |
| 1114 | 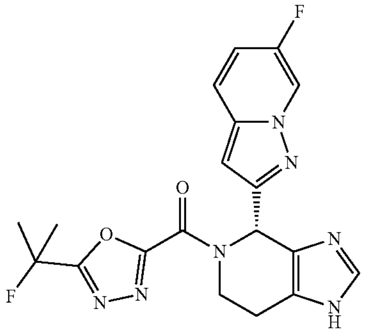 | (S)-(5-(2-fluoropropan-2-yl)-1,3,4-oxadiazol-2-yl)(4-(6-fluoropyrazolo[1,5-a]pyridin-2-yl)-6,7-dihydro-1H-imidazo[4,5-c]pyridin-5(4H)-yl)methanone |
| 1115 | 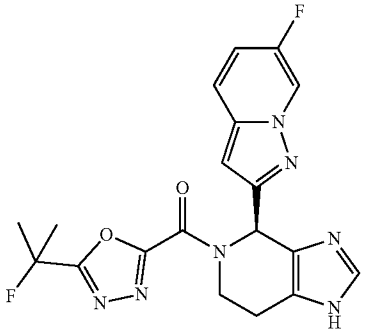 [SMILES: CC(C)(F)c1nnc(C(=O)N2CCc3[nH]cnc3[C@@H]2c2cc3ccc(F)cn3n2)o1] | (R)-(5-(2-fluoropropan-2-yl)-1,3,4-oxadiazol-2-yl)(4-(6-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1116 | 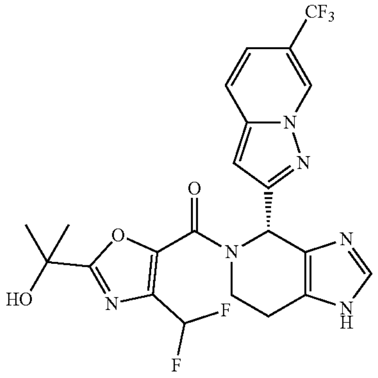 [SMILES: CC(C)(O)c1nc(C(F)F)c(C(=O)N2CCc3[nH]cnc3[C@H]2c2cc3ccc(C(F)(F)F)cn3n2)o1] | (S)-(4-(difluoromethyl)-2-(2-hydroxypropan-2-yl)oxazol-5-yl)(4-(6-(trifluoromethyl) pyrazolo[1,5-a]pyridin-2-yl)-6,7-dihydro-1H-imidazo [4,5-c]pyridin-5(4H)-yl)methanone |
| 1117 | 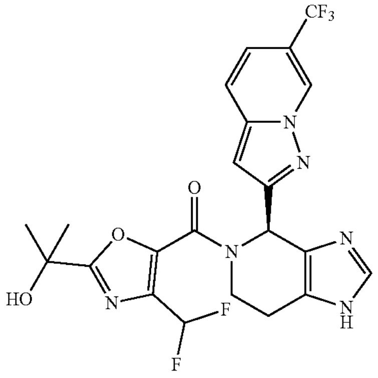 [SMILES: CC(C)(O)c1nc(C(F)F)c(C(=O)N2CCc3[nH]cnc3[C@@H]2c2cc3ccc(C(F)(F)F)cn3n2)o1] | (R)-(4-(difluoromethyl)-2-(2-hydroxypropan-2-yl)oxazol-5-yl)(4-(6-(trifluoromethyl)pyrazolo[1,5-a]pyridin-2-yl)-6,7-dihydro-1H-imidazo[4,5-c]pyridin-5(4H)-yl)methanone |
| 1118 | 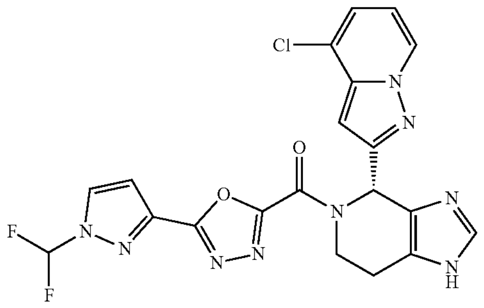 [SMILES: O=C(c1nnc(-c2ccn(C(F)F)n2)o1)N1CCc2[nH]cnc2[C@H]1c1cc2c(Cl)cccn2n1] | (S)-(4-(4-chloropyrazolo [1,5-a]pyridin-2-yl)-6,7-dihydro-1H-imidazo[4,5-c] pyridin-5(4H)-yl)(5-(1-(difluoromethyl)-1H-pyrazol-3-yl)-1,3,4-oxadiazol-2-yl)methanone |
| 1119 | 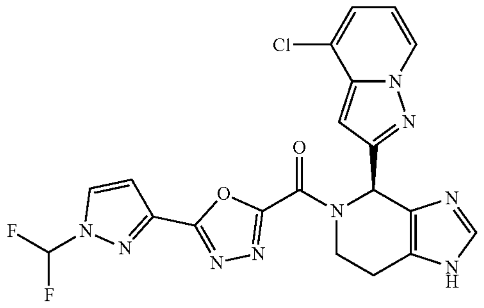 [SMILES: O=C(c1nnc(-c2ccn(C(F)F)n2)o1)N1CCc2[nH]cnc2[C@@H]1c1cc2c(Cl)cccn2n1] | (R)-(4-(4-chloropyrazolo [1,5-a]pyridin-2-yl)-6,7-dihydro-1H-imidazo[4,5-c] pyridin-5(4H)-yl)(5-(1-(difluoromethyl)-1H-pyrazol-3-yl)-1,3,4-oxadiazol-2-yl)methanone |

TABLE 1-continued

| Ex. # | Structure | Name |
|---|---|---|
| | Pyrazolo[1,5-a]pyridines | |
| 1120 | 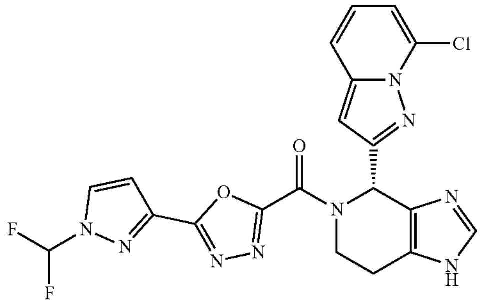 [SMILES: O=C(c1nnc(-c2ccn(C(F)F)n2)o1)N1CCc2[nH]cnc2[C@H]1c1cc2cccc(Cl)n2n1] | (S)-(4-(7-chloropyrazolo [1,5-a]pyridin-2-y]l)-6,7-dihydro-1H-imidazo[4,5-c] pyridin-5(4H)-yl)(5-(1-(difluoromethyl)-1H-pyrazol-4-yl)-1,3,4-oxadiazol-2-yl)methanone |
| 1121 | 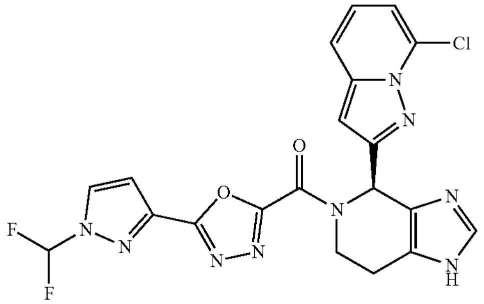 [SMILES: O=C(c1nnc(-c2ccn(C(F)F)n2)o1)N1CCc2[nH]cnc2[C@@H]1c1cc2cccc(Cl)n2n1] | (R)-(4-(7-chloropyrazolo [1,5-a]pyridin-2-yl)-6,7-dihydro-1H-imidazo[4,5-c] pyridin-5(4H)-yl)(5-(1-(difluoromethyl)-1H-pyrazol-4-yl)-1,3,4-oxadiazol-2-yl)methanone |
| 1122 | 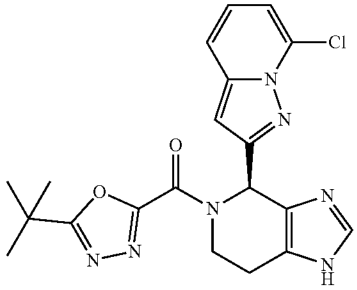 [SMILES: CC(C)(C)c1nnc(C(=O)N2CCc3[nH]cnc3[C@@H]2c2cc3cccc(Cl)n3n2)o1] | (R)-(5-(tert-butyl)-1,3,4-oxadiazol-2-yl)(4-(7-chloropyrazolo[1,5-a]pyridin-2-yl)-6,7-dihydro-1H-imidazo[4,5-c]pyridin-5(4H)-yl)methanone |
| 1123 | 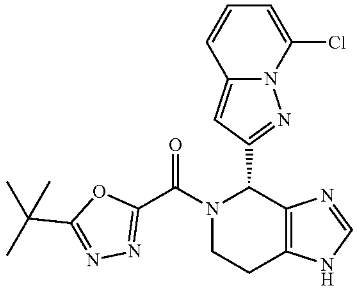 [SMILES: CC(C)(C)c1nnc(C(=O)N2CCc3[nH]cnc3[C@H]2c2cc3cccc(Cl)n3n2)o1] | (S)-(5-(tert-butyl)-1,3,4-oxadiazol-2-yl)(4-(7-chloropyrazolo[1,5-a]pyridin-2-yl)-6,7-dihydro-1H-imidazo[4,5-c]pyridin-5(4H)-yl)methanone |
| 1124 | 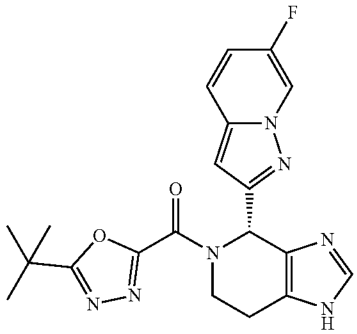 [SMILES: CC(C)(C)c1nnc(C(=O)N2CCc3[nH]cnc3[C@H]2c2cc3ccc(F)cn3n2)o1] | (S)-(5-(tert-butyl)-1,3,4-oxadiazol-2-yl)(4-(6-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1125 | 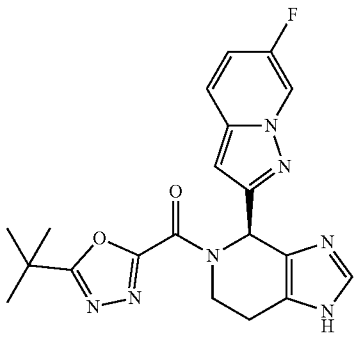 [SMILES: CC(C)(C)c1nnc(C(=O)N2CCc3[nH]cnc3[C@@H]2c2cc3ccc(F)cn3n2)o1] | (R)-(5-(tert-butyl)-1,3,4-oxadiazol-2-yl)(4-(6-fluoropyrazolo[1,5-a]pyridin-2-yl)-6,7-dihydro-1H-imidazo[4,5-c]pyridin-5(4H)-yl)methanone |
| 1126 | 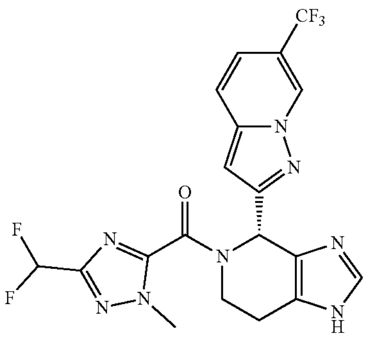 [SMILES: Cn1nc(C(F)F)nc1C(=O)N1CCc2[nH]cnc2[C@H]1c1cc2ccc(C(F)(F)F)cn2n1] | (S)-(3-(difluoromethyl)-1-methyl-1H-1,2,4-triazol-5-yl)(4-(6-(trifluoromethyl)pyrazolo[1,5-a]pyridin-2-yl)-6,7-dihydro-1H-imidazo[4,5-c]pyridin-5(4H)-yl)methanone |
| 1127 | 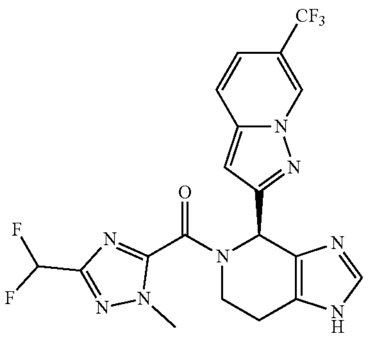 [SMILES: Cn1nc(C(F)F)nc1C(=O)N1CCc2[nH]cnc2[C@@H]1c1cc2ccc(C(F)(F)F)cn2n1] | (R)-(3-(difluoromethyl)-1-methyl-1H-1,2,4-triazol-5-yl)(4-(6-(trifluoromethyl)pyrazolo[1,5-a]pyridin-2-yl)-6,7-dihydro-1H-imidazo[4,5-c]pyridin-5(4H)-yl)methanone |
| 1128 | 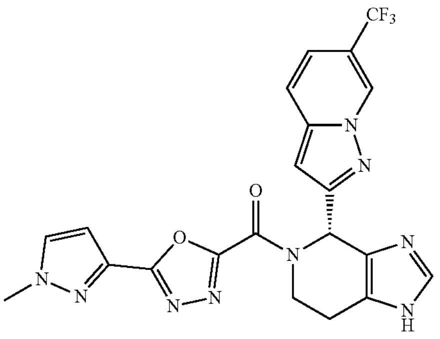 [SMILES: Cn1ccc(-c2nnc(C(=O)N3CCc4[nH]cnc4[C@H]3c3cc4ccc(C(F)(F)F)cn4n3)o2)n1] | (S)-(5-(1-methyl-1H-pyrazol-3-yl)-1,3,4-oxadiazol-2-yl)(4-(6-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1129 | 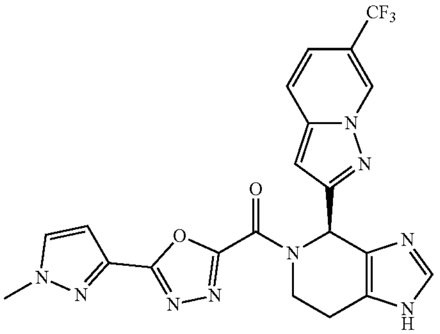 [SMILES: Cn1ccc(-c2nnc(C(=O)N3CCc4[nH]cnc4[C@@H]3c3cc4ccc(C(F)(F)F)cn4n3)o2)n1] | (R)-(5-(1-methyl-1H-pyrazol-3-yl)-1,3,4-oxadiazol-2-yl)(4-(6-(trifluoromethyl) pyrazolo[1,5-a]pyridin-2-yl)-6,7-dihydro-1H-imidazo [4,5-c]pyridin-5(4H)-yl)methanone |
| 1130 | 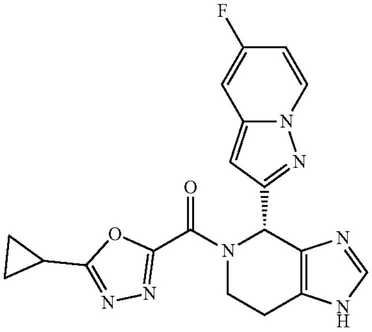 [SMILES: O=C(c1nnc(C2CC2)o1)N1CCc2[nH]cnc2[C@H]1c1cc2cc(F)ccn2n1] | (S)-(5-cyclopropyl-1,3,4-oxadiazol-2-yl)(4-(5-fluoropyrazolo[1,5-a]pyridin-2-yl)-6,7-dihydro-1H-imidazo[4,5-c]pyridin-5(4H)-yl)methanone |
| 1131 | 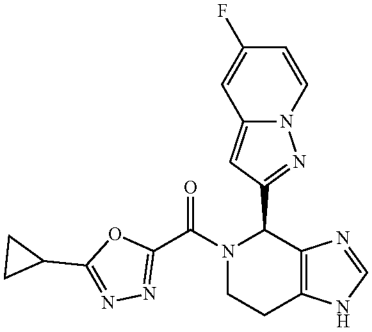 [SMILES: O=C(c1nnc(C2CC2)o1)N1CCc2[nH]cnc2[C@@H]1c1cc2cc(F)ccn2n1] | (R)-(5-cyclopropyl-1,3,4-oxadiazol-2-yl)(4-(5-fluoropyrazolo[1,5-a]pyridin-2-yl)-6,7-dihydro-1H-imidazo[4,5-c]pyridin-5(4H)-yl)methanone |
| 1132 | 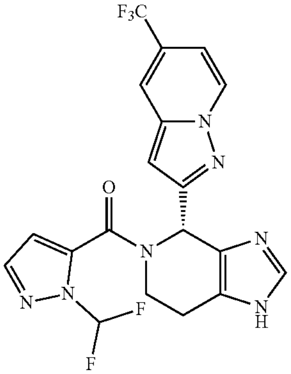 [SMILES: O=C(c1ccnn1C(F)F)N1CCc2[nH]cnc2[C@H]1c1cc2cc(C(F)(F)F)ccn2n1] | (S)-(1-(difluoromethyl)-1H-pyrazol-5-yl)(4-(5-(trifluoromethyl)pyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 1133 | 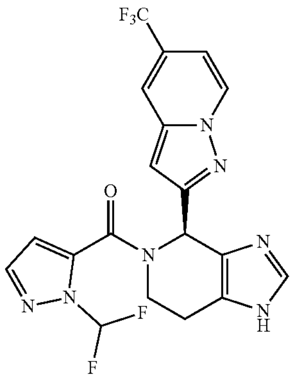 | (R)-(1-(difluoromethyl)-1H-pyrazol-5-yl)(4-(5-(trifluoromethyl)pyrazolo[1,5-a]pyridin-2-yl)-6,7-dihydro-1H-imidazo[4,5-c]pyridin-5(4H)-yl)methanone |
| 1134 | 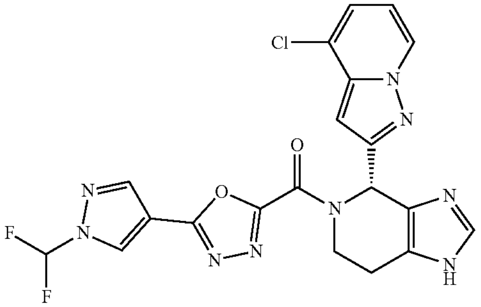 [SMILES: O=C(c1nnc(-c2cnn(C(F)F)c2)o1)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(5-(1-(difluoromethyl)-1H-pyrazol-4-yl)-1,3,4-oxadiazol-2-yl)methanone |
| 1135 | 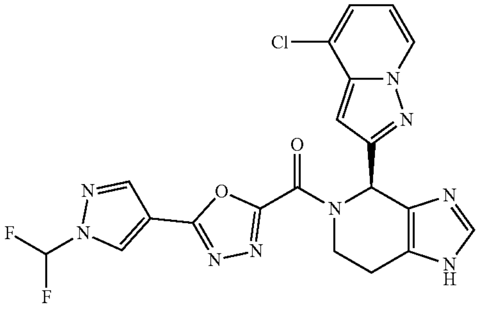 [SMILES: O=C(c1nnc(-c2cnn(C(F)F)c2)o1)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(5-(1-(difluoromethyl)-1H-pyrazol-4-yl)-1,3,4-oxadiazol-2-yl)methanone |
| 1136 | 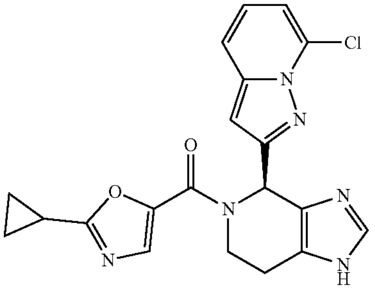 [SMILES: O=C(c1cnc(C2CC2)o1)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(5-cyclopropyl-1,3,4-oxadiazol-2-yl)methanone |

TABLE 1-continued

| Ex. # | Structure | Name |
|---|---|---|
| | Pyrazolo[1,5-a]pyridines | |
| 1137 | 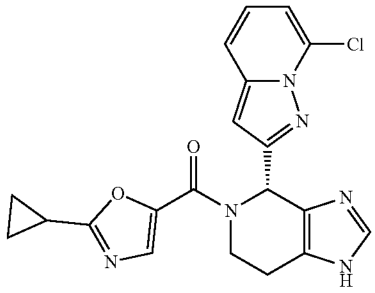 [SMILES: O=C(c1cnc(C2CC2)o1)N1CCc2[nH]cnc2[C@H]1c1cc2cccc(Cl)n2n1] | (S)-(4-(7-chloropyrazolo [1,5-a]pyridin-2-y])-6,7-dihydro-1H-imidazo[4,5-c] pyridin-5(4H)-yl)(5-cyclopropyl-1,3,4-oxadiazol-2-yl)methanone |
| 1138 | 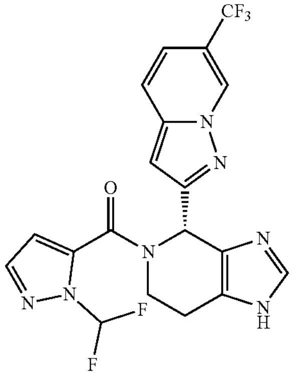 | (S)-(1-(difluoromethyl)-1H-pyrazol-5-yl)(4-(6-(trifluoromethyl)pyrazolo [1,5-a]pyridin-2-yl)-6,7-dihydro-1H-imidazo[4,5-c] pyridin-5(4H)-yl)methanone |
| 1139 | 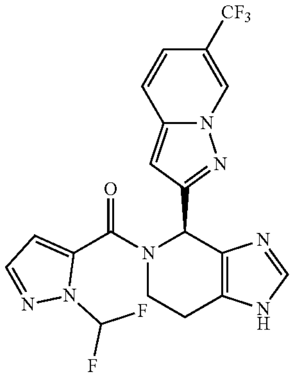 [SMILES: O=C(c1ccnn1C(F)F)N1CCc2[nH]cnc2[C@@H]1c1cc2ccc(C(F)(F)F)cn2n1] | (R)-(1-(difluoromethyl)-1H-pyrazol-5-yl)(4-(6-(trifluoromethyl)pyrazolo [1,5-a]pyridin-2-yl)-6,7-dihydro-1H-imidazo[4,5-c] pyridin-5(4H)-yl)methanone |
| 1140 | 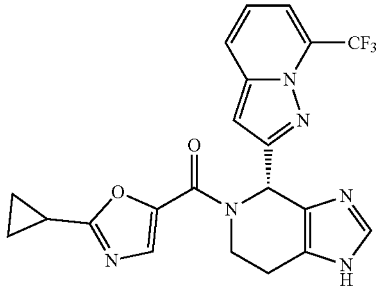 [SMILES: O=C(c1cnc(C2CC2)o1)N1CCc2[nH]cnc2[C@H]1c1cc2cccc(C(F)(F)F)n2n1] | (S)-(5-cyclopropyl-1,3,4-oxadiazol-2-yl)(4-(7-(trifluoromethyl)pyrazolo [1,5-a]pyridin-2-yl)-6,7-dihydro-1H-imidazo[4,5-c] pyridin-5(4H)-yl)methanone |

TABLE 1-continued

| Ex. # | Structure | Name |
|---|---|---|
| | Pyrazolo[1,5-a]pyridines | |
| 1141 | 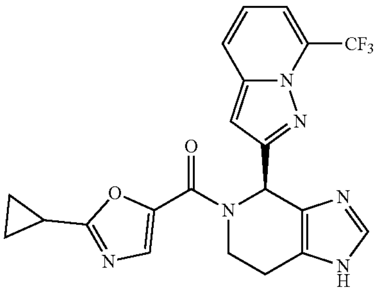 [SMILES: O=C(c1cnc(C2CC2)o1)N1CCc2[nH]cnc2[C@@H]1c1cc2cccc(C(F)(F)F)n2n1] | (R)-(5-cyclopropyl-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1142 | 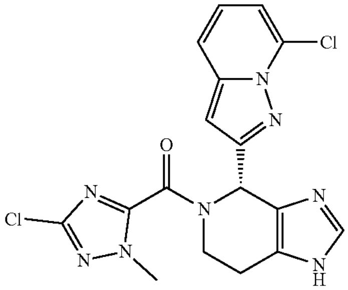 | (S)-(3-chloro-1-methyl-1H-1,2,4-triazol-5-yl)(4-(7-chloropyrazolo[1,5-a]pyridin-2-yl)-6,7-dihydro-1H-imidazo[4,5-c]pyridin-5(4H)-yl)methanone |
| 1143 | 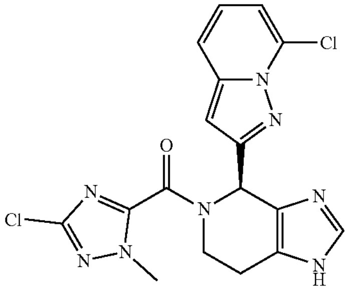 [SMILES: Cn1nc(Cl)nc1C(=O)N1CCc2[nH]cnc2[C@@H]1c1cc2cccc(Cl)n2n1] | (R)-(3-chloro-1-methyl-1H-1,2,4-triazol-5-yl)(4-(7-chloropyrazolo[1,5-a]pyridin-2-yl)-6,7-dihydro-1H-imidazo[4,5-c]pyridin-5(4H)-yl)methanone |
| 1144 | 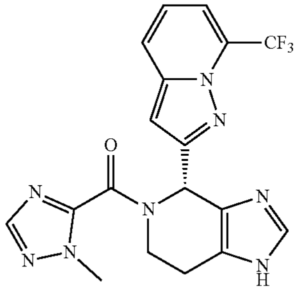 [SMILES: Cn1ncnc1C(=O)N1CCc2[nH]cnc2[C@H]1c1cc2cccc(C(F)(F)F)n2n1] | (S)-(1-methyl-1H-1,2,4-triazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1145 | 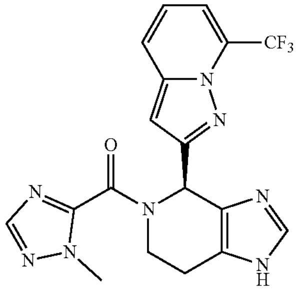 [SMILES: Cn1ncnc1C(=O)N1CCc2[nH]cnc2[C@@H]1c1cc2cccc(C(F)(F)F)n2n1] | (R)-(1-methyl-1H-1,2,4-triazol-5-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 1146 | 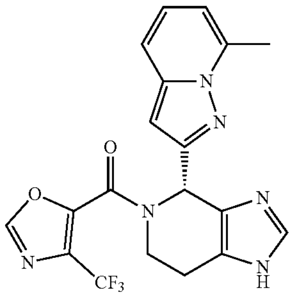 [SMILES: Cc1cccc2cc([C@@H]3c4nc[nH]c4CCN3C(=O)c3ocnc3C(F)(F)F)nn12] | (S)-(4-(7-methylpyrazolo [1,5-a]pyridin-2-yl)-6,7-dihydro-1H-imidazo[4,5-c] pyridin-5(4H)-yl)(4-(trifluoromethyl)oxazol-5-yl)methanone |
| 1147 | 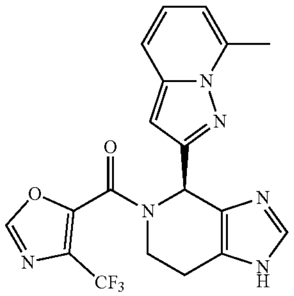 [SMILES: Cc1cccc2cc([C@H]3c4nc[nH]c4CCN3C(=O)c3ocnc3C(F)(F)F)nn12] | (R)-(4-(7-methylpyrazolo [1,5-a]pyridin-2-yl)-6,7-dihydro-1H-imidazo[4,5-c] pyridin-5(4H)-yl)(4-(trifluoromethyl)oxazol-5-yl)methanone |
| 1148 | 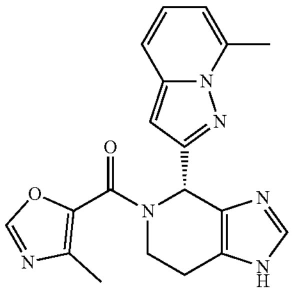 [SMILES: Cc1ncoc1C(=O)N1CCc2[nH]cnc2[C@H]1c1cc2cccc(C)n2n1] | (S)-(4-methyloxazol-5-yl) (4-(7-methylpyrazolo[1,5-a]pyridin-2-yl)-6,7-dihydro-1H-imidazo[4,5-c]pyridin-5(4H)-yl)methanone |
| 1149 | 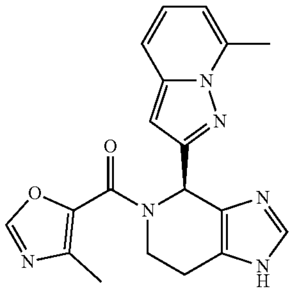 [SMILES: Cc1ncoc1C(=O)N1CCc2[nH]cnc2[C@@H]1c1cc2cccc(C)n2n1] | (R)-(4-methyloxazol-5-yl) (4-(7-methylpyrazolo[1,5-a]pyridin-2-yl)-6,7-dihydro-1H-imidazo[4,5-c]pyridin-5(4H)-yl)methanone |
| 1150 | 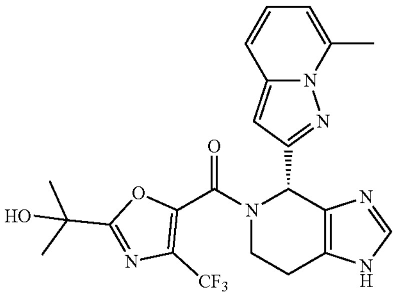 [SMILES: Cc1cccc2cc([C@@H]3c4nc[nH]c4CCN3C(=O)c3oc(C(C)(C)O)nc3C(F)(F)F)nn12] | (S)-(2-(2-hydroxypropan-2-yl)-4-(trifluoromethyl)oxazol-5-yl) (4-(7-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
| --- | --- | --- |
| | Pyrazolo[1,5-a]pyridines | |
| 1151 | 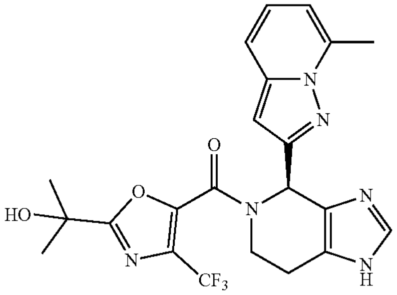 [SMILES: Cc1cccc2cc([C@H]3c4nc[nH]c4CCN3C(=O)c3oc(C(C)(C)O)nc3C(F)(F)F)nn12] | (R)-(2-(2-hydroxypropan-2-yl)-4-(trifluoromethyl)oxazol-5-yl)(4-(7-methylpyrazolo[1,5-a]pyridin-2-yl)-6,7-dihydro-1H-imidazo[4,5-c]pyridin-5(4H)-yl)methanone |
| 1152 | 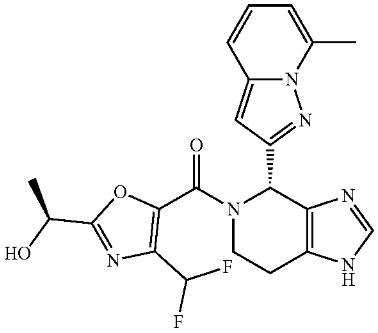 [SMILES: Cc1cccc2cc([C@@H]3c4nc[nH]c4CCN3C(=O)c3oc([C@H](C)O)nc3C(F)F)nn12] | (4-(difluoromethyl)-2-((S)-1-hydroxyethyl)oxazol-5-yl)((S)-4-(7-methylpyrazolo[1,5-a]pyridin-2-yl)-6,7-dihydro-1H-imidazo[4,5-c]pyridin-5(4H)-yl)methanone |
| 1153 | 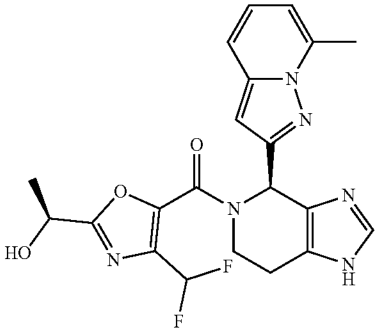 | (4-(difluoromethyl)-2-((S)-1-hydroxyethyl)oxazol-5-yl)((R)-4-(7-methylpyrazolo[1,5-a]pyridin-2-yl)-6,7-dihydro-1H-imidazo[4,5-c]pyridin-5(4H)-yl)methanone |
| 1154 | 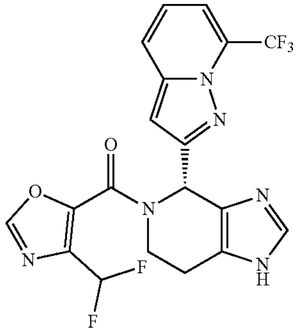 [SMILES: O=C(c1ocnc1C(F)F)N1CCc2[nH]cnc2[C@H]1c1cc2cccc(C(F)(F)F)n2n1] | (S)-(4-(difluoromethyl)oxazol-5-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1155 | 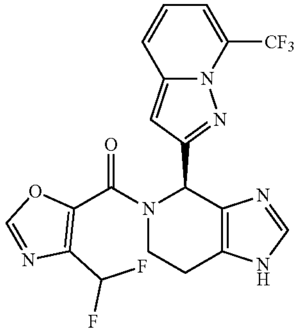 [SMILES: O=C(c1ocnc1C(F)F)N1CCc2[nH]cnc2[C@@H]1c1cc2cccc(C(F)(F)F)n2n1] | (R)-(4-(difluoromethyl) oxazol-5-yl)(4-(7-(trifluoromethyl)pyrazolo [1,5-a]pyridin-2-yl)-6,7-dihydro-1H-imidazo[4,5-c] pyridin-5(4H)-yl)methanone |
| 1156 | 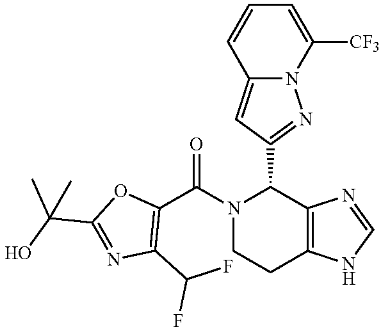 [SMILES: CC(C)(O)c1nc(C(F)F)c(C(=O)N2CCc3[nH]cnc3[C@H]2c2cc3cccc(C(F)(F)F)n3n2)o1] | (S)-(4-(difluoromethyl)-2-(2-hydroxypropan-2-yl)oxazol-5-yl)(4-(7-(trifluoromethyl) pyrazolo[1,5-a]pyridin-2-yl)-6,7-dihydro-1H-imidazo [4,5-c]pyridin-5(4H)-yl)methanone |
| 1157 | 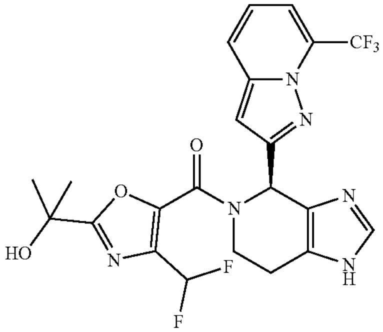 [SMILES: CC(C)(O)c1nc(C(F)F)c(C(=O)N2CCc3[nH]cnc3[C@@H]2c2cc3cccc(C(F)(F)F)n3n2)o1] | (R)-(4-(difluoromethyl)-2-(2-hydroxypropan-2-yl)oxazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1158 | 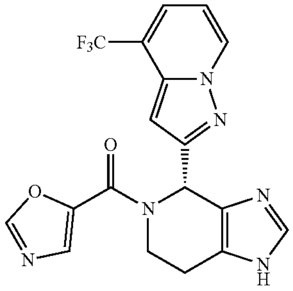 | (S)-oxazol-5-yl(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 1159 | 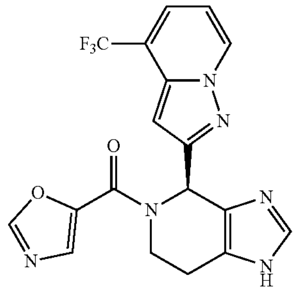 [SMILES: O=C(c1cnco1)N1CCc2[nH]cnc2[C@@H]1c1cc2c(C(F)(F)F)cccn2n1] | (R)-oxazol-5-yl(4-(4-(trifluoromethyl)pyrazolo[1,5-a]pyridin-2-yl)-6,7-dihydro-1H-imidazo[4,5-c]pyridin-5(4H)-yl)methanone |
| 1160 | 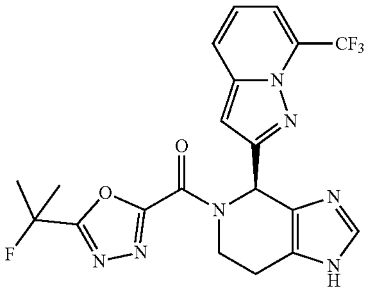 [SMILES: CC(C)(F)c1nnc(C(=O)N2CCc3[nH]cnc3[C@@H]2c2cc3cccc(C(F)(F)F)n3n2)o1] | (R)-(5-(2-fluoropropan-2-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1161 | 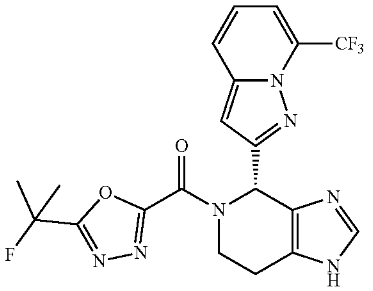 [SMILES: CC(C)(F)c1nnc(C(=O)N2CCc3[nH]cnc3[C@H]2c2cc3cccc(C(F)(F)F)n3n2)o1] | (S)-(5-(2-fluoropropan-2-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1162 | 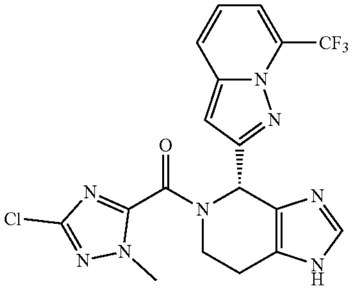 [SMILES: Cn1nc(Cl)nc1C(=O)N1CCc2[nH]cnc2[C@H]1c1cc2cccc(C(F)(F)F)n2n1] | (S)-(3-chloro-1-methyl-1H-1,2,4-triazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1163 | 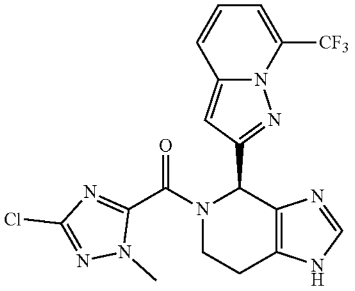 [SMILES: Cn1nc(Cl)nc1C(=O)N1CCc2[nH]cnc2[C@@H]1c1cc2cccc(C(F)(F)F)n2n1] | (R)-(3-chloro-1-methyl-1H-1,2,4-triazol-5-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1164 | 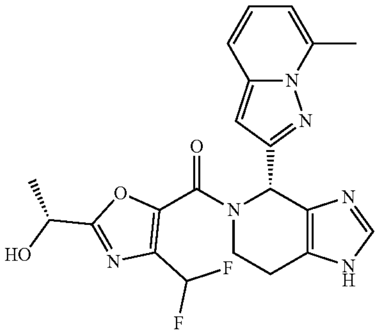 | (4-(difluoromethyl)-2-((R)-1-hydroxyethyl)oxazol-5-yl)((S)-4-(7-methylpyrazolo[1,5-a]pyridin-2-yl)-6,7-dihydro-1H-imidazo[4,5-c]pyridin-5(4H)-yl)methanone |
| 1165 | 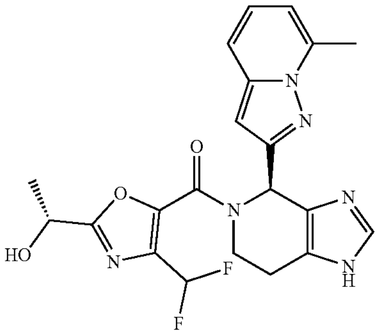 [SMILES: Cc1cccc2cc([C@H]3c4nc[nH]c4CCN3C(=O)c3oc([C@@H](C)O)nc3C(F)F)nn12] | (4-(difluoromethyl)-2-((R)-1-hydroxyethyl)oxazol-5-yl)((R)-4-(7-methylpyrazolo[1,5-a]pyridin-2-yl)-6,7-dihydro-1H-imidazo[4,5-c]pyridin-5(4H)-yl)methanone |
| 1166 | 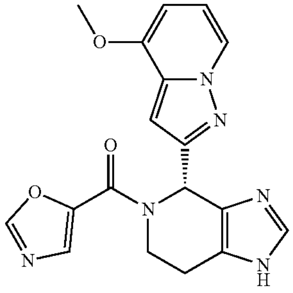 [SMILES: COc1cccn2nc([C@@H]3c4nc[nH]c4CCN3C(=O)c3cnco3)cc12] | (S)-(4-(4-methoxypyrazolo[1,5-a]pyridin-2-yl)-6,7-dihydro-1H-imidazo[4,5-c]pyridin-5(4H)-yl)(oxazol-5-yl)methanone |
| 1167 | 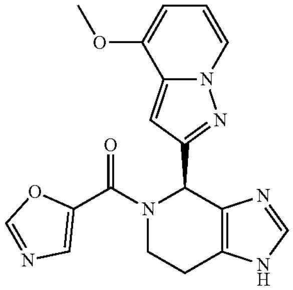 | (R)-(4-(4-methoxypyrazolo[1,5-a]pyridin-2-yl)-6,7-dihydro-1H-imidazo[4,5-c]pyridin-5(4H)-yl)(oxazol-5-yl)methanone |

TABLE 1-continued

| Pyrazolo[1,5-a]pyridines | | |
|---|---|---|
| Ex. # | Structure | Name |
| 1168 | 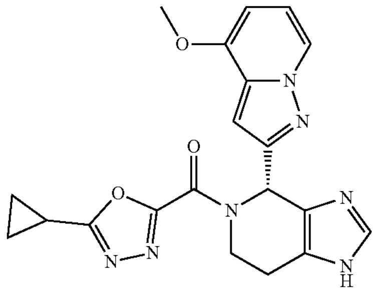 | (S)-(5-cyclopropyl-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 1169 | 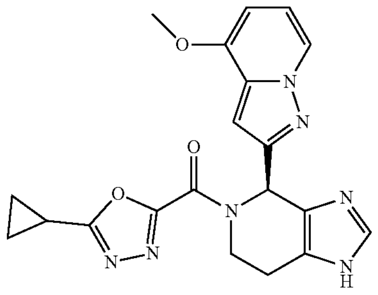 [SMILES: COc1cccn2nc([C@H]3c4nc[nH]c4CCN3C(=O)c3nnc(C4CC4)o3)cc12] | (R)-(5-cyclopropyl-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 1170 | 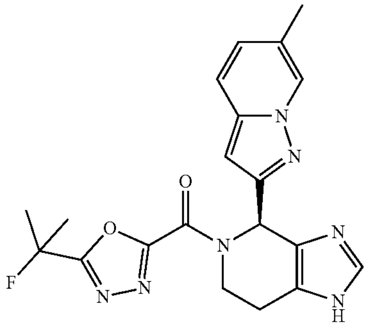 [SMILES: Cc1ccc2cc([C@H]3c4nc[nH]c4CCN3C(=O)c3nnc(C(C)(C)F)o3)nn2c1] | (R)-(5-(2-fluoropropan-2-yl)-1,3,4-oxadiazol-2-yl)(4-(6-methylpyrazolo[1,5-a]pyridin-2-yl)-6,7-dihydro-1H-imidazo[4,5-c]pyridin-5(4H)-yl)methanone |
| 1171 | 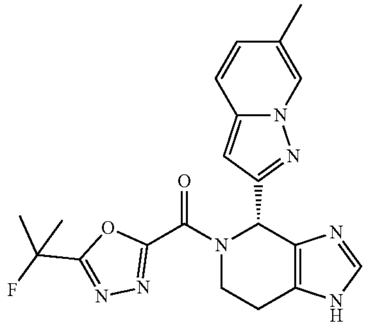 [SMILES: Cc1ccc2cc([C@@H]3c4nc[nH]c4CCN3C(=O)c3nnc(C(C)(C)F)o3)nn2c1] | (S)-(5-(2-fluoropropan-2-yl)-1,3,4-oxadiazol-2-yl)(4-(6-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1172 | 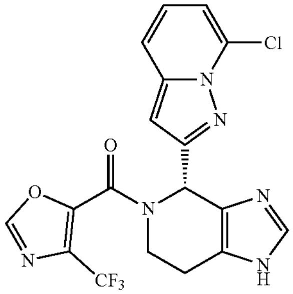 | (S)-(4-(7-chloropyrazolo [1,5-a]pyridin-2-yl)-6,7-dihydro-1H-imidazo[4,5-c] pyridin-5(4H)-yl)(4-(trifluoromethyl)oxazol-5-yl)methanone |
| 1173 | 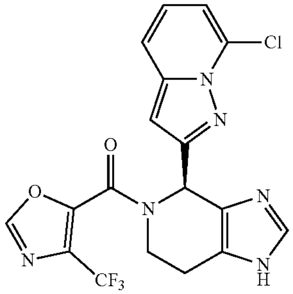 | (R)-(4-(7-chloropyrazolo [1,5-a]pyridin-2-yl)-6,7-dihydro-1H-imidazo[4,5-c] pyridin-5(4H)-yl)(4-(trifluoromethyl)oxazol-5-yl)methanone |
| 1174 | 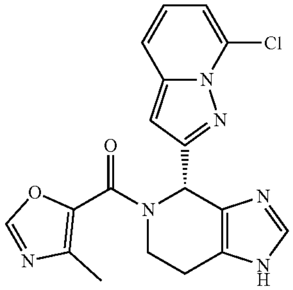 | (S)-(4-(7-chloropyrazolo [1,5-a]pyridin-2-yl)-6,7-dihydro-1H-imidazo[4,5-c] pyridin-5(4H)-yl)(4-methyloxazol-5-yl) methanone |
| 1175 | 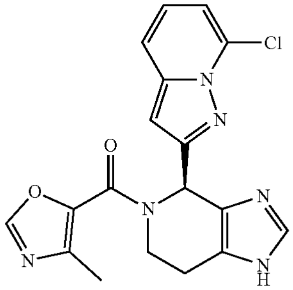 | (R)-(4-(7-chloropyrazolo [1,5-a]pyridin-2-yl)-6,7-dihydro-1H-imidazo[4,5-c] pyridin-5(4H)-yl)(4-methyloxazol-5-yl)methanone |
| 1176 | 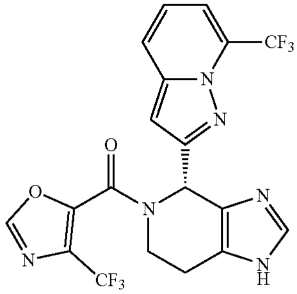 [SMILES: O=C(c1ocnc1C(F)(F)F)N1CCc2[nH]cnc2[C@H]1c1cc2cccc(C(F)(F)F)n2n1] | (S)-(4-(trifluoromethyl) oxazol-5-yl)(4-(7-(trifluoromethyl)pyrazolo [1,5-a]pyridin-2-yl)-6,7-dihydro-1H-imidazo[4,5-c] pyridin-5(4H)-yl)methanone |

TABLE 1-continued

| Ex. # | Structure | Name |
|---|---|---|
| | Pyrazolo[1,5-a]pyridines | |
| 1177 | 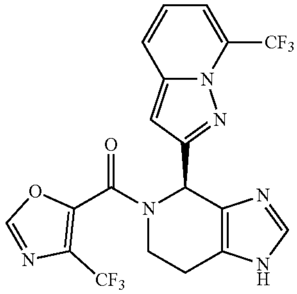 [SMILES: O=C(c1ocnc1C(F)(F)F)N1CCc2[nH]cnc2[C@@H]1c1cc2cccc(C(F)(F)F)n2n1] | (R)-(4-(trifluoromethyl) oxazol-5-yl)(4-(7-(trifluoromethyl)pyrazolo [1,5-a]pyridin-2-yl)-6,7-dihydro-1H-imidazo[4,5-c] pyridin-5(4H)-yl)methanone |
| 1178 | 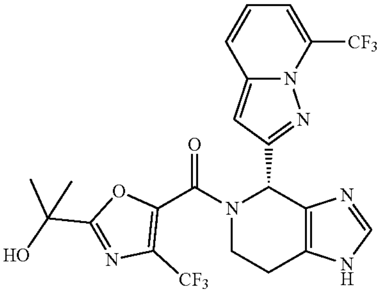 [SMILES: CC(C)(O)c1nc(C(F)(F)F)c(C(=O)N2CCc3[nH]cnc3[C@H]2c2cc3cccc(C(F)(F)F)n3n2)o1] | (S)-(2-(2-hydroxypropan-2-yl)-4-(trifluoromethyl) oxazol-5-yl)(4-(7-(trifluoromethyl)pyrazolo [1,5-a]pyridin-2-yl)-6,7-dihydro-1H-imidazo[4,5-c] pyridin-5(4H)-yl)methanone |
| 1179 | 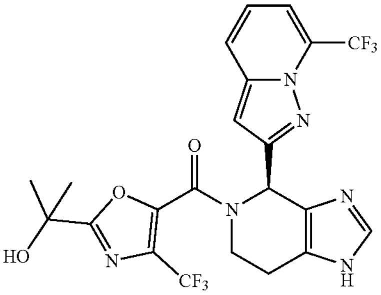 [SMILES: CC(C)(O)c1nc(C(F)(F)F)c(C(=O)N2CCc3[nH]cnc3[C@@H]2c2cc3cccc(C(F)(F)F)n3n2)o1] | (R)-(2-(2-hydroxypropan-2-yl)-4-(trifluoromethyl) oxazol-5-yl)(4-(7-(trifluoromethyl)pyrazolo [1,5-a]pyridin-2-yl)-6,7-dihydro-1H-imidazo[4,5-c] pyridin-5(4H)-yl)methanone |
| 1180 | 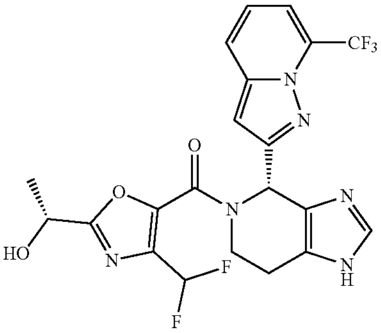 [SMILES: C[C@@H](O)c1nc(C(F)F)c(C(=O)N2CCc3[nH]cnc3[C@H]2c2cc3cccc(C(F)(F)F)n3n2)o1] | (4-(difluoromethyl)-2-((R)-1-hydroxyethyl)oxazol-5-yl)((S)-4-(7-(trifluoromethyl) pyrazolo[1,5-a]pyridin-2-yl)-6,7-dihydro-1H-imidazo [4,5-c]pyridin-5(4H)-yl)methanone |

TABLE 1-continued

| Pyrazolo[1,5-a]pyridines | | |
|---|---|---|
| Ex. # | Structure | Name |
| 1181 | 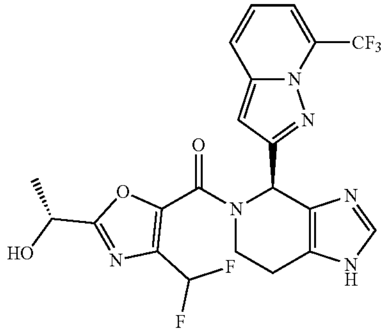 | (4-(difluoromethyl)-2-((R)-1-hydroxyethyl)oxazol-5-yl)((R)-4-(7-(trifluoromethyl)pyrazolo[1,5-a]pyridin-2-yl)-6,7-dihydro-1H-imidazo[4,5-c]pyridin-5(4H)-yl)methanone |
| 1182 | 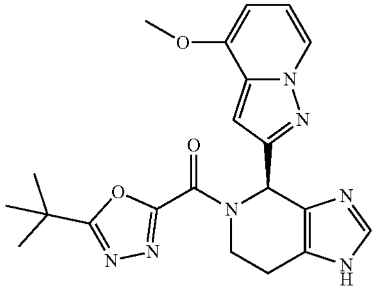 [SMILES: COc1cccn2nc([C@H]3c4nc[nH]c4CCN3C(=O)c3nnc(C(C)(C)C)o3)cc12] | (R)-(5-(tert-butyl)-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 1183 | 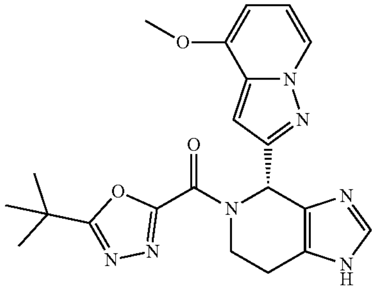 [SMILES: COc1cccn2nc([C@@H]3c4nc[nH]c4CCN3C(=O)c3nnc(C(C)(C)C)o3)cc12] | (S)-(5-(tert-butyl)-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 1184 | 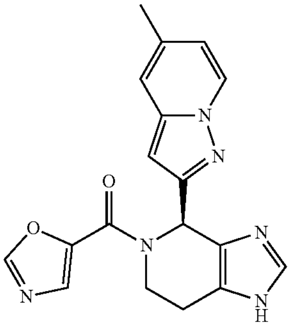 [SMILES: Cc1ccn2nc([C@H]3c4nc[nH]c4CCN3C(=O)c3cnco3)cc2c1] | (R)-(4-(5-methylpyrazolo[1,5-a]pyridin-2-yl)-6,7-dihydro-1H-imidazo[4,5-c]pyridin-5(4H)-yl)(oxazol-5-yl)methanone |

TABLE 1-continued

| Pyrazolo[1,5-a]pyridines | | |
|---|---|---|
| Ex. # | Structure | Name |
| 1185 | 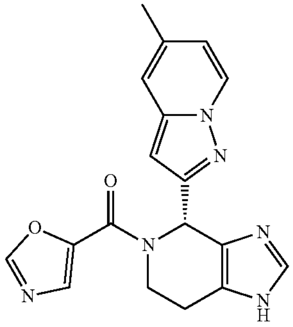 [SMILES: Cc1ccn2nc([C@@H]3c4nc[nH]c4CCN3C(=O)c3cnco3)cc2c1] | (S)-(4-(5-methylpyrazolo [1,5-a]pyridin-2-yl)-6,7-dihydro-1H-imidazo[4,5-c] pyridin-5(4H)-yl)(oxazol-5-yl)methanone |
| 1186 | 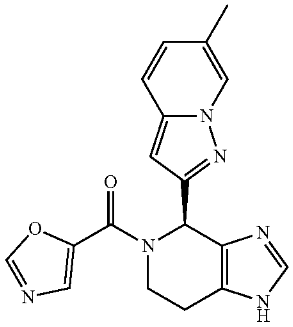 [SMILES: Cc1ccc2cc([C@H]3c4nc[nH]c4CCN3C(=O)c3cnco3)nn2c1] | (R)-(4-(6-methylpyrazolo [1,5-a]pyridin-2-yl)-6,7-dihydro-1H-imidazo[4,5-c] pyridin-5(4H)-yl)(oxazol-5-yl)methanone |
| 1187 | 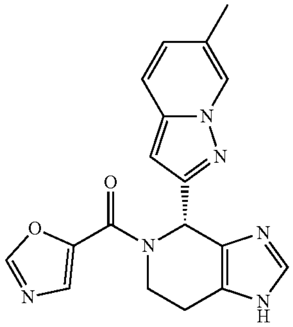 [SMILES: Cc1ccc2cc([C@@H]3c4nc[nH]c4CCN3C(=O)c3cnco3)nn2c1] | (S)-(4-(6-methylpyrazolo [1,5-a]pyridin-2-yl)-6,7-dihydro-1H-imidazo[4,5-c] pyridin-5(4H)-yl)(oxazol-5-yl)methanone |
| 1188 | 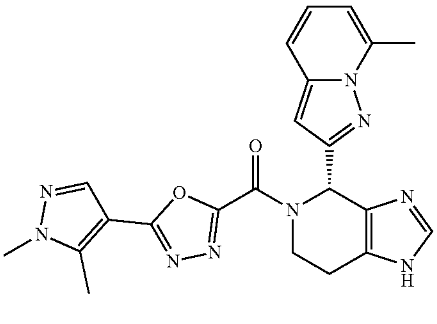 [SMILES: Cc1c(-c2nnc(C(=O)N3CCc4[nH]cnc4[C@H]3c3cc4cccc(C)n4n3)o2)cnn1C] | (S)-(5-(1,5-dimethyl-1H-pyrazol-4-yl)-1,3,4-oxadiazol-2-yl)(4-(7-methylpyrazolo[1,5-a] pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1189 | 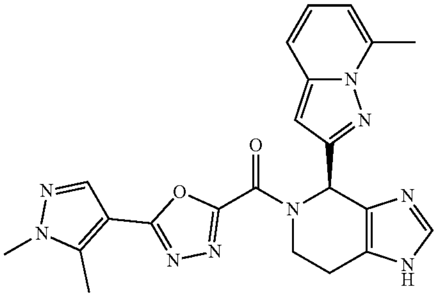 [SMILES: Cc1c(-c2nnc(C(=O)N3CCc4[nH]cnc4[C@@H]3c3cc4cccc(C)n4n3)o2)cnn1C] | (R)-(5-(1,5-dimethyl-1H-pyrazol-4-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 1190 | 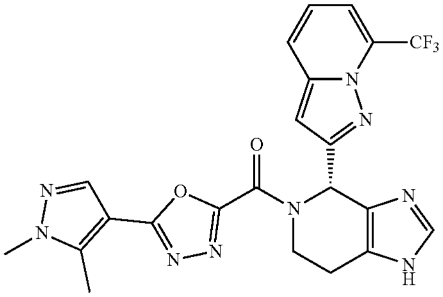 [SMILES: Cc1c(-c2nnc(C(=O)N3CCc4[nH]cnc4[C@H]3c3cc4cccc(C(F)(F)F)n4n3)o2)cnn1C] | (S)-(5-(1,5-dimethyl-1H-pyrazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1191 | 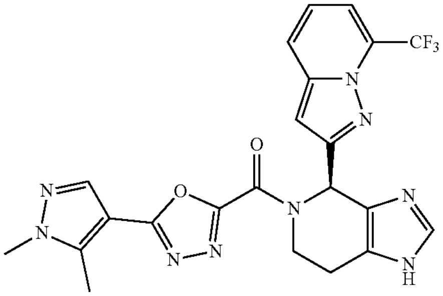 [SMILES: Cc1c(-c2nnc(C(=O)N3CCc4[nH]cnc4[C@@H]3c3cc4cccc(C(F)(F)F)n4n3)o2)cnn1C] | (R)-(5-(1,5-dimethyl-1H-pyrazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1192 | 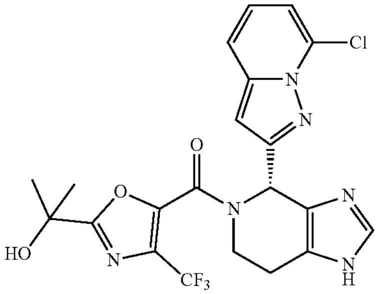 [SMILES: CC(C)(O)c1nc(C(F)(F)F)c(C(=O)N2CCc3[nH]cnc3[C@H]2c2cc3cccc(Cl)n3n2)o1] | (S)-(4-(7-chloropyrazolo[1,5-a]pyridin-2-yl)-6,7-dihydro-1H-imidazo[4,5-c]pyridin-5(4H)-yl)(2-(2-hydroxypropan-2-yl)-4-(trifluoromethyl)oxazol-5-yl)methanone |
| 1193 | 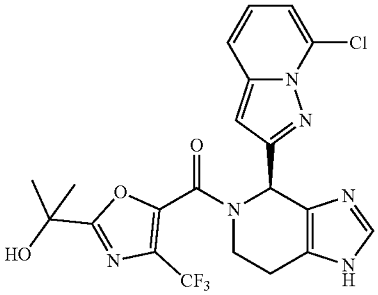 [SMILES: CC(C)(O)c1nc(C(F)(F)F)c(C(=O)N2CCc3[nH]cnc3[C@@H]2c2cc3cccc(Cl)n3n2)o1] | (R)-(4-(7-chloropyrazolo[1,5-a]pyridin-2-yl)-6,7-dihydro-1H-imidazo[4,5-c]pyridin-5(4H)-yl)(2-(2-hydroxypropan-2-yl)-4-(trifluoromethyl)oxazol-5-yl)methanone |

TABLE 1-continued

| Pyrazolo[1,5-a]pyridines | | |
|---|---|---|
| Ex. # | Structure | Name |
| 1194 | 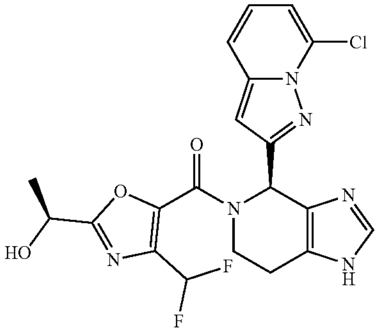 [SMILES: C[C@H](O)c1nc(C(F)F)c(C(=O)N2CCc3[nH]cnc3[C@@H]2c2cc3cccc(Cl)n3n2)o1] | ((R)-4-(7-chloropyrazolo[1,5-a]pyridin-2-yl)-6,7-dihydro-1H-imidazo[4,5-c]pyridin-5(4H)-yl)(4-(difluoromethyl)-2-((S)-1-hydroxyethyl)oxazol-5-yl)methanone |
| 1195 | 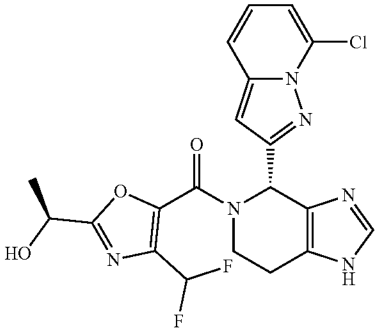 [SMILES: C[C@H](O)c1nc(C(F)F)c(C(=O)N2CCc3[nH]cnc3[C@H]2c2cc3cccc(Cl)n3n2)o1] | ((S)-4-(7-chloropyrazolo[1,5-a]pyridin-2-yl)-6,7-dihydro-1H-imidazo[4,5-c]pyridin-5(4H)-yl)(4-(difluoromethyl)-2-((S)-1-hydroxyethyl)oxazol-5-yl)methanone |
| 1196 | 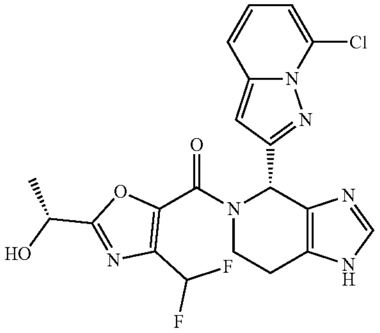 [SMILES: C[C@@H](O)c1nc(C(F)F)c(C(=O)N2CCc3[nH]cnc3[C@H]2c2cc3cccc(Cl)n3n2)o1] | ((S)-4-(7-chloropyrazolo[1,5-a]pyridin-2-yl)-6,7-dihydro-1H-imidazo[4,5-c]pyridin-5(4H)-yl)(4-(difluoromethyl)-2-((R)-1-hydroxyethyl)oxazol-5-yl)methanone |
| 1197 | 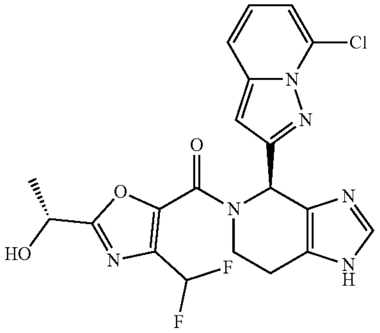 [SMILES: C[C@@H](O)c1nc(C(F)F)c(C(=O)N2CCc3[nH]cnc3[C@@H]2c2cc3cccc(Cl)n3n2)o1] | ((R)-4-(7-chloropyrazolo[1,5-a]pyridin-2-yl)-6,7-dihydro-1H-imidazo[4,5-c]pyridin-5(4H)-yl)(4-(difluoromethyl)-2-((R)-1-hydroxyethyl)oxazol-5-yl)methanone |

TABLE 1-continued

| Pyrazolo[1,5-a]pyridines | | |
|---|---|---|
| Ex. # | Structure | Name |
| 1198 | 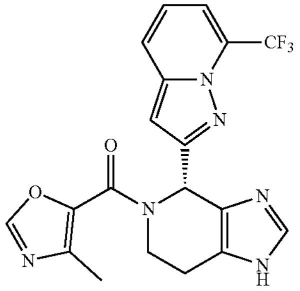 [SMILES: Cc1ncoc1C(=O)N1CCc2[nH]cnc2[C@H]1c1cc2cccc(C(F)(F)F)n2n1] | (S)-(4-(trifluoromethyl)oxazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1199 | 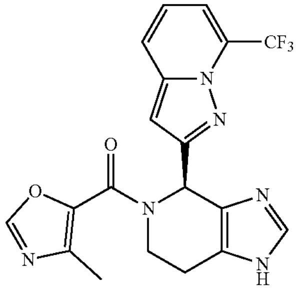 [SMILES: Cc1ncoc1C(=O)N1CCc2[nH]cnc2[C@@H]1c1cc2cccc(C(F)(F)F)n2n1] | (R)-(4-methyloxazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1200 | 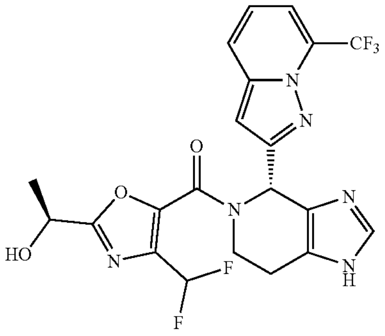 [SMILES: C[C@H](O)c1nc(C(F)F)c(C(=O)N2CCc3[nH]cnc3[C@H]2c2cc3cccc(C(F)(F)F)n3n2)o1] | (4-(difluoromethyl)-2-((S)-1-hydroxyethyl)oxazol-5-yl)((S)-4-(7-(trifluoromethyl)pyrazolo[1,5-a]pyridin-2-yl)-6,7-dihydro-1H-imidazo[4,5-c]pyridin-5(4H)-yl)methanone |
| 1201 | 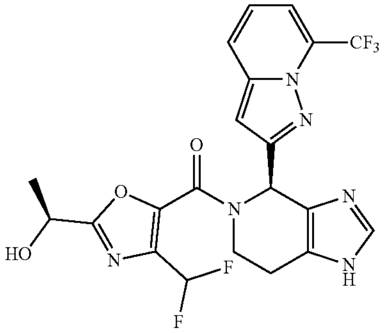 [SMILES: C[C@H](O)c1nc(C(F)F)c(C(=O)N2CCc3[nH]cnc3[C@@H]2c2cc3cccc(C(F)(F)F)n3n2)o1] | (4-(difluoromethyl)-2-((S)-1-hydroxyethyl)oxazol-5-yl)((R)-4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1202 | 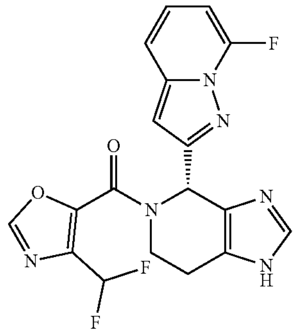 | (S)-(4-(difluoromethyl) oxazol-5-yl)(4-(7-fluoropyrazolo[1,5-a]pyridin-2-yl)-6,7-dihydro-1H-imidazo[4,5-c]pyridin-5(4H)-yl)methanone |
| 1203 | 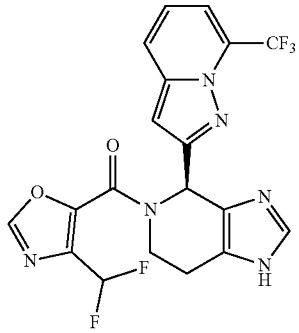 [SMILES: O=C(c1ocnc1C(F)F)N1CCc2[nH]cnc2[C@@H]1c1cc2cccc(C(F)(F)F)n2n1] | (R)-(4-(difluoromethyl) oxazol-5-yl)(4-(7-fluoropyrazolo[1,5-a]pyridin-2-yl)-6,7-dihydro-1H-imidazo[4,5-c]pyridin-5(4H)-yl)methanone |
| 1204 | 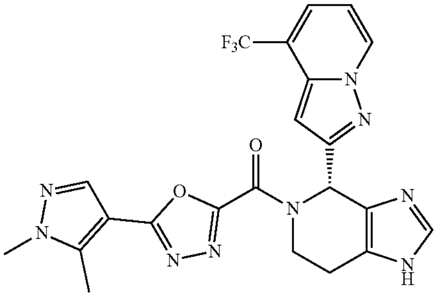 [SMILES: Cc1c(-c2nnc(C(=O)N3CCc4[nH]cnc4[C@H]3c3cc4c(C(F)(F)F)cccn4n3)o2)cnn1C] | (S)-(5-(1,5-dimethyl-1H-pyrazol-4-yl)-1,3,4-oxadiazol-2-yl)(4-(4-(trifluoromethyl) pyrazolo[1,5-a]pyridin-2-yl)-6,7-dihydro-1H-imidazo [4,5-c]pyridin-5(4H)-yl)methanone |
| 1205 | 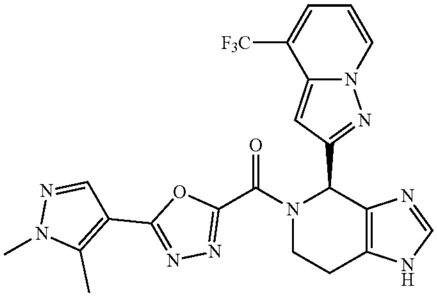 | (R)-(5-(1,5-dimethyl-1H-pyrazol-4-yl)-1,3,4-oxadiazol-2-yl)(4-(4-(trifluoromethyl) pyrazolo[1,5-a]pyridin-2-yl)-6,7-dihydro-1H-imidazo [4,5-c]pyridin-5(4H)-yl)methanone |

TABLE 1-continued

| Ex. # | Structure | Name |
| --- | --- | --- |
| Pyrazolo[1,5-a]pyridines | | |
| 1206 | 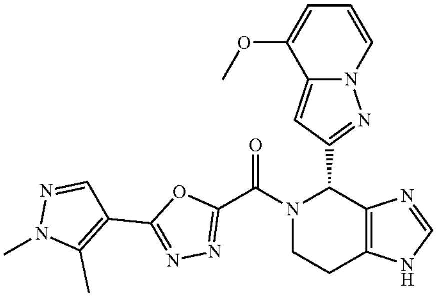 | (S)-(5-(1,5-dimethyl-1H-pyrazol-4-yl)-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 1207 | 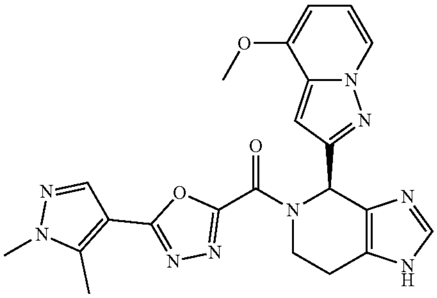 | (R)-(5-(1,5-dimethyl-1H-pyrazol-4-yl)-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 1208 | 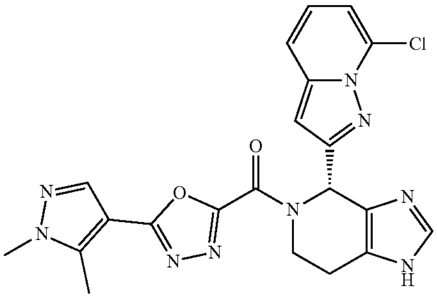 | (S)-(4-(7-chloropyrazolo[1,5-a]pyridin-2-yl)-6,7-dihydro-1H-imidazo[4,5-c]pyridin-5(4H)-yl)(5-(1,5-dimethyl-1H-pyrazol-4-yl)-1,3,4-oxadiazol-2-yl)methanone |
| 1209 | 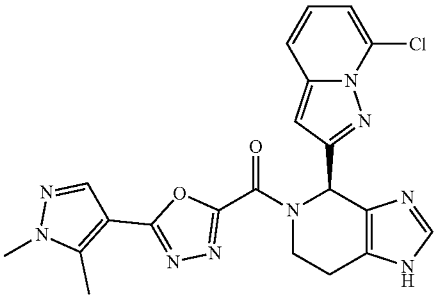 | (R)-(4-(7-chloropyrazolo[1,5-a]pyridin-2-yl)-6,7-dihydro-1H-imidazo[4,5-c]pyridin-5(4H)-yl)(5-(1,5-dimethyl-1H-pyrazol-4-yl)-1,3,4-oxadiazol-2-yl)methanone |
| 1210 | 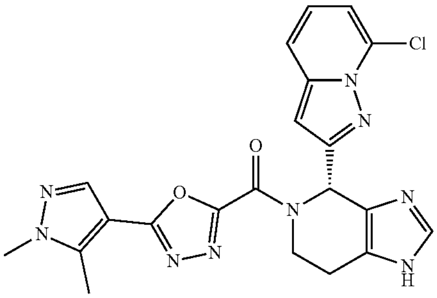 | (S)-(4-(7-chloropyrazolo[1,5-a]pyridin-2-yl)-6,7-dihydro-1H-imidazo[4,5-c]pyridin-5(4H)-yl)(2-(2-hydroxypropan-2-yl)-4-methyloxazol-5-yl)methanone |

TABLE 1-continued

| Ex. # | Structure | Name |
|---|---|---|
| Pyrazolo[1,5-a]pyridines | | |
| 1211 | 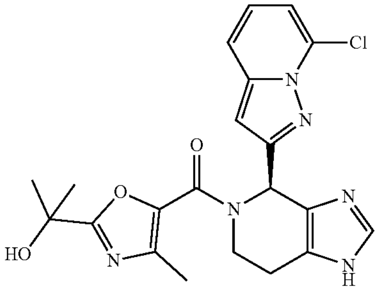 [SMILES: Cc1nc(C(C)(C)O)oc1C(=O)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(2-(2-hydroxypropan-2-yl)-4-methyloxazol-5-yl)methanone |
| 1212 | 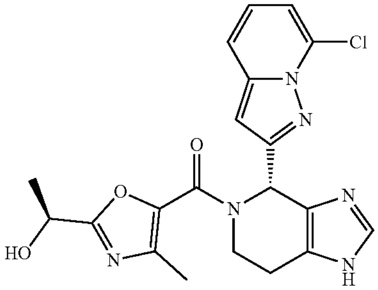 [SMILES: Cc1nc([C@H](C)O)oc1C(=O)N1CCc2[nH]cnc2[C@H]1c1cc2cccc(Cl)n2n1] | ((S)-4-(7-chloropyrazolo[1,5-a]pyridin-2-y]l)-6,7-dihydro-1H-imidazo[4,5-c]pyridin-5(4H)-yl)(2-((S)-1-hydroxyethyl)-4-methyloxazol-5-yl)methanone |
| 1213 | 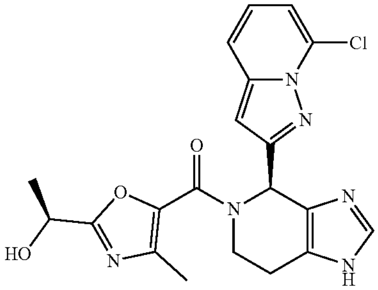 [SMILES: Cc1nc([C@H](C)O)oc1C(=O)N1CCc2[nH]cnc2[C@@H]1c1cc2cccc(Cl)n2n1] | ((R)-4-(7-chloropyrazolo[1,5-a]pyridin-2-yl)-6,7-dihydro-1H-imidazo[4,5-c]pyridin-5(4H)-yl)(2-((S)-1-hydroxyethyl)-4-methyloxazol-5-yl)methanone |
| 1214 | 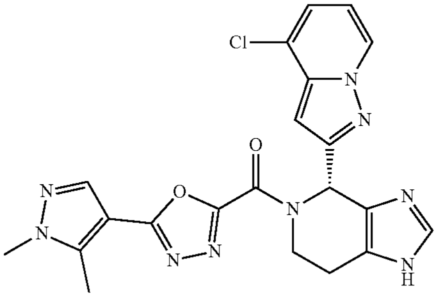 | (S)-(4-(4-chloropyrazolo[1,5-a]pyridin-2-yl)-6,7-dihydro-1H-imidazo[4,5-c]pyridin-5(4H)-yl)(5-(1,5-dimethyl-1H-pyrazol-4-yl)-1,3,4-oxadiazol-2-yl)methanone |
| 1215 | 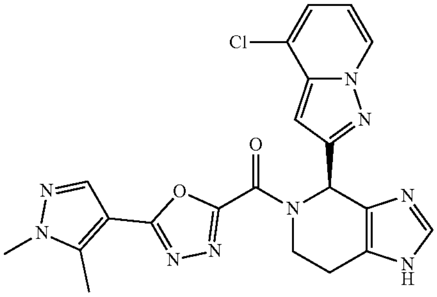 | (R)-(4-(4-chloropyrazolo[1,5-a]pyridin-2-yl)-6,7-dihydro-1H-imidazo[4,5-c]pyridin-5(4H)-yl)(5-(1,5-dimethyl-1H-pyrazol-4-yl)-1,3,4-oxadiazol-2-yl)methanone |

TABLE 1-continued

| Ex. # | Structure | Name |
|---|---|---|
| Pyrazolo[1,5-a]pyridines | | |
| 1216 | 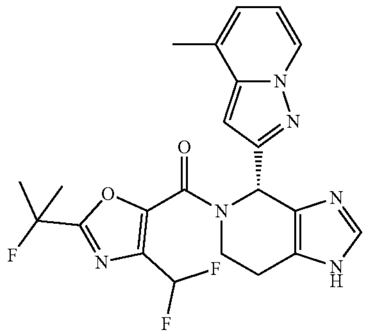 | (S)-(4-(difluoromethyl)-2-(2-fluoropropan-2-yl)oxazol-5-yl)(4-(4-methylpyrazolo[1,5-a]pyridin-2-yl)-6,7-dihydro-1H-imidazo[4,5-c]pyridin-5(4H)-yl)methanone |
| 1217 | 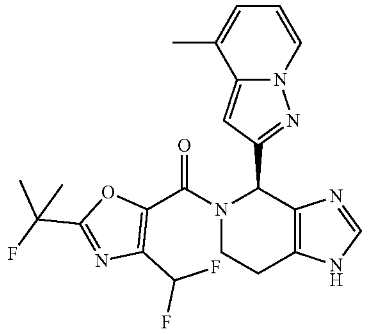 | (R)-(4-(difluoromethyl)-2-(2-fluoropropan-2-yl)oxazol-5-yl)(4-(4-methylpyrazolo[1,5-a]pyridin-2-yl)-6,7-dihydro-1H-imidazo[4,5-c]pyridin-5(4H)-yl)methanone |
| 1218 | 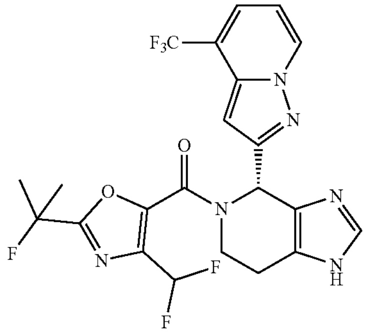 | (S)-(4-(difluoromethyl)-2-(2-fluoropropan-2-yl)oxazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1219 | 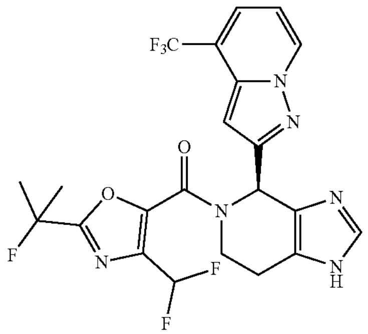 | (R)-(4-(difluoromethyl)-2-(2-fluoropropan-2-yl)oxazol-5-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1220 | 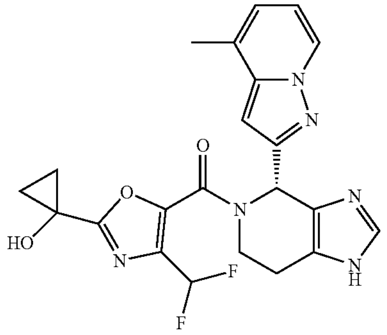 [SMILES: Cc1cccn2nc([C@@H]3c4nc[nH]c4CCN3C(=O)c3oc(C4(O)CC4)nc3C(F)F)cc12] | (S)-(4-(difluoromethyl)-2-(1-hydroxycyclopropyl)oxazol-5-yl)(4-(4-methylpyrazolo[1,5-a]pyridin-2-yl)-6,7-dihydro-1H-imidazo[4,5-c]pyridin-5(4H)-yl)methanone |
| 1221 | 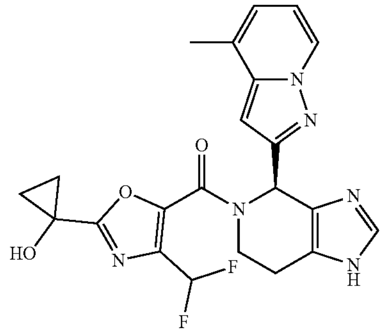 | (R)-(4-(difluoromethyl)-2-(1-hydroxycyclopropyl) oxazol-5-yl)(4-(4-methylpyrazolo[1,5-a]pyridin-2-yl)-6,7-dihydro-1H-imidazo[4,5-c]pyridin-5(4H)-yl)methanone |
| 1222 | 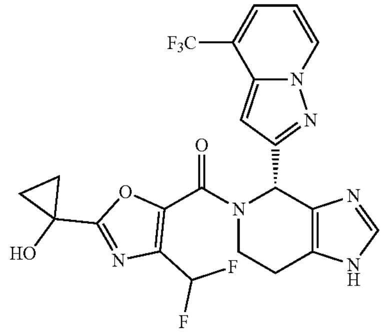 | (S)-(4-(difluoromethyl)-2-(1-hydroxycyclopropyl) oxazol-5-yl)(4-(4-(trifluoromethyl)pyrazolo [1,5-a]pyridin-2-yl)-6,7-dihydro-1H-imidazo[4,5-c] pyridin-5(4H)-yl)methanone |
| 1223 | 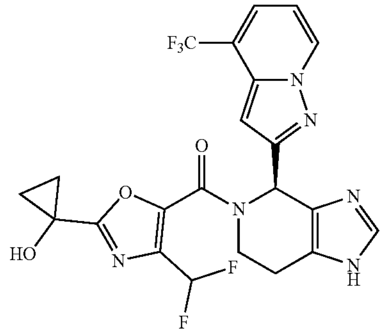 | (R)-(4-(difluoromethyl)-2-(1-hydroxycyclopropyl) oxazol-5-yl)(4-(4-(trifluoromethyl)pyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 1224 | 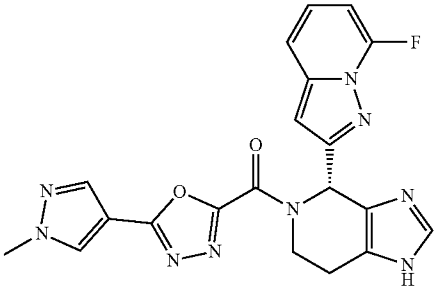 | (S)-(4-(7-fluoropyrazolo[1,5-a] pyridin-2-yl)-6,7-dihydro-1H-imidazo[4,5-c]pyridin-5(4H)-yl)(5-(1-methyl-1H-pyrazol-4-yl)-1,3,4-oxadiazol-2-yl) methanone |
| 1225 | 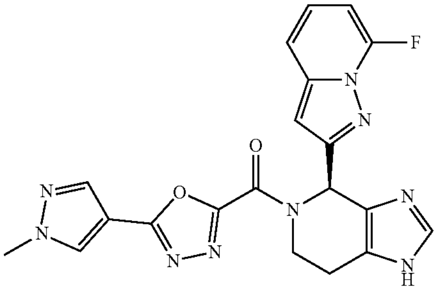 [SMILES: Cn1cc(-c2nnc(C(=O)N3CCc4[nH]cnc4[C@@H]3c3cc4cccc(F)n4n3)o2)cn1] | (R)-(4-(7-fluoropyrazolo [1,5-a]pyridin-2-yl)-6,7-dihydro-1H-imidazo[4,5-c] pyridin-5(4H)-yl)(5-(1-methyl-1H-pyrazol-4-yl)-1,3,4-oxadiazol-2-yl)methanone |
| 1226 | 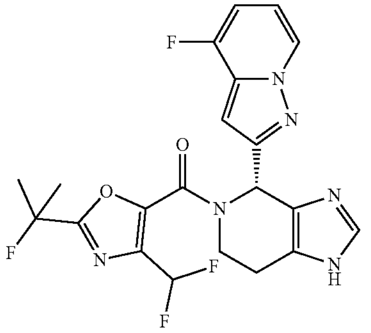 [SMILES: CC(C)(F)c1nc(C(F)F)c(C(=O)N2CCc3[nH]cnc3[C@H]2c2cc3c(F)cccn3n2)o1] | (S)-(4-(difluoromethyl)-2-(2-fluoropropan-2-yl)oxazol-5-yl)(4-(4-fluoropyrazolo[1,5-a] pyridin-2-yl)-6,7-dihydro-1H-imidazo[4,5-c]pyridin-5(4H)-yl)methanone |
| 1227 | 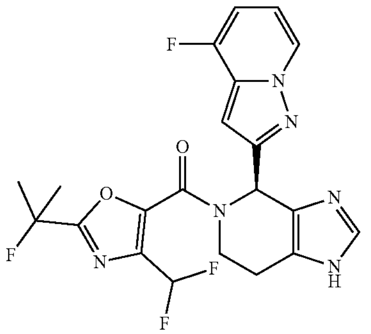 [SMILES: CC(C)(F)c1nc(C(F)F)c(C(=O)N2CCc3[nH]cnc3[C@@H]2c2cc3c(F)cccn3n2)o1] | (R)-(4-(difluoromethyl)-2-(2-fluoropropan-2-yl)oxazol-5-yl)(4-(4-fluoropyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 1228 | 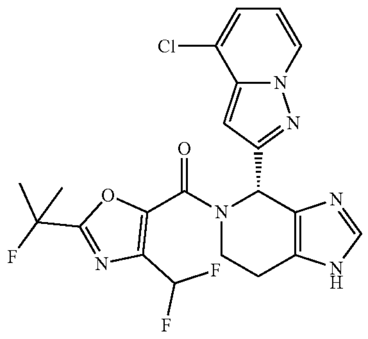 [SMILES: CC(C)(F)c1nc(C(F)F)c(C(=O)N2CCc3[nH]cnc3[C@H]2c2cc3c(Cl)cccn3n2)o1] | (S)-(4-(4-chloropyrazolo [1,5-a]pyridin-2-y]l)-6,7-dihydro-1H-imidazo[4,5-c] pyridin-5(4H)-yl)(4-(difluoromethyl)-2-(2-fluoropropan-2-yl)oxazol-5-yl)methanone |
| 1229 | 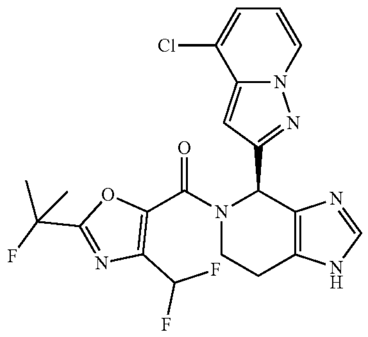 [SMILES: CC(C)(F)c1nc(C(F)F)c(C(=O)N2CCc3[nH]cnc3[C@@H]2c2cc3c(Cl)cccn3n2)o1] | (R)-(4-(4-chloropyrazolo [1,5-a]pyridin-2-yl)-6,7-dihydro-1H-imidazo [4,5-c]pyridin-5(4H)-yl)(4-(difluoromethyl)-2-(2-fluoropropan-2-yl)oxazol-5-yl)methanone |
| 1230 | 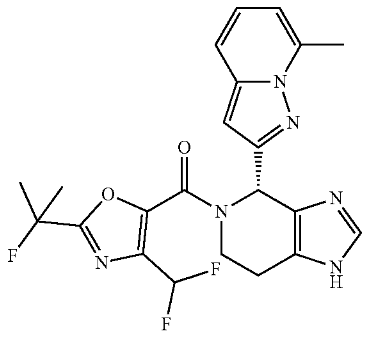 [SMILES: Cc1cccc2cc([C@@H]3c4nc[nH]c4CCN3C(=O)c3oc(C(C)(C)F)nc3C(F)F)nn12] | (S)-(4-(difluoromethyl)-2-(2-fluoropropan-2-yl)oxazol-5-yl)(4-(7-methylpyrazolo[1,5-a] pyridin-2-yl)-6,7-dihydro-1H-imidazo[4,5-c]pyridin-5(4H)-yl)methanone |
| 1231 | 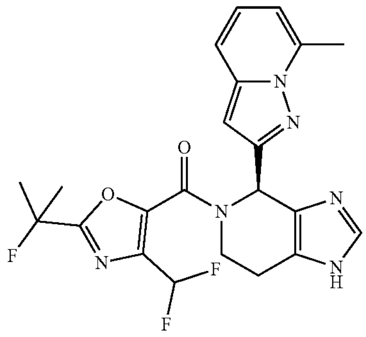 [SMILES: Cc1cccc2cc([C@H]3c4nc[nH]c4CCN3C(=O)c3oc(C(C)(C)F)nc3C(F)F)nn12] | (R)-(4-(difluoromethyl)-2-(2-fluoropropan-2-yl)oxazol-5-yl)(4-(7-methylpyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 1232 | 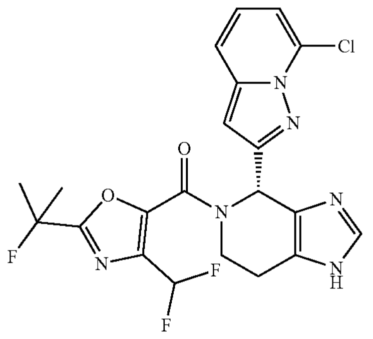 [SMILES: CC(C)(F)c1nc(C(F)F)c(C(=O)N2CCc3[nH]cnc3[C@H]2c2cc3cccc(Cl)n3n2)o1] | (S)-(4-(7-chloropyrazolo[1,5-a]pyridin-2-yl)-6,7-dihydro-1H-imidazo[4,5-c]pyridin-5(4H)-yl)(4-(difluoromethyl)-2-(2-fluoropropan-2-yl)oxazol-5-yl)methanone |
| 1233 | 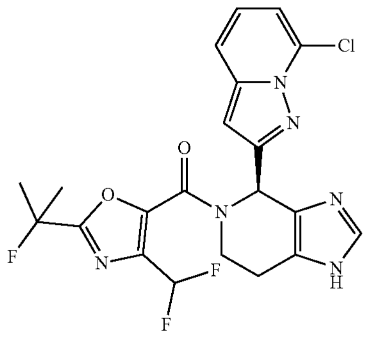 [SMILES: CC(C)(F)c1nc(C(F)F)c(C(=O)N2CCc3[nH]cnc3[C@@H]2c2cc3cccc(Cl)n3n2)o1] | (R)-(4-(7-chloropyrazolo[1,5-a]pyridin-2-yl)-6,7-dihydro-1H-imidazo[4,5-c]pyridin-5(4H)-yl)(4-(difluoromethyl)-2-(2-fluoropropan-2-yl)oxazol-5-yl)methanone |
| 1234 | 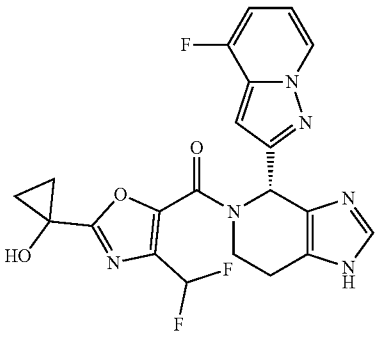 | (S)-(4-(difluoromethyl)-2-(1-hydroxycyclopropyl)oxazol-5-yl)(4-(4-fluoropyrazolo[1,5-a]pyridin-2-yl)-6,7-dihydro-1H-imidazo[4,5-c]pyridin-5(4H)-yl)methanone |
| 1235 | 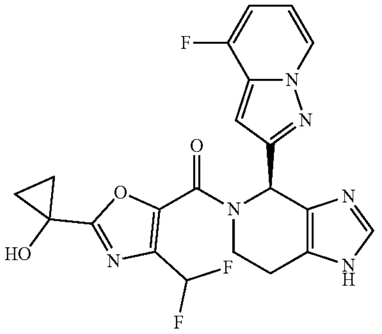 | (R)-(4-(difluoromethyl)-2-(1-hydroxycyclopropyl)oxazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1236 | 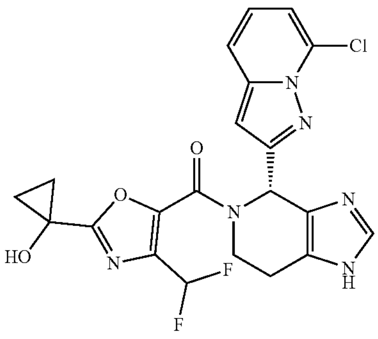 [SMILES: O=C(c1oc(C2(O)CC2)nc1C(F)F)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(4-(difluoromethyl)-2-(1-hydroxycyclopropyl)oxazol-5-yl)methanone |
| 1237 | 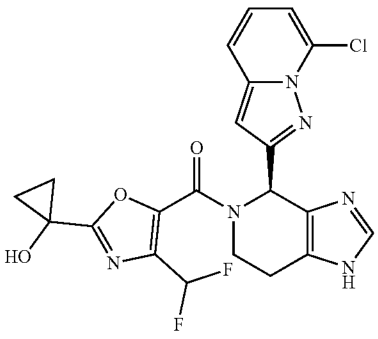 | (R)-(4-(7-chloropyrazolo[1,5-a]pyridin-2-yl)-6,7-dihydro-1H-imidazo[4,5-c]pyridin-5(4H)-yl)(4-(difluoromethyl)-2-(1-hydroxycyclopropyl)oxazol-5-yl)methanone |
| 1238 | 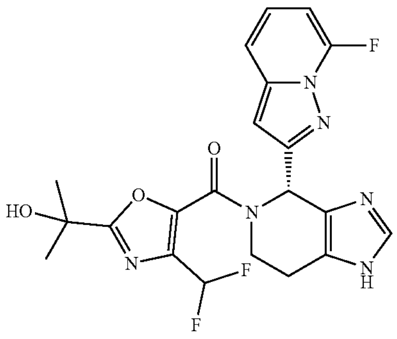 [SMILES: CC(C)(O)c1nc(C(F)F)c(C(=O)N2CCc3[nH]cnc3[C@H]2c2cc3cccc(F)n3n2)o1] | (S)-(4-(difluoromethyl)-2-(2-hydroxypropan-2-yl)oxazol-5-yl)(4-(7-fluoropyrazolo[1,5-a]pyridin-2-yl)-6,7-dihydro-1H-imidazo[4,5-c]pyridin-5(4H)-yl)methanone |
| 1239 | 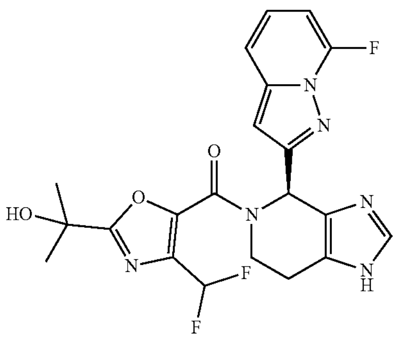 [SMILES: CC(C)(O)c1nc(C(F)F)c(C(=O)N2CCc3[nH]cnc3[C@@H]2c2cc3cccc(F)n3n2)o1] | (R)-(4-(difluoromethyl)-2-(2-hydroxypropan-2-yl)oxazol-5-yl)(4-(7-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1240 | 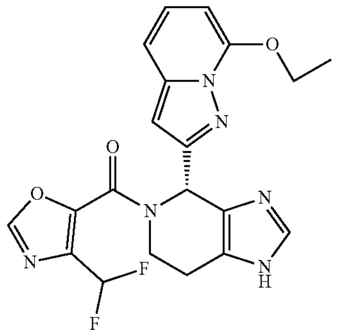 [SMILES: CCOc1cccc2cc([C@@H]3c4nc[nH]c4CCN3C(=O)c3ocnc3C(F)F)nn12] | (S)-(4-(difluoromethyl) oxazol-5-yl)(4-(7-ethoxypyrazolo[1,5-a]pyridin-2-yl)-6,7-dihydro-1H-imidazo[4,5-c]pyridin-5(4H)-yl)methanone |
| 1241 | 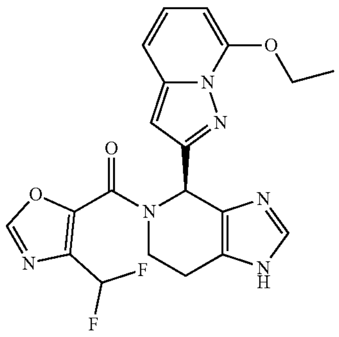 [SMILES: CCOc1cccc2cc([C@H]3c4nc[nH]c4CCN3C(=O)c3ocnc3C(F)F)nn12] | (R)-(4-(difluoromethyl) oxazol-5-yl)(4-(7-ethoxypyrazolo[1,5-a]pyridin-2-yl)-6,7-dihydro-1H-imidazo[4,5-c]pyridin-5(4H)-yl)methanone |
| 1242 | 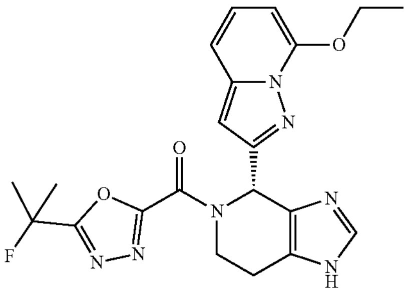 [SMILES: CCOc1cccc2cc([C@@H]3c4nc[nH]c4CCN3C(=O)c3nnc(C(C)(C)F)o3)nn12] | (S)-(4-(7-ethoxypyrazolo [1,5-a]pyridin-2-yl)-6,7-dihydro-1H-imidazo[4,5-c] pyridin-5(4H)-yl)(5-(2-fluoropropan-2-yl)-1,3,4-oxadiazol-2-yl)methanone |
| 1243 | 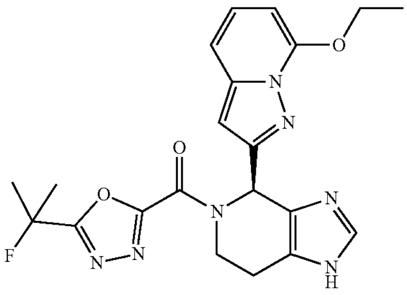 [SMILES: CCOc1cccc2cc([C@H]3c4nc[nH]c4CCN3C(=O)c3nnc(C(C)(C)F)o3)nn12] | (R)-(4-(7-ethoxypyrazolo [1,5-a]pyridin-2-yl)-6,7-dihydro-1H-imidazo[4,5-c] pyridin-5(4H)-yl)(5-(2-fluoropropan-2-yl)-1,3,4-oxadiazol-2-yl)methanone |

TABLE 1-continued

| Pyrazolo[1,5-a]pyridines | | |
|---|---|---|
| Ex. # | Structure | Name |
| 1244 | 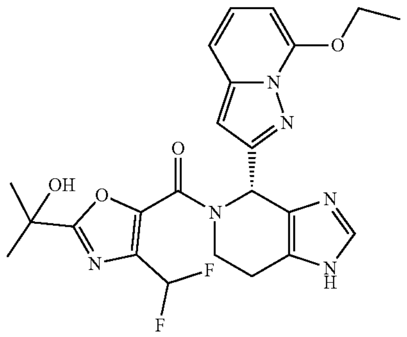 [SMILES: CCOc1cccc2cc([C@@H]3c4nc[nH]c4CCN3C(=O)c3oc(C(C)(C)O)nc3C(F)F)nn12] | (R)-(4-(difluoromethyl)-2-(2-hydroxypropan-2-yl)oxazol-5-yl)(4-(7-ethoxypyrazolo[1,5-a]pyridin-2-yl)-6,7-dihydro-1H-imidazo[4,5-c]pyridin-5(4H)-yl)methanone |
| 1245 | 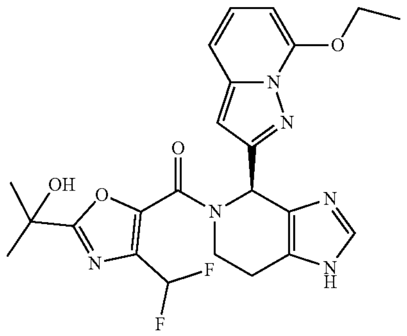 [SMILES: CCOc1cccc2cc([C@H]3c4nc[nH]c4CCN3C(=O)c3oc(C(C)(C)O)nc3C(F)F)nn12] | (S)-(4-(difluoromethyl)-2-(2-hydroxypropan-2-yl)oxazol-5-yl)(4-(7-ethoxypyrazolo[1,5-a]pyridin-2-yl)-6,7-dihydro-1H-imidazo[4,5-c]pyridin-5(4H)-yl)methanone |
| 1246 | 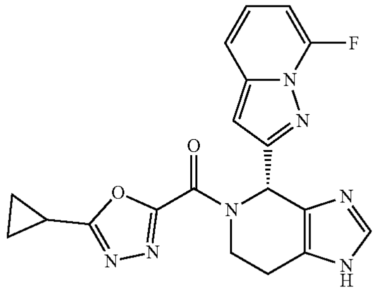 | (S)-(5-cyclopropyl-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1247 | 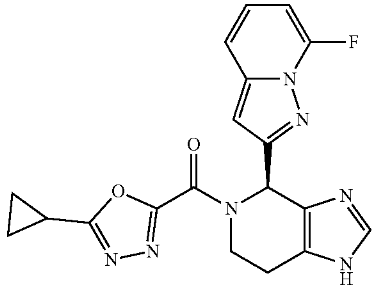 | (R)-(5-cyclopropyl-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1248 | 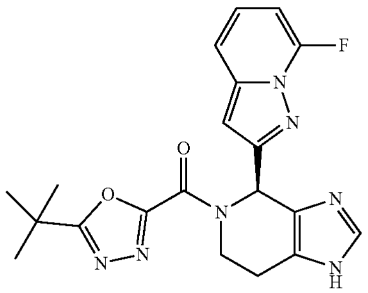 [SMILES: CC(C)(C)c1nnc(C(=O)N2CCc3[nH]cnc3[C@@H]2c2cc3cccc(F)n3n2)o1] | (R)-(5-(tert-butyl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1249 | 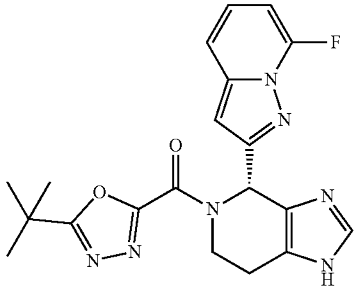 [SMILES: CC(C)(C)c1nnc(C(=O)N2CCc3[nH]cnc3[C@H]2c2cc3cccc(F)n3n2)o1] | (S)-(5-(tert-butyl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1250 | 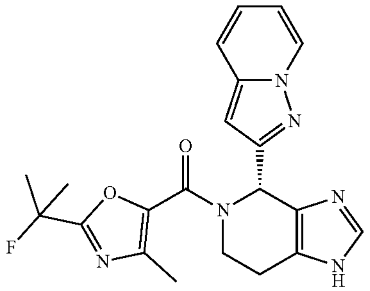 [SMILES: Cc1nc(C(C)(C)F)oc1C(=O)N1CCc2[nH]cnc2[C@H]1c1cc2ccccn2n1] | (S)-(2-(2-fluoropropan-2-yl)-4-methyloxazol-5-yl)(4-(pyrazolo[1,5-a]pyridin-2-yl)-6,7-dihydro-1H-imidazo[4,5-c]pyridin-5(4H)-yl)methanone |
| 1251 | 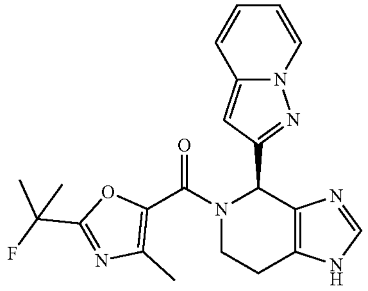 [SMILES: Cc1nc(C(C)(C)F)oc1C(=O)N1CCc2[nH]cnc2[C@@H]1c1cc2ccccn2n1] | (R)-(2-(2-fluoropropan-2-yl)-4-methyloxazol-5-yl)(4-(pyrazolo[1,5-a]pyridin-2-yl)-6,7-dihydro-1H-imidazo[4,5-c]pyridin-5(4H)-yl)methanone |
| 1252 | 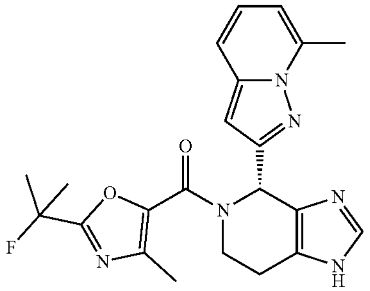 [SMILES: Cc1nc(C(C)(C)F)oc1C(=O)N1CCc2[nH]cnc2[C@H]1c1cc2cccc(C)n2n1] | (S)-(2-(2-fluoropropan-2-yl)-4-methyloxazol-5-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1253 | 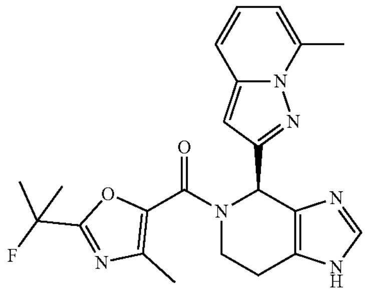 [SMILES: Cc1nc(C(C)(C)F)oc1C(=O)N1CCc2[nH]cnc2[C@@H]1c1cc2cccc(C)n2n1] | (R)-(2-(2-fluoropropan-2-yl)-4-methyloxazol-5-yl)(4-(7-methylpyrazolo[1,5-a]pyridin-2-yl)-6,7-dihydro-1H-imidazo[4,5-c]pyridin-5(4H)-yl)methanone |
| 1254 | 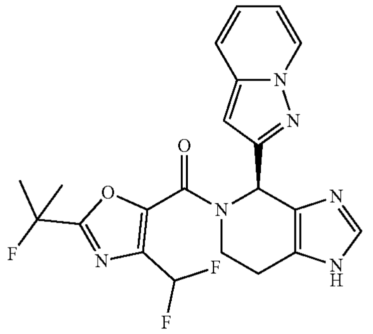 [SMILES: CC(C)(F)c1nc(C(F)F)c(C(=O)N2CCc3[nH]cnc3[C@@H]2c2cc3ccccn3n2)o1] | (R)-(4-(difluoromethyl)-2-(2-fluoropropan-2-yl)oxazol-5-yl)(4-(pyrazolo[1,5-a]pyridin-2-yl)-6,7-dihydro-1H-imidazo[4,5-c]pyridin-5(4H)-yl)methanone |
| 1255 | 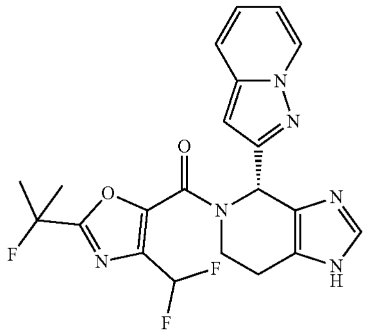 [SMILES: CC(C)(F)c1nc(C(F)F)c(C(=O)N2CCc3[nH]cnc3[C@H]2c2cc3ccccn3n2)o1] | (S)-(4-(difluoromethyl)-2-(2-fluoropropan-2-yl)oxazol-5-yl)(4-(pyrazolo[1,5-a]pyridin-2-yl)-6,7-dihydro-1H-imidazo[4,5-c]pyridin-5(4H)-yl)methanone |
| 1256 | 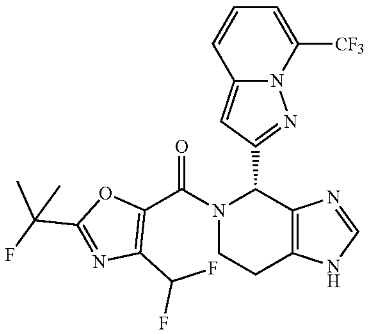 [SMILES: CC(C)(F)c1nc(C(F)F)c(C(=O)N2CCc3[nH]cnc3[C@H]2c2cc3cccc(C(F)(F)F)n3n2)o1] | (S)-(5-(2-fluoropropan-2-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| Pyrazolo[1,5-a]pyridines | | |
| 1257 | 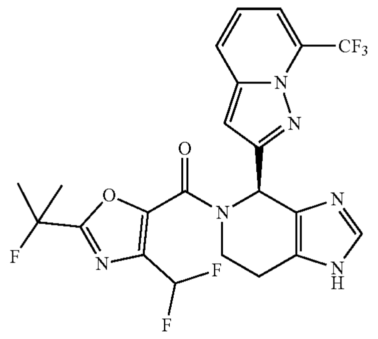 [SMILES: CC(C)(F)c1nc(C(F)F)c(C(=O)N2CCc3[nH]cnc3[C@@H]2c2cc3cccc(C(F)(F)F)n3n2)o1] | (R)-(5-(2-fluoropropan-2-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1258 | 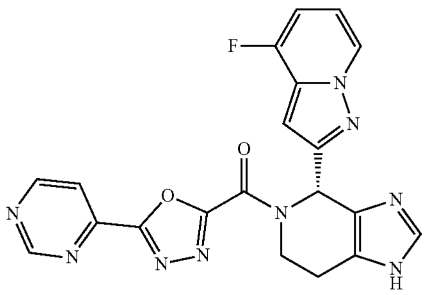 [SMILES: O=C(c1nnc(-c2ccncn2)o1)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(5-(pyrimidin-4-yl)-1,3,4-oxadiazol-2-yl)methanone |
| 1259 | 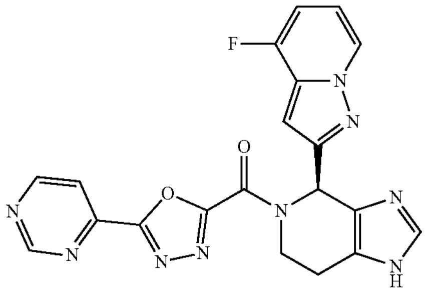 [SMILES: O=C(c1nnc(-c2ccncn2)o1)N1CCc2[nH]cnc2[C@@H]1c1cc2c(F)cccn2n1] | (R)-(4-(4-fluoropyrazolo[1,5-a]pyridin-2-y]l)-6,7-dihydro-1H-imidazo[4,5-c]pyridin-5(4H)-yl)(5-(pyrimidin-4-yl)-1,3,4-oxadiazol-2-yl)methanone |
| 1260 | 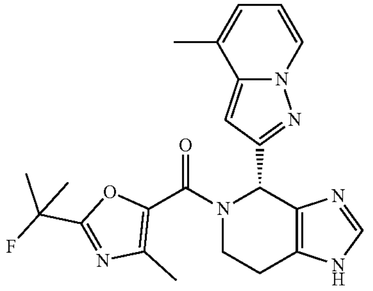 [SMILES: Cc1nc(C(C)(C)F)oc1C(=O)N1CCc2[nH]cnc2[C@H]1c1cc2c(C)cccn2n1] | (S)-(2-(2-fluoropropan-2-yl)-4-methyloxazol-5-yl)(4-(4-methylpyrazolo[1,5-a]pyridin-2-yl)-6,7-dihydro-1H-imidazo[4,5-c]pyridin-5(4H)-yl)methanone |
| 1261 | 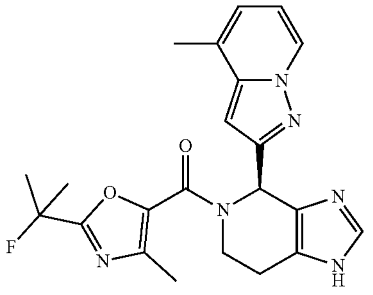 [SMILES: Cc1nc(C(C)(C)F)oc1C(=O)N1CCc2[nH]cnc2[C@@H]1c1cc2c(C)cccn2n1] | (R)-(2-(2-fluoropropan-2-yl)-4-methyloxazol-5-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1262 | 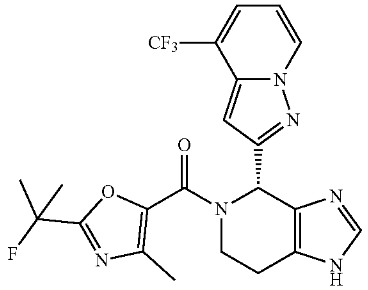 [SMILES: Cc1nc(C(C)(C)F)oc1C(=O)N1CCc2[nH]cnc2[C@H]1c1cc2c(C(F)(F)F)cccn2n1] | (S)-(2-(2-fluoropropan-2-yl)-4-methyloxazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1263 | 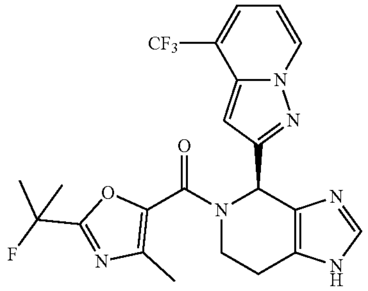 [SMILES: Cc1nc(C(C)(C)F)oc1C(=O)N1CCc2[nH]cnc2[C@@H]1c1cc2c(C(F)(F)F)cccn2n1] | (R)-(2-(2-fluoropropan-2-yl)-4-methyloxazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1264 | 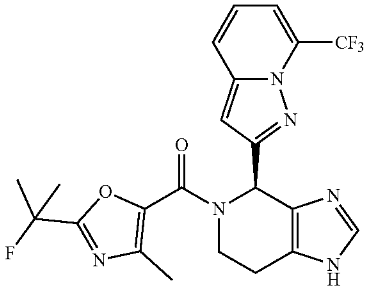 [SMILES: Cc1nc(C(C)(C)F)oc1C(=O)N1CCc2[nH]cnc2[C@@H]1c1cc2cccc(C(F)(F)F)n2n1] | (R)-(2-(2-fluoropropan-2-yl)-4-methyloxazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1265 | 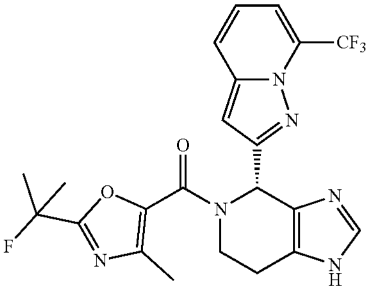 [SMILES: Cc1nc(C(C)(C)F)oc1C(=O)N1CCc2[nH]cnc2[C@H]1c1cc2cccc(C(F)(F)F)n2n1] | (S)-(2-(2-fluoropropan-2-yl)-4-methyloxazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1266 | 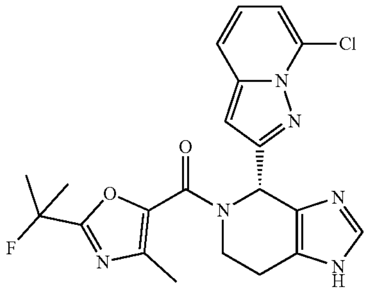 [SMILES: Cc1nc(C(C)(C)F)oc1C(=O)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(2-(2-fluoropropan-2-yl)-4-methyloxazol-5-yl)methanone |

TABLE 1-continued

| Pyrazolo[1,5-a]pyridines | | |
|---|---|---|
| Ex. # | Structure | Name |
| 1267 | 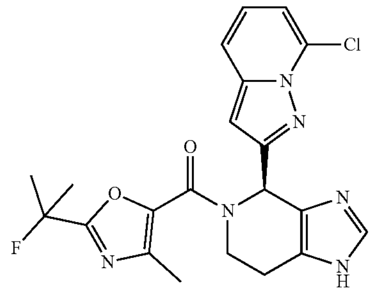 [SMILES: Cc1nc(C(C)(C)F)oc1C(=O)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(2-(2-fluoropropan-2-yl)-4-methyloxazol-5-yl)methanone |
| 1268 | 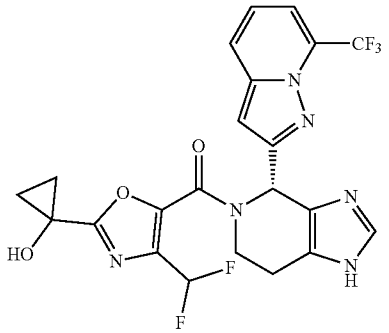 [SMILES: O=C(c1oc(C2(O)CC2)nc1C(F)F)N1CCc2[nH]cnc2[C@H]1c1cc2cccc(C(F)(F)F)n2n1] | (S)-(4-(difluoromethyl)-2-(1-hydroxycyclopropyl)oxazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1269 | 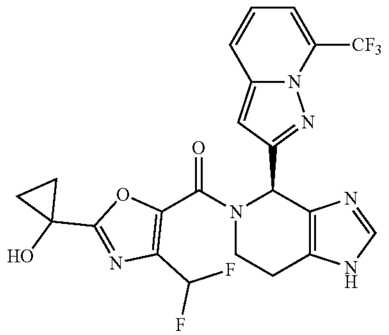 [SMILES: O=C(c1oc(C2(O)CC2)nc1C(F)F)N1CCc2[nH]cnc2[C@@H]1c1cc2cccc(C(F)(F)F)n2n1] | (R)-(4-(difluoromethyl)-2-(1-hydroxycyclopropyl)oxazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1270 | 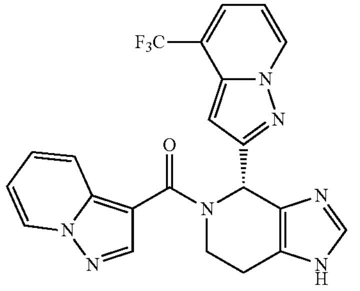 [SMILES: O=C(c1cnn2ccccc12)N1CCc2[nH]cnc2[C@H]1c1cc2c(C(F)(F)F)cccn2n1] | (S)-pyrazolo[1,5-a]pyridin-3-yl(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1271 | 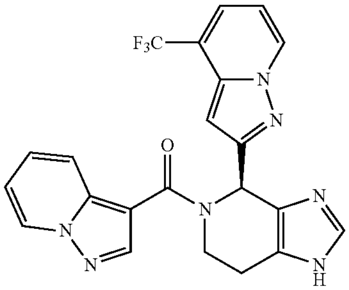 [SMILES: O=C(c1cnn2ccccc12)N1CCc2[nH]cnc2[C@@H]1c1cc2c(C(F)(F)F)cccn2n1] | (R)-pyrazolo[1,5-a]pyridin-3-yl(4-(4-(trifluoromethyl)pyrazolo[1,5-a]pyridin-2-yl)-6,7-dihydro-1H-imidazo[4,5-c]pyridin-5(4H)-yl)methanone |
| 1272 | 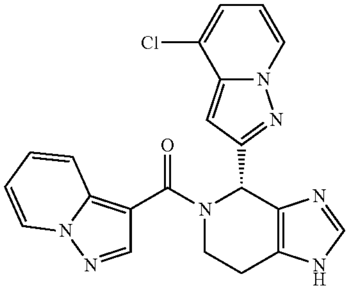 | (S)-(4-(4-chloropyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 1273 | 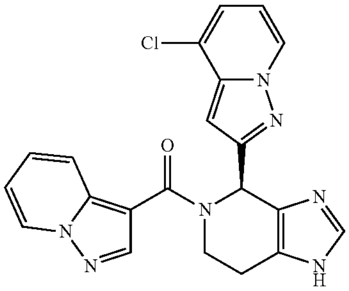 | (R)-(4-(4-chloropyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 1274 | 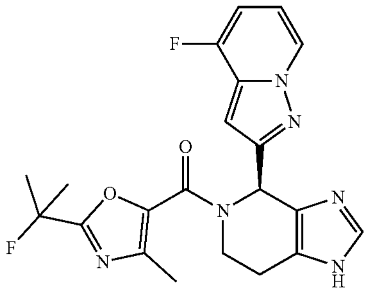 | (R)-(2-(2-fluoropropan-2-yl)-4-methyloxazol-5-yl)(4-(4-fluoropyrazolo[1,5-a]pyridin-2-yl)-6,7-dihydro-1H-imidazo[4,5-c]pyridin-5(4H)-yl)methanone |
| 1275 | 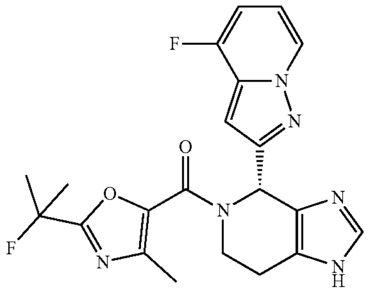 [SMILES: Cc1nc(C(C)(C)F)oc1C(=O)N1CCc2[nH]cnc2[C@H]1c1cc2c(F)cccn2n1] | (S)-(2-(2-fluoropropan-2-yl)-4-methyloxazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1276 | 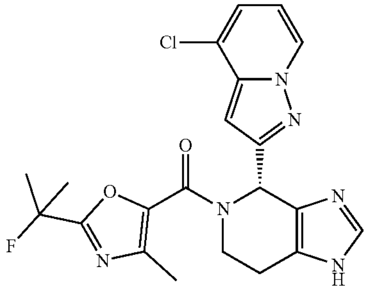 [SMILES: Cc1nc(C(C)(C)F)oc1C(=O)N1CCc2[nH]cnc2[C@H]1c1cc2c(Cl)cccn2n1] | (S)-(4-(4-chloropyrazolo [1,5-a]pyridin-2-y]l)-6,7-dihydro-1H-imidazo[4,5-c] pyridin-5(4H)-yl)(2-(2-fluoropropan-2-yl)-4-methyloxazol-5-yl)methanone |
| 1277 | 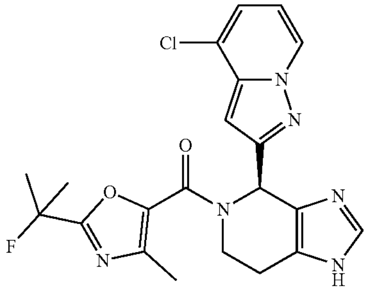 | (R)-(4-(4-chloropyrazolo [1,5-a]pyridin-2-yl)-6,7-dihydro-1H-imidazo[4,5-c] pyridin-5(4H)-yl)(2-(2-fluoropropan-2-yl)-4-methyloxazol-5-yl)methanone |
| 1278 | 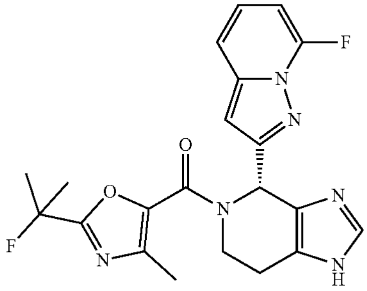 | (S)-(2-(2-fluoropropan-2-yl)-4-methyloxazol-5-yl)(4-(7-fluoropyrazolo[1,5-a]pyridin-2-yl)-6,7-dihydro-1H-imidazo[4,5-c]pyridin-5(4H)-yl)methanone |
| 1279 | 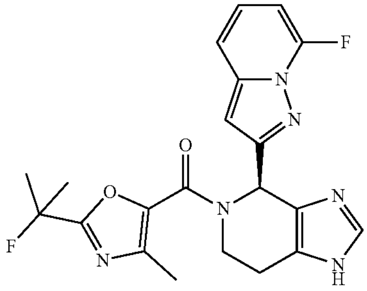 [SMILES: Cc1nc(C(C)(C)F)oc1C(=O)N1CCc2[nH]cnc2[C@@H]1c1cc2cccc(F)n2n1] | (R)-(2-(2-fluoropropan-2-yl)-4-methyloxazol-5-yl)(4-(7-fluoropyrazolo[1,5-a]pyridin-2-yl)-6,7-dihydro-1H-imidazo[4,5-c]pyridin-5(4H)-yl)methanone |
| 1280 | 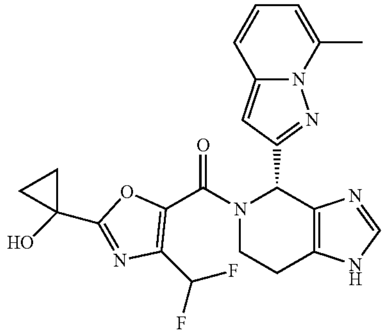 [SMILES: Cc1cccc2cc([C@@H]3c4nc[nH]c4CCN3C(=O)c3oc(C4(O)CC4)nc3C(F)F)nn12] | (S)-(4-(difluoromethyl)-2-(1-hydroxycyclopropyl) oxazol-5-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1281 | 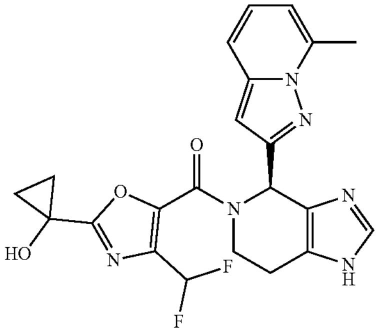 [SMILES: Cc1cccc2cc([C@H]3c4nc[nH]c4CCN3C(=O)c3oc(C4(O)CC4)nc3C(F)F)nn12] | (R)-(4-(difluoromethyl)-2-(1-hydroxycyclopropyl) oxazol-5-yl)(4-(7-methylpyrazolo[1,5-a]pyridin-2-yl)-6,7-dihydro-1H-imidazo[4,5-c]pyridin-5(4H)-yl)methanone |
| 1282 | 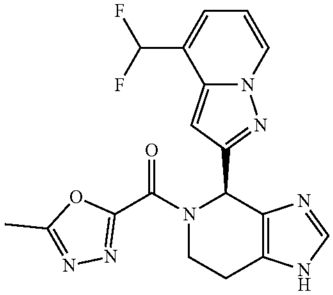 [SMILES: Cc1nnc(C(=O)N2CCc3[nH]cnc3[C@@H]2c2cc3c(C(F)F)cccn3n2)o1] | (R)-(4-(4-(difluoromethyl) pyrazolo[1,5-a]pyridin-2-y]l)-6,7-dihydro-1H-imidazo [4,5-c]pyridin-5(4H)-yl)(5-methyl-1,3,4-oxadiazol-2-yl)methanone |
| 1283 | 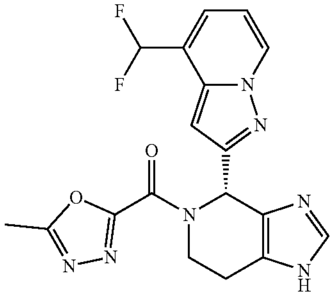 [SMILES: Cc1nnc(C(=O)N2CCc3[nH]cnc3[C@H]2c2cc3c(C(F)F)cccn3n2)o1] | (S)-(4-(4-(difluoromethyl) pyrazolo[1,5-a]pyridin-2-yl)-6,7-dihydro-1H-imidazo[4,5-c] pyridin-5(4H)-yl)(5-methyl-1,3,4-oxadiazol-2-yl)methanone |
| 1284 | 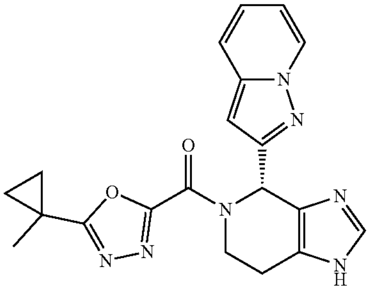 [SMILES: CC1(c2nnc(C(=O)N3CCc4[nH]cnc4[C@H]3c3cc4ccccn4n3)o2)CC1] | (S)-(5-(1-methylcyclopropyl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 1285 | 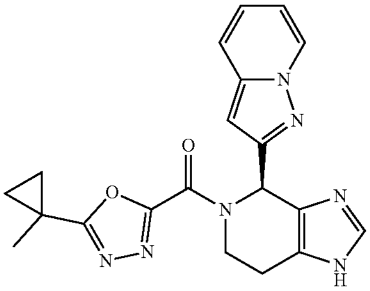 [SMILES: CC1(c2nnc(C(=O)N3CCc4[nH]cnc4[C@@H]3c3cc4ccccn4n3)o2)CC1] | (R)-(5-(1-methylcyclopropyl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 1286 | 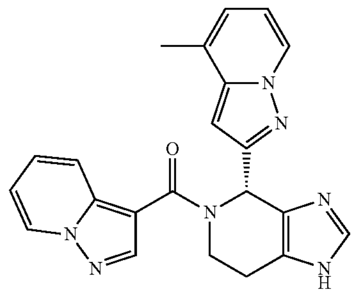 [SMILES: Cc1cccn2nc([C@@H]3c4nc[nH]c4CCN3C(=O)c3cnn4ccccc34)cc12] | (S)-(4-(4-methylpyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 1287 | 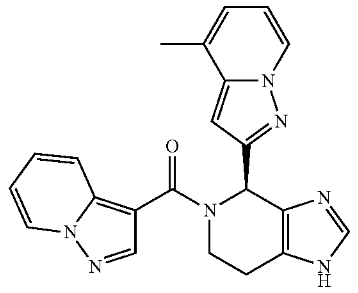 [SMILES: Cc1cccn2nc([C@H]3c4nc[nH]c4CCN3C(=O)c3cnn4ccccc34)cc12] | (R)-(4-(4-methylpyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 1288 | 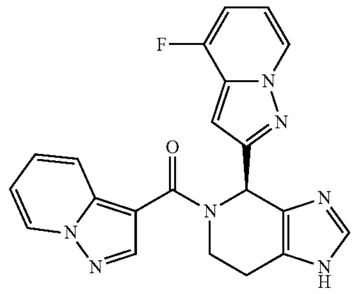 [SMILES: O=C(c1cnn2ccccc12)N1CCc2[nH]cnc2[C@@H]1c1cc2c(F)cccn2n1] | (R)-(4-(4-fluoropyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 1289 | 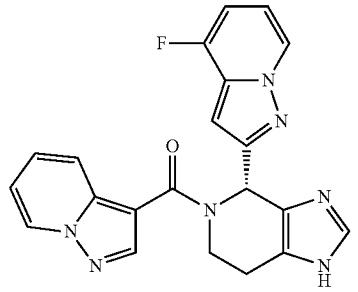 [SMILES: O=C(c1cnn2ccccc12)N1CCc2[nH]cnc2[C@H]1c1cc2c(F)cccn2n1] | (S)-(4-(4-fluoropyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 1290 | 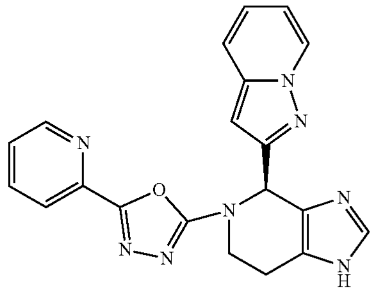 [SMILES: c1ccc(-c2nnc(N3CCc4[nH]cnc4[C@@H]3c3cc4ccccn4n3)o2)nc1] | (R)-2-(4-(pyrazolo[1,5-a]pyridin-2-yl)-6,7-dihydro-1H-imidazo[4,5-c]pyridin-5(4H)-yl)-5-(pyridin-2-yl)-1,3,4-oxadiazole |

TABLE 1-continued

Pyrazolo[1,5-a]pyridines

| Ex. # | Structure | Name |
|---|---|---|
| 1291 | 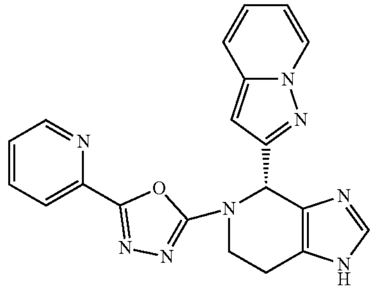 [SMILES: c1ccc(-c2nnc(N3CCc4[nH]cnc4[C@H]3c3cc4ccccn4n3)o2)nc1] | (S)-2-(4-(pyrazolo[1,5-a]pyridin-2-yl)-6,7-dihydro-1H-imidazo[4,5-c]pyridin-5(4H)-yl)-5-(pyridin-2-yl)-1,3,4-oxadiazole |
| 1292 | 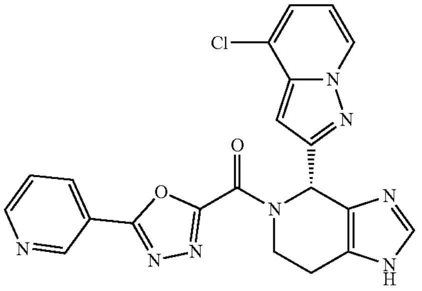 [SMILES: O=C(c1nnc(-c2cccnc2)o1)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1293 | 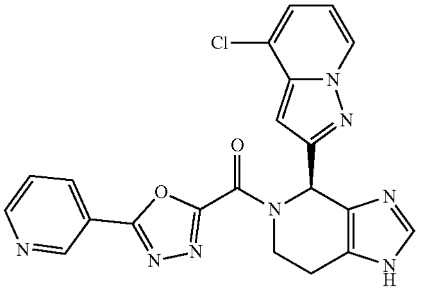 [SMILES: O=C(c1nnc(-c2cccnc2)o1)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1294 | 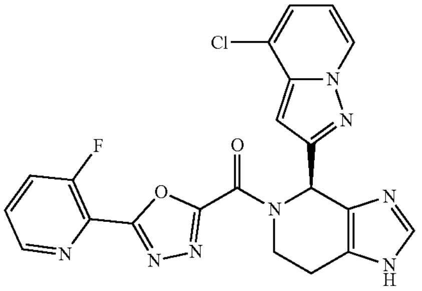 [SMILES: O=C(c1nnc(-c2ncccc2F)o1)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(5-(3-fluoropyridin-2-yl)-1,3,4-oxadiazol-2-yl)methanone |
| 1295 | 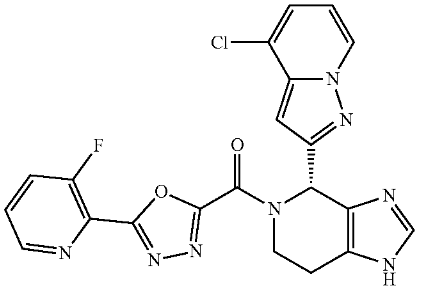 [SMILES: O=C(c1nnc(-c2ncccc2F)o1)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(5-(3-fluoropyridin-2-yl)-1,3,4-oxadiazol-2-yl)methanone |

TABLE 1-continued

Pyrazolo[1,5-a]pyridines

| Ex. # | Structure | Name |
| --- | --- | --- |
| 1296 | 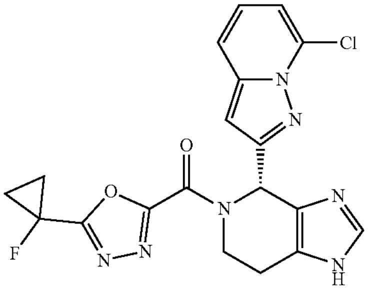 [SMILES: O=C(c1nnc(C2(F)CC2)o1)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(5-(1-methylcyclopropyl)-1,3,4-oxadiazol-2-yl)methanone |
| 1297 | 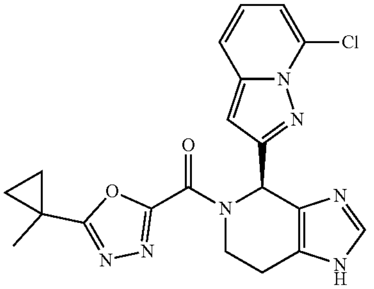 [SMILES: CC1(c2nnc(C(=O)N3CCc4[nH]cnc4[C@@H]3c3cc4cccc(Cl)n4n3)o2)CC1] | (R)-(4-(7-chloropyrazolo[1,5-a]pyridin-2-yl)-6,7-dihydro-1H-imidazo[4,5-c]pyridin-5(4H)-yl)(5-(1-methylcyclopropyl)-1,3,4-oxadiazol-2-yl)methanone |
| 1298 | 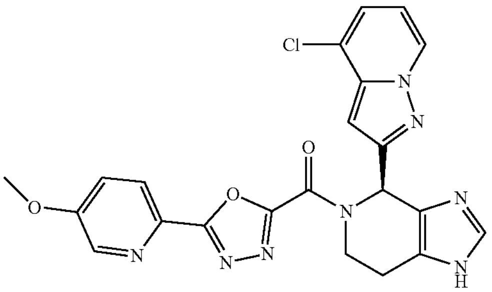 [SMILES: COc1ccc(-c2nnc(C(=O)N3CCc4[nH]cnc4[C@@H]3c3cc4c(Cl)cccn4n3)o2)nc1] | (R)-(4-(4-chloropyrazolo[1,5-a]pyridin-2-yl)-6,7-dihydro-1H-imidazo[4,5-c]pyridin-5(4H)-yl)(5-(5-methoxypyridin-2-yl)-1,3,4-oxadiazol-2-yl)methanone |
| 1299 | 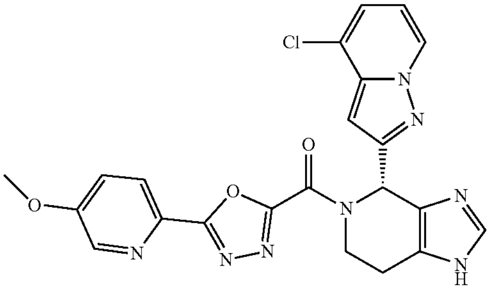 [SMILES: COc1ccc(-c2nnc(C(=O)N3CCc4[nH]cnc4[C@H]3c3cc4c(Cl)cccn4n3)o2)nc1] | (S)-(4-(4-chloropyrazolo[1,5-a]pyridin-2-yl)-6,7-dihydro-1H-imidazo[4,5-c]pyridin-5(4H)-yl)(5-(5-methoxypyridin-2-yl)-1,3,4-oxadiazol-2-yl)methanone |
| 1300 | 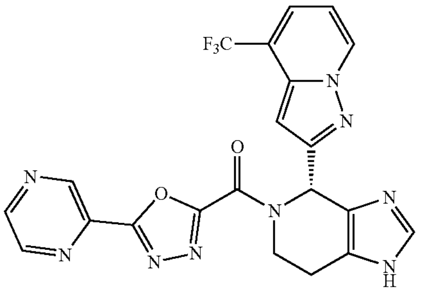 | (S)-(5-(pyrazin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1301 | 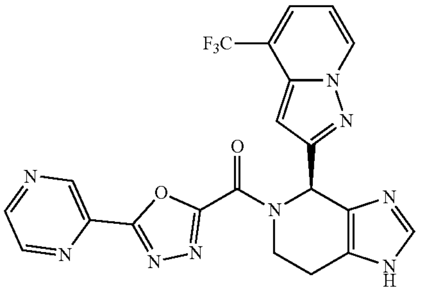 [SMILES: O=C(c1nnc(-c2cnccn2)o1)N1CCc2[nH]cnc2[C@@H]1c1cc2c(C(F)(F)F)cccn2n1] | (R)-(5-(pyrazin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1302 | 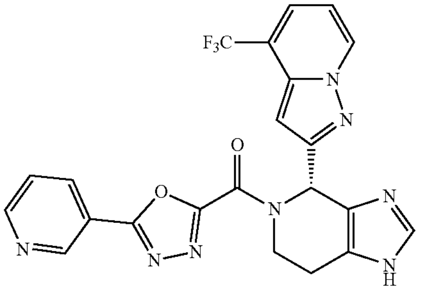 | (S)-(5-(pyridin-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1303 | 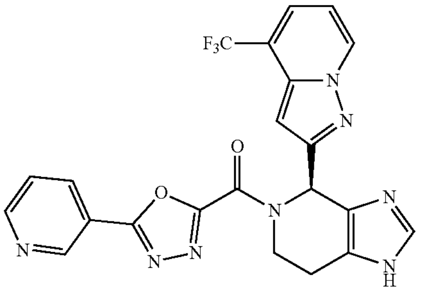 | (R)-(5-(pyridin-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1304 | 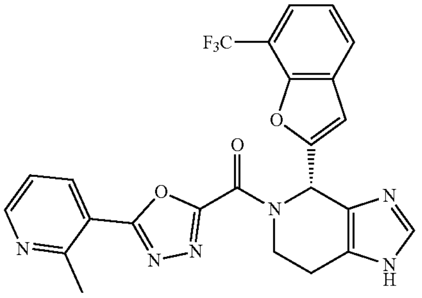 [SMILES: Cc1ncccc1-c1nnc(C(=O)N2CCc3[nH]cnc3[C@H]2c2cc3cccc(C(F)(F)F)c3o2)o1] | (S)-(5-(2-methylpyridin-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1305 | 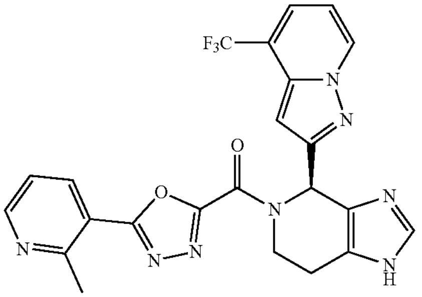 | (R)-(5-(2-methylpyridin-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1306 | 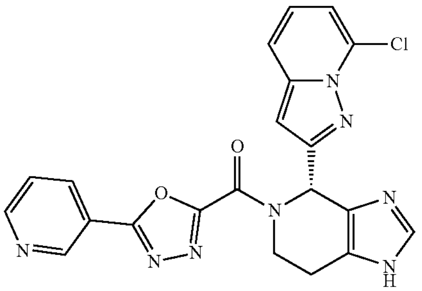 [SMILES: O=C(c1nnc(-c2cccnc2)o1)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1307 | 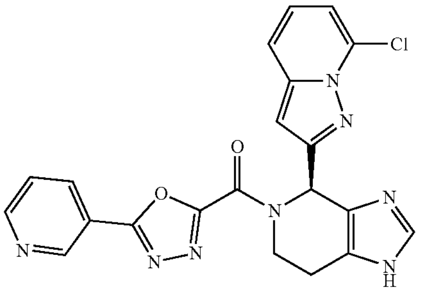 | (R)-(4-(7-chloropyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1308 | 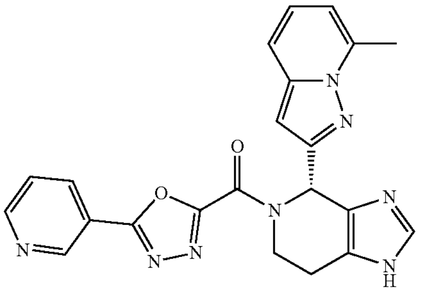 | (S)-(4-(7-methylpyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1309 | 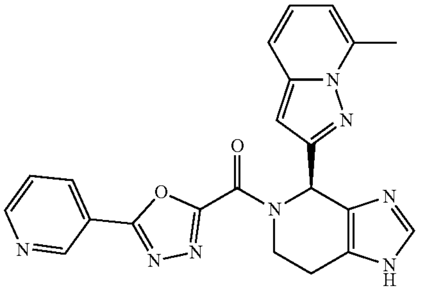 | (R)-(4-(7-methylpyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1310 | 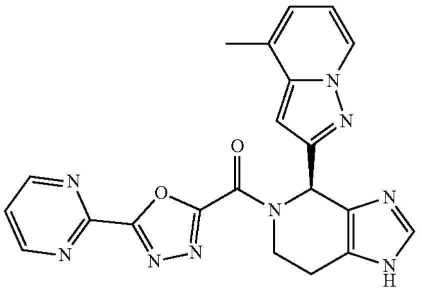 [SMILES: Cc1cccn2nc([C@H]3c4nc[nH]c4CCN3C(=O)c3nnc(-c4ncccn4)o3)cc12] | (R)-(4-(4-methylpyrazolo[1,5-a]pyridin-2-yl)-6,7-dihydro-1H-imidazo[4,5-c]pyridin-5(4H)-yl)(5-(pyrimidin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1311 | 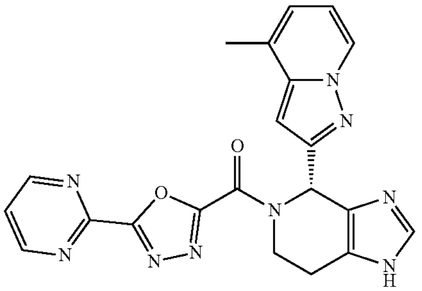 [SMILES: Cc1cccn2nc([C@@H]3c4nc[nH]c4CCN3C(=O)c3nnc(-c4ncccn4)o3)cc12] | (S)-(4-(4-methylpyrazolo [1,5-a]pyridin-2-yl)-6,7-dihydro-1H-imidazo[4,5-c] pyridin-5(4H)-yl)(5-(pyrimidin-2-yl)-1,3,4-oxadiazol-2-yl)methanone |
| 1312 | 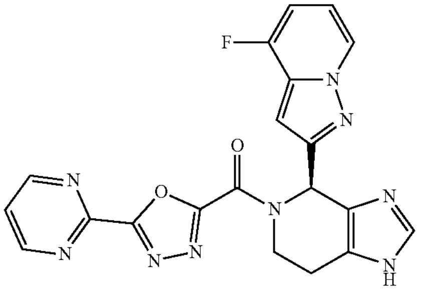 [SMILES: O=C(c1nnc(-c2ncccn2)o1)N1CCc2[nH]cnc2[C@@H]1c1cc2c(F)cccn2n1] | (R)-(4-(4-fluoropyrazolo [1,5-a]pyridin-2-yl)-6,7-dihydro-1H-imidazo[4,5-c] pyridin-5(4H)-yl)(5-(pyrimidin-2-yl)-1,3,4-oxadiazol-2-yl)methanone |
| 1313 | 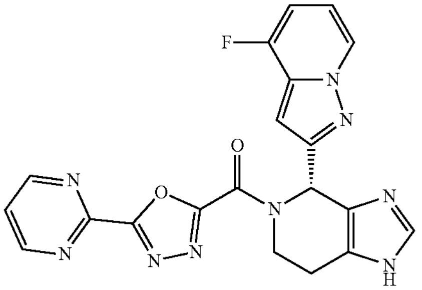 | (S)-(4-(4-fluoropyrazolo[1,5-a] pyridin-2-yl)-6,7-dihydro-1H-imidazo[4,5-c]pyridin-5(4H)-yl)(5-(pyrimidin-2-yl)-1,3,4-oxadiazol-2-yl)methanone |
| 1314 | 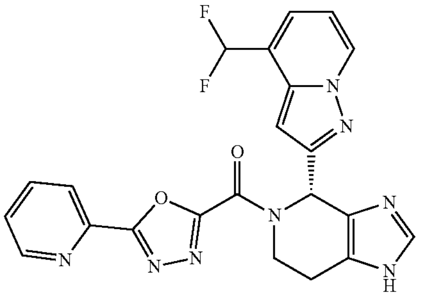 [SMILES: O=C(c1nnc(-c2ccccn2)o1)N1CCc2[nH]cnc2[C@H]1c1cc2c(C(F)F)cccn2n1] | (S)-(4-(4-(difluoromethyl) pyrazolo[1,5-a]pyridin-2-yl)-6,7-dihydro-1H-imidazo [4,5-c]pyridin-5(4H)-yl)(5-(pyridin-2-yl)-1,3,4-oxadiazol-2-yl)methanone |
| 1315 | 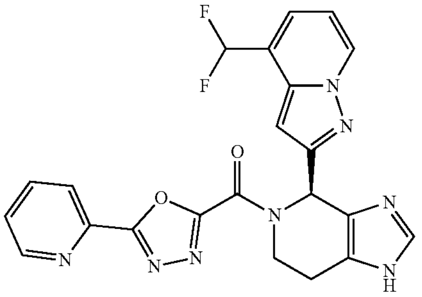 [SMILES: O=C(c1nnc(-c2ccccn2)o1)N1CCc2[nH]cnc2[C@@H]1c1cc2c(C(F)F)cccn2n1] | (R)-(4-(4-(difluoromethyl) pyrazolo[1,5-a]pyridin-2-yl)-6,7-dihydro-1H-imidazo [4,5-c]pyridin-5(4H)-yl)(5-(pyridin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1316 | 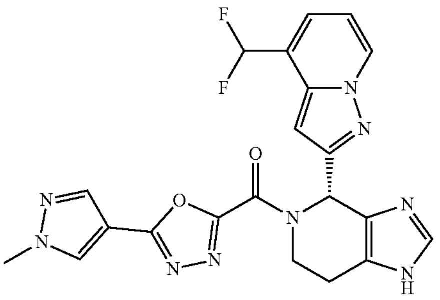 [SMILES: Cn1cc(-c2nnc(C(=O)N3CCc4[nH]cnc4[C@H]3c3cc4c(C(F)F)cccn4n3)o2)cn1] | (S)-(4-(4-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-4-yl)-1,3,4-oxadiazol-2-yl)methanone |
| 1317 | 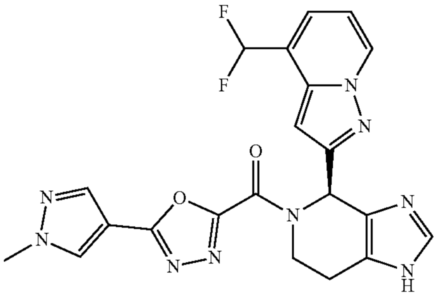 [SMILES: Cn1cc(-c2nnc(C(=O)N3CCc4[nH]cnc4[C@@H]3c3cc4c(C(F)F)cccn4n3)o2)cn1] | (R)-(4-(4-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-4-yl)-1,3,4-oxadiazol-2-yl)methanone |
| 1318 | 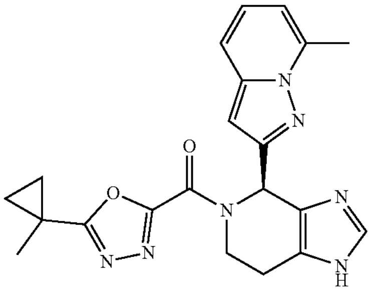 [SMILES: Cc1cccc2cc([C@H]3c4nc[nH]c4CCN3C(=O)c3nnc(C4(C)CC4)o3)nn12] | (R)-(5-(1-methylcyclopropyl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 1319 | 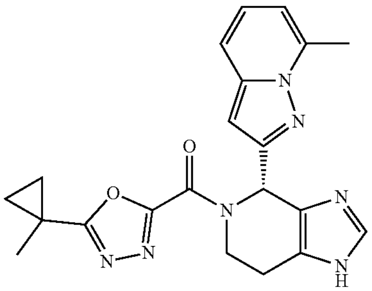 [SMILES: Cc1cccc2cc([C@@H]3c4nc[nH]c4CCN3C(=O)c3nnc(C4(C)CC4)o3)nn12] | (S)-(5-(1-methylcyclopropyl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 1320 | 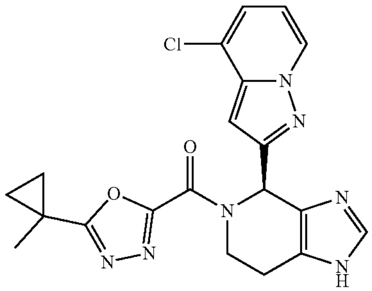 [SMILES: CC1(c2nnc(C(=O)N3CCc4[nH]cnc4[C@@H]3c3cc4c(Cl)cccn4n3)o2)CC1] | (R)-(4-(4-chloropyrazolo [1,5-a]pyridin-2-yl)-6,7-dihydro-1H-imidazo[4,5-c] pyridin-5(4H)-yl)(5-(1-methylcyclopropyl)-1,3,4-oxadiazol-2-yl)methanone |

TABLE 1-continued

| Pyrazolo[1,5-a]pyridines | | |
|---|---|---|
| Ex. # | Structure | Name |
| 1321 | 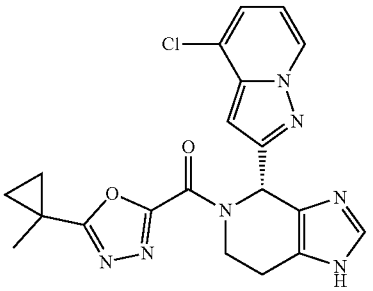 [SMILES: CC1(c2nnc(C(=O)N3CCc4[nH]cnc4[C@H]3c3cc4c(Cl)cccn4n3)o2)CC1] | (S)-(4-(4-chloropyrazolo[1,5-a]pyridin-2-yl)-6,7-dihydro-1H-imidazo[4,5-c]pyridin-5(4H)-yl)(5-(1-methylcyclopropyl)-1,3,4-oxadiazol-2-yl)methanone |
| 1322 | 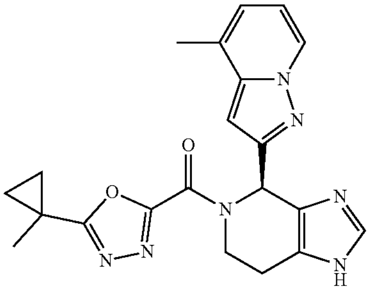 [SMILES: Cc1cccn2nc([C@H]3c4nc[nH]c4CCN3C(=O)c3nnc(C4(C)CC4)o3)cc12] | (R)-(5-(1-methylcyclopropyl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1323 | 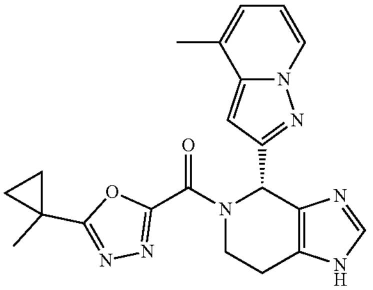 [SMILES: Cc1cccn2nc([C@@H]3c4nc[nH]c4CCN3C(=O)c3nnc(C4(C)CC4)o3)cc12] | (S)-(5-(1-methylcyclopropyl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1324 | 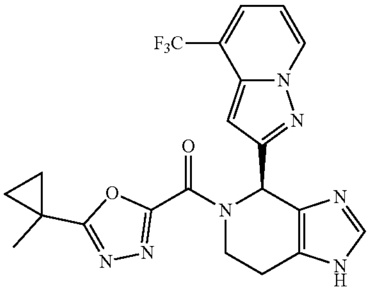 [SMILES: CC1(c2nnc(C(=O)N3CCc4[nH]cnc4[C@@H]3c3cc4c(C(F)(F)F)cccn4n3)o2)CC1] | (R)-(5-(1-methylcyclopropyl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1325 | 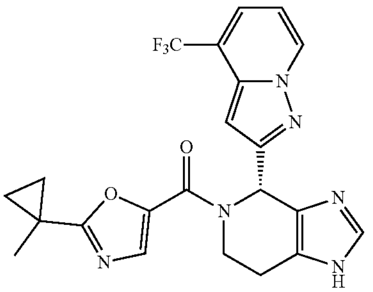 [SMILES: CC1(c2ncc(C(=O)N3CCc4[nH]cnc4[C@H]3c3cc4c(C(F)(F)F)cccn4n3)o2)CC1] | (S)-(5-(1-methylcyclopropyl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1326 | 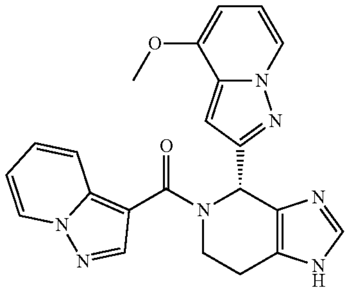 [SMILES: COc1cccn2nc([C@@H]3c4nc[nH]c4CCN3C(=O)c3cnn4ccccc34)cc12] | (S)-(4-(4-methoxypyrazolo [1,5-a]pyridin-2-yl)-6,7-dihydro-1H-imidazo [4,5-c]pyridin-5(4H)-yl)(pyrazolo[1,5-a] pyridin-3-yl)methanone |
| 1327 | 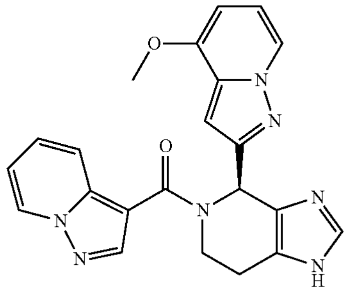 [SMILES: COc1cccn2nc([C@H]3c4nc[nH]c4CCN3C(=O)c3cnn4ccccc34)cc12] | (R)-(4-(4-methoxypyrazolo [1,5-a]pyridin-2-yl)-6,7-dihydro-1H-imidazo [4,5-c]pyridin-5(4H)-yl)(pyrazolo[1,5-a] pyridin-3-yl)methanone |
| 1328 | 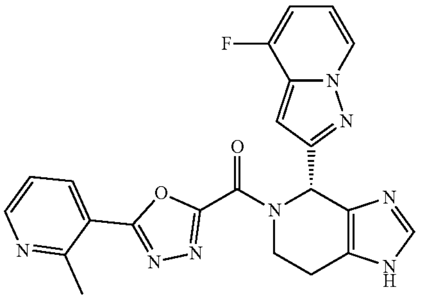 [SMILES: Cc1ncccc1-c1nnc(C(=O)N2CCc3[nH]cnc3[C@H]2c2cc3c(F)cccn3n2)o1] | (S)-(4-(4-fluoropyrazolo[1,5-a] pyridin-2-yl)-6,7-dihydro-1H-imidazo[4,5-c]pyridin-5(4H)-yl)(5-(2-methylpyridin-3-yl)-1,3,4-oxadiazol-2-yl)methanone |
| 1329 | 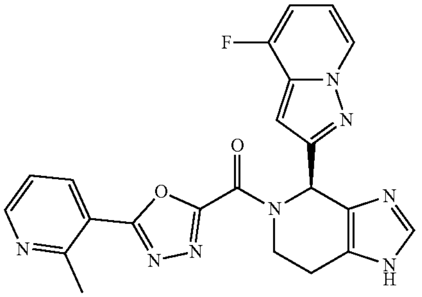 [SMILES: Cc1ncccc1-c1nnc(C(=O)N2CCc3[nH]cnc3[C@@H]2c2cc3c(F)cccn3n2)o1] | (R)-(4-(4-fluoropyrazolo [1,5-a]pyridin-2-yl)-6,7-dihydro-1H-imidazo[4,5-c] pyridin-5(4H)-yl)(5-(2-methylpyridin-3-yl)-1,3,4-oxadiazol-2-yl)methanone |
| 1330 | 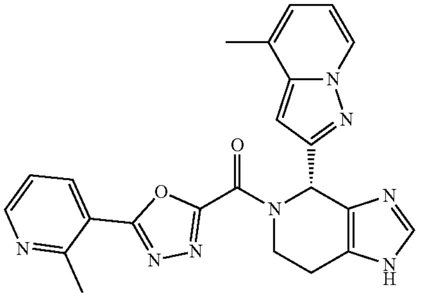 [SMILES: Cc1ncccc1-c1nnc(C(=O)N2CCc3[nH]cnc3[C@H]2c2cc3c(C)cccn3n2)o1] | (S)-(4-(4-methylpyrazolo [1,5-a]pyridin-2-yl)-6,7-dihydro-1H-imidazo[4,5-c] pyridin-5(4H)-yl)(5-(2-methylpyridin-3-yl)-1,3,4-oxadiazol-2-yl)methanone |

TABLE 1-continued

| Pyrazolo[1,5-a]pyridines | | |
|---|---|---|
| Ex. # | Structure | Name |
| 1331 | 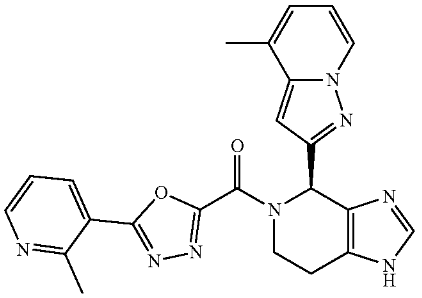 [SMILES: Cc1ncccc1-c1nnc(C(=O)N2CCc3[nH]cnc3[C@@H]2c2cc3c(C)cccn3n2)o1] | (R)-(4-(4-methylpyrazolo [1,5-a]pyridin-2-yl)-6,7-dihydro-1H-imidazo[4,5-c] pyridin-5(4H)-yl)(5-(2-methylpyridin-3-yl)-1,3,4-oxadiazol-2-yl)methanone |
| 1332 | 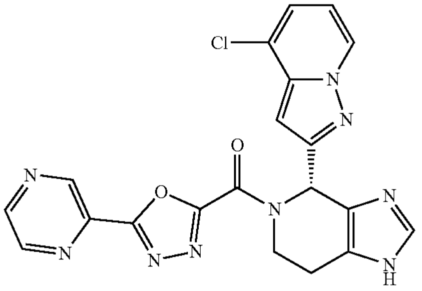 [SMILES: O=C(c1nnc(-c2cnccn2)o1)N1CCc2[nH]cnc2[C@H]1c1cc2c(Cl)cccn2n1] | (S)-(4-(4-chloropyrazolo [1,5-a]pyridin-2-yl)-6,7-dihydro-1H-imidazo[4,5-c] pyridin-5(4H)-yl)(5-(pyrazin-2-yl)-1,3,4-oxadiazol-2-yl)methanone |
| 1333 | 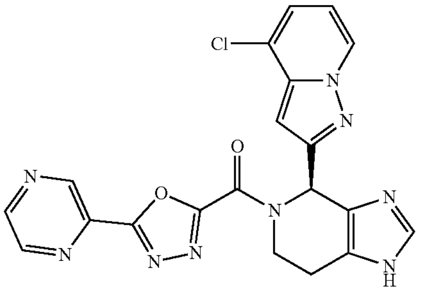 [SMILES: O=C(c1nnc(-c2cnccn2)o1)N1CCc2[nH]cnc2[C@@H]1c1cc2c(Cl)cccn2n1] | (R)-(4-(4-chloropyrazolo [1,5-a]pyridin-2-yl)-6,7-dihydro-1H-imidazo[4,5-c] pyridin-5(4H)-yl)(5-(pyrazin-2-yl)-1,3,4-oxadiazol-2-yl)methanone |
| 1334 | 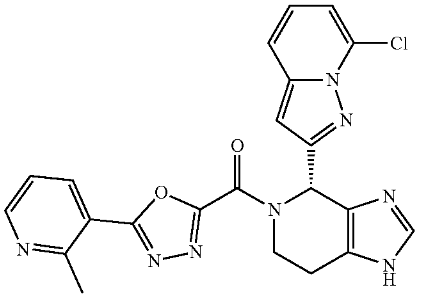 | (S)-(4-(7-chloropyrazolo [1,5-a]pyridin-2-yl)-6,7-dihydro-1H-imidazo[4,5-c] pyridin-5(4H)-yl)(5-(2-methylpyridin-3-yl)-1,3,4-oxadiazol-2-yl)methanone |
| 1335 | 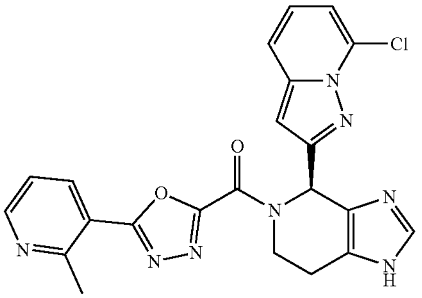 | (R)-(4-(7-chloropyrazolo [1,5-a]pyridin-2-yl)-6,7-dihydro-1H-imidazo[4,5-c] pyridin-5(4H)-yl)(5-(2-methylpyridin-3-yl)-1,3,4-oxadiazol-2-yl)methanone |

TABLE 1-continued

| Pyrazolo[1,5-a]pyridines | | |
|---|---|---|
| Ex. # | Structure | Name |
| 1336 | 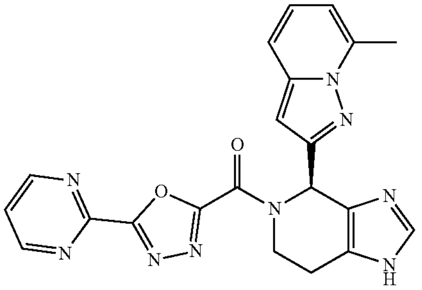 [SMILES: Cc1cccc2cc([C@H]3c4nc[nH]c4CCN3C(=O)c3nnc(-c4ncccn4)o3)nn12] | (R)-(4-(7-methylpyrazolo [1,5-a]pyridin-2-yl)-6,7-dihydro-1H-imidazo[4,5-c] pyridin-5(4H)-yl)(5-(pyrimidin-2-yl)-1,3,4-oxadiazol-2-yl)methanone |
| 1337 | 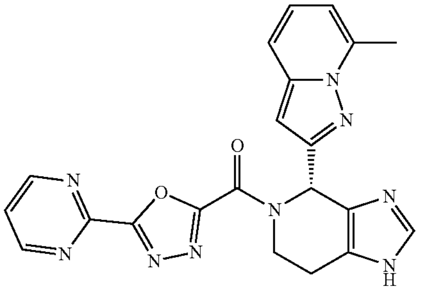 [SMILES: Cc1cccc2cc([C@@H]3c4nc[nH]c4CCN3C(=O)c3nnc(-c4ncccn4)o3)nn12] | (S)-(4-(7-methylpyrazolo [1,5-a]pyridin-2-yl)-6,7-dihydro-1H-imidazo[4,5-c] pyridin-5(4H)-yl)(5-(pyrimidin-2-yl)-1,3,4-oxadiazol-2-yl)methanone |
| 1338 | 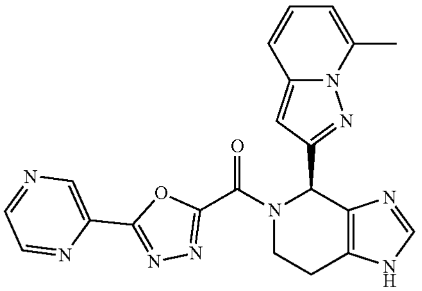 [SMILES: Cc1cccc2cc([C@H]3c4nc[nH]c4CCN3C(=O)c3nnc(-c4cnccn4)o3)nn12] | (R)-(4-(7-methylpyrazolo [1,5-a]pyridin-2-yl)-6,7-dihydro-1H-imidazo[4,5-c] pyridin-5(4H)-yl)(5-(pyrazin-2-yl)-1,3,4-oxadiazol-2-yl)methanone |
| 1339 | 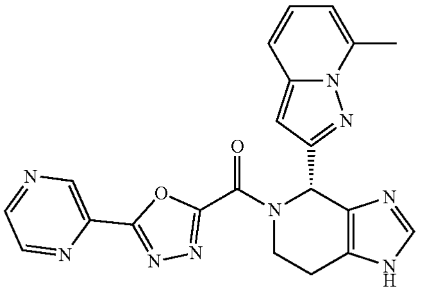 [SMILES: Cc1cccc2cc([C@@H]3c4nc[nH]c4CCN3C(=O)c3nnc(-c4cnccn4)o3)nn12] | (S)-(4-(7-methylpyrazolo [1,5-a]pyridin-2-yl)-6,7-dihydro-1H-imidazo[4,5-c] pyridin-5(4H)-yl)(5-(pyrazin-2-yl)-1,3,4-oxadiazol-2-yl)methanone |
| 1340 | 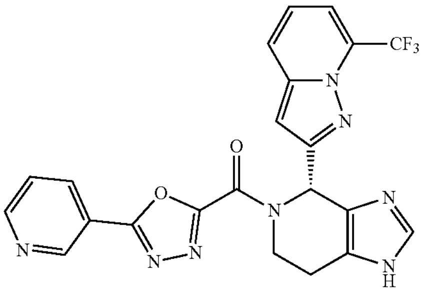 [SMILES: O=C(c1nnc(-c2cccnc2)o1)N1CCc2[nH]cnc2[C@H]1c1cc2cccc(C(F)(F)F)n2n1] | (S)-(5-(pyridin-3-yl)-1,3,4-oxadiazol-2-yl)(4-(7-(trifluoromethyl)pyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 1341 | 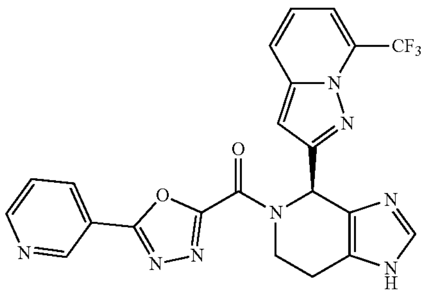 [SMILES: O=C(c1nnc(-c2cccnc2)o1)N1CCc2[nH]cnc2[C@@H]1c1cc2cccc(C(F)(F)F)n2n1] | (R)-(5-(pyridin-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1342 | 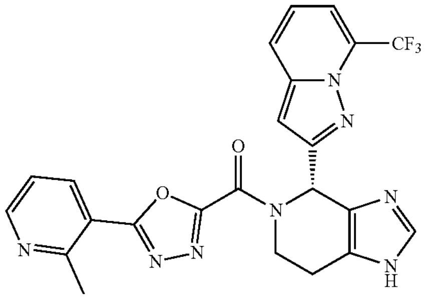 [SMILES: Cc1ncccc1-c1nnc(C(=O)N2CCc3[nH]cnc3[C@H]2c2cc3cccc(C(F)(F)F)n3n2)o1] | (S)-(5-(2-methylpyridin-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1343 | 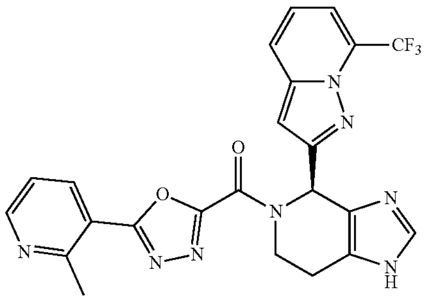 [SMILES: Cc1ncccc1-c1nnc(C(=O)N2CCc3[nH]cnc3[C@@H]2c2cc3cccc(C(F)(F)F)n3n2)o1] | (R)-(5-(2-methylpyridin-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1344 | 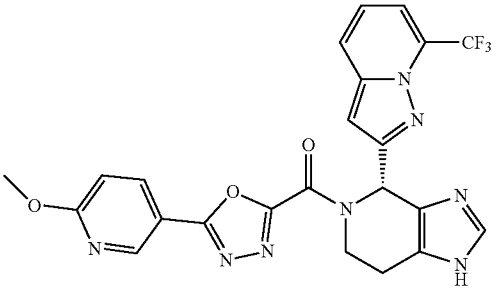 [SMILES: COc1ccc(-c2nnc(C(=O)N3CCc4[nH]cnc4[C@H]3c3cc4cccc(C(F)(F)F)n4n3)o2)cn1] | (S)-(5-(6-methoxypyridin-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1345 | 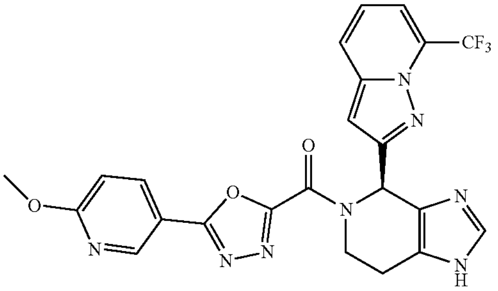 [SMILES: COc1ccc(-c2nnc(C(=O)N3CCc4[nH]cnc4[C@@H]3c3cc4cccc(C(F)(F)F)n4n3)o2)cn1] | (R)-(5-(6-methoxypyridin-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1346 | 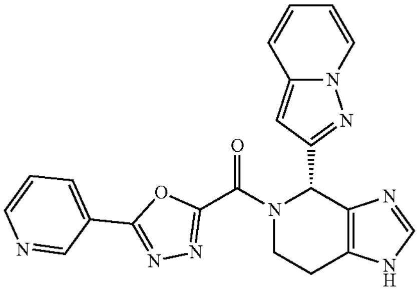 [SMILES: O=C(c1nnc(-c2cccnc2)o1)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1347 | 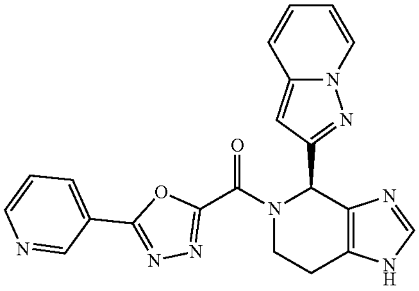 [SMILES: O=C(c1nnc(-c2cccnc2)o1)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1348 | 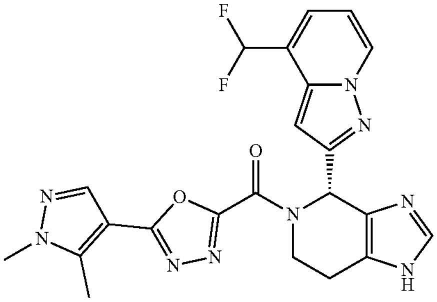 [SMILES: Cc1c(-c2nnc(C(=O)N3CCc4[nH]cnc4[C@H]3c3cc4c(C(F)F)cccn4n3)o2)cnn1C] | (S)-(4-(4-(difluoromethyl)pyrazolo[1,5-a]pyridin-2-yl)-6,7-dihydro-1H-imidazo[4,5-c]pyridin-5(4H)-yl)(5-(1,5-dimethyl-1H-pyrazol-4-yl)-1,3,4-oxadiazol-2-yl)methanone |
| 1349 | 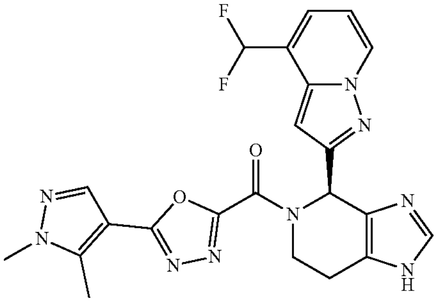 [SMILES: Cc1c(-c2nnc(C(=O)N3CCc4[nH]cnc4[C@@H]3c3cc4c(C(F)F)cccn4n3)o2)cnn1C] | (R)-(4-(4-(difluoromethyl)pyrazolo[1,5-a]pyridin-2-y]l)-6,7-dihydro-1H-imidazo[4,5-c]pyridin-5(4H)-yl)(5-(1,5-dimethyl-1H-pyrazol-4-yl)-1,3,4-oxadiazol-2-yl)methanone |
| 1350 | 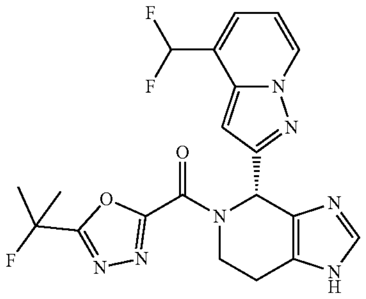 [SMILES: CC(C)(F)c1nnc(C(=O)N2CCc3[nH]cnc3[C@H]2c2cc3c(C(F)F)cccn3n2)o1] | (S)-(4-(4-(difluoromethyl)pyrazolo[1,5-a]pyridin-2-yl)-6,7-dihydro-1H-imidazo[4,5-c]pyridin-5(4H)-yl)(5-(2-fluoropropan-2-yl)-1,3,4-oxadiazol-2-yl)methanone |

TABLE 1-continued

| Ex. # | Structure | Name |
|---|---|---|
| | Pyrazolo[1,5-a]pyridines | |
| 1351 | 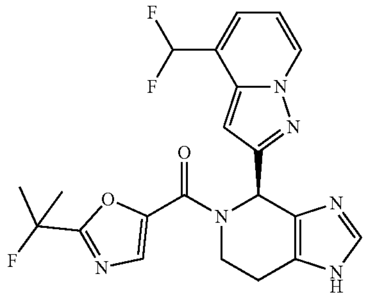 [SMILES: CC(C)(F)c1ncc(C(=O)N2CCc3[nH]cnc3[C@@H]2c2cc3c(C(F)F)cccn3n2)o1] | (R)-(4-(4-(difluoromethyl) pyrazolo[1,5-a]pyridin-2-y]l)-6,7-dihydro-1H-imidazo [4,5-c]pyridin-5(4H)-yl)(5-(2-fluoropropan-2-yl)-1,3,4-oxadiazol-2-yl)methanone |
| 1352 | 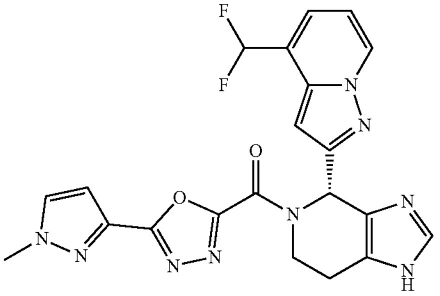 [SMILES: Cn1ccc(-c2nnc(C(=O)N3CCc4[nH]cnc4[C@H]3c3cc4c(C(F)F)cccn4n3)o2)n1] | (S)-(4-(4-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-3-yl)-1,3,4-oxadiazol-2-yl)methanone |
| 1353 | 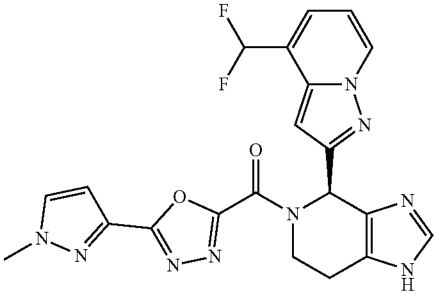 [SMILES: Cn1ccc(-c2nnc(C(=O)N3CCc4[nH]cnc4[C@@H]3c3cc4c(C(F)F)cccn4n3)o2)n1] | (R)-(4-(4-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-3-yl)-1,3,4-oxadiazol-2-yl)methanone |
| 1354 | 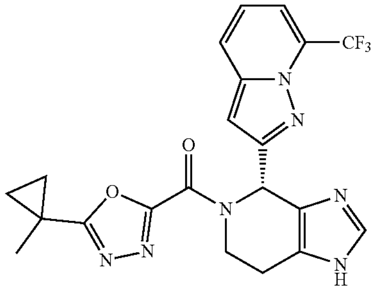 [SMILES: CC1(c2nnc(C(=O)N3CCc4[nH]cnc4[C@H]3c3cc4cccc(C(F)(F)F)n4n3)o2)CC1] | (S)-(5-(1-methylcyclopropyl)-1,3,4-oxadiazol-2-yl)(4-(7-(trifluoromethyl)pyrazolo [1,5-a]pyridin-2-yl)-6,7-dihydro-1H-imidazo[4,5-c] pyridin-5(4H)-yl)methanone |
| 1355 | 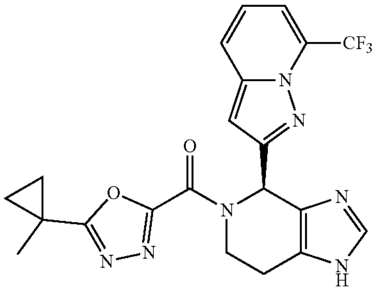 [SMILES: CC1(c2nnc(C(=O)N3CCc4[nH]cnc4[C@@H]3c3cc4cccc(C(F)(F)F)n4n3)o2)CC1] | (R)-(5-(1-methylcyclopropyl)-1,3,4-oxadiazol-2-yl)(4-(7-(trifluoromethyl)pyrazolo [1,5-a]pyridin-2-yl)-6,7-dihydro-1H-imidazo[4,5-c] pyridin-5(4H)-yl)methanone |

TABLE 1-continued

| Ex. # | Structure | Name |
|---|---|---|
| | Pyrazolo[1,5-a]pyridines | |
| 1356 | 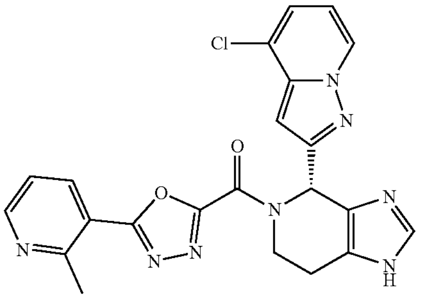 [SMILES: Cc1ncccc1-c1nnc(C(=O)N2CCc3[nH]cnc3[C@H]2c2cc3c(Cl)cccn3n2)o1] | (S)-(4-(4-chloropyrazolo[1,5-a]pyridin-2-yl)-6,7-dihydro-1H-imidazo[4,5-c]pyridin-5(4H)-yl)(5-(2-methylpyridin-3-yl)-1,3,4-oxadiazol-2-yl)methanone |
| 1357 | 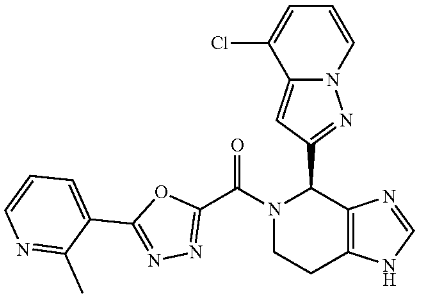 [SMILES: Cc1ncccc1-c1nnc(C(=O)N2CCc3[nH]cnc3[C@@H]2c2cc3c(Cl)cccn3n2)o1] | (R)-(4-(4-chloropyrazolo[1,5-a]pyridin-2-yl)-6,7-dihydro-1H-imidazo[4,5-c]pyridin-5(4H)-yl)(5-(2-methylpyridin-3-yl)-1,3,4-oxadiazol-2-yl)methanone |
| 1358 | 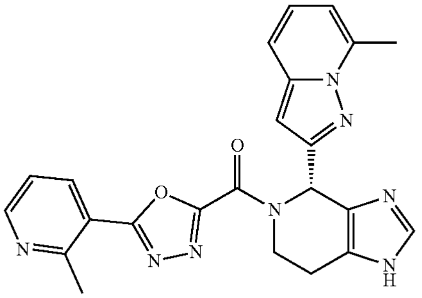 [SMILES: Cc1ncccc1-c1nnc(C(=O)N2CCc3[nH]cnc3[C@H]2c2cc3cccc(C)n3n2)o1] | (S)-(4-(7-methylpyrazolo[1,5-a]pyridin-2-yl)-6,7-dihydro-1H-imidazo[4,5-c]pyridin-5(4H)-yl)(5-(2-methylpyridin-3-yl)-1,3,4-oxadiazol-2-yl)methanone |
| 1359 | 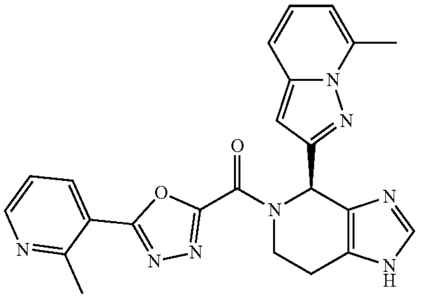 [SMILES: Cc1ncccc1-c1nnc(C(=O)N2CCc3[nH]cnc3[C@@H]2c2cc3cccc(C)n3n2)o1] | (R)-(4-(7-methylpyrazolo[1,5-a]pyridin-2-yl)-6,7-dihydro-1H-imidazo[4,5-c]pyridin-5(4H)-yl)(5-(2-methylpyridin-3-yl)-1,3,4-oxadiazol-2-yl)methanone |
| 1360 | 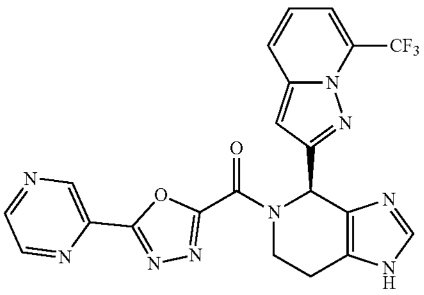 [SMILES: O=C(c1nnc(-c2cnccn2)o1)N1CCc2[nH]cnc2[C@@H]1c1cc2cccc(C(F)(F)F)n2n1] | (R)-(5-(pyrazin-2-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1361 | 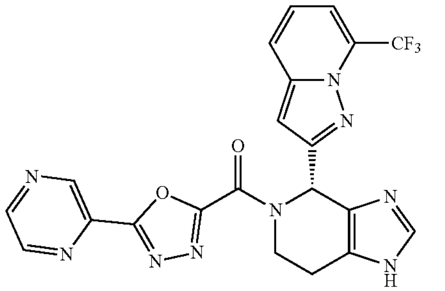 [SMILES: O=C(c1nnc(-c2cnccn2)o1)N1CCc2[nH]cnc2[C@H]1c1cc2cccc(C(F)(F)F)n2n1] | (S)-(5-(pyrazin-2-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1362 | 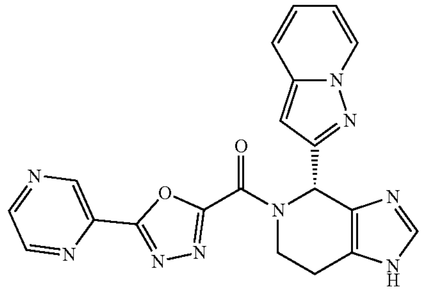 [SMILES: O=C(c1nnc(-c2cnccn2)o1)N1CCc2[nH]cnc2[C@H]1c1cc2ccccn2n1] | (S)-(5-(pyrazin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 1363 | 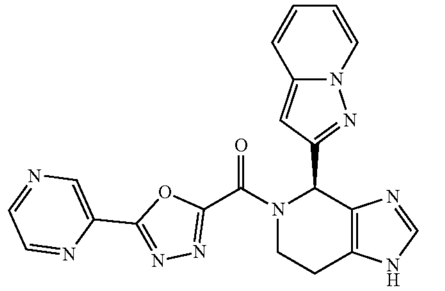 [SMILES: O=C(c1nnc(-c2cnccn2)o1)N1CCc2[nH]cnc2[C@@H]1c1cc2ccccn2n1] | (R)-(5-(pyrazin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 1364 | 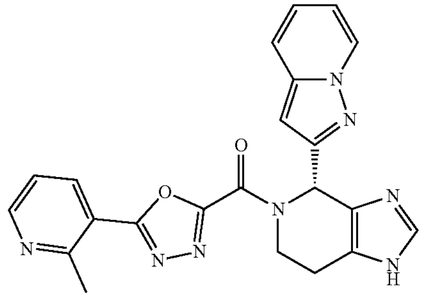 [SMILES: Cc1ncccc1-c1nnc(C(=O)N2CCc3[nH]cnc3[C@H]2c2cc3ccccn3n2)o1] | (S)-(5-(2-methylpyridin-3-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone imidazo[4,5-c]pyridin-5(4H)-yl)methanone |
| 1365 | 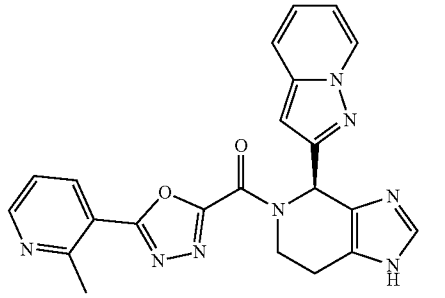 [SMILES: Cc1ncccc1-c1nnc(C(=O)N2CCc3[nH]cnc3[C@@H]2c2cc3ccccn3n2)o1] | (R)-(5-(2-methylpyridin-3-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| Pyrazolo[1,5-a]pyridines | | |
| 1366 | 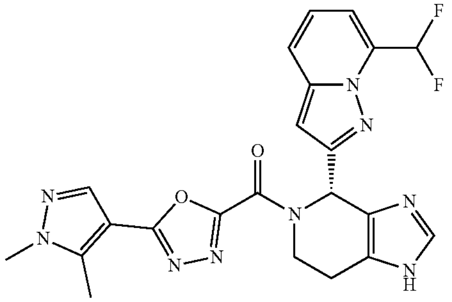 [SMILES: Cc1c(-c2nnc(C(=O)N3CCc4[nH]cnc4[C@H]3c3cc4cccc(C(F)F)n4n3)o2)cnn1C] | (S)-(4-(7-(difluoromethyl) pyrazolo[1,5-a]pyridin-2-yl)-6,7-dihydro-1H-imidazo[4,5-c] pyridin-5(4H)-yl)(5-(1,5-dimethyl-1H-pyrazol-4-yl)-1,3,4-oxadiazol-2-yl)methanone |
| 1367 | 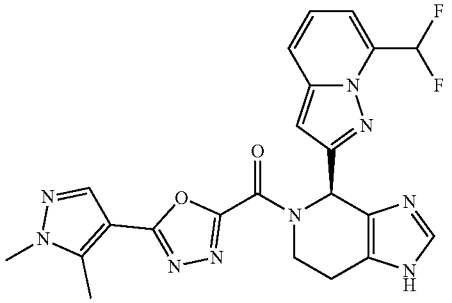 [SMILES: Cc1c(-c2nnc(C(=O)N3CCc4[nH]cnc4[C@@H]3c3cc4cccc(C(F)F)n4n3)o2)cnn1C] | (R)-(4-(7-(difluoromethyl) pyrazolo[1,5-a]pyridin-2-yl)-6,7-dihydro-1H-imidazo[4,5-c] pyridin-5(4H)-yl)(5-(1,5-dimethyl-1H-pyrazol-4-yl)-1,3,4-oxadiazol-2-yl)methanone |
| 1368 | 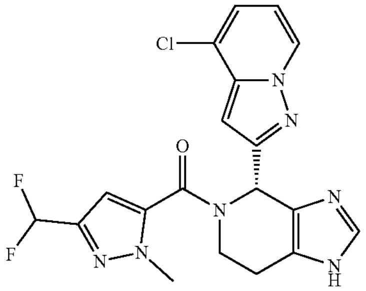 [SMILES: Cn1nc(C(F)F)cc1C(=O)N1CCc2[nH]cnc2[C@H]1c1cc2c(Cl)cccn2n1] | (S)-(4-(4-chloropyrazolo [1,5-a]pyridin-2-yl)-6,7-dihydro-1H-imidazo[4,5-c] pyridin-5(4H)-yl)(3-(difluoromethyl)-1-methyl-1H-pyrazol-5-yl)methanone |
| 1369 | 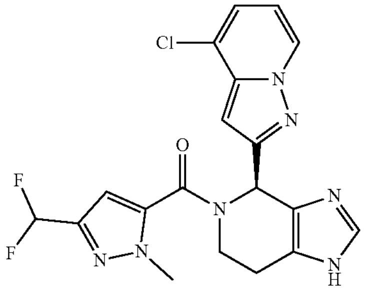 [SMILES: Cn1nc(C(F)F)cc1C(=O)N1CCc2[nH]cnc2[C@@H]1c1cc2c(Cl)cccn2n1] | (R)-(4-(4-chloropyrazolo [1,5-a]pyridin-2-yl)-6,7-dihydro-1H-imidazo [4,5-c]pyridin-5(4H)-yl)(3-(difluoromethyl)-1-methyl-1H-pyrazol-5-yl)methanone |
| 1370 | 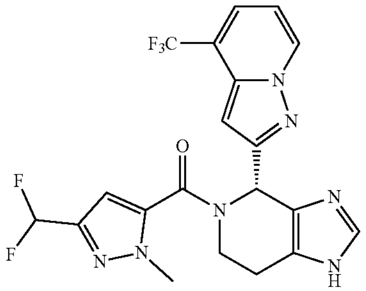 [SMILES: Cn1nc(C(F)F)cc1C(=O)N1CCc2[nH]cnc2[C@H]1c1cc2c(C(F)(F)F)cccn2n1] | (S)-(3-(difluoromethyl)-1-methyl-1H-pyrazol-5-yl)(4-(4-(trifluoromethyl)pyrazolo [1,5-a]pyridin-2-yl)-6,7-dihydro-1H-imidazo[4,5-c] pyridin-5(4H)-yl)methanone |

TABLE 1-continued

Pyrazolo[1,5-a]pyridines

| Ex. # | Structure | Name |
|---|---|---|
| 1371 | 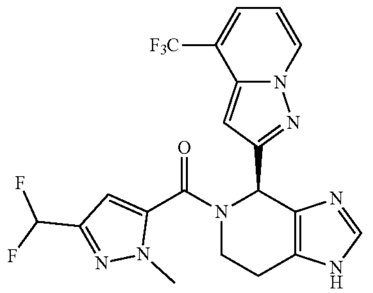 [SMILES: Cn1nc(C(F)F)cc1C(=O)N1CCc2[nH]cnc2[C@@H]1c1cc2c(C(F)(F)F)cccn2n1] | (R)-(3-(difluoromethyl)-1-methyl-1H-pyrazol-5-yl)(4-(4-(trifluoromethyl)pyrazolo[1,5-a]pyridin-2-yl)-6,7-dihydro-1H-imidazo[4,5-c]pyridin-5(4H)-yl)methanone |
| 1372 | 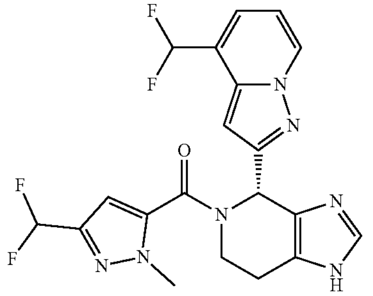 [SMILES: Cn1nc(C(F)F)cc1C(=O)N1CCc2[nH]cnc2[C@H]1c1cc2c(C(F)F)cccn2n1] | (S)-(3-(difluoromethyl)-1-methyl-1H-pyrazol-5-yl)(4-(4-(difluoromethyl)pyrazolo[1,5-a]pyridin-2-yl)-6,7-dihydro-1H-imidazo[4,5-c]pyridin-5(4H)-yl)methanone |
| 1373 | 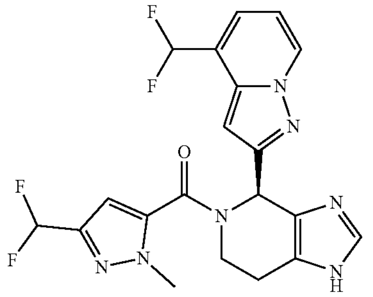 [SMILES: Cn1nc(C(F)F)cc1C(=O)N1CCc2[nH]cnc2[C@@H]1c1cc2c(C(F)F)cccn2n1] | (R)-(3-(difluoromethyl)-1-methyl-1H-pyrazol-5-yl)(4-(4-(difluoromethyl)pyrazolo[1,5-a]pyridin-2-yl)-6,7-dihydro-1H-imidazo[4,5-c]pyridin-5(4H)-yl)methanone |
| 1374 | 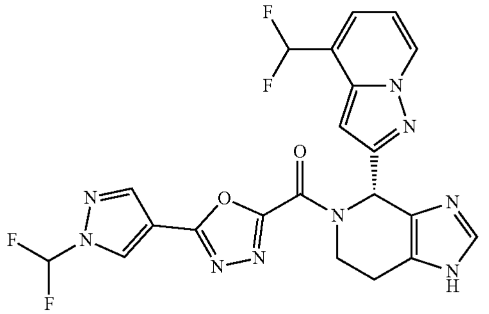 [SMILES: O=C(c1nnc(-c2cnn(C(F)F)c2)o1)N1CCc2[nH]cnc2[C@H]1c1cc2c(C(F)F)cccn2n1] | (S)-(5-(1-(difluoromethyl)-1H-pyrazol-4-yl)-1,3,4-oxadiazol-2-yl)(4-(4-(difluoromethyl)pyrazolo[1,5-a]pyridin-2-yl)-6,7-dihydro-1H-imidazo[4,5-c]pyridin-5(4H)-yl)methanone |
| 1375 | 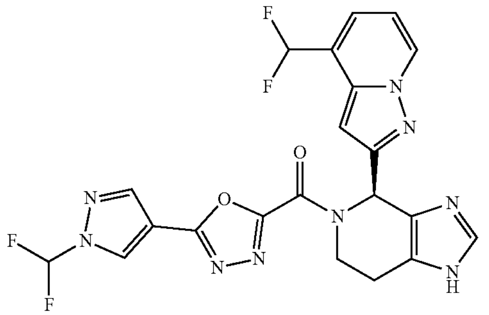 [SMILES: O=C(c1nnc(-c2cnn(C(F)F)c2)o1)N1CCc2[nH]cnc2[C@@H]1c1cc2c(C(F)F)cccn2n1] | (R)-(5-(1-(difluoromethyl)-1H-pyrazol-4-yl)-1,3,4-oxadiazol-2-yl)(4-(4-(difluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1376 | 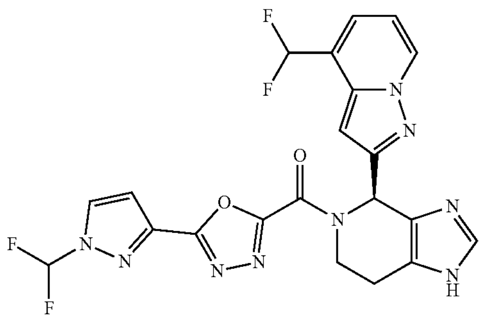 [SMILES: O=C(c1nnc(-c2ccn(C(F)F)n2)o1)N1CCc2[nH]cnc2[C@@H]1c1cc2c(C(F)F)cccn2n1] | (R)-(5-(1-(difluoromethyl)-1H-pyrazol-3-yl)-1,3,4-oxadiazol-2-yl)(4-(4-(difluoromethyl)pyrazolo[1,5-a]pyridin-2-yl)-6,7-dihydro-1H-imidazo[4,5-c]pyridin-5(4H)-yl)methanone |
| 1377 | 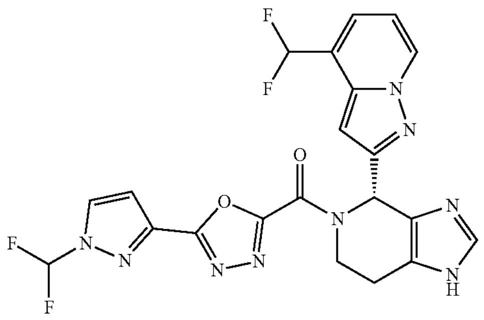 [SMILES: O=C(c1nnc(-c2ccn(C(F)F)n2)o1)N1CCc2[nH]cnc2[C@H]1c1cc2c(C(F)F)cccn2n1] | (S)-(5-(1-(difluoromethyl)-1H-pyrazol-3-yl)-1,3,4-oxadiazol-2-yl)(4-(4-(difluoromethyl)pyrazolo[1,5-a]pyridin-2-yl)-6,7-dihydro-1H-imidazo[4,5-c]pyridin-5(4H)-yl)methanone |
| 1378 | 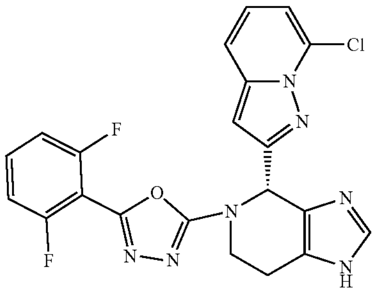 [SMILES: Fc1cccc(F)c1-c1nnc(N2CCc3[nH]cnc3[C@H]2c2cc3cccc(Cl)n3n2)o1] | (S)-(4-(4-fluoropyrazolo[1,5-a]pyridin-2-yl)-6,7-dihydro-1H-imidazo[4,5-c]pyridin-5(4H)-yl)(5-(1-methylcyclopropyl)-1,3,4-oxadiazol-2-yl)methanone |
| 1379 | 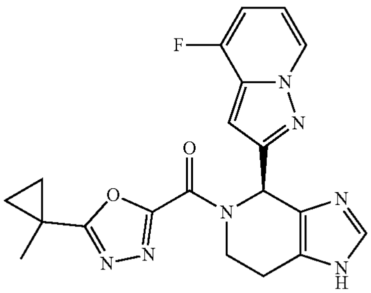 [SMILES: CC1(c2nnc(C(=O)N3CCc4[nH]cnc4[C@@H]3c3cc4c(F)cccn4n3)o2)CC1] | (R)-(4-(4-fluoropyrazolo[1,5-a]pyridin-2-yl)-6,7-dihydro-1H-imidazo[4,5-c]pyridin-5(4H)-yl)(5-(1-methylcyclopropyl)-1,3,4-oxadiazol-2-yl)methanone |
| 1380 | 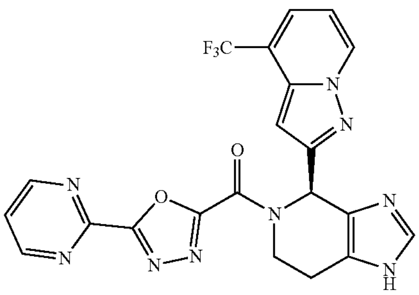 | (R)-(5-(pyrimidin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1381 | 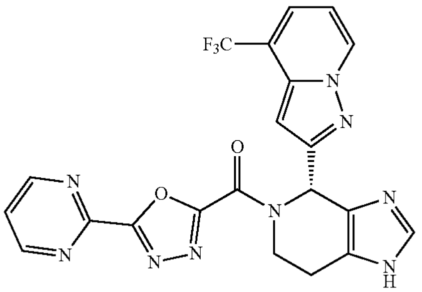 | (S)-(5-(pyrimidin-2-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1382 | 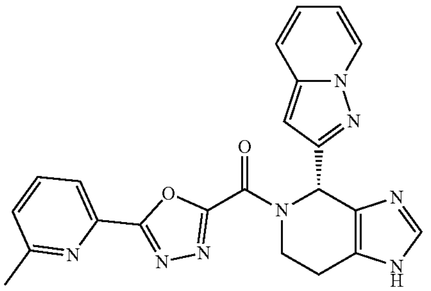 [SMILES: Cc1cccc(-c2nnc(C(=O)N3CCc4[nH]cnc4[C@H]3c3cc4ccccn4n3)o2)n1] | (S)-(5-(6-methylpyridin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 1383 | 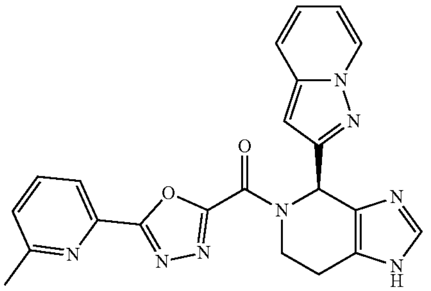 [SMILES: Cc1cccc(-c2nnc(C(=O)N3CCc4[nH]cnc4[C@@H]3c3cc4ccccn4n3)o2)n1] | (R)-(5-(6-methylpyridin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 1384 | 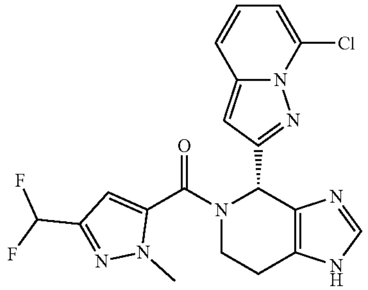 [SMILES: Cn1nc(C(F)F)cc1C(=O)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(3-(difluoromethyl)-1-methyl-1H-pyrazol-5-yl)methanone |
| 1385 | 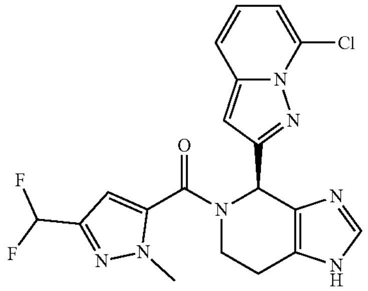 [SMILES: Cn1nc(C(F)F)cc1C(=O)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(3-(difluoromethyl)-1-methyl-1H-pyrazol-5-yl)methanone |

TABLE 1-continued

| Ex. # | Structure | Name |
|---|---|---|
| | Pyrazolo[1,5-a]pyridines | |
| 1386 | 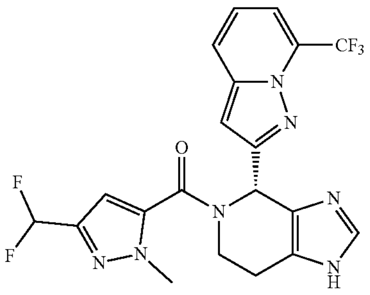 [SMILES: Cn1nc(C(F)F)cc1C(=O)N1CCc2[nH]cnc2[C@H]1c1cc2cccc(C(F)(F)F)n2n1] | (S)-(3-(difluoromethyl)-1-methyl-1H-pyrazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1387 | 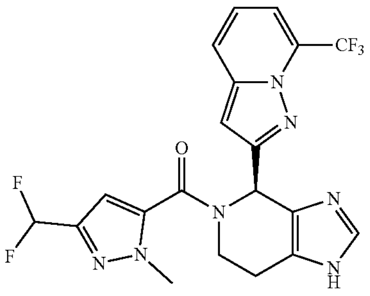 [SMILES: Cn1nc(C(F)F)cc1C(=O)N1CCc2[nH]cnc2[C@@H]1c1cc2cccc(C(F)(F)F)n2n1] | (R)-(3-(difluoromethyl)-1-methyl-1H-pyrazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 1388 | 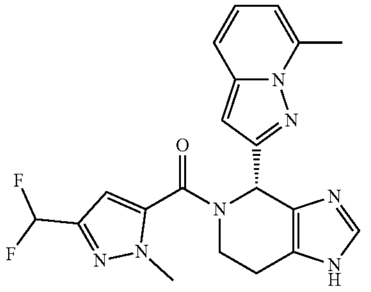 [SMILES: Cc1cccc2cc([C@@H]3c4nc[nH]c4CCN3C(=O)c3cc(C(F)F)nn3C)nn12] | (S)-(3-(difluoromethyl)-1-methyl-1H-pyrazol-5-yl)(4-(7-methylpyrazolo[1,5-a]pyridin-2-yl)-6,7-dihydro-1H-imidazo[4,5-c]pyridin-5(4H)-yl)methanone |
| 1389 | 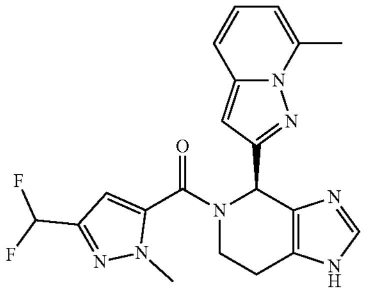 [SMILES: Cc1cccc2cc([C@H]3c4nc[nH]c4CCN3C(=O)c3cc(C(F)F)nn3C)nn12] | (R)-(3-(difluoromethyl)-1-methyl-1H-pyrazol-5-yl)(4-(7-methylpyrazolo[1,5-a]pyridin-2-yl)-6,7-dihydro-1H-imidazo[4,5-c]pyridin-5(4H)-yl)methanone |
| 1390 | 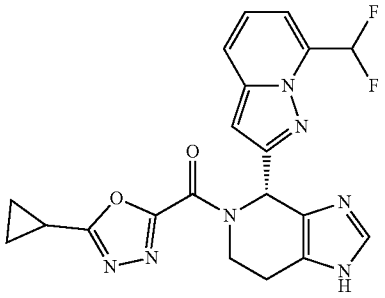 [SMILES: O=C(c1nnc(C2CC2)o1)N1CCc2[nH]cnc2[C@H]1c1cc2cccc(C(F)F)n2n1] | (S)-(5-cyclopropyl-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
| --- | --- | --- |
| Pyrazolo[1,5-a]pyridines | | |
| 1391 | 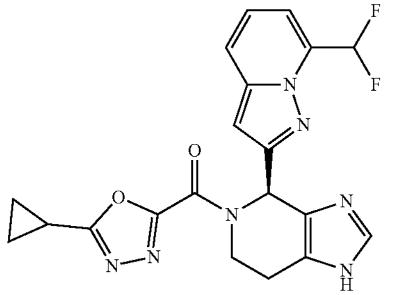 [SMILES: O=C(c1nnc(C2CC2)o1)N1CCc2[nH]cnc2[C@@H]1c1cc2cccc(C(F)F)n2n1] | (R)-(5-cyclopropyl-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |
| 1392 | 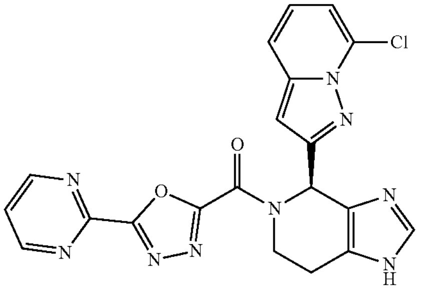 [SMILES: O=C(c1nnc(-c2ncccn2)o1)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(5-(pyrimidin-2-yl)-1,3,4-oxadiazol-2-yl)methanone |
| 1393 | 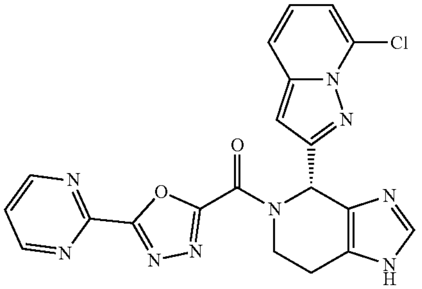 [SMILES: O=C(c1nnc(-c2ncccn2)o1)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(5-(pyrimidin-2-yl)-1,3,4-oxadiazol-2-yl)methanone |
| 1394 | 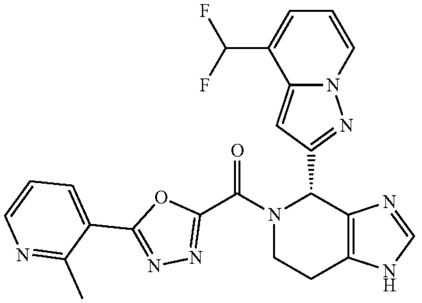 [SMILES: Cc1ncccc1-c1nnc(C(=O)N2CCc3[nH]cnc3[C@H]2c2cc3c(C(F)F)cccn3n2)o1] | (S)-(4-(4-(difluoromethyl)pyrazolo[1,5-a]pyridin-2-yl)-6,7-dihydro-1H-imidazo[4,5-c]pyridin-5(4H)-yl)(5-(2-methylpyridin-3-yl)-1,3,4-oxadiazol-2-yl)methanone |
| 1395 | 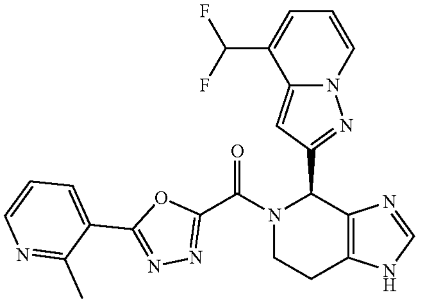 [SMILES: Cc1ncccc1-c1nnc(C(=O)N2CCc3[nH]cnc3[C@@H]2c2cc3c(C(F)F)cccn3n2)o1] | (R)-(4-(4-(difluoromethyl)pyrazolo[1,5-a]pyridin-2-yl)-6,7-dihydro-1H-imidazo[4,5-c]pyridin-5(4H)-yl)(5-(2-methylpyridin-3-yl)-1,3,4-oxadiazol-2-yl)methanone |

TABLE 1-continued

| Pyrazolo[1,5-a]pyridines | | |
|---|---|---|
| Ex. # | Structure | Name |
| 1396 | 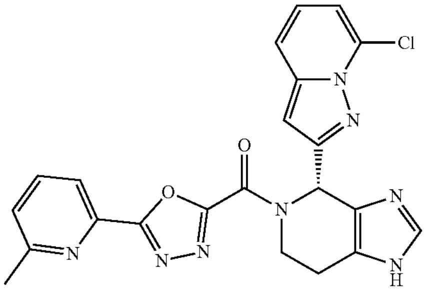 [SMILES: Cc1cccc(-c2nnc(C(=O)N3CCc4[nH]cnc4[C@H]3c3cc4cccc(Cl)n4n3)o2)n1] | (S)-(4-(7-chloropyrazolo [1,5-a]pyridin-2-yl)-6,7-dihydro-1H-imidazo[4,5-c] pyridin-5(4H)-yl)(5-(6-methylpyridin-2-yl)-1,3,4-oxadiazol-2-yl)methanone |
| 1397 | 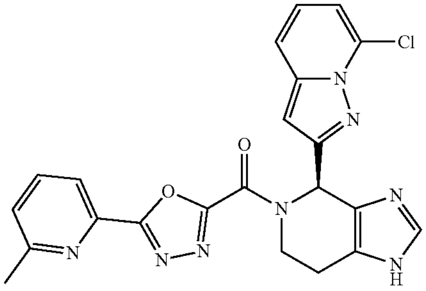 [SMILES: Cc1cccc(-c2nnc(C(=O)N3CCc4[nH]cnc4[C@@H]3c3cc4cccc(Cl)n4n3)o2)n1] | (R)-(4-(7-chloropyrazolo [1,5-a]pyridin-2-yl)-6,7-dihydro-1H-imidazo[4,5-c] pyridin-5(4H)-yl)(5-(6-methylpyridin-2-yl)-1,3,4-oxadiazol-2-yl)methanone |
| 1398 | 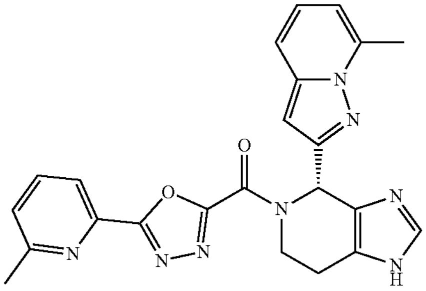 [SMILES: Cc1cccc(-c2nnc(C(=O)N3CCc4[nH]cnc4[C@H]3c3cc4cccc(C)n4n3)o2)n1] | (S)-(4-(7-methylpyrazolo [1,5-a]pyridin-2-yl)-6,7-dihydro-1H-imidazo[4,5-c] pyridin-5(4H)-yl)(5-(6-methylpyridin-2-yl)-1,3,4-oxadiazol-2-yl)methanone |
| 1399 | 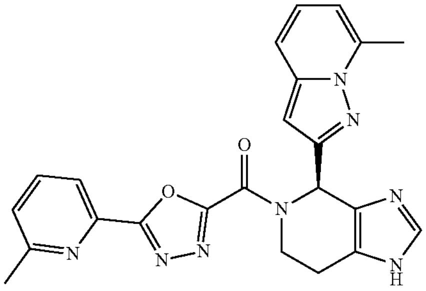 [SMILES: Cc1cccc(-c2nnc(C(=O)N3CCc4[nH]cnc4[C@@H]3c3cc4cccc(C)n4n3)o2)n1] | (R)-(4-(7-methylpyrazolo [1,5-a]pyridin-2-yl)-6,7-dihydro-1H-imidazo[4,5-c] pyridin-5(4H)-yl)(5-(6-methylpyridin-2-yl)-1,3,4-oxadiazol-2-yl)methanone |
| 1400 | 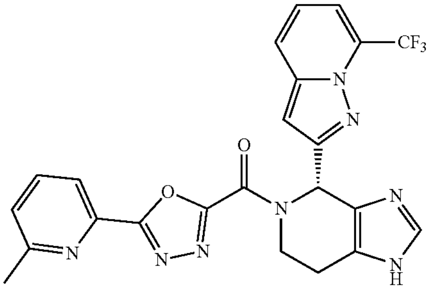 [SMILES: Cc1cccc(-c2nnc(C(=O)N3CCc4[nH]cnc4[C@H]3c3cc4cccc(C(F)(F)F)n4n3)o2)n1] | (S)-(5-(6-methylpyridin-2-yl)-1,3,4-oxadiazol-2-yl)(4-(7-(trifluoromethyl)pyrazolo [1,5-a]pyridin-2-yl)-6,7-dihydro-1H-imidazo[4,5-c] pyridin-5(4H)-yl)methanone |

TABLE 1-continued

| Ex. # | Structure | Name |
|---|---|---|
| | Pyrazolo[1,5-a]pyridines | |
| 1401 | 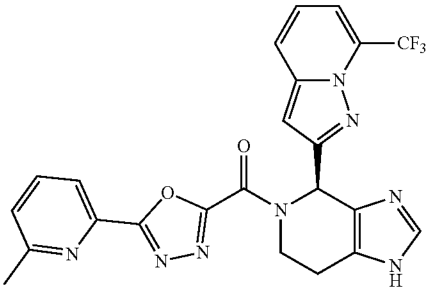 [SMILES: Cc1cccc(-c2nnc(C(=O)N3CCc4[nH]cnc4[C@@H]3c3cc4cccc(C(F)(F)F)n4n3)o2)n1] | (R)-(5-(6-methylpyridin-2-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1402 | 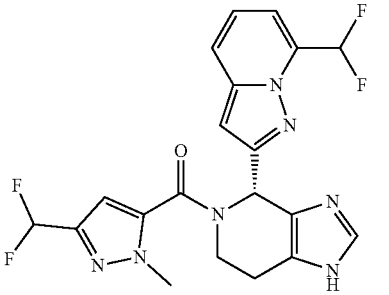 [SMILES: Cn1nc(C(F)F)cc1C(=O)N1CCc2[nH]cnc2[C@H]1c1cc2cccc(C(F)F)n2n1] | (S)-(3-(difluoromethyl)-1-methyl-1H-pyrazol-5-yl)(4-(7-(difluoromethyl)pyrazolo[1,5-a]pyridin-2-yl)-6,7-dihydro-1H-imidazo[4,5-c]pyridin-5(4H)-yl)methanone |
| 1403 | 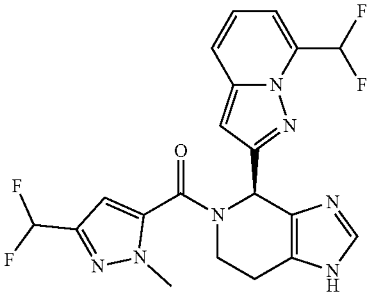 [SMILES: Cn1nc(C(F)F)cc1C(=O)N1CCc2[nH]cnc2[C@@H]1c1cc2cccc(C(F)F)n2n1] | (R)-(3-(difluoromethyl)-1-methyl-1H-pyrazol-5-yl)(4-(7-(difluoromethyl)pyrazolo[1,5-a]pyridin-2-yl)-6,7-dihydro-1H-imidazo[4,5-c]pyridin-5(4H)-yl)methanone |
| 1404 | 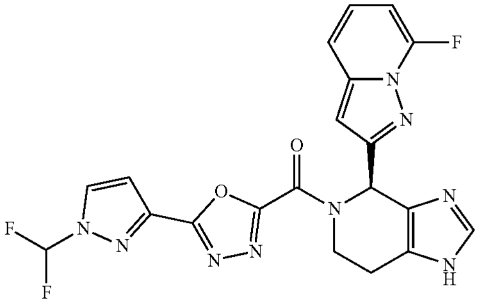 | (R)-(5-(1-(difluoromethyl)-1H-pyrazol-3-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1405 | 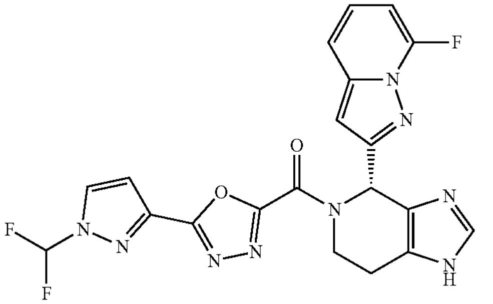 [SMILES: O=C(c1nnc(-c2ccn(C(F)F)n2)o1)N1CCc2[nH]cnc2[C@H]1c1cc2cccc(F)n2n1] | (S)-(5-(1-(difluoromethyl)-1H-pyrazol-3-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1406 | 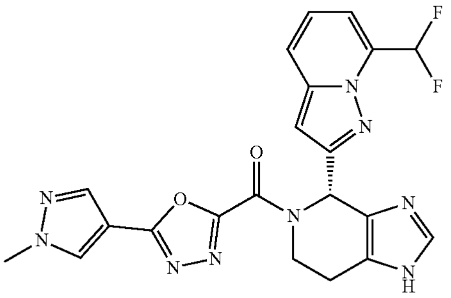 [SMILES: Cn1cc(-c2nnc(C(=O)N3CCc4[nH]cnc4[C@H]3c3cc4cccc(C(F)F)n4n3)o2)cn1] | (S)-(4-(7-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-4-yl)-1,3,4-oxadiazol-2-yl)methanone |
| 1407 | 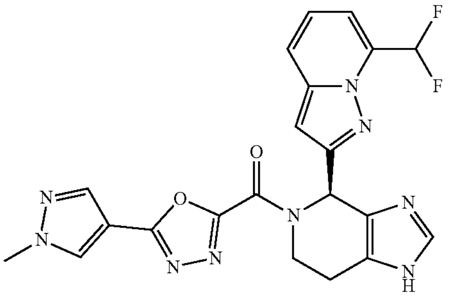 [SMILES: Cn1cc(-c2nnc(C(=O)N3CCc4[nH]cnc4[C@@H]3c3cc4cccc(C(F)F)n4n3)o2)cn1] | (R)-(4-(7-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-4-yl)-1,3,4-oxadiazol-2-yl)methanone |
| 1408 | 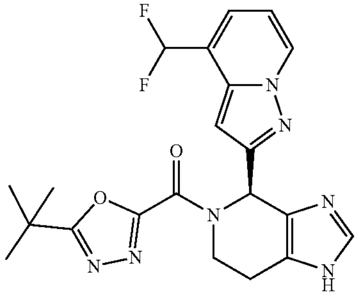 [SMILES: CC(C)(C)c1nnc(C(=O)N2CCc3[nH]cnc3[C@@H]2c2cc3c(C(F)F)cccn3n2)o1] | (R)-(5-(tert-butyl)-1,3,4-oxadiazol-2-yl)(4-(4-(difluoromethyl)pyrazolo [1,5-a]pyridin-2-yl)-6,7-dihydro-1H-imidazo[4,5-c] pyridin-5(4H)-yl)methanone |
| 1409 | 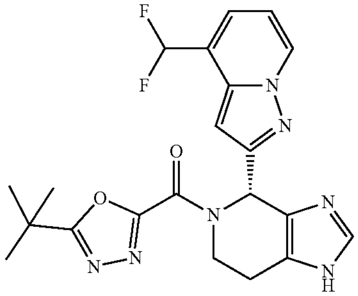 [SMILES: CC(C)(C)c1nnc(C(=O)N2CCc3[nH]cnc3[C@H]2c2cc3c(C(F)F)cccn3n2)o1] | (S)-(5-(tert-butyl)-1,3,4-oxadiazol-2-yl)(4-(4-(difluoromethyl)pyrazolo [1,5-a]pyridin-2-yl)-6,7-dihydro-1H-imidazo[4,5-c] pyridin-5(4H)-yl)methanone |
| 1410 | 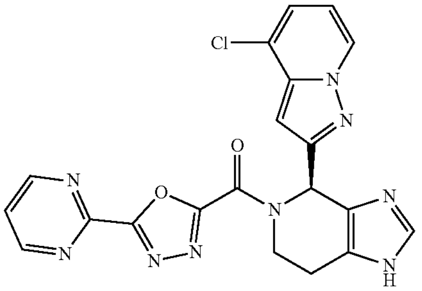 [SMILES: O=C(c1nnc(-c2ncccn2)o1)N1CCc2[nH]cnc2[C@@H]1c1cc2c(Cl)cccn2n1] | (R)-(4-(4-chloropyrazolo [1,5-a]pyridin-2-yl)-6,7-dihydro-1H-imidazo[4,5-c] pyridin-5(4H)-yl)(5-(pyrimidin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1411 | 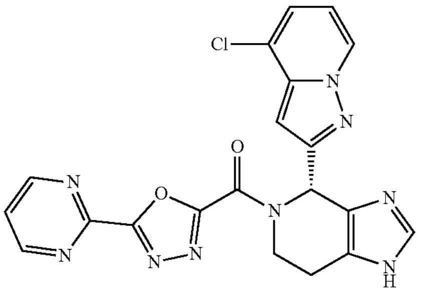 [SMILES: O=C(c1nnc(-c2ncccn2)o1)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(5-(pyrimidin-2-yl)-1,3,4-oxadiazol-2-yl)methanone |
| 1412 | 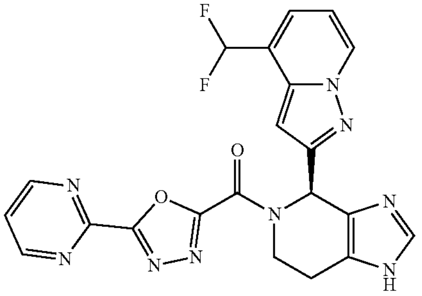 [SMILES: O=C(c1nnc(-c2ncccn2)o1)N1CCc2[nH]cnc2[C@@H]1c1cc2c(C(F)F)cccn2n1] | (R)-(4-(4-(difluoromethyl)pyrazolo[1,5-a]pyridin-2-yl)-6,7-dihydro-1H-imidazo[4,5-c]pyridin-5(4H)-yl)(5-(pyrimidin-2-yl)-1,3,4-oxadiazol-2-yl)methanone |
| 1413 | 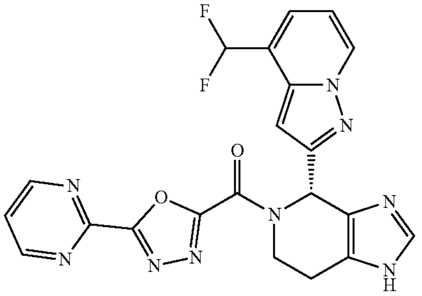 [SMILES: O=C(c1nnc(-c2ncccn2)o1)N1CCc2[nH]cnc2[C@H]1c1cc2c(C(F)F)cccn2n1] | (S)-(4-(4-(difluoromethyl)pyrazolo[1,5-a]pyridin-2-yl)-6,7-dihydro-1H-imidazo[4,5-c]pyridin-5(4H)-yl)(5-(pyrimidin-2-yl)-1,3,4-oxadiazol-2-yl)methanone |
| 1414 | 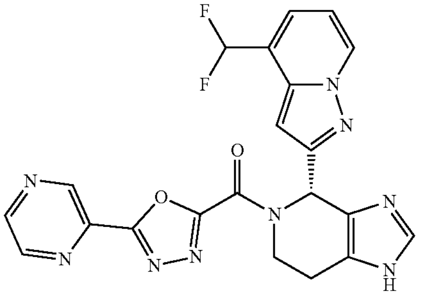 [SMILES: O=C(c1nnc(-c2cnccn2)o1)N1CCc2[nH]cnc2[C@H]1c1cc2c(C(F)F)cccn2n1] | (S)-(4-(4-(difluoromethyl)pyrazolo[1,5-a]pyridin-2-yl)-6,7-dihydro-1H-imidazo[4,5-c]pyridin-5(4H)-yl)(5-(pyrazin-2-yl)-1,3,4-oxadiazol-2-yl)methanone |
| 1415 | 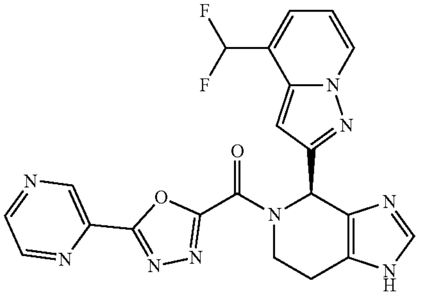 [SMILES: O=C(c1nnc(-c2cnccn2)o1)N1CCc2[nH]cnc2[C@@H]1c1cc2c(C(F)F)cccn2n1] | (R)-(4-(4-(difluoromethyl)pyrazolo[1,5-a]pyridin-2-yl)-6,7-dihydro-1H-imidazo[4,5-c]pyridin-5(4H)-yl)(5-(pyrazin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1416 | 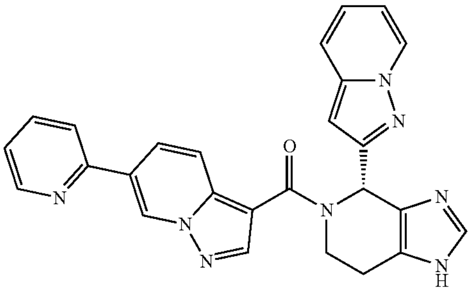 [SMILES: O=C(c1cnn2cc(-c3ccccn3)ccc12)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(6-(pyridin-2-yl)pyrazolo[1,5-a]pyridin-3-yl)methanone |
| 1417 | 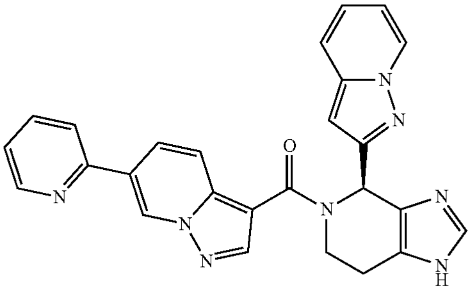 [SMILES: O=C(c1cnn2cc(-c3ccccn3)ccc12)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(6-(pyridin-2-yl)pyrazolo[1,5-a]pyridin-3-yl)methanone |
| 1418 | 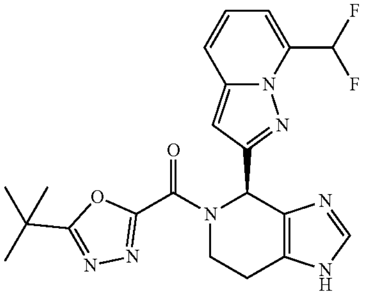 [SMILES: CC(C)(C)c1nnc(C(=O)N2CCc3[nH]cnc3[C@@H]2c2cc3cccc(C(F)F)n3n2)o1] | (R)-(5-(tert-butyl)-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |
| 1419 | 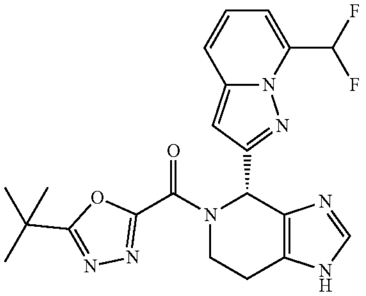 [SMILES: CC(C)(C)c1nnc(C(=O)N2CCc3[nH]cnc3[C@H]2c2cc3cccc(C(F)F)n3n2)o1] | (S)-(5-(tert-butyl)-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |
| 1420 | 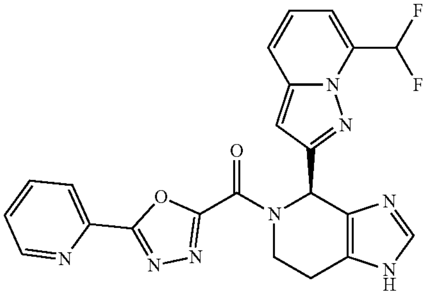 [SMILES: O=C(c1nnc(-c2ccccn2)o1)N1CCc2[nH]cnc2[C@@H]1c1cc2cccc(C(F)F)n2n1] | (R)-(4-(7-(difluoromethyl)pyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1421 | 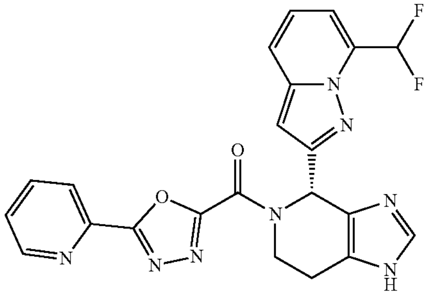 | (S)-(4-(7-(difluoromethyl) pyrazolo[1,5-a]pyridin-2-yl)-6,7-dihydro-1H-imidazo [4,5-c]pyridin-5(4H)-yl)(5-(pyridin-2-yl)-1,3,4-oxadiazol-2-yl)methanone |
| 1422 | 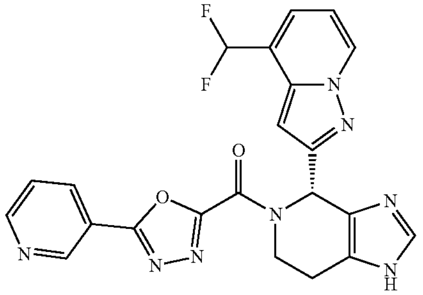 [SMILES: O=C(c1nnc(-c2cccnc2)o1)N1CCc2[nH]cnc2[C@H]1c1cc2c(C(F)F)cccn2n1] | (S)-(4-(4-(difluoromethyl) pyrazolo[1,5-a]pyridin-2-yl)-6,7-dihydro-1H-imidazo [4,5-c]pyridin-5(4H)-yl)(5-(pyridin-3-yl)-1,3,4-oxadiazol-2-yl)methanone |
| 1423 | 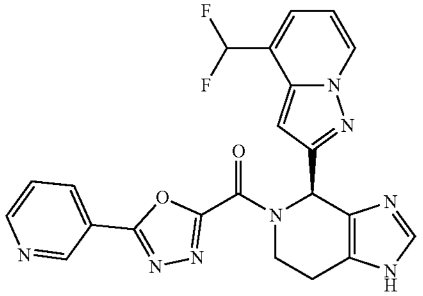 [SMILES: O=C(c1nnc(-c2cccnc2)o1)N1CCc2[nH]cnc2[C@@H]1c1cc2c(C(F)F)cccn2n1] | (R)-(4-(4-(difluoromethyl) pyrazolo[1,5-a]pyridin-2-yl)-6,7-dihydro-1H-imidazo [4,5-c]pyridin-5(4H)-yl)(5-(pyridin-3-yl)-1,3,4-oxadiazol-2-yl)methanone |
| 1424 | 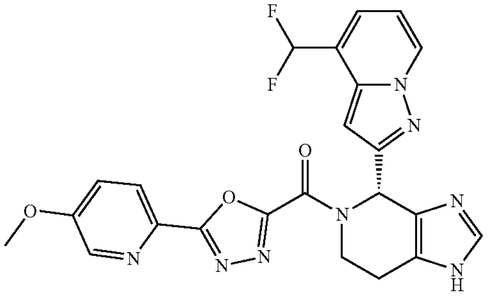 [SMILES: COc1ccc(-c2nnc(C(=O)N3CCc4[nH]cnc4[C@H]3c3cc4c(C(F)F)cccn4n3)o2)nc1] | (S)-(4-(4-(difluoromethyl) pyrazolo[1,5-a]pyridin-2-yl)-6,7-dihydro-1H-imidazo [4,5-c]pyridin-5(4H)-yl)(5-(5-methoxypyridin-2-yl)-1,3,4-oxadiazol-2-yl)methanone |
| 1425 | 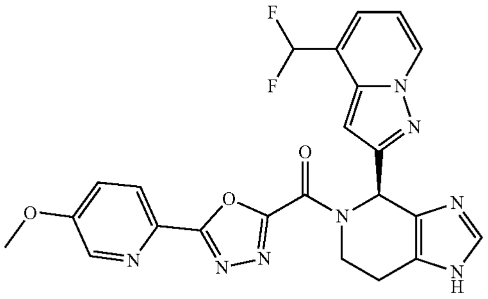 [SMILES: COc1ccc(-c2nnc(C(=O)N3CCc4[nH]cnc4[C@@H]3c3cc4c(C(F)F)cccn4n3)o2)nc1] | (R)-(4-(4-(difluoromethyl) pyrazolo[1,5-a]pyridin-2-y]l)-6,7-dihydro-1H-imidazo [4,5-c]pyridin-5(4H)-yl)(5-(5-methoxypyridin-2-yl)-1,3,4-oxadiazol-2-yl)methanone |

TABLE 1-continued

Pyrazolo[1,5-a]pyridines

| Ex. # | Structure | Name |
|---|---|---|
| 1426 | 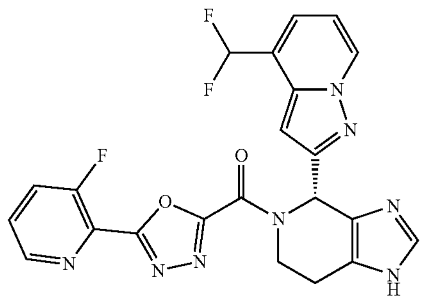 [SMILES: O=C(c1nnc(-c2ncccc2F)o1)N1CCc2[nH]cnc2[C@H]1c1cc2c(C(F)F)cccn2n1] | (S)-(4-(4-(difluoromethyl) pyrazolo[1,5-a]pyridin-2-yl)-6,7-dihydro-1H-imidazo [4,5-c]pyridin-5(4H)-yl)(5-(3-fluoropyridin-2-yl)-1,3,4-oxadiazol-2-yl)methanone |
| 1427 | 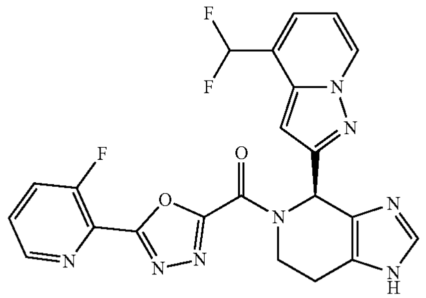 [SMILES: O=C(c1nnc(-c2ncccc2F)o1)N1CCc2[nH]cnc2[C@@H]1c1cc2c(C(F)F)cccn2n1] | (R)-(4-(4-(difluoromethyl) pyrazolo[1,5-a]pyridin-2-yl)-6,7-dihydro-1H-imidazo [4,5-c]pyridin-5(4H)-yl)(5-(3-fluoropyridin-2-yl)-1,3,4-oxadiazol-2-yl)methanone |
| 1428 | 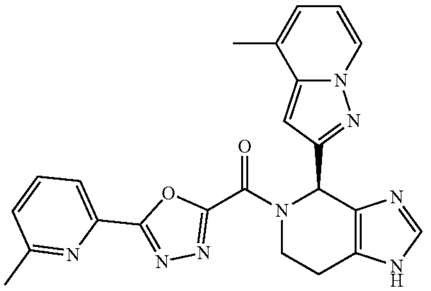 [SMILES: Cc1cccc(-c2nnc(C(=O)N3CCc4[nH]cnc4[C@@H]3c3cc4c(C)cccn4n3)o2)n1] | (R)-(4-(4-methylpyrazolo [1,5-a]pyridin-2-yl)-6,7-dihydro-1H-imidazo[4,5-c] pyridin-5(4H)-yl)(5-(6-methylpyridin-2-yl)-1,3,4-oxadiazol-2-yl)methanone |
| 1429 | 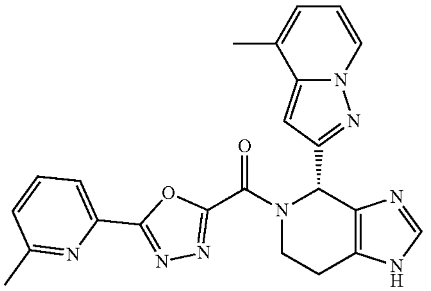 [SMILES: Cc1cccc(-c2nnc(C(=O)N3CCc4[nH]cnc4[C@H]3c3cc4c(C)cccn4n3)o2)n1] | (S)-(4-(4-methylpyrazolo [1,5-a]pyridin-2-yl)-6,7-dihydro-1H-imidazo[4,5-c] pyridin-5(4H)-yl)(5-(6-methylpyridin-2-yl)-1,3,4-oxadiazol-2-yl)methanone |
| 1430 | 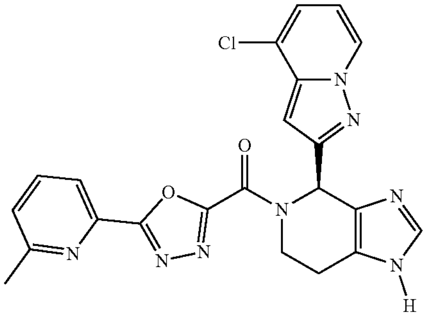 [SMILES: Cc1cccc(-c2nnc(C(=O)N3CCc4[nH]cnc4[C@@H]3c3cc4c(Cl)cccn4n3)o2)n1] | (R)-(4-(4-chloropyrazolo [1,5-a]pyridin-2-yl)-6,7-dihydro-1H-imidazo[4,5-c] pyridin-5(4H)-yl)(5-(6-methylpyridin-2-yl)-1,3,4-oxadiazol-2-yl)methanone |

TABLE 1-continued

Pyrazolo[1,5-a]pyridines

| Ex. # | Structure | Name |
|---|---|---|
| 1431 | 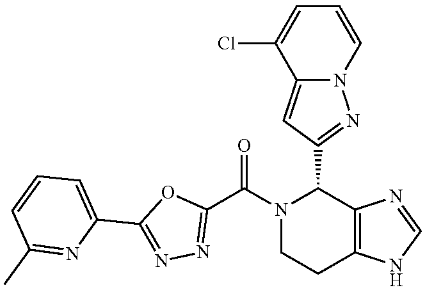 | (S)-(4-(4-chloropyrazolo [1,5-a]pyridin-2-yl)-6,7-dihydro-1H-imidazo[4,5-c] pyridin-5(4H)-yl)(5-(6-methylpyridin-2-yl)-1,3,4-oxadiazol-2-yl)methanone |
| 1432 | 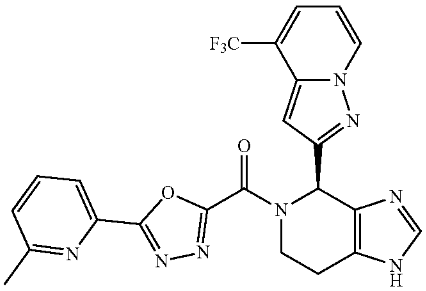 [SMILES: Cc1cccc(-c2nnc(C(=O)N3CCc4[nH]cnc4[C@@H]3c3cc4c(C(F)(F)F)cccn4n3)o2)n1] | (R)-(5-(6-methylpyridin-2-yl)-1,3,4-oxadiazol-2-yl)(4-(4-(trifluoromethyl)pyrazolo [1,5-a]pyridin-2-yl)-6,7-dihydro-1H-imidazo[4,5-c] pyridin-5(4H)-yl)methanone |
| 1433 | 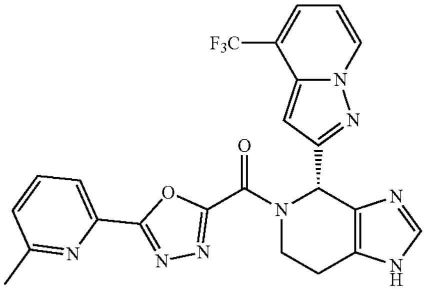 [SMILES: Cc1cccc(-c2nnc(C(=O)N3CCc4[nH]cnc4[C@H]3c3cc4c(C(F)(F)F)cccn4n3)o2)n1] | (S)-(5-(6-methylpyridin-2-yl)-1,3,4-oxadiazol-2-yl)(4-(4-(trifluoromethyl)pyrazolo [1,5-a]pyridin-2-yl)-6,7-dihydro-1H-imidazo[4,5-c] pyridin-5(4H)-yl)methanone |
| 1434 | 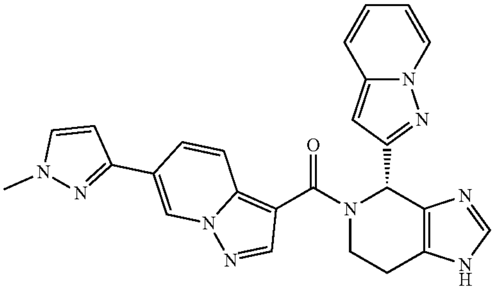 [SMILES: Cn1ccc(-c2ccc3c(C(=O)N4CCc5[nH]cnc5[C@H]4c4cc5ccccn5n4)cnn3c2)n1] | (S)-(6-(1-methyl-1H-pyrazol-3-yl)pyrazolo[1,5-a]pyridin-3-yl)(4-(pyrazolo [1,5-a]pyridin-2-yl)-6,7-dihydro-1H-imidazo[4,5-c] pyridin-5(4H)-yl)methanone |
| 1435 | 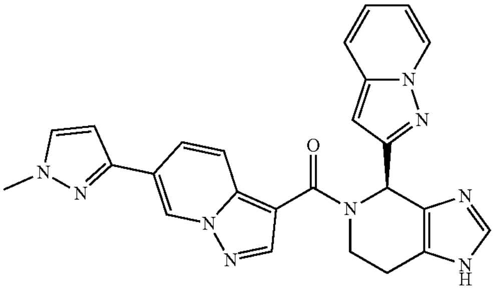 [SMILES: Cn1ccc(-c2ccc3c(C(=O)N4CCc5[nH]cnc5[C@@H]4c4cc5ccccn5n4)cnn3c2)n1] | (R)-(6-(1-methyl-1H-pyrazol-3-yl)pyrazolo[1,5-a]pyridin-3-yl)(4-(pyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 1436 | 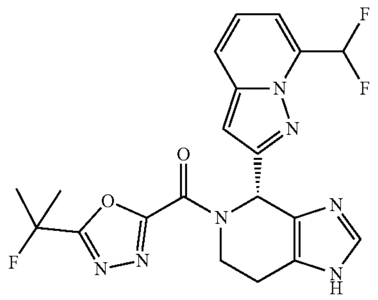 [SMILES: CC(C)(F)c1nnc(C(=O)N2CCc3[nH]cnc3[C@H]2c2cc3cccc(C(F)F)n3n2)o1] | (S)-(4-(7-(difluoromethyl) pyrazolo[1,5-a]pyridin-2-yl)-6,7-dihydro-1H-imidazo[4,5-c] pyridin-5(4H)-yl)(5-(2-fluoropropan-2-yl)-1,3,4-oxadiazol-2-yl)methanone |
| 1437 | 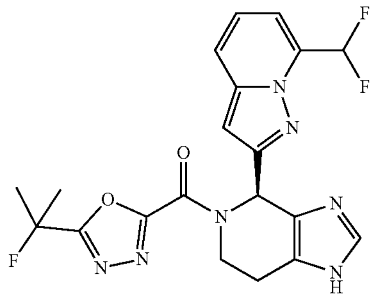 [SMILES: CC(C)(F)c1nnc(C(=O)N2CCc3[nH]cnc3[C@@H]2c2cc3cccc(C(F)F)n3n2)o1] | (R)-(4-(7-(difluoromethyl) pyrazolo[1,5-a]pyridin-2-yl)-6,7-dihydro-1H-imidazo[ 4,5-c]pyridin-5(4H)-yl)(5-(2-fluoropropan-2-yl)-1,3,4-oxadiazol-2-yl)methanone |
| 1438 | 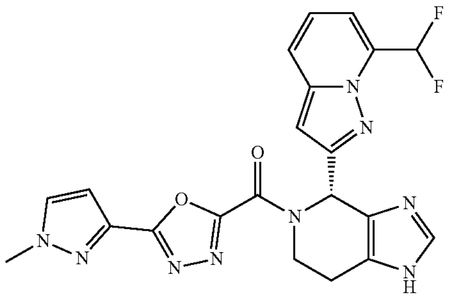 [SMILES: Cn1ccc(-c2nnc(C(=O)N3CCc4[nH]cnc4[C@H]3c3cc4cccc(C(F)F)n4n3)o2)n1] | (S)-(4-(7-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-3-yl)-1,3,4-oxadiazol-2-yl)methanone |
| 1439 | 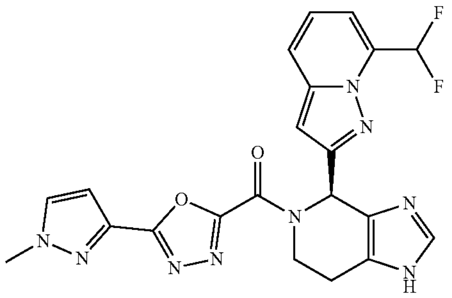 [SMILES: Cn1ccc(-c2nnc(C(=O)N3CCc4[nH]cnc4[C@@H]3c3cc4cccc(C(F)F)n4n3)o2)n1] | (R)-(4-(7-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-3-yl)-1,3,4-oxadiazol-2-yl)methanone |
| 1440 | 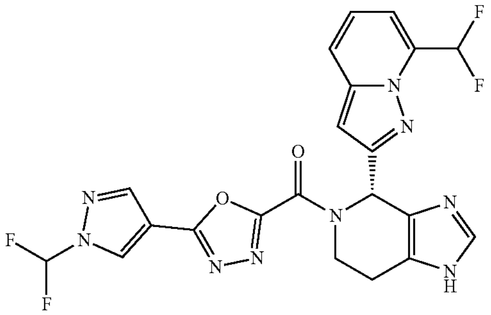 [SMILES: O=C(c1nnc(-c2cnn(C(F)F)c2)o1)N1CCc2[nH]cnc2[C@H]1c1cc2cccc(C(F)F)n2n1] | (S)-(5-(1-(difluoromethyl)-1H-pyrazol-4-yl)-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1441 | 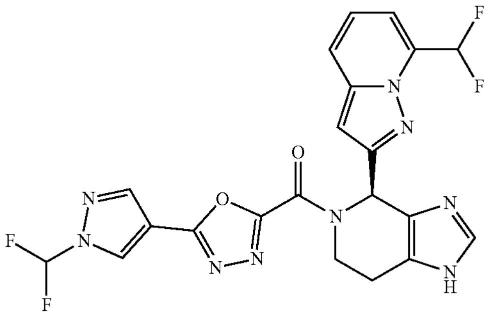 [SMILES: O=C(c1nnc(-c2cnn(C(F)F)c2)o1)N1CCc2[nH]cnc2[C@@H]1c1cc2cccc(C(F)F)n2n1] | (R)-(5-(1-(difluoromethyl)-1H-pyrazol-4-yl)-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |
| 1442 | 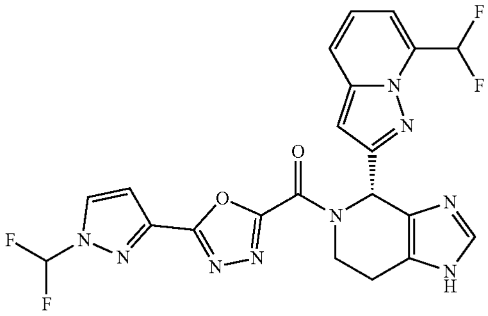 [SMILES: O=C(c1nnc(-c2ccn(C(F)F)n2)o1)N1CCc2[nH]cnc2[C@H]1c1cc2cccc(C(F)F)n2n1] | (S)-(5-(1-(difluoromethyl)-1H-pyrazol-3-yl)-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |
| 1443 | 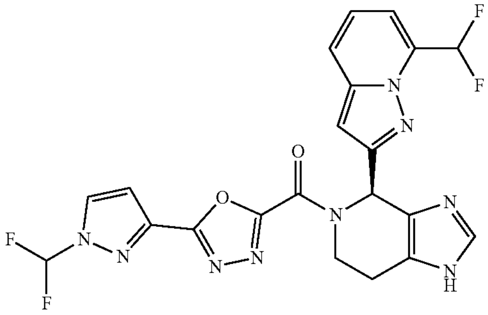 [SMILES: O=C(c1nnc(-c2ccn(C(F)F)n2)o1)N1CCc2[nH]cnc2[C@@H]1c1cc2cccc(C(F)F)n2n1] | (R)-(5-(1-(difluoromethyl)-1H-pyrazol-3-yl)-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |
| 1444 | 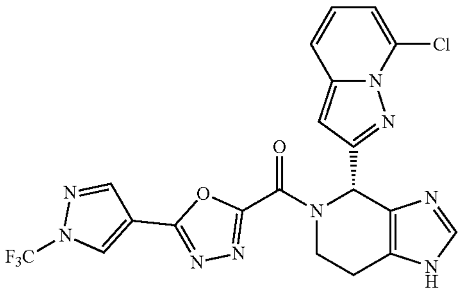 [SMILES: O=C(c1nnc(-c2cnn(C(F)(F)F)c2)o1)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |
| 1445 | 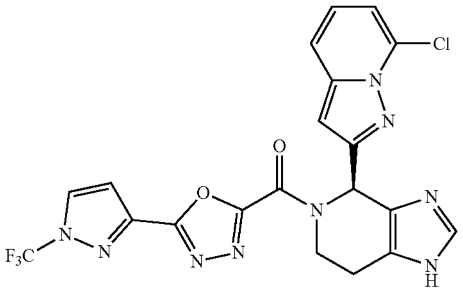 [SMILES: O=C(c1nnc(-c2ccn(C(F)(F)F)n2)o1)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |

TABLE 1-continued

| Ex. # | Structure | Name |
|---|---|---|
| | Pyrazolo[1,5-a]pyridines | |
| 1446 | 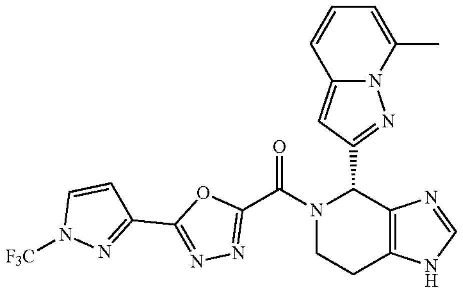 [SMILES: Cc1cccc2cc([C@@H]3c4nc[nH]c4CCN3C(=O)c3nnc(-c4ccn(C(F)(F)F)n4)o3)nn12] | (S)-(4-(7-methylpyrazolo[1,5-a]pyridin-2-yl)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |
| 1447 | 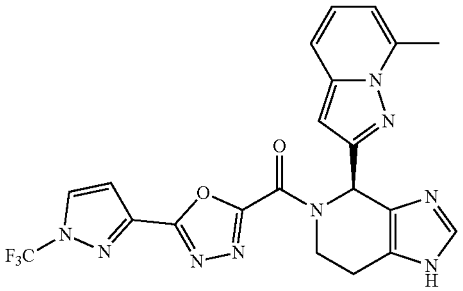 [SMILES: Cc1cccc2cc([C@H]3c4nc[nH]c4CCN3C(=O)c3nnc(-c4ccn(C(F)(F)F)n4)o3)nn12] | (R)-(4-(7-methylpyrazolo[1,5-a]pyridin-2-yl)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |
| 1448 | 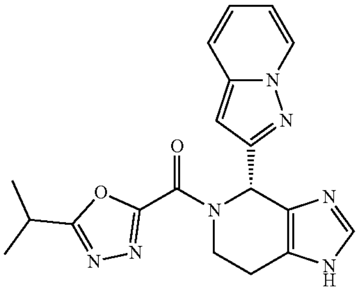 [SMILES: CC(C)c1nnc(C(=O)N2CCc3[nH]cnc3[C@H]2c2cc3ccccn3n2)o1] | (S)-(5-isopropyl-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 1449 | 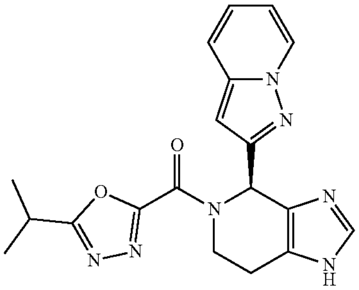 [SMILES: CC(C)c1nnc(C(=O)N2CCc3[nH]cnc3[C@@H]2c2cc3ccccn3n2)o1] | (R)-(5-isopropyl-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 1450 | 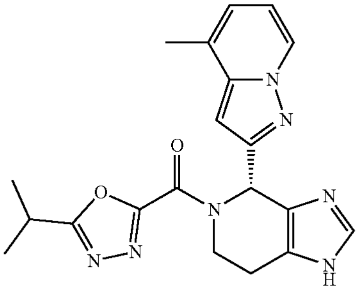 [SMILES: Cc1cccn2nc([C@@H]3c4nc[nH]c4CCN3C(=O)c3nnc(C(C)C)o3)cc12] | (S)-(5-isopropyl-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
| --- | --- | --- |
| | Pyrazolo[1,5-a]pyridines | |
| 1451 | 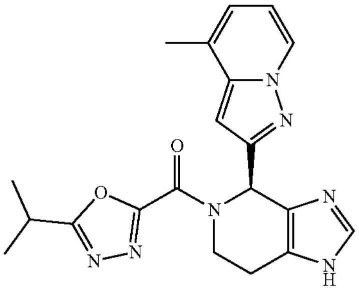 [SMILES: Cc1cccn2nc([C@H]3c4nc[nH]c4CCN3C(=O)c3nnc(C(C)C)o3)cc12] | (R)-(5-isopropyl-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1452 | 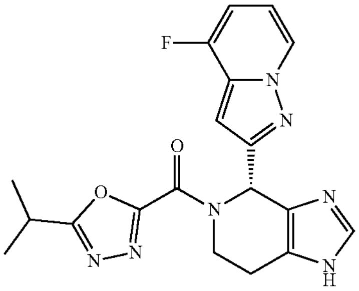 [SMILES: CC(C)c1nnc(C(=O)N2CCc3[nH]cnc3[C@H]2c2cc3c(F)cccn3n2)o1] | (S)-(4-(4-fluoropyrazolo[1,5-a]pyridin-2-yl)-6,7-dihydro-1H-imidazo[4,5-c]pyridin-5(4H)-yl)(5-isopropyl-1,3,4-oxadiazol-2-yl)methanone |
| 1453 | 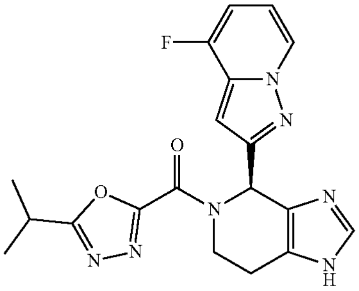 [SMILES: CC(C)c1nnc(C(=O)N2CCc3[nH]cnc3[C@@H]2c2cc3c(F)cccn3n2)o1] | (R)-(4-(4-fluoropyrazolo[1,5-a]pyridin-2-yl)-6,7-dihydro-1H-imidazo[4,5-c]pyridin-5(4H)-yl)(5-isopropyl-1,3,4-oxadiazol-2-yl)methanone |
| 1454 | 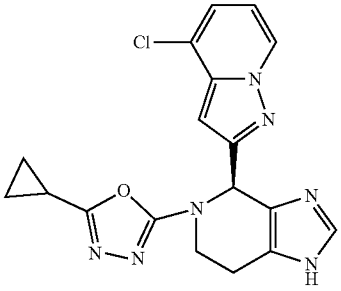 [SMILES: Clc1cccn2nc([C@H]3c4nc[nH]c4CCN3c3nnc(C4CC4)o3)cc12] | (R)-2-(4-(4-chloropyrazolo[1,5-a]pyridin-2-yl)-1,4,6,7-tetrahydro-5H-imidazo[4,5-c]pyridin-5-yl)-5-cyclopropyl-1,3,4-oxadiazole |
| 1455 | 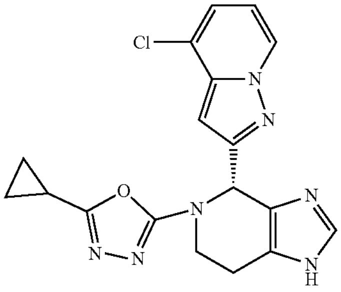 [SMILES: Clc1cccn2nc([C@@H]3c4nc[nH]c4CCN3c3nnc(C4CC4)o3)cc12] | (S)-2-(4-(4-chloropyrazolo[1,5-a]pyridin-2-yl)-1,4,6,7-tetrahydro-5H-imidazo[4,5-c]pyridin-5-yl)-5-cyclopropyl-1,3,4-oxadiazole |

TABLE 1-continued

| Ex. # | Structure | Name |
|---|---|---|
| | Pyrazolo[1,5-a]pyridines | |
| 1456 | 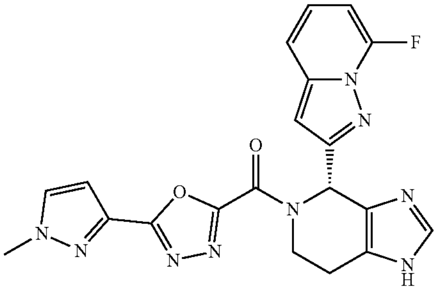 [SMILES: Cn1ccc(-c2nnc(C(=O)N3CCc4[nH]cnc4[C@H]3c3cc4cccc(F)n4n3)o2)n1] | (S)-(4-(7-fluoropyrazolo[1,5-a] pyridin-2-yl)-6,7-dihydro-1H-imidazo[4,5-c]pyridin-5(4H)-yl)(5-(1-methyl-1H-pyrazol-3-yl)-1,3,4-oxadiazol-2-yl)methanone |
| 1457 | 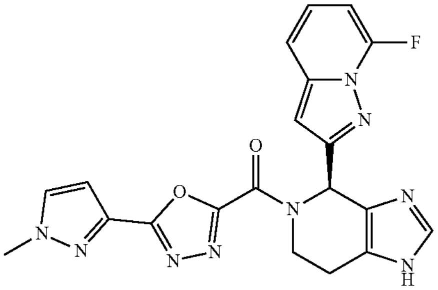 [SMILES: Cn1ccc(-c2nnc(C(=O)N3CCc4[nH]cnc4[C@@H]3c3cc4cccc(F)n4n3)o2)n1] | (R)-(4-(7-fluoropyrazolo [1,5-a]pyridin-2-yl)-6,7-dihydro-1H-imidazo[4,5-c] pyridin-5(4H)-yl)(5-(1-methyl-1H-pyrazol-3-yl)-1,3,4-oxadiazol-2-yl)methanone |
| 1458 | 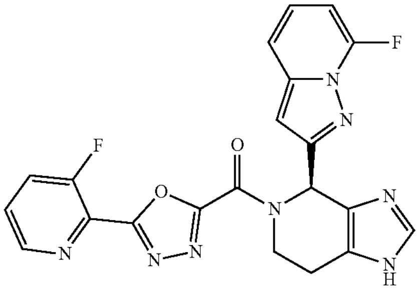 [SMILES: O=C(c1nnc(-c2ncccc2F)o1)N1CCc2[nH]cnc2[C@@H]1c1cc2cccc(F)n2n1] | (R)-(4-(7-fluoropyrazolo [1,5-a]pyridin-2-y])-6,7-dihydro-1H-imidazo[4,5-c] pyridin-5(4H)-yl)(5-(3-fluoropyridin-2-yl)-1,3,4-oxadiazol-2-yl)methanone |
| 1459 | 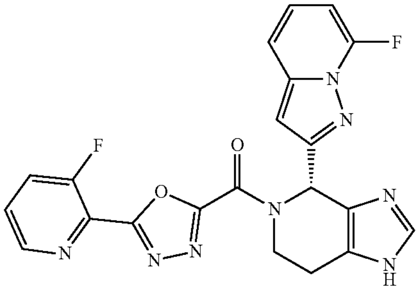 [SMILES: O=C(c1nnc(-c2ncccc2F)o1)N1CCc2[nH]cnc2[C@H]1c1cc2cccc(F)n2n1] | (S)-(4-(7-fluoropyrazolo[1,5-a] pyridin-2-yl)-6,7-dihydro-1H-imidazo[4,5-c]pyridin-5(4H)-yl)(5-(3-fluoropyridin-2-yl)-1,3,4-oxadiazol-2-yl)methanone |
| 1460 | 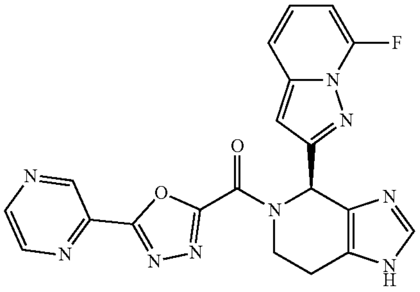 | (R)-(4-(7-fluoropyrazolo [1,5-a]pyridin-2-yl)-6,7-dihydro-1H-imidazo[4,5-c] pyridin-5(4H)-yl)(5-(pyrazin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1461 | 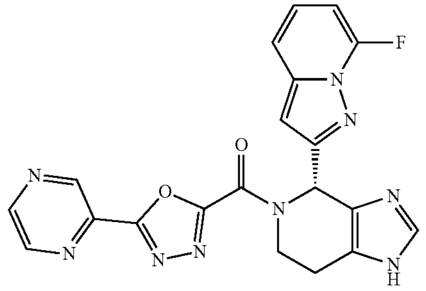 [SMILES: O=C(c1nnc(-c2cnccn2)o1)N1CCc2[nH]cnc2[C@H]1c1cc2cccc(F)n2n1] | (S)-(4-(7-fluoropyrazolo[1,5-a]pyridin-2-yl)-6,7-dihydro-1H-imidazo[4,5-c]pyridin-5(4H)-yl)(5-(pyrazin-2-yl)-1,3,4-oxadiazol-2-yl)methanone |
| 1462 | 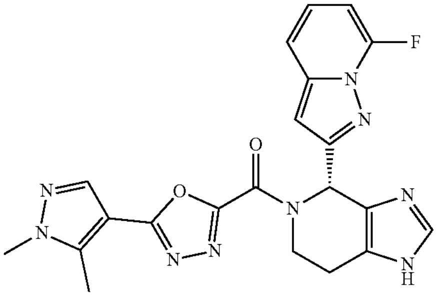 | (S)-(5-(1,5-dimethyl-1H-pyrazol-4-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1463 | 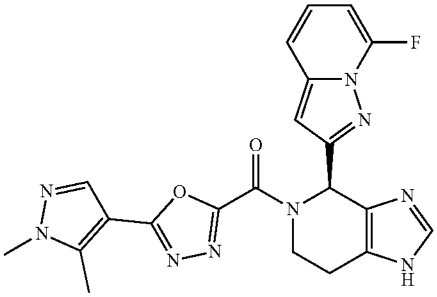 | (R)-(5-(1,5-dimethyl-1H-pyrazol-4-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1464 | 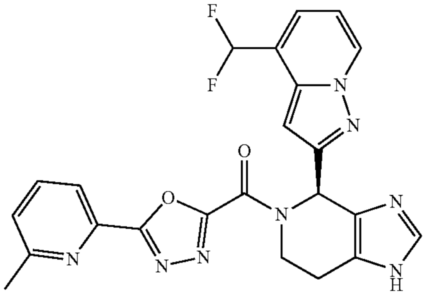 [SMILES: Cc1cccc(-c2nnc(C(=O)N3CCc4[nH]cnc4[C@@H]3c3cc4c(C(F)F)cccn4n3)o2)n1] | (R)-(4-(4-(difluoromethyl)pyrazolo[1,5-a]pyridin-2-yl)-6,7-dihydro-1H-imidazo[4,5-c]pyridin-5(4H)-yl)(5-(6-methylpyridin-2-yl)-1,3,4-oxadiazol-2-yl)methanone |
| 1465 | 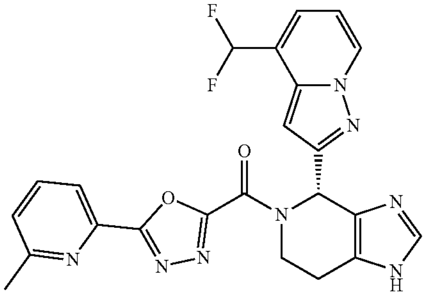 [SMILES: Cc1cccc(-c2nnc(C(=O)N3CCc4[nH]cnc4[C@H]3c3cc4c(C(F)F)cccn4n3)o2)n1] | (S)-(4-(4-(difluoromethyl)pyrazolo[1,5-a]pyridin-2-yl)-6,7-dihydro-1H-imidazo[4,5-c]pyridin-5(4H)-yl)(5-(6-methylpyridin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1466 | 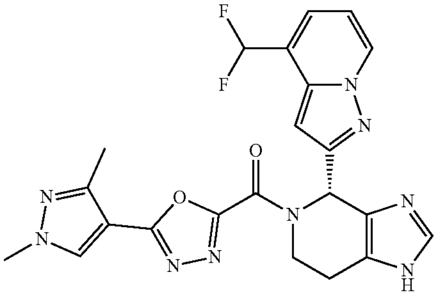 [SMILES: Cc1nn(C)cc1-c1nnc(C(=O)N2CCc3[nH]cnc3[C@H]2c2cc3c(C(F)F)cccn3n2)o1] | (S)-(4-(4-(difluoromethyl) pyrazolo[1,5-a]pyridin-2-yl)-6,7-dihydro-1H-imidazo[4,5-c] pyridin-5(4H)-yl)(5-(1,3-dimethyl-1H-pyrazol-4-yl)-1,3,4-oxadiazol-2-yl)methanone |
| 1467 | 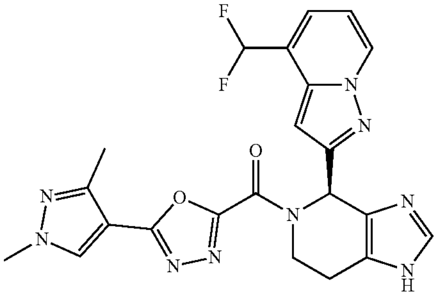 [SMILES: Cc1nn(C)cc1-c1nnc(C(=O)N2CCc3[nH]cnc3[C@@H]2c2cc3c(C(F)F)cccn3n2)o1] | (R)-(4-(4-(difluoromethyl) pyrazolo[1,5-a]pyridin-2-yl)-6,7-dihydro-1H-imidazo [4,5-c]pyridin-5(4H)-yl)(5-(1,3-dimethyl-1H-pyrazol-4-yl)-1,3,4-oxadiazol-2-yl)methanone |
| 1468 | 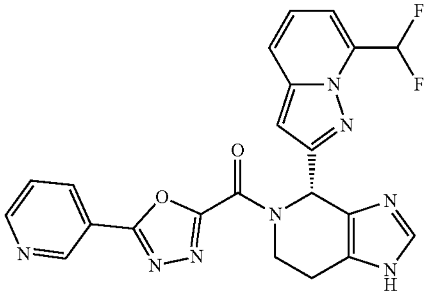 [SMILES: O=C(c1nnc(-c2cccnc2)o1)N1CCc2[nH]cnc2[C@H]1c1cc2cccc(C(F)F)n2n1] | (S)-(4-(7-(difluoromethyl) pyrazolo[1,5-a]pyridin-2-yl)-6,7-dihydro-1H-imidazo [4,5-c]pyridin-5(4H)-yl)(5-(pyridin-3-yl)-1,3,4-oxadiazol-2-yl)methanone |
| 1469 | 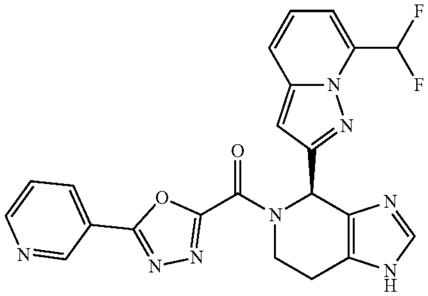 [SMILES: O=C(c1nnc(-c2cccnc2)o1)N1CCc2[nH]cnc2[C@@H]1c1cc2cccc(C(F)F)n2n1] | (R)-(4-(7-(difluoromethyl) pyrazolo[1,5-a]pyridin-2-yl)-6,7-dihydro-1H-imidazo [4,5-c]pyridin-5(4H)-yl)(5-(pyridin-3-yl)-1,3,4-oxadiazol-2-yl)methanone |
| 1470 | 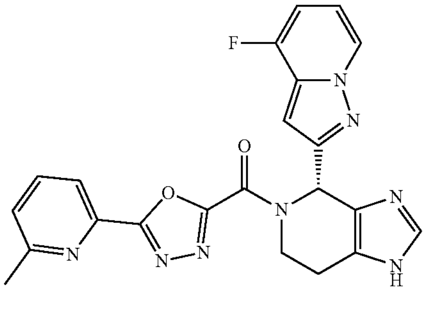 [SMILES: Cc1cccc(-c2nnc(C(=O)N3CCc4[nH]cnc4[C@H]3c3cc4c(F)cccn4n3)o2)n1] | (S)-(4-(4-fluoropyrazolo[1,5-a] pyridin-2-yl)-6,7-dihydro-1H-imidazo[4,5-c]pyridin-5(4H)-yl)(5-(6-methylpyridin-2-yl)-1,3,4-oxadiazol-2-yl) methanone |

TABLE 1-continued

| Ex. # | Structure | Name |
|---|---|---|
| | Pyrazolo[1,5-a]pyridines | |
| 1471 | 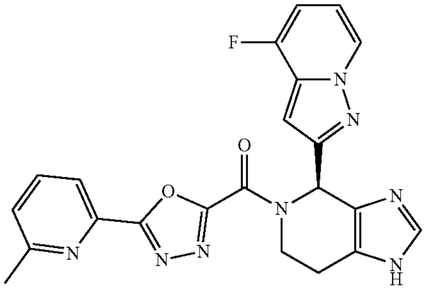 [SMILES: Cc1cccc(-c2nnc(C(=O)N3CCc4[nH]cnc4[C@@H]3c3cc4c(F)cccn4n3)o2)n1] | (R)-(4-(4-fluoropyrazolo[1,5-a]pyridin-2-yl)-6,7-dihydro-1H-imidazo[4,5-c]pyridin-5(4H)-yl)(5-(6-methylpyridin-2-yl)-1,3,4-oxadiazol-2-yl)methanone |
| 1472 | 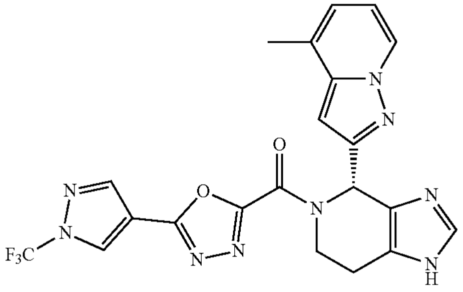 [SMILES: Cc1cccn2nc([C@@H]3c4nc[nH]c4CCN3C(=O)c3nnc(-c4cnn(C(F)(F)F)c4)o3)cc12] | (S)-(4-(4-methylpyrazolo[1,5-a]pyridin-2-yl)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |
| 1473 | 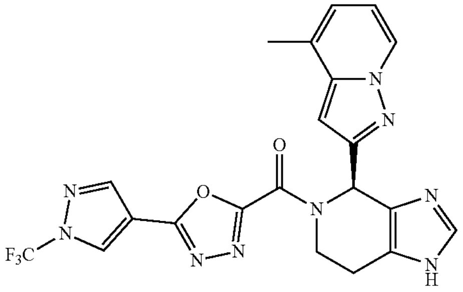 [SMILES: Cc1cccn2nc([C@H]3c4nc[nH]c4CCN3C(=O)c3nnc(-c4cnn(C(F)(F)F)c4)o3)cc12] | (R)-(4-(4-methylpyrazolo[1,5-a]pyridin-2-y]l)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |
| 1474 | 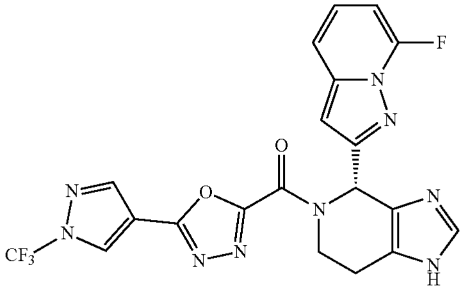 [SMILES: O=C(c1nnc(-c2cnn(C(F)(F)F)c2)o1)N1CCc2[nH]cnc2[C@H]1c1cc2cccc(F)n2n1] | (S)-(4-(7-fluoropyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1475 | 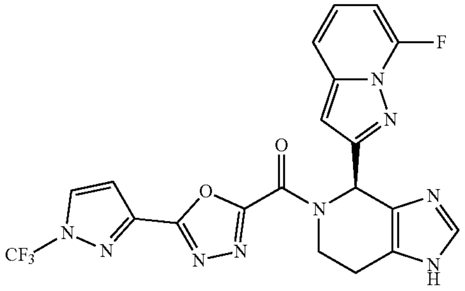 | (R)-(4-(7-fluoropyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |

TABLE 1-continued

| Ex. # | Structure | Name |
|---|---|---|
| | Pyrazolo[1,5-a]pyridines | |
| 1476 | 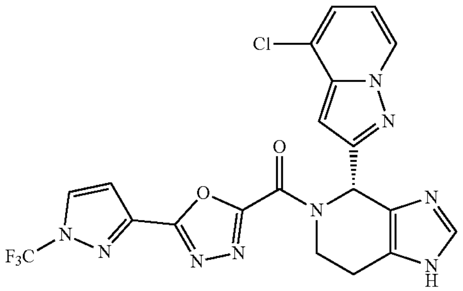 [SMILES: O=C(c1nnc(-c2ccn(C(F)(F)F)n2)o1)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1477 | 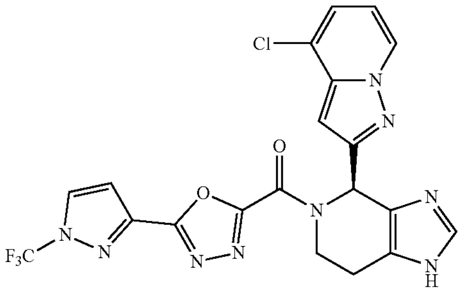 [SMILES: O=C(c1nnc(-c2ccn(C(F)(F)F)n2)o1)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1478 | 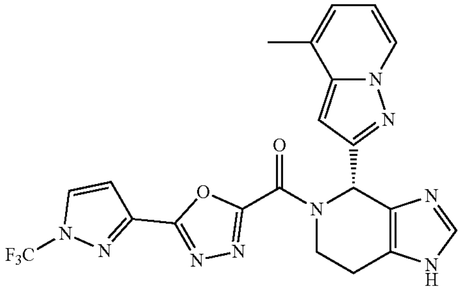 | (S)-(4-(4-methylpyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1479 | 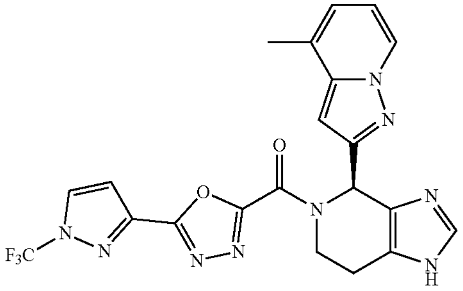 [SMILES: Cc1cccn2nc([C@H]3c4nc[nH]c4CCN3C(=O)c3nnc(-c4ccn(C(F)(F)F)n4)o3)cc12] | (R)-(4-(4-methylpyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1480 | 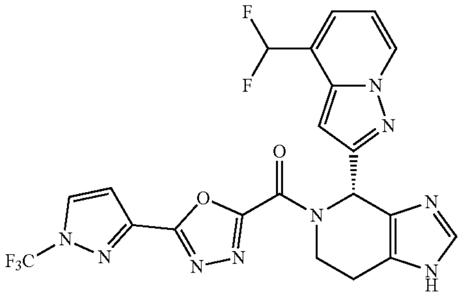 [SMILES: O=C(c1nnc(-c2ccn(C(F)(F)F)n2)o1)N1CCc2[nH]cnc2[C@H]1c1cc2c(C(F)F)cccn2n1] | (S)-(4-(4-(difluoromethyl)pyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |

TABLE 1-continued

| Ex. # | Structure | Name |
|---|---|---|
| | Pyrazolo[1,5-a]pyridines | |
| 1481 | 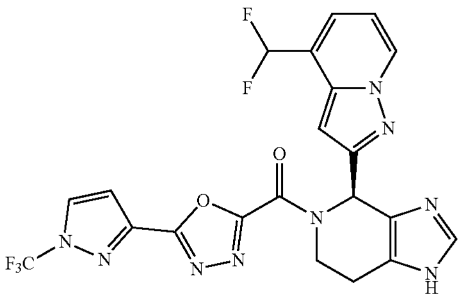 [SMILES: O=C(c1nnc(-c2ccn(C(F)(F)F)n2)o1)N1CCc2[nH]cnc2[C@@H]1c1cc2c(C(F)F)cccn2n1] | (R)-(4-(4-(difluoromethyl) pyrazolo[1,5-a]pyridin-2-yl)-6,7-dihydro-1H-imidazo [4,5-c]pyridin-5(4H)-yl)(5-(1-(trifluoromethyl)-1H-pyrazol-3-yl)-1,3,4-oxadiazol-2-yl)methanone |
| 1482 | 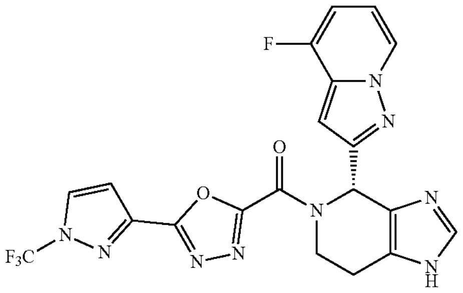 [SMILES: O=C(c1nnc(-c2ccn(C(F)(F)F)n2)o1)N1CCc2[nH]cnc2[C@H]1c1cc2c(F)cccn2n1] | (S)-(4-(4-fluoropyrazolo[1,5-a] pyridin-2-yl)-6,7-dihydro-1H-imidazo[4,5-c] pyridin-5(4H)-yl)(5-(1-(trifluoromethyl)-1H-pyrazol-3-yl)-1,3,4-oxadiazol-2-yl)methanone |
| 1483 | 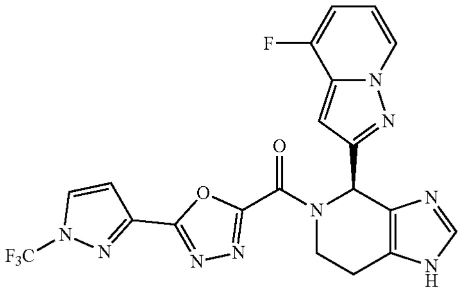 [SMILES: O=C(c1nnc(-c2ccn(C(F)(F)F)n2)o1)N1CCc2[nH]cnc2[C@@H]1c1cc2c(F)cccn2n1] | (R)-(4-(4-fluoropyrazolo [1,5-a]pyridin-2-yl)-6,7-dihydro-1H-imidazo[4,5-c] pyridin-5(4H)-yl)(5-(1-(trifluoromethyl)-1H-pyrazol-3-yl)-1,3,4-oxadiazol-2-yl)methanone |
| 1484 | 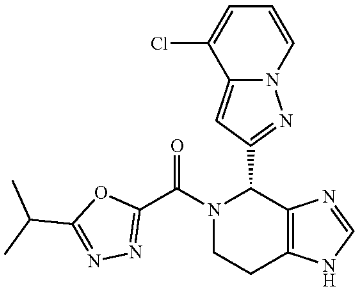 [SMILES: CC(C)c1nnc(C(=O)N2CCc3[nH]cnc3[C@H]2c2cc3c(Cl)cccn3n2)o1] | (S)-(4-(4-chloropyrazolo [1,5-a]pyridin-2-yl)-6,7-dihydro-1H-imidazo[4,5-c] pyridin-5(4H)-yl)(5-isopropyl-1,3,4-oxadiazol-2-yl)methanone |
| 1485 | 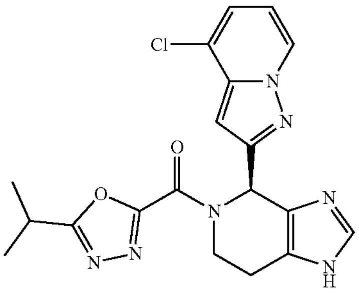 [SMILES: CC(C)c1nnc(C(=O)N2CCc3[nH]cnc3[C@@H]2c2cc3c(Cl)cccn3n2)o1] | (R)-(4-(4-chloropyrazolo [1,5-a]pyridin-2-yl)-6,7-dihydro-1H-imidazo[4,5-c] pyridin-5(4H)-yl)(5-isopropyl-1,3,4-oxadiazol-2-yl)methanone |

TABLE 1-continued

| Ex. # | Structure | Name |
|---|---|---|
| | Pyrazolo[1,5-a]pyridines | |
| 1486 | 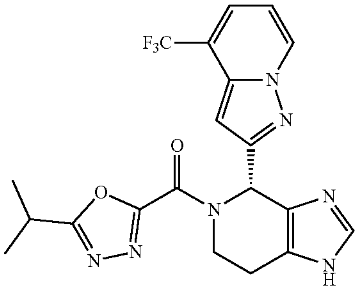 [SMILES: CC(C)c1nnc(C(=O)N2CCc3[nH]cnc3[C@H]2c2cc3c(C(F)(F)F)cccn3n2)o1] | (S)-(5-isopropyl-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1487 | 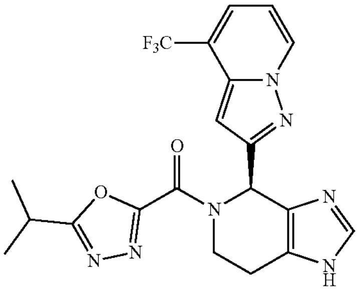 [SMILES: CC(C)c1nnc(C(=O)N2CCc3[nH]cnc3[C@@H]2c2cc3c(C(F)(F)F)cccn3n2)o1] | (R)-(5-isopropyl-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1488 | 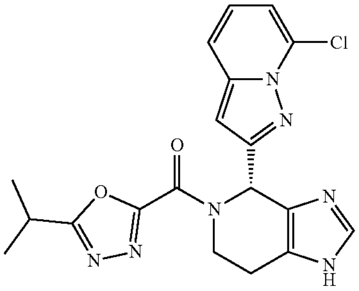 | (S)-(4-(7-chloropyrazolo[1,5-a]pyridin-2-yl)-6,7-dihydro-1H-imidazo[4,5-c]pyridin-5(4H)-yl)(5-isopropyl-1,3,4-oxadiazol-2-yl)methanone |
| 1489 | 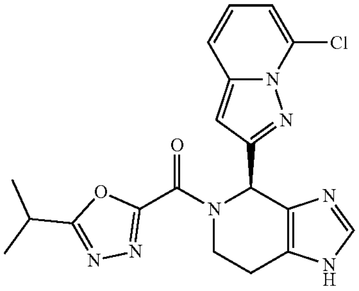 | (R)-(4-(7-chloropyrazolo[1,5-a]pyridin-2-yl)-6,7-dihydro-1H-imidazo[4,5-c]pyridin-5(4H)-yl)(5-isopropyl-1,3,4-oxadiazol-2-yl)methanone |
| 1490 | 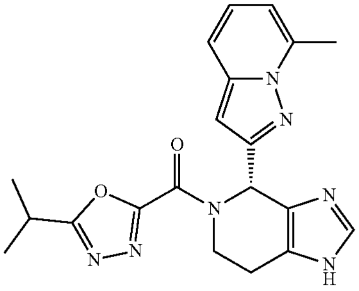 [SMILES: Cc1cccc2cc([C@@H]3c4nc[nH]c4CCN3C(=O)c3nnc(C(C)C)o3)nn12] | (S)-(5-isopropyl-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1491 | 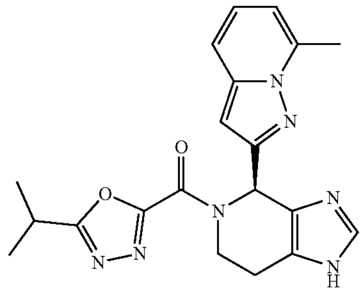 [SMILES: Cc1cccc2cc([C@H]3c4nc[nH]c4CCN3C(=O)c3nnc(C(C)C)o3)nn12] | (R)-(5-isopropyl-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 1492 | 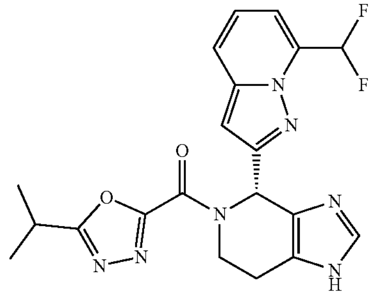 [SMILES: CC(C)c1nnc(C(=O)N2CCc3[nH]cnc3[C@H]2c2cc3cccc(C(F)F)n3n2)o1] | (S)-(4-(7-(difluoromethyl) pyrazolo[1,5-a]pyridin-2-yl)-6,7-dihydro-1H-imidazo [4,5-c]pyridin-5(4H)-yl)(5-isopropyl-1,3,4-oxadiazol-2-yl)methanone |
| 1493 | 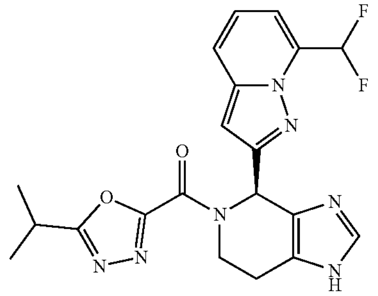 [SMILES: CC(C)c1nnc(C(=O)N2CCc3[nH]cnc3[C@@H]2c2cc3cccc(C(F)F)n3n2)o1] | (R)-(4-(7-(difluoromethyl) pyrazolo[1,5-a]pyridin-2-y]l)-6,7-dihydro-1H-imidazo [4,5-c]pyridin-5(4H)-yl)(5-isopropyl-1,3,4-oxadiazol-2-yl)methanone |
| 1494 | 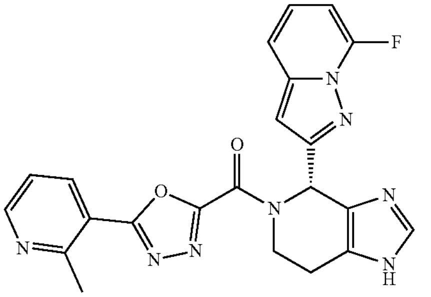 [SMILES: Cc1ncccc1-c1nnc(C(=O)N2CCc3[nH]cnc3[C@H]2c2cc3cccc(F)n3n2)o1] | (S)-(4-(7-fluoropyrazolo [1,5-a]pyridin-2-yl)-6,7-dihydro-1H-imidazo[4,5-c]pyridin-5(4H)-yl)(5-(2-methylpyridin-3-yl)-1,3,4-oxadiazol-2-yl)methanone |
| 1495 | 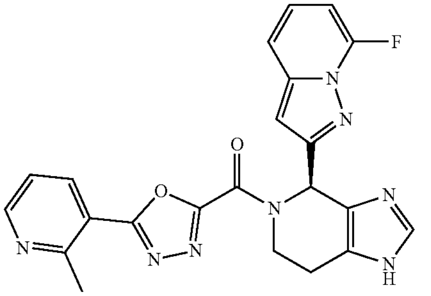 [SMILES: Cc1ncccc1-c1nnc(C(=O)N2CCc3[nH]cnc3[C@@H]2c2cc3cccc(F)n3n2)o1] | (R)-(4-(7-fluoropyrazolo [1,5-a]pyridin-2-yl)-6,7-dihydro-1H-imidazo [4,5-c]pyridin-5(4H)-yl)(5-(2-methylpyridin-3-yl)-1,3,4-oxadiazol-2-yl)methanone |

TABLE 1-continued

| Pyrazolo[1,5-a]pyridines | | |
|---|---|---|
| Ex. # | Structure | Name |
| 1496 | 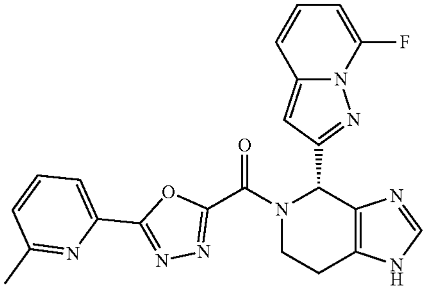 [SMILES: Cc1cccc(-c2nnc(C(=O)N3CCc4[nH]cnc4[C@H]3c3cc4cccc(F)n4n3)o2)n1] | (S)-(4-(7-fluoropyrazolo[1,5-a]pyridin-2-yl)-6,7-dihydro-1H-imidazo[4,5-c]pyridin-5(4H)-yl)(5-(6-methylpyridin-2-yl)-1,3,4-oxadiazol-2-yl)methanone |
| 1497 | 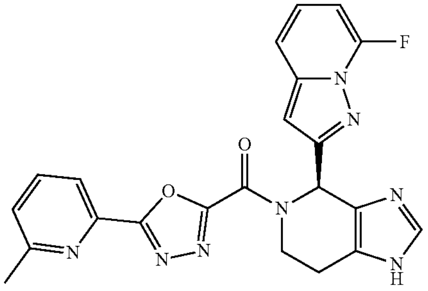 | (R)-(4-(7-fluoropyrazolo[1,5-a]pyridin-2-y])-6,7-dihydro-1H-imidazo[4,5-c]pyridin-5(4H)-yl)(5-(6-methylpyridin-2-yl)-1,3,4-oxadiazol-2-yl)methanone |
| 1498 | 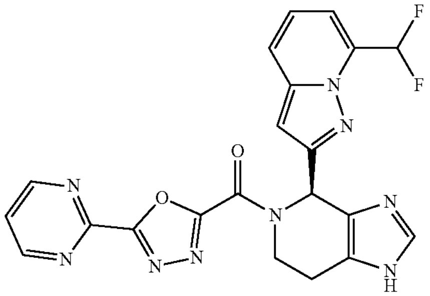 [SMILES: O=C(c1nnc(-c2ncccn2)o1)N1CCc2[nH]cnc2[C@@H]1c1cc2cccc(C(F)F)n2n1] | (R)-(4-(7-(difluoromethyl)pyrazolo[1,5-a]pyridin-2-y]l)-6,7-dihydro-1H-imidazo[4,5-c]pyridin-5(4H)-yl)(5-(pyrimidin-2-yl)-1,3,4-oxadiazol-2-yl)methanone |
| 1499 | 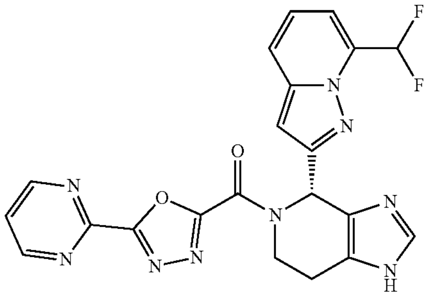 [SMILES: O=C(c1nnc(-c2ncccn2)o1)N1CCc2[nH]cnc2[C@H]1c1cc2cccc(C(F)F)n2n1] | (S)-(4-(7-(difluoromethyl)pyrazolo[1,5-a]pyridin-2-yl)-6,7-dihydro-1H-imidazo[4,5-c]pyridin-5(4H)-yl)(5-(pyrimidin-2-yl)-1,3,4-oxadiazol-2-yl)methanone |
| 1500 | 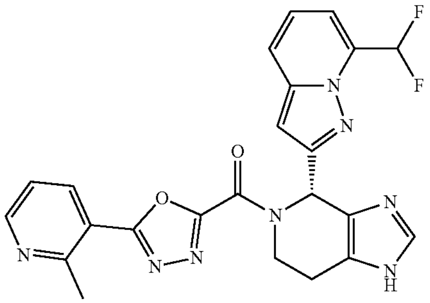 [SMILES: Cc1ncccc1-c1nnc(C(=O)N2CCc3[nH]cnc3[C@H]2c2cc3cccc(C(F)F)n3n2)o1] | (S)-(4-(7-(difluoromethyl)pyrazolo[1,5-a]pyridin-2-yl)-6,7-dihydro-1H-imidazo[4,5-c]pyridin-5(4H)-yl)(5-(2-methylpyridin-3-yl)-1,3,4-oxadiazol-2-yl)methanone |

TABLE 1-continued

| Ex. # | Structure | Name |
|---|---|---|
| | Pyrazolo[1,5-a]pyridines | |
| 1501 | 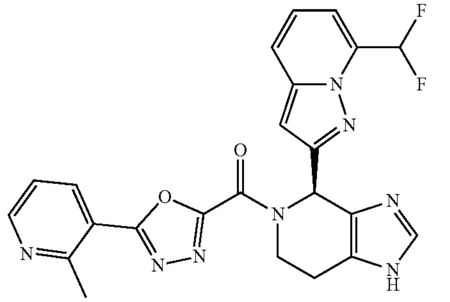 [SMILES: Cc1ncccc1-c1nnc(C(=O)N2CCc3[nH]cnc3[C@@H]2c2cc3cccc(C(F)F)n3n2)o1] | (R)-(4-(7-(difluoromethyl) pyrazolo[1,5-a]pyridin-2-yl)-6,7-dihydro-1H-imidazo [4,5-c]pyridin-5(4H)-yl)(5-(2-methylpyridin-3-yl)-1,3,4-oxadiazol-2-yl)methanone |
| 1502 | 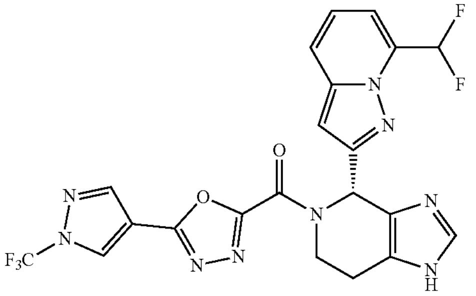 [SMILES: O=C(c1nnc(-c2cnn(C(F)(F)F)c2)o1)N1CCc2[nH]cnc2[C@H]1c1cc2cccc(C(F)F)n2n1] | (S)-(4-(7-(difluoromethyl) pyrazolo[1,5-a]pyridin-2-yl)-6,7-dihydro-1H-imidazo [4,5-c]pyridin-5(4H)-yl)(5-(1-(trifluoromethyl)-1H-pyrazol-4-yl)-1,3,4-oxadiazol-2-yl)methanone |
| 1503 | 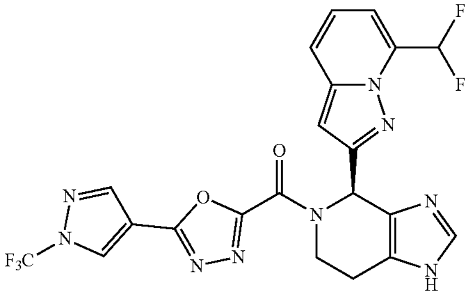 [SMILES: O=C(c1nnc(-c2cnn(C(F)(F)F)c2)o1)N1CCc2[nH]cnc2[C@@H]1c1cc2cccc(C(F)F)n2n1] | (R)-(4-(7-(difluoromethyl) pyrazolo[1,5-a]pyridin-2-yl)-6,7-dihydro-1H-imidazo [4,5-c]pyridin-5(4H)-yl)(5-(1-(trifluoromethyl)-1H-pyrazol-4-yl)-1,3,4-oxadiazol-2-yl)methanone |
| 1504 | 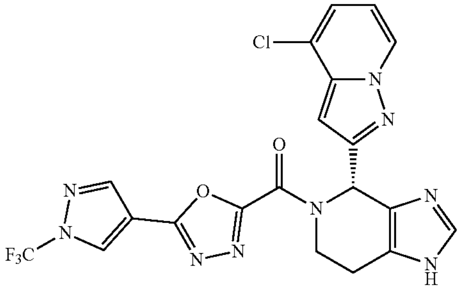 | (S)-(4-(4-chloropyrazolo [1,5-a]pyridin-2-yl)-6,7-dihydro-1H-imidazo[4,5-c] pyridin-5(4H)-yl)(5-(1-(trifluoromethyl)-1H-pyrazol-4-yl)-1,3,4-oxadiazol-2-yl)methanone |
| 1505 | 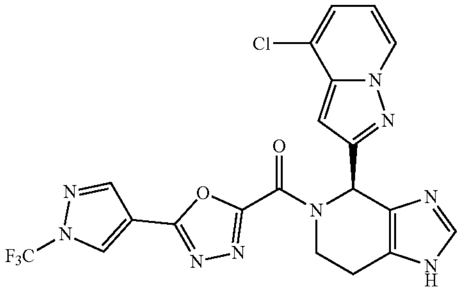 [SMILES: O=C(c1nnc(-c2cnn(C(F)(F)F)c2)o1)N1CCc2[nH]cnc2[C@@H]1c1cc2c(Cl)cccn2n1] | (R)-(4-(4-chloropyrazolo [1,5-a]pyridin-2-yl)-6,7-dihydro-1H-imidazo[4,5-c] pyridin-5(4H)-yl)(5-(1-(trifluoromethyl)-1H-pyrazol-4-yl)-1,3,4-oxadiazol-2-yl)methanonepyrazol-4-yl)-1,3,4-oxadiazol-2-yl)methanone |

TABLE 1-continued

| Ex. # | Structure | Name |
|---|---|---|
| | Pyrazolo[1,5-a]pyridines | |
| 1506 | 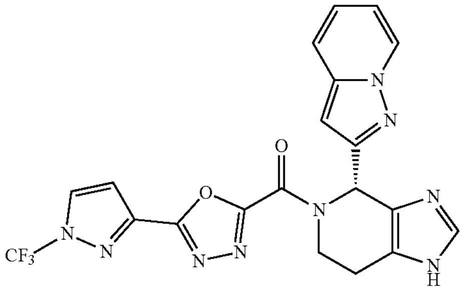 [SMILES: O=C(c1nnc(-c2ccn(C(F)(F)F)n2)o1)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1507 | 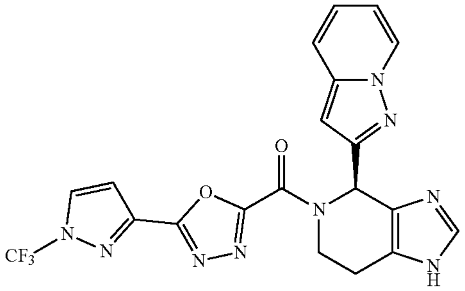 [SMILES: O=C(c1nnc(-c2ccn(C(F)(F)F)n2)o1)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1508 | 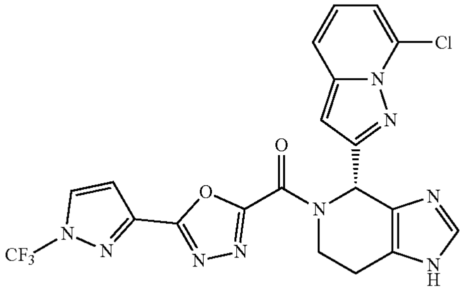 [SMILES: O=C(c1nnc(-c2ccn(C(F)(F)F)n2)o1)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1509 | 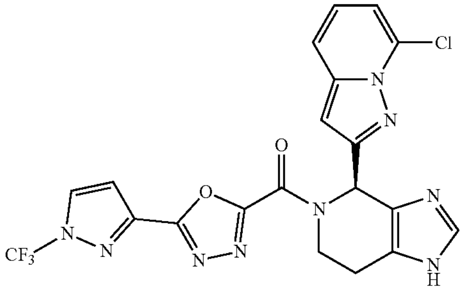 [SMILES: O=C(c1nnc(-c2ccn(C(F)(F)F)n2)o1)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1510 | 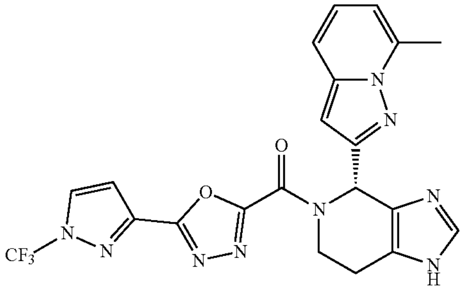 [SMILES: Cc1cccc2cc([C@@H]3c4nc[nH]c4CCN3C(=O)c3nnc(-c4ccn(C(F)(F)F)n4)o3)nn12] | (S)-(4-(7-methylpyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |

TABLE 1-continued

| Ex. # | Structure | Name |
|---|---|---|
| | Pyrazolo[1,5-a]pyridines | |
| 1511 | 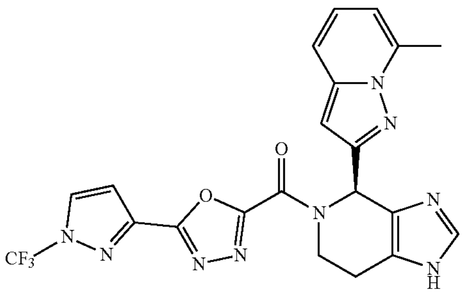 [SMILES: Cc1cccc2cc([C@H]3c4nc[nH]c4CCN3C(=O)c3nnc(-c4ccn(C(F)(F)F)n4)o3)nn12] | (R)-(4-(7-methylpyrazolo[1,5-a]pyridin-2-yl)-6,7-dihydro-1H-imidazo[4,5-c]pyridin-5(4H)-yl)(5-(1-(trifluoromethyl)-1H-pyrazol-3-yl)-1,3,4-oxadiazol-2-yl)methanone |
| 1512 | 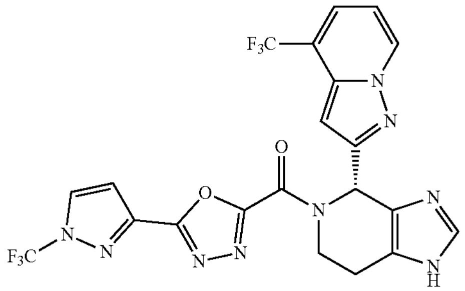 [SMILES: O=C(c1nnc(-c2ccn(C(F)(F)F)n2)o1)N1CCc2[nH]cnc2[C@H]1c1cc2c(C(F)(F)F)cccn2n1] | (S)-(5-(1-(trifluoromethyl)-1H-pyrazol-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1513 | 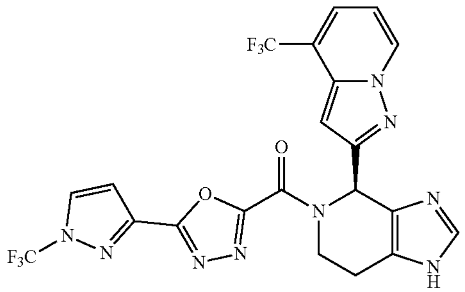 [SMILES: O=C(c1nnc(-c2ccn(C(F)(F)F)n2)o1)N1CCc2[nH]cnc2[C@@H]1c1cc2c(C(F)(F)F)cccn2n1] | (R)-(5-(1-(trifluoromethyl)-1H-pyrazol-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1514 | 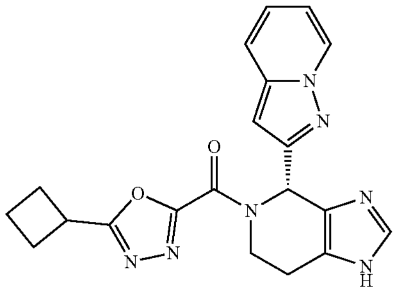 [SMILES: O=C(c1nnc(C2CCC2)o1)N1CCc2[nH]cnc2[C@H]1c1cc2ccccn2n1] | (S)-(5-cyclobutyl-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 1515 | 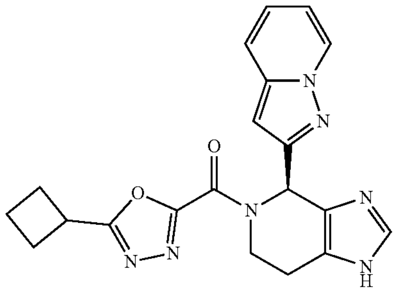 [SMILES: O=C(c1nnc(C2CCC2)o1)N1CCc2[nH]cnc2[C@@H]1c1cc2ccccn2n1] | (R)-(5-cyclobutyl-1,3,4-oxadiazol-2-yl)(4-(pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1516 | 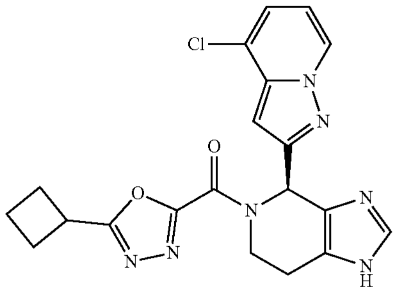 | (R)-(4-(4-chloropyrazolo [1,5-a]pyridin-2-yl)-6,7-dihydro-1H-imidazo [4,5-c]pyridin-5(4H)-yl)(5-cyclobutyl-1,3,4-oxadiazol-2-yl)methanone |
| 1517 | 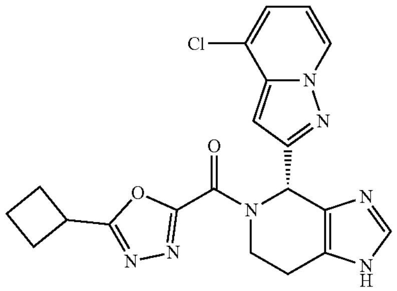 | (S)-(4-(4-chloropyrazolo [1,5-a]pyridin-2-yl)-6,7-dihydro-1H-imidazo[4,5-c] pyridin-5(4H)-yl)(5-cyclobutyl-1,3,4-oxadiazol-2-yl)methanone |
| 1518 | 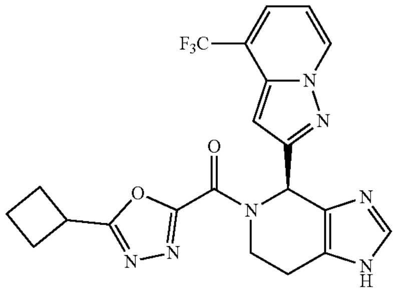 [SMILES: O=C(c1nnc(C2CCC2)o1)N1CCc2[nH]cnc2[C@@H]1c1cc2c(C(F)(F)F)cccn2n1] | (R)-(5-cyclobutyl-1,3,4-oxadiazol-2-yl)(4-(4-(trifluoromethyl)pyrazolo [1,5-a]pyridin-2-yl)-6,7-dihydro-1H-imidazo[4,5-c] pyridin-5(4H)-yl)methanone |
| 1519 | 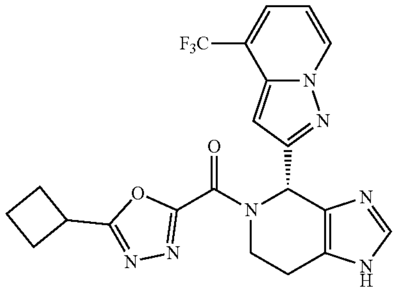 | (S)-(5-cyclobutyl-1,3,4-oxadiazol-2-yl)(4-(4-(trifluoromethyl)pyrazolo [1,5-a]pyridin-2-yl)-6,7-dihydro-1H-imidazo[4,5-c] pyridin-5(4H)-yl)methanone |
| 1520 | 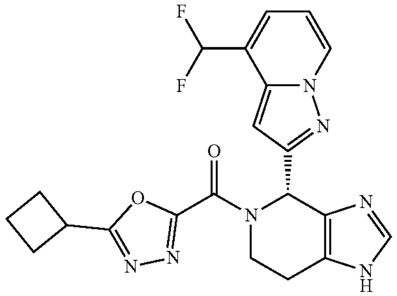 [SMILES: O=C(c1nnc(C2CCC2)o1)N1CCc2[nH]cnc2[C@H]1c1cc2c(C(F)F)cccn2n1] | (S)-(5-cyclobutyl-1,3,4-oxadiazol-2-yl)(4-(4-(difluoromethyl)pyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 1521 | 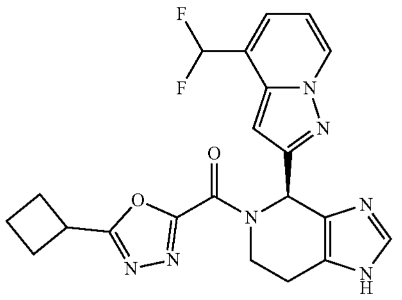 [SMILES: O=C(c1nnc(C2CCC2)o1)N1CCc2[nH]cnc2[C@@H]1c1cc2c(C(F)F)cccn2n1] | (R)-(5-cyclobutyl-1,3,4-oxadiazol-2-yl)(4-(4-(difluoromethyl)pyrazolo[1,5-a]pyridin-2-yl)-6,7-dihydro-1H-imidazo[4,5-c]pyridin-5(4H)-yl)methanone |
| 1522 | 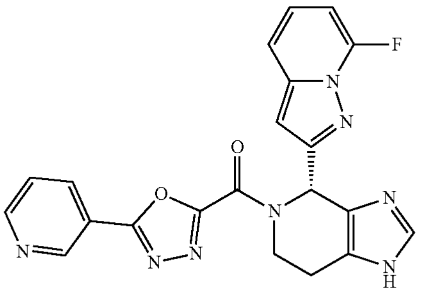 | (S)-(4-(7-fluoropyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1523 | 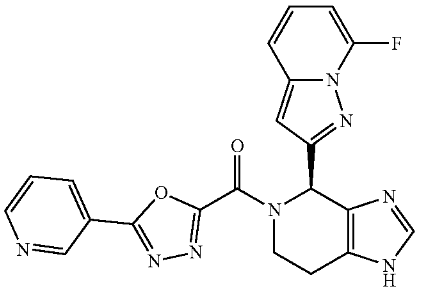 [SMILES: O=C(c1nnc(-c2cccnc2)o1)N1CCc2[nH]cnc2[C@@H]1c1cc2cccc(F)n2n1] | (R)-(4-(7-fluoropyrazolo[1,5-a]pyridin-2-yl)-6,7-dihydro-1H-imidazo[4,5-c]pyridin-5(4H)-yl)(5-(pyridin-3-yl)-1,3,4-oxadiazol-2-yl)methanone |
| 1524 | 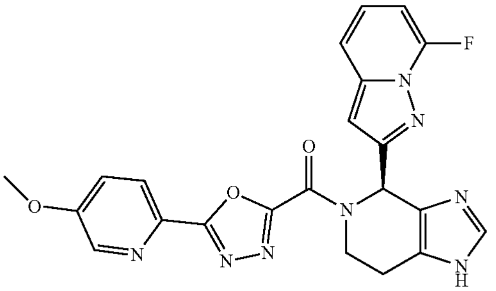 [SMILES: COc1ccc(-c2nnc(C(=O)N3CCc4[nH]cnc4[C@@H]3c3cc4cccc(F)n4n3)o2)nc1] | (R)-(4-(7-fluoropyrazolo[1,5-a]pyridin-2-yl)-6,7-dihydro-1H-imidazo[4,5-c]pyridin-5(4H)-yl)(5-(5-methoxypyridin-2-yl)-1,3,4-oxadiazol-2-yl)methanone |
| 1525 | 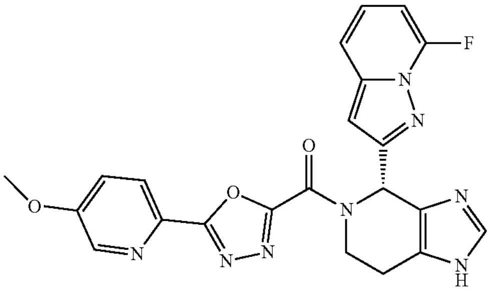 [SMILES: COc1ccc(-c2nnc(C(=O)N3CCc4[nH]cnc4[C@H]3c3cc4cccc(F)n4n3)o2)nc1] | (S)-(4-(7-fluoropyrazolo[1,5-a]pyridin-2-yl)-6,7-dihydro-1H-imidazo[4,5-c]pyridin-5(4H)-yl)(5-(5-methoxypyridin-2-yl)-1,3,4-oxadiazol-2-yl)methanone |

TABLE 1-continued

| Pyrazolo[1,5-a]pyridines | | |
|---|---|---|
| Ex. # | Structure | Name |
| 1526 | 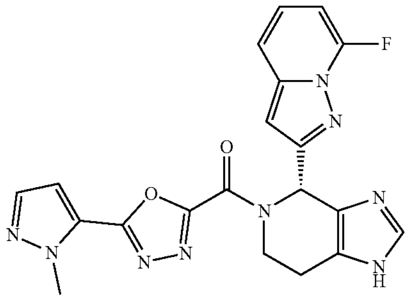 [SMILES: Cn1nccc1-c1nnc(C(=O)N2CCc3[nH]cnc3[C@H]2c2cc3cccc(F)n3n2)o1] | (S)-(4-(7-fluoropyrazolo[1,5-a]pyridin-2-yl)-6,7-dihydro-1H-imidazo[4,5-c]pyridin-5(4H)-yl)(5-(1-methyl-1H-pyrazol-5-yl)-1,3,4-oxadiazol-2-yl)methanone |
| 1527 | 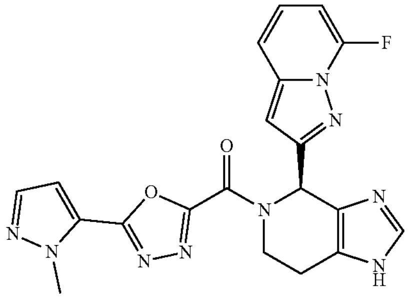 [SMILES: Cn1nccc1-c1nnc(C(=O)N2CCc3[nH]cnc3[C@@H]2c2cc3cccc(F)n3n2)o1] | (R)-(4-(7-fluoropyrazolo[1,5-a]pyridin-2-y]l)-6,7-dihydro-1H-imidazo[4,5-c]pyridin-5(4H)-yl)(5-(1-methyl-1H-pyrazol-5-yl)-1,3,4-oxadiazol-2-yl)methanone |
| 1528 | 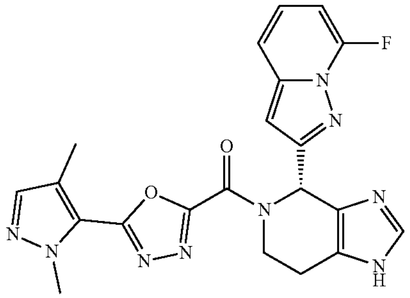 [SMILES: Cc1cnn(C)c1-c1nnc(C(=O)N2CCc3[nH]cnc3[C@H]2c2cc3cccc(F)n3n2)o1] | (S)-(5-(1,4-dimethyl-1H-pyrazol-5-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1529 | 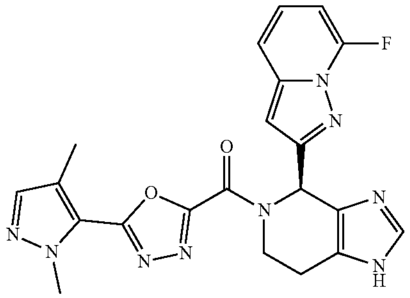 [SMILES: Cc1cnn(C)c1-c1nnc(C(=O)N2CCc3[nH]cnc3[C@@H]2c2cc3cccc(F)n3n2)o1] | (R)-(5-(1,4-dimethyl-1H-pyrazol-5-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1530 | 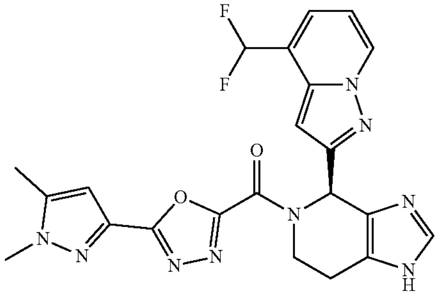 [SMILES: Cc1cc(-c2nnc(C(=O)N3CCc4[nH]cnc4[C@@H]3c3cc4c(C(F)F)cccn4n3)o2)nn1C] | (R)-(4-(4-(difluoromethyl)pyrazolo[1,5-a]pyridin-2-yl)-6,7-dihydro-1H-imidazo[4,5-c]pyridin-5(4H)-yl)(5-(1,5-dimethyl-1H-pyrazol-3-yl)-1,3,4-oxadiazol-2-yl)methanone |

TABLE 1-continued

| Ex. # | Structure | Name |
|---|---|---|
| Pyrazolo[1,5-a]pyridines | | |
| 1531 | 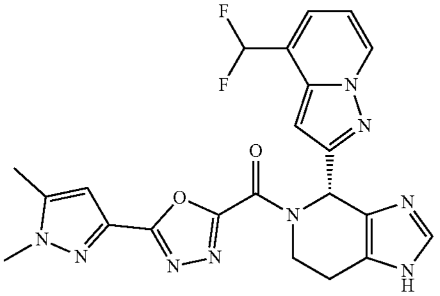 [SMILES: Cc1cc(-c2nnc(C(=O)N3CCc4[nH]cnc4[C@H]3c3cc4c(C(F)F)cccn4n3)o2)nn1C] | (S)-(4-(4-(difluoromethyl) pyrazolo[1,5-a]pyridin-2-yl)-6,7-dihydro-1H-imidazo[4,5-c] pyridin-5(4H)-yl)(5-(1,5-dimethyl-1H-pyrazol-3-yl)-1,3,4-oxadiazol-2-yl)methanone |
| 1532 | 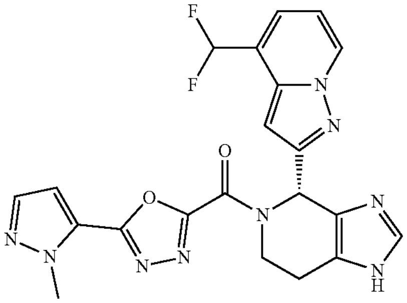 [SMILES: Cn1nccc1-c1nnc(C(=O)N2CCc3[nH]cnc3[C@H]2c2cc3c(C(F)F)cccn3n2)o1] | (S)-(4-(4-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-5-yl)-1,3,4-oxadiazol-2-yl)methanone |
| 1533 | 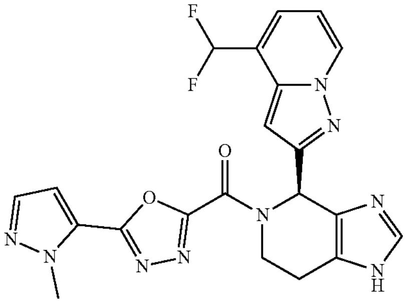 [SMILES: Cn1nccc1-c1nnc(C(=O)N2CCc3[nH]cnc3[C@@H]2c2cc3c(C(F)F)cccn3n2)o1] | (R)-(4-(4-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-5-yl)-1,3,4-oxadiazol-2-yl)methanone |
| 1534 | 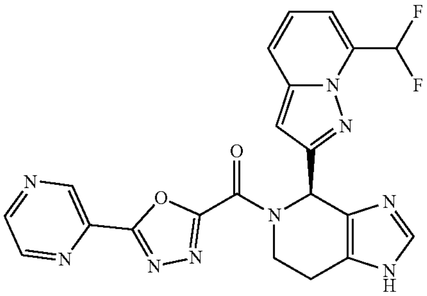 [SMILES: O=C(c1nnc(-c2cnccn2)o1)N1CCc2[nH]cnc2[C@@H]1c1cc2cccc(C(F)F)n2n1] | (R)-(4-(7-(difluoromethyl) pyrazolo[1,5-a]pyridin-2-yl)-6,7-dihydro-1H-imidazo [4,5-c]pyridin-5(4H)-yl)(5-(pyrazin-2-yl)-1,3,4-oxadiazol-2-yl)methanone |
| 1535 | 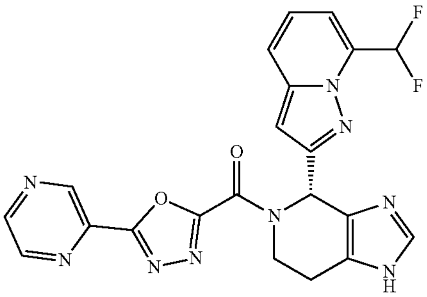 [SMILES: O=C(c1nnc(-c2cnccn2)o1)N1CCc2[nH]cnc2[C@H]1c1cc2cccc(C(F)F)n2n1] | (S)-(4-(7-(difluoromethyl) pyrazolo[1,5-a]pyridin-2-yl)-6,7-dihydro-1H-imidazo[4,5-c] pyridin-5(4H)-yl)(5-(pyrazin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1536 | 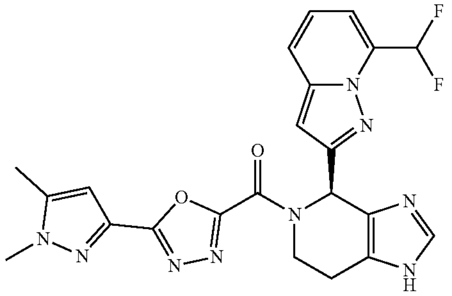 [SMILES: Cc1cc(-c2nnc(C(=O)N3CCc4[nH]cnc4[C@@H]3c3cc4cccc(C(F)F)n4n3)o2)nn1C] | (R)-(4-(7-(difluoromethyl) pyrazolo[1,5-a]pyridin-2-yl)-6,7-dihydro-1H-imidazo[4,5-c] pyridin-5(4H)-yl)(5-(1,5-dimethyl-1H-pyrazol-3-yl)-1,3,4-oxadiazol-2-yl)methanone |
| 1537 | 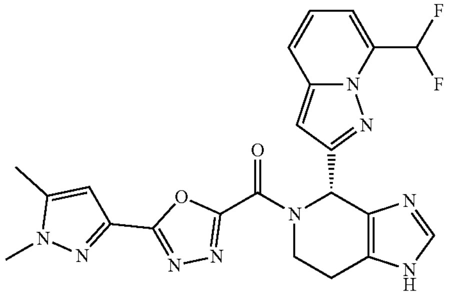 [SMILES: Cc1cc(-c2nnc(C(=O)N3CCc4[nH]cnc4[C@H]3c3cc4cccc(C(F)F)n4n3)o2)nn1C] | (S)-(4-(7-(difluoromethyl) pyrazolo[1,5-a]pyridin-2-yl)-6,7-dihydro-1H-imidazo[4,5-c] pyridin-5(4H)-yl)(5-(1,5-dimethyl-1H-pyrazol-3-yl)-1,3,4-oxadiazol-2-yl)methanone |
| 1538 | 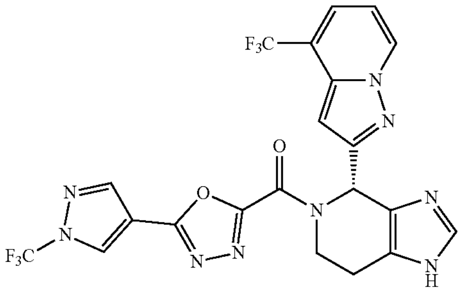 | (S)-(5-(1-(trifluoromethyl)-1H-pyrazol-4-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1539 | 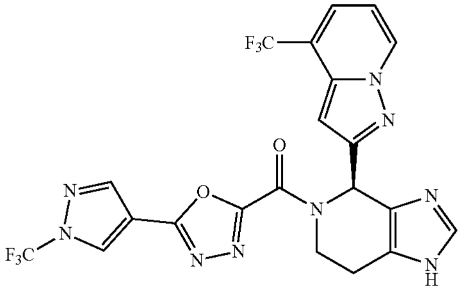 | (R)-(5-(1-(trifluoromethyl)-1H-pyrazol-4-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1540 | 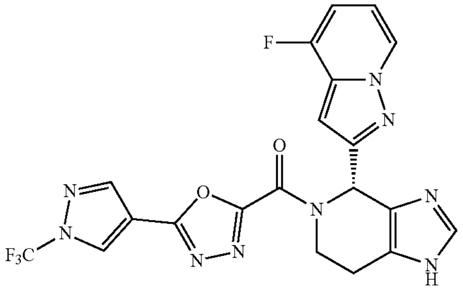 | (S)-(4-(4-fluoropyrazolo [1,5-a]pyridin-2-yl)-6,7-dihydro-1H-imidazo[4,5-c] pyridin-5(4H)-yl)(5-(1-(trifluoromethyl)-1H-pyrazol-4-yl)-1,3,4-oxadiazol-2-yl)methanone |

TABLE 1-continued

| Pyrazolo[1,5-a]pyridines | | |
|---|---|---|
| Ex. # | Structure | Name |
| 1541 | 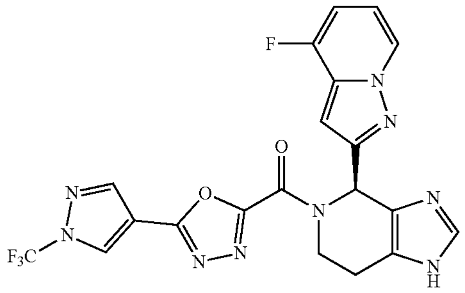 | (R)-(4-(4-fluoropyrazolo [1,5-a]pyridin-2-yl)-6,7-dihydro-1H-imidazo[4,5-c] pyridin-5(4H)-yl)(5-(1-(trifluoromethyl)-1H-pyrazol-4-yl)-1,3,4-oxadiazol-2-yl)methanone |
| 1542 | 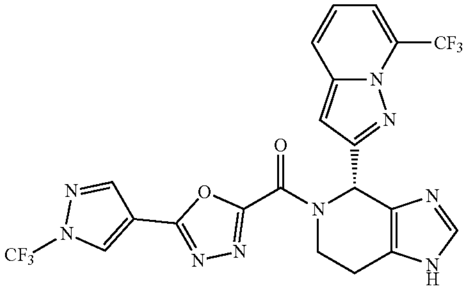 [SMILES: O=C(c1nnc(-c2cnn(C(F)(F)F)c2)o1)N1CCc2[nH]cnc2[C@H]1c1cc2cccc(C(F)(F)F)n2n1] | (S)-(5-(1-(trifluoromethyl)-1H-pyrazol-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1543 | 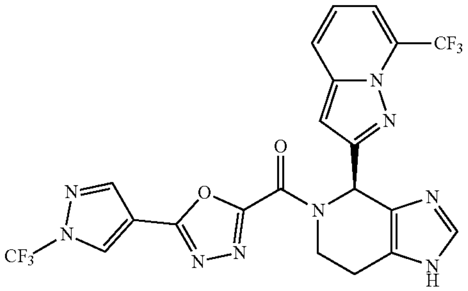 [SMILES: O=C(c1nnc(-c2cnn(C(F)(F)F)c2)o1)N1CCc2[nH]cnc2[C@@H]1c1cc2cccc(C(F)(F)F)n2n1] | (R)-(5-(1-(trifluoromethyl)-1H-pyrazol-3-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 1544 | 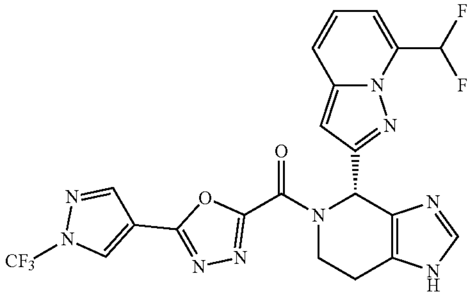 [SMILES: O=C(c1nnc(-c2cnn(C(F)(F)F)c2)o1)N1CCc2[nH]cnc2[C@H]1c1cc2cccc(C(F)F)n2n1] | (S)-(4-(7-(difluoromethyl) pyrazolo[1,5-a]pyridin-2-yl)-6,7-dihydro-1H-imidazo [4,5-c]pyridin-5(4H)-yl)(5-(1-(trifluoromethyl)-1H-pyrazol-3-yl)-1,3,4-oxadiazol-2-yl)methanone |
| 1545 | 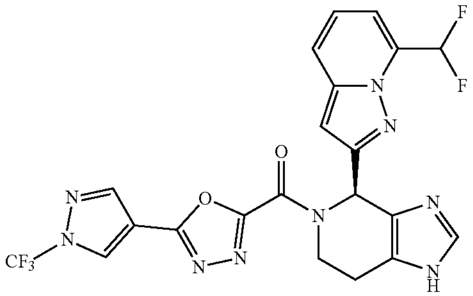 [SMILES: O=C(c1nnc(-c2cnn(C(F)(F)F)c2)o1)N1CCc2[nH]cnc2[C@@H]1c1cc2cccc(C(F)F)n2n1] | (R)-(4-(7-(difluoromethyl) pyrazolo[1,5-a]pyridin-2-y]l)-6,7-dihydro-1H-imidazo [4,5-c]pyridin-5(4H)-yl)(5-(1-(trifluoromethyl)-1H-pyrazol-3-yl)-1,3,4-oxadiazol-2-yl)methanone |

TABLE 1-continued

| Pyrazolo[1,5-a]pyridines | | |
|---|---|---|
| Ex. # | Structure | Name |
| 1546 | 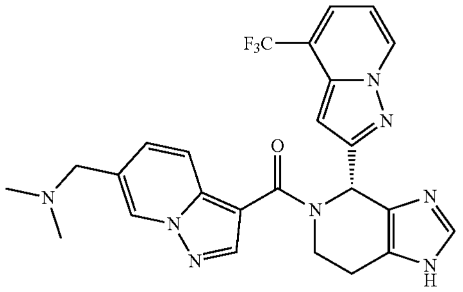 | (S)-(6-((dimethylamino) methyl)pyrazolo[1,5-a]pyridin-3-yl)(4-(4-(trifluoromethyl) pyrazolo[1,5-a]pyridin-2-yl)-6,7-dihydro-1H-imidazo [4,5-c]pyridin-5(4H)-yl)methanone |
| 1547 | 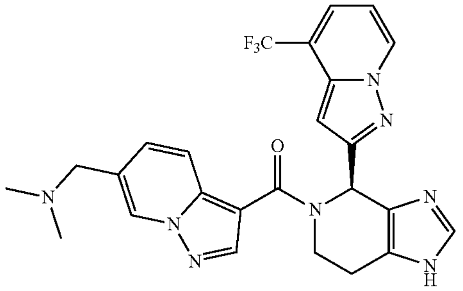 [SMILES: CN(C)Cc1ccc2c(C(=O)N3CCc4[nH]cnc4[C@@H]3c3cc4c(C(F)(F)F)cccn4n3)cnn2c1] | (R)-(6-((dimethylamino) methyl)pyrazolo[1,5-a]pyridin-3-yl)(4-(4-(trifluoromethyl) pyrazolo[1,5-a]pyridin-2-yl)-6,7-dihydro-1H-imidazo [4,5-c]pyridin-5(4H)-yl)methanone |
| 1548 | 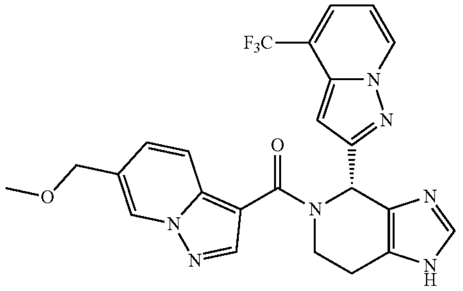 [SMILES: COCc1ccc2c(C(=O)N3CCc4[nH]cnc4[C@H]3c3cc4c(C(F)(F)F)cccn4n3)cnn2c1] | (S)-(6-(methoxymethyl) pyrazolo[1,5-a]pyridin-3-yl)(4-(4-(trifluoromethyl)pyrazolo [1,5-a]pyridin-2-yl)-6,7-dihydro-1H-imidazo[4,5-c] pyridin-5(4H)-yl)methanone |
| 1549 | 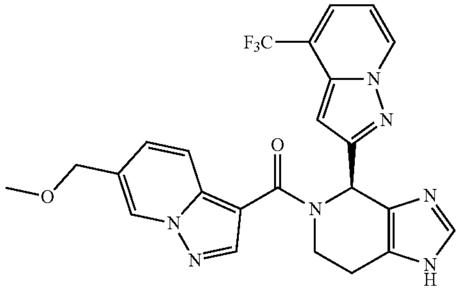 | (R)-(6-(methoxymethyl)pyrazolo [1,5-a]pyridin-3-y]l)(4-(4-(trifluoromethyl)pyrazolo [1,5-a]pyridin-2-yl)-6,7-dihydro-1H-imidazo[4,5-c] pyridin-5(4H)-yl)methanone |
| 1550 | 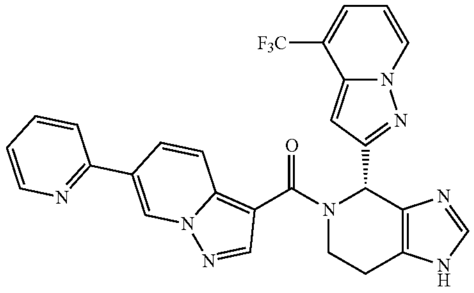 [SMILES: O=C(c1cnn2cc(-c3ccccn3)ccc12)N1CCc2[nH]cnc2[C@H]1c1cc2c(C(F)(F)F)cccn2n1] | (S)-(6-(pyridin-2-yl)pyrazolo [1,5-a]pyridin-3-yl)(4-(4-(trifluoromethyl)pyrazolo [1,5-a]pyridin-2-yl)-6,7-dihydro-1H-imidazo[4,5-c] pyridin-5(4H)-yl)methanone |

TABLE 1-continued

| Ex. # | Structure | Name |
|---|---|---|
| | Pyrazolo[1,5-a]pyridines | |
| 1551 | 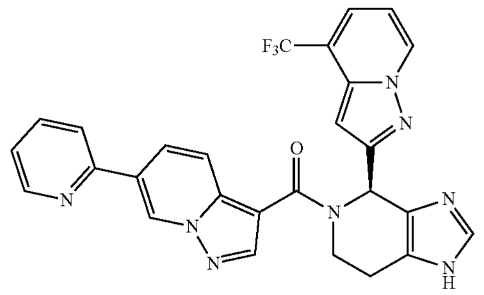 [SMILES: O=C(c1cnn2cc(-c3ccccn3)ccc12)N1CCc2[nH]cnc2[C@@H]1c1cc2c(C(F)(F)F)cccn2n1] | (R)-(6-(pyridin-2-yl)pyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 1552 | 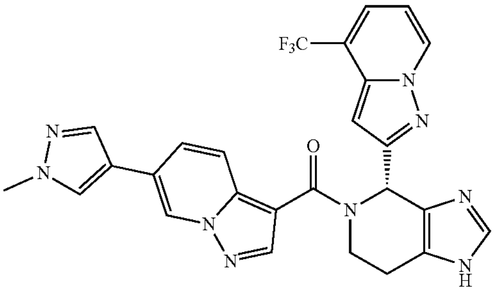 | (S)-(6-(1-methyl-1H-pyrazol-4-yl)pyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 1553 | 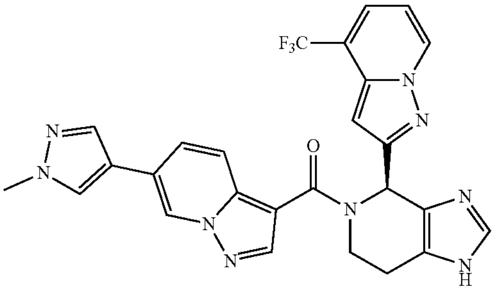 | (R)-(6-(1-methyl-1H-pyrazol-4-yl)pyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 1554 | 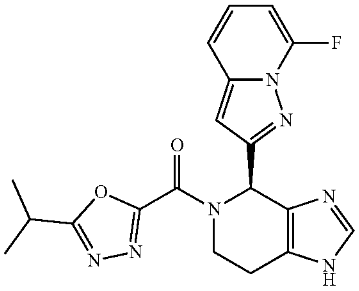 [SMILES: CC(C)c1nnc(C(=O)N2CCc3[nH]cnc3[C@@H]2c2cc3cccc(F)n3n2)o1] | (R)-(4-(7-fluoropyrazolo[1,5-a]pyridin-2-y]l)-6,7-dihydro-1H-imidazo[4,5-c]pyridin-5(4H)-yl)(5-isopropyl-1,3,4-oxadiazol-2-yl)methanone |
| 1555 | 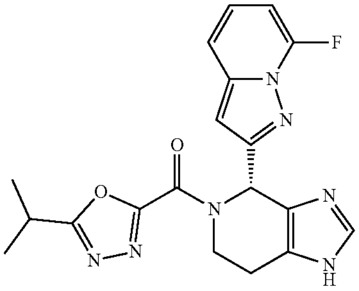 [SMILES: CC(C)c1nnc(C(=O)N2CCc3[nH]cnc3[C@H]2c2cc3cccc(F)n3n2)o1] | (S)-(4-(7-fluoropyrazolo[1,5-a]pyridin-2-yl)-6,7-dihydro-1H-imidazo[4,5-c]pyridin-5(4H)-yl)(5-isopropyl-1,3,4-oxadiazol-2-yl)methanone |

TABLE 1-continued

| Ex. # | Structure | Name |
|---|---|---|
| Pyrazolo[1,5-a]pyridines | | |
| 1556 | 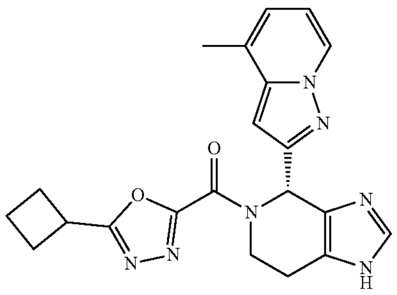 [SMILES: Cc1cccn2nc([C@@H]3c4nc[nH]c4CCN3C(=O)c3nnc(C4CCC4)o3)cc12] | (S)-(5-cyclobutyl-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1557 | 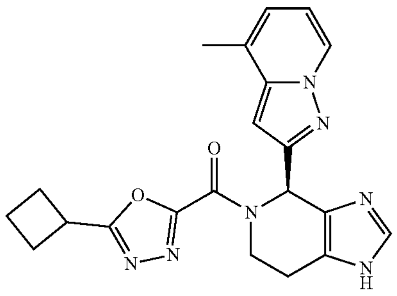 [SMILES: Cc1cccn2nc([C@H]3c4nc[nH]c4CCN3C(=O)c3nnc(C4CCC4)o3)cc12] | (R)-(5-cyclobutyl-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1558 | 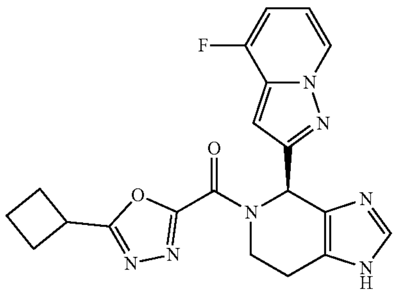 [SMILES: O=C(c1nnc(C2CCC2)o1)N1CCc2[nH]cnc2[C@@H]1c1cc2c(F)cccn2n1] | (R)-(5-cyclobutyl-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 1559 | 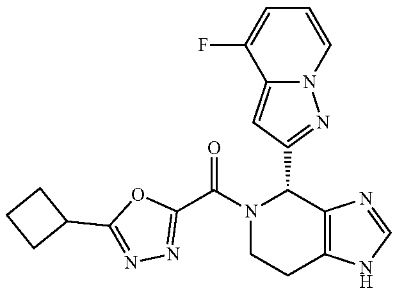 [SMILES: O=C(c1nnc(C2CCC2)o1)N1CCc2[nH]cnc2[C@H]1c1cc2c(F)cccn2n1] | (S)-(5-cyclobutyl-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 1560 | 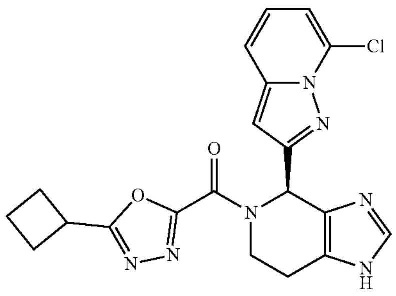 [SMILES: O=C(c1nnc(C2CCC2)o1)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(5-cyclobutyl-1,3,4-oxadiazol-2-yl)methanone |

TABLE 1-continued

Pyrazolo[1,5-a]pyridines

| Ex. # | Structure | Name |
|---|---|---|
| 1561 | 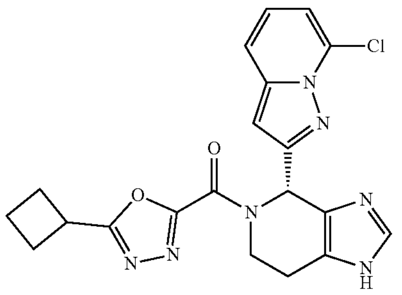 [SMILES: O=C(c1nnc(C2CCC2)o1)N1CCc2[nH]cnc2[C@H]1c1cc2cccc(Cl)n2n1] | (S)-(4-(7-chloropyrazolo [1,5-a]pyridin-2-yl)-6,7-dihydro-1H-imidazo [4,5-c]pyridin-5(4H)-yl)(5-cyclobutyl-1,3,4-oxadiazol-2-yl)methanone |
| 1562 | 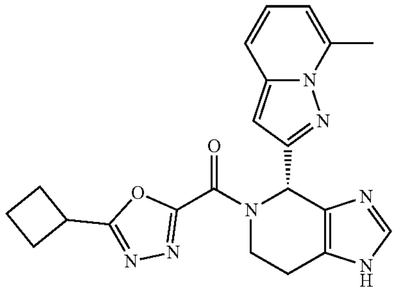 [SMILES: Cc1cccc2cc([C@@H]3c4nc[nH]c4CCN3C(=O)c3nnc(C4CCC4)o3)nn12] | (S)-(5-cyclobutyl-1,3,4-oxadiazol-2-yl)(4-(7-methylpyrazolo[1,5-a] pyridin-2-yl)-6,7-dihydro-1H-imidazo[4,5-c]pyridin-5(4H)-yl)methanone |
| 1563 | 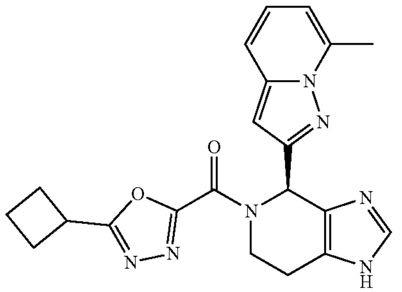 [SMILES: Cc1cccc2cc([C@H]3c4nc[nH]c4CCN3C(=O)c3nnc(C4CCC4)o3)nn12] | (R)-(5-cyclobutyl-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 1564 | 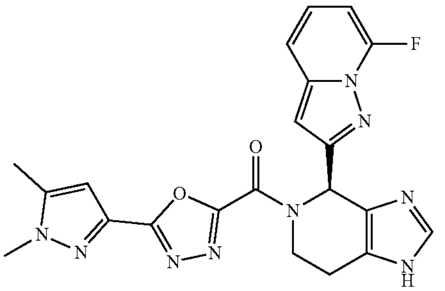 [SMILES: Cc1cc(-c2nnc(C(=O)N3CCc4[nH]cnc4[C@@H]3c3cc4cccc(F)n4n3)o2)nn1C] | (R)-(5-(1,5-dimethyl-1H-pyrazol-3-yl)-1,3,4-oxadiazol-2-yl)(4-(7-fluoropyrazolo [1,5-a]pyridin-2-yl)-6,7-dihydro-1H-imidazo[4,5-c] pyridin-5(4H)-yl)methanone |
| 1565 | 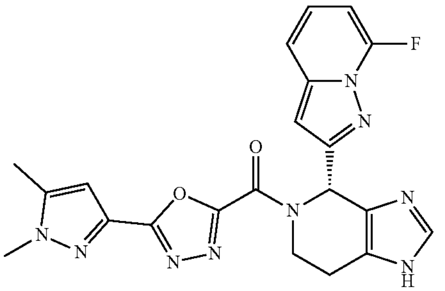 [SMILES: Cc1cc(-c2nnc(C(=O)N3CCc4[nH]cnc4[C@H]3c3cc4cccc(F)n4n3)o2)nn1C] | (S)-(5-(1,5-dimethyl-1H-pyrazol-3-yl)-1,3,4-oxadiazol-2-yl)(4-(7-fluoropyrazolo[1,5-a] pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1566 | 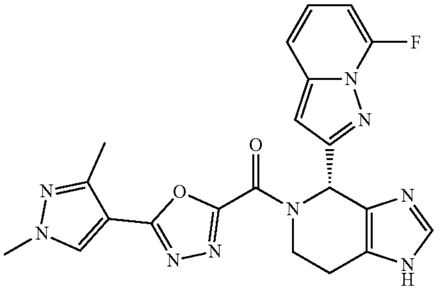 [SMILES: Cc1nn(C)cc1-c1nnc(C(=O)N2CCc3[nH]cnc3[C@H]2c2cc3cccc(F)n3n2)o1] | (S)-(5-(1,3-dimethyl-1H-pyrazol-4-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1567 | 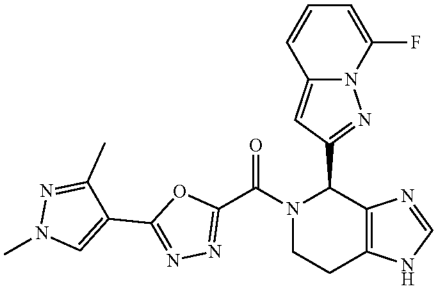 [SMILES: Cc1nn(C)cc1-c1nnc(C(=O)N2CCc3[nH]cnc3[C@@H]2c2cc3cccc(F)n3n2)o1] | (R)-(5-(1,3-dimethyl-1H-pyrazol-4-yl)-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1568 | 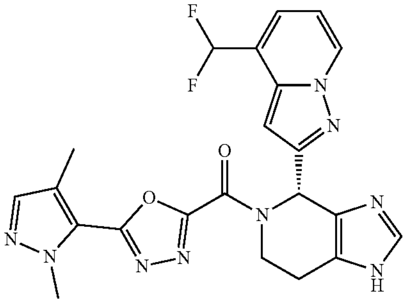 [SMILES: Cc1cnn(C)c1-c1nnc(C(=O)N2CCc3[nH]cnc3[C@H]2c2cc3c(C(F)F)cccn3n2)o1] | (S)-(4-(4-(difluoromethyl)pyrazolo[1,5-a]pyridin-2-yl)-6,7-dihydro-1H-imidazo[4,5-c]pyridin-5(4H)-yl)(5-(1,4-dimethyl-1H-pyrazol-5-yl)-1,3,4-oxadiazol-2-yl)methanone |
| 1569 | 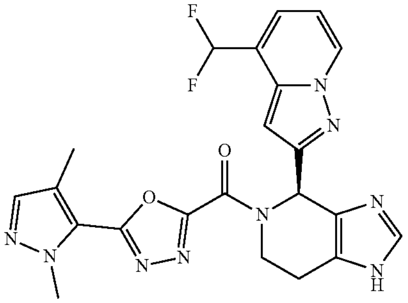 [SMILES: Cc1cnn(C)c1-c1nnc(C(=O)N2CCc3[nH]cnc3[C@@H]2c2cc3c(C(F)F)cccn3n2)o1] | (R)-(4-(4-(difluoromethyl)pyrazolo[1,5-a]pyridin-2-yl)-6,7-dihydro-1H-imidazo[4,5-c]pyridin-5(4H)-yl)(5-(1,4-dimethyl-1H-pyrazol-5-yl)-1,3,4-oxadiazol-2-yl)methanone |
| 1570 | 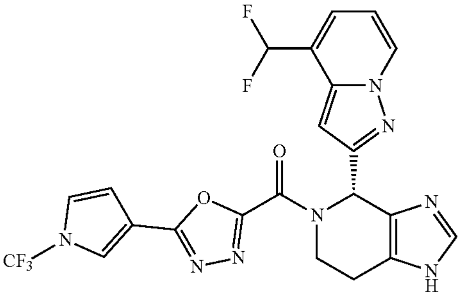 [SMILES: O=C(c1nnc(-c2ccn(C(F)(F)F)c2)o1)N1CCc2[nH]cnc2[C@H]1c1cc2c(C(F)F)cccn2n1] | (S)-(4-(4-(difluoromethyl)pyrazolo[1,5-a]pyridin-2-yl)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |

TABLE 1-continued

| Ex. # | Structure | Name |
|---|---|---|
| | Pyrazolo[1,5-a]pyridines | |
| 1571 | 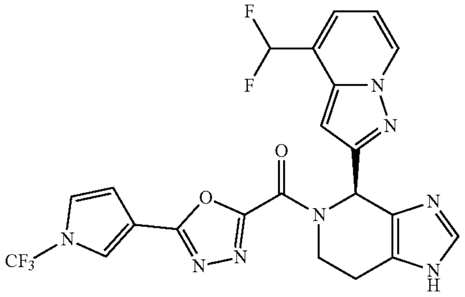 [SMILES: O=C(c1nnc(-c2ccn(C(F)(F)F)c2)o1)N1CCc2[nH]cnc2[C@@H]1c1cc2c(C(F)F)cccn2n1] | (R)-(4-(4-(difluoromethyl)pyrazolo[1,5-a]pyridin-2-yl)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |
| 1572 | 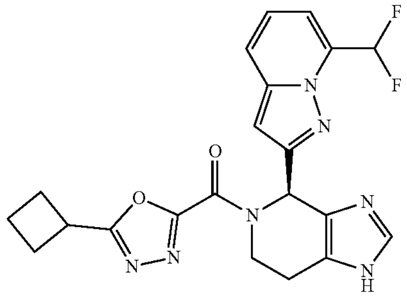 [SMILES: O=C(c1nnc(C2CCC2)o1)N1CCc2[nH]cnc2[C@@H]1c1cc2cccc(C(F)F)n2n1] | (R)-(5-cyclobutyl-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |
| 1573 | 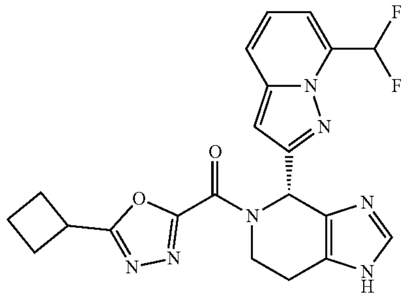 [SMILES: O=C(c1nnc(C2CCC2)o1)N1CCc2[nH]cnc2[C@H]1c1cc2cccc(C(F)F)n2n1] | (S)-(5-cyclobutyl-1,3,4-oxadiazol-2-yl)(4-(7-(difluoromethyl)pyrazolo[1,5-a]pyridin-2-yl)-6,7-dihydro-1H-imidazo[4,5-c]pyridin-5(4H)-yl)methanone |
| 1574 | 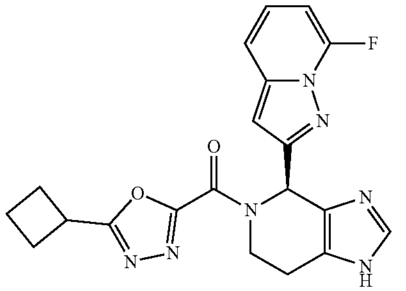 | (R)-(5-cyclobutyl-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |
| 1575 | 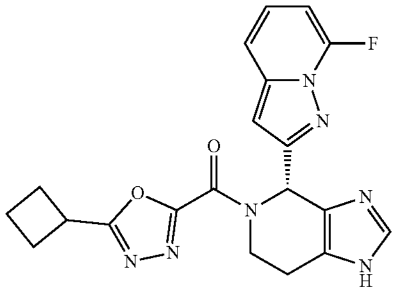 | (S)-(5-cyclobutyl-1,3,4-oxadiazol-2-yl)(4-(7-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1576 | 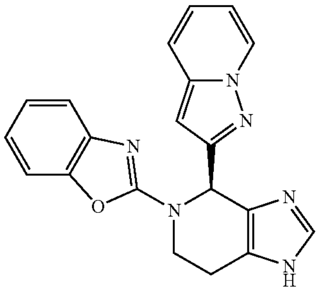 [SMILES: c1ccc2oc(N3CCc4[nH]cnc4[C@@H]3c3cc4ccccn4n3)nc2c1] | (R)-2-(4-(pyrazolo[1,5-a]pyridin-2-yl)-6,7-dihydro-1H-imidazo[4,5-c]pyridin-5(4H)-yl)benzo[d]oxazole |
| 1577 | 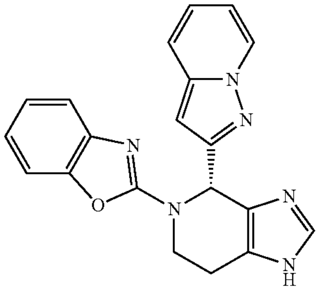 [SMILES: c1ccc2oc(N3CCc4[nH]cnc4[C@H]3c3cc4ccccn4n3)nc2c1] | (S)-2-(4-(pyrazolo[1,5-a]pyridin-2-yl)-6,7-dihydro-1H-imidazo[4,5-c]pyridin-5(4H)-yl)benzo[d]oxazole |
| 1578 | 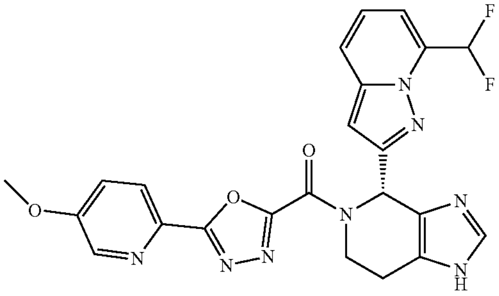 [SMILES: COc1ccc(-c2nnc(C(=O)N3CCc4[nH]cnc4[C@H]3c3cc4cccc(C(F)F)n4n3)o2)nc1] | (S)-(4-(7-(difluoromethyl)pyrazolo[1,5-a]pyridin-2-yl)-6,7-dihydro-1H-imidazo[4,5-c]pyridin-5(4H)-yl)(5-(5-methoxypyridin-2-yl)-1,3,4-oxadiazol-2-yl)methanone |
| 1579 | 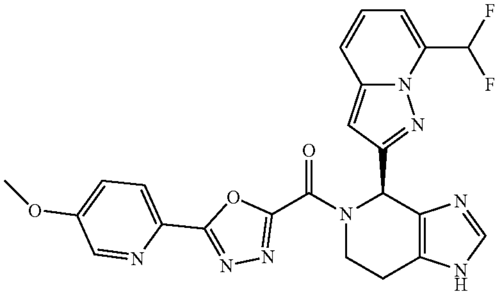 [SMILES: COc1ccc(-c2nnc(C(=O)N3CCc4[nH]cnc4[C@@H]3c3cc4cccc(C(F)F)n4n3)o2)nc1] | (R)-(4-(7-(difluoromethyl)pyrazolo[1,5-a]pyridin-2-yl)-6,7-dihydro-1H-imidazo[4,5-c]pyridin-5(4H)-yl)(5-(5-methoxypyridin-2-yl)-1,3,4-oxadiazol-2-yl)methanone |
| 1580 | 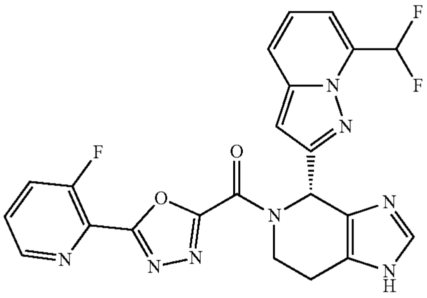 [SMILES: O=C(c1nnc(-c2ncccc2F)o1)N1CCc2[nH]cnc2[C@H]1c1cc2cccc(C(F)F)n2n1] | (S)-(4-(7-(difluoromethyl)pyrazolo[1,5-a]pyridin-2-yl)-6,7-dihydro-1H-imidazo[4,5-c]pyridin-5(4H)-yl)(5-(3-fluoropyridin-2-yl)-1,3,4-oxadiazol-2-yl)methanone |

TABLE 1-continued

Pyrazolo[1,5-a]pyridines

| Ex. # | Structure | Name |
|---|---|---|
| 1581 | 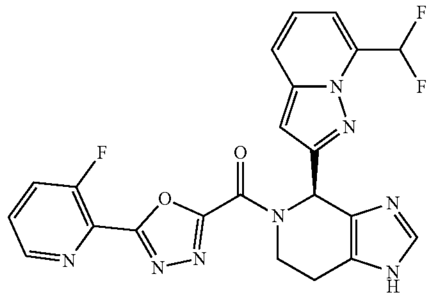 [SMILES: O=C(c1nnc(-c2ncccc2F)o1)N1CCc2[nH]cnc2[C@@H]1c1cc2cccc(C(F)F)n2n1] | (R)-(4-(7-(difluoromethyl) pyrazolo[1,5-a]pyridin-2-yl)-6,7-dihydro-1H-imidazo [4,5-c]pyridin-5(4H)-yl)(5-(3-fluoropyridin-2-yl)-1,3,4-oxadiazol-2-yl)methanone |
| 1582 | 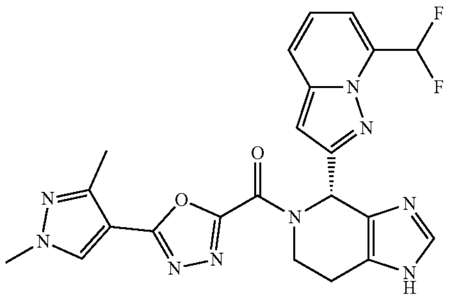 [SMILES: Cc1nn(C)cc1-c1nnc(C(=O)N2CCc3[nH]cnc3[C@H]2c2cc3cccc(C(F)F)n3n2)o1] | (S)-(4-(7-(difluoromethyl) pyrazolo[1,5-a]pyridin-2-yl)-6,7-dihydro-1H-imidazo [4,5-c]pyridin-5(4H)-yl)(5-(1,3-dimethyl-1H-pyrazol-4-yl)-1,3,4-oxadiazol-2-yl)methanone |
| 1583 | 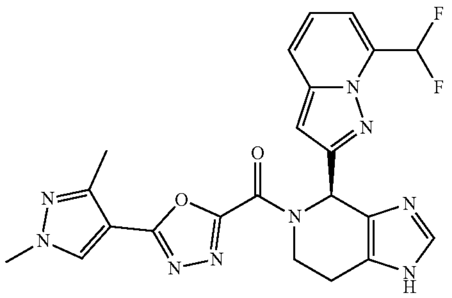 [SMILES: Cc1nn(C)cc1-c1nnc(C(=O)N2CCc3[nH]cnc3[C@@H]2c2cc3cccc(C(F)F)n3n2)o1] | (R)-(4-(7-(difluoromethyl) pyrazolo[1,5-a]pyridin-2-yl)-6,7-dihydro-1H-imidazo [4,5-c]pyridin-5(4H)-yl)(5-(1,3-dimethyl-1H-pyrazol-4-yl)-1,3,4-oxadiazol-2-yl)methanone |
| 1584 | 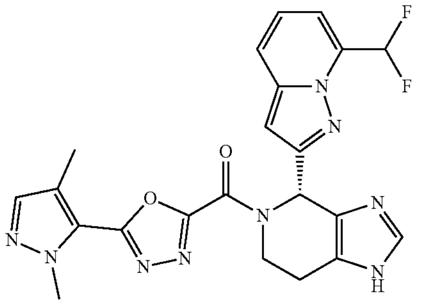 [SMILES: Cc1cnn(C)c1-c1nnc(C(=O)N2CCc3[nH]cnc3[C@H]2c2cc3cccc(C(F)F)n3n2)o1] | (S)-(4-(7-(difluoromethyl) pyrazolo[1,5-a]pyridin-2-yl)-6,7-dihydro-1H-imidazo [4,5-c]pyridin-5(4H)-yl)(5-(1,4-dimethyl-1H-pyrazol-5-yl)-1,3,4-oxadiazol-2-yl)methanone |
| 1585 | 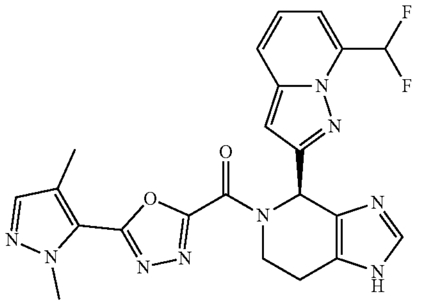 [SMILES: Cc1cnn(C)c1-c1nnc(C(=O)N2CCc3[nH]cnc3[C@@H]2c2cc3cccc(C(F)F)n3n2)o1] | (R)-(4-(7-(difluoromethyl) pyrazolo[1,5-a]pyridin-2-yl)-6,7-dihydro-1H-imidazo [4,5-c]pyridin-5(4H)-yl)(5-(1,4-dimethyl-1H-pyrazol-5-yl)-1,3,4-oxadiazol-2-yl)methanone |

TABLE 1-continued

| Ex. # | Structure | Name |
| --- | --- | --- |
| | Pyrazolo[1,5-a]pyridines | |
| 1586 | 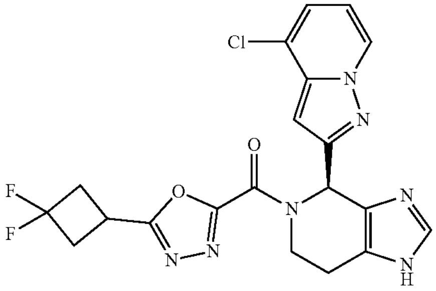 [SMILES: O=C(c1nnc(C2CC(F)(F)C2)o1)N1CCc2[nH]cnc2[C@@H]1c1cc2c(Cl)cccn2n1] | (R)-(4-(4-chloropyrazolo[1,5-a]pyridin-2-yl)-6,7-dihydro-1H-imidazo[4,5-c]pyridin-5(4H)-yl)(5-(3,3-difluorocyclobutyl)-1,3,4-oxadiazol-2-yl)methanone |
| 1587 | 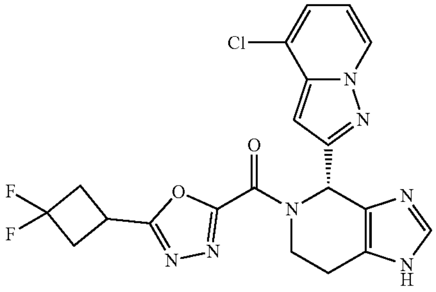 [SMILES: O=C(c1nnc(C2CC(F)(F)C2)o1)N1CCc2[nH]cnc2[C@H]1c1cc2c(Cl)cccn2n1] | (S)-(4-(4-chloropyrazolo[1,5-a]pyridin-2-yl)-6,7-dihydro-1H-imidazo[4,5-c]pyridin-5(4H)-yl)(5-(3,3-difluorocyclobutyl)-1,3,4-oxadiazol-2-yl)methanone |
| 1588 | 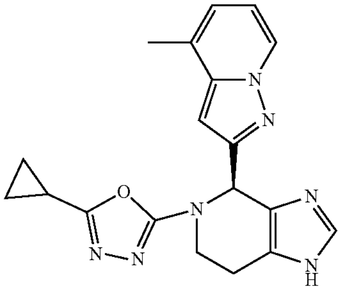 [SMILES: Cc1cccn2nc([C@H]3c4nc[nH]c4CCN3c3nnc(C4CC4)o3)cc12] | (R)-2-cyclopropyl-5-(4-(4-methylpyrazolo[1,5-a]pyridin-2-yl)-6,7-dihydro-1H-imidazo[4,5-c]pyridin-5(4H)-yl)-1,3,4-oxadiazole |
| 1589 | 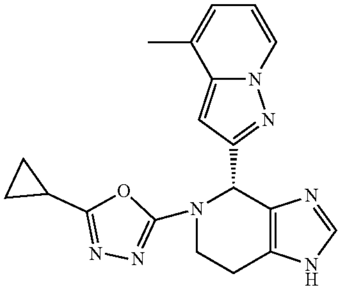 [SMILES: Cc1cccn2nc([C@@H]3c4nc[nH]c4CCN3c3nnc(C4CC4)o3)cc12] | (S)-2-cyclopropyl-5-(4-(4-methylpyrazolo[1,5-a]pyridin-2-yl)-6,7-dihydro-1H-imidazo[4,5-c]pyridin-5(4H)-yl)-1,3,4-oxadiazole |
| 1590 | 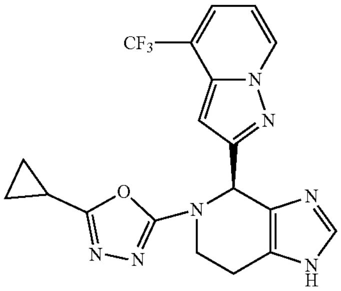 [SMILES: FC(F)(F)c1cccn2nc([C@H]3c4nc[nH]c4CCN3c3nnc(C4CC4)o3)cc12] | (R)-2-cyclopropyl-5-(4-(4-(trifluoromethyl)pyrazolo[1,5-a]pyridin-2-yl)-6,7-dihydro-1H-imidazo[4,5-c]pyridin-5(4H)-yl)-1,3,4-oxadiazole |

TABLE 1-continued

| Pyrazolo[1,5-a]pyridines | | |
|---|---|---|
| Ex. # | Structure | Name |
| 1591 | 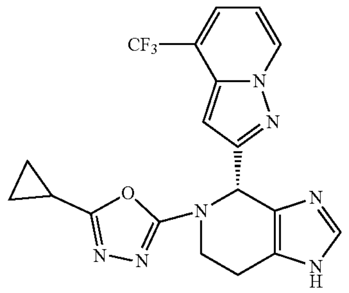 [SMILES: FC(F)(F)c1cccn2nc([C@@H]3c4nc[nH]c4CCN3c3nnc(C4CC4)o3)cc12] | (S)-2-cyclopropyl-5-(4-(4-(trifluoromethyl)pyrazolo[1,5-a]pyridin-2-yl)-6,7-dihydro-1H-imidazo[4,5-c]pyridin-5(4H)-yl)-1,3,4-oxadiazole |
| 1592 | 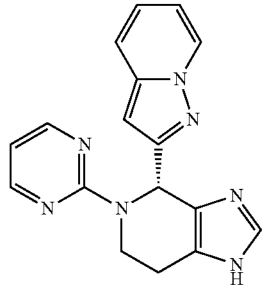 [SMILES: c1cnc(N2CCc3[nH]cnc3[C@H]2c2cc3ccccn3n2)nc1] | (S)-4-(pyrazolo[1,5-a]pyridin-2-yl)-5-(pyrimidin-2-yl)-4,5,6,7-tetrahydro-1H-imidazo[4,5-c]pyridine |
| 1593 | 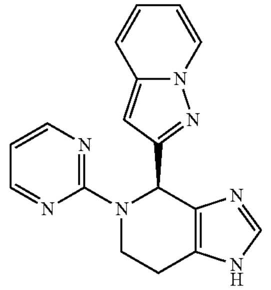 [SMILES: c1cnc(N2CCc3[nH]cnc3[C@@H]2c2cc3ccccn3n2)nc1] | (R)-4-(pyrazolo[1,5-a]pyridin-2-yl)-5-(pyrimidin-2-y]l)-4,5,6,7-tetrahydro-1H-imidazo[4,5-c]pyridine |
| 1594 | 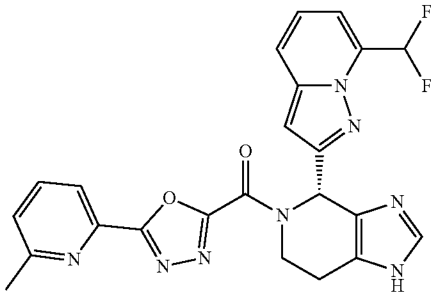 [SMILES: Cc1cccc(-c2nnc(C(=O)N3CCc4[nH]cnc4[C@H]3c3cc4cccc(C(F)F)n4n3)o2)n1] | (S)-(4-(7-(difluoromethyl) pyrazolo[1,5-a]pyridin-2-yl)-6,7-dihydro-1H-imidazo [4,5-c]pyridin-5(4H)-yl)(5-(6-methylpyridin-2-yl)-1,3,4-oxadiazol-2-yl)methanone |
| 1595 | 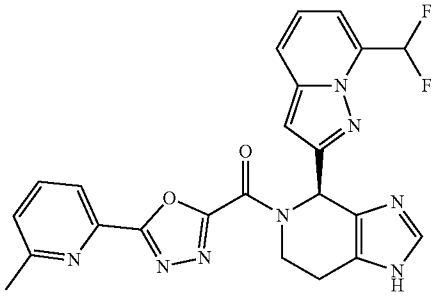 [SMILES: Cc1cccc(-c2nnc(C(=O)N3CCc4[nH]cnc4[C@@H]3c3cc4cccc(C(F)F)n4n3)o2)n1] | (R)-(4-(7-(difluoromethyl) pyrazolo[1,5-a]pyridin-2-yl)-6,7-dihydro-1H-imidazo [4,5-c]pyridin-5(4H)-yl)(5-(6-methylpyridin-2-yl)-1,3,4-oxadiazol-2-yl)methanone |

TABLE 1-continued

| Pyrazolo[1,5-a]pyridines | | |
|---|---|---|
| Ex. # | Structure | Name |
| 1596 | 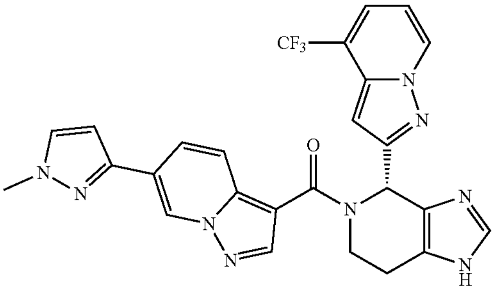 [SMILES: Cn1ccc(-c2ccc3c(C(=O)N4CCc5[nH]cnc5[C@H]4c4cc5c(C(F)(F)F)cccn5n4)cnn3c2)n1] | (S)-(6-(1-methyl-1H-pyrazol-3-yl)pyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 1597 | 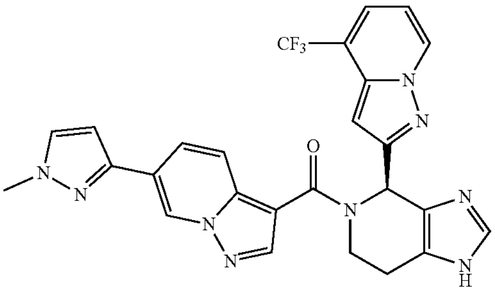 [SMILES: Cn1ccc(-c2ccc3c(C(=O)N4CCc5[nH]cnc5[C@@H]4c4cc5c(C(F)(F)F)cccn5n4)cnn3c2)n1] | (R)-(6-(1-methyl-1H-pyrazol-3-yl)pyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 1598 | 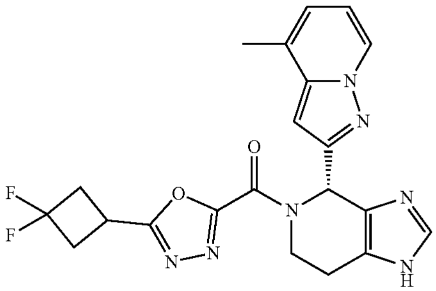 [SMILES: Cc1cccn2nc([C@@H]3c4nc[nH]c4CCN3C(=O)c3nnc(C4CC(F)(F)C4)o3)cc12] | (S)-(5-(3,3-difluorocyclobutyl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1599 | 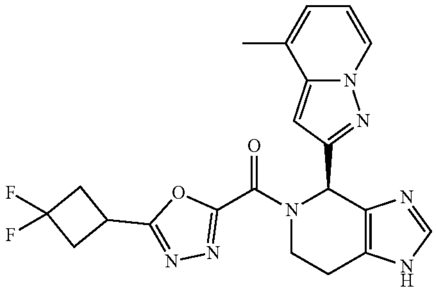 [SMILES: Cc1cccn2nc([C@H]3c4nc[nH]c4CCN3C(=O)c3nnc(C4CC(F)(F)C4)o3)cc12] | (R)-(5-(3,3-difluorocyclobutyl)-1,3,4-oxadiazol-2-yl)(4-(4-methylpyrazolo[1,5-a]pyridin-2-yl)-6,7-dihydro-1H-imidazo[4,5-c]pyridin-5(4H)-yl)methanone |
| 1600 | 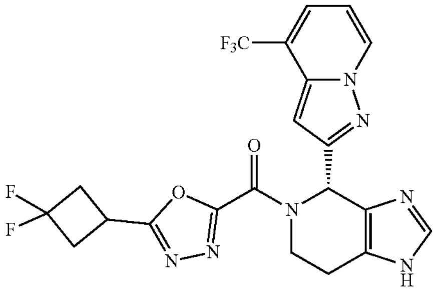 [SMILES: O=C(c1nnc(C2CC(F)(F)C2)o1)N1CCc2[nH]cnc2[C@H]1c1cc2c(C(F)(F)F)cccn2n1] | (S)-(5-(3,3-difluorocyclobutyl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| Pyrazolo[1,5-a]pyridines | | |
| 1601 | 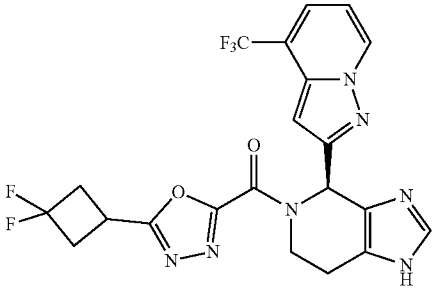 [SMILES: O=C(c1nnc(C2CC(F)(F)C2)o1)N1CCc2[nH]cnc2[C@@H]1c1cc2c(C(F)(F)F)cccn2n1] | (R)-(5-(3,3-difluorocyclobutyl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone |
| 1602 | 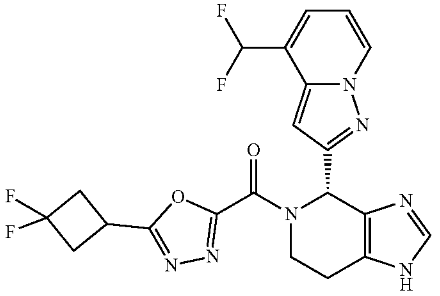 [SMILES: O=C(c1nnc(C2CC(F)(F)C2)o1)N1CCc2[nH]cnc2[C@H]1c1cc2c(C(F)F)cccn2n1] | (S)-(5-(3,3-difluorocyclobutyl)-1,3,4-oxadiazol-2-yl)(4-(4-(difluoromethyl)pyrazolo[1,5-a]pyridin-2-yl)-6,7-dihydro-1H-imidazo[4,5-c]pyridin-5(4H)-yl)methanone |
| 1603 | 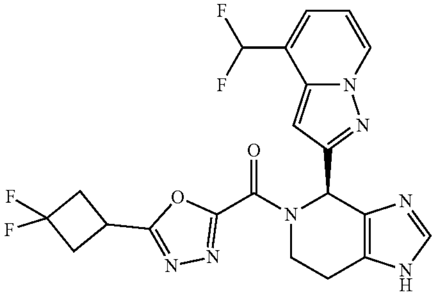 [SMILES: O=C(c1nnc(C2CC(F)(F)C2)o1)N1CCc2[nH]cnc2[C@@H]1c1cc2c(C(F)F)cccn2n1] | (R)-(5-(3,3-difluorocyclobutyl)-1,3,4-oxadiazol-2-yl)(4-(4-(difluoromethyl)pyrazolo[1,5-a]pyridin-2-yl)-6,7-dihydro-1H-imidazo[4,5-c]pyridin-5(4H)-yl)methanone |
| 1604 | 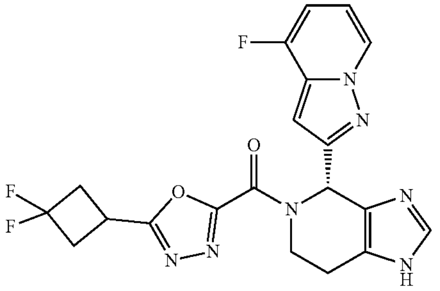 [SMILES: O=C(c1nnc(C2CC(F)(F)C2)o1)N1CCc2[nH]cnc2[C@H]1c1cc2c(F)cccn2n1] | (S)-(5-(3,3-difluorocyclobutyl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |
| 1605 | 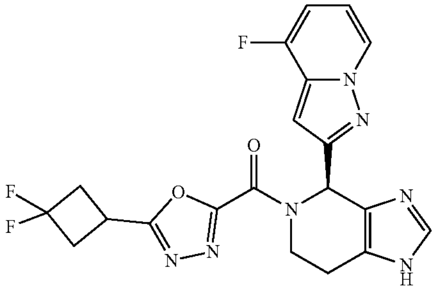 [SMILES: O=C(c1nnc(C2CC(F)(F)C2)o1)N1CCc2[nH]cnc2[C@@H]1c1cc2c(F)cccn2n1] | (R)-(5-(3,3-difluorocyclobutyl)-1,3,4-oxadiazol-2-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| Pyrazolo[1,5-a]pyridines | | |
| 1606 | 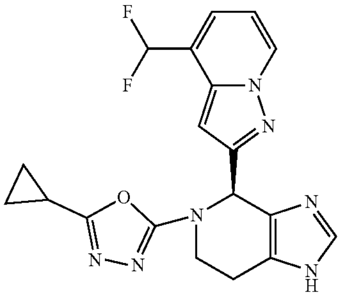 [SMILES: FC(F)c1cccn2nc([C@H]3c4nc[nH]c4CCN3c3nnc(C4CC4)o3)cc12] | (R)-2-cyclopropyl-5-(4-(4-(difluoromethyl)pyrazolo[1,5-a]pyridin-2-yl)-6,7-dihydro-1H-imidazo[4,5-c]pyridin-5(4H)-yl)-1,3,4-oxadiazole |
| 1607 | 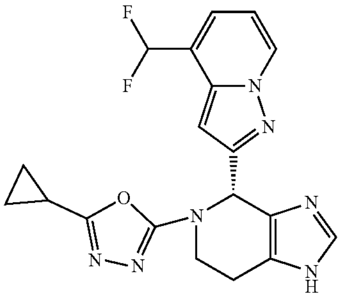 [SMILES: FC(F)c1cccn2nc([C@@H]3c4nc[nH]c4CCN3c3nnc(C4CC4)o3)cc12] | (S)-2-cyclopropyl-5-(4-(4-(difluoromethyl)pyrazolo[1,5-a]pyridin-2-yl)-6,7-dihydro-1H-imidazo[4,5-c]pyridin-5(4H)-yl)-1,3,4-oxadiazole |
| 1608 | 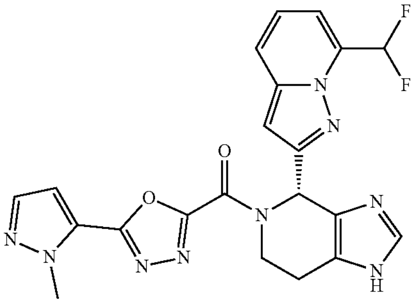 [SMILES: Cn1nccc1-c1nnc(C(=O)N2CCc3[nH]cnc3[C@H]2c2cc3cccc(C(F)F)n3n2)o1] | (S)-(4-(7-(difluoromethyl) pyrazolo[1,5-a]pyridin-2-yl)-6,7-dihydro-1H-imidazo[4,5-c] pyridin-5(4H)-yl)(5-(1-methyl-1H-pyrazol-5-yl)-1,3,4-oxadiazol-2-yl)methanone |
| 1609 | 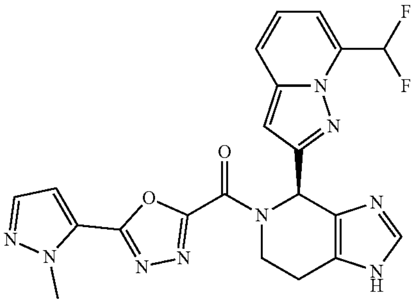 [SMILES: Cn1nccc1-c1nnc(C(=O)N2CCc3[nH]cnc3[C@@H]2c2cc3cccc(C(F)F)n3n2)o1] | (R)-(4-(7-(difluoromethyl) pyrazolo[1,5-a]pyridin-2-yl)-6,7-dihydro-1H-imidazo [4,5-c]pyridin-5(4H)-yl)(5-(1-methyl-1H-pyrazol-5-yl)-1,3,4-oxadiazol-2-yl)methanone |
| 1610 | 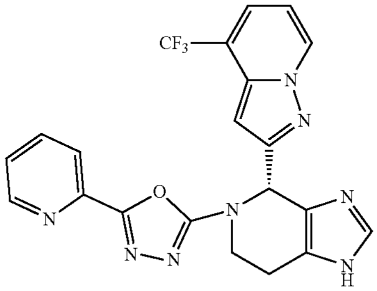 [SMILES: FC(F)(F)c1cccn2nc([C@@H]3c4nc[nH]c4CCN3c3nnc(-c4ccccn4)o3)cc12] | (S)-2-(pyridin-2-yl)-5-(4-(4-(trifluoromethyl)pyrazolo [1,5-a]pyridin-2-yl)-6,7-dihydro-1H-imidazo[4,5-c] pyridin-5(4H)-yl)-1,3,4-oxadiazole |

TABLE 1-continued

| Ex. # | Structure | Name |
| --- | --- | --- |
| | Pyrazolo[1,5-a]pyridines | |
| 1611 | 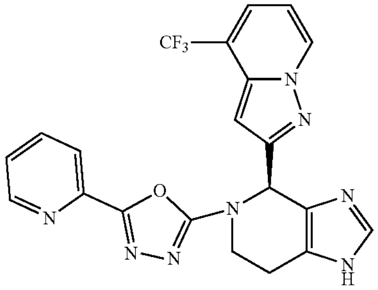 [SMILES: FC(F)(F)c1cccn2nc([C@H]3c4nc[nH]c4CCN3c3nnc(-c4ccccn4)o3)cc12] | (R)-2-(pyridin-2-yl)-5-(4-(4-(trifluoromethyl)pyrazolo[1,5-a]pyridin-2-yl)-6,7-dihydro-1H-imidazo[4,5-c]pyridin-5(4H)-yl)-1,3,4-oxadiazole |
| 1612 | 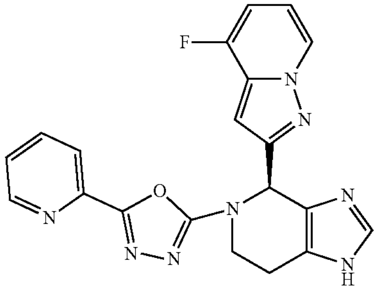 [SMILES: Fc1cccn2nc([C@H]3c4nc[nH]c4CCN3c3nnc(-c4ccccn4)o3)cc12] | (R)-2-(4-(4-fluoropyrazolo[1,5-a]pyridin-2-yl)-6,7-dihydro-1H-imidazo[4,5-c]pyridin-5(4H)-yl)-5-(pyridin-2-yl)-1,3,4-oxadiazole |
| 1613 | 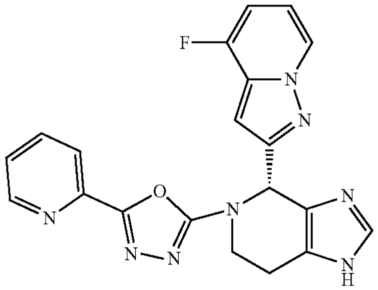 [SMILES: Fc1cccn2nc([C@@H]3c4nc[nH]c4CCN3c3nnc(-c4ccccn4)o3)cc12] | (S)-2-(4-(4-fluoropyrazolo[1,5-a]pyridin-2-yl)-6,7-dihydro-1H-imidazo[4,5-c]pyridin-5(4H)-yl)-5-(pyridin-2-yl)-1,3,4-oxadiazole |
| 1614 | 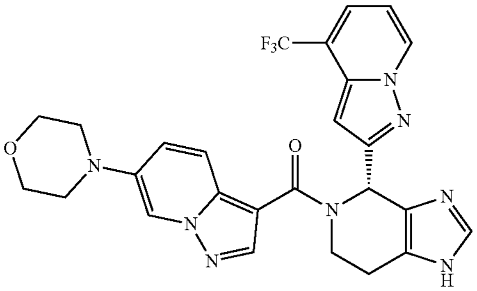 [SMILES: O=C(c1cnn2cc(N3CCOCC3)ccc12)N1CCc2[nH]cnc2[C@H]1c1cc2c(C(F)(F)F)cccn2n1] | (S)-(6-morpholinopyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 1615 | 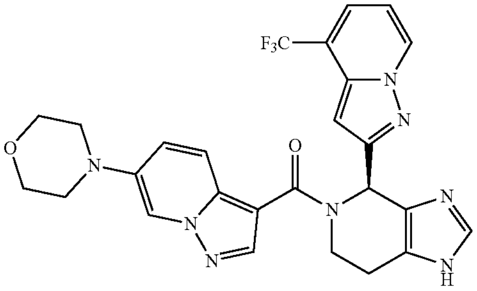 [SMILES: O=C(c1cnn2cc(N3CCOCC3)ccc12)N1CCc2[nH]cnc2[C@@H]1c1cc2c(C(F)(F)F)cccn2n1] | (R)-(6-morpholinopyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
| --- | --- | --- |
| Pyrazolo[1,5-a]pyridines | | |
| 1616 | 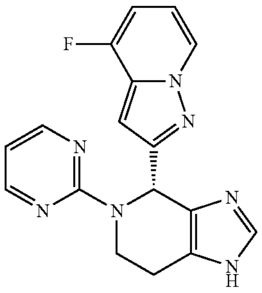 [SMILES: Fc1cccn2nc([C@@H]3c4nc[nH]c4CCN3c3ncccn3)cc12] | (S)-4-(4-fluoropyrazolo[1,5-a]pyridin-2-yl)-5-(pyrimidin-2-yl)-4,5,6,7-tetrahydro-1H-imidazo[4,5-c]pyridine |
| 1617 | 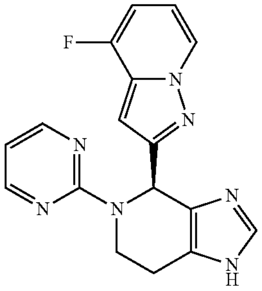 [SMILES: Fc1cccn2nc([C@H]3c4nc[nH]c4CCN3c3ncccn3)cc12] | (R)-4-(4-fluoropyrazolo[1,5-a]pyridin-2-yl)-5-(pyrimidin-2-yl)-4,5,6,7-tetrahydro-1H-imidazo[4,5-c]pyridine |
| 1618 | 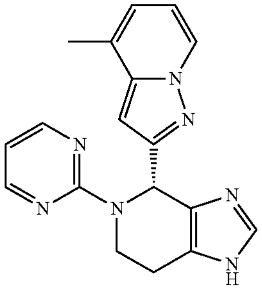 [SMILES: Cc1cccn2nc([C@@H]3c4nc[nH]c4CCN3c3ncccn3)cc12] | (S)-4-(4-methylpyrazolo[1,5-a]pyridin-2-yl)-5-(pyrimidin-2-yl)-4,5,6,7-tetrahydro-1H-imidazo[4,5-c]pyridine |
| 1619 | 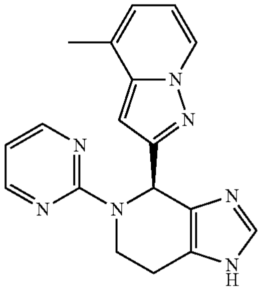 [SMILES: Cc1cccn2nc([C@H]3c4nc[nH]c4CCN3c3ncccn3)cc12] | (R)-4-(4-methylpyrazolo[1,5-a]pyridin-2-yl)-5-(pyrimidin-2-yl)-4,5,6,7-tetrahydro-1H-imidazo[4,5-c]pyridine |
| 1620 | 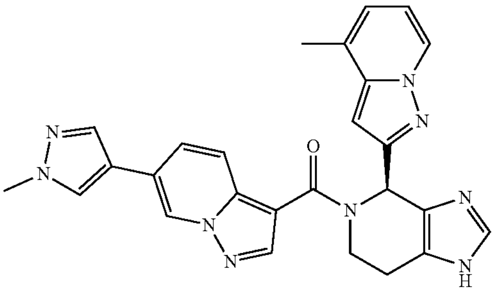 | (R)-(6-(1-methyl-1H-pyrazol-3-yl)pyrazolo[1,5-a]pyridin-3-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1621 | 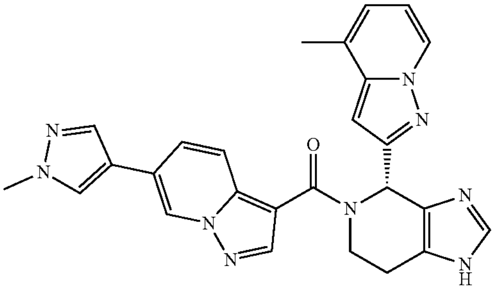 | (S)-(6-(1-methyl-1H-pyrazol-3-yl)pyrazolo[1,5-a]pyridin-3-yl)(4-(4-methylpyrazolo[1,5-a]pyridin-2-yl)-6,7-dihydro-1H-imidazo[4,5-c]pyridin-5(4H)-yl)methanone |
| 1622 | 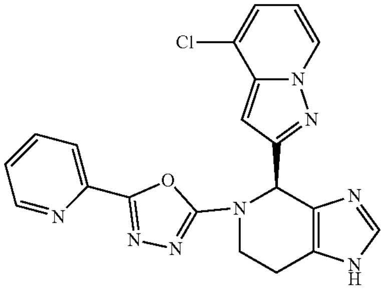 [SMILES: Clc1cccn2nc([C@H]3c4nc[nH]c4CCN3c3nnc(-c4ccccn4)o3)cc12] | (R)-2-(4-(4-chloropyrazolo[1,5-a]pyridin-2-yl)-6,7-dihydro-1H-imidazo[4,5-c]pyridin-5(4H)-yl)-5-(pyridin-2-yl)-1,3,4-oxadiazole |
| 1623 | 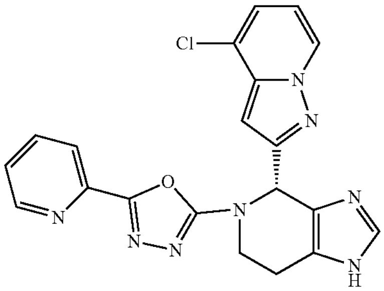 [SMILES: Clc1cccn2nc([C@@H]3c4nc[nH]c4CCN3c3nnc(-c4ccccn4)o3)cc12] | (S)-2-(4-(4-chloropyrazolo[1,5-a]pyridin-2-y]l)-6,7-dihydro-1H-imidazo[4,5-c]pyridin-5(4H)-yl)-5-(pyridin-2-yl)-1,3,4-oxadiazole |
| 1624 | 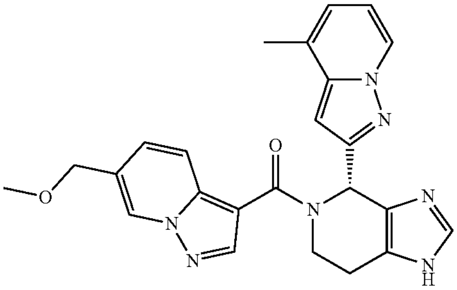 | (S)-(6-(methoxymethyl)pyrazolo[1,5-a]pyridin-3-yl)(4-(4-methylpyrazolo[1,5-a]pyridin-2-yl)-6,7-dihydro-1H-imidazo[4,5-c]pyridin-5(4H)-yl)methanone |
| 1625 | 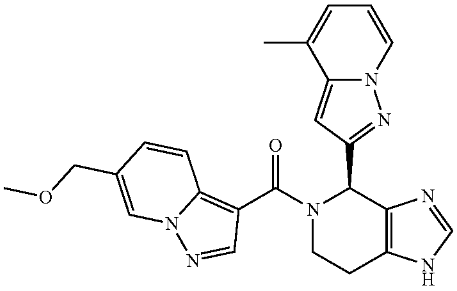 [SMILES: COCc1ccc2c(C(=O)N3CCc4[nH]cnc4[C@@H]3c3cc4c(C)cccn4n3)cnn2c1] | (R)-(6-(methoxymethyl)pyrazolo[1,5-a]pyridin-3-yl)(4-(4-methylpyrazolo[1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 1626 | 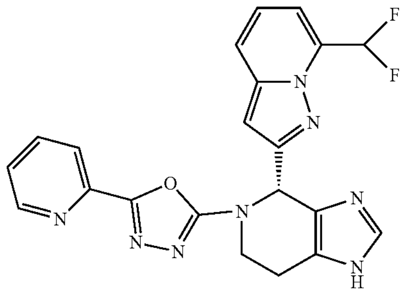 [SMILES: FC(F)c1cccc2cc([C@@H]3c4nc[nH]c4CCN3c3nnc(-c4ccccn4)o3)nn12] | (S)-2-(4-(7-(difluoromethyl) pyrazolo[1,5-a]pyridin-2-yl)-6,7-dihydro-1H-imidazo [4,5-c]pyridin-5(4H)-yl)-5-(pyridin-2-yl)-1,3,4-oxadiazole |
| 1627 | 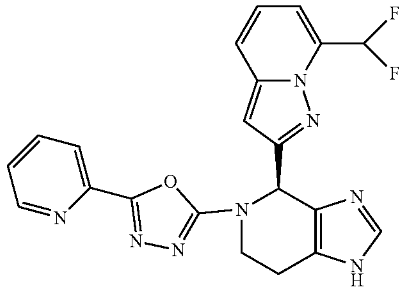 [SMILES: FC(F)c1cccc2cc([C@H]3c4nc[nH]c4CCN3c3nnc(-c4ccccn4)o3)nn12] | (R)-2-(4-(7-(difluoromethyl) pyrazolo[1,5-a]pyridin-2-yl)-6,7-dihydro-1H-imidazo [4,5-c]pyridin-5(4H)-yl)-5-(pyridin-2-yl)-1,3,4-oxadiazole |
| 1628 | 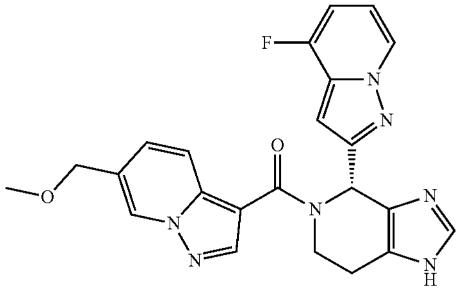 | (S)-(4-(4-fluoropyrazolo [1,5-a]pyridin-2-yl)-6,7-dihydro-1H-imidazo[4,5-c] pyridin-5(4H)-yl)(6-(methoxymethyl)pyrazolo [1,5-a]pyridin-3-yl) methanone |
| 1629 | 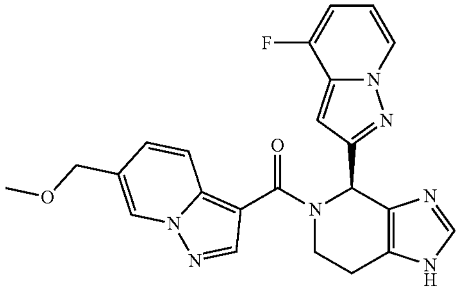 [SMILES: COCc1ccc2c(C(=O)N3CCc4[nH]cnc4[C@@H]3c3cc4c(F)cccn4n3)cnn2c1] | (R)-(4-(4-fluoropyrazolo [1,5-a]pyridin-2-yl)-6,7-dihydro-1H-imidazo [4,5-c]pyridin-5(4H)-yl)(6-(methoxymethyl)pyrazolo [1,5-a]pyridin-3-yl)methanone |
| 1630 | 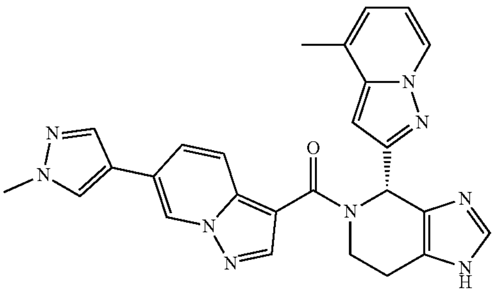 | (S)-(6-(1-methyl-1H-pyrazol-4-yl)pyrazolo[1,5-a]pyridin-3-yl)(4-(4-methylpyrazolo[1,5-a]pyridin-2-yl)-6,7-dihydro-1H-imidazo [4,5-c]pyridin-5(4H)-yl)methanone |

TABLE 1-continued

Pyrazolo[1,5-a]pyridines

| Ex. # | Structure | Name |
| --- | --- | --- |
| 1631 | 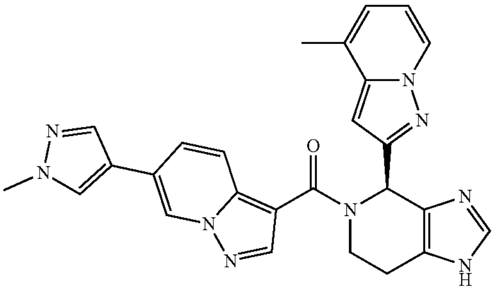 | (R)-(6-(1-methyl-1H-pyrazol-4-yl)pyrazolo[1,5-a]pyridin-3-yl)(4-(4-methylpyrazolo[1,5-a]pyridin-2-yl)-6,7-dihydro-1H-imidazo[4,5-c]pyridin-5(4H)-yl)methanone |
| 1632 | 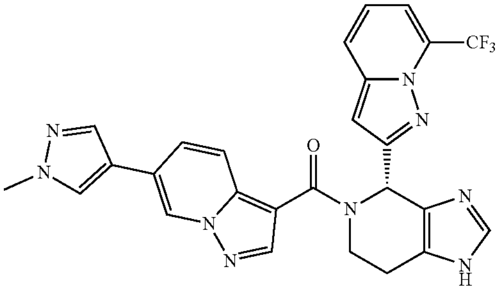 [SMILES: Cn1cc(-c2ccc3c(C(=O)N4CCc5[nH]cnc5[C@H]4c4cc5cccc(C(F)(F)F)n5n4)cnn3c2)cn1] | (S)-(6-(1-methyl-1H-pyrazol-3-yl)pyrazolo[1,5-a]pyridin-3-yl)(4-(7-(trifluoromethyl)pyrazolo[1,5-a]pyridin-2-yl)-6,7-dihydro-1H-imidazo[4,5-c]pyridin-5(4H)-yl)methanone |
| 1633 | 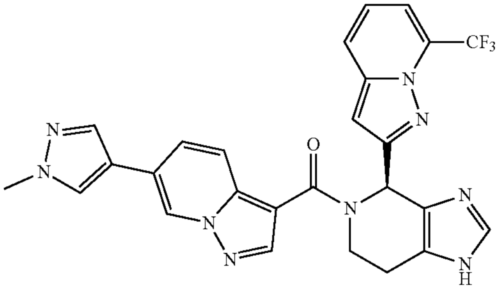 [SMILES: Cn1cc(-c2ccc3c(C(=O)N4CCc5[nH]cnc5[C@@H]4c4cc5cccc(C(F)(F)F)n5n4)cnn3c2)cn1] | (R)-(6-(1-methyl-1H-pyrazol-3-yl)pyrazolo[1,5-a]pyridin-3-yl)(4-(7-(trifluoromethyl)pyrazolo[1,5-a]pyridin-2-yl)-6,7-dihydro-1H-imidazo[4,5-c]pyridin-5(4H)-yl)methanone |
| 1634 | 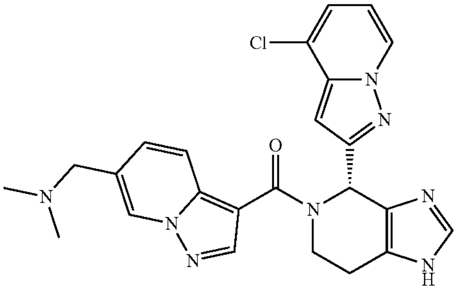 | (S)-(4-(4-chloropyrazolo[1,5-a]pyridin-2-yl)-6,7-dihydro-1H-imidazo[4,5-c]pyridin-5(4H)-yl)(6-((dimethylamino)methyl)pyrazolo[1,5-a]pyridin-3-yl)methanone |
| 1635 | 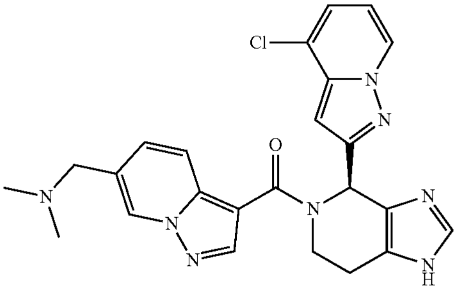 [SMILES: CN(C)Cc1ccc2c(C(=O)N3CCc4[nH]cnc4[C@@H]3c3cc4c(Cl)cccn4n3)cnn2c1] | (R)-(4-(4-chloropyrazolo[1,5-a]pyridin-2-yl)-6,7-dihydro-1H-imidazo[4,5-c]pyridin-5(4H)-yl)(6-((dimethylamino)methyl)pyrazolo[1,5-a]pyridin-3-yl)methanone |

TABLE 1-continued

| Ex. # | Structure | Name |
|---|---|---|
| | Pyrazolo[1,5-a]pyridines | |
| 1636 | 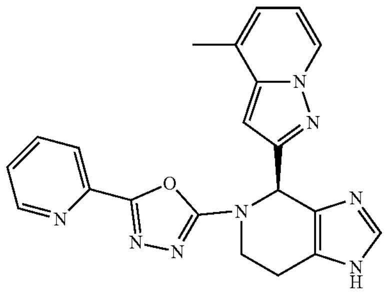 [SMILES: Cc1cccn2nc([C@H]3c4nc[nH]c4CCN3c3nnc(-c4ccccn4)o3)cc12] | (R)-2-(4-(4-methylpyrazolo[1,5-a]pyridin-2-yl)-6,7-dihydro-1H-imidazo[4,5-c]pyridin-5(4H)-yl)-5-(pyridin-2-yl)-1,3,4-oxadiazole |
| 1637 | 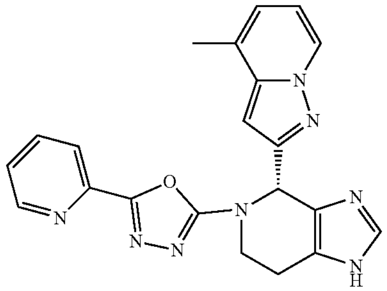 [SMILES: Cc1cccn2nc([C@@H]3c4nc[nH]c4CCN3c3nnc(-c4ccccn4)o3)cc12] | (S)-2-(4-(4-methylpyrazolo[1,5-a]pyridin-2-yl)-6,7-dihydro-1H-imidazo[4,5-c]pyridin-5(4H)-yl)-5-(pyridin-2-yl)-1,3,4-oxadiazole |
| 1638 | 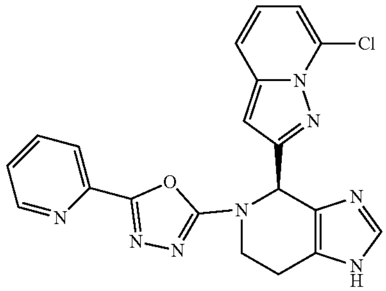 [SMILES: Clc1cccc2cc([C@H]3c4nc[nH]c4CCN3c3nnc(-c4ccccn4)o3)nn12] | (R)-2-(4-(7-chloropyrazolo[1,5-a]pyridin-2-yl)-6,7-dihydro-1H-imidazo[4,5-c]pyridin-5(4H)-yl)-5-(pyridin-2-yl)-1,3,4-oxadiazole |
| 1639 | 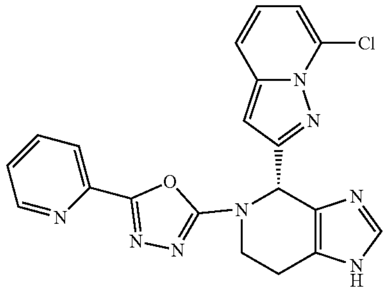 [SMILES: Clc1cccc2cc([C@@H]3c4nc[nH]c4CCN3c3nnc(-c4ccccn4)o3)nn12] | (S)-2-(4-(7-chloropyrazolo[1,5-a]pyridin-2-yl)-6,7-dihydro-1H-imidazo[4,5-c]pyridin-5(4H)-yl)-5-(pyridin-2-yl)-1,3,4-oxadiazole |
| 1640 | 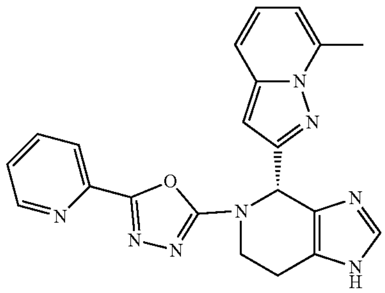 [SMILES: Cc1cccc2cc([C@@H]3c4nc[nH]c4CCN3c3nnc(-c4ccccn4)o3)nn12] | (S)-2-(4-(7-methylpyrazolo[1,5-a]pyridin-2-yl)-6,7-dihydro-1H-imidazo[4,5-c]pyridin-5(4H)-yl)-5-(pyridin-2-yl)-1,3,4-oxadiazole |

TABLE 1-continued

| Ex. # | Structure | Name |
|---|---|---|
| | Pyrazolo[1,5-a]pyridines | |
| 1641 | 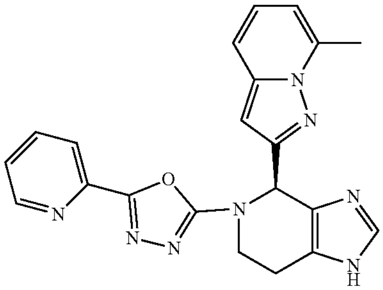 [SMILES: Cc1cccc2cc([C@H]3c4nc[nH]c4CCN3c3nnc(-c4ccccn4)o3)nn12] | (R)-2-(4-(7-methylpyrazolo[1,5-a]pyridin-2-yl)-6,7-dihydro-1H-imidazo[4,5-c]pyridin-5(4H)-yl)-5-(pyridin-2-yl)-1,3,4-oxadiazole |
| 1642 | 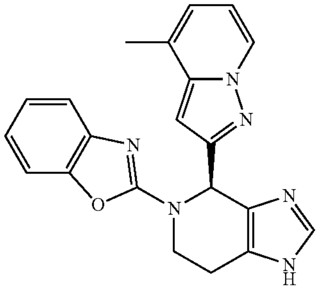 [SMILES: Cc1cccn2nc([C@H]3c4nc[nH]c4CCN3c3nc4ccccc4o3)cc12] | (R)-2-(4-(4-methylpyrazolo[1,5-a]pyridin-2-yl)-6,7-dihydro-1H-imidazo[4,5-c]pyridin-5(4H)-yl)benzo[d]oxazole |
| 1643 | 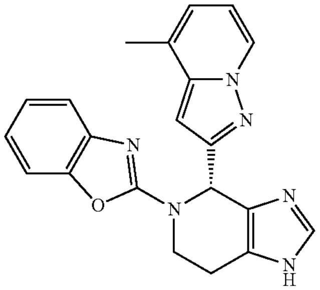 [SMILES: Cc1cccn2nc([C@@H]3c4nc[nH]c4CCN3c3nc4ccccc4o3)cc12] | (S)-2-(4-(4-methylpyrazolo[1,5-a]pyridin-2-yl)-6,7-dihydro-1H-imidazo[4,5-c]pyridin-5(4H)-yl)benzo[d]oxazole |
| 1644 | 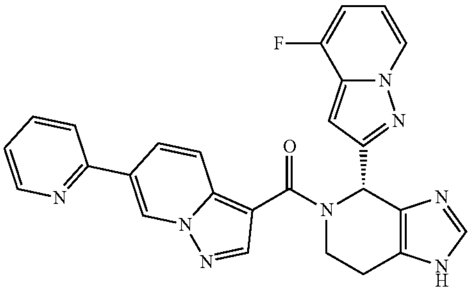 | (S)-(4-(4-fluoropyrazolo[1,5-a]pyridin-2-yl)-6,7-dihydro-1H-imidazo[4,5-c]pyridin-5(4H)-yl)(6-(pyridin-2-yl)pyrazolo[1,5-a]pyridin-3-yl)methanone |
| 1645 | 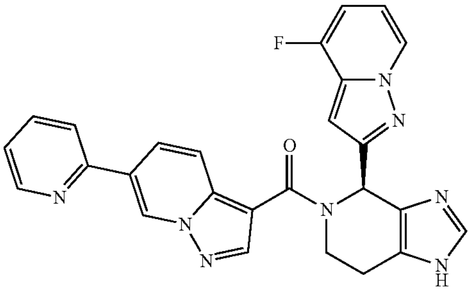 [SMILES: O=C(c1cnn2cc(-c3ccccn3)ccc12)N1CCc2[nH]cnc2[C@@H]1c1cc2c(F)cccn2n1] | (R)-(4-(4-fluoropyrazolo[1,5-a]pyridin-2-y]l)-6,7-dihydro-1H-imidazo[4,5-c]pyridin-5(4H)-yl)(6-(pyridin-2-yl)pyrazolo[1,5-a]pyridin-3-yl)methanone |

TABLE 1-continued

| Pyrazolo[1,5-a]pyridines | | |
|---|---|---|
| Ex. # | Structure | Name |
| 1646 | 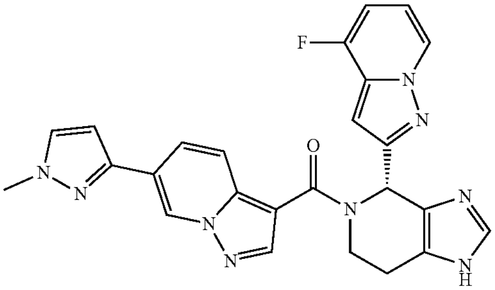 | (S)-(4-(4-fluoropyrazolo[1,5-a]pyridin-2-yl)-6,7-dihydro-1H-imidazo[4,5-c]pyridin-5(4H)-yl)(6-(1-methyl-1H-pyrazol-3-yl)pyrazolo[1,5-a]pyridin-3-yl)methanone |
| 1647 | 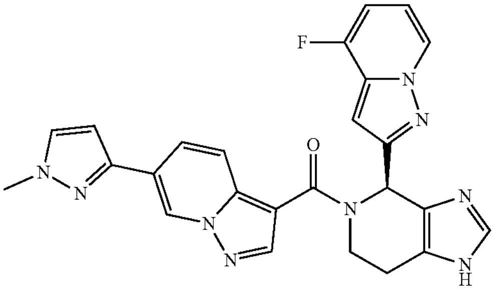 | (R)-(4-(4-fluoropyrazolo[1,5-a]pyridin-2-yl)-6,7-dihydro-1H-imidazo[4,5-c]pyridin-5(4H)-yl)(6-(1-methyl-1H-pyrazol-3-yl)pyrazolo[1,5-a]pyridin-3-yl)methanone |
| 1648 | 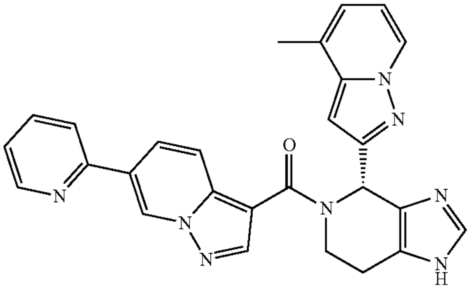 [SMILES: Cc1cccn2nc([C@@H]3c4nc[nH]c4CCN3C(=O)c3cnn4cc(-c5ccccn5)ccc34)cc12] | (S)-(4-(4-methylpyrazolo[1,5-a]pyridin-2-yl)-6,7-dihydro-1H-imidazo[4,5-c]pyridin-5(4H)-yl)(6-(pyridin-2-yl)pyrazolo[1,5-a]pyridin-3-yl)methanone |
| 1649 | 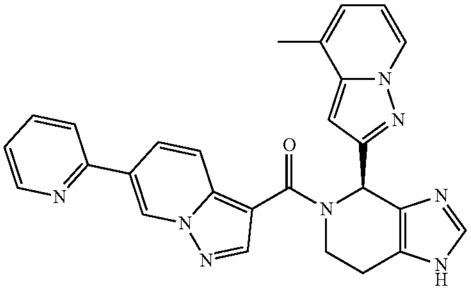 [SMILES: Cc1cccn2nc([C@H]3c4nc[nH]c4CCN3C(=O)c3cnn4cc(-c5ccccn5)ccc34)cc12] | (R)-(4-(4-methylpyrazolo[1,5-a]pyridin-2-yl)-6,7-dihydro-1H-imidazo[4,5-c]pyridin-5(4H)-yl)(6-(pyridin-2-yl)pyrazolo[1,5-a]pyridin-3-yl)methanone |
| 1650 | 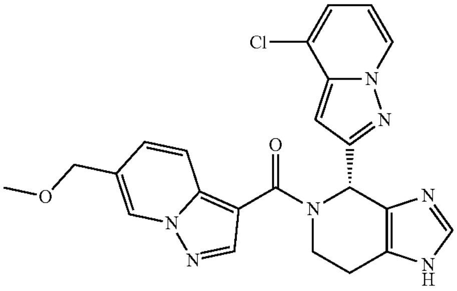 [SMILES: COCc1ccc2c(C(=O)N3CCc4[nH]cnc4[C@H]3c3cc4c(Cl)cccn4n3)cnn2c1] | (S)-(4-(4-chloropyrazolo[1,5-a]pyridin-2-yl)-6,7-dihydro-1H-imidazo[4,5-c]pyridin-5(4H)-yl)(6-(methoxymethyl)pyrazolo[1,5-a]pyridin-3-yl)methanone |

TABLE 1-continued

| Pyrazolo[1,5-a]pyridines | | |
|---|---|---|
| Ex. # | Structure | Name |
| 1651 | 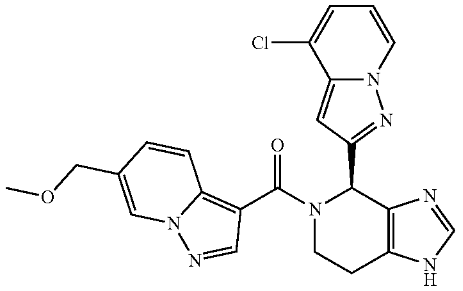 [SMILES: COCc1ccc2c(C(=O)N3CCc4[nH]cnc4[C@@H]3c3cc4c(Cl)cccn4n3)cnn2c1] | (R)-(4-(4-chloropyrazolo [1,5-a]pyridin-2-yl)-6,7-dihydro-1H-imidazo [4,5-c]pyridin-5(4H)-yl)(6-(methoxymethyl)pyrazolo [1,5-a]pyridin-3-yl)methanone |
| 1652 | 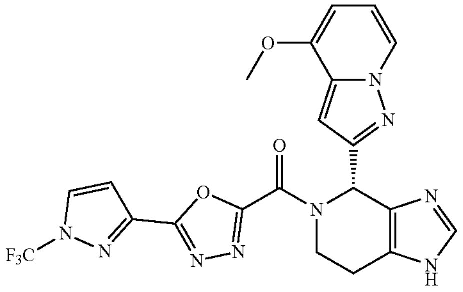 [SMILES: COc1cccn2nc([C@@H]3c4nc[nH]c4CCN3C(=O)c3nnc(-c4ccn(C(F)(F)F)n4)o3)cc12] | (S)-(4-(4-methoxypyrazolo [1,5-a]pyridin-2-yl)-6,7-dihydro-1H-imidazo[4,5-c] pyridin-5(4H)-yl)(5-(1-(trifluoromethyl)-1H-pyrazol-3-yl)-1,3,4-oxadiazol-2-yl)methanone |
| 1653 | 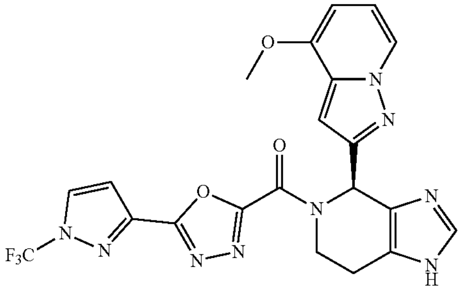 [SMILES: COc1cccn2nc([C@H]3c4nc[nH]c4CCN3C(=O)c3nnc(-c4ccn(C(F)(F)F)n4)o3)cc12] | (R)-(4-(4-methoxypyrazolo [1,5-a]pyridin-2-yl)-6,7-dihydro-1H-imidazo[4,5-c] pyridin-5(4H)-yl)(5-(1-(trifluoromethyl)-1H-pyrazol-3-yl)-1,3,4-oxadiazol-2-yl)methanone |
| 1654 | 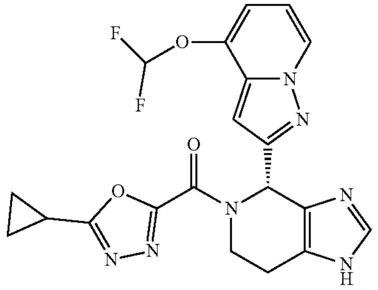 [SMILES: O=C(c1nnc(C2CC2)o1)N1CCc2[nH]cnc2[C@H]1c1cc2c(OC(F)F)cccn2n1] | (S)-(5-cyclopropyl-1,3,4-oxadiazol-2-yl)(4-(4-(difluoromethoxy)pyrazolo [1,5-a]pyridin-2-yl)-6,7-dihydro-1H-imidazo[4,5-c] pyridin-5(4H)-yl)methanone |
| 1655 | 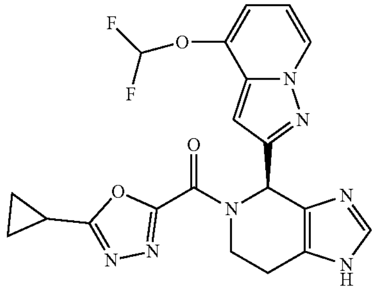 [SMILES: O=C(c1nnc(C2CC2)o1)N1CCc2[nH]cnc2[C@@H]1c1cc2c(OC(F)F)cccn2n1] | (R)-(5-cyclopropyl-1,3,4-oxadiazol-2-yl)(4-(4-(difluoromethoxy)pyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 1656 | 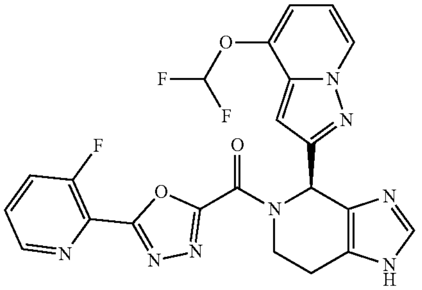 [SMILES: O=C(c1nnc(-c2ncccc2F)o1)N1CCc2[nH]cnc2[C@@H]1c1cc2c(OC(F)F)cccn2n1] | (R)-(4-(4-(difluoromethoxy) pyrazolo[1,5-a]pyridin-2-yl)-6,7-dihydro-1H-imidazo [4,5-c]pyridin-5(4H)-yl)(5-(3-fluoropyridin-2-yl)-1,3,4-oxadiazol-2-yl)methanone |
| 1657 | 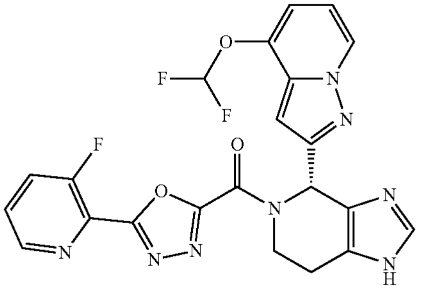 [SMILES: O=C(c1nnc(-c2ncccc2F)o1)N1CCc2[nH]cnc2[C@H]1c1cc2c(OC(F)F)cccn2n1] | (S)-(4-(4-(difluoromethoxy) pyrazolo[1,5-a]pyridin-2-yl)-6,7-dihydro-1H-imidazo [4,5-c]pyridin-5(4H)-yl)(5-(3-fluoropyridin-2-yl)-1,3,4-oxadiazol-2-yl)methanone |
| 1658 | 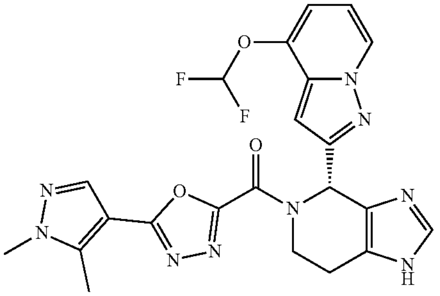 [SMILES: Cc1c(-c2nnc(C(=O)N3CCc4[nH]cnc4[C@H]3c3cc4c(OC(F)F)cccn4n3)o2)cnn1C] | (S)-(4-(4-(difluoromethoxy) pyrazolo[1,5-a]pyridin-2-yl)-6,7-dihydro-1H-imidazo [4,5-c]pyridin-5(4H)-yl)(5-(1,5-dimethyl-1H-pyrazol-4-yl)-1,3,4-oxadiazol-2-yl)methanone |
| 1659 | 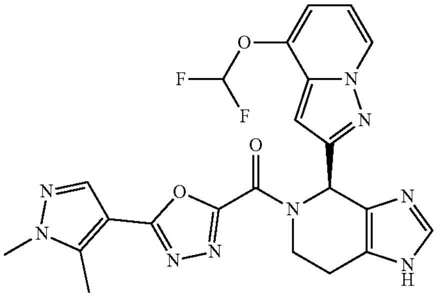 [SMILES: Cc1c(-c2nnc(C(=O)N3CCc4[nH]cnc4[C@@H]3c3cc4c(OC(F)F)cccn4n3)o2)cnn1C] | (R)-(4-(4-(difluoromethoxy) pyrazolo[1,5-a]pyridin-2-yl)-6,7-dihydro-1H-imidazo [4,5-c]pyridin-5(4H)-yl)(5-(1,5-dimethyl-1H-pyrazol-4-yl)-1,3,4-oxadiazol-2-yl)methanone |
| 1660 | 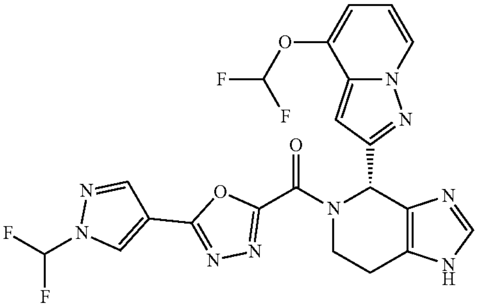 [SMILES: O=C(c1nnc(-c2cnn(C(F)F)c2)o1)N1CCc2[nH]cnc2[C@H]1c1cc2c(OC(F)F)cccn2n1] | (S)-(4-(4-(difluoromethoxy) pyrazolo[1,5-a]pyridin-2-yl)-6,7-dihydro-1H-imidazo [4,5-c]pyridin-5(4H)-yl)(5-(1-(difluoromethyl)-1H-pyrazol-4-yl)-1,3,4-oxadiazol-2-yl)methanone |

TABLE 1-continued

Pyrazolo[1,5-a]pyridines

| Ex. # | Structure | Name |
|---|---|---|
| 1661 | 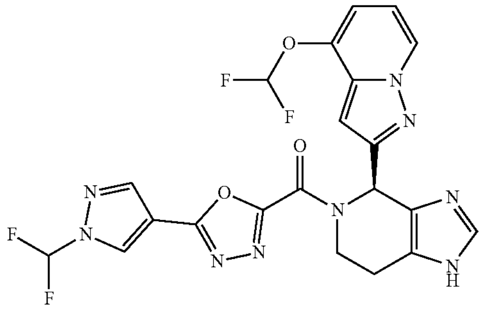 [SMILES: O=C(c1nnc(-c2cnn(C(F)F)c2)o1)N1CCc2[nH]cnc2[C@@H]1c1cc2c(OC(F)F)cccn2n1] | (R)-(4-(4-(difluoromethoxy) pyrazolo[1,5-a]pyridin-2-yl)-6,7-dihydro-1H-imidazo [4,5-c]pyridin-5(4H)-yl)(5-(1-(difluoromethyl)-1H-pyrazol-4-yl)-1,3,4-oxadiazol-2-yl)methanone |
| 1662 | 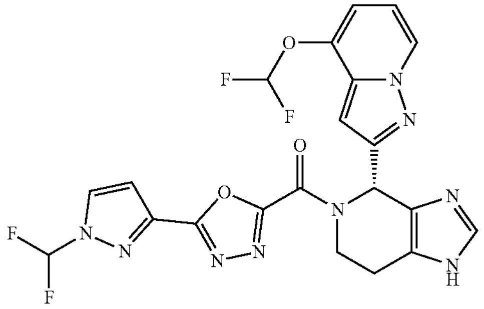 [SMILES: O=C(c1nnc(-c2ccn(C(F)F)n2)o1)N1CCc2[nH]cnc2[C@H]1c1cc2c(OC(F)F)cccn2n1] | (S)-(4-(4-(difluoromethoxy) pyrazolo[1,5-a]pyridin-2-yl)-6,7-dihydro-1H-imidazo [4,5-c]pyridin-5(4H)-yl)(5-(1-(difluoromethyl)-1H-pyrazol-3-yl)-1,3,4-oxadiazol-2-yl)methanone |
| 1663 | 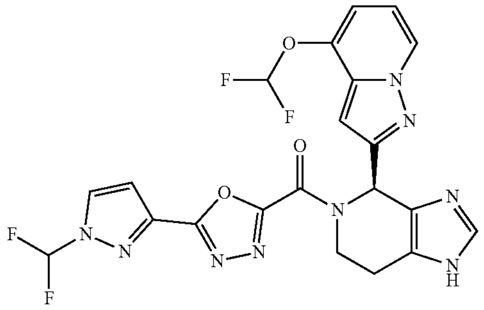 [SMILES: O=C(c1nnc(-c2ccn(C(F)F)n2)o1)N1CCc2[nH]cnc2[C@@H]1c1cc2c(OC(F)F)cccn2n1] | (R)-(4-(4-(difluoromethoxy) pyrazolo[1,5-a]pyridin-2-yl)-6,7-dihydro-1H-imidazo [4,5-c]pyridin-5(4H)-yl)(5-(1-(difluoromethyl)-1H-pyrazol-3-yl)-1,3,4-oxadiazol-2-yl)methanone |
| 1664 | 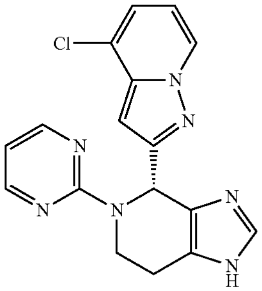 | (S)-4-(4-chloropyrazolo [1,5-a]pyridin-2-yl)-5-(pyrimidin-2-yl)-4,5,6,7-tetrahydro-1H-imidazo[4,5-c]pyridine |
| 1665 | 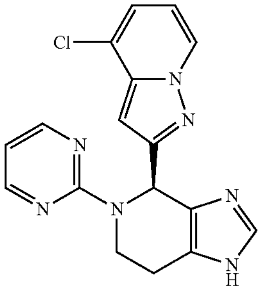 | (R)-4-(4-chloropyrazolo [1,5-a]pyridin-2-yl)-5-(pyrimidin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 1666 | 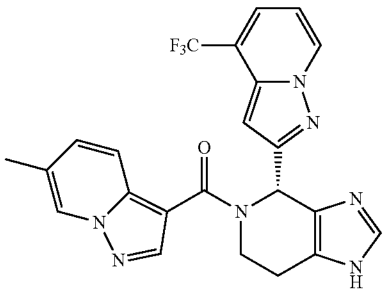 [SMILES: Cc1ccc2c(C(=O)N3CCc4[nH]cnc4[C@H]3c3cc4c(C(F)(F)F)cccn4n3)cnn2c1] | (S)-(6-methylpyrazolo [1,5-a]pyridin-3-yl)(4-(4-(trifluoromethyl)pyrazolo [1,5-a]pyridin-2-yl)-6,7-dihydro-1H-imidazo[4,5-c] pyridin-5(4H)-yl)methanone |
| 1667 | 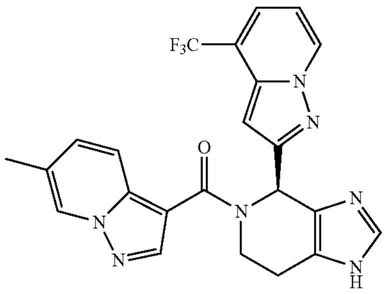 [SMILES: Cc1ccc2c(C(=O)N3CCc4[nH]cnc4[C@@H]3c3cc4c(C(F)(F)F)cccn4n3)cnn2c1] | (R)-(6-methylpyrazolo [1,5-a]pyridin-3-yl)(4-(4-(trifluoromethyl)pyrazolo [1,5-a]pyridin-2-yl)-6,7-dihydro-1H-imidazo[4,5-c] pyridin-5(4H)-yl)methanone |
| 1668 | 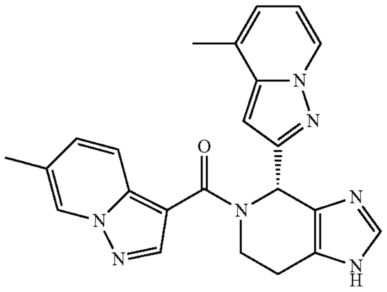 [SMILES: Cc1ccc2c(C(=O)N3CCc4[nH]cnc4[C@H]3c3cc4c(C)cccn4n3)cnn2c1] | (S)-(4-(4-methylpyrazolo [1,5-a]pyridin-2-yl)-6,7-dihydro-1H-imidazo [4,5-c]pyridin-5(4H)-yl)(6-methylpyrazolo[1,5-a] pyridin-3-yl)methanone |
| 1669 | 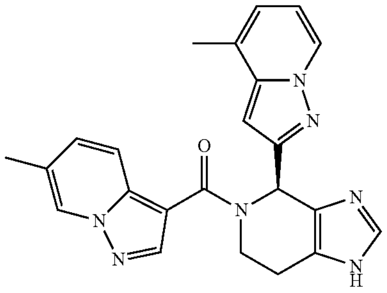 [SMILES: Cc1ccc2c(C(=O)N3CCc4[nH]cnc4[C@@H]3c3cc4c(C)cccn4n3)cnn2c1] | (R)-(4-(4-methylpyrazolo [1,5-a]pyridin-2-yl)-6,7-dihydro-1H-imidazo [4,5-c]pyridin-5(4H)-yl)(6-methylpyrazolo[1,5-a] pyridin-3-yl)methanone |
| 1670 | 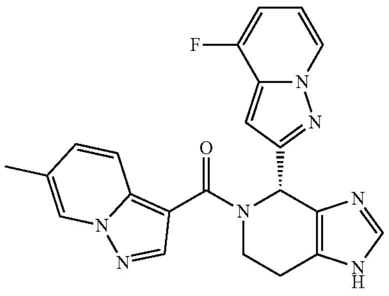 [SMILES: Cc1ccc2c(C(=O)N3CCc4[nH]cnc4[C@H]3c3cc4c(F)cccn4n3)cnn2c1] | (S)-(4-(4-fluoropyrazolo[1,5-a] pyridin-2-yl)-6,7-dihydro-1H-imidazo[4,5-c] pyridin-5(4H)-yl)(6-methylpyrazolo[1,5-a] pyridin-3-yl)methanone |

TABLE 1-continued

| Pyrazolo[1,5-a]pyridines | | |
|---|---|---|
| Ex. # | Structure | Name |
| 1671 | 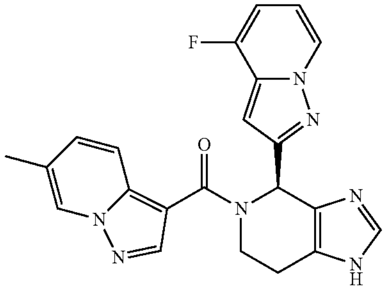 [SMILES: Cc1ccc2c(C(=O)N3CCc4[nH]cnc4[C@@H]3c3cc4c(F)cccn4n3)cnn2c1] | (R)-(4-(4-fluoropyrazolo [1,5-a]pyridin-2-y]l)-6,7-dihydro-1H-imidazo [4,5-c]pyridin-5(4H)-yl)(6-methylpyrazolo[1,5-a] pyridin-3-yl)methanone |
| 1672 | 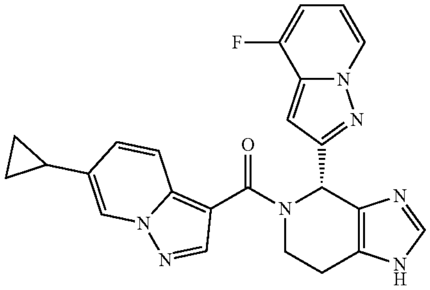 [SMILES: O=C(c1cnn2cc(C3CC3)ccc12)N1CCc2[nH]cnc2[C@H]1c1cc2c(F)cccn2n1] | (S)-(6-cyclopropylpyrazolo [1,5-a]pyridin-3-yl)(4-(4-fluoropyrazolo[1,5-a] pyridin-2-yl)-6,7-dihydro-1H-imidazo[4,5-c]pyridin-5(4H)-yl)methanone |
| 1673 | 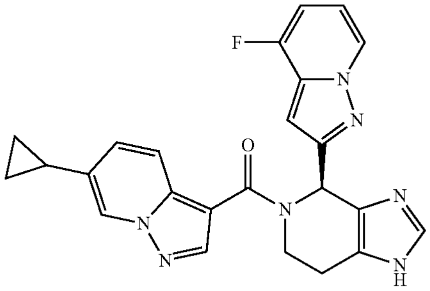 [SMILES: O=C(c1cnn2cc(C3CC3)ccc12)N1CCc2[nH]cnc2[C@@H]1c1cc2c(F)cccn2n1] | (R)-(6-cyclopropylpyrazolo [1,5-a]pyridin-3-yl)(4-(4-fluoropyrazolo[1,5-a]pyridin-2-yl)-6,7-dihydro-1H-imidazo[4,5-c]pyridin-5(4H)-yl)methanone |
| 1674 | 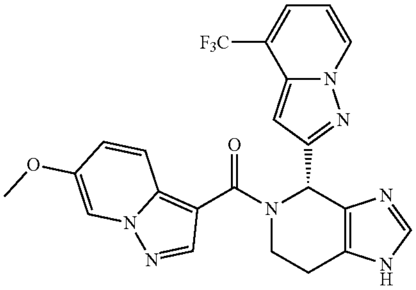 [SMILES: COc1ccc2c(C(=O)N3CCc4[nH]cnc4[C@H]3c3cc4c(C(F)(F)F)cccn4n3)cnn2c1] | (S)-(6-methoxypyrazolo [1,5-a]pyridin-3-yl)(4-(4-(trifluoromethyl)pyrazolo [1,5-a]pyridin-2-yl)-6,7-dihydro-1H-imidazo[4,5-c] pyridin-5(4H)-yl)methanone |
| 1675 | 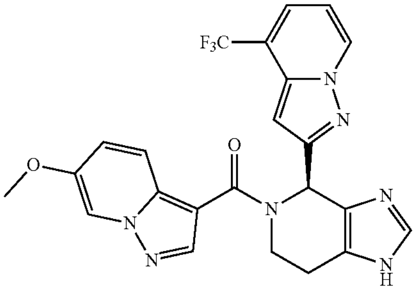 | (R)-(6-methoxypyrazolo [1,5-a]pyridin-3-yl)(4-(4-(trifluoromethyl)pyrazolo [1,5-a]pyridin-2-yl)-6,7-dihydro-1H-imidazo[4,5-c] pyridin-5(4H)-yl)methanone |

TABLE 1-continued

| Ex. # | Structure | Name |
|---|---|---|
| | Pyrazolo[1,5-a]pyridines | |
| 1676 | 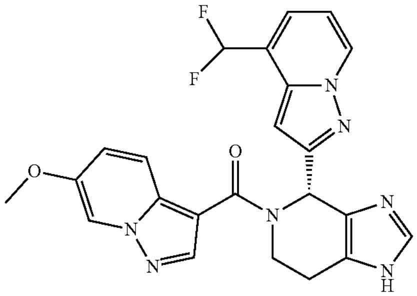 [SMILES: COc1ccc2c(C(=O)N3CCc4[nH]cnc4[C@H]3c3cc4c(C(F)F)cccn4n3)cnn2c1] | (S)-(4-(4-(difluoromethyl) pyrazolo[1,5-a]pyridin-2-yl)-6,7-dihydro-1H-imidazo [4,5-c]pyridin-5(4H)-yl)(6-methoxypyrazolo[1,5-a] pyridin-3-yl)methanone |
| 1677 | 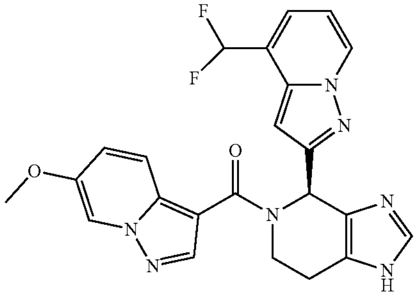 [SMILES: COc1ccc2c(C(=O)N3CCc4[nH]cnc4[C@@H]3c3cc4c(C(F)F)cccn4n3)cnn2c1] | (R)-(4-(4-(difluoromethyl) pyrazolo[1,5-a]pyridin-2-y]l)-6,7-dihydro-1H-imidazo [4,5-c]pyridin-5(4H)-yl)(6-methoxypyrazolo[1,5-a] pyridin-3-yl)methanone |
| 1678 | 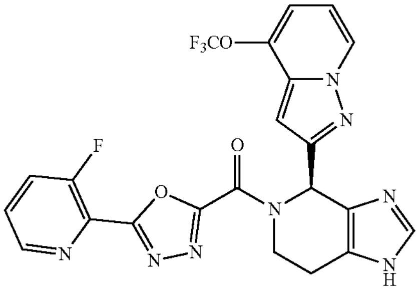 | (R)-(5-(3-fluoropyridin-2-yl)-1,3,4-oxadiazol-2-yl)(4-(4-(trifluoromethoxy)pyrazolo [1,5-a]pyridin-2-yl)-6,7-dihydro-1H-imidazo[4,5-c] pyridin-5(4H)-yl)methanone |
| 1679 | 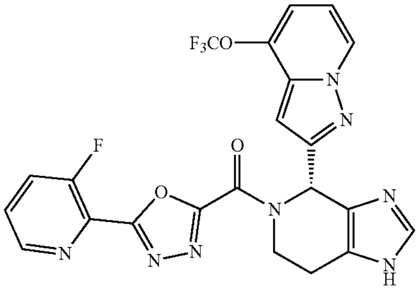 [SMILES: O=C(c1nnc(-c2ncccc2F)o1)N1CCc2[nH]cnc2[C@H]1c1cc2c(OC(F)(F)F)cccn2n1] | (S)-(5-(3-fluoropyridin-2-yl)-1,3,4-oxadiazol-2-yl)(4-(4-(trifluoromethoxy)pyrazolo [1,5-a]pyridin-2-yl)-6,7-dihydro-1H-imidazo[4,5-c] pyridin-5(4H)-yl)methanone |
| 1680 | 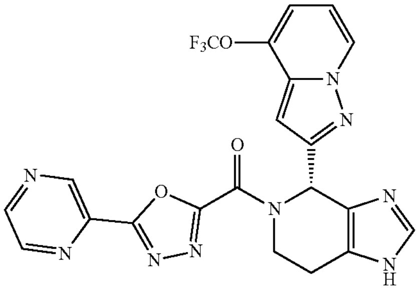 | (S)-(5-(pyrazin-2-yl)-1,3,4-oxadiazol-2-yl)(4-(4-(trifluoromethoxy)pyrazolo [1,5-a]pyridin-2-yl)-6,7-dihydro-1H-imidazo[4,5-c] pyridin-5(4H)-yl)methanone |

TABLE 1-continued

| Ex. # | Structure | Name |
|---|---|---|
| | Pyrazolo[1,5-a]pyridines | |
| 1681 | 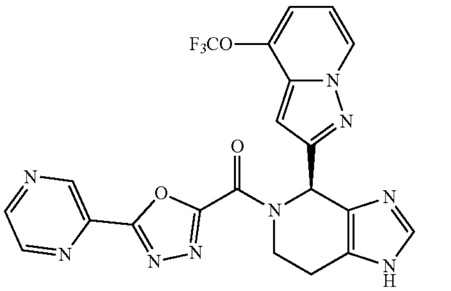 [SMILES: O=C(c1nnc(-c2cnccn2)o1)N1CCc2[nH]cnc2[C@@H]1c1cc2c(OC(F)(F)F)cccn2n1] | (R)-(5-(pyrazin-2-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1682 | 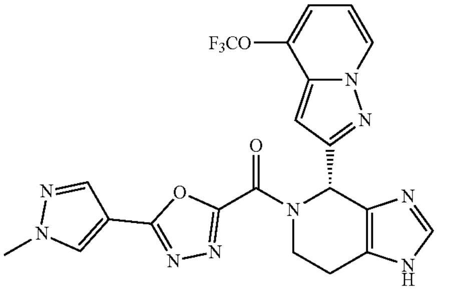 [SMILES: Cn1cc(-c2nnc(C(=O)N3CCc4[nH]cnc4[C@H]3c3cc4c(OC(F)(F)F)cccn4n3)o2)cn1] | (S)-(5-(1-methyl-1H-pyrazol-4-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1683 | 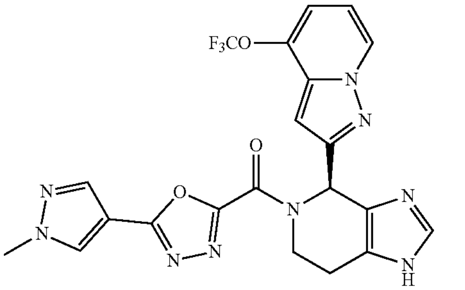 [SMILES: Cn1cc(-c2nnc(C(=O)N3CCc4[nH]cnc4[C@@H]3c3cc4c(OC(F)(F)F)cccn4n3)o2)cn1] | (R)-(5-(1-methyl-1H-pyrazol-4-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1684 | 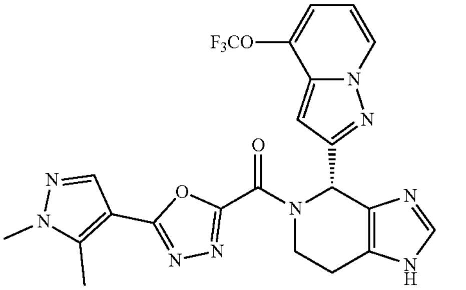 [SMILES: Cc1c(-c2nnc(C(=O)N3CCc4[nH]cnc4[C@H]3c3cc4c(OC(F)(F)F)cccn4n3)o2)cnn1C] | (S)-(5-(1,5-dimethyl-1H-pyrazol-4-yl)-1,3,4-oxadiazol-2-yl)-(4-(4-(trifluoromethoxy)pyrazolo[1,5-a]pyridin-2-yl)-6,7-dihydro-1H-imidazo[4,5-c]pyridin-5(4H)-yl)methanone |
| 1685 | 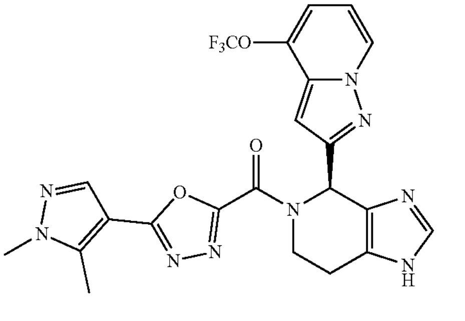 [SMILES: Cc1c(-c2nnc(C(=O)N3CCc4[nH]cnc4[C@@H]3c3cc4c(OC(F)(F)F)cccn4n3)o2)cnn1C] | (R)-(5-(1,5-dimethyl-1H-pyrazol-4-yl)-1,3,4-oxadiazol-2-yl)-(4-(4-(trifluoromethoxy)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1686 | 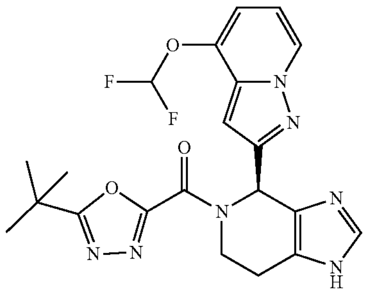 [SMILES: CC(C)(C)c1nnc(C(=O)N2CCc3[nH]cnc3[C@@H]2c2cc3c(OC(F)F)cccn3n2)o1] | (R)-(5-(tert-butyl)-1,3,4-oxadiazol-2-yl)(4-(4-(difluoromethoxy)pyrazolo[1,5-a]pyridin-2-yl)-6,7-dihydro-1H-imidazo[4,5-c]pyridin-5(4H)-yl)methanone |
| 1687 | 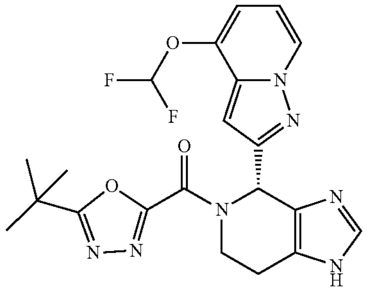 [SMILES: CC(C)(C)c1nnc(C(=O)N2CCc3[nH]cnc3[C@H]2c2cc3c(OC(F)F)cccn3n2)o1] | (S)-(5-(tert-butyl)-1,3,4-oxadiazol-2-yl)(4-(4-(difluoromethoxy)pyrazolo[1,5-a]pyridin-2-yl)-6,7-dihydro-1H-imidazo[4,5-c]pyridin-5(4H)-yl)methanone |
| 1688 | 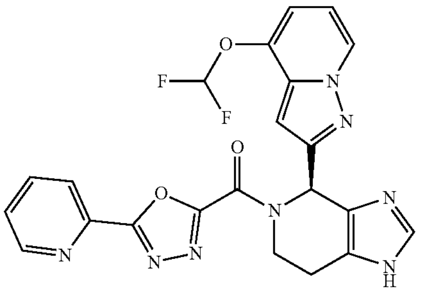 [SMILES: O=C(c1nnc(-c2ccccn2)o1)N1CCc2[nH]cnc2[C@@H]1c1cc2c(OC(F)F)cccn2n1] | (R)-(4-(4-(difluoromethoxy)pyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 1689 | 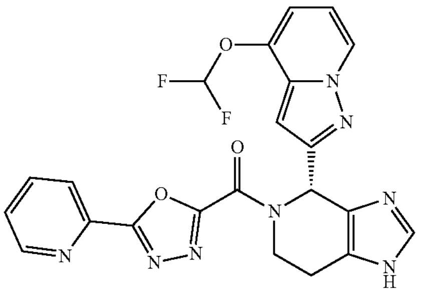 [SMILES: O=C(c1nnc(-c2ccccn2)o1)N1CCc2[nH]cnc2[C@H]1c1cc2c(OC(F)F)cccn2n1] | (S)-(4-(4-(difluoromethoxy)pyrazolo[1,5-a]pyridin-2-yl)-6,7-dihydro-1H-imidazo[4,5-c]pyridin-5(4H)-yl)(5-(pyridin-2-yl)-1,3,4-oxadiazol-2-yl)methanone |
| 1690 | 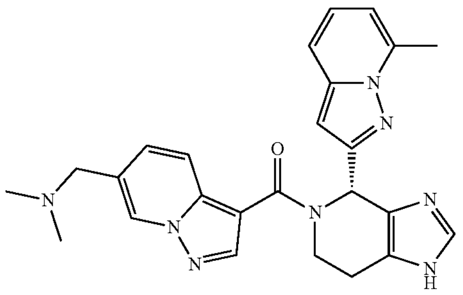 [SMILES: Cc1cccc2cc([C@@H]3c4nc[nH]c4CCN3C(=O)c3cnn4cc(CN(C)C)ccc34)nn12] | (S)-(6-((dimethylamino)methyl)pyrazolo[1,5-a]pyridin-3-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1691 | 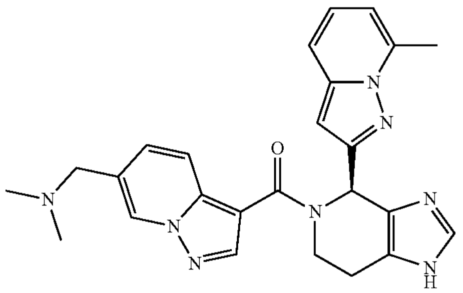 [SMILES: Cc1cccc2cc([C@H]3c4nc[nH]c4CCN3C(=O)c3cnn4cc(CN(C)C)ccc34)nn12] | (S)-(6-((dimethylamino) methyl)pyrazolo[1,5-a]pyridin-3-yl)(4-(7-methylpyrazolo [1,5-a]pyridin-2-yl)-6,7-dihydro-1H-imidazo[4,5-c] pyridin-5(4H)-yl)methanone |
| 1692 | 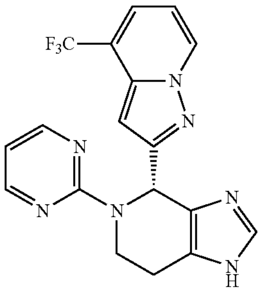 [SMILES: FC(F)(F)c1cccn2nc([C@@H]3c4nc[nH]c4CCN3c3ncccn3)cc12] | (S)-5-(pyrimidin-2-yl)-4-(4-(trifluoromethyl)pyrazolo [1,5-a]pyridin-2-yl)-4,5,6,7-tetrahydro-1H-imidazo [4,5-c]pyridine |
| 1693 | 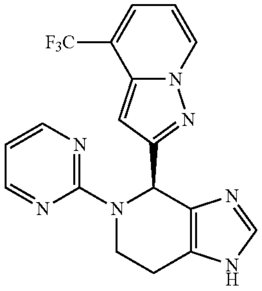 [SMILES: FC(F)(F)c1cccn2nc([C@H]3c4nc[nH]c4CCN3c3ncccn3)cc12] | (R)-5-(pyrimidin-2-yl)-4-(4-(trifluoromethyl)pyrazolo [1,5-a]pyridin-2-yl)-4,5,6,7-tetrahydro-1H-imidazo [4,5-c]pyridine |
| 1694 | 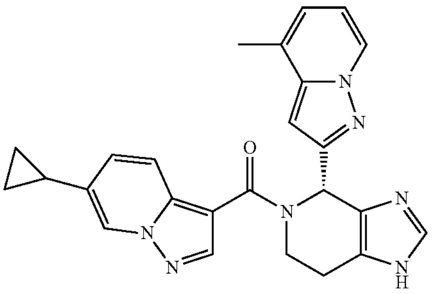 [SMILES: Cc1cccn2nc([C@@H]3c4nc[nH]c4CCN3C(=O)c3cnn4cc(C5CC5)ccc34)cc12] | (S)-(6-cyclopropylpyrazolo [1,5-a]pyridin-3-yl)(4-(4-methylpyrazolo[1,5-a] pyridin-2-yl)-6,7-dihydro-1H-imidazo[4,5-c]pyridin-5(4H)-yl)methanone |
| 1695 | 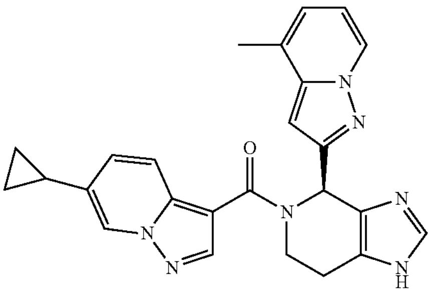 [SMILES: Cc1cccn2nc([C@H]3c4nc[nH]c4CCN3C(=O)c3cnn4cc(C5CC5)ccc34)cc12] | (R)-(6-cyclopropylpyrazolo [1,5-a]pyridin-3-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1696 | 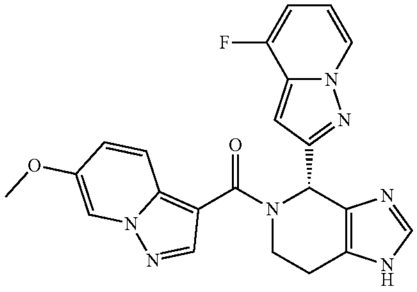 [SMILES: COc1ccc2c(C(=O)N3CCc4[nH]cnc4[C@H]3c3cc4c(F)cccn4n3)cnn2c1] | (S)-(4-(4-fluoropyrazolo[1,5-a]pyridin-2-yl)-6,7-dihydro-1H-imidazo[4,5-c]pyridin-5(4H)-yl)(6-methoxypyrazolo[1,5-a]pyridin-3-yl)methanone |
| 1697 | 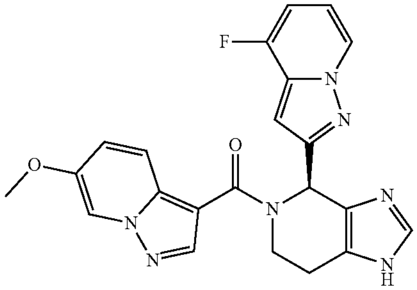 | (R)-(4-(4-fluoropyrazolo[1,5-a]pyridin-2-yl)-6,7-dihydro-1H-imidazo[4,5-c]pyridin-5(4H)-yl)(6-methoxypyrazolo[1,5-a]pyridin-3-yl)methanone |
| 1698 | 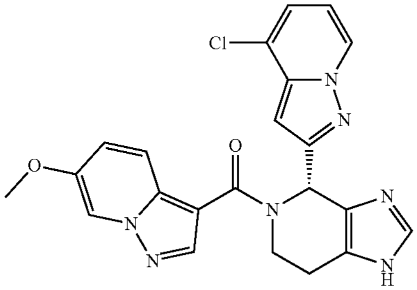 [SMILES: COc1ccc2c(C(=O)N3CCc4[nH]cnc4[C@H]3c3cc4c(Cl)cccn4n3)cnn2c1] | (S)-(4-(4-chloropyrazolo[1,5-a]pyridin-2-yl)-6,7-dihydro-1H-imidazo[4,5-c]pyridin-5(4H)-yl)(6-methoxypyrazolo[1,5-a]pyridin-3-yl)methanone |
| 1699 | 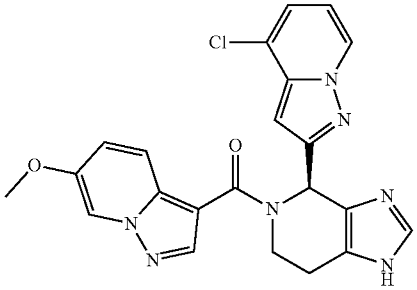 [SMILES: COc1ccc2c(C(=O)N3CCc4[nH]cnc4[C@@H]3c3cc4c(Cl)cccn4n3)cnn2c1] | (R)-(4-(4-chloropyrazolo[1,5-a]pyridin-2-yl)-6,7-dihydro-1H-imidazo[4,5-c]pyridin-5(4H)-yl)(6-methoxypyrazolo[1,5-a]pyridin-3-yl)methanone |
| 1700 | 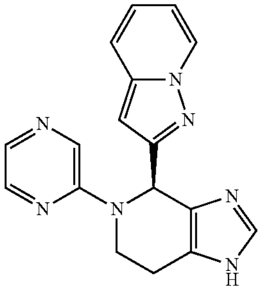 [SMILES: c1ccn2nc([C@H]3c4nc[nH]c4CCN3c3cnccn3)cc2c1] | (R)-5-(pyrazin-2-yl)-4-(pyrazolo[1,5-a]pyridin-2-yl)-4,5,6,7-tetrahydro-1H-imidazo[4,5-c]pyridine |

TABLE 1-continued

| Ex. # | Structure | Name |
|---|---|---|
| Pyrazolo[1,5-a]pyridines | | |
| 1701 | 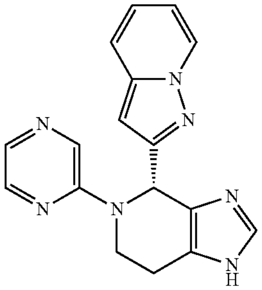 [SMILES: c1ccn2nc([C@@H]3c4nc[nH]c4CCN3c3cnccn3)cc2c1] | (S)-5-(pyrazin-2-yl)-4-(pyrazolo[1,5-a]pyridin-2-yl)-4,5,6,7-tetrahydro-1H-imidazo[4,5-c]pyridine |
| 1702 | 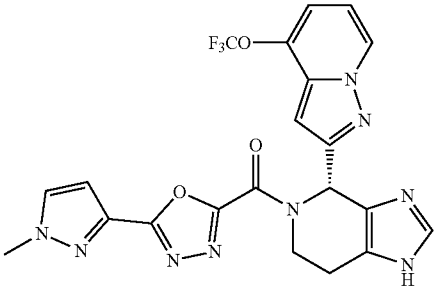 [SMILES: Cn1ccc(-c2nnc(C(=O)N3CCc4[nH]cnc4[C@H]3c3cc4c(OC(F)(F)F)cccn4n3)o2)n1] | (S)-(5-(1-methyl-1H-pyrazol-3-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1703 | 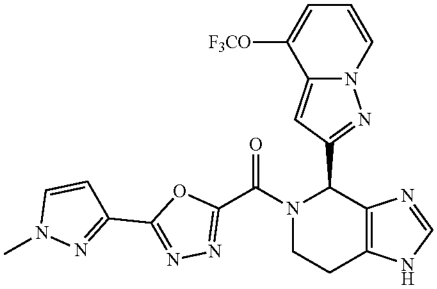 [SMILES: Cn1ccc(-c2nnc(C(=O)N3CCc4[nH]cnc4[C@@H]3c3cc4c(OC(F)(F)F)cccn4n3)o2)n1] | (R)-(5-(1-methyl-1H-pyrazol-3-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1704 | 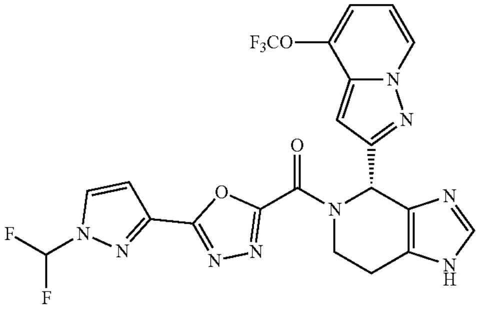 | (S)-(5-(1-(difluoromethyl)-1H-pyrazol-3-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1705 | 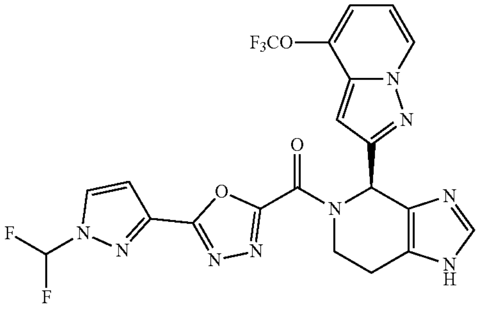 [SMILES: O=C(c1nnc(-c2ccn(C(F)F)n2)o1)N1CCc2[nH]cnc2[C@@H]1c1cc2c(OC(F)(F)F)cccn2n1] | (R)-(5-(1-(difluoromethyl)-1H-pyrazol-3-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 1706 | 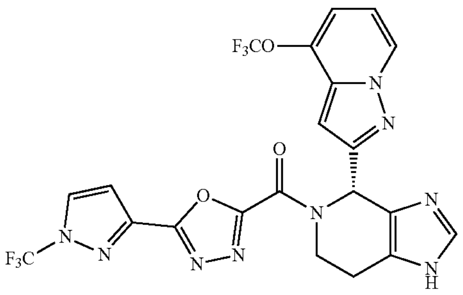 [SMILES: O=C(c1nnc(-c2ccn(C(F)(F)F)n2)o1)N1CCc2[nH]cnc2[C@H]1c1cc2c(OC(F)(F)F)cccn2n1] | (S)-(4-(4-(trifluoromethoxy) pyrazolo[1,5-a]pyridin-2-yl)-6,7-dihydro-1H-imidazo[4,5-c] pyridin-5(4H)-yl)(5-(1-(trifluoromethyl)-1H-pyrazol-3-yl)-1,3,4-oxadiazol-2-yl)methanone |
| 1707 | 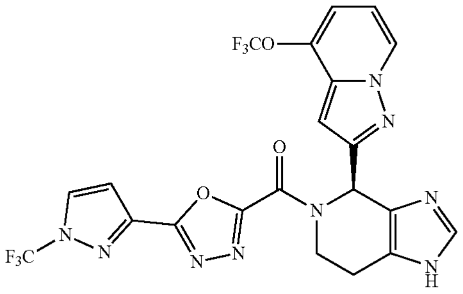 [SMILES: O=C(c1nnc(-c2ccn(C(F)(F)F)n2)o1)N1CCc2[nH]cnc2[C@@H]1c1cc2c(OC(F)(F)F)cccn2n1] | (R)-(4-(4-(trifluoromethoxy) pyrazolo[1,5-a]pyridin-2-yl)-6,7-dihydro-1H-imidazo [4,5-c]pyridin-5(4H)-yl)(5-(1-(trifluoromethyl)-1H-pyrazol-3-yl)-1,3,4-oxadiazol-2-yl)methanone |
| 1708 | 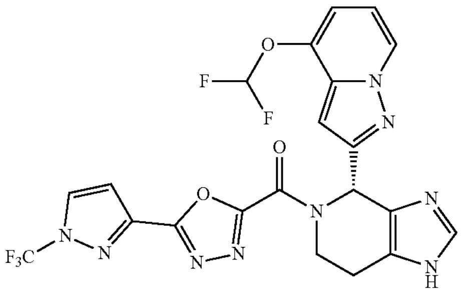 [SMILES: O=C(c1nnc(-c2ccn(C(F)(F)F)n2)o1)N1CCc2[nH]cnc2[C@H]1c1cc2c(OC(F)F)cccn2n1] | (S)-(4-(4-(difluoromethoxy) pyrazolo[1,5-a]pyridin-2-yl)-6,7-dihydro-1H-imidazo [4,5-c]pyridin-5(4H)-yl)(5-(1-(trifluoromethyl)-1H-pyrazol-3-yl)-1,3,4-oxadiazol-2-yl)methanone |
| 1709 | 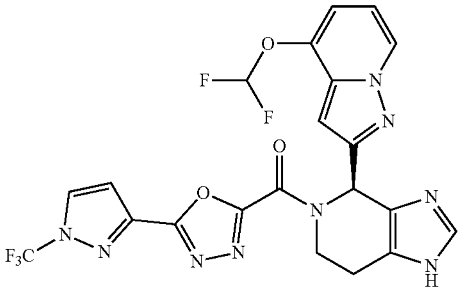 [SMILES: O=C(c1nnc(-c2ccn(C(F)(F)F)n2)o1)N1CCc2[nH]cnc2[C@@H]1c1cc2c(OC(F)F)cccn2n1] | (R)-(4-(4-(difluoromethoxy) pyrazolo[1,5-a]pyridin-2-yl)-6,7-dihydro-1H-imidazo [4,5-c]pyridin-5(4H)-yl)(5-(1-(trifluoromethyl)-1H-pyrazol-3-yl)-1,3,4-oxadiazol-2-yl)methanone |
| 1710 | 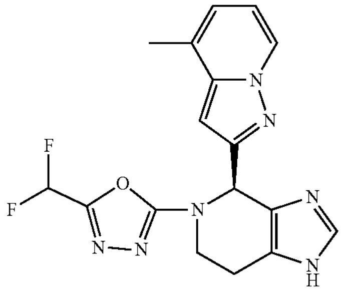 [SMILES: Cc1cccn2nc([C@H]3c4nc[nH]c4CCN3c3nnc(C(F)F)o3)cc12] | (R)-2-(difluoromethyl)-5-(4-(4-methylpyrazolo[1,5-a]pyridin-2-yl)-6,7-dihydro-1H-imidazo[4,5-c]pyridin-5(4H)-yl)-1,3,4-oxadiazole |

TABLE 1-continued

| Pyrazolo[1,5-a]pyridines | | |
|---|---|---|
| Ex. # | Structure | Name |
| 1711 | 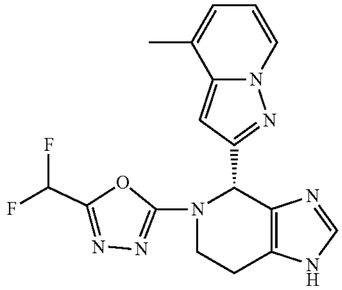 [SMILES: Cc1cccn2nc([C@@H]3c4nc[nH]c4CCN3c3nnc(C(F)F)o3)cc12] | (S)-2-(difluoromethyl)-5-(4-(4-methylpyrazolo[1,5-a]pyridin-2-yl)-6,7-dihydro-1H-imidazo[4,5-c]pyridin-5(4H)-yl)-1,3,4-oxadiazole |
| 1712 | 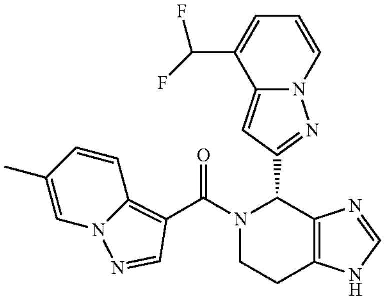 [SMILES: Cc1ccc2c(C(=O)N3CCc4[nH]cnc4[C@H]3c3cc4c(C(F)F)cccn4n3)cnn2c1] | (S)-(4-(4-(difluoromethyl) pyrazolo[1,5-a]pyridin-2-yl)-6,7-dihydro-1H-imidazo [4,5-c]pyridin-5(4H)-yl)(6-methylpyrazolo[1,5-a] pyridin-3-yl)methanone |
| 1713 | 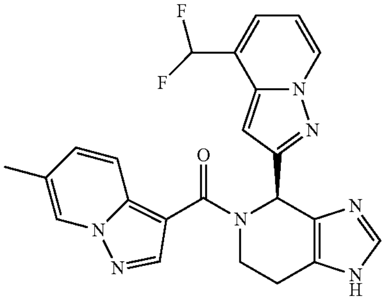 [SMILES: Cc1ccc2c(C(=O)N3CCc4[nH]cnc4[C@@H]3c3cc4c(C(F)F)cccn4n3)cnn2c1] | (R)-(4-(4-(difluoromethyl) pyrazolo[1,5-a]pyridin-2-yl)-6,7-dihydro-1H-imidazo [4,5-c]pyridin-5(4H)-yl)(6-methylpyrazolo[1,5-a] pyridin-3-yl)methanone |
| 1714 | 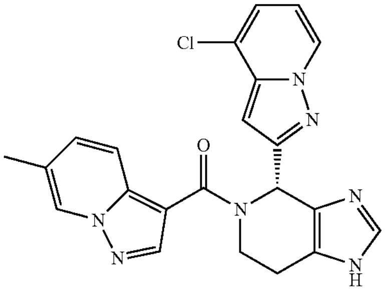 [SMILES: Cc1ccc2c(C(=O)N3CCc4[nH]cnc4[C@H]3c3cc4c(Cl)cccn4n3)cnn2c1] | (S)-(4-(4-chloropyrazolo [1,5-a]pyridin-2-yl)-6,7-dihydro-1H-imidazo [4,5-c]pyridin-5(4H)-yl)(6-methylpyrazolo[1,5-a] pyridin-3-yl)methanone |
| 1715 | 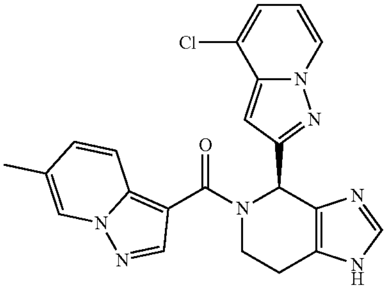 [SMILES: Cc1ccc2c(C(=O)N3CCc4[nH]cnc4[C@@H]3c3cc4c(Cl)cccn4n3)cnn2c1] | (R)-(4-(4-chloropyrazolo [1,5-a]pyridin-2-yl)-6,7-dihydro-1H-imidazo [4,5-c]pyridin-5(4H)-yl)(6-methylpyrazolo[1,5-a] pyridin-3-yl)methanone |

TABLE 1-continued

| Pyrazolo[1,5-a]pyridines | | |
|---|---|---|
| Ex. # | Structure | Name |
| 1716 | 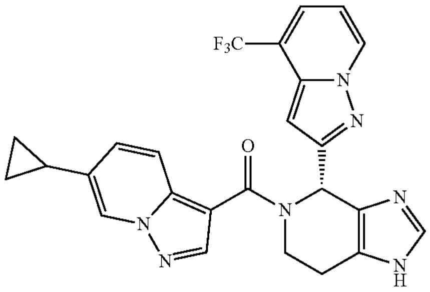 | (S)-(6-cyclopropylpyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 1717 | 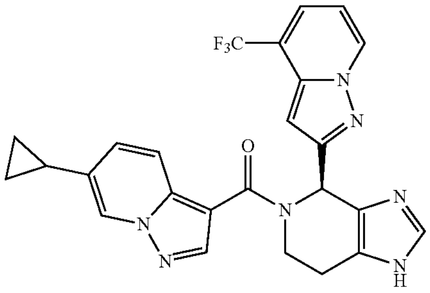 | (R)-(6-cyclopropylpyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 1718 | 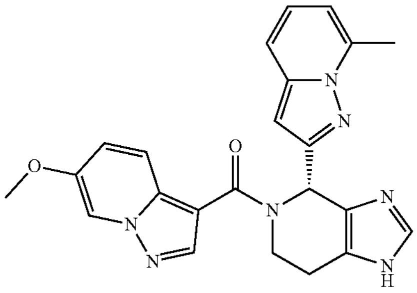 [SMILES: COc1ccc2c(C(=O)N3CCc4[nH]cnc4[C@H]3c3cc4cccc(C)n4n3)cnn2c1] | (S)-(6-methoxypyrazolo[1,5-a]pyridin-3-yl)(4-(7-methylpyrazolo[1,5-a]pyridin-2-yl)-6,7-dihydro-1H-imidazo[4,5-c]pyridin-5(4H)-yl)methanone |
| 1719 | 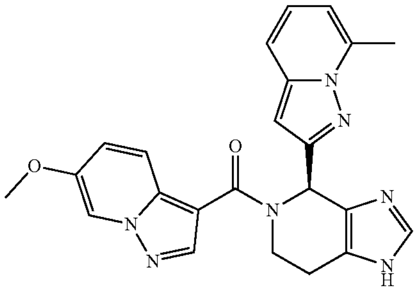 [SMILES: COc1ccc2c(C(=O)N3CCc4[nH]cnc4[C@@H]3c3cc4cccc(C)n4n3)cnn2c1] | (R)-(6-methoxypyrazolo[1,5-a]pyridin-3-yl)(4-(7-methylpyrazolo[1,5-a]pyridin-2-yl)-6,7-dihydro-1H-imidazo[4,5-c]pyridin-5(4H)-yl)methanone |
| 1720 | 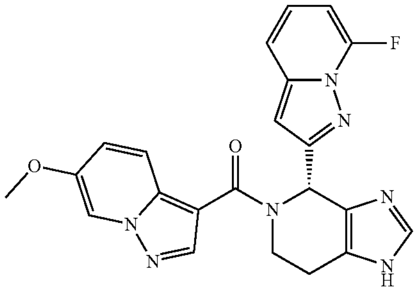 [SMILES: COc1ccc2c(C(=O)N3CCc4[nH]cnc4[C@H]3c3cc4cccc(F)n4n3)cnn2c1] | (S)-(4-(7-fluoropyrazolo[1,5-a]pyridin-2-yl)-6,7-dihydro-1H-imidazo[4,5-c]pyridin-5(4H)-yl)(6-methoxypyrazolo[1,5-a]pyridin-3-yl)methanone |

TABLE 1-continued

| Pyrazolo[1,5-a]pyridines | | |
|---|---|---|
| Ex. # | Structure | Name |
| 1721 | 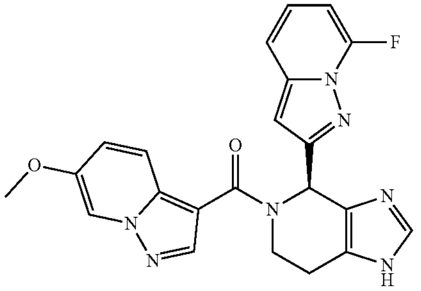 [SMILES: COc1ccc2c(C(=O)N3CCc4[nH]cnc4[C@@H]3c3cc4cccc(F)n4n3)cnn2c1] | (R)-(4-(7-fluoropyrazolo[1,5-a]pyridin-2-yl)-6,7-dihydro-1H-imidazo[4,5-c]pyridin-5(4H)-yl)(6-methoxypyrazolo[1,5-a]pyridin-3-yl)methanone |
| 1722 | 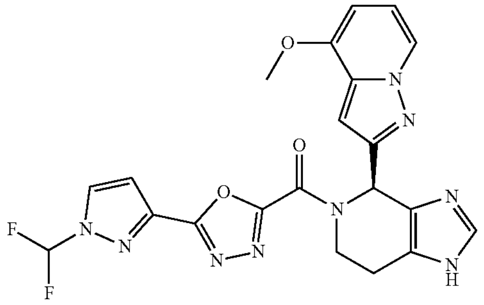 [SMILES: COc1cccn2nc([C@H]3c4nc[nH]c4CCN3C(=O)c3nnc(-c4ccn(C(F)F)n4)o3)cc12] | (R)-(5-(1-(difluoromethyl)-1H-pyrazol-3-yl)-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 1723 | 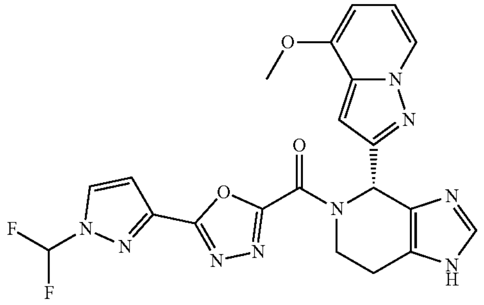 [SMILES: COc1cccn2nc([C@@H]3c4nc[nH]c4CCN3C(=O)c3nnc(-c4ccn(C(F)F)n4)o3)cc12] | (S)-(5-(1-(difluoromethyl)-1H-pyrazol-3-yl)-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 1724 | 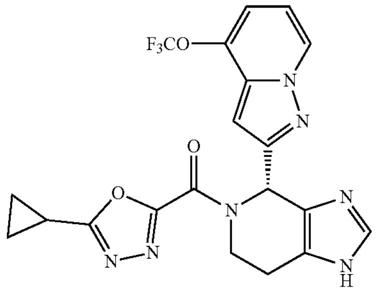 | (S)-(5-cyclopropyl-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1725 | 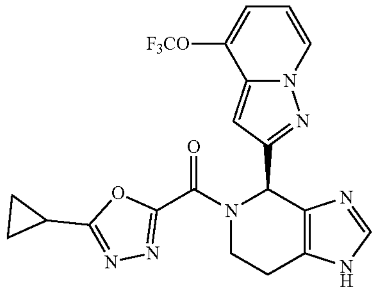 [SMILES: O=C(c1nnc(C2CC2)o1)N1CCc2[nH]cnc2[C@@H]1c1cc2c(OC(F)(F)F)cccn2n1] | (R)-(5-cyclopropyl-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1726 | 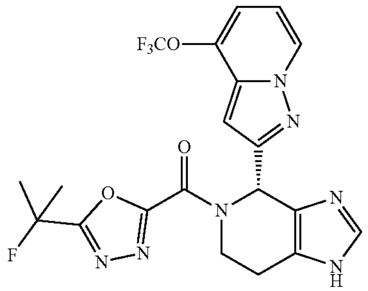 [SMILES: CC(C)(F)c1nnc(C(=O)N2CCc3[nH]cnc3[C@H]2c2cc3c(OC(F)(F)F)cccn3n2)o1] | (S)-(5-(2-fluoropropan-2-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1727 | 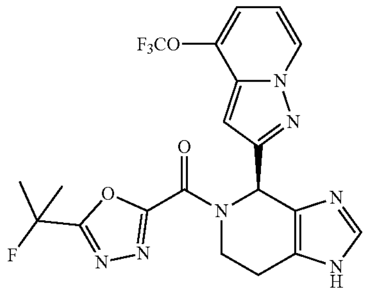 [SMILES: CC(C)(F)c1nnc(C(=O)N2CCc3[nH]cnc3[C@@H]2c2cc3c(OC(F)(F)F)cccn3n2)o1] | (R)-(5-(2-fluoropropan-2-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1728 | 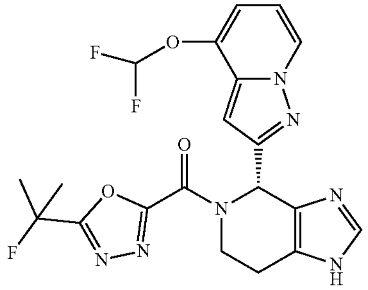 [SMILES: CC(C)(F)c1nnc(C(=O)N2CCc3[nH]cnc3[C@H]2c2cc3c(OC(F)F)cccn3n2)o1] | (S)-(4-(4-(difluoromethoxy)pyrazolo[1,5-a]pyridin-2-yl)-6,7-dihydro-1H-imidazo[4,5-c]pyridin-5(4H)-yl)(5-(2-fluoropropan-2-yl)-1,3,4-oxadiazol-2-yl)methanone |
| 1729 | 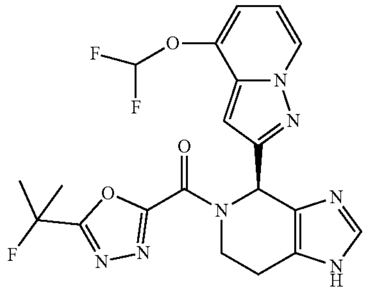 [SMILES: CC(C)(F)c1nnc(C(=O)N2CCc3[nH]cnc3[C@@H]2c2cc3c(OC(F)F)cccn3n2)o1] | (R)-(4-(4-(difluoromethoxy)pyrazolo[1,5-a]pyridin-2-yl)-6,7-dihydro-1H-imidazo[4,5-c]pyridin-5(4H)-yl)(5-(2-fluoropropan-2-yl)-1,3,4-oxadiazol-2-yl)methanone |
| 1730 | 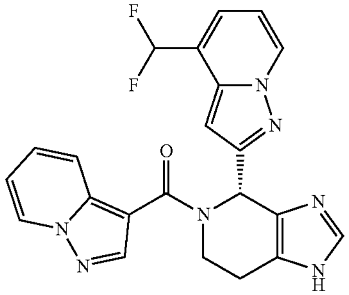 [SMILES: O=C(c1cnn2ccccc12)N1CCc2[nH]cnc2[C@H]1c1cc2c(C(F)F)cccn2n1] | (S)-(4-(4-(difluoromethyl)pyrazolo[1,5-a]pyridin-2-yl)-6,7-dihydro-1H-imidazo[4,5-c]pyridin-5(4H)-yl)(pyrazolo[1,5-a]pyridin-3-yl)methanone |

TABLE 1-continued

| Ex. # | Structure | Name |
|---|---|---|
| | Pyrazolo[1,5-a]pyridines | |
| 1731 | 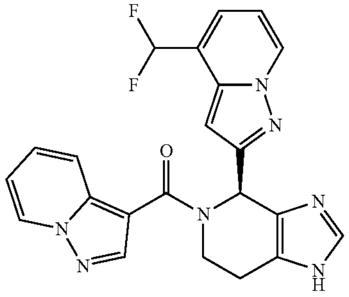 [SMILES: O=C(c1cnn2ccccc12)N1CCc2[nH]cnc2[C@@H]1c1cc2c(C(F)F)cccn2n1] | (R)-(4-(4-(difluoromethyl) pyrazolo[1,5-a]pyridin-2-yl)-6,7-dihydro-1H-imidazo [4,5-c]pyridin-5(4H)-yl)(pyrazolo[1,5-a]pyridin-3-yl)methanone |
| 1732 | 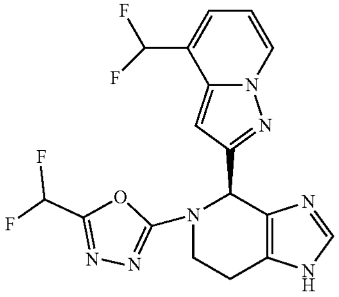 [SMILES: FC(F)c1nnc(N2CCc3[nH]cnc3[C@@H]2c2cc3c(C(F)F)cccn3n2)o1] | (R)-2-(difluoromethyl)-5-(4-(4-(difluoromethyl) pyrazolo[1,5-a]pyridin-2-yl)-6,7-dihydro-1H-imidazo[4,5-c]pyridin-5(4H)-yl)-1,3,4-oxadiazole |
| 1733 | 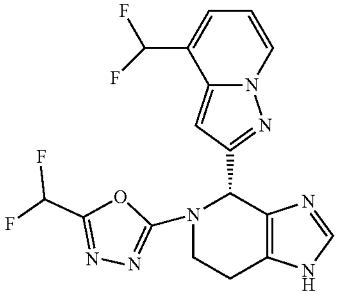 [SMILES: FC(F)c1nnc(N2CCc3[nH]cnc3[C@H]2c2cc3c(C(F)F)cccn3n2)o1] | (S)-2-(difluoromethyl)-5-(4-(4-(difluoromethyl) pyrazolo[1,5-a]pyridin-2-yl)-6,7-dihydro-1H-imidazo [4,5-c]pyridin-5(4H)-yl)-1,3,4-oxadiazole |
| 1734 | 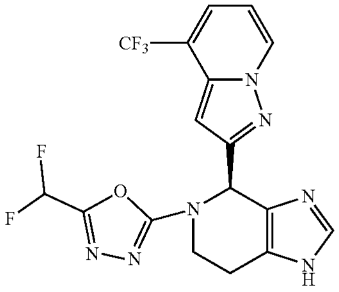 [SMILES: FC(F)c1nnc(N2CCc3[nH]cnc3[C@@H]2c2cc3c(C(F)(F)F)cccn3n2)o1] | (R)-2-(difluoromethyl)-5-(4-(4-(trifluoromethyl)pyrazolo [1,5-a]pyridin-2-yl)-6,7-dihydro-1H-imidazo[4,5-c] pyridin-5(4H)-yl)-1,3,4-oxadiazole |
| 1735 | 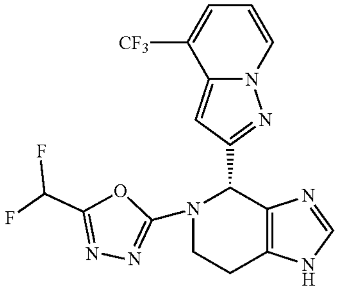 [SMILES: FC(F)c1nnc(N2CCc3[nH]cnc3[C@H]2c2cc3c(C(F)(F)F)cccn3n2)o1] | (S)-2-(difluoromethyl)-5-(4-(4-(trifluoromethyl)pyrazolo [1,5-a]pyridin-2-yl)-6,7-dihydro-1H-imidazo[4,5-c] pyridin-5(4H)-yl)-1,3,4-oxadiazole |

TABLE 1-continued

| Pyrazolo[1,5-a]pyridines | | |
|---|---|---|
| Ex. # | Structure | Name |
| 1736 | 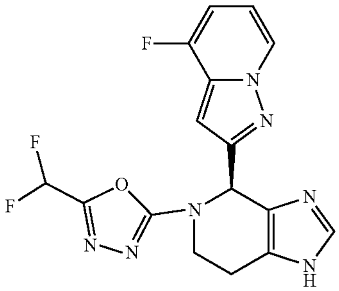 [SMILES: Fc1cccn2nc([C@H]3c4nc[nH]c4CCN3c3nnc(C(F)F)o3)cc12] | (R)-2-(difluoromethyl)-5-(4-(4-fluoropyrazolo[1,5-a]pyridin-2-yl)-6,7-dihydro-1H-imidazo[4,5-c]pyridin-5(4H)-yl)-1,3,4-oxadiazole |
| 1737 | 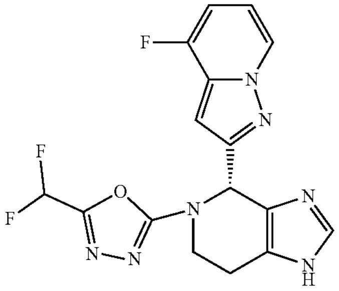 [SMILES: Fc1cccn2nc([C@@H]3c4nc[nH]c4CCN3c3nnc(C(F)F)o3)cc12] | (S)-2-(difluoromethyl)-5-(4-(4-fluoropyrazolo[1,5-a]pyridin-2-yl)-6,7-dihydro-1H-imidazo[4,5-c]pyridin-5(4H)-yl)-1,3,4-oxadiazole |
| 1738 | 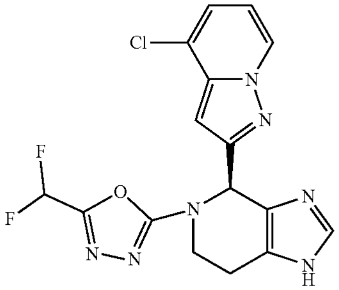 [SMILES: FC(F)c1nnc(N2CCc3[nH]cnc3[C@@H]2c2cc3c(Cl)cccn3n2)o1] | (R)-2-(4-(4-chloropyrazolo[1,5-a]pyridin-2-yl)-6,7-dihydro-1H-imidazo[4,5-c]pyridin-5(4H)-yl)-5-(difluoromethyl)-1,3,4-oxadiazole |
| 1739 | 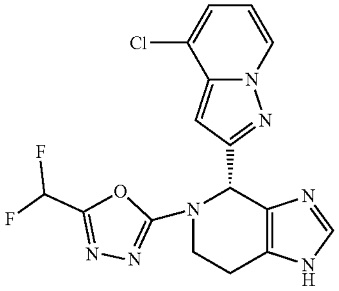 | (S)-2-(4-(4-chloropyrazolo[1,5-a]pyridin-2-yl)-6,7-dihydro-1H-imidazo[4,5-c]pyridin-5(4H)-yl)-5-(difluoromethyl)-1,3,4-oxadiazole |
| 1740 | 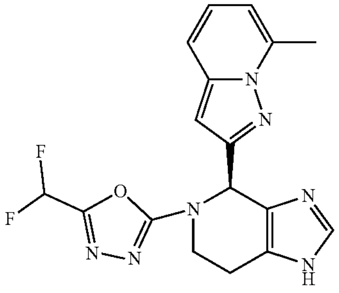 [SMILES: Cc1cccc2cc([C@H]3c4nc[nH]c4CCN3c3nnc(C(F)F)o3)nn12] | (R)-2-(difluoromethyl)-5-(4-(7-methylpyrazolo[1,5-a]pyridin-2-yl)-6,7-dihydro-1H-imidazo[4,5-c]pyridin-5(4H)-yl)-1,3,4-oxadiazole |

TABLE 1-continued

| Pyrazolo[1,5-a]pyridines | | |
|---|---|---|
| Ex. # | Structure | Name |
| 1741 | 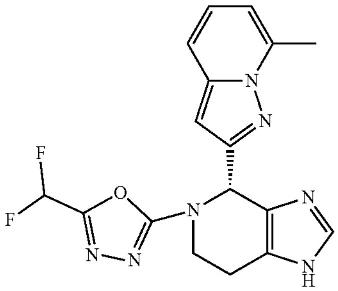 [SMILES: Cc1cccc2cc([C@@H]3c4nc[nH]c4CCN3c3nnc(C(F)F)o3)nn12] | (S)-2-(difluoromethyl)-5-(4-(7-methylpyrazolo[1,5-a]pyridin-2-yl)-6,7-dihydro-1H-imidazo[4,5-c]pyridin-5(4H)-yl)-1,3,4-oxadiazole |
| 1742 | 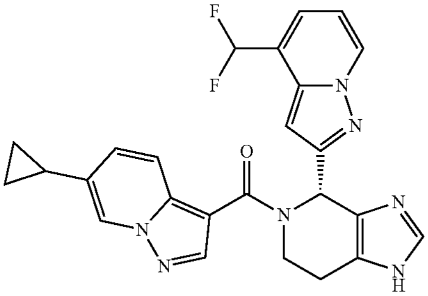 [SMILES: O=C(c1cnn2cc(C3CC3)ccc12)N1CCc2[nH]cnc2[C@H]1c1cc2c(C(F)F)cccn2n1] | (S)-(6-cyclopropylpyrazolo[1,5-a]pyridin-3-yl)(4-(4-(difluoromethyl)pyrazolo[1,5-a]pyridin-2-yl)-6,7-dihydro-1H-imidazo[4,5-c]pyridin-5(4H)-yl)methanone |
| 1743 | 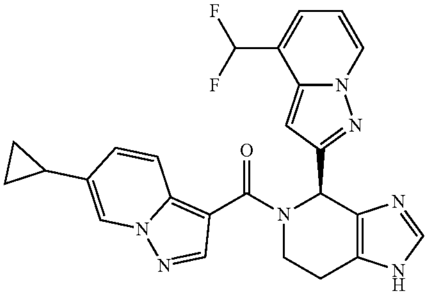 [SMILES: O=C(c1cnn2cc(C3CC3)ccc12)N1CCc2[nH]cnc2[C@@H]1c1cc2c(C(F)F)cccn2n1] | (R)-(6-cyclopropylpyrazolo[1,5-a]pyridin-3-yl)(4-(4-(difluoromethyl)pyrazolo[1,5-a]pyridin-2-yl)-6,7-dihydro-1H-imidazo[4,5-c]pyridin-5(4H)-yl)methanone |
| 1744 | 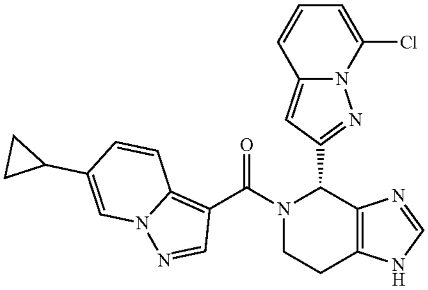 [SMILES: O=C(c1cnn2cc(C3CC3)ccc12)N1CCc2[nH]cnc2[C@H]1c1cc2cccc(Cl)n2n1] | (S)-(4-(7-chloropyrazolo[1,5-a]pyridin-2-yl)-6,7-dihydro-1H-imidazo[4,5-c]pyridin-5(4H)-yl)(6-cyclopropylpyrazolo[1,5-a]pyridin-3-yl)methanone |
| 1745 | 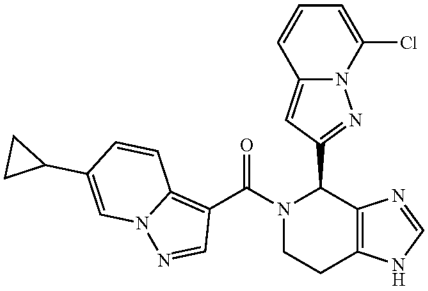 [SMILES: O=C(c1cnn2cc(C3CC3)ccc12)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(6-cyclopropylpyrazolo[1,5-a]pyridin-3-yl)methanone |

TABLE 1-continued

Pyrazolo[1,5-a]pyridines

| Ex. # | Structure | Name |
|---|---|---|
| 1746 | 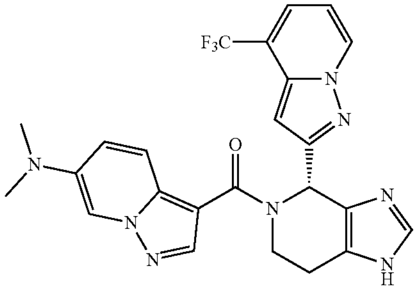 [SMILES: CN(C)c1ccc2c(C(=O)N3CCc4[nH]cnc4[C@H]3c3cc4c(C(F)(F)F)cccn4n3)cnn2c1] | (S)-(6-(dimethylamino) pyrazolo[1,5-a]pyridin-3-yl)(4-(4-(trifluoromethyl)pyrazolo [1,5-a]pyridin-2-yl)-6,7-dihydro-1H-imidazo[4,5-c] pyridin-5(4H)-yl)methanone |
| 1747 | 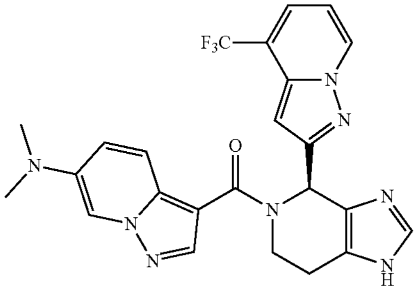 [SMILES: CN(C)c1ccc2c(C(=O)N3CCc4[nH]cnc4[C@@H]3c3cc4c(C(F)(F)F)cccn4n3)cnn2c1] | (R)-(6-(dimethylamino) pyrazolo[1,5-a]pyridin-3-yl)(4-(4-(trifluoromethyl)pyrazolo [1,5-a]pyridin-2-yl)-6,7-dihydro-1H-imidazo[4,5-c] pyridin-5(4H)-yl)methanone |
| 1748 | 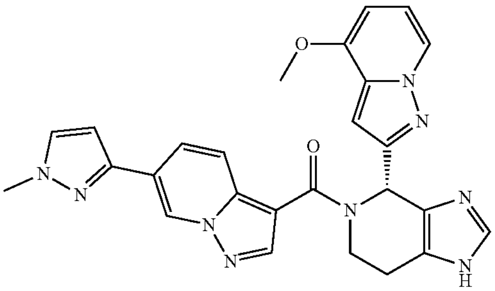 [SMILES: COc1cccn2nc([C@@H]3c4nc[nH]c4CCN3C(=O)c3cnn4cc(-c5ccn(C)n5)ccc34)cc12] | (S)-(4-(4-methoxypyrazolo [1,5-a]pyridin-2-yl)-6,7-dihydro-1H-imidazo[4,5-c] pyridin-5(4H)-yl)(6-(1-methyl-1H-pyrazol-3-yl) pyrazolo[1,5-a]pyridin-3-yl)methanone |
| 1749 | 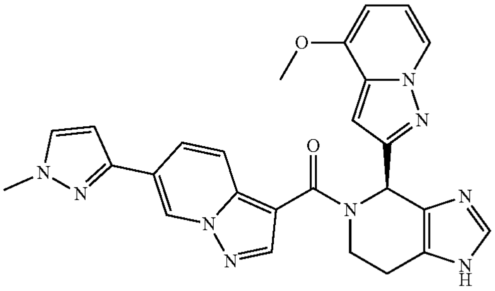 [SMILES: COc1cccn2nc([C@H]3c4nc[nH]c4CCN3C(=O)c3cnn4cc(-c5ccn(C)n5)ccc34)cc12] | (R)-(4-(4-methoxypyrazolo [1,5-a]pyridin-2-yl)-6,7-dihydro-1H-imidazo[4,5-c] pyridin-5(4H)-yl)(6-(1-methyl-1H-pyrazol-3-yl) pyrazolo[1,5-a]pyridin-3-yl)methanone |
| 1750 | 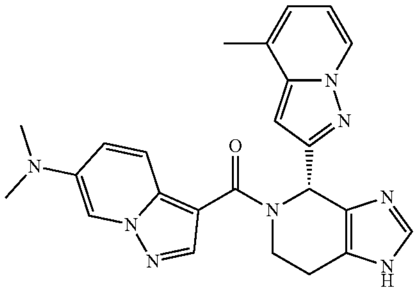 [SMILES: Cc1cccn2nc([C@@H]3c4nc[nH]c4CCN3C(=O)c3cnn4cc(N(C)C)ccc34)cc12] | (S)-(6-(dimethylamino) pyrazolo[1,5-a]pyridin-3-yl)(4-(4-methylpyrazolo[1,5-a] pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1751 | 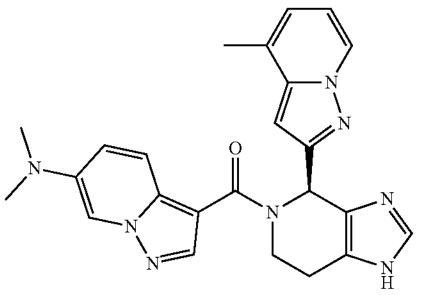 [SMILES: Cc1cccn2nc([C@H]3c4nc[nH]c4CCN3C(=O)c3cnn4cc(N(C)C)ccc34)cc12] | (R)-(6-(dimethylamino) pyrazolo[1,5-a]pyridin-3-yl)(4-(4-methylpyrazolo[1,5-a] pyridin-2-yl)-6,7-dihydro-1H-imidazo[4,5-c]pyridin-5(4H)-yl)methanone |
| 1752 | 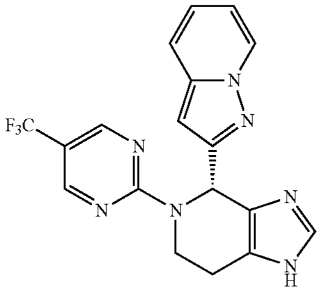 | (S)-4-(pyrazolo[1,5-a] pyridin-2-yl)-5-(5-(trifluoromethyl)pyrimidin-2-yl)-4,5,6,7-tetrahydro-1H-imidazo[4,5-c]pyridine |
| 1753 | 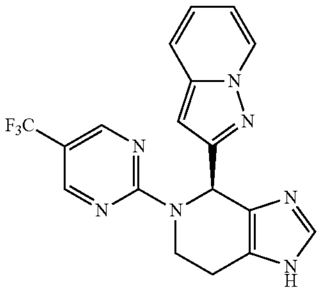 [SMILES: FC(F)(F)c1cnc(N2CCc3[nH]cnc3[C@@H]2c2cc3ccccn3n2)nc1] | (R)-4-(pyrazolo[1,5-a] pyridin-2-yl)-5-(5-(trifluoromethyl)pyrimidin-2-yl)-4,5,6,7-tetrahydro-1H-imidazo[4,5-c]pyridine |
| 1754 | 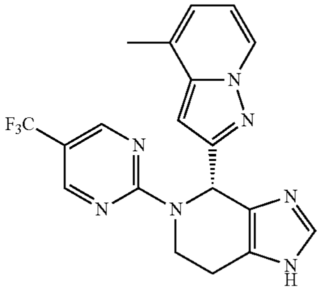 [SMILES: Cc1cccn2nc([C@@H]3c4nc[nH]c4CCN3c3ncc(C(F)(F)F)cn3)cc12] | (S)-4-(4-methylpyrazolo [1,5-a]pyridin-2-yl)-5-(5-(trifluoromethyl)pyrimidin-2-yl)-4,5,6,7-tetrahydro-1H-imidazo[4,5-c]pyridine |
| 1755 | 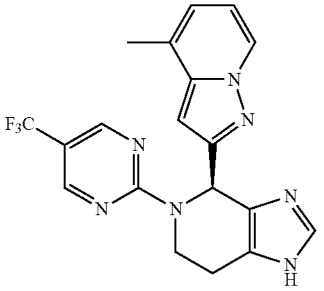 [SMILES: Cc1cccn2nc([C@H]3c4nc[nH]c4CCN3c3ncc(C(F)(F)F)cn3)cc12] | (R)-4-(4-methylpyrazolo [1,5-a]pyridin-2-yl)-5-(5-(trifluoromethyl)pyrimidin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 1756 | 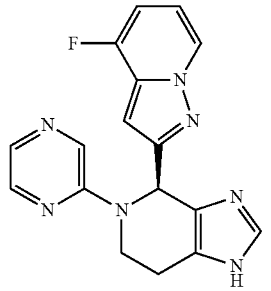 [SMILES: Fc1cccn2nc([C@H]3c4nc[nH]c4CCN3c3cnccn3)cc12] | (R)-4-(4-fluoropyrazolo[1,5-a]pyridin-2-yl)-5-(pyrazin-2-yl)-4,5,6,7-tetrahydro-1H-imidazo[4,5-c]pyridine |
| 1757 | 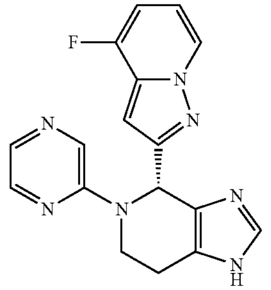 [SMILES: Fc1cccn2nc([C@@H]3c4nc[nH]c4CCN3c3cnccn3)cc12] | (S)-4-(4-fluoropyrazolo[1,5-a]pyridin-2-yl)-5-(pyrazin-2-yl)-4,5,6,7-tetrahydro-1H-imidazo[4,5-c]pyridine |
| 1758 | 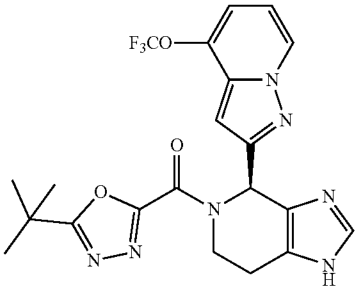 | (R)-(5-(tert-butyl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1759 | 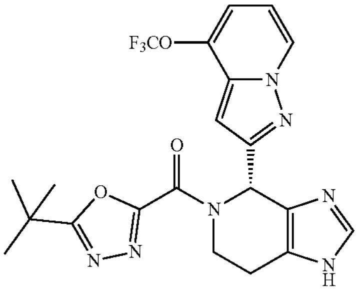 [SMILES: CC(C)(C)c1nnc(C(=O)N2CCc3[nH]cnc3[C@H]2c2cc3c(OC(F)(F)F)cccn3n2)o1] | (S)-(5-(tert-butyl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1760 | 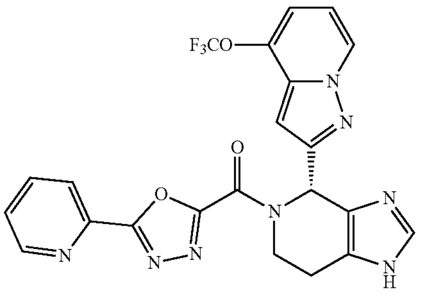 [SMILES: O=C(c1nnc(-c2ccccn2)o1)N1CCc2[nH]cnc2[C@H]1c1cc2c(OC(F)(F)F)cccn2n1] | (S)-(5-(pyridin-2-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1761 | 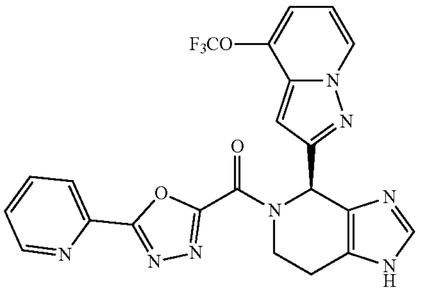 | (R)-(5-(pyridin-2-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1762 | 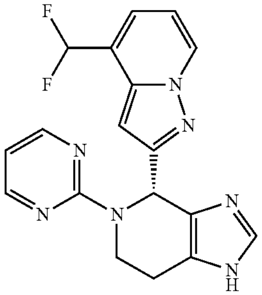 | (S)-4-(4-(difluoromethyl)pyrazolo[1,5-a]pyridin-2-yl)-5-(pyrimidin-2-yl)-4,5,6,7-tetrahydro-1H-imidazo[4,5-c]pyridine |
| 1763 | 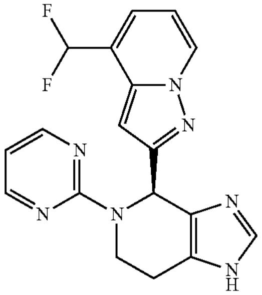 [SMILES: FC(F)c1cccn2nc([C@H]3c4nc[nH]c4CCN3c3ncccn3)cc12] | (R)-4-(4-(difluoromethyl)pyrazolo[1,5-a]pyridin-2-yl)-5-(pyrimidin-2-yl)-4,5,6,7-tetrahydro-1H-imidazo[4,5-c]pyridine |
| 1764 | 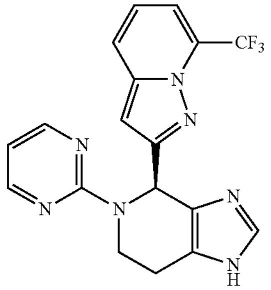 [SMILES: FC(F)(F)c1cccc2cc([C@H]3c4nc[nH]c4CCN3c3ncccn3)nn12] | (R)-5-(pyrimidin-2-yl)-4-(7-(trifluoromethyl)pyrazolo[1,5-a]pyridin-2-yl)-4,5,6,7-tetrahydro-1H-imidazo[4,5-c]pyridine |
| 1765 | 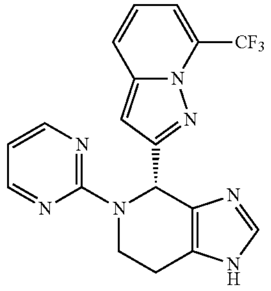 [SMILES: FC(F)(F)c1cccc2cc([C@@H]3c4nc[nH]c4CCN3c3ncccn3)nn12] | (S)-5-(pyrimidin-2-yl)-4-(7-(trifluoromethyl)pyrazolo[1,5-a]pyridin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 1766 | 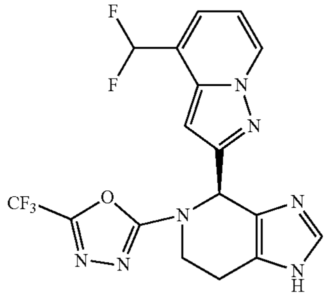 [SMILES: FC(F)c1cccn2nc([C@H]3c4nc[nH]c4CCN3c3nnc(C(F)(F)F)o3)cc12] | (R)-2-(4-(4-(difluoromethyl) pyrazolo[1,5-a]pyridin-2-yl)-6,7-dihydro-1H-imidazo [4,5-c]pyridin-5(4H)-yl)-5-(trifluoromethyl)-1,3,4-oxadiazole |
| 1767 | 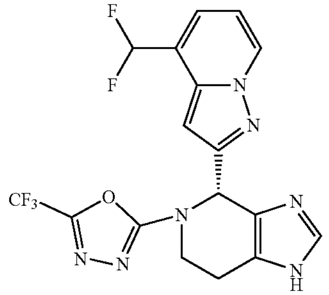 [SMILES: FC(F)c1cccn2nc([C@@H]3c4nc[nH]c4CCN3c3nnc(C(F)(F)F)o3)cc12] | (S)-2-(4-(4-(difluoromethyl) pyrazolo[1,5-a]pyridin-2-yl)-6,7-dihydro-1H-imidazo [4,5-c]pyridin-5(4H)-yl)-5-(trifluoromethyl)-1,3,4-oxadiazole |
| 1768 | 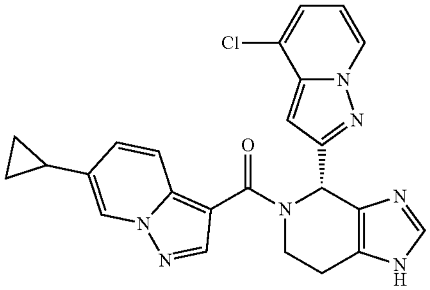 [SMILES: O=C(c1cnn2cc(C3CC3)ccc12)N1CCc2[nH]cnc2[C@H]1c1cc2c(Cl)cccn2n1] | (S)-(4-(4-chloropyrazolo [1,5-a]pyridin-2-yl)-6,7-dihydro-1H-imidazo [4,5-c]pyridin-5(4H)-yl)(6-cyclopropylpyrazolo[1,5-a] pyridin-3-yl)methanone |
| 1769 | 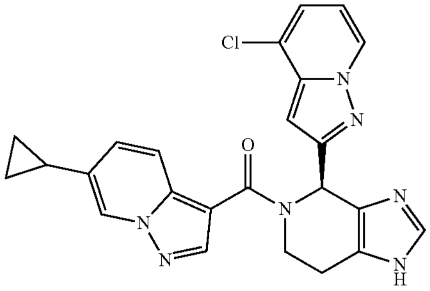 [SMILES: O=C(c1cnn2cc(C3CC3)ccc12)N1CCc2[nH]cnc2[C@@H]1c1cc2c(Cl)cccn2n1] | (R)-(4-(4-chloropyrazolo [1,5-a]pyridin-2-yl)-6,7-dihydro-1H-imidazo[4,5-c] pyridin-5(4H)-yl)(6-cyclopropylpyrazolo[1,5-a] pyridin-3-yl)methanone |
| 1770 | 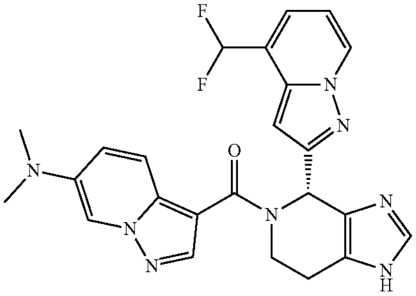 [SMILES: CN(C)c1ccc2c(C(=O)N3CCc4[nH]cnc4[C@H]3c3cc4c(C(F)F)cccn4n3)cnn2c1] | (S)-(4-(4-(difluoromethyl) pyrazolo[1,5-a]pyridin-2-yl)-6,7-dihydro-1H-imidazo [4,5-c]pyridin-5(4H)-yl)(6-(dimethylamino)pyrazolo [1,5-a]pyridin-3-yl)methanone |

TABLE 1-continued

| Pyrazolo[1,5-a]pyridines | | |
|---|---|---|
| Ex. # | Structure | Name |
| 1771 | 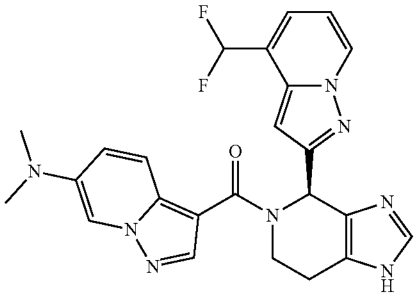 [SMILES: CN(C)c1ccc2c(C(=O)N3CCc4[nH]cnc4[C@@H]3c3cc4c(C(F)F)cccn4n3)cnn2c1] | (R)-(4-(4-(difluoromethyl) pyrazolo[1,5-a]pyridin-2-yl)-6,7-dihydro-1H-imidazo [4,5-c]pyridin-5(4H)-yl)(6-(dimethylamino)pyrazolo [1,5-a]pyridin-3-yl)methanone |
| 1772 | 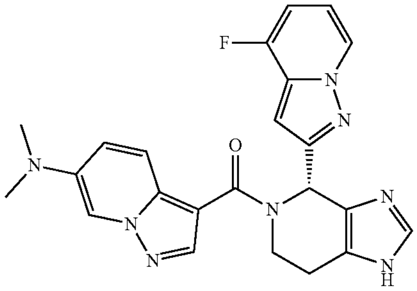 [SMILES: CN(C)c1ccc2c(C(=O)N3CCc4[nH]cnc4[C@H]3c3cc4c(F)cccn4n3)cnn2c1] | (S)-(6-(dimethylamino) pyrazolo[1,5-a]pyridin-3-yl)(4-(4-fluoropyrazolo[1,5-a] pyridin-2-yl)-6,7-dihydro-1H-imidazo[4,5-c]pyridin-5(4H)-yl)methanone |
| 1773 | 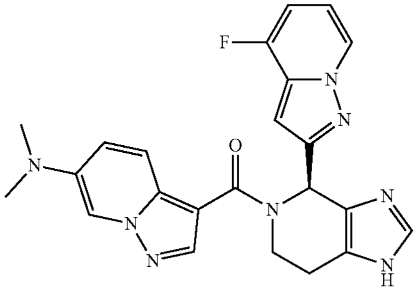 | (R)-(6-(dimethylamino) pyrazolo[1,5-a]pyridin-3-yl)(4-(4-fluoropyrazolo[1,5-a]pyridin-2-yl)-6,7-dihydro-1H-imidazo[4,5-c]pyridin-5(4H)-yl)methanone |
| 1774 | 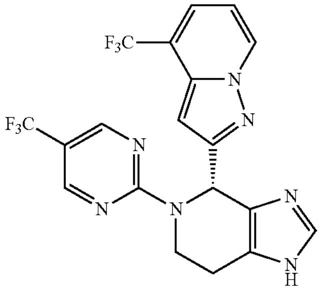 [SMILES: FC(F)(F)c1cnc(N2CCc3[nH]cnc3[C@H]2c2cc3c(C(F)(F)F)cccn3n2)nc1] | (S)-4-(4-(trifluoromethyl) pyrazolo[1,5-a]pyridin-2-yl)-5-(5-(trifluoromethyl)pyrimidin-2-yl)-4,5,6,7-tetrahydro-1H-imidazo[4,5-c]pyridine |
| 1775 | 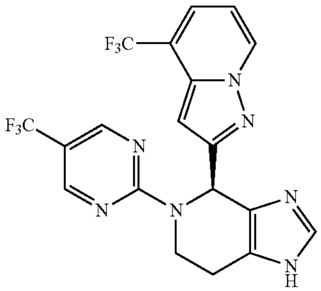 [SMILES: FC(F)(F)c1cnc(N2CCc3[nH]cnc3[C@@H]2c2cc3c(C(F)(F)F)cccn3n2)nc1] | (R)-4-(4-(trifluoromethyl) pyrazolo[1,5-a]pyridin-2-yl)-5-(5-(trifluoromethyl)pyrimidin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 1776 | 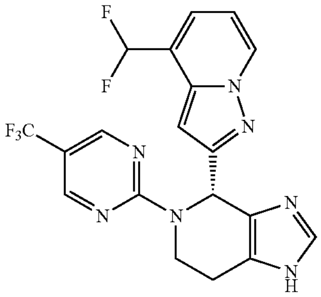 | (S)-4-(4-(difluoromethyl) pyrazolo[1,5-a]pyridin-2-yl)-5-(5-(trifluoromethyl)pyrimidin-2-yl)-4,5,6,7-tetrahydro-1H-imidazo[4,5-c]pyridine |
| 1777 | 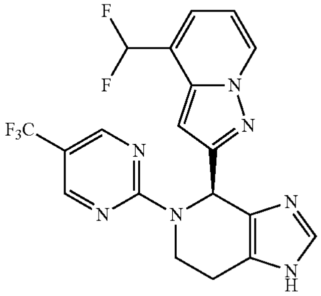 [SMILES: FC(F)c1cccn2nc([C@H]3c4nc[nH]c4CCN3c3ncc(C(F)(F)F)cn3)cc12] | (R)-4-(4-(difluoromethyl) pyrazolo[1,5-a]pyridin-2-yl)-5-(5-(trifluoromethyl)pyrimidin-2-yl)-4,5,6,7-tetrahydro-1H-imidazo[4,5-c]pyridine |
| 1778 | 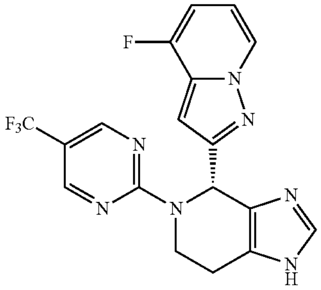 [SMILES: Fc1cccn2nc([C@@H]3c4nc[nH]c4CCN3c3ncc(C(F)(F)F)cn3)cc12] | (S)-4-(4-fluoropyrazolo [1,5-a]pyridin-2-yl)-5-(5-(trifluoromethyl)pyrimidin-2-yl)-4,5,6,7-tetrahydro-1H-imidazo[4,5-c]pyridine |
| 1779 | 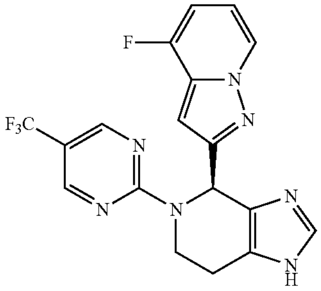 [SMILES: Fc1cccn2nc([C@H]3c4nc[nH]c4CCN3c3ncc(C(F)(F)F)cn3)cc12] | (R)-4-(4-fluoropyrazolo [1,5-a]pyridin-2-yl)-5-(5-(trifluoromethyl)pyrimidin-2-yl)-4,5,6,7-tetrahydro-1H-imidazo[4,5-c]pyridine |
| 1780 | 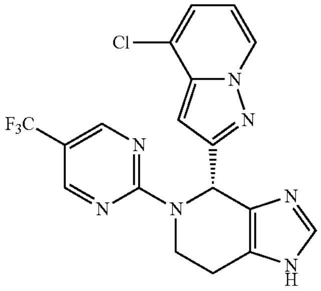 [SMILES: FC(F)(F)c1cnc(N2CCc3[nH]cnc3[C@H]2c2cc3c(Cl)cccn3n2)nc1] | (S)-4-(4-chloropyrazolo [1,5-a]pyridin-2-yl)-5-(5-(trifluoromethyl)pyrimidin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 1781 | 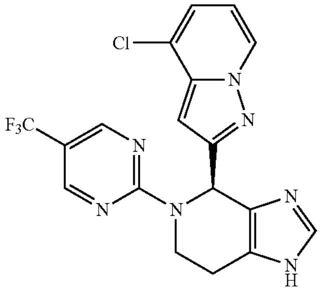 [SMILES: FC(F)(F)c1cnc(N2CCc3[nH]cnc3[C@@H]2c2cc3c(Cl)cccn3n2)nc1] | (R)-4-(4-chloropyrazolo[1,5-a]pyridin-2-yl)-5-(5-(trifluoromethyl)pyrimidin-2-yl)-4,5,6,7-tetrahydro-1H-imidazo[4,5-c]pyridine |
| 1782 | 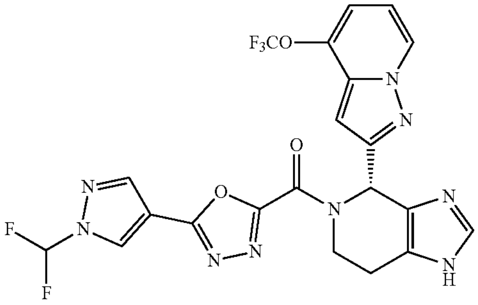 [SMILES: O=C(c1nnc(-c2cnn(C(F)F)c2)o1)N1CCc2[nH]cnc2[C@H]1c1cc2c(OC(F)(F)F)cccn2n1] | (S)-(5-(1-(difluoromethyl)-1H-pyrazol-4-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1783 | 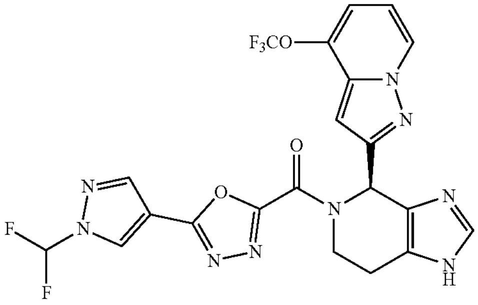 [SMILES: O=C(c1nnc(-c2cnn(C(F)F)c2)o1)N1CCc2[nH]cnc2[C@@H]1c1cc2c(OC(F)(F)F)cccn2n1] | (R)-(5-(1-(difluoromethyl)-1H-pyrazol-4-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 1784 | 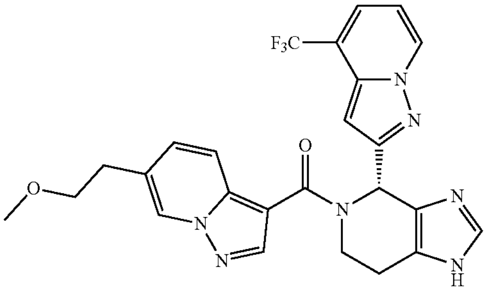 [SMILES: COCCc1ccc2c(C(=O)N3CCc4[nH]cnc4[C@H]3c3cc4c(C(F)(F)F)cccn4n3)cnn2c1] | (S)-(6-(2-methoxyethyl)pyrazolo[1,5-a]pyridin-3-yl)(4-(4-(trifluoromethyl)pyrazolo[1,5-a]pyridin-2-yl)-1,4,6,7-tetrahydro-5H-imidazo[4,5-c]pyridin-5-yl)methanone |
| 1785 | 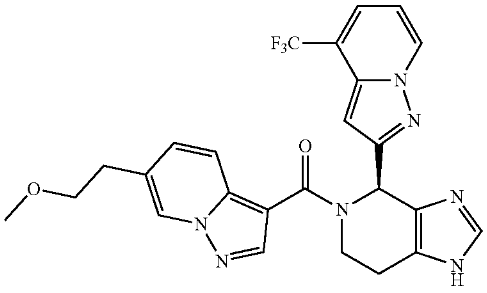 [SMILES: COCCc1ccc2c(C(=O)N3CCc4[nH]cnc4[C@@H]3c3cc4c(C(F)(F)F)cccn4n3)cnn2c1] | (R)-(6-(2-methoxyethyl)pyrazolo[1,5-a]pyridin-3-yl)(4-(4-(trifluoromethyl)pyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
|---|---|---|
| | Pyrazolo[1,5-a]pyridines | |
| 1786 | 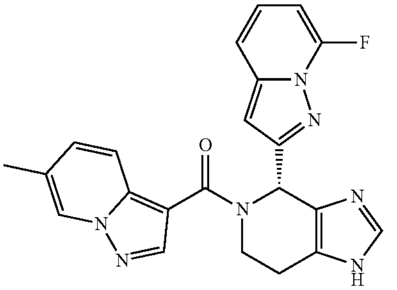 [SMILES: Cc1ccc2c(C(=O)N3CCc4[nH]cnc4[C@H]3c3cc4cccc(F)n4n3)cnn2c1] | (S)-(4-(7-fluoropyrazolo[1,5-a]pyridin-2-yl)-6,7-dihydro-1H-imidazo[4,5-c]pyridin-5(4H)-yl)(6-methylpyrazolo[1,5-a]pyridin-3-yl)methanone |
| 1787 | 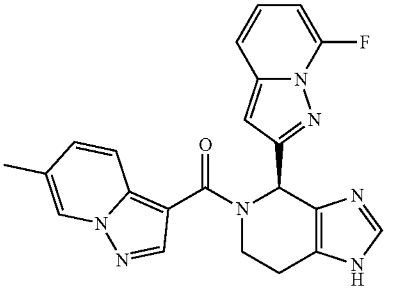 [SMILES: Cc1ccc2c(C(=O)N3CCc4[nH]cnc4[C@@H]3c3cc4cccc(F)n4n3)cnn2c1] | (R)-(4-(7-fluoropyrazolo[1,5-a]pyridin-2-yl)-6,7-dihydro-1H-imidazo[4,5-c]pyridin-5(4H)-yl)(6-methylpyrazolo[1,5-a]pyridin-3-yl)methanone |
| 1788 | 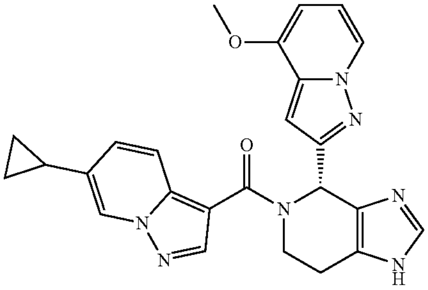 [SMILES: COc1cccn2nc([C@@H]3c4nc[nH]c4CCN3C(=O)c3cnn4cc(C5CC5)ccc34)cc12] | (S)-(6-cyclopropylpyrazolo[1,5-a]pyridin-3-yl)(4-(4-methoxypyrazolo[1,5-a]pyridin-2-yl)-6,7-dihydro-1H-imidazo[4,5-c]pyridin-5(4H)-yl)methanone |
| 1789 | 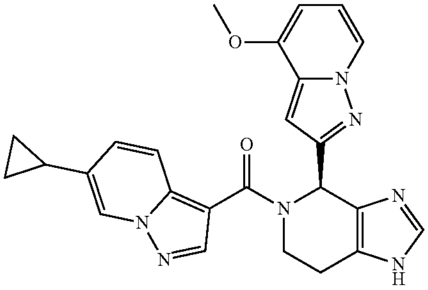 [SMILES: COc1cccn2nc([C@H]3c4nc[nH]c4CCN3C(=O)c3cnn4cc(C5CC5)ccc34)cc12] | (R)-(6-cyclopropylpyrazolo[1,5-a]pyridin-3-yl)(4-(4-methoxypyrazolo[1,5-a]pyridin-2-yl)-6,7-dihydro-1H-imidazo[4,5-c]pyridin-5(4H)-yl)methanone |
| 1790 | 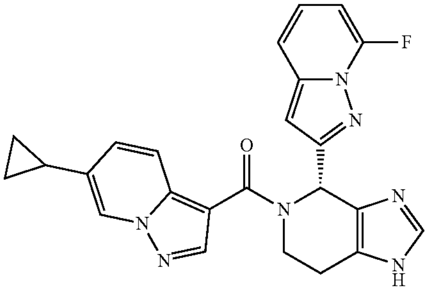 | (S)-(6-cyclopropylpyrazolo[1,5-a]pyridin-3-yl)(4-(7-fluoropyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1791 | 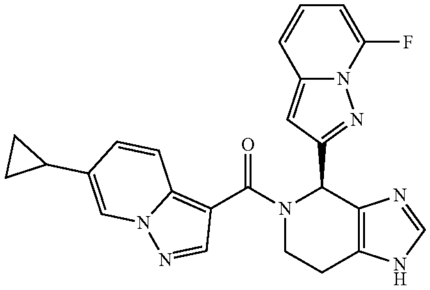 | (R)-(6-cyclopropylpyrazolo[1,5-a]pyridin-3-yl)(4-(7-fluoropyrazolo[1,5-a]pyridin-2-yl)-6,7-dihydro-1H-imidazo[4,5-c]pyridin-5(4H)-yl)methanone |
| 1792 | 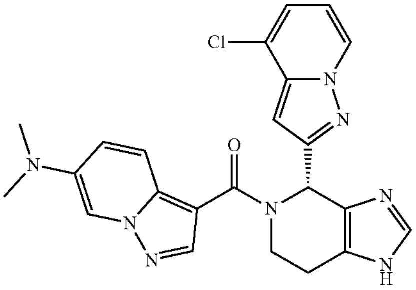 [SMILES: CN(C)c1ccc2c(C(=O)N3CCc4[nH]cnc4[C@H]3c3cc4c(Cl)cccn4n3)cnn2c1] | (S)-(4-(4-chloropyrazolo[1,5-a]pyridin-2-yl)-6,7-dihydro-1H-imidazo[4,5-c]pyridin-5(4H)-yl)(6-(dimethylamino)pyrazolo[1,5-a]pyridin-3-yl)methanone |
| 1793 | 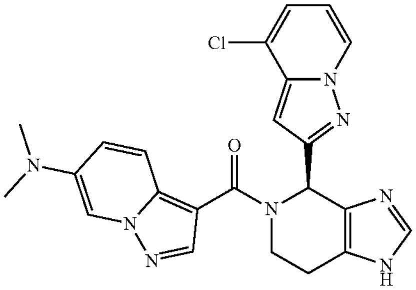 [SMILES: CN(C)c1ccc2c(C(=O)N3CCc4[nH]cnc4[C@@H]3c3cc4c(Cl)cccn4n3)cnn2c1] | (R)-(4-(4-chloropyrazolo[1,5-a]pyridin-2-yl)-6,7-dihydro-1H-imidazo[4,5-c]pyridin-5(4H)-yl)(6-(dimethylamino)pyrazolo[1,5-a]pyridin-3-yl)methanone |
| 1794 | 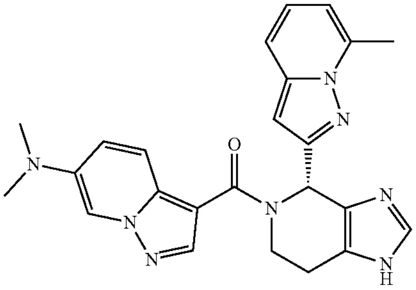 [SMILES: Cc1cccc2cc([C@@H]3c4nc[nH]c4CCN3C(=O)c3cnn4cc(N(C)C)ccc34)nn12] | (S)-(6-(dimethylamino)pyrazolo[1,5-a]pyridin-3-y]l)(4-(7-methylpyrazolo[1,5-a]pyridin-2-yl)-6,7-dihydro-1H-imidazo[4,5-c]pyridin-5(4H)-yl)methanone |
| 1795 | 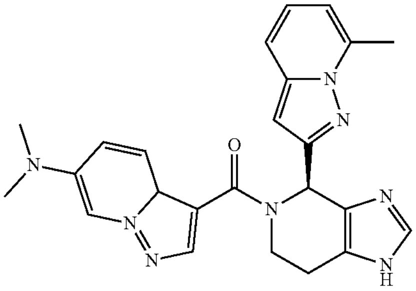 | (R)-(6-(dimethylamino)pyrazolo[1,5-a]pyridin-3-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 1796 | 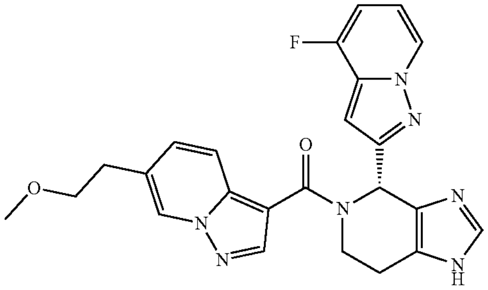 | (S)-(4-(4-fluoropyrazolo[1,5-a]pyridin-2-yl)-6,7-dihydro-1H-imidazo[4,5-c]pyridin-5(4H)-yl)(6-(2-methoxyethyl)pyrazolo[1,5-a]pyridin-3-yl)methanone |
| 1797 | 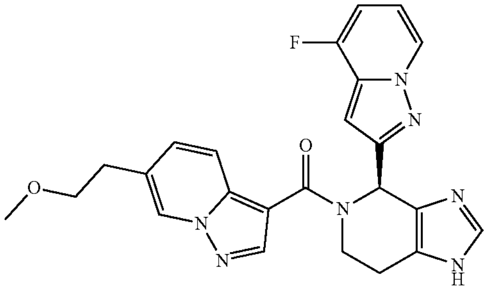 [SMILES: COCCc1ccc2c(C(=O)N3CCc4[nH]cnc4[C@@H]3c3cc4c(F)cccn4n3)cnn2c1] | (R)-(4-(4-fluoropyrazolo[1,5-a]pyridin-2-yl)-6,7-dihydro-1H-imidazo[4,5-c]pyridin-5(4H)-yl)(6-(2-methoxyethyl)pyrazolo[1,5-a]pyridin-3-yl)methanone |
| 1798 | 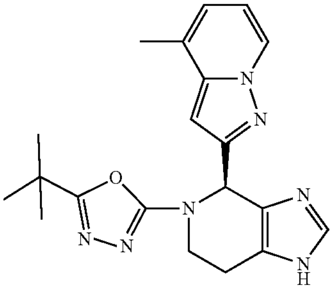 [SMILES: Cc1cccn2nc([C@H]3c4nc[nH]c4CCN3c3nnc(C(C)(C)C)o3)cc12] | (R)-2-(tert-butyl)-5-(4-(4-methylpyrazolo[1,5-a]pyridin-2-yl)-6,7-dihydro-1H-imidazo[4,5-c]pyridin-5(4H)-yl)-1,3,4-oxadiazole |
| 1799 | 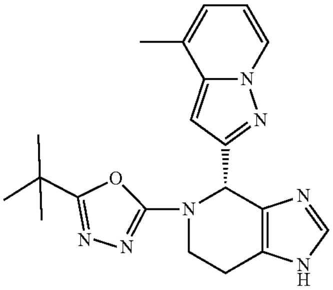 [SMILES: Cc1cccn2nc([C@@H]3c4nc[nH]c4CCN3c3nnc(C(C)(C)C)o3)cc12] | (S)-2-(tert-butyl)-5-(4-(4-methylpyrazolo[1,5-a]pyridin-2-yl)-6,7-dihydro-1H-imidazo[4,5-c]pyridin-5(4H)-yl)-1,3,4-oxadiazole |
| 1800 | 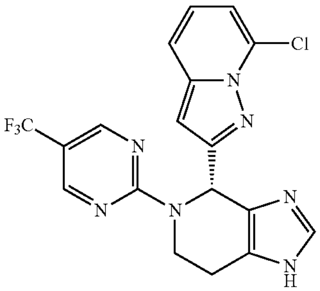 [SMILES: FC(F)(F)c1cnc(N2CCc3[nH]cnc3[C@H]2c2cc3cccc(Cl)n3n2)nc1] | (S)-4-(7-chloropyrazolo[1,5-a]pyridin-2-yl)-5-(5-(trifluoromethyl)pyrimidin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 1801 | 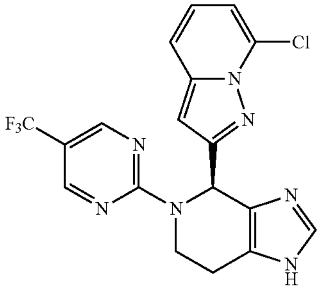 [SMILES: FC(F)(F)c1cnc(N2CCc3[nH]cnc3[C@@H]2c2cc3cccc(Cl)n3n2)nc1] | (R)-4-(7-chloropyrazolo[1,5-a]pyridin-2-yl)-5-(5-(trifluoromethyl)pyrimidin-2-yl)-4,5,6,7-tetrahydro-1H-imidazo[4,5-c]pyridine |
| 1802 | 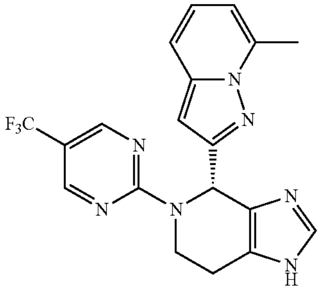 [SMILES: Cc1cccc2cc([C@@H]3c4nc[nH]c4CCN3c3ncc(C(F)(F)F)cn3)nn12] | (S)-4-(7-methylpyrazolo[1,5-a]pyridin-2-yl)-5-(5-(trifluoromethyl)pyrimidin-2-yl)-4,5,6,7-tetrahydro-1H-imidazo[4,5-c]pyridine |
| 1803 | 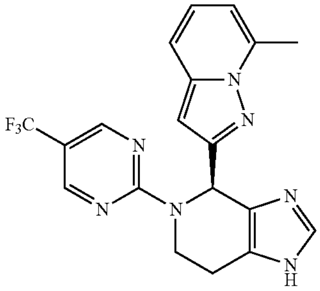 [SMILES: Cc1cccc2cc([C@H]3c4nc[nH]c4CCN3c3ncc(C(F)(F)F)cn3)nn12] | (R)-4-(7-methylpyrazolo[1,5-a]pyridin-2-yl)-5-(5-(trifluoromethyl)pyrimidin-2-yl)-4,5,6,7-tetrahydro-1H-imidazo[4,5-c]pyridine |
| 1804 | 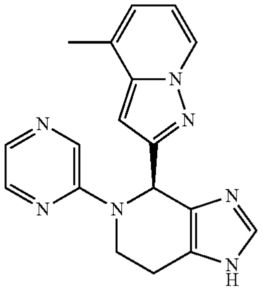 [SMILES: Cc1cccn2nc([C@H]3c4nc[nH]c4CCN3c3cnccn3)cc12] | (R)-4-(4-methylpyrazolo[1,5-a]pyridin-2-yl)-5-(pyrazin-2-yl)-4,5,6,7-tetrahydro-1H-imidazo[4,5-c]pyridine |
| 1805 | 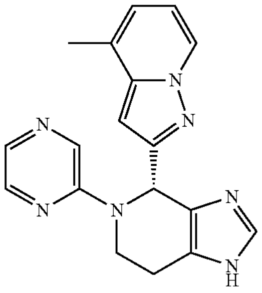 [SMILES: Cc1cccn2nc([C@@H]3c4nc[nH]c4CCN3c3cnccn3)cc12] | (S)-4-(4-methylpyrazolo[1,5-a]pyridin-2-yl)-5-(pyrazin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 1806 | 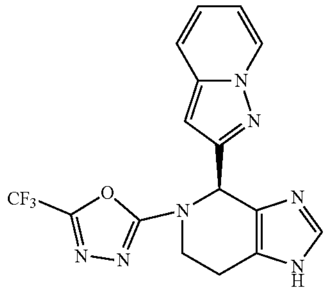 [SMILES: FC(F)(F)c1nnc(N2CCc3[nH]cnc3[C@@H]2c2cc3ccccn3n2)o1] | (R)-2-(4-(pyrazolo[1,5-a]pyridin-2-yl)-6,7-dihydro-1H-imidazo[4,5-c]pyridin-5(4H)-yl)-5-(trifluoromethyl)-1,3,4-oxadiazole |
| 1807 | 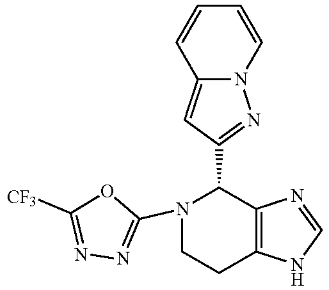 [SMILES: FC(F)(F)c1nnc(N2CCc3[nH]cnc3[C@H]2c2cc3ccccn3n2)o1] | (S)-2-(4-(pyrazolo[1,5-a]pyridin-2-yl)-6,7-dihydro-1H-imidazo[4,5-c]pyridin-5(4H)-yl)-5-(trifluoromethyl)-1,3,4-oxadiazole |
| 1808 | 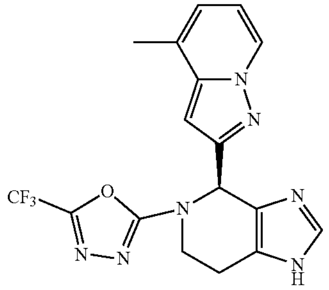 [SMILES: Cc1cccn2nc([C@H]3c4nc[nH]c4CCN3c3nnc(C(F)(F)F)o3)cc12] | (R)-2-(4-(4-methylpyrazolo[1,5-a]pyridin-2-yl)-6,7-dihydro-1H-imidazo[4,5-c]pyridin-5(4H)-yl)-5-(trifluoromethyl)-1,3,4-oxadiazole |
| 1809 | 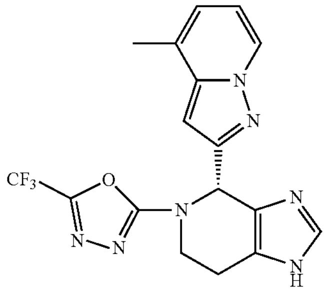 [SMILES: Cc1cccn2nc([C@@H]3c4nc[nH]c4CCN3c3nnc(C(F)(F)F)o3)cc12] | (S)-2-(4-(4-methylpyrazolo[1,5-a]pyridin-2-yl)-6,7-dihydro-1H-imidazo[4,5-c]pyridin-5(4H)-yl)-5-(trifluoromethyl)-1,3,4-oxadiazole |
| 1810 | 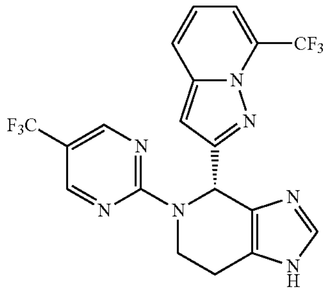 [SMILES: FC(F)(F)c1cnc(N2CCc3[nH]cnc3[C@H]2c2cc3cccc(C(F)(F)F)n3n2)nc1] | (S)-4-(7-(trifluoromethyl)pyrazolo[1,5-a]pyridin-2-yl)-5-(5-(trifluoromethyl)pyrimidin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 1811 | 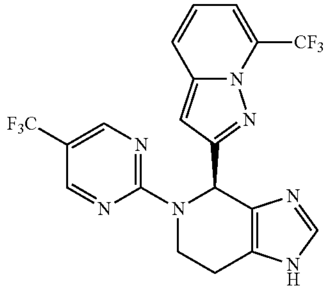 [SMILES: FC(F)(F)c1cnc(N2CCc3[nH]cnc3[C@@H]2c2cc3cccc(C(F)(F)F)n3n2)nc1] | (R)-4-(7-(trifluoromethyl) pyrazolo[1,5-a]pyridin-2-yl)-5-(5-(trifluoromethyl)pyrimidin-2-yl)-4,5,6,7-tetrahydro-1H-imidazo[4,5-c]pyridine |
| 1812 | 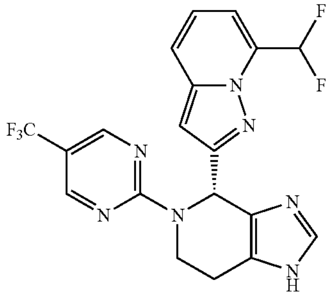 [SMILES: FC(F)c1cccc2cc([C@@H]3c4nc[nH]c4CCN3c3ncc(C(F)(F)F)cn3)nn12] | (S)-4-(7-(difluoromethyl) pyrazolo[1,5-a]pyridin-2-yl)-5-(5-(trifluoromethyl)pyrimidin-2-yl)-4,5,6,7-tetrahydro-1H-imidazo[4,5-c]pyridine |
| 1813 | 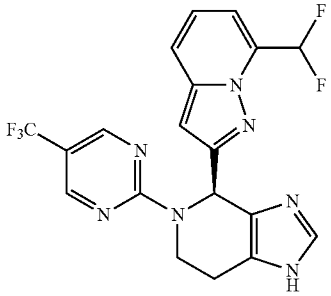 [SMILES: FC(F)c1cccc2cc([C@H]3c4nc[nH]c4CCN3c3ncc(C(F)(F)F)cn3)nn12] | (R)-4-(7-(difluoromethyl) pyrazolo[1,5-a]pyridin-2-yl)-5-(5-(trifluoromethyl)pyrimidin-2-yl)-4,5,6,7-tetrahydro-1H-imidazo[4,5-c]pyridine |
| 1814 | 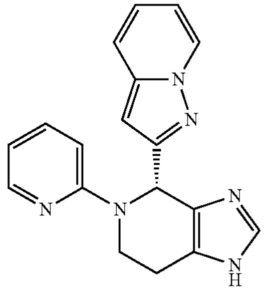 [SMILES: c1ccc(N2CCc3[nH]cnc3[C@H]2c2cc3ccccn3n2)nc1] | (S)-4-(pyrazolo[1,5-a] pyridin-2-yl)-5-(pyridin-2-yl)-4,5,6,7-tetrahydro-1H-imidazo[4,5-c]pyridine |
| 1815 | 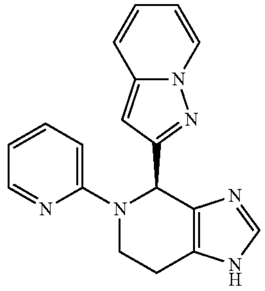 [SMILES: c1ccc(N2CCc3[nH]cnc3[C@@H]2c2cc3ccccn3n2)nc1] | (R)-4-(pyrazolo[1,5-a] pyridin-2-yl)-5-(pyridin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 1816 | 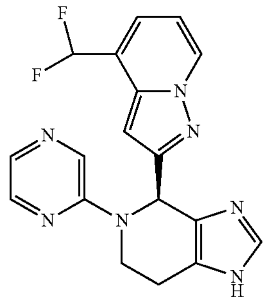 [SMILES: FC(F)c1cccn2nc([C@H]3c4nc[nH]c4CCN3c3cnccn3)cc12] | (R)-4-(4-(difluoromethyl) pyrazolo[1,5-a]pyridin-2-yl)-5-(pyrazin-2-yl)-4,5,6,7-tetrahydro-1H-imidazo[4,5-c]pyridine |
| 1817 | 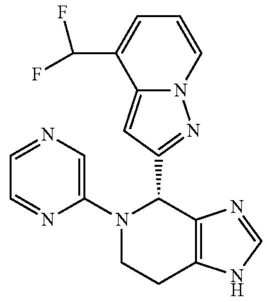 [SMILES: FC(F)c1cccn2nc([C@@H]3c4nc[nH]c4CCN3c3cnccn3)cc12] | (S)-4-(4-(difluoromethyl) pyrazolo[1,5-a]pyridin-2-yl)-5-(pyrazin-2-yl)-4,5,6,7-tetrahydro-1H-imidazo[4,5-c]pyridine |
| 1818 | 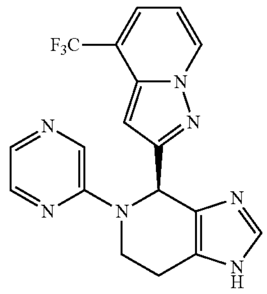 [SMILES: FC(F)(F)c1cccn2nc([C@H]3c4nc[nH]c4CCN3c3cnccn3)cc12] | (R)-5-(pyrazin-2-yl)-4-(4-(trifluoromethyl)pyrazolo[1,5-a]pyridin-2-yl)-4,5,6,7-tetrahydro-1H-imidazo[4,5-c]pyridine |
| 1819 | 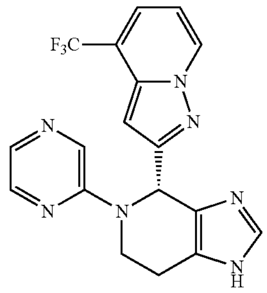 [SMILES: FC(F)(F)c1cccn2nc([C@@H]3c4nc[nH]c4CCN3c3cnccn3)cc12] | (S)-5-(pyrazin-2-yl)-4-(4-(trifluoromethyl)pyrazolo[1,5-a]pyridin-2-yl)-4,5,6,7-tetrahydro-1H-imidazo[4,5-c]pyridine |
| 1820 | 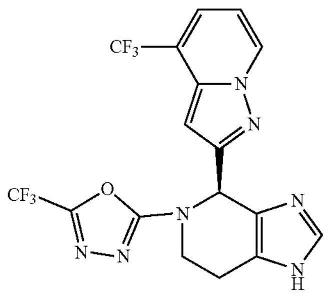 [SMILES: FC(F)(F)c1nnc(N2CCc3[nH]cnc3[C@@H]2c2cc3c(C(F)(F)F)cccn3n2)o1] | (R)-2-(trifluoromethyl)-5-(4-(4-(trifluoromethyl)pyrazolo [1,5-a]pyridin-2-yl)-6,7-dihydro-1H-imidazo[4,5-c] pyridin-5(4H)-yl)-1,3,4-oxadiazole |

TABLE 1-continued

| Ex. # | Structure | Name |
|---|---|---|
| | Pyrazolo[1,5-a]pyridines | |
| 1821 | 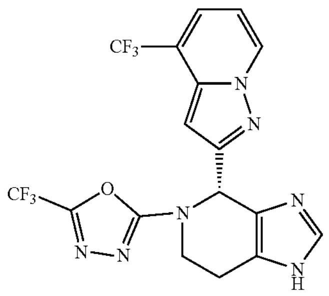 [SMILES: FC(F)(F)c1nnc(N2CCc3[nH]cnc3[C@H]2c2cc3c(C(F)(F)F)cccn3n2)o1] | (S)-2-(trifluoromethyl)-5-(4-(4-(trifluoromethyl)pyrazolo[1,5-a]pyridin-2-yl)-6,7-dihydro-1H-imidazo[4,5-c]pyridin-5(4H)-yl)-1,3,4-oxadiazole |
| 1822 | 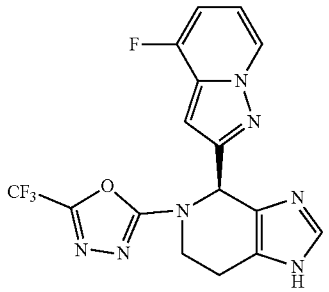 [SMILES: Fc1cccn2nc([C@H]3c4nc[nH]c4CCN3c3nnc(C(F)(F)F)o3)cc12] | (R)-2-(4-(4-fluoropyrazolo[1,5-a]pyridin-2-yl)-6,7-dihydro-1H-imidazo[4,5-c]pyridin-5(4H)-yl)-5-(trifluoromethyl)-1,3,4-oxadiazole |
| 1823 | 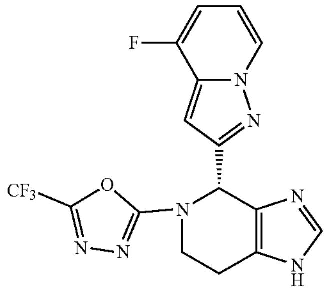 [SMILES: Fc1cccn2nc([C@@H]3c4nc[nH]c4CCN3c3nnc(C(F)(F)F)o3)cc12] | ((S)-2-(4-(4-fluoropyrazolo[1,5-a]pyridin-2-yl)-6,7-dihydro-1H-imidazo[4,5-c]pyridin-5(4H)-yl)-5-(trifluoromethyl)-1,3,4-oxadiazole |
| 1824 | 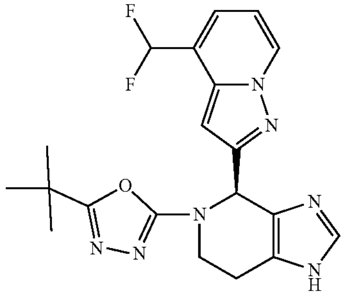 [SMILES: CC(C)(C)c1nnc(N2CCc3[nH]cnc3[C@@H]2c2cc3c(C(F)F)cccn3n2)o1] | (R)-2-(tert-butyl)-5-(4-(4-(difluoromethyl)pyrazolo[1,5-a]pyridin-2-yl)-6,7-dihydro-1H-imidazo[4,5-c]pyridin-5(4H)-yl)-1,3,4-oxadiazole |
| 1825 | 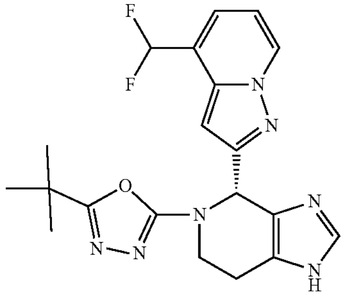 [SMILES: CC(C)(C)c1nnc(N2CCc3[nH]cnc3[C@H]2c2cc3c(C(F)F)cccn3n2)o1] | (S)-2-(tert-butyl)-5-(4-(4-(difluoromethyl)pyrazolo[1,5-a]pyridin-2-yl)-6,7-dihydro-1H-imidazo[4,5-c]pyridin-5(4H)-yl)-1,3,4-oxadiazole |

TABLE 1-continued

| Ex. # | Structure | Name |
|---|---|---|
| | Pyrazolo[1,5-a]pyridines | |
| 1826 | 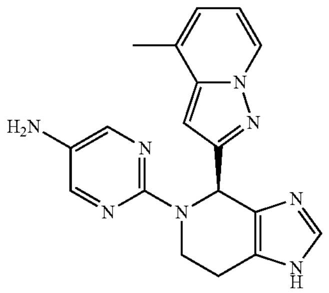 | (R)-2-(4-(4-methylpyrazolo[1,5-a]pyridin-2-yl)-6,7-dihydro-1H-imidazo[4,5-c]pyridin-5(4H)-yl)pyrimidin-5-amine |
| 1827 | 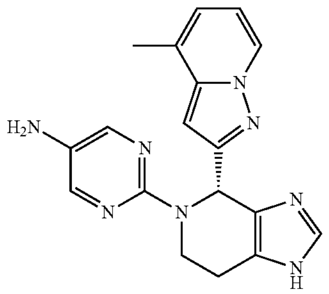 | (S)-2-(4-(4-methylpyrazolo[1,5-a]pyridin-2-yl)-6,7-dihydro-1H-imidazo[4,5-c]pyridin-5(4H)-yl)pyrimidin-5-amine |
| 1828 | 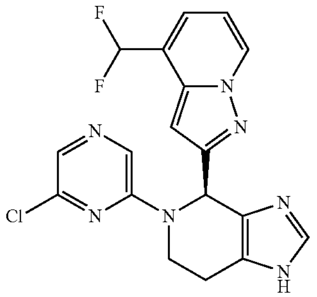 [SMILES: FC(F)c1cccn2nc([C@H]3c4nc[nH]c4CCN3c3cncc(Cl)n3)cc12] | (R)-5-(6-chloropyrazin-2-yl)-4-(4-(difluoromethyl)pyrazolo[1,5-a]pyridin-2-yl)-4,5,6,7-tetrahydro-1H-imidazo[4,5-c]pyridine |
| 1829 | 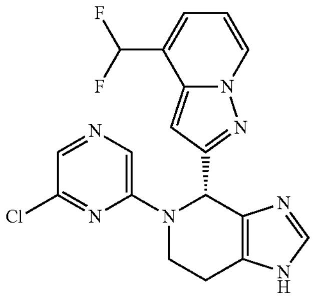 [SMILES: FC(F)c1cccn2nc([C@@H]3c4nc[nH]c4CCN3c3cncc(Cl)n3)cc12] | (S)-5-(6-chloropyrazin-2-yl)-4-(4-(difluoromethyl)pyrazolo[1,5-a]pyridin-2-yl)-4,5,6,7-tetrahydro-1H-imidazo[4,5-c]pyridine |
| 1830 | 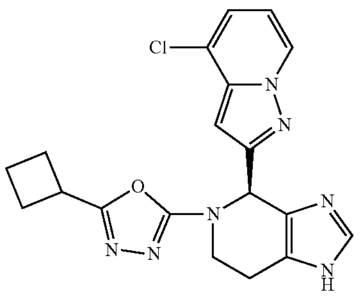 [SMILES: Clc1cccn2nc([C@H]3c4nc[nH]c4CCN3c3nnc(C4CCC4)o3)cc12] | (R)-2-(4-(4-chloropyrazolo[1,5-a]pyridin-2-yl)-6,7-dihydro-1H-imidazo[4,5-c]pyridin-5(4H)-yl)-5-cyclobutyl-1,3,4-oxadiazole |

TABLE 1-continued

Pyrazolo[1,5-a]pyridines

| Ex. # | Structure | Name |
|---|---|---|
| 1831 | 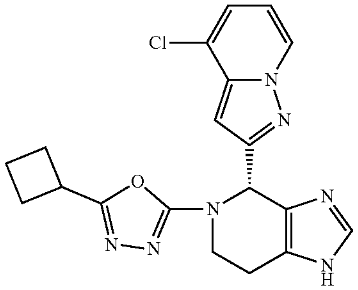 [SMILES: Clc1cccn2nc([C@@H]3c4nc[nH]c4CCN3c3nnc(C4CCC4)o3)cc12] | (S)-2-(4-(4-chloropyrazolo [1,5-a]pyridin-2-yl)-6,7-dihydro-1H-imidazo[4,5-c] pyridin-5(4H)-yl)-5-cyclobutyl-1,3,4-oxadiazole |
| 1832 | 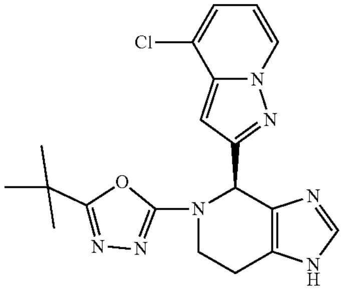 [SMILES: CC(C)(C)c1nnc(N2CCc3[nH]cnc3[C@@H]2c2cc3c(Cl)cccn3n2)o1] | (R)-2-(tert-butyl)-5-(4-(4-chloropyrazolo[1,5-a]pyridin-2-yl)-6,7-dihydro-1H-imidazo[4,5-c]pyridin-5(4H)-yl)-1,3,4-oxadiazole |
| 1833 | 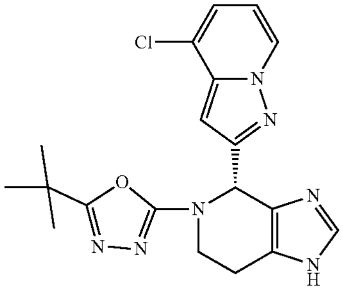 [SMILES: CC(C)(C)c1nnc(N2CCc3[nH]cnc3[C@H]2c2cc3c(Cl)cccn3n2)o1] | (S)-2-(tert-butyl)-5-(4-(4-chloropyrazolo[1,5-a]pyridin-2-yl)-6,7-dihydro-1H-imidazo[4,5-c]pyridin-5(4H)-yl)-1,3,4-oxadiazole |
| 1834 | 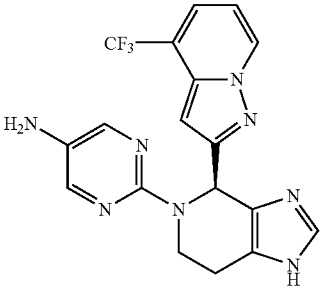 [SMILES: Nc1cnc(N2CCc3[nH]cnc3[C@@H]2c2cc3c(C(F)(F)F)cccn3n2)nc1] | (R)-2-(4-(4-(trifluoromethyl) pyrazolo[1,5-a]pyridin-2-yl)-1,4,6,7-tetrahydro-5H-imidazo[4,5-c]pyridin-5-yl)pyrimidin-5-amine |
| 1835 | 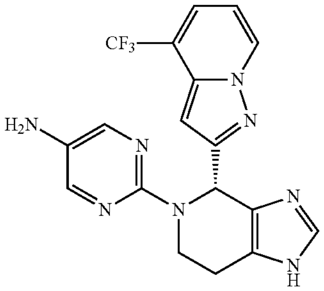 [SMILES: Nc1cnc(N2CCc3[nH]cnc3[C@H]2c2cc3c(C(F)(F)F)cccn3n2)nc1] | (S)-2-(4-(4-(trifluoromethyl) pyrazolo[1,5-a]pyridin-2-yl)-1,4,6,7-tetrahydro-5H-imidazo[4,5-c]pyridin-5-yl)pyrimidin-5-amine |

TABLE 1-continued

| Pyrazolo[1,5-a]pyridines | | |
|---|---|---|
| Ex. # | Structure | Name |
| 1836 | 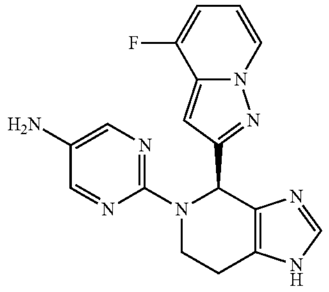 [SMILES: Nc1cnc(N2CCc3[nH]cnc3[C@@H]2c2cc3c(F)cccn3n2)nc1] | (R)-2-(4-(4-fluoropyrazolo [1,5-a]pyridin-2-yl)-1,4,6,7-tetrahydro-5H-imidazo[4,5-c] pyridin-5-yl)pyrimidin-5-amine |
| 1837 | 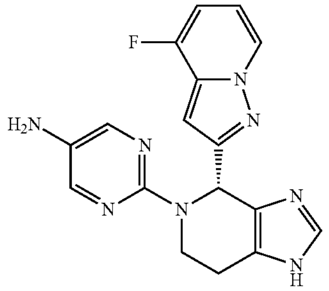 [SMILES: Nc1cnc(N2CCc3[nH]cnc3[C@H]2c2cc3c(F)cccn3n2)nc1] | (S)-2-(4-(4-fluoropyrazolo [1,5-a]pyridin-2-yl)-1,4,6,7-tetrahydro-5H-imidazo[4,5-c] pyridin-5-yl)pyrimidin-5-amine |
| 1838 | 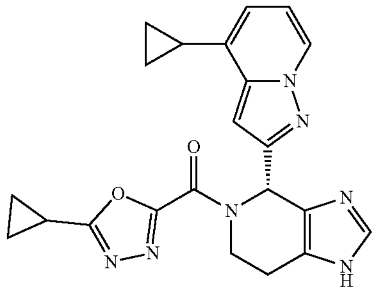 [SMILES: O=C(c1nnc(C2CC2)o1)N1CCc2[nH]cnc2[C@H]1c1cc2c(C3CC3)cccn2n1] | (S)-(5-cyclopropyl-1,3,4-oxadiazol-2-yl)(4-(4-cyclopropylpyrazolo[1,5-a] pyridin-2-yl)-1,4,6,7-tetrahydro-5H-imidazo[4,5-c] pyridin-5-yl)methanone |
| 1839 | 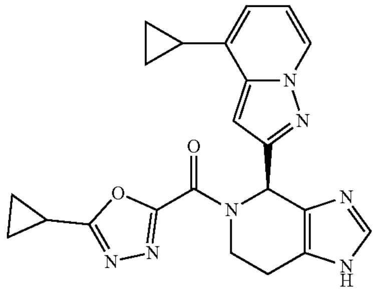 [SMILES: O=C(c1nnc(C2CC2)o1)N1CCc2[nH]cnc2[C@@H]1c1cc2c(C3CC3)cccn2n1] | (R)-(5-cyclopropyl-1,3,4-oxadiazol-2-yl)(4-(4-cyclopropylpyrazolo[1,5-a] pyridin-2-yl)-1,4,6,7-tetrahydro-5H-imidazo[4,5-c] pyridin-5-yl)methanone |
| 1840 | 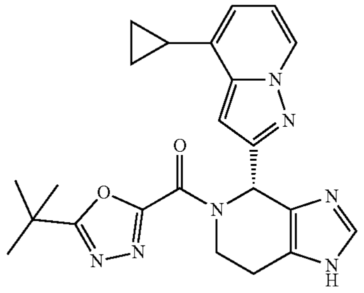 [SMILES: CC(C)(C)c1nnc(C(=O)N2CCc3[nH]cnc3[C@H]2c2cc3c(C4CC4)cccn3n2)o1] | (S)-(5-(tert-butyl)-1,3,4-oxadiazol-2-yl)(4-(4-cyclopropylpyrazolo[1,5-a] pyridin-2-yl)-1,4,6,7-tetrahydro-5H-imidazo[4,5-c] pyridin-5-yl)methanone |

TABLE 1-continued

| Ex. # | Structure | Name |
|---|---|---|
| | Pyrazolo[1,5-a]pyridines | |
| 1841 | 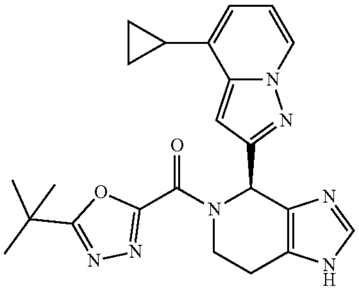 [SMILES: CC(C)(C)c1nnc(C(=O)N2CCc3[nH]cnc3[C@@H]2c2cc3c(C4CC4)cccn3n2)o1] | (R)-(5-(tert-butyl)-1,3,4-oxadiazol-2-yl)(4-(4-cyclopropylpyrazolo[1,5-a]pyridin-2-yl)-1,4,6,7-tetrahydro-5H-imidazo[4,5-c]pyridin-5-yl)methanone |
| 1842 | 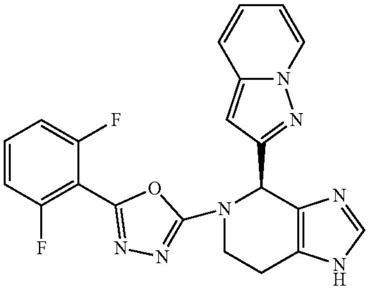 [SMILES: Fc1cccc(F)c1-c1nnc(N2CCc3[nH]cnc3[C@@H]2c2cc3ccccn3n2)o1] | (R)-2-(2,6-difluorophenyl)-5-(4-(pyrazolo[1,5-a]pyridin-2-yl)-6,7-dihydro-1H-imidazo[4,5-c]pyridin-5(4H)-yl)-1,3,4-oxadiazole |
| 1843 | 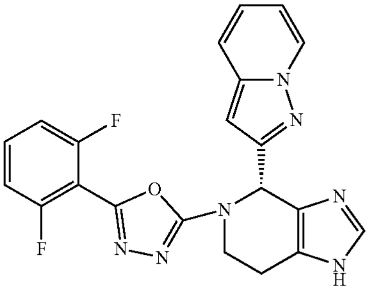 [SMILES: Fc1cccc(F)c1-c1nnc(N2CCc3[nH]cnc3[C@H]2c2cc3ccccn3n2)o1] | (S)-2-(2,6-difluorophenyl)-5-(4-(pyrazolo[1,5-a]pyridin-2-yl)-6,7-dihydro-1H-imidazo[4,5-c]pyridin-5(4H)-yl)-1,3,4-oxadiazole |
| 1844 | 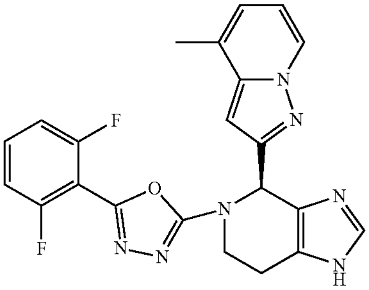 [SMILES: Cc1cccn2nc([C@H]3c4nc[nH]c4CCN3c3nnc(-c4c(F)cccc4F)o3)cc12] | (R)-2-(2,6-difluorophenyl)-5-(4-(4-methylpyrazolo[1,5-a]pyridin-2-yl)-6,7-dihydro-1H-imidazo[4,5-c]pyridin-5(4H)-yl)-1,3,4-oxadiazole |
| 1845 | 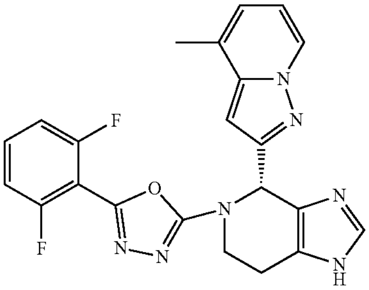 [SMILES: Cc1cccn2nc([C@@H]3c4nc[nH]c4CCN3c3nnc(-c4c(F)cccc4F)o3)cc12] | (S)-2-(2,6-difluorophenyl)-5-(4-(4-methylpyrazolo[1,5-a]pyridin-2-yl)-6,7-dihydro-1H-imidazo[4,5-c]pyridin-5(4H)-yl)-1,3,4-oxadiazole |

TABLE 1-continued

| Ex. # | Structure | Name |
|---|---|---|
| | Pyrazolo[1,5-a]pyridines | |
| 1846 | 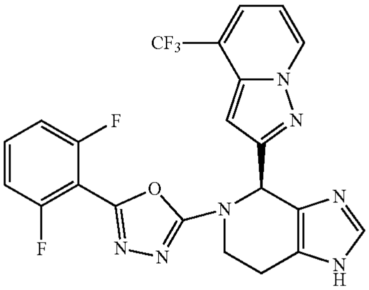 [SMILES: Fc1cccc(F)c1-c1nnc(N2CCc3[nH]cnc3[C@@H]2c2cc3c(C(F)(F)F)cccn3n2)o1] | (R)-2-(2,6-difluorophenyl)-5-(4-(4-(trifluoromethyl)pyrazolo[1,5-a]pyridin-2-yl)-6,7-dihydro-1H-imidazo[4,5-c]pyridin-5(4H)-yl)-1,3,4-oxadiazole |
| 1847 | 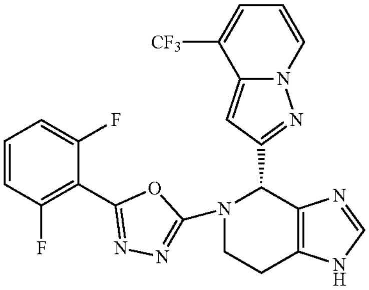 [SMILES: Fc1cccc(F)c1-c1nnc(N2CCc3[nH]cnc3[C@H]2c2cc3c(C(F)(F)F)cccn3n2)o1] | (S)-2-(2,6-difluorophenyl)-5-(4-(4-(trifluoromethyl)pyrazolo[1,5-a]pyridin-2-yl)-6,7-dihydro-1H-imidazo[4,5-c]pyridin-5(4H)-yl)-1,3,4-oxadiazole |
| 1848 | 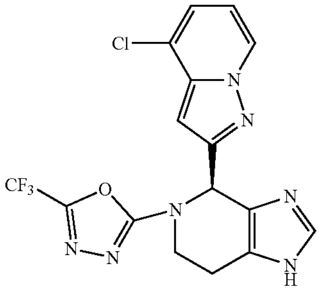 [SMILES: FC(F)(F)c1nnc(N2CCc3[nH]cnc3[C@@H]2c2cc3c(Cl)cccn3n2)o1] | (R)-2-(4-(4-chloropyrazolo[1,5-a]pyridin-2-yl)-6,7-dihydro-1H-imidazo[4,5-c]pyridin-5(4H)-yl)-5-(trifluoromethyl)-1,3,4-oxadiazole |
| 1849 | 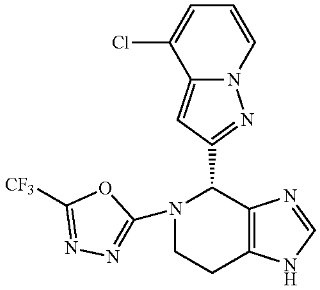 [SMILES: FC(F)(F)c1nnc(N2CCc3[nH]cnc3[C@H]2c2cc3c(Cl)cccn3n2)o1] | (S)-2-(4-(4-chloropyrazolo[1,5-a]pyridin-2-yl)-6,7-dihydro-1H-imidazo[4,5-c]pyridin-5(4H)-yl)-5-(trifluoromethyl)-1,3,4-oxadiazole |
| 1850 | 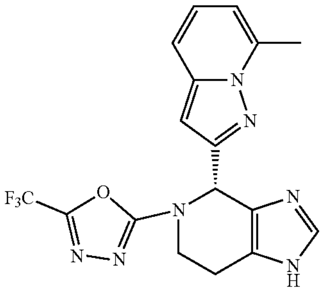 [SMILES: Cc1cccc2cc([C@@H]3c4nc[nH]c4CCN3c3nnc(C(F)(F)F)o3)nn12] | (S)-2-(4-(7-methylpyrazolo[1,5-a]pyridin-2-yl)-6,7-dihydro-1H-imidazo[4,5-c]pyridin-5(4H)-yl)-5-(trifluoromethyl)-1,3,4-oxadiazole |

TABLE 1-continued

| Ex. # | Structure | Name |
|---|---|---|
| | Pyrazolo[1,5-a]pyridines | |
| 1851 | 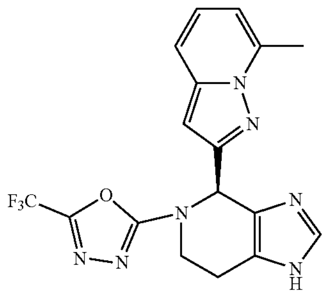 [SMILES: Cc1cccc2cc([C@H]3c4nc[nH]c4CCN3c3nnc(C(F)(F)F)o3)nn12] | (R)-2-(4-(7-methylpyrazolo [1,5-a]pyridin-2-y]l)-6,7-dihydro-1H-imidazo [4,5-c]pyridin-5(4H)-yl)-5-(trifluoromethyl)-1,3,4-oxadiazole |
| 1852 | 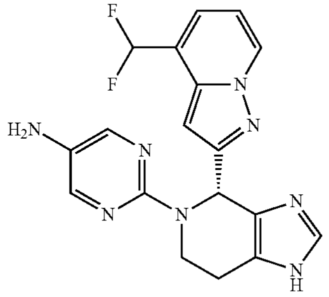 [SMILES: Nc1cnc(N2CCc3[nH]cnc3[C@H]2c2cc3c(C(F)F)cccn3n2)nc1] | (S)-2-(4-(4-(difluoromethyl) pyrazolo[1,5-a]pyridin-2-yl)-1,4,6,7-tetrahydro-5H-imidazo[4,5-c]pyridin-5-yl)pyrimidin-5-amine |
| 1853 | 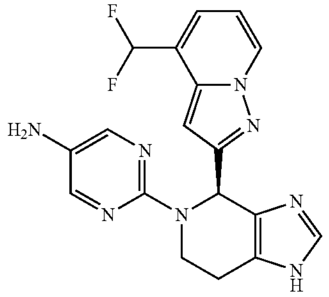 [SMILES: Nc1cnc(N2CCc3[nH]cnc3[C@@H]2c2cc3c(C(F)F)cccn3n2)nc1] | (R)-2-(4-(4-(difluoromethyl) pyrazolo[1,5-a]pyridin-2-yl)-1,4,6,7-tetrahydro-5H-imidazo[4,5-c]pyridin-5-yl)pyrimidin-5-amine |
| 1854 | 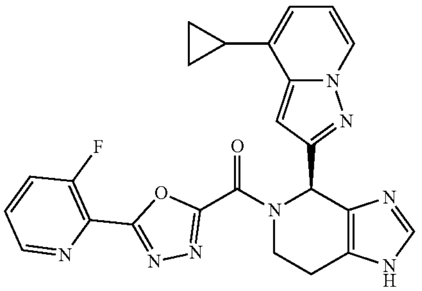 [SMILES: O=C(c1nnc(-c2ncccc2F)o1)N1CCc2[nH]cnc2[C@@H]1c1cc2c(C3CC3)cccn2n1] | (R)-(4-(4-cyclopropylpyrazolo [1,5-a]pyridin-2-yl)-1,4,6,7-tetrahydro-5H-imidazo[4,5-c]pyridin-5-yl)(5-(3-fluoropyridin-2-yl)-1,3,4-oxadiazol-2-yl) methanone |
| 1855 | 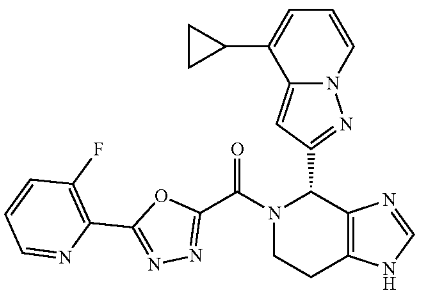 [SMILES: O=C(c1nnc(-c2ncccc2F)o1)N1CCc2[nH]cnc2[C@H]1c1cc2c(C3CC3)cccn2n1] | (S)-(4-(4-cyclopropylpyrazolo[1,5-a] pyridin-2-yl)-1,4,6,7-tetrahydro-5H-imidazo[4,5-c] pyridin-5-yl)(5-(3-fluoropyridin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1856 | 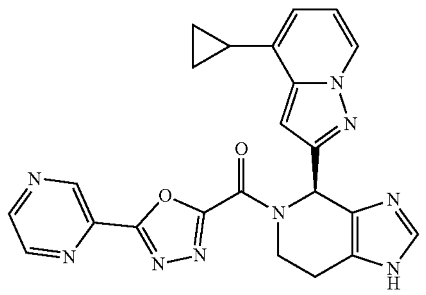 [SMILES: O=C(c1nnc(-c2cnccn2)o1)N1CCc2[nH]cnc2[C@@H]1c1cc2c(C3CC3)cccn2n1] | (R)-(4-(4-cyclopropylpyrazolo[1,5-a] pyridin-2-y]l)-1,4,6,7-tetrahydro-5H-imidazo[4,5-c]pyridin-5-yl)(5-(pyrazin-2-yl)-1,3,4-oxadiazol-2-yl)methanone |
| 1857 | 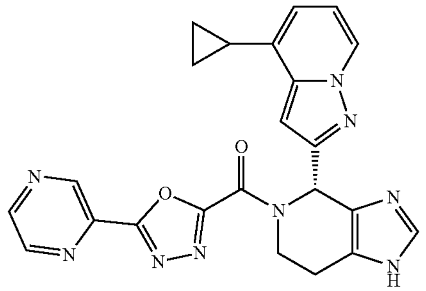 [SMILES: O=C(c1nnc(-c2cnccn2)o1)N1CCc2[nH]cnc2[C@H]1c1cc2c(C3CC3)cccn2n1] | (S)-(4-(4-cyclopropylpyrazolo [1,5-a]pyridin-2-yl)-1,4,6,7-tetrahydro-5H-imidazo[4,5-c]pyridin-5-yl)(5-(pyrazin-2-yl)-1,3,4-oxadiazol-2-yl)methanone |
| 1858 | 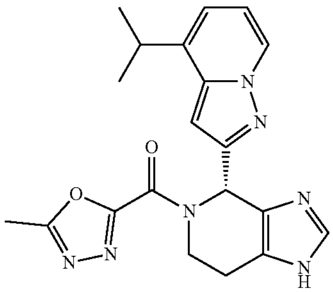 [SMILES: Cc1nnc(C(=O)N2CCc3[nH]cnc3[C@H]2c2cc3c(C(C)C)cccn3n2)o1] | (S)-(4-(4-isopropylpyrazolo [1,5-a]pyridin-2-yl)-1,4,6,7-tetrahydro-5H-imidazo [4,5-c]pyridin-5-yl)(5-methyl-1,3,4-oxadiazol-2-yl) methanone |
| 1859 | 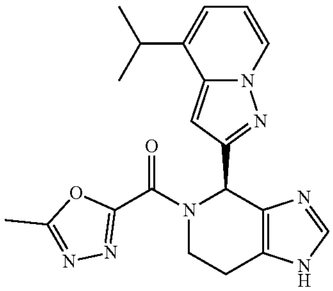 [SMILES: Cc1nnc(C(=O)N2CCc3[nH]cnc3[C@@H]2c2cc3c(C(C)C)cccn3n2)o1] | (R)-(4-(4-isopropylpyrazolo [1,5-a]pyridin-2-yl)-1,4,6,7-tetrahydro-5H-imidazo [4,5-c]pyridin-5-yl)(5-methyl-1,3,4-oxadiazol-2-yl)methanone |
| 1860 | 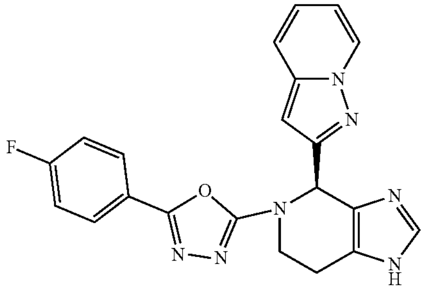 [SMILES: Fc1ccc(-c2nnc(N3CCc4[nH]cnc4[C@@H]3c3cc4ccccn4n3)o2)cc1] | (R)-2-(4-fluorophenyl)-5-(4-(pyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 1861 | 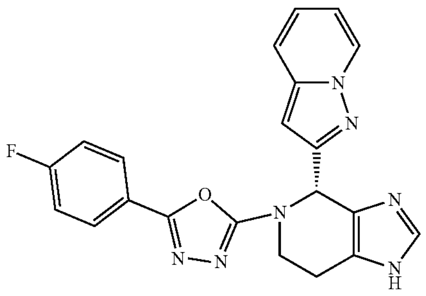 [SMILES: Fc1ccc(-c2nnc(N3CCc4[nH]cnc4[C@H]3c3cc4ccccn4n3)o2)cc1] | (S)-2-(4-fluorophenyl)-5-(4-(pyrazolo[1,5-a]pyridin-2-yl)-1,4,6,7-tetrahydro-5H-imidazo[4,5-c]pyridin-5-yl)-1,3,4-oxadiazole |
| 1862 | 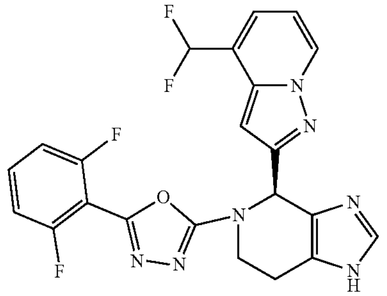 [SMILES: Fc1cccc(F)c1-c1nnc(N2CCc3[nH]cnc3[C@@H]2c2cc3c(C(F)F)cccn3n2)o1] | (R)-2-(4-(4-(difluoromethyl) pyrazolo[1,5-a]pyridin-2-yl)-1,4,6,7-tetrahydro-5H-imidazo[4,5-c]pyridin-5-yl)-5-(2,6-difluorophenyl)-1,3,4-oxadiazole |
| 1863 | 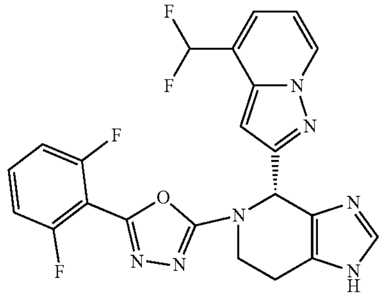 [SMILES: Fc1cccc(F)c1-c1nnc(N2CCc3[nH]cnc3[C@H]2c2cc3c(C(F)F)cccn3n2)o1] | (S)-2-(4-(4-(difluoromethyl) pyrazolo[1,5-a]pyridin-2-yl)-1,4,6,7-tetrahydro-5H-imidazo[4,5-c]pyridin-5-yl)-5-(2,6-difluorophenyl)-1,3,4-oxadiazole |
| 1864 | 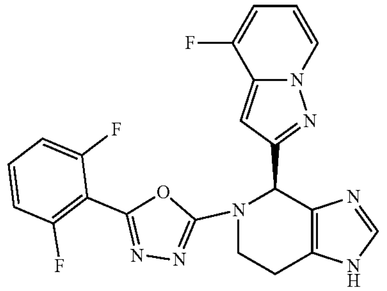 [SMILES: Fc1cccc(F)c1-c1nnc(N2CCc3[nH]cnc3[C@@H]2c2cc3c(F)cccn3n2)o1] | (R)-2-(2,6-difluorophenyl)-5-(4-(4-fluoropyrazolo[1,5-a]pyridin-2-yl)-1,4,6,7-tetrahydro-5H-imidazo[4,5-c]pyridin-5-yl)-1,3,4-oxadiazole |
| 1865 | 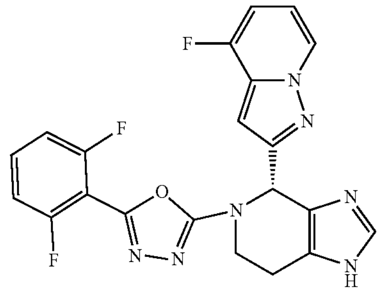 [SMILES: Fc1cccc(F)c1-c1nnc(N2CCc3[nH]cnc3[C@H]2c2cc3c(F)cccn3n2)o1] | (S)-2-(2,6-difluorophenyl)-5-(4-(4-fluoropyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 1866 | 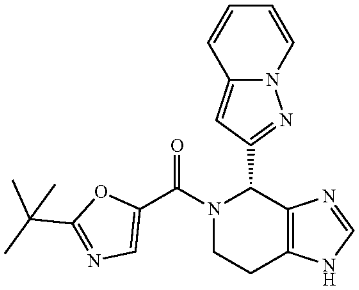 [SMILES: CC(C)(C)c1ncc(C(=O)N2CCc3[nH]cnc3[C@H]2c2cc3ccccn3n2)o1] | (S)-(2-(tert-butyl)oxazol-5-yl)(4-(pyrazolo[1,5-a]pyridin-2-yl)-1,4,6,7-tetrahydro-5H-imidazo[4,5-c]pyridin-5-yl)methanone |
| 1867 | 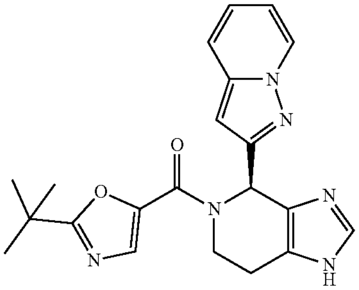 [SMILES: CC(C)(C)c1ncc(C(=O)N2CCc3[nH]cnc3[C@@H]2c2cc3ccccn3n2)o1] | (R)-(2-(tert-butyl)oxazol-5-yl)(4-(pyrazolo[1,5-a]pyridin-2-yl)-1,4,6,7-tetrahydro-5H-imidazo[4,5-c]pyridin-5-yl)methanone |
| 1868 | 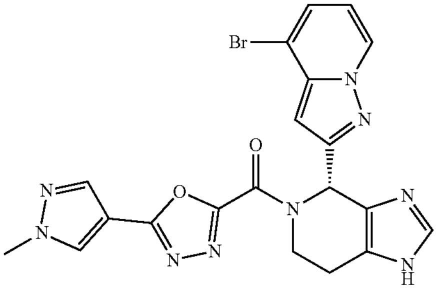 [SMILES: Cn1cc(-c2nnc(C(=O)N3CCc4[nH]cnc4[C@H]3c3cc4c(Br)cccn4n3)o2)cn1] | (S)-(4-(4-bromopyrazolo[1,5-a]pyridin-2-yl)-1,4,6,7-tetrahydro-5H-imidazo[4,5-c]pyridin-5-yl)(5-(1-methyl-1H-pyrazol-4-yl)-1,3,4-oxadiazol-2-yl)methanone |
| 1869 | 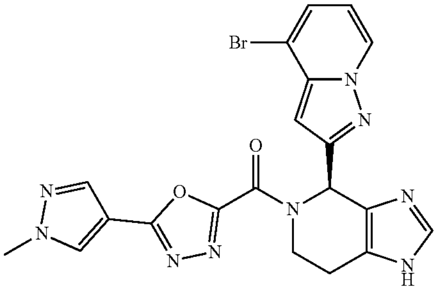 [SMILES: Cn1cc(-c2nnc(C(=O)N3CCc4[nH]cnc4[C@@H]3c3cc4c(Br)cccn4n3)o2)cn1] | (R)-(4-(4-bromopyrazolo[1,5-a]pyridin-2-yl)-1,4,6,7-tetrahydro-5H-imidazo[4,5-c]pyridin-5-yl)(5-(1-methyl-1H-pyrazol-4-yl)-1,3,4-oxadiazol-2-yl)methanone |
| 1870 | 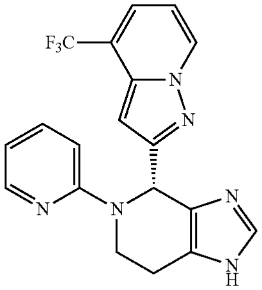 [SMILES: FC(F)(F)c1cccn2nc([C@@H]3c4nc[nH]c4CCN3c3ccccn3)cc12] | (S)-5-(pyridin-2-yl)-4-(4-(trifluoromethyl)pyrazolo[1,5-a]pyridin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 1871 | 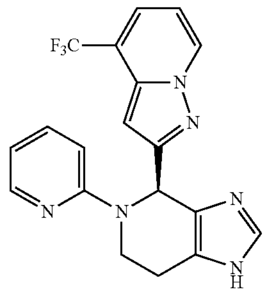 [SMILES: FC(F)(F)c1cccn2nc([C@H]3c4nc[nH]c4CCN3c3ccccn3)cc12] | (R)-5-(pyridin-2-yl)-4-(4-(trifluoromethyl)pyrazolo[1,5-a]pyridin-2-yl)-4,5,6,7-tetrahydro-1H-imidazo[4,5-c]pyridine |
| 1872 | 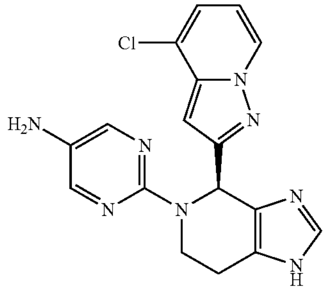 | (R)-2-(4-(4-chloropyrazolo[1,5-a]pyridin-2-yl)-1,4,6,7-tetrahydro-5H-imidazo[4,5-c]pyridin-5-yl)pyrimidin-5-amine |
| 1873 | 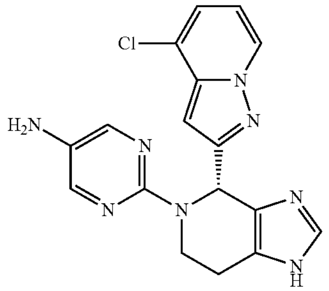 | (S)-2-(4-(4-chloropyrazolo[1,5-a]pyridin-2-yl)-1,4,6,7-tetrahydro-5H-imidazo[4,5-c]pyridin-5-yl)pyrimidin-5-amine |
| 1874 | 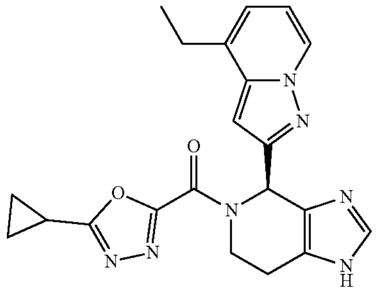 [SMILES: CCc1cccn2nc([C@H]3c4nc[nH]c4CCN3C(=O)c3nnc(C4CC4)o3)cc12] | (R)-(5-cyclopropyl-1,3,4-oxadiazol-2-yl)(4-(4-ethylpyrazolo[1,5-a]pyridin-2-yl)-1,4,6,7-tetrahydro-5H-imidazo[4,5-c]pyridin-5-yl)methanone |
| 1875 | 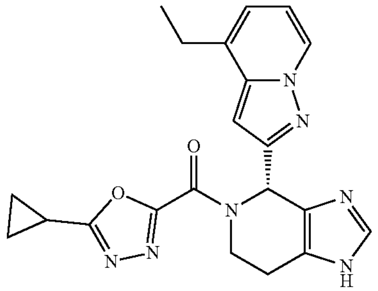 [SMILES: CCc1cccn2nc([C@@H]3c4nc[nH]c4CCN3C(=O)c3nnc(C4CC4)o3)cc12] | (S)-(5-cyclopropyl-1,3,4-oxadiazol-2-yl)(4-(4-ethylpyrazolo[1,5-a]pyridin-2-yl)-1,4,6,7-tetrahydro-5H-imidazo[4,5-c]pyridin-5-yl)methanone |

TABLE 1-continued

| Pyrazolo[1,5-a]pyridines | | |
|---|---|---|
| Ex. # | Structure | Name |
| 1876 | 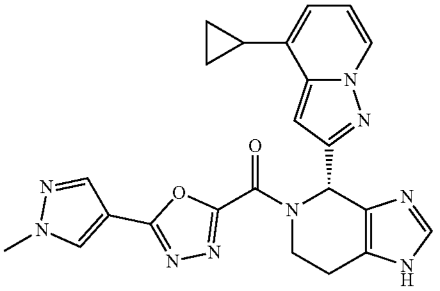 [SMILES: Cn1cc(-c2nnc(C(=O)N3CCc4[nH]cnc4[C@H]3c3cc4c(C5CC5)cccn4n3)o2)cn1] | (S)-(4-(4-cyclopropylpyrazolo[1,5-a]pyridin-2-yl)-1,4,6,7-tetrahydro-5H-imidazo[4,5-c]pyridin-5-yl)(5-(1-methyl-1H-pyrazol-4-yl)-1,3,4-oxadiazol-2-yl)methanone |
| 1877 | 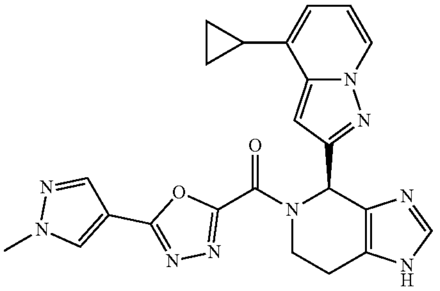 [SMILES: Cn1cc(-c2nnc(C(=O)N3CCc4[nH]cnc4[C@@H]3c3cc4c(C5CC5)cccn4n3)o2)cn1] | (R)-(4-(4-cyclopropylpyrazolo[1,5-a]pyridin-2-yl)-1,4,6,7-tetrahydro-5H-imidazo[4,5-c]pyridin-5-yl)(5-(1-methyl-1H-pyrazol-4-yl)-1,3,4-oxadiazol-2-yl)methanone |
| 1878 | 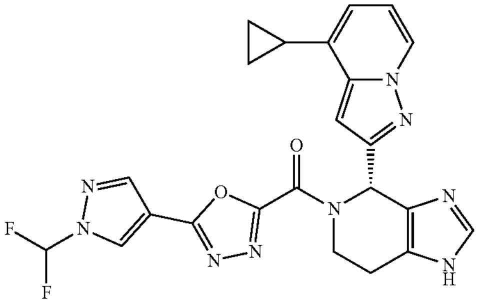 [SMILES: O=C(c1nnc(-c2cnn(C(F)F)c2)o1)N1CCc2[nH]cnc2[C@H]1c1cc2c(C3CC3)cccn2n1] | (S)-(4-(4-cyclopropylpyrazolo[1,5-a]pyridin-2-yl)-1,4,6,7-tetrahydro-5H-imidazo[4,5-c]pyridin-5-yl)(5-(1-(difluoromethyl)-1H-pyrazol-4-yl)-1,3,4-oxadiazol-2-yl)methanone |
| 1879 | 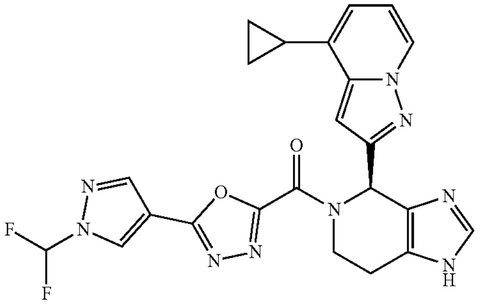 [SMILES: O=C(c1nnc(-c2cnn(C(F)F)c2)o1)N1CCc2[nH]cnc2[C@@H]1c1cc2c(C3CC3)cccn2n1] | (R)-(4-(4-cyclopropylpyrazolo[1,5-a]pyridin-2-yl)-1,4,6,7-tetrahydro-5H-imidazo[4,5-c]pyridin-5-yl)(5-(1-(difluoromethyl)-1H-pyrazol-4-yl)-1,3,4-oxadiazol-2-yl)methanone |
| 1880 | 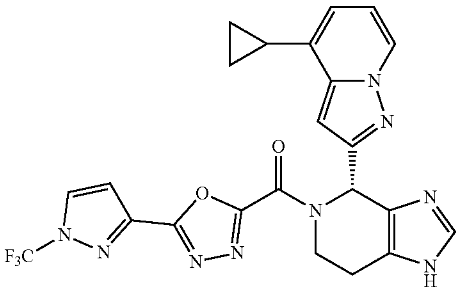 [SMILES: O=C(c1nnc(-c2ccn(C(F)(F)F)n2)o1)N1CCc2[nH]cnc2[C@H]1c1cc2c(C3CC3)cccn2n1] | (S)-(4-(4-cyclopropylpyrazolo[1,5-a]pyridin-2-yl)-1,4,6,7-tetrahydro-5H-imidazo[4,5-c]pyridin-5-yl)(5-(1-(trifluoromethyl)-1H-pyrazol-3-yl)-1,3,4-oxadiazol-2-yl)methanone |

TABLE 1-continued

| Ex. # | Structure | Name |
|---|---|---|
| | Pyrazolo[1,5-a]pyridines | |
| 1881 | 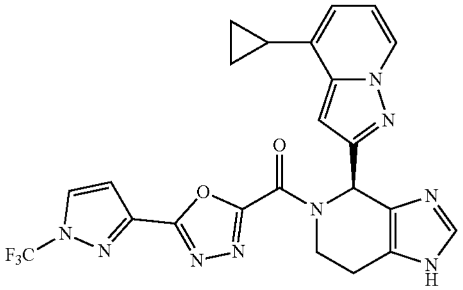 [SMILES: O=C(c1nnc(-c2ccn(C(F)(F)F)n2)o1)N1CCc2[nH]cnc2[C@@H]1c1cc2c(C3CC3)cccn2n1] | (R)-(4-(4-cyclopropylpyrazolo[1,5-a]pyridin-2-yl)-1,4,6,7-tetrahydro-5H-imidazo[4,5-c]pyridin-5-yl)(5-(1-(trifluoromethyl)-1H-pyrazol-3-yl)-1,3,4-oxadiazol-2-yl)methanone |
| 1882 | 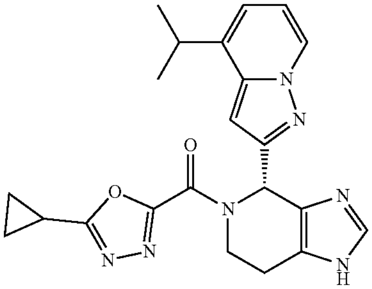 [SMILES: CC(C)c1cccn2nc([C@@H]3c4nc[nH]c4CCN3C(=O)c3nnc(C4CC4)o3)cc12] | (S)-(5-cyclopropyl-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 1883 | 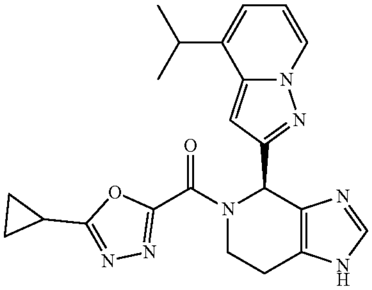 [SMILES: CC(C)c1cccn2nc([C@H]3c4nc[nH]c4CCN3C(=O)c3nnc(C4CC4)o3)cc12] | (R)-(5-cyclopropyl-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 1884 | 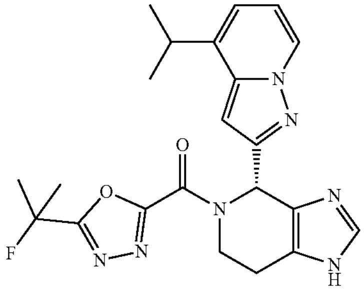 [SMILES: CC(C)c1cccn2nc([C@@H]3c4nc[nH]c4CCN3C(=O)c3nnc(C(C)(C)F)o3)cc12] | (S)-(5-(2-fluoropropan-2-yl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 1885 | 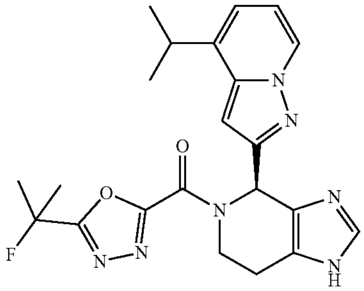 [SMILES: CC(C)c1cccn2nc([C@H]3c4nc[nH]c4CCN3C(=O)c3nnc(C(C)(C)F)o3)cc12] | (R)-(5-(2-fluoropropan-2-yl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |

TABLE 1-continued

| Pyrazolo[1,5-a]pyridines | | |
|---|---|---|
| Ex. # | Structure | Name |
| 1886 | 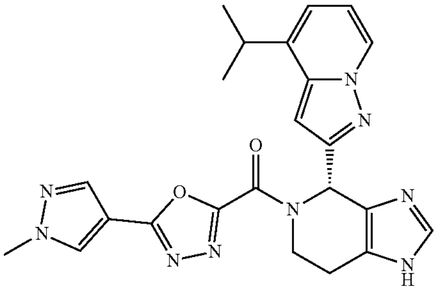 [SMILES: CC(C)c1cccn2nc([C@@H]3c4nc[nH]c4CCN3C(=O)c3nnc(-c4cnn(C)c4)o3)cc12] | (S)-(4-(4-isopropylpyrazolo[1,5-a]pyridin-2-yl)-1,4,6,7-tetrahydro-5H-imidazo[4,5-c]pyridin-5-yl)(5-(1-methyl-1H-pyrazol-4-yl)-1,3,4-oxadiazol-2-yl)methanone |
| 1887 | 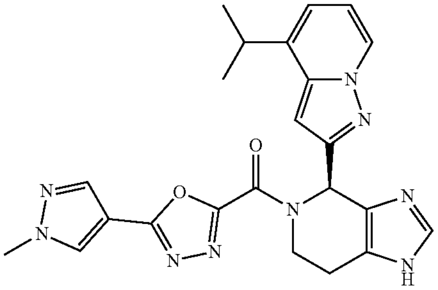 [SMILES: CC(C)c1cccn2nc([C@H]3c4nc[nH]c4CCN3C(=O)c3nnc(-c4cnn(C)c4)o3)cc12] | (R)-(4-(4-isopropylpyrazolo[1,5-a]pyridin-2-yl)-1,4,6,7-tetrahydro-5H-imidazo[4,5-c]pyridin-5-yl)(5-(1-methyl-1H-pyrazol-4-yl)-1,3,4-oxadiazol-2-yl)methanone |
| 1888 | 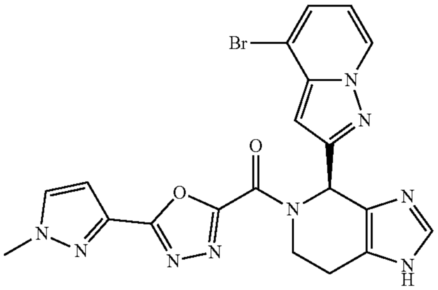 [SMILES: Cn1ccc(-c2nnc(C(=O)N3CCc4[nH]cnc4[C@@H]3c3cc4c(Br)cccn4n3)o2)n1] | (R)-(4-(4-bromopyrazolo[1,5-a]pyridin-2-yl)-1,4,6,7-tetrahydro-5H-imidazo[4,5-c]pyridin-5-yl)(5-(1-methyl-1H-pyrazol-3-yl)-1,3,4-oxadiazol-2-yl)methanone |
| 1889 | 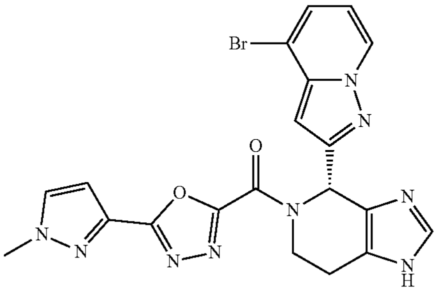 | (S)-(4-(4-bromopyrazolo[1,5-a]pyridin-2-yl)-1,4,6,7-tetrahydro-5H-imidazo[4,5-c]pyridin-5-yl)(5-(1-methyl-1H-pyrazol-3-yl)-1,3,4-oxadiazol-2-yl)methanone |
| 1890 | 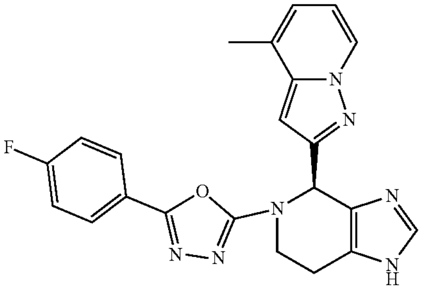 | (R)-2-(4-fluorophenyl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
|---|---|---|
| | Pyrazolo[1,5-a]pyridines | |
| 1891 | 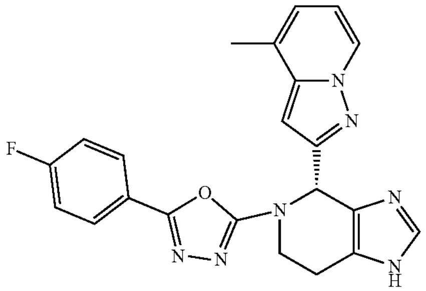 | (S)-2-(4-fluorophenyl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 1892 | 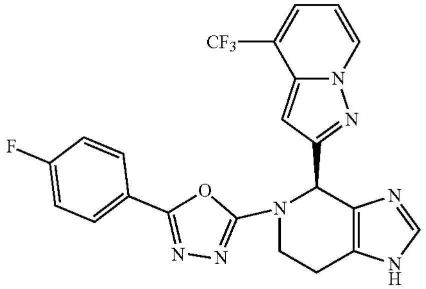 [SMILES: Fc1ccc(-c2nnc(N3CCc4[nH]cnc4[C@@H]3c3cc4c(C(F)(F)F)cccn4n3)o2)cc1] | (R)-2-(4-fluorophenyl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 1893 | 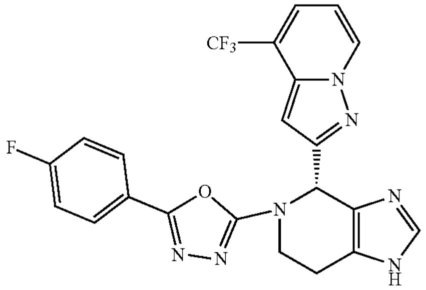 [SMILES: Fc1ccc(-c2nnc(N3CCc4[nH]cnc4[C@H]3c3cc4c(C(F)(F)F)cccn4n3)o2)cc1] | (S)-2-(4-fluorophenyl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 1894 | 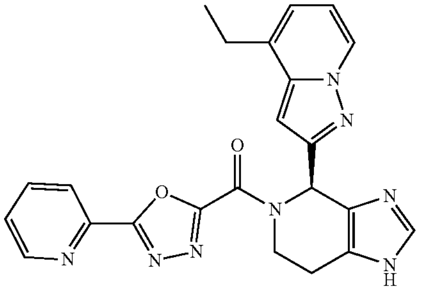 [SMILES: CCc1cccn2nc([C@H]3c4nc[nH]c4CCN3C(=O)c3nnc(-c4ccccn4)o3)cc12] | (R)-(4-(4-ethylpyrazolo[1,5-a]pyridin-2-yl)-1,4,6,7-tetrahydro-5H-imidazo[4,5-c]pyridin-5-yl)(5-(pyridin-2-yl)-1,3,4-oxadiazol-2-yl)metbanone |
| 1895 | 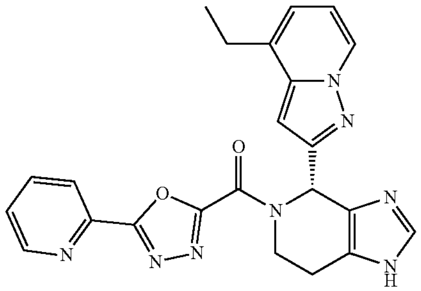 [SMILES: CCc1cccn2nc([C@@H]3c4nc[nH]c4CCN3C(=O)c3nnc(-c4ccccn4)o3)cc12] | (S)-(4-(4-ethylpyrazolo[1,5-a]pyridin-2-yl)-1,4,6,7-tetrahydro-5H-imidazo[4,5-c]pyridin-5-yl)(5-(pyridin-2-yl)-1,3,4-oxadiazol-2-yl)methanone |

TABLE 1-continued

| Ex. # | Structure | Name |
|---|---|---|
| Pyrazolo[1,5-a]pyridines | | |
| 1896 | 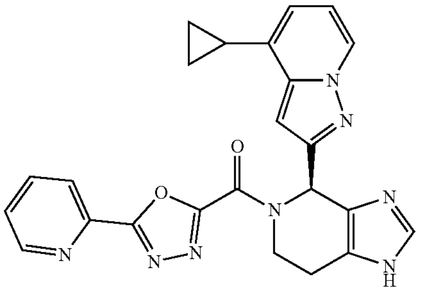 | (R)-(4-(4-cyclopropylpyrazolo [1,5-a]pyridin-2-y]l)-1,4,6,7-tetrahydro-5H-imidazo [4,5-c]pyridin-5-yl)(5-(pyridin-2-yl)-1,3,4-oxadiazol-2-yl)methanone |
| 1897 | 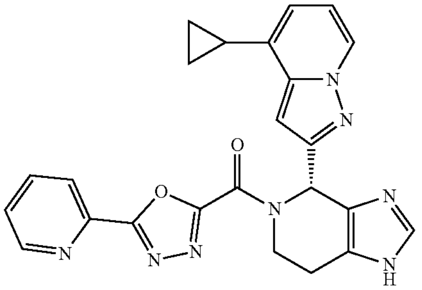 | (S)-(4-(4-cyclopropylpyrazolo [1,5-a]pyridin-2-yl)-1,4,6,7-tetrahydro-5H-imidazo [4,5-c]pyridin-5-yl)(5-(pyridin-2-yl)-1,3,4-oxadiazol-2-yl)methanone |
| 1898 | 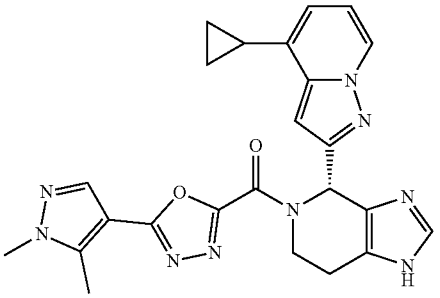 [SMILES: Cc1c(-c2nnc(C(=O)N3CCc4[nH]cnc4[C@H]3c3cc4c(C5CC5)cccn4n3)o2)cnn1C] | (S)-(4-(4-cyclopropylpyrazolo [1,5-a]pyridin-2-yl)-1,4,6,7-tetrahydro-5H-imidazo [4,5-c]pyridin-5-yl)(5-(1,5-dimethyl-1H-pyrazol-4-yl)-1,3,4-oxadiazol-2-yl)methanone |
| 1899 | 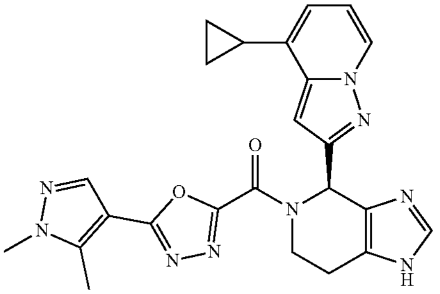 [SMILES: Cc1c(-c2nnc(C(=O)N3CCc4[nH]cnc4[C@@H]3c3cc4c(C5CC5)cccn4n3)o2)cnn1C] | (R)-(4-(4-cyclopropylpyrazolo [1,5-a]pyridin-2-yl)-1,4,6,7-tetrahydro-5H-imidazo [4,5-c]pyridin-5-yl)(5-(1,5-dimethyl-1H-pyrazol-4-yl)-1,3,4-oxadiazol-2-yl)methanone |
| 1900 | 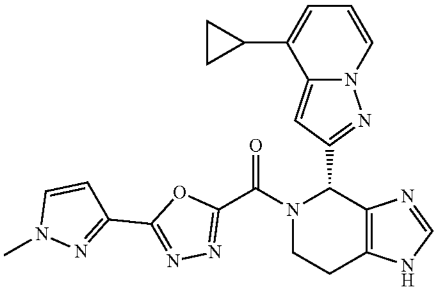 [SMILES: Cn1ccc(-c2nnc(C(=O)N3CCc4[nH]cnc4[C@H]3c3cc4c(C5CC5)cccn4n3)o2)n1] | (S)-(4-(4-cyclopropylpyrazolo [1,5-a]pyridin-2-yl)-1,4,6,7-tetrahydro-5H-imidazo [4,5-c]pyridin-5-yl)(5-(1-methyl-1H-pyrazol-3-yl)-1,3,4-oxadiazol-2-yl)methanone |

TABLE 1-continued

| Pyrazolo[1,5-a]pyridines | | |
|---|---|---|
| Ex. # | Structure | Name |
| 1901 | 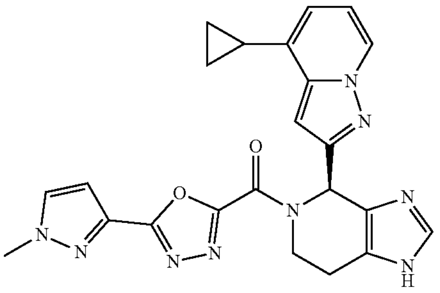 | (R)-(4-(4-cyclopropylpyrazolo[1,5-a]pyridin-2-y]l)-1,4,6,7-tetrahydro-5H-imidazo[4,5-c]pyridin-5-yl)(5-(1-methyl-1H-pyrazol-3-yl)-1,3,4-oxadiazol-2-yl)methanone |
| 1902 | 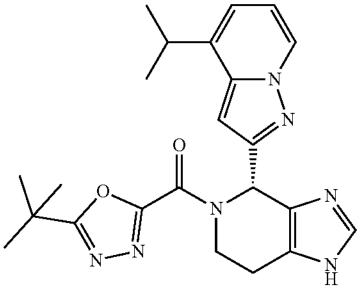 [SMILES: CC(C)c1cccn2nc([C@@H]3c4nc[nH]c4CCN3C(=O)c3nnc(C(C)(C)C)o3)cc12] | (S)-(5-(tert-butyl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 1903 | 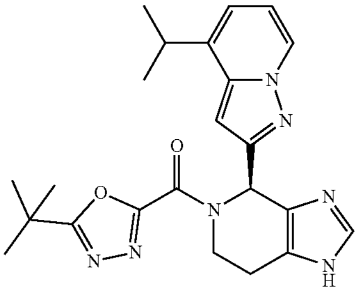 [SMILES: CC(C)c1cccn2nc([C@H]3c4nc[nH]c4CCN3C(=O)c3nnc(C(C)(C)C)o3)cc12] | (R)-(5-(tert-butyl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 1904 | 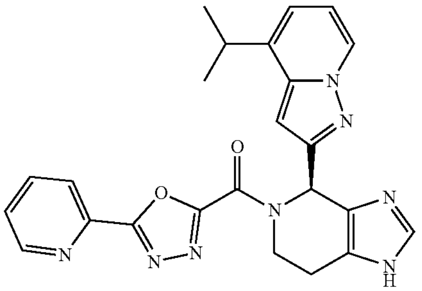 [SMILES: CC(C)c1cccn2nc([C@H]3c4nc[nH]c4CCN3C(=O)c3nnc(-c4ccccn4)o3)cc12] | (R)-(4-(4-isopropylpyrazolo[1,5-a]pyridin-2-yl)-1,4,6,7-tetrahydro-5H-imidazo[4,5-c]pyridin-5-yl)(5-(pyridin-2-yl)-1,3,4-oxadiazol-2-yl)methanone |
| 1905 | 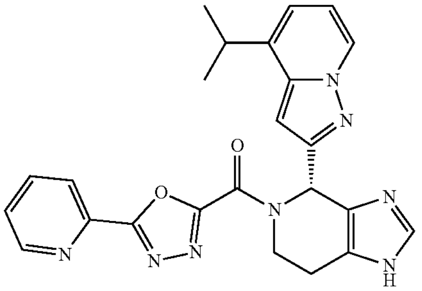 [SMILES: CC(C)c1cccn2nc([C@@H]3c4nc[nH]c4CCN3C(=O)c3nnc(-c4ccccn4)o3)cc12] | (S)-(4-(4-isopropylpyrazolo[1,5-a]pyridin-2-yl)-1,4,6,7-tetrahydro-5H-imidazo[4,5-c]pyridin-5-yl)(5-(pyridin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1906 | 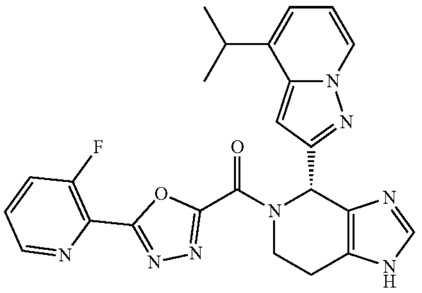 [SMILES: CC(C)c1cccn2nc([C@@H]3c4nc[nH]c4CCN3C(=O)c3nnc(-c4ncccc4F)o3)cc12] | (S)-(5-(3-fluoropyridin-2-yl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 1907 | 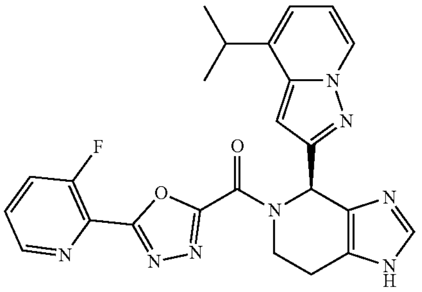 [SMILES: CC(C)c1cccn2nc([C@H]3c4nc[nH]c4CCN3C(=O)c3nnc(-c4ncccc4F)o3)cc12] | (R)-(5-(3-fluoropyridin-2-yl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 1908 | 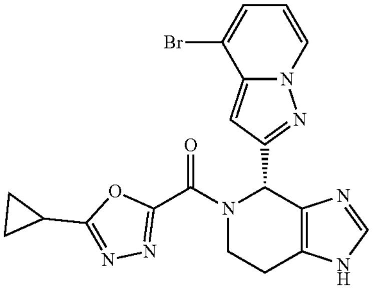 | (S)-(4-(4-bromopyrazolo[1,5-a]pyridin-2-yl)-1,4,6,7-tetrahydro-5H-imidazo[4,5-c]pyridin-5-yl)(5-cyclopropyl-1,3,4-oxadiazol-2-yl)methanone |
| 1909 | 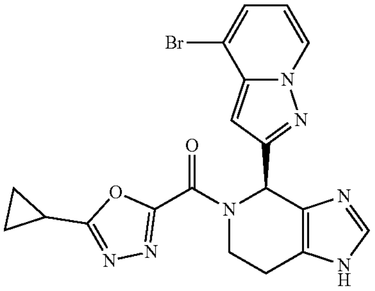 [SMILES: O=C(c1nnc(C2CC2)o1)N1CCc2[nH]cnc2[C@@H]1c1cc2c(Br)cccn2n1] | (R)-(4-(4-bromopyrazolo[1,5-a]pyridin-2-yl)-1,4,6,7-tetrahydro-5H-imidazo[4,5-c]pyridin-5-yl)(5-cyclopropyl-1,3,4-oxadiazol-2-yl)methanone |
| 1910 | 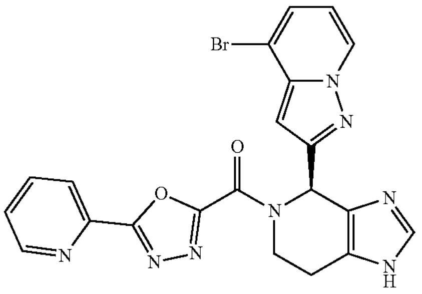 | (R)-(4-(4-bromopyrazolo[1,5-a]pyridin-2-yl)-1,4,6,7-tetrahydro-5H-imidazo[4,5-c]pyridin-5-yl)(5-(pyridin-2-yl)-1,3,4-oxadiazol-2-yl)methanone |

TABLE 1-continued

| Ex. # | Structure | Name |
|---|---|---|
| Pyrazolo[1,5-a]pyridines | | |
| 1911 | 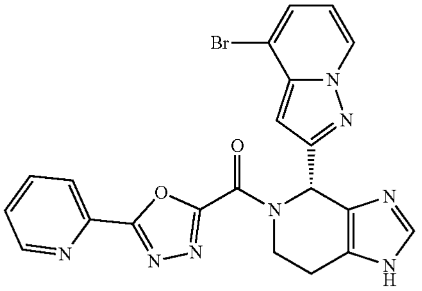 | (S)-(4-(4-bromopyrazolo[1,5-a]pyridin-2-yl)-1,4,6,7-tetrahydro-5H-imidazo[4,5-c]pyridin-5-yl)(5-(pyridin-2-yl)-1,3,4-oxadiazol-2-yl)methanone |
| 1912 | 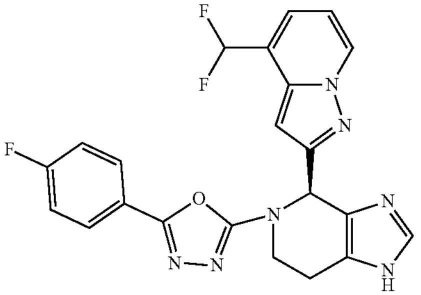 [SMILES: Fc1ccc(-c2nnc(N3CCc4[nH]cnc4[C@@H]3c3cc4c(C(F)F)cccn4n3)o2)cc1] | (R)-2-(4-(4-(difluoromethyl)pyrazolo[1,5-a]pyridin-2-yl)-1,4,6,7-tetrahydro-5H-imidazo[4,5-c]pyridin-5-yl)-5-(4-fluorophenyl)-1,3,4-oxadiazole |
| 1913 | 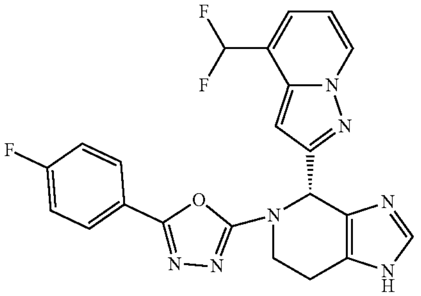 [SMILES: Fc1ccc(-c2nnc(N3CCc4[nH]cnc4[C@H]3c3cc4c(C(F)F)cccn4n3)o2)cc1] | (S)-2-(4-(4-(difluoromethyl)pyrazolo[1,5-a]pyridin-2-yl)-1,4,6,7-tetrahydro-5H-imidazo[4,5-c]pyridin-5-yl)-5-(4-fluorophenyl)-1,3,4-oxadiazole |
| 1914 | 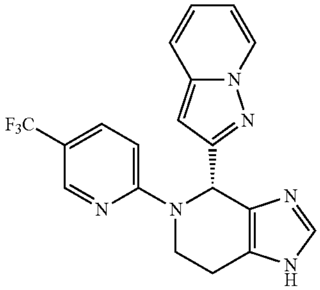 [SMILES: FC(F)(F)c1ccc(N2CCc3[nH]cnc3[C@H]2c2cc3ccccn3n2)nc1] | (S)-4-(pyrazolo[1,5-a]pyridin-2-yl)-5-(5-(trifluoromethyl)pyridin-2-yl)-4,5,6,7-tetrahydro-1H-imidazo[4,5-c]pyridine |
| 1915 | 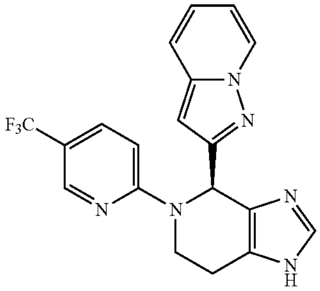 [SMILES: FC(F)(F)c1ccc(N2CCc3[nH]cnc3[C@@H]2c2cc3ccccn3n2)nc1] | (R)-4-(pyrazolo[1,5-a]pyridin-2-yl)-5-(5-(trifluoromethyl)pyridin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 1916 | 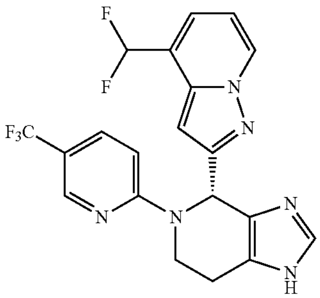 [SMILES: FC(F)c1cccn2nc([C@@H]3c4nc[nH]c4CCN3c3ccc(C(F)(F)F)cn3)cc12] | (S)-4-(4-(difluoromethyl) pyrazolo[1,5-a]pyridin-2-yl)-5-(5-(trifluoromethyl)pyridin-2-yl)-4,5,6,7-tetrahydro-1H-imidazo[4,5-c]pyridine |
| 1917 | 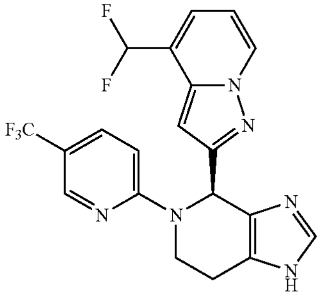 [SMILES: FC(F)c1cccn2nc([C@H]3c4nc[nH]c4CCN3c3ccc(C(F)(F)F)cn3)cc12] | (R)-4-(4-(difluoromethyl) pyrazolo[1,5-a]pyridin-2-yl)-5-(5-(trifluoromethyl)pyridin-2-yl)-4,5,6,7-tetrahydro-1H-imidazo[4,5-c]pyridine |
| 1918 | 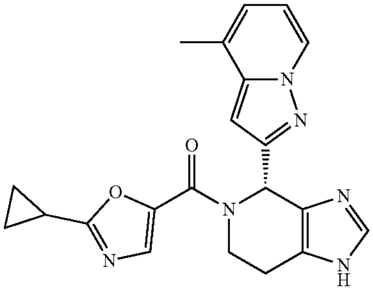 [SMILES: Cc1cccn2nc([C@@H]3c4nc[nH]c4CCN3C(=O)c3cnc(C4CC4)o3)cc12] | (S)-(2-cyclopropyloxazol-5-yl) (4-(4-methylpyrazolo[1,5-a]pyridin-2-yl)-1,4,6,7-tetrahydro-5H-imidazo[4,5-c]pyridin-5-yl)methanone |
| 1919 | 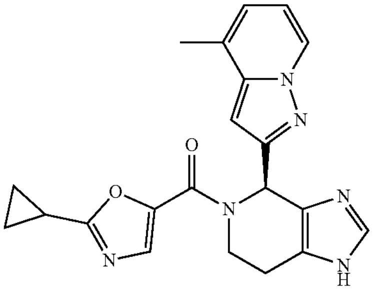 [SMILES: Cc1cccn2nc([C@H]3c4nc[nH]c4CCN3C(=O)c3cnc(C4CC4)o3)cc12] | (R)-(2-cyclopropyloxazol-5-yl)(4-(4-methylpyrazolo[1,5-a]pyridin-2-yl)-1,4,6,7-tetrahydro-5H-imidazo[4,5-c]pyridin-5-yl)methanone |
| 1920 | 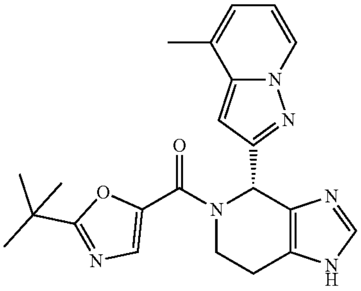 [SMILES: Cc1cccn2nc([C@@H]3c4nc[nH]c4CCN3C(=O)c3cnc(C(C)(C)C)o3)cc12] | (S)-(2-(tert-butyl)oxazol-5-yl)(4-(4-methylpyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
| --- | --- | --- |
| | Pyrazolo[1,5-a]pyridines | |
| 1921 | 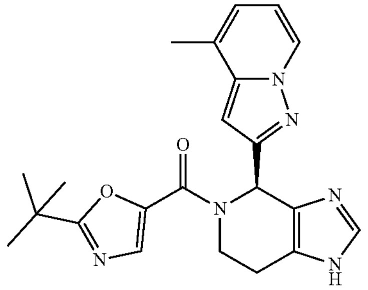 [SMILES: Cc1cccn2nc([C@H]3c4nc[nH]c4CCN3C(=O)c3cnc(C(C)(C)C)o3)cc12] | (R)-(2-(tert-butyl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 1922 | 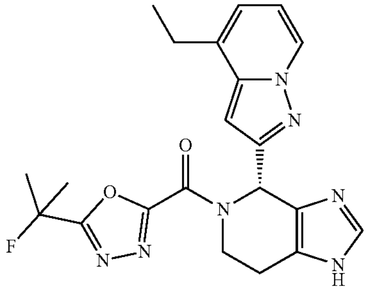 [SMILES: CCc1cccn2nc([C@@H]3c4nc[nH]c4CCN3C(=O)c3nnc(C(C)(C)F)o3)cc12] | (S)-(4-(4-ethylpyrazolo[1,5-a]pyridin-2-yl)-1,4,6,7-tetrahydro-5H-imidazo[4,5-c]pyridin-5-yl)(5-(2-fluoropropan-2-yl)-1,3,4-oxadiazol-2-yl)methanone |
| 1923 | 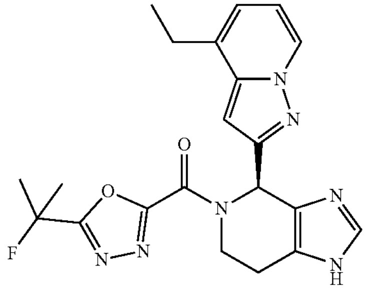 [SMILES: CCc1cccn2nc([C@H]3c4nc[nH]c4CCN3C(=O)c3nnc(C(C)(C)F)o3)cc12] | (R)-(4-(4-ethylpyrazolo[1,5-a]pyridin-2-yl)-1,4,6,7-tetrahydro-5H-imidazo[4,5-c]pyridin-5-yl)(5-(2-fluoropropan-2-yl)-1,3,4-oxadiazol-2-yl)methanone |
| 1924 | 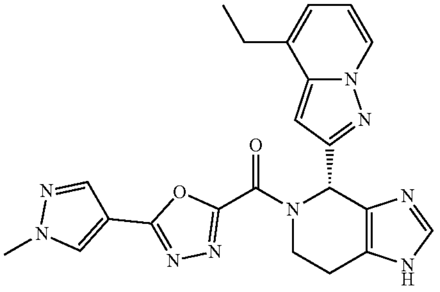 [SMILES: CCc1cccn2nc([C@@H]3c4nc[nH]c4CCN3C(=O)c3nnc(-c4cnn(C)c4)o3)cc12] | (S)-(4-(4-ethylpyrazolo[1,5-a]pyridin-2-yl)-1,4,6,7-tetrahydro-5H-imidazo[4,5-c]pyridin-5-yl)(5-(1-methyl-1H-pyrazol-4-yl)-1,3,4-oxadiazol-2-yl)methanone |
| 1925 | 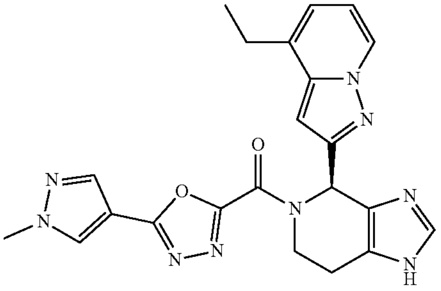 [SMILES: CCc1cccn2nc([C@H]3c4nc[nH]c4CCN3C(=O)c3nnc(-c4cnn(C)c4)o3)cc12] | (R)-(4-(4-ethylpyrazolo[1,5-a]pyridin-2-yl)-1,4,6,7-tetrahydro-5H-imidazo[4,5-c]pyridin-5-yl)(5-(1-methyl-1H-pyrazol-4-yl)-1,3,4-oxadiazol-2-yl)methanone |

TABLE 1-continued

| Pyrazolo[1,5-a]pyridines | | |
|---|---|---|
| Ex. # | Structure | Name |
| 1926 | 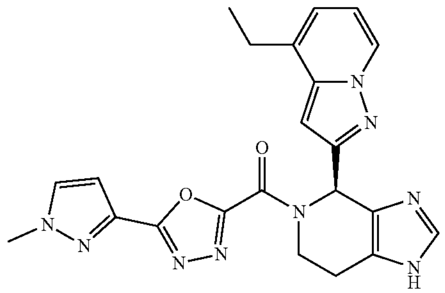 [SMILES: CCc1cccn2nc([C@H]3c4nc[nH]c4CCN3C(=O)c3nnc(-c4ccn(C)n4)o3)cc12] | (R)-(4-(4-ethylpyrazolo [1,5-a]pyridin-2-yl)-1,4,6,7-tetrahydro-5H-imidazo[4,5-c] pyridin-5-yl)(5-(1-methyl-1H-pyrazol-3-yl)-1,3,4-oxadiazol-2-yl)methanone |
| 1927 | 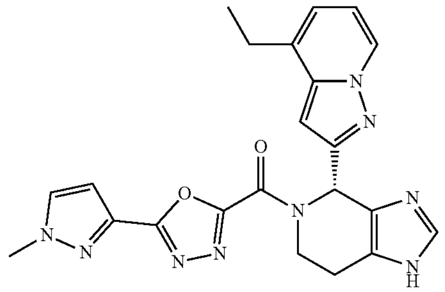 [SMILES: CCc1cccn2nc([C@@H]3c4nc[nH]c4CCN3C(=O)c3nnc(-c4ccn(C)n4)o3)cc12] | (S)-(4-(4-ethylpyrazolo [1,5-a]pyridin-2-yl)-1,4,6,7-tetrahydro-5H-imidazo[4,5-c] pyridin-5-yl)(5-(1-methyl-1H-pyrazol-3-yl)-1,3,4-oxadiazol-2-yl)methanone |
| 1928 | 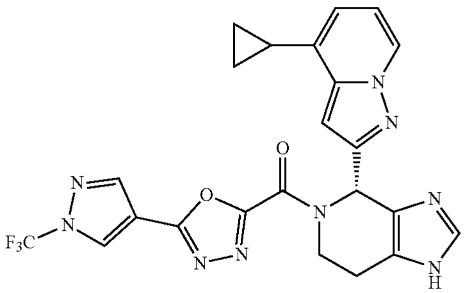 [SMILES: O=C(c1nnc(-c2cnn(C(F)(F)F)c2)o1)N1CCc2[nH]cnc2[C@H]1c1cc2c(C3CC3)cccn2n1] | (S)-(4-(4-cyclopropylpyrazolo [1,5-a]pyridin-2-yl)-1,4,6,7-tetrahydro-5H-imidazo [4,5-c]pyridin-5-yl)(5-(1-(trifluoromethyl)-1H-pyrazol-4-yl)-1,3,4-oxadiazol-2-yl)methanone |
| 1929 | 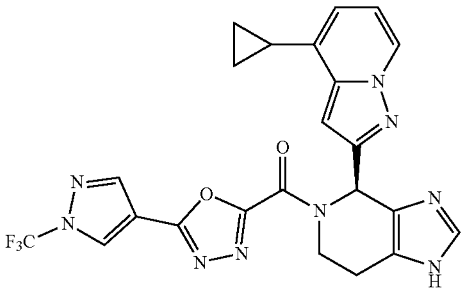 [SMILES: O=C(c1nnc(-c2cnn(C(F)(F)F)c2)o1)N1CCc2[nH]cnc2[C@@H]1c1cc2c(C3CC3)cccn2n1] | (R)-(4-(4-cyclopropylpyrazolo [1,5-a]pyridin-2-y]l)-1,4,6,7-tetrahydro-5H-imidazo [4,5-c]pyridin-5-yl)(5-(1-(trifluoromethyl)-1H-pyrazol-4-yl)-1,3,4-oxadiazol-2-yl)methanone |
| 1930 | 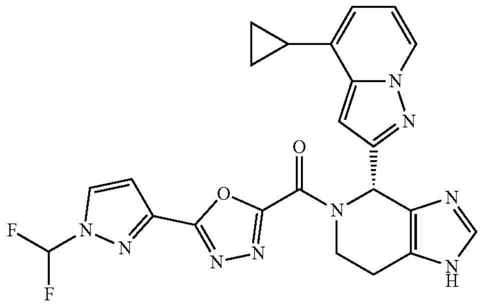 [SMILES: O=C(c1nnc(-c2ccn(C(F)F)n2)o1)N1CCc2[nH]cnc2[C@H]1c1cc2c(C3CC3)cccn2n1] | (S)-(4-(4-cyclopropylpyrazolo [1,5-a]pyridin-2-yl)-1,4,6,7-tetrahydro-5H-imidazo [4,5-c]pyridin-5-yl)(5-(1-(difluoromethyl)-1H-pyrazol-3-yl)-1,3,4-oxadiazol-2-yl)methanone |

TABLE 1-continued

| Pyrazolo[1,5-a]pyridines | | |
|---|---|---|
| Ex. # | Structure | Name |
| 1931 | 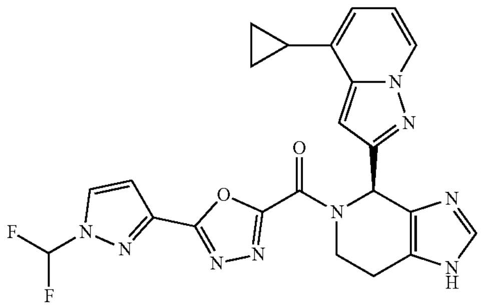 [SMILES: O=C(c1nnc(-c2ccn(C(F)F)n2)o1)N1CCc2[nH]cnc2[C@@H]1c1cc2c(C3CC3)cccn2n1] | (R)-(4-(4-cyclopropylpyrazolo[1,5-a]pyridin-2-yl)-1,4,6,7-tetrahydro-5H-imidazo[4,5-c]pyridin-5-yl)(5-(1-(difluoromethyl)-1H-pyrazol-3-yl)-1,3,4-oxadiazol-2-yl)methanone |
| 1932 | 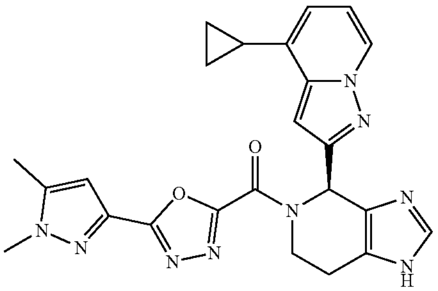 [SMILES: Cc1cc(-c2nnc(C(=O)N3CCc4[nH]cnc4[C@@H]3c3cc4c(C5CC5)cccn4n3)o2)nn1C] | (R)-(4-(4-cyclopropylpyrazolo[1,5-a]pyridin-2-yl)-1,4,6,7-tetrahydro-5H-imidazo[4,5-c]pyridin-5-yl)(5-(1,5-dimethyl-1H-pyrazol-3-yl)-1,3,4-oxadiazol-2-yl)methanone |
| 1933 | 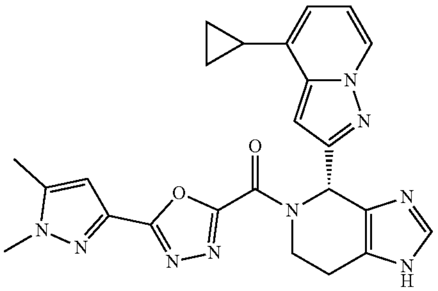 [SMILES: Cc1cc(-c2nnc(C(=O)N3CCc4[nH]cnc4[C@H]3c3cc4c(C5CC5)cccn4n3)o2)nn1C] | (S)-(4-(4-cyclopropylpyrazolo[1,5-a]pyridin-2-yl)-1,4,6,7-tetrahydro-5H-imidazo[4,5-c]pyridin-5-yl)(5-(1,5-dimethyl-1H-pyrazol-3-yl)-1,3,4-oxadiazol-2-yl)methanone |
| 1934 | 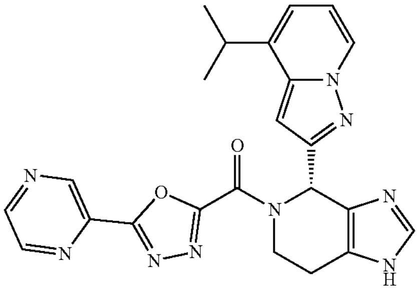 | (S)-(4-(4-isopropylpyrazolo[1,5-a]pyridin-2-yl)-1,4,6,7-tetrahydro-5H-imidazo[4,5-c]pyridin-5-yl)(5-(pyrazin-2-yl)-1,3,4-oxadiazol-2-yl)methanone |
| 1935 | 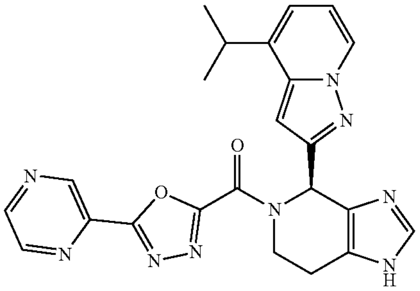 [SMILES: CC(C)c1cccn2nc([C@H]3c4nc[nH]c4CCN3C(=O)c3nnc(-c4cnccn4)o3)cc12] | (R)-(4-(4-isopropylpyrazolo[1,5-a]pyridin-2-yl)-1,4,6,7-tetrahydro-5H-imidazo[4,5-c]pyridin-5-yl)(5-(pyrazin-2-yl)-1,3,4-oxadiazol-2-yl)methanone |

TABLE 1-continued

| Ex. # | Structure | Name |
|---|---|---|
| | Pyrazolo[1,5-a]pyridines | |
| 1936 | 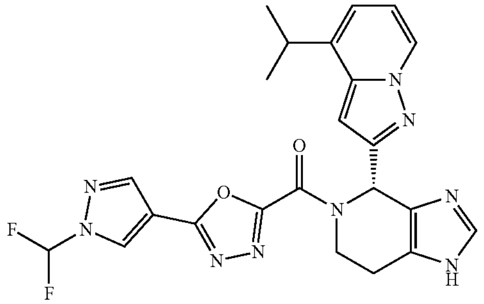 [SMILES: CC(C)c1cccn2nc([C@@H]3c4nc[nH]c4CCN3C(=O)c3nnc(-c4cnn(C(F)F)c4)o3)cc12] | (S)-(5-(1-(difluoromethyl)-1H-pyrazol-4-yl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 1937 | 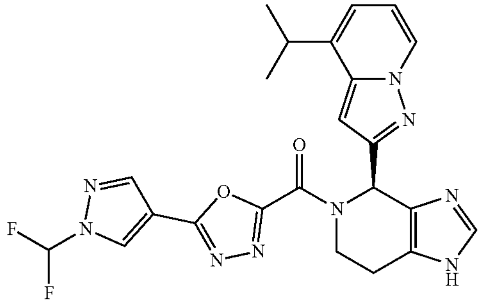 [SMILES: CC(C)c1cccn2nc([C@H]3c4nc[nH]c4CCN3C(=O)c3nnc(-c4cnn(C(F)F)c4)o3)cc12] | (R)-(5-(1-(difluoromethyl)-1H-pyrazol-4-yl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 1938 | 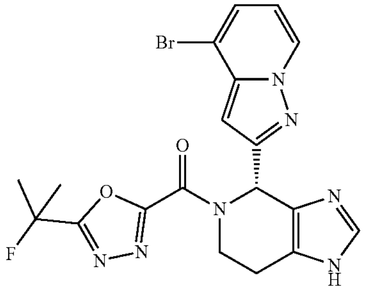 [SMILES: CC(C)(F)c1nnc(C(=O)N2CCc3[nH]cnc3[C@H]2c2cc3c(Br)cccn3n2)o1] | (S)-(4-(4-bromopyrazolo[1,5-a]pyridin-2-yl)-1,4,6,7-tetrahydro-5H-imidazo[4,5-c]pyridin-5-yl)(5-(2-fluoropropan-2-yl)-1,3,4-oxadiazol-2-yl)methanone |
| 1939 | 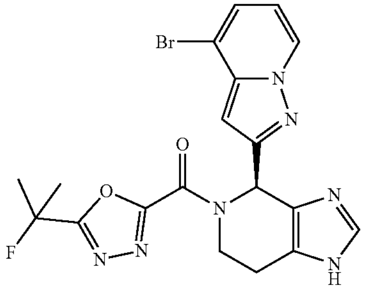 [SMILES: CC(C)(F)c1nnc(C(=O)N2CCc3[nH]cnc3[C@@H]2c2cc3c(Br)cccn3n2)o1] | (R)-(4-(4-bromopyrazolo[1,5-a]pyridin-2-yl)-1,4,6,7-tetrahydro-5H-imidazo[4,5-c]pyridin-5-yl)(5-(2-fluoropropan-2-yl)-1,3,4-oxadiazol-2-yl)methanone |
| 1940 | 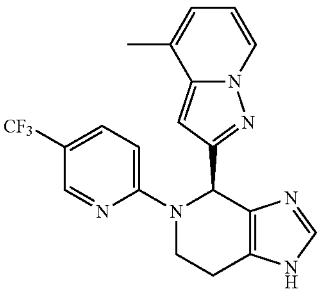 [SMILES: Cc1cccn2nc([C@H]3c4nc[nH]c4CCN3c3ccc(C(F)(F)F)cn3)cc12] | (R)-4-(4-methylpyrazolo[1,5-a]pyridin-2-yl)-5-(5-(trifluoromethyl)pyridin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 1941 | 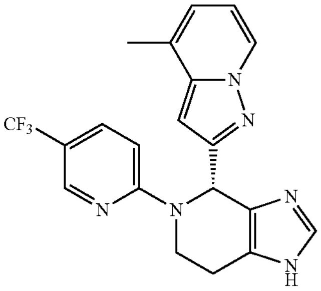 [SMILES: Cc1cccn2nc([C@@H]3c4nc[nH]c4CCN3c3ccc(C(F)(F)F)cn3)cc12] | (S)-4-(4-methylpyrazolo[1,5-a]pyridin-2-yl)-5-(5-(trifluoromethyl)pyridin-2-yl)-4,5,6,7-tetrahydro-1H-imidazo[4,5-c]pyridine |
| 1942 | 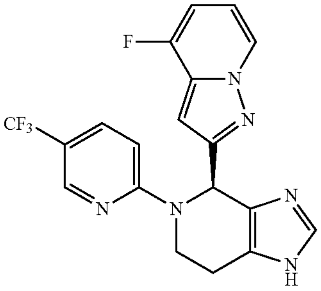 [SMILES: Fc1cccn2nc([C@H]3c4nc[nH]c4CCN3c3ccc(C(F)(F)F)cn3)cc12] | (R)-4-(4-fluoropyrazolo[1,5-a]pyridin-2-yl)-5-(5-(trifluoromethyl)pyridin-2-yl)-4,5,6,7-tetrahydro-1H-imidazo[4,5-c]pyridine |
| 1943 | 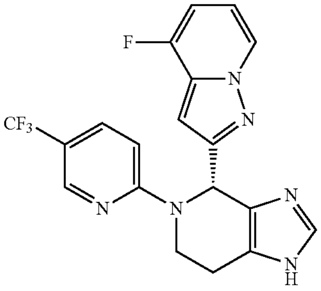 [SMILES: Fc1cccn2nc([C@@H]3c4nc[nH]c4CCN3c3ccc(C(F)(F)F)cn3)cc12] | (S)-4-(4-fluoropyrazolo[1,5-a]pyridin-2-yl)-5-(5-(trifluoromethyl)pyridin-2-yl)-4,5,6,7-tetrahydro-1H-imidazo[4,5-c]pyridine |
| 1944 | 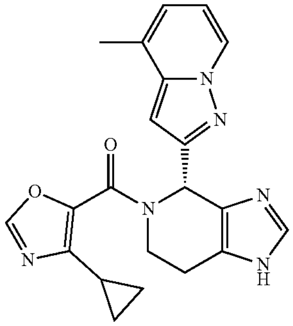 [SMILES: Cc1cccn2nc([C@@H]3c4nc[nH]c4CCN3C(=O)c3ocnc3C3CC3)cc12] | (S)-(4-cyclopropyloxazol-5-yl)(4-(4-methylpyrazolo[1,5-a]pyridin-2-yl)-1,4,6,7-tetrahydro-5H-imidazo[4,5-c]pyridin-5-yl)methanone |
| 1945 | 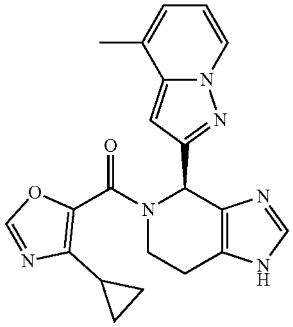 [SMILES: Cc1cccn2nc([C@H]3c4nc[nH]c4CCN3C(=O)c3ocnc3C3CC3)cc12] | (R)-(4-cyclopropyloxazol-5-yl)(4-(4-methylpyrazolo[1,5-a]pyridin-2-yl)-1,4,6,7-tetrahydro-5H-imidazo[4,5-c]pyridin-5-yl)methanone |

TABLE 1-continued

| Pyrazolo[1,5-a]pyridines | | |
|---|---|---|
| Ex. # | Structure | Name |
| 1946 | 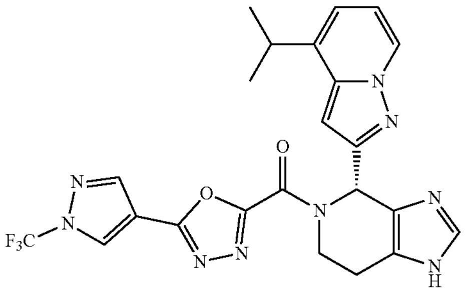 [SMILES: CC(C)c1cccn2nc([C@@H]3c4nc[nH]c4CCN3C(=O)c3nnc(-c4cnn(C(F)(F)F)c4)o3)cc12] | (S)-(4-(4-isopropylpyrazolo [1,5-a]pyridin-2-yl)-1,4,6,7-tetrahydro-5H-imidazo [4,5-c]pyridin-5-yl)(5-(1-(trifluoromethyl)-1H-pyrazol-4-yl)-1,3,4-oxadiazol-2-yl)methanone |
| 1947 | 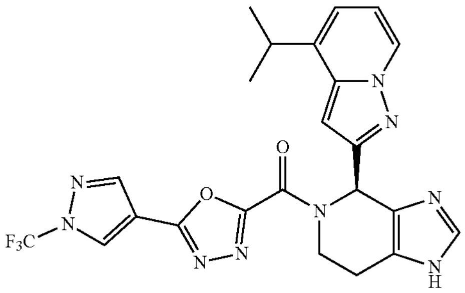 [SMILES: CC(C)c1cccn2nc([C@H]3c4nc[nH]c4CCN3C(=O)c3nnc(-c4cnn(C(F)(F)F)c4)o3)cc12] | (R)-(4-(4-isopropylpyrazolo [1,5-a]pyridin-2-yl)-1,4,6,7-tetrahydro-5H-imidazo [4,5-c]pyridin-5-yl)(5-(1-(trifluoromethyl)-1H-pyrazol-4-yl)-1,3,4-oxadiazol-2-yl)methanone |
| 1948 | 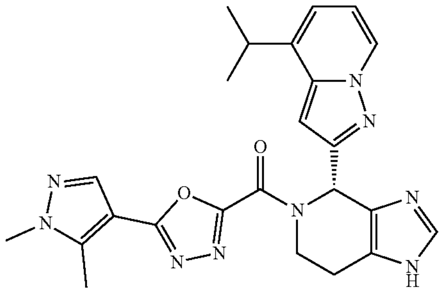 [SMILES: Cc1c(-c2nnc(C(=O)N3CCc4[nH]cnc4[C@H]3c3cc4c(C(C)C)cccn4n3)o2)cnn1C] | (S)-(5-(1,5-dimethyl-1H-pyrazol-4-yl)-1,3,4-oxadiazol-2-yl)(4-(4-isopropylpyrazolo [1,5-a]pyridin-2-yl)-1,4,6,7-tetrahydro-5H-imidazo[4,5-c] pyridin-5-yl)methanone |
| 1949 | 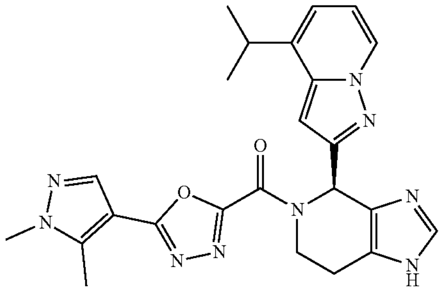 [SMILES: Cc1c(-c2nnc(C(=O)N3CCc4[nH]cnc4[C@@H]3c3cc4c(C(C)C)cccn4n3)o2)cnn1C] | (R)-(5-(1,5-dimethyl-1H-pyrazol-4-yl)-1,3,4-oxadiazol-2-yl)(4-(4-isopropylpyrazolo [1,5-a]pyridin-2-yl)-1,4,6,7-tetrahydro-5H-imidazo[4,5-c] pyridin-5-yl)methanone |
| 1950 | 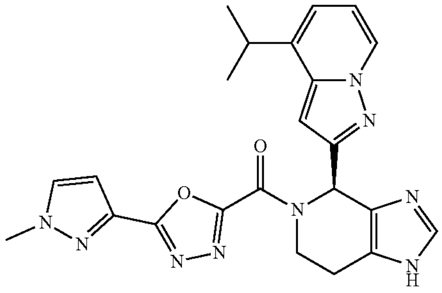 [SMILES: CC(C)c1cccn2nc([C@H]3c4nc[nH]c4CCN3C(=O)c3nnc(-c4ccn(C)n4)o3)cc12] | (R)-(4-(4-isopropylpyrazolo [1,5-a]pyridin-2-yl)-1,4,6,7-tetrahydro-5H-imidazo[4,5-c] pyridin-5-yl)(5-(1-methyl-1H-pyrazol-3-yl)-1,3,4-oxadiazol-2-yl)methanone |

TABLE 1-continued

| Pyrazolo[1,5-a]pyridines | | |
|---|---|---|
| Ex. # | Structure | Name |
| 1951 | 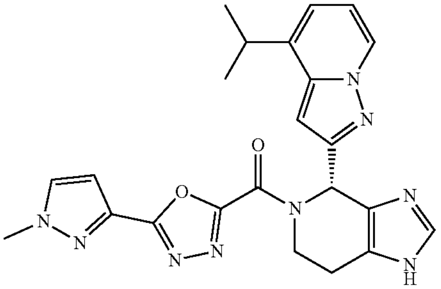 [SMILES: CC(C)c1cccn2nc([C@@H]3c4nc[nH]c4CCN3C(=O)c3nnc(-c4ccn(C)n4)o3)cc12] | (S)-(4-(4-isopropylpyrazolo[1,5-a]pyridin-2-yl)-1,4,6,7-tetrahydro-5H-imidazo[4,5-c]pyridin-5-yl)(5-(1-methyl-1H-pyrazol-3-yl)-1,3,4-oxadiazol-2-yl)methanone |
| 1952 | 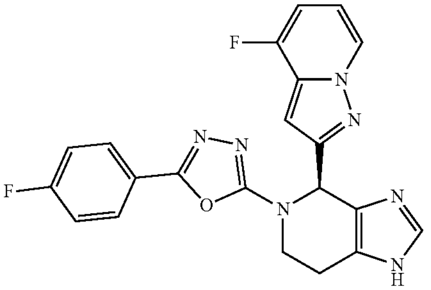 [SMILES: Fc1ccc(-c2nnc(N3CCc4[nH]cnc4[C@@H]3c3cc4c(F)cccn4n3)o2)cc1] | (R)-2-(4-fluorophenyl)-5-(4-(4-fluoropyrazolo[1,5-a]pyridin-2-yl)-1,4,6,7-tetrahydro-5H-imidazo[4,5-c]pyridin-5-yl)-1,3,4-oxadiazole |
| 1953 | 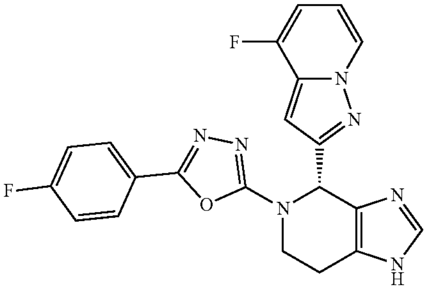 [SMILES: Fc1ccc(-c2nnc(N3CCc4[nH]cnc4[C@H]3c3cc4c(F)cccn4n3)o2)cc1] | (S)-2-(4-fluorophenyl)-5-(4-(4-fluoropyrazolo[1,5-a]pyridin-2-yl)-1,4,6,7-tetrahydro-5H-imidazo[4,5-c]pyridin-5-yl)-1,3,4-oxadiazole |
| 1954 | 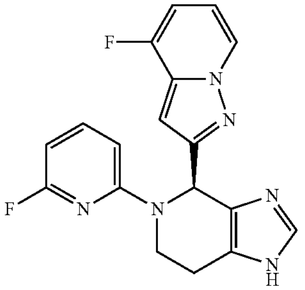 [SMILES: Fc1cccc(N2CCc3[nH]cnc3[C@@H]2c2cc3c(F)cccn3n2)n1] | (R)-4-(4-fluoropyrazolo[1,5-a]pyridin-2-yl)-5-(6-fluoropyridin-2-yl)-4,5,6,7-tetrahydro-1H-imidazo[4,5-c]pyridine |
| 1955 | 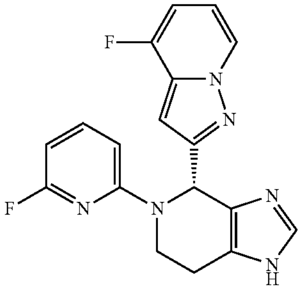 [SMILES: Fc1cccc(N2CCc3[nH]cnc3[C@H]2c2cc3c(F)cccn3n2)n1] | (S)-4-(4-fluoropyrazolo[1,5-a]pyridin-2-y])-5-(6-fluoropyridin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 1956 | 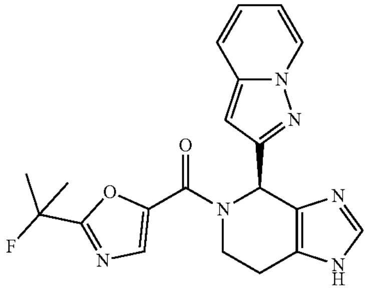 [SMILES: CC(C)(F)c1ncc(C(=O)N2CCc3[nH]cnc3[C@@H]2c2cc3ccccn3n2)o1] | (R)-(2-(2-fluoropropan-2-yl)oxazol-5-yl)(4-(pyrazolo[1,5-a]pyridin-2-yl)-1,4,6,7-tetrahydro-5H-imidazo[4,5-c]pyridin-5-yl)methanone |
| 1957 | 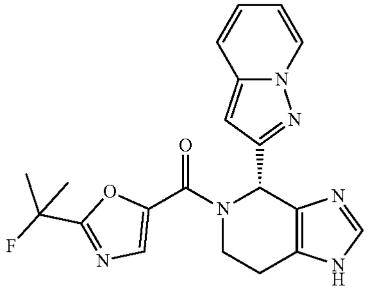 [SMILES: CC(C)(F)c1ncc(C(=O)N2CCc3[nH]cnc3[C@H]2c2cc3ccccn3n2)o1] | (S)-(2-(2-fluoropropan-2-yl)oxazol-5-yl)(4-(pyrazolo[1,5-a]pyridin-2-yl)-1,4,6,7-tetrahydro-5H-imidazo[4,5-c]pyridin-5-yl)methanone |
| 1958 | 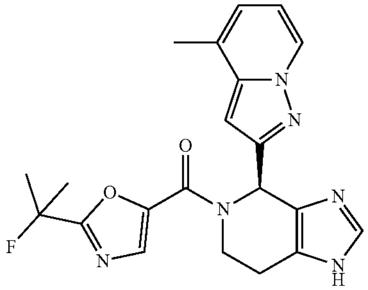 [SMILES: Cc1cccn2nc([C@H]3c4nc[nH]c4CCN3C(=O)c3cnc(C(C)(C)F)o3)cc12] | (R)-(2-(2-fluoropropan-2-yl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 1959 | 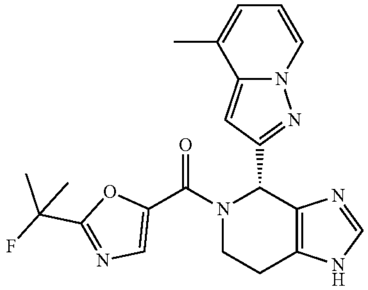 [SMILES: Cc1cccn2nc([C@@H]3c4nc[nH]c4CCN3C(=O)c3cnc(C(C)(C)F)o3)cc12] | (S)-(2-(2-fluoropropan-2-yl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 1960 | 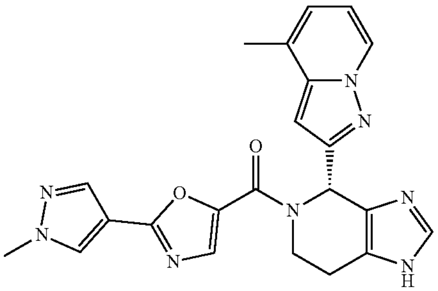 [SMILES: Cc1cccn2nc([C@@H]3c4nc[nH]c4CCN3C(=O)c3cnc(-c4cnn(C)c4)o3)cc12] | (S)-(2-(1-methyl-1H-pyrazol-4-yl)oxazol-5-yl)(4-(4-methylpyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
|---|---|---|
| Pyrazolo[1,5-a]pyridines | | |
| 1961 | 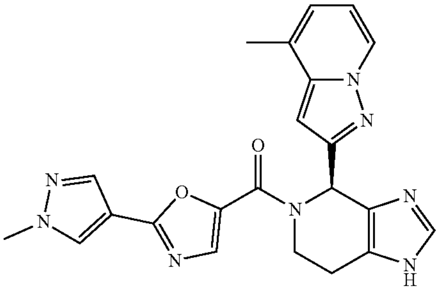 [SMILES: Cc1cccn2nc([C@H]3c4nc[nH]c4CCN3C(=O)c3cnc(-c4cnn(C)c4)o3)cc12] | (R)-(2-(1-methyl-1H-pyrazol-4-yl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 1962 | 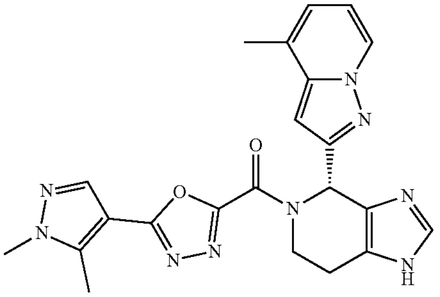 [SMILES: Cc1cccn2nc([C@@H]3c4nc[nH]c4CCN3C(=O)c3nnc(-c4cnn(C)c4C)o3)cc12] | (S)-(2-(1,5-dimethyl-1H-pyrazol-4-yl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 1963 | 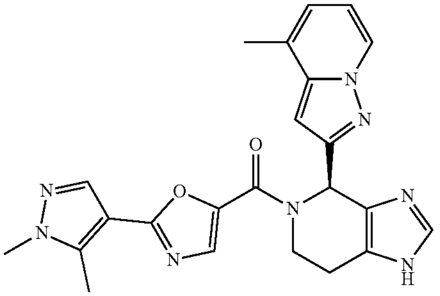 [SMILES: Cc1cccn2nc([C@H]3c4nc[nH]c4CCN3C(=O)c3cnc(-c4cnn(C)c4C)o3)cc12] | (R)-(2-(1,5-dimethyl-1H-pyrazol-4-yl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 1964 | 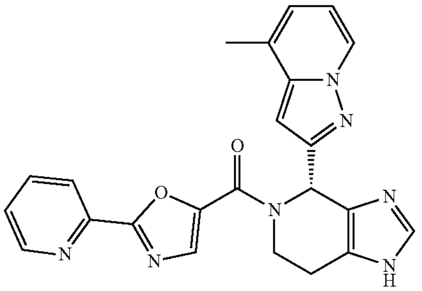 [SMILES: Cc1cccn2nc([C@@H]3c4nc[nH]c4CCN3C(=O)c3cnc(-c4ccccn4)o3)cc12] | (S)-(4-(4-methylpyrazolo[1,5-a]pyridin-2-yl)-1,4,6,7-tetrahydro-5H-imidazo[4,5-c]pyridin-5-yl)(2-(pyridin-2-yl)oxazol-5-yl)methanone |
| 1965 | 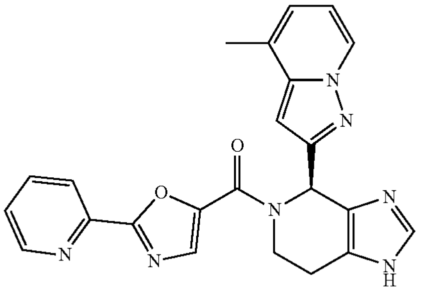 [SMILES: Cc1cccn2nc([C@H]3c4nc[nH]c4CCN3C(=O)c3cnc(-c4ccccn4)o3)cc12] | (R)-(4-(4-methylpyrazolo[1,5-a]pyridin-2-yl)-1,4,6,7-tetrahydro-5H-imidazo[4,5-c]pyridin-5-yl)(2-(pyridin-2-yl)oxazol-5-yl)methanone |

TABLE 1-continued

| Pyrazolo[1,5-a]pyridines | | |
|---|---|---|
| Ex. # | Structure | Name |
| 1966 | 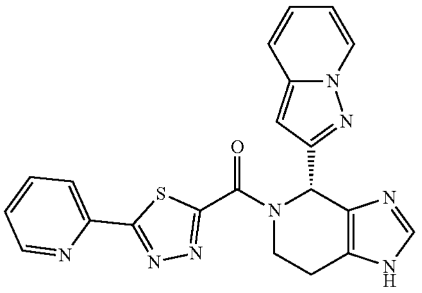 [SMILES: O=C(c1nnc(-c2ccccn2)s1)N1CCc2[nH]cnc2[C@H]1c1cc2ccccn2n1] | (S)-(4-(pyrazolo[1,5-a]pyridin-2-yl)-1,4,6,7-tetrahydro-5H-imidazo[4,5-c]pyridin-5-yl)(5-(pyridin-2-yl)-1,3,4-thiadiazol-2-yl)methanone |
| 1967 | 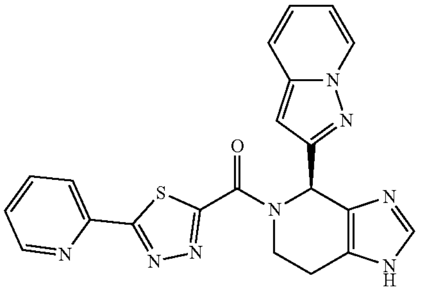 | (R)-(4-(pyrazolo[1,5-a]pyridin-2-yl)-1,4,6,7-tetrahydro-5H-imidazo[4,5-c]pyridin-5-yl)(5-(pyridin-2-yl)-1,3,4-thiadiazol-2-yl)methanone |
| 1968 | 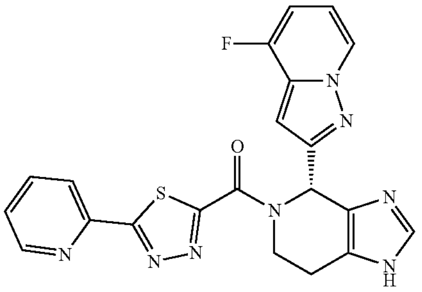 | (S)-(4-(4-fluoropyrazolo[1,5-a]pyridin-2-yl)-1,4,6,7-tetrahydro-5H-imidazo[4,5-c]pyridin-5-yl)(5-(pyridin-2-yl)-1,3,4-thiadiazol-2-yl)methanone |
| 1969 | 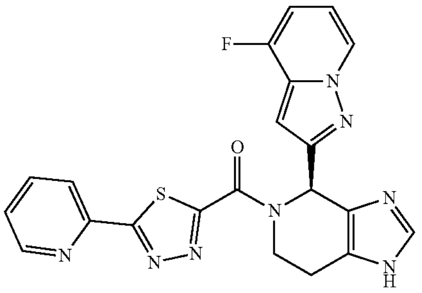 [SMILES: Cc1cccn2nc([C@H]3c4nc[nH]c4CCN3C(=O)c3nnc(-c4ccccn4)s3)cc12] | (R)-(4-(4-fluoropyrazolo[1,5-a]pyridin-2-yl)-1,4,6,7-tetrahydro-5H-imidazo[4,5-c]pyridin-5-yl)(5-(pyridin-2-yl)-1,3,4-thiadiazol-2-yl)methanone |
| 1970 | 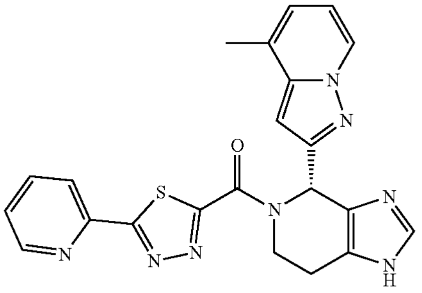 | (S)-(4-(4-methylpyrazolo[1,5-a]pyridin-2-yl)-1,4,6,7-tetrahydro-5H-imidazo[4,5-c]pyridin-5-yl)(5-(pyridin-2-yl)-1,3,4-thiadiazol-2-yl)methanone |

TABLE 1-continued

| Pyrazolo[1,5-a]pyridines | | |
|---|---|---|
| Ex. # | Structure | Name |
| 1971 | 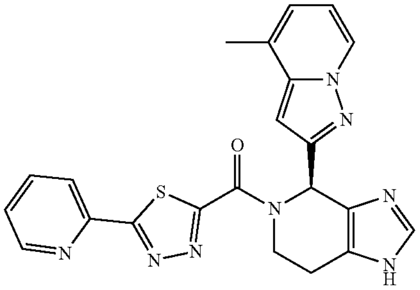 | (R)-(4-(4-methylpyrazolo [1,5-a]pyridin-2-yl)-1,4,6,7-tetrahydro-5H-imidazo[4,5-c] pyridin-5-yl)(5-(pyridin-2-yl)-1,3,4-thiadiazol-2-yl) methanone |
| 1972 | 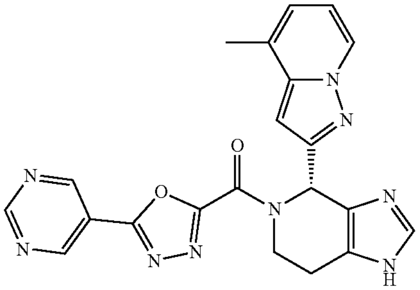 [SMILES: Cc1cccn2nc([C@@H]3c4nc[nH]c4CCN3C(=O)c3nnc(-c4cncnc4)o3)cc12] | (S)-(4-(4-methylpyrazolo [1,5-a]pyridin-2-yl)-1,4,6,7-tetrahydro-5H-imidazo[4,5-c] pyridin-5-yl)(5-(pyrimidin-5-yl)-1,3,4-oxadiazol-2-yl) methanone |
| 1973 | 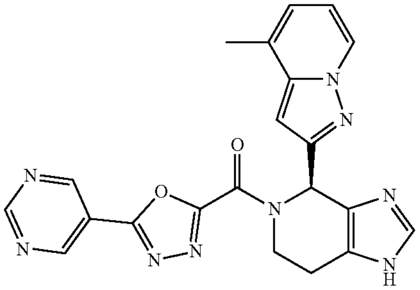 [SMILES: Cc1cccn2nc([C@H]3c4nc[nH]c4CCN3C(=O)c3nnc(-c4cncnc4)o3)cc12] | (R)-(4-(4-methylpyrazolo [1,5-a]pyridin-2-yl)-1,4,6,7-tetrahydro-5H-imidazo[4,5-c] pyridin-5-yl)(5-(pyrimidin-5-yl)-1,3,4-oxadiazol-2-yl) methanone |
| 1974 | 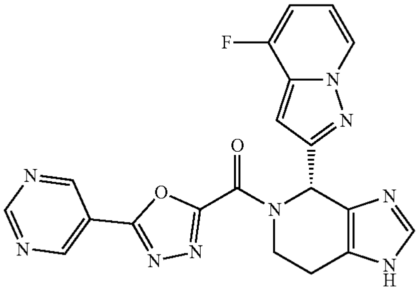 | (S)-(4-(4-fluoropyrazolo [1,5-a]pyridin-2-yl)-1,4,6,7-tetrahydro-5H-imidazo[4,5-c] pyridin-5-yl)(5-(pyrimidin-5-yl)-1,3,4-oxadiazol-2-yl) methanone |
| 1975 | 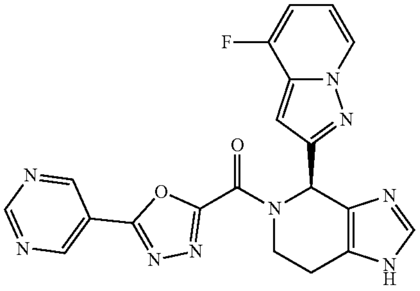 | (R)-(4-(4-fluoropyrazolo [1,5-a]pyridin-2-y]l)-1,4,6,7-tetrahydro-5H-imidazo[4,5-c] pyridin-5-yl)(5-(pyrimidin-5-yl)-1,3,4-oxadiazol-2-yl) methanone |

TABLE 1-continued

| Ex. # | Structure | Name |
|---|---|---|
| | Pyrazolo[1,5-a]pyridines | |
| 1976 | 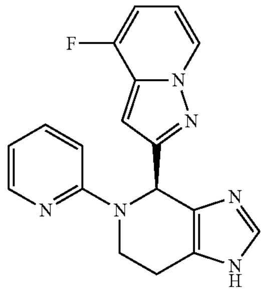 [SMILES: Fc1cccn2nc([C@H]3c4nc[nH]c4CCN3c3ccccn3)cc12] | (R)-4-(4-fluoropyrazolo[1,5-a]pyridin-2-yl)-5-(pyridin-2-yl)-4,5,6,7-tetrahydro-1H-imidazo[4,5-c]pyridine |
| 1977 | 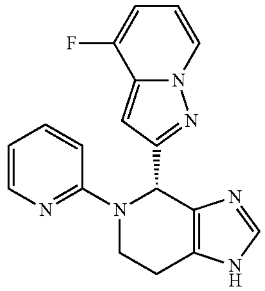 [SMILES: Fc1cccn2nc([C@@H]3c4nc[nH]c4CCN3c3ccccn3)cc12] | (S)-4-(4-fluoropyrazolo[1,5-a]pyridin-2-yl)-5-(pyridin-2-yl)-4,5,6,7-tetrahydro-1H-imidazo[4,5-c]pyridine |
| 1978 | 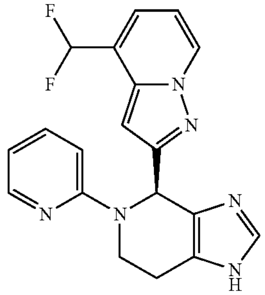 [SMILES: FC(F)c1cccn2nc([C@H]3c4nc[nH]c4CCN3c3ccccn3)cc12] | (R)-4-(4-(difluoromethyl)pyrazolo[1,5-a]pyridin-2-yl)-5-(pyridin-2-yl)-4,5,6,7-tetrahydro-1H-imidazo[4,5-c]pyridine |
| 1979 | 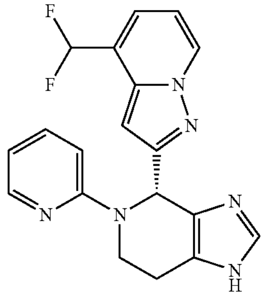 [SMILES: FC(F)c1cccn2nc([C@@H]3c4nc[nH]c4CCN3c3ccccn3)cc12] | (S)-4-(4-(difluoromethyl)pyrazolo[1,5-a]pyridin-2-yl)-5-(pyridin-2-yl)-4,5,6,7-tetrahydro-1H-imidazo[4,5-c]pyridine |
| 1980 | 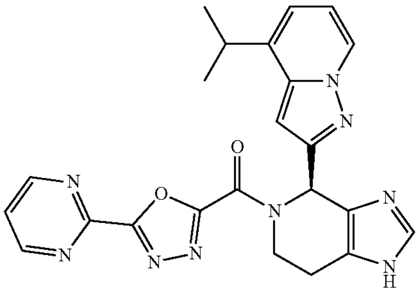 [SMILES: CC(C)c1cccn2nc([C@H]3c4nc[nH]c4CCN3C(=O)c3nnc(-c4ncccn4)o3)cc12] | (R)-(4-(4-isopropylpyrazolo[1,5-a]pyridin-2-yl)-1,4,6,7-tetrahydro-5H-imidazo[4,5-c]pyridin-5-yl)(5-(pyrimidin-2-yl)-1,3,4-oxadiazol-2-yl)methanone |

TABLE 1-continued

Pyrazolo[1,5-a]pyridines

| Ex. # | Structure | Name |
|---|---|---|
| 1981 | 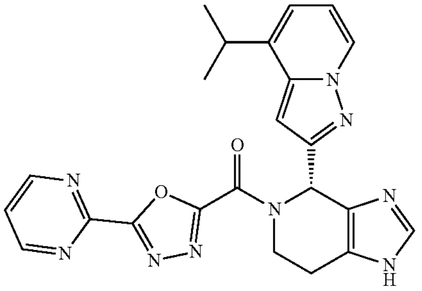 | (S)-(4-(4-isopropylpyrazolo [1,5-a]pyridin-2-yl)-1,4,6,7-tetrahydro-5H-imidazo[4,5-c] pyridin-5-yl)(5-(pyrimidin-2-yl)-1,3,4-oxadiazol-2-yl) methanone |
| 1982 | 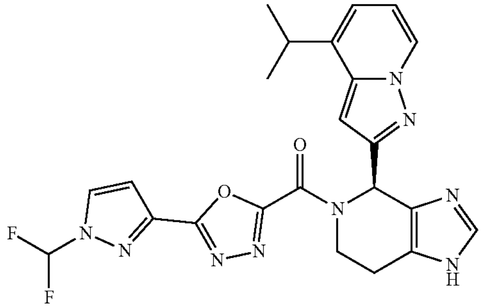 | (R)-(5-(1-(difluoromethyl)-1H-pyrazol-3-yl)-1,3,4-oxadiazol-2-yl)(4-(4-isopropylpyrazolo[1,5-a] pyridin-2-yl)-1,4,6,7-tetrahydro-5H-imidazo[4,5-c]pyridin-5-yl)methanone |
| 1983 | 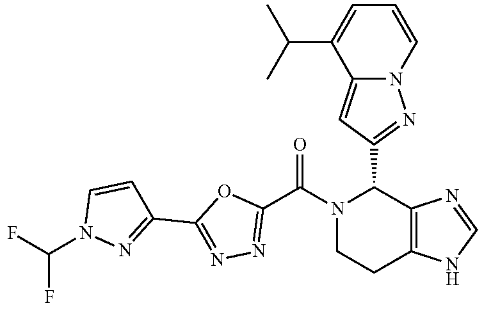 [SMILES: CC(C)c1cccn2nc([C@@H]3c4nc[nH]c4CCN3C(=O)c3nnc(-c4ccn(C(F)F)n4)o3)cc12] | (S)-(5-(1-(difluoromethyl)-1H-pyrazol-3-yl)-1,3,4-oxadiazol-2-yl)(4-(4-isopropylpyrazolo[1,5-a] pyridin-2-yl)-1,4,6,7-tetrahydro-5H-imidazo[4,5-c]pyridin-5-yl)methanone |
| 1984 | 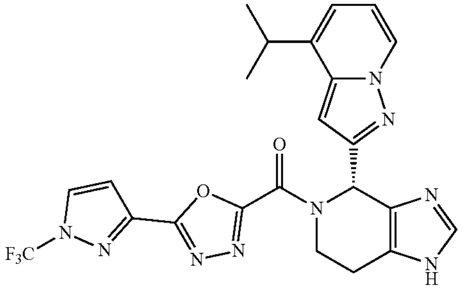 [SMILES: CC(C)c1cccn2nc([C@@H]3c4nc[nH]c4CCN3C(=O)c3nnc(-c4ccn(C(F)(F)F)n4)o3)cc12] | (S)-(4-(4-isopropylpyrazolo [1,5-a]pyridin-2-yl)-1,4,6,7-tetrahydro-5H-imidazo [4,5-c]pyridin-5-yl)(5-(1-(trifluoromethyl)-1H-pyrazol-3-yl)-1,3,4-oxadiazol-2-yl)methanone |
| 1985 | 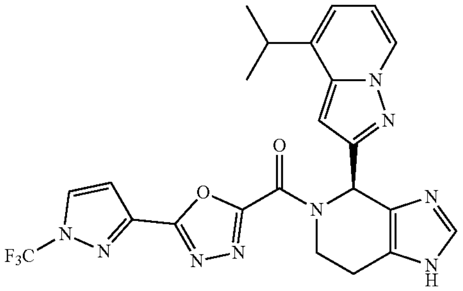 [SMILES: CC(C)c1cccn2nc([C@H]3c4nc[nH]c4CCN3C(=O)c3nnc(-c4ccn(C(F)(F)F)n4)o3)cc12] | (R)-(4-(4-isopropylpyrazolo [1,5-a]pyridin-2-yl)-1,4,6,7-tetrahydro-5H-imidazo [4,5-c]pyridin-5-yl)(5-(1-(trifluoromethyl)-1H-pyrazol-3-yl)-1,3,4-oxadiazol-2-yl)methanone |

TABLE 1-continued

| Ex. # | Structure | Name |
|---|---|---|
| | Pyrazolo[1,5-a]pyridines | |
| 1986 | 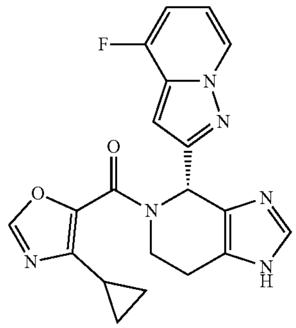 [SMILES: O=C(c1ocnc1C1CC1)N1CCc2[nH]cnc2[C@H]1c1cc2c(F)cccn2n1] | (S)-(4-cyclopropyloxazol-5-yl)(4-(4-fluoropyrazolo[1,5-a]pyridin-2-yl)-1,4,6,7-tetrahydro-5H-imidazo[4,5-c]pyridin-5-yl)methanone |
| 1987 | 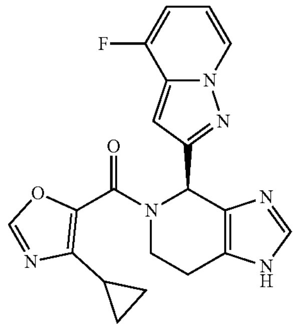 | (R)-(4-cyclopropyloxazol-5-yl)(4-(4-fluoropyrazolo[1,5-a]pyridin-2-yl)-1,4,6,7-tetrahydro-5H-imidazo[4,5-c]pyridin-5-yl)methanone |
| 1988 | 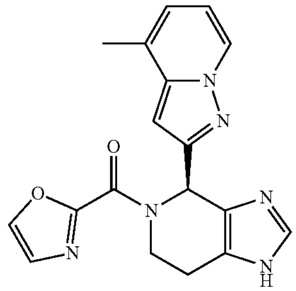 [SMILES: Cc1cccn2nc([C@H]3c4nc[nH]c4CCN3C(=O)c3ncco3)cc12] | (R)-(4-(4-methylpyrazolo[1,5-a]pyridin-2-yl)-1,4,6,7-tetrahydro-5H-imidazo[4,5-c]pyridin-5-yl)(oxazol-2-yl)methanone |
| 1989 | 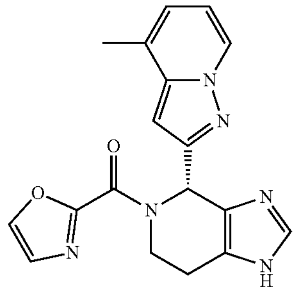 [SMILES: Cc1cccn2nc([C@@H]3c4nc[nH]c4CCN3C(=O)c3ncco3)cc12] | (S)-(4-(4-methylpyrazolo[1,5-a]pyridin-2-yl)-1,4,6,7-tetrahydro-5H-imidazo[4,5-c]pyridin-5-yl)(oxazol-2-yl)methanone |
| 1990 | 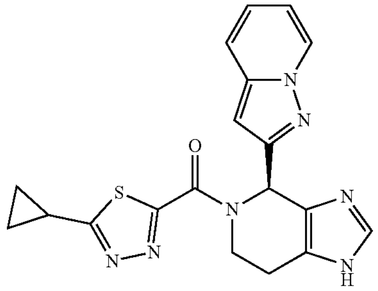 [SMILES: O=C(c1nnc(C2CC2)s1)N1CCc2[nH]cnc2[C@@H]1c1cc2ccccn2n1] | (R)-(5-cyclopropyl-1,3,4-thiadiazol-2-yl)(4-(pyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
|---|---|---|
| | Pyrazolo[1,5-a]pyridines | |
| 1991 | 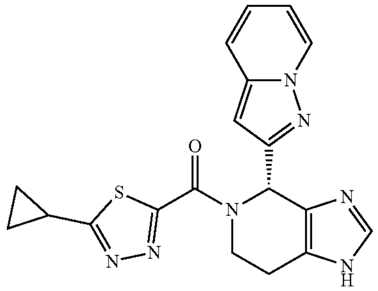 [SMILES: O=C(c1nnc(C2CC2)s1)N1CCc2[nH]cnc2[C@H]1c1cc2ccccn2n1] | (S)-(5-cyclopropyl-1,3,4-thiadiazol-2-yl)(4-(pyrazolo[1,5-a]pyridin-2-yl)-1,4,6,7-tetrahydro-5H-imidazo[4,5-c]pyridin-5-yl)methanone |
| 1992 | 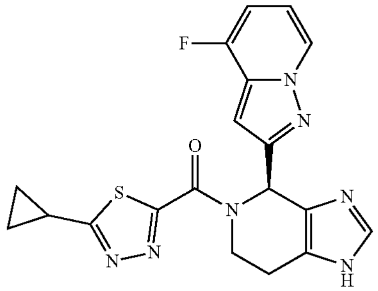 [SMILES: O=C(c1nnc(C2CC2)s1)N1CCc2[nH]cnc2[C@@H]1c1cc2c(F)cccn2n1] | (R)-(5-cyclopropyl-1,3,4-thiadiazol-2-yl)(4-(4-fluoropyrazolo[1,5-a]pyridin-2-yl)-1,4,6,7-tetrahydro-5H-imidazo[4,5-c]pyridin-5-yl)methanone |
| 1993 | 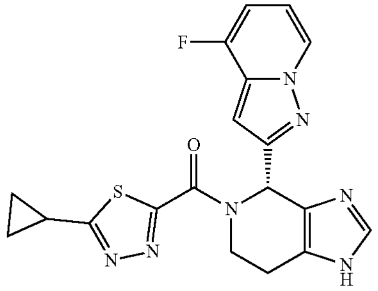 | (S)-(5-cyclopropyl-1,3,4-thiadiazol-2-yl)(4-(4-fluoropyrazolo[1,5-a]pyridin-2-yl)-1,4,6,7-tetrahydro-5H-imidazo[4,5-c]pyridin-5-yl)methanone |
| 1994 | 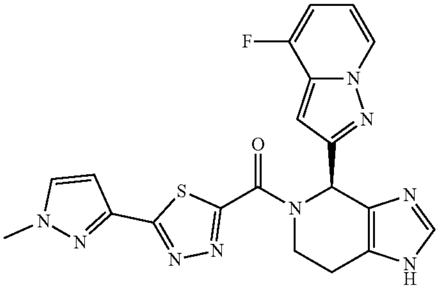 | (R)-(4-(4-fluoropyrazolo[1,5-a]pyridin-2-yl)-1,4,6,7-tetrahydro-5H-imidazo[4,5-c]pyridin-5-yl)(5-(1-methyl-1H-pyrazol-3-yl)-1,3,4-thiadiazol-2-yl)methanone |
| 1995 | 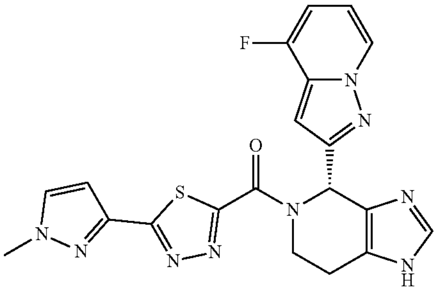 | (S)-(4-(4-fluoropyrazolo[1,5-a]pyridin-2-yl)-1,4,6,7-tetrahydro-5H-imidazo[4,5-c]pyridin-5-yl)(5-(1-methyl-1H-pyrazol-3-yl)-1,3,4-thiadiazol-2-yl)methanone |

TABLE 1-continued

| Pyrazolo[1,5-a]pyridines | | |
|---|---|---|
| Ex. # | Structure | Name |
| 1996 | 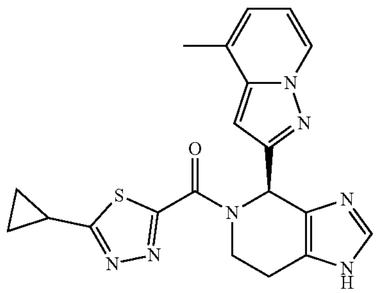 | (R)-(5-cyclopropyl-1,3,4-thiadiazol-2-yl)(4-(4-methylpyrazolo[1,5-a]pyridin-2-yl)-1,4,6,7-tetrahydro-5H-imidazo[4,5-c]pyridin-5-yl)methanone |
| 1997 | 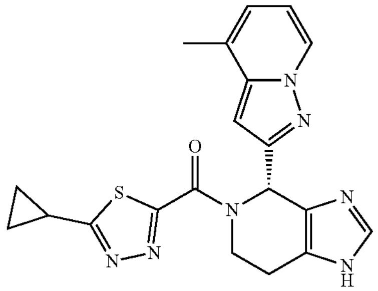 [SMILES: Cc1cccn2nc([C@@H]3c4nc[nH]c4CCN3C(=O)c3nnc(C4CC4)s3)cc12] | (S)-(5-cyclopropyl-1,3,4-thiadiazol-2-yl)(4-(4-methylpyrazolo[1,5-a]pyridin-2-yl)-1,4,6,7-tetrahydro-5H-imidazo[4,5-c]pyridin-5-yl)methanone |
| 1998 | 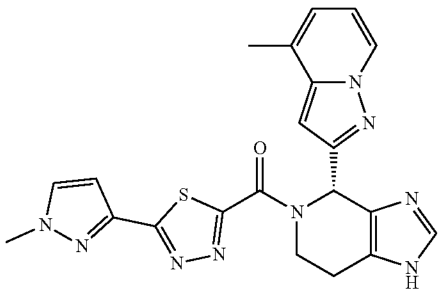 [SMILES: Cc1cccn2nc([C@@H]3c4nc[nH]c4CCN3C(=O)c3nnc(-c4ccn(C)n4)s3)cc12] | (S)-(5-(1-methyl-1H-pyrazol-3-yl)-1,3,4-thiadiazol-2-yl)(4-(4-methylpyrazolo[1,5-a]pyridin-2-yl)-1,4,6,7-tetrahydro-5H-imidazo[4,5-c]pyridin-5-yl)methanone |
| 1999 | 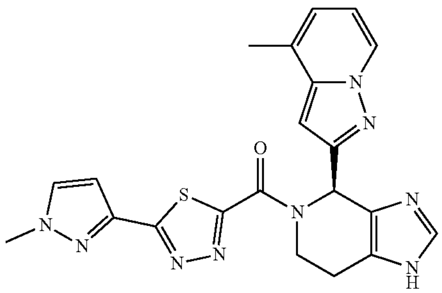 | (R)-(5-(1-methyl-1H-pyrazol-3-yl)-1,3,4-thiadiazol-2-yl)(4-(4-methylpyrazolo[1,5-a]pyridin-2-yl)-1,4,6,7-tetrahydro-5H-imidazo[4,5-c]pyridin-5-yl)methanone |
| 2000 | 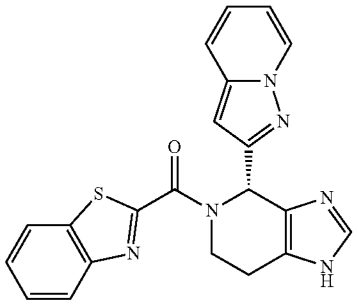 | (S)-benzo[d]thiazol-2-yl(4-(pyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
|---|---|---|
| | Pyrazolo[1,5-a]pyridines | |
| 2001 | 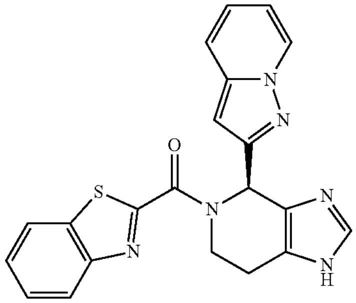 | (R)-benzo[d]thiazol-2-yl(4-(pyrazolo[1,5-a]pyridin-2-yl)-1,4,6,7-tetrahydro-5H-imidazo[4,5-c]pyridin-5-yl)methanone |
| 2002 | 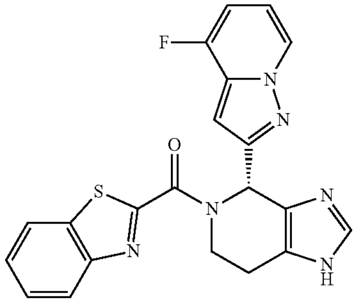 | (S)-benzo[d]thiazol-2-yl (4-(4-fluoropyrazolo[1,5-a]pyridin-2-yl)-1,4,6,7-tetrahydro-5H-imidazo[4,5-c]pyridin-5-yl)methanone |
| 2003 | 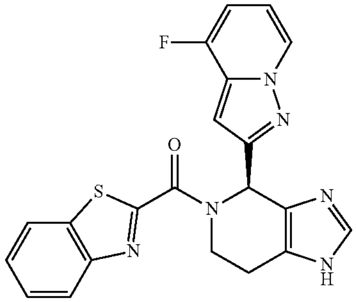 | (R)-benzo[d]thiazol-2-yl (4-(4-fluoropyrazolo[1,5-a]pyridin-2-yl)-1,4,6,7-tetrahydro-5H-imidazo[4,5-c]pyridin-5-yl)methanone |
| 2004 | 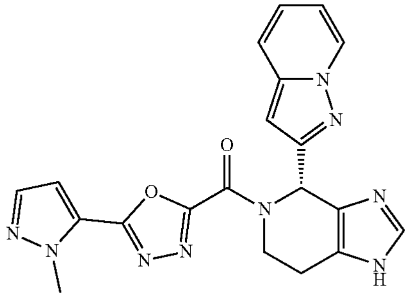 [SMILES: Cn1nccc1-c1nnc(C(=O)N2CCc3[nH]cnc3[C@H]2c2cc3ccccn3n2)o1] | (S)-(5-(1-methyl-1H-pyrazol-5-yl)-1,3,4-oxadiazol-2-yl)(4-(pyrazolo[1,5-a]pyridin-2-yl)-1,4,6,7-tetrahydro-5H-imidazo[4,5-c]pyridin-5-yl)methanone |
| 2005 | 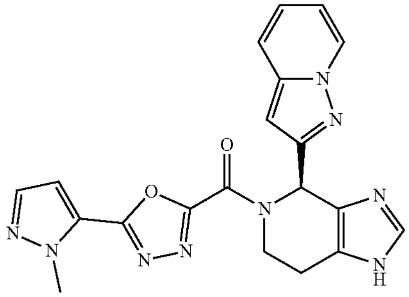 [SMILES: Cn1nccc1-c1nnc(C(=O)N2CCc3[nH]cnc3[C@@H]2c2cc3ccccn3n2)o1] | (R)-(5-(1-methyl-1H-pyrazol-5-yl)-1,3,4-oxadiazol-2-yl)(4-(pyrazolo[1,5-a]pyridin-2-yl)-1,4,6,7-tetrahydro-5H-imidazo[4,5-c]pyridin-5-yl)methanone |

TABLE 1-continued

Pyrazolo[1,5-a]pyridines

| Ex. # | Structure | Name |
|---|---|---|
| 2006 | 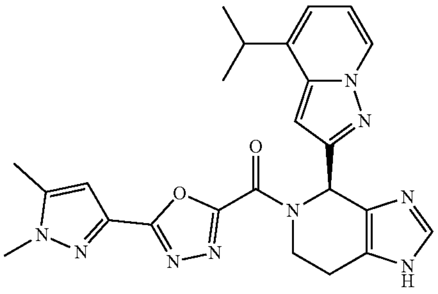 [SMILES: Cc1cc(-c2nnc(C(=O)N3CCc4[nH]cnc4[C@@H]3c3cc4c(C(C)C)cccn4n3)o2)nn1C] | (R)-(S-(1,5-dimethyl-1H-pyrazol-3-yl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 2007 | 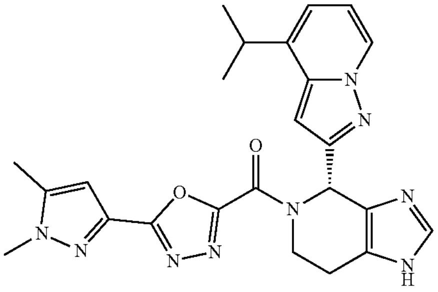 [SMILES: Cc1cc(-c2nnc(C(=O)N3CCc4[nH]cnc4[C@H]3c3cc4c(C(C)C)cccn4n3)o2)nn1C] | (S)-(5-(1,5-dimethyl-1H-pyrazol-3-yl)-1,3,4-oxadiazol-2-yl)(4-(4-isopropylpyrazolo[1,5-a]pyridin-2-yl)-1,4,6,7-tetrahydro-5H-imidazo[4,5-c]pyridin-5-yl)methanone |
| 2008 | 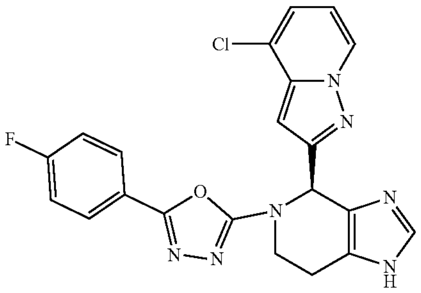 [SMILES: Fc1ccc(-c2nnc(N3CCc4[nH]cnc4[C@@H]3c3cc4c(Cl)cccn4n3)o2)cc1] | (R)-2-(4-(4-chloropyrazolo[1,5-a]pyridin-2-yl)-1,4,6,7-tetrahydro-5H-imidazo[4,5-c]pyridin-5-yl)-5-(4-fluorophenyl)-1,3,4-oxadiazole |
| 2009 | 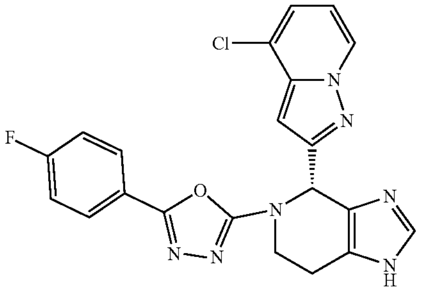 [SMILES: Fc1ccc(-c2nnc(N3CCc4[nH]cnc4[C@H]3c3cc4c(Cl)cccn4n3)o2)cc1] | (S)-2-(4-(4-chloropyrazolo[1,5-a]pyridin-2-yl)-1,4,6,7-tetrahydro-5H-imidazo[4,5-c]pyridin-5-yl)-5-(4-fluorophenyl)-1,3,4-oxadiazole |
| 2010 | 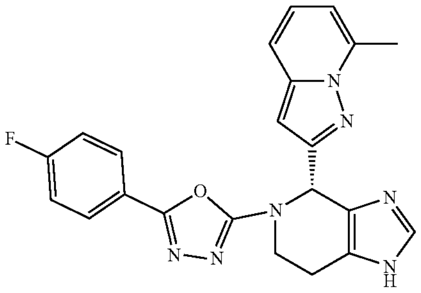 [SMILES: Cc1cccc2cc([C@@H]3c4nc[nH]c4CCN3c3nnc(-c4ccc(F)cc4)o3)nn12] | (S)-2-(4-fluorophenyl)-5-(4-(7-methylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
|---|---|---|
| | Pyrazolo[1,5-a]pyridines | |
| 2011 | 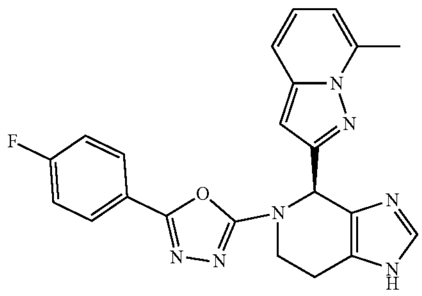 [SMILES: Cc1cccc2cc([C@H]3c4nc[nH]c4CCN3c3nnc(-c4ccc(F)cc4)o3)nn12] | (R)-2-(4-fluorophenyl)-5-(4-(7-methylpyrazolo[1,5-a]pyridin-2-yl)-1,4,6,7-tetrahydro-5H-imidazo[4,5-c]pyridin-5-yl)-1,3,4-oxadiazole |
| 2012 | 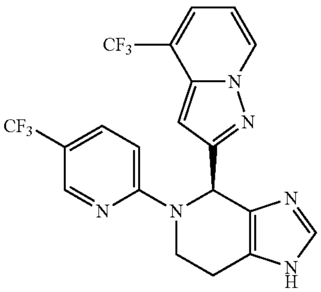 [SMILES: FC(F)(F)c1ccc(N2CCc3[nH]cnc3[C@@H]2c2cc3c(C(F)(F)F)cccn3n2)nc1] | (R)-4-(4-(trifluoromethyl) pyrazolo[1,5-a]pyridin-2-yl)-5-(5-(trifluoromethyl)pyridin-2-yl)-4,5,6,7-tetrahydro-1H-imidazo[4,5-c]pyridine |
| 2013 | 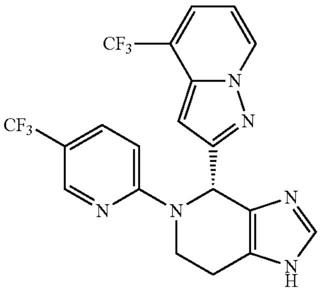 [SMILES: FC(F)(F)c1ccc(N2CCc3[nH]cnc3[C@H]2c2cc3c(C(F)(F)F)cccn3n2)nc1] | (S)-4-(4-(trifluoromethyl) pyrazolo[1,5-a]pyridin-2-yl)-5-(5-(trifluoromethyl)pyridin-2-yl)-4,5,6,7-tetrahydro-1H-imidazo[4,5-c]pyridine |
| 2014 | 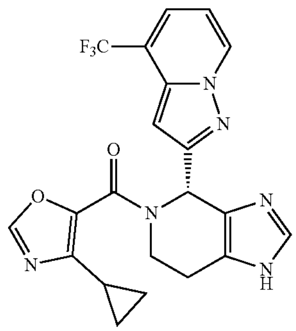 [SMILES: O=C(c1ocnc1C1CC1)N1CCc2[nH]cnc2[C@H]1c1cc2c(C(F)(F)F)cccn2n1] | (S)-(4-cyclopropyloxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2015 | 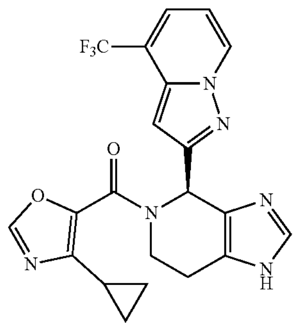 [SMILES: O=C(c1ocnc1C1CC1)N1CCc2[nH]cnc2[C@@H]1c1cc2c(C(F)(F)F)cccn2n1] | (R)-(4-cyclopropyloxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |

TABLE 1-continued

| Ex. # | Structure | Name |
|---|---|---|
| | Pyrazolo[1,5-a]pyridines | |
| 2016 | 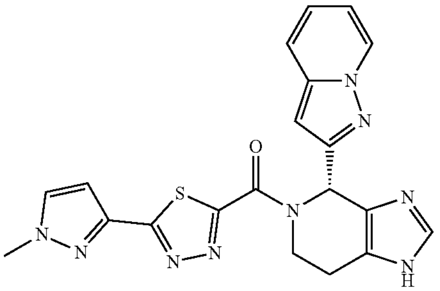 | (S)-(5-(1-methyl-1H-pyrazol-3-yl)-1,3,4-thiadiazol-2-yl)(4-(pyrazolo[1,5-a]pyridin-2-yl)-1,4,6,7-tetrahydro-5H-imidazo[4,5-c]pyridin-5-yl)methanone |
| 2017 | 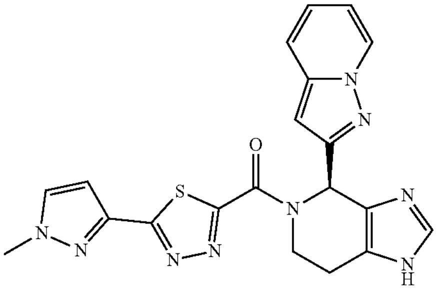 | (R)-(5-(1-methyl-1H-pyrazol-3-yl)-1,3,4-thiadiazol-2-yl)(4-(pyrazolo[1,5-a]pyridin-2-yl)-1,4,6,7-tetrahydro-5H-imidazo[4,5-c]pyridin-5-yl)methanone |
| 2018 | 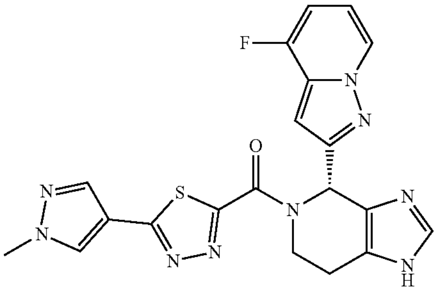 | (S)-(4-(4-fluoropyrazolo[1,5-a]pyridin-2-yl)-1,4,6,7-tetrahydro-5H-imidazo[4,5-c]pyridin-5-yl)(5-(1-methyl-1H-pyrazol-4-yl)-1,3,4-thiadiazol-2-yl)methanone |
| 2019 | 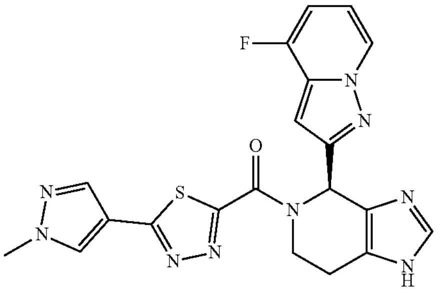 | (R)-(4-(4-fluoropyrazolo[1,5-a]pyridin-2-yl)-1,4,6,7-tetrahydro-5H-imidazo[4,5-c]pyridin-5-yl)(5-(1-methy]-1H-pyrazol-4-yl)-1,3,4-thiadiazol-2-yl)methanone |
| 2020 | 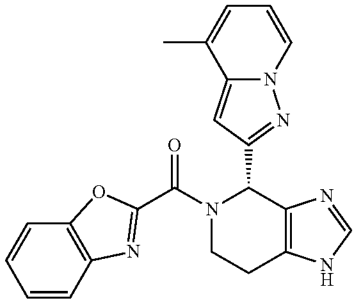 | (S)-benzo[d]oxazol-2-yl(4-(4-methylpyrazolo[1,5-a]pyridin-2-yl)-1,4,6,7-tetrahydro-5H-imidazo[4,5-c]pyridin-5-yl)methanone |

TABLE 1-continued

Pyrazolo[1,5-a]pyridines

| Ex. # | Structure | Name |
|---|---|---|
| 2021 | 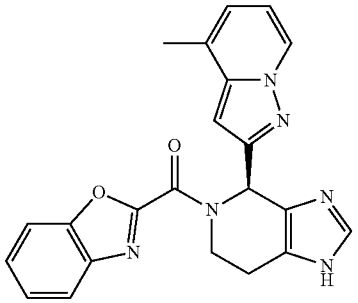 | (R)-benzo[d]oxazol-2-yl (4-(4-methylpyrazolo[1,5-a]pyridin-2-yl)-1,4,6,7-tetrahydro-5H-imidazo[4,5-c]pyridin-5-yl)methanone |
| 2022 | 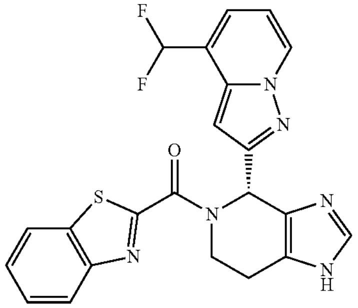 [SMILES: O=C(c1nc2ccccc2s1)N1CCc2[nH]cnc2[C@H]1c1cc2c(C(F)F)cccn2n1] | (S)-benzo[d]thiazol-2-yl(4-(4-(difluoromethyl)pyrazolo [1,5-a]pyridin-2-yl)-1,4,6,7-tetrahydro-5H-imidazo[4,5-c] pyridin-5-yl)methanone |
| 2023 | 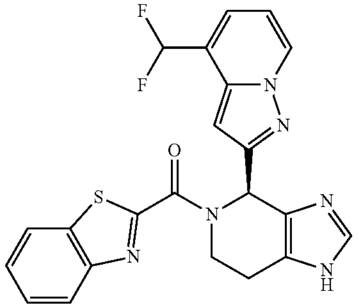 [SMILES: O=C(c1nc2ccccc2s1)N1CCc2[nH]cnc2[C@@H]1c1cc2c(C(F)F)cccn2n1] | (R)-benzo[d]thiazol-2-y]l(4-(4-(difluoromethyl)pyrazolo [1,5-a]pyridin-2-yl)-1,4,6,7-tetrahydro-5H-imidazo[4,5-c] pyridin-5-yl)methanone |
| 2024 | 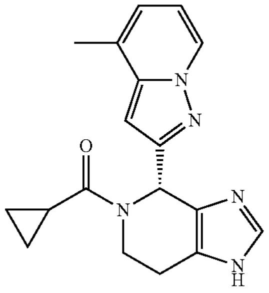 [SMILES: Cc1cccn2nc([C@@H]3c4nc[nH]c4CCN3C(=O)C3CC3)cc12] | (S)-cyclopropyl(4-(4-methylpyrazolo[1,5-a]pyridin-2-yl)-1,4,6,7-tetrahydro-5H-imidazo[4,5-c]pyridin-5-yl)methanone |
| 2025 | 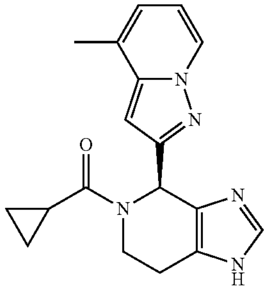 [SMILES: Cc1cccn2nc([C@H]3c4nc[nH]c4CCN3C(=O)C3CC3)cc12] | (R)-cyclopropyl(4-(4-methylpyrazolo[1,5-a]pyridin-2-yl)-1,4,6,7-tetrahydro-5H-imidazo[4,5-c]pyridin-5-yl)methanone |

TABLE 1-continued

| Pyrazolo[1,5-a]pyridines | | |
|---|---|---|
| Ex. # | Structure | Name |
| 2026 | 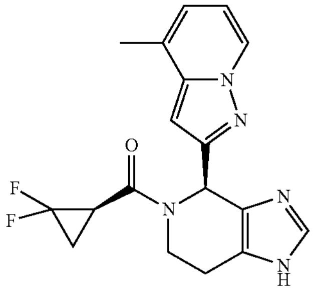 [SMILES: Cc1cccn2nc([C@H]3c4nc[nH]c4CCN3C(=O)[C@H]3CC3(F)F)cc12] | ((R)-2,2-difluorocyclopropyl) ((R)-4-(4-methylpyrazolo[1,5-a]pyridin-2-yl)-1,4,6,7-tetrahydro-5H-imidazo[4,5-c]pyridin-5-yl)methanone |
| 2027 | 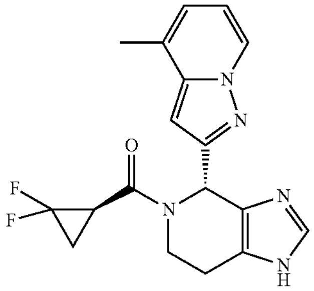 [SMILES: Cc1cccn2nc([C@@H]3c4nc[nH]c4CCN3C(=O)[C@H]3CC3(F)F)cc12] | ((R)-2,2-difluorocyclopropyl) ((S)-4-(4-methylpyrazolo[1,5-a]pyridin-2-yl)-1,4,6,7-tetrahydro-5H-imidazo[4,5-c]pyridin-5-yl)methanone |
| 2028 | 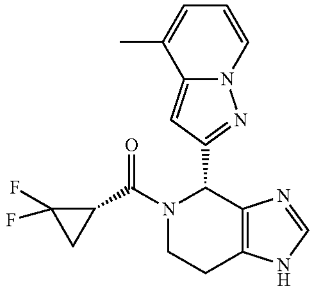 [SMILES: Cc1cccn2nc([C@@H]3c4nc[nH]c4CCN3C(=O)[C@@H]3CC3(F)F)cc12] | ((S)-2,2-difluorocyclopropyl) ((S)-4-(4-methylpyrazolo[1,5-a]pyridin-2-yl)-1,4,6,7-tetrahydro-5H-imidazo[4,5-c]pyridin-5-yl)methanone |
| 2029 | 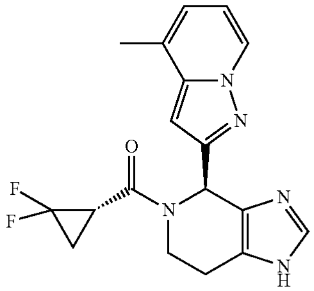 [SMILES: Cc1cccn2nc([C@H]3c4nc[nH]c4CCN3C(=O)[C@@H]3CC3(F)F)cc12] | ((S)-2,2-difluorocyclopropyl) ((R)-4-(4-methylpyrazolo[1,5-a]pyridin-2-yl)-1,4,6,7-tetrahydro-5H-imidazo[4,5-c]pyridin-5-yl)methanone |
| 2030 | 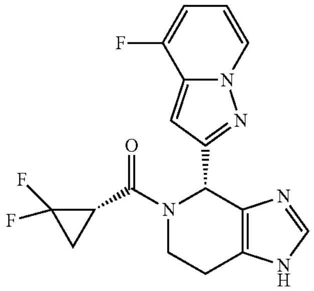 [SMILES: O=C([C@@H]1CC1(F)F)N1CCc2[nH]cnc2[C@H]1c1cc2c(F)cccn2n1] | ((S)-2,2-difluorocyclopropyl) ((S)-4-(4-fluoropyrazolo[1,5-a]pyridin-2-yl)-1,4,6,7-tetrahydro-5H-imidazo[4,5-c]pyridin-5-yl)methanone |

TABLE 1-continued

Pyrazolo[1,5-a]pyridines

| Ex. # | Structure | Name |
|---|---|---|
| 2031 | 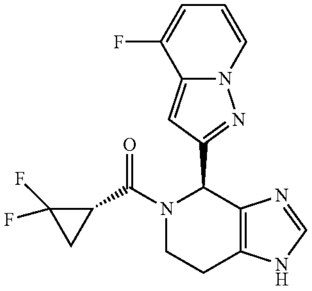 [SMILES: O=C([C@@H]1CC1(F)F)N1CCc2[nH]cnc2[C@@H]1c1cc2c(F)cccn2n1] | ((S)-2,2-difluorocyclopropyl)((R)-4-(4-fluoropyrazolo[1,5-a]pyridin-2-yl)-1,4,6,7-tetrahydro-5H-imidazo[4,5-c]pyridin-5-yl)methanone |
| 2032 | 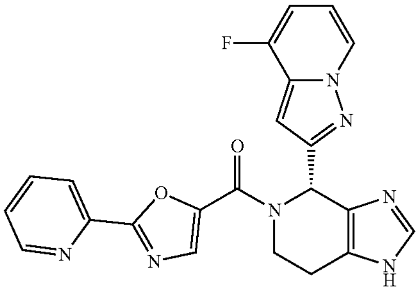 [SMILES: O=C(c1cnc(-c2ccccn2)o1)N1CCc2[nH]cnc2[C@H]1c1cc2c(F)cccn2n1] | (S)-(4-(4-fluoropyrazolo[1,5-a]pyridin-2-yl)-1,4,6,7-tetrahydro-5H-imidazo[4,5-c]pyridin-5-yl)(2-(pyridin-2-yl)oxazol-5-yl)methanone |
| 2033 | 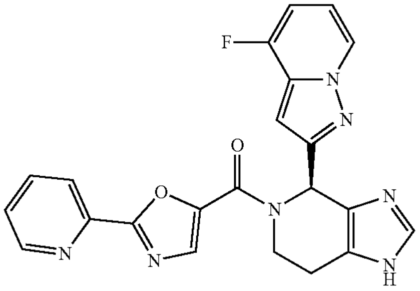 [SMILES: O=C(c1cnc(-c2ccccn2)o1)N1CCc2[nH]cnc2[C@@H]1c1cc2c(F)cccn2n1] | (R)-(4-(4-fluoropyrazolo[1,5-a]pyridin-2-yl)-1,4,6,7-tetrahydro-5H-imidazo[4,5-c]pyridin-5-yl)(2-(pyridin-2-yl)oxazol-5-yl)methanone |
| 2034 | 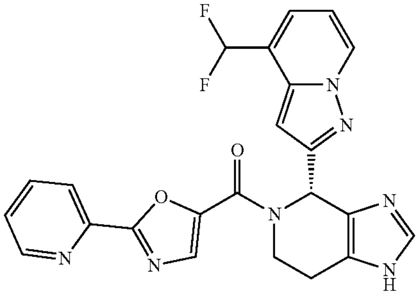 [SMILES: O=C(c1cnc(-c2ccccn2)o1)N1CCc2[nH]cnc2[C@H]1c1cc2c(C(F)F)cccn2n1] | (S)-(4-(4-(difluoromethyl)pyrazolo[1,5-a]pyridin-2-yl)-1,4,6,7-tetrahydro-5H-imidazo[4,5-c]pyridin-5-yl)(2-(pyridin-2-yl)oxazol-5-yl)methanone |
| 2035 | 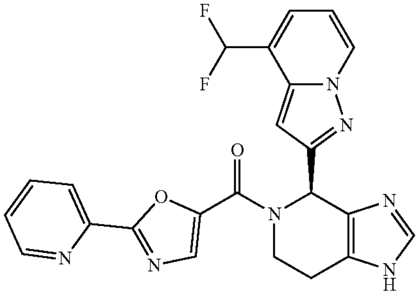 [SMILES: O=C(c1cnc(-c2ccccn2)o1)N1CCc2[nH]cnc2[C@@H]1c1cc2c(C(F)F)cccn2n1] | (R)-(4-(4-(difluoromethyl)pyrazolo[1,5-a]pyridin-2-yl)-1,4,6,7-tetrahydro-5H-imidazo[4,5-c]pyridin-5-yl)(2-(pyridin-2-yl)oxazol-5-yl)methanone |

TABLE 1-continued

| Ex. # | Structure | Name |
|---|---|---|
| | Pyrazolo[1,5-a]pyridines | |
| 2036 | 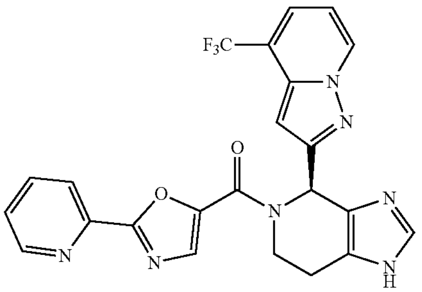 [SMILES: O=C(c1cnc(-c2ccccn2)o1)N1CCc2[nH]cnc2[C@@H]1c1cc2c(C(F)(F)F)cccn2n1] | (S)-(2-(pyridin-2-yl) oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2037 | 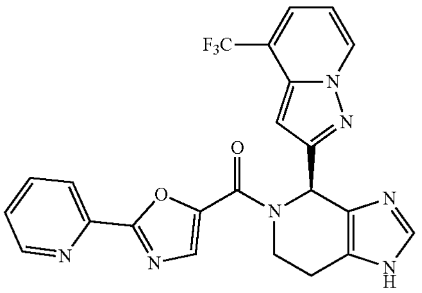 | (R)-(2-(pyridin-2-yl) oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2038 | 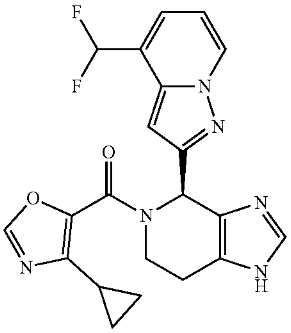 [SMILES: O=C(c1ocnc1C1CC1)N1CCc2[nH]cnc2[C@@H]1c1cc2c(C(F)F)cccn2n1] | (R)-(4-cyclopropyloxazol-5-yl)(4-(4-(difluoromethyl)pyrazolo [1,5-a]pyridin-2-yl)-1,4,6,7-tetrahydro-5H-imidazo[4,5-c] pyridin-5-yl)methanone |
| 2039 | 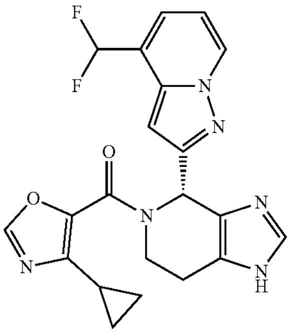 [SMILES: O=C(c1ocnc1C1CC1)N1CCc2[nH]cnc2[C@H]1c1cc2c(C(F)F)cccn2n1] | (S)-(4-cyclopropyloxazol-5-yl)(4-(4-(difluoromethyl)pyrazolo [1,5-a]pyridin-2-yl)-1,4,6,7-tetrahydro-5H-imidazo[4,5-c] pyridin-5-yl)methanone |

TABLE 1-continued

| Pyrazolo[1,5-a]pyridines | | |
|---|---|---|
| Ex. # | Structure | Name |
| 2040 | 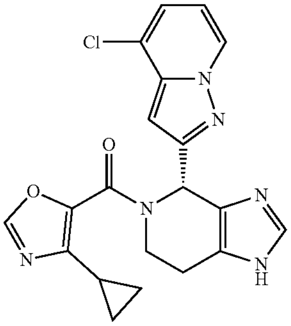 [SMILES: O=C(c1ocnc1C1CC1)N1CCc2[nH]cnc2[C@H]1c1cc2c(Cl)cccn2n1] | (S)-(4-(4-chloropyrazolo [1,5-a]pyridin-2-yl)-1,4,6,7-tetrahydro-5H-imidazo [4,5-c]pyridin-5-yl)(4-cyclopropyloxazol-5-yl) methanone |
| 2041 | 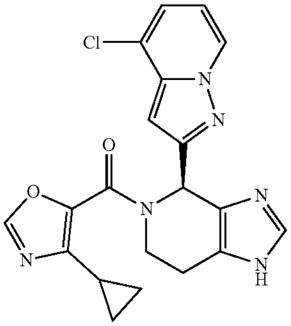 | (R)-(4-(4-chloropyrazolo [1,5-a]pyridin-2-yl)-1,4,6,7-tetrahydro-5H-imidazo [4,5-c]pyridin-5-yl)(4-cyclopropyloxazol-5-yl) methanone |
| 2042 | 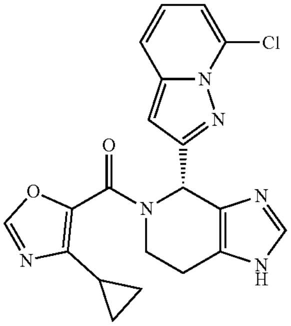 [SMILES: O=C(c1ocnc1C1CC1)N1CCc2[nH]cnc2[C@H]1c1cc2cccc(Cl)n2n1] | (S)-(4-(7-chloropyrazolo [1,5-a]pyridin-2-yl)-1,4,6,7-tetrahydro-5H-imidazo [4,5-c]pyridin-5-yl)(4-cyclopropyloxazol-5-yl) methanone |
| 2043 | 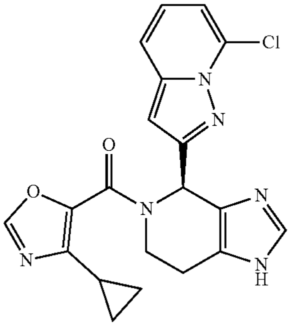 | (R)-(4-(7-chloropyrazolo [1,5-a]pyridin-2-yl)-1,4,6,7-tetrahydro-5H-imidazo [4,5-c]pyridin-5-yl)(4-cyclopropyloxazol-5-yl) methanone |

TABLE 1-continued

| Ex. # | Structure | Name |
|---|---|---|
| | Pyrazolo[1,5-a]pyridines | |
| 2044 | 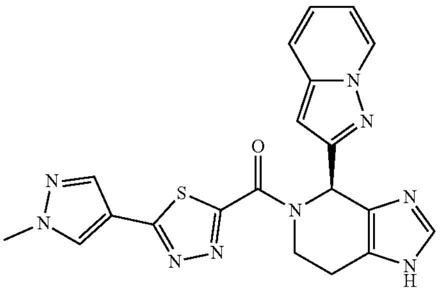 [SMILES: Cn1cc(-c2nnc(C(=O)N3CCc4[nH]cnc4[C@@H]3c3cc4ccccn4n3)s2)cn1] | (R)-(5-(1-methyl-1H-pyrazol-4-yl)-1,3,4-thiadiazol-2-yl)(4-(pyrazolo[1,5-a]pyridin-2-yl)-1,4,6,7-tetrahydro-5H-imidazo[4,5-c]pyridin-5-yl)methanone |
| 2045 | 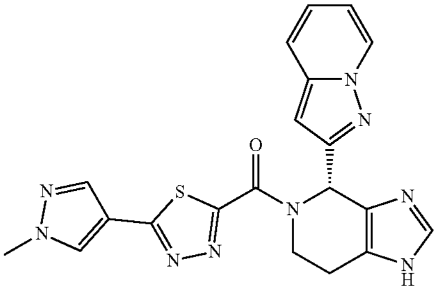 | (S)-(5-(1-methyl-1H-pyrazol-4-yl)-1,3,4-thiadiazol-2-yl)(4-(pyrazolo[1,5-a]pyridin-2-yl)-1,4,6,7-tetrahydro-5H-imidazo[4,5-c]pyridin-5-yl)methanone |
| 2046 | 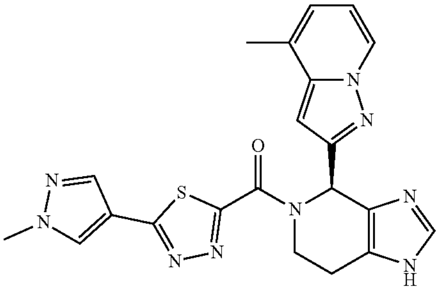 [SMILES: Cc1cccn2nc([C@H]3c4nc[nH]c4CCN3C(=O)c3nnc(-c4cnn(C)c4)s3)cc12] | (R)-(5-(1-methyl-1H-pyrazol-4-yl)-1,3,4-thiadiazol-2-yl)(4-(4-methylpyrazolo[1,5-a]pyridin-2-yl)-1,4,6,7-tetrahydro-5H-imidazo[4,5-c]pyridin-5-yl)methanone |
| 2047 | 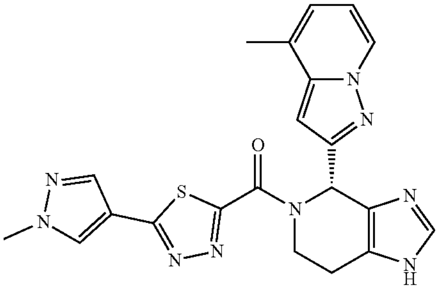 [SMILES: Cc1cccn2nc([C@@H]3c4nc[nH]c4CCN3C(=O)c3nnc(-c4cnn(C)c4)s3)cc12] | (S)-(5-(1-methyl-1H-pyrazol-4-yl)-1,3,4-thiadiazol-2-yl)(4-(4-methylpyrazolo[1,5-a]pyridin-2-yl)-1,4,6,7-tetrahydro-5H-imidazo[4,5-c]pyridin-5-yl)methanone |
| 2048 | 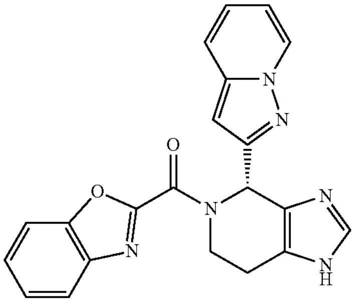 [SMILES: O=C(c1nc2ccccc2o1)N1CCc2[nH]cnc2[C@H]1c1cc2ccccn2n1] | (S)-benzo[d]oxazol-2-yl(4-(pyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
|---|---|---|
| | Pyrazolo[1,5-a]pyridines | |
| 2049 | 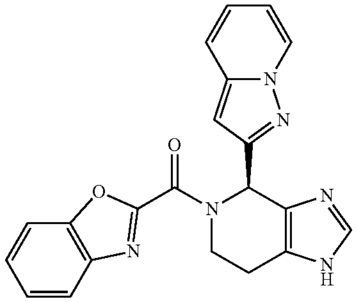 [SMILES: O=C(c1nc2ccccc2o1)N1CCc2[nH]cnc2[C@@H]1c1cc2ccccn2n1] | (R)-benzo[d]oxazol-2-yl(4-(pyrazolo[1,5-a]pyridin-2-yl)-1,4,6,7-tetrahydro-5H-imidazo[4,5-c]pyridin-5-yl)methanone |
| 2050 | 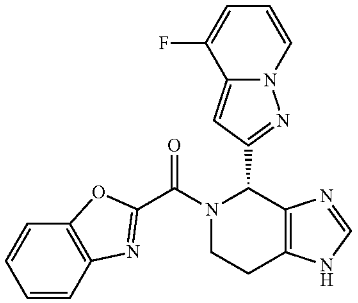 | (S)-benzo[d]oxazol-2-yl (4-(4-fluoropyrazolo[1,5-a]pyridin-2-yl)-1,4,6,7-tetrahydro-5H-imidazo[4,5-c]pyridin-5-yl)methanone |
| 2051 | 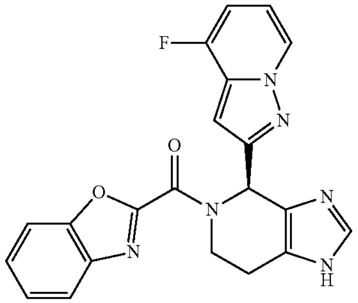 | (R)-benzo[d]oxazol-2-yl (4-(4-fluoropyrazolo[1,5-a]pyridin-2-yl)-1,4,6,7-tetrahydro-5H-imidazo[4,5-c]pyridin-5-yl)methanone |
| 2052 | 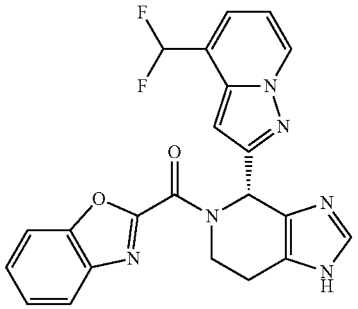 [SMILES: O=C(c1nc2ccccc2o1)N1CCc2[nH]cnc2[C@H]1c1cc2c(C(F)F)cccn2n1] | (S)-benzo[d]oxazol-2-yl(4-(4-(difluoromethyl)pyrazolo[1,5-a]pyridin-2-yl)-1,4,6,7-tetrahydro-5H-imidazo[4,5-c]pyridin-5-yl)methanone |
| 2053 | 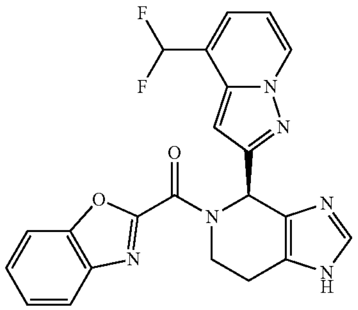 [SMILES: O=C(c1nc2ccccc2o1)N1CCc2[nH]cnc2[C@@H]1c1cc2c(C(F)F)cccn2n1] | (R)-benzo[d]oxazol-2-yl(4-(4-(difluoromethyl)pyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
| --- | --- | --- |
| Pyrazolo[1,5-a]pyridines | | |
| 2054 | 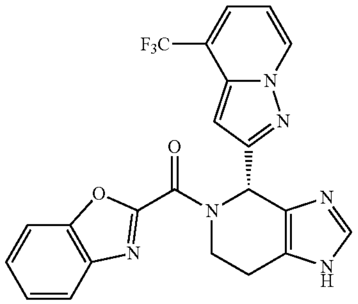 [SMILES: O=C(c1nc2ccccc2o1)N1CCc2[nH]cnc2[C@H]1c1cc2c(C(F)(F)F)cccn2n1] | (S)-benzo[d]oxazol-2-yl(4-(4-(trifluoromethyl)pyrazolo[1,5-a]pyridin-2-yl)-1,4,6,7-tetrahydro-5H-imidazo[4,5-c]pyridin-5-yl)methanone |
| 2055 | 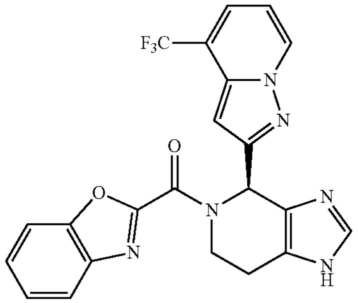 [SMILES: O=C(c1nc2ccccc2o1)N1CCc2[nH]cnc2[C@@H]1c1cc2c(C(F)(F)F)cccn2n1] | (R)-benzo[d]oxazol-2-yl(4-(4-(trifluoromethyl)pyrazolo[1,5-a]pyridin-2-yl)-1,4,6,7-tetrahydro-5H-imidazo[4,5-c]pyridin-5-yl)methanone |
| 2056 | 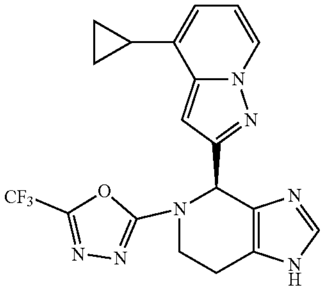 [SMILES: FC(F)(F)c1nnc(N2CCc3[nH]cnc3[C@@H]2c2cc3c(C4CC4)cccn3n2)o1] | (R)-2-(4-(4-cyclopropylpyrazolo[1,5-a]pyridin-2-yl)-1,4,6,7-tetrahydro-5H-imidazo[4,5-c]pyridin-5-yl)-5-(trifluoromethyl)-1,3,4-oxadiazole |
| 2057 | 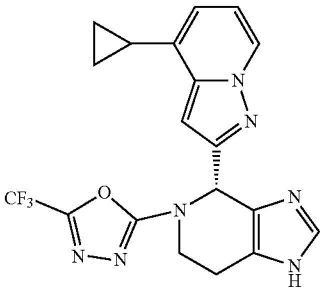 [SMILES: FC(F)(F)c1nnc(N2CCc3[nH]cnc3[C@H]2c2cc3c(C4CC4)cccn3n2)o1] | (S)-2-(4-(4-cyclopropylpyrazolo[1,5-a]pyridin-2-yl)-1,4,6,7-tetrahydro-5H-imidazo[4,5-c]pyridin-5-yl)-5-(trifluoromethyl)-1,3,4-oxadiazole |
| 2058 | 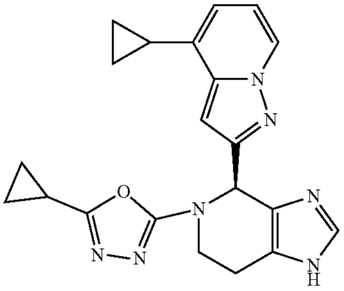 [SMILES: c1cc(C2CC2)c2cc([C@H]3c4nc[nH]c4CCN3c3nnc(C4CC4)o3)nn2c1] | (R)-2-cyclopropyl-5-(4-(4-cyclopropylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
|---|---|---|
| | Pyrazolo[1,5-a]pyridines | |
| 2059 | 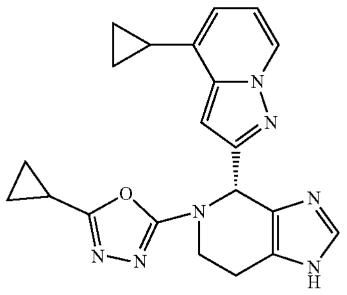 [SMILES: c1cc(C2CC2)c2cc([C@@H]3c4nc[nH]c4CCN3c3nnc(C4CC4)o3)nn2c1] | (S)-2-cyclopropyl-5-(4-(4-cyclopropylpyrazolo[1,5-a]pyridin-2-yl)-1,4,6,7-tetrahydro-5H-imidazo[4,5-c]pyridin-5-yl)-1,3,4-oxadiazole |
| 2060 | 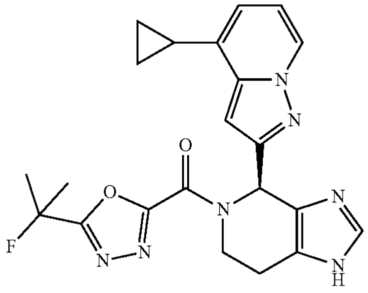 [SMILES: CC(C)(F)c1nnc(C(=O)N2CCc3[nH]cnc3[C@@H]2c2cc3c(C4CC4)cccn3n2)o1] | (R)-(4-(4-cyclopropylpyrazolo[1,5-a]pyridin-2-y]l)-1,4,6,7-tetrahydro-5H-imidazo[4,5-c]pyridin-5-yl)(5-(2-fluoropropan-2-yl)-1,3,4-oxadiazol-2-yl)methanone |
| 2061 | 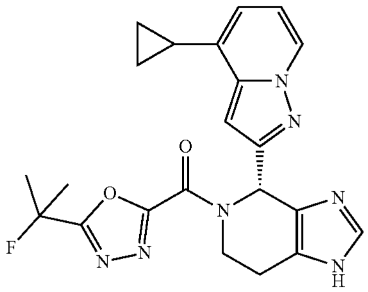 [SMILES: CC(C)(F)c1nnc(C(=O)N2CCc3[nH]cnc3[C@H]2c2cc3c(C4CC4)cccn3n2)o1] | (S)-(4-(4-cyclopropylpyrazolo[1,5-a]pyridin-2-yl)-1,4,6,7-tetrahydro-5H-imidazo[4,5-c]pyridin-5-yl)(5-(2-fluoropropan-2-yl)-1,3,4-oxadiazol-2-yl)methanone |
| 2062 | 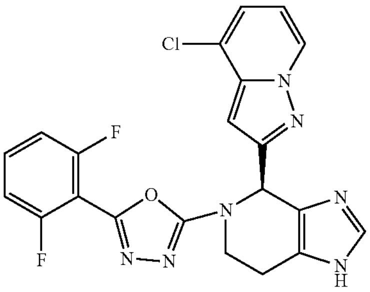 [SMILES: Fc1cccc(F)c1-c1nnc(N2CCc3[nH]cnc3[C@@H]2c2cc3c(Cl)cccn3n2)o1] | (R)-2-(4-(4-chloropyrazolo[1,5-a]pyridin-2-yl)-1,4,6,7-tetrahydro-5H-imidazo[4,5-c]pyridin-5-yl)-5-(2,6-difluorophenyl)-1,3,4-oxadiazole |
| 2063 | 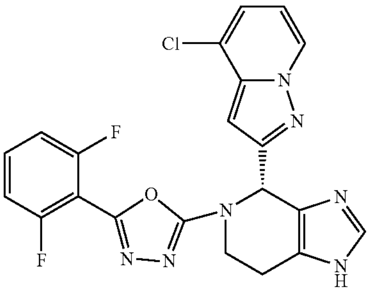 [SMILES: Fc1cccc(F)c1-c1nnc(N2CCc3[nH]cnc3[C@H]2c2cc3c(Cl)cccn3n2)o1] | (S)-2-(4-(4-chloropyrazolo[1,5-a]pyridin-2-yl)-1,4,6,7-tetrahydro-5H-imidazo[4,5-c]pyridin-5-yl)-5-(2,6-difluorophenyl)-1,3,4-oxadiazole |

TABLE 1-continued

| Ex. # | Structure | Name |
|---|---|---|
| | Pyrazolo[1,5-a]pyridines | |
| 2064 | 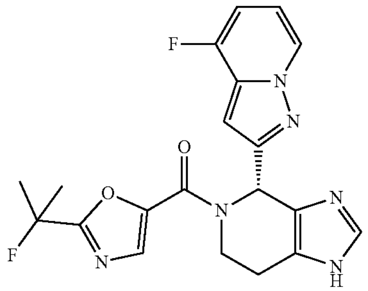 [SMILES: CC(C)(F)c1ncc(C(=O)N2CCc3[nH]cnc3[C@H]2c2cc3c(F)cccn3n2)o1] | (S)-(2-(2-fluoropropan-2-yl)oxazol-5-yl)(4-(4-fluoropyrazolo[1,5-a]pyridin-2-yl)-1,4,6,7-tetrahydro-5H-imidazo[4,5-c]pyridin-5-yl)methanone |
| 2065 | 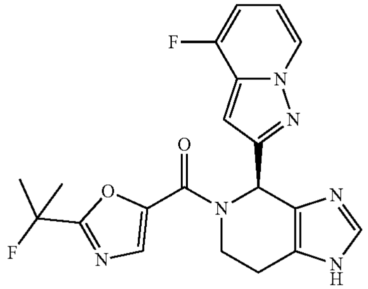 [SMILES: CC(C)(F)c1ncc(C(=O)N2CCc3[nH]cnc3[C@@H]2c2cc3c(F)cccn3n2)o1] | (R)-(2-(2-fluoropropan-2-yl)oxazol-5-yl)(4-(4-fluoropyrazolo[1,5-a]pyridin-2-yl)-1,4,6,7-tetrahydro-5H-imidazo[4,5-c]pyridin-5-yl)methanone |
| 2066 | 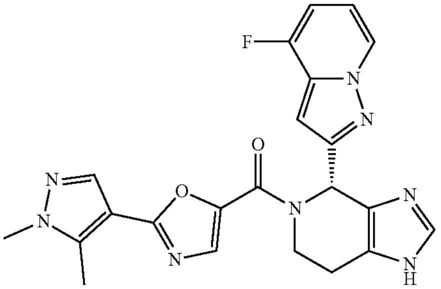 [SMILES: Cc1c(-c2ncc(C(=O)N3CCc4[nH]cnc4[C@H]3c3cc4c(F)cccn4n3)o2)cnn1C] | (S)-(2-(1,5-dimethyl-1H-pyrazol-4-yl)oxazol-5-yl)(4-(4-fluoropyrazolo[1,5-a]pyridin-2-yl)-1,4,6,7-tetrahydro-5H-imidazo[4,5-c]pyridin-5-yl)methanone |
| 2067 | 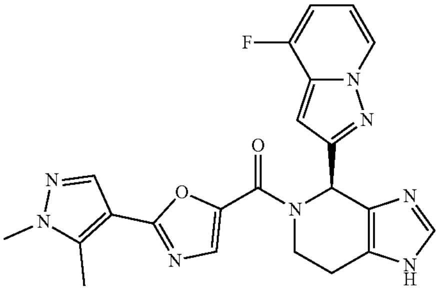 [SMILES: Cc1c(-c2ncc(C(=O)N3CCc4[nH]cnc4[C@@H]3c3cc4c(F)cccn4n3)o2)cnn1C] | (R)-(2-(1,5-dimethyl-1H-pyrazol-4-yl)oxazol-5-yl)(4-(4-fluoropyrazolo[1,5-a]pyridin-2-yl)-1,4,6,7-tetrahydro-5H-imidazo[4,5-c]pyridin-5-yl)methanone |
| 2068 | 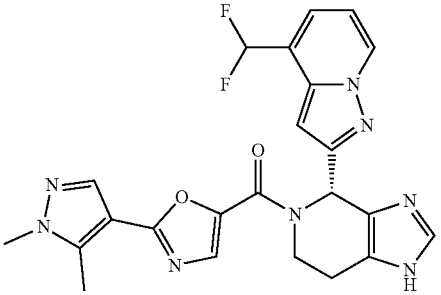 [SMILES: Cc1c(-c2ncc(C(=O)N3CCc4[nH]cnc4[C@H]3c3cc4c(C(F)F)cccn4n3)o2)cnn1C] | (S)-(4-(4-(difluoromethyl)pyrazolo[1,5-a]pyridin-2-yl)-1,4,6,7-tetrahydro-5H-imidazo[4,5-c]pyridin-5-yl)(2-(1,5-dimethyl-1H-pyrazol-4-yl)oxazol-5-yl)methanone |

TABLE 1-continued

Pyrazolo[1,5-a]pyridines

| Ex. # | Structure | Name |
|---|---|---|
| 2069 | 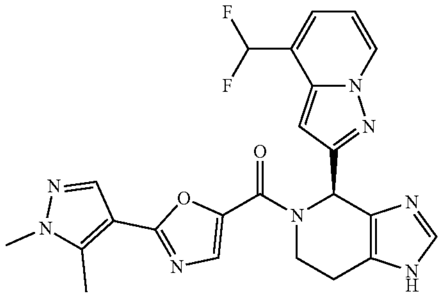 [SMILES: Cc1c(-c2ncc(C(=O)N3CCc4[nH]cnc4[C@@H]3c3cc4c(C(F)F)cccn4n3)o2)cnn1C] | (R)-(4-(4-(difluoromethyl) pyrazolo[1,5-a]pyridin-2-yl)-1,4,6,7-tetrahydro-5H-imidazo [4,5-c]pyridin-5-yl)(2-(1,5-dimethyl-1H-pyrazol-4-yl)oxazol-5-yl)methanone |
| 2070 | 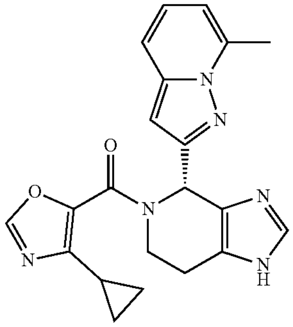 [SMILES: Cc1cccc2cc([C@@H]3c4nc[nH]c4CCN3C(=O)c3ocnc3C3CC3)nn12] | (S)-(4-cyclopropyloxazol-5-yl)(4-(7-methylpyrazolo[1,5-a]pyridin-2-yl)-1,4,6,7-tetrahydro-5H-imidazo[4,5-c]pyridin-5-yl)methanone |
| 2071 | 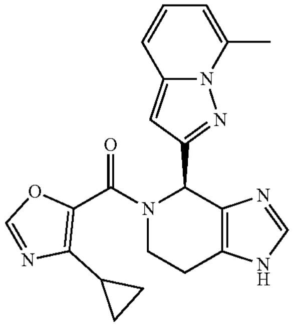 [SMILES: Cc1cccc2cc([C@H]3c4nc[nH]c4CCN3C(=O)c3ocnc3C3CC3)nn12] | (R)-(4-cyclopropyloxazol-5-yl)(4-(7-methylpyrazolo[1,5-a]pyridin-2-yl)-1,4,6,7-tetrahydro-5H-imidazo[4,5-c]pyridin-5-yl)methanone |
| 2072 | 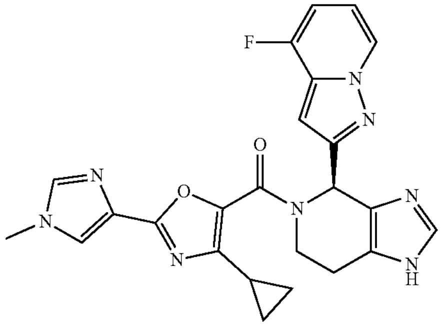 [SMILES: Cn1cnc(-c2nc(C3CC3)c(C(=O)N3CCc4[nH]cnc4[C@@H]3c3cc4c(F)cccn4n3)o2)c1] | (R)-(4-cyclopropyl-2-(1-methyl-1H-pyrazol-4-yl)oxazol-5-yl)(4-(4-fluoropyrazolo [1,5-a]pyridin-2-yl)-1,4,6,7-tetrahydro-5H-imidazo [4,5-c]pyridin-5-yl)methanone |

TABLE 1-continued

| Ex. # | Structure | Name |
|---|---|---|
| | Pyrazolo[1,5-a]pyridines | |
| 2073 | 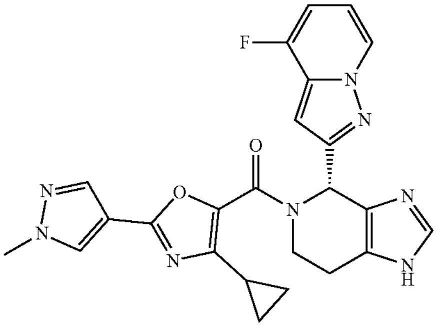 [SMILES: Cn1cc(-c2nc(C3CC3)c(C(=O)N3CCc4[nH]cnc4[C@H]3c3cc4c(F)cccn4n3)o2)cn1] | (S)-(4-cyclopropyl-2-(1-methyl-1H-pyrazol-4-yl)oxazol-5-yl)(4-(4-fluoropyrazolo[1,5-a]pyridin-2-yl)-1,4,6,7-tetrahydro-5H-imidazo[4,5-c]pyridin-5-yl)methanone |
| 2074 | 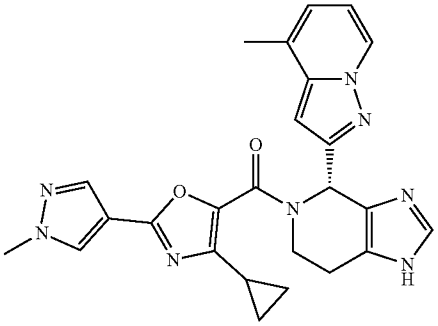 [SMILES: Cc1cccn2nc([C@@H]3c4nc[nH]c4CCN3C(=O)c3oc(-c4cnn(C)c4)nc3C3CC3)cc12] | (S)-(4-cyclopropyl-2-(1-methyl-1H-pyrazol-4-yl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 2075 | 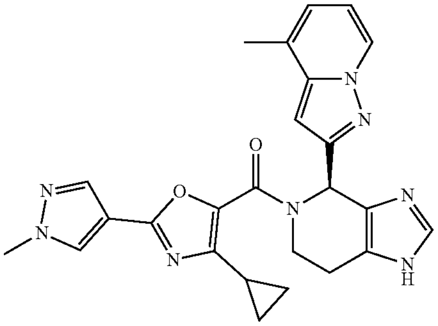 [SMILES: Cc1cccn2nc([C@H]3c4nc[nH]c4CCN3C(=O)c3oc(-c4cnn(C)c4)nc3C3CC3)cc12] | (R)-(4-cyclopropyl-2-(1-methyl-1H-pyrazol-4-yl)oxazol-5-yl)(4-(4-fluoropyrazolo[1,5-a]pyridin-2-yl)-1,4,6,7-tetrahydro-5H-imidazo[4,5-c]pyridin-5-yl)methanone |
| 2076 | 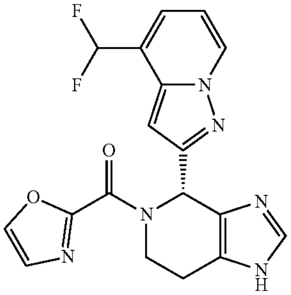 [SMILES: O=C(c1ncco1)N1CCc2[nH]cnc2[C@H]1c1cc2c(C(F)F)cccn2n1] | (S)-(4-(4-(difluoromethyl)pyrazolo[1,5-a]pyridin-2-yl)-1,4,6,7-tetrahydro-5H-imidazo[4,5-c]pyridin-5-yl)(oxazol-2-yl)methanone |

TABLE 1-continued

| Pyrazolo[1,5-a]pyridines | | |
|---|---|---|
| Ex. # | Structure | Name |
| 2077 | 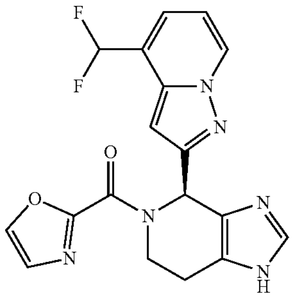 [SMILES: O=C(c1ncco1)N1CCc2[nH]cnc2[C@@H]1c1cc2c(C(F)F)cccn2n1] | (R)-(4-(4-(difluoromethyl) pyrazolo[1,5-a]pyridin-2-yl)-1,4,6,7-tetrahydro-5H-imidazo[4,5-c]pyridin-5-yl)(oxazol-2-yl)methanone |
| 2078 | 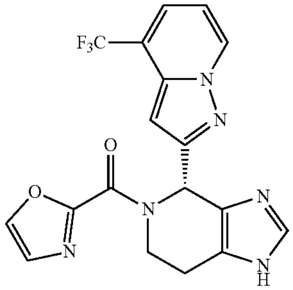 [SMILES: O=C(c1ncco1)N1CCc2[nH]cnc2[C@H]1c1cc2c(C(F)(F)F)cccn2n1] | (S)-oxazol-2-yl(4-(4-(trifluoromethyl)pyrazolo[1,5-a]pyridin-2-yl)-1,4,6,7-tetrahydro-5H-imidazo[4,5-c]pyridin-5-yl)methanone |
| 2079 | 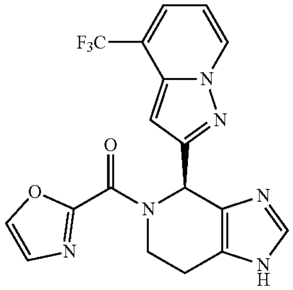 | (R)-oxazol-2-yl(4-(4-(trifluoromethyl)pyrazolo[1,5-a]pyridin-2-yl)-1,4,6,7-tetrahydro-5H-imidazo[4,5-c]pyridin-5-yl)methanone |
| 2080 | 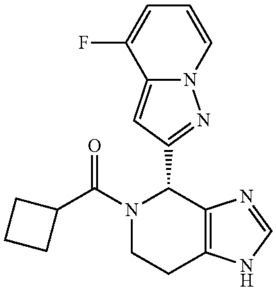 [SMILES: O=C(C1CCC1)N1CCc2[nH]cnc2[C@H]1c1cc2c(F)cccn2n1] | (S)-cyclobutyl(4-(4-fluoropyrazolo[1,5-a]pyridin-2-yl)-1,4,6,7-tetrahydro-5H-imidazo[4,5-c]pyridin-5-yl)methanone |
| 2081 | 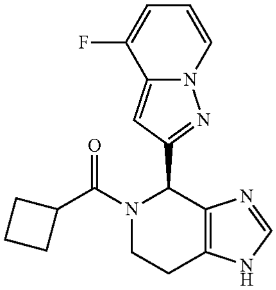 [SMILES: O=C(C1CCC1)N1CCc2[nH]cnc2[C@@H]1c1cc2c(F)cccn2n1] | (R)-cyclobutyl(4-(4-fluoropyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
|---|---|---|
| | Pyrazolo[1,5-a]pyridines | |
| 2082 | 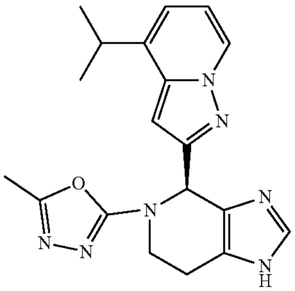 [SMILES: Cc1nnc(N2CCc3[nH]cnc3[C@@H]2c2cc3c(C(C)C)cccn3n2)o1] | (R)-2-(4-(4-isopropylpyrazolo[1,5-a]pyridin-2-yl)-1,4,6,7-tetrahydro-5H-imidazo[4,5-c]pyridin-5-yl)-5-methyl-1,3,4-oxadiazole |
| 2083 | 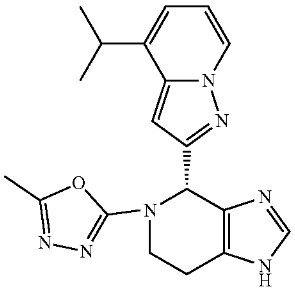 [SMILES: Cc1nnc(N2CCc3[nH]cnc3[C@H]2c2cc3c(C(C)C)cccn3n2)o1] | (S)-2-(4-(4-isopropylpyrazolo[1,5-a]pyridin-2-yl)-1,4,6,7-tetrahydro-5H-imidazo[4,5-c]pyridin-5-yl)-5-methyl-1,3,4-oxadiazole |
| 2084 | 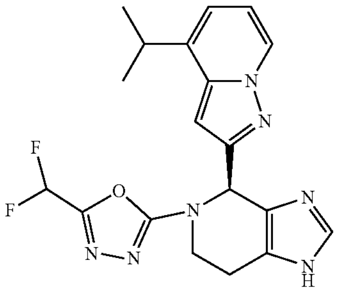 [SMILES: CC(C)c1cccn2nc([C@H]3c4nc[nH]c4CCN3c3nnc(C(F)F)o3)cc12] | (R)-2-(difluoromethyl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |
| 2085 | 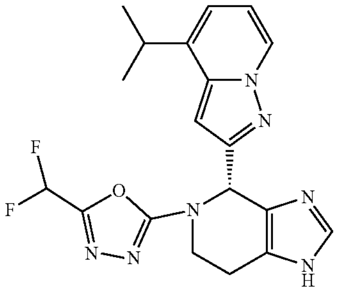 [SMILES: CC(C)c1cccn2nc([C@@H]3c4nc[nH]c4CCN3c3nnc(C(F)F)o3)cc12] | (S)-2-(difluoromethyl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |
| 2086 | 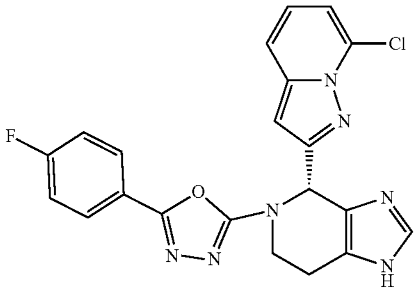 [SMILES: Fc1ccc(-c2nnc(N3CCc4[nH]cnc4[C@H]3c3cc4cccc(Cl)n4n3)o2)cc1] | (S)-2-(4-(7-chloropyrazolo[1,5-a]pyridin-2-yl)-1,4,6,7-tetrahydro-5H-imidazo[4,5-c]pyridin-5-yl)-5-(4-fluorophenyl)-1,3,4-oxadiazole |

TABLE 1-continued

| Pyrazolo[1,5-a]pyridines | | |
|---|---|---|
| Ex. # | Structure | Name |
| 2087 | 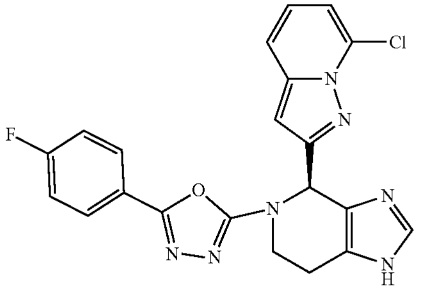 [SMILES: Fc1ccc(-c2nnc(N3CCc4[nH]cnc4[C@@H]3c3cc4cccc(Cl)n4n3)o2)cc1] | (R)-2-(4-(7-chloropyrazolo[1,5-a]pyridin-2-yl)-1,4,6,7-tetrahydro-5H-imidazo[4,5-c]pyridin-5-yl)-5-(4-fluorophenyl)-1,3,4-oxadiazole |
| 2088 | 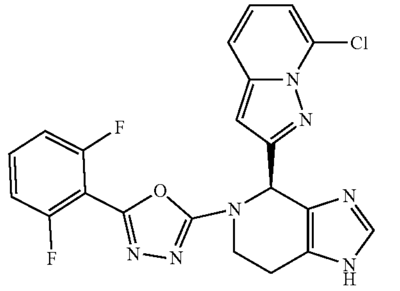 [SMILES: Fc1cccc(F)c1-c1nnc(N2CCc3[nH]cnc3[C@@H]2c2cc3cccc(Cl)n3n2)o1] | (R)-2-(4-(7-chloropyrazolo[1,5-a]pyridin-2-yl)-1,4,6,7-tetrahydro-5H-imidazo[4,5-c]pyridin-5-yl)-5-(2,6-difluorophenyl)-1,3,4-oxadiazole |
| 2089 | 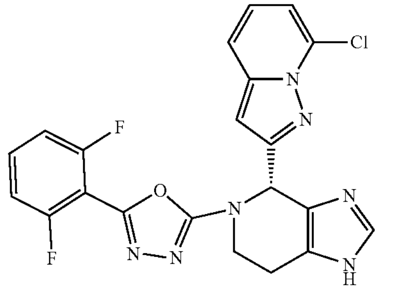 [SMILES: Fc1cccc(F)c1-c1nnc(N2CCc3[nH]cnc3[C@H]2c2cc3cccc(Cl)n3n2)o1] | (S)-2-(4-(7-chloropyrazolo[1,5-a]pyridin-2-yl)-1,4,6,7-tetrahydro-5H-imidazo[4,5-c]pyridin-5-yl)-5-(2,6-difluorophenyl)-1,3,4-oxadiazole |
| 2090 | 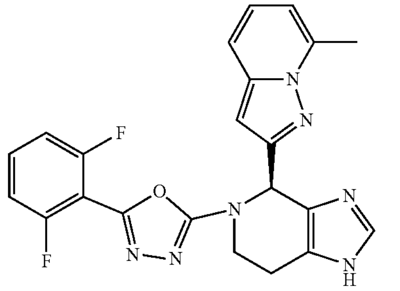 [SMILES: Cc1cccc2cc([C@H]3c4nc[nH]c4CCN3c3nnc(-c4c(F)cccc4F)o3)nn12] | (R)-2-(2,6-difluorophenyl)-5-(4-(7-methylpyrazolo[1,5-a]pyridin-2-yl)-1,4,6,7-tetrahydro-5H-imidazo[4,5-c]pyridin-5-yl)-1,3,4-oxadiazole |
| 2091 | 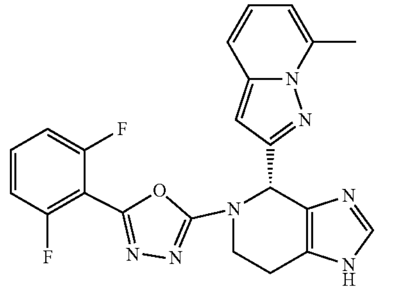 [SMILES: Cc1cccc2cc([C@@H]3c4nc[nH]c4CCN3c3nnc(-c4c(F)cccc4F)o3)nn12] | (S)-2-(2,6-difluorophenyl)-5-(4-(7-methylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2092 | 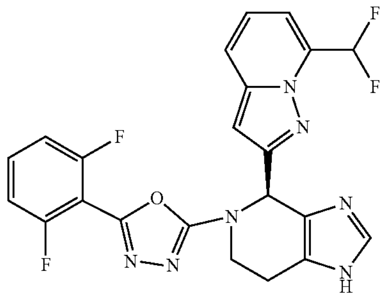 [SMILES: Fc1cccc(F)c1-c1nnc(N2CCc3[nH]cnc3[C@@H]2c2cc3cccc(C(F)F)n3n2)o1] | (R)-2-(4-(7-(difluoromethyl) pyrazolo[1,5-a]pyridin-2-yl)-1,4,6,7-tetrahydro-5H-imidazo[4,5-c]pyridin-5-yl)-5-(2,6-difluorophenyl)-1,3,4-oxadiazole |
| 2093 | 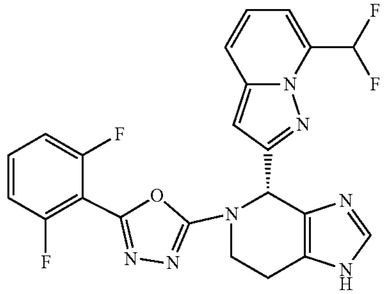 [SMILES: Fc1cccc(F)c1-c1nnc(N2CCc3[nH]cnc3[C@H]2c2cc3cccc(C(F)F)n3n2)o1] | (S)-2-(4-(7-(difluoromethyl) pyrazolo[1,5-a]pyridin-2-yl)-1,4,6,7-tetrahydro-5H-imidazo[4,5-c]pyridin-5-yl)-5-(2,6-difluorophenyl)-1,3,4-oxadiazole |
| 2094 | 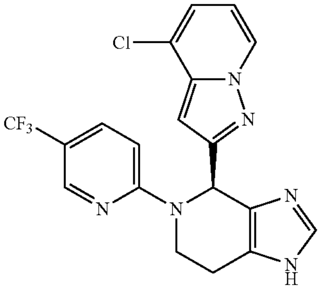 [SMILES: FC(F)(F)c1ccc(N2CCc3[nH]cnc3[C@@H]2c2cc3c(Cl)cccn3n2)nc1] | (R)-4-(4-chloropyrazolo [1,5-a]pyridin-2-yl)-5-(5-(trifluoromethyl)pyridin-2-yl)-4,5,6,7-tetrahydro-1H-imidazo[4,5-c]pyridine |
| 2095 | 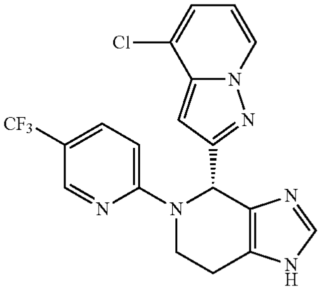 [SMILES: FC(F)(F)c1ccc(N2CCc3[nH]cnc3[C@H]2c2cc3c(Cl)cccn3n2)nc1] | (S)-4-(4-chloropyrazolo [1,5-a]pyridin-2-yl)-5-(5-(trifluoromethyl)pyridin-2-yl)-4,5,6,7-tetrahydro-1H-imidazo[4,5-c]pyridine |
| 2096 | 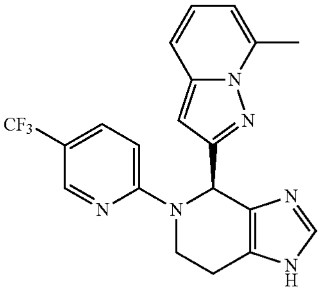 [SMILES: Cc1cccc2cc([C@H]3c4nc[nH]c4CCN3c3ccc(C(F)(F)F)cn3)nn12] | (R)-4-(7-methylpyrazolo [1,5-a]pyridin-2-yl)-5-(5-(trifluoromethyl)pyridin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 2097 | 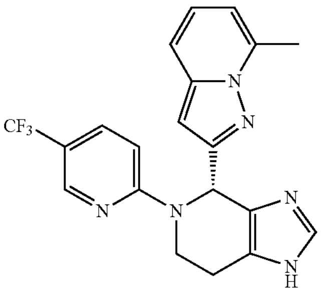 [SMILES: Cc1cccc2cc([C@@H]3c4nc[nH]c4CCN3c3ccc(C(F)(F)F)cn3)nn12] | (S)-4-(7-methylpyrazolo[1,5-a]pyridin-2-yl)-5-(5-(trifluoromethyl)pyridin-2-yl)-4,5,6,7-tetrahydro-1H-imidazo[4,5-c]pyridine |
| 2098 | 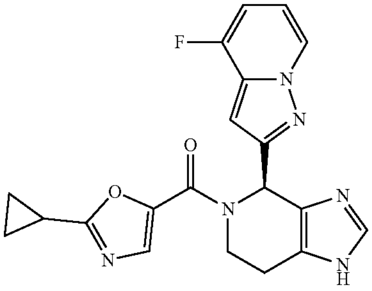 [SMILES: O=C(c1cnc(C2CC2)o1)N1CCc2[nH]cnc2[C@@H]1c1cc2c(F)cccn2n1] | (S)-(2-cyclopropyloxazol-5-yl)(4-(4-fluoropyrazolo[1,5-a]pyridin-2-yl)-1,4,6,7-tetrahydro-5H-imidazo[4,5-c]pyridin-5-yl)methanone |
| 2099 | 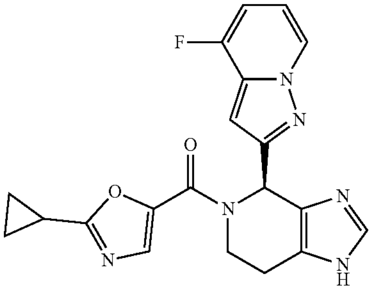 | (R)-(2-cyclopropyloxazol-5-yl)(4-(4-fluoropyrazolo[1,5-a]pyridin-2-yl)-1,4,6,7-tetrahydro-5H-imidazo[4,5-c]pyridin-5-yl)methanone |
| 2100 | 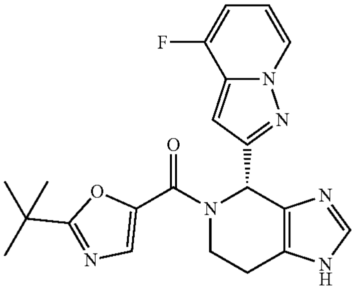 [SMILES: CC(C)(C)c1ncc(C(=O)N2CCc3[nH]cnc3[C@H]2c2cc3c(F)cccn3n2)o1] | (S)-(2-(tert-butyl)oxazol-5-yl)(4-(4-fluoropyrazolo[1,5-a]pyridin-2-yl)-1,4,6,7-tetrahydro-5H-imidazo[4,5-c]pyridin-5-yl)methanone |
| 2101 | 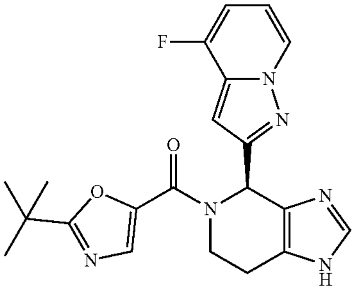 [SMILES: CC(C)(C)c1ncc(C(=O)N2CCc3[nH]cnc3[C@@H]2c2cc3c(F)cccn3n2)o1] | (R)-(2-(tert-butyl)oxazol-5-yl)(4-(4-fluoropyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
| --- | --- | --- |
| Pyrazolo[1,5-a]pyridines | | |
| 2102 | 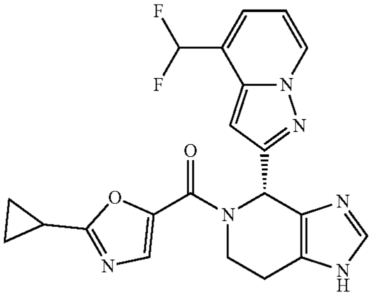 [SMILES: O=C(c1cnc(C2CC2)o1)N1CCc2[nH]cnc2[C@H]1c1cc2c(C(F)F)cccn2n1] | (S)-(2-cyclopropyloxazol-5-yl)(4-(4-(difluoromethyl)pyrazolo[1,5-a]pyridin-2-yl)-1,4,6,7-tetrahydro-5H-imidazo[4,5-c]pyridin-5-yl)methanone |
| 2103 | 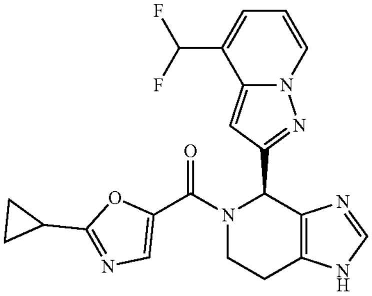 [SMILES: O=C(c1cnc(C2CC2)o1)N1CCc2[nH]cnc2[C@@H]1c1cc2c(C(F)F)cccn2n1] | (R)-(2-cyclopropyloxazol-5-yl)(4-(4-(difluoromethyl)pyrazolo[1,5-a]pyridin-2-yl)-1,4,6,7-tetrahydro-5H-imidazo[4,5-c]pyridin-5-yl)methanone |
| 2104 | 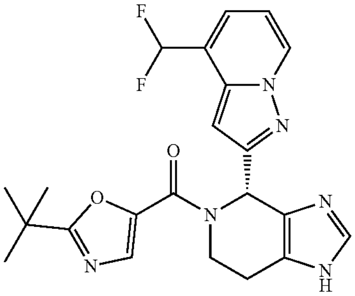 [SMILES: CC(C)(C)c1ncc(C(=O)N2CCc3[nH]cnc3[C@H]2c2cc3c(C(F)F)cccn3n2)o1] | (S)-(2-(tert-butyl)oxazol-5-yl)(4-(4-(difluoromethyl)pyrazolo[1,5-a]pyridin-2-yl)-1,4,6,7-tetrahydro-5H-imidazo[4,5-c]pyridin-5-yl)methanone |
| 2105 | 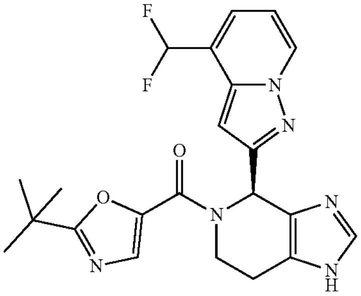 [SMILES: CC(C)(C)c1ncc(C(=O)N2CCc3[nH]cnc3[C@@H]2c2cc3c(C(F)F)cccn3n2)o1] | (R)-(2-(tert-butyl)oxazol-5-yl)(4-(4-(difluoromethyl)pyrazolo[1,5-a]pyridin-2-yl)-1,4,6,7-tetrahydro-5H-imidazo[4,5-c]pyridin-5-yl)methanone |
| 2106 | 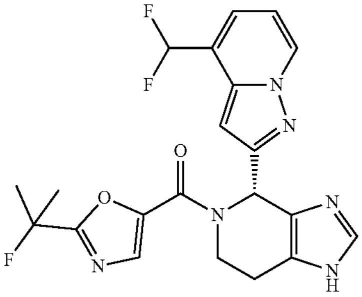 | (S)-(4-(4-(difluoromethyl)pyrazolo[1,5-a]pyridin-2-yl)-1,4,6,7-tetrahydro-5H-imidazo[4,5-c]pyridin-5-yl)(2-(2-fluoropropan-2-yl)oxazol-5-yl)methanone |

TABLE 1-continued

Pyrazolo[1,5-a]pyridines

| Ex. # | Structure | Name |
| --- | --- | --- |
| 2107 | 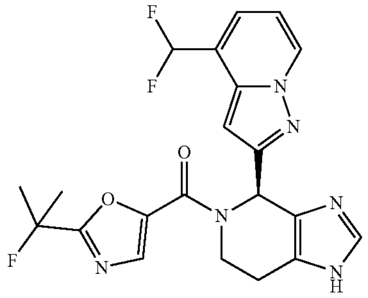 [SMILES: CC(C)(F)c1ncc(C(=O)N2CCc3[nH]cnc3[C@@H]2c2cc3c(C(F)F)cccn3n2)o1] | (R)-(4-(4-(difluoromethyl) pyrazolo[1,5-a]pyridin-2-yl)-1,4,6,7-tetrahydro-5H-imidazo [4,5-c]pyridin-5-yl)(2-(2-fluoropropan-2-yl)oxazol-5-yl)methanone |
| 2108 | 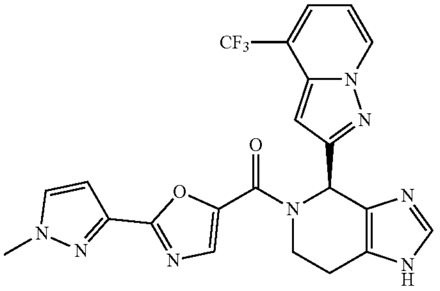 | (R)-(2-(1-methyl-1H-pyrazol-3-yl)oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2109 | 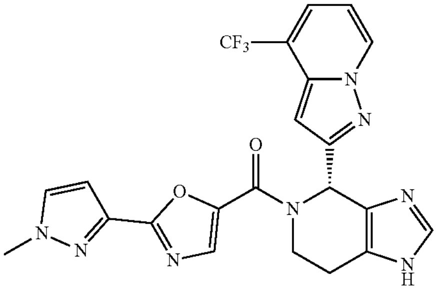 | (S)-(2-(1-methyl-1H-pyrazol-3-yl)oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2110 | 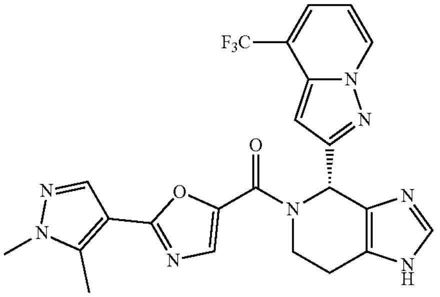 | (S)-(2-(1,5-dimethyl-1H-pyrazol-4-yl)oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2111 | 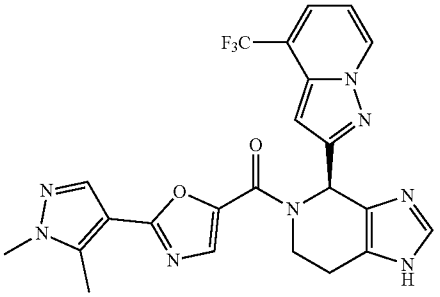 | (R)-(2-(1,5-dimethyl-1H-pyrazol-4-yl)oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |

TABLE 1-continued

| Ex. # | Structure | Name |
| --- | --- | --- |
| Pyrazolo[1,5-a]pyridines | | |
| 2112 | 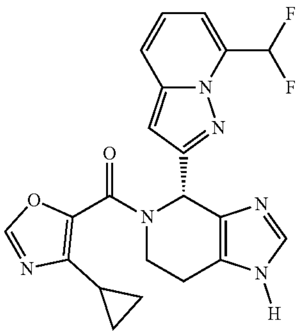 [SMILES: O=C(c1ocnc1C1CC1)N1CCc2[nH]cnc2[C@H]1c1cc2cccc(C(F)F)n2n1] | (S)-(4-cyclopropyloxazol-5-yl)(4-(7-(difluoromethyl)pyrazolo[1,5-a]pyridin-2-yl)-1,4,6,7-tetrahydro-5H-imidazo[4,5-c]pyridin-5-yl)methanone |
| 2113 | 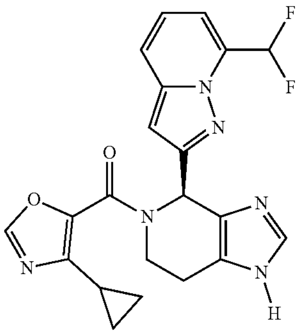 [SMILES: O=C(c1ocnc1C1CC1)N1CCc2[nH]cnc2[C@@H]1c1cc2cccc(C(F)F)n2n1] | (R)-(4-cyclopropyloxazol-5-yl)(4-(7-(difluoromethyl)pyrazolo[1,5-a]pyridin-2-yl)-1,4,6,7-tetrahydro-5H-imidazo[4,5-c]pyridin-5-yl)methanone |
| 2114 | 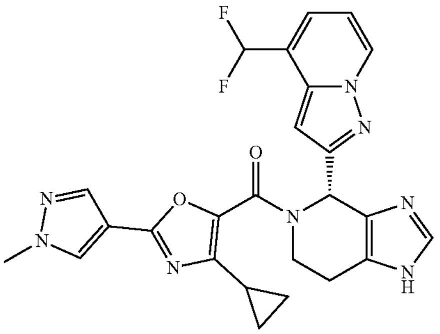 [SMILES: Cn1cc(-c2nc(C3CC3)c(C(=O)N3CCc4[nH]cnc4[C@H]3c3cc4c(C(F)F)cccn4n3)o2)cn1] | (S)-(4-cyclopropyl-2-(1-methyl-1H-pyrazol-4-yl)oxazol-5-yl)(4-(4-(difluoromethyl)pyrazolo[1,5-a]pyridin-2-yl)-1,4,6,7-tetrahydro-5H-imidazo[4,5-c]pyridin-5-yl)methanone |
| 2115 | 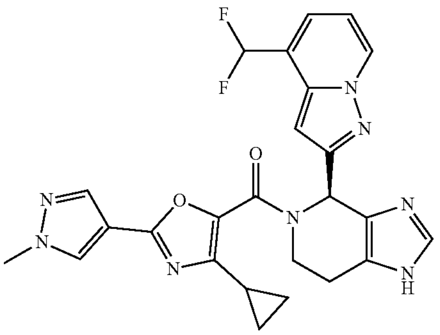 [SMILES: Cn1cc(-c2nc(C3CC3)c(C(=O)N3CCc4[nH]cnc4[C@@H]3c3cc4c(C(F)F)cccn4n3)o2)cn1] | (R)-(4-cyclopropyl-2-(1-methyl-1H-pyrazol-4-yl)oxazol-5-yl)(4-(4-(difluoromethyl)pyrazolo[1,5-a]pyridin-2-yl)-1,4,6,7-tetrahydro-5H-imidazo[4,5-c]pyridin-5-yl)methanone |

TABLE 1-continued

| Pyrazolo[1,5-a]pyridines | | |
|---|---|---|
| Ex. # | Structure | Name |
| 2116 | 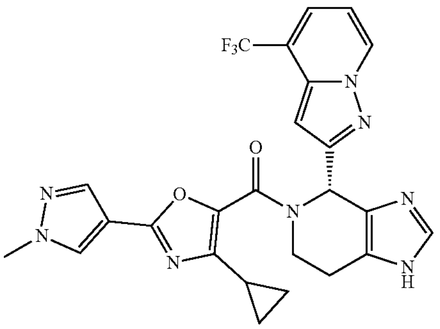 [SMILES: Cn1cc(-c2nc(C3CC3)c(C(=O)N3CCc4[nH]cnc4[C@H]3c3cc4c(C(F)(F)F)cccn4n3)o2)cn1] | (S)-(4-cyclopropyl-2-(1-methyl-1H-pyrazol-4-yl)oxazol-5-yl)(4-(4-(trifluoromethyl) pyrazolo[1,5-a]pyridin-2-yl)-1,4,6,7-tetrahydro-5H-imidazo[4,5-c]pyridin-5-yl)methanone |
| 2117 | 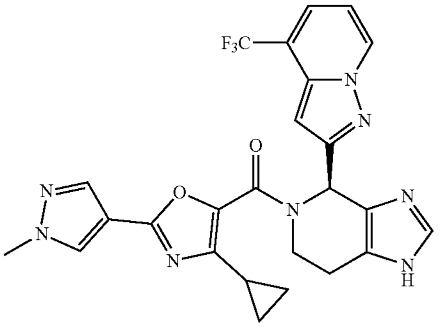 [SMILES: Cn1cc(-c2nc(C3CC3)c(C(=O)N3CCc4[nH]cnc4[C@@H]3c3cc4c(C(F)(F)F)cccn4n3)o2)cn1] | (R)-(4-cyclopropyl-2-(1-methyl-1H-pyrazol-4-yl)oxazol-5-yl)(4-(4-(trifluoromethyl) pyrazolo[1,5-a]pyridin-2-yl)-1,4,6,7-tetrahydro-5H-i midazo[4,5-c]pyridin-5-yl)methanone |
| 2118 | 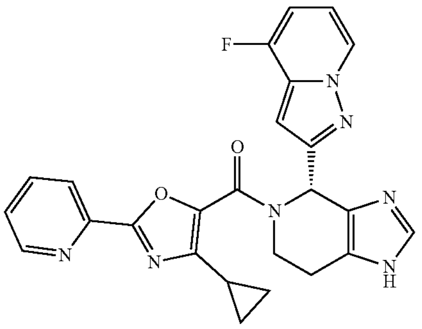 | (S)-(4-cyclopropyl-2-(pyridin-2-yl)oxazol-5-yl)(4-(4-fluoropyrazolo[1,5-a]pyridin-2-yl)-1,4,6,7-tetrahydro-5H-imidazo[4,5-c]pyridin-5-yl)methanone |
| 2119 | 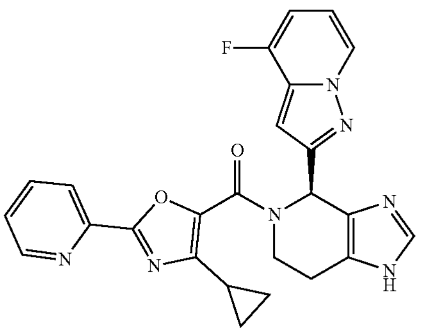 | (R)-(4-cyclopropyl-2-(pyridin-2-yl)oxazol-5-yl)(4-(4-fluoropyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
|---|---|---|
| | Pyrazolo[1,5-a]pyridines | |
| 2120 | 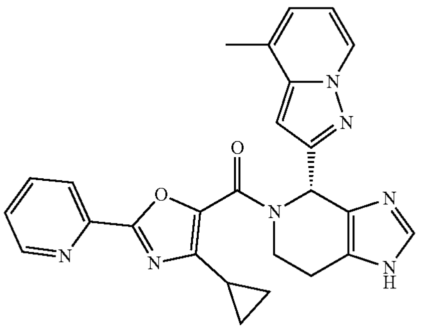 [SMILES: Cc1cccn2nc([C@@H]3c4nc[nH]c4CCN3C(=O)c3oc(-c4ccccn4)nc3C3CC3)cc12] | (S)-(4-cyclopropyl-2-(pyridin-2-yl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 2121 | 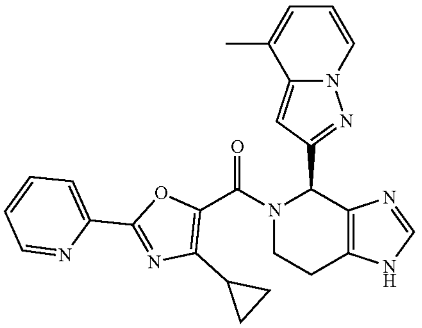 [SMILES: Cc1cccn2nc([C@H]3c4nc[nH]c4CCN3C(=O)c3oc(-c4ccccn4)nc3C3CC3)cc12] | (R)-(4-cyclopropyl-2-(pyridin-2-yl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 2122 | 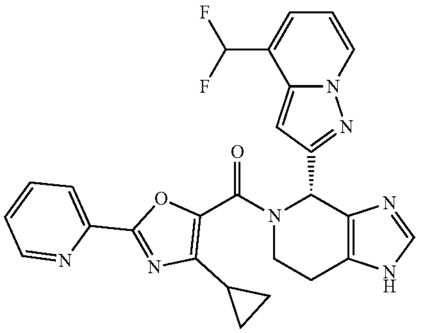 [SMILES: O=C(c1oc(-c2ccccn2)nc1C1CC1)N1CCc2[nH]cnc2[C@H]1c1cc2c(C(F)F)cccn2n1] | (S)-(4-cyclopropyl-2-(pyridin-2-yl)oxazol-5-yl)(4-(4-(difluoromethyl)pyrazolo[1,5-a]pyridin-2-yl)-1,4,6,7-tetrahydro-5H-imidazo[4,5-c]pyridin-5-yl)methanone |
| 2123 | 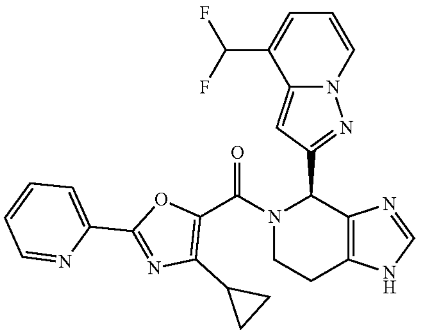 [SMILES: O=C(c1oc(-c2ccccn2)nc1C1CC1)N1CCc2[nH]cnc2[C@@H]1c1cc2c(C(F)F)cccn2n1] | (R)-(4-cyclopropyl-2-(pyridin-2-yl)oxazol-5-yl)(4-(4-(difluoromethyl)pyrazolo[1,5-a]pyridin-2-yl)-1,4,6,7-tetrahydro-5H-imidazo[4,5-c]pyridin-5-yl)methanone |

TABLE 1-continued

| Pyrazolo[1,5-a]pyridines | | |
|---|---|---|
| Ex. # | Structure | Name |
| 2124 | 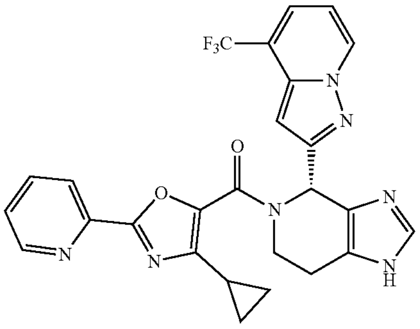 [SMILES: O=C(c1oc(-c2ccccn2)nc1C1CC1)N1CCc2[nH]cnc2[C@H]1c1cc2c(C(F)(F)F)cccn2n1] | (S)-(4-cyclopropyl-2-(pyridin-2-yl)oxazol-5-yl)(4-(4-(trifluoromethyl)pyrazolo[1,5-a]pyridin-2-yl)-1,4,6,7-tetrahydro-5H-imidazo[4,5-c]pyridin-5-yl)methanone |
| 2125 | 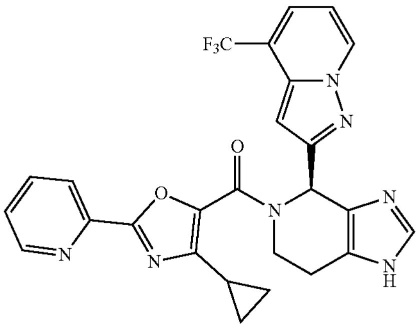 [SMILES: O=C(c1oc(-c2ccccn2)nc1C1CC1)N1CCc2[nH]cnc2[C@@H]1c1cc2c(C(F)(F)F)cccn2n1] | (R)-(4-cyclopropyl-2-(pyridin-2-yl)oxazol-5-yl)(4-(4-(trifluoromethyl)pyrazolo[1,5-a]pyridin-2-y])-1,4,6,7-tetrahydro-5H-imidazo[4,5-c]pyridin-5-yl)methanone |
| 2126 | 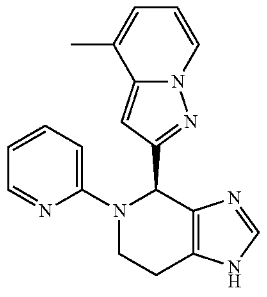 [SMILES: Cc1cccn2nc([C@H]3c4nc[nH]c4CCN3c3ccccn3)cc12] | (R)-4-(4-methylpyrazolo[1,5-a]pyridin-2-yl)-5-(pyridin-2-yl)-4,5,6,7-tetrahydro-1H-imidazo[4,5-c]pyridine |
| 2127 | 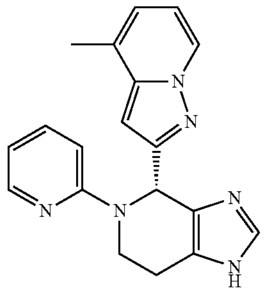 [SMILES: Cc1cccn2nc([C@@H]3c4nc[nH]c4CCN3c3ccccn3)cc12] | (S)-4-(4-methylpyrazolo[1,5-a]pyridin-2-yl)-5-(pyridin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 2128 | 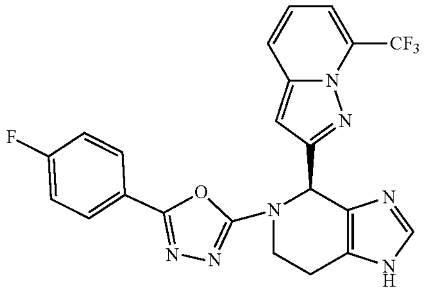 [SMILES: Fc1ccc(-c2nnc(N3CCc4[nH]cnc4[C@@H]3c3cc4cccc(C(F)(F)F)n4n3)o2)cc1] | (R)-2-(4-fluorophenyl)-5-(4-(7-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2129 | 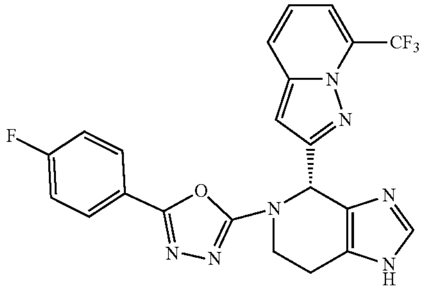 [SMILES: Fc1ccc(-c2nnc(N3CCc4[nH]cnc4[C@H]3c3cc4cccc(C(F)(F)F)n4n3)o2)cc1] | (S)-2-(4-fluorophenyl)-5-(4-(7-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2130 | 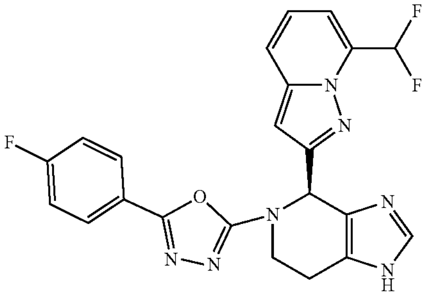 [SMILES: Fc1ccc(-c2nnc(N3CCc4[nH]cnc4[C@@H]3c3cc4cccc(C(F)F)n4n3)o2)cc1] | (R)-2-(4-(7-(difluoromethyl)pyrazolo[1,5-a]pyridin-2-yl)-1,4,6,7-tetrahydro-5H-imidazo[4,5-c]pyridin-5-yl)-5-(4-fluorophenyl)-1,3,4-oxadiazole |
| 2131 | 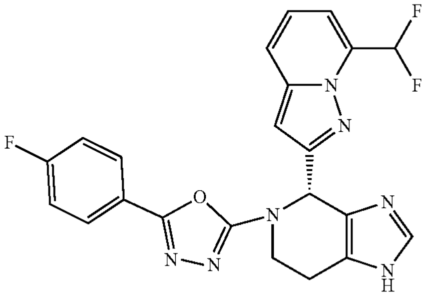 [SMILES: Fc1ccc(-c2nnc(N3CCc4[nH]cnc4[C@H]3c3cc4cccc(C(F)F)n4n3)o2)cc1] | (S)-2-(4-(7-(difluoromethyl)pyrazolo[1,5-a]pyridin-2-y]l)-1,4,6,7-tetrahydro-5H-imidazo[4,5-c]pyridin-5-yl)-5-(4-fluorophenyl)-1,3,4-oxadiazole |
| 2132 | 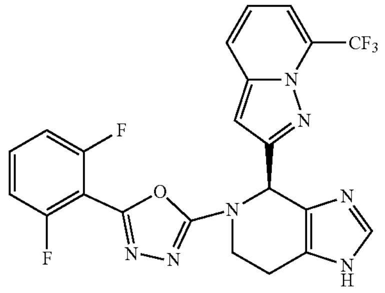 [SMILES: Fc1cccc(F)c1-c1nnc(N2CCc3[nH]cnc3[C@@H]2c2cc3cccc(C(F)(F)F)n3n2)o1] | (R)-2-(2,6-difluorophenyl)-5-(4-(7-(trifluoromethyl)pyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
|---|---|---|
| | Pyrazolo[1,5-a]pyridines | |
| 2133 | 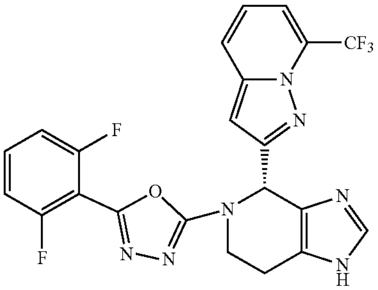 [SMILES: Fc1cccc(F)c1-c1nnc(N2CCc3[nH]cnc3[C@H]2c2cc3cccc(C(F)(F)F)n3n2)o1] | (S)-2-(2,6-difluorophenyl)-5-(4-(7-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2134 | 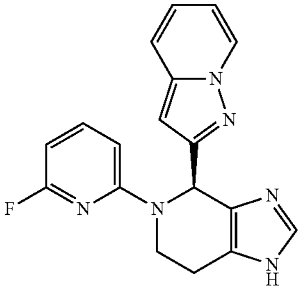 [SMILES: Fc1cccc(N2CCc3[nH]cnc3[C@@H]2c2cc3ccccn3n2)n1] | (R)-5-(6-fluoropyridin-2-yl)-4-(pyrazolo[1,5-a]pyridin-2-yl)-4,5,6,7-tetrahydro-1H-imidazo[4,5-c]pyridine |
| 2135 | 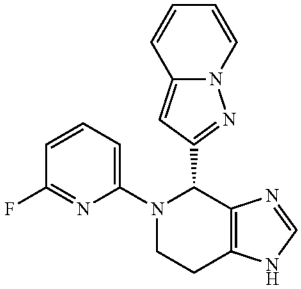 [SMILES: Fc1cccc(N2CCc3[nH]cnc3[C@H]2c2cc3ccccn3n2)n1] | (S)-5-(6-fluoropyridin-2-yl)-4-(pyrazolo[1,5-a]pyridin-2-yl)-4,5,6,7-tetrahydro-1H-imidazo[4,5-c]pyridine |
| 2136 | 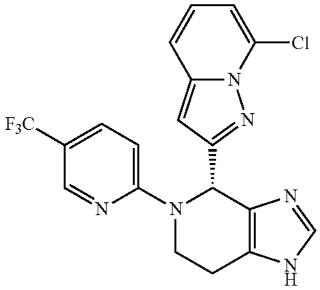 [SMILES: FC(F)(F)c1ccc(N2CCc3[nH]cnc3[C@H]2c2cc3cccc(Cl)n3n2)nc1] | (S)-4-(7-chloropyrazolo[1,5-a]pyridin-2-yl)-5-(5-(trifluoromethyl)pyridin-2-yl)-4,5,6,7-tetrahydro-1H-imidazo[4,5-c]pyridine |
| 2137 | 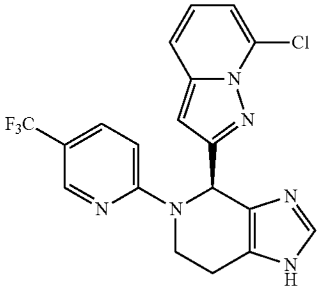 [SMILES: FC(F)(F)c1ccc(N2CCc3[nH]cnc3[C@@H]2c2cc3cccc(Cl)n3n2)nc1] | (R)-4-(7-chloropyrazolo[1,5-a]pyridin-2-yl)-5-(5-(trifluoromethyl)pyridin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 2138 | 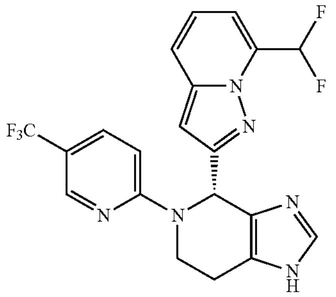 [SMILES: FC(F)c1cccc2cc([C@@H]3c4nc[nH]c4CCN3c3ccc(C(F)(F)F)cn3)nn12] | (S)-4-(7-(difluoromethyl) pyrazolo[1,5-a]pyridin-2-yl)-5-(5-(trifluoromethyl)pyridin-2-yl)-4,5,6,7-tetrahydro-1H-imidazo[4,5-c]pyridine |
| 2139 | 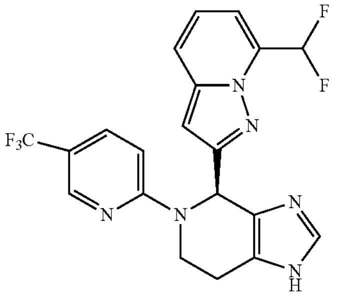 [SMILES: FC(F)c1cccc2cc([C@H]3c4nc[nH]c4CCN3c3ccc(C(F)(F)F)cn3)nn12] | (R)-4-(7-(difluoromethyl) pyrazolo[1,5-a]pyridin-2-yl)-5-(5-(trifluoromethyl)pyridin-2-yl)-4,5,6,7-tetrahydro-1H-imidazo[4,5-c]pyridine |
| 2140 | 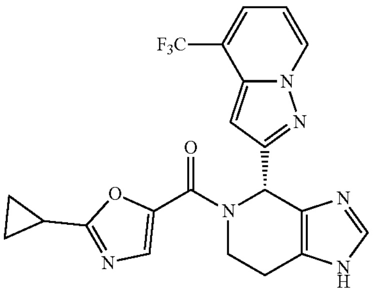 [SMILES: O=C(c1cnc(C2CC2)o1)N1CCc2[nH]cnc2[C@H]1c1cc2c(C(F)(F)F)cccn2n1] | (S)-(2-cyclopropyloxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2141 | 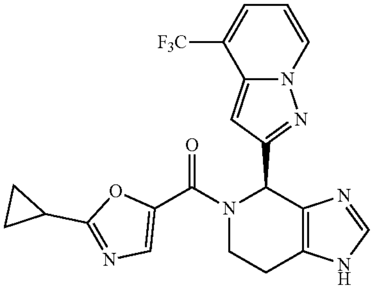 [SMILES: O=C(c1cnc(C2CC2)o1)N1CCc2[nH]cnc2[C@@H]1c1cc2c(C(F)(F)F)cccn2n1] | (R)-(2-cyclopropyloxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2142 | 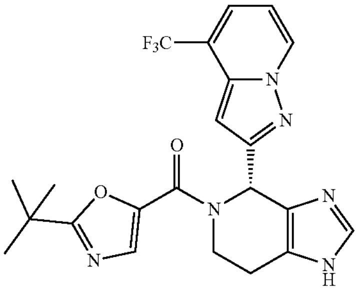 [SMILES: CC(C)(C)c1ncc(C(=O)N2CCc3[nH]cnc3[C@H]2c2cc3c(C(F)(F)F)cccn3n2)o1] | (S)-(2-(tert-butyl) oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |

TABLE 1-continued

| Pyrazolo[1,5-a]pyridines | | |
|---|---|---|
| Ex. # | Structure | Name |
| 2143 | 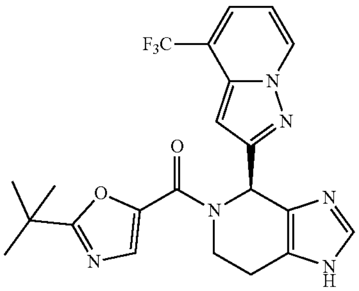 [SMILES: CC(C)(C)c1ncc(C(=O)N2CCc3[nH]cnc3[C@@H]2c2cc3c(C(F)(F)F)cccn3n2)o1] | (R)-(2-(tert-butyl) oxazol-5-yl)(4-(4-(trifluoromethyl)pyrazolo [1,5-a]pyridin-2-yl)-1,4,6,7-tetrahydro-5H-imidazo [4,5-c]pyridin-5-yl)methanone |
| 2144 | 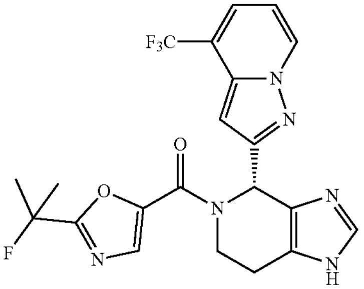 | (S)-(2-(2-fluoropropan-2-yl)oxazol-5-yl)(4-(4-(trifluoromethyl)pyrazolo [1,5-a]pyridin-2-yl)-1,4,6,7-tetrahydro-5H-imidazo [4,5-c]pyridin-5-yl)methanone |
| 2145 | 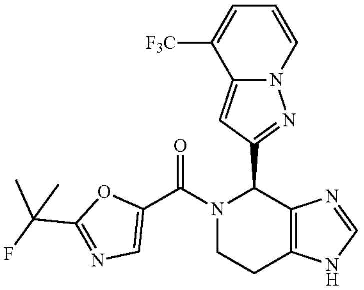 [SMILES: CC(C)(F)c1ncc(C(=O)N2CCc3[nH]cnc3[C@@H]2c2cc3c(C(F)(F)F)cccn3n2)o1] | (R)-(2-(2-fluoropropan-2-yl)oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2146 | 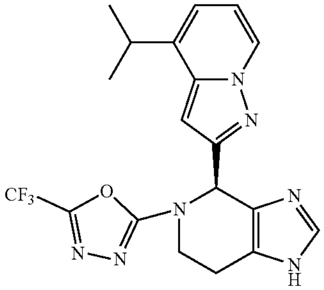 [SMILES: CC(C)c1cccn2nc([C@H]3c4nc[nH]c4CCN3c3nnc(C(F)(F)F)o3)cc12] | (R)-2-(4-(4-isopropylpyrazolo [1,5-a]pyridin-2-y]l)-1,4,6,7-tetrahydro-5H-imidazo [4,5-c]pyridin-5-yl)-5-(trifluoromethyl)-1,3,4-oxadiazole |
| 2147 | 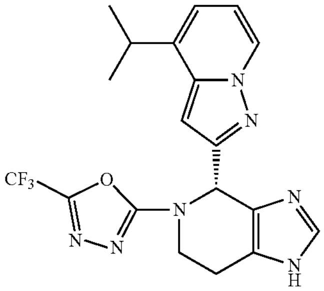 [SMILES: CC(C)c1cccn2nc([C@@H]3c4nc[nH]c4CCN3c3nnc(C(F)(F)F)o3)cc12] | (S)-2-(4-(4-isopropylpyrazolo [1,5-a]pyridin-2-yl)-1,4,6,7-tetrahydro-5H-imidazo [4,5-c]pyridin-5-yl)-5-(trifluoromethyl)-1,3,4-oxadiazole |

TABLE 1-continued

| Pyrazolo[1,5-a]pyridines | | |
|---|---|---|
| Ex. # | Structure | Name |
| 2148 | 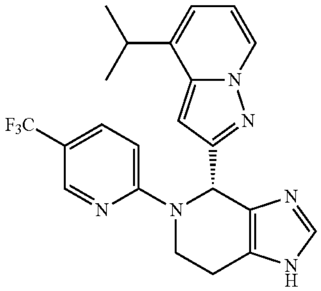 [SMILES: CC(C)c1cccn2nc([C@@H]3c4nc[nH]c4CCN3c3ccc(C(F)(F)F)cn3)cc12] | (S)-4-(4-isopropylpyrazolo[1,5-a]pyridin-2-yl)-5-(5-(trifluoromethyl)pyridin-2-yl)-4,5,6,7-tetrahydro-1H-imidazo[4,5-c]pyridine |
| 2149 | 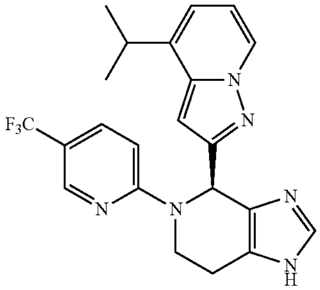 [SMILES: CC(C)c1cccn2nc([C@H]3c4nc[nH]c4CCN3c3ccc(C(F)(F)F)cn3)cc12] | (R)-4-(4-isopropylpyrazolo[1,5-a]pyridin-2-yl)-5-(5-(trifluoromethyl)pyridin-2-yl)-4,5,6,7-tetrahydro-1H-imidazo[4,5-c]pyridine |
| 2150 | 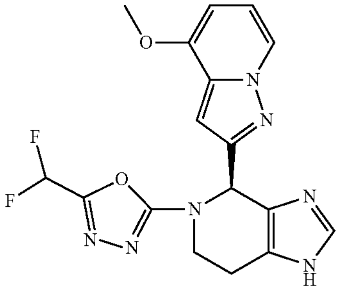 [SMILES: COc1cccn2nc([C@H]3c4nc[nH]c4CCN3c3nnc(C(F)F)o3)cc12] | (R)-2-(difluoromethyl)-5-(4-(4-methoxypyrazolo[1,5-a]pyridin-2-yl)-1,4,6,7-tetrahydro-5H-imidazo[4,5-c]pyridin-5-yl)-1,3,4-oxadiazole |
| 2151 | 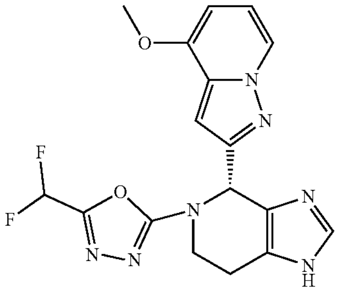 [SMILES: COc1cccn2nc([C@@H]3c4nc[nH]c4CCN3c3nnc(C(F)F)o3)cc12] | (S)-2-(difluoromethyl)-5-(4-(4-methoxypyrazolo[1,5-a]pyridin-2-yl)-1,4,6,7-tetrahydro-5H-imidazo[4,5-c]pyridin-5-yl)-1,3,4-oxadiazole |
| 2152 | 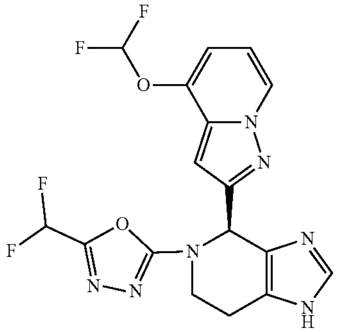 [SMILES: FC(F)Oc1cccn2nc([C@H]3c4nc[nH]c4CCN3c3nnc(C(F)F)o3)cc12] | (R)-2-(4-(4-(difluoromethoxy)pyrazolo[1,5-a]pyridin-2-yl)-1,4,6,7-tetrahydro-5H-imidazo[4,5-c]pyridin-5-yl)-5-(difluoromethyl)-1,3,4-oxadiazole |

TABLE 1-continued

| Pyrazolo[1,5-a]pyridines | | |
|---|---|---|
| Ex. # | Structure | Name |
| 2153 | 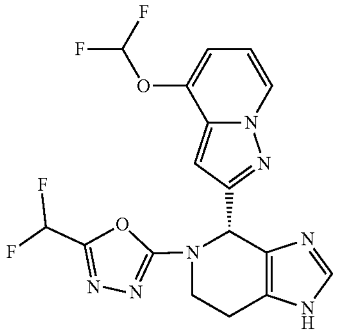 [SMILES: FC(F)Oc1cccn2nc([C@@H]3c4nc[nH]c4CCN3c3nnc(C(F)F)o3)cc12] | (S)-2-(4-(4-(difluoromethoxy) pyrazolo[1,5-a]pyridin-2-yl)-1,4,6,7-tetrahydro-5H-imidazo[4,5-c]pyridin-5-yl)-5-(difluoromethyl)-1,3,4-oxadiazole |
| 2154 | 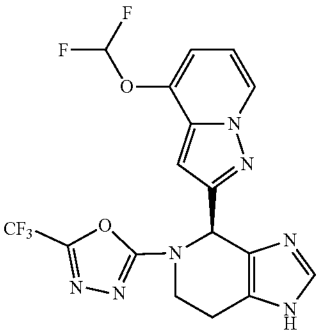 [SMILES: FC(F)Oc1cccn2nc([C@H]3c4nc[nH]c4CCN3c3nnc(C(F)(F)F)o3)cc12] | (R)-2-(4-(4-(difluoromethoxy) pyrazolo[1,5-a]pyridin-2-yl)-1,4,6,7-tetrahydro-5H-imidazo[4,5-c]pyridin-5-yl)-5-(trifluoromethyl)-1,3,4-oxadiazole |
| 2155 | 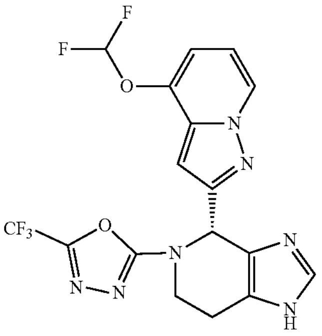 [SMILES: FC(F)Oc1cccn2nc([C@@H]3c4nc[nH]c4CCN3c3nnc(C(F)(F)F)o3)cc12] | (S)-2-(4-(4-(difluoromethoxy) pyrazolo[1,5-a]pyridin-2-yl)-1,4,6,7-tetrahydro-5H-imidazo[4,5-c]pyridin-5-yl)-5-(trifluoromethyl)-1,3,4-oxadiazole |
| 2156 | 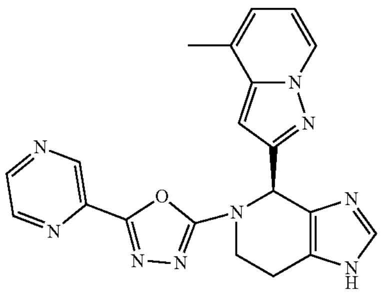 [SMILES: Cc1cccn2nc([C@H]3c4nc[nH]c4CCN3c3nnc(-c4cnccn4)o3)cc12] | (R)-2-(4-(4-methylpyrazolo [1,5-a]pyridin-2-yl)-1,4,6,7-tetrahydro-5H-imidazo[4,5-c] pyridin-5-yl)-5-(pyrazin-2-yl)-1,3,4-oxadiazole |

TABLE 1-continued

| Pyrazolo[1,5-a]pyridines | | |
|---|---|---|
| Ex. # | Structure | Name |
| 2157 | 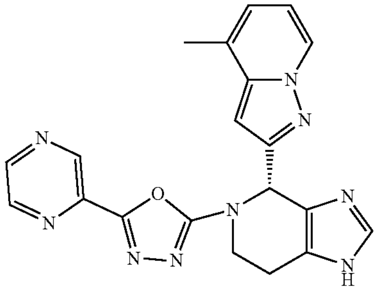 [SMILES: Cc1cccn2nc([C@@H]3c4nc[nH]c4CCN3c3nnc(-c4cnccn4)o3)cc12] | (S)-2-(4-(4-methylpyrazolo[1,5-a]pyridin-2-yl)-1,4,6,7-tetrahydro-5H-imidazo[4,5-c]pyridin-5-yl)-5-(pyrazin-2-yl)-1,3,4-oxadiazole |
| 2158 | 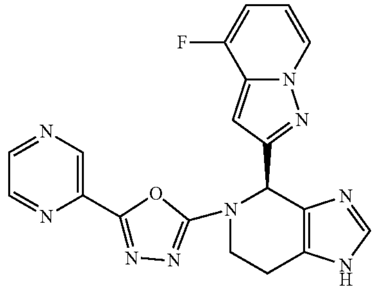 [SMILES: Fc1cccn2nc([C@H]3c4nc[nH]c4CCN3c3nnc(-c4cnccn4)o3)cc12] | (R)-2-(4-(4-fluoropyrazolo[1,5-a]pyridin-2-yl)-1,4,6,7-tetrahydro-5H-imidazo[4,5-c]pyridin-5-yl)-5-(pyrazin-2-yl)-1,3,4-oxadiazole |
| 2159 | 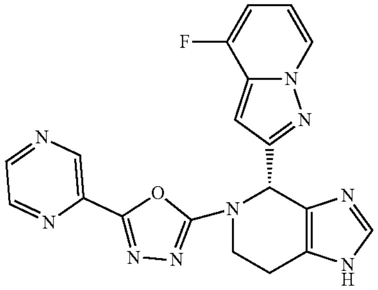 [SMILES: Fc1cccn2nc([C@@H]3c4nc[nH]c4CCN3c3nnc(-c4cnccn4)o3)cc12] | (S)-2-(4-(4-fluoropyrazolo[1,5-a]pyridin-2-yl)-1,4,6,7-tetrahydro-5H-imidazo[4,5-c]pyridin-5-yl)-5-(pyrazin-2-yl)-1,3,4-oxadiazole |
| 2160 | 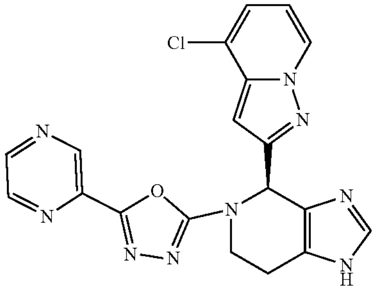 [SMILES: Clc1cccn2nc([C@H]3c4nc[nH]c4CCN3c3nnc(-c4cnccn4)o3)cc12] | (R)-2-(4-(4-chloropyrazolo[1,5-a]pyridin-2-yl)-1,4,6,7-tetrahydro-5H-imidazo[4,5-c]pyridin-5-yl)-5-(pyrazin-2-yl)-1,3,4-oxadiazole |
| 2161 | 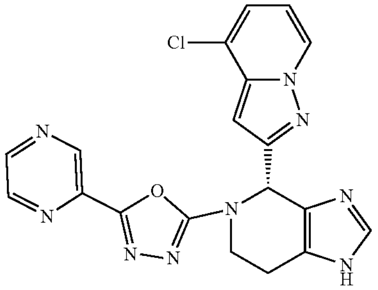 [SMILES: Clc1cccn2nc([C@@H]3c4nc[nH]c4CCN3c3nnc(-c4cnccn4)o3)cc12] | (S)-2-(4-(4-chloropyrazolo[1,5-a]pyridin-2-yl)-1,4,6,7-tetrahydro-5H-imidazo[4,5-c]pyridin-5-yl)-5-(pyrazin-2-yl)-1,3,4-oxadiazole |

TABLE 1-continued

| Ex. # | Structure | Name |
|---|---|---|
| | Pyrazolo[1,5-a]pyridines | |
| 2162 | 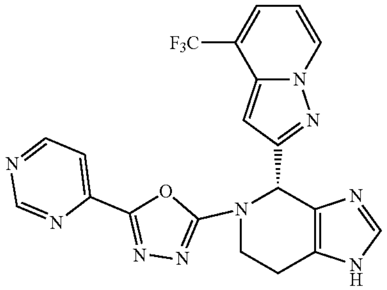 [SMILES: FC(F)(F)c1cccn2nc([C@@H]3c4nc[nH]c4CCN3c3nnc(-c4ccncn4)o3)cc12] | (S)-2-(pyrimidin-4-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2163 | 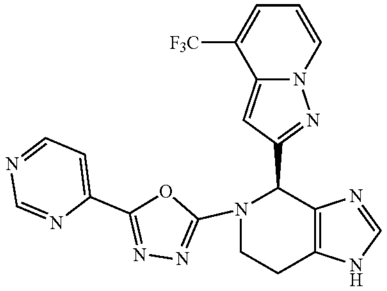 [SMILES: FC(F)(F)c1cccn2nc([C@H]3c4nc[nH]c4CCN3c3nnc(-c4ccncn4)o3)cc12] | (R)-2-(pyrimidin-4-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2164 | 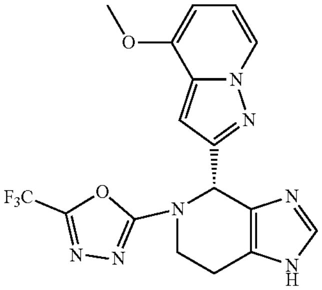 [SMILES: COc1cccn2nc([C@@H]3c4nc[nH]c4CCN3c3nnc(C(F)(F)F)o3)cc12] | (S)-2-(4-(4-methoxypyrazolo[1,5-a]pyridin-2-yl)-1,4,6,7-tetrahydro-5H-imidazo[4,5-c]pyridin-5-yl)-5-(trifluoromethyl)-1,3,4-oxadiazole |
| 2165 | 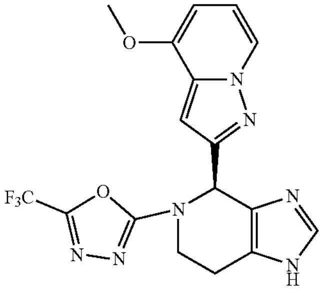 [SMILES: COc1cccn2nc([C@H]3c4nc[nH]c4CCN3c3nnc(C(F)(F)F)o3)cc12] | (R)-2-(4-(4-methoxypyrazolo[1,5-a]pyridin-2-yl)-1,4,6,7-tetrahydro-5H-imidazo[4,5-c]pyridin-5-yl)-5-(trifluoromethyl)-1,3,4-oxadiazole |
| 2166 | 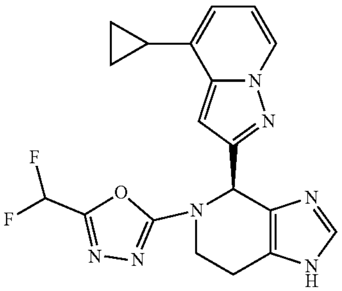 [SMILES: FC(F)c1nnc(N2CCc3[nH]cnc3[C@@H]2c2cc3c(C4CC4)cccn3n2)o1] | (R)-2-(4-(4-cyclopropylpyrazolo[1,5-a]pyridin-2-yl)-1,4,6,7-tetrahydro-5H-imidazo[4,5-c]pyridin-5-yl)-5-(difluoromethyl)-1,3,4-oxadiazole |

TABLE 1-continued

| Pyrazolo[1,5-a]pyridines | | |
|---|---|---|
| Ex. # | Structure | Name |
| 2167 | 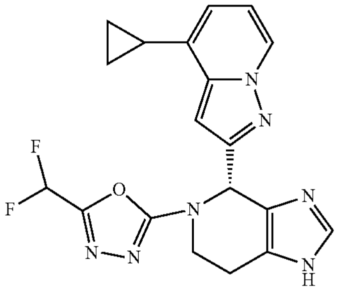 [SMILES: FC(F)c1nnc(N2CCc3[nH]cnc3[C@H]2c2cc3c(C4CC4)cccn3n2)o1] | (S)-2-(4-(4-cyclopropylpyrazolo [1,5-a]pyridin-2-y]l)-1,4,6,7-tetrahydro-5H-imidazo [4,5-c]pyridin-5-yl)-5-(difluoromethyl)-1,3,4-oxadiazole |
| 2168 | 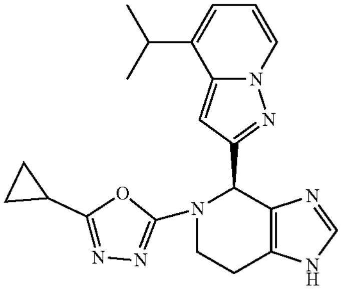 [SMILES: CC(C)c1cccn2nc([C@H]3c4nc[nH]c4CCN3c3nnc(C4CC4)o3)cc12] | (R)-2-cyclopropyl-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |
| 2169 | 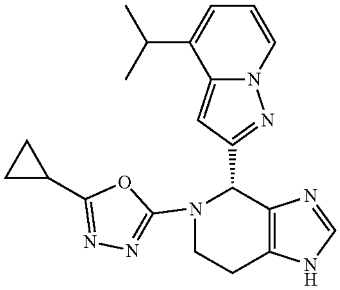 [SMILES: CC(C)c1cccn2nc([C@@H]3c4nc[nH]c4CCN3c3nnc(C4CC4)o3)cc12] | (S)-2-cyclopropyl-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |
| 2170 | 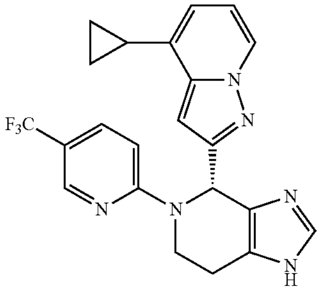 [SMILES: FC(F)(F)c1ccc(N2CCc3[nH]cnc3[C@H]2c2cc3c(C4CC4)cccn3n2)nc1] | (S)-4-(4-cyclopropylpyrazolo [1,5-a]pyridin-2-yl)-5-(5-(trifluoromethyl)pyridin-2-yl)-4,5,6,7-tetrahydro-1H-imidazo[4,5-c]pyridine |
| 2171 | 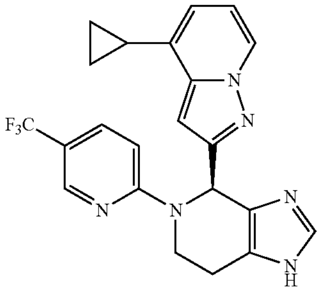 | (R)-4-(4-cyclopropylpyrazolo [1,5-a]pyridin-2-yl)-5-(5-(trifluoromethyl)pyridin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 2172 | 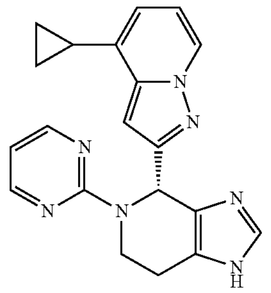 [SMILES: c1cnc(N2CCc3[nH]cnc3[C@H]2c2cc3c(C4CC4)cccn3n2)nc1] | (S)-4-(4-cyclopropylpyrazolo [1,5-a]pyridin-2-yl)-5-(pyrimidin-2-yl)-4,5,6,7-tetrahydro-1H-imidazo[4,5-c]pyridine |
| 2173 | 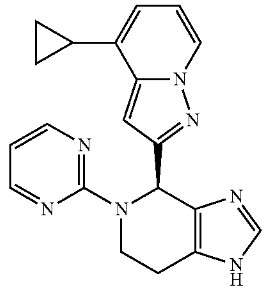 [SMILES: c1cnc(N2CCc3[nH]cnc3[C@@H]2c2cc3c(C4CC4)cccn3n2)nc1] | (R)-4-(4-cyclopropylpyrazolo [1,5-a]pyridin-2-yl)-5-(pyrimidin-2-yl)-4,5,6,7-tetrahydro-1H-imidazo[4,5-c]pyridine |
| 2174 | 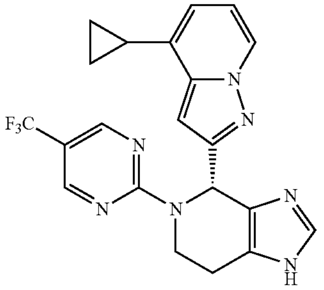 | (S)-4-(4-cyclopropylpyrazolo [1,5-a]pyridin-2-yl)-5-(5-(trifluoromethyl)pyrimidin-2-yl)-4,5,6,7-tetrahydro-1H-imidazo[4,5-c]pyridine |
| 2175 | 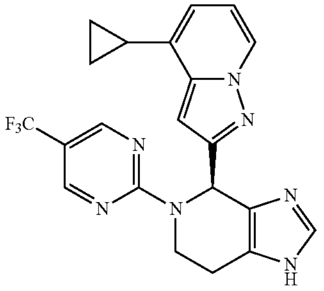 [SMILES: FC(F)(F)c1cnc(N2CCc3[nH]cnc3[C@@H]2c2cc3c(C4CC4)cccn3n2)nc1] | (R)-4-(4-cyclopropylpyrazolo [1,5-a]pyridin-2-yl)-5-(5-(trifluoromethyl)pyrimidin-2-yl)-4,5,6,7-tetrahydro-1H-imidazo[4,5-c]pyridine |
| 2176 | 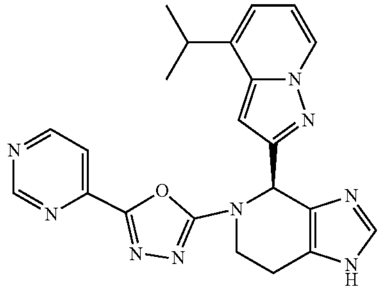 [SMILES: CC(C)c1cccn2nc([C@H]3c4nc[nH]c4CCN3c3nnc(-c4ccncn4)o3)cc12] | (R)-2-(4-(4-isopropylpyrazolo [1,5-a]pyridin-2-yl)-1,4,6,7-tetrahydro-5H-imidazo [4,5-c]pyridin-5-yl)-5-(pyrazin-2-yl)-1,3,4-oxadiazole |

TABLE 1-continued

| Pyrazolo[1,5-a]pyridines | | |
|---|---|---|
| Ex. # | Structure | Name |
| 2177 | 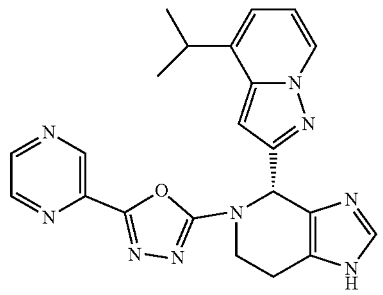 [SMILES: CC(C)c1cccn2nc([C@@H]3c4nc[nH]c4CCN3c3nnc(-c4cnccn4)o3)cc12] | (S)-2-(4-(4-isopropylpyrazolo[1,5-a]pyridin-2-yl)-1,4,6,7-tetrahydro-5H-imidazo[4,5-c]pyridin-5-yl)-5-(pyrazin-2-yl)-1,3,4-oxadiazole |
| 2178 | 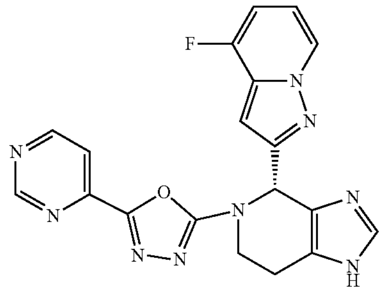 [SMILES: Fc1cccn2nc([C@@H]3c4nc[nH]c4CCN3c3nnc(-c4ccncn4)o3)cc12] | (S)-2-(4-(4-fluoropyrazolo[1,5-a]pyridin-2-yl)-1,4,6,7-tetrahydro-5H-imidazo[4,5-c]pyridin-5-yl)-5-(pyrimidin-4-yl)-1,3,4-oxadiazole |
| 2179 | 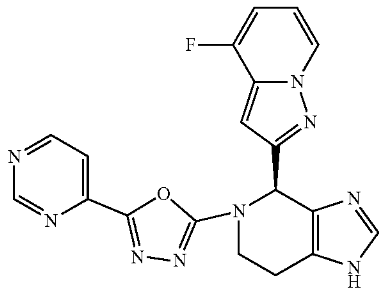 [SMILES: Fc1cccn2nc([C@H]3c4nc[nH]c4CCN3c3nnc(-c4ccncn4)o3)cc12] | (R)-2-(4-(4-fluoropyrazolo[1,5-a]pyridin-2-yl)-1,4,6,7-tetrahydro-5H-imidazo[4,5-c]pyridin-5-yl)-5-(pyrimidin-4-yl)-1,3,4-oxadiazole |
| 2180 | 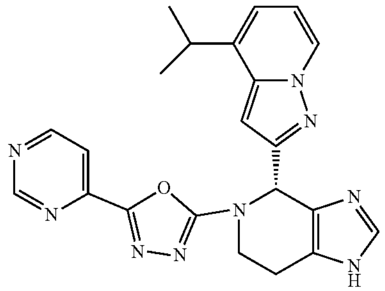 [SMILES: CC(C)c1cccn2nc([C@@H]3c4nc[nH]c4CCN3c3nnc(-c4ccncn4)o3)cc12] | (S)-2-(4-(4-isopropylpyrazolo[1,5-a]pyridin-2-yl)-1,4,6,7-tetrahydro-5H-imidazo[4,5-c]pyridin-5-yl)-5-(pyrimidin-4-yl)-1,3,4-oxadiazole |
| 2181 | 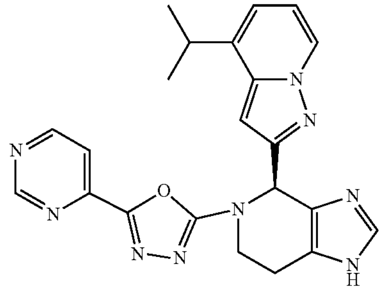 [SMILES: CC(C)c1cccn2nc([C@H]3c4nc[nH]c4CCN3c3nnc(-c4ccncn4)o3)cc12] | (R)-2-(4-(4-isopropylpyrazolo[1,5-a]pyridin-2-yl)-1,4,6,7-tetrahydro-5H-imidazo[4,5-c]pyridin-5-yl)-5-(pyrimidin-4-yl)-1,3,4-oxadiazole |

TABLE 1-continued

Pyrazolo[1,5-a]pyridines

| Ex. # | Structure | Name |
|---|---|---|
| 2182 | 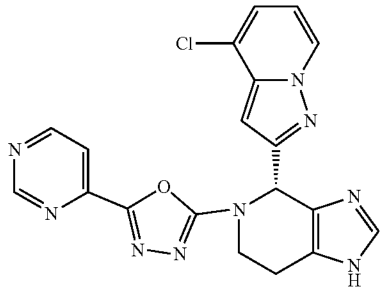 [SMILES: Clc1cccn2nc([C@@H]3c4nc[nH]c4CCN3c3nnc(-c4ccncn4)o3)cc12] | (S)-2-(4-(4-chloropyrazolo[1,5-a]pyridin-2-yl)-1,4,6,7-tetrahydro-5H-imidazo[4,5-c]pyridin-5-yl)-5-(pyrimidin-4-yl)-1,3,4-oxadiazole |
| 2183 | 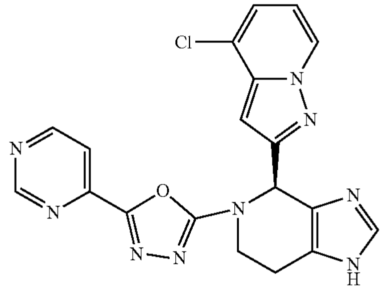 [SMILES: Clc1cccn2nc([C@H]3c4nc[nH]c4CCN3c3nnc(-c4ccncn4)o3)cc12] | (R)-2-(4-(4-chloropyrazolo[1,5-a]pyridin-2-yl)-1,4,6,7-tetrahydro-5H-imidazo[4,5-c]pyridin-5-yl)-5-(pyrimidin-4-yl)-1,3,4-oxadiazole |
| 2184 | 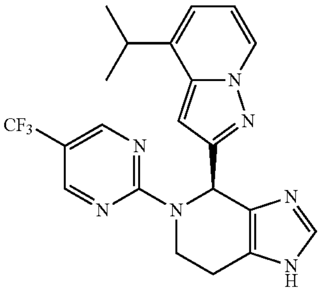 [SMILES: CC(C)c1cccn2nc([C@H]3c4nc[nH]c4CCN3c3ncc(C(F)(F)F)cn3)cc12] | (R)-4-(4-isopropylpyrazolo[1,5-a]pyridin-2-yl)-5-(5-(trifluoromethyl)pyrimidin-2-yl)-4,5,6,7-tetrahydro-1H-imidazo[4,5-c]pyridine |
| 2185 | 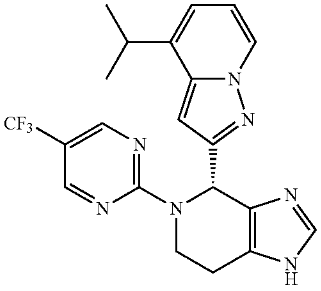 | (S)-4-(4-isopropylpyrazolo[1,5-a]pyridin-2-yl)-5-(5-(trifluoromethyl)pyrimidin-2-yl)-4,5,6,7-tetrahydro-1H-imidazo[4,5-c]pyridine |
| 2186 | 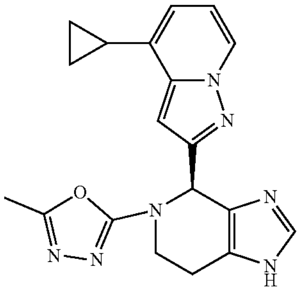 [SMILES: Cc1nnc(N2CCc3[nH]cnc3[C@@H]2c2cc3c(C4CC4)cccn3n2)o1] | (R)-2-(4-(4-cyclopropylpyrazolo[1,5-a]pyridin-2-yl)-1,4,6,7-tetrahydro-5H-imidazo[4,5-c]pyridin-5-yl)-5-methyl-1,3,4-oxadiazole |

TABLE 1-continued

| Ex. # | Structure | Name |
|---|---|---|
| | Pyrazolo[1,5-a]pyridines | |
| 2187 | 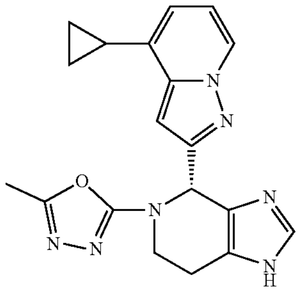 [SMILES: Cc1nnc(N2CCc3[nH]cnc3[C@H]2c2cc3c(C4CC4)cccn3n2)o1] | (S)-2-(4-(4-cyclopropylpyrazolo[1,5-a]pyridin-2-yl)-1,4,6,7-tetrahydro-5H-imidazo[4,5-c]pyridin-5-yl)-5-methyl-1,3,4-oxadiazole |
| 2188 | 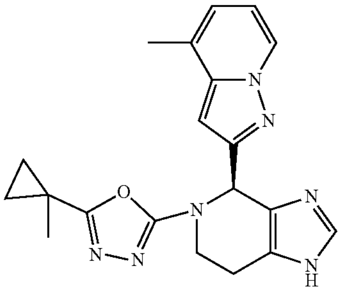 [SMILES: Cc1cccn2nc([C@H]3c4nc[nH]c4CCN3c3nnc(C4(C)CC4)o3)cc12] | (R)-2-(1-methylcyclopropyl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2189 | 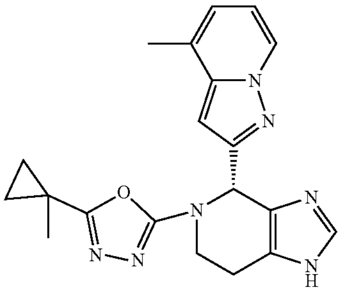 [SMILES: Cc1cccn2nc([C@@H]3c4nc[nH]c4CCN3c3nnc(C4(C)CC4)o3)cc12] | (S)-2-(1-methylcyclopropyl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2190 | 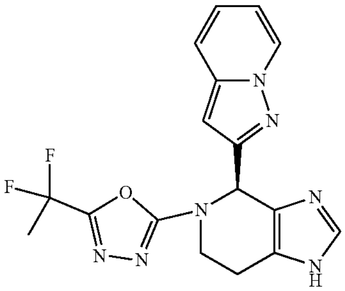 | (R)-2-(1,1-difluoroethyl)-5-(4-(pyrazolo[1,5-a]pyridin-2-yl)-1,4,6,7-tetrahydro-5H-imidazo[4,5-c]pyridin-5-yl)-1,3,4-oxadiazole |
| 2191 | 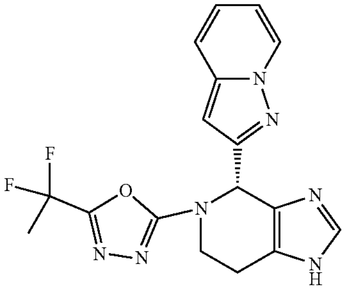 [SMILES: CC(F)(F)c1nnc(N2CCc3[nH]cnc3[C@H]2c2cc3ccccn3n2)o1] | (S)-2-(1,1-difluoroethyl)-5-(4-(pyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
|---|---|---|
| | Pyrazolo[1,5-a]pyridines | |
| 2192 | 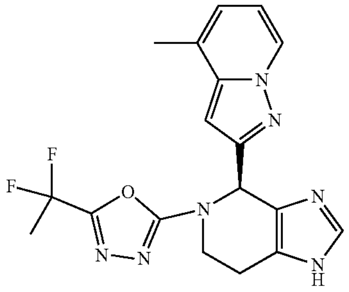 [SMILES: Cc1cccn2nc([C@H]3c4nc[nH]c4CCN3c3nnc(C(C)(F)F)o3)cc12] | (R)-2-(1,1-difluoroethyl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2193 | 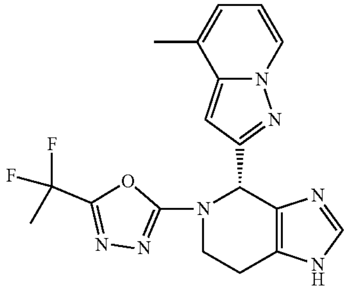 | (S)-2-(1,1-difluoroethyl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2194 | 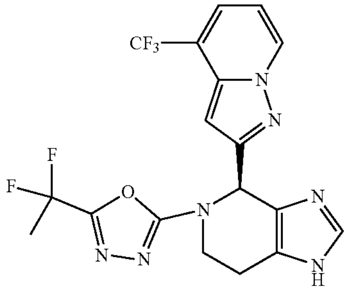 [SMILES: CC(F)(F)c1nnc(N2CCc3[nH]cnc3[C@@H]2c2cc3c(C(F)(F)F)cccn3n2)o1] | (R)-2-(1,1-difluoroethyl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2195 | 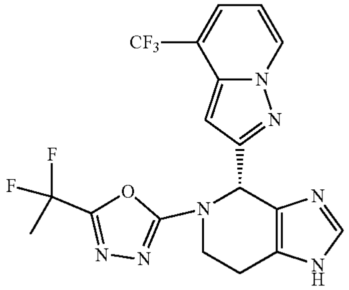 [SMILES: CC(F)(F)c1nnc(N2CCc3[nH]cnc3[C@H]2c2cc3c(C(F)(F)F)cccn3n2)o1] | (S)-2-(1,1-difluoroethyl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2196 | 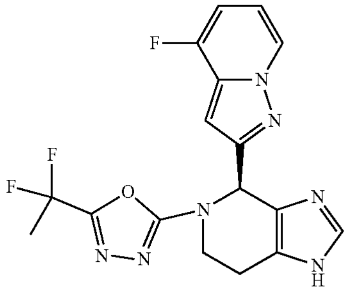 [SMILES: CC(F)(F)c1nnc(N2CCc3[nH]cnc3[C@@H]2c2cc3c(F)cccn3n2)o1] | (R)-2-(1,1-difluoroethyl)-5-(4-(4-fluoropyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2197 | 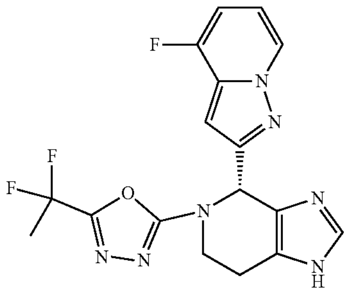 [SMILES: CC(F)(F)c1nnc(N2CCc3[nH]cnc3[C@H]2c2cc3c(F)cccn3n2)o1] | (S)-2-(1,1-difluoroethyl)-5-(4-(4-fluoropyrazolo[1,5-a]pyridin-2-yl)-1,4,6,7-tetrahydro-5H-imidazo[4,5-c]pyridin-5-yl)-1,3,4-oxadiazole |
| 2198 | 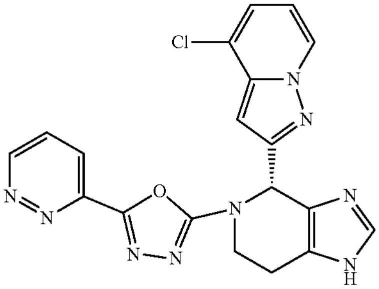 [SMILES: Clc1cccn2nc([C@@H]3c4nc[nH]c4CCN3c3nnc(-c4cccnn4)o3)cc12] | (S)-2-(4-(4-chloropyrazolo[1,5-a]pyridin-2-yl)-1,4,6,7-tetrahydro-5H-imidazo[4,5-c]pyridin-5-yl)-5-(pyridazin-3-yl)-1,3,4-oxadiazole |
| 2199 | 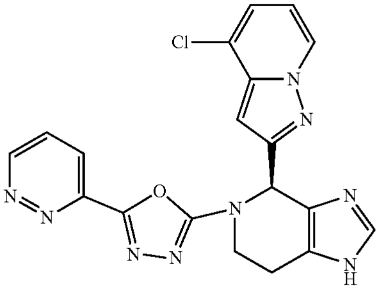 [SMILES: Clc1cccn2nc([C@H]3c4nc[nH]c4CCN3c3nnc(-c4cccnn4)o3)cc12] | (R)-2-(4-(4-chloropyrazolo[1,5-a]pyridin-2-yl)-1,4,6,7-tetrahydro-5H-imidazo[4,5-c]pyridin-5-yl)-5-(pyridazin-3-yl)-1,3,4-oxadiazole |
| 2200 | 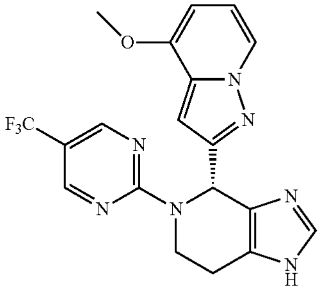 [SMILES: COc1cccn2nc([C@@H]3c4nc[nH]c4CCN3c3ncc(C(F)(F)F)cn3)cc12] | (S)-4-(4-methoxypyrazolo[1,5-a]pyridin-2-yl)-5-(5-(trifluoromethyl)pyrimidin-2-yl)-4,5,6,7-tetrahydro-1H-imidazo[4,5-c]pyridine |
| 2201 | 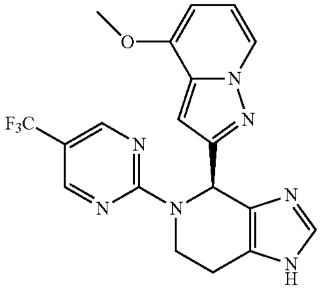 [SMILES: COc1cccn2nc([C@H]3c4nc[nH]c4CCN3c3ncc(C(F)(F)F)cn3)cc12] | (R)-4-(4-methoxypyrazolo[1,5-a]pyridin-2-yl)-5-(5-(trifluoromethyl)pyrimidin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 2202 | 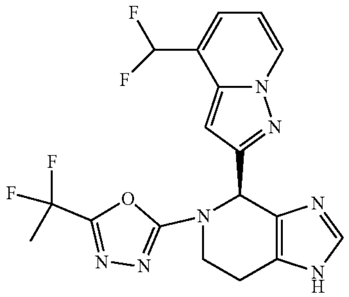 [SMILES: CC(F)(F)c1nnc(N2CCc3[nH]cnc3[C@@H]2c2cc3c(C(F)F)cccn3n2)o1] | (R)-2-(1,1-difluoroethyl)-5-(4-(4-(difluoromethyl)pyrazolo[1,5-a]pyridin-2-yl)-1,4,6,7-tetrahydro-5H-imidazo[4,5-c]pyridin-5-yl)-1,3,4-oxadiazole |
| 2203 | 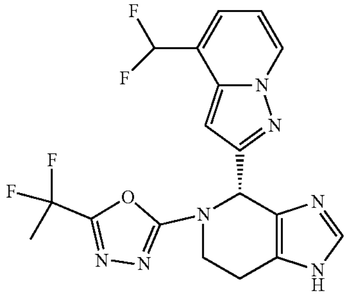 [SMILES: CC(F)(F)c1nnc(N2CCc3[nH]cnc3[C@H]2c2cc3c(C(F)F)cccn3n2)o1] | (S)-2-(1,1-difluoroethyl)-5-(4-(4-(difluoromethyl)pyrazolo[1,5-a]pyridin-2-yl)-1,4,6,7-tetrahydro-5H-imidazo[4,5-c]pyridin-5-yl)-1,3,4-oxadiazole |
| 2204 | 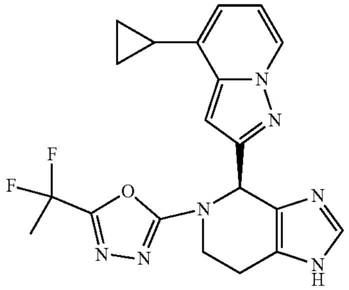 [SMILES: CC(F)(F)c1nnc(N2CCc3[nH]cnc3[C@@H]2c2cc3c(C4CC4)cccn3n2)o1] | (R)-2-(4-(4-cyclopropylpyrazolo[1,5-a]pyridin-2-y]l)-1,4,6,7-tetrahydro-5H-imidazo[4,5-c]pyridin-5-yl)-5-(1,1-difluoroethyl)-1,3,4-oxadiazole |
| 2205 | 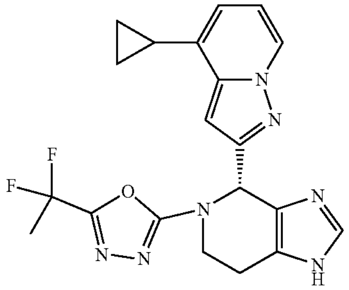 [SMILES: CC(F)(F)c1nnc(N2CCc3[nH]cnc3[C@H]2c2cc3c(C4CC4)cccn3n2)o1] | (S)-2-(4-(4-cyclopropylpyrazolo[1,5-a]pyridin-2-yl)-1,4,6,7-tetrahydro-5H-imidazo[4,5-c]pyridin-5-yl)-5-(1,1-difluoroethyl)-1,3,4-oxadiazole |
| 2206 | 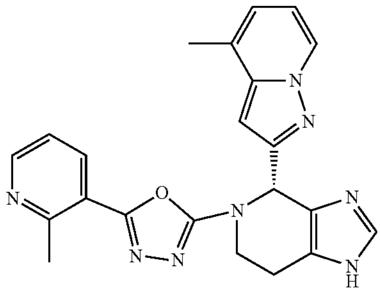 [SMILES: Cc1ncccc1-c1nnc(N2CCc3[nH]cnc3[C@H]2c2cc3c(C)cccn3n2)o1] | (S)-2-(4-(4-methylpyrazolo[1,5-a]pyridin-2-yl)-1,4,6,7-tetrahydro-5H-imidazo[4,5-c]pyridin-5-yl)-5-(2-methylpyridin-3-yl)-1,3,4-oxadiazole |

TABLE 1-continued

| Ex. # | Structure | Name |
|---|---|---|
| | Pyrazolo[1,5-a]pyridines | |
| 2207 | 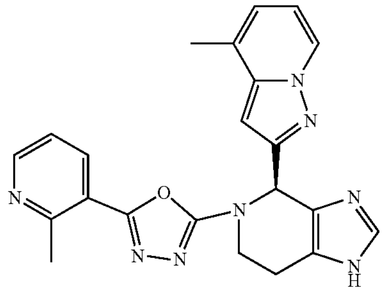 [SMILES: Cc1ncccc1-c1nnc(N2CCc3[nH]cnc3[C@@H]2c2cc3c(C)cccn3n2)o1] | (R)-2-(4-(4-methylpyrazolo[1,5-a]pyridin-2-yl)-1,4,6,7-tetrahydro-5H-imidazo[4,5-c]pyridin-5-yl)-5-(2-methylpyridin-3-yl)-1,3,4-oxadiazole |
| 2208 | 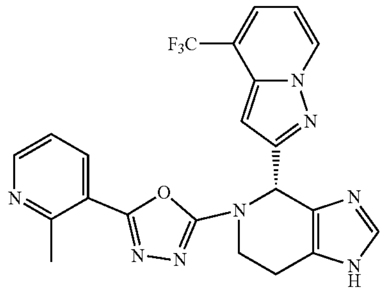 [SMILES: Cc1ncccc1-c1nnc(N2CCc3[nH]cnc3[C@H]2c2cc3c(C(F)(F)F)cccn3n2)o1] | (S)-2-(2-methylpyridin-3-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2209 | 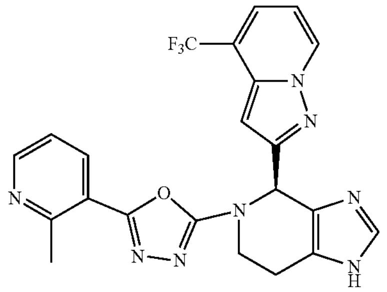 [SMILES: Cc1ncccc1-c1nnc(N2CCc3[nH]cnc3[C@@H]2c2cc3c(C(F)(F)F)cccn3n2)o1] | (R)-2-(2-methylpyridin-3-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2210 | 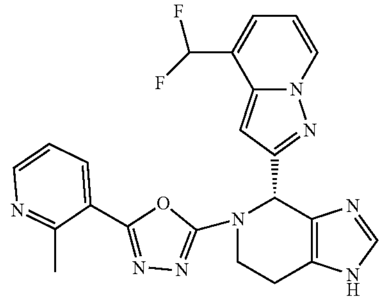 [SMILES: Cc1ncccc1-c1nnc(N2CCc3[nH]cnc3[C@H]2c2cc3c(C(F)F)cccn3n2)o1] | (S)-2-(4-(4-(difluoromethyl)pyrazolo[1,5-a]pyridin-2-yl)-1,4,6,7-tetrahydro-5H-imidazo[4,5-c]pyridin-5-yl)-5-(2-methylpyridin-3-yl)-1,3,4-oxadiazole |
| 2211 | 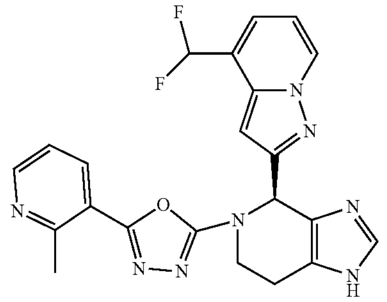 [SMILES: Cc1ncccc1-c1nnc(N2CCc3[nH]cnc3[C@@H]2c2cc3c(C(F)F)cccn3n2)o1] | (R)-2-(4-(4-(difluoromethyl)pyrazolo[1,5-a]pyridin-2-yl)-1,4,6,7-tetrahydro-5H-imidazo[4,5-c]pyridin-5-yl)-5-(2-methylpyridin-3-yl)-1,3,4-oxadiazole |

TABLE 1-continued

| Ex. # | Structure | Name |
|---|---|---|
| | Pyrazolo[1,5-a]pyridines | |
| 2212 | 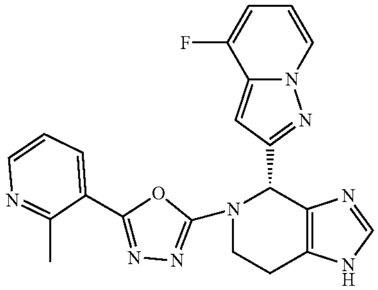 [SMILES: Cc1ncccc1-c1nnc(N2CCc3[nH]cnc3[C@H]2c2cc3c(F)cccn3n2)o1] | (S)-2-(4-(4-fluoropyrazolo [1,5-a]pyridin-2-yl)-1,4,6,7-tetrahydro-5H-imidazo [4,5-c]pyridin-5-yl)-5-(2-methylpyridin-3-yl)-1,3,4-oxadiazole |
| 2213 | 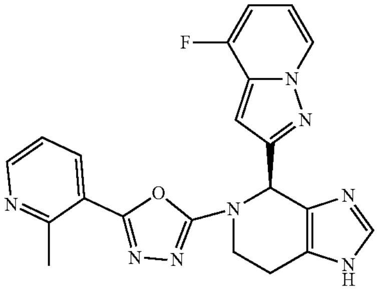 [SMILES: Cc1ncccc1-c1nnc(N2CCc3[nH]cnc3[C@@H]2c2cc3c(F)cccn3n2)o1] | (R)-2-(4-(4-fluoropyrazolo [1,5-a]pyridin-2-yl)-1,4,6,7-tetrahydro-5H-imidazo [4,5-c]pyridin-5-yl)-5-(2-methylpyridin-3-yl)-1,3,4-oxadiazole |
| 2214 | 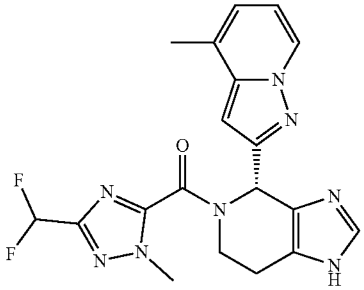 | (S)-(3-(difluoromethyl)-1-methyl-1H-1,2,4-triazol-5-yl)(4-(4-methylpyrazolo[1,5-a] pyridin-2-yl)-6,7-dihydro-1H-imidazo[4,5-c]pyridin-5(4H)-yl)methanone |
| 2215 | 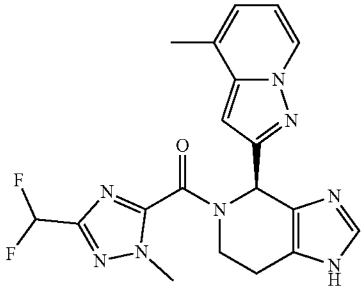 | (R)-(3-(difluoromethyl)-1-methyl-1H-1,2,4-triazol-5-yl)(4-(4-methylpyrazolo[1,5-a] pyridin-2-yl)-6,7-dihydro-1H-imidazo[4,5-c]pyridin-5(4H)-yl)methanone |
| 2216 | 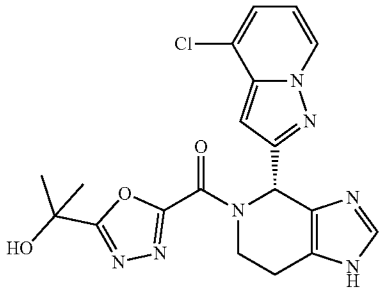 [SMILES: CC(C)(O)c1nnc(C(=O)N2CCc3[nH]cnc3[C@H]2c2cc3c(Cl)cccn3n2)o1] | (S)-(4-(4-chloropyrazolo [1,5-a]pyridin-2-y])-6,7-dihydro-1H-imidazo[4,5-c] pyridin-5(4H)-yl)(2-(2-hydroxypropan-2-yl)oxazol-5-yl)methanone |

TABLE 1-continued

| Ex. # | Structure | Name |
|---|---|---|
| | Pyrazolo[1,5-a]pyridines | |
| 2217 | 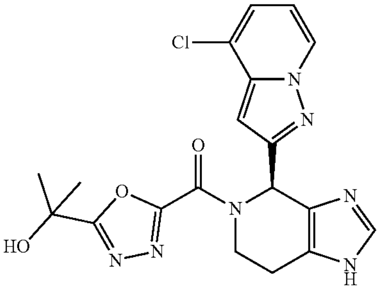 [SMILES: CC(C)(O)c1nnc(C(=O)N2CCc3[nH]cnc3[C@@H]2c2cc3c(Cl)cccn3n2)o1] | (R)-(4-(4-chloropyrazolo[1,5-a]pyridin-2-yl)-6,7-dihydro-1H-imidazo[4,5-c]pyridin-5(4H)-yl)(2-(2-hydroxypropan-2-yl)oxazol-5-yl)methanone |
| 2218 | 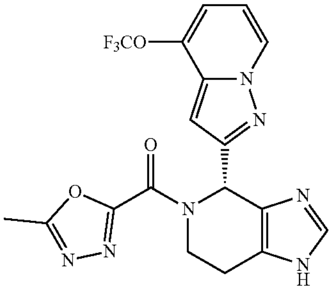 [SMILES: Cc1nnc(C(=O)N2CCc3[nH]cnc3[C@H]2c2cc3c(OC(F)(F)F)cccn3n2)o1] | (S)-(5-methyl-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 2219 | 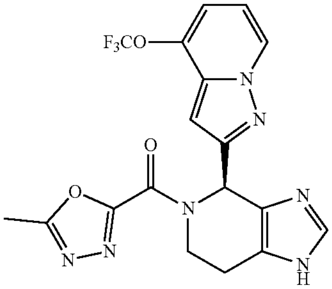 [SMILES: Cc1nnc(C(=O)N2CCc3[nH]cnc3[C@@H]2c2cc3c(OC(F)(F)F)cccn3n2)o1] | (R)-(5-methyl-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 2220 | 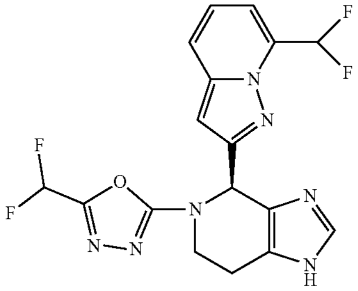 [SMILES: FC(F)c1nnc(N2CCc3[nH]cnc3[C@@H]2c2cc3cccc(C(F)F)n3n2)o1] | (R)-2-(difluoromethyl)-5-(4-(7-(difluoromethyl)pyrazolo[1,5-a]pyridin-2-yl)-1,4,6,7-tetrahydro-5H-imidazo[4,5-c]pyridin-5-yl)-1,3,4-oxadiazole |
| 2221 | 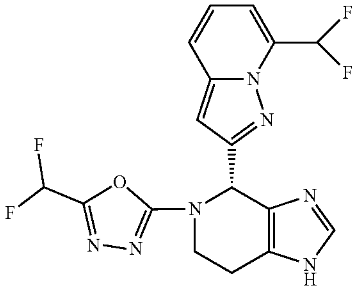 [SMILES: FC(F)c1nnc(N2CCc3[nH]cnc3[C@H]2c2cc3cccc(C(F)F)n3n2)o1] | (S)-2-(difluoromethyl)-5-(4-(7-(difluoromethyl)pyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
| --- | --- | --- |
| | Pyrazolo[1,5-a]pyridines | |
| 2222 | 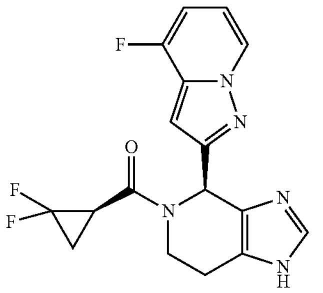 | ((R)-2,2-difluorocyclopropyl) ((R)-4-(4-fluoropyrazolo[1,5-a]pyridin-2-yl)-1,4,6,7-tetrahydro-5H-imidazo[4,5-c]pyridin-5-yl)methanone |
| 2223 | 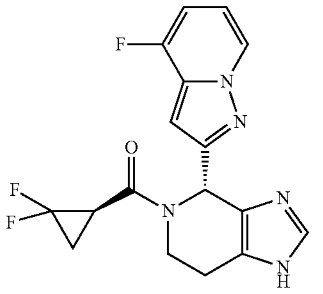 | ((R)-2,2-difluorocyclopropyl) ((S)-4-(4-fluoropyrazolo[1,5-a]pyridin-2-yl)-1,4,6,7-tetrahydro-5H-imidazo[4,5-c]pyridin-5-yl)methanone |
| 2224 | 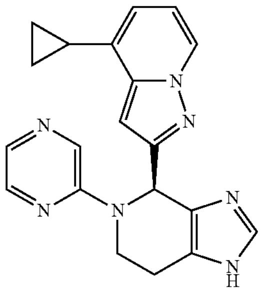 [SMILES: c1cc(C2CC2)c2cc([C@H]3c4nc[nH]c4CCN3c3cnccn3)nn2c1] | (R)-4-(4-cyclopropylpyrazolo [1,5-a]pyridin-2-yl)-5-(pyrazin-2-yl)-4,5,6,7-tetrahydro-1H-imidazo[4,5-c]pyridine |
| 2225 | 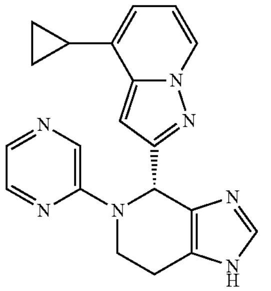 | (S)-4-(4-cyclopropylpyrazolo [1,5-a]pyridin-2-yl)-5-(pyrazin-2-yl)-4,5,6,7-tetrahydro-1H-imidazo[4,5-c]pyridine |
| 2226 | 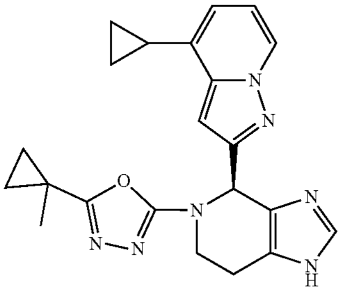 [SMILES: CC1(c2nnc(N3CCc4[nH]cnc4[C@@H]3c3cc4c(C5CC5)cccn4n3)o2)CC1] | (R)-2-(4-(4-cyclopropylpyrazolo [1,5-a]pyridin-2-yl)-1,4,6,7-tetrahydro-5H-imidazo [4,5-c]pyridin-5-yl)-5-(1-methylcyclopropyl)-1,3,4-oxadiazole |

TABLE 1-continued

| Ex. # | Structure | Name |
|---|---|---|
| | Pyrazolo[1,5-a]pyridines | |
| 2227 | 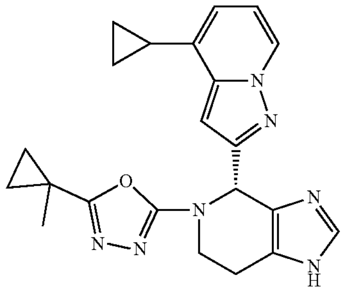 [SMILES: CC1(c2nnc(N3CCc4[nH]cnc4[C@H]3c3cc4c(C5CC5)cccn4n3)o2)CC1] | (S)-2-(4-(4-cyclopropylpyrazolo[1,5-a]pyridin-2-yl)-1,4,6,7-tetrahydro-5H-imidazo[4,5-c]pyridin-5-yl)-5-(1-methylcyclopropyl)-1,3,4-oxadiazole |
| 2228 | 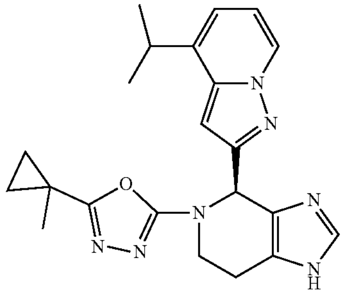 [SMILES: CC(C)c1cccn2nc([C@H]3c4nc[nH]c4CCN3c3nnc(C4(C)CC4)o3)cc12] | (R)-2-(4-(4-isopropylpyrazolo[1,5-a]pyridin-2-yl)-1,4,6,7-tetrahydro-5H-imidazo[4,5-c]pyridin-5-yl)-5-(1-methylcyclopropyl)-1,3,4-oxadiazole |
| 2229 | 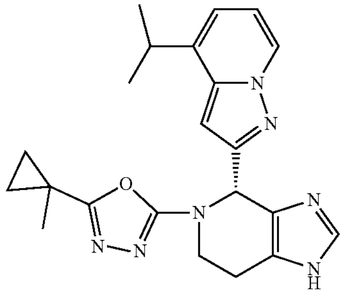 [SMILES: CC(C)c1cccn2nc([C@@H]3c4nc[nH]c4CCN3c3nnc(C4(C)CC4)o3)cc12] | (S)-2-(4-(4-isopropylpyrazolo[1,5-a]pyridin-2-yl)-1,4,6,7-tetrahydro-5H-imidazo[4,5-c]pyridin-5-yl)-5-(1-methylcyclopropyl)-1,3,4-oxadiazole |
| 2230 | 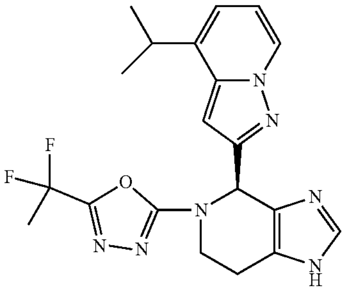 [SMILES: CC(C)c1cccn2nc([C@H]3c4nc[nH]c4CCN3c3nnc(C(C)(F)F)o3)cc12] | (R)-2-(1,1-difluoroethyl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |
| 2231 | 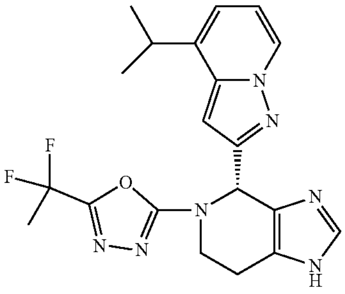 [SMILES: CC(C)c1cccn2nc([C@@H]3c4nc[nH]c4CCN3c3nnc(C(C)(F)F)o3)cc12] | (S)-2-(1,1-difluoroethyl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2232 | 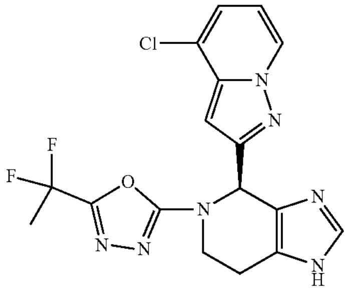 [SMILES: CC(F)(F)c1nnc(N2CCc3[nH]cnc3[C@@H]2c2cc3c(Cl)cccn3n2)o1] | (R)-2-(4-(4-chloropyrazolo [1,5-a]pyridin-2-yl)-1,4,6,7-tetrahydro-5H-imidazo [4,5-c]pyridin-5-yl)-5-(1,1-difluoroethyl)-1,3,4-oxadiazole |
| 2233 | 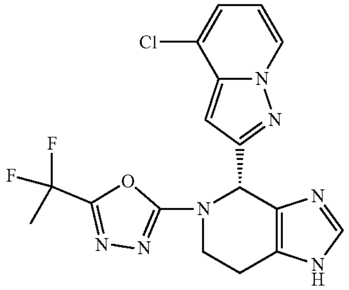 [SMILES: CC(F)(F)c1nnc(N2CCc3[nH]cnc3[C@H]2c2cc3c(Cl)cccn3n2)o1] | (S)-2-(4-(4-chloropyrazolo [1,5-a]pyridin-2-yl)-1,4,6,7-tetrahydro-5H-imidazo [4,5-c]pyridin-5-yl)-5-(1,1-difluoroethyl)-1,3,4-oxadiazole |
| 2234 | 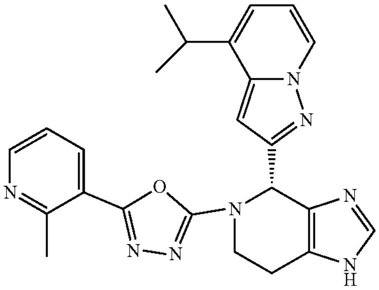 [SMILES: Cc1ncccc1-c1nnc(N2CCc3[nH]cnc3[C@H]2c2cc3c(C(C)C)cccn3n2)o1] | (S)-2-(4-(4-isopropylpyrazolo [1,5-a]pyridin-2-yl)-1,4,6,7-tetrahydro-5H-imidazo [4,5-c]pyridin-5-yl)-5-(2-methylpyridin-3-yl)-1,3,4-oxadiazole |
| 2235 | 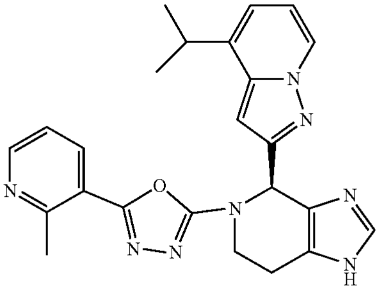 [SMILES: Cc1ncccc1-c1nnc(N2CCc3[nH]cnc3[C@@H]2c2cc3c(C(C)C)cccn3n2)o1] | (R)-2-(4-(4-isopropylpyrazolo [1,5-a]pyridin-2-yl)-1,4,6,7-tetrahydro-5H-imidazo [4,5-c]pyridin-5-yl)-5-(2-methylpyridin-3-yl)-1,3,4-oxadiazole |
| 2236 | 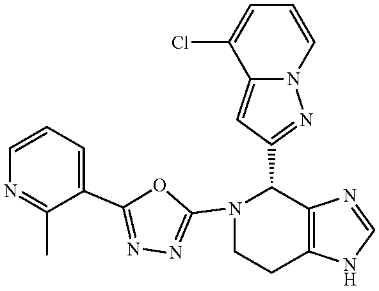 [SMILES: Cc1ncccc1-c1nnc(N2CCc3[nH]cnc3[C@H]2c2cc3c(Cl)cccn3n2)o1] | (S)-2-(4-(4-chloropyrazolo [1,5-a]pyridin-2-yl)-1,4,6,7-tetrahydro-5H-imidazo [4,5-c]pyridin-5-yl)-5-(2-methylpyridin-3-yl)-1,3,4-oxadiazole |

TABLE 1-continued

| Pyrazolo[1,5-a]pyridines | | |
|---|---|---|
| Ex. # | Structure | Name |
| 2237 | 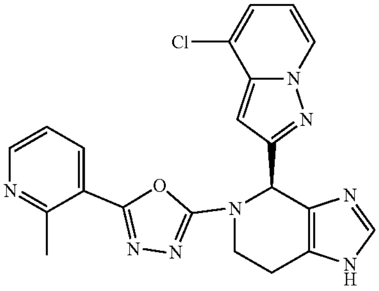 [SMILES: Cc1ncccc1-c1nnc(N2CCc3[nH]cnc3[C@@H]2c2cc3c(Cl)cccn3n2)o1] | (R)-2-(4-(4-chloropyrazolo[1,5-a]pyridin-2-yl)-1,4,6,7-tetrahydro-5H-imidazo[4,5-c]pyridin-5-yl)-5-(2-methylpyridin-3-yl)-1,3,4-oxadiazole |
| 2238 | 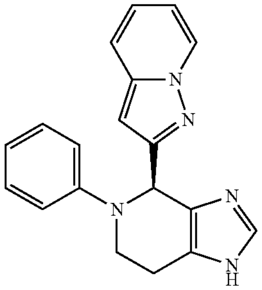 [SMILES: c1ccc(N2CCc3[nH]cnc3[C@@H]2c2cc3ccccn3n2)cc1] | (R)-5-phenyl-4-(pyrazolo[1,5-a]pyridin-2-y]l)-4,5,6,7-tetrahydro-1H-imidazo[4,5-c]pyridine |
| 2239 | 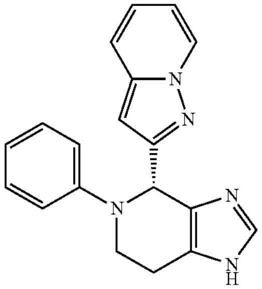 [SMILES: c1ccc(N2CCc3[nH]cnc3[C@H]2c2cc3ccccn3n2)cc1] | (S)-5-phenyl-4-(pyrazolo[1,5-a]pyridin-2-yl)-4,5,6,7-tetrahydro-1H-imidazo[4,5-c]pyridine |
| 2240 | 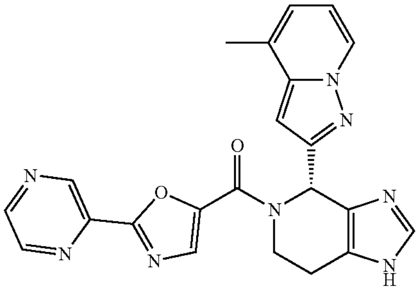 [SMILES: Cc1cccn2nc([C@@H]3c4nc[nH]c4CCN3C(=O)c3cnc(-c4cnccn4)o3)cc12] | (S)-(4-(4-methylpyrazolo[1,5-a]pyridin-2-yl)-1,4,6,7-tetrahydro-5H-imidazo[4,5-c]pyridin-5-yl)(2-(pyrazin-2-yl)oxazol-5-yl)methanone |
| 2241 | 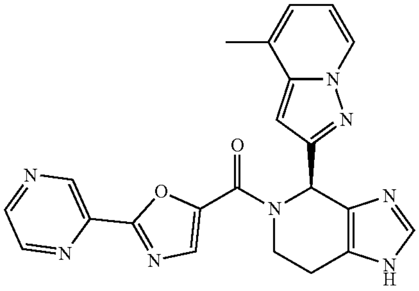 [SMILES: Cc1cccn2nc([C@H]3c4nc[nH]c4CCN3C(=O)c3cnc(-c4cnccn4)o3)cc12] | (R)-(4-(4-methylpyrazolo[1,5-a]pyridin-2-yl)-1,4,6,7-tetrahydro-5H-imidazo[4,5-c]pyridin-5-yl)(2-(pyrazin-2-yl)oxazol-5-yl)methanone |

TABLE 1-continued

| Ex. # | Structure | Name |
|---|---|---|
| | Pyrazolo[1,5-a]pyridines | |
| 2242 | 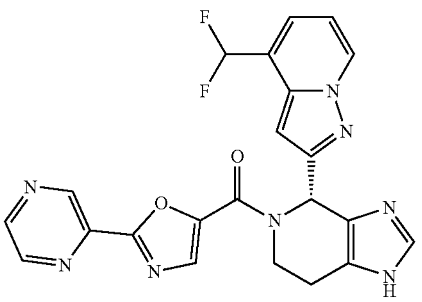 | (S)-(4-(4-(difluoromethyl) pyrazolo[1,5-a]pyridin-2-yl)-1,4,6,7-tetrahydro-5H-imidazo [4,5-c]pyridin-5-yl)(2-(pyrazin-2-yl)oxazol-5-yl) methanone |
| 2243 | 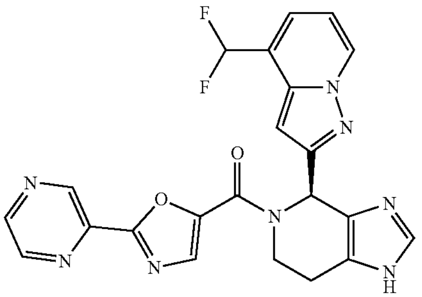 | (R)-(4-(4-(difluoromethyl) pyrazolo[1,5-a]pyridin-2-y]l)-1,4,6,7-tetrahydro-5H-imidazo [4,5-c]pyridin-5-yl)(2-(pyrazin-2-yl)oxazol-5-yl) methanone |
| 2244 | 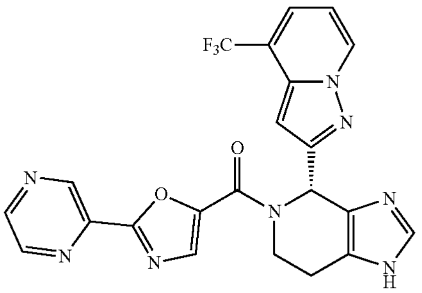 | (S)-(2-(pyrazin-2-yl) oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2245 | 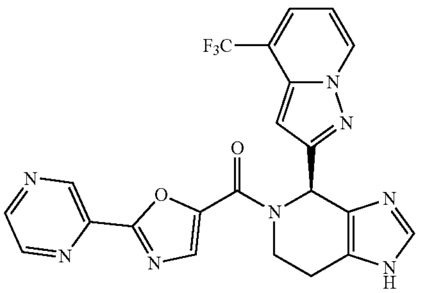 [SMILES: O=C(c1cnc(-c2cnccn2)o1)N1CCc2[nH]cnc2[C@@H]1c1cc2c(C(F)(F)F)cccn2n1] | (R)-(2-(pyrazin-2-yl) oxazol-5-yl)(4-(4-(trifluoromethyl)pyrazolo [1,5-a]pyridin-2-yl)-1,4,6,7-tetrahydro-5H-imidazo[4,5-c] pyridin-5-yl)methanone |
| 2246 | 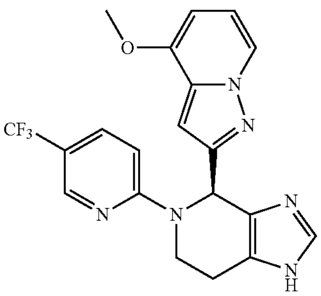 [SMILES: COc1cccn2nc([C@H]3c4nc[nH]c4CCN3c3ccc(C(F)(F)F)cn3)cc12] | (R)-4-(4-methoxypyrazolo [1,5-a]pyridin-2-yl)-5-(5-(trifluoromethyl)pyridin-2-yl)-4,5,6,7-tetrahydro-1H-imidazo[4,5-c]pyridine |

TABLE 1-continued

| Ex. # | Structure | Name |
|---|---|---|
| Pyrazolo[1,5-a]pyridines | | |
| 2247 | 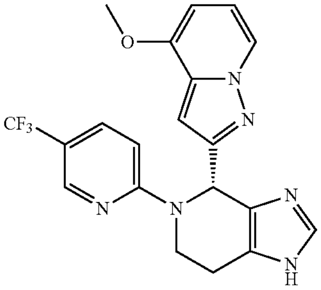 [SMILES: COc1cccn2nc([C@@H]3c4nc[nH]c4CCN3c3ccc(C(F)(F)F)cn3)cc12] | (S)-4-(4-methoxypyrazolo[1,5-a]pyridin-2-yl)-5-(5-(trifluoromethyl)pyridin-2-yl)-4,5,6,7-tetrahydro-1H-imidazo[4,5-c]pyridine |
| 2248 | 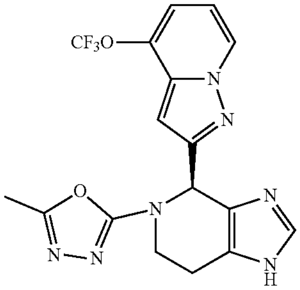 | (R)-2-methyl-5-(4-(4-(trifluoromethoxy)pyrazolo[1,5-a]pyridin-2-yl)-1,4,6,7-tetrahydro-5H-imidazo[4,5-c]pyridin-5-yl)-1,3,4-oxadiazole |
| 2249 | 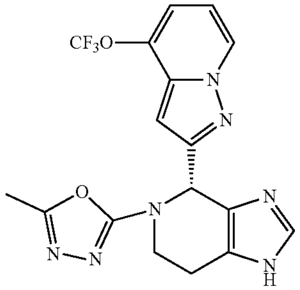 | (S)-2-methyl-5-(4-(4-(trifluoromethoxy)pyrazolo[1,5-a]pyridin-2-yl)-1,4,6,7-tetrahydro-5H-imidazo[4,5-c]pyridin-5-yl)-1,3,4-oxadiazole |
| 2250 | 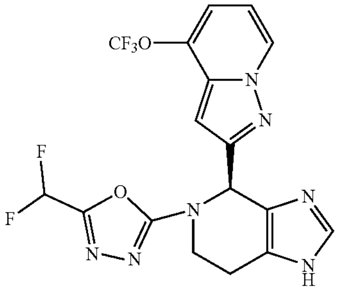 | (R)-2-(difluoromethyl)-5-(4-(4-(trifluoromethoxy)pyrazolo[1,5-a]pyridin-2-yl)-1,4,6,7-tetrahydro-5H-imidazo[4,5-c]pyridin-5-yl)-1,3,4-oxadiazole |
| 2251 | 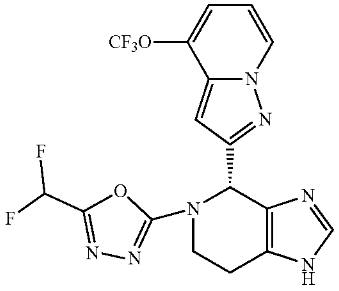 | (S)-2-(difluoromethyl)-5-(4-(4-(trifluoromethoxy)pyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2252 | 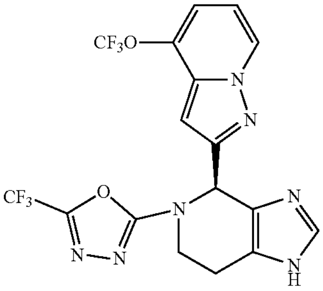 | (R)-2-(4-(4-(trifluoromethoxy )pyrazolo[1,5-a]pyridin-2-yl)-1,4,6,7-tetrahydro-5H-imidazo[4,5-c]pyridin-5-yl)-5-(trifluoromethyl)-1,3,4-oxadiazole |
| 2253 | 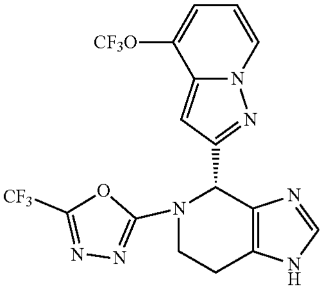 | (S)-2-(4-(4-(trifluoromethoxy) pyrazolo[1,5-a]pyridin-2-yl)-1,4,6,7-tetrahydro-5H-imidazo[4,5-c]pyridin-5-yl)-5-(trifluoromethyl)-1,3,4-oxadiazole |
| 2254 | 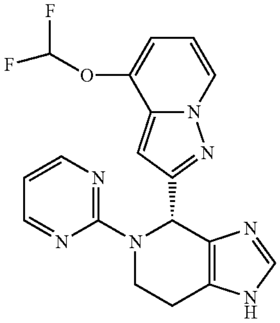 [SMILES: FC(F)Oc1cccn2nc([C@@H]3c4nc[nH]c4CCN3c3ncccn3)cc12] | (S)-4-(4-(difluoromethoxy) pyrazolo[1,5-a]pyridin-2-yl)-5-(pyrimidin-2-yl)-4,5,6,7-tetrahydro-1H-imidazo[4,5-c]pyridine |
| 2255 | 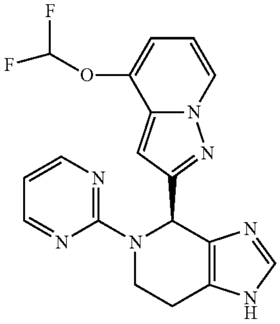 [SMILES: FC(F)Oc1cccn2nc([C@H]3c4nc[nH]c4CCN3c3ncccn3)cc12] | (R)-4-(4-(difluoromethoxy) pyrazolo[1,5-a]pyridin-2-yl)-5-(pyrimidin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 2256 | 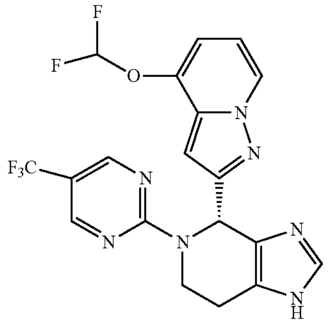 [SMILES: FC(F)Oc1cccn2nc([C@@H]3c4nc[nH]c4CCN3c3ncc(C(F)(F)F)cn3)cc12] | (S)-4-(4-(difluoromethoxy) pyrazolo[1,5-a]pyridin-2-yl)-5-(5-(trifluoromethyl)pyrimidin-2-yl)-4,5,6,7-tetrahydro-1H-imidazo[4,5-c]pyridine |
| 2257 | 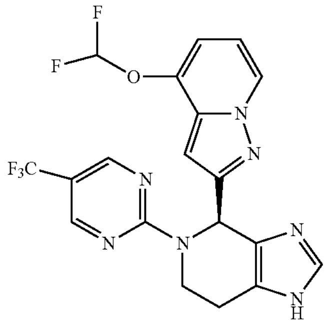 [SMILES: FC(F)Oc1cccn2nc([C@H]3c4nc[nH]c4CCN3c3ncc(C(F)(F)F)cn3)cc12] | (R)-4-(4-(difluoromethoxy) pyrazolo[1,5-a]pyridin-2-yl)-5-(5-(trifluoromethyl)pyrimidin-2-yl)-4,5,6,7-tetrahydro-1H-imidazo[4,5-c]pyridine |
| 2258 | 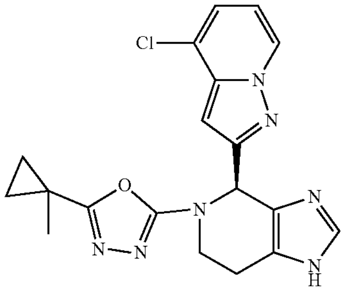 [SMILES: CC1(c2nnc(N3CCc4[nH]cnc4[C@@H]3c3cc4c(Cl)cccn4n3)o2)CC1] | (R)-2-(4-(4-chloropyrazolo [1,5-a]pyridin-2-yl)-1,4,6,7-tetrahydro-5H-imidazo [4,5-c]pyridin-5-yl)-5-(1-methylcyclopropyl)-1,3,4-oxadiazole |
| 2259 | 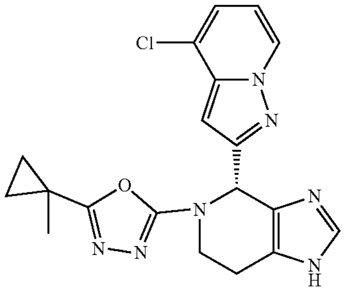 [SMILES: CC1(c2nnc(N3CCc4[nH]cnc4[C@H]3c3cc4c(Cl)cccn4n3)o2)CC1] | (S)-2-(4-(4-chloropyrazolo [1,5-a]pyridin-2-yl)-1,4,6,7-tetrahydro-5H-imidazo [4,5-c]pyridin-5-yl)-5-(1-methylcyclopropyl)-1,3,4-oxadiazole |
| 2260 | 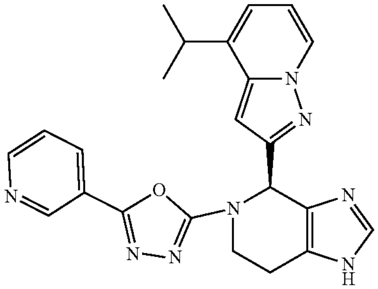 [SMILES: CC(C)c1cccn2nc([C@H]3c4nc[nH]c4CCN3c3nnc(-c4cccnc4)o3)cc12] | (R)-2-(4-(4-isopropylpyrazolo [1,5-a]pyridin-2-yl)-1,4,6,7-tetrahydro-5H-imidazo [4,5-c]pyridin-5-yl)-5-(pyridin-3-yl)-1,3,4-oxadiazole |

TABLE 1-continued

| Ex. # | Structure | Name |
|---|---|---|
| | Pyrazolo[1,5-a]pyridines | |
| 2261 | 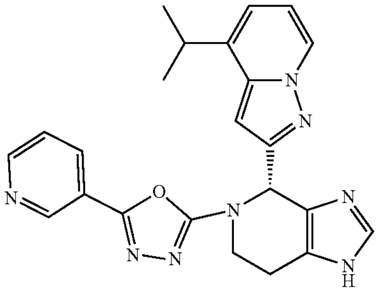 [SMILES: CC(C)c1cccn2nc([C@@H]3c4nc[nH]c4CCN3c3nnc(-c4cccnc4)o3)cc12] | (S)-2-(4-(4-isopropylpyrazolo[1,5-a]pyridin-2-yl)-1,4,6,7-tetrahydro-5H-imidazo[4,5-c]pyridin-5-yl)-5-(pyridin-3-yl)-1,3,4-oxadiazole |
| 2262 | 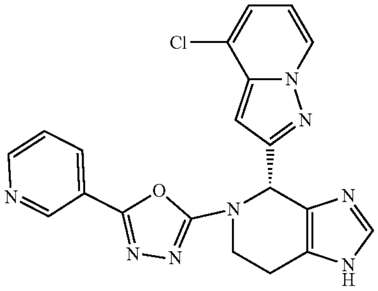 [SMILES: Clc1cccn2nc([C@@H]3c4nc[nH]c4CCN3c3nnc(-c4cccnc4)o3)cc12] | (S)-2-(4-(4-chloropyrazolo[1,5-a]pyridin-2-yl)-1,4,6,7-tetrahydro-5H-imidazo[4,5-c]pyridin-5-yl)-5-(pyridin-3-yl)-1,3,4-oxadiazole |
| 2263 | 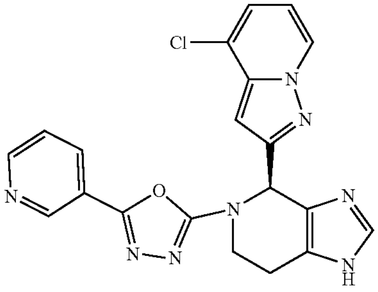 [SMILES: Clc1cccn2nc([C@H]3c4nc[nH]c4CCN3c3nnc(-c4cccnc4)o3)cc12] | (R)-2-(4-(4-chloropyrazolo[1,5-a]pyridin-2-yl)-1,4,6,7-tetrahydro-5H-imidazo[4,5-c]pyridin-5-yl)-5-(pyridin-3-yl)-1,3,4-oxadiazole |
| 2264 | 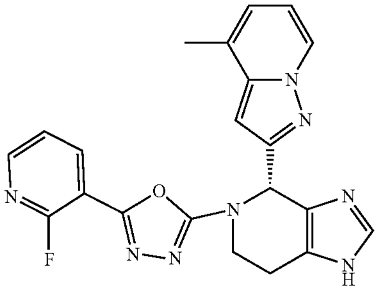 [SMILES: Cc1cccn2nc([C@@H]3c4nc[nH]c4CCN3c3nnc(-c4cccnc4F)o3)cc12] | (S)-2-(2-fluoropyridin-3-yl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2265 | 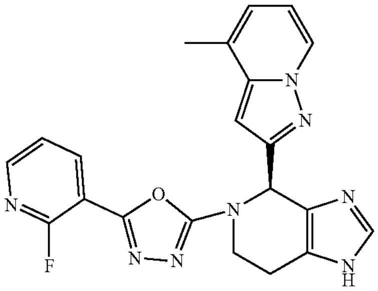 [SMILES: Cc1cccn2nc([C@H]3c4nc[nH]c4CCN3c3nnc(-c4cccnc4F)o3)cc12] | (R)-2-(2-fluoropyridin-3-yl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2266 | 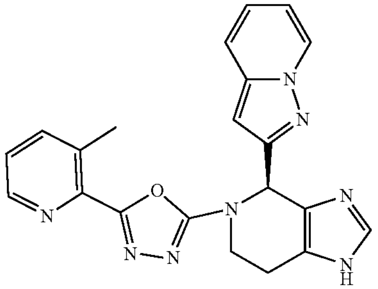 [SMILES: Cc1cccnc1-c1nnc(N2CCc3[nH]cnc3[C@@H]2c2cc3ccccn3n2)o1] | (R)-2-(3-methylpyridin-2-yl)-5-(4-(pyrazolo[1,5-a]pyridin-2-yl)-1,4,6,7-tetrahydro-5H-imidazo[4,5-c]pyridin-5-yl)-1,3,4-oxadiazole |
| 2267 | 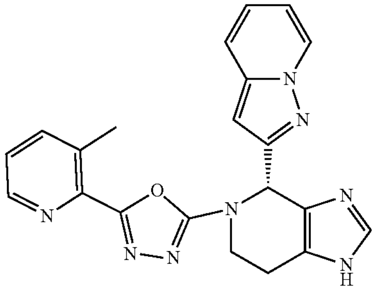 [SMILES: Cc1cccnc1-c1nnc(N2CCc3[nH]cnc3[C@H]2c2cc3ccccn3n2)o1] | (S)-2-(3-methylpyridin-2-yl)-5-(4-(pyrazolo[1,5-a]pyridin-2-yl)-1,4,6,7-tetrahydro-5H-imidazo[4,5-c]pyridin-5-yl)-1,3,4-oxadiazole |
| 2268 | 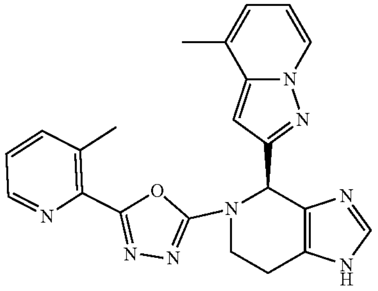 [SMILES: Cc1cccnc1-c1nnc(N2CCc3[nH]cnc3[C@@H]2c2cc3c(C)cccn3n2)o1] | (R)-2-(4-(4-methylpyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |
| 2269 | 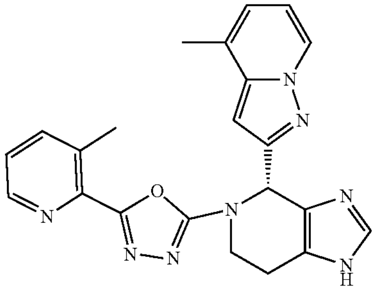 [SMILES: Cc1cccnc1-c1nnc(N2CCc3[nH]cnc3[C@H]2c2cc3c(C)cccn3n2)o1] | (S)-2-(4-(4-methylpyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |
| 2270 | 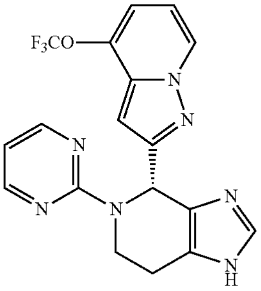 [SMILES: FC(F)(F)Oc1cccn2nc([C@@H]3c4nc[nH]c4CCN3c3ncccn3)cc12] | (S)-5-(pyrimidin-2-yl)-4-(4-(trifluoromethoxy)pyrazolo[1,5-a]pyridin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 2271 | 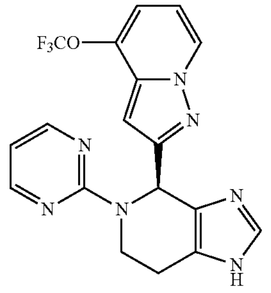 [SMILES: FC(F)(F)Oc1cccn2nc([C@H]3c4nc[nH]c4CCN3c3ncccn3)cc12] | (R)-5-(pyrimidin-2-yl)-4-(4-(trifluoromethoxy)pyrazolo[1,5-a]pyridin-2-yl)-4,5,6,7-tetrahydro-1H-imidazo[4,5-c]pyridine |
| 2272 | 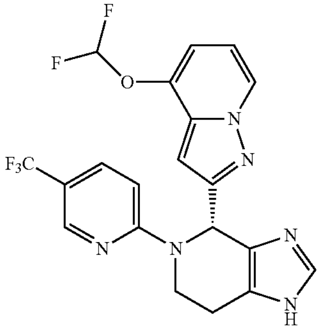 [SMILES: FC(F)Oc1cccn2nc([C@@H]3c4nc[nH]c4CCN3c3ccc(C(F)(F)F)cn3)cc12] | (S)-4-(4-(difluoromethoxy)pyrazolo[1,5-a]pyridin-2-yl)-5-(5-(trifluoromethyl)pyridin-2-yl)-4,5,6,7-tetrahydro-1H-imidazo[4,5-c]pyridine |
| 2273 | 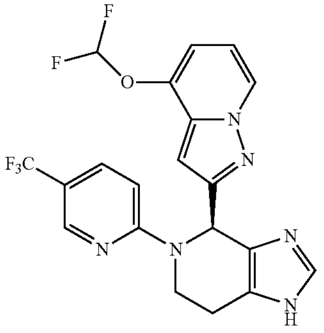 [SMILES: FC(F)Oc1cccn2nc([C@H]3c4nc[nH]c4CCN3c3ccc(C(F)(F)F)cn3)cc12] | (R)-4-(4-(difluoromethoxy)pyrazolo[1,5-a]pyridin-2-yl)-5-(5-(trifluoromethyl)pyridin-2-yl)-4,5,6,7-tetrahydro-1H-imidazo[4,5-c]pyridine |
| 2274 | 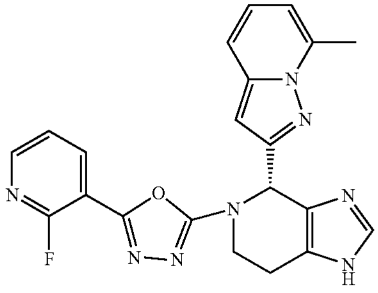 [SMILES: Cc1cccc2cc([C@@H]3c4nc[nH]c4CCN3c3nnc(-c4cccnc4F)o3)nn12] | (S)-2-(2-fluoropyridin-3-yl)-5-(4-(7-methylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
| --- | --- | --- |
| | Pyrazolo[1,5-a]pyridines | |
| 2275 | 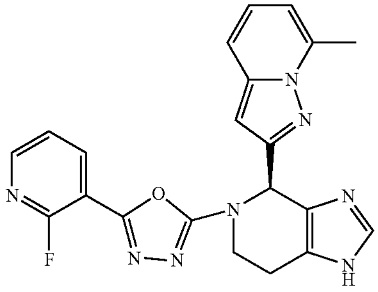 | (R)-2-(2-fluoropyridin-3-yl)-5-(4-(7-methylpyrazolo[1,5-a]pyridin-2-yl)-1,4,6,7-tetrahydro-5H-imidazo[4,5-c]pyridin-5-yl)-1,3,4-oxadiazole |
| 2276 | 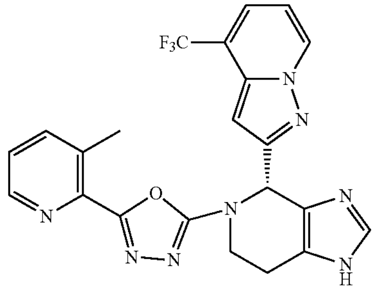 [SMILES: Cc1cccnc1-c1nnc(N2CCc3[nH]cnc3[C@H]2c2cc3c(C(F)(F)F)cccn3n2)o1] | (S)-2-(3-methylpyridin-2-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2277 | 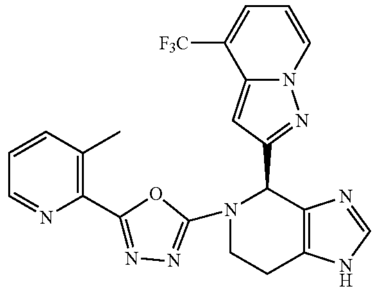 [SMILES: Cc1cccnc1-c1nnc(N2CCc3[nH]cnc3[C@@H]2c2cc3c(C(F)(F)F)cccn3n2)o1] | (R)-2-(3-methylpyridin-2-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2278 | 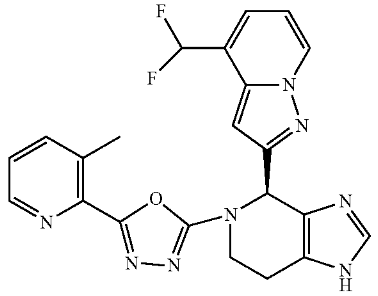 [SMILES: Cc1cccnc1-c1nnc(N2CCc3[nH]cnc3[C@@H]2c2cc3c(C(F)F)cccn3n2)o1] | (R)-2-(4-(4-(difluoromethyl)pyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |
| 2279 | 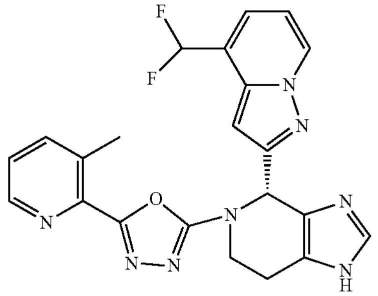 [SMILES: Cc1cccnc1-c1nnc(N2CCc3[nH]cnc3[C@H]2c2cc3c(C(F)F)cccn3n2)o1] | (S)-2-(4-(4-(difluoromethyl)pyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |

TABLE 1-continued

| Pyrazolo[1,5-a]pyridines | | |
|---|---|---|
| Ex. # | Structure | Name |
| 2280 | 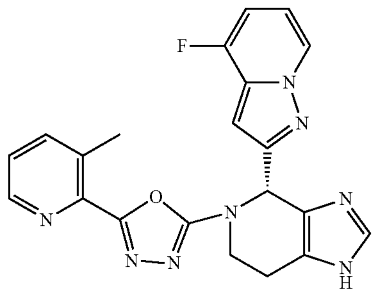 [SMILES: Cc1cccnc1-c1nnc(N2CCc3[nH]cnc3[C@H]2c2cc3c(F)cccn3n2)o1] | (S)-2-(4-(4-fluoropyrazolo [1,5-a]pyridin-2-yl)-1,4,6,7-tetrahydro-5H-imidazo [4,5-c]pyridin-5-yl)-5-(3-methylpyridin-2-yl)-1,3,4-oxadiazole |
| 2281 | 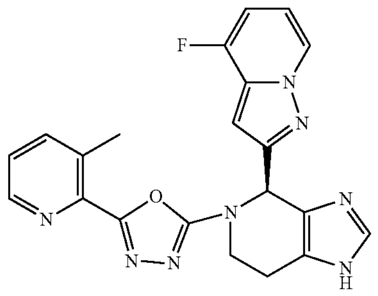 [SMILES: Cc1cccnc1-c1nnc(N2CCc3[nH]cnc3[C@@H]2c2cc3c(F)cccn3n2)o1] | (R)-2-(4-(4-fluoropyrazolo [1,5-a]pyridin-2-yl)-1,4,6,7-tetrahydro-5H-imidazo [4,5-c]pyridin-5-yl)-5-(3-methylpyridin-2-yl)-1,3,4-oxadiazole |
| 2282 | 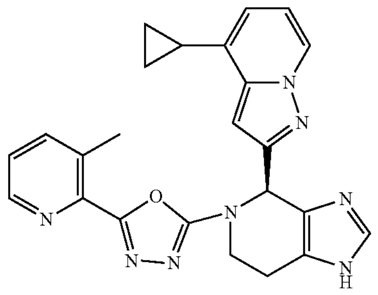 [SMILES: Cc1cccnc1-c1nnc(N2CCc3[nH]cnc3[C@@H]2c2cc3c(C4CC4)cccn3n2)o1] | (R)-2-(4-(4-cyclopropylpyrazolo [1,5-a]pyridin-2-yl)-1,4,6,7-tetrahydro-5H-imidazo [4,5-c]pyridin-5-yl)-5-(3-methylpyridin-2-yl)-1,3,4-oxadiazole |
| 2283 | 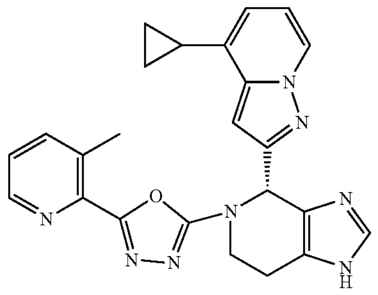 [SMILES: Cc1cccnc1-c1nnc(N2CCc3[nH]cnc3[C@H]2c2cc3c(C4CC4)cccn3n2)o1] | (S)-2-(4-(4-cyclopropylpyrazolo [1,5-a]pyridin-2-yl)-1,4,6,7-tetrahydro-5H-imidazo [4,5-c]pyridin-5-yl)-5-(3-methylpyridin-2-yl)-1,3,4-oxadiazole |
| 2284 | 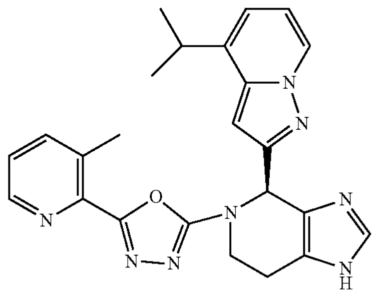 [SMILES: Cc1cccnc1-c1nnc(N2CCc3[nH]cnc3[C@@H]2c2cc3c(C(C)C)cccn3n2)o1] | (R)-2-(4-(4-isopropylpyrazolo [1,5-a]pyridin-2-yl)-1,4,6,7-tetrahydro-5H-imidazo [4,5-c]pyridin-5-yl)-5-(3-methylpyridin-2-yl)-1,3,4-oxadiazole |

TABLE 1-continued

| Ex. # | Structure | Name |
|---|---|---|
| | Pyrazolo[1,5-a]pyridines | |
| 2285 | 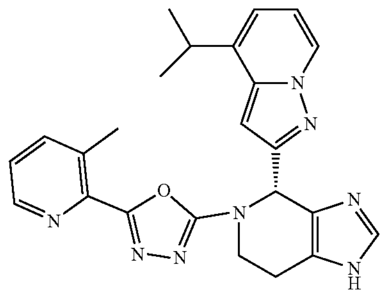 [SMILES: Cc1cccnc1-c1nnc(N2CCc3[nH]cnc3[C@H]2c2cc3c(C(C)C)cccn3n2)o1] | (S)-2-(4-(4-isopropylpyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |
| 2286 | 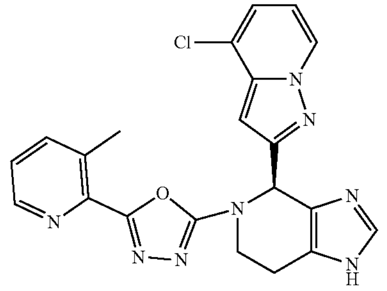 [SMILES: Cc1cccnc1-c1nnc(N2CCc3[nH]cnc3[C@@H]2c2cc3c(Cl)cccn3n2)o1] | (R)-2-(4-(4-chloropyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |
| 2287 | 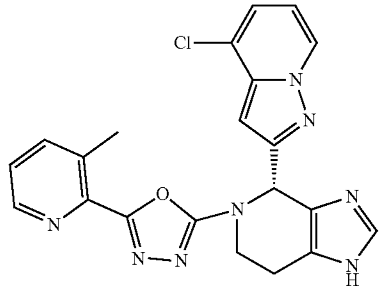 [SMILES: Cc1cccnc1-c1nnc(N2CCc3[nH]cnc3[C@H]2c2cc3c(Cl)cccn3n2)o1] | (S)-2-(4-(4-chloropyrazolo[1,5-a]pyridin-2-y]l)-1,4,6,7-tetrahydro-5H-imidazo[4,5-c]pyridin-5-yl)-5-(3-methylpyridin-2-yl)-1,3,4-oxadiazole |
| 2288 | 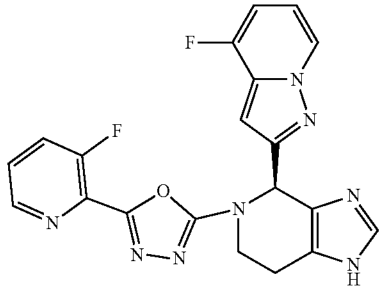 [SMILES: Fc1cccnc1-c1nnc(N2CCc3[nH]cnc3[C@@H]2c2cc3c(F)cccn3n2)o1] | (R)-2-(4-(4-fluoropyrazolo[1,5-a]pyridin-2-yl)-1,4,6,7-tetrahydro-5H-imidazo[4,5-c]pyridin-5-yl)-5-(3-fluoropyridin-2-yl)-1,3,4-oxadiazole |
| 2289 | 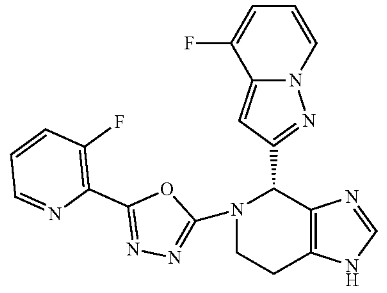 [SMILES: Fc1cccnc1-c1nnc(N2CCc3[nH]cnc3[C@H]2c2cc3c(F)cccn3n2)o1] | (S)-2-(4-(4-fluoropyrazolo[1,5-a]pyridin-2-yl)-1,4,6,7-tetrahydro-5H-imidazo[4,5-c]pyridin-5-yl)-5-(3-fluoropyridin-2-yl)-1,3,4-oxadiazole |

TABLE 1-continued

| Ex. # | Structure | Name |
|---|---|---|
| | Pyrazolo[1,5-a]pyridines | |
| 2290 | 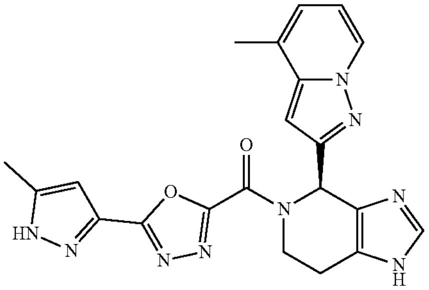 [SMILES: Cc1cc(-c2nnc(C(=O)N3CCc4[nH]cnc4[C@@H]3c3cc4c(C)cccn4n3)o2)n[nH]1] | (R)-(5-(5-methyl-1H-pyrazol-3-yl)-1,3,4-oxadiazol-2-yl)(4-(4-methylpyrazolo[1,5-a]pyridin-2-yl)-1,4,6,7-tetrahydro-5H-imidazo[4,5-c]pyridin-5-yl)methanone |
| 2291 | 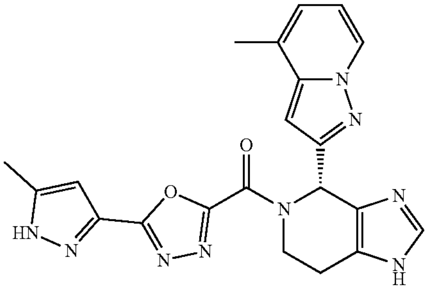 [SMILES: Cc1cc(-c2nnc(C(=O)N3CCc4[nH]cnc4[C@H]3c3cc4c(C)cccn4n3)o2)n[nH]1] | (S)-(5-(5-methyl-1H-pyrazol-3-yl)-1,3,4-oxadiazol-2-yl)(4-(4-methylpyrazolo[1,5-a]pyridin-2-yl)-1,4,6,7-tetrahydro-5H-imidazo[4,5-c]pyridin-5-yl)methanone |
| 2292 | 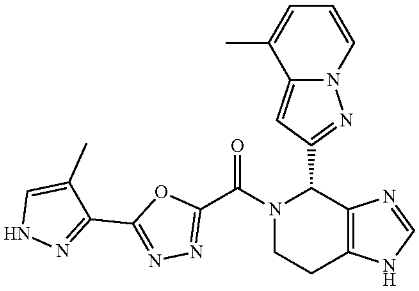 [SMILES: Cc1c[nH]nc1-c1nnc(C(=O)N2CCc3[nH]cnc3[C@H]2c2cc3c(C)cccn3n2)o1] | (S)-(5-(4-methyl-1H-pyrazol-3-yl)-1,3,4-oxadiazol-2-yl)(4-(4-methylpyrazolo[1,5-a]pyridin-2-yl)-1,4,6,7-tetrahydro-5H-imidazo[4,5-c]pyridin-5-yl)methanone |
| 2293 | 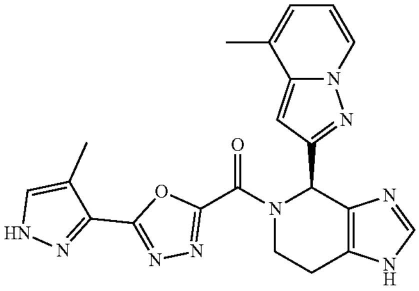 | (R)-(5-(4-methyl-1H-pyrazol-3-yl)-1,3,4-oxadiazol-2-yl)(4-(4-methylpyrazolo[1,5-a]pyridin-2-yl)-1,4,6,7-tetrahydro-5H-imidazo[4,5-c]pyridin-5-yl)methanone |
| 2294 | 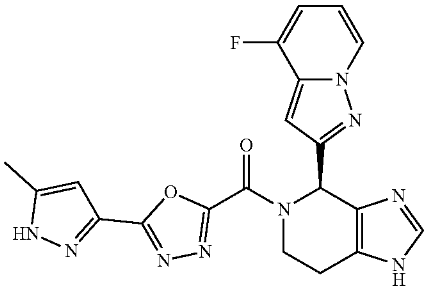 [SMILES: Cc1cc(-c2nnc(C(=O)N3CCc4[nH]cnc4[C@@H]3c3cc4c(F)cccn4n3)o2)n[nH]1] | (R)-(4-(4-fluoropyrazolo[1,5-a]pyridin-2-yl)-1,4,6,7-tetrahydro-5H-imidazo[4,5-c]pyridin-5-yl)(5-(5-methyl-1H-pyrazol-3-yl)-1,3,4-oxadiazol-2-yl)methanone |

TABLE 1-continued

| Pyrazolo[1,5-a]pyridines | | |
|---|---|---|
| Ex. # | Structure | Name |
| 2295 | 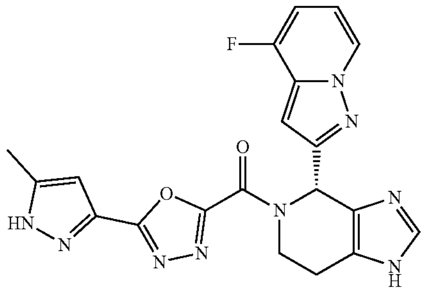 [SMILES: Cc1cc(-c2nnc(C(=O)N3CCc4[nH]cnc4[C@H]3c3cc4c(F)cccn4n3)o2)n[nH]1] | (S)-(4-(4-fluoropyrazolo [1,5-a]pyridin-2-yl)-1,4,6,7-tetrahydro-5H-imidazo[4,5-c] pyridin-5-yl)(5-(5-methyl-1H-pyrazol-3-yl)-1,3,4-oxadiazol-2-yl)methanone |
| 2296 | 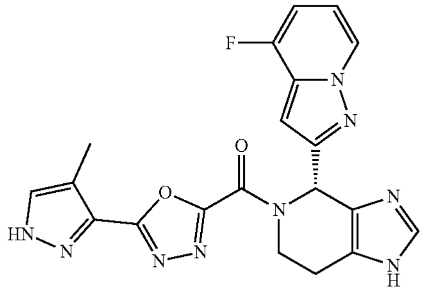 [SMILES: Cc1c[nH]nc1-c1nnc(C(=O)N2CCc3[nH]cnc3[C@H]2c2cc3c(F)cccn3n2)o1] | (S)-(4-(4-fluoropyrazolo [1,5-a]pyridin-2-yl)-1,4,6,7-tetrahydro-5H-imidazo[4,5-c] pyridin-5-yl)(5-(4-methyl-1H-pyrazol-3-yl)-1,3,4-oxadiazol-2-yl)methanone |
| 2297 | 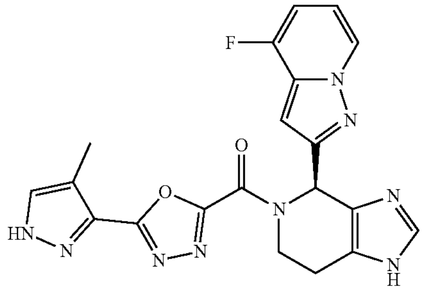 [SMILES: Cc1c[nH]nc1-c1nnc(C(=O)N2CCc3[nH]cnc3[C@@H]2c2cc3c(F)cccn3n2)o1] | (R)-(4-(4-fluoropyrazolo [1,5-a]pyridin-2-yl)-1,4,6,7-tetrahydro-5H-imidazo[4,5-c] pyridin-5-yl)(5-(4-methyl-1H-pyrazol-3-yl)-1,3,4-oxadiazol-2-yl)methanone |
| 2298 | 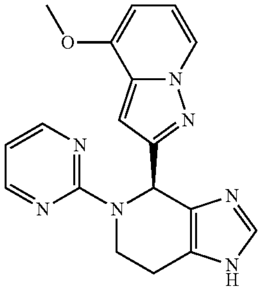 [SMILES: COc1cccn2nc([C@H]3c4nc[nH]c4CCN3c3ncccn3)cc12] | (R)-4-(4-methoxypyrazolo [1,5-a]pyridin-2-yl)-5-(pyrimidin-2-yl)-4,5,6,7-tetrahydro-1H-imidazo[4,5-c]pyridine |
| 2299 | 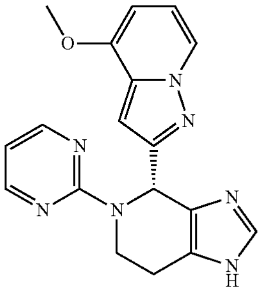 [SMILES: COc1cccn2nc([C@@H]3c4nc[nH]c4CCN3c3ncccn3)cc12] | (S)-4-(4-methoxypyrazolo [1,5-a]pyridin-2-yl)-5-(pyrimidin-2-yl)-4,5,6,7-tetrahydro-1H-imidazo[4,5-c]pyridine |

TABLE 1-continued

| Pyrazolo[1,5-a]pyridines | | |
|---|---|---|
| Ex. # | Structure | Name |
| 2300 | 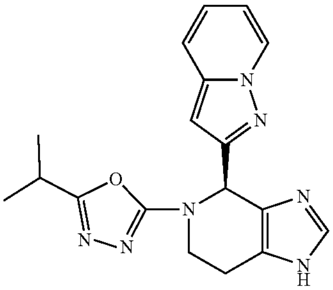 [SMILES: CC(C)c1nnc(N2CCc3[nH]cnc3[C@@H]2c2cc3ccccn3n2)o1] | (R)-2-isopropyl-5-(4-(pyrazolo[1,5-a]pyridin-2-yl)-1,4,6,7-tetrahydro-5H-imidazo[4,5-c]pyridin-5-yl)-1,3,4-oxadiazole |
| 2301 | 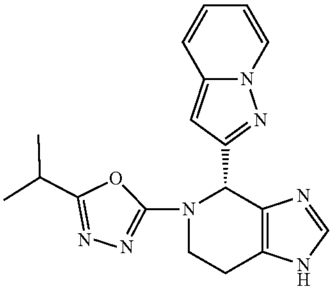 [SMILES: CC(C)c1nnc(N2CCc3[nH]cnc3[C@H]2c2cc3ccccn3n2)o1] | (S)-2-isopropyl-5-(4-(pyrazolo[1,5-a]pyridin-2-yl)-1,4,6,7-tetrahydro-5H-imidazo[4,5-c]pyridin-5-yl)-1,3,4-oxadiazole |
| 2302 | 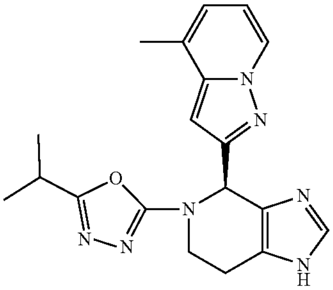 [SMILES: Cc1cccn2nc([C@H]3c4nc[nH]c4CCN3c3nnc(C(C)C)o3)cc12] | (R)-2-isopropyl-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2303 | 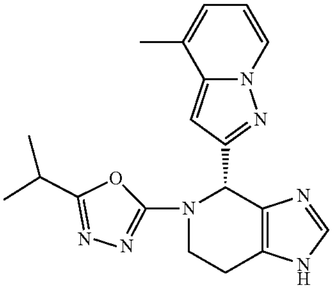 [SMILES: Cc1cccn2nc([C@@H]3c4nc[nH]c4CCN3c3nnc(C(C)C)o3)cc12] | (S)-2-isopropyl-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2304 | 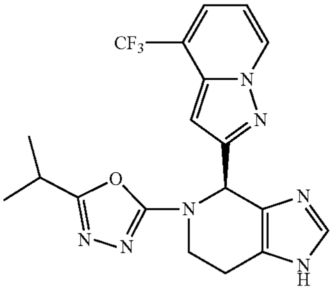 [SMILES: CC(C)c1nnc(N2CCc3[nH]cnc3[C@@H]2c2cc3c(C(F)(F)F)cccn3n2)o1] | (R)-2-isopropyl-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2305 | 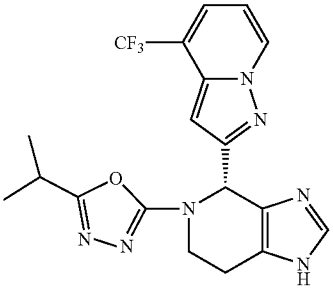 [SMILES: CC(C)c1nnc(N2CCc3[nH]cnc3[C@H]2c2cc3c(C(F)(F)F)cccn3n2)o1] | (S)-2-isopropyl-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2306 | 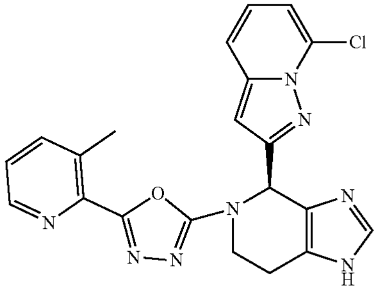 [SMILES: Cc1cccnc1-c1nnc(N2CCc3[nH]cnc3[C@@H]2c2cc3cccc(C)n3n2)o1] | (R)-2-(4-(7-chloropyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |
| 2307 | 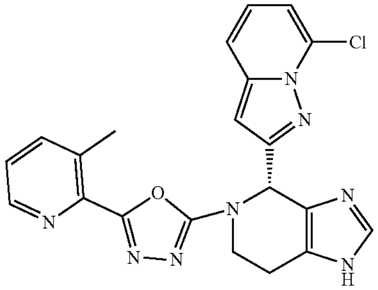 | (S)-2-(4-(7-chloropyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |
| 2308 | 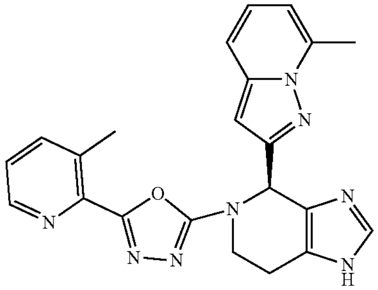 | (R)-2-(4-(7-methylpyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |
| 2309 | 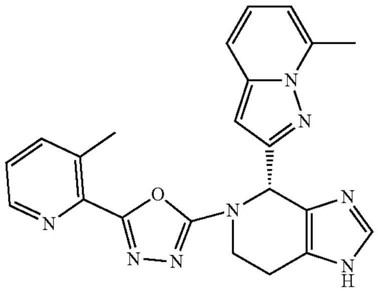 [SMILES: Cc1cccnc1-c1nnc(N2CCc3[nH]cnc3[C@H]2c2cc3cccc(C)n3n2)o1] | (S)-2-(4-(7-methylpyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |

TABLE 1-continued

| Pyrazolo[1,5-a]pyridines | | |
|---|---|---|
| Ex. # | Structure | Name |
| 2310 | 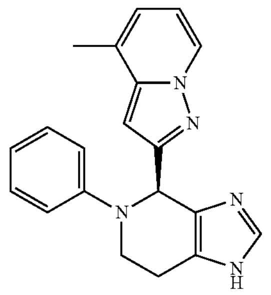 [SMILES: Cc1cccn2nc([C@H]3c4nc[nH]c4CCN3c3ccccc3)cc12] | (R)-4-(4-methylpyrazolo [1,5-a]pyridin-2-yl)-5-phenyl-4,5,6,7-tetrahydro-1H-imidazo[4,5-c]pyridine |
| 2311 | 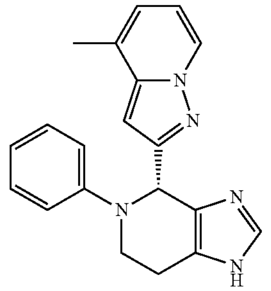 [SMILES: Cc1cccn2nc([C@@H]3c4nc[nH]c4CCN3c3ccccc3)cc12] | (S)-4-(4-methylpyrazolo [1,5-a]pyridin-2-yl)-5-phenyl-4,5,6,7-tetrahydro-1H-imidazo[4,5-c]pyridine |
| 2312 | 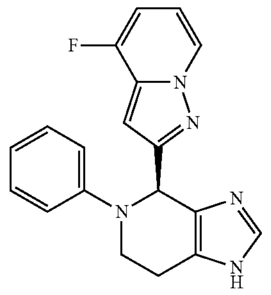 [SMILES: Fc1cccn2nc([C@H]3c4nc[nH]c4CCN3c3ccccc3)cc12] | (R)-4-(4-fluoropyrazolo [1,5-a]pyridin-2-yl)-5-phenyl-4,5,6,7-tetrahydro-1H -imidazo[4,5-c]pyridine |
| 2313 | 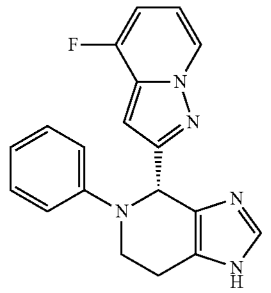 [SMILES: Fc1cccn2nc([C@@H]3c4nc[nH]c4CCN3c3ccccc3)cc12] | (S)-4-(4-fluoropyrazolo [1,5-a]pyridin-2-yl)-5-phenyl-4,5,6,7-tetrahydro-1H-imidazo[4,5-c]pyridine |
| 2314 | 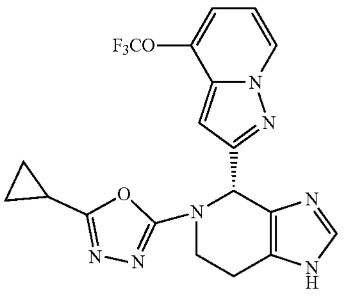 [SMILES: FC(F)(F)Oc1cccn2nc([C@@H]3c4nc[nH]c4CCN3c3nnc(C4CC4)o3)cc12] | (S)-2-cyclopropyl-5-(4-(4-(trifluoromethoxy)pyrazolo [1,5-a]pyridin-2-yl)-1,4,6,7-tetrahydro-5H-imidazo [4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2315 | 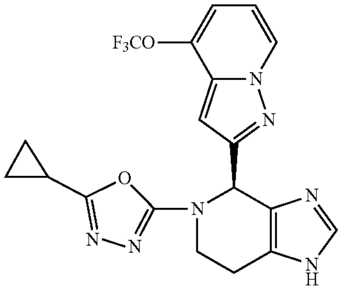 [SMILES: FC(F)(F)Oc1cccn2nc([C@H]3c4nc[nH]c4CCN3c3nnc(C4CC4)o3)cc12] | (R)-2-cyclopropyl-5-(4-(4-(trifluoromethoxy)pyrazolo[1,5-a]pyridin-2-yl)-1,4,6,7-tetrahydro-5H-imidazo[4,5-c]pyridin-5-yl)-1,3,4-oxadiazole |
| 2316 | 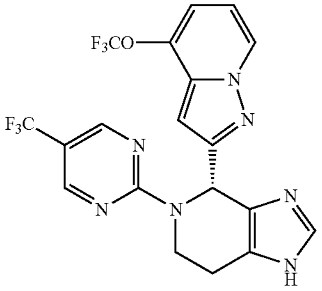 | (S)-4-(4-(trifluoromethoxy)pyrazolo[1,5-a]pyridin-2-yl)-5-(5-(trifluoromethyl)pyrimidin-2-yl)-4,5,6,7-tetrahydro-1H-imidazo[4,5-c]pyridine |
| 2317 | 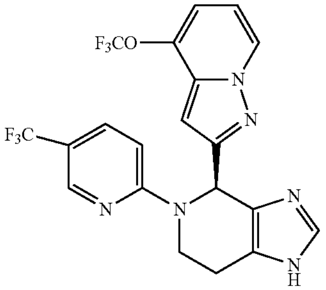 [SMILES: FC(F)(F)Oc1cccn2nc([C@H]3c4nc[nH]c4CCN3c3ccc(C(F)(F)F)cn3)cc12] | (R)-4-(4-(trifluoromethoxy)pyrazolo[1,5-a]pyridin-2-yl)-5-(5-(trifluoromethyl)pyrimidin-2-yl)-4,5,6,7-tetrahydro-1H-imidazo[4,5-c]pyridine |
| 2318 | 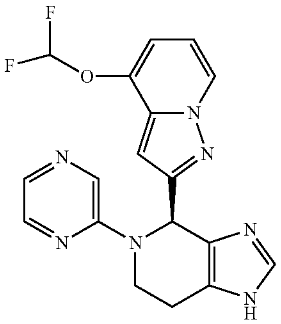 [SMILES: FC(F)Oc1cccn2nc([C@H]3c4nc[nH]c4CCN3c3cnccn3)cc12] | (R)-4-(4-(difluoromethoxy)pyrazolo[1,5-a]pyridin-2-yl)-5-(pyrazin-2-yl)-4,5,6,7-tetrahydro-1H-imidazo[4,5-c]pyridine |
| 2319 | 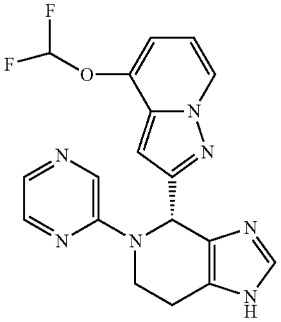 | (S)-4-(4-(difluoromethoxy)pyrazolo[1,5-a]pyridin-2-yl)-5-(pyrazin-2-yl)-4,5,6,7-tetrahydro-1H-imidazo[4,5-c]pyridine |

TABLE 1-continued

Pyrazolo[1,5-a]pyridines

| Ex. # | Structure | Name |
|---|---|---|
| 2320 | 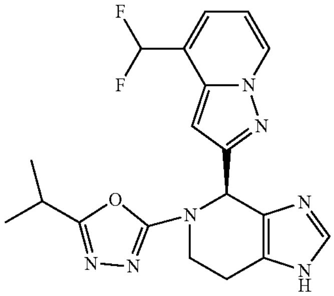 [SMILES: CC(C)c1nnc(N2CCc3[nH]cnc3[C@@H]2c2cc3c(C(F)F)cccn3n2)o1] | (R)-2-(4-(4-(difluoromethyl) pyrazolo[1,5-a]pyridin-2-yl)-1,4,6,7-tetrahydro-5H-imidazo[4,5-c]pyridin-5-yl)-5-isopropyl-1,3,4-oxadiazole |
| 2321 | 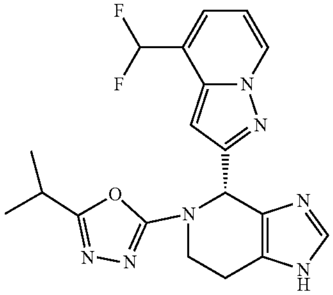 [SMILES: CC(C)c1nnc(N2CCc3[nH]cnc3[C@H]2c2cc3c(C(F)F)cccn3n2)o1] | (S)-2-(4-(4-(difluoromethyl) pyrazolo[1,5-a]pyridin-2-yl)-1,4,6,7-tetrahydro-5H-imidazo [4,5-c]pyridin-5-yl)-5-isopropyl-1,3,4-oxadiazole |
| 2322 | 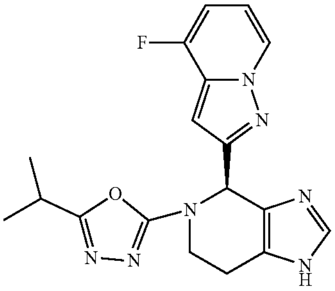 [SMILES: CC(C)c1nnc(N2CCc3[nH]cnc3[C@@H]2c2cc3c(F)cccn3n2)o1] | (R)-2-(4-(4-fluoropyrazolo [1,5-a]pyridin-2-yl)-1,4,6,7-tetrahydro-5H-imidazo [4,5-c]pyridin-5-yl)-5-isopropyl-1,3,4-oxadiazole |
| 2323 | 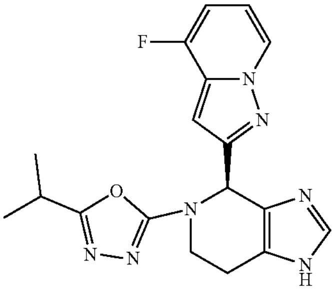 [SMILES: CC(C)c1nnc(N2CCc3[nH]cnc3[C@@H]2c2cc3c(F)cccn3n2)o1] | (S)-2-(4-(4-fluoropyrazolo [1,5-a]pyridin-2-yl)-1,4,6,7-tetrahydro-5H-imidazo [4,5-c]pyridin-5-yl)-5-isopropyl-1,3,4-oxadiazole |
| 2324 | 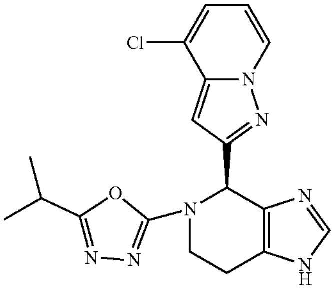 [SMILES: CC(C)c1nnc(N2CCc3[nH]cnc3[C@@H]2c2cc3c(Cl)cccn3n2)o1] | (R)-2-(4-(4-chloropyrazolo [1,5-a]pyridin-2-yl)-1,4,6,7-tetrahydro-5H-imidazo [4,5-c]pyridin-5-yl)-5-isopropyl-1,3,4-oxadiazole |

TABLE 1-continued

| Ex. # | Structure | Name |
|---|---|---|
| | Pyrazolo[1,5-a]pyridines | |
| 2325 | 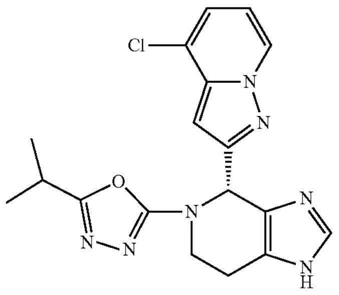 | (S)-2-(4-(4-chloropyrazolo [1,5-a]pyridin-2-yl)-1,4,6,7-tetrahydro-5H-imidazo[4,5-c] pyridin-5-yl)-5-isopropyl-1,3,4-oxadiazole |
| 2326 | 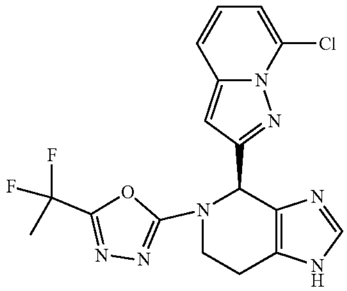 [SMILES: CC(F)(F)c1nnc(N2CCc3[nH]cnc3[C@@H]2c2cc3cccc(Cl)n3n2)o1] | (R)-2-(4-(7-chloropyrazolo [1,5-a]pyridin-2-yl)-1,4,6,7-tetrahydro-5H-imidazo[4,5-c] pyridin-5-yl)-5-(1,1-difluoroethyl)-1,3,4-oxadiazole |
| 2327 | 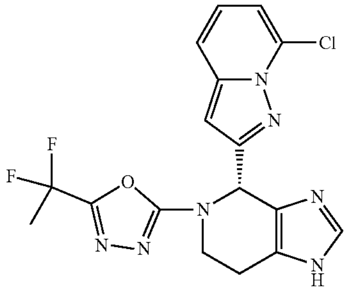 [SMILES: CC(F)(F)c1nnc(N2CCc3[nH]cnc3[C@H]2c2cc3cccc(Cl)n3n2)o1] | (S)-2-(4-(7-chloropyrazolo [1,5-a]pyridin-2-yl)-1,4,6,7-tetrahydro-5H-imidazo [4,5-c]pyridin-5-yl)-5-(1,1-difluoroethyl)-1,3,4-oxadiazole |
| 2328 | 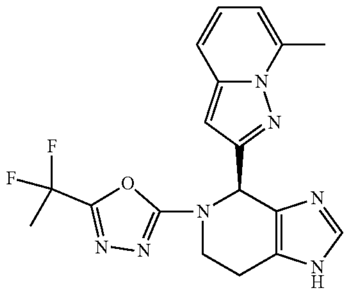 [SMILES: Cc1cccc2cc([C@H]3c4nc[nH]c4CCN3c3nnc(C(C)(F)F)o3)nn12] | (R)-2-(1,1-difluoroethyl)-5-(4-(7-methylpyrazolo[1,5-a]pyridin-2-yl)-1,4,6,7-tetrahydro-5H-imidazo[4,5-c]pyridin-5-yl)-1,3,4-oxadiazole |
| 2329 | 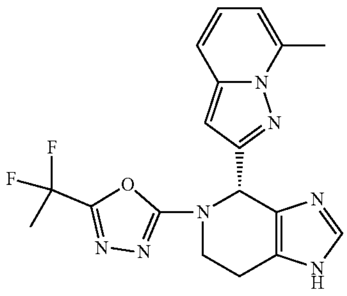 [SMILES: Cc1cccc2cc([C@@H]3c4nc[nH]c4CCN3c3nnc(C(C)(F)F)o3)nn12] | (S)-2-(1,1-difluoroethyl)-5-(4-(7-methylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
|---|---|---|
| Pyrazolo[1,5-a]pyridines | | |
| 2330 | 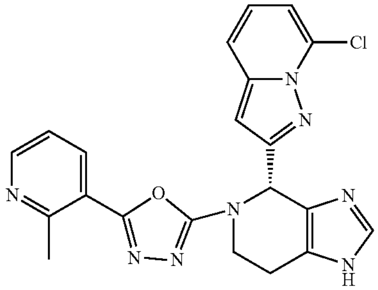 [SMILES: Cc1ncccc1-c1nnc(N2CCc3[nH]cnc3[C@H]2c2cc3cccc(Cl)n3n2)o1] | (S)-2-(4-(7-chloropyrazolo [1,5-a]pyridin-2-yl)-1,4,6,7-tetrahydro-5H-imidazo [4,5-c]pyridin-5-yl)-5-(2-methylpyridin-3-yl)-1,3,4-oxadiazole |
| 2331 | 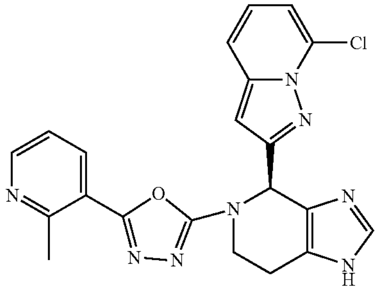 [SMILES: Cc1ncccc1-c1nnc(N2CCc3[nH]cnc3[C@@H]2c2cc3cccc(Cl)n3n2)o1] | (R)-2-(4-(7-chloropyrazolo [1,5-a]pyridin-2-yl)-1,4,6,7-tetrahydro-5H-imidazo [4,5-c]pyridin-5-yl)-5-(2-methylpyridin-3-yl)-1,3,4-oxadiazole |
| 2332 | 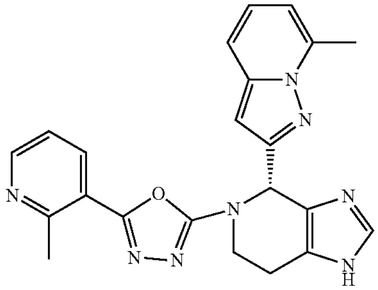 [SMILES: Cc1ncccc1-c1nnc(N2CCc3[nH]cnc3[C@H]2c2cc3cccc(C)n3n2)o1] | (S)-2-(4-(7-methylpyrazolo [1,5-a]pyridin-2-yl)-1,4,6,7-tetrahydro-5H-imidazo [4,5-c]pyridin-5-yl)-5-(2-methylpyridin-3-yl)-1,3,4-oxadiazole |
| 2333 | 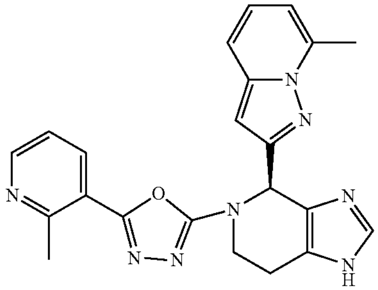 [SMILES: Cc1ncccc1-c1nnc(N2CCc3[nH]cnc3[C@@H]2c2cc3cccc(C)n3n2)o1] | (R)-2-(4-(7-methylpyrazolo [1,5-a]pyridin-2-y]l)-1,4,6,7-tetrahydro-5H-imidazo [4,5-c]pyridin-5-yl)-5-(2-methylpyridin-3-yl)-1,3,4-oxadiazole |
| 2334 | 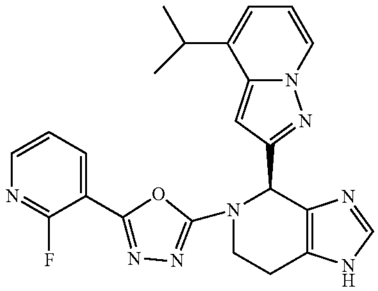 [SMILES: CC(C)c1cccn2nc([C@H]3c4nc[nH]c4CCN3c3nnc(-c4cccnc4F)o3)cc12] | (R)-2-(2-fluoropyridin-3-yl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2335 | 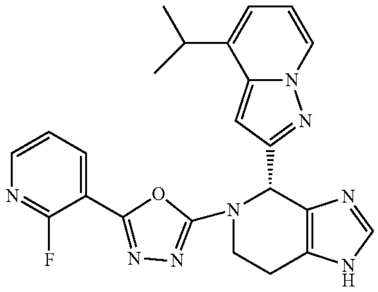 [SMILES: CC(C)c1cccn2nc([C@@H]3c4nc[nH]c4CCN3c3nnc(-c4cccnc4F)o3)cc12] | (S)-2-(2-fluoropyridin-3-yl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |
| 2336 | 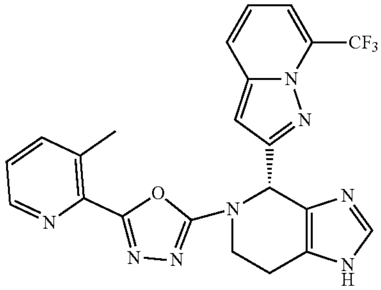 [SMILES: Cc1cccnc1-c1nnc(N2CCc3[nH]cnc3[C@H]2c2cc3cccc(C(F)(F)F)n3n2)o1] | (S)-2-(3-methylpyridin-2-yl)-5-(4-(7-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2337 | 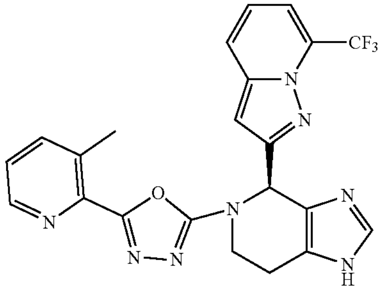 [SMILES: Cc1cccnc1-c1nnc(N2CCc3[nH]cnc3[C@@H]2c2cc3cccc(C(F)(F)F)n3n2)o1] | (R)-2-(3-methylpyridin-2-yl)-5-(4-(7-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2338 | 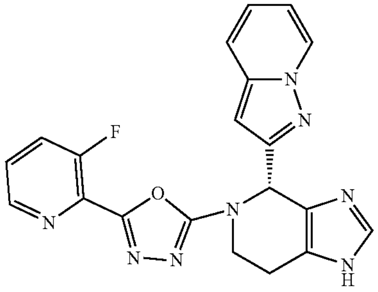 [SMILES: Fc1cccnc1-c1nnc(N2CCc3[nH]cnc3[C@H]2c2cc3ccccn3n2)o1] | (S)-2-(3-fluoropyridin-2-yl)-5-(4-(pyrazolo[1,5-a]pyridin-2-yl)-1,4,6,7-tetrahydro-5H-imidazo[4,5-c]pyridin-5-yl)-1,3,4-oxadiazole |
| 2339 | 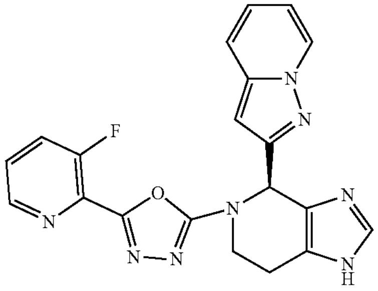 [SMILES: Fc1cccnc1-c1nnc(N2CCc3[nH]cnc3[C@@H]2c2cc3ccccn3n2)o1] | (R)-2-(3-fluoropyridin-2-yl)-5-(4-(pyrazolo[1,5-a]pyridin-2-yl)-1,4,6,7-tetrahydro-5H-imidazo[4,5-c]pyridin-5-yl)-1,3,4-oxadiazole |

TABLE 1-continued

Pyrazolo[1,5-a]pyridines

| Ex. # | Structure | Name |
|---|---|---|
| 2340 | 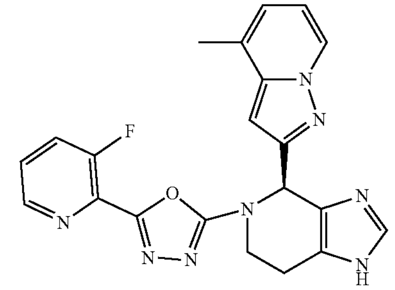 | (R)-2-(3-fluoropyridin-2-yl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2341 | 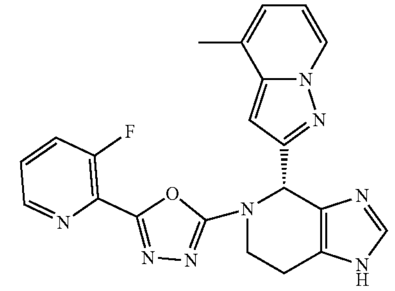 [SMILES: Cc1cccn2nc([C@@H]3c4nc[nH]c4CCN3c3nnc(-c4ncccc4F)o3)cc12] | (S)-2-(3-fluoropyridin-2-yl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2342 | 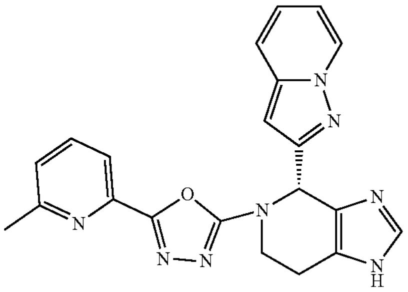 [SMILES: Cc1cccc(-c2nnc(N3CCc4[nH]cnc4[C@H]3c3cc4ccccn4n3)o2)n1] | (S)-2-(6-methylpyridin-2-yl)-5-(4-(pyrazolo[1,5-a]pyridin-2-yl)-1,4,6,7-tetrahydro-5H-imidazo[4,5-c]pyridin-5-yl)-1,3,4-oxadiazole |
| 2343 | 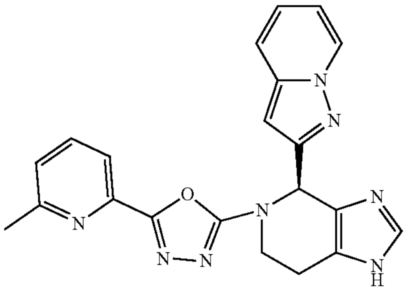 [SMILES: Cc1cccc(-c2nnc(N3CCc4[nH]cnc4[C@@H]3c3cc4ccccn4n3)o2)n1] | (R)-2-(6-methylpyridin-2-yl)-5-(4-(pyrazolo[1,5-a]pyridin-2-yl)-1,4,6,7-tetrahydro-5H-imidazo[4,5-c]pyridin-5-yl)-1,3,4-oxadiazole |
| 2344 | 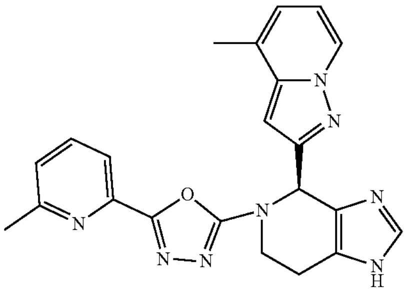 [SMILES: Cc1cccc(-c2nnc(N3CCc4[nH]cnc4[C@@H]3c3cc4c(C)cccn4n3)o2)n1] | (R)-2-(4-(4-methylpyrazolo[1,5-a]pyridin-2-y]l)-1,4,6,7-tetrahydro-5H-imidazo[4,5-c]pyridin-5-yl)-5-(6-methylpyridin-2-yl)-1,3,4-oxadiazole |

TABLE 1-continued

| Ex. # | Structure | Name |
|---|---|---|
| | Pyrazolo[1,5-a]pyridines | |
| 2345 | 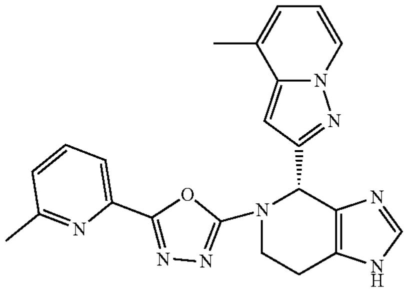 [SMILES: Cc1cccc(-c2nnc(N3CCc4[nH]cnc4[C@H]3c3cc4c(C)cccn4n3)o2)n1] | (S)-2-(4-(4-methylpyrazolo[1,5-a]pyridin-2-yl)-1,4,6,7-tetrahydro-5H-imidazo[4,5-c]pyridin-5-yl)-5-(6-methylpyridin-2-yl)-1,3,4-oxadiazole |
| 2346 | 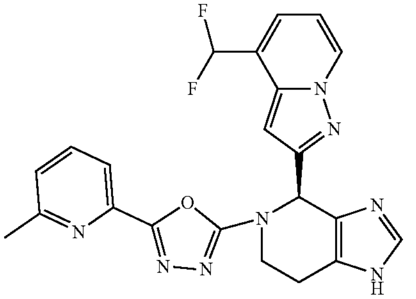 [SMILES: Cc1cccc(-c2nnc(N3CCc4[nH]cnc4[C@@H]3c3cc4c(C(F)F)cccn4n3)o2)n1] | (R)-2-(4-(4-(difluoromethyl)pyrazolo[1,5-a]pyridin-2-yl)-1,4,6,7-tetrahydro-5H-imidazo[4,5-c]pyridin-5-yl)-5-(6-methylpyridin-2-yl)-1,3,4-oxadiazole |
| 2347 | 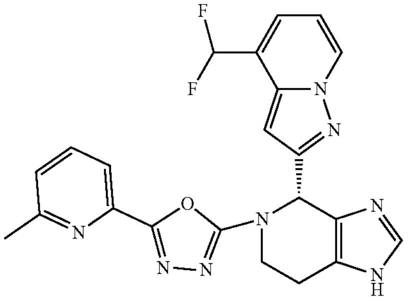 [SMILES: Cc1cccc(-c2nnc(N3CCc4[nH]cnc4[C@H]3c3cc4c(C(F)F)cccn4n3)o2)n1] | (S)-2-(4-(4-(difluoromethyl)pyrazolo[1,5-a]pyridin-2-yl)-1,4,6,7-tetrahydro-5H-imidazo[4,5-c]pyridin-5-yl)-5-(6-methylpyridin-2-yl)-1,3,4-oxadiazole |
| 2348 | 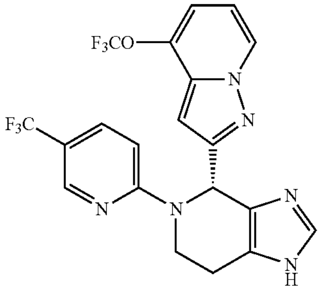 [SMILES: FC(F)(F)Oc1cccn2nc([C@@H]3c4nc[nH]c4CCN3c3ccc(C(F)(F)F)cn3)cc12] | (S)-4-(4-(trifluoromethoxy)pyrazolo[1,5-a]pyridin-2-yl)-5-(5-(trifluoromethyl)pyridin-2-yl)-4,5,6,7-tetrahydro-1H-imidazo[4,5-c]pyridine |
| 2349 | 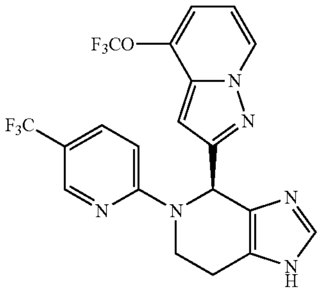 [SMILES: FC(F)(F)Oc1cccn2nc([C@H]3c4nc[nH]c4CCN3c3ccc(C(F)(F)F)cn3)cc12] | (R)-4-(4-(trifluoromethoxy)pyrazolo[1,5-a]pyridin-2-yl)-5-(5-(trifluoromethyl)pyridin-2-yl)-4,5,6,7-tetrahydro-1H-imidazo[4,5-c]pyridine |

TABLE 1-continued

| Ex. # | Structure | Name |
|---|---|---|
| | Pyrazolo[1,5-a]pyridines | |
| 2350 | 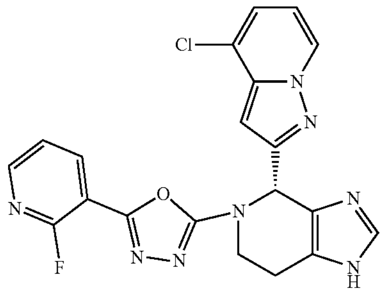 [SMILES: Fc1ncccc1-c1nnc(N2CCc3[nH]cnc3[C@H]2c2cc3c(Cl)cccn3n2)o1] | (S)-2-(4-(4-chloropyrazolo [1,5-a]pyridin-2-y]l)-1,4,6,7-tetrahydro-5H-imidazo [4,5-c]pyridin-5-yl)-5-(2-fluoropyridin-3-yl)-1,3,4-oxadiazole |
| 2351 | 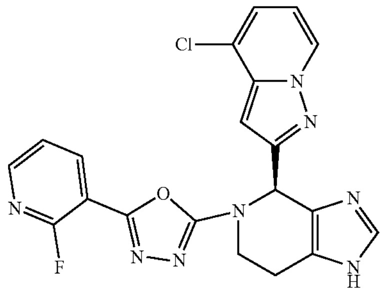 [SMILES: Fc1ncccc1-c1nnc(N2CCc3[nH]cnc3[C@@H]2c2cc3c(Cl)cccn3n2)o1] | (R)-2-(4-(4-chloropyrazolo [1,5-a]pyridin-2-yl)-1,4,6,7-tetrahydro-5H-imidazo [4,5-c]pyridin-5-yl)-5-(2-fluoropyridin-3-yl)-1,3,4-oxadiazole |
| 2352 | 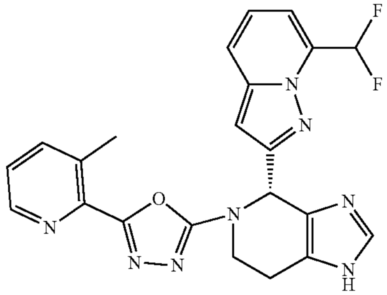 [SMILES: Cc1cccnc1-c1nnc(N2CCc3[nH]cnc3[C@H]2c2cc3cccc(C(F)F)n3n2)o1] | (S)-2-(4-(7-(difluoromethyl) pyrazolo[1,5-a]pyridin-2-yl)-1,4,6,7-tetrahydro-5H-imidazo [4,5-c]pyridin-5-yl)-5-(3-methylpyridin-2-yl)-1,3,4-oxadiazole |
| 2353 | 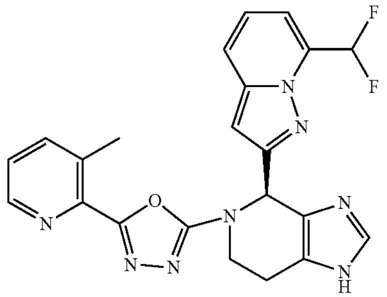 [SMILES: Cc1cccnc1-c1nnc(N2CCc3[nH]cnc3[C@@H]2c2cc3cccc(C(F)F)n3n2)o1] | (R)-2-(4-(7-(difluoromethyl) pyrazolo[1,5-a]pyridin-2-yl)-1,4,6,7-tetrahydro-5H-imidazo[4,5-c]pyridin-5-yl)-5-(3-methylpyridin-2-yl)-1,3,4-oxadiazole |
| 2354 | 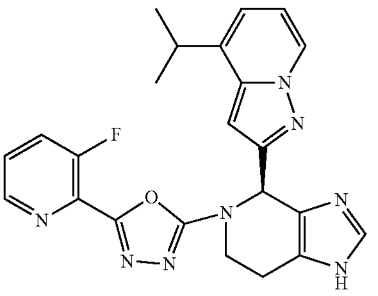 [SMILES: CC(C)c1cccn2nc([C@H]3c4nc[nH]c4CCN3c3nnc(-c4ncccc4F)o3)cc12] | (R)-2-(3-fluoropyridin-2-yl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
|---|---|---|
| | Pyrazolo[1,5-a]pyridines | |
| 2355 | 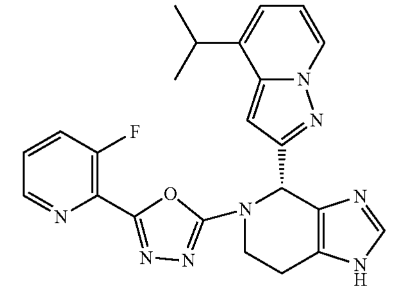 [SMILES: CC(C)c1cccn2nc([C@@H]3c4nc[nH]c4CCN3c3nnc(-c4ncccc4F)o3)cc12] | (S)-2-(3-fluoropyridin-2-yl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |
| 2356 | 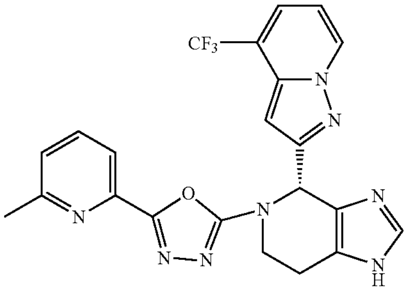 [SMILES: Cc1cccc(-c2nnc(N3CCc4[nH]cnc4[C@H]3c3cc4c(C(F)(F)F)cccn4n3)o2)n1] | (R)-2-(6-methylpyridin-2-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2357 | 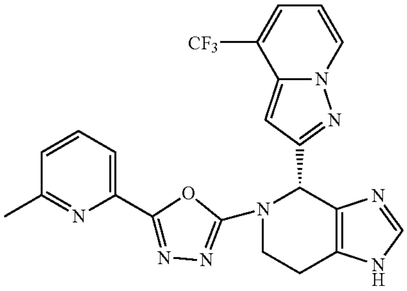 [SMILES: Cc1cccc(-c2nnc(N3CCc4[nH]cnc4[C@H]3c3cc4c(C(F)(F)F)cccn4n3)o2)n1] | (S)-2-(6-methylpyridin-2-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2358 | 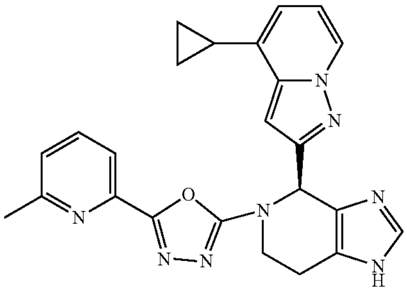 [SMILES: Cc1cccc(-c2nnc(N3CCc4[nH]cnc4[C@@H]3c3cc4c(C5CC5)cccn4n3)o2)n1] | (R)-2-(4-(4-cyclopropylpyrazolo[1,5-a]pyridin-2-yl)-1,4,6,7-tetrahydro-5H-imidazo[4,5-c]pyridin-5-yl)-5-(6-methylpyridin-2-yl)-1,3,4-oxadiazole |
| 2359 | 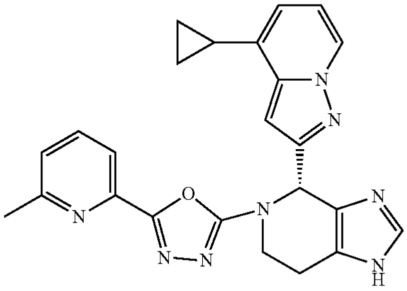 [SMILES: Cc1cccc(-c2nnc(N3CCc4[nH]cnc4[C@H]3c3cc4c(C5CC5)cccn4n3)o2)n1] | (S)-2-(4-(4-cyclopropylpyrazolo[1,5-a]pyridin-2-yl)-1,4,6,7-tetrahydro-5H-imidazo[4,5-c]pyridin-5-yl)-5-(6-methylpyridin-2-yl)-1,3,4-oxadiazole |

TABLE 1-continued

| Pyrazolo[1,5-a]pyridines | | |
|---|---|---|
| Ex. # | Structure | Name |
| 2360 | 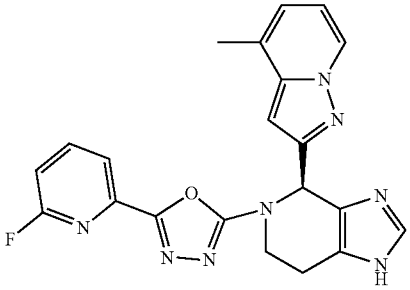 [SMILES: Cc1cccn2nc([C@H]3c4nc[nH]c4CCN3c3nnc(-c4cccc(F)n4)o3)cc12] | (R)-2-(6-fluoropyridin-2-yl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2361 | 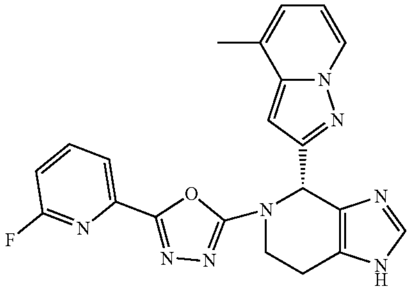 [SMILES: Cc1cccn2nc([C@@H]3c4nc[nH]c4CCN3c3nnc(-c4cccc(F)n4)o3)cc12] | (S)-2-(6-fluoropyridin-2-yl)-5-(4-(4-methylpyrazolo[1,5-a]pyridin-2-yl)-1,4,6,7-tetrahydro-5H-imidazo[4,5-c]pyridin-5-yl)-1,3,4-oxadiazole |
| 2362 | 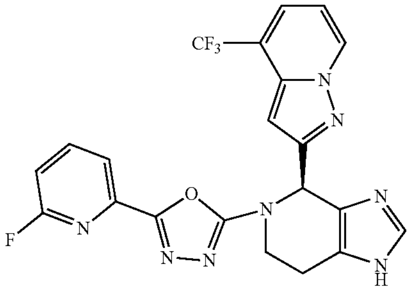 [SMILES: Fc1cccc(-c2nnc(N3CCc4[nH]cnc4[C@@H]3c3cc4c(C(F)(F)F)cccn4n3)o2)n1] | (R)-2-(6-fluoropyridin-2-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2363 | 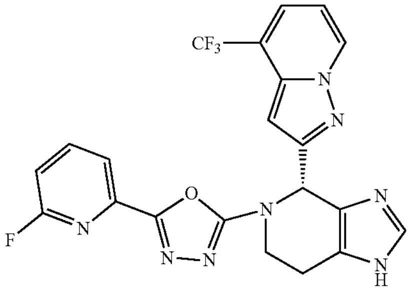 [SMILES: Fc1cccc(-c2nnc(N3CCc4[nH]cnc4[C@H]3c3cc4c(C(F)(F)F)cccn4n3)o2)n1] | (S)-2-(6-fluoropyridin-2-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2364 | 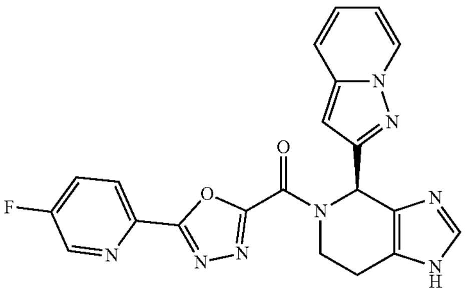 [SMILES: O=C(c1nnc(-c2ccc(F)cn2)o1)N1CCc2[nH]cnc2[C@@H]1c1cc2ccccn2n1] | (R)-(5-(5-fluoropyridin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
| --- | --- | --- |
| Pyrazolo[1,5-a]pyridines | | |
| 2365 | 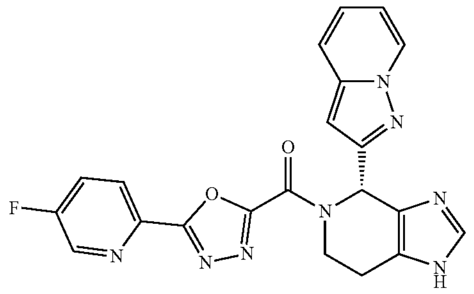 [SMILES: O=C(c1nnc(-c2ccc(F)cn2)o1)N1CCc2[nH]cnc2[C@H]1c1cc2ccccn2n1] | (S)-(5-(5-fluoropyridin-2-yl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |
| 2366 | 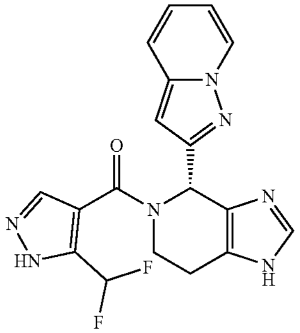 [SMILES: O=C(c1cn[nH]c1C(F)F)N1CCc2[nH]cnc2[C@H]1c1cc2ccccn2n1] | (S)-(5-(difluoromethyl)-1H-pyrazol-4-yl)(4-(pyrazolo[1,5-a]pyridin-2-yl)-6,7-dihydro-1H-imidazo[4,5-c]pyridin-5(4H)-yl)methanone |
| 2367 | 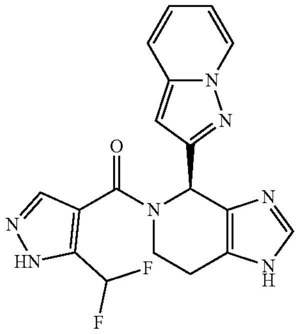 [SMILES: O=C(c1cn[nH]c1C(F)F)N1CCc2[nH]cnc2[C@@H]1c1cc2ccccn2n1] | (R)-(5-(difluoromethyl)-1H-pyrazol-4-yl)(4-(pyrazolo[1,5-a]pyridin-2-yl)-6,7-dihydro-1H-imidazo[4,5-c]pyridin-5(4H)-yl)methanone |
| 2368 | 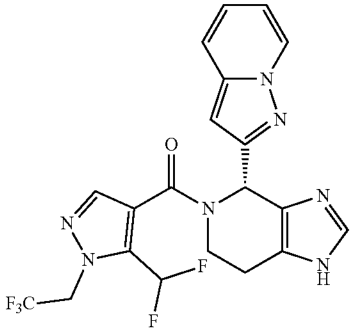 [SMILES: O=C(c1cnn(CC(F)(F)F)c1C(F)F)N1CCc2[nH]cnc2[C@H]1c1cc2ccccn2n1] | (S)-(5-(difluoromethyl)-1-(2,2,2-trifluoroethyl)-1H-pyrazol-4-yl)(4-(pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 2369 | 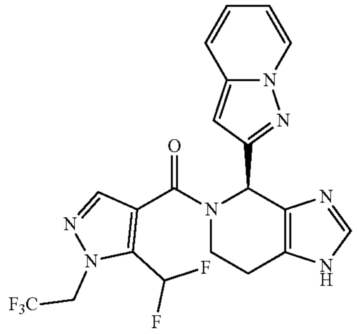 [SMILES: O=C(c1cnn(CC(F)(F)F)c1C(F)F)N1CCc2[nH]cnc2[C@@H]1c1cc2ccccn2n1] | (R)-(5-(difluoromethyl)-1-(2,2,2-trifluoroethyl)-1H-pyrazol-4-yl)(4-(pyrazolo[1,5-a]pyridin-2-yl)-6,7-dihydro-1H-imidazo[4,5-c]pyridin-5(4H)-yl)methanone |
| 2370 | 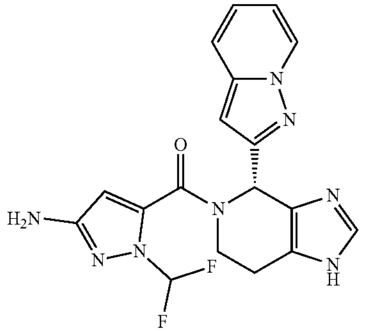 [SMILES: Nc1cc(C(=O)N2CCc3[nH]cnc3[C@H]2c2cc3ccccn3n2)n(C(F)F)n1] | (S)-(3-amino-1-(difluoromethyl)-1H-pyrazol-5-yl)(4-(pyrazolo[1,5-a]pyridin-2-yl)-6,7-dihydro-1H-imidazo[4,5-c]pyridin-5(4H)-yl)methanone |
| 2371 | 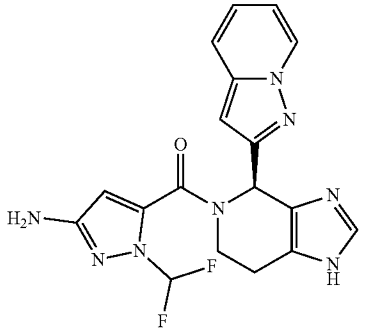 [SMILES: Nc1cc(C(=O)N2CCc3[nH]cnc3[C@@H]2c2cc3ccccn3n2)n(C(F)F)n1] | (R)-(3-amino-1-(difluoromethyl)-1H-pyrazol-5-yl)(4-(pyrazolo[1,5-a]pyridin-2-yl)-6,7-dihydro-1H-imidazo[4,5-c]pyridin-5(4H)-yl)methanone |
| 2372 | 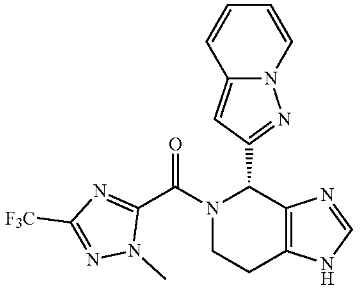 [SMILES: Cn1nc(C(F)(F)F)nc1C(=O)N1CCc2[nH]cnc2[C@H]1c1cc2ccccn2n1] | (S)-(1-methyl-3-(trifluoromethyl)-1H-1,2,4-triazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 2373 | 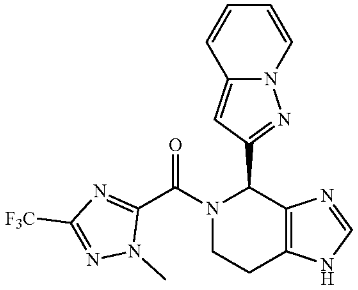 [SMILES: Cn1nc(C(F)(F)F)nc1C(=O)N1CCc2[nH]cnc2[C@@H]1c1cc2ccccn2n1] | (R)-(1-methyl-3-(trifluoromethyl)-1H-1,2,4-triazol-5-yl)(4-(pyrazolo[1,5-a]pyridin-2-yl)-6,7-dihydro-1H-imidazo[4,5-c]pyridin-5(4H)-yl)methanone |
| 2374 | 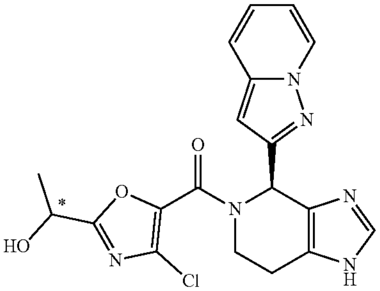 [SMILES: CC(O)c1nc(Cl)c(C(=O)N2CCc3[nH]cnc3[C@@H]2c2cc3ccccn3n2)o1] | (4-chloro-2-(1-hydroxyethyl) oxazol-5-yl)((R)-4-(pyrazolo[1,5-a]pyridin-2-yl)-6,7-dihydro-1H-imidazo[4,5-c]pyridin-5(4H)-yl)methanone Diastereomer #2 (Rt = 7.091 min) |
| 2375 | 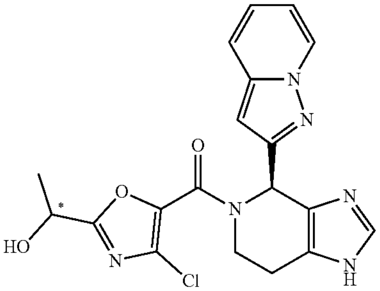 [SMILES: CC(O)c1nc(Cl)c(C(=O)N2CCc3[nH]cnc3[C@@H]2c2cc3ccccn3n2)o1] | (4-chloro-2-(1-hydroxyethyl) oxazol-5-yl)((R)-4-(pyrazolo[1,5-a]pyridin-2-yl)-6,7-dihydro-1H-imidazo[4,5-c]pyridin-5(4H)-yl)methanone Diastereomer #1 (Rt = 6.819 min) |
| 2376 | 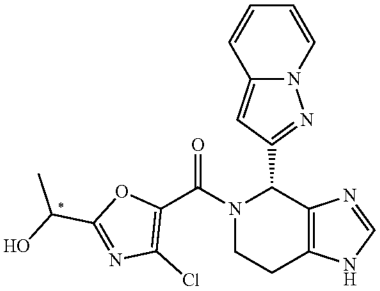 [SMILES: CC(O)c1nc(Cl)c(C(=O)N2CCc3[nH]cnc3[C@H]2c2cc3ccccn3n2)o1] | (4-chloro-2-(1-hydroxyethyl) oxazol-5-yl)((S)-4-(pyrazolo[1,5-a]pyridin-2-yl)-6,7-dihydro-1H-imidazo[4,5-c]pyridin-5(4H)-yl)methanone |
| 2377 | 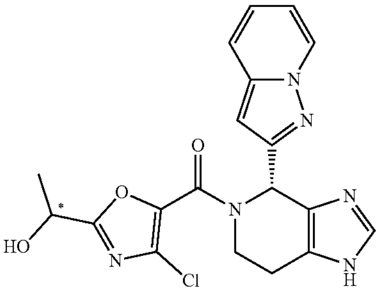 [SMILES: CC(O)c1nc(Cl)c(C(=O)N2CCc3[nH]cnc3[C@H]2c2cc3ccccn3n2)o1] | (4-chloro-2-(1-hydroxyethyl) oxazol-5-yl)((S)-4-(pyrazolo[1,5-a]pyridin-2-yl)-6,7-dihydro-1H-imidazo[4,5-c]pyridin-5(4H)-yl)methanone Diastereomer #2 (Rt = 6.340 min) |

TABLE 1-continued

| Ex. # | Structure | Name |
|---|---|---|
| Pyrazolo[1,5-a]pyridines | | |
| 2378 | 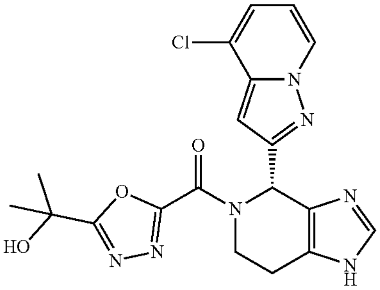 [SMILES: CC(C)(O)c1nnc(C(=O)N2CCc3[nH]cnc3[C@H]2c2cc3c(Cl)cccn3n2)o1] | (S)-(4-(4-chloropyrazolo[1,5-a]pyridin-2-yl)-6,7-dihydro-1H-imidazo[4,5-c]pyridin-5(4H)-yl)(5-(2-hydroxypropan-2-yl)-1,3,4-oxadiazol-2-yl)methanone |
| 2379 | 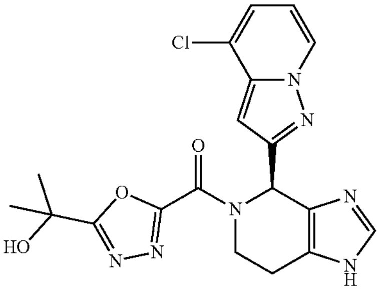 [SMILES: CC(C)(O)c1nnc(C(=O)N2CCc3[nH]cnc3[C@@H]2c2cc3c(Cl)cccn3n2)o1] | (R)-(4-(4-chloropyrazolo[1,5-a]pyridin-2-yl)-6,7-dihydro-1H-imidazo[4,5-c]pyridin-5(4H)-yl)(5-(2-hydroxypropan-2-yl)-1,3,4-oxadiazol-2-yl)methanone |
| 2380 | 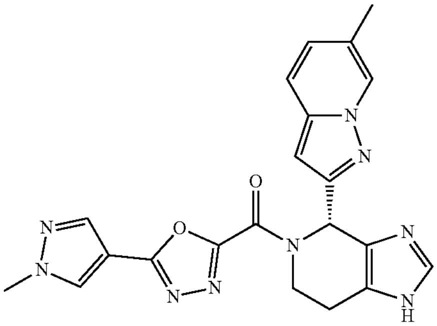 [SMILES: Cc1ccc2cc([C@@H]3c4nc[nH]c4CCN3C(=O)c3nnc(-c4cnn(C)c4)o3)nn2c1] | (S)-(5-(1-methyl-1H-pyrazol-4-yl)-1,3,4-oxadiazol-2-yl)(4-(6-methylpyrazolo[1,5-a]pyridin-2-yl)-6,7-dihydro-1H-imidazo[4,5-c]pyridin-5(4H)-yl)methanone |
| 2381 | 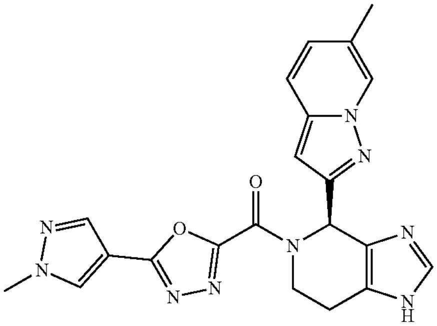 [SMILES: Cc1ccc2cc([C@H]3c4nc[nH]c4CCN3C(=O)c3nnc(-c4cnn(C)c4)o3)nn2c1] | (R)-(5-(1-methyl-1H-pyrazol-4-yl)-1,3,4-oxadiazol-2-yl)(4-(6-methylpyrazolo[1,5-a]pyridin-2-yl)-6,7-dihydro-1H-imidazo[4,5-c]pyridin-5(4H)-yl)methanone |
| 2382 | 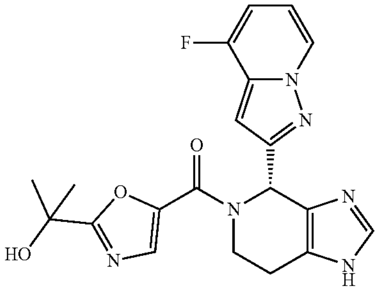 [SMILES: CC(C)(O)c1ncc(C(=O)N2CCc3[nH]cnc3[C@H]2c2cc3c(F)cccn3n2)o1] | (S)-(4-(4-fluoropyrazolo[1,5-a]pyridin-2-yl)-6,7-dihydro-1H-imidazo[4,5-c]pyridin-5(4H)-yl)(2-(2-hydroxypropan-2-yl)oxazol-5-yl)methanone |

TABLE 1-continued

| Pyrazolo[1,5-a]pyridines | | |
|---|---|---|
| Ex. # | Structure | Name |
| 2383 | 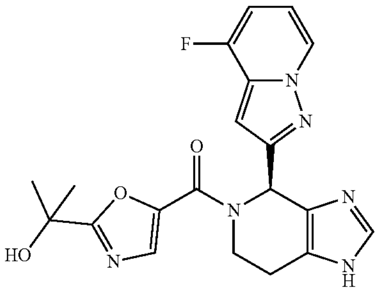 [SMILES: CC(C)(O)c1ncc(C(=O)N2CCc3[nH]cnc3[C@@H]2c2cc3c(F)cccn3n2)o1] | (R)-(4-(4-fluoropyrazolo [1,5-a]pyridin-2-y]l)-6,7-dihydro-1H-imidazo[4,5-c] pyridin-5(4H)-yl)(2-(2-hydroxypropan-2-yl) oxazol-5-yl)methanone |
| 2384 | 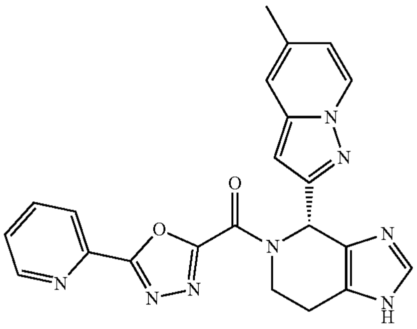 [SMILES: Cc1ccn2nc([C@@H]3c4nc[nH]c4CCN3C(=O)c3nnc(-c4ccccn4)o3)cc2c1] | (S)-(4-(5-methylpyrazolo [1,5-a]pyridin-2-yl)-6,7-dihydro-1H-imidazo[4,5-c] pyridin-5(4H)-yl)(5-(pyridin-2-yl)-1,3,4-oxadiazol-2-yl)methanone |
| 2385 | 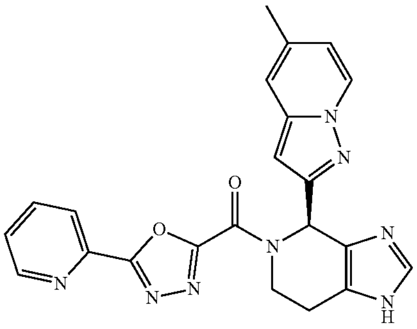 [SMILES: Cc1ccn2nc([C@H]3c4nc[nH]c4CCN3C(=O)c3nnc(-c4ccccn4)o3)cc2c1] | (R)-(4-(5-methylpyrazolo [1,5-a]pyridin-2-yl)-6,7-dihydro-1H-imidazo[4,5-c] pyridin-5(4H)-yl)(5-(pyridin-2-yl)-1,3,4-oxadiazol-2-yl)methanone |
| 2386 | 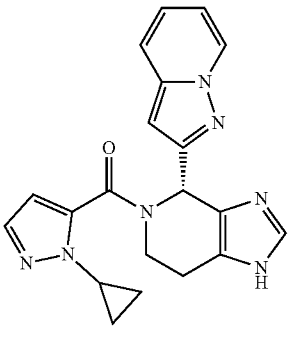 [SMILES: O=C(c1ccnn1C1CC1)N1CCc2[nH]cnc2[C@H]1c1cc2ccccn2n1] | (S)-(1-cyclopropyl-1H-pyrazol-5-yl)(4-(pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 2387 | 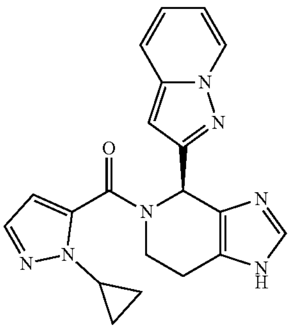 [SMILES: O=C(c1ccnn1C1CC1)N1CCc2[nH]cnc2[C@@H]1c1cc2ccccn2n1] | (R)-(1-cyclopropyl-1H-pyrazol-5-yl)(4-(pyrazolo[1,5-a]pyridin-2-yl)-6,7-dihydro-1H-imidazo[4,5-c]pyridin-5(4H)-yl)methanone |
| 2388 | 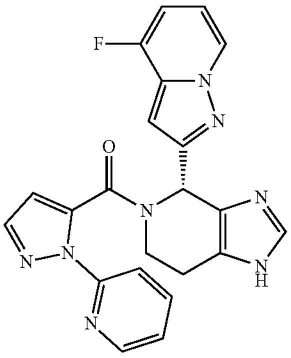 | (S)-(4-(4-fluoropyrazolo[1,5-a]pyridin-2-yl)-6,7-dihydro-1H-imidazo[4,5-c]pyridin-5(4H)-yl)(1-(pyridin-2-y])-1H-pyrazol-5-yl)methanone |
| 2389 | 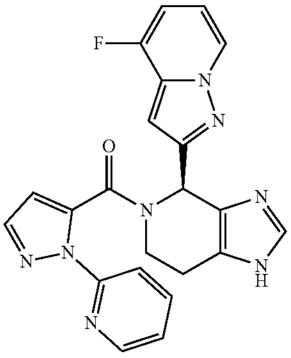 | (R)-(4-(4-fluoropyrazolo[1,5-a]pyridin-2-yl)-6,7-dihydro-1H-imidazo[4,5-c]pyridin-5(4H)-yl)(1-(pyridin-2-yl)-1H-pyrazol-5-yl)methanone |
| 2390 | 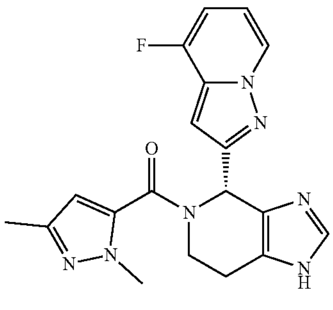 [SMILES: Cc1cc(C(=O)N2CCc3[nH]cnc3[C@H]2c2cc3c(F)cccn3n2)n(C)n1] | (S)-(1,3-dimethyl-1H-pyrazol-5-yl)(4-(4-fluoropyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 2391 | 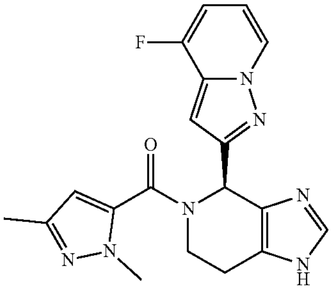 [SMILES: Cc1cc(C(=O)N2CCc3[nH]cnc3[C@@H]2c2cc3c(F)cccn3n2)n(C)n1] | (R)-(1,3-dimethyl-1H-pyrazol-5-yl)(4-(4-fluoropyrazolo[1,5-a]pyridin-2-yl)-6,7-dihydro-1H-imidazo[4,5-c]pyridin-5(4H)-yl)methanone |
| 2392 | 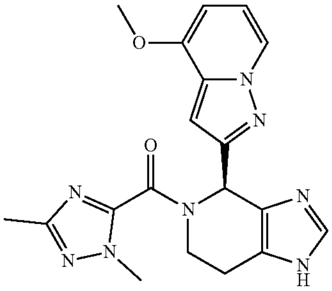 [SMILES: COc1cccn2nc([C@H]3c4nc[nH]c4CCN3C(=O)c3nc(C)nn3C)cc12] | (R)-(1,3-dimethyl-1H-1,2,4-triazol-5-yl)(4-(4-methoxypyrazolo[1,5-a]pyridin-2-yl)-6,7-dihydro-1H-imidazo[4,5-c]pyridin-5(4H)-yl)methanone |
| 2393 | 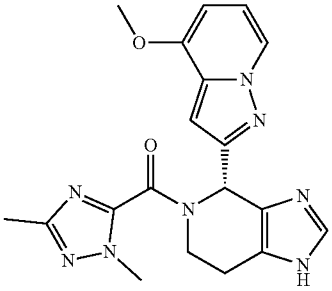 [SMILES: COc1cccn2nc([C@@H]3c4nc[nH]c4CCN3C(=O)c3nc(C)nn3C)cc12] | (S)-(1,3-dimethyl-1H-1,2,4-triazol-5-yl)(4-(4-methoxypyrazolo[1,5-a]pyridin-2-yl)-6,7-dihydro-1H-imidazo[4,5-c]pyridin-5(4H)-yl)methanone |
| 2394 | 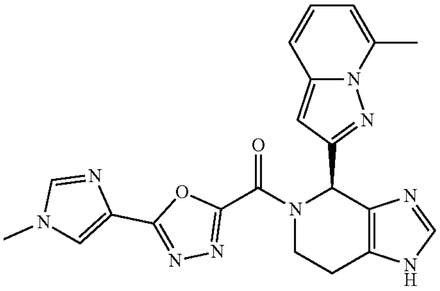 [SMILES: Cc1cccc2cc([C@H]3c4nc[nH]c4CCN3C(=O)c3nnc(-c4cn(C)cn4)o3)nn12] | (R)-(5-(1-methyl-1H-imidazol-4-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |
| 2395 | 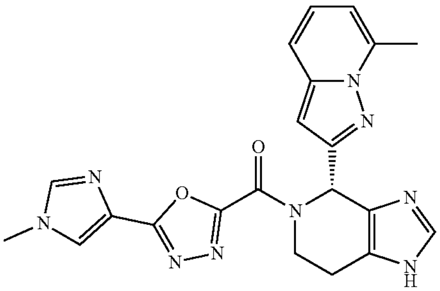 [SMILES: Cc1cccc2cc([C@@H]3c4nc[nH]c4CCN3C(=O)c3nnc(-c4cn(C)cn4)o3)nn12] | (S)-(5-(1-methyl-1H-imidazol-4-yl)-1,3,4-oxadiazol-2-yl)(4-(7-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 2396 | 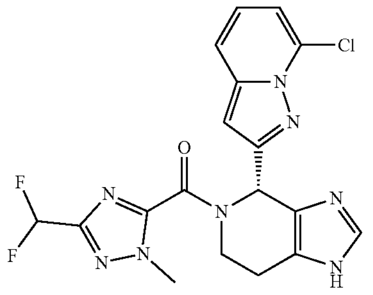 [SMILES: Cn1nc(C(F)F)nc1C(=O)N1CCc2[nH]cnc2[C@H]1c1cc2cccc(Cl)n2n1] | (S)-(4-(7-chloropyrazolo [1,5-a]pyridin-2-yl)-6,7-dihydro-1H-imidazo[4,5-c] pyridin-5(4H)-yl)(3-(difluoromethyl)-1-methyl-1H-1,2,4-triazol-5-yl)methanone |
| 2397 | 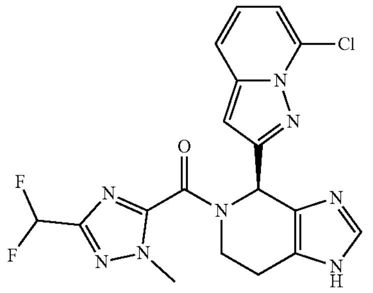 | (R)-(4-(7-chloropyrazolo [1,5-a]pyridin-2-yl)-6,7-dihydro-1H-imidazo[4,5-c] pyridin-5(4H)-yl)(3-(difluoromethyl)-1-methyl-1H-1,2,4-triazol-5-yl)methanone |
| 2398 | 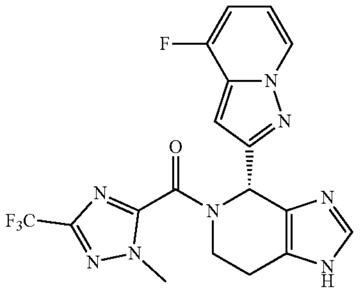 [SMILES: Cn1nc(C(F)(F)F)nc1C(=O)N1CCc2[nH]cnc2[C@H]1c1cc2c(F)cccn2n1] | (S)-(4-(4-fluoropyrazolo[1,5-a] pyridin-2-yl)-6,7-dihydro-1H-imidazo[4,5-c]pyridin-5(4H)-yl)(1-methyl-3-(trifluoromethyl)-1H-1,2,4-triazol-5-yl)methanone |
| 2399 | 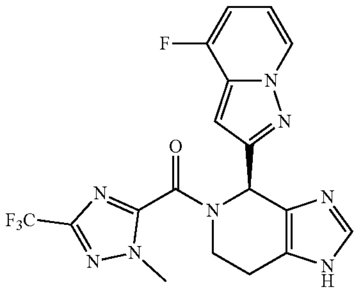 [SMILES: Cn1nc(C(F)(F)F)nc1C(=O)N1CCc2[nH]cnc2[C@@H]1c1cc2c(F)cccn2n1] | (R)-(4-(4-fluoropyrazolo [1,5-a]pyridin-2-yl)-6,7-dihydro-1H-imidazo[4,5-c]pyridin-5(4H)-yl)(1-methyl-3-(trifluoromethyl)-1H-1,2,4-triazol-5-yl)methanone |

TABLE 1-continued

| Ex. # | Structure | Name |
|---|---|---|
| | Pyrazolo[1,5-a]pyridines | |
| 2400 | 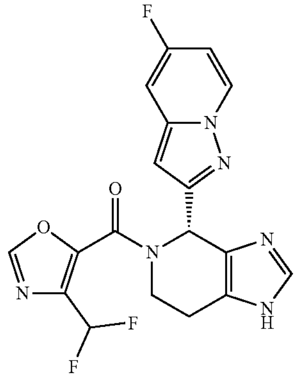 [SMILES: O=C(c1ocnc1C(F)F)N1CCc2[nH]cnc2[C@H]1c1cc2cc(F)ccn2n1] | (S)-(4-(difluoromethyl) oxazol-5-yl)(4-(5-fluoropyrazolo[1,5-a]pyridin-2-yl)-6,7-dihydro-1H-imidazo[4,5-c]pyridin-5(4H)-yl)methanone |
| 2401 | 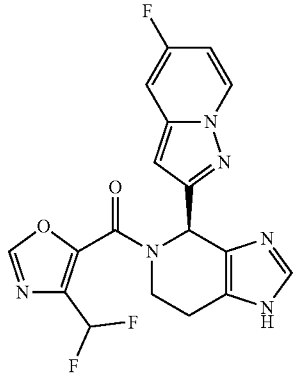 [SMILES: O=C(c1ocnc1C(F)F)N1CCc2[nH]cnc2[C@@H]1c1cc2cc(F)ccn2n1] | (R)-(4-(difluoromethyl)oxazol-5-yl)(4-(5-fluoropyrazolo[1,5-a]pyridin-2-yl)-6,7-dihydro-1H-imidazo[4,5-c]pyridin-5(4H)-yl)methanone |
| 2402 | 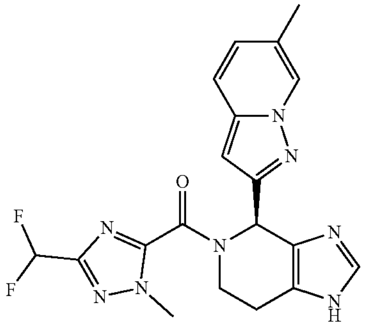 [SMILES: Cc1ccc2cc([C@H]3c4nc[nH]c4CCN3C(=O)c3nc(C(F)F)nn3C)nn2c1] | (R)-(3-(difluoromethyl)-1-methyl-1H-1,2,4-triazol-5-yl)(4-(6-methylpyrazolo[1,5-a]pyridin-2-yl)-6,7-dihydro-1H-imidazo[4,5-c]pyridin-5(4H)-yl)methanone |
| 2403 | 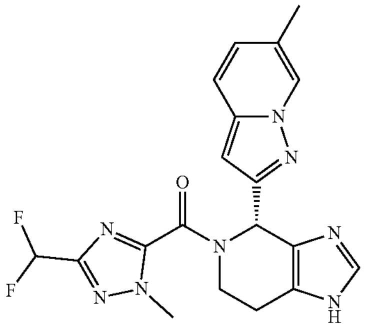 [SMILES: Cc1ccc2cc([C@@H]3c4nc[nH]c4CCN3C(=O)c3nc(C(F)F)nn3C)nn2c1] | (S)-(3-(difluoromethyl)-1-methyl-1H-1,2,4-triazol-5-yl)(4-(6-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 2404 | 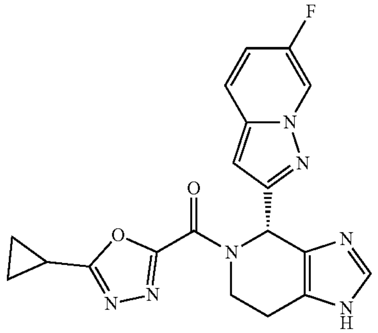 [SMILES: O=C(c1nnc(C2CC2)o1)N1CCc2[nH]cnc2[C@H]1c1cc2ccc(F)cn2n1] | (S)-(5-cyclopropyl-1,3,4-oxadiazol-2-yl)(4-(6-fluoropyrazolo[1,5-a]pyridin-2-yl)-6,7-dihydro-1H-imidazo[4,5-c]pyridin-5(4H)-yl)methanone |
| 2405 | 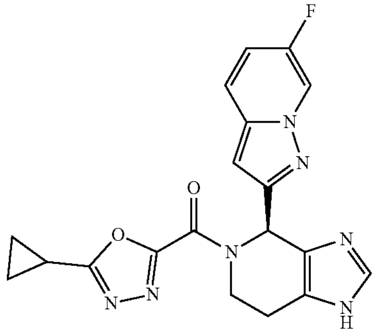 [SMILES: O=C(c1nnc(C2CC2)o1)N1CCc2[nH]cnc2[C@@H]1c1cc2ccc(F)cn2n1] | (R)-(5-cyclopropyl-1,3,4-oxadiazol-2-yl)(4-(6-fluoropyrazolo[1,5-a]pyridin-2-yl)-6,7-dihydro-1H-imidazo[4,5-c]pyridin-5(4H)-yl)methanone |
| 2406 | 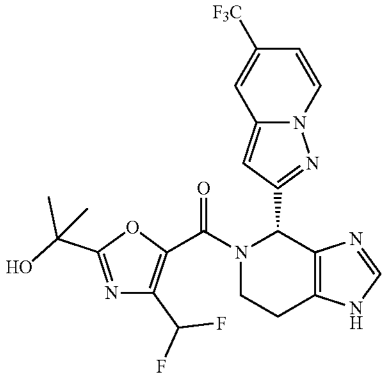 [SMILES: CC(C)(O)c1nc(C(F)F)c(C(=O)N2CCc3[nH]cnc3[C@H]2c2cc3cc(C(F)(F)F)ccn3n2)o1] | (S)-(4-(difluoromethyl)-2-(2-hydroxypropan-2-yl)oxazol-5-yl)(4-(5-(trifluoromethyl)pyrazolo[1,5-a]pyridin-2-yl)-6,7-dihydro-1H-imidazo[4,5-c]pyridin-5(4H)-yl)methanone |
| 2407 | 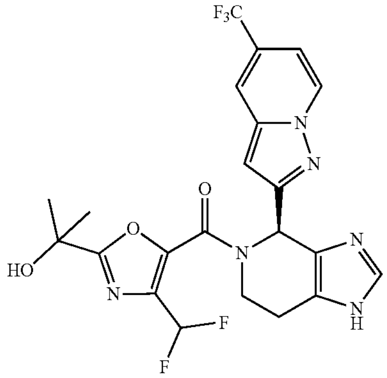 [SMILES: CC(C)(O)c1nc(C(F)F)c(C(=O)N2CCc3[nH]cnc3[C@@H]2c2cc3cc(C(F)(F)F)ccn3n2)o1] | (R)-(4-(difluoromethyl)-2-(2-hydroxypropan-2-yl)oxazol-5-yl)(4-(5-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 2408 | 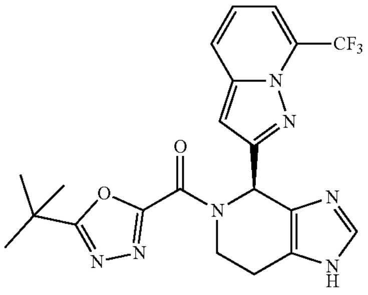 [SMILES: CC(C)(C)c1nnc(C(=O)N2CCc3[nH]cnc3[C@@H]2c2cc3cccc(C(F)(F)F)n3n2)o1] | (R)-(5-(tert-butyl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 2409 | 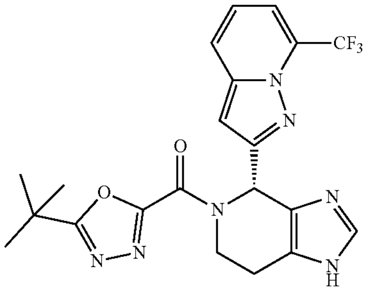 [SMILES: CC(C)(C)c1nnc(C(=O)N2CCc3[nH]cnc3[C@H]2c2cc3cccc(C(F)(F)F)n3n2)o1] | (S)-(5-(tert-butyl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 2410 | 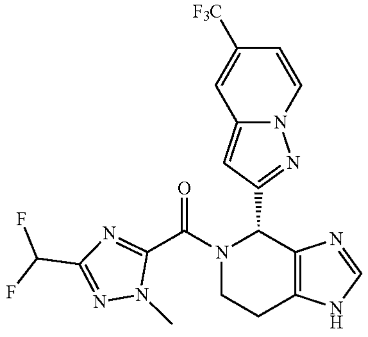 [SMILES: Cn1nc(C(F)F)nc1C(=O)N1CCc2[nH]cnc2[C@H]1c1cc2cc(C(F)(F)F)ccn2n1] | (S)-(3-(difluoromethyl)-1-methyl-1H-1,2,4-triazol-5-yl)(4-(5-(trifluoromethyl)pyrazolo[1,5-a]pyridin-2-yl)-6,7-dihydro-1H-imidazo[4,5-c]pyridin-5(4H)-yl)methanone |
| 2411 | 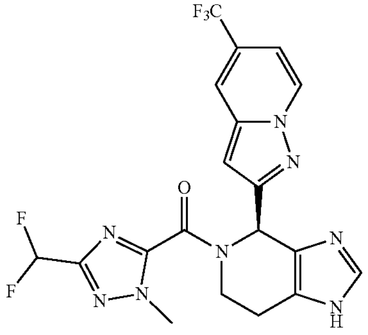 [SMILES: Cn1nc(C(F)F)nc1C(=O)N1CCc2[nH]cnc2[C@@H]1c1cc2cc(C(F)(F)F)ccn2n1] | (R)-(3-(difluoromethyl)-1-methyl-1H-1,2,4-triazol-5-yl)(4-(5-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 2412 | 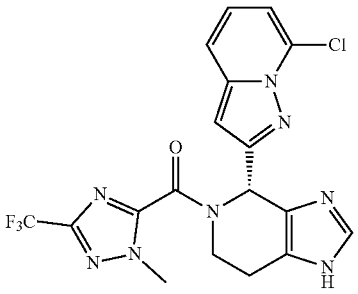 [SMILES: Cn1nc(C(F)(F)F)nc1C(=O)N1CCc2[nH]cnc2[C@H]1c1cc2cccc(Cl)n2n1] | (S)-(4-(7-chloropyrazolo [1,5-a]pyridin-2-yl)-6,7-dihydro-1H-imidazo[4,5-c] pyridin-5(4H)-yl)(1-methyl-3-(trifluoromethyl)-1H-1,2,4-triazol-5-yl)methanone |
| 2413 | 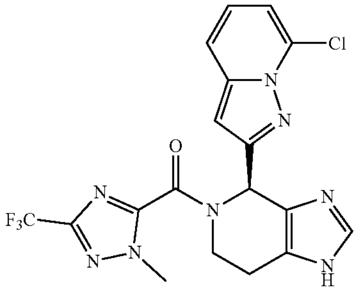 [SMILES: Cn1nc(C(F)(F)F)nc1C(=O)N1CCc2[nH]cnc2[C@@H]1c1cc2cccc(Cl)n2n1] | (R)-(4-(7-chloropyrazolo [1,5-a]pyridin-2-yl)-6,7-dihydro-1H-imidazo[4,5-c] pyridin-5(4H)-yl)(1-methyl-3-(trifluoromethyl)-1H-1,2,4-triazol-5-yl)methanone |
| 2414 | 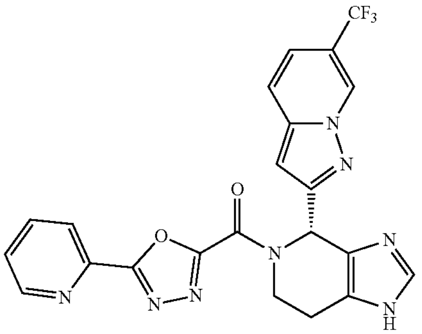 [SMILES: O=C(c1nnc(-c2ccccn2)o1)N1CCc2[nH]cnc2[C@H]1c1cc2ccc(C(F)(F)F)cn2n1] | (S)-(5-(pyridin-2-yl)-1,3,4-oxadiazol-2-yl)(4-(6-(trifluoromethyl)pyrazolo [1,5-a]pyridin-2-yl)-6,7-dihydro-1H-imidazo[4,5-c] pyridin-5(4H)-yl)methanone |
| 2415 | 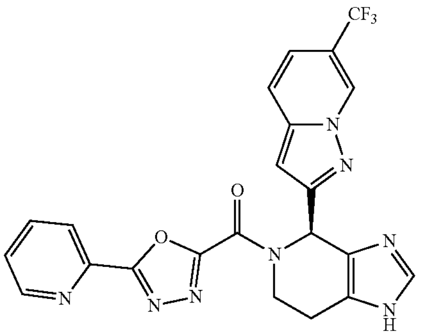 [SMILES: O=C(c1nnc(-c2ccccn2)o1)N1CCc2[nH]cnc2[C@@H]1c1cc2ccc(C(F)(F)F)cn2n1] | (R)-(5-(pyridin-2-yl)-1,3,4-oxadiazol-2-yl)(4-(6-(trifluoromethyl)pyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 2416 | 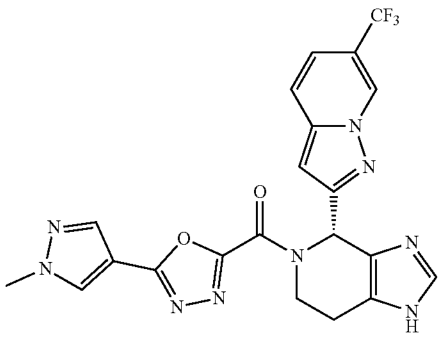 [SMILES: Cn1cc(-c2nnc(C(=O)N3CCc4[nH]cnc4[C@H]3c3cc4ccc(C(F)(F)F)cn4n3)o2)cn1] | (S)-(5-(1-methyl-1H-pyrazol-4-yl)-1,3,4-oxadiazol-2-yl)(4-(6-(trifluoromethyl)pyrazolo[1,5-a]pyridin-2-yl)-6,7-dihydro-1H-imidazo[4,5-c]pyridin-5(4H)-yl)methanone |
| 2417 | 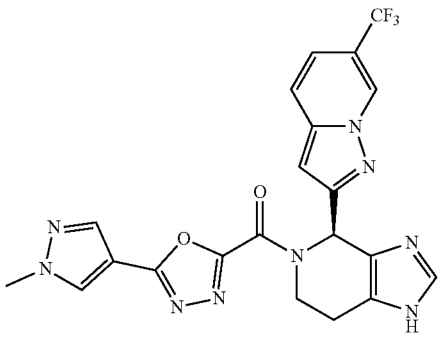 [SMILES: Cn1cc(-c2nnc(C(=O)N3CCc4[nH]cnc4[C@@H]3c3cc4ccc(C(F)(F)F)cn4n3)o2)cn1] | (R)-(5-(1-methyl-1H-pyrazol-4-yl)-1,3,4-oxadiazol-2-yl)(4-(6-(trifluoromethyl)pyrazolo[1,5-a]pyridin-2-yl)-6,7-dihydro-1H-imidazo[4,5-c]pyridin-5(4H)-yl)methanone |
| 2418 | 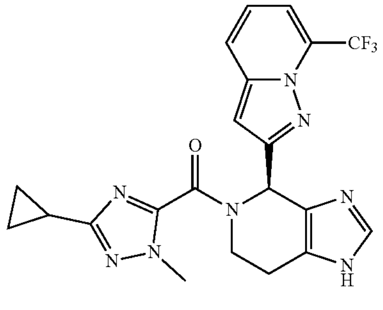 [SMILES: Cn1nc(C2CC2)nc1C(=O)N1CCc2[nH]cnc2[C@@H]1c1cc2cccc(C(F)(F)F)n2n1] | (R)-(3-cyclopropyl-1-methyl-1H-1,2,4-triazol-5-yl)(4-(7-(trifluoromethyl)pyrazolo[1,5-a]pyridin-2-yl)-6,7-dihydro-1H-imidazo[4,5-c]pyridin-5(4H)-yl)methanone |
| 2419 | 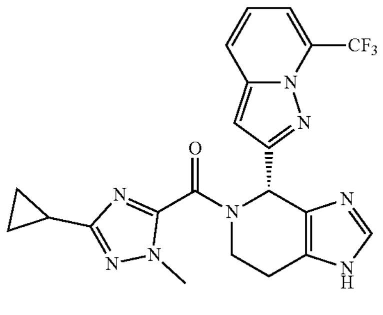 [SMILES: Cn1nc(C2CC2)nc1C(=O)N1CCc2[nH]cnc2[C@H]1c1cc2cccc(C(F)(F)F)n2n1] | (S)-(3-cyclopropyl-1-methyl-1H-1,2,4-triazol-5-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 2420 | 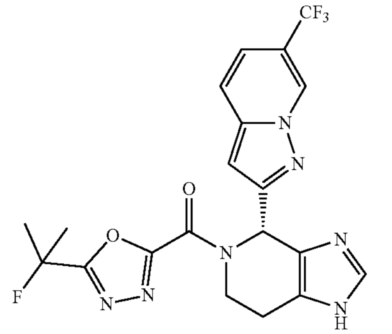 [SMILES: CC(C)(F)c1nnc(C(=O)N2CCc3[nH]cnc3[C@H]2c2cc3ccc(C(F)(F)F)cn3n2)o1] | (S)-(5-(2-fluoropropan-2-yl)-1,3,4-oxadiazol-2-yl)(4-(6-(trifluoromethyl)pyrazolo[1,5-a]pyridin-2-yl)-6,7-dihydro-1H-imidazo[4,5-c]pyridin-5(4H)-yl)methanone |
| 2421 | 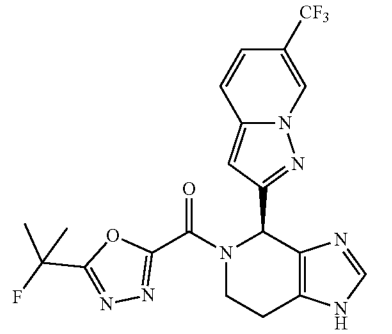 [SMILES: CC(C)(F)c1nnc(C(=O)N2CCc3[nH]cnc3[C@@H]2c2cc3ccc(C(F)(F)F)cn3n2)o1] | (R)-(5-(2-fluoropropan-2-yl)-1,3,4-oxadiazol-2-yl)(4-(6-(trifluoromethyl)pyrazolo[1,5-a]pyridin-2-yl)-6,7-dihydro-1H-imidazo[4,5-c]pyridin-5(4H)-yl)methanone |
| 2422 | 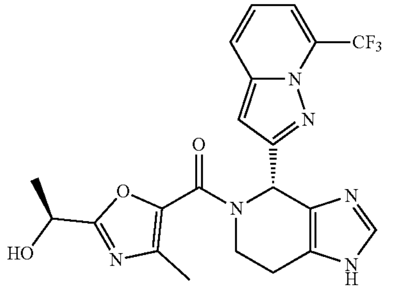 [SMILES: Cc1nc([C@H](C)O)oc1C(=O)N1CCc2[nH]cnc2[C@H]1c1cc2cccc(C(F)(F)F)n2n1] | (2-((S)-1-hydroxyethyl)-4-methyloxazol-5-yl)((S)-4-(7-(trifluoromethyl)pyrazolo[1,5-a]pyridin-2-yl)-6,7-dihydro-1H-imidazo[4,5-c]pyridin-5(4H)-yl)methanone |
| 2423 | 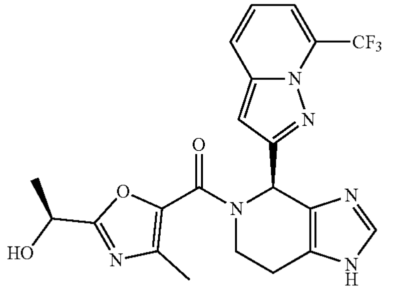 [SMILES: Cc1nc([C@H](C)O)oc1C(=O)N1CCc2[nH]cnc2[C@@H]1c1cc2cccc(C(F)(F)F)n2n1] | (2-((S)-1-hydroxyethyl)-4-methyloxazol-5-yl)((R)-4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 2424 | 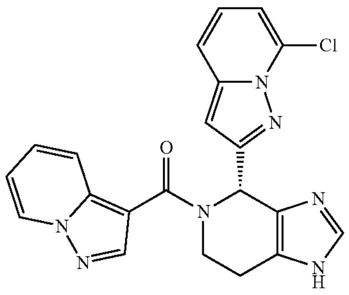 | (S)-(4-(7-chloropyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 2425 | 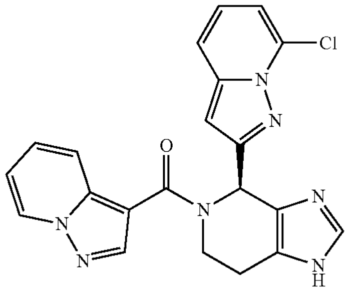 [SMILES: O=C(c1cnn2ccccc12)N1CCc2[nH]cnc2[C@@H]1c1cc2cccc(Cl)n2n1] | (R)-(4-(7-chloropyrazolo[1,5-a]pyridin-2-yl)-6,7-dihydro-1H-imidazo[4,5-c]pyridin-5(4H)-yl)(pyrazolo[1,5-a]pyridin-3-yl)methanone |
| 2426 | 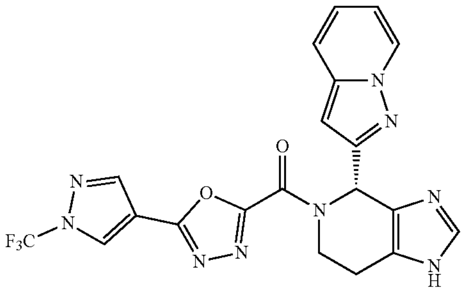 [SMILES: O=C(c1nnc(-c2cnn(C(F)(F)F)c2)o1)N1CCc2[nH]cnc2[C@H]1c1cc2ccccn2n1] | (S)-(4-(pyrazolo[1,5-a]pyridin-2-yl)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |
| 2427 | 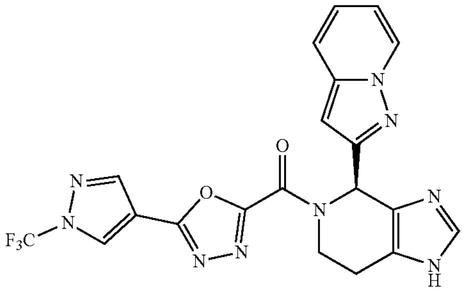 [SMILES: O=C(c1nnc(-c2cnn(C(F)(F)F)c2)o1)N1CCc2[nH]cnc2[C@@H]1c1cc2ccccn2n1] | (R)-(4-(pyrazolo[1,5-a]pyridin-2-yl)-6,7-dihydro-1H-imidazo[4,5-c]pyridin-5(4H)-yl)(5-(1-(trifluoromethyl)-1H-pyrazol-4-yl)-1,3,4-oxadiazol-2-yl)methanone |
| 2428 | 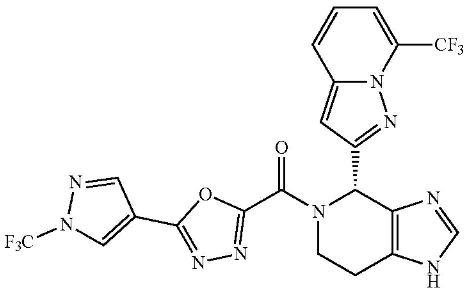 [SMILES: O=C(c1nnc(-c2cnn(C(F)(F)F)c2)o1)N1CCc2[nH]cnc2[C@H]1c1cc2cccc(C(F)(F)F)n2n1] | (S)-(5-(1-(trifluoromethyl)-1H-pyrazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 2429 | 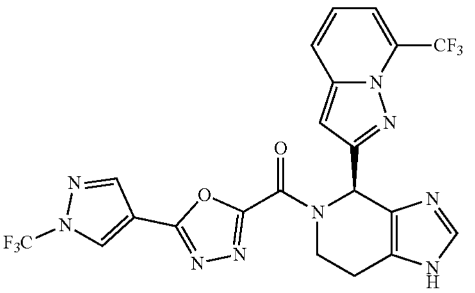 [SMILES: O=C(c1nnc(-c2cnn(C(F)(F)F)c2)o1)N1CCc2[nH]cnc2[C@@H]1c1cc2cccc(C(F)(F)F)n2n1] | (R)-(5-(1-(trifluoromethyl)-1H-pyrazol-4-yl)-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 2430 | 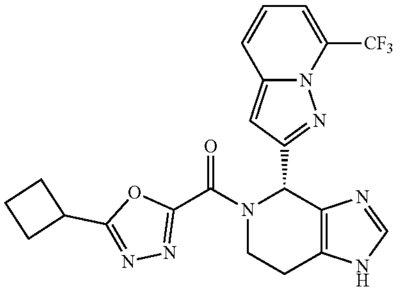 [SMILES: O=C(c1nnc(C2CCC2)o1)N1CCc2[nH]cnc2[C@H]1c1cc2cccc(C(F)(F)F)n2n1] | (S)-(5-cyclobutyl-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 2431 | 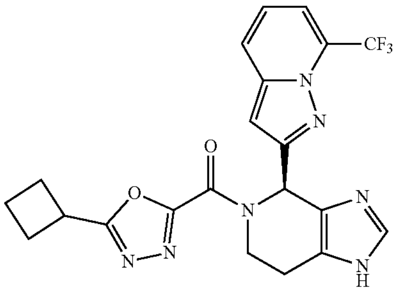 [SMILES: O=C(c1nnc(C2CCC2)o1)N1CCc2[nH]cnc2[C@@H]1c1cc2cccc(C(F)(F)F)n2n1] | (R)-(5-cyclobutyl-1,3,4-oxadiazol-2-yl)(4-(7-(trifluoromethyl)pyrazolo[1,5-a]pyridin-2-yl)-6,7-dihydro-1H-imidazo[4,5-c]pyridin-5(4H)-yl)methanone |
| 2432 | 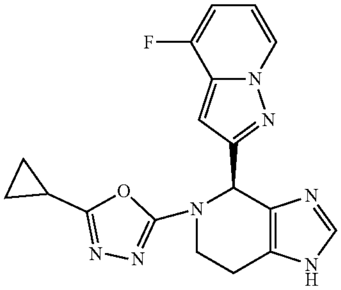 [SMILES: Fc1cccn2nc([C@H]3c4nc[nH]c4CCN3c3nnc(C4CC4)o3)cc12] | (R)-2-cyclopropyl-5-(4-(4-fluoropyrazolo[1,5-a]pyridin-2-yl)-6,7-dihydro-1H-imidazo[4,5-c]pyridin-5(4H)-yl)-1,3,4-oxadiazole |
| 2433 | 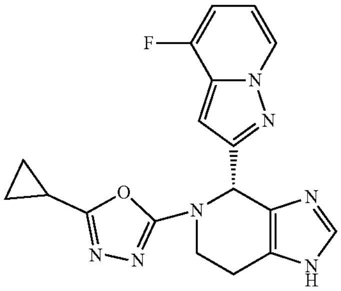 | (S)-2-cyclopropyl-5-(4-(4-fluoropyrazolo[1,5-a]pyridin-2-yl)-6,7-dihydro-1H-imidazo[4,5-c]pyridin-5(4H)-yl)-1,3,4-oxadiazole |

TABLE 1-continued

| Pyrazolo[1,5-a]pyridines | | |
|---|---|---|
| Ex. # | Structure | Name |
| 2434 | 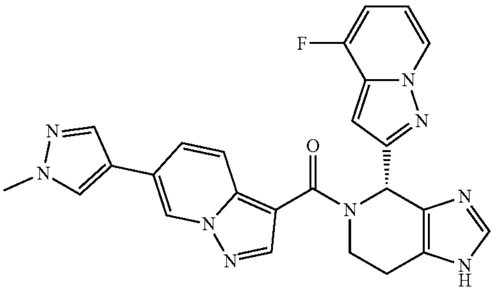 [SMILES: Cn1cc(-c2ccc3c(C(=O)N4CCc5[nH]cnc5[C@H]4c4cc5c(F)cccn5n4)cnn3c2)cn1] | (S)-(4-(4-fluoropyrazolo[1,5-a]pyridin-2-yl)-6,7-dihydro-1H-imidazo[4,5-c]pyridin-5(4H)-yl)(6-(1-methyl-1H-pyrazol-4-yl)pyrazolo[1,5-a]pyridin-3-yl)methanone |
| 2435 | 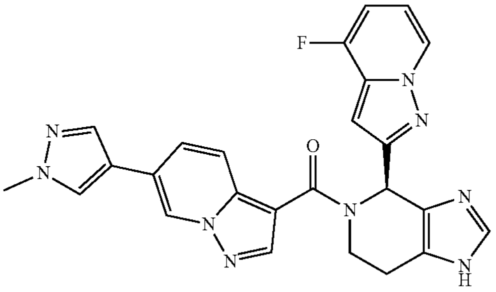 [SMILES: Cn1cc(-c2ccc3c(C(=O)N4CCc5[nH]cnc5[C@@H]4c4cc5c(F)cccn5n4)cnn3c2)cn1] | (R)-(4-(4-fluoropyrazolo[1,5-a]pyridin-2-yl)-6,7-dihydro-1H-imidazo[4,5-c]pyridin-5(4H)-yl)(6-(1-methyl-1H-pyrazol-4-yl)pyrazolo[1,5-a]pyridin-3-yl)methanone |
| 2436 | 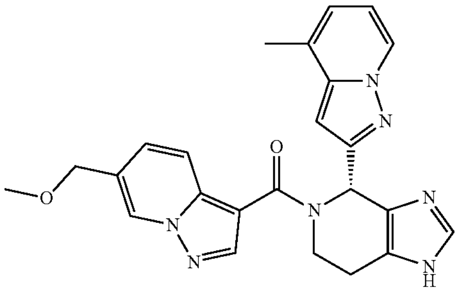 [SMILES: COCc1ccc2c(C(=O)N3CCc4[nH]cnc4[C@H]3c3cc4c(C)cccn4n3)cnn2c1] | (S)-(6-(methoxymethyl)pyrazolo[1,5-a]pyridin-3-yl)(4-(4-methylpyrazolo[1,5-a]pyridin-2-yl)-6,7-dihydro-1H-imidazo[4,5-c]pyridin-5(4H)-yl)methanone |
| 2437 | 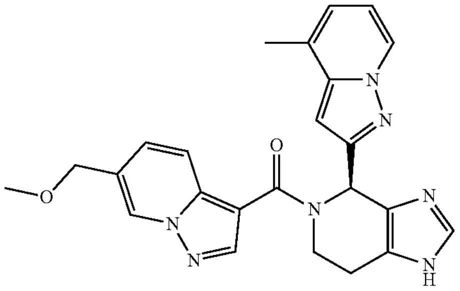 [SMILES: COCc1ccc2c(C(=O)N3CCc4[nH]cnc4[C@@H]3c3cc4c(C)cccn4n3)cnn2c1] | (R)-(6-(methoxymethyl)pyrazolo[1,5-a]pyridin-3-yl)(4-(4-methylpyrazolo[1,5-a]pyridin-2-yl)-6,7-dihydro-1H-imidazo[4,5-c]pyridin-5(4H)-yl)methanone |
| 2438 | 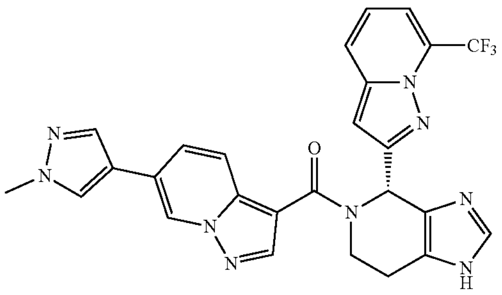 [SMILES: Cn1cc(-c2ccc3c(C(=O)N4CCc5[nH]cnc5[C@H]4c4cc5cccc(C(F)(F)F)n5n4)cnn3c2)cn1] | (S)-(6-(1-methyl-1H-pyrazol-4-yl)pyrazolo[1,5-a]pyridin-3-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 2439 | 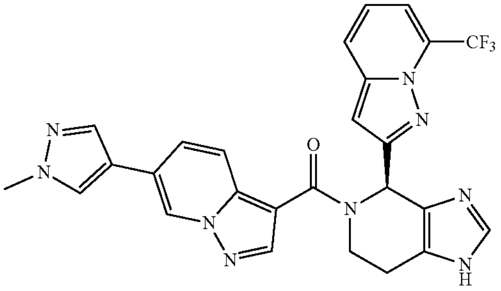 [SMILES: Cn1cc(-c2ccc3c(C(=O)N4CCc5[nH]cnc5[C@@H]4c4cc5cccc(C(F)(F)F)n5n4)cnn3c2)cn1] | (R)-(6-(1-methyl-1H-pyrazol-4-yl)pyrazolo[1,5-a]pyridin-3-yl)(4-(7-(trifluoromethyl)pyrazolo[1,5-a]pyridin-2-yl)-6,7-dihydro-1H-imidazo[4,5-c]pyridin-5(4H)-yl)methanone |
| 2440 | 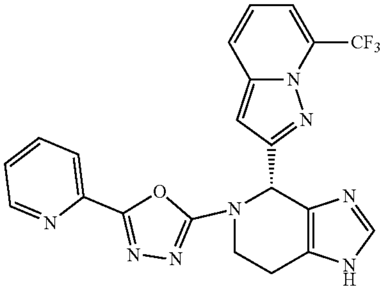 [SMILES: FC(F)(F)c1cccc2cc([C@@H]3c4nc[nH]c4CCN3c3nnc(-c4ccccn4)o3)nn12] | (S)-2-(pyridin-2-yl)-5-(4-(7-(trifluoromethyl)pyrazolo[1,5-a]pyridin-2-yl)-6,7-dihydro-1H-imidazo[4,5-c]pyridin-5(4H)-yl)-1,3,4-oxadiazole |
| 2441 | 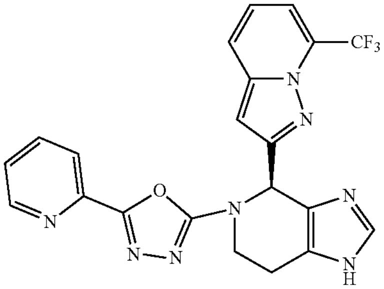 [SMILES: FC(F)(F)c1cccc2cc([C@H]3c4nc[nH]c4CCN3c3nnc(-c4ccccn4)o3)nn12] | (R)-2-(pyridin-2-yl)-5-(4-(7-(trifluoromethyl)pyrazolo[1,5-a]pyridin-2-yl)-6,7-dihydro-1H-imidazo[4,5-c]pyridin-5(4H)-yl)-1,3,4-oxadiazole |
| 2442 | 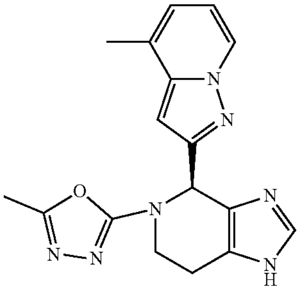 [SMILES: Cc1nnc(N2CCc3[nH]cnc3[C@@H]2c2cc3c(C)cccn3n2)o1] | (R)-2-methyl-5-(4-(4-methylpyrazolo[1,5-a]pyridin-2-yl)-6,7-dihydro-1H-imidazo[4,5-c]pyridin-5(4H)-yl)-1,3,4-oxadiazole |
| 2443 | 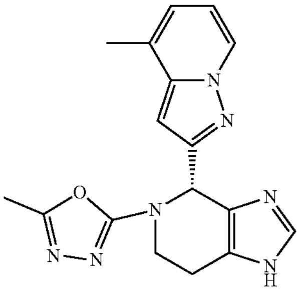 [SMILES: Cc1nnc(N2CCc3[nH]cnc3[C@H]2c2cc3c(C)cccn3n2)o1] | (S)-2-methyl-5-(4-(4-methylpyrazolo[1,5-a]pyridin-2-yl)-6,7-dihydro-1H-imidazo[4,5-c]pyridin-5(4H)-yl)-1,3,4-oxadiazole |

TABLE 1-continued

Pyrazolo[1,5-a]pyridines

| Ex. # | Structure | Name |
|---|---|---|
| 2444 | 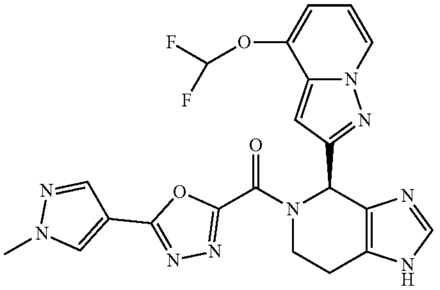 [SMILES: Cn1cc(-c2nnc(C(=O)N3CCc4[nH]cnc4[C@@H]3c3cc4c(OC(F)F)cccn4n3)o2)cn1] | (R)-(4-(4-(difluoromethoxy) pyrazolo[1,5-a]pyridin-2-yl)-6,7-dihydro-1H-imidazo [4,5-c]pyridin-5(4H)-yl)(5-(1-methyl-1H-pyrazol-4-yl)-1,3,4-oxadiazol-2-yl)methanone |
| 2445 | 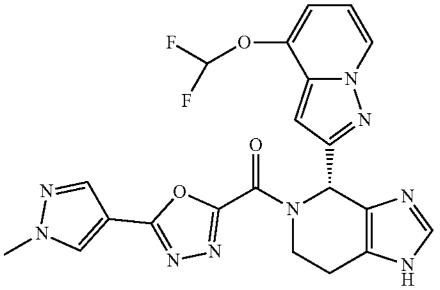 [SMILES: Cn1cc(-c2nnc(C(=O)N3CCc4[nH]cnc4[C@H]3c3cc4c(OC(F)F)cccn4n3)o2)cn1] | (S)-(4-(4-(difluoromethoxy) pyrazolo[1,5-a]pyridin-2-yl)-6,7-dihydro-1H-imidazo [4,5-c]pyridin-5(4H)-yl)(5-(1-methyl-1H-pyrazol-4-yl)-1,3,4-oxadiazol-2-yl)methanone |
| 2446 | 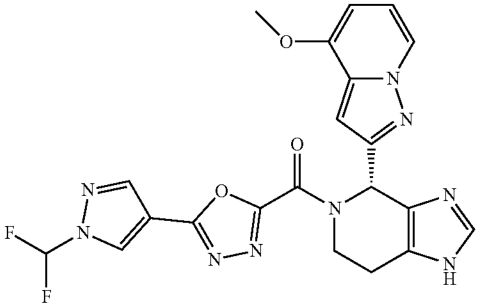 | (S)-(5-(1-(difluoromethyl)-1H-pyrazol-4-yl)-1,3,4-oxadiazol-2-yl)(4-(4-methoxypyrazolo[1,5-a]pyridin-2-yl)-6,7-dihydro-1H-imidazo [4,5-c]pyridin-5(4H)-yl)methanone |
| 2447 | 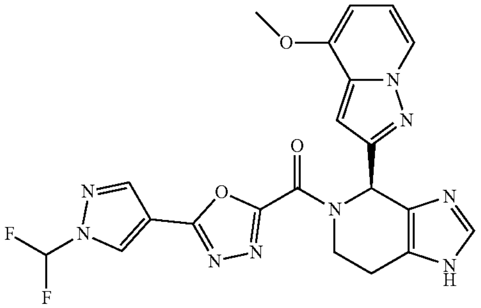 [SMILES: COc1cccn2nc([C@H]3c4nc[nH]c4CCN3C(=O)c3nnc(-c4cnn(C(F)F)c4)o3)cc12] | (R)-(5-(1-(difluoromethyl)-1H-pyrazol-4-yl)-1,3,4-oxadiazol-2-yl)(4-(4-methoxypyrazolo[1,5-a]pyridin-2-yl)-6,7-dihydro-1H-imidazo[4,5-c]pyridin-5(4H)-yl)methanone |
| 2448 | 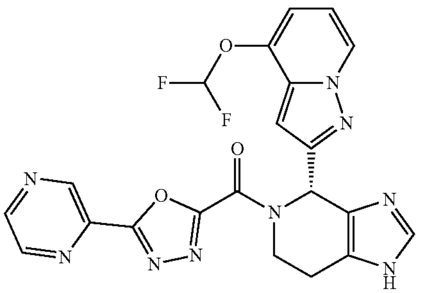 [SMILES: O=C(c1nnc(-c2cnccn2)o1)N1CCc2[nH]cnc2[C@H]1c1cc2c(OC(F)F)cccn2n1] | (S)-(4-(4-(difluoromethoxy) pyrazolo[1,5-a]pyridin-2-yl)-6,7-dihydro-1H-imidazo [4,5-c]pyridin-5(4H)-yl)(5-(pyrazin-2-yl)-1,3,4-oxadiazol-2-yl)methanone |

TABLE 1-continued

| Pyrazolo[1,5-a]pyridines | | |
|---|---|---|
| Ex. # | Structure | Name |
| 2449 | 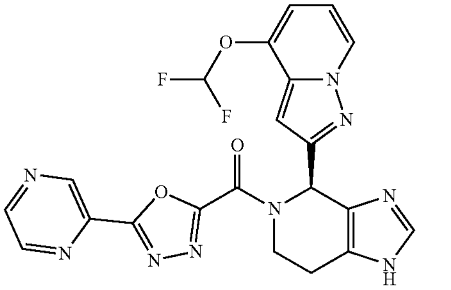 | (R)-(4-(4-(difluoromethoxy) pyrazolo[1,5-a]pyridin-2-yl)-6,7-dihydro-1H-imidazo [4,5-c]pyridin-5(4H)-yl)(5-(pyrazin-2-yl)-1,3,4-oxadiazol-2-yl)methanone |
| 2450 | 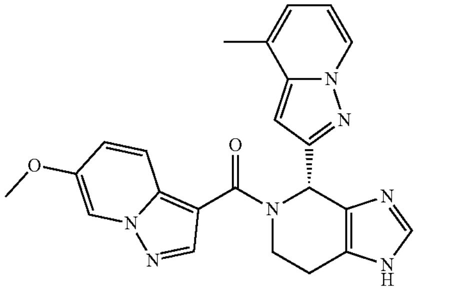 [SMILES: COc1ccc2c(C(=O)N3CCc4[nH]cnc4[C@H]3c3cc4c(C)cccn4n3)cnn2c1] | (S)-(6-methoxypyrazolo [1,5-a]pyridin-3-yl)(4-(4-methylpyrazolo[1,5-a]pyridin-2-yl)-6,7-dihydro-1H-imidazo[4,5-c]pyridin-5(4H)-yl)methanone |
| 2451 | 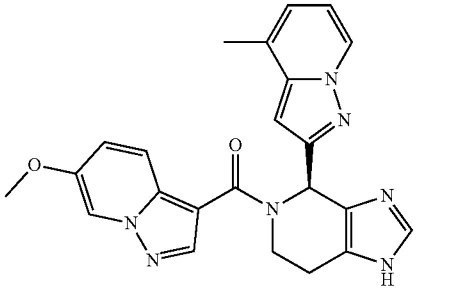 [SMILES: COc1ccc2c(C(=O)N3CCc4[nH]cnc4[C@@H]3c3cc4c(C)cccn4n3)cnn2c1] | (R)-(6-methoxypyrazolo [1,5-a]pyridin-3-yl)(4-(4-methylpyrazolo[1,5-a]pyridin-2-yl)-6,7-dihydro-1H-imidazo[4,5-c]pyridin-5(4H)-yl)methanone |
| 2452 | 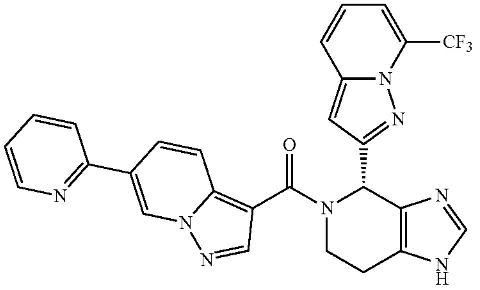 [SMILES: O=C(c1cnn2cc(-c3ccccn3)ccc12)N1CCc2[nH]cnc2[C@H]1c1cc2cccc(C(F)(F)F)n2n1] | (S)-(6-(pyridin-2-yl)pyrazolo [1,5-a]pyridin-3-yl)(4-(7-(trifluoromethyl)pyrazolo [1,5-a]pyridin-2-yl)-6,7-dihydro-1H-imidazo[4,5-c]pyridin-5(4H)-yl)methanone |
| 2453 | 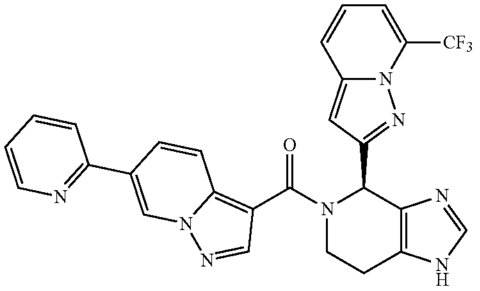 [SMILES: O=C(c1cnn2cc(-c3ccccn3)ccc12)N1CCc2[nH]cnc2[C@@H]1c1cc2cccc(C(F)(F)F)n2n1] | (R)-(6-(pyridin-2-yl)pyrazolo [1,5-a]pyridin-3-yl)(4-(7-(trifluoromethyl)pyrazolo [1,5-a]pyridin-2-yl)-6,7-dihydro-1H-imidazo[4,5-c]pyridin-5(4H)-yl)methanone |

TABLE 1-continued

Pyrazolo[1,5-a]pyridines

| Ex. # | Structure | Name |
|---|---|---|
| 2454 | 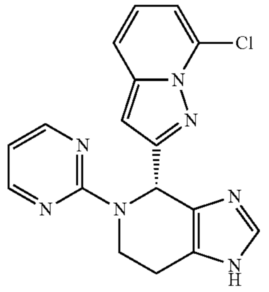 [SMILES: Clc1cccc2cc([C@@H]3c4nc[nH]c4CCN3c3ncccn3)nn12] | (S)-4-(7-chloropyrazolo [1,5-a]pyridin-2-yl)-5- (pyrimidin-2-yl)-4,5,6,7- tetrahydro-1H-imidazo[4,5- c]pyridine |
| 2455 | 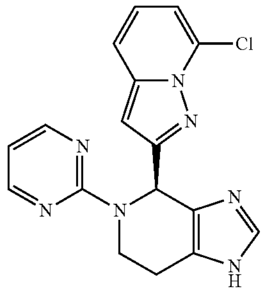 [SMILES: Clc1cccc2cc([C@H]3c4nc[nH]c4CCN3c3ncccn3)nn12] | (R)-4-(7-chloropyrazolo [1,5-a]pyridin-2-yl)-5- (pyrimidin-2-yl)-4,5,6,7- tetrahydro-1H-imidazo[4,5- c]pyridine |
| 2456 | 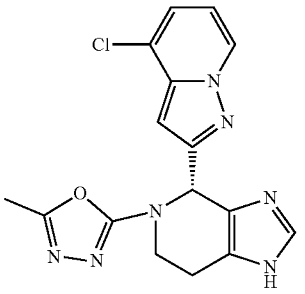 [SMILES: Cc1nnc(N2CCc3[nH]cnc3[C@H]2c2cc3c(Cl)cccn3n2)o1] | (S)-2-(4-(4-chloropyrazolo [1,5-a]pyridin-2-yl)-6,7- dihydro-1H-imidazo[4,5-c] pyridin-5(4H)-yl)-5-methyl- 1,3,4-oxadiazole |
| 2457 | 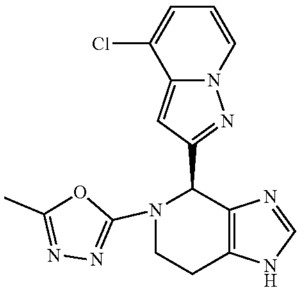 [SMILES: Cc1nnc(N2CCc3[nH]cnc3[C@@H]2c2cc3c(Cl)cccn3n2)o1] | (R)-2-(4-(4-chloropyrazolo [1,5-a]pyridin-2-yl)-6,7- dihydro-1H-imidazo[4,5-c] pyridin-5(4H)-yl)-5-methyl- 1,3,4-oxadiazole |
| 2458 | 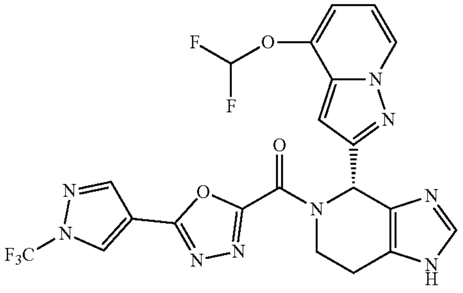 [SMILES: O=C(c1nnc(-c2cnn(C(F)(F)F)c2)o1)N1CCc2[nH]cnc2[C@H]1c1cc2c(OC(F)F)cccn2n1] | (S)-(4-(4-(difluoromethoxy) pyrazolo[1,5-a]pyridin-2-yl)- 6,7-dihydro-1H-imidazo [4,5-c]pyridin-5(4H)-yl)(5-(1- (trifluoromethyl)-1H-pyrazol- 4-yl)-1,3,4-oxadiazol-2- yl)methanone |

TABLE 1-continued

| Pyrazolo[1,5-a]pyridines | | |
|---|---|---|
| Ex. # | Structure | Name |
| 2459 | 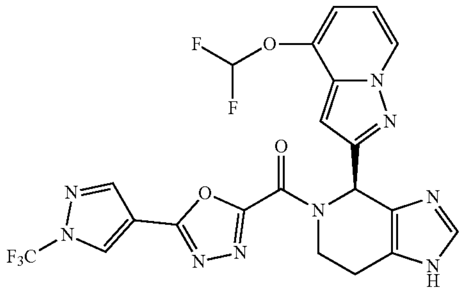 [SMILES: O=C(c1nnc(-c2cnn(C(F)(F)F)c2)o1)N1CCc2[nH]cnc2[C@@H]1c1cc2c(OC(F)F)cccn2n1] | (R)-(4-(4-(difluoromethoxy) pyrazolo[1,5-a]pyridin-2-yl)-6,7-dihydro-1H-imidazo [4,5-c]pyridin-5(4H)-yl)(5-(1-(trifluoromethyl)-1H-pyrazol-4-yl)-1,3,4-oxadiazol-2-yl)methanone |
| 2460 | 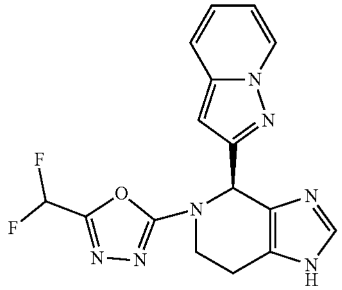 [SMILES: FC(F)c1nnc(N2CCc3[nH]cnc3[C@@H]2c2cc3ccccn3n2)o1] | (R)-2-(difluoromethyl)-5-(4-(pyrazolo[1,5-a]pyridin-2-yl)-6,7-dihydro-1H-imidazo [4,5-c]pyridin-5(4H)-yl)-1,3,4-oxadiazole |
| 2461 | 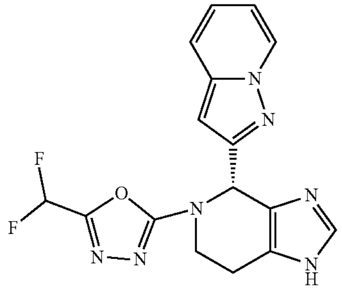 [SMILES: FC(F)c1nnc(N2CCc3[nH]cnc3[C@H]2c2cc3ccccn3n2)o1] | (S)-2-(difluoromethyl)-5-(4-(pyrazolo[1,5-a]pyridin-2-yl)-6,7-dihydro-1H-imidazo [4,5-c]pyridin-5(4H)-yl)-1,3,4-oxadiazole |
| 2462 | 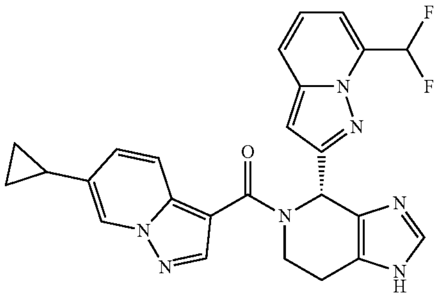 [SMILES: O=C(c1cnn2cc(C3CC3)ccc12)N1CCc2[nH]cnc2[C@H]1c1cc2cccc(C(F)F)n2n1] | (S)-(6-cyclopropylpyrazolo [1,5-a]pyridin-3-yl)(4-(7-(difluoromethyl)pyrazolo [1,5-a]pyridin-2-yl)-6,7-dihydro-1H-imidazo[4,5-c] pyridin-5(4H)-yl)methanone |
| 2463 | 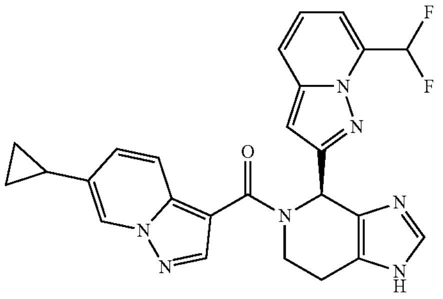 [SMILES: O=C(c1cnn2cc(C3CC3)ccc12)N1CCc2[nH]cnc2[C@@H]1c1cc2cccc(C(F)F)n2n1] | (R)-(6-cyclopropylpyrazolo [1,5-a]pyridin-3-yl)(4-(7-(difluoromethyl)pyrazolo [1,5-a]pyridin-2-yl)-6,7-dihydro-1H-imidazo[4,5-c] pyridin-5(4H)-yl)methanone |

TABLE 1-continued

| Pyrazolo[1,5-a]pyridines | | |
|---|---|---|
| Ex. # | Structure | Name |
| 2464 | 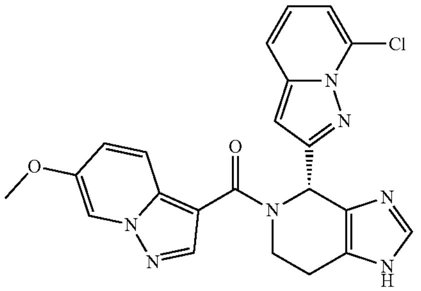 [SMILES: COc1ccc2c(C(=O)N3CCc4[nH]cnc4[C@H]3c3cc4cccc(Cl)n4n3)cnn2c1] | (S)-(4-(7-chloropyrazolo[1,5-a]pyridin-2-yl)-6,7-dihydro-1H-imidazo[4,5-c]pyridin-5(4H)-yl)(6-methoxypyrazolo[1,5-a]pyridin-3-yl)methanone |
| 2465 | 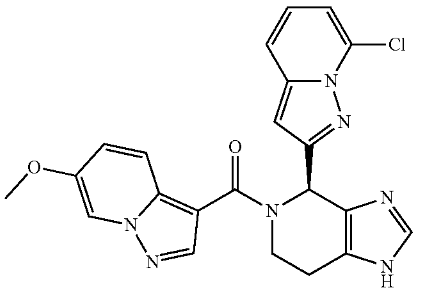 [SMILES: COc1ccc2c(C(=O)N3CCc4[nH]cnc4[C@@H]3c3cc4cccc(Cl)n4n3)cnn2c1] | (R)-(4-(7-chloropyrazolo[1,5-a]pyridin-2-yl)-6,7-dihydro-1H-imidazo[4,5-c]pyridin-5(4H)-yl)(6-methoxypyrazolo[1,5-a]pyridin-3-yl)methanone |
| 2466 | 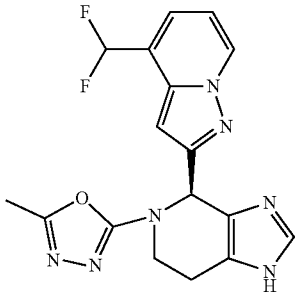 [SMILES: Cc1nnc(N2CCc3[nH]cnc3[C@@H]2c2cc3c(C(F)F)cccn3n2)o1] | (R)-2-(4-(4-(difluoromethyl)pyrazolo[1,5-a]pyridin-2-yl)-6,7-dihydro-1H-imidazo[4,5-c]pyridin-5(4H)-yl)-5-methyl-1,3,4-oxadiazole |
| 2467 | 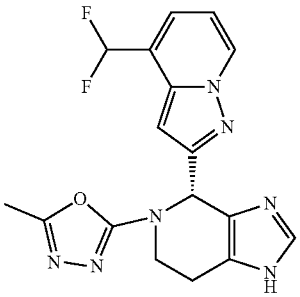 [SMILES: Cc1nnc(N2CCc3[nH]cnc3[C@H]2c2cc3c(C(F)F)cccn3n2)o1] | (S)-2-(4-(4-(difluoromethyl)pyrazolo[1,5-a]pyridin-2-yl)-6,7-dihydro-1H-imidazo[4,5-c]pyridin-5(4H)-yl)-5-methyl-1,3,4-oxadiazole |
| 2468 | 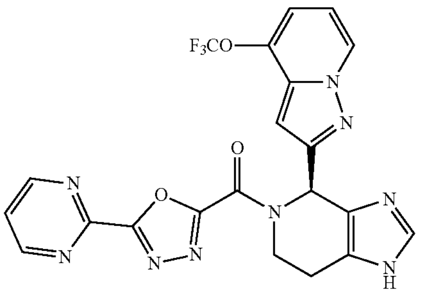 [SMILES: O=C(c1nnc(-c2ncccn2)o1)N1CCc2[nH]cnc2[C@@H]1c1cc2c(OC(F)(F)F)cccn2n1] | (R)-(5-(pyrimidin-2-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
| --- | --- | --- |
| | Pyrazolo[1,5-a]pyridines | |
| 2469 | 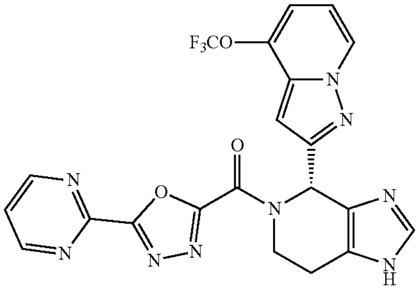 | (S)-(5-(pyrimidin-2-yl)-1,3,4-oxadiazol-2-yl)(4-(4-(trifluoromethoxy)pyrazolo[1,5-a]pyridin-2-yl)-6,7-dihydro-1H-imidazo[4,5-c]pyridin-5(4H)-yl)methanone |
| 2470 | 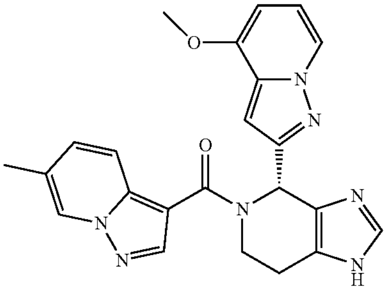 [SMILES: COc1cccn2nc([C@@H]3c4nc[nH]c4CCN3C(=O)c3cnn4cc(C)ccc34)cc12] | (S)-(4-(4-methoxypyrazolo[1,5-a]pyridin-2-yl)-6,7-dihydro-1H-imidazo[4,5-c]pyridin-5(4H)-yl)(6-methylpyrazolo[1,5-a]pyridin-3-yl)methanone |
| 2471 | 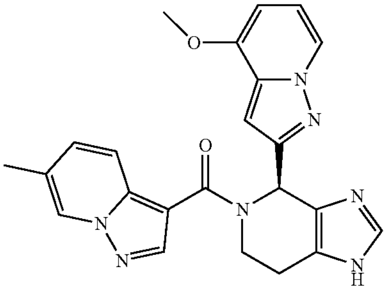 [SMILES: COc1cccn2nc([C@H]3c4nc[nH]c4CCN3C(=O)c3cnn4cc(C)ccc34)cc12] | (R)-(4-(4-methoxypyrazolo[1,5-a]pyridin-2-yl)-6,7-dihydro-1H-imidazo[4,5-c]pyridin-5(4H)-yl)(6-methylpyrazolo[1,5-a]pyridin-3-yl)methanone |
| 2472 | 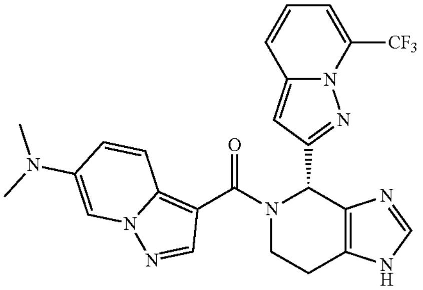 [SMILES: CN(C)c1ccc2c(C(=O)N3CCc4[nH]cnc4[C@H]3c3cc4cccc(C(F)(F)F)n4n3)cnn2c1] | (S)-(6-(dimethylamino)pyrazolo[1,5-a]pyridin-3-yl)(4-(7-(trifluoromethyl)pyrazolo[1,5-a]pyridin-2-yl)-6,7-dihydro-1H-imidazo[4,5-c]pyridin-5(4H)-yl)methanone |
| 2473 | 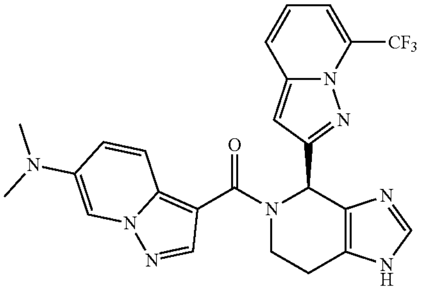 [SMILES: CN(C)c1ccc2c(C(=O)N3CCc4[nH]cnc4[C@@H]3c3cc4cccc(C(F)(F)F)n4n3)cnn2c1] | (R)-(6-(dimethylamino)pyrazolo[1,5-a]pyridin-3-yl)(4-(7-(trifluoromethyl)pyrazolo[1,5-a]pyridin-2-yl)-6,7-dihydro-1H-imidazo[4,5-c]pyridin-5(4H)-yl)methanone |

TABLE 1-continued

| Ex. # | Structure | Name |
|---|---|---|
| | Pyrazolo[1,5-a]pyridines | |
| 2474 | 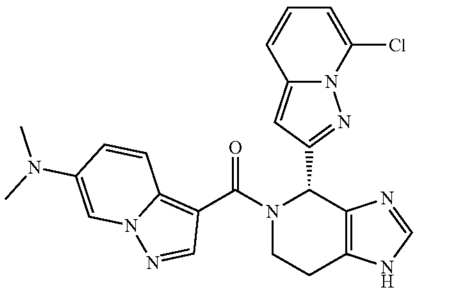 [SMILES: CN(C)c1ccc2c(C(=O)N3CCc4[nH]cnc4[C@H]3c3cc4cccc(Cl)n4n3)cnn2c1] | (S)-(4-(7-chloropyrazolo[1,5-a]pyridin-2-yl)-6,7-dihydro-1H-imidazo[4,5-c]pyridin-5(4H)-yl)(6-(dimethylamino)pyrazolo[1,5-a]pyridin-3-yl)methanone |
| 2475 | 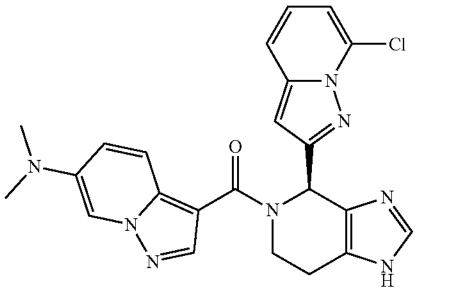 [SMILES: CN(C)c1ccc2c(C(=O)N3CCc4[nH]cnc4[C@@H]3c3cc4cccc(Cl)n4n3)cnn2c1] | (R)-(4-(7-chloropyrazolo[1,5-a]pyridin-2-yl)-6,7-dihydro-1H-imidazo[4,5-c]pyridin-5(4H)-yl)(6-(dimethylamino)pyrazolo[1,5-a]pyridin-3-yl)methanone |
| 2476 | 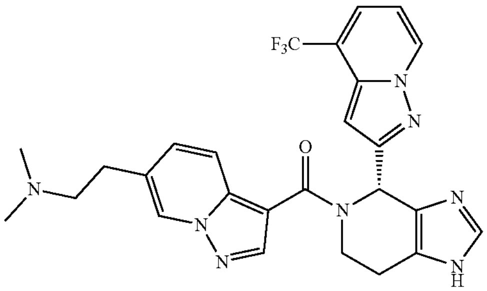 [SMILES: CN(C)CCc1ccc2c(C(=O)N3CCc4[nH]cnc4[C@H]3c3cc4c(C(F)(F)F)cccn4n3)cnn2c1] | (S)-(6-(2-(dimethylamino)ethyl)pyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 2477 | 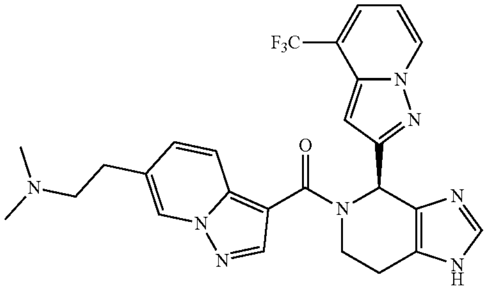 [SMILES: CN(C)CCc1ccc2c(C(=O)N3CCc4[nH]cnc4[C@@H]3c3cc4c(C(F)(F)F)cccn4n3)cnn2c1] | (R)-(6-(2-(dimethylamino)ethyl)pyrazolo[1,5-a]pyridin-3-yl)(4-(4-(trifluoromethyl)pyrazolo[1,5-a]pyridin-2-yl)-6,7-dihydro-1H-imidazo[4,5-c]pyridin-5(4H)-yl)methanone |
| 2478 | 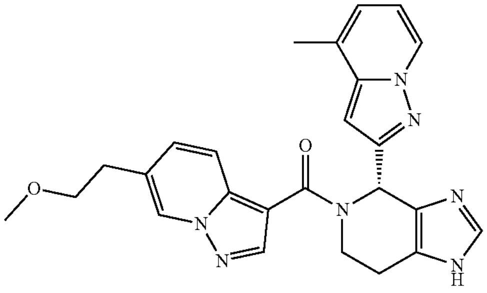 [SMILES: COCCc1ccc2c(C(=O)N3CCc4[nH]cnc4[C@H]3c3cc4c(C)cccn4n3)cnn2c1] | (S)-(6-(2-methoxyethyl)pyrazolo[1,5-a]pyridin-3-yl)(4-(4-methylpyrazolo[1,5-a]pyridin-2-yl)-6,7-dihydro-1H-imidazo[4,5-c]pyridin-5(4H)-yl)methanone |

TABLE 1-continued

| Pyrazolo[1,5-a]pyridines | | |
|---|---|---|
| Ex. # | Structure | Name |
| 2479 | 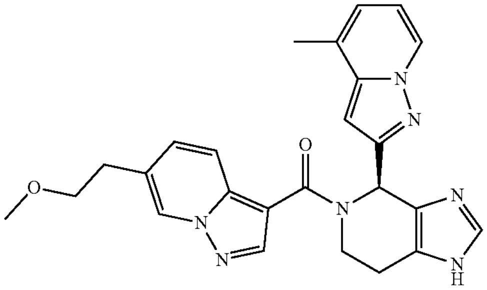 [SMILES: COCCc1ccc2c(C(=O)N3CCc4[nH]cnc4[C@@H]3c3cc4c(C)cccn4n3)cnn2c1] | (R)-(6-(2-methoxyethyl)pyrazolo[1,5-a]pyridin-3-yl)(4-(4-methylpyrazolo[1,5-a]pyridin-2-yl)-6,7-dihydro-1H-imidazo[4,5-c]pyridin-5(4H)-yl)methanone |
| 2480 | 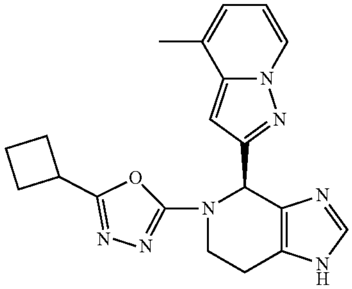 [SMILES: Cc1cccn2nc([C@H]3c4nc[nH]c4CCN3c3nnc(C4CCC4)o3)cc12] | (R)-2-cyclobutyl-5-(4-(4-methylpyrazolo[1,5-a]pyridin-2-yl)-6,7-dihydro-1H-imidazo[4,5-c]pyridin-5(4H)-yl)-1,3,4-oxadiazole |
| 2481 | 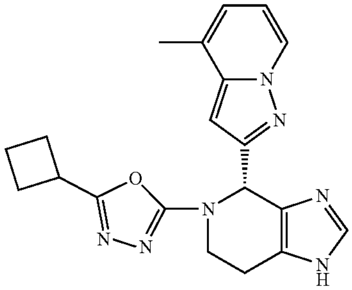 [SMILES: Cc1cccn2nc([C@@H]3c4nc[nH]c4CCN3c3nnc(C4CCC4)o3)cc12] | (S)-2-cyclobutyl-5-(4-(4-methylpyrazolo[1,5-a]pyridin-2-yl)-6,7-dihydro-1H-imidazo[4,5-c]pyridin-5(4H)-yl)-1,3,4-oxadiazole |
| 2482 | 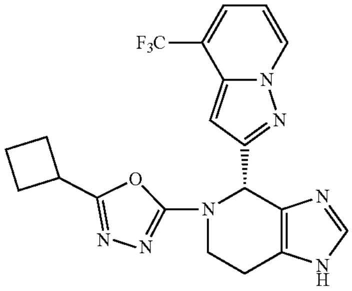 [SMILES: FC(F)(F)c1cccn2nc([C@@H]3c4nc[nH]c4CCN3c3nnc(C4CCC4)o3)cc12] | (S)-2-cyclobutyl-5-(4-(4-(trifluoromethyl)pyrazolo[1,5-a]pyridin-2-yl)-6,7-dihydro-1H-imidazo[4,5-c]pyridin-5(4H)-yl)-1,3,4-oxadiazole |
| 2483 | 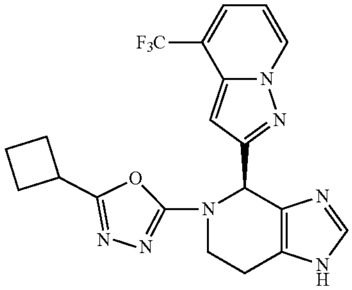 [SMILES: FC(F)(F)c1cccn2nc([C@H]3c4nc[nH]c4CCN3c3nnc(C4CCC4)o3)cc12] | (R)-2-cyclobutyl-5-(4-(4-(trifluoromethyl)pyrazolo[1,5-a]pyridin-2-yl)-6,7-dihydro-1H-imidazo[4,5-c]pyridin-5(4H)-yl)-1,3,4-oxadiazole |

TABLE 1-continued

Pyrazolo[1,5-a]pyridines

| Ex. # | Structure | Name |
| --- | --- | --- |
| 2484 | 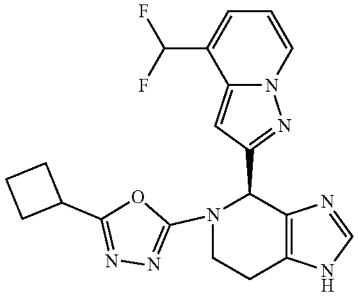 [SMILES: FC(F)c1cccn2nc([C@H]3c4nc[nH]c4CCN3c3nnc(C4CCC4)o3)cc12] | (R)-2-cyclobutyl-5-(4-(4-(difluoromethyl)pyrazolo[1,5-a]pyridin-2-yl)-6,7-dihydro-1H-imidazo[4,5-c]pyridin-5(4H)-yl)-1,3,4-oxadiazole |
| 2485 | 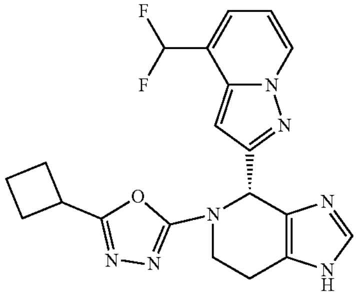 [SMILES: FC(F)c1cccn2nc([C@@H]3c4nc[nH]c4CCN3c3nnc(C4CCC4)o3)cc12] | (S)-2-cyclobutyl-5-(4-(4-(difluoromethyl)pyrazolo[1,5-a]pyridin-2-yl)-6,7-dihydro-1H-imidazo[4,5-c]pyridin-5(4H)-yl)-1,3,4-oxadiazole |
| 2486 | 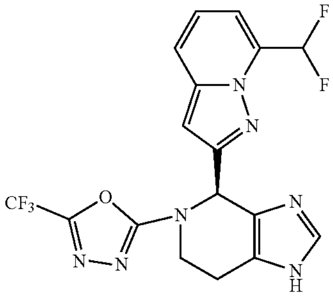 [SMILES: FC(F)c1cccc2cc([C@H]3c4nc[nH]c4CCN3c3nnc(C(F)(F)F)o3)nn12] | (R)-2-(4-(7-(difluoromethyl) pyrazolo[1,5-a]pyridin-2-yl)-6,7-dihydro-1H-imidazo [4,5-c]pyridin-5(4H)-yl)-5-(trifluoromethyl)-1,3,4-oxadiazole |
| 2487 | 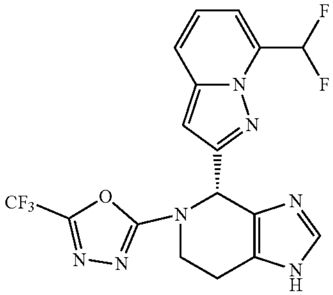 [SMILES: FC(F)c1cccc2cc([C@@H]3c4nc[nH]c4CCN3c3nnc(C(F)(F)F)o3)nn12] | (S)-2-(4-(7-(difluoromethyl) pyrazolo[1,5-a]pyridin-2-yl)-6,7-dihydro-1H-imidazo [4,5-c]pyridin-5(4H)-yl)-5-(trifluoromethyl)-1,3,4-o xadiazole |
| 2488 | 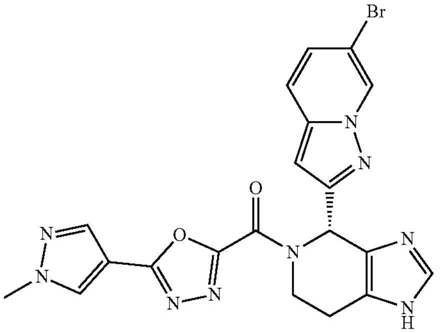 | (S)-(4-(6-bromopyrazolo [1,5-a]pyridin-2-yl)-1,4,6,7-tetrahydro-5H-imidazo[4,5-c] pyridin-5-yl)(5-(1-methyl-1H-pyrazol-4-yl)-1,3,4-oxadiazol-2-yl)methanone |

TABLE 1-continued

| Pyrazolo[1,5-a]pyridines | | |
|---|---|---|
| Ex. # | Structure | Name |
| 2489 | 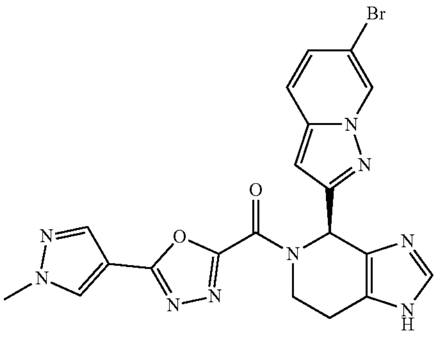 [SMILES: Cn1cc(-c2nnc(C(=O)N3CCc4[nH]cnc4[C@@H]3c3cc4ccc(Br)cn4n3)o2)cn1] | (R)-(4-(6-bromopyrazolo [1,5-a]pyridin-2-yl)-1,4,6,7-tetrahydro-5H-imidazo[4,5-c] pyridin-5-yl)(5-(1-methyl-1H-pyrazol-4-yl)-1,3,4-oxadiazol-2-yl)methanone |
| 2490 | 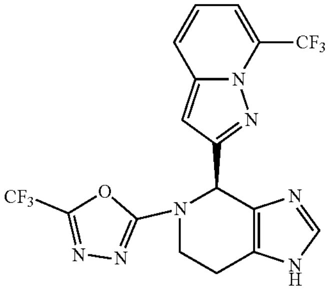 [SMILES: FC(F)(F)c1nnc(N2CCc3[nH]cnc3[C@@H]2c2cc3cccc(C(F)(F)F)n3n2)o1] | (R)-2-(trifluoromethyl)-5-(4-(7-(trifluoromethyl)pyrazolo[1,5-a] pyridin-2-yl)-1,4,6,7-tetrahydro-5H-imidazo[4,5-c] pyridin-5-yl)-1,3,4-oxadiazole |
| 2491 | 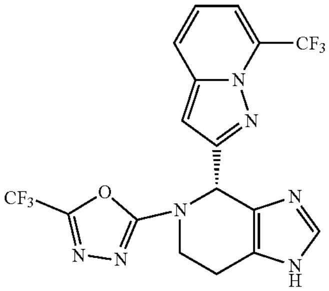 [SMILES: FC(F)(F)c1nnc(N2CCc3[nH]cnc3[C@H]2c2cc3cccc(C(F)(F)F)n3n2)o1] | (S)-2-(trifluoromethyl)-5-(4-(7-(trifluoromethyl)pyrazolo [1,5-a]pyridin-2-yl)-1,4,6,7-tetrahydro-5H-imidazo [4,5-c]pyridin-5-yl)-1,3,4-oxadiazole |
| 2492 | 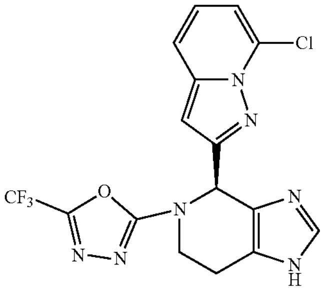 [SMILES: FC(F)(F)c1nnc(N2CCc3[nH]cnc3[C@@H]2c2cc3cccc(Cl)n3n2)o1] | (R)-2-(4-(7-chloropyrazolo [1,5-a]pyridin-2-yl)-1,4,6,7-tetrahydro-5H-imidazo [4,5-c]pyridin-5-yl)-5-(trifluoromethyl)-1,3,4-oxadiazole |
| 2493 | 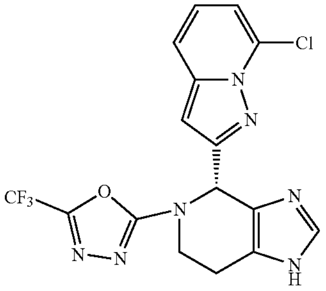 [SMILES: FC(F)(F)c1nnc(N2CCc3[nH]cnc3[C@H]2c2cc3cccc(Cl)n3n2)o1] | (S)-2-(4-(7-chloropyrazolo [1,5-a]pyridin-2-yl)-1,4,6,7-tetrahydro-5H-imidazo[4,5-c] pyridin-5-yl)-5-(trifluoromethyl)-1,3,4-oxadiazole |

TABLE 1-continued

Pyrazolo[1,5-a]pyridines

| Ex. # | Structure | Name |
|---|---|---|
| 2494 | 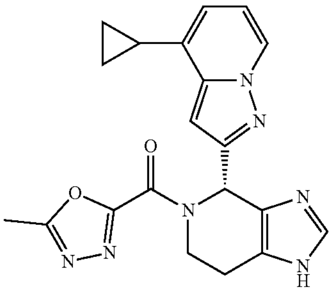 [SMILES: Cc1nnc(C(=O)N2CCc3[nH]cnc3[C@H]2c2cc3c(C4CC4)cccn3n2)o1] | (S)-(4-(4-cyclopropylpyrazolo[1,5-a]pyridin-2-yl)-1,4,6,7-tetrahydro-5H-imidazo[4,5-c]pyridin-5-yl)(5-methyl-1,3,4-oxadiazol-2-yl)methanone |
| 2495 | 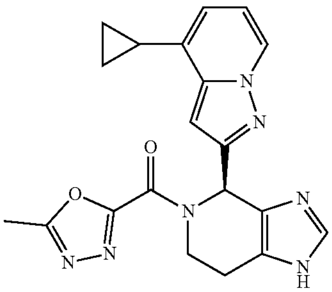 [SMILES: Cc1nnc(C(=O)N2CCc3[nH]cnc3[C@@H]2c2cc3c(C4CC4)cccn3n2)o1] | (R)-(4-(4-cyclopropylpyrazolo[1,5-a]pyridin-2-yl)-1,4,6,7-tetrahydro-5H-imidazo[4,5-c]pyridin-5-yl)(5-methyl-1,3,4-oxadiazol-2-yl)methanone |
| 2496 | 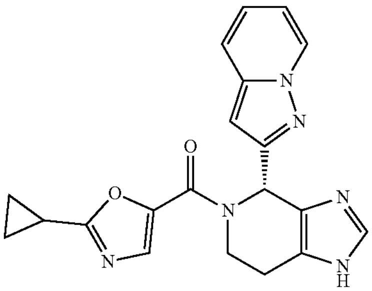 [SMILES: O=C(c1cnc(C2CC2)o1)N1CCc2[nH]cnc2[C@H]1c1cc2ccccn2n1] | (S)-(2-cyclopropyloxazol-5-yl)(4-(pyrazolo[1,5-a]pyridin-2-yl)-1,4,6,7-tetrahydro-5H-imidazo[4,5-c]pyridin-5-yl)methanone |
| 2497 | 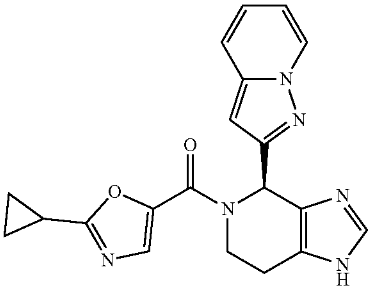 [SMILES: O=C(c1cnc(C2CC2)o1)N1CCc2[nH]cnc2[C@@H]1c1cc2ccccn2n1] | (R)-(2-cyclopropyloxazol-5-yl)(4-(pyrazolo[1,5-a]pyridin-2-yl)-1,4,6,7-tetrahydro-5H-imidazo[4,5-c]pyridin-5-yl)methanone |
| 2498 | 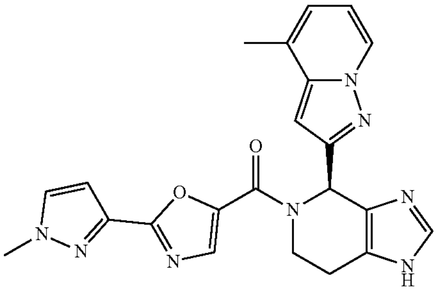 [SMILES: Cc1cccn2nc([C@H]3c4nc[nH]c4CCN3C(=O)c3cnc(-c4ccn(C)n4)o3)cc12] | (R)-(2-(1-methyl-1H-pyrazol-3-yl)oxazol-5-yl)(4-(4-methylpyrazolo[1,5-a]pyridin-2-yl)-1,4,6,7-tetrahydro-5H-imidazo[4,5-c]pyridin-5-yl)methanone |

TABLE 1-continued

| Ex. # | Structure | Name |
|---|---|---|
| | Pyrazolo[1,5-a]pyridines | |
| 2499 | 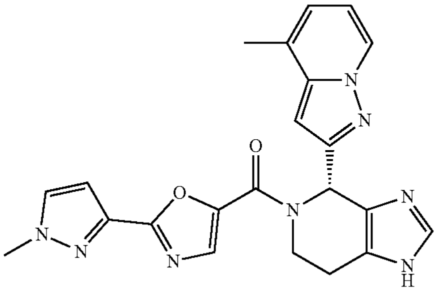 [SMILES: Cc1cccn2nc([C@@H]3c4nc[nH]c4CCN3C(=O)c3cnc(-c4ccn(C)n4)o3)cc12] | (S)-(2-(1-methyl-1H-pyrazol-3-yl)oxazol-5-yl)(4-(4-methylpyrazolo[1,5-a]pyridin-2-yl)-1,4,6,7-tetrahydro-5H-imidazo[4,5-c]pyridin-5-yl)methanone |
| 2500 | 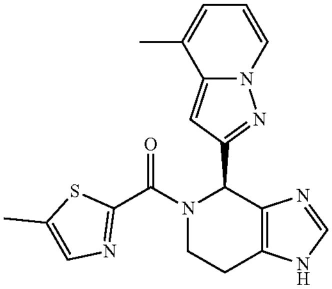 [SMILES: Cc1cnc(C(=O)N2CCc3[nH]cnc3[C@@H]2c2cc3c(C)cccn3n2)s1] | (R)-(5-methyl-1,3,4-thiadiazol-2-yl)(4-(4-methylpyrazolo[1,5-a]pyridin-2-yl)-1,4,6,7-tetrahydro-5H-imidazo[4,5-c]pyridin-5-yl)methanone |
| 2501 | 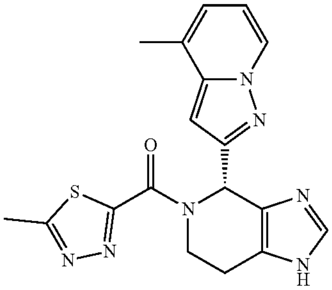 [SMILES: Cc1nnc(C(=O)N2CCc3[nH]cnc3[C@H]2c2cc3c(C)cccn3n2)s1] | (S)-(5-methyl-1,3,4-thiadiazol-2-yl)(4-(4-methylpyrazolo[1,5-a]pyridin-2-yl)-1,4,6,7-tetrahydro-5H-imidazo[4,5-c]pyridin-5-yl)methanone |
| 2502 | 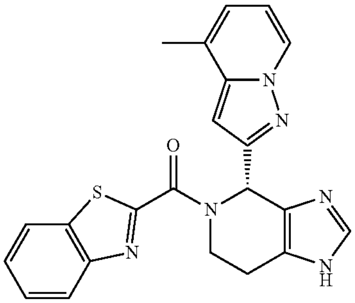 [SMILES: Cc1cccn2nc([C@@H]3c4nc[nH]c4CCN3C(=O)c3nc4ccccc4s3)cc12] | (S)-benzo[d]thiazol-2-yl (4-(4-methylpyrazolo[1,5-a]pyridin-2-yl)-1,4,6,7-tetrahydro-5H-imidazo[4,5-c]pyridin-5-yl)methanone |
| 2503 | 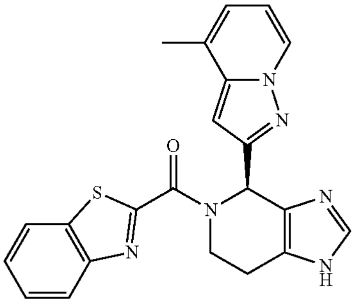 [SMILES: Cc1cccn2nc([C@H]3c4nc[nH]c4CCN3C(=O)c3nc4ccccc4s3)cc12] | (R)-benzo[d]thiazol-2-yl (4-(4-methylpyrazolo[1,5-a]pyridin-2-yl)-1,4,6,7-tetrahydro-5H-imidazo[4,5-c]pyridin-5-yl)methanone |

TABLE 1-continued

| Pyrazolo[1,5-a]pyridines | | |
|---|---|---|
| Ex. # | Structure | Name |
| 2504 | 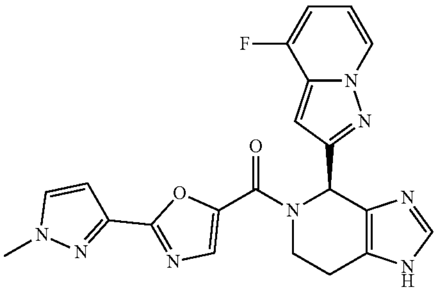 | (R)-(4-(4-fluoropyrazolo[1,5-a]pyridin-2-yl)-1,4,6,7-tetrahydro-5H-imidazo[4,5-c]pyridin-5-yl)(2-(1-methyl-1H-pyrazol-3-yl)oxazol-5-yl)methanone |
| 2505 | 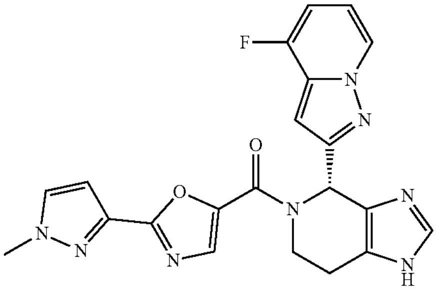 | (S)-(4-(4-fluoropyrazolo[1,5-a]pyridin-2-yl)-1,4,6,7-tetrahydro-5H-imidazo[4,5-c]pyridin-5-yl)(2-(1-methyl-1H-pyrazol-3-yl)oxazol-5-yl)methanone |
| 2506 | 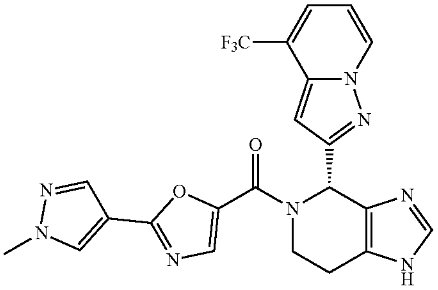 | (S)-(2-(1-methyl-1H-pyrazol-4-yl)oxazol-5-yl)(4-(4-(trifluoromethyl)pyrazolo[1,5-a]pyridin-2-yl)-1,4,6,7-tetrahydro-5H-imidazo[4,5-c]pyridin-5-yl)methanone |
| 2507 | 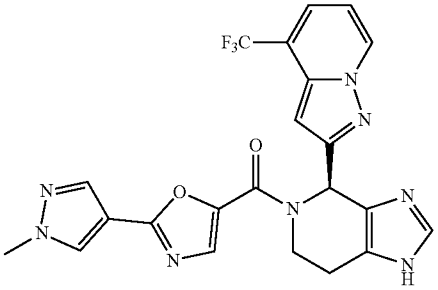 | (R)-(2-(1-methyl-1H-pyrazol-4-yl)oxazol-5-yl)(4-(4-(trifluoromethyl)pyrazolo[1,5-a]pyridin-2-yl)-1,4,6,7-tetrahydro-5H-imidazo[4,5-c]pyridin-5-yl)methanone |
| 2508 | 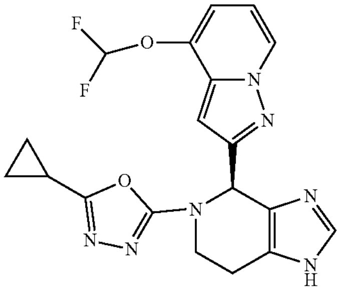 [SMILES: FC(F)Oc1cccn2nc([C@H]3c4nc[nH]c4CCN3c3nnc(C4CC4)o3)cc12] | (R)-2-cyclopropyl-5-(4-(4-(difluoromethoxy)pyrazolo[1,5-a]pyridin-2-yl)-1,4,6,7-tetrahydro-5H-imidazo[4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2509 | 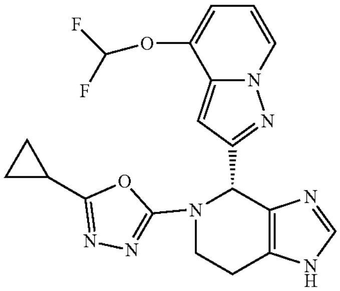 [SMILES: FC(F)Oc1cccn2nc([C@@H]3c4nc[nH]c4CCN3c3nnc(C4CC4)o3)cc12] | (S)-2-cyclopropyl-5-(4-(4-(difluoromethoxy)pyrazolo[1,5-a]pyridin-2-yl)-1,4,6,7-tetrahydro-5H-imidazo[4,5-c]pyridin-5-yl)-1,3,4-oxadiazole |
| 2510 | 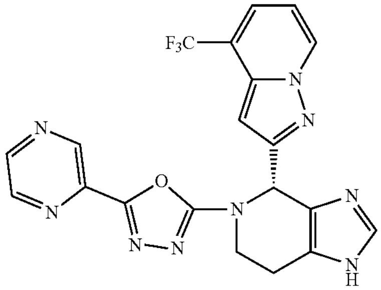 [SMILES: FC(F)(F)c1cccn2nc([C@@H]3c4nc[nH]c4CCN3c3nnc(-c4cnccn4)o3)cc12] | (S)-2-(pyrazin-2-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2511 | 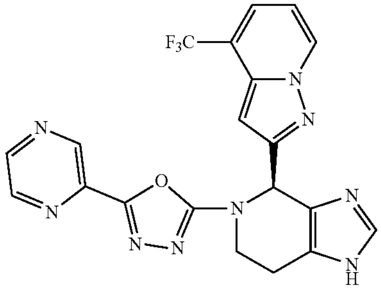 [SMILES: FC(F)(F)c1cccn2nc([C@H]3c4nc[nH]c4CCN3c3nnc(-c4cnccn4)o3)cc12] | (R)-2-(pyrazin-2-yl)-5-(4-(4-(trifluoromethyl)pyrazolo[1,5-a]pyridin-2-yl)-1,4,6,7-tetrahydro-5H-imidazo[4,5-c]pyridin-5-yl)-1,3,4-oxadiazole |
| 2512 | 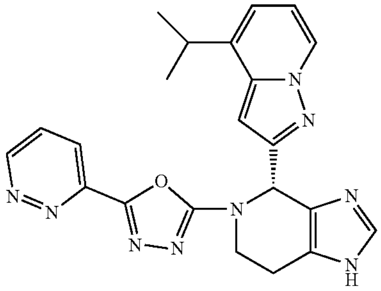 [SMILES: CC(C)c1cccn2nc([C@@H]3c4nc[nH]c4CCN3c3nnc(-c4cccnn4)o3)cc12] | (S)-2-(4-(4-isopropylpyrazolo[1,5-a]pyridin-2-yl)-1,4,6,7-tetrahydro-5H-imidazo[4,5-c]pyridin-5-yl)-5-(pyridazin-3-yl)-1,3,4-oxadiazole |
| 2513 | 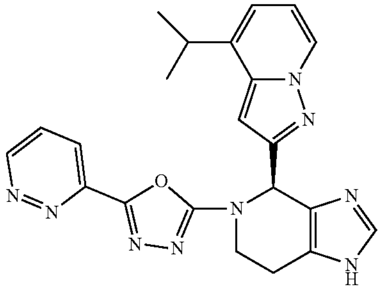 [SMILES: CC(C)c1cccn2nc([C@H]3c4nc[nH]c4CCN3c3nnc(-c4cccnn4)o3)cc12] | (R)-2-(4-(4-isopropylpyrazolo[1,5-a]pyridin-2-yl-1,4,6,7-tetrahydro-5H-imidazo[4,5-c]pyridin-5-yl)-5-(pyridazin-3-yl)-1,3,4-oxadiazole |

TABLE 1-continued

| Ex. # | Structure | Name |
|---|---|---|
| | Pyrazolo[1,5-a]pyridines | |
| 2514 | 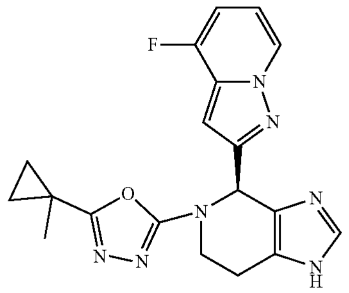 [SMILES: CC1(c2nnc(N3CCc4[nH]cnc4[C@@H]3c3cc4c(F)cccn4n3)o2)CC1] | (R)-2-(4-(4-fluoropyrazolo [1,5-a]pyridin-2-y]l)-1,4,6,7-tetrahydro-5H-imidazo [4,5-c]pyridin-5-yl)-5-(1-methylcyclopropyl)-1,3,4-oxadiazole |
| 2515 | 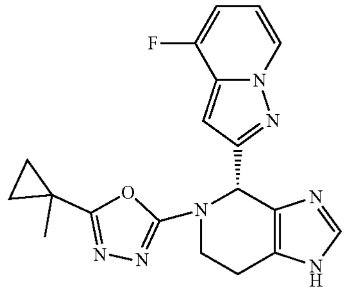 [SMILES: CC1(c2nnc(N3CCc4[nH]cnc4[C@H]3c3cc4c(F)cccn4n3)o2)CC1] | (S)-2-(4-(4-fluoropyrazolo [1,5-a]pyridin-2-yl)-1,4,6,7-tetrahydro-5H-imidazo [4,5-c]pyridin-5-yl)-5-(1-methylcyclopropyl)-1,3,4-oxadiazole |
| 2516 | 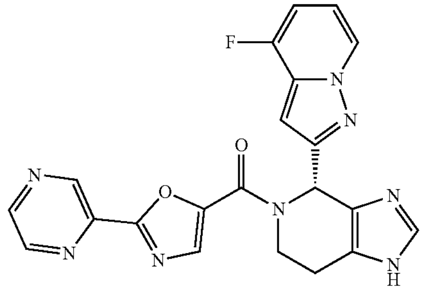 | (S)-(4-(4-fluoropyrazolo [1,5-a]pyridin-2-yl)-1,4,6,7-tetrahydro-5H-imidazo[4,5-c] pyridin-5-yl)(2-(pyrazin-2-yl)oxazol-5-yl)methanone |
| 2517 | 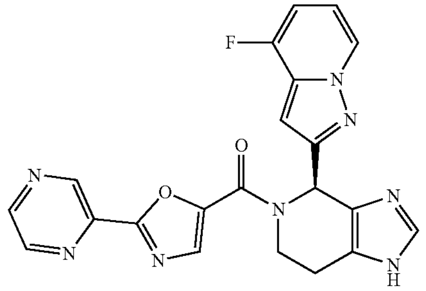 | (R)-(4-(4-fluoropyrazolo [1,5-a]pyridin-2-yl)-1,4,6,7-tetrahydro-5H-imidazo[4,5-c] pyridin-5-yl)(2-(pyrazin-2-yl)oxazol-5-yl)methanone |
| 2518 | 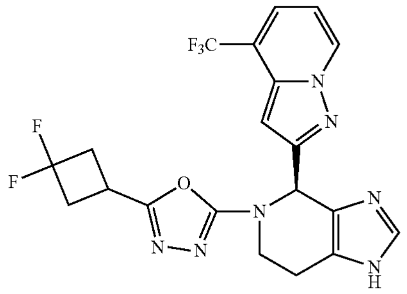 [SMILES: FC1(F)CC(c2nnc(N3CCc4[nH]cnc4[C@@H]3c3cc4c(C(F)(F)F)cccn4n3)o2)C1] | (R)-2-(3,3-difluorocyclobutyl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |

TABLE 1-continued

| Ex. # | Structure | Name |
|---|---|---|
| | Pyrazolo[1,5-a]pyridines | |
| 2519 | 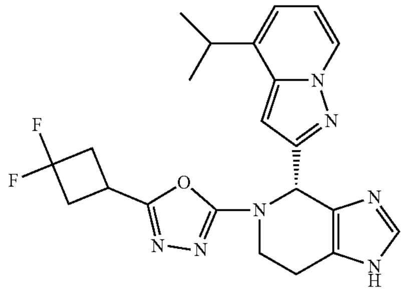 [SMILES: CC(C)c1cccn2nc([C@@H]3c4nc[nH]c4CCN3c3nnc(C4CC(F)(F)C4)o3)cc12] | (S)-2-(3,3-difluorocyclobutyl)-5-(4-(4-isopropylpyrazolo[1,5-a]pyridin-2-yl)-1,4,6,7-tetrahydro-5H-imidazo[4,5-c]pyridin-5-yl)-1,3,4-oxadiazole |
| 2520 | 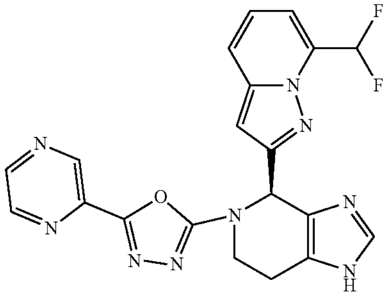 [SMILES: FC(F)c1cccc2cc([C@H]3c4nc[nH]c4CCN3c3nnc(-c4cnccn4)o3)nn12] | (R)-2-(4-(7-(difluoromethyl) pyrazolo[1,5-a]pyridin-2-yl)-1,4,6,7-tetrahydro-5H-imidazo[4,5-c]pyridin-5-yl)-5-(pyrazin-2-yl)-1,3,4-oxadiazole |
| 2521 | 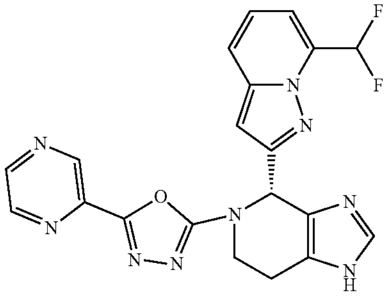 [SMILES: FC(F)c1cccc2cc([C@@H]3c4nc[nH]c4CCN3c3nnc(-c4cnccn4)o3)nn12] | (S)-2-(4-(7-(difluoromethyl) pyrazolo[1,5-a]pyridin-2-yl)-1,4,6,7-tetrahydro-5H-imidazo[4,5-c]pyridin-5-yl)-5-(pyrazin-2-yl)-1,3,4-oxadiazole |
| 2522 | 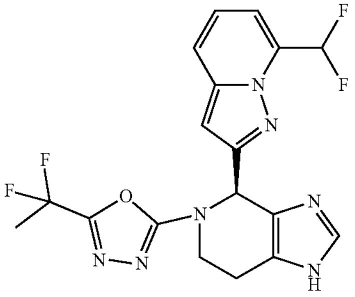 [SMILES: CC(F)(F)c1nnc(N2CCc3[nH]cnc3[C@@H]2c2cc3cccc(C(F)F)n3n2)o1] | (R)-2-(1,1-difluoroethyl)-5-(4-(7-(difluoromethyl)pyrazolo [1,5-a]pyridin-2-yl)-1,4,6,7-tetrahydro-5H-imidazo [4,5-c]pyridin-5-yl)-1,3,4-oxadiazole |
| 2523 | 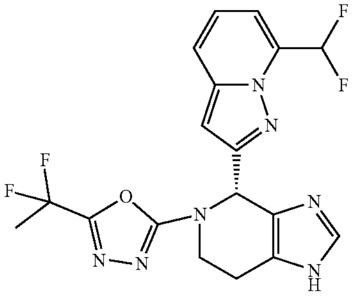 [SMILES: CC(F)(F)c1nnc(N2CCc3[nH]cnc3[C@H]2c2cc3cccc(C(F)F)n3n2)o1] | (S)-2-(1,1-difluoroethyl)-5-(4-(7-(difluoromethyl)pyrazolo [1,5-a]pyridin-2-yl)-1,4,6,7-tetrahydro-5H-imidazo [4,5-c]pyridin-5-yl)-1,3,4-oxadiazole |

TABLE 1-continued

| Pyrazolo[1,5-a]pyridines | | |
|---|---|---|
| Ex. # | Structure | Name |
| 2524 | 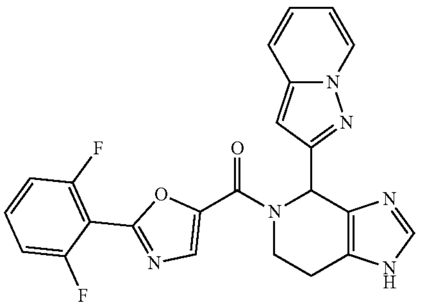 [SMILES: O=C(c1cnc(-c2c(F)cccc2F)o1)N1CCc2[nH]cnc2C1c1cc2ccccn2n1] | (5-(2,6-difluorophenyl)-1,3,4-oxadiazol-2-yl)(4-(pyrazolo[1,5-a]pyridin-2-yl)-6,7-dihydro-1H-imidazo[4,5-c]pyridin-5(4H)-yl)methanone |

In further embodiments, the compound of Formula I is one or more of the compounds in Table 1 that is the S-enantiomer, or a pharmaceutically acceptable salt thereof.

In still further embodiments, the compound of Formula I s one or more of Examples 605, 626, 640, 670, 688, 708, 710, 726, 728, 733, 748, 760, 762, 764, 791, 836, 840, 906, 922, 938, 942, 944, 946, 948, 950, 952, 954, 957, 958, 960, 962, 964, 966, 969, 971, 972, 975, 976, 979, 980, 982, 984, 988, 1381, 1438, 1461, 1506, 1531, 1548, 1589, 1607, 1613, 1628, 1652, 1657, 1728, 1737, 1757, 1807, 1809, 1823, 1843, 1849, 1850, 1943, 1953, 1986, 2218, 2221, and 2223, or a pharmaceutically acceptable salt thereof. In yet other embodiments, the compound of Formula I is one or more of Examples 640, 670, 688, 708, 710, 726, 728, 733, 748, 760, 762, 764, 836, 840, 906, 922, 938, 942, 944, 946, 948, 950, 952, 954, 957, 960, 962, 969, 971, 972, 975, 976, 979, 980, 984, 988, 1438, 1461, 1506, 1548, 1628, 1652, 1657, 1728, 1737, 1757, 1809, 1849, 1850, 1953, 1986, 2218, and 2221, or a pharmaceutically acceptable salt thereof. In still other embodiments, the compound of Formula I is one or more of Examples 640, 670, 688, 708, 710, 726, 728, 733, 748, 760, 762, 764, 836, 840, 906, 922, 938, 942, 944, 946, 948, 950, 952, 954, 957, 960, 962, 969, 971, 972, 975, 976, 979, 980, 984, 988, 1438, 1461, 1506, 1548, 1628, 1652, 1657, 1728, 1986, and 2218, or a pharmaceutically acceptable salt thereof.

| Abbreviations and terms list: | |
|---|---|
| aq | aqueous |
| min | minute(s) |

-continued

| Abbreviations and terms list: | |
|---|---|
| hrs | hours |
| mL | milliliter |
| μL | microliter |
| mmol | millimole(s) |
| μmol | micromole(s) |
| mol | mole(s) |
| M | molar |
| eq | equivalents |
| LCMS | Liquid chromatography mass spectrometry |
| NMR | nuclear magnetic resonance |
| TLC | thin layer chromatography |
| HPLC | high-performance liquid chromatography |
| SFC | supercritical fluid chromatography |
| sat | saturated |
| ° C. | degrees Celsius |
| rt | room temperature |
| $N_2$ | nitrogen gas |
| Hz | Hertz |
| δ | chemical shift |
| s | singlet |
| d | doublet |
| t | triplet |
| q | quartet |
| m | multiplet |
| br | broad |
| dd | doublet of doublets |
| ddd | doublet of doublet or doublets |
| td | triplet of doublets |
| dt | doublet of triplets |
| $CDCl_3$ | chloroform-d |
| $CD_3OD$ | methanol-$d_4$ |
| DMSO-$d_6$ | dimethyl sulfoxide-$d_6$ |

| Solvents and reagents: | |
|---|---|
| DCE | 1,2-dichloroethane |
| DCM | dichloromethane |
| DMAc | dimethylacetamide |
| DME | dimethoxyethane |
| DMF | dimethylformamide |
| EtOH | ethyl alcohol |
| EtOAc | ethyl acetate |
| i-PrOH or IPA | isopropanol |
| MeOH | methyl alcohol |
| TAA | tert-amyl alcohol |
| MeCN or ACN | acetonitrile |
| PE | petroleum ether |
| TBME | tert-butyl methyl ether |

-continued

| Solvents and reagents: | |
|---|---|
| $H_2O$ | water |
| THF | tetrahydrofuran |
| HOAc | acetic acid |
| HCl | hydrochloric acid |
| $H_2SO_4$ | sulfuric acid |
| FA | formic acid |
| TFA | trifluoroacetic acid |
| TsOH | p-toluenesulfonic acid |
| TosCl or TsCl | p-toluenesulfonyl chloride |
| $NH_4Cl$ | ammonium chloride |
| KOH | Potassium hydroxide |
| LiOH | lithium hydroxide |
| $K_2CO_3$ | potassium carbonate |
| $Na_2CO_3$ | sodium carbonate |
| $Cs_2CO_3$ | cesium carbonate |
| $Na_2SO_4$ | sodium sulfate |
| $NaHCO_3$ | sodium bicarbonate |
| $Na_2S_2O_3$ | sodium thiosulfate |
| $Et_3N$ or TEA | triethylamine |
| DIPEA | N,N-diisopropylethylamine |
| Py | pyridine |
| KOAc | potassium acetate |
| KF | potassium fluoride |
| CsF | cesium fluoride |
| $NH_3$ | ammonia |
| LDA | lithium diisopropylamine |
| LiHMDS | lithium bis(trimethylsilyl)amide |
| MeMgBr | methylmagnesium bromide |
| iPrMgCl•LiCl | isopropylmagnesium chloride lithium chloride complex |
| PFIB | perfluoroisobutene |
| BuOK | potassium t-butoxide |
| CAN | cerium ammonium nitrate |
| DIBAL-H | diisobutylaluminium hydride |
| NaOMe | sodium methoxide |
| DMP | Dess-Martin periodinane |
| $MnO_2$ | manganese(IV) oxide |
| IBX | 2-iodoxybenzoic acid |
| t-BuONO | tert-butyl nitrite |
| PIDA | (diacetoxyiodo)benzene |
| NFSI | N-fluorodi(benzenesulfonyl)amine |
| NBS | N-bromosuccinimide |
| NCS | N-chlorosuccinimide |
| Mel | methyl iodide |
| $LiBH_4$ | lithium borohydride |
| $NaBH_4$ | sodium borohydride |
| $NaBH(OAc)_3$ | Sodium triacetoxyborohydride |
| EDCI | 1-ethyl-3-(3-dimethylaminopropyl)carbodiimide |
| HOBt | 1-hydroxybenzotriazole |
| HATU | 1-[Bis(dimethylamino)methylene]-1H-1,2,3-triazolo[4,5-b]pyridinium 3-oxid hexafluorophosphate |
| T3P | Propanephosphonic acid anhydride |
| CDI | carbonyldiimidazole |
| Thio-CDI | 1,1'-Thiocarbonyldiimidazole |
| DPPA | diphenylphosphoryl azide |
| $BCl_3$ | boron trichloride |
| $Boc_2O$ | di-tert-butyl dicarbonate |
| DHP | Dihydropyran |
| Pd/C | palladium on carbon |
| $Pd(PPh_3)_2Cl_2$ | bis(triphenylphosphine)palladium(II) dichloride |
| $Pd_2(dba)_3$ | tris(dibenzylideneacetone)dipalladium |
| $Pd(dppf)Cl_2$ | (1,1'-Bis(diphenylphosphino)ferrocene)palladium(II) dichloride |
| $Pd(OAc)_2$ | palladium(II) acetate |
| Xantphos | 4,5-Bis(diphenylphosphino)-9,9-dimethylxanthene |
| t-BuXPhos-Pd-G3 | [(2-Di-tert-butylphosphino-2',4',6'-triisopropyl-1,1'-biphenyl)-2-(2'-amino-1,1'-biphenyl)] palladium(II) methanesulfonate |
| CPhos-Pd-G3 | [(2-Dicyclohexylphosphine-2',6'-bis(N,N-dimethylamino)-1,1'-biphenyl)-2-(2'-amino-1,1'-biphenyl)] palladium(II) methanesulfonate |
| $PPh_3$ | triphenylphosphine |
| DEAD | diethyl azodicarboxylate |
| $Pin_2B_2$ | bis(pinacolato)diborane |
| CuI | copper iodide |
| $CuBr_2$ | copper (II) bromide |
| $Zn(CN)_2$ | zinc cyanide |
| $H_2$ | hydrogen gas |
| $SiO_2$ | silica |
| TFAA | Trifluoroacetic anhydride |

-continued

| Solvents and reagents: | |
|---|---|
| $K_2OsO_4 \cdot 2H_2O$ | potassium osmate(VI) dihydrate |
| $NaIO_4$ | sodium periodate |

General Experimental

In the following examples, the reagents and solvents were purchased from commercial sources (such as Alfa, Acros, AstaTech, CombiBlocks, Enamine, Sigma Aldrich, TCI, PharmaBock, Bide Pharmatech Ltd., Accela ChemBio, Aladdin, Shanghai Haohong Pharmaceutical Co., Ltd, Amkchem, Beijing Ouhe Technology Co., Ltd, Haoyuan Chemexpress Co., Ltd, Hualun, Coolpharm, Scochem, Titan and WuXi LabNetwork, and used without further purification unless otherwise specified. Flash chromatography was performed on a CombiFlashRf 150 (ISCO) via column with silica gel particles of 200-300 mesh. HPLC was performed on an Agilent 1100 Liquid Chromatography (Agilent, USA) and a Shimadzu LC 20/20A (Shimadzu, Japan). Supercritical fluid chromatography was performed on a Waters Prep SFC 150 AP/80Q/200/350 system (Waters, USA). Analytical and preparative thin layer chromatography plates (TLC) were HSGF 254 (0.15-0.2 mm thickness, Shanghai Anbang Company, China). Nuclear magnetic resonance (NMR) spectra were obtained on a Brucker AV-400 NMR or Bruker AVIII 500 MHz NMR (Bruker, Switzerland). Chemical shifts were reported in parts per million (ppm, δ) downfield from tetramethylsilane. Mass spectra were given with electrospray ionization (ESI) from a Waters LCT TOF Mass Spectrometer (Waters, USA). LC-MS was performed on an Agilent Prime-6125B/Agilent LC1260-MS6150/Agilent LC1260-MS6125B/Agilent LC1200-MS6110 (Agilent, USA) and a Shimadzu LC20-MS2020. Microwave reactions were run on an Initiator 2.5 Microwave Synthesizer (Biotage, Sweden).

Intermediate (1-(1H-imidazol-5-yl)cyclopropyl)methanamine hydrochloride

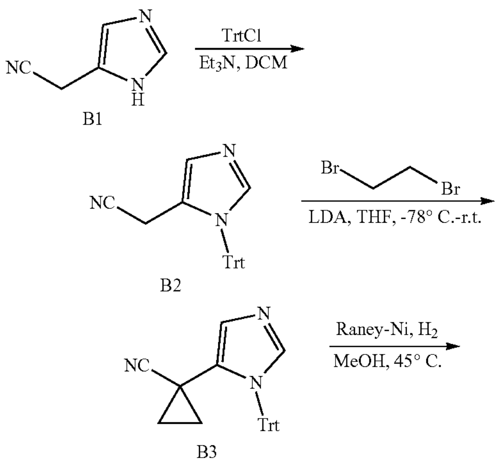

-continued

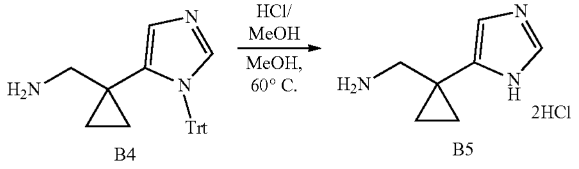

Step 1: Preparation of 2-(3-tritylimidazol-4-yl)acetonitrile (B2)

B2 was prepared starting with 2-(1H-imidazol-5-yl)acetonitrile (B1) in accordance with literature procedures. See, e.g., WO2008/003766 (page 19).

Step 2: Preparation of 1-(3-tritylimidazol-4-yl)cyclopropanecarbonitrile (B3)

To a solution of 2-(3-tritylimidazol-4-yl)acetonitrile (B2) (10 g, 28.6 mmol) in THF (200 mL) was added LDA (2 M, 42.9 mL, 3 eq) dropwise at −78° C. After addition was complete, the reaction mixture was stirred at −20° C. to −10° C. for 1 hr. The reaction mixture was then cooled to −78° C., and 1,2-dibromoethane (10.75 g, 57.2 mmol, 4.32 mL, 2 eq) was added dropwise at −78° C. After the addition was complete, the reaction mixture was warmed to rt slowly and stirred for another 2 hrs. Reaction progress was tracked using TLC (PE:EtOAc=1:1). The reaction mixture was quenched with sat. $NH_4Cl$ solution (200 mL) and stirred at rt for 0.5 hr. The aqueous portion was extracted with EtOAc (100 mL×3), and the combined organic layers were dried over $Na_2SO_4$, filtered, and concentrated to dryness. The residue (combined with two other reactions performed using 10 g of B2) was purified by flash silica gel chromatography (ISCO®, 120 g SepaFlash®, Silica Flash Column, eluent of 0~40% EtOAc/PE, gradient @40 mL/min) to give B3 (23.4 g, 72% yield). $^1H$ NMR (400 MHz, DMSO-$d_6$) δ 7.30-7.52 (m, 10H), 7.09 (dd, 6H), 6.84 (d, 1H), 1.51-1.66 (m, 2H), 1.29-1.46 (m, 2H).

Step 3: Preparation of 1-(3-tritylimidazol-4-yl)cyclopropyl]methanamine (B4)

A mixture of 1-(3-tritylimidazol-4-yl)cyclopropanecarbonitrile (B3) (19 g, 50.6 mmol), Raney-Ni (4.60 g, 53.7 mmol, 1.06 eq), $NH_3 \cdot H_2O$ (591 mg, 5.06 mmol, 650 μL, 30% purity, 0.1 eq) in MeOH (200 mL) was degassed and purged with $H_2$ 3 times, and then the reaction mixture was stirred at 45° C. for 16 hrs under $H_2$ (45 psi) atmosphere. Reaction progress was tracked using TLC (DCM:MeOH=10:1). The reaction mixture was filtered, and additional Raney-Ni (4.60 g, 53.7 mmol, 1.06 eq) was added. The reaction mixture was stirred at 45° C. under $H_2$ (45 psi) atmosphere for another 24 hrs. The reaction mixture was filtered through a pad of Celite, and the filtrate was concentrated to dryness to give B4 (18 g), which was used without further purification. $^1$H NMR (400 MHz, DMSO-$d_6$) δ 7.33-7.44 (m, 9H), 7.18-7.25 (m, 1H), 7.04-7.13 (m, 6H), 6.64-6.71 (m, 1H), 3.17 (br s, 2H), 2.58-2.74 (m, 2H), 0.60-0.82 (m, 4H).

Step 4: Preparation of [1-(1H-imidazol-5-yl)cyclopropyl]methanamine hydrochloride (B5)

To a solution of [1-(3-tritylimidazol-4-yl)cyclopropyl]methanamine (B4) (18 g, 47.4 mmol) in MeOH (100 mL) was added HCU/MeOH (4 M, 100 mL, 8.4 eq). The reaction mixture was stirred at 60° C. for 16 hrs. Reaction progress was tracked using LC-MS. The reaction mixture was concentrated to dryness, and the residue was triturated with EtOAc(40 mL) and stirred for 15 min. The precipitate was collected by filtration and then dried in vacuo to give B5 (8.5 g, 2HCl salt). $^1$H NMR (400 MHz, DMSO-$d_6$) δ 14.73 (br s, 1H), 9.04 (s, 1H), 8.27 (br s, 2H), 7.51 (s, 1H), 2.98-3.22 (m, 2H), 0.90-1.23 (m, 4H).

Intermediate 2-(1H-imidazol-5-yl)-2-methylpropan-1-amine hydrochloride

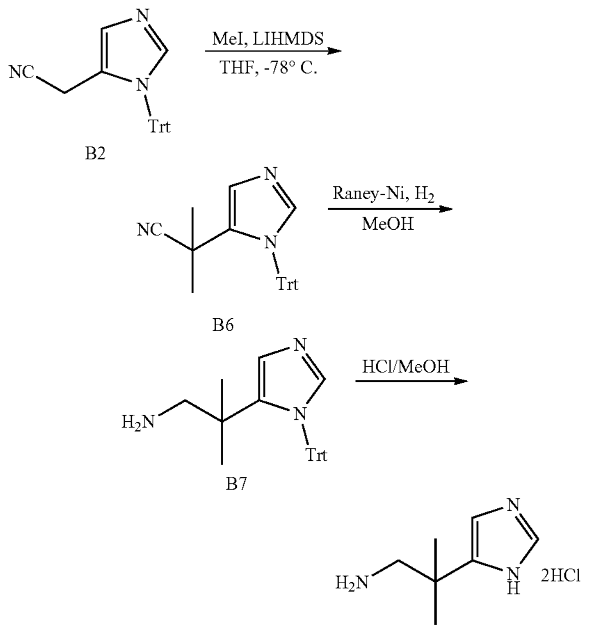

B2, B6, B7, B8

Step 1: Preparation of (2-methyl-2-(3-tritylimidazol-4-yl)propanenitrile (B6)

To a solution of 2-(3-tritylimidazol-4-yl)acetonitrile (B2) (12 g, 34.3 mmol) in THF (400 mL) was drop-wise added LiHMDS (1 M, 96.2 mL, 2.8 eq) at −78° C. The reaction mixture was stirred at −78° C. for 15 min, and then MeI was added (14.62 g, 103 mmol, 6.41 mL, 3 eq). The reaction mixture was stirred at −78° C. for 1 hr, and then warmed to rt for 18 hrs. Reaction progress was tracked using TLC (PE:EtOAc=1:1). The reaction mixture was cooled to 0° C., quenched by the addition of sat. $NH_4Cl$ solution (15 mL) and then $H_2O$ (60 mL) was added. The aqueous portion was extracted with EtOAc (60 mL×3). The combined organic layers were washed with brine (60 mL), dried over $Na_2SO_4$, and concentrated to dryness. The residue (combined with the residue from another reaction performed using 2 g of B2) was purified by flash silica gel chromatography (ISCO®; 80 g SepaFlash® Silica Flash Column, eluent of 0~80% EtOAc/PE, gradient @60 mL/min) to give B6 (14 g, 92% yield). $^1$H NMR (400 MHz, $CDCl_3$) δ 7.41 (d, 1H), 7.32-7.39 (m, 9H), 7.08-7.16 (m, 6H), 6.81 (d, 1H), 1.69 (s, 6H).

Step 2: Preparation of (2-methyl-2-(3-tritylimidazol-4-yl)propan-1-amine (B7)

To a solution of 2-methyl-2-(3-tritylimidazol-4-yl)propanenitrile (B6) (14 g, 37.1 mmol) in MeOH (350 mL) was added Raney-Ni (2 g, 23.3 mmol, 0.63 eq) under $N_2$. The reaction mixture was degassed under vacuum and purged with $H_2$ several times. The reaction mixture was stirred under $H_2$ (50 psi) at 40° C. for 36 hrs. Reaction progress was tracked using TLC (PE:EtOAc=1:1). The reaction mixture was filtered through of pad of celite, and the filtrate was concentrated to dryness to afford B7 (12 g, 85% yield). $^1$H NMR (400 MHz, $CDCl_3$) δ 7.38 (s, 1H), 7.29-7.36 (m, 9H), 7.10-7.18 (m, 6H), 6.55 (s, 1H), 3.49 (br s, 1H), 2.74 (s, 2H), 1.20 (s, 6H); LCMS: m/z 382.2 $[M+H]^+$.

Step 3: Preparation of (2-(1H-imidazol-5-yl)-2-methyl-propan-1-amine (B8)

To a solution of 2-methyl-2-(3-tritylimidazol-4-yl)propan-1-amine (B7) (14 g, 36.7 mmol) in MeOH (150 mL) was added HCl/MeOH (4 M, 150 mL, 16.4 eq), and the reaction mixture was stirred at 50° C. for 18 hrs. Reaction progress was tracked using TLC (EtOAc). The reaction mixture was concentrated to dryness, and 200 mL of EtOAc was added. The mixture was stirred at 60° C. for 1 hr. The precipitate was collected by filtration and rinsed with EtOAc, and then dried in vacuo to give B8 (7.0 g, 90% yield, 2HCl salt). $^1$H NMR (400 MHz, $CD_3OD$) δ 8.96 (s, 1H), 7.52 (s, 1H), 3.20-3.27 (m, 2H), 1.49 (s, 6H).

Intermediate 2-(1H-imidazol-5-yl)propan-1-amine hydrochloride

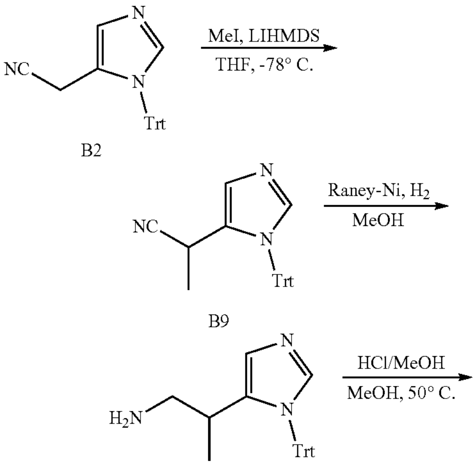

B2, B9, B10

-continued

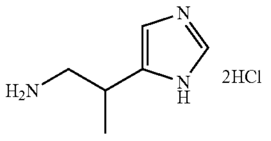

B11

Step 1: Preparation of 2-(3-tritylimidazol-4-yl)propanenitrile (B9)

To a solution of 2-(3-tritylimidazol-4-yl)acetonitrile (B2) (15 g, 42.9 mmol) in THF (120 mL) was added LiHMDS (1 M, 51.5 mL, 1.2 eq) dropwise at −78° C. After addition, the reaction mixture was stirred for 0.5 hr, and then MeI (10.97 g, 77.3 mmol, 4.81 mL, 1.8 eq) was added dropwise at −78° C. The reaction mixture was stirred at −78° C. for 2 hrs. Reaction progress was tracked using TLC (PE:EtOAc=2:1). The reaction mixture was quenched by the addition of sat. $NH_4Cl$ solution (120 mL) and stirred for 15 min. The aqueous portion was extracted with EtOAc (400 mL), and the organic layer washed by water (100 mL) and brine (60 mL), dried over $Na_2SO_4$, filtered, and concentrated to dryness. The residue (combined with the residue from another reaction performed using 15 g of B2) was purified by column chromatography on silica gel (PE:EtOAc=20:1 to 2:1) to give B9 (33.5 g, 75% yield). $^1$H NMR (400 MHz, DMSO-$d_6$) δ 7.38-7.45 (m, 10H), 7.06-7.13 (m, 6H), 6.82-6.92 (m, 1H), 4.12-4.23 (m, 1H), 1.48 (d, 3H).

Step 2: Preparation of 2-(3-tritylimidazol-4-yl)propan-1-amine (B10)

A mixture of 2-(3-tritylimidazol-4-yl)propanenitrile (B9) (16.5 g, 45.4 mmol), Raney-Ni (4.08 g, 47.7 mmol, 1.05 eq), $NH_3 \cdot H_2O$ (910 mg, 7.79 mmol, 1 mL, 30% purity) in MeOH (300 mL) was degassed under vacuum and purged with $H_2$ 3 times. The reaction mixture was stirred at 45° C. for 16 hrs under $H_2$ (45 psi) atmosphere. Reaction progress was tracked using TLC (PE:EtOAc=2:1). The reaction mixture was filtered through a pad of Celite and the filtrate was concentrated to dryness to afford B10 (33 g), which was used without further purification. $^1$H NMR (400 MHz, $CD_3OD$) δ 7.36-7.44 (m, 10H), 7.13-7.20 (m, 6H), 6.72 (br s, 1H), 2.57-2.92 (m, 3H), 1.21 (br d, 3H).

Step 3: Preparation of 2-(1H-imidazol-5-yl)propan-1-amine (B11)

To a solution of 2-(3-tritylimidazol-4-yl)propan-1-amine (B10) (23 g, 62.6 mmol) in MeOH (100 mL) was added HCU/MeOH (4 M, 100 mL). The mixture was stirred at rt for 12 hrs. Reaction progress was tracked using TLC (EtOAc). The reaction mixture (combined with the reaction mixture from another reaction performed using 23 g of B10) was concentrated to dryness. $H_2O$ (40 mL) was added to the residue, and the aqueous layer washed with EtOAc (50 mL). The aqueous layer was lyophilized to give B11 (21 g, 2HCl). $^1$H NMR (400 MHz, $CD_3OD$) δ 8.96 (d, 1H), 7.56 (s, 1H), 3.43-3.51 (m, 1H), 3.17-3.32 (m, 2H), 1.29-1.53 (m, 3H).

Intermediate 2-[(2R)-2-(1H-imidazol-5-yl)propyl]isoindoline-1,3-dione and 2-[(2S)-2-(1H-imidazol-5-yl)propyl]isoindoline-1,3-dione

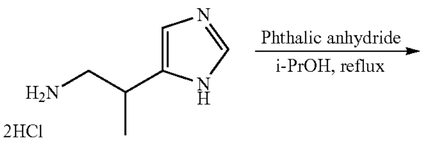

B11

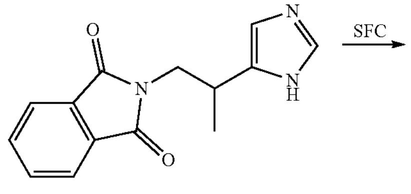

B13

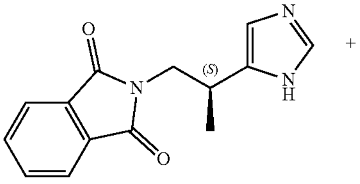

B13A

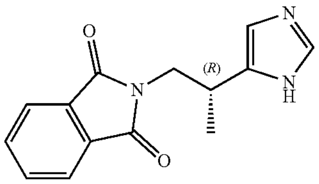

B13B

Step 1: Preparation of 2-[2-(1H-imidazol-5-yl)propyl]isoindoline-1,3-dione (B13)

To a solution of 2-(1H-imidazol-5-yl)propan-1-amine (B11) (10 g, 50.5 mmol, 2HCl) and phthalic anhydride (7.85 g, 53.0 mmol, 1.05 eq) in i-PrOH (400 mL) was added $Et_3N$ (15.32 g, 151 mmol, 21.1 mL, 3 eq). The reaction mixture was stirred at 100° C. for 18 hrs under $N_2$ atmosphere. After cooling, the reaction mixture was concentrated to dryness. Water (200 mL) was then added, and the mixture was stirred at rt for 10 mins. The precipitate was collected by filtration, rinsed with water (100 mL), and dried in vacuo to afford B13 (13 g), which was used without further purification. $^1$H NMR (400 MHz, DMSO-$d_6$) δ 7.71-7.89 (m, 4H), 7.49 (s, 1H), 6.79 (s, 1H), 3.70-3.76 (m, 1H), 3.60-3.65 (m, 1H), 3.15-3.23 (m, 1H), 1.16 (d, 3H).

Step 2: SFC Separation

Compound 2-[2-(1H-imidazol-5-yl)propyl]isoindoline-1,3-dione (13 g) was separated by SFC separation (column: DAICEL CHIRALPAK AD(250 mm*50 mm, 10 um); mobile phase: [0.1% $NH_3H_2O$ ETOH]; B %: 40%-40%, min) to afford Enantiomer 1 (4.8 g, 37% yield, Rt=3.953 min) and Enantiomer 2 (5.2 g, 40% yield, Rt=4.652 min).

Enantiomer 1: 2-[(2R)-2-(1H-imidazol-5-yl)propyl]isoindoline-1,3-dione (B13A). $^1$H NMR (400 MHz, $CD_3OD$) δ 7.73-7.89 (m, 4H), 7.56 (d, 1H), 6.82 (s, 1H), 3.84-3.93 (m, 1H), 3.70-3.82 (m, 1H), 3.36-3.39 (m, 1H), 1.31 (d, 3H); SFC: 98.4% ee.

Enantiomer 2: 2-[(2S)-2-(1H-imidazol-5-yl)propyl]isoindoline-1,3-dione (B13B). $^1$H NMR (400 MHz, $CD_3OD$) δ 7.77-7.88 (m, 4H), 7.55 (d, 1H), 6.82 (s, 1H), 3.84-3.97 (m, 1H), 3.72-3.82 (m, 1H), 3.36-3.42 (m, 1H), 1.31 (d, 3H), SFC: 99.1% ee.

Intermediate Pyrazolo[1,5-a]pyridine-2-carbaldehyde

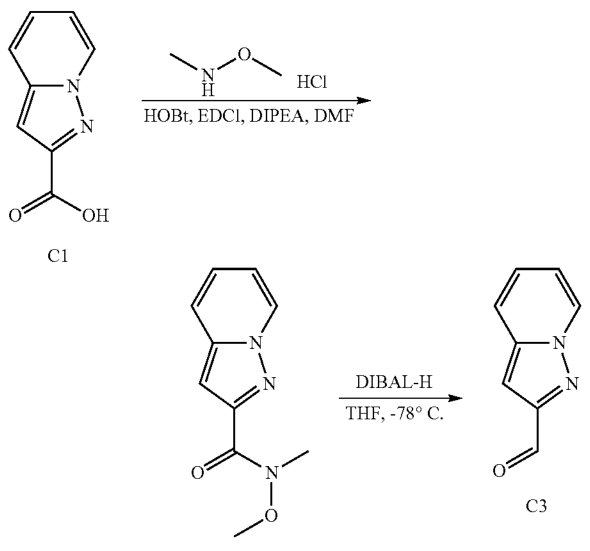

C1

C2

C3

Step 1: Preparation of N-methoxy-N-methyl-pyrazolo[1,5-a]pyridine-2-carboxamide (C2)

To a solution of pyrazolo[1,5-a]pyridine-2-carboxylic acid (C1) (12.5 g, 77.1 mmol) and N-methoxymethanamine (9.42 g, 96.6 mmol, 1.25 eq, HCl) in DMF (200 mL) was added EDCI (22.17 g, 116 mmol, 1.5 eq), DIPEA (29.89 g, 231 mmol, 40.3 mL, 3 eq) and HOBt (15.63 g, 116 mmol, 1.5 eq). The reaction mixture was stirred at rt for 12 hrs. Reaction progress was checked using TLC (PE:EtOAc=1:1). The reaction mixture was combined with the reaction mixture from another reaction performed using 12.5 g of C1 and concentrated to dryness. The residue was dissolved in DCM (200 mL), and the organic layer washed with sat. $Na_2CO_3$ solution (100 mL) and brine (100 mL), dried over $Na_2SO_4$, filtered, and concentrated to dryness. The residue was purified by column chromatography on silica gel (PE: EtOAc=20:1 to 1:1) to give C2 (30.5 g, 96% yield). $^1$H NMR (400 MHz, $CDCl_3$) δ 8.47-8.54 (m, 1H), 7.59 (d, 1H), 7.16 (ddd, 1H), 7.02 (s, 1H), 6.86 (td, 1H), 3.81 (s, 3H), 3.51 (s, 3H).

Step 2: Preparation of pyrazolo[1,5-a]pyridine-2-carbaldehyde (C3)

To a solution of N-methoxy-N-methyl-pyrazolo[1,5-a]pyridine-2-carboxamide (C2) (15 g, 73.1 mmol) in THF (150 mL) was added DIBAL-H (1 M, 146.2 mL, 2 eq) dropwise at −78° C. under $N_2$, and then the reaction mixture was stirred at −78° C. for 2 hrs under $N_2$. Reaction progress was tracked using TLC (PE:EtOAc=1:1). The reaction mixture was combined with the reaction mixture from another reaction performed using 15 g of C2 and was quenched by the addition of sat. $NH_4Cl$ solution (200 mL) slowly and stirred for 15 min. 1 M HCl solution was added until a clear solution was observed. The aqueous portion was extracted with EtOAc (250 mL×3), and the combined organic layer was washed with water (100 mL) and brine (100 mL), dried over $Na_2SO_4$, filtered, and concentrated to dryness. The residue was purified by column chromatography on silica gel (PE:EtOAc=20:1 to 1:1) to give C3 (14.2 g). $^1$H NMR (400 MHz, DMSO-$d_6$) δ 10.14 (s, 1H), 8.81 (dd, 1H), 7.84 (d, 1H), 7.34 (t, 1H), 7.10-7.15 (m, 2H).

Intermediate 3-methylpyrazolo[1,5-a]pyridine-2-carbaldehyde was prepared following the general procedure described above for C3, starting with 3-methylpyrazolo[1,5-a]pyridine-2-carboxylic acid.

Intermediate 3-bromopyrazolo[1,5-a]pyridine-2-carbaldehyde was prepared following the general procedure described above for C3, starting with 3-bromopyrazolo[1,5-a]pyridine-2-carboxylic acid.

Intermediate 4-chloropyrazolo[1,5-a]pyridine-2-carbaldehyde was prepared following the general procedure described above for C3, starting with 4-chloropyrazolo[1,5-a]pyridine-2-carboxylic acid.

Intermediate 6-bromopyrazolo[1,5-a]pyridine-2-carbaldehyde was prepared following the general procedure described above for C3, starting with 6-bromopyrazolo[1,5-a]pyridine-2-carboxylic acid.

Intermediate 6-chloropyrazolo[1,5-a]pyridine-2-carbaldehyde was prepared following the general procedure described above for C3, starting with 6-chloropyrazolo[1,5-a]pyridine-2-carboxylic acid.

Intermediate 7-methylpyrazolo[1,5-a]pyridine-2-carbaldehyde was prepared following the general procedure described above for C3, starting with 7-methylpyrazolo[1,5-a]pyridine-2-carboxylic acid.

Intermediate 4-fluoropyrazolo[1,5-a]pyridine-2-carbaldehyde

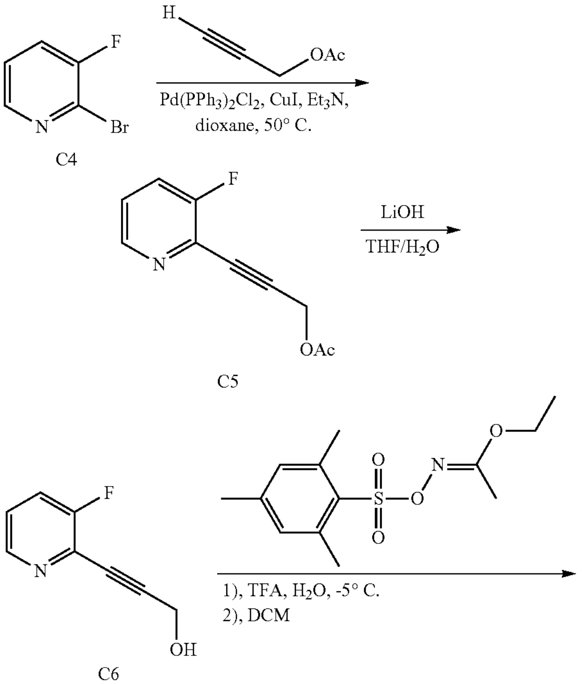

C4

C5

C6

-continued

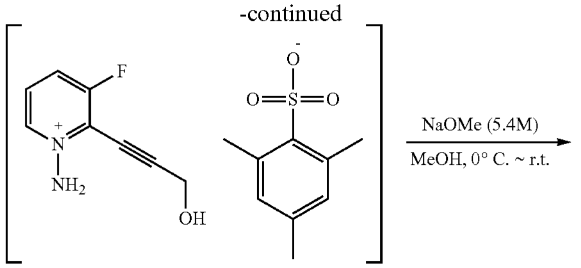

C7

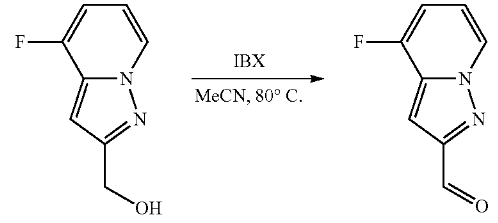

C8 C9

Step 1: Preparation of 3-(3-fluoro-2-pyridyl)prop-2-yn-1yl acetate (C5)

A mixture of 2-bromo-3-fluoro-pyridine (C4) (30 g, 170 mmol), prop-2-yn-1yl acetate (23.41 g, 239 mmol, 1.4 eq), $Pd(PPh_3)_2Cl_2$ (5.98 g, 8.52 mmol, 0.05 eq), CuI (1.62 g, 8.52 mmol, 0.05 eq) and TEA (51.75 g, 511 mmol, 71.2 mL, 3 eq) in dioxane (300 mL) was degassed and purged with $N_2$ 3 times, and then the reaction mixture was stirred at 50° C. for 6 hrs under $N_2$ atmosphere. Reaction progress was checked using TLC (PE:EtOAc=5:1). The reaction mixture was concentrated to dryness. EtOAc (600 mL) was added to the residue, and the organic portion washed with water (300 mL) and brine (300 mL), dried over $Na_2SO_4$, filtered, and concentrated to dryness. The residue was purified by flash silica gel chromatography (ISCO®; 120 g SepaFlash®, Silica Flash Column, eluent of 0~20% EtOAc/PE, gradient @120 mL/min) to give C5 (23.4 g, 71% yield). $^1$H NMR (400 MHz, $CDCl_3$) δ 8.43 (d, 1H), 7.46 (td, 1H), 7.32 (dt, 1H), 4.99 (s, 2H), 2.16 (s, 3H).

Step 2: Preparation of 3-(3-fluoro-2-pyridyl)prop-2-yn-1-ol (C6)

To a solution of 3-(3-fluoro-2-pyridyl)prop-2-ynyl acetate (C5) (23.4 g, 121 mmol) in THF (300 mL) and $H_2O$ (150 mL) and was added $LiOH·H_2O$ (5.34 g, 127 mmol, 1.05 eq) at 0° C. The reaction mixture was stirred at rt for 2 hrs. Reaction progress was checked using TLC (PE:EtOAc=1:1). EtOAc (600 mL) was added to the reaction mixture, and the organic layer washed with $H_2O$ (400 mL) and brine (400 mL), dried over $Na_2SO_4$, filtered and concentrated to dryness to afford C6 (17.5 g), which was used without further purification. $^1$H NMR (400 MHz, DMSO-$d_6$) δ 8.34-8.53 (m, 1H), 7.72-7.88 (m, 1H), 7.50 (dt, 1H), 5.54 (t, 1H), 4.38 (d, 2H).

Step 3: Preparation of 1-amino-3-fluoro-2-(3-hydroxyprop-1-yn-1-yl)pyridin-1-ium2,4,6-trimethylbenzenesulfonate (C7)

To a mixture of $H_2O$ (35 mL, 1.94 mol, 17.3 eq) and TFA (308.0 g, 2.70 mol, 200 mL, 24.0 eq) was added ethyl (1E)-N-(2,4,6-trimethylphenyl)sulfonyloxyethanimidate (33.70 g, 118 mmol, 1.05 eq) at 0° C., and the reaction mixture was stirred at 0° C. for 2 hrs. The reaction was quenched with ice-water (40 mL). The precipitate was filtered and washed with water (20 mL×2). The precipitate was then dissolved in DCM (200 mL) and dried over $Na_2SO_4$ and filtered. To the filtrate was added 3-(3-fluoro-2-pyridyl)prop-2-yn-1-ol (C6) (17 g, 112 mmol, 1 eq) at 0° C. The reaction mixture was warmed to rt for 16 hrs. Reaction progress was checked using TLC (PE:EtOAc=1:1). TBME (400 mL) was slowly added to the reaction mixture, and the precipitate was collected by filtration. The precipitate was rinsed with TBME (200 mL×2) to afford C7 (26 g), which was used without further purification. $^1$H NMR (400 MHz, DMSO-$d_6$) δ 8.66-8.88 (m, 3H), 8.32 (t, 1H), 8.01 (dt, 1H), 6.75 (s, 2H), 4.58 (s, 2H), 3.17 (s, 1H), 2.49 (s, 6H), 2.17 (s, 3H).

Step 4: Preparation of (4-fluoropyrazolo[1,5-a]pyridin-2-yl) methanol (C8)

To a solution of 1-amino-3-fluoro-2-(3-hydroxyprop-1-yn-1-yl)pyridin-1-ium 2,4,6-trimethylbenzenesulfonate (C7) (26 g, 71.0 mmol) in MeOH (250 mL) was added NaOMe (5.4 M, 26.3 mL, 2 eq) at 0° C. The reaction mixture was stirred at rt for 1 hr. The reaction progress was tracked by TLC (PE:EtOAc=1:1). The reaction mixture was quenched by the addition of ice-cold $H_2O$ (200 mL), concentrated to remove most of the MeOH, and extracted with EtOAc (200 mL×3). The combined organic layer was washed with brine (400 mL), dried over $Na_2SO_4$, filtered, and concentrated to dryness to give C8 (7.5 g), which was used without further purification. $^1$H NMR (400 MHz, $CDCl_3$) δ 8.27 (d, 1H), 6.62-6.88 (m, 3H), 4.94 (s, 2H).

Step 5: Preparation of 4-fluoropyrazolo[1,5-a]pyridine-2-carbaldehyde (C9)

To a solution of (4-fluoropyrazolo[1,5-a]pyridin-2-yl) methanol (C8) (7.5 g, 45.1 mmol) in MeCN (150 mL) was added IBX (15.17 g, 54.2 mmol, 1.2 eq). The reaction mixture was stirred at 80° C. for 3 hrs. Reaction progress was checked using TLC (PE:EtOAc=5:1). The reaction mixture was filtered and concentrated to dryness. The residue was purified by flash silica gel chromatography (ISCO®; 40 g SepaFlash® Silica Flash Column, Eluent of 0~4% EtOAc/PE, gradient @40 mL/min) to give C9 (4 g, 54% yield). $^1$H NMR (400 MHz, $CDCl_3$) δ 10.22 (s, 1H), 8.33-8.41 (m, 1H), 7.20 (d, 1H), 6.85-6.98 (m, 2H).

Intermediate 4-methylpyrazolo[1,5-a]pyridine-2-carbaldehyde was prepared following the general procedure described above for C9, starting with 2-bromo-3-methylpyridine.

Intermediate 4-(trifluoromethyl)pyrazolo[1,5-a]pyridine-2-carbaldehyde was prepared following the general procedure described above for C9, starting with 2-bromo-3-(trifluoromethyl)pyridine.

Intermediate 4-methoxypyrazolo[1,5-a]pyridine-2-carbaldehyde was prepared following the general procedure described above for C9, starting with 2-bromo-3-methoxypyridine.

Intermediate 5-methylpyrazolo[1,5-a]pyridine-2-carbaldehyde was prepared following the general procedure described above for C9, starting with 2-bromo-4-methylpyridine.

Intermediate 5-fluoropyrazolo[1,5-a]pyridine-2-carbaldehyde was prepared following the general procedure described above for C9, starting with 2-bromo-4-fluoropyridine.

Intermediate 5-(trifluoromethyl)pyrazolo[1,5-a]pyridine-2-carbaldehyde was prepared following the general procedure described above for C9, starting with 4-(trifluoromethyl)pyridine.

Intermediate 6-methylpyrazolo[1,5-a]pyridine-2-carbaldehyde was prepared following the general procedure described above for C9, starting with 2-bromo-5-methylpyridine.

Intermediate 6-fluoropyrazolo[1,5-a]pyridine-2-carbaldehyde was prepared following the general procedure described above for C9, starting with 2-bromo-5-fluoropyridine.

Intermediate 6-(trifluoromethyl)pyrazolo[1,5-a]pyridine-2-carbaldehyde was prepared following the general procedure described above for C9, starting with 2-bromo-5-(trifluoromethyl)pyridine.

Intermediate 7-(trifluoromethyl)pyrazolo[1,5-a]pyridine-2-carbaldehyde

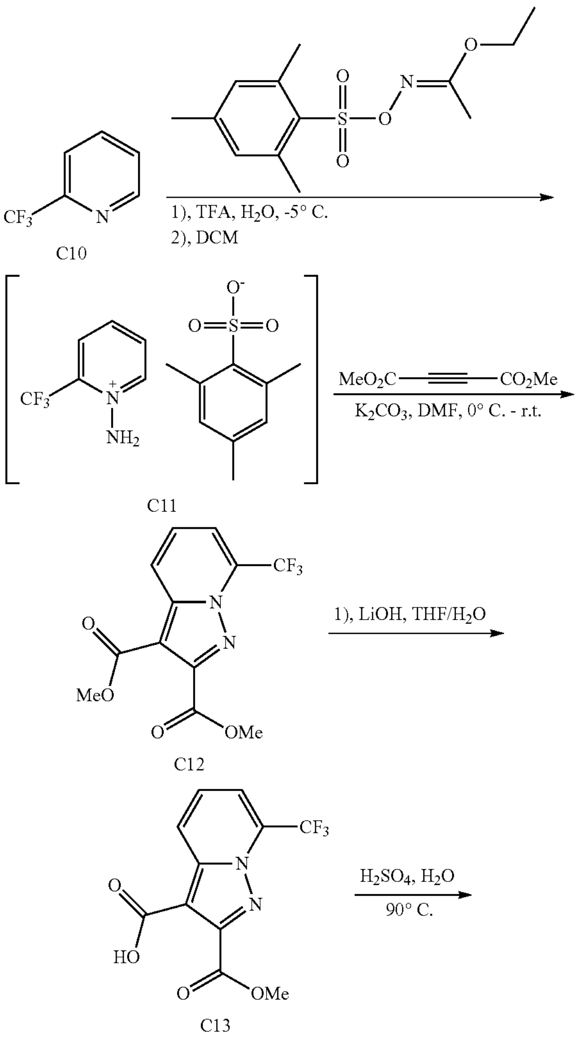

C10

C11

C12

C13

-continued

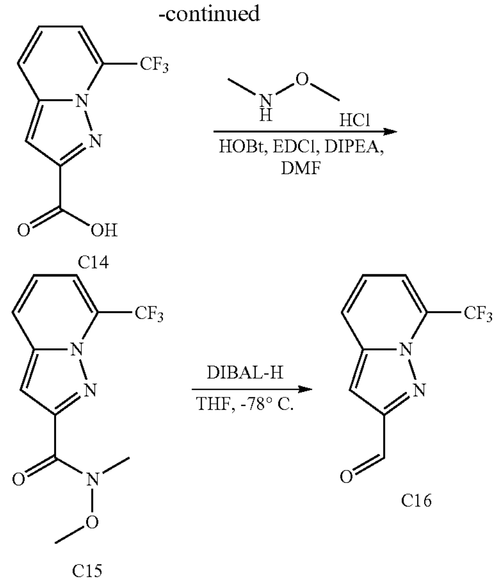

C14

C15

C16

Step 1: Preparation of 1-amino-2-(trifluoromethyl)pyridin-1-ium 2,4,6-trimethylbenzenesulfonate (C11)

To a mixture of TFA (215.60 g, 1.89 mol, 140 mL, 27.8 eq) and $H_2O$ (20.00 g, 1.11 mol, 20.0 mL, 16.3 eq) was added ethyl (1E)-N-(2,4,6-trimethylphenyl) sulfonyloxyethanimidate (21.34 g, 74.8 mmol, 1.1 eq) at 0° C., and the reaction mixture was stirred at 0° C. for 2 hrs. The reaction was quenched by the addition of ice-water (100 mL), and the precipitate was filtered and rinsed with water (50 mL×2). The precipitate was then dissolved in DCM (140 mL), dried over $Na_2SO_4$ and filtered. To the filtrate was added 2-(trifluoromethyl)pyridine (C10) (10 g, 68.0 mmol, 7.87 mL) at 0° C. The reaction mixture was warmed to rt and stirred for 16 hrs. TBME (100 mL) was slowly added to the reaction mixture, and the precipitate was collected and rinsed with TBME (40 mL×3), and then dried in vacuo to give C11 (8.5 g, 35% yield), which was used without further purification. $^1H$ NMR (400 MHz, DMSO-$d_6$) δ 9.06 (d, 1H), 8.40-8.60 (m, 2H), 8.20-8.26 (m, 1H), 8.12 (s, 2H), 6.60 (s, 2H), 2.34 (s, 6H), 2.02 (s, 3H).

Step 2: Preparation of dimethyl 7-(trifluoromethyl) pyrazolo[1,5-a]pyridine-2,3-dicarboxylate (C12)

To a mixture of 1-amino-2-(trifluoromethyl)pyridin-1-ium 2,4,6-trimethylbenzenesulfonate (C11) (8.5 g, 23.5 mmol) and $K_2CO_3$ (6.49 g, 46.9 mmol, 2 eq) in DMF (100 mL) was added dimethyl but-2-ynedioate (6.66 g, 46.9 mmol, 2 eq) at 0° C., The reaction mixture was warmed to rt and stirred for 16 hrs. Reaction progress was tracked by TLC (PE:EtOAc=1:1). Water (200 mL) was added, and the solution was stirred for 30 mins. The resulting precipitate was collected by vacuum filtration, rinsed with water, and dried. The residue was purified by flash silica gel chromatography (ISCO®; 80 g SepaFlash® Silica Flash Column, eluent of 0~40% EtOAc:PE @dv 60 mL/min) to give C12 (2.85 g, 40% yield). $^1H$ NMR (400 MHz, DMSO-$d_h$) δ 8.40 (d, 1H), 7.74-7.96 (m, 2H), 3.85-3.96 (m, 6H).

Step 3: Preparation of 2-(methoxycarbonyl)-7-(trifluoromethyl)pyrazolo[1,5-a]pyridine-3-carboxylic acid (C13)

To a solution of dimethyl 7-(trifluoromethyl)pyrazolo[1,5-a]pyridine-2,3-dicarboxylate (C12) (2.85 g, 9.43 mmol) in THF (20 mL) was added LiOH·$H_2O$ (1.58 g, 37.7 mmol, 4 eq) in $H_2O$ (20 mL), and the reaction mixture was stirred at rt for 16 hrs. Reaction progress was tracked using TLC (PE:EtOAc=1:1). The reaction mixture was concentrated in vacuo to remove most of THF, and the aqueous phase was adjusted to pH ~2 with 4 M HCl. The precipitate was collected by filtration and then dried in vacuo to give C13 (2.25 g), which was used without further purification. $^1$H NMR (400 MHz, DMSO-$d_6$) δ 8.43 (d, 1H), 7.85 (d, 1H), 7.71-7.76 (m, 1H).

Step 4: Preparation of 7-(trifluoromethyl)pyrazolo[1,5-a]pyridine-2-carboxylic acid (C14)

A mixture of 2-(methoxycarbonyl)-7-(trifluoromethyl)pyrazolo[1,5-a]pyridine-3-carboxylic acid (C13) (2.25 g, 8.21 mmol) in $H_2SO_4$ (41.40 g, 422 mmol, 22.5 mL, 51.4 eq) and $H_2O$ (11.25 g, 624 mmol, 11.3 mL, 76.1 eq) was stirred at 90° C. for 16 hrs. Reaction progress was tracked using LC-MS. The reaction mixture was cooled to rt, and water (60 mL) was added. The precipitate was collected by filtration and then dried in vacuo to give C14 (1.7 g), which was used without further purification. $^1$H NMR (400 MHz, DMSO-$d_6$) δ 8.14 (d, 1H), 7.71 (d, 1H), 7.41-7.49 (m, 1H), 7.32 (s, 1H).

Step 5: Preparation of N-methoxy-N-methyl-7-(trifluoromethyl)pyrazolo[1,5-a]pyridine-2-carboxamide (C15)

To a solution of 7-(trifluoromethyl)pyrazolo[1,5-a]pyridine-2-carboxylic acid (C14) (8.00 g, 34.8 mmol) and N-methoxymethanamine (10.17 g, 104 mmol, 3 eq, HCl) in DMF (80 mL) was added HOBt (7.05 g, 52.1 mmol, 1.5 eq), EDCI (10.00 g, 52.1 mmol, 1.5 eq) and DIPEA (13.48 g, 104 mmol, 18.2 mL, 3 eq). The mixture was stirred at rt for 16 hrs. Reaction progress was tracked using TLC (DCM:MeOH=10:1). DCM (150 mL) was added, and the organic portion washed with sat. $Na_2CO_3$ solution (100 mL×2) and brine (100 mL), dried over $Na_2SO_4$, filtered, and concentrated to dryness. The residue was purified by flash silica gel chromatography (ISCO®; 80 g SepaFlash® Silica Flash Column, eluent of 0~10% MeOH:DCM @60 mL/min) to give C15 (6 g, 60% yield). $^1$H NMR (400 MHz, DMSO-$d_6$) δ 8.11 (d, 1H), 7.67 (d, 1H), 7.37-7.49 (m, 1H), 7.21 (s, 1H), 3.77 (s, 3H), 2.50-2.52 (M, 3H); LCMS: m/z 274.1 [M+H]$^+$.

Step 6: Preparation of 7-(trifluoromethyl)pyrazolo[1,5-a]pyridine-2-carbaldehyde (C16)

To a solution of N-methoxy-N-methyl-7-(trifluoromethyl)pyrazolo[1,5-a]pyridine-2-carboxamide (C15) (6 g, 22.0 mmol) in THF (60 mL) was added DIBAL-H (1 M, 65.9 mL, 3 eq) dropwise at −78° C. under $N_2$, and then the reaction mixture was stirred at −78° C. for 2 hrs under $N_2$. Reaction progress was tracked using TLC (PE:EtOAc=5:1). The reaction mixture was quenched by the addition of sat. $NH_4Cl$ solution (150 mL), and then 4 M HCl solution (80 mL) was added. The aqueous portion was extracted with EtOAc (100 mL×2), and the combined organic layer was washed with water (80 mL) and brine (80 mL). The organic layer was dried over $Na_2SO_4$, filtered, and evaporated to dryness. The residue was purified by flash silica gel chromatography (ISCO®; 40 g SepaFlash® Silica Flash Column, eluent of 0~30% EtOAc:PE @40 mL/min) to give C16 (3.95 g, 68% yield). $^1$H NMR (400 MHz, DMSO-$d_6$) δ 10.20 (s, 1H), 8.20 (d, 1H), 7.79 (d, 1H), 7.49 (dd, 1H), 7.40 (s, 1H).

Intermediate 7-chloropyrazolo[1,5-a]pyridine-2-carbaldehyde was prepared following the general procedure described above for C16, starting with 2-chloropyridine.

Intermediate 5-(trifluoromethyl)pyrazolo[1,5-a]pyridine-2-carbaldehyde was prepared following the general procedure described above for C16, starting with 4-(trifluoromethyl)pyridine.

Intermediate 7-fluoropyrazolo[1,5-a]pyridine-2-carbaldehyde

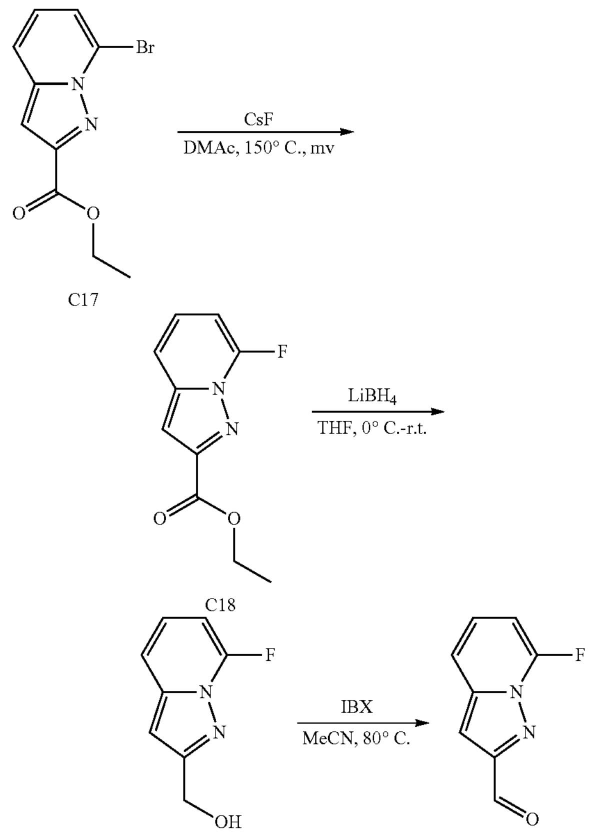

C17 C18 C19 C20

Step 1: Preparation of ethyl 7-fluoropyrazolo[1,5-a]pyridine-2-carboxylate (C18)

To a solution of ethyl 7-bromopyrazolo[1,5-a]pyridine-2-carboxylate (C17) (1 g, 3.72 mmol) in DMA (8 mL) was added CsF (1.69 g, 11.2 mmol, 411 μL, 3 eq), the reaction mixture was stirred at 150° C. for 1 hr under microwave. Reaction progress was tracked using LCMS. DCM (60 mL) was added to the reaction mixture, and the organic portion washed with water (30 mL) and brine (30 mL), dried over $Na_2SO_4$, filtered, and concentrated to dryness. The residue was purified by column chromatography ($SiO_2$, PE/EtOAc=1/0 to 4/1) to give C18 (450 mg, 29% yield). $^1$H NMR (400 MHz, $CDCl_3$) δ 7.48 (d, 1H), 7.18-7.26 (m, 2H), 6.64 (ddd, 1H), 4.52 (q, 2H), 1.48 (t, 3H); LCMS: m/z 208.8 $[M+H]^+$.

Step 2: Preparation of (7-fluoropyrazolo[1,5-a]pyridin-2-yl)methanol (C19)

To a solution of ethyl 7-fluoropyrazolo[1,5-a]pyridine-2-carboxylate (C18) (450 mg, 2.16 mmol) in THF (4 mL) and EtOH (2 mL) was added $LiBH_4$ (260 mg, 11.9 mmol, 5.5 eq) at 0° C. The reaction mixture was stirred at rt for 2 hrs. Reaction progress was tracked using LCMS. The reaction mixture was quenched by the addition of sat. $NH_4Cl$ solution (10 mL), and the aqueous portion extracted with EtOAc (30 mL). The organic layer was washed with water (20 mL) and brine (20 mL), dried over $Na_2SO_4$, filtered, and concentrated to dryness to give C19 (360 mg), which was used without further purification. LCMS: m/z 167.0 $[M+H]^+$.

Step 3: Preparation of 7-fluoropyrazolo[1,5-a]pyridine-2-carbaldehyde (C20)

To a solution of (7-fluoropyrazolo[1,5-a]pyridin-2-yl) methanol (C19) (360 mg, 2.17 mmol) in MeCN (5 mL) was added IBX (971 mg, 3.47 mmol, 1.6 eq), and the reaction mixture was stirred at 80° C. for 1 hr. Reaction progress was tracked using LCMS. The reaction mixture was filtrated and concentrated to dryness to give C20 (355 mg), which was used without further purification. $^1H$ NMR (400 MHz, $CDCl_3$) δ 10.26-10.46 (m, 1H), 7.52 (dd, 1H), 7.22-7.28 (m, 1H), 7.16 (d, 1H), 6.69 (ddd, 1H); LCMS: m/z 165.0 $[M+H]^+$.

Intermediate 4-(difluoromethyl)oxazole-5-carboxylic Acid According to General Scheme 4

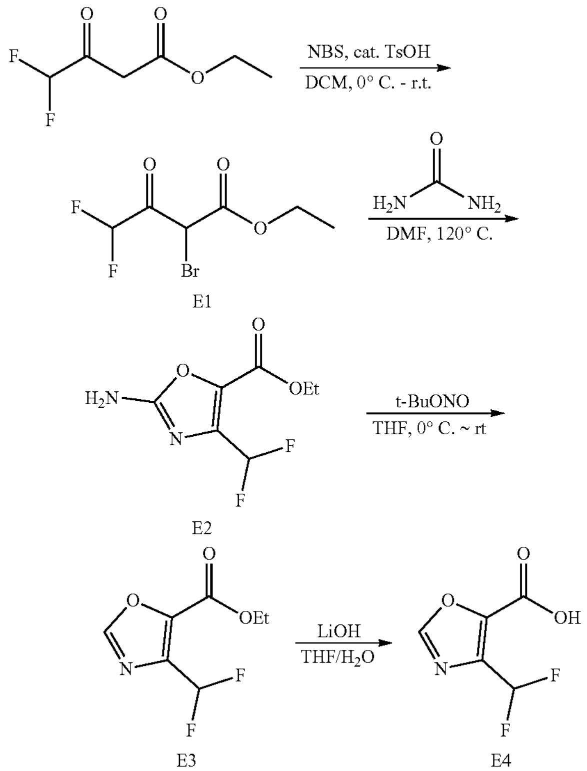

E1

E2

E3

E4

Step 1: Preparation of ethyl 2-bromo-4,4-difluoro-3-oxo-butanoate (E1)

To a solution of ethyl 4,4-difluoro-3-oxo-butanoate (20 g, 120 mmol) in DCM (240 mL) was added TsOH (4.15 g, 24.1 mmol, 0.2 eq) and NBS (22.50 g, 126 mmol, 1.05 eq) in portions at 0° C. After addition was complete, the reaction mixture was stirred at rt for 1 hr. The reaction progress was checked using TLC (PE:EtOAc=5:1). DCM was added (100 mL), and the organic portion was washed with sat. $Na_2CO_3$ solution (100 mL) and brine (150 mL), dried over $Na_2SO_4$, filtered, and concentrated to dryness to afford E1 (34 g), which was used without further purification. $^1H$ NMR (400 MHz, DMSO-$d_6$) δ 5.81-6.16 (m, 1H), 4.34-4.41 (m, 1H), 4.12-4.20 (m, 2H), 1.17-1.23 (m, 3H).

Step 2: Preparation of ethyl 2-amino-4-(difluoromethyl) oxazole-5-carboxylate (E2)

A mixture of E1 (37 g, 151 mmol) and urea (45.34 g, 755 mmol, 40.5 mL, 5 eq) in DMF (30 mL) was stirred at 120° C. for 12 hrs. The reaction progress was checked using LC-MS. The reaction mixture was cooled to rt and poured into 100 mL of water. The reaction mixture was stirred for 15 min at 0° C., and the precipitate was collected by filtration, rinsed with water (50 mL), dried in vacuo to give E2 (15.5 g, 63% yield for steps 1 and 2). LC-MS: m/z 207.2 $(M+H)^+$; $^1H$ NMR (400 MHz, DMSO-$d_6$) δ 7.86 (s, 2H), 6.84-7.44 (m, 1H), 4.27 (q, 2H), 1.28 (t, 3H).

Step 3: Preparation of ethyl 4-(difluoromethyl)oxazole-5-carboxylate (E3)

To a solution of ethyl 2-amino-4-(difluoromethyl)oxazole-5-carboxylate (20 g, 97.0 mmol) in THF (300 mL) was added t-BuONO (30.01 g, 291 mmol, 34.6 mL, 3 eq) dropwise at 0° C., the reaction mixture was stirred at rt for 12 hrs. DCM (3M) mL) was added, and the organic portion was washed with water (200 mL) and brine (200 mL), dried over $Na_2SO_4$, filtered, and concentrated to dryness. The residue was purified by column chromatography ($SiO_2$, PE/EtOAc=1/0 to 10/1) to give E3 (12.7 g, 69% yield). $^1H$ NMR (400 MHz, $CDCl_3$) δ 8.05 (s, 1H), 6.93-7.27 (m, 1H), 4.44 (q, 2H), 1.40 (t, 3H).

Step 5: Preparation of 4-(difluoromethyl)oxazole-5-carboxylic acid (E4)

To a solution of ethyl 4-(difluoromethyl)oxazole-5-carboxylate (12.7 g, 66.5 mmol) in THF (100 mL) and $H_2O$ (20 mL) was added $LiOH{\cdot}H_2O$ (3.07 g, 73.1 mmol, 1.1 eq). The reaction mixture was stirred at rt for 1 hr and then concentrated in vacuo to remove THF. Water (80 mL) was added, and the aqueous portion extracted with TBME (50 mL). The aqueous layer was then adjusted to pH-6 by the addition of 0.5 M HCl. The aqueous layer was concentrated to dryness to give E4 (11 g), which was used without further purification. $^1H$ NMR (400 MHz, DMSO-$d_6$) δ 8.30 (s, 1H), 7.34-7.76 (m, 1H).

Intermediate ethyl 2-bromo-4-(difluoromethyl)oxazole-5-carboxylate according to General Scheme 4

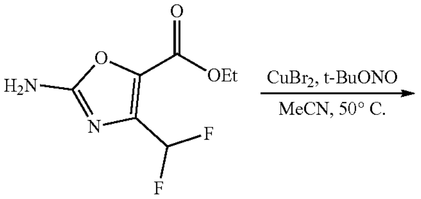

E2

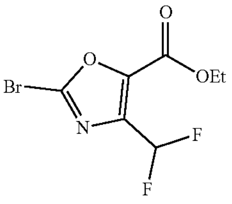

E5

Preparation of ethyl 2-bromo-4-(difluoromethyl)oxazole-5-carboxylate (E5)

To a solution of ethyl 2-amino-4-(difluoromethyl)oxazole-5-carboxylate (E2) (25 g, 121 mmol) in MeCN (200 mL) was added $CuBr_2$ (40.63 g, 182 mmol, 8.5 mL, 1.5 eq) at 0° C. The mixture turned dark green and further stirred for 15 min at rt. t-BuONO (18.76 g, 182 mmol, 21.6 mL, 1.5 eq) was added at 0° C. The reaction was stirred at rt for 2 hrs, and then was heated to 50° C. and stirred for 12 hrs. Reaction progress was tracked using TLC (EtOAc:PE=5:1). The reaction mixture was filtered. DCM (2(0) mL) was added to the filtrate, and the organic layer was washed by water (100 mL) and brine (100 mL), dried over $Na_2SO_4$, filtered, and concentrated to dryness. The residue was purified by flash silica gel chromatography (ISCO®; 120 g SepaFlash® Silica Flash Column, Eluent of 0~20% EtOAc/PE gradient a; 100 mL/min) to afford E5 (19 g, 58% yield). $^1H$ NMR (400 MHz, $CDCl_3$) δ 7.02 (t, 1H), 4.39 (q, 2H), 1.35 (t, 3H).

Intermediate 4-(difluoromethyl)-2-(1-hydroxy-1-methyl-ethyl)oxazole-5-carboxylic acid according to General Scheme 6, Method A

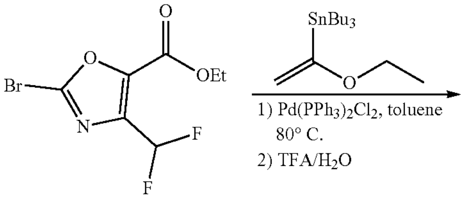

E5

-continued

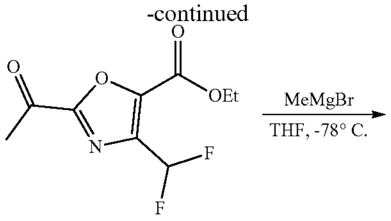

E6

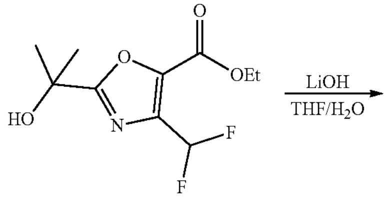

E7

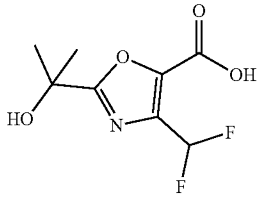

E8

Step 1: Preparation of ethyl 2-acetyl-4-(difluoromethyl)oxazole-5-carboxylate (E6)

To a solution of ethyl 2-bromo-4-(difluoromethyl)oxazole-5-carboxylate (E5) (10 g, 37.0 mmol) in toluene (150 mL) was added $Pd(PPh_3)_2Cl_2$ (2.60 g, 3.70 mmol, 0.1 eq) and tributyl(1-ethoxyvinyl)stannane (17.39 g, 48.1 mmol, 16.3 mL, 1.3 eq). The mixture was stirred at 85° C. for 12 hrs under $N_2$ atmosphere. The reaction progress was checked using TLC (PE:EtOAc). EtOAc (100 mL) was added to the reaction mixture, and the organic portion washed with sat. KF solution (150 mL) and brine (100 mL), dried over $Na_2SO_4$, filtered, and concentrated to dryness. The residue was dissolved in THF (60 mL) and treated with HCl (4 M, 60 mL), and then was stirred at 40° C. for 12 hrs. The reaction progress was checked by TLC (Petroleum ether: EtOAc=10:1). EtOAc (100 mL) was added to the reaction mixture, and the organic portion washed with water (50 mL) and brine (50 mL), dried over $Na_2SO_4$, filtered, and concentrated to dryness. The residue was purified by flash silica gel chromatography (ISCO®; 40 g SepaFlash® Silica Flash Column, eluent of 0~20% EtOAc/PE gradient @40 mL/min) to give E6 (7.1 g, 82% yield). $^1H$ NMR (400 MHz, $CDCl_3$) δ 7.00-7.36 (m, 1H), 4.48 (q, 2H), 2.66-2.86 (m, 3H), 1.43 (t, 3H).

Step 2: Preparation of ethyl 4-(difluoromethyl)-2-(1-hydroxy-1-methyl-ethyl)oxazole-5-carboxylate (E7)

To a solution of E6 (2.5 g, 10.7 mmol) in THF (120 mL) was added MeMgBr (3 M, 7.15 mL, 2 eq) at −78° C. The mixture was stirred at −78° C. for 1 hr. The reaction progress was checked by TLC (PE:EtOAc=2:1). The reaction mixture was quenched by addition of sat. $NH_4Cl$ solution (50 mL)

and then water (100 mL) was added. The aqueous portion was extracted with EtOAc (100 mL×3). The combined organic layers were dried over $Na_2SO_4$, filtered, and concentrated to dryness. The residue was purified by flash silica gel chromatography (ISCO®; 40 g SepaFlash® Silica Flash Column, eluent of 0~12% EtOAc/PE gradient @, 40 mL/min) to give E7 (3.2 g, 60% yield). $^1$H NMR (400 MHz, $CDCl_3$) δ 6.94-7.29 (m, 1H), 4.46 (q, 2H), 2.86 (s, 1H), 1.72 (s, 6H), 1.44 (t, 3H). The starting material E6 (300 mg) was also recovered.

Step 3: Preparation of 4-(difluoromethyl)-2-(1-hydroxy-1-methyl-ethyl)oxazole-5-carboxylic acid (E8)

To a solution of E7 (3.9 g, 15.7 mmol) in THF (40 mL) and $H_2O$ (40 mL) was added $LiOH{\cdot}H_2O$ (690 mg, 16.4 mmol, 1.05 eq). The mixture was stirred at rt for 1 hr. The reaction progress was checked using TLC (PE:EtOAc=5:1). The reaction mixture was concentrated to remove THF. The aqueous mixture was then adjusted to pH-3 by the addition of IM HCl, and then lyophilized in vacuo to give E8 (4 g), which was used without further purification. $^1$H NMR (400 MHz, DMSO-$d_6$) δ 7.35-7.71 (m, 1H), 5.68 (br s, 1H), 1.50 (s, 6H).

Intermediate 2-(I-hydroxycyclobutyl)-4-(trifluoromethyl)oxazole-5-carboxylic acid

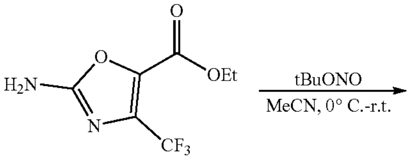

E9

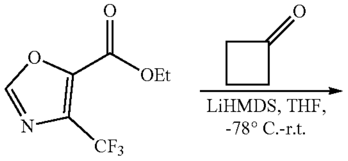

E10

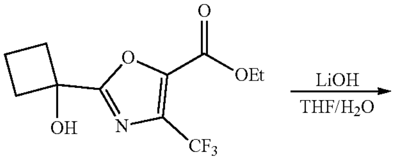

E11

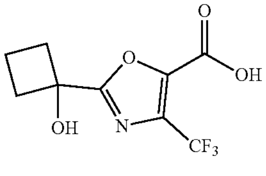

E12

Step 1: Preparation of ethyl 4-(trifluoromethyl)oxazole-5-carboxylate (E10)

To a solution of ethyl 2-amino-4-(trifluoromethyl)oxazole-5-carboxylate (2.00 g, 8.92 mmol) in THF (60 mL) was added t-BuONO (1.84 g, 17.9 mmol, 2.12 mL, 2 eq). The reaction mixture was stirred at 55° C. for 24 hrs. EtOAc (120 mL) was added to the reaction mixture, and the organic portion washed with water (100 mL) and brine (100 mL), dried over $Na_2SO_4$, filtered, and concentrated to dryness. The residue was purified by column chromatography ($SiO_2$, PE/EtOAc=1/0 to 8/1) to give E10 (1.2 g, 64% yield). $^1$H NMR (400 MHz, $CDCl_3$) δ 7.96 (s, 1H), 4.39 (q, 2H), 1.34 (t, 3H).

Step 2: Preparation of ethyl 2-(1-hydroxycyclobutyl)-4-(trifluoromethyl)oxazole-5-carboxylate (E11)

To a solution of ethyl 4-(trifluoromethyl)oxazole-5-carboxylate (1.2 g, 5.74 mmol) in THF (30 mL) was added LiHMDS (1 M, 8.61 mL, 1.5 eq) at −78° C., and the reaction mixture was stirred at −78° C. for 0.5 hr. Cyclobutanone (1.21 g, 17.2 mmol, 1.29 mL, 3 eq) in THF (5 mL) was added to the reaction mixture, and the mixture was stirred at −78° C. for 2 hrs under $N_2$ atmosphere. The reaction mixture was quenched by the addition of sat. $NH_4Cl$ solution (30 mL), and the aqueous portion extracted with EtOAc (100 mL). The organic layer washed by water (70 mL) and brine (70 mL), dried over $Na_2SO_4$, filtered, and concentrated to dryness. The residue was purified by column chromatography ($SiO_2$, PE/EtOAc=1/0 to 10/1) to give E11 (600 mg, 37% yield). $^1$H NMR (400 MHz, $CDCl_3$) δ 4.29 (q, 2H), 2.78-2.94 (m, 1H), 2.52-2.65 (m, 2H), 2.24-2.38 (m, 2H), 1.78-1.98 (m, 3H), 1.26 (t, 3H).

Step 3: Preparation of 2-(1-hydroxycyclobutyl)-4-(trifluoromethyl)oxazole-5-carboxylic acid (E12)

To a solution of ethyl 2-(1-hydroxycyclobutyl)-4-(trifluoromethyl)oxazole-5-carboxylate (600 mg, 2.15 mmol) in $H_2O$ (2 mL) and THF (10 mL) was added $LiOH{\cdot}H_2O$ (99.2 mg, 2.36 mmol, 1.1 eq) at 0° C. The reaction mixture was stirred at rt for 2 hrs and concentrated in vacuo to remove THF. Water (10 mL) was added, and the aqueous portion extracted with TBME (30 mL). The aqueous layer was then adjusted to pH-6 by the addition of 0.5 M HCl and concentrated to dryness to give E12 (540 mg), which was used without further purification. $^1$H NMR (400 MHz, $CD_3OD$) δ 2.54-2.67 (m, 2H), 2.19-2.34 (m, 2H), 1.81-1.95 (m, 1H), 1.66-1.80 (m, 1H).

Intermediate ethyl 4-bromo-2-(2-hydroxypropan-2-yl)oxazole-5-carboxylate according to General Scheme 6

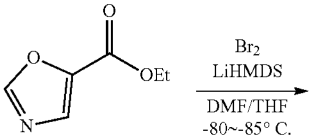

E13

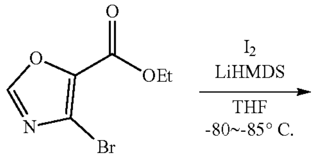

E14

-continued

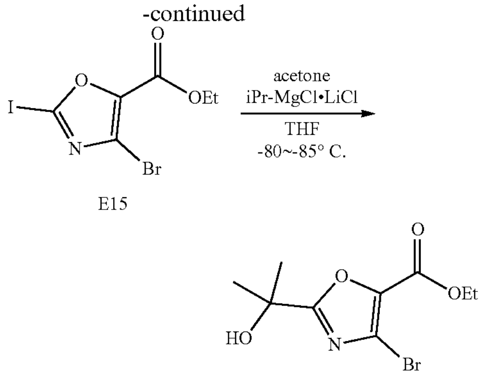

E15

E16

Step 1: Preparation of Ethyl 4-bromooxazole-5-carboxylate (E14)

Ethyl oxazole-5-carboxylate (E13) (500 mg, 3.54 mmol) was added in THF (2.50 mL) and DMF (2.50 mL) at approximately 10° C. The reaction mixture was cooled to −80° C. and LiHMDS (1 M, 4.61 mL, 1.30 eq) was added dropwise at approximately −80° C. The reaction mixture was stirred at approximately −80° C. for 0.5 hr. $Br_2$ (736 mg, 4.61 mmol, 1.3 eq) was then added dropwise at approximately −80° C. The reaction mixture was stirred at approximately −80° C. for 0.5 hr. The reaction progress was checked using LC-MS. The reaction mixture was combined with 19 other reactions performed using 500 mg of E13. The combined reaction mixture was poured into sat. citric acid at approximately −10° C. The aqueous portion was extracted with EtOAc (50 mL×3). The combined organic layer was washed with brine (50 mL), dried with $Na_2SO_4$, filtered, and concentrated to dryness. The residue was purified by column chromatography ($SiO_2$, PE/EtOAc=1/0 to 0/1) to give E14 (3.00 g, 19% yield). $^1H$ NMR (400 MHz, DMSO-$d_6$) δ 8.70 (s, 1H), 4.29-4.34 (m, 2H), 1.29 (t, 3H); LC-MS: m/z 219.9 & 221.9 $(M+H)^+$.

Step 2: Preparation of Ethyl 4-bromo-2-iodooxazole-5-carboxylate (E15)

Ethyl 4-bromooxazole-5-carboxylate (E14) (3.15 g, 14.3 mmol, 1.00 eq) was added in THF (15.0 mL) at rt. LiHMDS (I M, 17.2 mL, 1.20 eq) was added dropwise at approximately −80° C. $I_2$ (5.45 g, 21.5 mmol, 1.50 eq) in THF (15.0 mL) was then added dropwise at approximately −80° C. The reaction mixture was stirred at approximately −80° C. for 1 hr. The reaction progress was checked using TLC (PE/EtOAc). The reaction mixture was poured into saturated citric acid (30 mL) at approximately −10° C. The aqueous phase was extracted with ethyl acetate (30 mL×3). The combined organic layer was washed with brine (30 mL), dried with $Na_2SO_4$, filtered, and concentrated to dryness. The residue was purified by column chromatography ($SiO_2$, PE/EtOAc=1/0 to 0/1) to afford E15 (1.10 g, 22% yield). $^1H$ NMR (400 MHz, DMSO-$d_6$) δ: 4.29-4.35 (m, 2H), 1.30 (t, 3H). LC-MS: m/z 345.8 & 347.9 $(M+H)^+$.

Step 3: Preparation of Ethyl 4-bromo-2-(2-hydroxypropan-2-yl)oxazole-5-carboxylate (E16)

Ethyl 4-bromo-2-iodooxazole-5-carboxylate (E15) (1.10 g 3.18 mmol) was added in THF (10 mL) at approximately 10° C. under $N_2$. The reaction mixture was degassed under vacuum and purged with $N_2$ three times. The mixture was cooled to −80° C., and iPr-MgCl·LiCl (1.3 M, 2.45 mL, 1 eq) was added dropwise at approximately −80° C. The reaction mixture was stirred at approximately −80° C. for 0.5 hr, and then acetone (222 mg, 3.82 mmol, 1.20 eq) was added dropwise at approximately −80° C. The mixture was stirred at approximately −80° C. for 0.5 hr. The reaction progress was checked using TLC (PE/EtOAc=5/1). The reaction mixture was poured into sat. citric acid solution (5 mL) at approximately −10° C. The aqueous portion was extracted with ethyl acetate (5 mL×3). The combined organic layer was washed with brine (5 mL), dried with $Na_2SO_4$, filtered, and concentrated to dryness. The residue was purified by column chromatography ($SiO_2$, PE/EtOAc=1/0 to 0/1) and further purified by prep-HPLC (column: Phenomenex luna C18 80×40 mm×3 um; mobile phase: [water (0.04% HCl)-ACN]; B %: 18%-45%, 7 min) to afford E16 (140 mg, 16% yield). $^1H$ NMR (400 MHz, DMSO-$d_6$) δ: 5.93 (s, 1H), 4.30-4.37 (m, 2H), 1.50 (s, 6H), 1.32 (t, 3H). LC-MS: m/z 277.9 & 279.9 $(M+H)^+$.

Intermediate ethyl 4-chloro-2-(2-hydroxypropan-2-yl)oxazole-5-carboxylate according to General Scheme 6

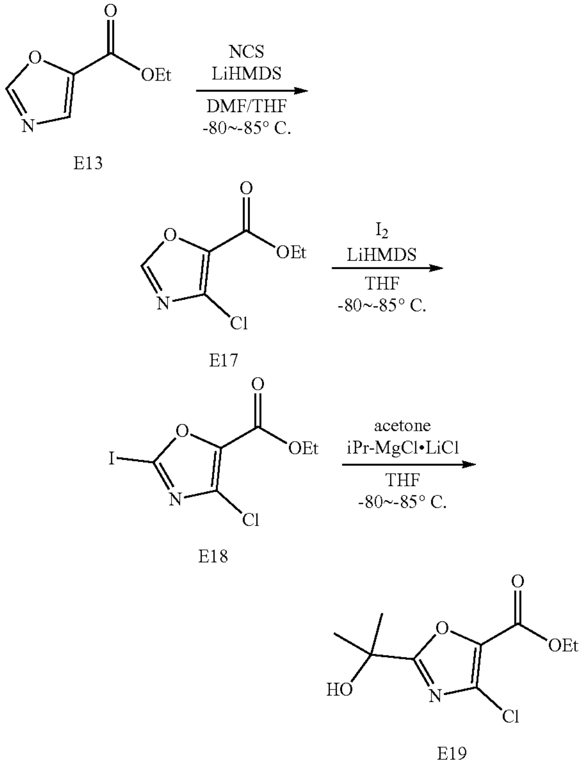

E13

E17

E18

E19

Step 1: Preparation of Ethyl 4-chlorooxazole-5-carboxylate (E17)

Ethyl oxazole-5-carboxylate (E13) (10.0 g, 70.9 mmol) was added in DMF (50 mL) at approximately 10° C. The reaction mixture was cooled to −80° C., and LiHMDS (1 M, 92.1 mL, 1.3 eq) was added dropwise at approximately −80°

C. The reaction mixture was stirred at approximately −80° C. for 0.5 hr, and NCS (12.3 g, 92.1 mmol, 1.3 eq) in THF (50 mL) was then added dropwise at approximately −80° C. The mixture was stirred at approximately −80° C. for 0.5 hr. The reaction progress was checked using TLC (PE/EtOAc=5/1). The reaction mixture was combined for workup with seven other reactions each performed using 10 g of E13. The combined reaction mixture was poured into sat citric acid solution (100 mL) at approximately −10° C. The aqueous portion was extracted with ethyl acetate (100 mL×3). The combined organic layer was washed with brine (50 mL), dried with $Na_2SO_4$, filtered, and concentrated to dryness. The residue was purified by column chromatography ($SiO_2$, PE/EtOAc=1/0 to 0/1) to afford E17 (18.0 g, 18% yield). $^1H$ NMR (400 MHz, $CDCl_3$) δ 7.94 (s, 1H), 4.44 (q, 2H), 1.42 (t, 3H); LC-MS: m/z 176.0 $(M+H)^+$.

Step 2: Preparation of Ethyl 4-chloro-2-iodooxazole-5-carboxylate (E18)

Three reactions were carried out in parallel. Ethyl 4-chlorooxazole-5-carboxylate (E17) (6.00 g, 34.2 mmol) was dissolved in THF (30 mL) at rt. LiHMDS (1 M, 41.0 mL, 1.2 eq) was added dropwise at approximately −80° C., followed by the dropwise addition of $I_2$ (13.0 g, 51.3 mmol, 1.5 eq) in THF (30 mL) at approximately −80° C. The reaction mixture was stirred at approximately −80° C. for 1 hr. The reaction progress was checked using TLC (PE/EtOAc=5/1). The three parallel reactions were combined together for workup. The combined reaction mixture was poured into sat. citric acid solution (100 mL) at approximately −5° C. The aqueous portion was extracted with ethyl acetate (100 mL×3). The combined organic layer was washed with brine (50 mL), dried with $Na_2SO_4$, filtered, and concentrated to dryness. The residue was purified by column chromatography ($SiO_2$, PE/EtOAc=1/0 to 0/1) to afford E18 (10.0 g, 32% yield). $^1H$ NMR (400 MHz, DMSO-$d_6$) δ 4.20-4.27 (m, 2H), 1.21 (t, 3H); LC-MS: m/z 301.9 $(M+H)^+$.

Step 3: Preparation of Ethyl 4-chloro-2-(2-hydroxypropan-2-yl)oxazole-5-carboxylate (E19)

Two reactions were carried out in parallel. Compound E18 (5.00 g, 16.6 mmol) was added in THF (50 mL) at approximately 10° C. under $N_2$. The suspension was degassed under vacuum and purged with $N_2$ three times. The mixture was cooled to −80° C., and iPr-MgCl·LiCl (1.3 M, 12.8 mL, 1 eq) was added dropwise at approximately −80° C. The mixture was stirred at approximately −80° C. for 0.5 hr, and acetone (1.16 g, 19.9 mmol, 1.2 eq) was then added dropwise at approximately −80° C. The mixture was stirred at approximately −80° C. for 0.5 hr. The reaction progress was checked using TLC (PE/EtOAc=5/1). The two parallel reactions were combined together for workup. The combined reaction mixture was poured into sat. citric acid solution (50 mL) at approximately −10° C. The aqueous portion was extracted with ethyl acetate (50 mL×3). The combined organic layer was washed with brine (50 mL), dried with $Na_2SO_4$, filtered, and concentrated to dryness. The residue was purified by column chromatography ($SiO_2$, PE/EtOAc=1/0 to 0/1) and further purified by prep-HPLC (column: Phenomenex luna C18 (250×70 mm, 15 um); mobile phase: [water (0.05% HCl)-ACN]; B %: 20%-50%, 23 min) to afford E19 (1.80 g, 23% yield). $^1H$ NMR (400 MHz, DMSO-$d_6$) δ: 5.92 (s, 1H), 4.32-4.37 (m, 2H), 1.51 (s, 6H), 1.31 (t, 3H); LC-MS: m/z 234.0 $(M+H)^+$.

Intermediate 4-(difluoromethyl)-2-(2-cyanopropan-2-yl)oxazole-5-carboxylic acid

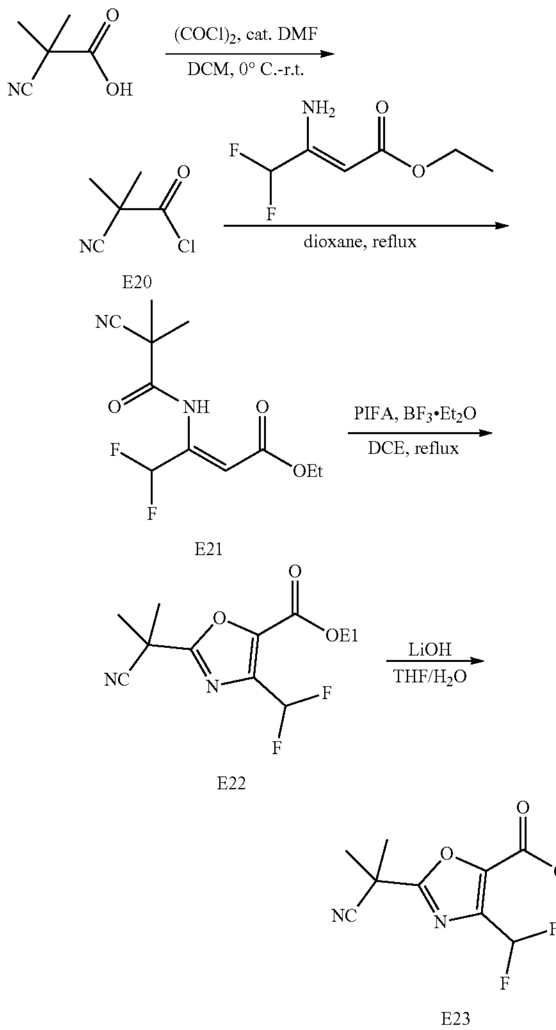

Step 1: Preparation of 2-cyano-2-methyl-propanoyl chloride (E20)

To a solution of 2-cyano-2-methyl-propanoic acid (2 g, 17.7 mmol) and DMF (129 mg, 1.77 mmol, 136 μL, 0.1 eq) in DCM (20 mL) was added oxalyl chloride (2.69 g, 21.2 mmol, 1.86 mL, 1.2 eq) dropwise at 0° C., and then the reaction mixture was stirred at rt for 1 hr. The reaction mixture was concentrated to dryness to afford E20 (2.5 g), which was used without further purification.

Step 2: Preparation of ethyl (Z)-3-[(2-cyano-2-methyl-propanoyl)amino]-4,4-difluoro-but-2-enoate (E21)

To a solution of ethyl (Z)-3-amino-4,4-difluoro-but-2-enoate (2 g, 12.1 mmol) in dioxane (20 mL) was added a solution of 2-cyano-2-methyl-propanoyl chloride (E20) (2.39 g, 18.2 mmol, 1.5 eq) in dioxane (20 mL) at rt. The reaction mixture was stirred at 110° C. for 12 hrs. The reaction progress was checked using TLC (PE/Ethyl acetate=5/1). The reaction mixture was concentrated to dryness, and the residue was purified by flash silica gel chromatography (ISCO®; 40 g SepaFlash® Silica Flash Column, eluent of 0~7% EtOAc/PE gradient @40 mL/min) to give E21 (2.4 g, 76% yield). $^1$H NMR (400 MHz, DMSO-$d_6$) δ 10.90 (s, 1H), 6.95-7.27 (m, 1H), 5.81 (s, 1H), 4.12-4.29 (m, 2H), 1.51-1.69 (m, 6H), 1.20 (t, 3H); LCMS: m/z 259.1 $[M+H]^+$.

Step 3: Preparation of ethyl 2-(1-cyano-1-methyl-ethyl)-4-(difluoromethyl)oxazole-5-carboxylate (E22)

To a solution of ethyl (Z)-3-[(2-cyano-2-methyl-propanoyl)amino]-4,4-difluoro-but-2-enoate (E21) (2.4 g, 9.22 mmol) in DCE (20 mL) was added $BF_3 \cdot Et_2O$ (2.62 g, 18.4 mmol, 2.28 mL, 2 eq) and PIDA (4.16 g, 12.9 mmol, 1.4 eq) at rt. The mixture was stirred at 90° C. for 18 hrs. The reaction progress was checked by TLC (PE/EtOAc). The reaction mixture was concentrated to dryness. DCM (100 mL) was added to the residue, and the organic layer washed with sat. $Na_2CO_3$ solution (10 mL) and brine (50 mL), dried over $Na_2SO_4$, filtered, and concentrated to dryness. The residue was purified by flash silica gel chromatography (ISCO®; 12 g SepaFlash® Silica Flash Column, eluent of 0~7% EtOAc/PE gradient a 30 mL/min) to give E22 (0.25 g, 11% yield). $^1$H NMR (400 MHz, DMSO-$d_6$) δ 7.03-7.55 (m, 1H), 4.35 (q, 2H), 1.77 (s, 6H), 1.29 (t, 3H).

Step 4: Preparation of 2-(1-cyano-1-methyl-ethyl)-4-(difluoromethyl)oxazole-5-carboxylic acid (E23)

To a solution of ethyl 2-(1-cyano-1-methyl-ethyl)-4-(difluoromethyl)oxazole-5-carboxylate (E22) (0.25 g, 968 μmol) in THF (3 mL) and $H_2O$ (1 mL) was added $LiOH \cdot H_2O$ (48.8 mg, 1.16 mmol, 1.2 eq). The mixture was stirred at rt for 18 hrs. Reaction completeness was checked using TLC (PE:EtOAc=5:1). The reaction mixture was concentrated under reduced pressure to remove THF. The aqueous portion was adjusted with 2 M HCl to pH ~7, and then lyophilized under vacuo to give E23 (0.22 g, 99% yield). $^1$H NMR (400 MHz, DMSO-$d_6$) δ 7.23-7.74 (m, 1H), 1.73 (s, 6H).

Intermediate 4-(difluoromethyl)-2-(pyrimidin-2-yl)oxazole-5-carboxylic acid according to General Scheme 5, Method B

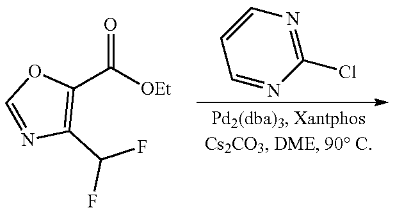

E4

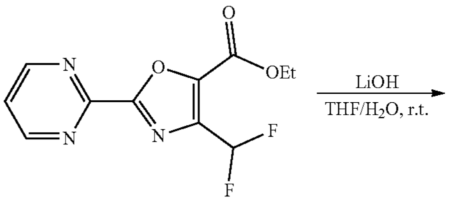

E24

-continued

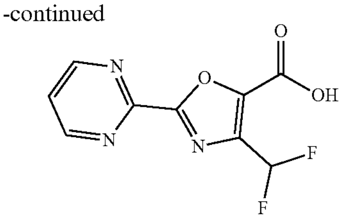

E25

Step 1: Preparation of ethyl 4-(difluoromethyl)-2-pyrimidin-2-yl-oxazole-5-carboxylate (E24)

To a solution of ethyl 4-(difluoromethyl)oxazole-5-carboxylate (E4) (1 g, 5.23 mmol), $Pd_2(dba)_3$ (240 mg, 262 μmol, 0.05 eq), (5-diphenylphosphanyl-9,9-dimethyl-xanthen-4-yl)-diphenyl-phosphane (151 mg, 262 μmol, 0.05 eq) and $Cs_2CO_3$ (3.41 g, 10.5 mmol, 2 eq) in 1,2-dimethoxyethane (3 mL) was added 2-chloropyrimidine (599 mg, 5.23 mmol) under $N_2$ atmosphere. The reaction mixture was stirred at 90° C. for 12 hrs. DCM (50 mL) was added to the reaction mixture, and the organic portion washed by water (40 mL) and brine (40 mL), dried over $Na_2SO_4$, filtered, and concentrated to dryness. The residue was purified by column chromatography ($SiO_2$, PE/EtOAc=1/0 to 1/1) to give E24 (400 mg, 25% yield). $^1$H NMR (400 MHz, $CDCl_3$) δ 9.02 (br d, 2H), 7.52 (t, 1H), 7.38 (s, 1H), 7.24 (s, 1H), 7.11 (s, 1H), 4.54 (q, 2H), 1.48 (t, 3H).

Step 2: Preparation of 4-(difluoromethyl)-2-pyrimidin-2-yl-oxazole-5-carboxylic acid (E25)

To a solution of ethyl 4-(difluoromethyl)-2-pyrimidin-2-yl-oxazole-5-carboxylate (E24) (450 mg, 1.67 mmol) in THF (2 mL) and $H_2O$ (2 mL) was added $LiOH \cdot H_2O$ (77.2 mg, 1.84 mmol, 1.1 eq). The reaction mixture was stirred at rt for 1 hr. The reaction mixture was concentrated to remove THF, and $H_2O$ (10 mL) was added. The aqueous layer was extracted with TBME (30 mL). The aqueous layer was then adjusted to pH-6 with 0.5 M HCl and extracted with DCM/MeOH (30/3 mL) 3 times. The combined DCM/MeOH organic layer was dried over $Na_2SO_4$, filtered, and concentrated to dryness to afford E25 (350 mg), which was used without further purification. $^1$H NMR (400 MHz, DMSO-$d_6$) δ 9.06 (d, 2H), 7.75 (t, 1H), 7.20-7.57 (M, 1H).

Intermediate 2-(1-hydroxy-1-methyl-ethyl)-4-methyl-oxazole-5-carboxylic acid according to General Scheme 4 and General Scheme 6, Method A

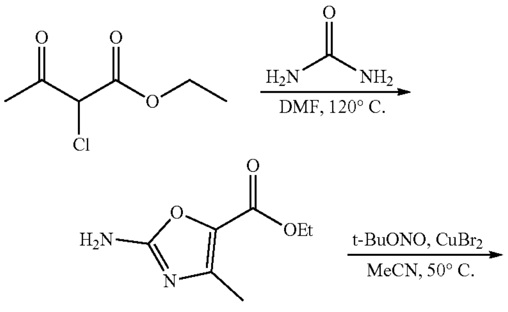

E26

-continued

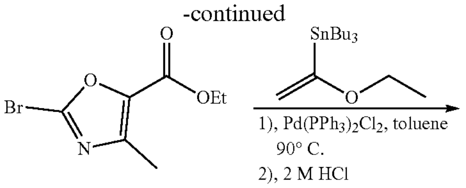

E27

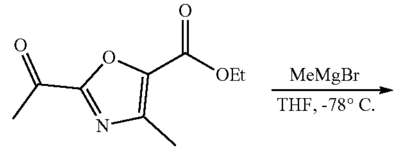

E28

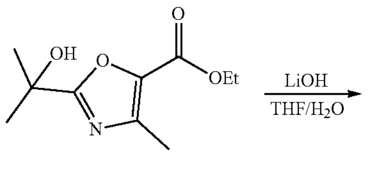

E29

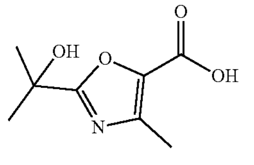

E30

Step 1: Preparation of ethyl 2-amino-4-methyl-oxazole-5-carboxylate (E26)

A mixture of ethyl 2-chloro-3-oxo-butanoate (55 g, 334 mmol, 46.2 mL) and urea (100.34 g, 1.67 mol, 89.6 mL, 5 eq) in DMF (100 mL) was stirred at 120° C. for 12 hours. Reaction progress was checked using TLC (PE:EtOAc=5:1). The reaction mixture was cooled to rt, poured into $H_2O$ (400 ml), and stirred at 0° C. for 30 min. The solid was collected by filtration, rinsed with water (30 mL), and then dried in vacuo to give E26 (22.2 g, 39% yield). $^1H$ NMR (400 MHz, $CD_3OD$) δ 4.29 (q, 2H), 2.32 (s, 3H), 1.35 (t, 3H).

Step 2: Preparation of ethyl 2-bromo-4-methyl-oxazole-5-carboxylate (E27)

To a solution of E26 (11.1 g, 65.2 mmol) in MeCN (120 mL) was added $CuBr_2$ (21.85 g, 97.9 mmol, 4.58 mL, 1.5 eq) at 0° C. The mixture turned dark green and was further stirred for 15 min at rt. t-BuONO (10.09 g, 97.9 mmol, 11.6 mL, 1.5 eq) was added. The reaction was stirred at rt for 2 hrs and then heated at 50° C. for 4 hrs. Reaction progress was checked using TLC (Petroleum ether:EtOAc=3:1). The reaction mixture was concentrated to dryness. The residue was purified by flash silica gel chromatography (ISCO®; 120 g SepaFlash® Silica Flash Column, eluent of 0~5% EtOAc/PE gradient @100 mL/min) to give E27 (8.5 g, 56% yield). $^1H$ NMR (400 MHz, $CDCl_3$) δ 4.25-4.35 (m, 2H), 2.45 (s, 3H), 1.32 (t, 3H).

Step 3: Preparation of ethyl 2-acetyl-4-methyloxazole-5-carboxylate (E28)

A mixture of E27 (9.5 g, 40.6 mmol), tributyl(1-ethoxyvinyl) stannane (17.59 g, 48.7 mmol, 16.4 mL, 1.2 eq) and $Pd(PPh_3)_2Cl_2$ (2.85 g, 4.06 mmol, 0.1 eq) in toluene (200 mL) was stirred at 90° C. for 12 hrs under $N_2$ atmosphere. Reaction progress was checked using TLC (Petroleum ether: EtOAc=5:1). EtOAc (300 ml) was added, followed by sat. KF solution (500 ml). The resulting mixture was stirred at rt for 40 min, the mixture filtered, and the filtrate separated. The organic layer was washed with brine (100 mL), dried over $Na_2SO_4$, filtered, and concentrated to dryness. The residue was dissolved in THF (300 ml), and 4 N HCl (300 ml) was added. The mixture was stirred at rt for 12 hrs. LCMS indicated the desired mass was detected. The reaction mixture was extracted with DCM (100 mL×3). The combined organic layer was dried over $Na_2SO_4$, filtered, and concentrated to dryness. The residue was purified by flash silica gel chromatography (ISCO®; 24 g SepaFlash® Silica Flash Column, eluent of 0~10% EtOAc/PE gradient @35 mL/min) to give E28 (6.8 g, 85% yield). $^1H$ NMR (400 MHz, $CDCl_3$) δ 4.35 (q, 2H), 2.62 (s, 3H), 2.48 (s, 3H), 1.34 (t, 3H); LCMS: m/z 198.1 $(M+H)^+$.

Step 4: Preparation of ethyl 2-(2-hydroxypropan-2-yl)-4-methyloxazole-5-carboxylate (E29)

To a solution of E28 (2.5 g, 12.7 mmol) in THF (25 mL) was added MeMgBr (3 M, 12.7 mL, 3 eq) dropwise under $N_2$ at −78° C. The reaction was stirred at −78° C. for 1.5 hr. Reaction progress was checked using TLC (Petroleum ether: EtOAc=5:1, by UV). The reaction was quenched by the addition of sat. $NH_4Cl$ solution (30 mL) slowly and then the organic portion extracted with EtOAc (30 mL×3). The combined organic phase was washed with brine (30 mL), dried over $Na_2SO_4$, filtered, and concentrated to dryness. The residue was purified by column chromatography ($SiO_2$, Petroleum ether/EtOAc=1/0 to 1/1) to give E29 (1.7 g, 63% yield). $^1H$ NMR (400 MHz, $CDCl_3$) δ 4.39 (q, 2H), 2.47 (s, 3H), 1.67 (s, 6H), 1.40 (t, 3H).

Alternatively, E29 can be prepared by reacting 2-hydroxy-2-methylpropanamide with ethyl 2-chloro-3-oxo-butanoate in a neat reaction at 150° C. for 6 hrs.

Step 5: Preparation of ethyl 2-(2-hydroxypropan-2-yl)-4-methyloxazole-5-carboxylic acid (E30)

To a solution of E29 (3.4 g, 16.0 mmol) in THF (30 mL) and $H_2O$ (15 mL) was added $LiOH·H_2O$ (803 mg, 19.1 mmol, 1.2 eq). The reaction was stirred at rt for 1.5 hr. Reaction progress was tracked using LCMS. The reaction mixture was adjusted to pH 7 with HCl (1 M) and concentrated to dryness to afford E30 (4 g), which was used without further purification. $^1H$ NMR (400 MHz, DMSO-$d_6$) δ 5.67 (s, 1H), 2.30 (s, 2H), 1.44 (s, 6H); LCMS: m/z 186.1 $(M+H)^+$.

Intermediate 4-cyclopropyl-2-(2-hydroxypropan-2-yl)oxazole-5-carboxylic acid according to General Scheme 4

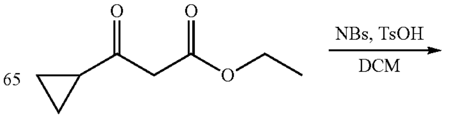

-continued

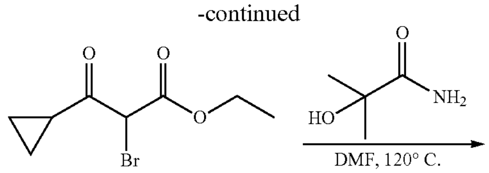

E31

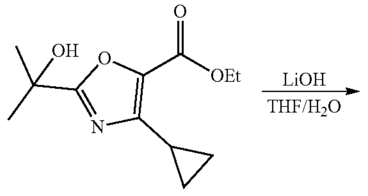

E32

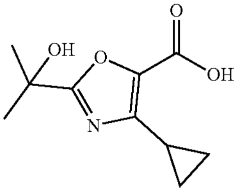

E33

Step 1: Preparation of ethyl 2-bromo-3-cyclopropyl-3-oxo-propanoate (E31)

To a solution of ethyl 3-cyclopropyl-3-oxo-propanoate (8 g, 51.2 mmol) in DCM (100 mL) was added NBS (9.12 g, 51.2 mmol) and TsOH·$H_2O$ (1.95 g, 10.2 mmol, 0.2 eq). The reaction mixture was stirred at rt for 2 hrs. Reaction progress was tracked using TLC (PE:EtOAc=10:1). The reaction mixture was concentrated to dryness. EtOAc (120 mL) was added to the residue, and the mixture filtered. The filtrate was washed with sat. $NaHCO_3$ solution (2×100 mL) and water (100 mL), dried over $Na_2SO_4$, filtered, and concentrated to dryness. The residue was purified by column chromatography ($SiO_2$, PE/EtOAc=1:0 to 10:1) to give E31 (12 g, 100% yield). $^1$H NMR (400 MHz, DMSO-$d_6$) δ 5.71 (s, 1H), 4.18 (q, 2H), 2.14-2.28 (m, 1H), 1.18 (t, 3H), 1.01-1.08 (m, 2H), 0.89-0.96 (m, 2H); LCMS: m/z 235.0 $[M+H]^+$.

Step 2: Preparation of ethyl 4-cyclopropyl-2-(1-hydroxy-1-methyl-ethyl)oxazole-5-carboxylate (E32)

To a solution of ethyl 2-bromo-3-cyclopropyl-3-oxo-propanoate (E31) (1 g, 4.25 mmol) in DMF (2 mL) was added 2-hydroxy-2-methyl-propanamide (2.19 g, 21.3 mmol, 5 eq). The mixture was stirred at 110° C. for 40 hrs. Reaction progress was tracked using LC-MS. The reaction mixture was adjusted to pH-8 by addition of sat. aq. $NaHCO_3$ at 0° C. $H_2O$ (50 mL) was added, and the aqueous portion extracted with EtOAc (3×50 mL). The combined organic layers were dried over $Na_2SO_4$, filtered, and concentrated to dryness. The residue was purified by column chromatography ($SiO_2$, PE/EtOAc=1:0 to 2:1) to give E32 (0.15 g, 14% yield). $^1$H NMR (400 MHz, DMSO-$d_6$) δ 5.70 (s, 1H), 4.29 (q, 2H), 2.40-2.45 (m, 1H), 1.43 (s, 6H), 1.27 (t, 3H), 0.94-1.04 (m, 2H), 0.79-0.92 (m, 2H); LCMS: m/z 240.0 $[M+H]^+$.

Step 3: Preparation of 4-cyclopropyl-2-(1-hydroxy-1-methyl-ethyl)oxazole-5-carboxylic acid (E33)

To a solution of ethyl 4-cyclopropyl-2-(1-hydroxy-1-methyl-ethyl)oxazole-5-carboxylate (E32) (590 mg, 2.47 mmol) in THF (4 mL) and $H_2O$ (4 mL) was added LiOH·$H_2O$ (114 mg, 2.71 mmol, 1.1 eq). The reaction mixture was stirred at rt for 16 hrs. Reaction progress was tracked using LC-MS. The reaction mixture was concentrated to remove THF. The aqueous portion was adjusted to pH-7 by the addition of HCl (1 M) and then lyophilized to give E33 (550 mg, 90% yield). $^1$H NMR (400 MHz, DMSO-$d_6$) δ 2.70-2.84 (m, 1H), 1.39 (s, 6H), 0.62-0.81 (m, 4H); LCMS: m/z 212.0 $[M+H]^+$.

Intermediate 4-cyanooxazole-5-carboxylic acid

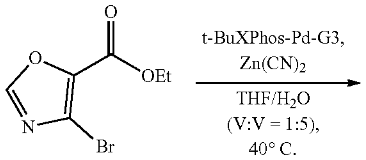

E14

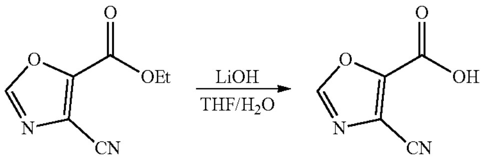

E34 E35

Step 1: Preparation of ethyl 4-cyanooxazole-5-carboxylate (E34)

To a solution of ethyl 4-bromooxazole-5-carboxylate (E14) (10 g, 45.5 mmol) in THF (30 mL) and $H_2O$ (150 mL) was added $Zn(CN)_2$ (3.74 g, 31.8 mmol, 2.02 mL, 0.7 eq) and t-BuXPhos-Pd-G3 (1.81 g, 2.27 mmol, 0.05 eq). The reaction mixture was degassed under vacuum and purged with $N_2$ 3 times, and then the mixture was stirred at 40° C. for 16 hrs under $N_2$. Reaction progress was tracked using TLC (PE:EtOAc=5:1). EtOAc(300 mL) was added to the reaction mixture, and the organic layer washed with $H_2O$ (50 mL) and brine (50 mL), dried over $Na_2SO_4$, filtered, and concentrated to dryness. The residue was purified by column chromatography ($SiO_2$, PE/EtOAc=100/1 to 10/1) to give E34 (7.5 g, 99% yield). $^1$H NMR (400 MHz, DMSO-$d_6$) δ 8.89 (s, 1H), 4.37 (q, 2H), 1.30 (t, 3H).

Step 2: Preparation of (4-cyanooxazole-5-carbonyl)oxylithium (E35)

To a solution of E34 (5 g, 30.1 mmol) in THF (40 mL) and $H_2O$ (80 mL) was added LiOH·$H_2O$ (1.33 g, 31.6 mmol, 1.05 eq). The mixture was stirred at rt for 2 hrs. Reaction progress was tracked using TLC (PE:EtOAc=5:1). The reaction mixture was concentrated in vacuo to remove most of the THF and then lyophilized in vacuo to give E35 (4.5 g), which was used without further purification. $^1$H NMR (400 MHz, DMSO-$d_6$) δ 8.47 (s, 1H).

Intermediate [5-[1-(2,2,2-trifluoroethyl)pyrazol-4-yl]-1,3,4-oxadiazole-2-carbonyl]oxylithium according to General Scheme 9

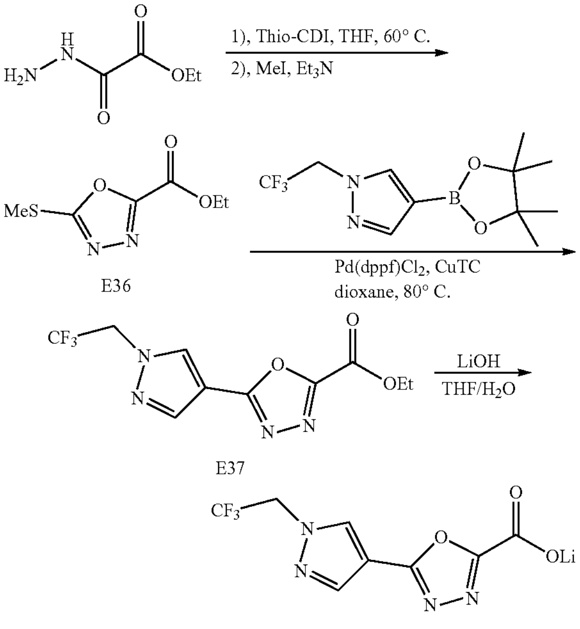

E36

E37

E38

Step 1: Preparation of ethyl 5-methylsulfanyl-1,3,4-oxadiazole-2-carboxylate (E36)

A mixture of ethyl 2-hydrazino-2-oxo-acetate (16 g, 121 mmol) and di(1H-imidazol-1-yl)methanethione (25.90 g, 145 mmol, 1.2 eq) in THF (300 mL) was stirred at rt for 12 hrs, and then heated to 75° C. for 4 hrs. After cooling to rt, $K_2CO_3$ (50.21 g, 363 mmol, 3 eq) and $CH_3I$ (85.95 g, 606 mmol, 37.7 mL, 5 eq) were added. The resulting mixture was stirred at rt for 2 hrs. Reaction progress was tracked using TLC (PE:EtOAc=1:1). The reaction mixture was combined with another reaction performed with 8.5 g of ethyl 2-hydrazino-2-oxo-acetate and quenched by the addition of $H_2O$ (100 mL). DCM (500 mL) was added, and the organic layer was separated and washed with brine (2×100 mL), dried over $Na_2SO_4$, filtered, and concentrated to dryness. The residue was purified by flash silica gel chromatography (Eluent of 0~25% PE:EtOAc @40 mL/min) to give E36 (25 g). $^1H$ NMR (400 MHz, $CDCl_3$) δ 4.43 (q, 2H), 2.72 (s, 3H), 1.38 (t, 3H).

Step 2: Preparation of ethyl 5-[1-(2,2,2-trifluoroethyl)pyrazol-4-yl]-1,3,4-oxadiazole-2-carboxylate (E37)

A mixture of E36 (233 mg, 1.24 mmol), 4-(4,4,5,5-tetramethyl-1,3,2-dioxaborolan-2-yl)-1-(2,2,2-trifluoroethyl)pyrazole (410 mg, 1.49 mmol, 1.2 eq), $Na_2CO_3$ (394 mg, 3.71 mmol, 3 eq), thiophene-2-carbonyloxycopper (472 mg, 2.48 mmol, 2 eq) and $Pd(dppf)Cl_2$ (181 mg, 248 μmol, 0.2 eq) in dioxane (9 mL) was degassed and purged with $N_2$ 3 times, and then the reaction mixture was stirred at 75° C. for 16 hrs under $N_2$. Reaction progress was tracked using TLC (PE:EtOAc=2:1). EtOAc (100 mL) was added to the reaction mixture, and the organic layer washed with water (30 mL) and brine (30 mL), dried over $Na_2SO_4$, filtered, and concentrated to dryness. The residue was purified by column chromatography ($SiO_2$, PE/EtOAc=1/0 to 2/1) to give E37 (140 mg, 39% yield). $^1H$ NMR (400 MHz, $CD_3OD$) δ 8.61 (s, 1H), 8.22 (s, 1H), 5.12 (q, 2H), 4.51 (q, 2H), 1.44 (t, 3H); LCMS: m/z 291.1 $(M+H)^+$.

Step 3: Preparation of [5-[1-(2,2,2-trifluoroethyl)pyrazol-4-yl]-1,3,4-oxadiazole-2-carbonyl]oxylithium (E38)

To a solution of E37 (140 mg, 482 μmol) in THF (1.5 mL) was added $LiOH \cdot H_2O$ (22.3 mg, 531 μmol, 1.1 eq) in $H_2O$ (3 mL). The reaction mixture was stirred at rt for 2 hrs. Reaction progress was tracked using TLC (DCM:MeOH). The reaction mixture was concentrated in vacuo to remove most of the THF and then lyophilized in vacuo to give E38 (115 mg), which was used without further purification. $^1H$ NMR (400 MHz, DMSO-d) δ 8.58 (s, 1H), 8.14 (s, 1H), 5.27 (q, 2H).

Alternatively, ethyl 5-[1-(2,2,2-trifluoroethyl)pyrazol-4-yl]-1,3,4-oxadiazole-2-carboxylate (E37) can be prepared accordingly to the following scheme.

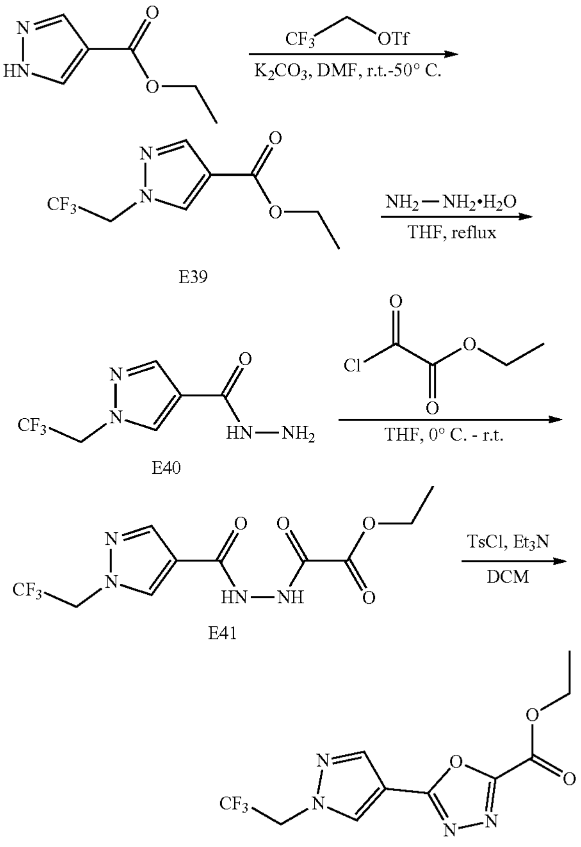

E39

E40

E41

E37

Step A: Preparation of ethyl 1-(2,2,2-trifluoroethyl)pyrazole-4-carboxylate (E39)

To a solution of ethyl 1H-pyrazole-4-carboxylate (10 g, 71.4 mmol) and $K_2CO_3$ (19.72 g, 142 mmol, 2 eq) in DMF (45 mL) was added 2,2,2-trifluoroethyl trifluoromethanesulfonate (21.53 g, 92.8 mmol, 1.3 eq) dropwise, and then the resulting mixture was stirred at 50° C. for 6 hrs. Reaction progress was tracked using TLC (PE:EtOAc=1:1). EtOAc (300 mL) was added to the reaction mixture, and the organic layer washed with $H_2O$ (100 mL) and brine (2×100 mL), dried over $Na_2SO_4$, filtered, and concentrated to dryness. The residue was purified by flash silica gel chromatography (ISCO®; 40 g SepaFlash® Silica Flash Column, eluent of 0~12% PE/EtOAc @60 mL/min) to give E39 (16 g). $^1H$ NMR (400 MHz, $CDCl_3$) δ 8.01 (d, 2H), 4.73 (q, 2H), 4.32 (q, 2H), 1.36 (t, 3H).

Step B: Preparation of 1-(2,2,2-trifluoroethyl)pyrazole-4-carbohydrazide (E40)

To a solution of E39 (16 g, 72.0 mmol) in THF (100 mL) was added $NH_2NH_2{\cdot}H_2O$ (7.73 g, 151 mmol, 7.5 mL, 98% purity, 2.1 eq), and then the reaction mixture was stirred at 80° C. for 15 hrs. Reaction progress was tracked using TLC (PE:EtOAc=1:1). The reaction mixture was concentrated to dryness. The residue was triturated with TBME (50 mL) and stirred for 15 min. The precipitate was collected by filtration, and then dried in vacuo to give E40 (13 g). $^1H$ NMR (400 MHz, $CD_3OD$) δ 8.19 (s, 1H), 7.93 (s, 1H), 4.98 (q, 2H).

Step C: Preparation of ethyl N-[[1-(2,2,2-trifluoroethyl)pyrazole-4-carbonyl]amino]carbamate (E41)

To a solution of E40 (3 g, 14.4 mmol) in THF (70 mL) was added ethyl 2-chloro-2-oxo-acetate (2.36 g, 17.3 mmol, 1.9 mL, 1.2 eq) dropwise at 0° C., and then the reaction mixture was stirred at rt for 3 hrs. The precipitate was collected by filtration and rinsed with TBME (30 mL), and then dried in vacuo to give E41 (1.5 g, 37% yield). $^1H$ NMR (400 MHz, $CDCl_3$) δ 9.75 (br s, 1H), 9.06 (br s, 1H), 8.25 (s, 1H), 7.99 (s, 1H), 4.76 (q, 2H), 4.42 (q, 2H), 1.42 (t, 3H).

Step D: Preparation of ethyl 5-[1-(2,2,2-trifluoroethyl)pyrazol-4-yl]-1,3,4-oxadiazole-2-carboxylate (E37)

To a solution of E41 (1.5 g, 5.35 mmol) and $Et_3N$ (271 mg, 2.68 mmol, 373 μL, 0.5 eq) in DCM (30 mL) was added TsCl (491 mg, 6.96 mmol, 1.3 eq) in portions at 0° C., and then the resulting mixture was stirred at rt for 18 hrs. Reaction progress was tracked using TLC (PE:EtOAc=1:1). DCM (100 mL) was added to the reaction mixture, and the organic layer washed with sat. $Na_2CO_3$ solution (60 mL) and brine (60 mL), dried over $Na_2SO_4$, filtered, and concentrated to dryness. The residue was purified by flash silica gel chromatography (ISCO®; 40 g SepaFlash® Silica Flash Column, Eluent of 0~16% PE/EtOAc @40 mL/min) to give E37 (0.65 g, 42% yield). $^1H$ NMR (400 MHz, $CDCl_3$) δ 8.16-8.29 (m, 2H), 4.80 (q, 2H), 4.53 (q, 2H), 1.47 (t, 3H).

Intermediate lithium 5-morpholino-1,3,4-oxadiazole-2-carboxylate according to General Scheme 10

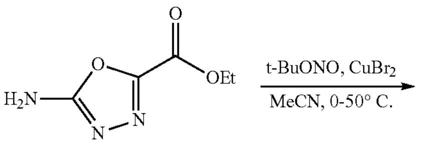

-continued

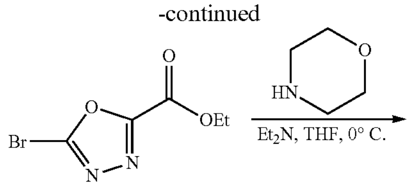

E42

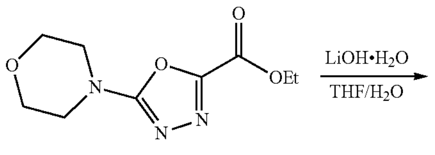

E43

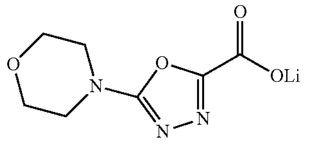

E44

Step 1: Preparation of ethyl 5-bromo-1,3,4-oxadiazole-2-carboxylate (E42)

To a solution of ethyl 5-amino-1,3,4-oxadiazole-2-carboxylate (5 g, 31.8 mmol) in MeCN (60 mL) was added $CuBr_2$ (10.66 g, 47.7 mmol, 2.2 mL, 1.5 eq) at 0° C. The reaction mixture turned dark green and was stirred for 15 min at rt. t-BuONO (4.92 g, 47.7 mmol, 5.7 mL, 1.5 eq) was added at 0° C., and the reaction mixture was stirred at rt for 2 hrs, then heated at 50° C. for another 12 hrs. The reaction progress was checked using TLC (PE/EtOAc=1/1). The reaction mixture was filtered and concentrated to dryness. The residue was purified by flash silica gel chromatography (ISCO®; 40 g SepaFlash® K Silica Flash Column, eluent of 0~50% EtOAc/PE gradient @40 mL/min) to give E42 (4.5 g, 64% yield). $^1H$ NMR (400 MHz, $CDCl_3$) δ 4.52 (q, 2H), 1.45 (t, 3H).

Step 2: Preparation of ethyl 5-morpholino-1,3,4-oxadiazole-2-carboxylate (E43)

To a solution of ethyl 5-bromo-1,3,4-oxadiazole-2-carboxylate (E42) (1 g, 4.52 mmol) and morpholine (473 mg, 5.43 mmol, 478 μL, 1.2 eq) in THF (40 mL) was added DIPEA (1.17 g, 9.05 mmol, 1.6 mL, 2 eq) at 0° C. The mixture was stirred at rt for 1 hr. The reaction progress was checked using TLC (PE/EtOAc=1/1). EtOAc (100 mL) was added to the reaction mixture, and the organic portion washed with water (30 mL) and brine (30 mL×2), dried over $Na_2SO_4$, filtered, and concentrated to dryness. The residue was purified by flash silica gel chromatography (ISCO®; 12 g SepaFlash® Silica Flash Column, Eluent of 0~30% EtOAc/PE gradient @35 mL/min) to give E43 (800 mg, 78% yield). $^1H$ NMR (400 MHz, DMSO-$d_6$) δ 4.37 (q, 2H), 3.68-3.74 (m, 4H), 3.48-3.52 (m, 4H), 1.31 (t, 3H).

Step 3: Preparation of (5-morpholino-1,3,4-oxadiazole-2-carbonyl)oxylithium (E44)

To a solution of ethyl 5-morpholino-1,3,4-oxadiazole-2-carboxylate (E43) (800 mg, 3.52 mmol) in THF (8 mL) and $H_2O$ (12 mL) was added $LiOH{\cdot}H_2O$ (162 mg, 3.87 mmol, 1.1 eq). The reaction mixture was stirred at rt for 12 hrs. The reaction progress was checked using TLC (PE/EtOAc=I/1). The reaction mixture was concentrated to dryness to afford E44 (600 mg), which was used without further purification. $^1H$ NMR (400 MHz, DMSO-$d_6$) δ 3.62-3.74 (m, 4H), 3.36 (br d, 4H).

Intermediate [5-(5-fluoro-2-pyridyl)-1,3,4-oxadiazole-2-carbonyl]oxylithium according to General Scheme 9, Method A

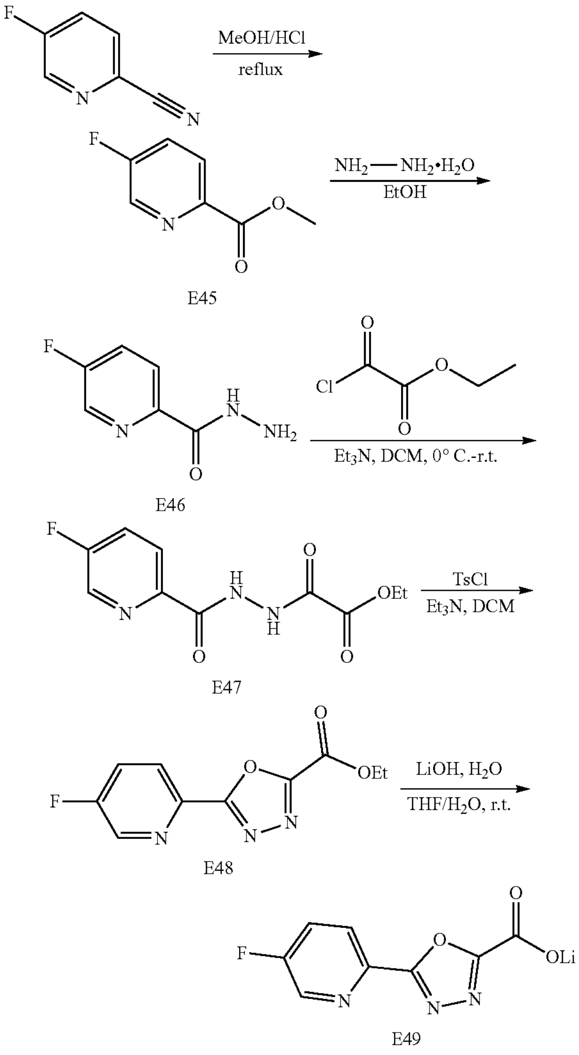

E45

E46

E47

E48

E49

Step 1: Preparation of methyl 5-fluoropyridine-2-carboxylate (E45)

A solution of 5-fluoropyridine-2-carbonitrile (15 g, 123 mmol) in HCl/MeOH (4 M, 180 mL, 5.9 eq) was stirred at 60° C. for 12 hrs. The reaction mixture was concentrated in vacuo, and the residue was dissolved in EtOAc (150 mL), washed with sat. $NaHCO_3$ solution (50 mL) and brine (20 mL). The organic layer was dried over $Na_2SO_4$, filtered, and concentrated to dryness. The residue was purified by flash silica gel chromatography (ISCO®; 80 g SepaFlash® Silica Flash Column, Eluent of 0~25% EtOAc/PE gradient a; 60 mL/min) to give E45 (15.24 g, 80% yield). $^1H$ NMR (400 MHz, $CDCl_3$) δ 8.58 (d, 1H), 8.20 (dd, 1H), 7.53 (ddd, 1H), 4.00 (s, 3H).

Step 2: Preparation of 5-fluoropyridine-2-carbohydrazide (E46)

A mixture of methyl 5-fluoropyridine-2-carboxylate (E45) (16 g, 103 mmol), $NH_2NH_2{\cdot}H_2O$ (11.06 g, 217 mmol, 10.7 mL, 98% purity, 2.1 eq) in EtOH (70 mL) was degassed and purged with $N_2$ for 3 times, and then the reaction mixture was stirred at rt for 3 hrs under $N_2$ atmosphere. The reaction mixture was concentrated to dryness to give E46 (15 g, 94% yield). $^1H$ NMR (400 MHz, DMSO-$d_6$) δ 9.89 (br s, 1H), 8.61 (d, 1H), 8.07 (dd, 1H), 7.88 (td, 1H), 4.57 (br s, 2H).

Step 3: Preparation of ethyl 2-[2-(5-fluoropyridine-2-carbonyl)hydrazino]-2-oxo-acetate (E47)

To a mixture of 5-fluoropyridine-2-carbohydrazide (E46) (13.5 g, 87.0 mmol) and TEA (17.61 g, 174 mmol, 24.2 mL, 2 eq) in DCM (500 mL) was added ethyl 2-chloro-2-oxo-acetate (15.45 g, 113 mmol, 12.7 mL, 1.3 eq) over a period of 10 min at 0° C. The reaction mixture was stirred for 2 hrs at rt. $H_2O$ (100 mL) was added to the reaction mixture, and the aqueous portion extracted with DCM (300 mL×3). The combined organic layer was washed with brine (100 mL), dried over $Na_2SO_4$, filtered, and concentrated to dryness. The residue was purified by flash silica gel chromatography (ISCO®; 80 g SepaFlash® Silica Flash Column, Eluent of 0~2.5% EtOAc/PE gradient @60 mL/min) to give E47 (16 g, 53% yield). $^1H$ NMR (400 MHz, $CDCl_3$) δ 10.03-10.15 (m, 1H), 9.65 (br d, 1H), 8.35-8.42 (m, 1H), 8.11-8.18 (m, 1H), 7.51 (td, 2H), 4.35 (q, 1H), 1.34 (t, 3H); LCMS: m/z 256.2 $[M+H]^+$.

Step 4: Preparation of ethyl 5-(5-fluoro-2-pyridyl)-1,3,4-oxadiazole-2-carboxylate (E48)

To a solution of ethyl 2-[2-(5-fluoropyridine-2-carbonyl) hydrazino]-2-oxo-acetate (E47) (16 g, 62.7 mmol) in DCM (350 mL) was added TEA (8.25 g, 81.5 mmol, 11.3 mL, 1.3 eq) and TosCl (5.98 g, 31.4 mmol, 0.5 eq) in 3 portions at 0° C. The mixture was stirred at rt for 3 hrs. Sat. $NaHCO_3$ solution (200 mL) was added, and the aqueous portion extracted with DCM (400 mL×3). The combined organic layer was washed with brine (200 mL), dried over $Na_2SO_4$, filtered, and concentrated to dryness. The residue was purified by flash silica gel chromatography (ISCO®; 120 g SepaFlash® Silica Flash Column, Eluent of 0~2.5% MeOH/DCM@85 mL/min) to give E48 (8.2 g, 49% yield). $^1H$ NMR (400 MHz, $CDCl_3$) δ 8.71 (d, 1H), 8.39 (dd, 1H), 7.66 (ddd, 1H), 4.59 (q, 2H), 1.51 (t, 3H); LCMS: m/z 238.2 $[M+H]^+$.

Step 5: Preparation of [5-(5-fluoro-2-pyridyl)-1,3,4-oxadiazole-2-carbonyl]oxylithium (E49)

To a solution of ethyl 5-(5-fluoro-2-pyridyl)-1,3,4-oxadiazole-2-carboxylate (E48) (12 g, 50.6 mmol) in THF (140 mL) and $H_2O$ (180 mL) was added $LiOH{\cdot}H_2O$ (2.23 g, 53.1 mmol, 1.05 eq). The mixture was stirred at rt for 2 hrs. The reaction mixture was concentrated in vacuo to remove most of THF, and the aqueous portion was lyophilized in vacuo to give E49 (11.5 g), which was used without further purification. $^1$H NMR (400 MHz, DMSO-$d_6$) δ 8.79 (d, 1H), 8.24 (dd, 1H), 7.99 (td, 1H).

Intermediate 5-(difluoromethyl)-1-(2,2,2-trifluoroethyl)pyrazole-4-carboxylic acid

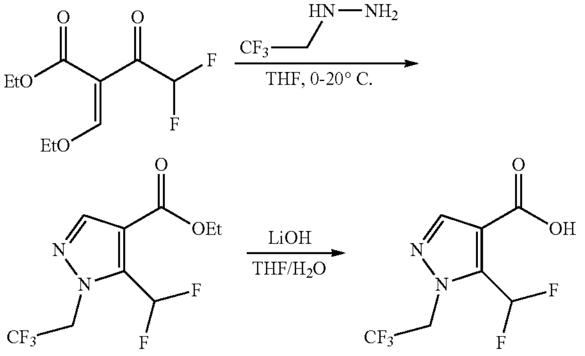

E50

E51

Step 1: Preparation of ethyl 5-(difluoromethyl)-1-(2,2,2-trifluoroethyl)pyrazole-4-carboxylate (E50)

To a solution of (Z)-ethyl 2-(ethoxymethylene)-4,4-difluoro-3-oxobutanoate (1 g, 4.52 mmol) in THF (8 mL) was added 2,2,2-trifluoroethylhydrazine (670 mg, 5.88 mmol, 1.3 eq) dropwise at 0° C. The reaction mixture was stirred at 0° C. for 1 hr, and then stirred at rt for 16 hrs. Reaction progress was checked using LCMS. The reaction mixture was concentrated to dryness, and the residue was purified by flash silica gel chromatography (Eluent: 0~5% EtOAc/PE gradient) to give E50 (850 mg, 69% yield). $^1$H NMR (400 MHz, $CDCl_3$) δ 8.02 (s, 1H), 7.38-7.75 (m, 1H), 4.95 (q, 2H), 4.37 (q, 2H), 1.40 (t, 3H); LCMS: m/z 273.1 $[M+H]^+$.

Step 2: Preparation of 5-(difluoromethyl)-1-(2,2,2-trifluoroethyl)pyrazole-4-carboxylic acid (E51)

To a solution of ethyl 5-(difluoromethyl)-1-(2,2,2-trifluoroethyl)pyrazole-4-carboxylate (E50) (910 mg, 3.34 mmol) in THF (5 mL) and $H_2O$ (5 mL) was added $LiOH{\cdot}H_2O$ (224 mg, 5.35 mmol, 1.6 eq). The mixture was stirred at rt for 2 hrs. The reaction progress was checked using TLC (PE:EtOAc=2:1). The reaction mixture was concentrated to remove THF. The aqueous portion was adjusted to pH-6 by the addition of HCl (1 MV). The resulting precipitate was collected by filtration and then dried in vacuo to give E51 (816 mg, 100% yield). $^1$H NMR (400 MHz, DMSO-$d_6$) δ 8.08 (s, 1H), 7.45-7.78 (m, 1H), 5.30 (q, 2H).

Intermediate ethyl 2-(2-pyridyl)pyrazole-3-carboxylate

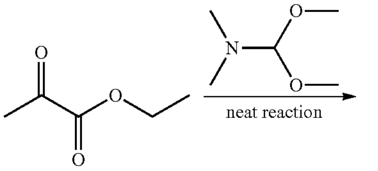

-continued

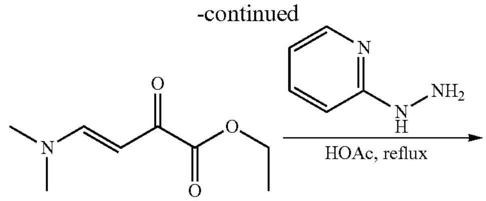

E52

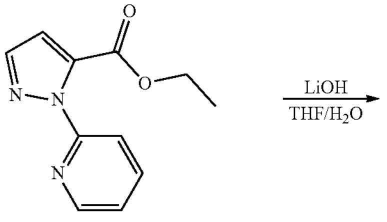

E53

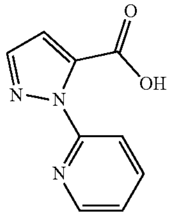

E54

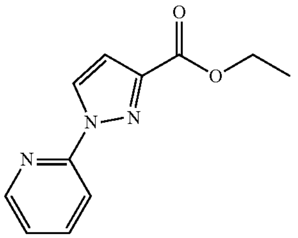

E53a

Step 1: Preparation of ethyl (E)-4-(dimethylamino)-2-oxo-but-3-enoate (E52)

Ethyl 2-oxopropanoate (2 g, 17.2 mmol, 1.9 mL) and 1,1-dimethoxy-N,N-dimethyl-methanamine (2.09 g, 17.6 mmol, 2.3 mL, 1.02 eq) were stirred at rt for 12 hrs. The reaction progress was checked using TLC (PE:EtOAc=10:1). The reaction mixture was concentrated to dryness to give E52 (2.4 g), which was used without further purification.

Step 2: Preparation of ethyl 2-(2-pyridyl)pyrazole-3-carboxylate (E53)

A mixture of ethyl (E)-4-(dimethylamino)-2-oxo-but-3-enoate (E52) (2.4 g, 14.0 mmol) and 2-pyridylhydrazine (1.53 g, 14.0 mmol) in HOAc (100 mL) was stirred at 110° C. for 12 hrs. The reaction progress was checked using TLC (PE:EtOAc=10:1). The reaction mixture was adjusted to pH ~9 by the addition of sat. $Na_2CO_3$ solution. The aqueous portion was extracted with EtOAc (300 mL). The organic layer was dried over $Na_2SO_4$, filtered, and concentrated to dryness. The residue was purified by column chromatography ($SiO_2$, PE/EtOAc=100/1 to 50/1) to give E53 (1.03 g, 34% yield). $^1$H NMR (400 MHz, DMSO-$d_6$) δ 8.48 (dt, 1H), 8.05 (td, 1H), 7.83-7.96 (m, 1H), 7.76 (d, 1H), 7.49 (ddd, 1H), 6.96-7.05 (m, 1H), 4.21 (q, 2H), 1.05-1.23 (m, 3H); LCMS: m/z 218.1 $[M+H]^+$.

Ethyl 1-(2-pyridyl)pyrazole-3-carboxylate (E53a) was also obtained (190 mg, 6% yield). $^1H$ NMR (400 MHz, DMSO-$d_6$) δ 8.70-8.81 (m, 1H), 8.54 (dd, 1H), 7.92-8.13 (m, 2H), 7.47 (ddd, 1H), 7.02 (d, 1H), 4.35 (q, 2H), 1.34 (t, 3H). The regiochemistry of E53 and E53a were confirmed by HSQC and HMBC NMR analysis.

Step 3: Preparation of 2-(2-pyridyl)pyrazole-3-carboxylic acid (E54)

To a solution of ethyl 2-(2-pyridyl)pyrazole-3-carboxylate (E53) (1 g, 4.60 mmol) in THF (10 mL) and $H_2O$ (10 mL) was added LiOH·$H_2O$ (386 mg, 9.21 mmol, 2 eq), and the reaction mixture was stirred at rt for 12 hrs. The reaction progress was checked using TLC (PE/EtOAc=1/I). The reaction mixture was concentrated under reduced pressure to remove THF. The aqueous portion was adjusted to pH-7 by the addition of 2 M HCl and lyophilized in vacuo to give (E54) (1.2 g), which was used without further purification. $^1H$ NMR (400 MHz, DMSO-$d_6$) δ 8.36-8.44 (m, 1H), 7.88 (td, 1H), 7.44-7.53 (m, 2H), 7.35 (ddd, 1H), 6.44 (d, 1H).

Intermediate [5-(difluoromethyl)-2-methyl-1,2,4-triazole-3-carbonyl]oxylithium

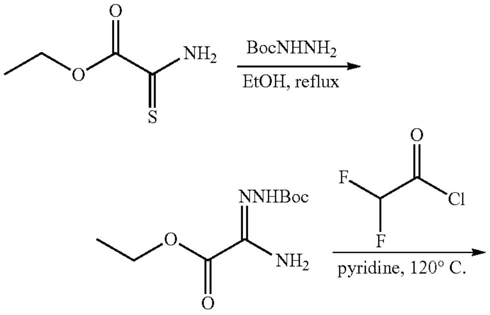

E55

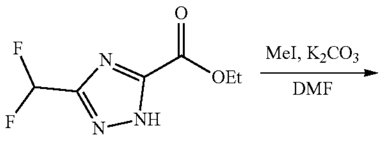

E56

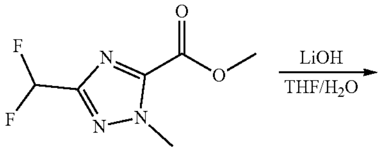

E57

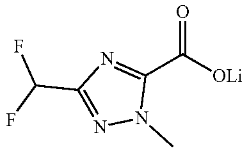

E58

Step 1: Preparation of tert-butyl (Z)-2-(1-amino-2-ethoxy-2-oxoethylidene)hydrazine-1-carboxylate (E55)

Tert-butyl (Z)-2-(1-amino-2-ethoxy-2-oxoethylidene)hydrazine-1-carboxylate was prepared from ethyl 2-amino-2-thioxoacetate following the procedure in Bioorg. Med. Chem., 26 (2016) 3223-3225. The reaction was heated to reflux.

Step 2: Preparation of ethyl 3-(difluoromethyl)-1H-1,2,4-triazole-5-carboxylate (E56)

Reagent 2,2-difluoroacetyl chloride was prepared by adding oxalyl dichloride (18.90 g, 149 mmol, 13.0 mL, 1.1 eq) dropwise at 0° C. to a solution of 2,2-difluoroacetic acid (13 g, 135 mmol, 8.5 mL) and DMF (989 mg, 13.5 mmol, 1.0 mL, 0.1 eq) in DCM (80 mL). The reaction mixture was stirred at rt for 1 hr, and the solution was used without further purification.

To a solution of tert-butyl (Z)-2-(1-amino-2-ethoxy-2-oxoethylidene)hydrazine-1-carboxylate (E55) (13 g, 56.2 mmol) in pyridine (90 mL) was added 2,2-difluoroacetyl chloride (15.47 g, 135 mmol, 2.4 eq). The reaction mixture was heated to 120° C. and stirred for 12 hrs. Reaction progress was checked using LCMS. The reaction mixture was concentrated to dryness. DCM (200 mL) was added to the residue, and the organic portion washed with 1 M HCl (30 mL) and brine (60 mL), dried over $Na_2SO_4$, filtered, and concentrated to dryness. The residue was purified by column chromatography on silica gel (PE:EtOAc=20:1 to 2:1) to give E56 (8.87 g, 83% yield). $^1H$ NMR (400 MHz, DMSO-$d_6$) δ 7.01-7.32 (m, 1H), 4.36 (q, 2H), 1.30 (t, 3H); LCMS: m/z 192.0 $[M+H]^+$.

Step 3: Preparation of ethyl 5-(difluoromethyl)-2-methyl-1,2,4-triazole-3-carboxylate (E57)

To a solution of ethyl 3-(difluoromethyl)-1H-1,2,4-triazole-5-carboxylate (E56) (10 g, 52.3 mmol) in DMF (80 mL) was added MeI (22.28 g, 157 mmol, 9.8 mL, 3 eq) and $K_2CO_3$ (21.69 g, 157 mmol, 3 eq). The mixture was stirred at rt for 12 hrs. Reaction progress was checked using TLC (PE:EtOAc=1:1). The reaction mixture was filtered, and the precipitate was rinsed with EtOAc (150 mL). The filtrate was washed with water (30 mL) and brine (30 mL), dried over $Na_2SO_4$, filtered, and concentrated to dryness. The residue was purified by column chromatography on silica gel (PE:EtOAc=20:1 to 1:1) to give E57 (4.46 g, 42% yield). $^1H$ NMR (400 MHz, DMSO-$d_6$) δ 6.99-7.34 (m, 1H), 4.39 (q, 2H), 4.11-4.22 (m, 3H), 1.35 (t, 3H).

Step 4: Preparation of [5-(difluoromethyl)-2-methyl-1,2,4-triazole-3-carbonyl]oxylithium (E58)

To a solution of ethyl 5-(difluoromethyl)-2-methyl-1,2,4-triazole-3-carboxylate (E57) (2.35 g, 11.5 mmol) in THF (40 mL) and $H_2O$ (10 mL) was added LiOH·$H_2O$ (505 mg, 12.0 mmol, 1.05 eq). The reaction mixture was stirred at rt for 1 hr. Reaction progress was checked using TLC (PE:EtOAc=2:1). The reaction mixture was concentrated in vacuo to remove THF. $H_2O$ (20 mL) was added, and the aqueous portion extracted with TBME (20 mL), and then lyophilized in vacuo to give E58 (2.15 g), which was used without further purification. $^1H$ NMR (400 MHz, DMSO-$d_6$) δ 6.75-7.21 (m, 1H), 4.09 (s, 3H).

Intermediate ethyl 3-(1-hydroxy-1-methyl-ethyl)-1,2,4-oxadiazole-5-carboxylate

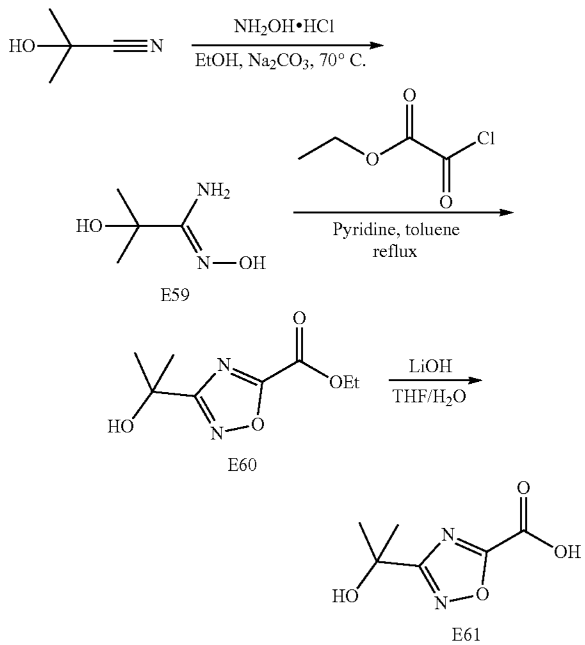

E59

E60

E61

Step 1: Preparation of N',2-dihydroxy-2-methyl-propenamidine (E59)

To a solution of 2-hydroxy-2-methyl-propanenitrile (2.14 g, 25.2 mmol, 2.3 mL) in EtOH (20 mL) was added hydroxylamino hydrochloride (3.49 g, 50.3 mmol, 2 eq) and $Na_2CO_3$ (5.33 g, 50.3 mmol, 2 eq), and then the reaction was stirred at 70° C. for 16 hrs. The reaction mixture was concentrated to dryness. EtOAc (200 mL) was added to the residue, and the organic portion washed twice with water (50 mL) and brine (50 mL), dried over $Na_2SO_4$, filtered, and concentrated to dryness to afford E59 (1 g), which was used without further purification. $^1H$ NMR (400 MHz, DMSO-$d_6$) δ 10.11 (s, 1H), 8.86 (s, 1H), 5.03 (br s, 1H), 1.70 (s, 3H), 1.66 (s, 3H).

Step 2: Preparation of ethyl 3-(1-hydroxy-1-methyl-ethyl)-1,2,4-oxadiazole-5-carboxylate (E60)

To a solution of N',2-dihydroxy-2-methyl-propanamidine (E59) (520 mg, 4.40 mmol) and pyridine (696 mg, 8.80 mmol, 711 μL, 2 eq) in toluene (15 mL) was added ethyl 2-chloro-2-oxo-acetate (601 mg, 4.40 mmol, 493 μL) at 0° C. The reaction mixture was stirred at rt for 1 hr, and then stirred at 100° C. for 15 hrs. Reaction progress was checked using LCMS. The reaction mixture was concentrated to dryness. The residue was purified by column chromatography ($SiO_2$, PE/EtOAc=1/0 to 2/1) and further purified by prep-HPLC (column: Boston Uni C18 40*150*5 um; mobile phase: [water(0.225% FA)-ACN]; B %: 16%-46%, 7.7 min) to give E60 (250 mg, 28% yield). $^1H$ NMR (400 MHz, $CDCl_3$) δ 4.52 (q, 2H), 2.65 (br s, 1H), 1.67 (s, 6H), 1.45 (t, 3H); LCMS: m/z 201.1 $[M+H]^+$.

Step 3: Preparation of ethyl 3-(1-hydroxy-1-methyl-ethyl)-1,2,4-oxadiazole-5-carboxylate (E61)

To a solution of ethyl 3-(1-hydroxy-1-methyl-ethyl)-1,2,4-oxadiazole-5-carboxylate (E60) (200 mg, 999 μmol) in THF (5 mL) and $H_2O$ (5 mL) was added $LiOH·H_2O$ (41.9 mg, 999 μmol), and then the reaction mixture was stirred at rt for 1 hr. The solvent was removed in vacuo, and the aqueous portion was lyophilized in vacuo to give E61 (170 mg), which was used without further purification.

Intermediates E62, E63, E64, E65, E66, and E67

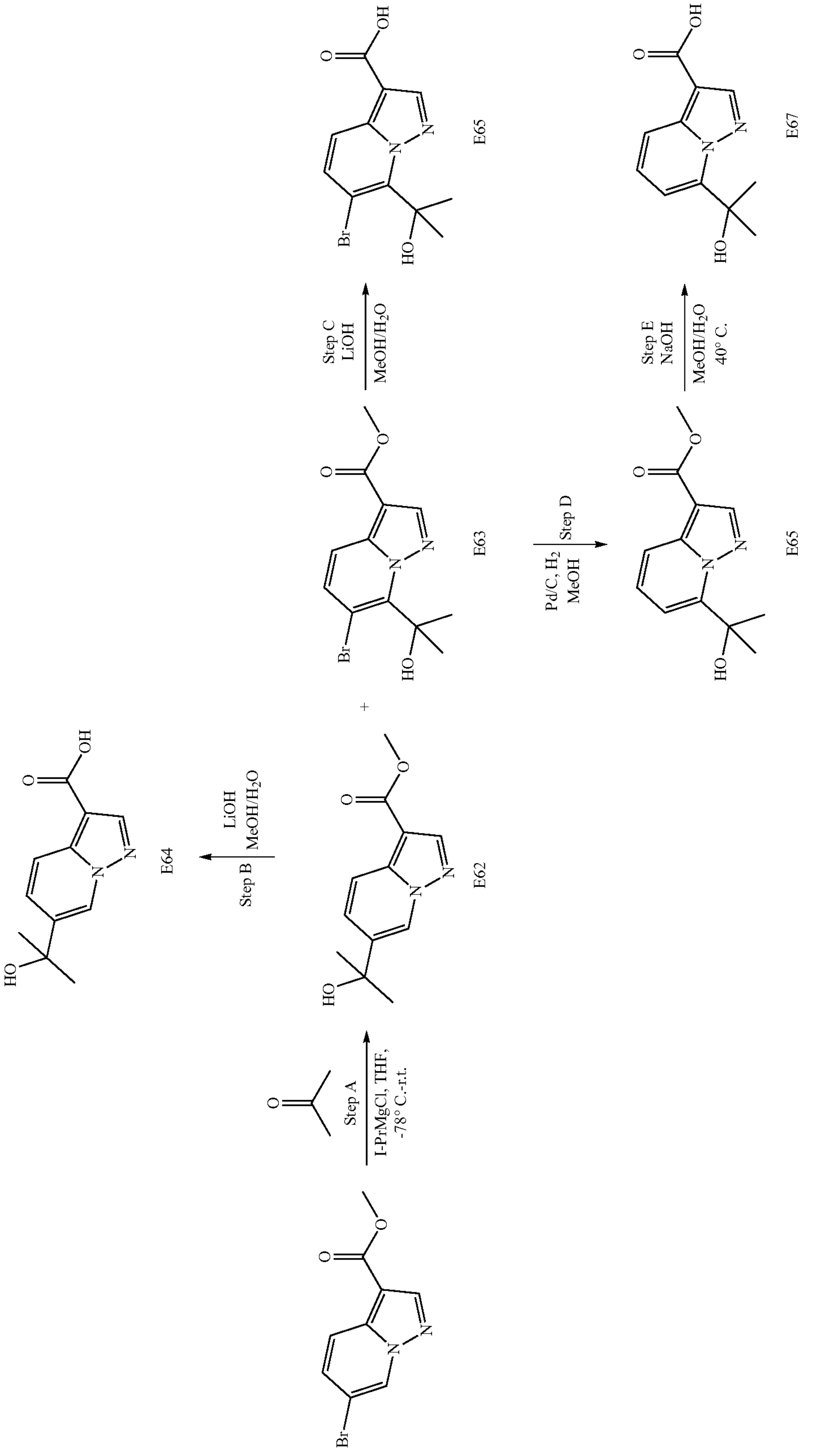
E62
E63
E64
E65
E65
E67

Step A: Preparation of methyl 6-(2-hydroxypropan-2-yl)pyrazolo[1,5-a]pyridine-3-carboxylate (E62) and methyl 6-bromo-7-(2-hydroxypropan-2-yl)pyrazolo[1,5-a]pyridine-3-carboxylate (E63)

To a solution of methyl 6-bromopyrazolo[1,5-a]pyridine-3-carboxylate (1 g, 3.92 mmol) in THF (10 mL) was added i-PrMgCl—LiCl (1.3 M, 6.03 mL, 2 eq) at −78° C. The reaction mixture was stirred at −78° C. for 15 min, then acetone (1.37 g, 23.5 mmol, 1.7 mL, 6 eq) was added dropwise to the reaction mixture. The reaction mixture was stirred at ~78° C. for 1 hr. Reaction progress was checked using LCMS. The reaction mixture was dropwise added to 10 mL of aq. $NH_4Cl$ solution. Water (30 mL) was added, and the aqueous portion extracted with EtOAc (25 mL×2). The combined organic layers were washed with brine (20 mL), dried over $Na_2SO_4$, filtered, and concentrated to dryness. The residue was purified by column chromatography ($SiO_2$, PE/EtOAc=1/0 to 20:1) to give E62 (320 mg, 34% yield) and E63 (300 mg, 23% yield).

E62: $^1$H NMR (400 MHz, $CD_3OD$) δ 8.40-8.54 (m, 1H), 8.14 (dd, 1H), 7.57 (dd, 1H), 7.27 (dd, 1H), 3.88-4.03 (m, 3H), 1.77-1.92 (m, 6H); LCMS: m/z 235.2 $[M+H]^+$.

E63: $^1$H NMR (400 MHz, $CD_3OD$) δ 8.46 (s, 1H), 8.02 (d, 1H), 7.76 (d, 1H), 3.93 (s, 3H), 1.95 (s, 6H); LCMS' m/z 313.0 $[M+H]^+$.

Step B: Preparation of 6-(2-hydroxypropan-2-yl)pyrazolo[1,5-a]pyridine-3-carboxylic acid (E64)

To a solution of methyl 6-(1-hydroxy-1-methyl-ethyl)pyrazolo[1,5-a]pyridine-3-carboxylate (E62) (50) mg, 2.13 mmol) in MeOH (3 mL) and $H_2O$ (1 mL) was added $LiOH{\cdot}H_2O$ (116 mg, 2.77 mmol, 1.3 eq). The reaction mixture was stirred at 40° C. for 12 hrs. Reaction progress was checked using LCMS. The reaction mixture was concentrated in vacuo to remove MeOH, and water (50 mL) was added. The aqueous portion was extracted with TBME (30 mL), and the aqueous layer was then adjusted to pH ~6 by the addition of 0.5 M HCl. The resulting suspension was extracted with DCM/MeOH (100/10 mL) 3 times. The combined DCM/MeOH organic layer was dried over $Na_2SO_4$, filtered, and concentrated to dryness to afford E64 (420 mg, 89% yield). LCMS: m/z 221.1 $[M+H]^+$.

Step C: Preparation of 6-bromo-7-(2-hydroxypropan-2-yl)pyrazolo[1,5-a]pyridine-3-carboxylic acid (E65)

To a solution of methyl 6-bromo-7-(2-hydroxypropan-2-yl)pyrazolo[1,5-a]pyridine-3-carboxylate (E63) (120 mg, 383 μmol) in MeOH (2 mL) and $H_2O$ (1 mL) was added $LiOH{\cdot}H_2O$ (17.69 mg, 422 μmol, 1.1 eq), the mixture was stirred at 40° C. for 12 hr. Reaction progress was checked using LCMS. The reaction mixture was concentrated in vacuo to remove MeOH, and water (10 mL) was added. The aqueous portion was extracted with TBME (30 mL) and was then adjusted to pH ~6 by the addition of 0.5 M HCl. The resulting suspension was extracted with DCM/MeOH (30/3 mL) 3 times. The combined DCM/MeOH organic layer was dried over $Na_2SO_4$, filtered, and concentrated to dryness to afford E65 (100 mg, 87% yield). $^1$H NMR (400 MHz, $CD_3OD$) δ 8.44 (s, 1H), 8.07 (d, 1H), 7.74 (d, 1H), 1.96 (s, 6H); LCMS: m/z 301.1 $[M+H]^+$.

Step D: Preparation of methyl 7-(2-hydroxypropan-2-yl)pyrazolo[1,5-a]pyridine-3-carboxylate (E66)

To a solution of methyl 6-bromo-7-(2-hydroxypropan-2-yl)pyrazolo[1,5-a]pyridine-3-carboxylate (E63) (450 mg, 1.44 mmol) in MeOH (10 mL) was added Pd/C (100 mg, 10% purity) under $N_2$. The resulting mixture was degassed under vacuum and purged with $H_2$ 3 times, and then the mixture was stirred at rt for 1 hr under $H_2$ (15 psi). Reaction progress was checked using LCMS. The reaction mixture was filtered through a pad of Celite, and the filtrate was concentrated in vacuo to afford E66 (350 mg), which was used without further purification. LCMS: m/z 234.9 $[M+H]^+$.

Step E: Preparation of 7-(2-hydroxypropan-2-yl)pyrazolo[1,5-a]pyridine-3-carboxylic acid (E67)

To a solution of methyl 7-(2-hydroxypropan-2-yl)pyrazolo[1,5-a]pyridine-3-carboxylate (E66) (350 mg, 1.49 mmol) in MeOH (5 mL) and $H_2O$ (1 mL) was added NaOH (89.64 mg, 2.24 mmol, 1.5 eq), the mixture was stirred at 40° C. for 12 hrs. Reaction progress was checked using LCMS. The reaction mixture was concentrated in vacuo to remove MeOH, and water (10 mL) was added. The aqueous portion was extracted with TBME (30 mL), and then adjusted to pH ~6 by the addition of 0.5 M HCl. The resulting suspension was extracted with DCM/MeOH (30/3 mL) 3 times. The combined DCM/MeOH organic layer was dried over $Na_2SO_4$, filtered, and concentrated to dryness to afford E67 (320 mg), which was used without further purification. LCMS: m/z 220.9 $[M+H]^+$.

Intermediate E72 According to General Scheme 7, Methods C and D

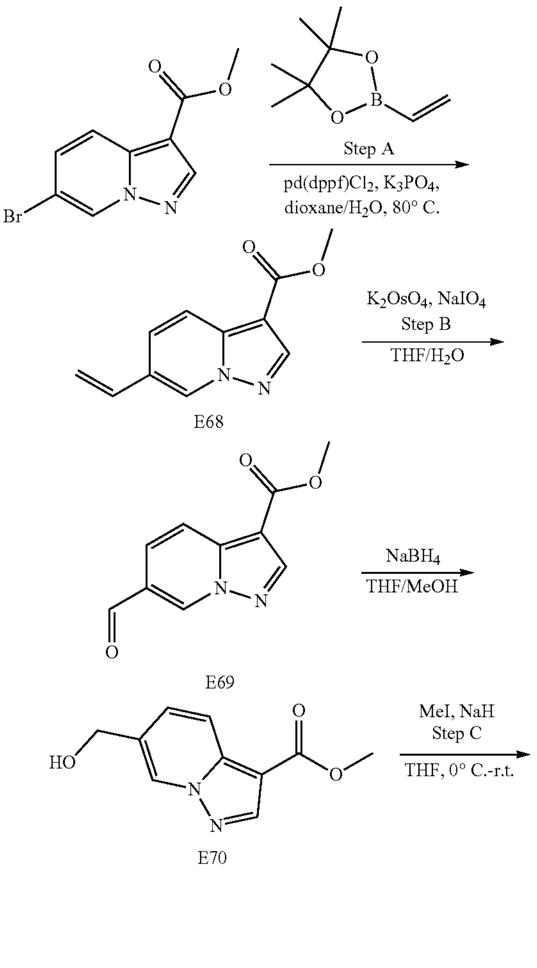

E68
E69
E70

-continued

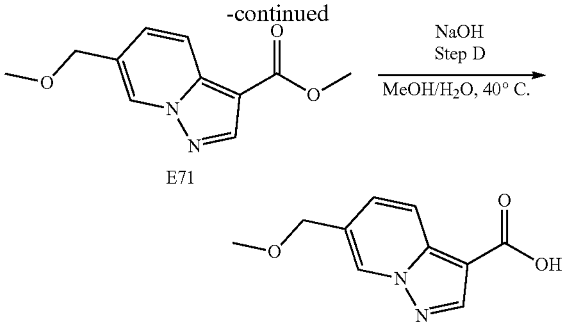

E71

E72

Step A: Preparation of methyl 6-vinylpyrazolo[1,5-a]pyridine-3-carboxylate (E68)

A mixture of 4,4,5,5-tetramethyl-2-vinyl-1,3,2-dioxaborolane (8.15 g, 52.9 mmol, 8.98 mL), methyl 6-bromopyrazolo[1,5-a]pyridine-3-carboxylate (9 g, 35.3 mmol), $K_3PO_4$ (22.47 g, 106 mmol) and Pd(dppf)$Cl_2$ (1.29 g, 1.76 mmol) in dioxane (80 mL) and $H_2O$ (40 mL) was stirred at 80° C. for 12 hrs under $N_2$. Reaction progress was checked using LCMS. The reaction mixture was combined with another 1 g batch reaction, and DCM (200 mL) was added. The organic layer was washed with brine (2×80 mL), dried over $Na_2SO_4$, filtered, and concentrated to dryness. The residue was purified by column chromatography ($SiO_2$, PE/EtOAc=1/0 to 4/1) to give E68 (6.4 g, 80.2% yield). $^1$H NMR (400 MHz, $CDCl_3$) δ 8.37 (s, 1H), 8.30 (s, 1H), 8.03 (d, 1H), 7.52 (dd, 1H), 6.61 (dd, 1H), 5.76 (d, 1H), 5.34 (d, 1H), 3.84 (s, 3H); LCMS: m/z 203.1 $[M+H]^+$.

Step B: Preparation of methyl 6-formylpyrazolo[1,5-a]pyridine-3-carboxylate (E69)

To a solution of methyl 6-vinylpyrazolo[1,5-a]pyridine-3-carboxylate (E68) (6.4 g, 31.7 mmol) in THF (80 mL) and $H_2O$ (80 mL) was added $K_2OsO_4 \cdot 2H_2O$ (583 mg, 1.58 mmol) and $NaIO_4$ (16.92 g, 79.1 mmol, 4.38 mL) at 0° C., and then the reaction mixture was stirred at rt for 12 hrs. Reaction progress was checked using LCMS. DCM (200 mL) was added to the reaction mixture, and the organic layer was washed with brine (2×80 mL), dried over $Na_2SO_4$, filtered, and concentrated to dryness. The residue was purified by column chromatography ($SiO_2$, DCM/EtOAc=1/0 to 6/1) to give E69 (5.9 g, 91.3% yield). $^1$H NMR (400 MHz, $CDCl_3$) δ 9.94 (s, 1H), 8.90-8.98 (m, 1H), 8.48 (s, 1H), 8.18 (d, 1H), 7.80 (dd, 1H), 3.88 (s, 3H); LCMS: m/z 204.9 $[M+H]^+$.

Step C: Preparation of methyl 6-(hydroxymethyl)pyrazolo[1,5-a]pyridine-3-carboxylate (E70)

To a solution of methyl 6-formylpyrazolo[1,5-a]pyridine-3-carboxylate (E69) (2.4 g, 11.8 mmol) in THF (30 mL) and MeOH (30 mL) was added $NaBH_4$ (1.78 g, 47.0 mmol) at 0° C., and then the reaction mixture was stirred at rt for 1 hr. Reaction progress was checked using LCMS. The reaction mixture was quenched by the addition of sat. aq. $NH_4Cl$ (50 mL), and the aqueous portion extracted with EtOAc (100 mL). The organic layer was washed with water (50 mL) and brine (40 mL), dried over $Na_2SO_4$, filtered, and concentrated to dryness to give E70 (2.3 g, 94.9% yield). $^1$H NMR (400 MHz, $CDCl_3$) δ 8.54 (s, 1H), 8.38 (s, 1H), 8.11 (d, 1H), 7.41 (dd, 1H), 4.78 (s, 2H), 3.93 (s, 3H); LCMS: m/z 207.0 $[M+H]^+$.

Step D: Preparation of methyl 6-(methoxymethyl)pyrazolo[1,5-a]pyridine-3-carboxylate (E71)

To a solution of methyl 6-(hydroxymethyl)pyrazolo[1,5-a]pyridine-3-carboxylate (E70) (2.2 g, 10.7 mmol) in THF (50 mL) was added NaH (512 mg, 12.8 mmol, 60% purity) at 0° C. The reaction mixture was stirred at 0° C. for 15 min, and then MeI (1.82 g, 12.8 mmol, 797 μL) was added to the reaction mixture. The reaction mixture was stirred at rt for 1 hr, and reaction progress was checked using LCMS. The reaction mixture was quenched by the addition of sat. aq. $NH_4Cl$ (40 mL), and the aqueous portion extracted with DCM (2×60 mL). The combined organic layer was washed by water (30 mL) and brine (30 mL), dried over $Na_2SO_4$, filtered, and concentrated to dryness. The residue was purified by column chromatography ($SiO_2$, PE/EtOAc=1/0 to 5/1) to give E71 (1.8 g, 76.6% yield). $^1$H NMR (400 MHz, $CDCl_3$) δ 8.52 (s, 1H), 8.41 (s, 1H), 8.16 (d, 1H), 7.42 (dd, 1H), 4.53 (s, 2H), 3.94 (s, 3H), 3.46 (s, 3H); LCMS: m/z 221.1 $[M+H]^+$.

Step E: Preparation of 6-(methoxymethyl)pyrazolo[1,5-a]pyridine-3-carboxylic acid (E72)

To a solution of methyl 6-(methoxymethyl)pyrazolo[1,5-a]pyridine-3-carboxylate (E71) (1.8 g, 8.17 mmol) in MeOH (40 mL) and $H_2O$ (40 mL) was added NaOH (719 mg, 18.0 mmol), and the reaction mixture was stirred at 40° C. for 12 hrs. Reaction progress was checked using LCMS. The reaction mixture was concentrated to remove MeOH, and then $H_2O$ (10 mL) was added. The pH of the aqueous mixture was adjusted to ~6 by the addition of 0.5 M HCl, and the aqueous mixture was filtered. The precipitate was dried in vacuo to give E72 (1.6 g, 94.9% yield). $^1$H NMR (400 MHz, $CDCl_3$) δ 8.57 (s, 1H), 8.45-8.51 (m, 1H), 8.21 (d, 1H), 7.48 (dd, 1H), 4.55 (s, 2H), 3.48 (s, 3H); LCMS: m/z 206.7 $[M+H]^+$.

Intermediate E78 according to General Scheme 9, Method A

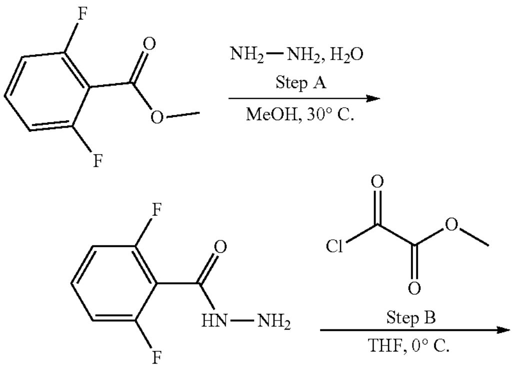

E73

-continued

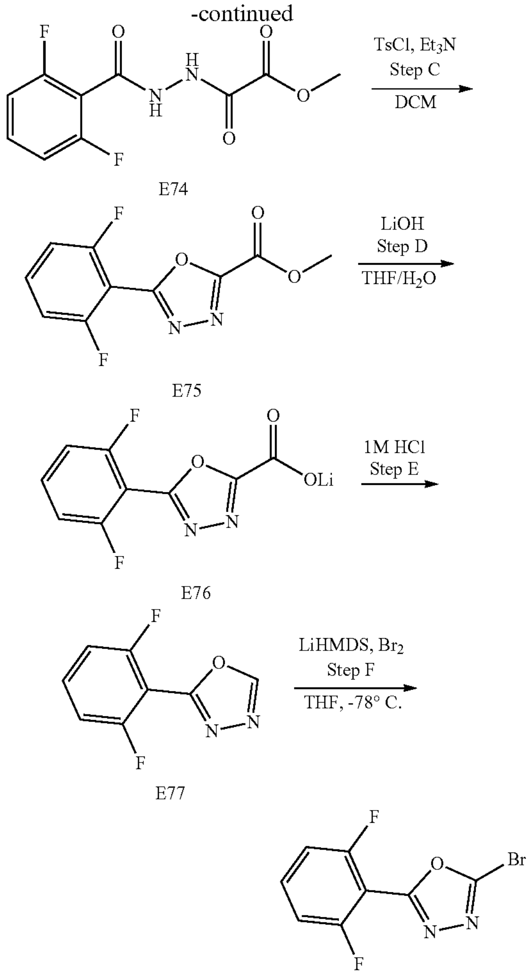

E74

E75

E76

E77

E78

Step A: Preparation of 2,6-difluorobenzohydrazide (E73)

To a solution of methyl 2,6-difluorobenzoate (25 g, 145 mmol) in MeOH (250 mL) was added $NH_2NH_2{\cdot}H_2O$ (18.18 g, 363 mmol, 17.7 mL), and the reaction mixture was stirred at 60° C. for 12 hrs. Reaction progress was checked using TLC. Additional $NH_2NH_2{\cdot}H_2O$ (7.27 g, 145 mmol, 7.05 mL) was added, and the reaction mixture was stirred at 60° C. for another 3 hrs. The reaction mixture was concentrated in vacuo to give E73 (25 g), which was used without further purification. $^1H$ NMR (400 MHz, $CDCl_3$) δ 7.37 (s, 1H), 6.93 (t, 2H), 3.45-3.89 (m, 2H).

Step B: Preparation of methyl 2-[2-(2,6-difluorobenzoyl)hydrazino]-2-oxo-acetate (E74)

To a solution of 2,6-difluorobenzohydrazide (E73) (25 g, 145 mmol) in THF (250 mL) was added methyl 2-chloro-2-oxo-acetate (19.57 g, 160 mmol, 14.7 mL) at 0° C., and the reaction mixture was stirred at 0° C. for 1 hr. Reaction progress was checked using TLC. The reaction mixture was filtered. The precipitate was washed with MTBE (800 mL), and then dried in vacuo to give E74 (37 g). $^1H$ NMR (400 MHz, DMSO-$d_6$) δ 7.59 (ddd, 2H), 7.21 (t, 1H), 3.83 (s, 2H).

Step C: Preparation of methyl 5-(2,6-difluorophenyl)-1,3,4-oxadiazole-2-carboxylate (E75)

To a solution of methyl 2-[2-(2,6-difluorobenzoyl)hydrazino]-2-oxo-acetate (E74) (15 g, 58.1 mmol) in DCM (250 mL) was added $Et_3N$ (23.52 g, 232 mmol, 32.4 mL) and TosCl (14.40 g, 75.5 mmol) in portions at 0° C. The reaction mixture was allowed to warm to rt and stirred at rt for 12 hrs. Reaction progress was checked using TLC. DCM (100 mL) was added to the reaction mixture, and the organic layer was washed with sat. aq. $NaHCO_3$ (100 mL) and water (100 mL), dried over $Na_2SO_4$, filtered, and concentrated to dryness. The residue was purified by column chromatography ($SiO_2$, PE/EtOAc=1/0 to 1/1) to give E75 (4.3 g, 30.8% yield). $^1H$ NMR (400 MHz, $CDCl_3$) δ 7.61 (tt, 1H), 7.14 (t, 2H), 4.10 (s, 3H).

Step D: Preparation of 5-(2,6-difluorophenyl)-1,3,4-oxadiazole-2-carboxylic acid (E76)

To a solution of methyl 5-(2,6-difluorophenyl)-1,3,4-oxadiazole-2-carboxylate (E75) (300 mg, 1.25 mmol) in $H_2O$ (2 mL) and THF (4 mL) was added $LiOH{\cdot}H_2O$ (52.4 mg, 1.25 mmol). The reaction mixture was stirred at rt for 1 hr. Reaction progress was checked using LCMS. The reaction mixture was concentrated in vacuo to give E76 (300 mg), which was used without further purification. LCMS: m/z 226.8 $[M+H]^+$ Step E: Preparation of 2-(2,6-difluorophenyl)-1,3,4-oxadiazole (E77)

To a solution of 5-(2,6-difluorophenyl)-1,3,4-oxadiazole-2-carboxylic acid (E76) (4 g, 17.7 mmol) in $H_2O$ (20 mL) was added HCl (1 M, 35.4 mL), and the reaction mixture was stirred at rt for 1 hr. Reaction progress was checked using LCMS and TLC. DCM (60 mL) was added to the reaction mixture, and the organic layer washed by water (20 mL), dried over $Na_2SO_4$, filtered, and concentrated to dryness. The residue was purified by column chromatography ($SiO_2$, PE/EtOAc=1/0 to 1/1) to give E77 (1.5 g, 46.6% yield). $^1H$ NMR (400 MHz, $CDCl_3$) δ 8.63 (s, 1H), 7.57 (tt, 1H), 7.12 (t, 2H); LCMS: m/z 182.8 $[M+H]^+$.

Step F: Preparation of 2-bromo-5-(2,6-difluorophenyl)-1,3,4-oxadiazole (E78)

To a solution of 2-(2,6-difluorophenyl)-1,3,4-oxadiazole (E77) (1.5 g, 8.24 mmol) in THF (50 mL) was added LiHMDS (1 M, 16.5 mL) dropwise at −78° C. The reaction mixture was stirred at −78° C. for 30 min, then $Br_2$ (2.63 g, 16.5 mmol, 849 μL) was added to the reaction mixture at −78° C. dropwise. The reaction mixture was stirred at −78° C. for 2 hrs. Reaction progress was checked using TLC. Sat. aq. $NH_4Cl$ (100 mL) was added to the reaction mixture, and the aqueous portion extracted with DCM (3×50 mL). The combined organic layer was washed with brine (40 mL), dried over $Na_2SO_4$, filtered and concentrated to dryness. The residue was purified by column chromatography ($SiO_2$, PE/EtOAc=1/0 to 3/1) to give E78 (1.6 g, 54.2% yield). $^1H$ NMR (400 MHz, DMSO-$d_6$) δ 7.79 (tt, 1H), 7.41 (t, 2H); LCMS: m/z 341.2 $[M+H]^+$.

Preparation of Examples 640 and 641 according to General Scheme 1, Method C

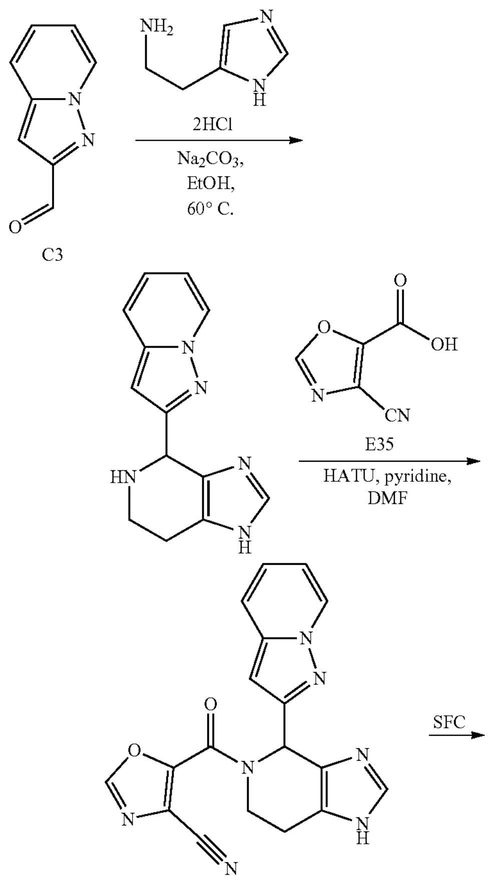

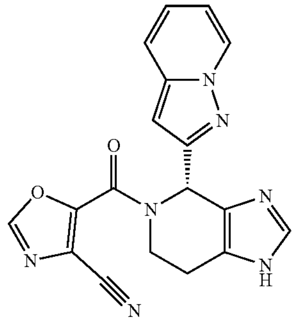

Example 640

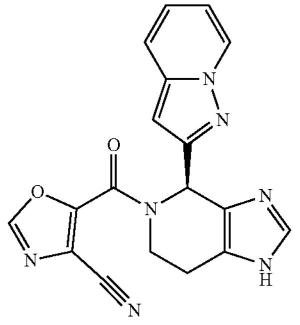

Example 641

Step 1: Preparation of 4-(pyrazolo[1,5-a]pyridin-2-yl)-4,5,6,7-tetrahydro-1H-imidazo[4,5-c]pyridine A mixture of pyrazolo[1,5-a]pyridine-2-carbaldehyde (C3) (9.2 g, 63.0 mmol), 2-(1H-imidazol-5-yl)ethanamine (15.06 g, 81.8 nmol, 1.3 eq, 2HCl salt) and $K_2CO_3$ (17.40 g, 126 mmol, 2 eq) in EtOH (300 mL) was stirred at 80° C. for 16 hrs under $N_2$. Reaction progress was checked using LCMS. The reaction mixture was combined with another reaction mixture performed using 5 g of C3 and filtered, and the filtrate was concentrated to dryness. The residue was purified by column chromatography on silica gel (DCM: MeOH=20:1 to 10:1) to give 4-pyrazolo[1,5-a]pyridin-2-yl-4,5,6,7-tetrahydro-1H-imidazo[4,5-c]pyridine (11.4 g). $^1$H NMR (400 MH-z, $CD_3OD$) δ 8.48 (d, 1H), 7.54-7.62 (m, 2H), 7.09-7.29 (m, 1H), 6.82-6.90 (m, 1H), 6.44 (s, 1H), 5.28 (s, 1H), 3.28 (dt, 1H), 3.04-3.12 (m, 1H), 2.73-2.80 (m, 2H); LC-MS: m/z 240.2 $(M+H)^+$.

Step 2: Preparation of 5-(4-pyrazolo[1,5-a]pyridin-2-yl-1,4,6,7-tetrahydroimidazo[4,5-c]pyridine-5-carbonyl)oxazole-4-carbonitrile To a solution of 4-pyrazolo[1,5-a]pyridin-2-yl-4,5,6,7-tetrahydro-1H-imidazo[4,5-c]pyridine (4 g, 16.7 mmol) and (4-cyanooxazole-5-carbonyl)oxylithiumn (E35) (3.37 g, 23.4 mmol, 1.4 eq) in DMF (90 mL) was added HATU (7.63 g, 20.1 mmol, 1.2 eq) and pyridine (3.97 g, 50.2 mmol, 4.1 mL, 3 eq). The reaction mixture was stirred at rt for 2 hrs. Reaction progress was checked using LCMS, and the reaction mixture was stirred at rt for another 12 hrs. Reaction progress was checked using TLC (DCM:MeOH=10:1). DCM (300 mL) was added, and the organic portion was washed with sat. $NaHCO_3$ solution (100 mL) and brine (100 mL), dried over $Na_2SO_4$, filtered, and concentrated to dryness. The residue was purified by flash silica gel chromatography (ISCO®; 40 g SepaFlash® Silica Flash Column, Eluent of 0~8.5% MeOH/DCM @35 mL/min) to give 5-(4-pyrazolo[1,5-a]pyridin-2-yl-1,4,6,7-tetrahydroimidazo[4,5-c]pyridine-5-carbonyl)oxazole-4-carbonitrile (2.6 g). $^1$H NMR (400 MHz, $CD_3OD$) δ 8.51 (s, 1H), 8.46 (d, 1H), 7.69 (s, 1H), 7.57-7.65 (m, 1H), 7.17-7.23 (m, 1H), 6.83-6.91 (m, 2H), 6.59-6.72 (m, 1H), 4.40 (br d, 1H), 3.77 (br d, 1H), 3.19 (s, 1H), 2.85 (br s, 1H); LC-MS: m/z 360.2 $(M+H)^+$.

Step 3: SFC Separation 5-(4-pyrazolo[1,5-a]pyridin-2-yl-1,4,6,7-tetrahydroimidazo[4,5-c]pyridine-5-carbonyl)oxazole-4-carbonitrile (2.6 g) was separated by SFC (column: DAICEL CHIRALPAK AD(250 mm*50 mm, 10 um); mobile phase: [Neu-ETOH]; B %: 45%-45%, min) to afford Enantiomer 1 (650 mg, Rt=1.884 min) and Enantiomer 2 (450 mg, Rt=2.124 min).

Enantiomer 1 (Example 640): (S)-5-(4-(pyrazolo[1,5-a]pyridin-2-yl)-4,5,6,7-tetrahydro-1H-imidazo[4,5-c]pyridine-5-carbonyl)oxazole-4-carbonitrile. $^1$H NMR (400 MHz, $CD_3OD$) δ 8.52 (s, 1H), 8.46 (dd, 1H), 7.71 (s, 1H), 7.62 (br d, 1H), 7.17-7.26 (m, 1H), 6.85-6.92 (m, 1.7H), 6.48-6.69 (m, 1.3H), 4.77-4.87 (m, 0.4H), 4.40 (br d, 0.6H), 3.79 (br s, 1H), 3.10-3.19 (m, 1H), 2.79-2.91 (m, 1H); LC-MS: m/z 360.1 $(M+H)^+$; SFC: 94.1% ee.

Enantiomer 2 (Example 641): (R)-5-(4-(pyrazolo[1,5-a]pyridin-2-yl)-4,5,6,7-tetrahydro-1H-imidazo[4,5-c]pyridine-5-carbonyl)oxazole-4-carbonitrile. $^1$H NMR (400 MHz, $CD_3OD$) δ 8.51 (s, 1H), 8.46 (dd, 1H), 7.71 (s, 1H), 7.62 (br d, 1H), 7.13-7.26 (m, 1H), 6.84-6.94 (m, 1.7H), 6.49-6.70 (m, 1.3H), 4.77-4.87 (m, 0.4H), 4.40 (br d, 0.6H), 3.71-3.91 (m, 1H), 3.08-3.19 (m, 1H), 2.79-2.89 (m, 1H); LC-MS: m/z 360.2 $(M+H)^+$; SFC: 96.7% ee.

Preparation of Examples 836 and 837 according to General Scheme 1, Method C

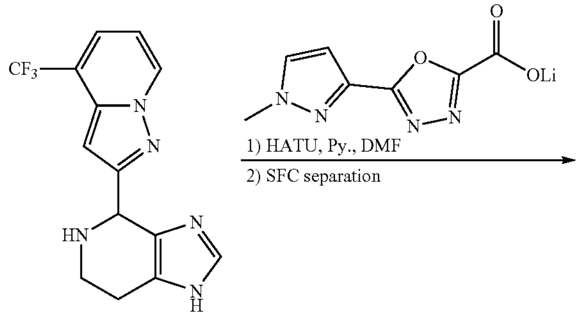

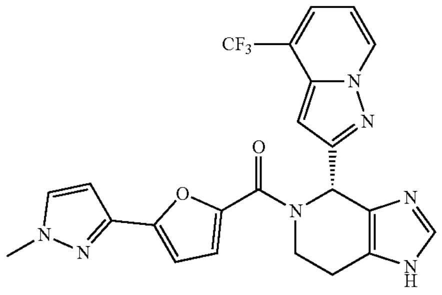

Example 836

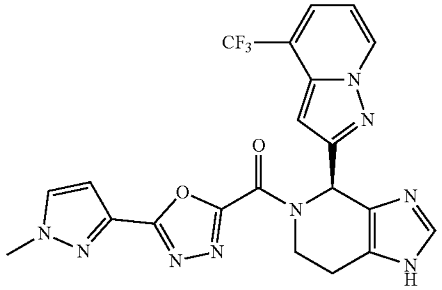

Example 837

Step 1: Preparation of (5-(1-methyl-1H-pyrazol-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone To a solution of 4-[4-(trifluoromethyl)pyrazolo[1,5-a]pyridin-2-yl]-4,5,6,7-tetrahydro-1H-imidazo[4,5-c]pyridine (150 mg, 488 μmol) and 54(1-methylpyrazol-3-yl)-1,3,4-oxadiazole-2-carboxylic acid (prepared in accordance with General Scheme 9, Method A, starting with methyl 1-methyl-1H-pyrazole-3-carboxylate) (142 mg, 732 μmol) in DMSO (3 mL) was added pyridine (116 mg, 1.46 mmol, 118 μL) and HATU (241 mg, 635 μmol) at rt. The reaction mixture was stirred at rt for 16 hrs. Reaction progress was checked using LCMS. The reaction mixture was submitted to prep-HPLC (column: Welch Xtimate C18 150*30 mm*5 um; mobile phase: [water(0.05% $NH_3H_2O$+10 mM $NH_4HCO_3$)-ACN]; B %; 27%-57%, 9 min) to give (5-(1-methyl-1H-pyrazol-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone. (100 mg, 42.4% yield). LCMS: m/z 484.1 $[M+H]^+$.

Step 2: SFC Separation

Compound (5-(1-methyl-1H-pyrazol-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone (100 mg, 207 μmol) was separated by SFC (column: Phenomenex-Cellulose-2 (250 mm*50 mm, 10 um); mobile phase: [0.1% $NH_3H_2O$ EtOH]; B %; 50%-50%, min) to afford Enantiomer 1 (46.1 mg, 46.1% yield, Rt=5.268 min) and Enantiomer 2 (46.2 mg, 45.6% yield, Rt=10.218 min).

Enantiomer 1 (Example 836): (S)-(5-(1-methyl-1H-pyrazol-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone. $^1H$ NMR (400 MHz, $CD_3OD$) δ 8.59-8.76 (m, 1H), 7.81 (d, 1H), 7.74 (s, 1H), 7.53-7.66 (m, 1H), 6.86-7.12 (m, 3H), 6.76-6.84 (m, 1H), 5.08 (br dd, 1H), 4.03 (s, 3H), 3.72-3.84 (m, 0.6H), 3.41 (td, 0.4H), 3.13-3.27 (m, 0.6H), 2.95-3.09 (m, 0.4H), 2.77-2.94 (m, 1H); LCMS: m/z 484.2 $[M+H]^+$; SFC: 100% ee.

Enantiomer 2 (Example 837): (R)-(5-(1-methyl-1H-pyrazol-3-yl)-1,3,4-oxadiazol-2-yl)(4-(4-(trifluoromethyl)pyrazolo[1,5-a]pyridin-2-yl)-6,7-dihydro-1H-imidazo[4,5-c]pyridin-5(4H)-yl)methanone. $^1H$ NMR (400 MHz, $CD_3OD$) δ 8.42-8.69 (m, 1H), 7.60-7.79 (m, 2H), 7.41-7.57 (m, 1H), 6.80-6.97 (m, 3H), 6.60-6.75 (m, 1H), 4.96 (br dd, 1H), 3.92 (s, 3H), 3.60-3.73 (m, 0.5H), 3.24-3.37 (m, 0.5H), 3.03-3.17 (m, 0.5H), 2.84-3.00 (m, 0.5H), 2.68-2.80 (m, 1H); LCMS: m/z 484.2 $[M+H]^+$; SFC: 98.7% ee.

Preparation of Examples 1628 and 1629 according to General Scheme 1, Method C

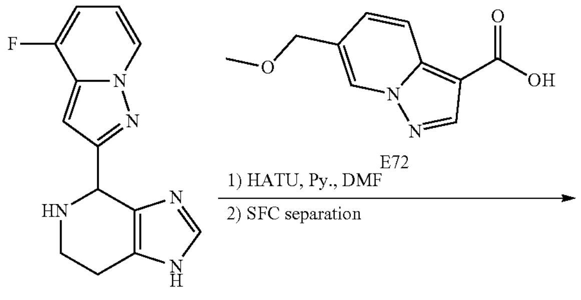

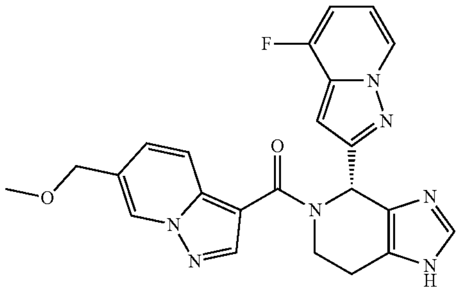

Example 1628

-continued

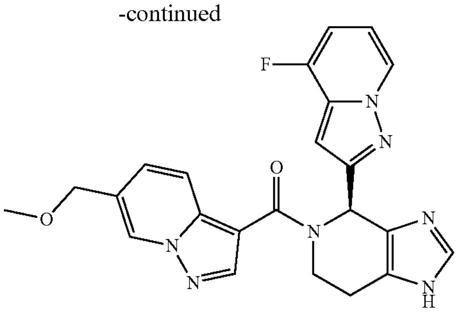

Example 1629

Step 1: Preparation of (4-(4-fluoropyrazolo[1,5-a]pyridin-2-yl)-6,7-dihydro-1H-imidazo[4,5-c]pyridin-5(4H)-yl)(6-(methoxymethyl)pyrazolo[1,5-a]pyridin-3-yl)methanone To a solution of 6-(methoxymethyl)pyrazolo[1,5-a]pyridine-3-carboxylic acid (E72) (144 mg, 700 μmol) and 4-(4-fluoropyrazolo[1,5-a]pyridin-2-yl)-4,5,6,7-tetrahydro-1H-imidazo[4,5-c]pyridine (150 mg, 583 μmol) in DMF (3 mL) was added HATU (333 mg, 875 μmol) and Py (185 mg, 2.33 mmol, 188.2 μL), and the reaction mixture was stirred at rt for 12 hrs. Reaction progress was checked using LCMS. DCM (30 mL) was added to the reaction mixture, and the organic layer washed with sat. aq. $Na_2CO_3$ solution (10 mL) and brine (10 mL), dried over $Na_2SO_4$, filtered and concentrated to dryness. The residue was purified by prep-HPLC (column: Boston Prime C18 150*30 mm*5 um; mobile phase: [water($NH_3H_2O$+$NH_4HCO_3$)-ACN]; B %: 25%-55%, 7 min) to give (4-(4-fluoropyrazolo[1,5-a]pyridin-2-yl)-6,7-dihydro-1H-imidazo[4,5-c]pyridin-5(4H)-yl)(6-(methoxymethyl)pyrazolo[1,5-a]pyridin-3-yl)methanone (108 mg, 41.6% yield). LCMS: m/z 446.2 $[M+H]^+$.

Step 2: SFC Separation

The compound (4-(4-fluoropyrazolo[1,5-a]pyridin-2-yl)-6,7-dihydro-1H-imidazo[4,5-c]pyridin-5(4H)-yl)(6-(methoxymethyl)pyrazolo[1,5-a]pyridin-3-yl)methanone (100 mg, 224 μmol) was separated by SFC (column: Phenomenex-Cellulose-2 (250 mm*30 mm, 10 um); mobile phase: 10.1% $NH_3H_2O$ EtOH]; B %; 55%, isocratic elution mode) to give Enantiomer 1 (20.1 mg, 19.5% yield, Rt=1.879 min) and Enantiomer 2 (23.3 mg, 22.7% yield, Rt=4.054 min).

Enantiomer 1 (Example 1628): (S)-(4-(4-fluoropyrazolo[1,5-a]pyridin-2-yl)-6,7-dihydro-1H-imidazo[4,5-c]pyridin-5(4H)-yl)(6-(methoxymethyl)pyrazolo[1,5-a]pyridin-3-yl)methanone. $^1H$ NMR (400 MHz, $CD_3OD$) δ 8.32-8.78 (m, 3H), 7.97 (d, 1H), 7.68 (s, 1H), 7.45 (d, 1H), 6.54-7.10 (m, 4H), 4.62-4.75 (m, 1H), 4.55 (s, 2H), 3.40-3.60 (m, 4H), 3.02-3.17 (m, 1H), 2.79 (br dd, 1H); LCMS: m/z 446.1 $[M+H]^+$; SFC: 100%.

Enantiomer 2 (Example 1629): (R)-(4-(4-fluoropyrazolo[1,5-a]pyridin-2-yl)-6,7-dihydro-1H-imidazo[4,5-c]pyridin-5(4H)-yl)(6-(methoxymethyl)pyrazolo[1,5-a]pyridin-3-yl)methanone. $^1H$ NMR (400 MHz, $CD_3OD$) δ 8.31-8.88 (m, 3H), 7.97 (d, 1H), 7.68 (s, 1H), 7.45 (dd, 1H), 6.55-7.06 (m, 4H), 4.62-4.73 (m, 1H), 4.55 (s, 2H), 3.40-3.76 (m, 4H), 2.99-3.17 (m, 1H), 2.79 (br dd, 1H); LCMS: m/z 446.2 $[M+H]^+$; SFC: 99.8%.

Preparation of Examples 1756 and 1757 according to General Scheme 1, Method A2

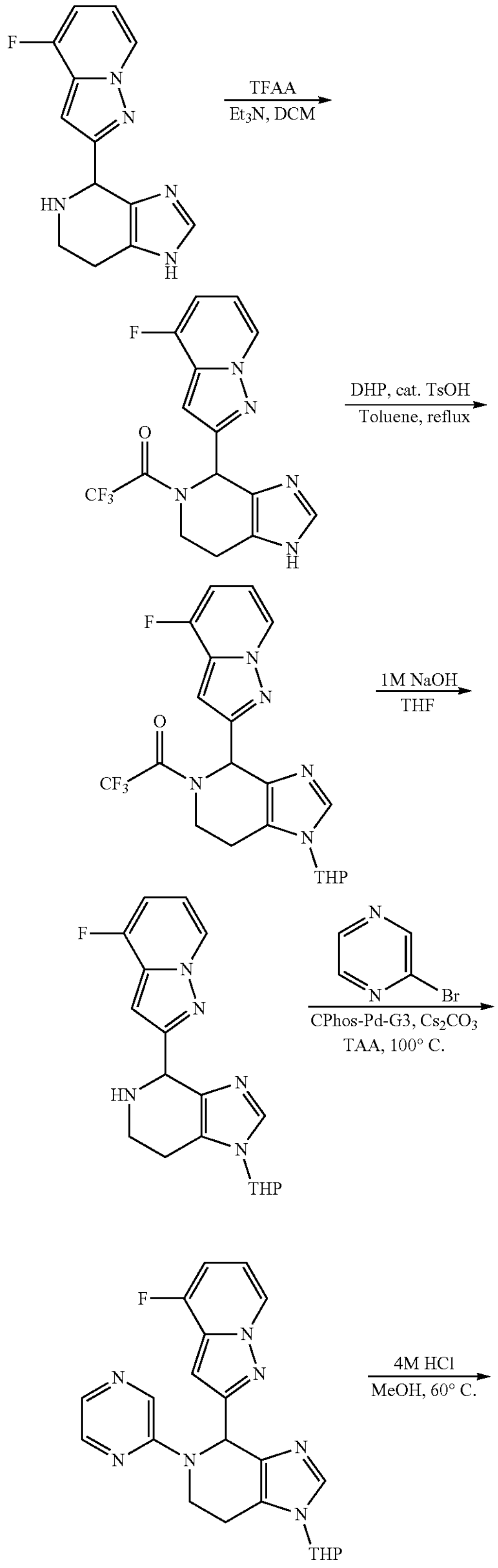

-continued

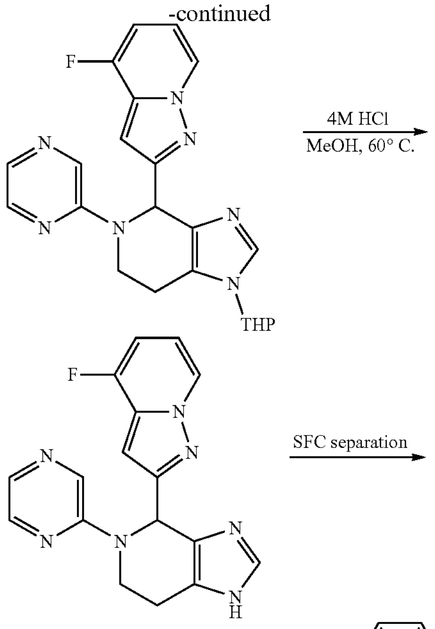

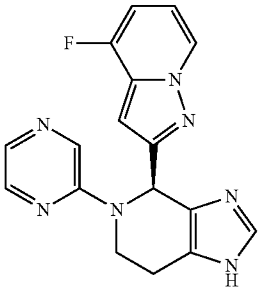

Example 1756

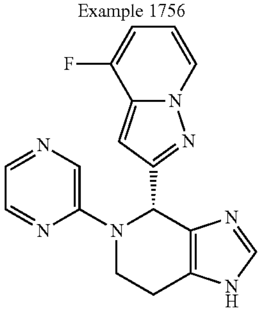

Example 1757

Step 1: Preparation of 2,2,2-trifluoro-1-[4-(4-fluoro-pyrazolo[1,5-a]pyridin-2-yl)-1,4,6,7-tetrahydroimidazo[4,5-c]pyridin-5-yl]ethanone To a solution of 4-(4-fluoropyrazolo[1,5-a]pyridin-2-yl)-4,5,6,7-tetrahydro-1H-imidazo[4,5-c]pyridine (7.3 g, 28.4 mmol) and $Et_3N$ (11.49 g, 114 mmol, 15.8 mL) in DCM (150 mL) was added TFAA (15.50 g, 73.8 mmol, 10.3 mL) dropwise at 0° C. After the addition was complete, the reaction mixture was stirred at rt for 3 hrs. Reaction progress was checked using TLC. DCM (150 mL) was added to the reaction mixture, and the organic layer was washed with water (100 mL) and brine (100 mL), dried over $Na_2SO_4$, filtered and concentrated to dryness. The residue was purified by flash silica gel chromatography (ISCO®; 80 g SepaFlash® Silica Flash Column, Eluent of 0~15% MeOH/DCM @60 mL/min) to give compound 2,2,2-trifluoro-1-[4-(4-fluoropyrazolo[1,5-a]pyridin-2-yl)-1,4,6,7-tetrahydro-imidazo[4,5-c]pyridin-5-yl]ethanone (10 g, 94.4% yield). $^1H$ NMR (400 MHz, DMSO-$d_6$) δ 8.55-8.68 (m, 1H), 7.60-7.76 (m, 1H), 7.15 (dd, 1H), 6.90 (td, 1H), 6.66-6.73 (m, 1H), 6.63 (s, 1H), 4.10 (br s, 1H), 3.67-3.80 (m, 1H), 2.70-2.88 (m, 2H); LCMS: m/z 354.2 $[M+H]^+$.

Step 2: Preparation of 2,2,2-trifluoro-1-[4-(4-fluoro-pyrazolo[1,5-a]pyridin-2-yl)-1-tetrahydropyran-2-yl-6,7-dihydro-4H-imidazo[4,5-c]pyridin-5-yl]ethanone To a solution of 2,2,2-trifluoro-1-[4-(4-fluoropyrazolo[1,5-a]pyridin-2-yl)-1,4,6,7-tetrahydroimidazo[4,5-c]pyridin-5-yl]ethanone (10 g, 28.3 mmol) and DHP (7.14 g, 84.9 mmol, 7.76 mL) in toluene (140 mL) was added TsOH (487 mg, 2.83 mmol), and the reaction mixture was stirred at 120° C. for 12 hrs. Reaction progress was checked using LCMS and TLC. EtOAc (150 ml) was added, and the organic layer washed with brine (40 ml×2), dried over $Na_2SO_4$, filtered, and concentrated to dryness. The residue was purified by flash silica gel chromatography (ISCO®; 80 g SepaFlash® Silica Flash Column, Eluent of 0~10% MeOH/DCM gradient @60 mL/min) to give compound 2,2,2-trifluoro-1-[4-(4-fluoropyrazolo[1,5-a]pyridin-2-yl)-1-tetrahydropyran-2-yl-6,7-dihydro-4H-imidazo[4,5-c]pyridin-5-yl]ethanone (8.9 g, 64.8% yield). $^1H$ NMR (400 MHz, DMSO-$d_6$) δ 8.54-8.66 (m, 1H), 7.73-7.90 (m, 1H), 7.11-7.20 (m, 1H), 6.67-6.93 (m, 2H), 6.12-6.61 (m, 1H), 5.14-5.37 (m, 1H), 3.92-4.16 (m, 2H), 3.60-3.84 (m, 2H), 2.80-2.97 (m, 2H), 1.87-2.06 (m, 3H), 1.49-1.70 (m, 3H); LCMS: m/z 438.3 $[M+H]^+$.

Step 3: Preparation of 4-(4-fluoropyrazolo[1,5-a]pyridin-2-yl)-1-tetrahydropyran-2-yl-4,5,6,7-tetrahydroimidazo[4,5-c]pyridine A mixture of 2,2,2-trifluoro-1-[4-(4-fluoropyrazolo[1,5-a]pyridin-2-yl)-1-tetrahydropyran-2-yl-6,7-dihydro-4H-imidazo[4,5-c]pyridin-5-yl]ethanone (8.8 g, 20.1 mmol) and $K_2CO_3$ (12.51 g, 90.5 mmol) in MeOH (100 mL) was degassed and purged with $N_2$ for 3 times, and then the reaction mixture was stirred at rt for 12 hrs under $N_2$ atmosphere. Reaction progress was checked using LCMS and TLC. DCM (150 mL) was added to the reaction mixture, and the organic layer washed with $H_2O$ (2×40 mL), dried over $Na_2SO_4$, filtered, and concentrated to dryness. The residue was purified by flash silica gel chromatography (ISCO®; 80 g SepaFlash® Silica Flash Column, Eluent of 0~10% MeOH:DCM @60 mL/min) to give compound 4-(4-fluoropyrazolo[1,5-a]pyridin-2-yl)-1-tetrahydropyran-2-yl-4,5,6,7-tetrahydroimidazo[4,5-c]pyridine (5.8 g, 79.4% yield). $^1H$ NMR (400 MHz, DMSO-$d_6$) δ 8.52 (d, 1H), 7.62 (d, 1H), 7.02-7.10 (m, 1H), 6.77-6.85 (m, 1H), 6.49 (d, 1H), 5.15-5.24 (m, 1H), 5.06 (d, 1H), 3.95-4.11 (m, 2H), 3.56-3.69 (m, 1H), 2.94 (br dd, 1H), 2.57-2.70 (m, 2H), 1.89-2.06 (m, 3H), 1.46-1.70 (m, 3H); LCMS: m/z 342.2 $[M+H]^+$.

Step 4: Preparation of 4-(4-fluoropyrazolo[1,5-a]pyridin-2-yl)-5-pyrazin-2-yl-1-tetrahydropyran-2-yl-6,7-dihydro-4H-imidazo[4,5-c]pyridine A mixture of 2-bromopyrazine (1.40 g, 8.79 mmol), 4-(4-fluoropyrazolo[1,5-a]pyridin-2-yl)-1-tetrahydropyran-2-yl-4,5,6,7-tetrahydroimidazo[4,5-c]pyridine (1.5 g, 4.39 mmol), CPhos-Pd-G3 (177.15 mg, 220 μmol), $Cs_2CO_3$ (4.29 g, 13.2 mmol) in tert-amyl alcohol (20 mL) was degassed and purged with $N_2$ for 3 times, and then the reaction mixture was stirred at 100° C. for 12 hrs under $N_2$ atmosphere. Reaction progress was checked using LCMS. DCM (100 mL) was added to the reaction mixture, and the organic layer washed with water (40 mL) and brine (40 mL), dried over $Na_2SO_4$, filtered, and concentrated to dryness. The residue was purified by flash silica gel chromatography (ISCO®; 24 g SepaFlash® Silica Flash Column, Eluent of 0~10% MeOH:DCM @30 mL/min) to give 4-(4-fluoropyrazolo[1,5-a]pyridin-2-yl)-5-pyrazin-2-yl-1-tetrahydropyran-2-yl-6,7-dihydro-4H-imidazo[4,5-c]pyridine (1 g, 50.3% yield). LCMS: m/z 420.2 $[M+H]^+$.

Step 5: Preparation of 4-(4-fluoropyrazolo[1,5-a]pyridin-2-yl)-5-(pyrazin-2-yl)-4,5,6,7-tetrahydro-1H-imidazo[4,5-c]pyridine To a solution of 4-(4-fluoropyrazolo[1,5-a]pyridin-2-yl)-5-pyrazin-2-yl-1-tetrahydropyran-2-yl-6,7-dihydro-4H-imidazo[4,5-c]pyridine (1 g, 2.38 mmol) in MeOH (15 mL) was added HCl (4 M, 20.0 mL) at rt. The reaction mixture was stirred at 70° C. for 12 hrs. Reaction progress was checked using LCMS. DCM (100 mL) was added, and the organic layer washed with sat. aq. $Na_2CO_3$ (50 mL×2) and brine (50 mL), dried over $Na_2SO_4$, filtered, and concentrated to dryness. The residue was purified by flash silica gel chromatography (ISCO®; 24 g SepaFlash® Silica Flash Column, Eluent of 0~10% MeOH:DCM @30 mL/min) to give 4-(4-fluoropyrazolo[1,5-a]pyridin-2-yl)-5-(pyrazin-2-yl)-4,5,6,7-tetrahydro-1H-imidazo[4,5-c]pyridine (500 mg, 58.3% yield). LCMS: m/z 336.2 $[M+H]^+$.

Step 6: SFC Separation

The compound 4-(4-fluoropyrazolo[1,5-a]pyridin-2-yl)-5-(pyrazin-2-yl)-4,5,6,7-tetrahydro-1H-imidazo[4,5-c]pyridine (1.2 g, 3.58 mmol) was separated by SFC (column: DAICEL CHIRALPAK AD(250 mm*30 mm, 10 um); mobile phase: [$CO_2$-EtOH(0.1% $NH_3H_2O$)]; B %; 40%, isocratic elution mode) to give Enantiomer 1 (370 mg, 28.8% yield, Rt=0.530 min) and Enantiomer 2 (433 mg, 33.4% yield, Rt=0.931 min).

Enantiomer 1 (Example 1756): (R)-4-(4-fluoropyrazolo[1,5-a]pyridin-2-yl)-5-(pyrazin-2-yl)-4,5,6,7-tetrahydro-1H-imidazo[4,5-c]pyridine. $^1H$ NMR (400 MHz, $CD_3OD$) δ 8.46 (s, 1H), 8.34 (d, 1H), 8.16 (s, 1H), 7.80 (d, 1H), 7.65 (s, 1H), 6.88-7.00 (m, 1H), 6.77-6.87 (m, 2H), 6.66 (s, 1H), 4.71 (br dd, 1H), 3.56-3.67 (m, 1H), 2.92-3.05 (m, 1H), 2.76 (dd, 1H); LCMS: m/z 336.1 $[M+H]^+$; SFC: 100% ee.

Enantiomer 2 (Example 1757): (S)-4-(4-fluoropyrazolo[1,5-a]pyridin-2-yl)-5-(pyrazin-2-yl)-4,5,6,7-tetrahydro-1H-imidazo[4,5-c]pyridine. $^1H$ NMR (400 MHz, $CD_3OD$) δ 8.46 (d, 1H), 8.30-8.37 (m, 1H), 8.13-8.19 (m, 1H), 7.80 (d, 1H), 7.65 (s, 1H), 6.94 (dd, 1H), 6.77-6.87 (m, 2H), 6.65 (s, 1H), 4.71 (dd, 1H), 3.61 (ddd, 1H), 2.92-3.03 (m, 1H), 2.76 (dd, 1H); LCMS: m/z 336.2 $[M+H]^+$; SFC: 99.7% ee.

Preparation of Examples 1842 and 1843 according to General Scheme 1, Method A1

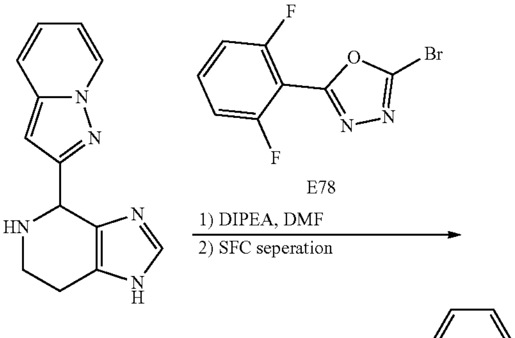

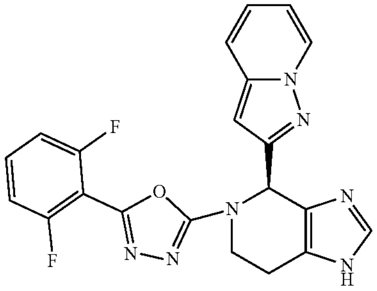

Example 1842

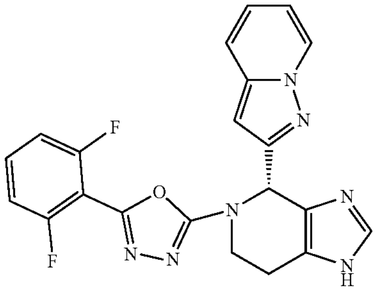

Example 1843

Step 1: Preparation of 2-(2,6-difluorophenyl)-5-(4-(pyrazolo[1,5-a]pyridin-2-yl)-6,7-dihydro-1H-imidazo[4,5-c]pyridin-5(4H)-yl)-1,3,4-oxadiazole To a solution of 4-pyrazolo[1,5-a]pyridin-2-yl-4,5,6,7-tetrahydro-1H-imidazo[4,5-c]pyridine (200 mg, 836 μmol) in DMF (2 mL) was added DIPEA (432 mg, 3.34 mmol, 582 μL) and 2-bromo-5-(2,6-difluorophenyl)-1,3,4-oxadiazole (E78) (262 mg, 1.00 mmol), and the reaction mixture was stirred at rt for 12 hrs. Reaction progress was checked using TLC. DCM (20 mL) was added to the reaction mixture, and the organic layer was washed by water (20 mL), dried over $Na_2SO_4$, filtered, and concentrated to dryness. The residue was purified by prep-HPLC (column: Welch Xtimate C18 150*30 mm*5 um; mobile phase: [water($NH_3H_2O$+$NH_4HCO_3$)-ACN]; B %: 30%-60%, 7 min) to afford 2-(2,6-difluorophenyl)-5-(4-(pyrazolo[1,5-a]pyridin-2-yl)-6,7-dihydro-1H-imidazo[4,5-c]pyridin-5(4H)-yl)-1,3,4-oxadiazole (150 mg, 40.8% yield). LCMS: m/z 420.1 $[M+H]^+$.

Step 2: SFC Separation

The compound 2-(2,6-difluorophenyl)-5-(4-(pyrazolo[1,5-a]pyridin-2-yl)-6,7-dihydro-1H-imidazo[4,5-c]pyridin-5

(4H)-yl)-1,3,4-oxadiazole (100 mg, 238 μmol) was separated by SFC (column: DAICEL CHIRALPAK AD(250 mm*30 mm, 10 um); mobile phase: [0.1% $NH_3H_2O$ EtOH]; B %: 45%-45%, 45 min) to give Enantiomer 1 (46.8 mg, 46.6% yield, Rt=1.780 min) and Enantiomer 2 (47.0 mg, 46.8% yield, Rt=1.990 min).

Enantiomer 1 (Example 1842): (R)-2-(2,6-difluorophenyl)-5-(4-(pyrazolo[1,5-a]pyridin-2-yl)-6,7-dihydro-1H-imidazo[4,5-c]pyridin-5(4H)-yl)-1,3,4-oxadiazole. $^1$H NMR 400 MHz, $CD_3OD$) δ 8.45 (d, 1H), 7.49-7.76 (m, 3H), 7.09-7.30 (m, 3H), 6.86 (td, 1H), 6.60 (s, 1H), 6.41 (s, 1H), 435 (dd, 1H), 3.73-3.88 (m, 1H), 2.99-3.17 (m, 1H), 2.84 (dd, 1H); LCMS: m/z 420.2 $[M+H]^+$; SFC: 99.3% ee.

Enantiomer 2 (Example 1843): (S)-2-(2,6-difluorophenyl)-5-(4-(pyrazolo[1,5-a]pyridin-2-yl)-6,7-dihydro-1H-imidazo[4,5-c]pyridin-5(4H)-yl)-1,3,4-oxadiazole. $^1$H NMR (400 MHz, $CD_3OD$) δ 8.45 (d, 1H), 7.49-7.79 (m, 3H), 7.12-7.30 (m, 3H), 6.86 (td, 1H), 6.61 (s, 1H), 6.41 (s, 1H), 4.36 (dd, 1H), 3.68-3.90 (m, 1H), 3.00-3.17 (m, 1H), 2.85 (dd, 1H); LCMS: m/z 420.1 $[M+H]^+$; SFC: 99.2% ee.

The compounds of Table 1 were characterized using proton NMR and LCMS and the enantiomeric excess determined. See Table 2.

TABLE 2

| Ex. # | $^1$H NMR (400 MHz unless otherwise noted) | LCMS: m/z | % ee |
|---|---|---|---|
| 600 | ($CD_3OD$) δ 8.22-8.79 (m, 3 H), 7.98 (d, 1 H), 7.67 (s, 1 H), 7.60 (d, 1 H), 7.39-7.49 (m, 1 H), 7.15-7.24 (m, 1 H), 7.02-7.13 (m, 1 H), 6.87 (br s, 1 H), 6.56 (br s, 1 H), 4.64 (br s, 1 H), 3.38-3.77 (m, 1 H), 2.97-3.18 (m, 1 H), 2.97-3.18 (m, 1 H), 2.70-2.87 (m, 1 H) | 384.2 $[M + H]^+$ | 100% |
| 601 | ($CD_3OD$) δ 8.33-8.97 (m, 3 H), 7.98 (d, 1 H), 7.68 (br s, 1 H), 7.60 (d, 1 H), 7.44 (t, 1 H), 7.21 (t, 1 H), 7.07 (t, 1 H), 6.87 (br s, 1 H), 6.56 (br s, 1 H), 4.65 (br s, 1 H), 3.38-3.83 (m, 1 H), 3.02-3.16 (m, 1 H), 2.70-2.85 (m, 1 H) | 384.2 $[M + H]^+$ | 99.4% |
| 602 | ($CD_3OD$) δ 9.18 (s, 1 H), 8.19-8.81 (m, 2 H), 7.69 (s, 1 H), 7.61 (d, 1 H), 7.22 (br t, 1 H), 6.89 (t, 1.5 H), 6.30-6.69 (m, 1.5 H), 4.06-4.85 (m, 1 H), 3.77 (br s, 1 H), 2.95-3.10 (m, 1 H), 2.78 (d, 1 H) | 351.1 $[M + H]^+$ | 100% |
| 603 | ($CD_3OD$) δ 9.18 (s, 1 H), 8.16-8.80 (m, 2 H), 7.69 (s, 1 H), 7.61 (d, 1 H), 7.22 (t, 1 H), 6.80-6.95(m, 1.5 H), 6.25-6.72 (m, 1.5 H), 4.14-4.84 (m, 1 H), 3.52-3.89 (m, 1 H), 3.52-3.53 (m, 1 H), 2.95-3.15 (m, 1 H), 2.70-2.85 m, 1 H) | 351.1 $[M + H]^+$ | 100% |
| 604 | ($CD_3OD$) δ 8.70-8.85 (m, 1 H), 8.38-8.53 (m, 2 H), 8.31 (dd, 1 H), 8.09 (td, 1 H), 7.52-7.74 (m, 2.3 H), 7.17-7.32 (m, 1 H), 7.10 (s, 0.7 H), 6.83-6.96 (m, 1 H), 6.67-6.80 (m, 1 H), 5.12 (dd, 1 H), 3.69-3.86 (m, 0.7 H), 3.41-3.49 (m, 0.3 H), 3.19-3.28 (m, 0.4 H), 3.01-3.18 (m, 0.6 H), 2.91-2.99 (m, 1 H) | 413.0 $[M + H]^+$ | 99.5% |
| 605 | ($CD_3OD$) δ 8.72-8.81 (m, 1 H), 8.34-8.51 (m, 1 H), 8.25-8.33 (m, 1 H), 8.07 (td, 1 H), 7.45-7.76 (m, 3.4 H), 7.12-7.26 (m, 1 H), 6.97 (s, 0.6 H), 6.78-6.90 (m, 1 H), 6.52-6.74 (m, 1 H), 4.99 (br dd, 1 H), 3.72-3.88 (m, 0.7 H), 3.42 (td, 0.3 H), 3.14-3.23 (m, 0.5 H), 2.92-3.07 (m, 0.5 H), 2.79-2.89 (m, 1 H) | 413.0 $[M + H]^+$ | 100% |
| 606 | ($CD_3OD$) δ 8.44 (d, 1 H), 8.25 (s, 1 H), 7.51-7.72 (m, 2 H), 7.10-7.24 (m, 1 H), 6.84 (t, 1.6 H), 6.61 (br s, 1.4 H), 4.30 (br s, 1 H), 3.53-3.86 (m, 1 H), 2.93-3.11 (m, 1 H), 2.78 (br d, 1 H), 2.38 (s, 3 H) | 349.0 $[M + H]^+$ | 100% |
| 607 | ($CD_3OD$) δ 8.44 (d, 1 H), 8.25 (s, 1 H), 7.51-7.73 (m, 2 H), 7.10-7.30 (m, 1 H), 6.73-6.95 (m, 1.7 H), 6.60 (br s, 1.3 H), 4.31 (br s, 1 H), 3.51-3.81 (m, 1 H), 2.95-3.17 (m, 1 H), 2.69-2.89 (m, 1 H), 2.38 (s, 3 H) | 349.0 $[M + H]^+$ | 99.8% |
| 608 | ($CD_3OD$) δ 8.39-8.56 (m, 1 H), 8.10-8.17 (m, 1 H), 7.67 (br d, 1 H), 7.58 (d, 1 H), 7.18-7.23 (m, 1 H), 6.84-6.93 (m, 1.6 H), 6.44-6.62 (m, 1.4 H), 4.77-4.89 (m, 1.4 H), 4.67-4.76 (m, 0.4 H), 4.39-4.47 (m, 0.6 H), 4.30 (dd, 0.6 H), 3.62-3.74 (m, 0.6 H), 3.19 (td, 0.4 H), 2.82-3.01 (m, 1 H), 2.67-2.81 (m, 1 H) | 433.1 $[M + H]^+$ | 100% |
| 609 | ($CD_3OD$) δ 8.40-8.55 (m, 1 H), 8.09-8.17 (m, 1 H), 7.65-7.69 (m, 1 H), 7.58 (d, 1 H), 7.17-7.23 (m, 1 H), 6.83-6.93 (m, 1.6 H), 6.44-6.59 (m, 1.4 H), 4.81-4.89 (m, 1.5 H), 4.68-4.77 (m, 0.4 H), 4.40-4.46 (m, 0.5 H), 4.30 (dd, 0.6 H), 3.69 (ddd, 0.6 H), 3.19 (td, 0.4 H), 2.81-3.01 (m, 1 H), 2.68-2.81 (m, 1 H) | 433.1 $[M + H]^+$ | 99.8% |
| 610 | ($CD_3OD$) δ 8.34-8.55 (m, 2 H), 7.49-7.74 (m, 2 H), 7.13-7.24 (m, 1 H), 6.79-6.94 (m, 2 H), 6.59 (s, 0.6 H), 6.38 (s, 0.2 H), 5.98 (br s, 0.2 H), 4.82 (br d, 0.3 H), 3.65-3.85 (m, 1.5 H), 3.39-3.49 (m, 0.2 H), 2.70-3.02 (m, 2 H) | 403.1 $[M + H]^+$ | 99.0% |
| 611 | ($CD_3OD$) δ 8.35-8.54 (m, 2 H), 7.45-7.75 (m, 2 H), 7.12-7.28 (m, 1 H), 6.79-6.96 (m, 2 H), 6.60 (s, 0.6 H), 6.39 (s, 0.2 H), 5.99 (br s, 0.2 H), 4.83 (br d, 0.3 H), 3.66-3.87 (m, 1.4 H), 3.45 (td, 0.3 H), 2.70-3.04 (m, 2 H) | 403.1 $[M + H]^+$ | 97.5% |
| 612 | ($CD_3OD$) δ 8.42-8.66 (m, 1.5 H), 8.18 (br s, 0.5 H), 7.65 (s, 1 H), 7.57 (br d, 1 H), 7.13-7.23 (m, 1 H), 6.85 (br s, 1 H), 6.28-6.66 (m, 2 H), 4.23 (br s, 1 H), 3.76 (br s, 1 H), 3.01 (br s, 1 H), 2.75 (br d, 1 H), 2.10 (t, 3 H) | 415.0 $[M + H]^+$ | 99.2% |
| 613 | ($CD_3OD$) δ 8.39-8.68 (m, 1.6 H), 8.18 (br s, 0.4 H), 7.65 (s, 1 H), 7.57 (br d, 1 H), 7.12-7.23 (m, 1 H), 6.86 (br s, 1 H), 6.22-6.65 (m, 2 H), 4.22 (br s, 1 H), 3.76 (br s, 1 H), 3.01 (br s, 1 H), 2.75 (br d, 1 H), 2.10 (t, 3 H) | 415.0 $[M + H]^+$ | 99.3% |

TABLE 2-continued

| Ex. # | $^1$H NMR (400 MHz unless otherwise noted) | LCMS: m/z | % ee |
|---|---|---|---|
| 614 | ($CD_3OD$) δ 8.40-8.52 (m, 1 H), 7.54-7.68 (m, 2 H), 7.16-7.24 (m, 1 H), 6.81-6.95 (m, 1.6 H), 6.55 (s, 0.6 H), 6.42 (s, 0.4 H), 6.26 (s, 0.4 H), 4.82-4.88 (m, 0.6 H), 4.16 (dd, 0.4 H), 3.56-3.68 (m, 0.6 H), 3.14 (td, 0.4 H), 2.41-2.99 (m, 4 H), 1.03-1.13 (m, 1 H), 0.48-0.62 (m, 2 H), 0.16-0.29 (m, 2 H) | 322.1 $[M + H]^+$ | 99.9% |
| 615 | ($CD_3OD$) δ 8.40-8.53 (m, 1 H), 7.53-7.69 (m, 2 H), 7.14-7.24 (m, 1 H), 6.80-6.95 (m, 1.6 H), 6.55 (s, 0.6 H), 6.42 (s, 0.4 H), 6.26 (s, 0.4 H), 4.81-4.87 (m, 0.4 H), 4.16 (dd, 1 H), 3.56-3.67 (m, 0.6 H), 3.08-3.20 (m, 0.4 H), 2.42-2.97 (m, 4 H), 1.03-1.15 (m, 1 H), 0.48-0.62 (m, 2 H), 0.17-0.29 (m, 2 H) | 322.2 $[M + H]^+$ | 99.9% |
| 616 | ($CD_3OD$) δ 8.57-8.68 (m, 1 H), 8.33-8.48 (m, 1 H), 7.91 (t, 1 H), 7.70-7.78 (m, 1 H), 7.68 (s, 1 H), 7.53-7.61 (m, 1 H), 7.46 (s, 0.3 H), 7.09-7.26 (m, 1 H), 6.95 (s, 0.7 H), 6.75-6.88 (m, 1 H), 6.53-6.68 (m, 1 H), 4.95 (br d, 1 H), 3.72-3.86 (m, 0.8 H), 3.37-3.46 (m, 0.2 H), 2.94-3.26 (m, 1 H), 2.83 (br d, 1 H) | 431.1 $[M + H]^+$ | 100% |
| 617 | ($CD_3OD$) δ 8.53-8.80 (m, 1 H), 8.31-8.50 (m, 1 H), 7.85-7.98 (m, 1 H), 7.70-7.77 (m, 1 H), 7.68 (s, 1 H), 7.52-7.62 (m, 1 H), 7.46 (s, 0.3 H), 7.10-7.23 (m, 1 H), 6.95 (s, 0.7 H), 6.75-6.88 (m, 1 H), 6.56-6.69 (m, 1 H), 4.95 (br d, 1 H), 3.72-3.84 (m, 0.7 H), 3.35-3.47 (m, 0.5 H), 2.93-3.21 (m, 1 H), 2.74-2.90 (m, 1 H) | 431.1 $[M + H]^+$ | 100% |
| 618 | ($CD_3OD$) δ 8.41 (d, 1 H), 8.11 (s, 1 H), 7.51-7.66 (m, 2 H), 7.11-7.20 (m, 1 H), 6.82 (td, 2 H), 6.56 (br s, 1 H), 4.34 (br s, 1 H), 3.51-3.86 (m, 1 H), 2.92-3.12 (m, 1 H), 2.76 (br dd, 1 H), 2.19-2.42 (m, 1 H), 0.84-1.03 (m, 4 H) | 375.0 $[M + H]^+$ | 99.8% |
| 619 | ($CD_3OD$) δ 8.42 (d, 1 H), 8.11 (s, 1 H), 7.51-7.67 (m, 2 H), 7.11-7.21 (m, 1 H), 6.77-6.85 (m, 2 H), 6.56 (br s, 1 H), 4.32 (br s, 1 H), 3.68 (br s, 1 H), 3.01 (br s, 1 H), 2.76 (br dd, 1 H), 2.32 (br s, 1 H), 0.84-1.00 (m, 4 H) | 375.0 $[M + H]^+$ | 99.7% |
| 620 | ($CD_3OD$) δ 8.42-8.48 (m, 1 H), 7.70 (s, 1 H), 7.57-7.63 (m, 1 H), 7.18-7.24 (m, 1 H), 6.83-6.95 (m, 2 H), 6.53-6.64 (m, 1 H), 4.99 (br dd, 1 H), 3.69-3.79 (m, 0.7 H), 3.35-3.44 (m, 0.3 H), 3.07-3.20 (m, 0.7 H), 2.91-3.04 (m, 0.3 H), 2.77-2.87 (m, 1 H), 2.26-2.39 (m, 1 H), 1.19-1.33 (m, 4 H) | 376.0 $[M + H]^+$ | 100% |
| 621 | ($CD_3OD$) δ 8.41-8.48 (m, 1 H), 7.69 (s, 1 H), 7.57-7.64 (m, 1 H), 7.18-7.24 (m, 1 H), 6.80-6.97 (m, 2 H), 6.53-6.65 (m, 1 H), 4.99 (br dd, 1 H), 3.74 (ddd, 0.7 H), 3.36-3.44 (m, 0.3 H), 3.07-3.20 (m, 0.7 H), 2.90-3.03 (m, 0.3 H), 2.75-2.88 (m, 1 H), 2.26-2.39 (m, 1 H), 1.17-1.32 (m, 4 H) | 376.0 $[M + H]^+$ | 99.9% |
| 622 | ($CD_3OD$) δ 8.65 (br d, 1 H), 8.43 (br d, 1 H), 7.89-8.18 (m, 2 H), 7.65 (br s, 1 H), 7.58 (br d, 1 H), 7.48-7.54 (m, 1 H), 7.13-7.22 (m, 1 H), 6.61-6.92 (m, 3 H), 4.49 (br s, 1 H), 3.76 (br s, 1 H), 3.18 (br s, 1 H), 2.80 (br d, 1 H), 2.40 (br s, 1 H), 0.87-1.14 (m, 4 H) | 452.2 $[M + H]^+$ | 99.7% |
| 623 | ($CD_3OD$) δ 8.65 (br d, 1 H), 8.43 (br d, 1 H), 7.85-8.16 (m, 2 H), 7.65 (s, 1 H), 7.57 (br d, 1 H), 7.47-7.54 (m, 1 H), 7.14-7.20 (m, 1 H), 6.58-6.93 (m, 3 H), 4.42-4.63 (m, 1 H), 3.76 (br s, 1 H), 3.18 (br s, 1 H), 2.80 (br d, 1 H), 2.40 (br s, 1 H), 0.89-1.14 (m, 4 H) | 452.2 $[M + H]^+$ | 99.6% |
| 624 | ($CD_3OD$) δ 8.42 (d, 1 H), 7.52-7.66 (m, 2 H), 7.13-7.21 (m, 1 H), 6.82 (t, 2 H), 6.59 (s, 1 H), 4.35 (br s, 1 H), 3.69 (br s, 1 H), 3.09 (br d, 1 H), 2.76 (br d, 1 H), 2.33 (br s, 1 H), 1.55 (br s, 6 H), 0.80-1.05 (m, 4 H) | 433.2 $[M + H]^+$ | 100% |
| 625 | ($CD_3OD$) δ 8.42 (d, 1 H), 7.52-7.66 (m, 2 H), 7.13-7.20 (m, 1 H), 6.82 (t, 2 H), 6.59 (s, 1 H), 4.34 (br s, 1 H), 3.66 (br s, 1 H), 2.90-3.17 (m, 1 H), 2.76 (br d, 1 H), 2.33 (br s, 1 H), 1.55 (br s, 6 H), 0.79-1.04 (m, 4 H) | 433.1 $[M + H]^+$ | 99.5% |
| 626 | ($CD_3OD$) δ 8.36-8.48 (m, 2 H), 8.10 (s, 1 H), 7.68 (s, 1 H), 7.53-7.63 (m, 1 H), 7.14-7.23 (m, 1 H), 6.94 (br s, 1 H), 6.81-6.89 (m, 1 H), 6.52-6.65 (m, 1 H), 4.96-5.10 (m, 0.7 H), 4.68-4.79 (m, 0.4 H), 4.00 (s, 3 H), 3.71-3.81 (m, 0.7 H), 3.36-3.51 (m, 0.4 H), 2.95-3.23 (m, 1 H), 2.83 (br d, 1 H) | 416.2 $[M + H]^+$ | 100% |
| 627 | ($CD_3OD$) δ 8.34-8.48 (m, 2 H), 8.11 (s, 1 H), 7.69 (s, 1 H), 7.53-7.63 (m, 1 H), 7.14-7.25 (m, 1 H), 6.96 (br s, 1 H), 6.80-6.90 (m, 1 H), 6.54-6.65 (m, 1 H), 5.06 (br dd, 0.7 H), 4.76-4.80 (m, 0.6 H), 4.01 (s, 3 H), 3.72-3.82 (m, 0.6 H), 3.40 (td, 0.4 H), 2.93-3.23 (m, 1 H), 2.83 (br d, 1 H) | 416.2 $[M + H]^+$ | 99.6% |
| 628 | ($CD_3OD$) δ 8.47 (br d, 1 H), 7.53-7.77 (m, 2 H), 7.15-7.27 (m, 1 H), 6.83-6.95 (m, 2 H), 6.44-6.67 (m, 1 H), 3.80 (br d, 1.5 H), 3.41-3.55 (m, 0.5 H), 2.74-3.07 (m, 2 H), 1.55-1.74 (m, 6 H) | 461.0 $[M + H]^+$ | 100% |
| 629 | ($CD_3OD$) δ 8.39-8.51 (m, 1 H), 7.55-7.72 (m, 2 H), 7.31-7.53 (m, 0.5 H), 7.15-7.26 (m, 1 H), 6.80-6.95 (m, 1.5 H), 6.42-6.65 (m, 1 H), 3.80 (br d, 1.4 H), 3.50 (br d, 0.6 H), 2.73-3.10 (m, 2 H), 1.51-1.73 (m, 6 H) | 461.0 $[M + H]^+$ | 99.6% |
| 630 | (DMSO-$d_6$) δ 11.89-12.21 (m, 1 H), 8.51-8.79 (m, 2 H), 7.44-7.76 (m, 2 H), 7.07-7.41 (m, 2 H), 6.28-6.94 (m, 3 H), 4.69 (br s, 0.4 H), 4.23 (br d, 0.6 H), 3.57-3.81 (m, 0.5 H), 3.17-3.29 (m, 0.5 H), 2.58-2.98 (m, 2 H) | 385.1 $[M + H]^+$ | 100% |

TABLE 2-continued

| Ex. # | $^1$H NMR (400 MHz unless otherwise noted) | LCMS: m/z | % ee |
|---|---|---|---|
| 631 | ($CD_3OD$) δ 8.39-8.48 (m, 2 H), 7.68 (s, 1 H), 7.59 (br d, 1 H), 6.99-7.30 (m, 2 H), 6.44-6.92 (m, 3 H), 4.96-5.10 (m, 0.5 H), 4.31 (br d, 0.7 H), 3.73 (br s, 0.5 H), 3.48 (br d, 0.3 H), 2.92-3.16 (m, 1 H), 2.80 (br d, 1 H) | 385.1 $[M + H]^+$ | 99.7% |
| 632 | ($CD_3OD$) δ 8.43 (br d, 1 H), 7.65 (s, 1 H), 7.57 (d, 1 H), 6.91-7.27 (m, 2 H), 6.73-6.91 (m, 1.6 H), 6.57 (br s, 1.4 H), 4.65-4.79 (m, 0.5 H), 4.30 (br s, 0.5 H), 3.37-3.91 (m, 1 H), 2.88-3.11 (m, 1 H), 2.79 (br d, 1 H), 2.00-2.34 (m, 1 H), 0.98-1.26 (m, 4 H) | 425.0 $[M + H]^+$ | 95.8% |
| 633 | ($CD_3OD$) δ 8.43 (br d, 1 H), 7.65 (s, 1 H), 7.57 (d, 1 H), 7.02-7.33 (m, 2 H), 6.73-7.01 (m, 2 H), 6.50-6.60 (m, 1 H), 4.69-4.80 (m, 0.5 H), 4.31 (br s, 0.5 H), 3.67 (br s, 1 H), 2.92-3.21 (m, 1 H), 2.79 (br d, 1 H), 1.97-2.38 (m, 1 H), 1.05-1.26 (m, 4 H) | 425.0 $[M + H]^+$ | 99.1% |
| 634 | ($CD_3OD$) δ 8.28-8.41 (m, 1 H), 7.41-7.57 (m, 2 H), 7.03-7.12 (m, 1 H), 6.83 (s, 0.6 H), 6.69-6.79 (m, 1 H), 6.29-6.47 (m, 1.4 H), 4.73 (br d, 0.5 H), 4.17 (br dd, 0.5 H), 3.41-3.54 (m, 0.6 H), 2.95-3.06 (m, 1 H), 2.55-2.90 (m, 3.4 H), 1.91-2.16 (m, 4 H), 1.50-1.76 (m, 2 H) | 352.2 $[M + H]^+$ | 100% |
| 635 | ($CD_3OD$) δ 8.37-8.54 (m, 1 H), 7.52-7.71 (m, 2 H), 7.13-7.25 (m, 1 H), 6.95 (s, 0.6 H), 6.79-6.90 (m, 1 H), 6.40-6.58 (m, 1.4 H), 4.85 (br d, 0.4 H), 4.30 (dd, 0.6 H), 3.59 (ddd, 0.6 H), 3.11-3.16 (m, 1 H), 2.67-3.03 (m, 3.4 H), 2.03-2.27 (m, 4 H), 1.62-1.88 (m, 2 H) | 352.2 $[M + H]^+$ | 99.5% |
| 636 | ($CD_3OD$) δ 8.40-8.54 (m, 1 H), 7.62-7.69 (m, 1 H), 7.58 (d, 1 H), 7.15-7.24 (m, 1 H), 6.79-6.93 (m, 2 H), 6.37-6.54 (m, 1 H), 4.82 (br dd, 1 H), 4.16 (br dd, 1 H), 3.47-3.66 (m, 1 H), 2.87-3.18 (m, 2 H), 2.68-2.82 (m, 3 H), 2.30-2.51 (m, 2 H), 2.19 (br d, 2 H) | 354.2 $[M + H]^+$ | 100% |
| 637 | ($CD_3OD$) δ 8.38-8.53 (m, 1 H), 7.61-7.69 (m, 1 H), 7.57 (d, 1 H), 7.14-7.23 (m, 1 H), 6.77-6.92 (m, 2 H), 6.36-6.54 (m, 1 H), 5.03-5.25 (m, 1 H), 4.15 (br dd, 1 H), 3.46-3.66 (m, 1 H), 2.85-3.15 (m, 2 H), 2.66-2.81 (m, 3 H), 2.29-2.60 (m, 2 H), 2.07-2.25 (m, 2 H) | 354.2 $[M + H]^+$ | 83.3% |
| 638 | ($CD_3OD$) δ 8.43 (br d, 1 H), 7.48-7.68 (m, 2 H), 7.10-7.23 (m, 1 H), 6.71-6.88 (m, 2 H), 6.40-6.59 (m, 1 H), 4.54-4.64 (m, 1 H), 3.46-3.65 (m, 1 H), 2.83-3.06 (m, 1 H), 2.67-2.79 (m, 1 H), 2.55-2.66 (m, 2 H), 2.02-2.16 (m, 2 H), 1.91-2.02 (m, 1 H), 1.77 (br d, 1 H) | 388.2 $[M + H]^+$ | 100% |
| 639 | ($CD_3OD$) δ 8.43 (br d, 1 H), 7.47-7.71 (m, 2 H), 7.09-7.22 (m, 1 H), 6.71-6.93 (m, 2 H), 6.40-6.59 (m, 1 H), 4.58 (br dd, 1 H), 3.58 (br t, 1 H), 2.80-3.04 (m, 1 H), 2.67-2.78 (m, 1 H), 2.55-2.66 (m, 2 H), 2.08 (br d, 2 H), 1.98 (dt, 1 H), 1.70-1.84 (m, 1 H) | 388.1 $[M + H]^+$ | 99.6% |
| 640 | Data provided above | | |
| 641 | Data provided above | | |
| 642 | ($CD_3OD$) δ 8.33-8.68 (m, 3 H), 7.96 (d, 2 H), 7.73 (br s, 1 H), 7.49-7.67 (m, 1.4 H), 7.17-7.31 (m, 1 H), 7.00 (br s, 0.6 H), 6.78-6.95 (m, 1 H), 6.56-6.74 (m, 1 H), 5.10 (br dd, 0.7 H), 4.96-4.99 (m, 0.3 H), 3.76-3.90 (m, 0.6 H), 3.40-3.53 (m, 0.4 H), 2.99-3.28 (m, 1 H), 2.88 (br d, 1 H) | 480.2 $[M + H]^+$ | 100% |
| 643 | ($CD_3OD$) δ 8.13-8.55 (m, 3 H), 7.83 (br d, 2 H), 7.32-7.74 (m, 2 H), 7.00-7.18 (m, 1 H), 6.66-6.96 (m, 2 H), 6.38-6.61 (m, 1 H), 4.97 (br dd, 1 H), 3.59-3.83 (m, 0.7 H), 3.28-3.36 (m, 0.3 H), 2.85-3.15 (m, 1 H), 2.77 (br s, 1 H) | 480.2 $[M + H]^+$ | 99.2% |
| 644 | ($CD_3OD$) δ 8.74 (br d, 1 H), 8.47 (br d, 1 H), 8.30 (br d, 1 H), 7.90-8.10 (m, 1 H), 7.54-7.77 (m, 3 H), 7.05-7.42 (m, 2 H), 6.58-6.97 (m, 3 H), 4.52 (br d, 1 H), 3.43-3.86 (m, 1 H), 2.92-3.25 (m, 1 H), 2.78-2.91 (m, 1 H) | 462.1 $[M + H]^+$ | 100% |
| 645 | ($CD_3OD$) δ 8.74 (br d, 1 H), 8.47 (br d, 1 H), 8.13-8.34 (m, 1 H), 7.89-8.10 (m, 1 H), 7.56-7.79 (m, 3 H), 7.05-7.40 (m, 2 H), 6.51-7.00 (m, 3 H), 4.51 (br d, 1 H), 3.45-3.87 (m, 1 H), 2.92-3.26 (m, 1 H), 2.86 (br d, 1 H) | 462.1 $[M + H]^+$ | 99.5% |
| 646 | ($CD_3OD$) δ 8.59 (s, 1 H), 8.37-8.48 (m, 1 H), 8.22 (s, 1 H), 7.54-7.72 (m, 2 H), 7.13-7.24 (m, 1 H), 6.78-6.99 (m, 2 H), 6.53-6.66 (m, 1 H), 5.02-5.17 (m, 3 H), 3.74-3.81 (m, 0.5 H), 3.38-3.47 (m, 0.5 H), 2.77-3.23 (m, 2 H) | 484.1 $[M + H]^+$ | 100% |
| 647 | ($CD_3OD$) δ 8.59 (s, 1 H), 8.37-8.47 (m, 1 H), 8.22 (s, 1 H), 7.54-7.72 (m, 2 H), 7.14-7.24 (m, 1 H), 6.80-6.99 (m, 2 H), 6.54-6.67 (m, 1 H), 5.02-5.16 (m, 3 H), 3.72-3.82 (m, 0.6 H), 3.38-3.45 (m, 0.4 H), 2.80-3.16 (m, 2 H) | 484.1 $[M + H]^+$ | 98.3% |
| 648 | ($CD_3OD$) δ 8.35-8.56 (m, 1 H), 8.06-8.15 (m, 1 H), 7.98-8.05 (m, 1 H), 7.71 (br s, 1 H), 7.49-7.66 (m, 2.4 H), 7.15-7.28 (m, 1 H), 6.98 (s, 0.6 H), 6.81-6.94 (m, 1 H), 6.56-6.71 (m, 1 H), 5.09 (dd, 0.7 H), 4.94-4.96 (m, 0.3 H), 3.71-3.88 (m, 0.7 H), 3.43 (td, 0.3 H), 3.13-3.26 (m, 0.7 H), 2.95-3.08 (m, 0.3 H), 2.86 (br d, 1 H) | 448.1 $[M + H]^+$ | 100% |

TABLE 2-continued

| Ex. # | $^1$H NMR (400 MHz unless otherwise noted) | LCMS: m/z | % ee |
|---|---|---|---|
| 649 | ($CD_3OD$) δ 8.35-8.63 (m, 1 H), 8.05-8.15 (m, 1 H), 7.97-8.05 (m, 1 H), 7.71 (br s, 1 H), 7.47-7.66 (m, 2.4 H), 7.08-7.32 (m, 1 H), 6.76-7.06 (m, 1.6 H), 6.51-6.74 (m, 1 H), 5.08 (br dd, 0.7 H), 4.95-5.00 (m, 0.3 H), 3.70-3.89 (m, 0.7 H), 3.38-3.48 (m, 0.3 H), 3.11-3.28 (m, 0.7 H), 2.96-3.09 (m, 0.3 H), 2.86 (br d, 1 H) | 448.1 $[M + H]^+$ | 100% |
| 650 | ($CD_3OD$) δ 8.93 (br d, 1 H), 8.24-8.57 (m, 2 H), 7.46-7.89 (m, 3 H), 7.21 (br s, 1 H), 6.74-7.07 (m, 2 H), 6.50-6.69 (m, 1 H), 5.05 (br s, 1 H), 3.79 (br s, 1 H), 2.75-3.26 (m, 2 H) | 452.0 $[M + H]^+$ | 100% |
| 651 | ($CD_3OD$) δ 8.94 (s, 1 H), 8.31-8.50 (m, 2 H), 7.48-7.86 (m, 3 H), 7.14-7.31 (m, 1 H), 6.78-7.03 (m, 2 H), 6.52-6.69 (m, 1 H), 5.07 (br dd, 1 H), 3.36-3.87 (m, 1 H), 2.79-3.25 (m, 2 H) | 452.0 $[M + H]^+$ | 99.6% |
| 652 | ($CD_3OD$) δ 8.39-8.52 (m, 1 H), 8.17-8.31 (m, 1 H), 7.71 (s, 1 H), 7.53-7.66 (m, 1.3 H), 7.16-7.38 (m, 3 H), 6.98 (s, 0.7 H), 6.82-6.93 (m, 1 H), 6.57-6.70 (m, 1 H), 5.03 (dd, 0.7 H), 4.94-4.96 (m, 0.3 H), 3.74-3.86 (m, 0.7 H), 3.43 (td, 0.3 H), 3.16-3.26 (m, 0.7 H), 2.97-3.07 (m, 0.3 H), 2.81-2.91 (m, 1 H) | 448.2 $[M + H]^+$ | 100% |
| 653 | ($CD_3OD$) δ 8.26-8.39 (m, 1 H), 8.11 (td, 1 H), 7.64 (br s, 1 H), 7.41-7.54 (m, 1.3 H), 7.07-7.25 (m, 3 H), 6.87 (s, 0.7 H), 6.71-6.80 (m, 1 H), 6.46-6.58 (m, 1 H), 4.92 (br dd, 0.7 H), 4.82-4.85 (m, 0.3 H), 3.63-3.73 (m, 0.7 H), 3.27-3.36 (m, 0.3 H), 3.06-3.14 (m, 0.7 H), 2.85-2.97 (m, 0.3 H), 2.69-2.80 (m, 1 H) | 448.2 $[M + H]^+$ | 98.6% |
| 654 | (DMSO-$d_6$) δ 11.97-12.17 (m, 1 H), 8.48-8.69 (m, 1 H), 7.88-8.08 (m, 1 H), 7.50-7.70 (m, 2 H), 7.33-7.40 (m, 1 H), 7.13-7.32 (m, 2 H), 7.08 (s, 0.2 H), 6.95 (br s, 1.2 H), 6.48-6.61 (m, 1.6 H), 4.67-4.86 (m, 1 H), 3.62-3.79 (m, 1 H), 2.71-3.11 (m, 2 H), 2.58-2.67 (m, 3 H) | 444.1 $[M + H]^+$ | 100% |
| 655 | (DMSO-$d_6$) δ 12.03-12.18 (m, 1 H), 8.54-8.70 (m, 1 H), 7.95-8.07 (m, 1 H), 7.57-7.71 (m, 2 H), 7.36-7.43 (m, 1 H), 7.27-7.35 (m, 2 H), 6.80-6.90 (m, 1 H), 6.55-6.63 (m, 1 H), 4.72-4.88 (m, 1 H), 3.61-3.85 (m, 1 H), 2.89-3.18 (m, 1 H), 2.79 (br d, 1 H), 2.61-2.69 (m, 3 H) | 444.1 $[M + H]^+$ | 100% |
| 656 | ($CD_3OD$) δ 8.42-8.56 (m, 1 H), 7.50-7.84 (m, 4 H), 6.73-7.26 (m, 4 H), 6.24-6.64 (m, 1 H), 4.81 (br s, 1 H), 4.07 (br d, 0.5 H), 3.71 (br t, 0.5 H), 2.99 (br s, 1 H), 2.75 (br d, 1 H) | 384.1 $[M + H]^+$ | 100% |
| 657 | ($CD_3OD$) δ 8.41-8.57 (m, 1 H), 7.48-7.85 (m, 4 H), 6.73-7.25 (m, 4 H), 6.23-6.66 (m, 1 H), 4.75-4.86 (m, 1 H), 4.01-4.12 (m, 0.5 H), 3.71 (br s, 0.5 H), 2.99 (br s, 1 H), 2.75 (br d, 1 H) | 384.1 $[M + H]^+$ | 99.7% |
| 658 | ($CD_3OD$) δ 8.34-8.58 (m, 1 H), 7.46-7.90 (m, 3.3 H), 7.10-7.34 (m, 1 H), 6.77-7.02 (m, 2.7 H), 6.47-6.73 (m, 1 H), 5.03 (br dd, 1 H), 4.05 (s, 3 H), 3.79 (br t, 1 H), 2.71-3.21 (m, 2 H) | 416.1 $[M + H]^+$ | 98.1% |
| 659 | ($CD_3OD$) δ 8.31-8.58 (m, 1 H), 7.44-7.96 (m, 3.3 H), 7.14-7.33 (m, 1 H), 6.80-7.10 (m, 2.7 H), 6.52-6.71 (m, 1 H), 5.03 (br dd, 1 H), 4.05 (s, 3 H), 3.70-3.88 (m, 1 H), 2.71-3.23 (m, 2 H) | 416.1 $[M + H]^+$ | 90.6% |
| 660 | ($CD_3OD$) δ 8.42-8.61 (m, 1 H), 7.48-7.75 (m, 3 H), 7.16-7.27 (m, 1 H), 6.76-7.03 (m, 2 H), 6.53-6.71 (m, 1 H), 6.35 (br s, 1 H), 4.04-4.19 (m, 1 H), 3.93 (s, 3 H), 3.61-3.79 (m, 1 H), 2.98 (br s, 1 H), 2.66-2.87 (m, 1 H) | 348.1 $[M + H]^+$ | 100% |
| 661 | ($CD_3OD$) δ 8.42-8.61 (m, 1 H), 7.47-7.75 (m, 3 H), 7.16-7.28 (m, 1 H), 6.76-7.03 (m, 2 H), 6.52-6.72 (m, 1 H), 6.34 (br s, 1 H), 4.03-4.20 (m, 1 H), 3.93 (s, 3 H), 3.59-3.78 (m, 1 H), 2.98 (br s, 1 H), 2.76 (br d, 1 H) | 348.1 $[M + H]^+$ | 96.8% |
| 662 | ($CD_3OD$) δ 8.30-8.64 (m, 1.5 H), 7.97 (br s, 0.5 H), 7.45-7.75 (m, 2 H), 7.14-7.23 (m, 1 H), 6.75-7.03 (m, 2.6 H), 6.17-6.64 (m, 1.4 H), 4.02-4.16 (m, 1 H), 3.96 (s, 3 H), 3.34-3.80 (m, 1 H), 2.93 (br t, 1 H), 2.70 (br dd, 1 H) | 398.1 $[M + H]^+$ | 100% |
| 663 | ($CD_3OD$) δ 8.25-8.66 (m, 1.5 H), 7.97 (br s, 0.5 H), 7.50-7.70 (m, 2 H), 7.12-7.27 (m, 1 H), 6.70-7.08 (m, 2.5 H), 6.08-6.69 (m, 1.5 H), 4.01-4.19 (m, 1 H), 3.96 (s, 3 H), 3.34-3.80 (m, 1 H), 2.93 (br t, 1 H), 2.60-2.77 (m, 1 H) | 398.1 $[M + H]^+$ | 99.3% |
| 664 | ($CD_3OD$) δ 8.17-8.60 (m, 1.5 H), 7.90 (br s, 0.5 H), 7.50-7.69 (m, 2 H), 7.18 (ddd, 1 H), 6.78-7.02 (m, 1.6 H), 6.12-6.68 (m, 1.4 H), 4.81 (br s, 0.5 H), 4.05 (br d, 0.5 H), 3.88 (s, 3 H), 3.71 (br s, 0.5 H), 3.15-3.30 (m, 0.5 H), 2.90-3.01 (m, 1 H), 2.72 (br dd, 1 H) | 382.2 $[M + H]^+$ | 100% |
| 665 | ($CD_3OD$) δ 8.19-8.58 (m, 1.5 H), 7.90 (br s, 0.5 H), 7.50-7.69 (m, 2 H), 7.17 (dd, 1 H), 6.78-7.01 (m, 1.6 H), 6.14-6.66 (m, 1.4 H), 4.69-4.83 (m, 0.6 H), 4.04 (br d, 0.4 H), 3.87 (s, 3 H), 3.69 (br s, 0.5 H), 3.24 (br s, 0.5 H), 2.88-3.00 (m, 1 H), 2.71 (br dd, 1 H) | 382.2 $[M + H]^+$ | 99.6% |
| 666 | ($CD_3OD$) δ 8.34-8.49 (m, 2 H), 7.52-7.86 (m, 3.3 H), 7.15-7.29 (m, 2 H), 6.83-7.00 (m, 1.7 H), 6.57-6.70 (m, 1 H), 5.03 (dd, 1 H), 3.72-3.86 (m, 0.7 H), 3.38-3.51 (m, 0.3 H), 2.96-3.27 (m, 1 H), 2.79-2.93 (m, 1 H) | 452.2 $[M + H]^+$ | 100% |
| 667 | ($CD_3OD$) δ 8.32-8.51 (m, 2 H), 7.53-7.85 (m, 3.5 H), 7.14-7.26 (m, 2 H), 6.81-7.01 (m, 1.5 H), 6.58-6.69 (m, 1 H), 5.03 (dd, 1 H), 3.80 (ddd, 0.7 H), 3.43 (td, 0.3 H), 2.97-3.27 (m, 1 H), 2.86 (br dd, 1 H) | 452.3 $[M + H]^+$ | 97.2% |

TABLE 2-continued

| Ex. # | $^1$H NMR (400 MHz unless otherwise noted) | LCMS: m/z | % ee |
|---|---|---|---|
| 668 | ($CD_3OD$) δ 9.04 (d, 1 H), 8.55 (s, 1 H), 8.37-8.49 (m, 1 H), 7.96 (d, 1 H), 7.67-7.74 (m, 1 H), 7.51-7.64 (m, 1.3 H), 7.15-7.24 (m, 1 H), 6.98 (s, 0.7 H), 6.80-6.90 (m, 1 H), 6.58-6.69 (m, 1 H), 5.03 (dd, 1 H), 3.81 (ddd, 0.7 H), 3.39-3.50 (m, 0.4 H), 3.11-3.23 (m, 0.6 H), 2.97-3.07 (m, 0.4 H), 2.78-2.92 (m, 1 H) | 481.1 $[M + H]^+$ | 100% |
| 669 | ($CD_3OD$) δ 9.04 (d, 1 H), 8.55 (s, 1 H), 8.37-8.50 (m, 1 H), 7.96 (d, 1 H), 7.70 (s, 1 H), 7.50-7.63 (m, 1.3 H), 7.14-7.25 (m, 1 H), 6.98 (s, 0.7 H), 6.80-6.90 (m, 1 H), 6.58-6.69 (m, 1 H), 5.02 (br dd, 1 H), 3.76-3.85 (m, 0.7 H), 3.40-3.49 (m, 0.3 H), 3.16-3.25 (m, 0.7 H), 2.97-3.07 (m, 0.3 H), 2.78-2.90 (m, 1 H) | 481.1 [M + H]+ | 98.4% |
| 670 | ($CD_3OD$) δ 8.34 (d, 1 H), 7.37-7.67 (m, 2 H), 6.99-7.19 (m, 2 H), 6.68-6.93 (m, 2 H), 6.51 (s, 1 H), 4.22 (br d, 1 H), 3.26-3.80 (m, 1 H), 2.59-3.10 (m, 2 H), 1.45-1.66 (m, 6 H) | 443.2 $[M + H]^+$ | 100% |
| 671 | ($CD_3OD$) δ 8.33 (br d, 1 H), 7.41-7.71 (m, 2 H), 6.99-7.19 (m, 2 H), 6.71-6.94 (m, 2 H), 6.51 (s, 1 H), 4.23 (br d, 1 H), 3.28-3.78 (m, 1 H), 2.58-3.11 (m, 2 H), 1.42-1.67 (m, 6 H) | 443.1 $[M + H]^+$ | 98.9% |
| 672 | ($CD_3OD$) δ 8.59 (s, 1 H), 8.32-8.50 (m, 1 H), 8.07-8.24 (m, 1 H), 7.80-7.95 (m, 1 H), 7.67 (s, 1 H), 7.43-7.62 (m, 1.4 H), 7.10-7.24 (m, 1 H), 6.94 (s, 0.6 H), 6.74-6.89 (m, 1 H), 6.49-6.68 (m, 1 H), 4.97 (br dd, 1 H), 3.67-3.86 (m, 0.7 H), 3.39 (td, 0.3 H), 3.17 (br s, 0.7 H), 2.91-3.04 (m, 0.3 H), 2.82 (br d, 1 H), 2.45 (s, 3 H) | 427.1 $[M + H]^+$ | 100% |
| 673 | ($CD_3OD$) δ 8.59 (s, 1 H), 8.30-8.48 (m, 1 H), 8.09-8.22 (m, 1 H), 7.83-7.93 (m, 1 H), 7.67 (s, 1 H), 7.42-7.63 (m, 1.4 H), 7.09-7.25 (m, 1 H), 6.94 (s, 0.6 H), 6.72-6.88 (m, 1 H), 6.49-6.68 (m, 1 H), 4.97 (br dd, 1 H), 3.77 (ddd, 0.7 H), 3.39 (td, 0.3 H), 3.10-3.23 (m, 0.7 H), 2.91-3.06 (m, 0.3 H), 2.82 (br dd, 1 H), 2.45 (s, 3 H) | 427.1 $[M + H]^+$ | 98.3% |
| 674 | ($CD_3OD$) δ 8.82-9.33 (m, 1 H), 8.35-8.61 (m, 2 H), 7.88-8.02 (m, 2 H), 7.51-7.72 (m, 2 H), 7.37 (br t, 1 H), 7.20 (dd, 1 H), 6.58-7.05 (m, 2 H), 6.22-6.39 (m, 1 H), 4.10 (br d, 1 H), 3.76 (br s, 1 H), 3.00 (br s, 1 H), 2.76 (br d, 1 H) | 445.2 $[M + H]^+$ | 100% |
| 675 | ($CD_3OD$) δ 8.81-9.31 (m, 1 H), 8.40-8.59 (m, 2 H), 7.90-8.01 (m, 2 H), 7.52-7.70 (m, 2 H), 7.37 (br t, 1 H), 7.20 (dd, 1 H), 6.61-7.04 (m, 2 H), 6.23-6.38 (m, 1 H), 4.10 (br d, 1 H), 3.76 (br s, 1 H), 3.00 (br t, 1 H), 2.75 (br d, 1 H) | 445.2 $[M + H]^+$ | 99.6% |
| 676 | ($CD_3OD$) δ 8.46 (d, 1 H), 7.68 (s, 1 H), 7.61 (br d, 1 H), 7.13-7.30 (m, 1 H), 6.87 (td, 1.3 Hz, 1.7 H), 6.48-6.73 (m, 1 H), 6.39 (br s, 0.3 H), 4.78 (br s, 0.3 H), 4.16 (br d, 0.7 H), 3.69-3.91 (m, 0.7 H), 3.42 (br s, 0.3 H), 2.92-3.24 (m, 1 H), 2.82 (br d, 1 H), 1.53-1.70 (m, 6 H) | 471.0 $[M + H]^+$ | 100% |
| 677 | ($CD_3OD$) δ 8.46 (d, 1 H), 7.68 (s, 1 H), 7.62 (br d, 1 H), 7.13-7.28 (m, 1 H), 6.87 (td, 1.6 H), 6.49-6.72 (m, 1 H), 6.38 (br s, 0.4 H), 4.79 (br s, 0.3 H), 4.16 (br d, 0.7 H), 3.70-3.88 (m, 0.7 H), 3.42 (br s, 0.3 H), 3.12 (br d, 1 H), 2.82 (br d, 1 H), 1.52-1.72 (m, 6 H) | 471.0 $[M + H]^+$ | 99.7% |
| 678 | ($CD_3OD$) δ 8.58 (s, 1 H), 8.36-8.50 (m, 1 H), 7.71 (s, 1 H), 7.49-7.65 (m, 1.3 H), 7.15-7.27 (m, 1 H), 6.80-7.02 (m, 1.7 H), 6.53-6.68 (m, 1 H), 4.99 (br dd, 1 H), 4.07 (s, 3 H), 3.72-3.85 (m, 0.7 H), 3.41 (td, 0.3 H), 3.13-3.26 (m, 0.7 H), 2.93-3.09 (m, 0.3 H), 2.77-2.92 (m, 1 H) | 484.1 $[M + H]^+$ | 100% |
| 679 | ($CD_3OD$) δ 8.58 (s, 1 H), 8.37-8.54 (m, 1 H), 7.71 (s, 1 H), 7.47-7.65 (m, 1.3 H), 7.14-7.27 (m, 1 H), 6.78-7.01 (m, 1.7 H), 6.52-6.71 (m, 1 H), 4.99 (br dd, 1 H), 4.07 (s, 3 H), 3.73-3.84 (m, 0.7 H), 3.37-3.45 (m, 0.3 H), 3.12-3.26 (m, 0.7 H), 2.94-3.07 (m, 0.3 H), 2.77-2.91 (m, 1 H) | 484.1 $[M + H]^+$ | 100% |
| 680 | ($CD_3OD$) δ 8.40-8.59 (m, 1 H), 7.50-7.71 (m, 2 H), 7.19 (ddd, 1 H), 6.74-7.01 (m, 2 H), 6.45-6.69 (m, 1 H), 6.31 (br d, 1 H), 4.80 (br s, 0.4 H), 3.98-4.14 (m, 0.6 H), 3.81-3.89 (m, 3 H), 3.61-3.78 (m, 0.7 H), 3.29 (br s, 0.3 H), 2.90-3.04 (m, 1 H), 2.75 (br d, 1 H) | 382.2 $[M + H]^+$ | 100% |
| 681 | ($CD_3OD$) δ 8.40-8.59 (m, 1 H), 7.51-7.72 (m, 2 H), 7.19 (ddd, 1 H), 6.72-7.00 (m, 2 H), 6.47-6.67 (m, 1 H), 6.31 (br d, 1 H), 4.81 (br s, 0.5 H), 4.00-4.13 (m, 0.5 H), 3.85 (s, 3 H), 3.62-3.77 (m, 0.6 H), 3.25 (br s, 0.4 H), 2.89-3.03 (m, 1 H), 2.75 (br d, 1 H) | 382.2 $[M + H]^+$ | 99.2% |
| 682 | ($CD_3OD$) δ 8.44-8.71 (m, 2 H), 7.68 (s, 1 H), 7.53 (br d, 1 H), 7.26 (dd, 1 H), 6.45-6.88 (m, 2 H), 4.39 (br d, 1 H), 3.35-3.94 (m, 1 H), 2.73-3.20 (m, 2 H) | 440.1 $[M + H]^+$ | 100% |
| 683 | ($CD_3OD$) δ 8.37-8.78 (m, 2 H), 7.68 (s, 1 H), 7.55 (br d, 1 H), 7.27 (dd, 1 H), 6.37-6.93 (m, 2 H), 4.39 (br d, 1 H), 3.34-3.94 (m, 1 H), 2.73-3.23 (m, 2 H) | 440.1 $[M + H]^+$ | 99.8% |
| 684 | ($CD_3OD$) δ 8.40-8.62 (m, 2 H), 7.52-7.72 (m, 2 H), 7.19 (dd, 1 H), 6.52-6.90 (m, 2 H), 4.38 (br d, 1 H), 3.33-3.92 (m, 1 H), 2.72-3.22 (m, 2 H) | 394.0 $[M + H]^+$ | 100% |
| 685 | ($CD_3OD$) δ 8.40-8.62 (m, 2 H), 7.52-7.76 (m, 2 H), 7.20 (dd, 1 H), 6.46-6.91 (m, 2 H), 4.39 (br d, 1 H), 3.35-3.90 (m, 1 H), 3.11 (br s, 1 H), 2.72-2.95 (m, 1 H) | 394.0 $[M + H]^+$ | 99.8% |

TABLE 2-continued

| Ex. # | $^1$H NMR (400 MHz unless otherwise noted) | LCMS: m/z | % ee |
|---|---|---|---|
| 686 | ($CD_3OD$) δ 8.38-8.54 (m, 2 H), 7.62-7.79 (m, 1 H), 7.30 (d, 1 H), 6.48-7.00 (m, 3 H), 4.40 (br d, 1 H), 3.77 (br s, 1 H), 2.77-3.19 (m, 2 H) | 394.2 $[M + H]^+$ | 98.6% |
| 687 | ($CD_3OD$) δ 8.39-8.56 (m, 2 H), 7.69 (s, 1 H), 7.30 (d, 1 H), 6.46-6.94 (m, 3 H), 4.41 (br d, 1 H), 3.78 (br d, 1 H), 2.77-3.20 (m, 2 H) | 394.2 $[M + H]^+$ | 94.5% |
| 688 | ($CD_3OD$) δ 8.33-8.48 (m, 2 H), 7.98-8.17 (m, 1 H), 7.53-7.72 (m, 1.3 H), 7.21-7.36 (m, 1 H), 6.60-7.03 (m, 2.7 H), 4.92-5.10 (m, 1 H), 4.00 (s, 3 H), 3.76 (ddd, 0.6 H), 3.35-3.44 (m, 0.4 H), 2.92-3.22 (m, 1 H), 2.79-2.89 (m, 1 H) | 450.2 $[M + H]^+$ | 100% |
| 689 | ($CD_3OD$) δ 8.35-8.49 (m, 2 H), 8.04-8.16 (m, 1 H), 7.50-7.74 (m, 1.3 H), 7.24-7.35 (m, 1 H), 6.68-6.97 (m, 2.7 H), 4.92-5.12 (m, 1 H), 4.00 (s, 3 H), 3.71-3.83 (m, 0.7 H), 3.40 (td, 0.3 H), 2.93-3.23 (m, 1 H), 2.77-2.90 (m, 1 H) | 450.2 $[M + H]^+$ | 99.3% |
| 690 | ($CD_3OD$) δ 8.44 (br d, 1 H), 7.54-7.70 (m, 2 H), 7.10-7.28 (m, 2 H), 6.81-7.01 (m, 2 H), 6.60 (br s, 1 H), 4.94-5.00 (m, 1 H), 4.33 (br d, 1 H), 3.72 (br s, 1 H), 2.92-3.20 (m, 1 H), 2.80 (br d, 1 H), 1.61 (br d, 3 H) | 429.3 $[M + H]^+$ | 99.6% |
| 691 | ($CD_3OD$) δ 8.44 (br d, 1 H), 7.53-7.71 (m, 2 H), 7.10-7.29 (m, 2 H), 6.79-7.02 (m, 2 H), 6.60 (s, 1 H), 4.94-5.01 (m, 1 H), 4.34 (br d, 1 H), 3.73 (br s, 1 H), 2.90-3.19 (m, 1 H), 2.81 (br d, 1 H), 1.50-1.68 (m, 3 H) | 429.2 $[M + H]^+$ | 99.7% |
| 692 | ($CD_3OD$) δ 8.44 (br d, 1 H), 7.68 (s, 1 H), 7.59 (br d, 1 H), 7.27 (s, 0.2 H), 7.16-7.23 (m, 1 H), 6.97-7.14 (m, 0.8 H), 6.85 (br t, 2 H), 6.61 (s, 1 H), 4.97 (br d, 1 H), 4.35 (br d, 1 H), 3.63-3.80 (m, 0.7 H), 3.37-3.49 (m, 0.3 H), 2.91-3.20 (m, 1 H), 2.81 (br d, 1 H), 1.60 (br d, 3 H) | 429.2 $[M + H]^+$ | 100% |
| 693 | ($CD_3OD$) δ 8.44 (br d, 1 H), 7.68 (s, 1 H), 7.59 (br d, 1 H), 7.26 (s, 0.2 H), 7.16-7.22 (m, 1 H), 6.98-7.14 (m, 0.8 H), 6.86 (br t, 2 H), 6.61 (s, 1 H), 4.97 (br d, 1 H), 4.34 (br d, 1 H), 3.72 (br s, 0.7 H), 3.48 (br s, 0.4 H), 2.89-3.19 (m, 1 H), 2.81 (br d, 1 H), 1.61 (br d, 3 H) | 429.2 $[M + H]^+$ | 100% |
| 694 | ($CD_3OD$) δ 8.40-8.48 (m, 1 H), 7.65-7.70 (m, 1 H), 7.51-7.61 (m, 1 H), 7.13-7.24 (m, 1 H), 6.80-6.94 (m, 2 H), 6.35-6.64 (m, 1 H), 4.83 (br s, 0.3, 4.44 (dd, 0.7 H), 4.02 (s, 3 H), 3.59-3.73 (m, 0.7 H), 3.09-3.27 (m, 1 H), 2.90-3.01 (m, 0.3 H), 2.70-2.85 (m, 1 H) | 383.2 $[M + H]^+$ | 99.0% |
| 695 | ($CD_3OD$) δ 8.40-8.48 (m, 1 H), 7.65-7.71 (m, 1 H), 7.50-7.61 (m, 1 H), 7.13-7.23 (m, 1 H), 6.79-6.93 (m, 2 H), 6.34-6.63 (m, 1 H), 4.83 (br s, 0.3, 4.44 (dd, 0.7 H), 4.02 (s, 3 H), 3.66 (ddd, 0.7 H), 3.08-3.27 (m, 1 H), 2.90-3.00 (m, 0.3 H), 2.70-2.85 (m, 1 H) | 383.2 $[M + H]^+$ | 98.6% |
| 696 | ($CD_3OD$) δ 8.49-8.63 (m, 1 H), 8.32 (br s, 1 H), 8.08 (s, 1 H), 7.53-7.70 (m, 2.3 H), 7.08-7.27 (m, 1 H), 6.91 (s, 0.7 H), 6.58-6.73 (m, 1 H), 5.07 (br dd, 0.5 H), 3.99 (s, 3 H), 3.66-3.85 (m, 1 H), 3.39 (td, 0.5 H), 2.73-3.24 (m, 2 H) | 450.2 $[M + H]^+$ | 100% |
| 697 | ($CD_3OD$) δ 8.50-8.62 (m, 1 H), 8.38 (s, 1 H), 8.03-8.15 (m, 1 H), 7.51-7.74 (m, 2.4 H), 7.13-7.30 (m, 1 H), 6.92 (s, 0.6 H), 6.60-6.73 (m, 1 H), 5.07 (br dd, 0.5 H), 4.00 (s, 3 H), 3.67-3.83 (m, 1 H), 3.33-3.48 (m, 0.5 H), 2.72-3.23 (m, 2 H) | 450.2 $[M + H]^+$ | 99.7% |
| 698 | ($CD_3OD$) δ 8.35 (d, 1 H), 7.38-7.71 (m, 2 H), 6.86-7.29 (m, 2 H), 6.38-6.81 (m, 3 H), 4.21 (br d, 1 H), 3.29-3.78 (m, 1 H), 2.58-3.15 (m, 2 H), 1.54-1.90 (m, 6 H) | 452.2 $[M + H]^+$ | 98.3% |
| 699 | ($CD_3OD$) δ 8.47 (d, 1 H), 7.52-7.79 (m, 2 H), 6.99-7.36 (m, 2 H), 6.45-6.93 (m, 3 H), 4.33 (br d, 1 H), 3.38-3.85 (m, 1 H), 2.69-3.27 (m, 2 H), 1.67-2.01 (m, 6 H)) | 452.2 $[M + H]^+$ | 98.4% |
| 700 | ($CD_3OD$) δ 8.44 (d, 1 H), 7.68 (s, 1 H), 6.94-7.35 (m, 2 H), 6.51-6.93 (m, 3 H), 4.36 (br d, 1 H), 3.33-3.82 (m, 1 H), 2.70-3.18 (m, 2 H), 1.54-1.73 (m, 6 H) | 477.2 $[M + H]^+$ | 94.7% |
| 701 | ($CD_3OD$) δ 8.44 (d, 1 H), 7.68 (s, 1 H), 6.94-7.38 (m, 2 H), 6.51-6.93 (m, 3 H), 4.35 (br d, 1 H), 3.37-3.88 (m, 1 H), 2.73-3.23 (m, 2 H), 1.55-1.74 (m, 6 H) | 477.2 $[M + H]^+$ | 99.4% |
| 702 | ($CD_3OD$) δ 8.44 (d, 1 H), 7.68 (s, 1 H), 7.30 (d, 1 H), 6.94-7.27 (m, 1 H), 6.85 (t, 1.7 H), 6.49-6.77 (m, 1.3 H), 4.97 (br d, 1.3 H), 4.36 (br d, 0.7 H), 3.36-3.85 (m, 1 H), 2.73-3.23 (m, 2 H), 1.49-1.71 (m, 3 H) | 463.0 $[M + H]^+$ | 98.1% |
| 703 | ($CD_3OD$) δ 8.43 (d, 1 H), 7.68 (s, 1 H), 7.30 (d, 1 H), 6.97-7.27 (m, 1 H), 6.85 (t, 1.6 H), 6.54-6.78 (m, 1.4 H), 4.97 (br d, 1.3 H), 4.37 (br d, 0.7 H), 3.37-3.81 (m, 1 H), 2.75-3.21 (m, 2 H), 1.46-1.67 (m, 3 H) | 463.0 $[M + H]^+$ | 96.7% |
| 704 | ($CD_3OD$) δ 8.44 (d, 1 H), 7.68 (s, 1 H), 7.30 (d, 1 H), 6.95-7.27 (m, 1 H), 6.85 (t, 1.6 H), 6.54-6.77 (m, 1.4 H), 4.40 (br d, 1 H), 3.36-3.83 (m, 1 H), 2.70-3.21 (m, 2 H), 1.20-1.46 (m, 4 H) | 475.2 $[M + H]^+$ | 98.7% |
| 705 | ($CD_3OD$) δ 8.44 (d, 1 H), 7.72 (br s, 1 H), 7.30 (d, 1 H), 6.95-7.27 (m, 1 H), 6.85 (t, 1.6 H), 6.74 (s, 1.4 H), 4.41 (br d, 1 H), 3.72 (br s, 1 H), 2.73-3.23 (m, 2 H), 1.23-1.44 (m, 4 H) | 475.1 $[M + H]^+$ | 99.2% |

TABLE 2-continued

| Ex. # | $^1$H NMR (400 MHz unless otherwise noted) | LCMS: m/z | % ee |
|---|---|---|---|
| 706 | ($CD_3OD$) δ 8.43 (d, 1 H), 7.67 (s, 1 H), 7.29 (d, 1 H), 6.34-6.98 (m, 3 H), 4.91 (br s, 1 H), 4.28-4.79 (m, 1 H), 3.37-3.83 (m, 1 H), 2.68-3.20 (m, 2 H), 2.37 (s, 3 H), 1.55 (br s, 3 H) | 427.2 $[M + H]^+$ | 98.7% |
| 707 | ($CD_3OD$) δ 8.43 (d, 1 H), 7.66 (s, 1 H), 7.28 (d, 1 H), 6.41-6.93 (m, 3 H), 4.88-4.94 (m, 1 H), 4.36 (br s, 1 H), 3.39-3.79 (m, 1 H), 2.68-3.21 (m, 2 H), 2.37 (s, 3 H), 1.55 (br s, 3 H) | 427.2 $[M + H]^+$ | 97.7% |
| 708 | ($CD_3OD$) δ 8.43 (d, 1 H), 7.66 (s, 1 H), 7.28 (d, 1 H), 6.41-6.93 (m, 3 H), 4.88-4.94 (m, 1 H), 4.36 (br s, 1 H), 3.39-3.79 (m, 1 H), 2.68-3.21 (m, 2 H), 2.37 (s, 3 H), 1.55 (br s, 3 H) | 427.2 $[M + H]^+$ | 97.7% |
| 709 | ($CD_3OD$) δ 8.43 (d, 1 H), 7.67 (s, 1 H), 7.29 (d, 1 H), 6.32-6.97 (m, 3 H), 4.89-4.93 (m, 1 H), 4.34 (br s, 1 H), 3.37-3.83 (m, 1 H), 2.68-3.23 (m, 2 H), 2.37 (s, 3 H), 1.56 (br s, 3 H) | 427.2 $[M + H]^+$ | 99.5% |
| 710 | ($CD_3OD$) δ 8.33 (d, 1 H), 7.67 (s, 1 H), 6.91-7.29 (m, 2 H), 6.49-6.90 (m, 3 H), 4.97 (br d, 1.3 H), 4.36 (br d, 0.7 H), 3.34-3.80 (m, 1 H), 2.70-3.21 (m, 2 H), 1.49-1.68 (m, 3 H) | 447.1 $[M + H]^+$ | 98.9% |
| 711 | ($CD_3OD$) δ 8.33 (d, 1 H), 7.67 (s, 1 H), 6.92-7.31 (m, 2 H), 6.51-6.90 (m, 3 H), 4.97 (br d, 1.4 H), 4.36 (br d, 0.6 H), 3.37-3.85 (m, 1 H), 2.68-3.21 (m, 2 H), 1.46-1.67 (m, 3 H) | 447.1 $[M + H]^+$ | 99.5% |
| 712 | ($CD_3OD$) δ 8.33 (d, 1 H), 7.61-7.72 (m, 1 H), 6.93-7.31 (m, 2 H), 6.52-6.90 (m, 3 H), 4.97 (br d, 1 H), 4.36 (br d, 1 H), 3.37-3.80 (m, 1 H), 2.72-3.21 (m, 2 H), 1.61 (br d, 3 H) | 447.1 $[M + H]^+$ | 95.9% |
| 713 | ($CD_3OD$) δ 8.33 (d, 1 H), 7.62-7.74 (m, 1 H), 6.91-7.30 (m, 2 H), 6.48-6.90 (m, 3 H), 4.97 (br d, 1 H), 4.30-4.45 (m, 1 H), 3.36-3.80 (m, 1 H), 2.72-3.22 (m, 2 H), 1.48-1.69 (m, 3 H) | 447.1 $[M + H]^+$ | 98.8% |
| 714 | ($CD_3OD$) δ 8.33 (d, 1 H), 7.67 (s, 1 H), 6.90-7.28 (m, 2 H), 6.49-6.89 (m, 3 H), 4.33 (br s, 1 H), 3.37-3.86 (m, 1 H), 2.74-3.20 (m, 2 H), 1.66 (br s, 6 H) | 461.1 $[M + H]^+$ | 99.7% |
| 715 | ($CD_3OD$) δ 8.33 (d, 1 H), 7.67 (s, 1 H), 6.90-7.30 (m, 2 H), 6.50-6.89 (m, 3 H), 4.34 (br d, 1 H), 3.36-3.84 (m, 1 H), 2.73-3.22 (m, 2 H), 1.56-1.71 (m, 6 H) | 461.1 $[M + H]^+$ | 99.6% |
| 716 | ($CD_3OD$) δ 8.40-8.57 (m, 1 H), 7.89 (br s, 1 H), 7.51-7.75 (m, 2 H), 7.17-7.30 (m, 1 H), 6.84-7.06 (m, 2 H), 6.58-6.80 (m, 1 H), 5.92-6.41 (m, 1 H), 4.85 (br d, 0.4 H), 3.70-3.83 (m, 1.2 H), 3.36-3.45 (m, 0.4 H), 2.67-3.09 (m, 2 H) | 402.20 $[M + H]^+$ | 100% |
| 717 | ($CD_3OD$) δ 8.41-8.59 (m, 1 H), 7.89 (br s, 1 H), 7.49-7.79 (m, 2 H), 7.14-7.30 (m, 1 H), 6.85-7.04 (m, 2 H), 6.59-6.82 (m, 1 H), 5.96-6.42 (m, 1 H), 4.85 (br d, 0.4 H), 3.69-3.83 (m, 1.2 H), 3.36-3.46 (m, 0.4 H), 2.64-3.04 (m, 2 H) | 402.20 $[M + H]^+$ | 100% |
| 718 | ($CD_3OD$) δ 8.36-8.50 (m, 2 H), 8.05-8.18 (m, 1 H), 7.53-7.76 (m, 1.3 H), 7.24-7.35 (m, 1 H), 6.92 (s, 0.7 H), 6.65-6.88 (m, 2 H), 5.07 (br dd, 1 H), 3.98 (s, 3 H), 3.67-3.82 (m, 0.7 H), 3.32-3.45 (m, 0.3 H), 2.92-3.21 (m, 1 H), 2.78-2.89 (m, 1 H) | 450.1 $[M + H]^+$ | 100% |
| 719 | ($CD_3OD$) δ 8.32-8.47 (m, 2 H), 8.09 (d, 1 H), 7.73-7.87 (m, 1 H), 7.22-7.61 (m, 1.3 H), 6.95 (s, 0.7 H), 6.67-6.89 (m, 2 H), 5.08 (br dd, 1 H), 3.98 (s, 3 H), 3.66-3.79 (m, 0.6 H), 3.33-3.42 (m, 0.4 H), 2.93-3.22 (m, 1 H), 2.84 (br d, 1 H) | 450.0 $[M + H]^+$ | 99.0% |
| 720 | ($CD_3OD$) δ 8.46 (d, 1 H), 7.70 (s, 1 H), 7.32 (d, 1 H), 6.82-7.00 (m, 1.7 H), 6.76 (br s, 1 H), 6.45 (br s, 0.3 H), 4.82 (br s, 0.4 H), 4.24 (br d, 0.6 H), 3.68-3.91 (m, 0.6 H), 3.41 (br s, 0.4 H), 2.92-3.25 (m, 1 H), 2.70-2.91 (m, 1 H), 1.51-1.70 (m, 6 H) | 461.2 $[M + H]^+$ | 100% |
| 721 | ($CD_3OD$) δ 8.46 (d, 1 H), 7.70 (s, 1 H), 7.31 (d, 1 H), 6.81-6.93 (m, 1.7 H), 6.76 (br s, 1 H), 6.45 (br s, 0.3 H), 4.79 (br s, 0.3 H), 4.24 (br d, 0.7 H), 3.78 (br t, 0.7 H), 3.41 (br s, 0.3 H), 3.15 (br s, 1 H), 2.84 (br d, 1 H), 1.52-1.72 (m, 6 H) | 461.1 $[M + H]^+$ | 100% |
| 722 | ($CD_3OD$) δ 8.44 (d, 1 H), 7.68 (s, 1 H), 7.30 (d, 1 H), 6.84 (t, 1.6 H), 6.25-6.76 (m, 1.4 H), 4.79 (br s, 0.4 H), 4.17 (br d, 0.6 H), 3.36-3.84 (m, 1 H), 2.75-3.23 (m, 2 H), 1.49-1.69 (m, 6 H) | 507.1 $[M + H]^+$ | 96.2% |
| 723 | ($CD_3OD$) δ 8.44 (d, 1 H), 7.68 (s, 1 H), 7.30 (d, 1 H), 6.84 (t, 1.6 H), 6.31-6.76 (m, 1.4 H), 4.82 (br s, 0.4 H), 4.17 (br d, 0.6 H), 3.36-3.83 (m, 1 H), 2.75-3.22 (m, 2 H), 1.52-1.71 (m, 6 H) | 507.2 $[M + H]^+$ | 98.3% |
| 724 | ($CD_3OD$) δ 8.43 (d, 1 H), 7.56-7.74 (m, 1 H), 7.29 (d, 1 H), 6.42-6.93 (m, 3 H), 4.24-4.44 (m, 1 H), 3.39-3.80 (m, 1 H), 2.70-3.23 (m, 2 H), 2.37 (s, 3 H), 1.62 (br s, 6 H) | 441.3 $[M + H]^+$ | 98.3% |
| 725 | ($CD_3OD$) δ 8.44 (d, 1 H), 7.67 (s, 1 H), 7.29 (d, 1 H), 6.43-6.95 (m, 3 H), 4.35 (br s, 1 H), 3.38-3.80 (m, 1 H), 2.73-3.22 (m, 2 H), 2.37 (s, 3 H), 1.62 (br s, 6 H) | 441.3 $[M + H]^+$ | 99.8% |
| 726 | ($CD_3OD$) δ 8.33 (d, 1 H), 7.66 (s, 1 H), 6.95 (dd, 1 H), 6.46-6.89 (m, 3 H), 4.89 (br d, 1 H), 4.35 (br s, 1 H), 3.38-3.80 (m, 1 H), 2.70-3.20 (m, 2 H), 2.36 (s, 3 H), 1.56 (br s, 3 H) | 411.2 [M + H] | 98.4% |
| 727 | ($CD_3OD$) δ 8.33 (d, 1 H), 7.66 (s, 1 H), 6.95 (dd, 1 H), 6.42-6.90 (m, 3 H), 4.90 (br d, 1 H), 4.36 (br s, 1 H), 3.36-3.79 (m, 1 H), 2.70-3.20 (m, 2 H), 2.37 (s, 3 H), 1.55 (br s, 3 H) | 411.2 [M + H] | 99.9% |
| 728 | ($CD_3OD$) δ 8.25-8.46 (m, 2 H), 8.10 (s, 1 H), 7.56-7.73 (m, 1.3 H), 6.92-7.00 (m, 1.7 H), 6.68-6.89 (m, 2 H), 5.09 (br dd, 1 H), 4.00 (s, 3 H), 3.70-3.83 (m, 0.7 H), 3.40 (td, 0.3 H), 2.93-3.22 (m, 1 H), 2.79-2.89 (m, 1 H) | 434.1 $[M + H]^+$ | 99.8% |

TABLE 2-continued

| Ex. # | $^1$H NMR (400 MHz unless otherwise noted) | LCMS: m/z | % ee |
|---|---|---|---|
| 729 | ($CD_3OD$) δ 8.26-8.42 (m, 2 H), 8.10 (s, 1 H), 7.56-7.72 (m, 1.3 H), 6.92-7.00 (m, 1.7 H), 6.68-6.89 (m, 2 H), 5.09 (br dd, 1 H), 4.00 (s, 3 H), 3.70-3.84 (m, 0.7 H), 3.40 (td, 0.3 H), 2.93-3.22 (m, 1 H), 2.77-2.90 (m, 1 H) | 434.1 $[M + H]^+$ | 97.8% |
| 730 | ($CD_3OD$) δ 8.24-8.40 (m, 1 H), 7.81 (d, 1 H), 7.70 (s, 1 H), 7.51 (s, 0.3 H), 6.90-7.03 (m, 2.7 H), 6.71-6.88 (m, 2 H), 5.04 (br dd, 1 H), 4.03 (s, 3 H), 3.78 (ddd, 0.6 H), 3.37-3.45 (m, 0.4 H), 2.79-3.24 (m, 2 H) | 434.2 $[M + H]^+$ | 100% |
| 731 | ($CD_3OD$) δ 8.25-8.39 (m, 1 H), 7.81 (d, 1 H), 7.69 (s, 1 H), 7.51 (br s, 0.3 H), 6.91-7.02 (m, 2.7 H), 6.72-6.88 (m, 2 H), 4.96-5.10 (m, 1 H), 4.03 (s, 3 H), 3.73-3.83 (m, 0.6 H), 3.38-3.45 (m, 0.4 H), 2.80-3.23 (m, 2 H) | 434.3 $[M + H]^+$ | 99.8% |
| 732 | ($CD_3OD$) δ 8.78 (d, 1 H), 8.25-8.42 (m, 2 H), 8.02-8.16 (m, 1 H), 7.43-7.77 (m, 2.3 H), 6.90-7.06 (m, 1.7 H), 6.73-6.90 (m, 2 H), 4.93-5.08 (m, 1 H), 3.74-3.87 (m, 0.7 H), 3.43 (td, 0.3 H), 2.82-3.26 (m, 2 H) | 431.3 $[M + H]^+$ | 98.9% |
| 733 | ($CD_3OD$) δ 8.78 (d, 1 H), 8.22-8.42 (m, 2 H), 8.08 (td, 1 H), 7.43-7.76 (m, 2.3 H), 6.91-7.03 (m, 1.7 H), 6.74-6.88 (m, 2 H), 4.93-5.06 (m, 1 H), 3.74-3.86 (m, 0.7 H), 3.38-3.50 (m, 0.3 H), 2.81-3.25 (m, 2 H) | 431.2 $[M + H]^+$ | 99.8% |
| 734 | ($CD_3OD$) δ 8.78 (dd, 1 H), 8.36-8.49 (m, 1 H), 8.31 (dd, 1 H), 8.08 (td, 1 H), 7.60-7.75 (m, 2 H), 7.49 (br s, 0.3 H), 7.23-7.38 (m, 1 H), 6.97 (s, 0.7 H), 6.69-6.90 (m, 2 H), 4.95-5.08 (m, 1 H), 3.79 (ddd, 0.7 H), 3.37-3.51 (m, 0.3 H), 2.78-3.24 (m, 2 H) | 447.3 $[M + H]^+$ | 99.6% |
| 735 | ($CD_3OD$) δ 8.77 (d, 1 H), 8.35-8.50 (m, 1 H), 8.31 (d, 1 H), 8.08 (td, 1 H), 7.62-7.76 (m, 2 H), 7.49 (br s, 0.3 H), 7.23-7.37 (m, 1 H), 6.97 (br s, 0.7 H), 6.71-6.88 (m, 2 H), 4.95-5.06 (m, 1 H), 3.72-3.86 (m, 0.7 H), 3.38-3.49 (m, 0.3 H), 2.82-3.26 (m, 2 H) | 447.3 $[M + H]^+$ | 100% |
| 736 | ($CD_3OD$) δ 8.30 (d, 1 H), 7.69 (br s, 1 H), 7.11-7.30 (m, 1 H), 6.99 (br d, 1 H), 6.86 (br s, 1 H), 6.79 (t, 1 H), 6.52-6.70 (m, 1 H), 4.69-4.83 (m, 0.4 H), 4.25-4.40 (m, 0.6 H), 3.74 (br t, 0.6 H), 3.43 (br s, 0.4 H), 2.91-3.21 (m, 1 H), 2.83 (br d, 1 H), 2.45 (s, 3 H), 1.49-1.76 (m, 6 H) | 457.4 $[M + H]^+$ | 100% |
| 737 | ($CD_3OD$) δ 8.30 (d, 1 H), 7.68 (br s, 1 H), 7.10-7.30 (m, 1 H), 6.99 (br d, 1 H), 6.86 (br s, 1 H), 6.78 (t, 1 H), 6.53-6.70 (m, 1 H), 4.80 (br s, 0.2 H), 4.24-4.40 (m, 0.6 H), 3.65-3.83 (m, 0.6 H), 3.44 (br s, 0.4 H), 2.92-3.23 (m, 1 H), 2.82 (br d, 1 H), 2.44 (s, 3 H), 1.50-1.74 (m, 6 H) | 457.4 $[M + H]^+$ | 99.5% |
| 738 | ($CD_3OD$) δ 8.30 (br d, 1 H), 7.68 (s, 1 H), 7.09-7.31 (m, 1 H), 6.99 (br d, 1 H), 6.86 (br s, 1 H), 6.78 (t, 1 H), 6.61 (br s, 1 H), 4.97 (q, 1 H), 4.77 (br s, 0.3 H), 4.35 (br d, 0.6 H), 3.74 (br t, 0.6 H), 3.44 (br s, 0.3 H), 2.90-3.19 (m, 1 H), 2.81 (br d, 1 H), 2.44 (s, 3 H), 1.61 (br d, 3 H) | 443.3 $[M + H]^+$ | 99.6% |
| 739 | ($CD_3OD$) δ 8.30 (br d, 1 H), 7.68 (s, 1 H), 7.09-7.31 (m, 1 H), 6.99 (br d, 1 H), 6.86 (br s, 1 H), 6.78 (t, 1 H), 6.51-6.70 (m, 1 H), 4.97 (q, 1 H), 4.78 (br s, 0.1 H), 4.35 (br d, 0.6 H), 3.64-3.81 (m, 0.6 H), 3.46 (br d, 0.4 H), 2.91-3.19 (m, 1 H), 2.81 (br d, 1 H), 2.44 (s, 3 H), 1.60 (br d, 3 H) | 443.3 $[M + H]^+$ | 99.3% |
| 740 | ($CD_3OD$) δ 8.77 (d, 1 H), 8.20-8.36 (m, 2 H), 8.08 (td, 1 H), 7.60-7.75 (m, 2 H), 7.50 (s, 0.3 H), 6.92-7.04 (m, 1.7 H), 6.71-6.84 (m, 1 H), 6.57-6.68 (m, 1 H), 5.00 (br dd, 1 H), 3.74-3.86 (m, 0.6 H), 3.43 (td, 0.3 H), 2.96-3.26 (m, 1 H), 2.79-2.90 (m, 1 H), 2.39-2.49 (m, 3 H) | 427.3 $[M + H]^+$ | 99.6% |
| 741 | ($CD_3OD$) δ 8.77 (d, 1 H), 8.20-8.36 (m, 2 H), 8.08 (td, 1 H), 7.61-7.74 (m, 2 H), 7.50 (s, 0.3 H), 6.93-7.04 (m, 1.7 H), 6.72-6.83 (m, 1 H), 6.57-6.68 (m, 1 H), 5.00 (br dd, 1 H), 3.73-3.87 (m, 0.6 H), 3.43 (td, 0.4 H), 2.95-3.27 (m, 1 H), 2.85 (br d, 1 H), 2.39-2.48 (m, 3 H) | 427.3 $[M + H]^+$ | 100% |
| 742 | ($CD_3OD$) δ 8.20-8.34 (m, 1 H), 7.81 (d, 1 H), 7.69 (s, 1 H), 7.52 (s, 0.5 H), 6.91-7.03 (m, 2.5 H), 6.71-6.85 (m, 1 H), 6.52-6.66 (m, 1 H), 5.01 (br dd, 1 H), 4.02 (s, 3 H), 3.72-3.83 (m, 0.7 H), 3.41 (td, 0.4 H), 3.12-3.24 (m, 0.8 H), 2.93-3.06 (m, 0.4 H), 2.75-2.88 (m, 1 H), 2.35-2.48 (m, 3 H) | 430.4 $[M + H]^+$ | 100% |
| 743 | ($CD_3OD$) δ 8.21-8.35 (m, 1 H), 7.81 (s, 1 H), 7.69 (s, 1 H), 7.52 (s, 0.5 H), 6.93-7.02 (m, 2.5 H), 6.71-6.82 (m, 1 H), 6.53-6.66 (m, 1 H), 5.01 (br dd, 0.4 H), 4.03 (s, 3 H), 3.72-3.84 (m, 0.7 H), 3.35-3.46 (m, 1 H), 3.12-3.24 (m, 0.6 H), 2.94-3.06 (m, 0.4 H), 2.83 (br d, 1 H), 2.40-2.49 (m, 3 H) | 430.4 $[M + H]^+$ | 100% |
| 744 | ($CD_3OD$) δ 8.25-8.43 (m, 1 H), 7.55-7.78 (m, 1 H), 6.93-7.02 (m, 1 H), 6.79-6.92 (m, 1.7 H), 6.55-6.75 (m, 1 H), 6.05 (br s, 0.3 H), 4.81-4.87 (m, 0.3 H), 3.67-3.86 (m, 1.4 H), 3.45 (td, 0.3 H), 2.71-3.08 (m, 2 H), 1.54-1.71 (m, 6 H) | 479.2 [M + H] | 98.4% |
| 745 | ($CD_3OD$) δ 8.29-8.40 (m, 1 H), 7.63-7.73 (m, 1 H), 6.92-7.02 (m, 1 H), 6.78-6.91 (m, 1.7 H), 6.58-6.75 (m, 1 H), 6.04 (br s, 0.3 H), 4.81-4.87 (m, 0.2 H), 3.68-3.86 (m, 1.4 H), 3.45 (td, 0.4 H), 2.72-3.07 (m, 2 H), 1.53-1.71 (m, 6 H) | 479.2 [M + H] | 98.9% |

TABLE 2-continued

| Ex. # | $^1$H NMR (400 MHz unless otherwise noted) | LCMS: m/z | % ee |
|---|---|---|---|
| 746 | ($CD_3OD$) δ 8.34 (d, 1 H), 7.67 (s, 1 H), 6.96 (dd, 1 H), 6.83 (td, 1.7 H), 6.63-6.78 (m, 1 H), 6.38 (br s, 0.3 H), 4.72-4.82 (m, 0.4 H), 4.16 (br d, 0.6 H), 3.37-3.84 (m, 1 H), 2.75-3.22 (m, 2 H), 1.52-1.66 (m, 6 H) | 489.2 [M + H] | 98.8% |
| 747 | ($CD_3OD$) δ 8.34 (d, 1 H), 7.67 (s, 1 H), 6.96 (dd, 1 H), 6.83 (td, 1.7 H), 6.64-6.78 (m, 1 H), 6.38 (br s, 0.3 H), 4.81 (br s, 0.4 H), 4.16 (br d, 0.6 H), 3.36-3.86 (m, 1 H), 2.75-3.20 (m, 2 H), 1.52-1.65 (m, 6 H) | 489.1 [M + H] | 99.7% |
| 748 | ($CD_3OD$) δ 8.39 (s, 1 H), 8.21-8.33 (m, 1 H), 8.10 (s, 1 H), 7.52-7.74 (m, 1 H), 6.92-7.03 (m, 2 H), 6.71-6.82 (m, 1 H), 6.53-6.65 (m, 1 H), 5.06 (dd, 1 H), 4.00 (s, 3 H), 3.70-3.85 (m, 0.7 H), 3.40 (td, 0.3 H), 3.10-3.23 (m, 0.7 H), 2.93-3.06 (m, 0.3 H), 2.78-2.88 (m, 1 H), 2.37-2.49 (m, 3 H) | 430.3 $[M + H]^+$ | 99.4% |
| 749 | ($CD_3OD$) δ 8.38 (s, 1 H), 8.20-8.34 (m, 1 H), 8.09 (s, 1 H), 7.54-7.73 (m, 1 H), 6.91-7.03 (m, 2 H), 6.70-6.82 (m, 1 H), 6.52-6.65 (m, 1 H), 5.06 (dd, 1 H), 4.00 (s, 3 H), 3.71-3.82 (m, 0.7 H), 3.40 (td, 0.3 H), 3.09-3.23 (m, 0.7 H), 2.91-3.04 (m, 0.3 H), 2.76-2.89 (m, 1 H), 2.36-2.49 (m, 3 H) | 430.3 $[M + H]^+$ | 98.6% |
| 750 | ($CD_3OD$) δ 8.29 (d, 1 H), 7.66 (s, 1 H), 6.98 (d, 1 H), 6.49-6.89 (m, 3 H), 4.90-4.94 (m, 1 H), 4.73 (br s, 0.3 H), 4.34 (br d, 0.7 H), 3.38-3.79 (m, 1 H), 3.09 (br s, 1 H), 2.79 (br d, 1 H), 2.44 (s, 3 H), 2.36 (s, 3 H), 1.55 (br s, 3 H) | 407.3 $[M + H]^+$ | 99.1% |
| 751 | ($CD_3OD$) δ 8.30 (d, 1 H), 7.66 (s, 1 H), 6.98 (d, 1 H), 6.72-6.89 (m, 1.7 H), 6.48-6.70 (m, 1.3 H), 4.89-4.93 (m, 1 H), 4.67-4.76 (m, 0.4 H), 4.32 (br s, 0.6 H), 3.39-3.81 (m, 1 H), 3.10 (br s, 1 H), 2.79 (br d, 1 H), 2.44 (s, 3 H), 2.36 (s, 3 H), 1.56 (br s, 3 H) | 407.4 $[M + H]^+$ | 99.4% |
| 752 | ($CD_3OD$) δ 8.29 (d, 1 H), 7.66 (s, 1 H), 6.98 (d, 1 H), 6.84 (br s, 0.6 H), 6.77 (t, 1 H), 6.48-6.70 (m, 1.4 H), 4.91-4.94 (m, 1 H), 4.72 (br s, 0.5 H), 4.34 (br s, 0.5 H), 3.54-3.81 (m, 1 H), 3.11 (br s, 1 H), 2.79 (br d, 1 H), 2.44 (s, 3 H), 2.36 (s, 3 H), 1.43-1.63 (m, 3 H) | 407.3 $[M + H]^+$ | 100% |
| 753 | ($CD_3OD$) δ 8.29 (d, 1 H), 7.66 (s, 1 H), 6.98 (d, 1 H), 6.84 (br s, 0.6 H), 6.77 (t, 1 H), 6.46-6.72 (m, 1.4 H), 4.90-4.94 (m, 1 H), 4.73 (br s, 0.4 H), 4.33 (br s, 0.6 H), 3.39-3.80 (m, 1 H), 3.10 (br s, 1 H), 2.79 (br d, 1 H), 2.44 (s, 3 H), 2.37 (s, 3 H), 1.55 (br s, 3 H) | 407.4 $[M + H]^+$ | 99.8% |
| 754 | ($CD_3OD$) δ 8.29 (d, 1 H), 7.75 (br s, 1 H), 6.98 (d, 1 H), 6.55-6.90 (m, 3 H), 4.60-4.78 (m, 0.5 H), 4.35 (br s, 0.5 H), 3.38-3.81 (m, 1 H), 3.12 (br d, 1 H), 2.80 (br d, 1 H), 2.32-2.50 (m, 6 H), 1.61 (br s, 6 H) | 421.4 $[M + H]^+$ | 100% |
| 755 | ($CD_3OD$) δ 8.29 (d, 1 H), 7.66 (s, 1 H), 6.97 (d, 1 H), 6.47-6.90 (m, 3 H), 4.63-4.77 (m, 0.5 H), 4.33 (br s, 0.5 H), 3.38-3.82 (m, 1 H), 3.11 (br s, 1 H), 2.79 (br d, 1 H), 2.33-2.48 (m, 6 H), 1.61 (br s, 6 H) | 421.4 $[M + H]^+$ | 99.8% |
| 756 | ($CD_3OD$) δ 8.34 (d, 1 H), 7.68 (s, 1 H), 6.96 (dd, 7.7 Hz, 1 H), 6.65-6.89 (m, 2.7 H), 6.43 (br s, 0.3 H), 4.15-4.82 (m, 1 H), 3.38-3.84 (m, 1 H), 2.79-3.18 (m, 2 H), 1.53-1.68 (m, 6 H) | 445.3 $[M + H]^+$ | 100% |
| 757 | ($CD_3OD$) δ 8.34 (d, 1 H), 7.68 (s, 1 H), 6.96 (dd, 1 H), 6.63-6.89 (m, 2.7 H), 6.43 (br s, 0.3 H), 4.13-4.81 (m, 1 H), 3.37-3.82 (m, 1 H), 2.78-3.18 (m, 2 H), 1.52-1.67 (m, 6 H) | 445.3 $[M + H]^+$ | 100% |
| 758 | ($CD_3OD$) δ 8.43 (s, 1 H), 8.34 (d, 1 H), 7.68 (s, 1 H), 6.91-7.31 (m, 2 H), 6.40-6.89 (m, 3 H), 4.28-4.83 (m, 1 H), 3.37-3.82 (m, 1 H), 2.74-3.16 (m, 2 H) | 403.3 [M + H] | 99.7% |
| 759 | ($CD_3OD$) δ 8.43 (s, 1 H), 8.34 (d, 1 H), 7.68 (s, 1 H), 6.92-7.31 (m, 2 H), 6.45-6.92 (m, 3 H), 4.27-4.83 (m, 1 H), 3.37-3.78 (m, 1 H), 2.77-3.13 (m, 2 H) | 403.2 [M + H] | 99.3% |
| 760 | ($CD_3OD$) δ 8.25-8.49 (m, 2 H), 7.58-8.13 (m, 2 H), 6.92-7.01 (m, 1 H), 6.53-6.91 (m, 3 H), 4.48 (br s, 1 H), 3.41-3.83 (m, 1 H), 2.74-3.15 (m, 2 H) | 353.2 $[M + H]^+$ | 100% |
| 761 | ($CD_3OD$) δ 8.26-8.50 (m, 2 H), 7.64-8.14 (m, 2 H), 6.92-7.01 (m, 1 H), 6.53-6.92 (m, 3 H), 4.39-4.79 (m, 1 H), 3.37-3.84 (m, 1 H), 2.73-3.17 (m, 2 H) | 353.3 $[M + H]^+$ | 99.3% |
| 762 | ($CD_3OD$) δ 8.35 (br d, 1 H), 7.70 (d, 1 H), 6.88-7.02 (m, 2 H), 6.50-6.88 (m, 2 H), 4.48 (dd, 1 H), 4.00-4.05 (m, 3 H), 3.62-3.71 (m, 0.6 H), 2.92-3.22 (m, 1.4 H), 2.71-2.87 (m, 1 H) | 401.2 $[M + H]^+$ | 100% |
| 763 | ($CD_3OD$) δ 8.35 (br d, 1 H), 7.70 (br d, 1 H), 6.88-7.01 (m, 2 H), 6.50-6.87 (m, 2 H), 4.48 (dd, 1 H), 3.98-4.07 (m, 3 H), 3.60-3.72 (m, 0.6 H), 2.92-3.24 (m, 1.4 H), 2.69-2.86 (m, 1 H) | 401.2 $[M + H]^+$ | 100% |
| 764 | ($CD_3OD$) δ 8.35 (t, 1 H), 7.70 (br d, 1 H), 6.68-7.03 (m, 4.6 H), 6.53 (s, 0.4 H), 4.47 (dd, 1 H), 4.06-4.16 (m, 3 H), 3.62-3.74 (m, 0.6 H), 2.93-3.24 (m, 1.4 H), 2.68-2.87 (m, 1 H) | 417.2 $[M + H]^+$ | 100% |
| 765 | ($CD_3OD$) δ 8.29-8.41 (m, 1 H), 7.70 (br s, 1 H), 6.70-7.02 (m, 4.7 H), 6.53 (s, 0.3 H), 4.47 (dd, 1 H), 4.06-4.15 (m, 3 H), 3.63-3.75 (m, 0.6 H), 2.93-3.23 (m, 1.4 H), 2.70-2.89 (m, 1 H) | 417.2 $[M + H]^+$ | 100% |
| 766 | ($CD_3OD$) δ 8.39 (s, 2 H), 7.59-8.16 (m, 2 H), 7.29 (d, 1 H), 6.53-6.91 (m, 3 H), 4.45-4.85 (m, 1 H), 3.74 (br s, 1 H), 2.71-3.17 (m, 2 H) | 369.2 $[M + H]^+$ | 100% |

TABLE 2-continued

| Ex. # | $^1$H NMR (400 MHz unless otherwise noted) | LCMS: m/z | % ee |
|---|---|---|---|
| 767 | ($CD_3OD$) δ 8.40 (s, 2 H), 7.68-8.13 (m, 2 H), 7.30 (d, 1 H), 6.57-6.93 (m, 3 H), 4.42-4.84 (m, 1 H), 3.74 (br s, 1 H), 2.77-3.17 (m, 2 H) | 369.2 $[M + H]^+$ | 99.1% |
| 768 | ($CD_3OD$) δ 8.24-8.43 (m, 2 H), 8.08 (br s, 0.4 H), 7.77 (br s, 0.6 H), 7.68 (s, 1 H), 6.99 (br d, 1 H), 6.88 (br s, 1 H), 6.78 (br t, 1 H), 6.40-6.69 (m, 1 H), 4.47 (br s, 1 H), 3.76 (br s, 1 H), 2.91-3.17 (m, 1 H), 2.80 (br s, 1 H), 2.44 (s, 3 H) | 348.9 $[M + H]^+$ | 100% |
| 769 | ($CD_3OD$) δ 8.23-8.45 (m, 2 H), 8.08 (br s, 0.4 H), 7.61-7.86 (m, 1.6 H), 6.99 (br d, 1 H), 6.88 (br s, 1 H), 6.78 (br t, 1 H), 6.41-6.67 (m, 1 H), 4.78 (br s, 0.5 H), 4.47 (br s, 0.5 H), 3.76 (br s, 0.6 H), 3.35 (br s, 0.4 H), 2.91-3.16 (m, 1 H), 2.77 (br d, 1 H), 2.44 (s, 3 H) | 349.0 $[M + H]^+$ | 99.8% |
| 770 | ($CD_3OD$) δ 8.19-8.35 (m, 2 H), 7.67 (s, 1 H), 6.98 (d, 1 H), 6.71-6.90 (m, 2 H), 6.61 (br s, 1 H), 4.31 (br s, 1 H), 3.71 (br s, 1 H), 2.92-3.15 (m, 1 H), 2.78 (br d, 1 H), 2.33-2.51 (m, 6 H) | 363.1 $[M + H]^+$ | 100% |
| 771 | ($CD_3OD$) δ 8.17-8.38 (m, 2 H), 7.67 (s, 1 H), 6.98 (d, 1 H), 6.73-6.90 (m, 2 H), 6.60 (br s, 1 H), 4.29 (br s, 1 H), 3.72 (br s, 1 H), 2.90-3.18 (m, 1 H), 2.78 (br d, 1 H), 2.32-2.49 (m, 6 H) | 363.0 $[M + H]^+$ | 99.5% |
| 772 | ($CD_3OD$) δ 8.46-8.53 (m, 1 H), 8.31-8.39 (m, 1 H), 7.66-7.75 (m, 1 H), 6.81-7.03 (m, 3 H), 6.74 (s, 0.6 H), 6.54 (s, 0.2 H), 6.03 (s, 0.2 H), 3.41-3.88 (m, 2 H), 2.76-3.00 (m, 2 H) | 421.0 $[M + H]^+$ | 99.6% |
| 773 | ($CD_3OD$) δ 8.44-8.49 (m, 1 H), 8.29-8.36 (m, 1 H), 7.64-7.72 (m, 1 H), 6.79-7.01 (m, 3 H), 6.72 (s, 0.6 H), 6.52 (s, 0.2 H), 6.01 (br s, 0.2 H), 3.37-3.88 (m, 2 H), 2.89-2.99 (m, 1 H), 2.74-2.86 (m, 1 H) | 421.0 $[M + H]^+$ | 99.4% |
| 774 | ($CD_3OD$) δ 8.33 (d, 1 H), 8.25 (s, 1 H), 7.67 (s, 1 H), 6.95 (dd, 1 H), 6.49-6.88 (m, 3 H), 4.21-4.83 (m, 1 H), 3.38-3.85 (m, 1 H), 3.06 (br s, 1 H), 2.78 (br d, 1 H), 2.38 (s, 3 H) | 367.1 $[M + H]^+$ | 99.2% |
| 775 | ($CD_3OD$) δ 8.33 (d, 1 H), 8.25 (s, 1 H), 7.67 (s, 1 H), 6.96 (dd, 1 H), 6.49-6.88 (m, 3 H), 4.26-4.83 (m, 1 H), 3.35-3.82 (m, 1 H), 2.96-3.14 (m, 1 H), 2.78 (br d, 1 H), 2.38 (s, 3 H) | 367.0 $[M + H]^+$ | 99.7% |
| 776 | ($CD_3OD$) δ 8.28-8.48 (m, 1 H), 7.50-7.84 (m, 3 H), 6.74-7.08 (m, 4 H), 6.15-6.56 (m, 1 H), 4.82 (br s, 0.5 H), 4.05-4.14 (m, 0.5 H), 3.64-3.78 (m, 0.5 H), 3.12-3.29 (m, 0.5 H), 2.70-3.06 (m, 2 H) | 402.0 $[M + H]^+$ | 99.5% |
| 777 | ($CD_3OD$) δ 8.29-8.47 (m, 1 H), 7.50-7.84 (m, 3 H), 6.25-7.11 (m, 5 H), 4.84 (br d, 0.5 H), 4.04-4.12 (m, 0.5 H), 3.61-3.78 (m, 0.5 H), 3.19-3.28 (m, 0.5 H), 2.92-3.06 (m, 1 H), 2.75 (br d, 1 H) | 402.0 $[M + H]^+$ | 99.3% |
| 778 | ($CD_3OD$) δ 8.78 (br d, 1 H), 8.26-8.36 (m, 1 H), 7.99-8.14 (m, 2 H), 7.59-7.74 (m, 2 H), 7.50 (s, 0.3 H), 6.97 (s, 0.7 H), 6.72-6.84 (m, 1 H), 6.63-6.71 (m, 1 H), 6.54-6.62 (m, 1 H), 5.00 (dd, 1 H), 3.86-4.06 (m, 3 H), 3.72-3.85 (m, 0.7 H), 3.43 (td, 0.3 H), 2.93-3.29 (m, 1 H), 2.86 (br dd, 1 H) | 443.0 $[M + H]^+$ | 100% |
| 779 | ($CD_3OD$) δ 8.78 (br d, 1 H), 8.28-8.34 (m, 1 H), 7.99-8.16 (m, 2 H), 7.61-7.78 (m, 2 H), 7.50 (s, 0.3 H), 6.97 (s, 0.7 H), 6.74-6.83 (m, 1 H), 6.63-6.72 (m, 1 H), 6.52-6.62 (m, 1 H), 5.00 (br dd, 1 H), 3.92-4.00 (m, 3 H), 3.72-3.84 (m, 0.7 H), 3.43 (td, 0.3 H), 2.96-3.27 (m, 1 H), 2.86 (br dd, 1 H) | 443.0 $[M + H]^+$ | 100% |
| 780 | ($CD_3OD$) δ 8.40-8.53 (m, 1 H), 7.70 (d, 1 H), 7.24-7.33 (m, 1 H), 6.67-7.00 (m, 3.7 H), 6.51 (s, 0.3 H), 4.92 (br d, 0.3 H), 4.47 (dd, 0.7 H), 4.05-4.15 (m, 3 H), 3.68 (ddd, 0.5 H), 2.93-3.27 (m, 1.5 H), 2.72-2.88 (m, 1 H) | 433.0 $[M + H]^+$ | 100% |
| 781 | ($CD_3OD$) δ 8.36-8.52 (m, 1 H), 7.70 (d, 1 H), 7.24-7.36 (m, 1 H), 6.65-7.01 (m, 3.7 H), 6.51 (s, 0.3 H), 4.92 (br d, 0.4 H), 4.47 (dd, 0.6 H), 4.05-4.17 (m, 3 H), 3.68 (ddd, 0.6 H), 2.92-3.27 (m, 1.4 H), 2.71-2.89 (m, 1 H) | 432.9 $[M + H]^+$ | 99.5% |
| 782 | ($CD_3OD$) δ 8.40-8.58 (m, 1 H), 7.49-7.85 (m, 3 H), 7.30 (d, 1 H), 6.71-7.11 (m, 3.2 H), 6.25-6.54 (m, 0.8 H), 4.83 (br s, 0.5 H), 4.02-4.14 (m, 0.5 H), 3.71 (br t, 0.5 H), 3.17-3.29 (m, 0.5 H), 2.93-3.06 (m, 1 H), 2.75 (br d, 1 H) | 417.9 $[M + H]^+$ | 99.6% |
| 783 | ($CD_3OD$) δ 8.36-8.59 (m, 1 H), 7.47-7.88 (m, 3 H), 7.30 (d, 1 H), 6.67-7.13 (m, 3.2 H), 6.18-6.57 (m, 0.8 H), 4.82 (br s, 0.5 H), 4.09 (br dd, 0.5 H), 3.62-3.79 (m, 0.5 H), 3.15-3.28 (m, 0.5 H), 2.90-3.07 (m, 1 H), 2.76 (br d, 1 H) | 418.0 $[M + H]^+$ | 99.6% |
| 784 | ($CD_3OD$) δ 8.27-8.50 (m, 2 H), 7.51-7.76 (m, 2 H), 7.03-7.25 (m, 2 H), 6.89-7.02 (m, 1 H), 6.81 (br t, 1 H), 4.26 (br s, 1 H), 4.06 (br s, 1 H), 3.05 (br d, 1 H), 2.86 (br d, 1 H), 2.34-2.63 (m, 3 H) | 399.0 $[M + H]^+$ | 100% |
| 785 | ($CD_3OD$) δ 8.42 (br s, 1 H), 8.31-8.38 (m, 1 H), 7.65 (s, 1 H), 7.53-7.62 (m, 1 H), 7.03-7.22 (m, 2 H), 6.95 (br d, 1 H), 6.82 (br s, 1 H), 4.26 (br s, 1 H), 4.06 (br s, 1 H), 2.99-3.12 (m, 1 H), 2.86 (dd, 1 H), 2.47 (br s, 3 H) | 399.0 $[M + H]^+$ | 99.8% |
| 786 | ($CD_3OD$) δ 8.35 (d, 1 H), 7.74 (s, 1 H), 7.59 (br d, 1 H), 7.15-7.20 (m, 1 H), 6.88-7.14 (m, 2 H), 6.82 (td, 1 H), 4.29 (br s, 1 H), 4.07 (br s, 1 H), 3.13 (br d, 1 H), 2.89 (dd, 1 H), 2.47 (br s, 3 H), 1.67 (s, 6 H) | 457.0 $[M + H]^+$ | 97.5% |

TABLE 2-continued

| Ex. # | $^1$H NMR (400 MHz unless otherwise noted) | LCMS: m/z | % ee |
|---|---|---|---|
| 787 | ($CD_3OD$) δ 8.35 (d, 1 H), 7.93 (br s, 1 H), 7.60 (br d, 1 H), 7.18 (t, 1 H), 6.89-7.10 (m, 2 H), 6.84 (td, 1 H), 4.32 (br s, 1 H), 4.05 (br s, 1 H), 3.15 (br s, 1 H), 2.80-2.97 (m, 1 H), 2.48 (br s, 3 H), 1.67 (s, 6 H) | 457.0 $[M + H]^+$ | 99.0% |
| 788 | ($CD_3OD$) δ 8.44 (d, 1 H), 8.22-8.38 (m, 2 H), 7.70 (s, 1 H), 7.51-7.63 (m, 1.3 H), 6.91-7.01 (m, 1.7 H), 6.74-6.88 (m, 2 H), 4.94-5.08 (m, 1 H), 3.99 (s, 3 H), 3.72-3.85 (m, 0.7 H), 3.42 (td, 0.3 H), 2.96-3.25 (m, 1 H), 2.78-2.91 (m, 1 H) | 461.1 $[M + H]^+$ | 96.7% |
| 789 | ($CD_3OD$) δ 8.44 (d, 1 H), 8.21-8.39 (m, 2 H), 7.70 (s, 1 H), 7.51-7.63 (m, 1.3 H), 6.92-7.01 (m, 1.7 H), 6.72-6.88 (m, 2 H), 4.93-5.08 (m, 1 H), 3.99 (s, 3 H), 3.73-3.85 (m, 0.7 H), 3.42 (td, 0.3 H), 2.97-3.24 (m, 1 H), 2.85 (br d, 1 H) | 461.2 $[M + H]^+$ | 90.1% |
| 790 | ($CD_3OD$) δ 8.64 (d, 1 H), 8.27-8.39 (m, 1 H), 7.94 (t, 1 H), 7.67-7.80 (m, 2 H), 7.46 (s, 0.4 H), 6.94-7.00 (m, 1.6 H), 6.71-6.89 (m, 2 H), 4.98 (br dd, 1 H), 3.74-3.85 (m, 0.7 H), 3.38-3.50 (m, 0.3 H), 2.97-3.26 (m, 1 H), 2.85 (br d, 1 H) | 449.1 $[M + H]^+$ | 98.8% |
| 791 | ($CD_3OD$) δ 8.64 (d, 1 H), 8.26-8.38 (m, 1 H), 7.93 (td, 1 H), 7.68-7.79 (m, 2 H), 7.46 (s, 0.4 H), 6.93-6,99 (m, 1.6 H), 6.76-6.89 (m, 2 H), 4.98 (dd, 1 H), 3.76-3.85 (m, 0.7 H), 3.43 (td, 0.3 H), 2.98-3.26 (m, 1 H), 2.81-2.91 (m, 1 H) | 449.1 $[M + H]^+$ | 98.4% |
| 792 | ($CD_3OD$) δ 8.43 (s, 1 H), 7.66 (s, 1 H), 7.45 (br s, 1 H), 6.96-7.30 (m, 2 H), 6.34-6.96 (m, 3 H), 4.18-4.43 (m, 1 H), 3.36-3.98 (m, 1 H), 2.89-3.16 (m, 1 H), 2.80 (dd, 1 H), 2.65 (br s, 3 H) | 399.2 $[M + H]^+$ | 100% |
| 793 | ($CD_3OD$) δ 8.43 (s, 1 H), 7.67 (s, 1 H), 7.46 (br d, 1 H), 6.97-7.29 (m, 2 H), 6.38-6.94 (m, 3 H), 4.29 (br s, 1 H), 3.35-3.97 (m, 1 H), 3.01 (br s, 1 H), 2.80 (dd, 1 H), 2.65 (br s, 3 H) | 399.1 $[M + H]^+$ | 100% |
| 794 | ($CD_3OD$) δ 7.66 (s, 1 H), 7.46 (br s, 1 H), 6.93-7.28 (m, 2 H), 6.41-6.90 (m, 3 H), 4.74-4.87 (m, 0.7 H), 4.33 (br s, 0.3 H), 3.36-3.93 (m, 1 H), 2.76-3.18 (m, 2 H), 2.55-2.72 (m, 3 H), 1.36-1.81 (m, 6 H) | 457.2 $[M + H]^+$ | 100% |
| 795 | ($CD_3OD$) δ 7.67 (s, 1 H), 7.45 (br s, 1 H), 6.94-7.27 (m, 2 H), 6.44-6.90 (m, 3 H), 4.75-4.86 (m, 0.5 H), 4.34 (br d, 0.5 H), 3.35-3.93 (m, 1 H), 2.74-3.17 (m, 2 H), 2.55-2.72 (m, 3 H), 1.54-1.72 (m, 6 H) | 457.2 $[M + H]^+$ | 99.2% |
| 796 | ($CD_3OD$) δ 8.92 (s, 1 H), 8.27-8.39 (m, 2 H), 7.46-7.85 (m, 2.3 H), 6.91-7.05 (m, 1.7 H), 6.71-6.88 (m, 2 H), 4.92-5.13 (m, 1 H), 3.37-3.84 (m, 1 H), 2.90-3.22 (m, 1 H), 2.84 (br d, 1 H) | 470.1 $[M + H]^+$ | 100% |
| 797 | ($CD_3OD$) δ 8.92 (s, 1 H), 8.25-8.40 (m, 2 H), 7.48-7.83 (m, 2.4 H), 6.92-7.01 (m, 1.6 H), 6.72-6.88 (m, 2 H), 4.92-5.14 (m, 1 H), 3.37-3.84 (m, 1 H), 2.95-3.24 (m, 1 H), 2.86 (br d, 1 H) | 470.1 $[M + H]^+$ | 99.4% |
| 798 | ($CD_3OD$) δ 8.74-8.82 (m, 1 H), 8.26-8.37 (m, 1 H), 8.09 (tt, 1 H), 7.60-7.75 (m, 2 H), 7.38-7.54 (m, 1.5 H), 7.04-7.18 (m, 1 H), 7.00 (s, 0.5 H), 6.60-6.77 (m, 1.6 H), 6.45 (s, 0.4 H), 4.92-5.04 (m, 1 H), 3.89-4.00 (m, 0.5 H), 3.35-3.43 (m, 0.5 H), 2.96-3.25 (m, 1 H), 2.82-2.92 (m, 1 H), 2.44-2.71 (m, 3 H) | 427.1 $[M + H]^+$ | 100% |
| 799 | ($CD_3OD$) δ 8.73-8.81 (m, 1 H), 8.27-8.35 (m, 1 H), 8.08 (tt, 1 H), 7.62-7.74 (m, 2 H), 7.37-7.52 (m, 1.5 H), 7.05-7.15 (m, 1 H), 7.00 (s, 0.5 H), 6.59-6.76 (m, 1.6 H), 6.44 (s, 0.4 H), 4.93-5.03 (m, 1 H), 3.93 (br t, 0.5 H), 3.35-3.43 (m, 0.5 H), 2.94-3.25 (m, 1 H), 2.82-2.91 (m, 1 H), 2.44-2.70 (m, 3 H) | 427.2 $[M + H]^+$ | 100% |
| 800 | ($CD_3OD$) δ 8.39 (d, 1 H), 8.09 (s, 1 H), 7.68 (d, 1 H), 7.38-7.52 (m, 1.5 H), 7.10 (ddd, 1 H), 6.97 (s, 0.5 H), 6.41-6.76 (m, 2 H), 4.91-5.11 (m, 1 H), 4.00 (d, 3 H), 3.85-3.95 (m, 0.6 H), 3.34-3.40 (m, 0.4 H), 2.93-3.22 (m, 1 H), 2.84 (dt, 1 H), 2.48-2.69 (m, 3 H) | 430.2 $[M + H]^+$ | 100% |
| 801 | ($CD_3OD$) δ 8.39 (s, 1 H), 8.10 (s, 1 H), 7.69 (d, 1 H), 7.39-7.52 (m, 1.5 H), 7.10 (ddd, 1 H), 6.98 (s, 0.5 H), 6.42-6.75 (m, 2 H), 4.92-5.11 (m, 1 H), 4.00 (d, 3 H), 3.86-3.95 (m, 0.5 H), 3.33-3.41 (m, 0.5 H), 2.94-3.21 (m, 1 H), 2.84 (dt, 1 H), 2.48-2.69 (m, 3 H) | 430.2 $[M + H]^+$ | 99.4% |
| 802 | ($CD_3OD$) δ 7.81 (dd, 1 H), 7.70 (d, 1 H), 7.36-7.52 (m, 1.5 H), 7.05-7.16 (m, 1 H), 6.98 (s, 1.5 H), 6.64-6.77 (m, 1 H), 6.35-6.63 (m, 1 H), 5.01 (br dd, 1 H), 4.03 (d, 3 H), 3.84-3.95 (m, 0.6 H), 3.33-3.39 (m, 0.4 H), 2.93-3.22 (m, 1 H), 2.78-2.90 (m, 1 H), 2.47-2.68 (m, 3 H) | 430.2 $[M + H]^+$ | 100% |
| 803 | ($CD_3OD$) δ 7.82 (dd, 1 H), 7.69 (d, 1 H), 7.38-7.53 (m, 1.5 H), 7.04-7.18 (m, 1 H), 6.99 (d, 1.5 H), 6.64-6.76 (m, 1 H), 6.41-6.64 (m, 1 H), 5.01 (br dd, 1 H), 4.03 (d, 3 H), 3.84-3.96 (m, 0.6 H), 3.34-3.39 (m, 0.4 H), 2.93-3.24 (m, 1 H), 2.80-2.91 (m, 1 H), 2.45-2.72 (m, 3 H) | 430.2 $[M + H]^+$ | 100% |
| 804 | ($CD_3OD$) δ 8.24 (s, 1 H), 7.67 (br s, 1 H), 7.49 (br d, 1 H), 7.11-7.28 (m, 0.7 H), 7.08 (d, 1 H), 6.99 (s, 0.3 H), 6.47-6.88 (m, 2 H), 4.31 (br d, 1 H), 3.73 (br s, 1 H), 2.91-3.20 (m, 1 H), 2.81 (br d, 1 H), 2.32 (s, 3 H), 1.51-1.72 (m, 6 H) | 457.1 $[M + H]^+$ | 100% |

TABLE 2-continued

| Ex. # | $^1$H NMR (400 MHz unless otherwise noted) | LCMS: m/z | % ee |
|---|---|---|---|
| 805 | ($CD_3OD$) δ 8.24 (s, 1 H), 7.66 (br s, 1 H), 7.49 (br d, 1 H), 7.11-7.29 (m, 0.8 H), 7.08 (d, 1 H), 6.99 (s, 0.2 H), 6.46-6.89 (m, 2 H), 4.31 (br d, 1 H), 3.73 (br s, 1 H), 2.90-3.20 (m, 1 H), 2.81 (br d, 1 H), 2.25-2.35 (m, 3 H), 1.52-1.76 (m, 6 H) | 457.2 $[M + H]^+$ | 99.2% |
| 806 | ($CD_3OD$) δ 8.24-8.37 (m, 1 H), 8.00 (s, 1 H), 7.81-7.89 (m, 1 H), 7.46-7.75 (m, 1.4 H), 6.93-7.09 (m, 1.6 H), 6.73-6.86 (m, 1 H), 6.53-6.70 (m, 1 H), 5.07 (dd, 1 H), 4.05-4.15 (m, 3 H), 3.37-3.85 (m, 1 H), 2.96-3.27 (m, 1 H), 2.79-2.93 (m, 1 H), 2.36-2.52 (m, 3 H) | 430.2 $[M + H]^+$ | 100% |
| 807 | ($CD_3OD$) δ 8.25-8.37 (m, 1 H), 8.00 (s, 1 H), 7.83-7.94 (m, 1 H), 7.54-7.80 (m, 1.3 H), 6.96-7.09 (m, 1.7 H), 6.73-6.87 (m, 1 H), 6.51-6.69 (m, 1 H), 5.07 (dd, 1 H), 4.09-4.19 (m, 3 H), 3.38-3.89 (m, 1 H), 2.95-3.26 (m, 1 H), 2.78-2.91 (m, 1 H), 2.40-2.52 (m, 3 H) | 430.2 $[M + H]^+$ | 93.0% |
| 808 | ($CD_3OD$) δ 8.31-8.45 (m, 1 H), 8.00 (s, 1 H), 7.83-7.91 (m, 1 H), 7.50-7.80 (m, 1,4 H), 6.94-7.06 (m, 1.6 H), 6.72-6.91 (m, 2 H), 5.10 (dd, 1 H), 4.10-4.20 (m, 3 H), 3.38-3.88 (m, 1 H), 2.96-3.29 (m, 1 H), 2.80-2.93 (m, 1 H) | 434.2 $[M + H]^+$ | 92.5% |
| 809 | ($CD_3OD$) δ 8.29-8.40 (m, 1 H), 7.99 (s, 1 H), 7.84-7.89 (m, 1 H), 7.50-7.76 (m, 1.4 H), 6.94-7.04 (m, 1.6 H), 6.74-6.90 (m, 2 H), 4.94-5.13 (m, 1 H), 4.10-4.14 (m, 3 H), 3.38-3.87 (m, 1 H), 2.97-3.28 (m, 1 H), 2.80-2.91 (m, 1 H) | 434.2 $[M + H]^+$ | 100% |
| 810 | ($CD_3OD$) δ 8.69 (d, 1 H), 7.69 (s, 1 H), 7.63 (br d, 1 H), 7.10-7.29 (m, 1 H), 6.96-7.01 (m, 1 H), 6.54-6.90 (m, 2 H), 4.37 (br d, 1 H), 3.74 (br s, 1 H), 2.71-3.21 (m, 2 H), 1.55-1.70 (m, 6 H) | 511.2 $[M + H]^+$ | 98.3% |
| 811 | ($CD_3OD$) δ 8.69 (d, 1 H), 7.61-7.71 (m, 2 H), 7.11-7.27 (m, 1 H), 6.99 (t, 1 H), 6.57-6.91 (m, 2 H), 4.37 (br d, 1 H), 3.64-3.84 (m, 1 H), 2.75-3.21 (m, 2 H), 1.53-1.69 (m, 6 H) | 511.2 $[M + H]^+$ | 99.6% |
| 812 | ($CD_3OD$) δ 8.77 (br d, 1 H), 8.15-8.39 (m, 2 H), 8.09 (br t, 1 H), 7.61-7.73 (m, 2 H), 7.40-7.57 (m, 1 H), 7.02-7.14 (m, 1 H), 6.96 (s, 1 H), 6.46-6.64 (m, 1 H), 4.98 (br dd, 1 H), 3.74-3.85 (m, 0.9 H), 3.40 (br d, 0.1 H), 2.93-3.26 (m, 1 H), 2.84 (br d, 1 H), 2.23-2.37 (m, 3 H) | 427.2 $[M + H]^+$ | 100% |
| 813 | ($CD_3OD$) δ 8.77 (dd, 1 H), 8.15-8.34 (m, 2 H), 8.03-8.12 (m, 1 H), 7.62-7.72 (m, 2 H), 7.41-7.53 (m, 1 H), 7.01-7.12 (m, 1 H), 6.95 (s, 1 H), 6.49-6.60 (m, 1 H), 4.98 (br dd, 1 H), 3.74-3.88 (m, 0.8 H), 3.38-3.49 (m, 0.2 H), 3.13-3.26 (m, 0.7 H), 2.93-3.06 (m, 0.3 H), 2.78-2.89 (m, 1 H), 2.23-2.36 (m, 3 H) | 427.2 $[M + H]^+$ | 99.9% |
| 814 | ($CD_3OD$) δ 8.15-8.29 (m, 1 H), 7.81 (d, 1 H), 7.68 (s, 1 H), 7.41-7.54 (m, 1 H), 7.03-7.12 (m, 1 H), 6.98-7.01 (m, 1 H), 6.94 (s, 1 H), 6.45-6.60 (m, 1 H), 5.00 (br dd, 1 H), 3.99-4.07 (m, 3 H), 3.71-3.82 (m, 0.7 H), 3.36-3.45 (m, 0.3 H), 2.93-3.23 (m, 1 H), 2.83 (br d, 1 H), 2.25-2.35 (m, 3 H) | 430.2 $[M + H]^+$ | 100% |
| 815 | ($CD_3OD$) δ 8.17-8.29 (m, 1 H), 7.78-7.84 (m, 1 H), 7.69 (s, 1 H), 7.41-7.56 (m, 1 H), 7.03-7.13 (m, 1 H), 6.97-7.02 (m, 1 H), 6.94 (s, 1 H), 6.42-6.61 (m, 1 H), 5.00 (br dd, 1 H), 4.00-4.06 (m, 3 H), 3.70-3.83 (m, 0.6 H), 3.34-3.45 (m, 0.4 H), 2.92-3.24 (m, 1 H), 2.74-2.89 (m, 1 H), 2.26-2.35 (m, 3 H) | 430.2 $[M + H]^+$ | 99.9% |
| 816 | ($CD_3OD$) δ 8.42 (d, 1 H), 8.18-8.32 (m, 2 H), 7.70 (s, 1 H), 7.49-7.62 (m, 1 H), 6.92-7.01 (m, 2 H), 6.69-6.80 (m, 1 H), 6.55-6.66 (m, 1 H), 5.01 (br dd, 1 H), 3.97 (s, 3 H), 3.68-3.87 (m, 0.7 H), 3.37-3.49 (m, 0.3 H), 2.93-3.25 (m, 1 H), 2.77-2.89 (m, 1 H), 2.35-2.48 (m, 3 H) | 457.2 $[M + H]^+$ | 100% |
| 817 | ($CD_3OD$) δ 8.43 (d, 1 H), 8.14-8.34 (m, 2 H), 7.69-7.78 (m, 1 H), 7.51-7.63 (m, 1 H), 6.92-7.03 (m, 2 H), 6.70-6.83 (m, 1 H), 6.53-6.68 (m, 1 H), 5.02 (br dd, 1 H), 3.98 (s, 3 H), 3.71-3.85 (m, 0.7 H), 3.42 (td, 0.3 H), 3.12-3.26 (m, 0.7 H), 2.95-3.07 (m, 0.3 H), 2.76-2.91 (m, 1 H), 2.39-2.49 (m, 3 H) | 457.2 $[M + H]^+$ | 100% |
| 818 | ($CD_3OD$) δ 8.58-8.66 (m, 1 H), 8.19-8.34 (m, 1 H), 7.83-7.98 (m, 1 H), 7.64-7.77 (m, 2 H), 7.46 (s, 0.3 H), 6.90-7.03 (m, 1.7 H), 6.70-6.82 (m, 1 H), 6.55-6.67 (m, 1 H), 4.92-5.01 (m, 1 H), 3.70-3.86 (m, 0.7 H), 3.44 (td, 0.3 H), 2.95-3.27 (m, 1 H), 2.76-2.91 (m, 1 H), 2.35-2.50 (m, 3 H) | 445.2 $[M + H]^+$ | 99.4% |
| 819 | ($CD_3OD$) δ 8.58-8.68 (m, 1 H), 8.20-8.34 (m, 1 H), 7.92 (t, 1 H), 7.65-7.80 (m, 2 H), 7.46 (s, 0.3 H), 6.90-7.02 (m, 1.7 H), 6.70-6.84 (m, 1 H), 6.56-6.69 (m, 1 H), 4.92-5.01 (m, 1 H), 3.72-3.86 (m, 0.7 H), 3.44 (td, 0.3 H), 3.15-3.27 (m, 0.7 H), 2.95-3.07 (m, 0.3 H), 2.85 (br dd, 1 H), 2.34-2.49 (m, 3 H) | 445.2 $[M + H]^+$ | 99.6% |
| 820 | ($CD_3OD$) δ 8.92 (s, 1 H), 8.21-8.40 (m, 2 H), 7.49-7.81 (m, 2 H), 6.92-7.03 (m, 2 H), 6.71-6.83 (m, 1 H), 6.51-6.67 (m, 1 H), 4.98-5.12 (m, 1 H), 3.70-3.87 (m, 0.7 H), 3.38-3.47 (m, 0.3 H), 2.94-3.23 (m, 1 H), 2.77-2.91 (m, 1 H), 2.37-2.48 (m, 3 H) | 466.2 $[M + H]^+$ | 98.8% |
| 821 | ($CD_3OD$) δ 8.77-9.00 (m, 1 H), 8.20-8.40 (m, 2 H), 7.48-7.82 (m, 2 H), 6.98 (br t, 2 H), 6.70-6.82 (m, 1 H), 6.54-6.68 (m, 1 H), 5.06 (br dd, 1 H), 3.67-3.86 (m, 0.7 H), 3.41 (td, 0.3 H), 2.93-3.26 (m, 1 H), 2.85 (br d, 1 H), 2.35-2.51 (m, 3 H) | 466.2 $[M + H]^+$ | 99.5% |

TABLE 2-continued

| Ex. # | $^1$H NMR (400 MHz unless otherwise noted) | LCMS: m/z | % ee |
|---|---|---|---|
| 822 | ($CD_3OD$) δ 8.20-8.37 (m, 2 H), 7.48-7.85 (m, 2 H), 7.17-7.25 (m, 1 H), 6.92-7.03 (m, 2 H), 6,70-6.82 (m, 1 H), 6.53-6.66 (m, 1 H), 5.02 (dd, 1 H), 3.73-3.86 (m, 0.7 H), 3.42 (td, 0.3 H), 2.94-3.25 (m, 1 H), 2.77-2.89 (m, 1 H), 2.38-2.48 (m, 3 H) | 466.2 $[M + H]^+$ | 100% |
| 823 | ($CD_3OD$) δ 8.21-8.35 (m, 2 H), 7.82 (s, 0.3 H), 7.69 (d, 1 H), 7.53 (s, 0.6 H), 7.18-7.23 (m, 1 H), 6.93-7.02 (m, 2 H), 6,71-6.81 (m, 1 H), 6.53-6.66 (m, 1 H), 5.02 (dd, 1 H), 3.72-3.85 (m, 0.7 H), 3.42 (td, 0.3 H), 2.95-3.25 (m, 1 H), 2.76-2.89 (m, 1 H), 2.39-2.48 (m, 3 H) | 466.2 $[M + H]^+$ | 100% |
| 824 | ($CD_3OD$) δ 8.26-8.39 (m, 2 H), 7.50-7.84 (m, 2.4 H), 7.21 (d, 1 H), 6.93-7.01 (m, 1.6 H), 6.70-6.88 (m, 2 H), 4.92-5.08 (m, 1 H), 3.74-3.86 (m, 0.7 H), 3.42 (br dd, 0.3 H), 3.15-3.24 (m, 0.7 H), 2.96-3.04 (m, 0.3 H), 2.80-2.91 (m, 1 H) | 470.2 $[M + H]^+$ | 99.5% |
| 825 | ($CD_3OD$) δ 8.23-8.43 (m, 2 H), 7.47-7.88 (m, 2.4 H), 7.21 (d, 1 H), 6.91-7.04 (m, 1.6 H), 6.72-6.89 (m, 2 H), 5.04 (br dd, 1 H), 3.73-3.85 (m, 0.5 H), 3.38-3.45 (m, 0.5 H), 3.12-3.24 (m, 0.8 H), 2.97-3.05 (m, 0.2 H), 2.78-2.91 (m, 1 H) | 470.2 $[M + H]^+$ | 100% |
| 826 | ($CD_3OD$) δ 8.63-8.80 (m, 2 H), 8.31 (d, 1 H), 8.09 (td, 1 H), 7.59-7.72 (m, 3 H), 6.72-7.10 (m, 3 H), 4.92-5.07 (m, 1 H), 3.38-3.85 (m, 1 H), 2.83-3.25 (m, 2 H) | 481.2 $[M + H]^+$ | 100% |
| 827 | ($CD_3OD$) δ 8.63-8.80 (m, 2 H), 8.31 (d, 1 H), 8.08 (td, 1 H), 7.58-7.72 (m, 3 H), 6.75-7.07 (m, 3 H), 4.93-5.07 (m, 1 H), 3.39-3.83 (m, 1 H), 2.84-3.26 (m, 2 H) | 481.2 [M + H]+ | 98.1% |
| 828 | ($CD_3OD$) δ 8.66-8.73 (m, 1 H), 8.39-8.43 (m, 1 H), 8.08-8.17 (m, 1 H), 7.72 (s, 1 H), 7.59-7.66 (m, 1 H), 6.93-7.05 (m, 2 H), 6.76-6.84 (m, 1 H), 4.94-5.16 (m, 1 H), 4.02 (s, 3 H), 3.41-3.81 (m, 1 H), 2.84-3.22 (m, 2 H) | 484.2 $[M + H]^+$ | 100% |
| 829 | ($CD_3OD$) δ 8.66-8.73 (m, 1 H), 8.39-8.43 (m, 1 H), 8.09-8.15 (m, 1 H), 7.62-7.73 (m, 2 H), 6.94-7.05 (m, 2 H), 6.77-6.83 (m, 1 H), 4.95-5.17 (m, 1 H), 4.02 (s, 3 H), 3.41-3.82 (m, 1 H), 2.84-3.22 (m, 2 H) | 484.2 $[M + H]^+$ | 98.2% |
| 830 | ($CD_3OD$) δ 8.83 (d, 2 H), 8.23-8.43 (m, 1 H), 8.03-8.19 (m, 2 H), 7.46-7.80 (m, 1.3 H), 6.90-7.06 (m, 1.7 H), 6.71-6.89 (m, 2 H), 5.07 (br dd, 0.7 H), 4.92-4.97 (m, 0.3 H), 3.80 (br t, 0.7 H), 3.43 (br t, 0.3 H), 2.96-3.25 (m, 1 H), 2.89 (br s, 1 H) | 431.2 $[M + H]^+$ | 100% |
| 831 | ($CD_3OD$) δ 8.83 (d, 2 H), 8.26-8.42 (m, 1 H), 8.12 (d, 2 H), 7.46-7.83 (m, 1.3 H), 6.91-7.08 (m, 1.7 H), 6.64-6.89 (m, 2 H), 5.07 (br dd, 0.7 H), 4.92-4.97 (m, 0.3 H), 3.80 (br t, 0.7 H), 3.38-3.50 (m, 0.3 H), 2.96-3.26 (m, 1 H), 2.87 (br s, 1 H) | 431.2 $[M + H]^+$ | 99.7% |
| 832 | ($CD_3OD$) δ 8.48 (s, 1 H), 8.25-8.39 (m, 1 H), 8.14 (s, 1 H), 7.52-7.76 (m, 1.4 H), 6.90-7.04 (m, 1.6 H), 6.78-6.89 (m, 1 H), 6.69-6.78 (m, 1 H), 5.10 (br dd, 0.5 H), 4.95 (br s, 0.5 H), 3.71-3.84 (m, 0.8 H), 3.38-3.43 (m, 0.2 H), 2.94-3.23 (m, 2 H), 2.84 (br d, 1 H), 2.48-2.65 (m, 4 H), 1.88-1.98 (m, 2 H) | 474.2 $[M + H]^+$ | 100% |
| 833 | ($CD_3OD$) δ 8.48 (s, 1 H), 8.24-8.39 (m, 1 H), 8.14 (s, 1 H), 7.55-7.75 (m, 1.4 H), 6.90-7.02 (m, 1.6 H), 6.80-6.88 (m, 1 H), 6.68-6.78 (m, 1 H), 4.98-5.15 (m, 1 H), 3.72-3.83 (m, 0.8 H), 3.42 (br d, 0.2 H), 2.93-3.26 (m, 2 H), 2.84 (br d, 1 H), 2.48-2.64 (m, 4 H), 1.88-1.97 (m, 2 H) | 474.2 $[M + H]^+$ | 99.4% |
| 834 | ($CD_3OD$) δ 8.98 (s, 1 H), 8.46 (s, 1 H), 8.26-8.39 (m, 1 H), 7.49-7.77 (m, 1 H), 6.90-7.03 (m, 2 H), 6.79-6.89 (m, 1 H), 6.72-6.78 (m, 1 H), 5.08 (dd, 1 H), 3.71-3.85 (m, 1 H), 3.36-3.52 (m, 1 H), 2.92-3.26 (m, 2 H), 2.85 (br d, 1 H), 1.41-1.55 (m, 2 H), 1.25-1.32 (m, 2 H) | 524.2 [M + H]+ | 100% |
| 835 | ($CD_3OD$) δ 8.98 (s, 1 H), 8.46 (s, 1 H), 8.24-8.38 (m, 1 H), 7.51-7.78 (m, 1 H), 6.90-7.02 (m, 2 H), 6.80-6.89 (m, 1 H), 6.71-6.78 (m, 1 H), 5.08 (br dd, 1 H), 3.65-3.92 (m, 1 H), 3.36-3.51 (m, 1 H), 2.94-3.24 (m, 2 H), 2.77-2.91 (m, 1 H), 1.42-1.53 (m, 2 H), 1.23-1.32 (m, 2 H) | 524.2 $[M + H]^+$ | 99.5% |
| 836 | Data provided above | | |
| 837 | Data provided above | | |
| 838 | ($CD_3OD$) δ 8.22-8.41 (m, 1 H), 7.94-8.07 (m, 1 H), 7.70 (s, 1 H), 6.74-7.07 (m, 3 H), 6.64 (s, 0.6 H), 6.34 (s, 0.4 H), 4.94 (br d, 0.4 H), 4.40 (dd, 0.6 H), 3.98-4.12 (m, 3 H), 3.65-3.75 (m, 0.5 H), 2.71-3.29 (m, 2.5 H), 2.37-2.51 (m, 3 H) | 363.2 $[M + H]^+$ | 100% |
| 839 | ($CD_3OD$) δ 8.14-8.27 (m, 1 H), 7.84-7.94 (m, 1 H), 7.59 (d, 1 H), 6.62-6.94 (m, 3 H), 6.52 (s, 0.6 H), 6.22 (s, 0.4 H), 4.82 (br s, 0.4 H), 4.28 (dd, 0.6 H), 3.84-4.01 (m, 3 H), 3.53-3.63 (m, 0.5 H), 2.59-3.17 (m, 2.5 H), 2.22-2.42 (m, 3 H) | 363.2 $[M + H]^+$ | 98.9% |
| 840 | ($CD_3OD$) δ 8.31-8.39 (m, 1 H), 8.00 (s, 1 H), 7.69 (d, 1 H), 6.73-7.02 (m, 3.5 H), 6.49 (s, 0.5 H), 4.90-4.94 (m, 0.5 H), 4.40 (dd, 0.5 H), 4.00-4.09 (m, 3 H), 3.61-3.72 (m, 0.5 H), 2.70-3.27 (m, 2.5 H) | 367.2 $[M + H]^+$ | 98.5% |
| 841 | ($CD_3OD$) δ 8.33-8.41 (m, 1 H), 8.02 (s, 1 H), 7.71 (d, 1 H), 6.74-7.02 (m, 3.5 H), 6.51 (s, 0.5 H), 4.92-4.96 (m, 0.5 H), 4.42 (dd, 0.5 H), 4.04-4.09 (m, 3 H), 3.64-3.73 (m, 0,5 H), 2.71-3.30 (m, 2.5 H) | 367.2 $[M + H]^+$ | 98.3% |

TABLE 2-continued

| Ex. # | $^{1}$H NMR (400 MHz unless otherwise noted) | LCMS: m/z | % ee |
|---|---|---|---|
| 842 | ($CD_3OD$) δ 8.33-8.45 (m, 1 H), 7.86-7.92 (m, 1 H), 7.70 (br d, 1 H), 6.94-7.03 (m, 2 H), 6.69-6.93 (m, 2.3 H), 6.48 (s, 0.3 H), 6.03 (s, 0.4 H), 4.86 (br d, 0.6 H), 3.69-3.88 (m, 1 H), 3.35-3.42 (m, 0.4 H), 2.69-3.05 (m, 2 H) | 420.1 $[M + H]^+$ | 96.9% |
| 843 | ($CD_3OD$) δ 8.31-8.47 (m, 1 H), 7.83-7.96 (m, 1 H), 7.70 (br d, 1 H), 6.94-7.04 (m, 2 H), 6.83-6.92 (m, 1 H), 6.71-6.81 (m, 1.3 H), 6.48 (s, 0.3 H), 6.03 (s, 0.4 H), 4.86 (br d, 0.6 H), 3.69-3.86 (m, 1 H), 3.34-3.43 (m, 0.4 H), 2.68-3.05 (m, 2 H) | 420.2 $[M + H]^+$ | 92.8% |
| 844 | ($CD_3OD$) δ 8.23-8.34 (m, 2 H), 7.52-7.72 (m, 1 H), 6.93-7.04 (m, 2 H), 6.52-6.85 (m, 2 H), 5.06 (br dd, 1 H), 3.92 (s, 3 H), 3.72-3.81 (m, 1 H), 2.79-3.22 (m, 2 H), 2.51-2.56 (m, 3 H), 2.40-2.47 (m, 3 H)) | 444.2 $[M + H]^+$ | 98.0% |
| 845 | ($CD_3OD$) δ 8.20-8.34 (m, 2 H), 7.53-7.71 (m, 1 H), 6.90-7.05 (m, 2 H), 6.48-6.83 (m, 2 H), 5.06 (br dd, 1 H), 3.92 (s, 3 H), 3.71-3.83 (m, 1 H), 2.77-3.22 (m, 2 H), 2.51-2.57 (m, 3 H), 2.38-2.49 (m, 3 H) | 444.2 $[M + H]^+$ | 98.3% |
| 846 | ($CD_3OD$) δ 8.24-8.38 (m, 2 H), 7.53-7.72 (m, 1 H), 6.68-7.02 (m, 4 H), 5.09 (dd, 1 H), 3.92 (s, 3 H), 3.70-3.80 (m, 1 H), 2.73-3.24 (m, 2 H), 2.45-2.59 (m, 3 H) | 448.2 $[M + H]^+$ | 98.2% |
| 847 | ($CD_3OD$) δ 8.27-8.37 (m, 2 H), 7.47-7.71 (m, 1 H), 6.65-7.04 (m, 4 H), 5.09 (br dd, 1 H), 3.92 (s, 3 H), 3.72-3.82 (m, 1 H), 2.74-3.28 (m, 2 H), 2.47-2.64 (m, 3 H) | 448.2 $[M + H]^+$ | 98.8% |
| 848 | ($CD_3OD$) δ 8.16-8.70 (m, 1 H), 7.70 (br s, 1 H), 7.50 (s, 1 H), 6.94-7.07 (m, 1.6 H), 6.68-6.93 (m, 2 H), 6.42-6.61 (m, 1 H), 6.16 (br s, 0.4 H), 3.95 (br dd, 1 H), 3.59-3.83 (m, 1.6 H), 3.35-3.45 (m, 0.4 H), 2.89-3.11 (m, 1 H), 2.68-2.89 (m, 1 H), 1.12 (br s, 1 H), 0.63-0.99 (m, 3 H) | 392.2 $[M + H]^+$ | 99.6% |
| 849 | ($CD_3OD$) δ 8.31-8.53 (m, 1 H), 7.70 (br s, 1 H), 7.50 (s, 1 H), 6.94-7.13 (m, 1.6 H), 6.68-6.93 (m, 2 H), 6.39-6.61 (m, 1 H), 6.16 (br s, 0.4 H), 3.95 (br dd, 1 H), 3.56-3.82 (m, 1.6 H), 3.36-3.45 (m, 0.4 H), 2.89-3.11 (m, 1 H), 2.70-2.87 (m, 1 H), 1.12 (br s, 1 H), 0.64-1.01 (m, 3 H) | 392.2 $[M + H]^+$ | 99.1% |
| 850 | ($CD_3OD$) δ 8.83 (br d, 2 H), 8.19-8.36 (m, 1 H), 8.12 (d, 2 H), 7.49-7.77 (m, 1 H), 6.94-7.04 (m, 2 H), 6.72-6.85 (m, 1 H), 6.52-6.67 (m, 1 H), 5.05 (br dd, 0.5 H), 3.72-3.89 (m, 1 H), 3.37-3.51 (m, 0.5 H), 2.95-3.26 (m, 1 H), 2.88 (br s, 1 H), 2.38-2.51 (m, 3 H) | 427.2 $[M + H]^+$ | 100% |
| 851 | ($CD_3OD$) δ 8.83 (br d, 2 H), 8.19-8.38 (m, 1 H), 8.12 (d, 2 H), 7.41-7.80 (m, 1 H), 6.91-7.06 (m, 2 H), 6.71-6.84 (m, 1 H), 6.49-6.68 (m, 1 H), 5.05 (br dd, 0.5 H), 3.71-3.90 (m, 1 H), 3.43 (br t, 0.5 H), 2.97-3.27 (m, 1 H), 2.88 (br s, 1 H), 2.38-2.50 (m, 3 H) | 427.2 $[M + H]^+$ | 98.3% |
| 852 | ($CD_3OD$) δ 8.99 (s, 1 H), 8.46 (s, 1 H), 8.20-8.36 (m, 1 H), 7.54-7.71 (m, 1 H), 6.74-7.09 (m, 3 H), 6.52-6.68 (m, 1 H), 4.96-5.20 (m, 1 H), 3.79 (br t, 1 H), 3.04-3.24 (m, 2 H), 2.85 (br d, 1 H), 2.42-2.46 (m, 3 H), 1.44-1.51 (m, 2 H), 1.28 (br d, 2 H) | 520.2 $[M + H]^+$ | 100% |
| 853 | ($CD_3OD$) δ 8.99 (s, 1 H), 8.46 (s, 1 H), 8.19-8.36 (m, 1 H), 7.57-7.97 (m, 1 H), 6.50-7.20 (m, 4 H), 5.03-5.15 (m, 1 H), 3.68-3.89 (m, 1 H), 2.99-3.26 (m, 2 H), 2.88 (br d, 1 H), 2.39-2.50 (m, 3 H), 1.44-1.52 (m, 2 H), 1.28 (br d, 2 H) | 520.2 $[M + H]^+$ | 99.3% |
| 854 | ($CD_3OD$) δ 8.14-8.38 (m, 1 H), 7.48-7.73 (m, 1 H), 6.71-7.08 (m, 4 H), 6.49-6.68 (m, 1 H), 5.00 (br dd, 1 H), 3.90 (s, 3 H), 3.71-3.84 (m, 1 H), 2.94-3.23 (m, 1 H), 2.83 (br d, 1 H), 2.38-2.47 (m, 6 H) | 444.2 $[M + H]^+$ | 96.4% |
| 855 | ($CD_3OD$) δ 8.21-8.35 (m, 1 H), 7.49-7.71 (m, 1 H), 6.71-7.08 (m, 4 H), 6.50-6.67 (m, 1 H), 5.00 (br dd, 1 H), 3.90 (s, 3 H), 3.36-3.83 (m, 1 H), 2.95-3.24 (m, 1 H), 2.83 (br d, 1 H), 2.36-2.48 (m, 6 H) | 444.2 $[M + H]^+$ | 90.2% |
| 856 | ($CD_3OD$) δ 8.33-8.58 (m, 1 H), 7.47-8.01 (m, 3 H), 7.19 (br t, 1 H), 6.15-7.02 (m, 4 H), 4.69 (br d, 2 H), 3.63-4.07 (m, 1 H), 2.66-3.18 (m, 2 H), 1.22-1.57 (m, 6 H) | 376.2 $[M + H]^+$ | 99.9% |
| 857 | ($CD_3OD$) δ 8.34-8.61 (m, 1 H), 7.44-7.78 (m, 3 H), 7.19 (br t, 1 H), 6.12-7.04 (m, 4 H), 4.69 (br d, 2 H), 3.60-4.03 (m, 1 H), 2.60-3.09 (m, 2 H), 1.25-1.51 (m, 6 H) | 376.2 $[M + H]^+$ | 99.9% |
| 858 | ($CD_3OD$) δ 8.23-8.53 (m, 1 H), 7.49-7.74 (m, 2 H), 6.07-7.13 (m, 5 H), 4.55-4.82 (m, 2 H), 3.60-4.09 (m, 1 H), 2.66-3.07 (m, 2 H), 1.25-1.53 (m, 6 H) | 394.2 $[M + H]^+$ | 99.5% |
| 859 | ($CD_3OD$) δ 8.23-8.49 (m, 1 H), 7.43-7.78 (m, 2 H), 6.15-7.04 (m, 5 H), 4.54-4.80 (m, 2 H), 3.61-4.14 (m, 1 H), 2.68-3.10 (m, 2 H), 1.42 (br d, 6 H) | 394.2 $[M + H]^+$ | 98.6% |
| 860 | ($CD_3OD$) δ 8.18-8.57 (m, 1 H), 7.70 (br s, 1 H), 7.50 (d, 1 H), 6.94-7.10 (m, 1.6 H), 6.77-6.87 (m, 1 H), 6.74 (br s, 0.4 H), 6.06-6.70 (m, 2 H), 3.92 (br dd, 1 H), 3.75 (br t, 0,6 H), 3.66 (br d, 1 H), 3.36-3.48 (m, 0.4 H), 2.88-3.12 (m, 1 H), 2.70-2.87 (m, 1 H), 2.33-2.53 (m, 3 H), 0.78-1.16 (m, 4 H) | 388.2 $[M + H]^+$ | 98.4% |

TABLE 2-continued

| Ex. # | $^1$H NMR (400 MHz unless otherwise noted) | LCMS: m/z | % ee |
|---|---|---|---|
| 861 | ($CD_3OD$) δ 8.23-8.56 (m, 1 H), 7.63-7.80 (m, 1 H), 7.50 (d, 1 H), 6.94-7.10 (m, 1.6 H), 6.78-6.86 (m, 1 H), 6.74 (br s, 0.4 H), 6.10-6.70 (m, 2 H), 3.92 (br dd, 1 H), 3.74 (br t, 0.6 H), 3.66 (br d, 1 H), 3.39 (br d, 0.4 H), 2.88-3.11 (m, 1 H), 2.67-2.87 (m, 1 H), 2.39-2.54 (m, 3 H), 0.77-1.16 (m, 4 H) | 388.2 $[M + H]^+$ | 99.2% |
| 862 | ($CD_3OD$) δ 8.32 (dd, 1 H), 7.66-7.89 (m, 4 H), 7.46-7.57 (m, 1 H), 7.02-7.13 (m, 1.6 H), 6.99 (s, 1 H), 6.73-6.86 (m, 1.4 H), 5.83-6.71 (m, 2 H), 3.42-3.77 (m, 2 H), 2.58-3.13 (m, 2 H), 2.36-2.51 (m, 3 H) | 425.2 $[M + H]^+$ | 88.7% |
| 863 | ($CD_3OD$) δ 8.24-8.36 (m, 1 H), 7.65-7.91 (m, 4 H), 7.44-7.56 (m, 1 H), 7.02-7.14 (m, 1.6 H), 6.94-7.00 (m, 1 H), 6.73-6.86 (m, 1.4 H), 5.83-6.72 (m, 2 H), 3.41-3.79 (m, 2 H), 2.56-3.13 (m, 2 H), 2.37-2.52 (m, 3 H) | 425.2 $[M + H]^+$ | 85.6% |
| 864 | ($CD_3OD$) δ 8.30-8.49 (m, 1 H), 7.69 (s, 1 H), 6.70-7.07 (m, 5 H), 6.28-6.65 (m, 1 H), 4.76-4.86 (m, 0.4 H), 4.03-4.18 (m, 0.6 H), 3.95 (s, 3 H), 3.72 (br t, 0.6 H), 3.26 (br s, 0.4 H), 2.90-3.05 (m, 1 H), 2.76 (br d, 1 H) | 416.2 $[M + H]^+$ | 100% |
| 865 | ($CD_3OD$) δ 8.29-8.50 (m, 1 H), 7.69 (s, 1 H), 6.73-7.06 (m, 5 H), 6.25-6.65 (m, 1 H), 4.77-4.86 (m, 0.4 H), 4.09 (br d, 0.6 H), 3.95 (s, 3 H), 3.72 (br t, 0.6 H), 3.27 (br s, 0.4 H), 2.90-3,07 (m, 1 H), 2.76 (br d, 1 H) | 416.2 $[M + H]^+$ | 100% |
| 866 | ($CD_3OD$) δ 8.25-8.42 (m, 1 H), 7.68 (s, 1 H), 6.87-7.05 (m, 2 H), 6.72-6.84 (m, 2 H), 6.62 (s, 1 H), 6.30 (br s, 1 H), 4.01-4.16 (m, 1 H), 3.94 (s, 3 H), 3.64-3.82 (m, 1 H), 2.96 (br d, 1 H), 2.76 (br d, 1 H), 2.36-2.48 (m, 3 H) | 412.2 $[M + H]^+$ | 98.4% |
| 867 | ($CD_3OD$) δ 8.26-8.42 (m, 1 H), 7.68 (s, 1 H), 6.86-7.06 (m, 2 H), 6.71-6.82 (m, 2 H), 6.62 (s, 1 H), 6.31 (br s, 1 H), 4.00-4.15 (m, 1 H), 3.94 (s, 3 H), 3.65-3.82 (m, 1 H), 2.96 (br d, 1 H), 2.76 (br d, 1 H), 2.34-2.50 (m, 3 H) | 412.2 $[M + H]^+$ | 97.6% |
| 868 | ($CD_3OD$) δ 8.47 (br s, 1 H), 7.49-7.99 (m, 4 H), 7.03-7.38 (m, 2 H), 6.43-6.96 (m, 3 H), 4.47 (br s, 1 H), 3.87-4.17 (m, 3 H), 3.37-3.85 (m, 1 H), 2.74-3.23 (m, 2 H) | 465.2 $[M + H]^+$ | 99.6% |
| 869 | ($CD_3OD$) δ 8.47 (br s, 1 H), 7.47-8.01 (m, 4 H), 7.04-7.38 (m, 2 H), 6.51-6.97 (m, 3 H), 4.44 (br s, 1 H), 3.91-4.17 (m, 3 H), 3.37-3.84 (m, 1 H), 2.74-3.22 (m, 2 H) | 465.2 $[M + H]^+$ | 99.7% |
| 870 | ($CD_3OD$) δ 8.60 (s, 1 H), 8.14-8.34 (m, 2 H), 7.89 (br d, 1 H), 7.45-7.73 (m, 1 H), 6.92-7.03 (m, 2 H), 6.70-6.83 (m, 1 H), 6.53-6.66 (m, 1 H), 4.99 (br dd, 1 H), 3.72-3.86 (m, 0.7 H), 3.36-3.49 (m, 0.3 H), 3.13-3.25 (m, 0.7 H), 2.95-3.06 (m, 0.3 H), 2.80-2.94 (m, 1 H), 2.38-2.50 (m, 6 H) | 441.2 $[M + H]^+$ | 100% |
| 871 | ($CD_3OD$) δ 8.61 (s, 1 H), 8.15-8.33 (m, 2 H), 7.90 (br d, 1 H), 7.46-7.73 (m, 1 H), 6.93-7.04 (m, 2 H), 6.71-6.84 (m, 1 H), 6.54-6.69 (m, 1 H), 4.99 (br dd, 1 H), 3.72-3.87 (m, 0.7 H), 3.37-3.51 (m, 0.3 H), 3.14-3.24 (m, 0.7 H), 2.94-3.07 (m, 0.3 H), 2.84 (br d, 1 H), 2.38-2.51 (m, 6 H) | 441.2 $[M + H]^+$ | 99.7% |
| 872 | ($CD_3OD$) δ 9.11 (s, 1 H), 8.46-8.55 (m, 1 H), 8.38-8.45 (m, 1 H), 8.19-8.34 (m, 1 H), 7.46-7.75 (m, 1 H), 6.91-7.04 (m, 2 H), 6.70-6.84 (m, 1 H), 6.55-6.67 (m, 1 H), 5.00 (br dd, 1 H), 3.75-3.85 (m, 0.7 H), 3.43 (td, 0.4 H), 2.95-3.26 (m, 1 H), 2.79-2.90 (m, 1 H), 2.36-2,50 (m, 3 H) | 495.2 $[M + H]^+$ | 100% |
| 873 | ($CD_3OD$) δ 9.11 (s, 1 H), 8.45-8.53 (m, 1 H), 8.36-8.44 (m, 1 H), 8.20-8.33 (m, 1 H), 7.66-7.78 (m, 1 H), 7.51 (s, 0.3 H), 6.91-7.05 (m, 1.7 H), 6.71-6.84 (m, 1 H), 6.55-6.68 (m, 1 H), 5.01 (br dd, 1 H), 3.70-3.87 (m, 0.7 H), 3.39-3.51 (m, 0.3 H), 2.95-3.26 (m, 1 H), 2.79-2.91 (m, 1 H), 2.37-2.52 (m, 3 H) | 495.2 $[M + H]^+$ | 100% |
| 874 | ($CD_3OD$) δ 8.69 (d, 1 H), 8.21-8.40 (m, 2 H), 7.87 (td, 1 H), 7.46-7.75 (m, 1 H), 6.93-7.02 (m, 2 H), 6.71-6.82 (m, 1 H), 6.55-6.67 (m, 1 H), 5.00 (br dd, 1 H), 3.72-3.86 (m, 0.7 H), 3.43 (td, 0.3 H), 3.13-3.25 (m, 0.7 H), 2.95-3.07 (m, 0.3 H), 2.78-2.89 (m, 1 H), 2.39-2.47 (m, 3 H) | 445.2 $[M + H]^+$ | 100% |
| 875 | ($CD_3OD$) δ 8.69 (d, 1 H), 8.19-8.40 (m, 2 H), 7.87 (td, 1 H), 7.45-7.74 (m, 1 H), 6.89-7.04 (m, 2 H), 6.71-6.83 (m, 1 H), 6.53-6.67 (m, 1 H), 5.00 (br dd, 1 H), 3.72-3.85 (m, 0.7 H), 3.43 (td, 0.3 H), 3.12-3.26 (m, 0.7 H), 2.94-3.07 (m, 0.3 H), 2.78-2.89 (m, 1 H), 2.38-2.46 (m, 3 H) | 445.2 $[M + H]^+$ | 99.4% |
| 876 | ($CD_3OD$) δ 8.62 (s, 1 H), 8.27-8.38 (m, 1 H), 8.15-8.23 (m, 1 H), 7.90 (br d, 1 H), 7.70 (s, 1 H), 7.50 (s, 0.3 H), 7.18 (br s, 0.2 H), 6.92-7.00 (m, 1.5 H), 6.75-6.87 (m, 2 H), 5.02 (br dd, 1 H), 3.76-3.85 (m, 0.7 H), 3.37-3.50 (m, 0.3 H), 2.78-3.26 (m, 2 H), 2.48 (s, 3 H) | 445.2 $[M + H]^+$ | 100% |
| 877 | ($CD_3OD$) δ 8.62 (s, 1 H), 8.26-8.39 (m, 1 H), 8.15-8.23 (m, 1 H), 7.87-7.94 (m, 1 H), 7.70 (s, 1 H), 7.50 (s, 0.3 H), 7.20 (br s, 0.2 H), 6.93-7.00 (m, 1.5 H), 6.75-6.87 (m, 2 H), 5.02 (br dd, 1 H), 3.74-3.85 (m, 0.6 H), 3.36-3.49 (m, 0.4 H), 2.80-3.25 (m, 2 H), 2.48 (s, 3 H) | 445.2 $[M + H]^+$ | 100% |

TABLE 2-continued

| Ex. # | $^1$H NMR (400 MHz unless otherwise noted) | LCMS: m/z | % ee |
|---|---|---|---|
| 878 | ($CD_3OD$) δ 9.11 (s, 1 H), 8.23-8.56 (m, 3 H), 7.43-7.78 (m, 1.3 H), 6.90-7.07 (m, 1.7 H), 6.74-6.88 (m, 2 H), 4.94-5.06 (m, 1 H), 3.75-3.86 (m, 0.7 H), 3.43 (td, 0.3 H), 2.81-3.27 (m, 2 H) | 499.2 $[M + H]^+$ | 100% |
| 879 | ($CD_3OD$) δ 9.11 (s, 1 H), 8.23-8.57 (m, 3 H), 7.46-7.78 (m, 1.3 H), 6.90-7.04 (m, 1.7 H), 6.71-6.87 (m, 2 H), 4.94-5.07 (m, 1 H), 3.75-3.87 (m, 0.6 H), 3.44 (td, 0.4 H), 2.82-3.25 (m, 2 H) | 499.2 $[M + H]^+$ | 100% |
| 880 | ($CD_3OD$) δ 8.70 (d, 1 H), 8.23-8.44 (m, 2 H), 7.88 (td, 1 H), 7.70 (s, 1 H), 7.51 (s, 0.3 H), 6.91-7.04 (m, 1.7 H), 6.72-6.89 (m, 2 H), 4.93-5.08 (m, 1 H), 3.79 (ddd, 0.7 H), 3.43 (td, 0.3 H), 2.81-3.25 (m, 2 H) | 449.2 $[M + H]^+$ | 100% |
| 881 | ($CD_3OD$) δ 8.70 (d, 1 H), 8.24-8.43 (m, 2 H), 7.88 (td, 1 H), 7.70 (s, 1 H), 7.51 (s, 0.3 H), 6.90-7.03 (m, 1.7 H), 6.73-6.88 (m, 2 H), 4.94-5.07 (m, 1 H), 3.73-3.86 (m, 0.7 H), 3.43 (td, 0.3 H), 2.79-3.25 (m, 2 H) | 449.2 $[M + H]^+$ | 100% |
| 882 | ($CD_3OD$) δ 8.20-8.41 (m, 1 H), 7.44-7.77 (m, 1 H), 6.66-7.11 (m, 5 H), 5.02 (br dd, 1 H), 3.90 (s, 3 H), 3.68-3.85 (m, 1 H), 2.81-3.25 (m, 2 H), 2.39 (s, 3 H) | 448.2 [M + H]+ | 99.7% |
| 883 | ($CD_3OD$) δ 8.20-8.43 (m, 1 H), 7.47-7.76 (m, 1 H), 6.62-7.12 (m, 5 H), 5.02 (br dd, 1 H), 3.90 (s, 3 H), 3.71-3.84 (m, 1 H), 2.76-3.24 (m, 2 H), 2.39 (s, 3 H) | 448.2 $[M + H]^+$ | 99.4% |
| 884 | ($CD_3OD$) δ 8.32-8.47 (m, 1 H), 7.68 (s, 1 H), 7.52 (br s, 1 H), 6.91-7.01 (m, 1.5 H), 6.72-6.89 (m, 2 H), 6.30-6.64 (m, 1.5 H), 4.11 (br d, 1 H), 3.47-3.97 (m, 4 H), 2.71-3.02 (m, 2 H) | 366.2 $[M + H]^+$ | 99.8% |
| 885 | ($CD_3OD$) δ 8.29-8.49 (m, 1 H), 7.69 (s, 1 H), 7.53 (br s, 1 H), 6.91-7.02 (m, 1.5 H), 6.73-6.89 (m, 2 H), 6.31-6.63 (m, 1.5 H), 4.10 (br s, 1 H), 3.93 (s, 4 H), 2.71-3.04 (m, 2 H) | 366.2 $[M + H]^+$ | 99.6% |
| 886 | ($CD_3OD$) δ 8.02-8.21 (m, 1 H), 7.34-7.72 (m, 1 H), 6.86-7.06 (m, 1 H), 6.73-6.85 (m, 2 H), 6.53-6.68 (m, 2 H), 6.31 (br d, 1 H), 4.72-4.85 (m, 1 H), 4.05 (br d, 0.5 H), 3.90-3.98 (m, 6 H), 3.70 (br t, 0.5 H), 2.97 (br s, 1 H), 2.67-2.83 (m, 1 H) | 428.2 $[M + H]^+$ | 99.1% |
| 887 | ($CD_3OD$) δ 8.04-8.20 (m, 1 H), 7.67 (s, 1 H), 6.87-7.06 (m, 1 H), 6.71-6.84 (m, 2 H), 6.64 (br d, 1 H), 6.57 (d, 1 H), 6.31 (br d, 1 H), 4.76-4.83 (m, 0.4 H), 4.00-4.13 (m, 0.6 H), 3.89-3.98 (m, 6 H), 3.70 (br t, 0.7 H), 3.27 (br s, 0.3 H), 2.90-3.04 (m, 1 H), 2.68-2.82 (m, 1 H) | 428.2 $[M + H]^+$ | 99.1% |
| 888 | ($CD_3OD$) δ 8.36 (br s, 1 H), 7.45-8.01 (m, 3 H), 7.03-7.36 (m, 1 H), 6.58-7.03 (m, 4 H), 4.47 (br d, 1 H), 3.92-4.16 (m, 3 H), 3.36-3.85 (m, 1 H), 2.74-3.22 (m, 2 H) | 483.2 $[M + H]^+$ | 99.3% |
| 889 | ($CD_3OD$) δ 8.36 (br s, 1 H), 7.49-8.01 (m, 3 H), 7.03-7.39 (m, 1 H), 6.60-7.03 (m, 4 H), 4.46 (br s, 1 H), 3.90-4.17 (m, 3 H), 3.37-3.86 (m, 1 H), 2.74-3.22 (m, 2 H) | 483.2 $[M + H]^+$ | 99.6% |
| 890 | ($CD_3OD$) δ 8.32 (br d, 1 H), 7.48-8.00 (m, 3 H), 6.94-7.38 (m, 2 H), 6.48-6.93 (m, 3 H), 4.47 (br s, 1 H), 3.90-4.16 (m, 3 H), 3.39-3.88 (m, 1 H), 2.74-3.25 (m, 2 H), 2.45 (s, 3 H) | 479.3 $[M + H]^+$ | 99.5% |
| 891 | ($CD_3OD$) δ 8.31 (br d, 1 H), 7.45-7.98 (m, 3 H), 6.96-7.38 (m, 2 H), 6.50-6.94 (m, 3 H), 4.46 (br s, 1 H), 3.90-4.16 (m, 3 H), 3.37-3.85 (m, 1 H), 2.74-3.21 (m, 2 H), 2.44 (s, 3 H) | 479.2 $[M + H]^+$ | 99.7% |
| 892 | ($CD_3OD$) δ 8.28-8.65 (m, 1 H), 7.43-7.78 (m, 2 H), 7.21 (dd, 1 H), 6.80-7.04 (m, 1.5 H), 6.49-6.74 (m, 1 H), 6.36 (br s, 1.3 H), 4.80-4.87 (m, 0.8 H), 4.05-4.21 (m, 0.5 H), 3.84 (s, 3 H), 3.70 (br t, 0.5 H), 2.66-3.04 (m, 2 H), 2.20-2.36 (m, 3 H) | 362.2 $[M + H]^+$ | 100% |
| 893 | ($CD_3OD$) δ 8.11-8.58 (m, 1 H), 7.28-7.70 (m, 2 H), 6.89-7.25 (m, 1 H), 6.66-6.88 (m, 1.5 H), 6.30-6.63 (m, 1 H), 6.23 (br s, 1.3 H), 4.65-4.76 (m, 1 H), 3.92-4.08 (m, 0.5 H), 3.53-3.77 (m, 3.5 H), 2.52-2.97 (m, 2 H), 2.02-2.24 (m, 3 H) | 362.2 $[M + H]^+$ | 99.7% |
| 894 | ($CD_3OD$) δ 9.31 (d, 1 H), 8.80 (dd, 1 H), 8.55 (dd, 1 H), 8.18-8.36 (m, 1 H), 7.63-7.74 (m, 2 H), 7.56 (s, 0.3 H), 6.94-7.04 (m, 1.7 H), 6.72-6.84 (m, 1 H), 6.53-6.67 (m, 1 H), 5.07 (dd, 1 H), 3.80 (ddd, 0.6 H), 3.37-3.51 (m, 0.4 H), 2.95-3.26 (m, 1 H), 2.76-2.92 (m, 1 H), 2.38-2.48 (m, 3 H) | 427.2 $[M + H]^+$ | 100% |
| 895 | ($CD_3OD$) δ 9.31 (d, 1 H), 8.80 (dd, 1 H), 8.55 (dt, 1 H), 8.20-8.35 (m, 1 H), 7.63-7.74 (m, 2 H), 7.56 (s, 0.3 H), 6.91-7.03 (m, 1.7 H), 6.72-6.85 (m, 1 H), 6.53-6.67 (m, 1 H), 5.07 (dd, 1 H), 3.76-3.86 (m, 0.6 H), 3.44 (td, 0.4 H), 2.95-3.26 (m, 1 H), 2.79-2.90 (m, 1 H), 2.37-2.50 (m, 3 H) | 427.2 $[M + H]^+$ | 99.3% |
| 896 | ($CD_3OD$) δ 9.31 (d, 1 H), 8.80 (dd, 1 H), 8.49-8.62 (m, 1 H), 8.24-8.42 (m, 1 H), 7.66-7.71 (m, 2 H), 7.57 (s, 0.3 H), 6.93-7.01 (m, 1.7 H), 6.73-6.88 (m, 2 H), 4.96-5.15 (m, 1 H), 3.75-3.86 (m, 0.7 H), 3.38-3.52 (m, 0.3 H), 2.82-3.23 (m, 2 H) | 431.2 $[M + H]^+$ | 99.8% |
| 897 | ($CD_3OD$) δ 9.31 (d, 1 H), 8.80 (dd, 1 H), 8.55 (dd, 1 H), 8.28-8.39 (m, 1 H), 7.65-7.73 (m, 2 H), 7.57 (s, 0.3 H), 6.90-7.03 (m, 1.7 H), 6.72-6.89 (m, 2 H), 5.10 (dd, 1 H), 3.72-3.87 (m, 0.7 H), 3.40-3.49 (m, 0.3 H), 2.81-3.24 (m, 2 H) | 431.1 $[M + H]^+$ | 98.3% |
| 898 | ($CD_3OD$) δ 8.05-8.17 (m, 1 H), 7.52-7.95 (m, 5 H), 7.08-7.21 (m, 1 H), 6.60-7.02 (m, 4 H), 5.84-6.59 (m, 1 H), 3.94-4.06 (m, 3 H), 3.37-3.83 (m, 2 H), 2.57-3.18 (m, 2 H) | 441.2 $[M + H]^+$ | 100% |

TABLE 2-continued

| Ex. # | $^1$H NMR (400 MHz unless otherwise noted) | LCMS: m/z | % ee |
|---|---|---|---|
| 899 | ($CD_3OD$) δ 8.01-8.16 (m, 1 H), 7.48-7.95 (m, 5 H), 7.04-7.21 (m, 1 H), 6.59-6.99 (m, 4 H), 5.82-6.57 (m, 1 H), 3.89-4.06 (m, 3 H), 3.39-3.80 (m, 2 H), 2.56-3.15 (m, 2 H) | 441.2 $[M + H]^+$ | 92.8% |
| 900 | ($CD_3OD$) δ 8.13-8.49 (m, 1 H), 7.65 (s, 1 H), 6.83-7.18 (m, 2 H), 6.75 (br s, 1 H), 6.44-6.63 (m, 1 H), 6.31 (br t, 1 H), 4.02-4.16 (m, 1 H), 3.80 (s, 3 H), 3.68 (br t, 1 H), 2.65-3.05 (m, 2 H), 2.33-2.48 (m, 3 H), 2.23 (br s, 3 H) | 376.2 $[M + H]^+$ | 100% |
| 901 | ($CD_3OD$) δ 8.20-8.42 (m, 1 H), 7.65 (s, 1 H), 6.87-7.07 (m, 2 H), 6.76 (br s, 1 H), 6.37-6.62 (m, 1 H), 6.19-6.36 (m, 1 H), 3.97-4.18 (m, 1 H), 3.54-3.86 (m, 4 H), 2.65-3.04 (m, 2 H), 2.33-2.48 (m, 3 H), 2.23 (br s, 3 H) | 376.2 $[M + H]^+$ | 99.3% |
| 902 | ($CD_3OD$) δ 7.83-8.43 (m, 3 H), 7.68 (s, 1 H), 7.02-7.36 (m, 1 H), 6.93-7.00 (m, 1 H), 6.61-6.90 (m, 3 H), 4.36-4.61 (m, 1 H), 3.97 (br s, 3 H), 3.76 (br s, 0.6 H), 3.36-3.51 (m, 0.4 H), 2.72-3.23 (m, 2 H) | 483.2 $[M + H]^+$ | 99.3% |
| 903 | ($CD_3OD$) δ 7.74-8.32 (m, 3 H), 7.59 (s, 1 H), 6.93-7.25 (m, 1 H), 6.87 (dd, 1 H), 6.51-6.79 (m, 3 H), 4.31-4.51 (m, 1 H), 3.87 (br s, 3 H), 3.66 (br s, 0.6 H), 3.24-3.43 (m, 0.4 H), 2.61-3.13 (m, 2 H) | 483.2 $[M + H]^+$ | 98.9% |
| 904 | ($CD_3OD$) δ 8.62-8.74 (m, 2 H), 7.88-8.08 (m, 2 H), 7.53-7.78 (m, 2 H), 6.84-7.07 (m, 3 H), 5.05 (br dd, 1 H), 3.40-3.82 (m, 1 H), 3.00-3.28 (m, 1 H), 2.86-2.95 (m, 1 H) | 499.2 [M + H]+ | 99.0% |
| 905 | ($CD_3OD$) δ 8.62-8.72 (m, 2 H), 7.46-7.96 (m, 4 H), 6.81-7.02 (m, 3 H), 4.98 (br dd, 1 H), 3.39-3.83 (m, 1 H), 2.98-3.27 (m, 1 H), 2.86 (br dd, 1 H) | 499.2 [M + H]+ | 94.9% |
| 906 | ($CD_3OD$) δ 8.89-8.94 (m, 1 H), 8.64-8.71 (m, 1 H), 8.30-8.38 (m, 1 H), 7.50-7.80 (m, 3.5 H), 6.77-7.01 (m, 2.5 H), 4.95-5.13 (m, 1 H), 3.36-3.81 (m, 1 H), 2.95-3.23 (m, 1 H), 2.80-2.89 (m, 1 H) | 520.2 $[M + H]^+$ | 100% |
| 907 | ($CD_3OD$) δ 8.90-8.94 (m, 1 H), 8.64-8.71 (m, 1 H), 8.26-8.41 (m, 1 H), 7.49-7.82 (m, 3.5 H), 6.77-7.02 (m, 2.5 H), 4.95-5.13 (m, 1 H), 3.39-3.82 (m, 1 H), 2.95-3.22 (m, 1 H), 2.79-2.89 (m, 1 H) | 520.2 [M + H]+ | 95.7% |
| 908 | ($CD_3OD$) δ 8.62-8.73 (m, 1 H), 8.33 (d, 1 H), 7.50-7.84 (m, 3 H), 6.74-7.24 (m, 4 H), 4.95-5.09 (m, 1 H), 3.36-3.82 (m, 1 H), 2.96-3.25 (m, 1 H), 2.79-2.90 (m, 1 H) | 520.2 [M + H]+ | 100% |
| 909 | ($CD_3OD$) δ 8.62-8.73 (m, 1 H), 8.33 (d, 1 H), 7.52-7.83 (m, 3 H), 6.76-7.22 (m, 4 H), 4.94-5.09 (m, 1 H), 3.36-3.83 (m, 1 H), 2.97-3.24 (m, 1 H), 2.79-2.92 (m, 1 H) | 520.2 [M + H]+ | 100% |
| 910 | ($CD_3OD$) δ 8.41-8.47 (m, 1 H), 8.25 (dd, 1 H), 7.56-7.73 (m, 2 H), 7.41-7.52 (m, 1.5 H), 6.98-7.15 (m, 1.5 H), 6.58-6.76 (m, 1.6 H), 6.44 (s, 0.4 H), 4.94-5.06 (m, 1 H), 3.99 (d, 3.7 H), 3.35-3.42 (m, 0.3 H), 2.82-3.24 (m, 2 H), 2.45-2.71 (m, 3 H) | 457.2 $[M + H]^+$ | 100% |
| 911 | ($CD_3OD$) δ 8.39-8.49 (m, 1 H), 8.25 (dd, 1 H), 7.56-7.76 (m, 2 H), 7.39-7.53 (m, 1.5 H), 6.97-7.18 (m, 1.5 H), 6.59-6.76 (m, 1.6 H), 6.44 (s, 0.4 H), 4.94-5.06 (m, 1 H), 3.99 (d, 3.6 H), 3.36-3.42 (m, 0.4 H), 2.80-3.24 (m, 2 H), 2.44-2.70 (m, 3 H) | 457.2 $[M + H]^+$ | 100% |
| 912 | ($CD_3OD$) δ 8.58-8.69 (m, 1 H), 7.87-7.99 (m, 1 H), 7.64-7.80 (m, 2 H), 7.36-7.52 (m, 1.4 H), 6.95-7.19 (m, 1.6 H), 6.58-6.76 (m, 1.6 H), 6.44 (s, 0.4 H), 4.93-4.99 (m, 1 H), 3.86-4.00 (m, 0.6 H), 3.34-3.42 (m, 0.4 H), 2.81-3.26 (m, 2 H), 2.44-2.70 (m, 3 H) | 445.2 $[M + H]^+$ | 100% |
| 913 | ($CD_3OD$) δ 8.64 (t, 1 H), 7.86-8.00 (m, 1 H), 7.60-7.80 (m, 2 H), 7.35-7.53 (m, 1.5 H), 6.93-7.18 (m, 1.5 H), 6.55-6.80 (m, 1.6 H), 6.44 (s, 0.4 H), 4.93-5.01 (m, 1 H), 3.93 (br t, 0.5 H), 3.34-3.44 (m, 0.5 H), 2.79-3.25 (m, 2 H), 2.41-2.75 (m, 3 H) | 445.2 $[M + H]^+$ | 100% |
| 914 | ($CD_3OD$) δ 8.92 (d, 1 H), 8.35 (s, 1 H), 7.39-7.84 (m, 3.5 H), 6.94-7.19 (m, 1.5 H), 6.40-6.77 (m, 2 H), 4.92-5.10 (m, 1 H), 3.85-3.99 (m, 0.6 H), 3.35-3.44 (m, 0.4 H), 2.81-3.23 (m, 2 H), 2.47-2.74 (m, 3 H) | 466.2 $[M + H]^+$ | 100% |
| 915 | ($CD_3OD$) δ 8.92 (d, 1 H), 8.35 (s, 1 H), 7.40-7.86 (m, 3.5 H), 6.90-7.22 (m, 1.5 H), 6.40-6.77 (m, 2 H), 4.93-5.11 (m, 1 H), 3.87-3.99 (m, 0.6 H), 3.34-3.44 (m, 0.4 H), 2.81-3.21 (m, 2 H), 2.46-2.72 (m, 3 H) | 466.2 $[M + H]^+$ | 100% |
| 916 | ($CD_3OD$) δ 8.28-8.36 (m, 1 H), 7.70 (d, 1 H), 6.74-7.08 (m, 3 H), 6.23-6.68 (m, 1 H), 4.93 (br s, 0.4 H), 4.36 (dd, 0.6 H), 3.96 (d, 3 H), 3.65-3.75 (m, 0.6 H), 3.26 (td, 0.4 H), 2.93-3.19 (m, 1 H), 2.72-2.88 (m, 1 H), 2.36-2.49 (m, 6 H) | 377.2 $[M + H]^+$ | 99.7% |
| 917 | ($CD_3OD$) δ 8.27-8.38 (m, 1 H), 7.70 (d, 1 H), 6.73-7.07 (m, 3 H), 6.22-6.66 (m, 1 H), 4.93 (br s, 0.4 H), 4.36 (dd, 0.6H), 3.96 (d, 3 H), 3.70 (ddd, 0.6 H), 3.26 (td, 0.4 H), 2.93-3.18 (m, 1 H), 2.71-2.88 (m, 1 H), 2.34-2.51 (m, 6 H) | 377.2 $[M + H]^+$ | 99.1% |
| 918 | ($CD_3OD$) δ 8.06-8.22 (m, 1 H), 7.69 (s, 1 H), 6.94 (br s, 0.6 H), 6.75-6.86 (m, 1 H), 6.46-6.72 (m, 2 H), 6.35 (br s, 1.4 H), 4.78-4.87 (m, 1 H), 4.04-4.19 (m, 0.5 H), 3.97 (br s, 3 H), 3.83 (s, 3 H), 3.62-3.75 (m, 0.5 H), 2.66-3.06 (m, 2 H), 2.27 (br s, 3 H) | 392.2 $[M + H]^+$ | 98.8% |
| 919 | ($CD_3OD$) δ 7.95-8.35 (m, 1 H), 7.69 (br s, 1 H), 6.94 (br s, 0.6 H), 6.80 (br s, 1 H), 6.47-6.73 (m, 2 H), 6.35 (br s, 1.4 H), 4.79- | 392.2 $[M + H]^+$ | 98.3% |

TABLE 2-continued

| Ex. # | $^1$H NMR (400 MHz unless otherwise noted) | LCMS: m/z | % ee |
|---|---|---|---|
| | 4.87 (m, 0.7 H), 4.12 (br d, 0.5 H), 3.97 (br s, 3 H), 3.83 (s, 3 H), 3.61-3.77 (m, 0.5 H), 3.24-3.32 (m, 0.3 H), 2.56-3.16 (m, 2 H), 2.27 (br s, 3 H) | | |
| 920 | ($CD_3OD$) δ 8.34 (d, 1 H), 7.56-8.05 (m, 3 H), 7.03-7.37 (m, 1 H), 6.68-7.02 (m, 4 H), 4.46-4.59 (m, 1 H), 3.83 (br s, 4 H), 2.79-3.25 (m, 2 H) | 483.2 $[M + H]^+$ | 99.0% |
| 921 | ($CD_3OD$) δ 8.34 (d, 1 H), 7.63-8.01 (m, 3 H), 7.04-7.45 (m, 1 H), 6.70-7.02 (m, 4 H), 4.44-4.59 (m, 1 H), 3.65-3.90 (m, 4 H), 2.74-3.25 (m, 2 H) | 483.2 $[M + H]^+$ | 96.9% |
| 922 | ($CD_3OD$) δ 8.08-8.25 (m, 1 H), 7.59 (s, 1 H), 7.30 (s, 0.3 H), 6.80-6.93 (m, 1.7 H), 6.61-6.75 (m, 1 H), 6.35-6.59 (m, 1 H), 4.80-4.87 (m, 1 H), 3.65 (ddd, 0.7 H), 3.29 (td, 0.3 H), 2.82-3.11 (m, 1 H), 2.72 (dd, 1 H), 2.28-2.37 (m, 3 H), 1.72-1.84 (m, 6 H) | 410.2 $[M + H]^+$ | 100% |
| 923 | ($CD_3OD$) δ 8.22-8.34 (m, 1 H), 7.69 (s, 1 H), 7.40 (s, 0.3 H), 6.90-7.03 (m, 1.7 H), 6.72-6.82 (m, 1 H), 6.46-6.66 (m, 1 H), 4.90-4.98 (m, 1 H), 3.68-3.80 (m, 0.7 H), 3.39 (td, 0.3 H), 2.92-3.21 (m, 1 H), 2.83 (br dd, 1 H), 2.38-2.48 (m, 3 H), 1.81-1.95 (m, 6 H) | 410.2 $[M + H]^+$ | 99.6% |
| 924 | ($CD_3OD$) δ 8.23-8.33 (m, 1 H), 7.68 (s, 1 H), 7.45 (s, 0.3 H), 6.94-7.02 (m, 1 H), 6.91 (s, 0.7 H), 6.70-6.83 (m, 1 H), 6.48-6.65 (m, 1 H), 4.97 (dd, 1 H), 3.72 (ddd, 0.7 H), 3.33-3.41 (m, 0.3 H), 2.89-3.19 (m, 1 H), 2.74-2.86 (m, 1 H), 2.38-2.47 (m, 3 H), 2.24-2.36 (m, 1 H), 1.14-1.32 (m, 4 H) | 390.2 $[M + H]^+$ | 100% |
| 925 | ($CD_3OD$) δ 8.22-8.33 (m, 1 H), 7.68 (s, 1 H), 7.45 (s, 0.3 H), 6.95-7.03 (m, 1 H), 6.91 (s, 0.7 H), 6.71-6.82 (m, 1 H), 6.47-6.64 (m, 1 H), 4.97 (dd, 1 H), 3.72 (ddd, 0.7 H), 3.37 (td, 0.3 H), 2.89-3.19 (m, 1 H), 2.70-2.87 (m, 1 H), 2.37-2.51 (m, 3 H), 2.21-2.36 (m, 1 H), 1.11-1.32 (m, 4 H) | 390.2 $[M + H]^+$ | 99.9% |
| 926 | ($CD_3OD$) δ 8.18-8.37 (m, 1 H), 7.70 (s, 1 H), 7.45-7.50 (m, 1 H), 6.70-7.10 (m, 3 H), 6.55-6.67 (m, 1 H), 5.06 (dd, 1 H), 4.19-4.27 (m, 3 H), 3.76-3.86 (m, 0.7 H), 3.38-3.49 (m, 0.3 H), 2.77-3.28 (m, 2 H), 2.34-2.46 (m, 6 H) | 444.2 $[M + H]^+$ | 100% |
| 927 | ($CD_3OD$) δ 8.21-8.38 (m, 1 H), 7.70 (s, 1 H), 7.43-7.53 (m, 1 H), 6.70-7.10 (m, 3 H), 6.55-6.68 (m, 1 H), 5.06 (br dd, 1 H), 4.17-4.28 (m, 3 H), 3.66-3.84 (m, 0.7 H), 3.38-3.49 (m, 0.3 H), 2.96-3.27 (m, 1 H), 2.80-2.90 (m, 1 H), 2.33-2.46 (m, 6 H) | 444,2 $[M + H]^+$ | 100% |
| 928 | ($CD_3OD$) δ 8.25-8.39 (m, 1 H), 7.70 (s, 1 H), 7.43-7.51 (m, 1 H), 6.79-7.15 (m, 3 H), 6.73-6.78 (m, 1 H), 5.09 (dd, 0.6 H), 4.20-4.25 (m, 3 H), 3.65-3.85 (m, 1 H), 3.35-3.46 (m, 0.4 H), 2.96-3.26 (m, 1 H), 2.79-2.88 (m, 1 H), 2.29-2.48 (m, 3 H) | 448.2 $[M + H]^+$ | 100% |
| 929 | ($CD_3OD$) δ 8.26-8.41 (m, 1 H), 7.70 (s, 1 H), 7.38-7.59 (m, 1 H), 6.78-7.12 (m, 3 H), 6.73-6.78 (m, 1 H), 4.92-5.12 (m, 1 H), 4.18-4.28 (m, 3 H), 3.72-3.88 (m, 0.7 H), 3.37-3.50 (m, 0.3 H), 2.77-3.26 (m, 2 H), 2.28-2.45 (m, 3 H) | 448.2 $[M + H]^+$ | 100% |
| 930 | ($CD_3OD$) δ 8.30 (br d, 1 H), 7.63-8.08 (m, 3 H), 6.36-7.44 (m, 5 H), 4.53 (br s, 1 H), 3.82 (br s, 4 H), 2.72-3.26 (m, 2 H), 2.45 (s, 3 H) | 479.2 $[M + H]^+$ | 99.3% |
| 931 | ($CD_3OD$) δ 8.30 (d, 1 H), 7.51-8.10 (m, 3 H), 6.46-7.40 (m, 5 H), 4.51 (br s, 1 H), 3.82 (br s, 4 H), 2.78-3.26 (m, 2 H), 2.45 (s, 3 H) | 479.3 $[M + H]^+$ | 97.7% |
| 932 | ($CD_3OD$) δ 8.63-8.72 (m, 1 H), 8.43 (d, 1 H), 8.25 (d, 1 H), 7.71 (s, 1 H), 7.58-7.65 (m, 2 H), 6.91-7.04 (m, 2 H), 6.77-6.83 (m, 1 H), 4.93-5.09 (m, 1 H), 3.98 (s, 3 H), 3.37-3.83 (m, 1 H), 2.96-3.25 (m, 1 H), 2.85 (br dd, 1 H) | 511.2 $[M + H]^+$ | 100% |
| 933 | ($CD_3OD$) δ 8.62-8.72 (m, 1 H), 8.43 (d, 1 H), 8.24 (d, 1 H), 7.71 (s, 1 H), 7.56-7.66 (m, 2 H), 6.89-7.05 (m, 2 H), 6.74-6.83 (m, 1 H), 4.93-5.09 (m, 1 H), 3.98 (s, 3 H), 3.37-3.83 (m, 1 H), 2.96-3.25 (m, 1 H), 2.79-2.91 (m, 1 H) | 511.2 [M + H]+ | 94.9% |
| 934 | ($CD_3OD$) δ 8.62-8.72 (m, 1 H), 7.97 (s, 1 H), 7.76-7.87 (m, 1 H), 7.59-7.71 (m, 2 H), 6.88-7.06 (m, 2 H), 6.76-6.84 (m, 1 H), 4.92-5.13 (m, 1 H), 4.07-4.11 (m, 3 H), 3.37-3.83 (m, 1 H), 2.96-3.23 (m, 1 H), 2.78-2.90 (m, 1 H) | 484.2 [M + H]+ | 100% |
| 935 | ($CD_3OD$) δ 8.63-8.73 (m, 1 H), 7.97 (s, 1 H), 7.79-7.88 (m, 1 H), 7.70 (s, 1 H), 7.59-7.66 (m, 1 H), 6.91-7.02 (m, 2 H), 6.76-6.83 (m, 1 H), 4.93-5.13 (m, 1 H), 4.08-4.11 (m, 3 H), 3.38-3.83 (m, 1 H), 2.96-3.24 (m, 1 H), 2.79-2.89 (m, 1 H) | 484.2 [M + H]+ | 92.0% |
| 936 | ($CD_3OD$) δ 8.33 (dd, 1 H), 7.83 (d, 0.2 H), 7.64-7.75 (m, 1.5 H), 7.37-7.55 (m, 1.8 H), 7.21 (t, 1 H), 7.03-7.15 (m, 1 H), 6.99 (s, 0.5 H), 6.58-6.76 (m, 1.6 H), 6.43 (s, 0.4 H), 4.92-5.06 (m, 1 H), 3.85-3.98 (m, 0.5 H), 3.33-3.41 (m, 0.5 H), 2.80-3.24 (m, 2 H), 2.44-2.72 (m, 3 H) | 466.2 $[M + H]^+$ | 100% |
| 937 | ($CD_3OD$) δ 8.33 (dd, 1 H), 7.83 (d, 0.3 H), 7.62-7.75 (m, 1.5 H), 7.37-7.57 (m, 1.7 H), 7.21 (t, 1 H), 7.03-7.17 (m, 1 H), 6.99 (s, 0.5 H), 6.57-6.79 (m, 1.6 H), 6.44 (s, 0.4 H), 4.93-5.07 (m, 1 H), 3.86-3.98 (m, 0.5 H), 3.34-3.41 (m, 0.5 H), 2.80-3.24 (m, 2 H), 2.44-2.72 (m, 3 H) | 466.2 $[M + H]^+$ | 99.5% |

TABLE 2-continued

| Ex. # | $^1$H NMR (400 MHz unless otherwise noted) | LCMS: m/z | % ee |
|---|---|---|---|
| 938 | ($CD_3OD$) δ 7.68 (d, 1 H), 7.27-7.53 (m, 1.4 H), 7.04-7.16 (m, 1 H), 6.96 (s, 0.6 H), 6.39-6.76 (m, 2 H), 4.90-4.97 (m, 1 H), 3.89 (br t, 1 H), 2.79-3.20 (m, 2 H), 2.53-2.72 (m, 3 H), 1.81-1.95 (m, 6 H) | 410.2 $[M + H]^+$ | 100% |
| 939 | ($CD_3OD$) δ 7.68 (d, 1 H), 7.29-7.52 (m, 1.4 H), 7.06-7.17 (m, 1 H), 6.96 (s, 0.6 H), 6.36-6.75 (m, 2 H), 4.90-4.94 (m, 1 H), 3.82-3.96 (m, 1 H), 2.78-3.20 (m, 2 H), 2.54-2.71 (m, 3 H), 1.80-1.95 (m, 6 H) | 410.2 $[M + H]^+$ | 99.1% |
| 940 | ($CD_3OD$) δ 7.66 (d, 1 H), 7.32-7.51 (m, 1.4 H), 7.06-7.16 (m, 1 H), 6.93 (br s, 0.6 H), 6.36-6.76 (m, 2 H), 4.97 (br dd, 1 H), 3.78-3.95 (m, 0.5 H), 3.33-3.38 (m, 0.5 H), 2.75-3.19 (m, 2 H), 2.55-2.73 (m, 3 H), 2.31 (tq, 1 H), 1.13-1.32 (m, 4 H) | 390.2 $[M + H]^+$ | 100% |
| 941 | ($CD_3OD$) δ 7.66 (d, 1 H), 7.28-7.54 (m, 1.4 H), 7.04-7.17 (m, 1 H), 6.94 (s, 0.6 H), 6.38-6.77 (m, 2 H), 4.97 (br dd, 1 H), 3.81-3.93 (m, 0.5 H), 3.34-3.40 (m, 0.5 H), 2.76-3.17 (m, 2 H), 2.56-2.72 (m, 3 H), 2.24-2.37 (m, 1 H), 1.10-1.40 (m, 4 H) | 390.2 $[M + H]^+$ | 99.9% |
| 942 | ($CD_3OD$) δ 8.62-8.72 (m, 1 H), 7.69 (s, 1 H), 7.59-7.65 (m, 1 H), 6.84-7.04 (m, 2 H), 6.70-6.80 (m, 1 H), 4.89-5.05 (m, 1 H), 3.35-3.77 (m, 1 H), 2.92-3.16 (m, 1 H), 2.76-2.86 (m, 1 H), 2.24-2.36 (m, 1 H), 1.18-1.29 (m, 4 H) | 444.2 [M + H]+ | 98.9% |
| 943 | ($CD_3OD$) δ 8.62-8.72 (m, 1 H), 7.57-7.73 (m, 2 H), 6.85-7.03 (m, 2 H), 6.67-6.81 (m, 1 H), 4.89-5.05 (m, 1 H), 3.34-3.76 (m, 1 H), 2.91-3.18 (m, 1 H), 2.76-2.86 (m, 1 H), 2.25-2.36 (m, 1 H), 1.19-1.29 (m, 4 H) | 444.2 [M + H]+ | 94.9% |
| 944 | ($CD_3OD$) δ 8.64-8.72 (m, 1 H), 7.76-7.81 (m, 1 H), 7.58-7.66 (m, 1 H), 6.88-7.07 (m, 2 H), 6.73-6.82 (m, 1 H), 4.90-5.04 (m, 1 H), 3.35-3.78 (m, 1 H), 2.95-3.19 (m, 1 H), 2.79-2.87 (m, 1 H), 2.63 (s, 3 H) | 418.2 [M + H]+ | 100% |
| 945 | ($CD_3OD$) δ 8.63-8.72 (m, 1 H), 7.77-7.86 (m, 1 H), 7.58-7.66 (m, 1 H), 6.89-7.04 (m, 2 H), 6.73-6.83 (m, 1 H), 4.90-5.06 (m, 1 H), 3.35-3.77 (m, 1 H), 2.94-3.19 (m, 1 H), 2.78-2.88 (m, 1 H), 2.63 (s, 3 H) | 418.2 [M + H]+ | 92.1% |
| 946 | ($CD_3OD$) δ 8.26-8.38 (m, 1 H), 7.68 (s, 1 H), 7.45 (s, 0.3 H), 6.87-7.01 (m, 1.7 H), 6.78-6.87 (m, 1 H), 6.65-6.75 (m, 1 H), 4.99 (dd, 1 H), 3.72 (ddd, 0.7 H), 3.35-3.42 (m, 0.3 H), 2.74-3.20 (m, 2 H), 2.26-2.38 (m, 1 H), 1.18-1.30 (m, 4 H) | 394.2 $[M + H]^+$ | 99.3% |
| 947 | ($CD_3OD$) δ 8.27-8.38 (m, 1 H), 7.69 (s, 1 H), 7.45 (s, 0.3 H), 6.87-7.02 (m, 1.7 H), 6.78-6.87 (m, 1 H), 6.63-6.77 (m, 1 H), 4.99 (dd, 1 H), 3.63-3.80 (m, 0.7 H), 3.37-3.44 (m, 0.3 H), 2.77-3.17 (m, 2 H), 2.24-2.40 (m, 1 H), 1.20-1.32 (m, 4 H) | 394.2 $[M + H]^+$ | 98.3% |
| 948 | ($CD_3OD$) δ 8.62-8.72 (m, 1 H), 7.69 (s, 1 H), 7.58-7.65 (m, 1 H), 6.93-7.44 (m, 2 H), 6.71-6.80 (m, 1 H), 4.90-5.03 (m, 1 H), 3.35-3.76 (m, 1 H), 2.80-3.15 (m, 2 H), 1.45-1.49 (m, 9 H) | 460.2 $[M + H]^+$ | 99.3% |
| 949 | ($CD_3OD$) δ 8.63-8.71 (m, 1 H), 7.69 (s, 1 H), 7.59-7.65 (m, 1 H), 6.94-7.44 (m, 2 H), 6.72-6.81 (m, 1 H), 4.90-5.03 (m, 1 H), 3.35-3.76 (m, 1 H), 2.80-3.17 (m, 2 H), 1.45-1.49 (m, 9 H) | 460.2 [M + H]+ | 98.2% |
| 950 | ($CD_3OD$) δ 8.70 (d, 1 H), 7.56-7.76 (m, 2 H), 7.41 (br s, 0.4 H), 6.92-7.03 (m, 1.6 H), 6.69-6.83 (m, 1 H), 4.98 (br dd, 1 H), 3.69-3.79 (m, 0.6 H), 3.35 (s, 0.4 H), 2.81-3.20 (m, 2 H), 1.75-2.02 (m, 6 H) | 464.2 $[M + H]^+$ | 97.2% |
| 951 | ($CD_3OD$) δ 8.69 (d, 1 H), 7.57-7.76 (m, 2 H), 7.41 (s, 0.4 H), 6.92-7.03 (m, 1.6 H), 6.71-6.81 (m, 1 H), 4.98 (br dd, 1 H), 3.69-3.79 (m, 0.6 H), 3.34-3.41 (m, 0.4 H), 2.79-3.21 (m, 2 H), 1.79-1.98 (m, 6 H) | 464.2 $[M + H]^+$ | 94.7% |
| 952 | ($CD_3OD$) δ 8.40 (s, 1 H), 8.10 (d, 1 H), 7.79-7.91 (m, 1 H), 7.66-7.75 (m, 1 H), 7.54-7.63 (m, 0.5 H), 7.24-7.38 (m, 2 H), 6.86 (s, 1 H), 6.66 (s, 0.5 H), 5.08-5.14 (m, 0.5 H), 4.94 (br s, 1 H), 4.02 (d, 3 H), 3.79-3.98 (m, 0.5 H), 2.99 (s, 1 H), 2.82-2.91 (m, 1 H) | 484.2 $[M + H]^+$ | 100% |
| 953 | ($CD_3OD$) δ 8.39 (s, 1 H), 8.09 (d, 1 H), 7.78-7.89 (m, 1 H), 7.65-7.74 (m, 1 H), 7.54-7.61 (m, 0.5 H), 7.32 (br d, 2 H), 6.85 (s, 1 H), 6.65 (s, 0.5 H), 5.10 (br dd, 0.5 H), 4.93-5.01 (m, 1 H), 4.00 (d, 3 H), 3.95 (br dd, 0.5 H), 2,94-3.18 (m, 1 H), 2.85 (br d, 1 H) | 484.2 $[M + H]^+$ | 99.2% |
| 954 | ($CD_3OD$) δ 8.23-8.40 (m, 1 H), 7.96-8.04 (m, 1 H), 7.53-7.76 (m, 1.3 H), 6.91-7.06 (m, 1.7 H), 6.65-6.89 (m, 2 H), 5.03-5.26 (m, 1 H), 3.69-3.93 (m, 3.7 H), 3.36-3.48 (m, 0.3 H), 2.92-3.25 (m, 1 H), 2.79-2.90 (m, 1 H), 2.57-2.75 (m, 3 H) | 448.2 $[M + H]^+$ | 98.7% |
| 955 | ($CD_3OD$) δ 8.24-8.40 (m, 1 H), 7.90-8.04 (m, 1 H), 7.51-7.74 (m, 1.4 H), 6.89-7.01 (m, 1.6 H), 6.64-6.88 (m, 2 H), 5.05-5.22 (m, 1 H), 3.67-3.91 (m, 3.5 H), 3.35-3.48 (m, 0.5 H), 2.91-3.24 (m, 1 H), 2.74-2.90 (m, 1 H), 2.58-2.72 (m, 3 H) | 448.2 $[M + H]^+$ | 96.7% |
| 956 | ($CD_3OD$) δ 9.40-9.53 (m, 1 H), 8.82-8.91 (m, 2 H), 8.22-8.37 (m, 1 H), 7.73 (s, 1 H), 7.52 (s, 0.3 H), 6.97-7.03 (m, 1.7 H), 6.73-6.88 (m, 1 H), 6.59-6.68 (m, 1 H), 5.02 (br dd, 0.5 H), 3.77-3.89 (m, 0.5 H), 3.46 (td, 0.5 H), 2.97-3.28 (m, 1.5 H), 2.80-2.93 (m, 1 H), 2.43-2.49 (m, 3 H) | 428.2 $[M + H]^+$ | 99.7% |

TABLE 2-continued

| Ex. # | $^1$H NMR (400 MHz unless otherwise noted) | LCMS: m/z | % ee |
|---|---|---|---|
| 957 | ($CD_3OD$) δ 9.34-9.52 (m, 1 H), 8.84 (br d, 2 H), 8.19-8.36 (m, 1 H), 7.70 (s, 1 H), 7.50 (s, 0.3 H), 6.96-7.01 (m, 1.7 H), 6.74-6.83 (m, 1 H), 6.59-6.66 (m, 1 H), 5.00 (br dd, 0.5 H), 3.75-3.87 (m, 0.5 H), 3.45 (td, 0.5 H), 2.95-3.27 (m, 1.5 H), 2.80-2.90 (m, 1 H), 2.42-2,46 (m, 3 H) | 428.2 $[M + H]^+$ | 99.3% |
| 958 | ($CD_3OD$) δ 8.42 (s, 1 H), 7.72 (s, 1 H), 7.60 (br d, 1 H), 7.12-7.31 (m, 2 H), 7.01-7.05 (m, 1 H), 6.56-6.93 (m, 2 H), 4.24-4.43 (m, 1 H), 3.77-3.95 (m, 1 H), 2.78-3.08 (m, 2 H) | 419.1 $[M + H]^+$ | 99.6% |
| 959 | ($CD_3OD$) δ 8.44 (s, 1 H), 7.71 (s, 1 H), 7.62 (br d, 1 H), 7.15-7.31 (m, 2 H), 7.03-7.06 (m, 1 H), 6.51-6.95 (m, 2 H), 4.25-4.43 (m, 1 H), 3.73-3.98 (m, 1 H), 2.80-3.11 (m, 2 H) | 419.1 $[M + H]^+$ | 99.9% |
| 960 | ($CD_3OD$) δ 7.67 (s, 1 H), 7.61 (br d, 1 H), 6.98-7.28 (m, 3 H), 6.78 (br s, 2 H), 4.26-4.48 (m, 1 H), 3.75-4.00 (m, 0.5 H), 3.35-3.52 (m, 0.5 H), 2.77-3.16 (m, 2 H), 1.57-1.70 (m, 6 H) | 477.1 $[M + H]^+$ | 100% |
| 961 | ($CD_3OD$) δ 7.67 (s, 1 H), 7.60 (br d, 1 H), 6.99-7.28 (m, 3 H), 6.62-6.90 (m, 2 H), 4.27-4.41 (m, 1 H), 3.80-3.97 (m, 0.5 H), 3.37-3.51 (m, 0.5 H), 2.77-3.16 (m, 2 H), 1.58-1.69 (m, 6 H) | 477.1 $[M + H]^+$ | 98.3% |
| 962 | ($CD_3OD$) δ 9.38-9.55 (m, 1 H), 8.81-8.95 (m, 2 H), 8.28-8.38 (m, 1 H), 7.70 (s, 1 H), 6.70-7.05 (m, 4 H), 5.03 (br dd, 0.5 H), 3.75-3.85 (m, 0.5 H), 3.43 (td, 0.5 H), 2.94-3.28 (m, 1.5 H), 2.80-2.91 (m, 1 H) | 432.1 $[M + H]^+$ | 100% |
| 963 | ($CD_3OD$) δ 9.45-9.52 (m, 1 H), 8.78-8.90 (m, 2 H), 8.26-8.44 (m, 1 H), 7.71 (s, 1 H), 6.74-7.08 (m, 4 H), 5.03 (br dd, 0.5 H), 3.72-3.88 (m, 0.5 H), 3.38-3.51 (m, 0.5 H), 2.98-3.26 (m, 1.5 H), 2.86 (br d, 1 H) | 432.1 $[M + H]^+$ | 99.7% |
| 964 | ($CD_3OD$) δ 8.35 (dd, 1 H), 7.62-7.84 (m, 2.5 H), 7.50-7.58 (m, 1 H), 7.14-7.25 (m, 2 H), 6.98-7.07 (m, 1.5 H), 6.60-6.84 (m, 1 H), 5.07 (br dd, 1 H), 3.89-3.97 (m, 0.5 H), 3.37-3.44 (m, 0.5 H), 2.85-3.24 (m, 2 H) | 486.1 $[M + H]^+$ | 99.7% |
| 965 | ($CD_3OD$) δ 8.30-8.38 (m, 1 H), 7.59-7.87 (m, 2.5 H), 7.49-7.58 (m, 1 H), 7.12-7.25 (m, 2 H), 6.97-7.07 (m, 1.5 H), 6.61-6.84 (m, 1 H), 5.07 (br dd, 1 H), 3.87-4.00 (m, 0.6 H), 3.38-3.44 (m, 0.4 H), 2.84-3.25 (m, 2 H) | 486.1 $[M + H]^+$ | 99.5% |
| 966 | ($CDCl_3$) δ 8.06-8.22 (m, 1 H), 7.53-7.63 (m, 1 H), 7.43 (s, 0.3 H), 7.30-7.38 (m, 1 H), 6.95 (s, 0.7 H), 6.93 (br d, 1 H), 6.50 (s, 1 H), 5.17 (br dd, 0.7 H), 4.94 (br dd, 0.3 H), 3.76-3.85 (m, 0.7 H), 3.44-3.51 (m, 0.3 H), 3.10-3.20 (m, 0.7 H), 2.94-3.05 (m, 0.5 H), 2.81 (br d, 0.5 H), 2.73 (br d, 0.3 H), 2.22-2.29 (m, 4 H), 1.19-1.28 (m, 4 H) | 390.2 $[M + H]^+$ | 100% |
| 967 | ($CDCl_3$) δ 8.08-8.21 (m, 1 H), 7.57-7.62 (m, 1 H), 7.45 (s, 0.3 H), 7.31-7.38 (m, 1 H), 6.96 (s, 0.7 H), 6.93 (br d, 1 H), 6.51 (s, 1 H), 5.18 (dd, 0.7 H), 4.96 (dd, 0.3 H), 3.76-3.87 (m, 0.7 H), 3.45-3.54 (m, 0.3 H), 3.11-3.21 (m, 0.7 H), 2.93-3.06 (m, 0.5 H), 2.82 (br d, 0.5 H), 2.74 (br d, 0.3 H), 2.26-2.31 (m, 4 H), 1.21-1.28 (m, 4 H) | 390.2 $[M + H]^+$ | 100% |
| 968 | ($CD_3OD$) δ 7.71 (d, 1 H), 7.56-7.65 (m, 1 H), 7.46 (s, 0.4 H), 7.14-7.23 (m, 1 H), 7.02-7.08 (m, 1 H), 6.97 (s, 0.6 H), 6.60-6.83 (m, 1 H), 4.95-5.03 (m, 1 H), 3.83-3.96 (m, 0.6 H), 3.36-3.43 (m, 0.4 H), 2.82-3.18 (m, 2 H), 1.87-1.94 (m, 6 H) | 430.2 $[M + H]^+$ | 99.6% |
| 969 | ($CD_3OD$) δ 7.59 (d, 1 H), 7.43-7.52 (m, 1 H), 7.33 (s, 0.4 H), 7.02-7.10 (m, 1 H), 6.92 (d, 1 H), 6.85 (s, 0.6 H), 6.50-6.69 (m, 1 H), 4.85-4.90 (m, 1 H), 3.72-3.82 (m, 0.6 H), 3.24-3.31 (m, 0.4 H), 2.71-3.05 (m, 2 H), 1.74-1.82 (m, 6 H) | 430.1 $[M + H]^+$ | 99.5% |
| 970 | ($CD_3OD$) δ 7.99-8.14 (m, 1 H), 7.70 (s, 1 H), 6.89-7.47 (m, 1 H), 6.77-6.83 (m, 1 H), 6.52-6.72 (m, 2 H), 4.97 (br d, 1 H), 3.89-4.02 (m, 3 H), 3.37-3.82 (m, 1 H), 2.75-3.23 (m, 2 H), 1.82-2.00 (m, 6 H) | 426.2 $[M + H]^+$ | 98.8% |
| 971 | ($CD_3OD$) δ 7.87-8.04 (m, 1 H), 7.59 (s, 1 H), 6.78-7.37 (m, 1 H), 6.68 (q, 1 H), 6.38-6.58 (m, 2 H), 4.85 (br d, 1 H), 3.79-3.90 (m, 3 H), 3.25-3.71 (m, 1 H), 2.65-3.12 (m, 2 H), 1.72-1.84 (m, 6 H) | 426.1 $[M + H]^+$ | 98.4% |
| 972 | ($CD_3OD$) δ 8.40-8.50 (m, 1 H), 7.99-8.03 (m, 1 H), 7.71 (s, 1 H), 7.53-7.66 (m, 1.3 H), 7.16-7.26 (m, 1 H), 6.97 (s, 0.7 H), 6.83-6.92 (m, 1 H), 6.57-6.67 (m, 1 H), 4.99-5.12 (m, 1 H), 3.90 (s, 3 H), 3.73-3.84 (m, 0.7 H), 3.42 (td, 0.3 H), 2.96-3.26 (m, 1 H), 2.80-2.91 (m, 1 H), 2.66-2.72 (m, 3 H) | 430.2 $[M + H]^+$ | 100% |
| 973 | ($CD_3OD$) δ 8.39-8.50 (m, 1 H), 8.00-8.03 (m, 1 H), 7.71 (br s, 1 H), 7.56-7.65 (m, 1.3 H), 7.17-7.25 (m, 1 H), 6.97 (s, 0.7 H), 6.83-6.92 (m, 1 H), 6.57-6.68 (m, 1 H), 5.09 (br dd, 1 H), 3.91 (s, 3 H), 3.72-3.84 (m, 0.7 H), 3.42 (td, 0.3 H), 2.96-3.26 (m, 1 H), 2.86 (br d, 1 H), 2.66-2.72 (m, 3 H) | 430.2 $[M + H]^+$ | 98.6% |
| 974 | ($CD_3OD$) δ 8.79 (d, 1 H), 8.28-8.41 (m, 1 H), 8.10 (td, 1 H), 7.63-7.79 (m, 2 H), 7.42-7.60 (m, 1.5 H), 7.18-7.34 (m, 1 H), 7.00 (s, 0.5 H), 6.71-6.87 (m, 1 H), 6.54-6.70 (m, 1 H), 5.06 (br dd, 1 H), 3.79-3.93 (m, 0.6 H), 3.46 (td, 0.4 H), 2.98-3.29 (m, 1 H), 2.82-2.95 (m, 1 H) | 431.1 $[M + H]^+$ | 99.7% |
| 975 | ($CD_3OD$) 8 8.79 (d, 1 H), 8.29-8.42 (m, 1 H), 8.11 (td, 1 H), 7.64-7.77 (m, 2 H), 7.40-7.59 (m, 1.4 H), 7.17-7.34 (m, 1 H), | 431.2 $[M + H]^+$ | 97.2% |

TABLE 2-continued

| Ex. # | $^{1}$H NMR (400 MHz unless otherwise noted) | LCMS: m/z | % ee |
|---|---|---|---|
| | 7.00 (s, 0.6 H), 6.71-6.89 (m, 1 H), 6.59-6.70 (m, 1 H), 5.06 (br dd, 1 H), 3.80-3.96 (m, 0.5 H), 3.41-3.53 (m, 0.5 H), 2.95-3.28 (m, 1 H), 2.88 (dd, 1 H) | | |
| 976 | ($CD_3OD$) δ 7.80 (dd, 1 H), 7.69 (d, 1 H), 7.49-7.62 (m, 1,5 H), 7.16 (dd, 1 H), 6.95-7.03 (m, 2.5 H), 6.60-6.78 (m, 1 H), 5.05 (br dd, 1 H), 4.02 (d, 3 H), 3.90 (ddd, 0.6 H), 3.33-3.41 (m, 0.4 H), 2.82-3.20 (m, 2 H) | 450.1 $[M + H]^+$ | 100% |
| 977 | ($CD_3OD$) δ 7.80 (dd, 1 H), 7.70 (br d, 1 H), 7.50-7.63 (m, 1.5 H), 7.10-7.21 (m, 1 H), 6.94-7.04 (m, 2.5 H), 6.60-6.80 (m, 1 H), 5.05 (br dd, 1 H), 4.02 (d, 3 H), 3.84-3.95 (m, 0.6 H), 3.34-3.41 (m, 0.4 H), 2.82-3.21 (m, 2 H) | 450.1 $[M + H]^+$ | 100% |
| 978 | ($CD_3OD$) δ 9.28-9.45 (m, 1 H), 8.64-8.86 (m, 2 H), 7.62 (br s, 1 H), 7.18-7.58 (m, 2 H), 6.82-7.18 (m, 2 H), 6.48-6.81 (m, 1 H), 4.82-5.00 (m, 1 H), 3.25-3.91 (m, 1 H), 2.72-3.16 (m, 2 H) | 448.1 $[M + H]^+$ | 98.7% |
| 979 | ($CD_3OD$) δ 9.42-9.54 (m, 1 H), 8.76-8.91 (m, 2 H), 7.74 (br d, 1 H), 7.43-7.70 (m, 2 H), 6.98-7.23 (m, 2 H), 6.62-6.86 (m, 1 H), 4.94-5.11 (m, 1 H), 3.38-4.01 (m, 1 H), 2.84-3.28 (m, 2 H) | 448.1 $[M + H]^+$ | 96.9% |
| 980 | ($CD_3OD$) δ 8.48-8.64 (m, 1 H), 7.69 (s, 1 H), 7.39-7.50 (m, 1.2 H), 7.08-7.13 (m, 0.4 H), 6.61-7.00 (m, 3.4 H), 5.00 (br dd, 1 H), 3.64-3.77 (m, 0.5 H), 3.39 (br d, 0.5 H), 2.77-3.18 (m, 2 H), 2.27-2.35 (m, 1 H), 1.19-1.31 (m, 4 H) | 426.2 $[M + H]^+$ | 100% |
| 981 | ($CD_3OD$) δ 8.52-8.61 (m, 1 H), 7.69 (s, 1 H), 7.38-7.49 (m, 1.2 H), 7.07-7.15 (m, 0.4 H), 6.68-7.00 (m, 3.4 H), 5.00 (br dd, 1 H), 3.66-3.78 (m, 0.5 H), 3.34-3.40 (m, 0.5 H), 2.78-3.19 (m, 2 H), 2.25-2.36 (m, 1 H), 1.20-1.30 (m, 4 H) | 426.2 $[M + H]^+$ | 100% |
| 982 | ($CD_3OD$) δ 8.62-8.69 (m, 1 H), 7.91-8.01 (m, 1 H), 7.68-7.80 (m, 2 H), 7.55-7.66 (m, 1 H), 7.48 (s, 0.4 H), 7.13-7.24 (m, 1 H), 6.97-7.08 (m, 1.6 H), 6.64-6.84 (m, 1 H), 4.98-5.10 (m, 1 H), 3.87-4.00 (m, 0.6 H), 3.38-3.48 (m, 0.4 H), 2.85-3.26 (m, 2 H) | 465.1 $[M + H]^+$ | 98.6% |
| 983 | ($CD_3OD$) δ 8.64 (d, 1 H), 7.94 (br t, 1 H), 7.68-7.79 (m, 2 H), 7.55-7.65 (m, 1 H), 7.47 (s, 0.4 H), 7.17 (dt, 1 H), 6.95-7.07 (m, 1.6 H), 6.61-6.84 (m, 1 H), 4.98-5.04 (m, 1 H), 3.93 (br s, 0.6 H), 3.36-3.46 (m, 0.4 H), 2.84-3.22 (m, 2 H) | 465.1 $[M + H]^+$ | 96.2% |
| 984 | ($CD_3OD$) δ 8.83-9.06 (m, 1 H), 8.37 (s, 1 H), 7.42-7.87 (m, 3.5 H), 7.19-7.33 (m, 1 H), 6.98 (s, 0.5 H), 6.80 (d, 0.5 H), 6.59-6.73 (m, 1.5 H), 5.12 (br dd, 1 H), 3.75-3.91 (m, 0.6 H), 3.39-3.48 (m, 0.4 H), 3.13-3.26 (m, 0.7 H), 3.02 (br t, 0.3 H), 2.87 (br d, 1 H) | 470.2 $[M + H]^+$ | 98.6% |
| 985 | ($CD_3OD$) δ 8.84-9.10 (m, 1 H), 8.37 (s, 1 H), 7.42-7.88 (m, 3.5 H), 7.19-7.34 (m, 1 H), 6.98 (s, 0.5 H), 6.80 (d, 0.5 H), 6.57-6.74 (m, 1.5 H), 5.12 (br dd, 1 H), 3.79-3.91 (m, 0.7 H), 3.40-3.49 (m, 0.3 H), 3.12-3.24 (m, 1 H), 2.87 (br d, 1 H) | 470.2 $[M + H]^+$ | 95.7% |
| 986 | ($CD_3OD$) δ 7.65-7.95 (m, 1 H), 7.21-7.52 (m, 2 H), 6.53-7.08 (m, 3 H), 4.99 (br d, 1 H), 3.38-3.88 (m, 1 H), 2.79-3.25 (m, 2 H), 1.79-2.01 (m, 6 H) | 414.2 $[M + H]^+$ | 99.4% |
| 987 | ($CD_3OD$) δ 7.63-8.07 (m, 1 H), 7.20-7.53 (m, 2 H), 6.53-7.16 (m, 3 H), 4.97-5.02 (m, 1 H), 3.36-3.86 (m, 1 H), 2.80-3.25 (m, 2 H), 1.82-1.99 (m, 6 H) | 414.2 $[M + H]^+$ | 95.1% |
| 988 | ($CD_3OD$) δ 8.19-8.35 (m, 1 H), 7.95-8.06 (m, 1 H), 7.52-7.74 (m, 1.4 H), 6.95-7.06 (m, 1,6 H), 6.55-6.86 (m, 2 H), 5.09 (br dd, 1 H), 3.70-3.99 (m, 3.7 H), 3.36-3.50 (m, 0.4 H), 2.94-3.28 (m, 1 H), 2.79-2.91 (m, 1 H), 2.60-2.74 (m, 3 H), 2.34-2.54 (m, 3 H) | 444.2 $[M + H]^+$ | 97.4% |
| 989 | ($CD_3OD$) δ 8.18-8.34 (m, 1 H), 7.93-8.04 (m, 1 H), 7.48-7.76 (m, 1.4 H), 6.95-7.06 (m, 1.6 H), 6.51-6.85 (m, 2 H), 5.07 (br dd, 1 H), 3.66-3.93 (m, 3.7 H), 3.35-3.48 (m, 0.3 H), 2.94-3.23 (m, 1 H), 2.78-2.92 (m, 1 H), 2.58-2.71 (m, 3 H), 2.31-2.51 (m, 3 H) | 444.2 $[M + H]^+$ | 97.7% |
| 990 | ($CD_3OD$) δ 8.46 (d, 1 H), 7.50-7.75 (m, 2 H), 7.18-7.24 (m, 1 H), 6.87 (td, 1.6 H), 6.33-6.72 (m, 1.4 H), 4.79 (br s, 0.4 H), 4.21 (br d, 0.6 H), 3.79 (br t, 0.6 H), 3.37-3.52 (m, 0.4 H), 2.91-3.21 (m, 1 H), 2.83 (br d, 1 H), 1.51-1.69 (m, 6 H) | 427.2 $[M + H]^+$ | 100% |
| 991 | ($CD_3OD$) δ 8.46 (d, 1 H), 7.54-7.76 (m, 2 H), 7.20 (t, 1 H), 6.86 (td, 1.6 H), 6.32-6.69 (m, 1.4 H), 4.80 (br s, 0.3 H), 4.21 (br d, 0.7 H), 3.79 (br t, 0.7 H), 3.41 (br s, 0.3 H), 2.92-3.22 (m, 1 H), 2.83 (br d, 1 H), 1.55-1.70 (m, 6 H) | 427.3 $[M + H]^+$ | 95.9% |
| 992 | ($CD_3OD$) δ 8.45 (br d, 1 H), 7.50-7.75 (m, 2 H), 7.10-7.28 (m, 1 H), 6.85 (br t, 1.5 H), 6.34-6.71 (m, 1.5 H), 4.27 (br d, 1 H), 3.34-3.91 (m, 1 H), 2.70-3.21 (m, 2 H), 2.37 (s, 3 H), 1.57-2.02 (m, 6 H) | 416.2 $[M + H]^+$ | 100% |
| 993 | ($CD_3OD$) δ 8.44 (br d, 1 H), 7.49-7.75 (m, 2 H), 7.18 (dd, 1 H), 6.36-6.92 (m, 3 H), 4.04-4.43 (m, 1 H), 3.35-3.84 (m, 1 H), 2.64-3.22 (m, 2 H), 2.37 (s, 3 H), 1.64-2.06 (m, 6 H) | 416.3 $[M + H]^+$ | 99.6% |
| 994 | ($CD_3OD$) δ 8.46 (dd, 1 H), 7.69 (s, 1 H), 7.61 (br d, 1 H), 7.11-7.30 (m, 2 H), 6.80-7.05 (m, 2 H), 6.63 (s, 1 H), 4.39 (br d, 1 H), 3.73 (br s, 1 H), 2.74-3.27 (m, 2 H), 1.26-1.58 (m, 4 H) | 441.2 $[M + H]^+$ | 99.3% |
| 995 | ($CD_3OD$) δ 8.34 (dd, 1 H), 7.57 (s, 1 H), 7.49 (br d, 1 H), 7.00-7.20 (m, 2 H), 6.68-6.92 (m, 2 H), 6.51 (s, 1 H), 4.13-4.37 (m, 1 H), 3.51-3.77 (m, 1 H), 2.65-3.12 (m, 2 H), 1.14-1.49 (m, 4 H) | 441.2 $[M + H]^+$ | 99.3% |

TABLE 2-continued

| Ex. # | $^1$H NMR (400 MHz unless otherwise noted) | LCMS: m/z | % ee |
|---|---|---|---|
| 996 | ($CD_3OD$) δ 8.42 (d, 1 H), 7.50-7.69 (m, 2 H), 7.17 (t, 1 H), 6.77-6.88 (m, 1.6 H), 6.29-6.64 (m, 1.4 H), 4.97-5.14 (m, 1 H), 4.75 (br d, 0.4 H), 4.12 (br d, 0.6 H), 3.74 (br t, 0.6 H), 3.38 (br s, 0.4 H), 2.90-3.13 (m, 1 H), 2.78 (br dd, 1 H), 1.55 (br d, 3 H) | 459.2 $[M + H]^+$ | 94.9% |
| 997 | ($CD_3OD$) δ 8.46 (d, 1 H), 7.57-7.80 (m, 2 H), 7.21 (t, 1 H), 6.82-6.91 (m, 1.7 H), 6.38-6.67 (m, 1.3 H), 4.97-5.11 (m, 1 H), 4.74-4.83 (m, 0.4 H), 4.18 (br d, 0.6 H), 3.78 (br t, 0.6 H), 3.42 (br s, 0.4 H), 2.92-3.20 (m, 1 H), 2.83 (br dd, 1 H), 1.59 (br d, 3 H) | 459.1 $[M + H]^+$ | 97.0% |
| 998 | ($CD_3OD$) δ 8.42 (d, 1 H), 7.51-7.70 (m, 2 H), 7.12-7.23 (m, 1 H), 6.79-6.89 (m, 1.6 H), 6.25-6.64 (m, 1.4 H), 4.94-5.11 (m, 1 H), 4.77 (br s, 0.4 H), 4.12 (br d, 0.6 H), 3.69-3.82 (m, 0.6 H), 3.38 (br s, 0.4 H), 2.89-3.16 (m, 1 H), 2.78 (br dd, 1 H), 1.55 (br d, 3 H) | 459.2 $[M + H]^+$ | 93.1% |
| 999 | ($CD_3OD$) δ 8.46 (d, 1 H), 7.54-7.74 (m, 2 H), 7.21 (br t, 1 H), 6.87 (t, 1.7 H), 6.35-6.69 (m, 1.3 H), 4.97-5.05 (m, 1 H), 4.74-4.84 (m, 0.4 H), 4.16 (br d, 0.6 H), 3.74-3.93 (m, 0.6 H), 3.42 (br s, 0.4 H), 2.93-3.19 (m, 1 H), 2.82 (br dd, 1 H), 1.59 (br d, 3 H) | 459.2 $[M + H]^+$ | 98.8% |
| 1000 | ($CD_3OD$) δ 8.34 (d, 1 H), 7.67 (s, 1 H), 6.96 (dd, 1 H), 6.47-6.87 (m, 3 H), 4.26-4.81 (m, 1 H), 3.35-3.78 (m, 1 H), 2.90-3.22 (m, 1 H), 2.80 (br d, 1 H), 2.37 (s, 3 H), 1.49-1.67 (m, 6 H) | 425.0 $[M + H]^+$ | 98.6% |
| 1001 | ($CD_3OD$) δ 8.34 (d, 1 H), 7.67 (s, 1 H), 6.96 (dd, 1 H), 6.45-6.87 (m, 3 H), 4.27-4.84 (m, 1 H), 3.35-3.79 (m, 1 H), 2.66-3.22 (m, 2 H), 2.37 (s, 3 H), 1.49-1.70 (m, 6 H) | 425.1 $[M + H]^+$ | 99.8% |
| 1002 | ($CD_3OD$) δ 8.69 (d, 1 H), 8.42 (s, 1 H), 7.70 (s, 1 H), 7.63 (d, 1 H), 7.10-7.31 (m, 1 H), 6.55-7.02 (m, 3 H), 4.33 (br s, 1 H), 3.73 (br s, 1 H), 2.73-3.14 (m, 2 H) | 453.1 $[M + H]^+$ | 99.7% |
| 1003 | ($CD_3OD$) δ 8.69 (d, 1 H), 8.42 (s, 1 H), 7.69 (s, 1 H), 7.63 (d, 1 H), 7.11-7.29 (m, 1 H), 6.56-7.02 (m, 3 H), 4.35 (br d, 1 H), 3.73 (br s, 1 H), 2.74-3.15 (m, 2 H) | 453.1 $[M + H]^+$ | 99.2% |
| 1004 | ($CD_3OD$) δ 8.44 (s, 1 H), 8.33 (d, 1 H), 7.72 (s, 1 H), 7.01-7.41 (m, 2 H), 6.61-6.92 (m, 2 H), 6.40-6.57 (m, 1 H), 4.26-4.84 (m, 1 H), 3.48-3.82 (m, 1 H), 3.08 (br s, 1 H), 2.81 (br d, 1 H), 2.38 (s, 3 H) | 399.2 $[M + H]^+$ | 99.7% |
| 1005 | ($CD_3OD$) δ 8.44 (s, 1 H), 8.33 (d, 1 H), 7.69 (s, 1 H), 7.00-7.41 (m, 2 H), 6.61-6.92 (m, 2 H), 6.49 (br s, 1 H), 4.24-4.79 (m, 1 H), 3.41-3.83 (m, 1 H), 2.96-3.16 (m, 1 H), 2.81 (br d, 1 H), 2.38 (s, 3 H) | 399.2 $[M + H]^+$ | 98.5% |
| 1006 | ($CD_3OD$) δ 8.74 (d, 1 H), 8.19-8.40 (m, 2 H), 8.06 (br s, 1 H), 7.59-7.78 (m, 2 H), 6.73-7.40 (m, 5 H), 4.80-4.86 (m, 0.4 H), 4.54 (br d, 0.6 H), 3.51-3.87 (m, 1 H), 2.99-3.32 (m, 1 H), 2.87 (br d, 1 H) | 480.2 $[M + H]^+$ | 100% |
| 1007 | ($CD_3OD$) δ 8.74 (d, 1 H), 8.16-8.50 (m, 2 H), 8.05 (br d, 1 H), 7.54-7.78 (m, 2 H), 6.64-7.47 (m, 5 H), 4.78-4.87 (m, 0.4 H), 4.54 (br d, 0.6 H), 3.53-3.90 (m, 1 H), 2.96-3.30 (m, 1 H), 2.87 (br d, 1 H) | 480.2 $[M + H]^+$ | 99.3% |
| 1008 | ($CD_3OD$) δ 7.87-8.40 (m, 3 H), 7.77 (br s, 1 H), 7.05-7.37 (m, 1 H), 6.94-7.04 (m, 1 H), 6.53-6.92 (m, 3 H), 4.50 (br s, 1 H), 3.98 (br s, 3 H), 3.77 (br s, 0.6 H), 3.49 (br s, 0.4 H), 2.71-3.26 (m, 2 H), 2.45 (s, 3 H) | 479.2 $[M + H]^+$ | 95.3% |
| 1009 | ($CD_3OD$) δ 7.85-8.39 (m, 3 H), 7.71 (s, 1 H), 7.04-7.35 (m, 1 H), 6.99 (d, 1 H), 6.48-6.92 (m, 3 H), 4.32-4.72 (m, 1 H), 3.97 (br s, 3 H), 3.68-3.85 (m, 0.6 H), 3.46 (br d, 0.4 H), 2.73-3.23 (m, 2 H), 2.44 (s, 3 H) | 479.2 $[M + H]^+$ | 92.8% |
| 1010 | ($CD_3OD$) δ 8.23-8.33 (m, 1 H), 7.43-7.71 (m, 1.3 H), 6.90-7.01 (m, 1.7 H), 6.72-6.81 (m, 1 H), 6.51-6.63 (m, 1 H), 4.90-4.97 (m, 1 H), 3.74 (ddd, 0.7 H), 3.38 (td, 0.3 H), 3.07-3.18 (m, 0.6 H), 2.90-3.02 (m, 0.4 H), 2.81 (br dd, 1 H), 2.60-2.65 (m, 3 H), 2.39-2.47 (m, 3 H) | 364.2 $[M + H]^+$ | 100% |
| 1011 | ($CD_3OD$) δ 8.23-8.35 (m, 1 H), 7.72-7.83 (m, 1 H), 7.49 (s, 0.3 H), 6.92-7.01 (m, 1.7 H), 6.71-6.83 (m, 1 H), 6.49-6.65 (m, 1 H), 4.92-4.99 (m, 1 H), 3.74 (ddd, 0.7 H), 3.38 (td, 0.3 H), 3.07-3.19 (m, 0.7 H), 2.92-3.02 (m, 0.3 H), 2.77-2.87 (m, 1 H), 2.59-2.67 (m, 3 H), 2.38-2.48 (m, 3 H) | 364.2 $[M + H]^+$ | 100% |
| 1012 | ($CD_3OD$) δ 8.31 (d, 1 H), 7.69 (s, 1.3 H), 6.89-7.07 (m, 1.7 H), 6.74-6.86 (m, 1 H), 6.54-6.66 (m, 1 H), 5.21 (dd, 0.7 H), 4.92-5.04 (m, 1 H), 3.53-3.88 (m, 5 H), 3.39 (br dd, 0.3 H), 2.75-3.22 (m, 2 H), 2.40-2.49 (m, 3 H), 1.86-2.17 (m, 4 H) | 451.3 $[M + H]^+$ | 100% |
| 1013 | ($CD_3OD$) δ 8.22-8.38 (m, 1 H), 7.57-7.80 (m, 1.3 H), 6.74-7.11 (m, 2.7 H), 6.56-6.70 (m, 1 H), 5.21 (dd, 0.7 H), 4.97 (br s, 1 H), 3.62-3.80 (m, 5 H), 3.37-3.45 (m, 0.3 H), 2.75-3.19 (m, 2 H), 2.41-2.51 (m, 3 H), 1.89-2.15 (m, 4 H) | 451.3 $[M + H]^+$ | 100% |
| 1014 | ($CD_3OD$) δ 8.35 (d, 1 H), 7.54-7.82 (m, 1.4 H), 6.81-7.12 (m, 2.6 H), 6.75 (s, 1 H), 5.23 (dd, 0.6 H), 4.97 (br d, 1 H), 3.61-3.82 (m, 5 H), 3.35-3.47 (m, 0.6 H), 2.74-3.22 (m, 2 H), 1.76-2.24 (m, 4 H) | 455.2 $[M + H]^+$ | 100% |
| 1015 | ($CD_3OD$) δ 8.23 (d, 1 H), 7.41-7.74 (m, 1.3 H), 6.68-6.91 (m, 2.7 H), 6.63 (s, 1 H), 5.11 (br dd, 1 H), 4.85 (br s, 1 H), 3.52- | 455.2 $[M + H]^+$ | 99.0% |

TABLE 2-continued

| Ex. # | $^1$H NMR (400 MHz unless otherwise noted) | LCMS: m/z | % ee |
|---|---|---|---|
| | 3.68 (m, 5 H), 3.24-3.30 (m, 0.6 H), 2.61-3.09 (m, 2 H), 1.74-2.01 (m, 4 H) | | |
| 1016 | ($CD_3OD$) δ 8.20-8.33 (m, 1 H), 7.51-7.73 (m, 2.3 H), 7.03-7.09 (m, 1 H), 6.93-7.01 (m, 1.7 H), 6.71-6.83 (m, 1 H), 6.54-6.67 (m, 1 H), 5.04 (dd, 1 H), 4.26-4.36 (m, 3 H), 3.79 (ddd, 0.7 H), 3.35-3.52 (m, 0.3 H), 2.76-3.25 (m, 2 H), 2.36-2.51 (m, 3 H) | 430.2 $[M + H]^+$ | 99.5% |
| 1017 | ($CD_3OD$) δ 8.20-8.33 (m, 1 H), 7.48-7.75 (m, 2.3 H), 7.04-7.11 (m, 1 H), 6.91-7.03 (m, 1.7 H), 6.71-6.83 (m, 1 H), 6.53-6.67 (m, 1 H), 4.98-5.12 (m, 1 H), 4.24-4.37 (m, 3 H), 3.71-3.86 (m, 0.7 H), 3.36-3.52 (m, 0.3 H), 2.73-3.26 (m, 2 H), 2.37-2.49 (m, 3 H) | 430.2 $[M + H]^+$ | 99.4% |
| 1018 | ($CD_3OD$) δ 8.26-8.37 (m, 1 H), 7.49-7.73 (m, 2.3 H), 7.05-7.11 (m, 1 H), 6.90-7.02 (m, 1.7 H), 6.78-6.87 (m, 1 H), 6.72-6.78 (m, 1 H), 5.07 (dd, 1 H), 4.28-4.33 (m, 3 H), 3.78 (ddd, 0.7 H), 3.41 (td, 0.3 H), 2.75-3.26 (m, 2 H) | 434.2 $[M + H]^+$ | 99.3% |
| 1019 | ($CD_3OD$) δ 8.25-8.38 (m, 1 H), 7.51-7.73 (m, 2.3 H), 7.05-7.11 (m, 1 H), 6.91-7.02 (m, 1.7 H), 6.78-6.87 (m, 1 H), 6.72-6.78 (m, 1 H), 5.07 (dd, 1 H), 4.25-4.36 (m, 3 H), 3.72-3.84 (m, 0.7 H), 3.36-3.48 (m, 0.3 H), 2.77-3.25 (m, 2 H) | 434.2 $[M + H]^+$ | 99.2% |
| 1020 | ($CD_3OD$) δ 7.68 (d, 1 H), 7.35-7.54 (m, 1.4 H), 7.04-7.19 (m, 1 H), 6.96 (s, 0.6 H), 6.67-6.75 (m, 1 H), 6.42-6.61 (m, 1 H), 4.92-4.99 (m, 1 H), 3.82-3.94 (m, 0.5 H), 3.34-3.40 (m, 0.5 H), 2.76-3.20 (m, 2 H), 2.57-2.70 (m, 3 H), 1.47 (d, 9 H) | 406.2 $[M + H]^+$ | 98.7% |
| 1021 | ($CD_3OD$) δ 7.68 (d, 1 H), 7.33-7.53 (m, 1.4 H), 7.05-7.18 (m, 1 H), 6.95 (s, 0.6 H), 6.66-6.75 (m, 1 H), 6.40-6.63 (m, 1 H), 4.92-4.99 (m, 1 H), 3.87 (br t, 0.5 H), 3.34-3.42 (m, 0.5 H), 2.77-3.19 (m, 2 H), 2.55-2.72 (m, 3 H), 1.47 (d, 9 H) | 406.3 $[M + H]^+$ | 95.3% |
| 1022 | ($CD_3OD$) δ 8.20-8.33 (m, 1 H), 7.69 (s, 1 H), 7.41 (s, 0.3 H), 6.91-7.04 (m, 1.7 H), 6.73-6.82 (m, 1 H), 6.50-6.66 (m, 1 H), 4.95 (br dd, 1 H), 3.69-3.78 (m, 0.5 H), 3.34-3.43 (m, 0.5 H), 2.92-3.20 (m, 1 H), 2.82 (br dd, 1 H), 2.38-2.50 (m, 3 H), 1.41-1.56 (m, 9 H) | 406.2 $[M + H]^+$ | 100% |
| 1023 | ($CD_3OD$) δ 8.22-8.32 (m, 1 H), 7.71-7.78 (m, 1 H), 7.42 (s, 0.3 H), 6.90-7.03 (m, 1.7 H), 6.72-6.83 (m, 1 H), 6.49-6.66 (m, 1 H), 4.96 (dd, 1 H), 3.67-3.80 (m, 0.6 H), 3.38 (td, 0.4 H), 2.90-3.21 (m, 1 H), 2.83 (br dd, 1 H), 2.36-2.50 (m, 3 H), 1.45-1.50 (m, 9 H) | 406.2 $[M + H]^+$ | 99.6% |
| 1024 | ($CD_3OD$) δ 8.27-8.36 (m, 1 H), 7.69 (s, 1 H), 7.41 (s, 0.4 H), 6.91-7.00 (m, 1.6 H), 6.78-6.88 (m, 1 H), 6.66-6.77 (m, 1 H), 4.94-4.99 (m, 1 H), 3.70-3.82 (m, 0.7 H), 3.37 (br s, 0.3 H), 2.83 (br dd, 2 H), 1.83-1.95 (m, 6 H) | 414.2 $[M + H]^+$ | 96.1% |
| 1025 | ($CD_3OD$) δ 8.26-8.40 (m, 1 H), 7.69 (s, 1 H), 7.41 (s, 0.4 H), 6.92-7.00 (m, 1.6 H), 6.79-6.87 (m, 1 H), 6.66-6.76 (m, 1 H), 4.93-5.00 (m, 1 H), 3.75 (br s, 1 H), 2.79-3.21 (m, 2 H), 1.79-1.95 (m, 6 H) | 414.2 $[M + H]^+$ | 95.0% |
| 1026 | ($CD_3OD$) δ 8.25-8.38 (m, 1 H), 7.69 (s, 1 H), 7.40 (br s, 0.3 H), 6.89-7.02 (m, 1.7 H), 6.78-6.88 (m, 1 H), 6.63-6.77 (m, 1 H), 4.91-5.03 (m, 1 H), 3.66-3.80 (m, 0.7 H), 3.35-3.44 (m, 0.3 H), 2.77-3.21 (m, 2 H), 1.45-1.51 (m, 9 H) | 410.2 $[M + H]^+$ | 100% |
| 1027 | ($CD_3OD$) δ 8.27-8.38 (m, 1 H), 7.69 (s, 1 H), 7.40 (br s, 0.3 H), 6.89-7.01 (m, 1.7 H), 6.78-6.87 (m, 1 H), 6.62-6.78 (m, 1 H), 4.90-5.01 (m, 1 H), 3.65-3.81 (m, 0.7 H), 3.35-3.42 (m, 0.3 H), 2.74-3.19 (m, 2 H), 1.44-1.52 (m, 9 H) | 410.2 $[M + H]^+$ | 100% |
| 1028 | ($CD_3OD$) δ 8.78 (t, 1 H), 8.31 (d, 1 H), 8.04-8.16 (m, 1 H), 7.80-7.91 (m, 1 H), 7.65-7.75 (m, 2 H), 7.54-7.61 (m, 0.5 H), 7.29 (br s, 2 H), 6.88 (s, 1 H), 6.68 (s, 0.5 H), 4.94-5.08 (m, 1 H), 3.90-4.07 (m, 0.5 H), 3.34-3.37 (m, 0.5 H), 2.84-3.26 (m, 2 H) | 481.2 $[M + H]^+$ | 100% |
| 1029 | ($CD_3OD$) δ 8.77 (t, 1 H), 8.30 (d, 1 H), 8.04-8.13 (m, 1 H), 7.78-7.90 (m, 1 H), 7.63-7.74 (m, 2 H), 7.57 (s, 0.5 H), 7.22-7.36 (m, 2 H), 6.85-7.01 (m, 1 H), 6.67 (s, 0.5 H), 4.93-5.04 (m, 1 H), 3.97 (br s, 0.5 H), 3.33-3.38 (m, 0.5 H), 2.83-3.25 (m, 2 H) | 481.2 $[M + H]^+$ | 99.8% |
| 1030 | ($CD_3OD$) δ 7.76-7.87 (m, 2 H), 7.69 (br d, 1 H), 7.58 (s, 0.5 H), 7.18-7.34 (m, 2 H), 6.82-6.99 (m, 2 H), 6.66 (s, 0.5 H), 4.96-5.08 (m, 1 H), 4.01 (d, 3.8 H), 3.36 (br d, 0.2 H), 3.17 (br s, 0.5 H), 2.96 (br dd, 0.5 H), 2.85 (br d, 1 H) | 484.2 $[M + H]^+$ | 100% |
| 1031 | ($CD_3OD$) δ 7.77-7.88 (m, 2 H), 7.54-7.59 (m, 1 H), 7.58 (s, 0.5 H), 7.20-7.34 (m, 2 H), 6.84-6.97 (m, 2 H), 6.66 (s, 0.5 H), 4.92-5.07 (m, 1 H), 4.01 (d, 3.8 H), 3.32-3.37 (m, 0.2 H), 3.10-3.21 (m, 0.5 H), 2.98 (s, 0.5 H), 2.81-2.89 (m, 1 H) | 484.2 $[M + H]^+$ | 100% |
| 1032 | ($CD_3OD$) δ 7.97 (d, 1 H), 7.80-7.90 (m, 2 H), 7.66-7.75 (m, 1 H), 7.54 (s, 0.5 H), 7.23-7.36 (m, 2 H), 6.85-6.99 (m, 1 H), 6.66 (s, 0.5 H), 5.08 (br dd, 0.5 H), 4.93-4.97 (m, 1 H), 4.09 (s, 3 H), 3.90-4.00 (m, 0.5 H), 2.94-3.04 (m, 1 H), 2.82-2.90 (m, 1 H) | 484.2 $[M + H]^+$ | 100% |
| 1033 | ($CD_3OD$) δ 7.97 (d, 1 H), 7.80-7.89 (m, 2 H), 7.79 (s, 1 H), 7.55 (s, 0.5 H), 7.22-7.36 (m, 2 H), 6.85-7.01 (m, 1 H), 6.68 (s, 0.5 H), 5.10 (dd, 0.5 H), 4.90-4.98 (m, 1 H), 4.09 (s, 3 H), 3.90-3.99 (m, 0.5 H), 2.94-3.04 (m, 1 H), 2.83-2.91 (m, 1 H) | 484.2 $[M + H]^+$ | 99.5% |

TABLE 2-continued

| Ex. # | $^1$H NMR (400 MHz unless otherwise noted) | LCMS: m/z | % ee |
|---|---|---|---|
| 1034 | ($CD_3OD$) δ 8.60-8.74 (m, 1 H), 7.88-8.00 (m, 1.5 H), 7.73-7.86 (m, 2 H), 7.54-7.72 (m, 1 H), 7.24-7.39 (m, 2 H), 6.68-7.03 (m, 1.5 H), 5.02 (br d, 1 H), 3.92-4.07 (m, 0.5 H), 3.37-3.42 (m, 0.5 H), 2.86-3.23 (m, 2 H) | 499.2 $[M + H]^+$ | 100% |
| 1035 | ($CD_3OD$) δ 8.65 (t, 1 H), 7.87-7.98 (m, 1.5 H), 7.71-7.84 (m, 2 H), 7.52-7.69 (m, 1 H), 7.21-7.38 (m, 2 H), 6.66-7.00 (m, 1.5 H), 4.96 (br t, 1 H), 3.89-4.05 (m, 0.5 H), 3.34-3.41 (m, 0.5 H), 2.84-3.22 (m, 2 H) | 499.2 $[M + H]^+$ | 100% |
| 1036 | ($CD_3OD$) δ 8.34 (dd, 1 H), 7.50-7.91 (m, 3.5 H), 7.19-7.39 (m, 3 H), 6.65-7.01 (m, 1.5 H), 4.97-5.09 (m, 1 H), 3.88-4.07 (m, 0.5 H), 3.33-3.51 (m, 0.5 H), 2.85-3.22 (m, 2 H) | 520.2 $[M + H]^+$ | 98.0% |
| 1037 | ($CD_3OD$) δ 8.33 (dd, 1 H), 7.51-7.90 (m, 3.5 H), 7.19-7.38 (m, 3 H), 6.64-7.01 (m, 1.5 H), 4.94-5.04 (m, 1 H), 3.97 (br d, 0.5 H), 3.33-3.39 (m, 0.5 H), 2.85-3.21 (m, 2 H) | 520.2 $[M + H]^+$ | 98.8% |
| 1038 | ($CD_3OD$) δ 8.46-8.50 (m, 1 H), 8.23-8.33 (m, 1 H), 8.14 (s, 1 H), 7.69 (s, 1 H), 7.57 (s, 0.3 H), 6.93-7.02 (m, 1.7 H), 6.73-6.82 (m, 1 H), 6.53-6.66 (m, 1 H), 4.99-5.11 (m, 2 H), 3.71-3.83 (m, 0.6 H), 3.36-3.47 (m, 0.4 H), 3.11-3.23 (m, 0.7 H), 2.92-3.06 (m, 0.3 H), 2.78-2.90 (m, 1 H), 2.57-2.67 (m, 2 H), 2.47-2.57 (m, 2 H), 2.39-2.47 (m, 3 H), 1.85-2.00 (m, 2 H) | 470.2 $[M + H]^+$ | 100% |
| 1039 | ($CD_3OD$) δ 8.46-8.50 (m, 1 H), 8.23-8.33 (m, 1 H), 8.14 (s, 1 H), 7.69 (s, 1 H), 7.57 (s, 0.3 H), 6.93-7.02 (m, 1.7 H), 6.73-6.82 (m, 1 H), 6.53-6.66 (m, 1 H), 4.99-5.11 (m, 2 H), 3.71-3.83 (m, 0.6 H), 3.36-3.47 (m, 0.4 H), 3.11-3.23 (m, 0.7 H), 2.92-3.06 (m, 0.3 H), 2.78-2.90 (m, 1 H), 2.57-2.67 (m, 2 H), 2.47-2.57 (m, 2 H), 2.39-2.47 (m, 3 H), 1.85-2.00 (m, 2 H) | 470.2 $[M + H]^+$ | 98.5% |
| 1040 | ($CD_3OD$) δ 8.91 (d, 1 H), 8.35 (d, 1 H), 7.73-7.91 (m, 2 H), 7.64-7.68 (m, 1 H), 7.50-7.57 (m, 0.6 H), 7.24-7.37 (m, 2 H), 6.84-6.99 (m, 1 H), 6.66 (s, 0.4 H), 5.10 (br dd, 1 H), 3.91-4.02 (m, 1 H), 2.84-3.18 (m, 2 H) | 520.1 $[M + H]^+$ | 100% |
| 1041 | ($CD_3OD$) δ 8.89 (d, 1 H), 8.33 (d, 1 H), 7.69-7.89 (m, 2 H), 7.63-7.68 (m, 1 H), 7.48-7.55 (m, 0.6 H), 7.22-7.37 (m, 2 H), 6.83-6.98 (m, 1 H), 6.64 (s, 0.4 H), 5.09 (dd, 1 H), 3.87-4.02 (m, 1 H), 2.84-3.20 (m, 2 H) | 520.1 $[M + H]^+$ | 98.3% |
| 1042 | ($CD_3OD$) δ 8.76 (dd, 1 H), 8.24-8.35 (m, 1 H), 8.07 (tdd, 1 H), 7.54-7.71 (m, 3 H), 7.48 (s, 0.4 H), 7.10-7.21 (m, 1 H), 6.94-7.04 (m, 1.6 H), 6.60-6.81 (m, 1 H), 4.96-5.07 (m, 1 H), 3.88-3.95 (m, 0.5 H), 3.38 (td, 0.5 H), 2.82-3.23 (m, 2 H) | 447.1 $[M + H]^+$ | 100% |
| 1043 | ($CD_3OD$) δ 8.76 (dd, 1 H), 8.24-8.35 (m, 1 H), 8.07 (tdd, 1 H), 7.54-7.71 (m, 3 H), 7.48 (s, 0.4 H), 7.10-7.21 (m, 1 H), 6.94-7.04 (m, 1.6 H), 6.60-6.81 (m, 1 H), 4.96-5.07 (m, 1 H), 3.88-3.95 (m, 0.5 H), 3.38 (td, 0.5 H), 2.82-3.23 (m, 2 H) | 447.1 $[M + H]^+$ | 97.2% |
| 1044 | ($CD_3OD$) δ 8.71 (br d, 1 H), 7.94-8.05 (m, 1 H), 7.70 (d, 1 H), 7.58-7.66 (m, 1 H), 6.50-7.02 (m, 3 H), 4.91-4.96 (m, 0.5 H), 4.42 (dd, 0.5 H), 4.03-4.08 (m, 3 H), 3.66 (ddd, 0.6 H), 3.10-3.25 (m, 1 H), 2.93-3.03 (m, 0.4 H), 2.70-2.86 (m, 1 H) | 417.1 $[M + H]^+$ | 100% |
| 1045 | ($CD_3OD$) δ 8.71 (br d, 1 H), 7.96-8.03 (m, 1 H), 7.67-7.72 (m, 1 H), 7.58-7.65 (m, 1 H), 6.51-7.01 (m, 3 H), 4.91-4.96 (m, 0.4 H), 4.42 (dd, 0.6 H), 4.03-4.07 (m, 3 H), 3.66 (ddd, 0.6 H), 3.11-3.25 (m, 1 H), 2.93-3.02 (m, 0.4 H), 2.71-2.86 (m, 1 H) | 417.2 $[M + H]^+$ | 99.7% |
| 1046 | ($CD_3OD$) δ 8.36-8.47 (m, 1 H), 7.69 (br s, 1 H), 7.40 (br s, 0.2 H), 7.23-7.33 (m, 1 H), 6.92 (br s, 0.6 H), 6.80-6.88 (m, 1 H), 6.62-6.76 (m, 1 H), 4.95-5.01 (m, 1 H), 3.62-3.86 (m, 0.7 H), 3.33-3.41 (m, 0.4 H), 2.72-3.23 (m, 2 H), 1.42-1.52 (m, 9 H) | 426.1 $[M + H]^+$ | 100% |
| 1047 | ($CD_3OD$) δ 8.37-8.47 (m, 1 H), 7.70 (s, 1 H), 7.41 (br s, 0.2 H), 7.26-7.33 (m, 1 H), 6.93 (s, 0.5 H), 6.81-6.89 (m, 1 H), 6.65-6.77 (m, 1 H), 4.95-5.01 (m, 1 H), 3.66-3.80 (m, 0.7 H), 3.37-3.42 (m, 0.2 H), 2.79-3.22 (m, 2 H), 1.42-1.54 (m, 9 H) | 426.1 $[M + H]^+$ | 99.8% |
| 1048 | ($CD_3OD$) δ 8.25-8.38 (m, 1 H), 7.67 (d, 1 H), 7.24-7.40 (m, 1 H), 6.67-6.98 (m, 3 H), 6.48 (s, 0.6 H), 6.22 (s, 0.4 H), 4.42 (dd, 0.5 H), 4.05-4.13 (m, 3 H), 3.67 (ddd, 0.5 H), 2.91-3.30 (m, 2 H), 2.70-2.86 (m, 1 H), 2.30-2.39 (m, 3 H) | 413.2 $[M + H]^+$ | 100% |
| 1049 | ($CD_3OD$) δ 8.30-8.37 (m, 1 H), 7.69 (d, 1 H), 7.27-7.42 (m, 1 H), 6.69-7.00 (m, 3 H), 6.50 (s, 0.6 H), 6.24 (s, 0.4 H), 4.44 (dd, 0.5 H), 4.07-4.14 (m, 3 H), 3.69 (ddd, 0.5 H), 2.93-3.31 (m, 2 H), 2.72-2.88 (m, 1 H), 2.33-2.41 (m, 3 H) | 413.2 $[M + H]^+$ | 98.0% |
| 1050 | ($CD_3OD$) δ 8.40-8.47 (m, 1 H), 8.00 (s, 1 H), 7.69 (d, 1 H), 7.24-7.31 (m, 1 H), 6.80-6.95 (m, 2 H), 6.74 (s, 0.6 H), 6.47 (s, 0.4 H), 4.39 (m, 1 H), 4.03-4.07 (m, 3 H), 3.66 (m, 0.6 H), 3.08-3.26 (m, 1 H), 2.92-3.01 (m, 0.4 H), 2.69-2.85 (m, 1 H) | 383.1 $[M + H]^+$ | 99.9% |
| 1051 | ($CD_3OD$) δ 8.40-8.47 (m, 1 H), 7.99 (s, 1 H), 7.69 (d, 1 H), 7.24-7.31 (m, 1 H), 6.80-6.95 (m, 2 H), 6.73 (s, 0.6 H), 6.46 (s, 0.4 H), 4.39 (m, 1 H), 4.03-4.06 (m, 3 H), 3.65 (m, 0.6 H), 3.08-3.26 (m, 1 H), 2.91-3.01 (m, 0,4 H), 2.69-2.85 (m, 1 H) | 383.1 $[M + H]^+$ | 99.7% |

TABLE 2-continued

| Ex. # | $^1H$ NMR (400 MHz unless otherwise noted) | LCMS: m/z | % ee |
|---|---|---|---|
| 1052 | ($CD_3OD$) δ 8.40-8.49 (m, 1 H), 7.73 (s, 1 H), 7.23-7.34 (m, 1 H), 6.81-6.97 (m, 2 H), 6.75 (s, 0.6 H), 6.55 (s, 0.4 H), 4.92 (br s, 0.4 H), 4.49 (m, 0.6 H), 4.12-4.19 (m, 3 H), 3.69 (m, 0.6 H), 3.13-3.29 (m, 1 H), 2.94-3.04 (m, 0.4 H), 2.74-2.89 (m, 1 H) | 451.1 $[M + H]^+$ | 99.9% |
| 1053 | ($CD_3OD$) δ 8.40-8.48 (m, 1 H), 7.70 (d, 1 H), 7.25-7.33 (m, 1 H), 6.80-6.98 (m, 2 H), 6.74 (s, 0.6 H), 6.53 (s, 0.3 H), 4.92 (br s, 0.5 H), 4.47 (m, 0.5 H), 4.11-4.20 (m, 3 H), 3.68 (m, 0.6 H), 3.11-3.29 (m, 1 H), 2.94-3.03 (m, 0.4 H), 2.73-2.88 (m, 1 H) | 451.1 $[M + H]^+$ | 98.0% |
| 1054 | ($CD_3OD$) δ 8.44 (m, 1 H), 7.70 (d, 1 H), 7.24-7.32 (m, 1 H), 6.80-6.94 (m, 2 H), 6.73 (s, 0.6 H), 6.51 (s, 0.3 H), 4.48 (m, 0.1 H), 3.99-4.06 (m, 3 H), 3.66 (m, 0.6 H), 3.09-3.25 (m, 1 H), 2.91-3.02 (m, 0.4 H), 2.71-2.86 (m, 1 H) | 417.1 $[M + H]^+$ | 100% |
| 1055 | ($CD_3OD$) δ 8.44 (m, 1 H), 7.66-7.73 (m, 1 H), 7.24-7.32 (m, 1 H), 6.81-6.95 (m, 2 H), 6.73 (s, 0.6 H), 6.51 (s, 0.4 H), 4.48 (m, 1 H), 4.02-4.05 (m, 3 H), 3.66 (m, 0.6 H), 3.09-3.25 (m, 1 H), 2.92-3.02 (m, 0.3 H), 2.72-2.86 (m, 1 H) | 417.1 $[M + H]^+$ | 99.3% |
| 1056 | ($CD_3OD$) δ 8.22-8.38 (m, 1 H), 7.69 (d, 1 H), 6.85-7.05 (m, 2 H), 6.72-6.81 (m, 1 H), 6.36-6.66 (m, 1 H), 4.45 (dd, 1 H), 4.14 (s, 3 H), 3.69 (ddd, 0.6 H), 3.10-3.29 (m, 1 H), 2.66-3.07 (m, 1.4 H), 2.33-2.49 (m, 3 H) | 431.2 $[M + H]^+$ | 100% |
| 1057 | ($CD_3OD$) δ 8.30 (dd, 1 H), 7.69 (d, 1 H), 6.86-7.05 (m, 2 H), 6.73-6.82 (m, 1 H), 6.31-6.65 (m, 1 H), 4.45 (dd, 1 H), 4.14 (s, 3 H), 3.69 (ddd, 0.6 H), 3.09-3.26 (m, 1 H), 2.70-3.07 (m, 1.4 H), 2.37-2.46 (m, 3 H) | 431.2 $[M + H]^+$ | 99.5% |
| 1058 | ($CD_3OD$) δ 8.23-8.33 (m, 1 H), 7.68 (d, 1 H), 6.86-7.08 (m, 1.6 H), 6.69-6.84 (m, 1.4 H), 6.30-6.67 (m, 1 H), 4.84 (br s, 0.5 H), 4.31 (dd, 0.5 H), 3.93 (d, 3 H), 3.57-3.72 (m, 0.5 H), 2.91-3.29 (m, 1.5 H), 2.68-2.87 (m, 1 H), 2.36-2.49 (m, 3 H), 1.93-2.08 (m, 1 H), 0.86-1.02 (m, 4 H) | 403.2 $[M + H]^+$ | 99.2% |
| 1059 | ($CD_3OD$) δ 8.20-8.35 (m, 1 H), 7.69 (d, 1 H), 6.87-7.06 (m, 1.6 H), 6.78 (q, 1.4 H), 6.29-6.66 (m, 1 H), 4.85 (br d, 0.5 H), 4.31 (dd, 0.5 H), 3.93 (d, 3 H), 3.67 (ddd, 0.5 H), 3.05-3.29 (m, 1 H), 2.67-3.01 (m, 1.5 H), 2.36-2.48 (m, 3 H), 1.96-2.08 (m, 1 H), 0.88-1.02 (m, 4 H) | 403.2 $[M + H]^+$ | 98.5% |
| 1060 | ($CD_3OD$) δ 8.67-8.73 (m, 1 H), 7.70 (d, 1 H), 7.62 (dd, 1 H), 6.55-7.05 (m, 4 H), 4.94 (br s, 0.4 H), 4.48 (dd, 0.6 H), 4.07-4.15 (m, 3 H), 3.68 (ddd, 0.6 H), 3.13-3.27 (m, 1 H), 2.94-3.04 (m, 0.4 H), 2.73-2.87 (m, 1 H) | 467.1 $[M + H]^+$ | 100% |
| 1061 | ($CD_3OD$) δ 8.67-8.73 (m, 1 H), 7.70 (d, 1 H), 7.57-7.67 (m, 1 H), 6.55-7.04 (m, 4 H), 4.94 (br s, 0.4 H), 4.48 (dd, 0.6 H), 4.08-4.14 (m, 3 H), 3.63-3.72 (m, 0.6 H), 3.13-3.27 (m, 1 H), 2.94-3,04 (m, 0.4 H), 2.73-2.87 (m, 1 H) | 467.2 $[M + H]^+$ | 99.7% |
| 1062 | ($CD_3OD$) δ 8.67-8.73 (m, 1 H), 7.71 (d, 1 H), 7.57-7.68 (m, 1 H), 6.91-7.02 (m, 2 H), 6.62-6.82 (m, 1 H), 4.94-4.97 (m, 0.4 H), 4.50 (dd, 0.6 H), 4.11-4.20 (m, 3 H), 3.68 (ddd, 0.6 H), 3.13-3.29 (m, 1 H), 2.94-3.04 (m, 0.4 H), 2.74-2.87 (m, 1 H) | 485.1 $[M + H]^+$ | 99.9% |
| 1063 | ($CD_3OD$) δ 8.67-8.73 (m, 1 H), 7.70 (d, 1 H), 7.56-7.68 (m, 1 H), 6.89-7.03 (m, 2 H), 6.59-6.83 (m, 1 H), 4.93 (br s, 0.4 H), 4.49 (dd, 0.6 H), 4.10-4.20 (m, 3 H), 3.68 (ddd, 0.6 H), 3.12-3.29 (m, 1 H), 2.94-3.05 (m, 0.4 H), 2.73-2.88 (m, 1 H) | 485.1 $[M + H]^+$ | 98.8% |
| 1064 | ($CD_3OD$) δ 7.55-7.91 (m, 4 H), 6.92-7.35 (m, 3 H), 6.80 (br d, 1 H), 6.21-6.56 (m, 1 H), 4.04 (br dd, 1 H), 3.66-3.83 (m, 1 H), 2.70-3.04 (m, 2 H) | 418.1 $[M + H]^+$ | 98.4% |
| 1065 | ($CD_3OD$) δ 7.51-7.98 (m, 4 H), 6.91-7.38 (m, 3 H), 6.79 (br d, 1 H), 6.27-6.56 (m, 1 H), 4.03 (br dd, 1 H), 3.74 (br s, 1 H), 2.68-3.06 (m, 2 H) | 418.1 $[M + H]^+$ | 97.4% |
| 1066 | ($CD_3OD$) δ 8.39 (s, 1 H), 8.10 (s, 1 H), 7.69 (d, 1 H), 7.62 (d, 1.5 H), 7.12-7.23 (m, 1 H), 6.95-7.07 (m, 1.5 H), 6.61-6.80 (m, 1 H), 5.10 (br dd, 1 H), 3.98-4.04 (m, 3 H), 3.82-3.96 (m, 0.6 H), 3.34-3.44 (m, 0.4 H), 2.82-3.20 (m, 2 H) | 450.1 $[M + H]^+$ | 99.6% |
| 1067 | ($CD_3OD$) δ 8.37 (br s, 1 H), 8.08 (s, 1 H), 7.69 (br d, 1 H), 7.52-7.63 (m, 1.5 H), 7.10-7.21 (m, 1 H), 6.93-7.05 (m, 1.5 H), 6.60-6.80 (m, 1 H), 5.09 (br dd, 1 H), 3.99 (br d, 3 H), 3.84-3.94 (m, 0.6 H), 3.35-3.42 (m, 0.4 H), 2.81-3.18 (m, 2 H) | 450.1 $[M + H]^+$ | 94.0% |
| 1068 | ($CD_3OD$) δ 8.11-8.80 (m, 2 H), 7.53-7.75 (m, 2 H), 6.97-7.28 (m, 2 H), 6.43-6.90 (m, 2 H), 4.69-4.86 (m, 0.4 H), 4.21-4.39 (m, 0.6 H), 3.35-3.90 (m, 1 H), 2.71-3.16 (m, 2 H) | 403.1 $[M + H]^+$ | 99.4% |
| 1069 | ($CD_3OD$) δ 8.26-8.61 (m, 2 H), 7.52-7.79 (m, 2 H), 6.94-7.34 (m, 2 H), 6.44-6.91 (m, 2 H), 4.04-4.56 (m, 1 H), 3.35-3.86 (m, 1 H), 2.75-3.18 (m, 2 H) | 403.1 $[M + H]^+$ | 100% |
| 1070 | ($CD_3OD$) δ 8.51 (br d, 1 H), 7.51-7.77 (m, 2 H), 6.93-7.31 (m, 2 H), 6.68 (s, 2 H), 4.32 (br d, 1 H), 3.73 (br s, 1 H), 2.72-3.20 (m, 2 H), 1.57-1.68 (m, 6 H) | 461.2 $[M + H]^+$ | 100% |
| 1071 | ($CD_3OD$) δ 8.51 (br d, 1 H), 7.53-7.74 (m, 2 H), 6.95-7.33 (m, 2 H), 6.48-6.95 (m, 2 H), 4.11-4.47 (m, 1 H), 3.37-3.90 (m, 1 H), 2.76-3.19 (m, 2 H), 1.57-1.70 (m, 6 H) | 461.2 $[M + H]^+$ | 100% |

TABLE 2-continued

| Ex. # | $^1$H NMR (400 MHz unless otherwise noted) | LCMS: m/z | % ee |
|---|---|---|---|
| 1072 | ($CD_3OD$) δ 8.44 (m, 1 H), 7.69 (d, 1 H), 7.29 (m, 1 H), 6.80-6.94 (m, 2 H), 6.73 (s, 0.5 H), 6.50 (s, 0.4 H), 4.82-4.85 (m, 0.5 H), 4.34 (m, 0.5 H), 3.94 (d, 3 H), 3.64 (m, 0.6 H), 3.22 (m, 0.4 H), 3.05-3.14 (m, 0.6 H), 2.91-3.01 (m, 0.4 H), 2.69-2.85 (m, 1 H), 1.98-2.06 (m, 1 H), 0.89-1.01 (m, 4 H) | 423.2 $[M + H]^+$ | 99.9% |
| 1073 | ($CD_3OD$) δ 8.45 (m, 1 H), 7.70 (d, 1 H), 7.30 (m, 1 H), 6.82-6.94 (m, 2 H), 6.74 (s, 0.5 H), 6.51 (s, 0.5 H), 4.86 (br s, 0.4 H), 4.34 (m, 0.6 H), 3.95 (d, 3 H), 3.65 (m, 0.6 H), 3.22 (m, 0.4 H), 3.05-3.15 (m, 0.6 H), 2.91-3.01 (m, 0.4 H), 2.70-2.86 (m, 1 H), 1.97-2.07 (m, 1 H), 0.90-1.01 (m, 4 H) | 423.1 $[M + H]^+$ | 99.8% |
| 1074 | ($CD_3OD$) δ 8.45 (m, 1 H), 7.70 (m, 1 H), 7.25-7.33 (m, 1 H), 6.80-6.98 (m, 2 H), 6.74 (s, 0.5 H), 6.45 (s, 0.4 H), 4.36 (m, 0.5 H), 3.96 (m, 3 H), 3.66 (m, 0.5 H), 2.70-3.23 (m, 2 H), 2.35 (m, 3 H) | 397.2 $[M + H]^+$ | 100% |
| 1075 | ($CD_3OD$) δ 8.45 (m, 1 H), 7.70 (d, 1 H), 7.29 (m, 1 H), 6.81-6.96 (m, 2 H), 6.74 (s, 0.6 H), 6.45 (s, 0.4 H), 4.36 (m, 0.5 H), 3.96 (d, 3 H), 3.61-3.71 (m, 0.5 H), 2.70-3.25 (m, 2 H), 2.33-2.38 (m, 3 H) | 397.2 $[M + H]^+$ | 99.4% |
| 1076 | ($CD_3OD$) δ 8.21-8.39 (m, 1 H), 7.69 (d, 1 H), 6.86-7.07 (m, 2 H), 6.73-6.84 (m, 1 H), 6.61 (s, 0.6 H), 6.36 (s, 0.4 H), 4.82-4.86 (m, 0.4 H), 4.45 (dd, 0.6 H), 3.91-4.09 (m, 3 H), 3.59-3.75 (m, 0.6 H), 3.06-3.29 (m, 1 H), 2.90-3.04 (m, 0.4 H), 2.68-2.86 (m, 1 H), 2.31-2.47 (m, 3 H) | 397.1 $[M + H]^+$ | 100% |
| 1077 | ($CD_3OD$) δ 8.20-8.39 (m, 1 H), 7.69 (br d, 1 H), 6.88-7.02 (m, 2 H), 6.78 (q, 1 H), 6.61 (s, 0.6 H), 6.36 (s, 0.4 H), 4.81-4.86 (m, 0.4 H), 4.45 (dd, 0.6 H), 3.98-4.07 (m, 3 H), 3.67 (ddd, 0.6 H), 3.08-3.29 (m, 1 H), 2.90-3.04 (m, 0.4 H), 2.70-2.88 (m, 1 H), 2.32-2.50 (m, 3 H) | 397.1 $[M + H]^+$ | 100% |
| 1078 | ($CD_3OD$) δ 8.70 (d, 1 H), 7.70 (d, 1 H), 7.57-7.67 (m, 1 H), 6.50-7.11 (m, 3 H), 4.97 (br s, 0.4 H), 4.49 (dd, 0.6 H), 3.97-4.13 (m, 3 H), 3.60-3.72 (m, 0.6 H), 3.09-3.24 (m, 1 H), 2.89-3.04 (m, 0.4 H), 2.70-2.88 (m, 1 H) | 451.1 $[M + H]^+$ | 100% |
| 1079 | ($CD_3OD$) δ 8.70 (br d, 1 H), 7.65-7.78 (m, 1 H), 7.57-7.65 (m, 1 H), 6.56-7.01 (m, 3 H), 4.97 (br s, 0.4 H), 4.50 (dd, 0.6 H), 4.01-4.06 (m, 3 H), 3.62-3.70 (m, 0.6 H), 3.09-3.25 (m, 1 H), 2.92-3.02 (m, 0.4 H), 2.69-2.87 (m, 1 H) | 451.1 $[M + H]^+$ | 99.2% |
| 1080 | ($CD_3OD$) δ 8.70 (dd, 1 H), 7.69 (d, 1 H), 7.59-7.66 (m, 1 H), 6.57-7.05 (m, 3 H), 4.86 (br s, 0.5 H), 4.35 (dd, 0.5 H), 3.94 (d, 3 H), 3.59-3.69 (m, 0.6 H), 3.05-3.27 (m, 1 H), 2.90-3.02 (m, 0.4 H), 2.70-2.86 (m, 1 H), 1.97-2.07 (m, 1 H), 0.89-1.00 (m, 4 H) | 457.2 $[M + H]^+$ | 97.0% |
| 1081 | ($CD_3OD$) δ 8.70 (dd, 1 H), 7.69 (d, 1 H), 7.62 (t, 1 H), 6.57-7.02 (m, 3 H), 4.94-5.00 (m, 0.5 H), 4.35 (dd, 0.5 H), 3.95 (d, 3 H), 3.59-3.69 (m, 0.6 H), 3.06-3.26 (m, 1 H), 2.90-3.02 (m, 0.4 H), 2.70-2.86 (m, 1 H), 1.98-2.06 (m, 1 H), 0.89-1.00 (m, 4 H) | 457.2 $[M + H]^+$ | 99.5% |
| 1082 | ($CD_3OD$) δ 8.71 (d, 1 H), 7.73 (d, 1 H), 7.58-7.66 (m, 1 H), 6.46-7.06 (m, 3 H), 4.94-4.97 (m, 0.5 H), 4.39 (dd, 0.5 H), 3.91-4.01 (m, 3 H), 3.61-3.71 (m, 0.6 H), 3.06-3.24 (m, 1 H), 2.91-3.02 (m, 0.4 H), 2.69-2.88 (m, 1 H), 2.31-2.40 (m, 3 H) | 431.2 $[M + H]^+$ | 100% |
| 1083 | ($CD_3OD$) δ 8.71 (d, 1 H), 7.70 (d, 1 H), 7.58-7.67 (m, 1 H), 6.41-7.07 (m, 3 H), 4.93 (br s, 0.5 H), 4.38 (dd, 0.5 H), 3.88-4.04 (m, 3 H), 3.59-3.71 (m, 0.6 H), 3.06-3.24 (m, 1 H), 2.91-3.02 (m, 0.4 H), 2.70-2.86 (m, 1 H), 2.35 (d, 3 H) | 431.2 $[M + H]^+$ | 99.6% |
| 1084 | ($CD_3OD$) δ 8.49 (dd, 1 H), 7.69 (s, 1 H), 6.99-7.32 (m, 2 H), 6.53-6.92 (m, 3 H), 4.35 (br d, 1 H), 3.74 (br s, 1 H), 2.97-3.23 (m, 1 H), 2.83 (br d, 1 H), 1.51-1.82 (m, 6 H) | 461.2 $[M + H]^+$ | 100% |
| 1085 | ($CD_3OD$) δ 8.49 (dd, 1 H), 7.69 (s, 1 H), 6.94-7.43 (m, 2 H), 6.48-6.88 (m, 3 H), 4.35 (br d, 1 H), 3.62-3.84 (m, 1 H), 2.94-3.24 (m, 1 H), 2.83 (br d, 1 H), 1.49-1.80 (m, 6 H) | 461.2 $[M + H]^+$ | 99.5% |
| 1086 | ($CD_3OD$) δ 7.69 (d, 1 H), 7.47 (dd, 1 H), 7.13 (dt, 1 H), 6.94 (s, 1 H), 6.73 (d, 1 H), 6.62 (s, 0.6 H), 6.34 (s, 0.4 H), 4.93 (br s, 0.5 H), 4.41 (dd, 0.5 H), 3.92-4.09 (m, 3 H), 3.72-3.86 (m, 0.5 H), 3.25-3.31 (m, 0.5 H), 3.08-3.21 (m, 0.7 H), 2.92-3.05 (m, 0.3 H), 2.73-2.90 (m, 1 H), 2.57-2.71 (m, 3 H) | 397.1 $[M + H]^+$ | 98.9% |
| 1087 | ($CD_3OD$) δ 7.69 (d, 1 H), 7.47 (dd, 1 H), 7.08-7.19 (m, 1 H), 6.94 (s, 1 H), 6.73 (d, 1 H), 6.62 (s, 0.5 H), 6.34 (s, 0.5 H), 4.97-4.98 (m, 0.5 H), 4.41 (dd, 0.5 H), 3.91-4.08 (m, 3 H), 3.73-3.86 (m, 0.5 H), 3.28 (br d, 0.5 H), 3.07-3.20 (m, 0.7 H), 2.92-3.04 (m, 0.3 H), 2.73-2.89 (m, 1 H), 2.60-2.72 (m, 3 H) | 397.2 $[M + H]^+$ | 96.9% |
| 1088 | ($CD_3OD$) δ 8.44-8.74 (m, 1 H), 7.48-7.87 (m, 4 H), 7.22 (br t, 1 H), 6.65-7.13 (m, 2 H), 6.19-6.53 (m, 1 H), 4.82 (br d, 0.7 H), 3.63-4.15 (m, 1 H), 3.16-3.27 (m, 0.3 H), 2.65-3.07 (m, 2 H) | 402.1 $[M + H]^+$ | 100% |
| 1089 | ($CD_3OD$) δ 8.33-8.76 (m, 1 H), 7.48-7.86 (m, 4 H), 7.22 (br t, 1 H), 6.64-7.13 (m, 2 H), 6.16-6.51 (m, 1 H), 4.73-4.85 (m, 0.7 H), 3.63-4.13 (m, 1 H), 3.17-3.27 (m, 0.3 H), 2.66-3.07 (m, 2 H) | 402.1 $[M + H]^+$ | 99.5% |

TABLE 2-continued

| Ex. # | $^1$H NMR (400 MHz unless otherwise noted) | LCMS: m/z | % ee |
|---|---|---|---|
| 1090 | ($CD_3OD$) δ 8.69-8.87 (m, 1 H), 8.43-8.59 (m, 1 H), 8.24-8.39 (m, 1 H), 8.08 (td, 1 H), 7.41-7.88 (m, 3.4 H), 7.13-7.41 (m, 1 H), 6.49-7.08 (m, 1.6 H), 4.99 (br dd, 1 H), 3.37-3.92 (m, 1 H), 2.75-3.27 (m, 2 H) | 431.2 $[M + H]^+$ | 100% |
| 1091 | ($CD_3OD$) δ 8.74-8.83 (m, 1 H), 8.43-8.59 (m, 1 H), 8.27-8.37 (m, 1 H), 8.08 (td, 1 H), 7.45-7.83 (m, 3.4 H), 7.11-7.32 (m, 1 H), 6.59-7.01 (m, 1.6 H), 5.00 (br dd, 1 H), 3.36-3.89 (m, 1 H), 2.76-3.25 (m, 2 H) | 431.1 $[M + H]^+$ | 99.2% |
| 1092 | ($CD_3OD$) δ 8.41-8.68 (m, 1 H), 7.49-7.89 (m, 3 H), 7.26-7.44 (m, 1 H), 6.18-7.10 (m, 4 H), 4.82-4.86 (m, 0.4 H), 3.99-4.18 (m, 0.6 H), 3.72 (br t, 0.6 H), 2.95-3.31 (m, 1.4 H), 2.76 (br d, 1 H) | 402.2 $[M + H]^+$ | 100% |
| 1093 | ($CD_3OD$) δ 8.30-8.53 (m, 1 H), 7.38-7.79 (m, 3 H), 7.10-7.29 (m, 1 H), 6.10-7.00 (m, 4 H), 4.69-4.75 (m, 0.4 H), 3.91-4.05 (m, 0.6 H), 3.60 (br t, 0.6 H), 2.84-3.19 (m, 1.4 H), 2.64 (br d, 1 H) | 402.1 $[M + H]^+$ | 99.9% |
| 1094 | ($CD_3OD$) δ 8.40-8.46 (m, 1 H), 7.70 (s, 1 H), 7.46 (s, 0.3 H), 7.27-7.33 (m, 1 H), 6.91 (s, 0.6 H), 6.82-6.88 (m, 1 H), 6.67-6.74 (m, 1 H), 5.00 (dd, 0.4 H), 3.68-3.75 (m, 0.6 H), 3.26-3.40 (m, 0.2 H), 3.13-2.79 (m, 1 H), 2.82 (br dd, 1 H), 2.28-2.36 (m, 1 H), 1.18-1.31 (m, 4 H) | 410.1 $[M + H]^+$ | 100% |
| 1095 | ($CD_3OD$) δ 8.40-8.46 (m, 1 H), 7.70 (s, 1 H), 7.46 (s, 0.3 H), 7.27-7.33 (m, 1 H), 6.91 (s, 0.6 H), 6.82-6.88 (m, 1 H), 6.67-6.74 (m, 1 H), 4.98-5.03 (m, 0.5 H), 3.68-3.75 (m, 1 H), 3.36-3.41 (m, 0.3 H), 2.91-3.18 (m, 1 H), 2.79-2.84 (m, 1 H), 2.28-2.36 (m, 1 H), 1.18-1.31 (m, 4 H) | 410.1 $[M + H]^+$ | 100% |
| 1096 | ($CD_3OD$) δ 8.44 (t, 1 H), 8.26 (dd, 1 H), 7.71 (d, 1 H), 7.55-7.66 (m, 2 H), 7.52 (s, 0.4 H), 7.13-7.24 (m, 1 H), 6.97-7.08 (m, 1.6 H), 6.61-6.83 (m, 1 H), 5.06 (br dd, 1 H), 4.00 (d, 3 H), 3.87-3.98 (m, 0.6 H), 3.36-3.45 (m, 0.4 H), 2.84-3.24 (m, 2 H) | 477.1 $[M + H]^+$ | 100% |
| 1097 | ($CD_3OD$) δ 8.45 (d, 1 H), 8.27 (dd, 1 H), 7.71 (d, 1 H), 7.59-7.67 (m, 2 H), 7.52 (s, 0.5 H), 7.15-7.22 (m, 1 H), 6.99-7.07 (m, 1.5 H), 6.60-6.85 (m, 1 H), 5.03-5.08 (m, 1 H), 4.00 (d, 3 H), 3.94 (br d, 1 H), 2.87-3.23 (m, 2 H) | 477.2 $[M + H]^+$ | 100% |
| 1098 | ($CD_3OD$) δ 7.98 (s, 1 H), 7.84 (dd, 1 H), 7.71 (d, 1 H), 7.48-7.66 (m, 1.5 H), 7.13-7.25 (m, 1 H), 6.97-7.06 (m, 1.5 H), 6.63-6.82 (m, 1 H), 5.10 (br dd, 1 H), 4.11 (s, 3 H), 3.87-3.99 (m, 0.6 H), 3.37-3.47 (m, 0.4 H), 2.87 (br dd, 2 H) | 450.1 $[M + H]^+$ | 98.1% |
| 1099 | ($CD_3OD$) δ 7.86 (s, 1 H), 7.72 (d, 1 H), 7.59 (d, 1 H), 7.36-7.54 (m, 1.5 H), 7.01-7.12 (m, 1 H), 6.85-6.94 (m, 1.5 H), 6.52-6.70 (m, 1 H), 4.87-5.04 (m, 1 H), 3.99 (s, 3 H), 3.75-3.89 (m, 0.6 H), 3.24-3.30 (m, 0.4 H), 2.73-3.12 (m, 2 H) | 450.1 $[M + H]^+$ | 94.5% |
| 1100 | ($CD_3OD$) δ 8.45-8.57 (m, 1 H), 8.38 (s, 1 H), 8.09 (s, 1 H), 7.51-7.75 (m, 2.4 H), 7.13-7.31 (m, 1 H), 6.92 (s, 0.6 H), 6.55-6.75 (m, 1 H), 5.05 (br dd, 1 H), 4.00 (s, 3 H), 3.34-3.81 (m, 1 H), 2.76-3.22 (m, 2 H) | 434.2 $[M + H]^+$ | 99.4% |
| 1101 | ($CD_3OD$) δ 8.45-8.54 (m, 1 H), 8.38 (s, 1 H), 8.09 (s, 1 H), 7.54-7.70 (m, 2.4 H), 7.12-7.28 (m, 1 H), 6.92 (s, 0.6 H), 6.54-6.76 (m, 1 H), 5.05 (br dd, 1 H), 4.00 (s, 3 H), 3.34-3.82 (m, 1 H), 2.76-3.22 (m, 2 H) | 434.2 $[M + H]^+$ | 98.8% |
| 1102 | ($CD_3OD$) δ 8.34-8.60 (m, 1 H), 7.81 (d, 1 H), 7.68 (s, 2 H), 7.50 (s, 0.4 H), 7.11-7.27 (m, 1 H), 6.86-7.01 (m, 1.6 H), 6.52-6.75 (m, 1 H), 5.00 (br dd, 0.7 H), 3.92-4.10 (m, 3 H), 3.35-3.83 (m, 1.3 H), 2.77-3.22 (m, 2 H) | 434.2 $[M + H]^+$ | 100% |
| 1103 | ($CD_3OD$) δ 8.37-8.62 (m, 1 H), 7.81 (d, 1 H), 7.56-7.72 (m, 2 H), 7.50 (s, 0.4 H), 7.12-7.28 (m, 1 H), 6.80-7.07 (m, 1.6 H), 6.56-6.75 (m, 1 H), 5.00 (br dd, 0.7 H), 3.92-4.07 (m, 3 H), 3.34-3.85 (m, 1.3 H), 2.80-3.22 (m, 2 H) | 434.1 $[M + H]^+$ | 100% |
| 1104 | ($CD_3OD$) δ 8.92 (s, 1 H), 8.42 (s, 1 H), 7.65-7.82 (m, 2 H), 7.35 (br d, 1 H), 6.99-7.28 (m, 1 H), 6.53-6.90 (m, 2 H), 4.34 (br d, 1 H), 3.66-3.80 (m, 0.7 H), 3.34-3.49 (m, 0.3 H), 2.93-3.16 (m, 1 H), 2.80 (br d, 1 H) | 453.1 $[M + H]^+$ | 99.6% |
| 1105 | ($CD_3OD$) δ 8.92 (s, 1 H), 8.42 (s, 1 H), 7.63-7.86 (m, 2 H), 7.35 (d, 1 H), 6.99-7.28 (m, 1 H), 6.47-6.92 (m, 2 H), 4.34 (br d, 1 H), 3.74 (br t, 0.7 H), 3.35-3.48 (m, 0.3 H), 2.91-3.15 (m, 1 H), 2.79 (br d, 1 H) | 453.1 $[M + H]^+$ | 98.6% |
| 1106 | ($CD_3OD$) δ 8.38-8.45 (m, 1 H), 7.69 (s, 1 H), 7.47 (s, 0.3 H), 7.24-7.32 (m, 1 H), 6.67-6.93 (m, 2.7 H), 4.96 (dd, 1 H), 3.68-3.77 (m, 0.7 H), 3.33-3.42 (m, 0.3 H), 2.91-3.17 (m, 1 H), 2.79-2.84 (m, 1 H), 2.60-2.66 (m, 3 H) | 384.1 $[M + H]^+$ | 100% |
| 1107 | ($CD_3OD$) δ 8.40-8.46 (m, 1 H), 7.71 (s, 1 H), 7.47 (s, 0.3 H), 7.26-7.32 (m, 1 H), 6.68-6.94 (m, 2.7 H), 4.94 - 4.99 (m, 1 H), 3.68-3.77 (m, 0.7 H), 3.33-3.41 (m, 0.4 H), 2.91-3.19 (m, 1 H), 2.79-2.84 (m, 1 H), 2.60-2.66 (m, 3 H) | 384.2 $[M + H]^+$ | 99.5% |
| 1108 | ($CD_3OD$) δ 8.38-8.47 (m, 1 H), 7.70 (s, 1 H), 7.40 (s, 0.3 H), 6.93 (s, 0.6 H), 6.64-6.88 (m, 2 H), 4.97 (br dd, 1 H), 3.74 (ddd, 0.6 H), 3.36-3.42 (m, 0.3 H), 2.80-3.21 (m, 2 H), 1.83-1.95 (m, 6 H) | 430.1 $[M + H]^+$ | 100% |

TABLE 2-continued

| Ex. # | $^1H$ NMR (400 MHz unless otherwise noted) | LCMS: m/z | % ee |
| --- | --- | --- | --- |
| 1109 | ($CD_3OD$) δ 8.37-8.47 (m, 1 H), 7.69 (s, 1 H), 7.40 (s, 0.3 H), 7.27-7.33 (m, 1 H), 6.93 (s, 0.6 H), 6.63-6.88 (m, 2 H), 4.92-4.99 (m, 1 H), 3.67-3.78 (m, 0.7 H), 3.34-3.42 (m, 0.4 H), 2.80-3.16 (m, 2 H), 1.84-1.93 (m, 6 H) | 430.1 $[M + H]^+$ | 99.4% |
| 1110 | ($CD_3OD$) δ 8.17-8.29 (m, 1 H), 7.67 (s, 1 H), 7.44-7.53 (m, 1 H), 7.39 (br s, 0.3 H), 7.02-7.11 (m, 1 H), 6.91 (br s, 0.7 H), 6.54 (s, 0.7 H), 6.45 (s, 0.3 H), 4.90-5.00 (m, 1 H), 3.72 (td, 0.7 H), 3.33-3.42 (m, 0.3 H), 3.07-3.21 (m, 0.7 H), 2.91-3.02 (m, 0.3 H), 2.81 (br d, 1 H), 2.26-2.36 (m, 3 H), 1.47 (s, 9 H) | 406.2 $[M + H]^+$ | 100% |
| 1111 | ($CD_3OD$) δ 8.16-8.33 (m, 1 H), 7.69 (d, 1 H), 7.43-7.53 (m, 1 H), 7.40 (s, 0.3 H), 7.04-7.13 (m, 1 H), 6.91 (s, 0.7 H), 6.43-6.59 (m, 1 H), 4.91-4.97 (m, 1 H), 3.68-3.77 (m, 0.7 H), 3.33-3.43 (m, 0.3 H), 3.06-3.19 (m, 0.7 H), 2.90-3.02 (m, 0.3 H), 2.81 (br d, 1 H), 2.28-2.35 (m, 3 H), 1.47 (s, 9 H) | 406.2 $[M + H]^+$ | 99.8% |
| 1112 | ($CDCl_3$) δ 8.12-8.29 (m, 1 H), 7.30-7.80 (m, 4 H), 6.96 (br d, 2 H), 6.43-6.63 (m, 1 H), 6.34 (br d, 1 H), 4.00-4.97 (m, 1 H), 3.23-3.80 (m, 1 H), 2.86-3.12 (m, 1 H), 2.67-2.78 (m, 1 H), 2.32 (br s, 3 H) | 398.2 $[M + H]^+$ | 98.6% |
| 1113 | ($CDCl_3$) δ 8.13-8.27 (m, 1 H), 7.31-7.80 (m, 4 H), 6.90-7.03 (m, 2 H), 6.39-6.67 (m, 1 H), 6.34 (br d, 1 H), 4.04-4.95 (m, 1 H), 3.24-3.83 (m, 1 H), 2.87-3.13 (m, 1 H), 2.65-2.80 (m, 1 H), 2.32 (br s, 3 H) | 398.2 $[M + H]^+$ | 100% |
| 1114 | ($CD_3OD$) δ 8.40-8.59 (m, 1 H), 7.53-7.78 (m, 2 H), 7.39 (s, 0.3 H), 7.13-7.30 (m, 1 H), 6.91 (s, 0.7 H), 6.47-6.78 (m, 1 H), 4.92-4.98 (m, 1 H), 3.36-3.81 (m, 1 H), 2.75-3.21 (m, 2 H), 1.82-1.96 (m, 6 H) | 414.2 $[M + H]^+$ | 100% |
| 1115 | ($CD_3OD$) δ 8.36-8.59 (m, 1 H), 7.55-7.74 (m, 2 H), 7.39 (s, 0.4 H), 7.14-7.28 (m, 1 H), 6.91 (s, 0.6 H), 6.54-6.76 (m, 1 H), 4.92-4.99 (m, 1 H), 3.35-3.79 (m, 1 H), 2.75-3.21 (m, 2 H), 1.84-1.95 (m, 6 H) | 414.2 $[M + H]^+$ | 99.4% |
| 1116 | ($CD_3OD$) δ 8.92 (s, 1 H), 7.77 (br d, 1 H), 7.68 (s, 1 H), 7.35 (br d, 1 H), 6.97-7.27 (m, 1 H), 6.78-6.87 (m, 1.6 H), 6.61 (br s, 0.4 H), 4.82 (br s, 0.4 H), 4.32-4.41 (m, 0.6 H), 3.74 (br t, 0.6 H), 3.36-3.49 (m, 0.4 H), 2.74-3.20 (m, 2 H), 1.55-1.69 (m, 6 H) | 511.2 $[M + H]^+$ | 100% |
| 1117 | ($CD_3OD$) δ 8.92 (s, 1 H), 7.77 (br d, 1 H), 7.68 (s, 1 H), 7.35 (d, 1 H), 6.97-7.27 (m, 1 H), 6.79-6.87 (m, 1.7 H), 6.61 (br d, 0.3 H), 4.81 (br s, 0.3 H), 4.36 (br d, 0.7 H), 3.69-3.79 (m, 0.7 H), 3.34-3.49 (m, 0.3 H), 2.77-3.18 (m, 2 H), 1.55-1.68 (m, 6 H) | 511.2 $[M + H]^+$ | 98.5% |
| 1118 | ($CD_3OD$) δ 8.31-8.48 (m, 2 H), 7.83 (s, 0.2 H), 7.49-7.72 (m, 2 H), 7.19-7.33 (m, 2 H), 6.70-6.99 (m, 2.6 H), 4.99-5.08 (m, 1 H), 3.72-3.83 (m, 0.6 H), 3.41 (td, 0.4 H), 2.94-3.25 (m, 1 H), 2.80-2.90 (m, 1 H) | 486.2 $[M + H]^+$ | 100% |
| 1119 | ($CD_3OD$) δ 8.29-8.48 (m, 2 H), 7.82 (s, 0.2 H), 7.49-7.74 (m, 2 H), 7.18-7.35 (m, 2 H), 6.69-6.99 (m, 2.8 H), 5.02-5.07 (m, 1 H), 3.72-3.82 (m, 0.7 H), 3.37-3.44 (m, 0.3 H), 2.96-3.26 (m, 1 H), 2.83-2.87 (m, 1 H) | 486.1 $[M + H]^+$ | 99.8% |
| 1120 | ($CD_3OD$) δ 8.93 (s, 1 H), 8.36 (s, 1 H), 7.51-7.74 (m, 3.4 H), 7.14-7.23 (m, 1 H), 6.98-7.08 (m, 1.6 H), 6.64-6.82 (m, 1 H), 5.11 (dd, 1 H), 3.88-3.97 (m, 0.6 H), 3.37-3.44 (m, 0.4 H), 2.99-3.24 (m, 1 H), 2.88 (dd, 1 H) | 486.1 $[M + H]^+$ | 100% |
| 1121 | ($CD_3OD$) δ 8.81 (s, 1 H), 8.24 (s, 1 H), 7.38-7.64 (m, 3.4 H), 7.02-7.12 (m, 1 H), 6.86-6.95 (m, 1.6 H), 6.53-6.70 (m, 1 H), 5.00 (br dd, 1 H), 3.74-3.86 (m, 0.6 H), 3.25-3.34 (m, 0.4 H), 2.86-3.13 (m, 1 H), 2.76 (dd, 1 H) | 486.1 $[M + H]^+$ | 100% |
| 1122 | ($CD_3OD$) δ 7.59 (d, 1 H), 7.45-7.54 (m, 1 H), 7.34 (s, 0.4 H), 7.04-7.12 (m, 1 H), 6.91-6.97 (m, 1 H), 6.86 (s, 0.6 H), 6.51-6.71 (m, 1 H), 4.89 (br dd, 1 H), 3.71-3.81 (m, 0.6 H), 3.25-3.32 (m, 0.4 H), 2.71-3.10 (m, 2 H), 1.37-1.39 (m, 9 H) | 426.2 $[M + H]^+$ | 100% |
| 1123 | ($CD_3OD$) δ 7.70 (d, 1 H), 7.57-7.65 (m, 1 H), 7.44 (s, 0.4 H), 7.16-7.23 (m, 1 H), 7.02-7.07 (m, 1 H), 6.97 (s, 0.6 H), 6.63-6.81 (m, 1 H), 5.00 (dd, 1 H), 3.81-3.93 (m, 0.6 H), 3.36-3.43 (m, 0.4 H), 2.81-3.21 (m, 2 H), 1.47-1.50 (m, 9 H) | 426.2 $[M + H]^+$ | 98.0% |
| 1124 | ($CD_3OD$) δ 8.39-8.55 (m, 1 H), 7.53-7.72 (m, 2 H), 7.39 (s, 0.3 H), 7.13-7.28 (m, 1 H), 6.90 (s, 0.7 H), 6.58-6.73 (m, 1 H), 4.96 (br s, 1 H), 3.68-3.77 (m, 0.7 H), 3.34-3.41 (m, 0.3 H), 2.78-3.18 (m, 2 H), 1.47 (s, 9 H) | 410.2 $[M + H]^+$ | 100% |
| 1125 | ($CD_3OD$) δ 8.39-8.61 (m, 1 H), 7.52-7.75 (m, 2 H), 7.39 (s, 0.3 H), 7.14-7.27 (m, 1 H), 6.90 (s, 0.7 H), 6.56-6.72 (m, 1 H), 4.96 (br d, 1 H), 3.63-3.81 (m, 0.7 H), 3.36-3.41 (m, 0.3 H), 2.74-3.21 (m, 2 H), 1.47 (s, 9 H) | 410.2 $[M + H]^+$ | 99.7% |
| 1126 | ($CD_3OD$) δ 8.90-8.96 (m, 1 H), 7.68-7.80 (m, 2 H), 7.31-7.37 (m, 1 H), 6.93-6.98 (m, 1 H), 6.79-6.85 (m, 1 H), 6.69-6.72 (m, 0.5 H), 6.62 (s, 0.5 H), 4.93 (br d, 0.4 H), 4.48 (dd, 0.6 H), 4.07-4.13 (m, 3 H), 3.68 (ddd, 0.6 H), 3.11-3.28 (m, 1 H), 2.93-3.04 (m, 0.4 H), 2.71-2.86 (m, 1 H) | 467.1 $[M + H]^+$ | 100% |

TABLE 2-continued

| Ex. # | $^1$H NMR (400 MHz unless otherwise noted) | LCMS: m/z | % ee |
|---|---|---|---|
| 1127 | ($CD_3OD$) δ 8.93 (br d, 1 H), 7.66-7.81 (m, 2 H), 7.31-7.38 (m, 1 H), 6.92-6.98 (m, 1 H), 6.79-6.85 (m, 1 H), 6.69-6.72 (m, 0.5 H), 6.62 (s, 0.5 H), 4.90-4.95 (m, 0.7 H), 4.48 (dd, 0.3 H), 4.08-4.12 (m, 3 H), 3.68 (ddd, 0.6 H), 3.12-3.28 (m, 1 H), 2.94-3.04 (m, 0.4 H), 2.71-2.86 (m, 1 H) | 467.1 $[M + H]^+$ | 100% |
| 1128 | ($CD_3OD$) δ 8.85-8.96 (m, 1 H), 7.67-7.84 (m, 3 H), 7.51 (s, 0.2 H), 7.31-7.38 (m, 0.8 H), 6.94-7.00 (m, 2 H), 6.76-6.83 (m, 1 H), 5.05 (br dd, 0.6 H), 4.95 (br d, 0.4 H), 4.03 (s, 3 H), 3.74-3.84 (m, 0.6 H), 3.36-3.46 (m, 0.4 H), 3.12-3.24 (m, 0.7 H), 2.94-3.06 (m, 0.3 H), 2.83 (br d, 1 H) | 484.2 $[M + H]^+$ | 89.9% |
| 1129 | ($CD_3OD$) δ 8.86-8.97 (m, 1 H), 7.68-7.83 (m, 3 H), 7.51 (br s, 0.3 H), 7.31-7.39 (m, 0.7 H), 6.93-7.01 (m, 2 H), 6.75-6.85 (m, 1 H), 5.05 (br dd, 0.7 H), 4.95 (br d, 0.3 H), 4.03 (s, 3 H), 3.74-3.84 (m, 0.7 H), 3.36-3.50 (m, 0.3 H), 3.10-3.24 (m, 0.8 H), 2.93-3.06 (m, 0.2 H), 2.79-2.88 (m, 1 H) | 484.2 $[M + H]^+$ | 94.9% |
| 1130 | ($CD_3OD$) δ 8.38-8.52 (m, 1 H), 7.23-7.74 (m, 2.3 H), 6.71-6.95 (m, 1.7 H), 6.51-6.67 (m, 1 H), 4.97-5.04 (m, 1 H), 3.73 (ddd, 0.6 H), 3.37-3.42 (m, 0.4 H), 2.91-3.20 (m, 1 H), 2.75-2.86 (m, 1 H), 2.24-2.41 (m, 1 H), 1.17-1.33 (m, 4 H) | 394.1 $[M + H]^+$ | 99.9% |
| 1131 | ($CD_3OD$) δ 8.38-8.55 (m, 1 H), 7.25-7.82 (m, 2.3 H), 6.75-7.01 (m, 1.7 H), 6.49-6.63 (m, 1 H), 4.96-5.06 (m, 1 H), 3.73 (ddd, 0.6 H), 3.35-3.43 (m, 0.4 H), 2.90-3.21 (m, 1 H), 2.74-2.88 (m, 1 H), 2.21-2.45 (m, 1 H), 1.20-1.38 (m, 4 H) | 394.2 $[M + H]^+$ | 99.9% |
| 1132 | ($CD_3OD$) δ 8.57-8.79 (m, 1 H), 8.04 (br d, 1 H), 7.44-7.87 (m, 3 H), 6.58-7.15 (m, 3.6 H), 6.31 (br s, 0.4 H), 4.82 (br s, 0.5 H), 4.09 (br dd, 0.5 H), 3.71 (br t, 0.5 H), 3.15-3.30 (m, 0.5 H), 2.68-3.06 (m, 2 H) | 452.2 $[M + H]^+$ | 100% |
| 1133 | ($CD_3OD$) δ 8.58-8.79 (m, 1 H), 8.04 (br d, 1 H), 7.46-7.88 (m, 3 H), 6.58-7.17 (m, 3.6 H), 6.31 (br s, 0.4 H), 4.82 (br s, 0.5 H), 4.09 (br dd, 0.5 H), 3.65-3.78 (m, 0.5 H), 3.17-3.29 (m, 0.5 H), 2.66-3.09 (m, 2 H) | 452.1 $[M + H]^+$ | 99.7% |
| 1134 | ($CD_3OD$) δ 8.90 (br s, 1 H), 8.30-8.48 (m, 2 H), 7.49-7.80 (m, 2 H), 7.22-7.33 (m, 1 H), 6.66-6.98 (m, 3 H), 5.03-5.11 (m, 1 H), 3.77 (br t, 0.7 H), 3.35-3.45 (m, 0.3 H), 3.11-3.23 (m, 1 H), 2.78-3.03 (m, 1 H) | 486.1 $[M + H]^+$ | 100% |
| 1135 | ($CD_3OD$) δ 8.90 (s, 1 H), 8.31-8.46 (m, 2 H), 7.47-7.81 (m, 2 H), 7.24-7.32 (m, 1 H), 6.69-6.99 (m, 3 H), 5.07 (br dd, 1 H), 3.71-3.82 (m, 0.7 H), 3.40 (td, 0.3 H), 3.12-3.23 (m, 1 H), 2.79-3.04 (m, 1 H) | 486.1 $[M + H]^+$ | 98.3% |
| 1136 | ($CD_3OD$) δ 7.82-7.92 (m, 1 H), 7.46-7.56 (m, 1 H), 7.40 (s, 0.3 H), 7.04-7.14 (m, 1 H), 6.85-6.97 (m, 1.7 H), 6.56-6.73 (m, 1 H), 4.95 (br dd, 1 H), 3.66-3.77 (m, 0.6 H), 3.24-3.32 (m, 0.4 H), 2.84-3.08 (m, 1 H), 2.70-2.81 (m, 1 H), 2.16-2.29 (m, 1 H), 1.15-1.19 (m, 2 H), 1.08-1.13 (m, 2 H) | 410.1 $[M + H]^+$ | 99.5% |
| 1137 | ($CD_3OD$) δ 7.60 (d, 1 H), 7.49 (dd, 1 H), 7.34 (s, 0.3 H), 7.03-7.11 (m, 1 H), 6.81-6.96 (m, 1.7 H), 6.50-6.69 (m, 1 H), 4.89 (br d, 1 H), 3.67-3.83 (m, 0.6 H), 3.26 (br s, 0.4 H), 3.02 (br d, 1 H), 2.72 (br dd, 1 H), 2.17-2.25 (m, 1 H), 1.14-1.19 (m, 2 H), 1.07-1.14 (m, 2 H) | 410.1 $[M + H]^+$ | 99.7% |
| 1138 | ($CD_3OD$) δ 8.87-9.07 (m, 1 H), 7.50-7.82 (m, 4 H), 7.35 (dd, 1 H), 6.89-7.09 (m, 1 H), 6.80 (br d, 1 H), 6.23-6.62 (m, 1 H), 4.78-4.84 (m, 0.5 H), 4.10 (br dd, 0.5 H), 3.72 (br t, 0.5 H), 3.21-3.30 (m, 0.5 H), 2.93-3.06 (m, 1 H), 2.75 (br d, 1 H) | 452.1 $[M + H]^+$ | 100% |
| 1139 | ($CD_3OD$) δ 8.87-9.09 (m, 1 H), 7.48-7.85 (m, 4 H), 7.35 (dd, 1 H), 6.90-7.09 (m, 1 H), 6.80 (br d, 1 H), 6.24-6.60 (m, 1 H), 4.77-4.83 (m, 0.5 H), 4.10 (br dd, 0.5 H), 3.72 (br t, 0.5 H), 3.21-3.30 (m, 0.5 H), 2.94-3.06 (m, 1 H), 2.75 (br d, 1 H) | 452.1 $[M + H]^+$ | 100% |
| 1140 | ($CD_3OD$) δ 7.74 (dd, 1 H), 7.51-7.65 (m, 1 H), 7.40 (s, 0.5 H), 7.11-7.29 (m, 2 H), 6.67-6.94 (m, 1 H), 6.53 (s, 0.5 H), 4.89 (br s, 1 H), 3.61-3.95 (m, 0.5 H), 2.67-3.19 (m, 2.5 H), 2.05-2.34 (m, 1 H), 1.09-1.21 (m, 4 H) | 444.2 $[M + H]^+$ | 100% |
| 1141 | ($CD_3OD$) δ 7.74 (dd, 1 H), 7.51-7.64 (m, 1 H), 7.21-7.44 (m, 1.5 H), 7.10-7.21 (m, 1 H), 6.81 (s, 0.5 H), 6.44-6.77 (m, 1 H), 4.90 (br dd, 1 H), 3.73-3.87 (m, 0.5 H), 2.68-3.18 (m, 2.5 H), 2.13-2.36 (m, 1 H), 1.09-1.20 (m, 4 H) | 444.1 $[M + H]^+$ | 97.6% |
| 1142 | ($CD_3OD$) δ 7.72 (d, 1 H), 7.55-7.66 (m, 1 H), 7.16-7.24 (m, 1 H), 7.02-7.11 (m, 1 H), 6.93 (s, 1 H), 6.48-6.84 (m, 1 H), 4.41 (br dd, 0.7 H), 4.06 (d, 3 H), 3.71-3.82 (m, 0.7 H), 2.79-3.22 (m, 2.6 H) | 417.1 $[M + H]^+$ | 99.4% |
| 1143 | ($CD_3OD$) δ 7.60 (br d, 1 H), 7.43-7.53 (m, 1 H), 7.02-7.11 (m, 1 H), 6.94 (d, 1 H), 6.81 (s, 1 H), 6.37-6.69 (m, 1 H), 4.28 (br dd, 0.7 H), 3.94 (d, 3 H), 3.59-3.69 (m, 0.7 H), 2.62-3.12 (m, 2.6 H) | 417.1 $[M + H]^+$ | 97.7% |
| 1144 | ($CD_3OD$) δ 8.02 (d, 1 H), 7.79-7.94 (m, 1 H), 7.72 (d, 1 H), 7.38 (d, 1 H), 7.18-7.32 (m, 1 H), 6.94-7.08 (m, 1 H), 6.88 (s, 0.5 H), 6.55 (s, 0.5 H), 4.99 (br s, 0.6 H), 4.23-4.29 (m, 0.4 H), 4.03 (d, 3 H), 3.75 (td, 0.6 H), 2.69-3.30 (m, 2.4 H) | 417.2 $[M + H]^+$ | 99.3% |

TABLE 2-continued

| Ex. # | $^{1}H$ NMR (400 MHz unless otherwise noted) | LCMS: m/z | % ee |
|---|---|---|---|
| 1145 | ($CD_3OD$) δ 7.90 (d, 1 H), 7.67-7.80 (m, 1 H), 7.59 (d, 1 H), 7.23-7.30 (m, 1 H), 7.10-7.22 (m, 1 H), 6.81-6.99 (m, 1 H), 6.76 (s, 0.5 H), 6.42 (s, 0.5 H), 4.86 (br d, 0.5 H), 4.14 (br dd, 0.5 H), 3.91 (d, 3 H), 3.58-3.67 (m, 0.5 H), 2.57-3.18 (m, 2.5 H) | 417.2 $[M + H]^+$ | 99.3% |
| 1146 | ($CD_3OD$) δ 8.39-8.64 (m, 1 H), 7.65-7.76 (m, 1 H), 7.41-7.56 (m, 1 H), 7.08-7.19 (m, 1 H), 6.93 (s, 0.7 H), 6.73 (d, 1 H), 6.59 (s, 0.7 H), 6.36 (s, 0.3 H), 6.09 (s, 0.3 H), 3.76-3.94 (m, 1.5 H), 3.43-3.57 (m, 0.5 H), 2.74-3.04 (m, 2 H), 2.62-2.72 (m, 3 H) | 417.1 $[M + H]^+$ | 99.8% |
| 1147 | ($CD_3OD$) δ 8.35-8.64 (m, 1 H), 7.64-7.75 (m, 1 H), 7.38-7.56 (m, 1 H), 7.05-7.20 (m, 1 H), 6.93 (s, 0.7 H), 6.73 (d, 1 H), 6.59 (s, 0.7 H), 6.36 (s, 0.3 H), 6.09 (br s, 0.3 H), 3.74-3.94 (m, 1.5 H), 3.41-3.54 (m, 0.5 H), 2.74-3.03 (m, 2 H), 2.60-2.71 (m, 3 H) | 417.1 $[M + H]^+$ | 99.8% |
| 1148 | ($CD_3OD$) δ 8.26 (s, 1 H), 7.67 (s, 1 H), 7.47 (br d, 1 H), 7.12 (dd, 1 H), 6.90 (br s, 0.6 H), 6.71 (d, 1 H), 6.60 (br s, 1.4 H), 4.64-4.73 (m, 0.5 H), 4.18-4.42 (m, 0.5 H), 3.72-4.00 (m, 0.6 H), 3.37-3.56 (m, 0.4 H), 2.90-3.12 (m, 1 H), 2.82 (br d, 1 H), 2.67 (s, 3 H), 2.38 (s, 3 H) | 363.2 $[M + H]^+$ | 100% |
| 1149 | ($CD_3OD$) δ 8.26 (s, 1 H), 7.67 (s, 1 H), 7.47 (br d, 1 H), 7.12 (dd, 1 H), 6.89 (br s, 0,6 H), 6.71 (d, 1 H), 6.59 (br s, 1.4 H), 4.70-4.86 (m, 0.4 H), 4.32 (br s, 0.6 H), 3.86 (br s, 0.6 H), 3.37-3.55 (m, 0.4 H), 3.02 (br s, 1 H), 2.80 (dd, 1 H), 2.66 (s, 3 H), 2.38 (s, 3 H) | 363.2 $[M + H]^+$ | 100% |
| 1150 | ($CD_3OD$) δ 7.58-7.84 (m, 1 H), 7.40-7.54 (m, 1 H), 7.07-7.19 (m, 1 H), 6.92 (s, 0.6 H), 6.73 (d, 1 H), 6.60 (s, 0.6 H), 6.40 (s, 0.4 H), 6.14 (br s, 0.4 H), 3.73-3.96 (m, 1.5 H), 3.40-3.56 (m, 0.5 H), 2.92-3.07 (m, 1 H), 2.75-2.91 (m, 1 H), 2.60-2.72 (m, 3 H), 1.59-1.69 (m, 6 H) | 475.2 $[M + H]^+$ | 99.3% |
| 1151 | ($CD_3OD$) δ 7.62-7.77 (m, 1 H), 7.42-7.55 (m, 1 H), 7.08-7.21 (m, 1 H), 6.92 (s, 0.6 H), 6.73 (d, 1 H), 6.60 (s, 0.6 H), 6.40 (s, 0.4 H), 6.14 (s, 0.4 H), 3.77-3.95 (m, 1.4 H), 3.49 (td, 0.6 H), 2.92-3.07 (m, 1 H), 2.75-2.90 (m, 1 H), 2.64-2.73 (m, 3 H), 1.61-1.69 (m, 6 H) | 475.2 $[M + H]^+$ | 99.2% |
| 1152 | ($CD_3OD$) δ 7.55 (s, 1 H), 7.36 (br d, 1 H), 6.95-7.17 (m, 2 H), 6.30-6.91 (m, 3 H), 4.84-4.90 (m, 1 H), 4.53-4.67 (m, 0.5 H), 4.17-4.32 (m, 0.5 H), 3.66-3.86 (m, 0.5 H), 3.27-3.42 (m, 0.5 H), 2.64-3.06 (m, 2 H), 2.44-2.63 (m, 3 H), 1.32-1.65 (m, 3 H) | 443.2 $[M + H]^+$ | 99.5% |
| 1153 | ($CD_3OD$) δ 7.55 (s, 1 H), 7.36 (br d, 1 H), 6.92-7.20 (m, 2 H), 6.33-6.88 (m, 3 H), 4.87 (q, 1 H), 4.50-4.67 (m, 0.5 H), 4.15-4.33 (m, 0.5 H), 3.66-3.85 (m, 0.5 H), 3.26-3.47 (m, 0.5 H), 2.64-3.09 (m, 2 H), 2.55 (br s, 3 H), 1.49 (br s, 3 H) | 443.2 $[M + H]^+$ | 98.8% |
| 1154 | ($CD_3OD$) δ 8.32 (s, 1 H), 7.48-7.81 (m, 2 H), 7.22-7.34 (m, 1 H), 6.48-7.20 (m, 4 H), 4.20 (br s, 1 H), 3.79 (br d, 1 H), 2.91 (br s, 1 H), 2.70 (dd, 1 H) | 453.1 $[M + H]^+$ | 99.4% |
| 1155 | ($CD_3OD$) δ 8.32 (s, 1 H), 7.54-7.85 (m, 2 H), 7.20-7.34 (m, 1 H), 6.47-7.19 (m, 4 H), 4.21 (br s, 1 H), 3.78 (br s, 1 H), 2.92 (br d, 1 H), 2.70 (dd, 1 H) | 453.1 $[M + H]^+$ | 97.8% |
| 1156 | ($CD_3OD$) δ 7.87 (br s, 1 H), 7.69 (s, 1 H), 7.35-7.41 (m, 1 H), 6.68-7.32 (m, 4 H), 4.36 (br d, 1 H), 3.92 (br s, 1 H), 2.92-3.15 (m, 1 H), 2.83 (br d, 1 H), 1.53-1.76 (m, 6 H) | 511.2 $[M + H]^+$ | 99.8% |
| 1157 | ($CD_3OD$) δ 7.87 (br s, 1 H), 7.69 (s, 1 H), 7.33-7.45 (m, 1 H), 6.61-7.33 (m, 4 H), 4.37 (br d, 1 H), 3.91 (br s, 1 H), 2.93-3.13 (m, 1 H), 2.83 (br d, 1 H), 1.52-1.76 (m, 6 H) | 511.2 $[M + H]^+$ | 96.9% |
| 1158 | ($CD_3OD$) δ 8.68 (br s, 1 H), 8.39 (s, 1 H), 7.74-8.09 (m, 1 H), 7.69 (s, 1 H), 7.62 (br d, 1 H), 6.63-7.03 (m, 3 H), 4.73-4.87 (m, 1 H), 4.51 (br s, 0.4 H), 3.75 (br s, 0.6 H), 3.09 (br s, 1 H), 2.82 (br d, 1 H) | 403.1 $[M + H]^+$ | 99.6% |
| 1159 | ($CD_3OD$) δ 8.68 (br s, 1 H), 8.39 (s, 1 H), 7.73-8.09 (m, 1 H), 7.69 (s, 1 H), 7.62 (br d, 1 H), 6.63-7.03 (m, 3 H), 4.73-4.87 (m, 1 H), 4.51 (br s, 0.4 H), 3.74 (br s, 0.6 H), 3.09 (br s, 1 H), 2.82 (br d, 1 H) | 403.1 $[M + H]^+$ | 99.7% |
| 1160 | ($CD_3OD$) δ 7.87 (dd, 1 H), 7.59-7.77 (m, 1 H), 7.53 (br s, 0.5 H), 7.24-7.43 (m, 2 H), 6.87 (s, 1 H), 6.67 (s, 0.5 H), 4.95-5.02 (m, 1 H), 3.96 (br s, 0.5 H), 2.73-3.31 (m, 2.5 H), 1.82-1.99 (m, 6 H) | 464.2 $[M + H]^+$ | 99.1% |
| 1161 | ($CD_3OD$) δ 7.74 (dd, 1 H), 7.50-7.65 (m, 1 H), 7.41 (s, 0.5 H), 7.08-7.27 (m, 2 H), 6.67-6.89 (m, 1 H), 6.55 (s, 0.5 H), 4.84-4.89 (m, 1 H), 3.75-3.91 (m, 0.5 H), 2.70-3.19 (m, 2.5 H), 1.72-1.86 (m, 6 H) | 464.2 $[M + H]^+$ | 98.0% |
| 1162 | ($CD_3OD$) δ 7.68-7.80 (m, 1 H), 7.60 (d, 1 H), 7.26 (br d, 1 H), 7.13-7.20 (m, 1 H), 7.01 (s, 0.5 H), 6.72-6.88 (m, 1 H), 6.44 (s, 0.5 H), 4.84 (br s, 0.5 H), 4.24 (dd, 0.5 H), 3.89 (d, 3 H), 3.56-3.73 (m, 0.5 H), 2.92-3.15 (m, 1 H), 2.79-2.92 (m, 0.5 H), 2.59-2.77 (m, 1 H) | 451.1 $[M + H]^+$ | 98.4% |
| 1163 | ($CD_3OD$) δ 7.81-7.91 (m, 1 H), 7.72 (d, 1 H), 7.34-7.43 (m, 1 H), 7.23-7.33 (m, 1 H), 7.13 (s, 0.5 H), 6.84-6.96 (m, 1 H), 6.57 (s, 0.5 H), 4.95 (br d, 0.5 H), 4.36 (dd, 0.5 H), 4.01 (d, 3 H), 3.70-3.81 (m, 0.5 H), 3.07-3.27 (m, 1 H), 2.91-3.03 (m, 0.5 H), 2.71-2.90 (m, 1 H) | 451.1 $[M + H]^+$ | 99.1% |

TABLE 2-continued

| Ex. # | $^1$H NMR (400 MHz unless otherwise noted) | LCMS: m/z | % ee |
|---|---|---|---|
| 1164 | ($CD_3OD$) δ 7.68 (s, 1 H), 7.47 (br s, 1 H), 6.97-7.28 (m, 2 H), 6.90 (br s, 0.4 H), 6.73 (br d, 1.3 H), 6.42-6.65 (m, 1.3 H), 4.96-5.01 (m, 1.8 H), 4.37 (br s, 0.2 H), 3.89 (br s, 0.5 H), 3.36-3.53 (m, 0.5 H), 2.90-3.12 (m, 1 H), 2.76-2.88 (m, 1 H), 2.68 (br s, 3 H), 1.62 (br s, 3 H) | 443.1 $[M + H]^+$ | 98.9% |
| 1165 | ($CD_3OD$) δ 7.70 (s, 1 H), 7.48 (br s, 1 H), 6.95-7.30 (m, 2 H), 6.90 (br s, 0.5 H), 6.73 (br d, 1.3 H), 6.43-6.66 (m, 1.2 H), 4.96-5.00 (m, 1.7 H), 4.38 (br s, 0.3 H), 3.88 (br s, 0.5 H), 3.50 (s, 0.5 H), 2.90-3.18 (m, 1 H), 2.83 (dd, 1 H), 2.68 (br s, 3 H), 1.61 (br s, 3 H) | 443.2 $[M + H]^+$ | 98.3% |
| 1166 | ($CD_3OD$) δ 8.29 (s, 1 H), 7.98 (br s, 1.5 H), 7.66 (br s, 0.5 H), 7.56 (s, 1 H), 6.58-6.85 (m, 2 H), 6.33-6.57 (m, 2 H), 4.37 (br s, 1 H), 3.85 (s, 3 H), 3.64 (br d, 1 H), 2.96 (br s, 1 H), 2.59-2.78 (m, 1 H) | 365.2 $[M + H]^+$ | 100% |
| 1167 | ($CD_3OD$) δ 8.29 (s, 1 H), 7.98 (br s, 1.5 H), 7.67 (br s, 0.5 H), 7.56 (s, 1 H), 6.57-6.82 (m, 2 H), 6.34-6.58 (m, 2 H), 4.36 (br s, 1 H), 3.85 (s, 3 H), 3.64 (br d, 1 H), 2.79-3.07 (m, 1 H), 2.59-2.79 (m, 1 H) | 365.1 $[M + H]^+$ | 99.2% |
| 1168 | ($CD_3OD$) δ 7.98-8.17 (m, 1 H), 7.69 (s, 1 H), 6.87-7.49 (m, 1 H), 6.74-6.84 (m, 1 H), 6.65 (s, 1 H), 6.56-6.62 (m, 1 H), 4.98 (br dd, 1 H), 3.92-4.00 (m, 3 H), 3.36-3.79 (m, 1 H), 2.77-3.21 (m, 2 H), 2.28-2.38 (m, 1 H), 1.20-1.33 (m, 4 H) | 406.2 $[M + H]^+$ | 98.8% |
| 1169 | ($CD_3OD$) δ 7.87-8.04 (m, 1 H), 7.57 (s, 1 H), 6.74-7.41 (m, 1 H), 6.65-6.71 (m, 1 H), 6.40-6.59 (m, 2 H), 4.86 (br dd, 1 H), 3.79-3.91 (m, 3 H), 3.24-3.66 (m, 1 H), 2.59-3.05 (m, 2 H), 2.08-2.33 (m, 1 H), 1.07-1.21 (m, 4 H) | 406.2 $[M + H]^+$ | 94.4% |
| 1170 | ($CD_3OD$) δ 8.17-8.28 (m, 1 H), 7.68 (s, 1 H), 7.45-7.53 (m, 1 H), 7.40 (s, 0.3 H), 7.05-7.12 (m, 1 H), 6.92 (s, 0.7 H), 6.43-6.58 (m, 1 H), 4.94 (br d, 1 H), 3.69-3.80 (m, 0.7 H), 3.34-3.43 (m, 0.3 H), 2.78-3.19 (m, 2 H), 2.28-2.35 (m, 3 H), 1.90-1.94 (m, 3 H), 1.84-1.88 (m, 3 H) | 410.2 $[M + H]^+$ | 100% |
| 1171 | ($CD_3OD$) δ 8.18-8.28 (m, 1 H), 7.68 (s, 1 H), 7.45-7.53 (m, 1 H), 7.40 (br s, 0.3 H), 7.04-7.13 (m, 1 H), 6.91 (br s, 0.7 H), 6.43-6.57 (m, 1 H), 4.93-4.96 (m, 1 H), 3.67-3.80 (m, 0.7 H), 3.34-3.44 (m, 0.3 H), 2.78-3.19 (m, 2 H), 2.27-2.37 (m, 3 H), 1.91 (d, 3 H), 1.86 (d, 3 H) | 410.2 $[M + H]^+$ | 98.5% |
| 1172 | ($CD_3OD$) δ 8.43-8.54 (m, 1 H), 7.56-7.69 (m, 2 H), 7.20 (br dd, 1 H), 7.06 (d, 1 H), 6.05-6.94 (m, 2 H), 3.45-3.99 (m, 2 H), 2.78-3.00 (m, 2 H) | 437.1 $[M + H]^+$ | 100% |
| 1173 | ($CD_3OD$) δ 8.40-8.51 (m, 1 H), 7.54-7.68 (m, 2 H), 7.14-7.23 (m, 1 H), 7.03 (d, 1 H), 6.05-6.94 (m, 2 H), 3.42-3.94 (m, 2 H), 2.76-2.99 (m, 2 H) | 437.1 $[M + H]^+$ | 100% |
| 1174 | ($CD_3OD$) δ 8.26 (s, 1 H), 7.67 (s, 1 H), 7.61 (br d, 1 H), 7.18 (dd, 1 H), 7.04 (dd, 1 H), 6.49-6.94 (m, 2 H), 4.25-4.44 (m, 1 H), 3.85 (td, 1 H), 2.76-3.07 (m, 2 H), 2.39 (s, 3 H) | 383.1 $[M + H]^+$ | 100% |
| 1175 | ($CD_3OD$) δ 8.26 (s, 1 H), 7.68 (br s, 1 H), 7.61 (br d, 1 H), 7.18 (t, 1 H), 7.00-7.05 (m, 1 H), 6.57-6.91 (m, 2 H), 4.35 (br s, 1 H), 3.74-3.97 (m, 1 H), 2.78-3.07 (m, 2 H), 2.39 (s, 3 H) | 383.1 $[M + H]^+$ | 99.7% |
| 1176 | ($CD_3OD$) δ 8.35 (s, 1 H), 7.56-7.83 (m, 2 H), 7.12-7.29 (m, 2 H), 6.70-6.84 (m, 1.4 H), 6.47 (s, 0.3 H), 6.03 (s, 0.3 H), 3.60-3.88 (m, 1.6 H), 3.37 (td, 0.4 H), 2.61-2.91 (m, 2 H) | 471.1 $[M + H]^+$ | 99.1% |
| 1177 | ($CD_3OD$) δ 8.48 (s, 1 H), 7.75-8.01 (m, 1 H), 7.64-7.73 (m, 1 H), 7.24-7.43 (m, 2 H), 6.80-6.95 (m, 1.4 H), 6.59 (s, 0.3 H), 6.14 (s, 0.3 H), 3.78-4.01 (m, 1.5 H), 3.42-3.55 (m, 0.5 H), 2.75-3.02 (m, 2 H) | 471.1 $[M + H]^+$ | 98.6% |
| 1178 | ($CD_3OD$) δ 7.80-7.95 (m, 1 H), 7.61-7.77 (m, 1 H), 7.23-7.48 (m, 2 H), 6.80-7.00 (m, 1.3 H), 6.66 (s, 0.3 H), 5.91-6.40 (m, 0.4 H), 4.96-5.00 (m, 0.2 H), 3.75-4.10 (m, 1.4 H), 3.51 (br d, 0.4 H), 2.90-3.08 (m, 1 H), 2.82 (br t, 1 H), 1.57-1.70 (m, 6 H) | 529.2 $[M + H]^+$ | 96.3% |
| 1179 | ($CD_3OD$) δ 7.81-7.93 (m, 1 H), 7.54-7.78 (m, 1 H), 7.13-7.46 (m, 2 H), 6.79-7.06 (m, 1.3 H), 6.66 (s, 0.4 H), 6.21 (br s, 0.3 H), 4.93-4.98 (m, 0.2 H), 3.77-4.00 (m, 1.4 H), 3.52 (td, 0.4 H), 2.75-3.08 (m, 2 H), 1.55-1.73 (m, 6 H) | 529.2 $[M + H]^+$ | 97.8% |
| 1180 | ($CD_3OD$) δ 7.88 (br d, 1 H), 7.68 (s, 1 H), 7.34-7.40 (m, 1 H), 7.25-7.33 (m, 1 H), 6.92-7.25 (m, 1 H), 6.68-6.91 (m, 2 H), 4.98 (br s, 1.5 H), 4.25-4.48 (m, 0.5 H), 3.78-4.02 (m, 0.5 H), 3.35-3.50 (m, 0.5 H), 2.90-3.22 (m, 1 H), 2.83 (br d, 1 H), 1.46-1.75 (m, 3 H) | 497.2 $[M + H]^+$ | 96.9% |
| 1181 | ($CD_3OD$) δ 7.87 (br d, 1 H), 7.68 (s, 1 H), 7.36 (d, 1 H), 7.25-7.33 (m, 1 H), 6.92-7.24 (m, 1 H), 6.69-6.91 (m, 2 H), 4.98 (br s, 1.5 H), 4.26-4.47 (m, 0.5 H), 3.78-4.02 (m, 0.5 H), 3.36-3.49 (m, 0.5 H), 2.90-3.20 (m, 1 H), 2.83 (br d, 1 H), 1.44-1.76 (m, 3 H) | 497.2 $[M + H]^+$ | 95.5% |
| 1182 | ($CD_3OD$) δ 7.85-8.07 (m, 1 H), 7.46-7.65 (m, 1 H), 7.28 (s, 0.3 H), 6.81 (s, 0.7 H), 6.63-6.72 (m, 1 H), 6.39-6.58 (m, 2 H), 4.85 (br d, 1 H), 3.80-3.89 (m, 3 H), 3.24-3.69 (m, 1 H), 2.65-3.10 (m, 2 H), 1.37 (s, 9 H) | 422.2 $[M + H]^+$ | 100% |

TABLE 2-continued

| Ex. # | $^1$H NMR (400 MHz unless otherwise noted) | LCMS: m/z | % ee |
|---|---|---|---|
| 1183 | ($CD_3OD$) δ 7.87-8.06 (m, 1 H), 7.58 (br s, 1 H), 7.28 (br s, 0.3 H), 6.81 (br s, 0.6 H), 6.63-6.72 (m, 1 H), 6.35-6.58 (m, 2 H), 4,81-4.93 (m, 1 H), 3.78-3.90 (m, 3 H), 3.24-3.70 (m, 1 H), 2.64-3.09 (m, 2 H), 1.37 (s, 9 H) | 422.2 $[M + H]^+$ | 99.7% |
| 1184 | ($CD_3OD$) δ 8.23-8.42 (m, 2 H), 7.70-8.14 (m, 1 H), 7.66 (s, 1 H), 7.34 (s, 1 H), 6.25-6.92 (m, 3 H), 4.75 (br s, 0.5 H), 4.46 (br s, 0.5 H), 3.74 (br s, 0.5 H), 3.35 (br s, 0.5 H), 2.66-3.19 (m, 2 H), 2.36 (s, 3 H) | 349.2 $[M + H]^+$ | 99.5% |
| 1185 | ($CD_3OD$) δ 8.25-8.44 (m, 2 H), 7.71-8.13 (m, 1 H), 7.67 (s, 1 H), 7.33 (s, 1 H), 6.28-6.93 (m, 3 H), 4.76 (br s, 0.5 H), 4.46 (br s, 0.5 H), 3.74 (br s, 0.5 H), 3.35 (br s, 0.5 H), 2.67-3.19 (m, 2 H), 2.36 (s, 3 H) | 349.2 $[M + H]^+$ | 98.4% |
| 1186 | ($CD_3OD$) δ 8.15-8.42 (m, 2 H), 7.66-8.10 (m, 2 H), 7.49 (d, 1 H), 7.08 (d, 1 H), 6.29-6.96 (m, 2 H), 4.69-4.85 (m, 1 H), 4.46 (br s, 0.5 H), 3.62-3.85 (m, 0.5 H), 2.73-3.13 (m, 2 H), 2.32 (s, 3 H) | 349.1 $[M + H]^+$ | 100% |
| 1187 | ($CD_3OD$) δ 8.11-8.41 (m, 2 H), 7.55-8.08 (m, 2 H), 7.49 (d, 1 H), 7.08 (d, 1 H), 6.29-6.96 (m, 2 H), 4.76 (br s, 1 H), 4.45 (br s, 0.5 H), 3.74 (br s, 0.5 H), 2.65-3.16 (m, 2 H), 2.32 (s, 3 H) | 349.2 $[M + H]^+$ | 99.4% |
| 1188 | ($CD_3OD$) δ 7.98 (br s, 1 H), 7.71 (d, 1 H), 7.40-7.50 (m, 1.5 H), 7.05-7.14 (m, 1 H), 6.98 (s, 0.5 H), 6.68 (br dd, 1 H), 6.61 (s, 0.6 H), 6.46 (s, 0.4 H), 5.03-5.12 (m, 0.6 H), 3.84-3.95 (m, 4 H), 3.33-3.42 (m, 0.4 H), 3.11-3.22 (m, 0.6 H), 2.93-3.03 (m, 0.4 H), 2.80-2.88 (m, 1 H), 2.64-2.68 (m, 5 H), 2.50 (s, 1 H) | 444.2 $[M + H]^+$ | 98.4% |
| 1189 | ($CD_3OD$) δ 7.98 (d, 1 H), 7.69 (d, 1 H), 7.40-7.50 (m, 1.5 H), 7.10 (dt, 1 H), 6.98 (s, 0.5 H), 6.69 (dd, 1 H), 6.61 (s, 0.6 H), 6.45 (s, 0.4 H), 5.08 (br dd, 0.6 H), 3.82-3.95 (m, 4 H), 3.34-3.41 (m, 0.4 H), 3.11-3.22 (m, 0.6 H), 2.93-3.04 (m, 0.4 H), 2.80-2.88 (m, 1 H), 2.64-2.68 (m, 5 H), 2.51 (s, 1 H) | 444.2 $[M + H]^+$ | 92.9% |
| 1190 | ($CD_3OD$) δ 7.99 (d, 1 H), 7.79-7,90 (m, 1 H), 7.73 (s, 0.5 H), 7.67 (s, 0.5 H), 7.58 (s, 0.5 H), 7.21-7.37 (m, 2 H), 6.96 (s, 0.5 H), 6.86 (s, 0.5 H), 6.66 (s, 0.5 H), 5.11 (br dd, 0.5 H), 4.93-4.99 (m, 1 H), 3.91-3.99 (m, 0.5 H), 3.89 (d, 3 H), 3.11-3.22 (m, 0.5 H), 2.93-3.04 (m, 0.5 H), 2.85 (br d, 1 H), 2.67 (s, 3 H) | 498.2 $[M + H]^+$ | 98.5% |
| 1191 | ($CD_3OD$) δ 7.99 (br d, 1 H), 7.79-7.90 (m, 1 H), 7.74 (br s, 0.5 H), 7.61-7.70 (m, 0.5 H), 7.59 (br s, 0.5 H), 7.22-7.37 (m, 2 H), 6.97 (br s, 0.5 H), 6.86 (s, 0.5 H), 6.66 (s, 0.5 H), 5.06-5.15 (m, 0.5 H), 4.96 (br d, 1 H), 3.92-4.00 (m, 0.5 H), 3.89 (br d, 3 H), 3.11-3.25 (m, 0.5 H), 2.92-3.05 (m, 0.5 H), 2.80-2.91 (m, 1 H), 2.67 (s, 3 H) | 498.2 $[M + H]^+$ | 95.2% |
| 1192 | ($CD_3OD$) δ 7.54-7.73 (m, 2 H), 7.20 (br t, 1 H), 7.06 (d, 1 H), 6.57-6.97 (m, 1.6 H), 6.14 (br s, 0.4 H), 3.78-4.03 (m, 1.5 H), 3.52 (td, 0.5 H), 2.72-3.08 (m, 2 H), 1.61-1.70 (m, 6 H) | 495.2 $[M + H]^+$ | 100% |
| 1193 | ($CD_3OD$) δ 7.45-7.59 (m, 2 H), 7.09 (br t, 1 H), 6.94 (d, 1 H), 6.42-6.85 (m, 1.6 H), 6.02 (br s, 0.4 H), 3.75 (br d, 1.5 H), 3.33-3.49 (m, 0.5 H), 2.64-2.94 (m, 2 H), 1.49-1.57 (m, 6 H) | 495.1 $[M + H]^+$ | 97.0% |
| 1194 | ($CD_3OD$) δ 7.57-7.71 (m, 2 H), 7.12-7.32 (m, 1.7 H), 6.98-7.10 (m, 1.3 H), 6.54-6.95 (m, 2 H), 4.96-5.02 (m, 1 H), 4.77-4.86 (m, 0.5 H), 4.40 (br d, 0.5 H), 3.88 (br s, 0.5 H), 3.38-3.54 (m, 0.5 H), 2.76-3.20 (m, 2 H), 1.49-1.72 (m, 3 H) | 463.1 $[M + H]^+$ | 100% |
| 1195 | ($CD_3OD$) δ 7.54-7.69 (m, 2 H), 7.10-7.30 (m, 1.8 H), 6.97-7.08 (m, 1.2 H), 6.58-6.96 (m, 2 H), 4.97 (br d, 1 H), 4.77-4.85 (m, 0.5 H), 4.38 (br d, 0.5 H), 3.86 (br s, 0.5 H), 3.45 (br d, 0.5 H), 2.74-3.18 (m, 2 H), 1.60 (br s, 3 H) | 463.1 $[M + H]^+$ | 91.7% |
| 1196 | ($CD_3OD$) δ 7.68 (s, 1 H), 7.62 (br d, 1 H), 7.14-7.31 (m, 2 H), 7.00-7.08 (m, 1 H), 6.61-6.92 (m, 2 H), 4.99 (br d, 1 H), 4.64-4.68 (m, 1 H), 4.34-4.44 (m, 0.5 H), 3.81-3.93 (m, 0.5 H), 2.80-3.14 (m, 2 H), 1.55-1.66 (m, 3 H) | 463.1 $[M + H]^+$ | 97.3% |
| 1197 | ($CD_3OD$) δ 7.68 (s, 1 H), 7.62 (br d, 1 H), 7.14-7.29 (m, 2 H), 7.01-7.07 (m, 1 H), 6.64-6.92 (m, 2 H), 4.99 (br d, 1 H), 4.64-4.67 (m, 1 H), 4.40 (br dd, 0.5 H), 3.88 (br s, 0.5 H), 2.81-3.17 (m, 2 H), 1.62 (br s, 3 H) | 463.1 $[M + H]^+$ | 98.7% |
| 1198 | ($CD_3OD$) δ 8.26 (s, 1 H), 7.86 (br d, 1 H), 7.68 (s, 1 H), 7.24-7.41 (m, 2 H), 6.86 (br s, 2 H), 4.33 (br s, 0.9 H), 3.55-4.05 (m, 1.1 H), 3.01 (br s, 1 H), 2.80 (dd, 1 H), 2.37 (s, 3 H) | 417.1 $[M + H]^+$ | 99.8% |
| 1199 | ($CD_3OD$) δ 8.14 (s, 1 H), 7.75 (br d, 1 H), 7.56 (s, 1 H), 7.08-7.31 (m, 2 H), 6.39-6.83 (m, 2 H), 4.22 (br s, 1 H), 3.51-3.90 (m, 1 H), 2.81-3.00 (m, 1 H), 2.68 (br dd, 1 H), 2.25 (s, 3 H) | 417.1 $[M + H]^+$ | 99.7% |
| 1200 | ($CD_3OD$) δ 7.75 (br d, 1 H), 7.57 (s, 1 H), 7.14-7.28 (m, 2 H), 6.55-7.12 (m, 3 H), 4.86 (br s, 1 H), 4.25 (br s, 1 H), 3.26-3.86 (m, 1 H), 2.82-3.03 (m, 1 H), 2.71 (dd, 1 H), 1.41-1.56 (m, 3 H) | 497.2 $[M + H]^+$ | 88.2% |
| 1201 | ($CD_3OD$) δ 7.87 (br d, 1 H), 7.68 (s, 1 H), 7.23-7.42 (m, 2 H), 6.60-7.23 (m, 3 H), 4.98 (br s, 1 H), 4.36 (br s, 1 H), 3.41-4.06 (m, 1 H), 2.94-3.17 (m, 1 H), 2.83 (br d, 1 H), 1.43-1.73 (m, 3 H) | 497.1 $[M + H]^+$ | 98.7% |
| 1202 | ($CD_3OD$) δ 8.44 (s, 1 H), 7.69 (s, 1 H), 7.48 (br d, 1 H), 7.00-7.33 (m, 2 H), 6.73-6.95 (m, 1.4 H), 6.48-6.72 (m, 1.6 H), 4.79- | 403.1 $[M + H]^+$ | 99.8% |

TABLE 2-continued

| Ex. # | $^1$H NMR (400 MHz unless otherwise noted) | LCMS: m/z | % ee |
|---|---|---|---|
| | 4.86 (m, 0.3 H), 4.36 (br d, 0.7 H), 3.71-3.97 (m, 0.7 H), 3.37-3.49 (m, 0.3 H), 3.08 (br s, 1 H), 2.82 (br d, 1 H) | | |
| 1203 | ($CD_3OD$) δ 8.44 (s, 1 H), 7.69 (s, 1 H), 7.48 (br d, 1 H), 6.99-7.33 (m, 2 H), 6.72-6.94 (m, 1.5 H), 6.51-6.71 (m, 1.5 H), 4.85 (br s, 0.3 H), 4.36 (br d, 0.7 H), 3.80 (br s, 0.7 H), 3.37-3.48 (m, 0.3 H), 3.09 (br s, 1 H), 2.82 (br d, 1 H) | 403.2 $[M + H]^+$ | 99.1% |
| 1204 | ($CD_3OD$) δ 8.59-8.76 (m, 1 H), 7.91-8.05 (m, 1 H), 7.70 (s, 1 H), 7.52-7.67 (m, 1.4 H), 6.91-7.05 (m, 1.6 H), 6.72-6.83 (m, 1 H), 4.94-5.15 (m, 1 H), 3.83-3.95 (m, 3 H), 3.68-3.82 (m, 0.7 H), 3.39 (td, 0.3 H), 2.79-3.25 (m, 2 H), 2.59-2.72 (m, 3 H) | 498.2 $[M + H]^+$ | 100% |
| 1205 | ($CD_3OD$) δ 8.57-8.79 (m, 1 H), 7.94-8.07 (m, 1 H), 7.70 (s, 1 H), 7.52-7.67 (m, 1.3 H), 6.90-7.06 (m, 1.7 H), 6.73-6.83 (m, 1 H), 5.12 (br dd, 1 H), 3.86-3.95 (m, 3 H), 3.69-3.83 (m, 0.7 H), 3.39 (td, 0.3 H), 2.78-3.25 (m, 2 H), 2.63-2.71 (m, 3 H) | 498.2 $[M + H]^+$ | 100% |
| 1206 | ($CD_3OD$) δ 7.93-8.15 (m, 2 H), 7.69 (s, 1 H), 7.53 (s, 0.3 H), 6.94 (s, 0.7 H), 6.73-6.85 (m, 1 H), 6.66 (s, 0.6 H), 6.53-6.63 (m, 1.4 H), 5.06 (dd, 1 H), 3.83-4.01 (m, 6 H), 3.70-3.79 (m, 0.7 H), 3.39 (td, 0.3 H), 2.77-3.24 (m, 2 H), 2.62-2.71 (m, 3 H) | 460.2 $[M + H]^+$ | 98.2% |
| 1207 | ($CD_3OD$) δ 7.95-8.16 (m, 2 H), 7.69 (s, 1 H), 7.53 (br s, 0.3 H), 6.93 (s, 0.7 H), 6.72-6.85 (m, 1 H), 6.66 (s, 0.7 H), 6.52-6.63 (m, 1.3 H), 5.06 (br dd, 1 H), 3.85-4.01 (m, 6 H), 3.70-3.82 (m, 0.7 H), 3.35-3.44 (m, 0.3 H), 2.79-3.23 (m, 2 H), 2.61-2.73 (m, 3 H) | 460.2 $[M + H]^+$ | 97.2% |
| 1208 | ($CD_3OD$) δ 7.98 (br s, 1 H), 7.65-7.72 (m, 1 H), 7.49-7,64 (m, 1.5 H), 7.11-7.21 (m, 1 H), 6.94-7.06 (m, 1.5 H), 6.78 (s, 0.5 H), 6.64 (s, 0.5 H), 5.11 (dd, 0.6 H), 4.95 (br d, 0.4 H), 3.93 (br d, 0.5 H), 3.88 (s, 3 H), 3.38 (td, 0.5 H), 3.12-3.23 (m, 0.6 H), 2.93-3.04 (m, 0,4 H), 2.85 (br dd, 1 H), 2.62-2.70 (m, 3 H) | 464.2 $[M + H]^+$ | 98.9% |
| 1209 | ($CD_3OD$) δ 7.95-8.03 (m, 1 H), 7.67-7.72 (m, 1 H), 7.50-7.65 (m, 1.5 H), 7.11-7.21 (m, 1 H), 6.94-7.08 (m, 1.5 H), 6.79 (d, 0.5 H), 6.64 (s, 0.5 H), 5.11 (dd, 0.6 H), 4.94-4.96 (m, 0.4 H), 3.92 (br d, 0.5 H), 3.89 (s, 3 H), 3.38 (td, 0.5 H), 3.11-3.24 (m, 0.6 H), 2.93-3.05 (m, 0.4 H), 2.85 (br dd, 1 H), 2.62-2.71 (m, 3 H) | 464.2 $[M + H]^+$ | 94.5% |
| 1210 | ($CD_3OD$) δ 7.55-7.76 (m, 2 H), 7.17 (dd, 1 H), 6.97-7.06 (m, 1 H), 6.49-6.94 (m, 2 H), 4.96-4.97 (m, 0.5 H), 4.36 (br s, 0.5 H), 3.85 (br s, 0.5 H), 3.38-3.44 (m, 0.5 H), 2.71-3.18 (m, 2 H), 2.36 (s, 3 H), 1.62 (br s, 6 H) | 441.2 $[M + H]^+$ | 98.9% |
| 1211 | ($CD_3OD$) δ 7.56-7.69 (m, 2 H), 7.14-7.26 (m, 1 H), 7.02 (d, 1 H), 6.42-6.98 (m, 2 H), 4.98-5.00 (m, 0.5 H), 4.35 (br s, 0.5 H), 3.85 (br s, 0.5 H), 3.38-3.48 (m, 0.5 H), 2.68-3.19 (m, 2 H), 2.36 (s, 3 H), 1.62 (br s, 6 H) | 441.2 $[M + H]^+$ | 97.8% |
| 1212 | ($CD_3OD$) δ 7.57-7.69 (m, 2 H), 7.17 (dd, 1 H), 7.02 (dd, 1 H), 6.50-6.94 (m, 2 H), 4.98-5.01 (m, 1.5 H), 4.36 (br s, 0.5 H), 3.84 (br s, 0.5 H), 3.37-3.43 (m, 0.5 H), 2.72-3.10 (m, 2 H), 2.36 (s, 3 H), 1.56 (br s, 3 H) | 427.1 $[M + H]^+$ | 98.6% |
| 1213 | ($CD_3OD$) δ 7.52-7.73 (m, 2 H), 7.09-7.24 (m, 1 H), 7.02 (d, 1 H), 6.47-6.90 (m, 2 H), 4.99-5.05 (m, 1.5 H), 4.37 (br s, 0.5 H), 3.84 (br s, 0.5 H), 3.38-3.47 (m, 0.5 H), 2.74-3.14 (m, 2 H), 2.36 (s, 3 H), 1.56 (br s, 3 H) | 427.1 $[M + H]^+$ | 99.5% |
| 1214 | ($CD_3OD$) δ 8.30-8.54 (m, 1 H), 7.91-8.07 (m, 1 H), 7.71 (s, 1 H), 7.56 (s, 0.3 H), 7.19-7.36 (m, 1 H), 6.95 (s, 0.6 H), 6.69-6.89 (m, 2 H), 5.10 (br dd, 1 H), 3.88 (s, 3 H), 3.72-3.80 (m, 0.6 H), 3.37-3.43 (m, 0.4 H), 2.78-3.24 (m, 2 H), 2.61-2.73 (m, 3 H) | 464.1 $[M + H]^+$ | 100% |
| 1215 | ($CD_3OD$) δ 8.31-8.50 (m, 1 H), 7.82-8.07 (m, 1 H), 7.70 (s, 1 H), 7.55 (s, 0.3 H), 7.30 (br t, 1 H), 6.95 (s, 0.7 H), 6.67-6.88 (m, 2 H), 5.10 (br dd, 1 H), 3.89 (s, 3 H), 3.72-3.80 (m, 0.5 H), 3.39-3.44 (m, 0.5 H), 2.82-3.23 (m, 2 H), 2.57-2.73 (m, 3 H) | 464.2 $[M + H]^+$ | 99.4% |
| 1216 | ($CD_3OD$) δ 8.30 (br d, 1 H), 7.68 (s, 1 H), 7.28 (s, 0.4 H), 7.15 (s, 0.6 H), 6.96-7.03 (m, 1 H), 6.73-6.90 (m, 2 H), 6.52-6.64 (m, 1 H), 4.29 (br d, 1 H), 3.75 (br t, 0.6 H), 3.36-3.47 (m, 0.4 H), 2.77-3.14 (m, 2 H), 2.44 (br s, 3 H), 1.72-1.91 (m, 6 H) | 459.2 $[M + H]^+$ | 99.7% |
| 1217 | ($CD_3OD$) δ 8.29 (br d, 1 H), 7.68 (br s, 1 H), 7.28 (s, 0.4 H), 7.15 (s, 0.6 H), 6.96-7.03 (m, 1 H), 6.71-6.89 (m, 2 H), 6.52-6.65 (m, 1 H), 4.29 (br d, 1 H), 3.75 (br t, 0.6 H), 3.37-3.50 (m, 0.4 H), 2.74-3.15 (m, 2 H), 2.44 (br s, 3 H), 1.68-1.93 (m, 6 H) | 459.2 $[M + H]^+$ | 98,6% |
| 1218 | ($CD_3OD$) δ 8.69 (d, 1 H), 7.61-7.71 (m, 2 H), 7.27 (s, 0.5 H), 7.14 (s, 0.5 H), 6.96-7.02 (m, 1 H), 6.76-6.90 (m, 1.5 H), 6.57 (br d, 0.5 H), 4.28-4.37 (m, 0.8 H), 3.69-3.80 (m, 1 H), 3.41-3.51 (m, 0.2 H), 2.79-3.15 (m, 2 H), 1.69-1.91 (m, 6 H) | 513.2 $[M + H]^+$ | 98.8% |
| 1219 | ($CD_3OD$) δ 8.69 (d, 1 H), 7.60-7.75 (m, 2 H), 7.27 (s, 0.5 H), 7.14 (s, 0.5 H), 6.96-7.02 (m, 1 H), 6.76-6.89 (m, 1.5 H), 6.57 (br s, 0.5 H), 4.25-4.40 (m, 1 H), 3,67-3.83 (m, 0.8 H), 3.40-3.51 (m, 0.2 H), 2.77-3.15 (m, 2 H), 1.67-1.93 (m, 6 H) | 513.2 $[M + H]^+$ | 98.5% |
| 1220 | ($CD_3OD$) δ 8.32 (d, 1 H), 7.69 (s, 1 H), 6.99-7.33 (m, 2 H), 6.43-6.90 (m, 3 H), 4.35-4.46 (m, 1 H), 3.45-3.79 (m, 1 H), 2.81-3.13 (m, 2 H), 2.46 (s, 3 H), 1.28-1.43 (m, 4 H) | 455.2 $[M + H]^+$ | 99.8% |

TABLE 2-continued

| Ex. # | $^1$H NMR (400 MHz unless otherwise noted) | LCMS: m/z | % ee |
|---|---|---|---|
| 1221 | ($CD_3OD$) δ 8.32 (d, 1 H), 7.69 (s, 1 H), 6.99-7.28 (m, 2 H), 6.55-6.89 (m, 3 H), 4.34-4.47 (m, 1 H), 3.65-3.81 (m, 1 H), 2.80-3.11 (m, 2 H), 2.46 (s, 3 H), 1.26-1.42 (m, 4 H) | 455.2 $[M + H]^+$ | 98.5% |
| 1222 | ($CD_3OD$) δ 8.71 (d, 1 H), 7.62-7.74 (m, 2 H), 6.98-7.28 (m, 2 H), 6.54-6.90 (m, 2 H), 4.44 (br d, 1 H), 3.74 (br s, 1 H), 2.81-3.17 (m, 2 H), 1.21-1.46 (m, 4 H) | 509.1 $[M + H]^+$ | 99.4% |
| 1223 | ($CD_3OD$) δ 8.71 (br d, 1 H), 7.60-7.76 (m, 2 H), 6.96-7.30 (m, 2 H), 6.53-6.92 (m, 2 H), 4.35-4.57 (m, 1 H), 3.76 (br d, 1 H), 2.81-3.16 (m, 2 H), 1.22-1.46 (m, 4 H) | 509.2 $[M + H]^+$ | 99.6% |
| 1224 | ($CD_3OD$) δ 8.41 (s, 1 H), 8.07-8.19 (m, 1 H), 7.71 (s, 1 H), 7.60 (s, 0.3 H), 7.42-7.53 (m, 1 H), 7.19-7.33 (m, 1 H), 6.98 (s, 0.7 H), 6.80 (d, 0.7 H), 6.58-6.73 (m, 1.3 H), 5.12 (dd, 1 H), 4.02 (s, 3 H), 3.73-3.91 (m, 0.7 H), 3.43 (td, 0.3 H), 3.13-3.25 (m, 0.7 H), 2.95-3.07 (m, 0.3 H), 2.80-2.90 (m, 1 H) | 434.2 $[M + H]^+$ | 100% |
| 1225 | ($CD_3OD$) δ 8.42 (s, 1 H), 8.09-8.18 (m, 1 H), 7.77 (s, 1 H), 7.61 (s, 0.3 H), 7.41-7.54 (m, 1 H), 7.20-7.36 (m, 1 H), 6.99 (s, 0.7 H), 6.70-6.87 (m, 1 H), 6.62-6.70 (m, 1 H), 5.13 (br dd, 1 H), 4.02 (s, 3 H), 3.75-3.91 (m, 0.7 H), 3.43 (td, 0.3 H), 3.13-3.26 (m, 0.7 H), 2.94-3.07 (m, 0.3 H), 2.87 (br dd, 1 H) | 434.2 $[M + H]^+$ | 97.8% |
| 1226 | ($CD_3OD$) δ 8.33 (d, 1 H), 7.68 (s, 1 H), 7.27 (s, 0.5 H), 7.14 (s, 0.5 H), 6.93-7.01 (m, 1 H), 6.68-6.85 (m, 2.5 H), 6.56 (br s, 0.5 H), 4.31 (br d, 1 H), 3.75 (br t, 0.6 H), 3.40 (br s, 0.4 H), 2.74-3.15 (m, 2 H), 1.68-1.90 (m, 6 H) | 463.2 $[M + H]^+$ | 99.1% |
| 1227 | ($CD_3OD$) δ 8.30-8.36 (m, 1 H), 7.70 (br s, 1 H), 7.27 (s, 0.5 H), 7.14 (s, 0.5 H), 6.91-7.02 (m, 1 H), 6.68-6.87 (m, 2.5 H), 6.57 (br s, 0.5 H), 4.31 (br dd, 1 H), 3.75 (br t, 0.6 H), 3.34-3.46 (m, 0.4 H), 2.74-3.16 (m, 2 H), 1.69-1.92 (m, 6 H) | 463.1 $[M + H]^+$ | 99.6% |
| 1228 | ($CD_3OD$) δ 8.45 (br d, 1 H), 7.69 (s, 1 H), 7.01-7.33 (m, 2 H), 6.70-6.89 (m, 2.5 H), 6.56 (br s, 0.5 H), 4.32 (br d, 1 H), 3.70-3.80 (m, 0.6 H), 3.38-3.50 (m, 0.4 H), 2.75-3.16 (m, 2 H), 1.72-1.91 (m, 6 H) | 479.1 $[M + H]^+$ | 99.6% |
| 1229 | ($CD_3OD$) δ 8.38-8.44 (m, 1 H), 7.68 (br s, 1 H), 6.99-7.30 (m, 2 H), 6.70-6.88 (m, 2.5 H), 6.55 (br s, 0.5 H), 4.26-4.37 (m, 1 H), 3.74 (br t, 0.6 H), 3.41 (br s, 0.4 H), 2.75-3.15 (m, 2 H), 1.69-1.89 (m, 6 H) | 479.1 $[M + H]^+$ | 98.9% |
| 1230 | ($CD_3OD$) δ 7.68 (s, 1 H), 7.47 (br s, 1 H), 6.97-7.31 (m, 2 H), 6.37-6.95 (m, 3 H), 4.65-4.75 (m, 0.4 H), 4.22-4.41 (m, 0.6 H), 3.45-3.97 (m, 1 H), 2.80-3.12 (m, 2 H), 2.65 (br d, 3 H), 1.65-2.03 (m, 6 H) | 459.2 $[M + H]^+$ | 99.1% |
| 1231 | ($CD_3OD$) δ 7.56 (s, 1 H), 7.35 (br d, 1 H), 6.85-7.20 (m, 2 H), 6.21-6.83 (m, 3 H), 4.54-4.64 (m, 0.4 H), 4.19 (br d, 0.6 H), 3.36-3.83 (m, 1 H), 2.67-3.01 (m, 2 H), 2.40-2.66 (m, 3 H), 1.48-2.07 (m, 6 H) | 459.2 $[M + H]^+$ | 96.3% |
| 1232 | ($CD_3OD$) δ 7.70 (s, 1 H), 7.61 (br s, 1 H), 7.10-7.44 (m, 2 H), 7.00-7.09 (m, 1 H), 6.61-6.93 (m, 2 H), 4.71-4.84 (m, 0.5 H), 4.23-4.45 (m, 0.5 H), 3.37-4.01 (m, 1 H), 2.73-3.21 (m, 2 H), 1.70-1.97 (m, 6 H) | 479.2 $[M + H]^+$ | 99.8% |
| 1233 | ($CD_3OD$) δ 7.69 (s, 1 H), 7.62 (br s, 1 H), 7.07-7.43 (m, 2 H), 7.02-7.07 (m, 1 H), 6.57-6.96 (m, 2 H), 4.75-4.88 (m, 0.5 H), 4.25-4.44 (m, 0.5 H), 3.38-3.99 (m, 1 H), 2.72-3.21 (m, 2 H), 1.72-1.96 (m, 6 H) | 479.1 $[M + H]^+$ | 99.4% |
| 1234 | ($CD_3OD$) δ 8.36 (d, 1 H), 7.70 (s, 1 H), 7.07-7.28 (m, 1 H), 6.96-7.01 (m, 1 H), 6.56-6.89 (m, 3 H), 4.29-4.55 (m, 1 H), 3.54-3.87 (m, 1 H), 2.80-3.14 (m, 2 H), 1.26-1.43 (m, 4 H) | 459.2 $[M + H]^+$ | 99.1% |
| 1235 | ($CD_3OD$) δ 8.36 (d, 1 H), 7.70 (s, 1 H), 7.09-7.32 (m, 1 H), 6.96-7.01 (m, 1 H), 6.58-6,90 (m, 3 H), 4.33-4.55 (m, 1 H), 3.51-3.84 (m, 1 H), 2.82-3.16 (m, 2 H), 1.26-1.43 (m, 4 H) | 459.1 $[M + H]^+$ | 93.9% |
| 1236 | ($CD_3OD$) δ 7.55-7.74 (m, 2 H), 7.00-7.28 (m, 3 H), 6.52-6.93 (m, 2 H), 5.02-5.17 (m, 0.2 H), 4.28-4.55 (m, 0.8 H), 3.52-4.00 (m, 1 H), 2.79-3.16 (m, 2 H), 1.26-1.46 (m, 4 H) | 475.1 $[M + H]^+$ | 99.6% |
| 1237 | ($CD_3OD$) δ 7.57-7.73 (m, 2 H), 6.99-7.29 (m, 3 H), 6.65-6.95 (m, 2 H), 4.99-5.12 (m, 0.2 H), 4.36-4.55 (m, 0.8 H), 3.51-4.01 (m, 1 H), 2.80-3.10 (m, 2 H), 1.26-1.43 (m, 4 H) | 475.1 $[M + H]^+$ | 98.0% |
| 1238 | ($CD_3OD$) δ 7.69 (s, 1 H), 7.48 (br d, 1 H), 6.96-7.33 (m, 2 H), 6.71-6.93 (m, 1.7 H), 6.66 (t, 1.3 H), 4.79-4.84 (m, 0.4 H), 4.38 (br d, 0.6 H), 3.81 (br s, 0.6 H), 3.45 (br s, 0.4 H), 2.95-3.23 (m, 1 H), 2.86 (br s, 1 H), 1.52-1.71 (m, 6 H) | 461.2 $[M + H]^+$ | 95.1% |
| 1239 | ($CD_3OD$) δ 7.73 (br s, 1 H), 7.49 (br d, 1 H), 6.97-7.34 (m, 2 H), 6.72-6.93 (m, 1.7 H), 6.58-6.71 (m, 1.3 H), 4.74-4.82 (m, 0.5 H), 4.39 (br d, 0.5 H), 3.80 (br s, 0.5 H), 3.37-3.49 (m, 0.5 H), 2.93-3.22 (m, 1 H), 2.85 (br d, 1 H), 1.59-1.71 (m, 6 H) | 461.2 $[M + H]^+$ | 97.3% |
| 1240 | ($CD_3OD$) δ 8.43 (s, 1 H), 7.68 (s, 1 H), 7.21 (br d, 3 H), 6.90 (br s, 0.7 H), 6.40-6.71 (m, 1.3 H), 6.23-6.38 (m, 1 H), 4.42 (q, 2.8 H), 3.82 (br s, 1.2 H), 3.07 (br s, 1 H), 2.82 (br d, 1 H), 1.57 (t, 3 H) | 429.2 $[M + H]^+$ | 99.6% |

TABLE 2-continued

| Ex. # | $^1$H NMR (400 MHz unless otherwise noted) | LCMS: m/z | % ee |
|---|---|---|---|
| 1241 | ($CD_3OD$) δ 8.43 (s, 1 H), 7.68 (s, 1 H), 7.21 (br d, 3 H), 6.90 (br s, 0.6 H), 6.61 (br s, 1.4 H), 6.26-6.37 (m, 1 H), 4.42 (q, 2.7 H), 3.82 (br s, 1.3 H), 3.07 (br s, 1 H), 2.81 (br d, 1 H), 1.57 (t, 3 H) | 429.1 $[M + H]^+$ | 98.3% |
| 1242 | ($CD_3OD$) δ 7.59-7.85 (m, 1 H), 6.89-7.55 (m, 3 H), 6.23-6.72 (m, 2 H), 4.33-4.51 (m, 2 H), 3.38-3.89 (m, 2 H), 2.78-3.25 (m, 2 H), 1.79-2.03 (m, 6 H), 1.46-1.65 (m, 3 H) | 440.2 $[M + H]^+$ | 99.7% |
| 1243 | ($CD_3OD$) δ 7.57 (s, 1 H), 6.78-7.47 (m, 3 H), 6.05-6.57 (m, 2 H), 4.22-4.37 (m, 2 H), 3.24-3.77 (m, 2 H), 2.67-3.10 (m, 2 H), 1.62-1.94 (m, 6 H), 1.33-1.56 (m, 3 H) | 440.2 $[M + H]^+$ | 98.5% |
| 1244 | ($CD_3OD$) δ 7.68 (s, 1 H), 7.21 (br d, 3 H), 6.80-7.12 (m, 0.8 H), 6.45-6.66 (m, 1.2 H), 6.25-6.39 (m, 1 H), 4.82 (br s, 0.3 H), 4.26-4.49 (m, 2.7 H), 3.83 (br s, 0.6 H), 3.37-3.48 (m, 0.4 H), 2.94-3.20 (m, 1 H), 2.83 (br d, 1 H), 1.55-1.70 (m, 9 H) | 487.2 $[M + H]^+$ | 99.9% |
| 1245 | ($CD_3OD$) δ 7.69 (s, 1 H), 7.11-7.41 (m, 3 H), 6.81-7.10 (m, 0.8 H), 6.48-6.67 (m, 1.2 H), 6.23-6.40 (m, 1 H), 4.76-4.81 (m, 0.3 H), 4.32-4.47 (m, 2.7 H), 3.83 (br s, 0.6 H), 3.38-3.48 (m, 0.4 H), 2.93-3.21 (m, 1 H), 2.84 (br d, 1 H), 1.54-1.71 (m, 9 H) | 487.2 $[M + H]^+$ | 99.8% |
| 1246 | ($CD_3OD$) δ 7.63-7.81 (m, 1 H), 7.42-7.55 (m, 1.4 H), 7.20-7.34 (m, 1 H), 6.93 (s, 0.6 H), 6.78 (d, 0.6 H), 6.59-6.73 (m, 1.4 H), 5.03 (br dd, 1 H), 3.71-3.87 (m, 0.6 H), 3.37-3.45 (m, 0.4 H), 3.08-3.23 (m, 0.7 H), 2.93-3.04 (m, 0.3 H), 2.83 (dd, 1 H), 2.27-2.41 (m, 1 H), 1.20-1.32 (m, 4 H) | 394.1 $[M + H]^+$ | 100% |
| 1247 | ($CD_3OD$) δ 7.70 (d, 1 H), 7.42-7.55 (m, 1.3 H), 7.21-7.33 (m, 1 H), 6.93 (s, 0.7 H), 6.78 (d, 0.7 H), 6.60-6.70 (m, 1.3 H), 5.03 (br dd, 1 H), 3.67-3.86 (m, 0.7 H), 3.37-3.44 (m, 0.3 H), 2.93-3.21 (m, 1 H), 2.75-2.89 (m, 1 H), 2.28-2.42 (m, 1 H), 1.23-1.32 (m, 4 H) | 394.2 $[M + H]^+$ | 97.1% |
| 1248 | ($CD_3OD$) δ 7.59-7.80 (m, 1 H), 7.40-7.53 (m, 1.3 H), 7.18-7.34 (m, 1 H), 6.95 (s, 0.7 H), 6.79 (d, 0.7 H), 6.59-6.72 (m, 1.3 H), 5.01 (br dd, 1 H), 3.70-3.92 (m, 0.7 H), 3.37-3.44 (m, 0.3 H), 3.08-3.22 (m, 0.7 H), 2.92-3.05 (m, 0.3 H), 2.86 (br s, 1 H), 1.45-1.53 (m, 9 H) | 410.2 $[M + H]^+$ | 100% |
| 1249 | ($CD_3OD$) δ 7.64-7.81 (m, 1 H), 7.41-7.55 (m, 1.3 H), 7.20-7.32 (m, 1 H), 6.95 (s, 0.7 H), 6.79 (d, 0.7 H), 6.66 (q, 1.3 H), 5.01 (br dd, 1 H), 3.71-3.92 (m, 0.6 H), 3.36-3.43 (m, 0.4 H), 3.10-3.23 (m, 0.7 H), 2.94-3.08 (m, 0.3 H), 2.84 (br dd, 1 H), 1.42-1.58 (m, 9 H) | 410.2 $[M + H]^+$ | 100% |
| 1250 | ($CD_3OD$) δ 8.46 (d, 1 H), 7.53-7.74 (m, 2 H), 7.21 (ddd, 1 H), 6.41-6.95 (m, 3 H), 4.05-4.55 (m, 1 H), 3.45-3.87 (m, 1 H), 2.77-3.18 (m, 2 H), 2.40 (s, 3 H), 1.66-1.90 (m, 6 H) | 409.2 $[M + H]^+$ | 99.8% |
| 1251 | ($CD_3OD$) δ 8.43-8.50 (m, 1 H), 7.55-7.76 (m, 2 H), 7.21 (ddd, 1 H), 6.40-6.96 (m, 3 H), 4.04-4.51 (m, 1 H), 3.47-3.88 (m, 1 H), 2.74-3.16 (m, 2 H), 2.40 (s, 3 H), 1.59-1.91 (m, 6 H) | 409.2 $[M + H]^+$ | 99.7% |
| 1252 | ($CD_3OD$) δ 7.67 (s, 1 H), 7.47 (br d, 1 H), 7.12 (dd, 1 H), 6.72 (d, 3 H), 4.14-4.52 (m, 1 H), 3.44-4.04 (m, 1 H), 2.78-3.12 (m, 2 H), 2.67 (s, 3 H), 2.38 (s, 3 H), 1.67-1.90 (m, 6 H) | 423.2 $[M + H]^+$ | 99.8% |
| 1253 | ($CD_3OD$) δ 7.67 (s, 1 H), 7.48 (br d, 1 H), 7.12 (dd, 1 H), 6.72 (d, 3 H), 4.10-4.52 (m, 1 H), 3.45-4.06 (m, 1 H), 2.78-3.14 (m, 2 H), 2.67 (s, 3 H), 2.38 (s, 3 H), 1.67-1.91 (m, 6 H) | 423.2 $[M + H]^+$ | 99.7% |
| 1254 | ($CD_3OD$) δ 8.43 (d, 1 H), 7.53-7.70 (m, 2 H), 6.99-7.30 (m, 2 H), 6.83-6.87 (m, 2 H), 6.53-6.62 (m, 1 H), 4.81 (br d, 0.4 H), 4.29 (br d, 0.6 H), 3.74 (br t, 0.6 H), 3.37-3.50 (m, 0.4 H), 2.71-3.15 (m, 2 H), 1.69-1.93 (m, 6 H) | 445.2 $[M + H]^+$ | 97.0% |
| 1255 | ($CD_3OD$) δ 8.44 (d, 1 H), 7.56-7.70 (m, 2 H), 7.00-7.30 (m, 2 H), 6.85 (br t, 2 H), 6.54-6.63 (m, 1 H), 4.77-4.83 (m, 0.4 H), 4.29 (br dd, 0.6 H), 3.74 (br t, 0.6 H), 3.37-3.47 (m, 0.4 H), 2.76-3.15 (m, 2 H), 1.69-1.90 (m, 6 H) | 445.2 $[M + H]^+$ | 98.4% |
| 1256 | ($CD_3OD$) δ 7.74 (br s, 1 H), 7.58 (s, 1 H), 7.12-7.34 (m, 2 H), 6.45-7.11 (m, 3 H), 4.01-4.41 (m, 0.7 H), 3.26-3.98 (m, 1.3 H), 2.80-3.07 (m, 1 H), 2.63-2.79 (m, 1 H), 1.45-1.98 (m, 6 H) | 485.2 $[M + H]^+$ | 99.3% |
| 1257 | ($CD_3OD$) δ 7.86 (br s, 1 H), 7.69 (s, 1 H), 7.33-7.40 (m, 1 H), 7.25-7.32 (m, 1 H), 6.62-7.24 (m, 3 H), 4.07-4.58 (m, 0.7 H), 3.34-4.07 (m, 1.3 H), 2.92-3.20 (m, 1 H), 2.83 (br dd, 1 H), 1.65-2.04 (m, 6 H) | 485.2 $[M + H]^+$ | 99.3% |
| 1258 | ($CD_3OD$) δ 9.42 (d, 1 H), 9.11 (d, 1 H), 8.27-8.42 (m, 2 H), 6.91-7.86 (m, 3 H), 6.75-6.90 (m, 2 H), 4.93-5.07 (m, 1 H), 3.43-3.89 (m, 1 H), 2.97-3.26 (m, 1 H), 2.88 (br dd, 1 H) | 432.1 $[M + H]^+$ | 100% |
| 1259 | ($CD_3OD$) δ 9.30 (d, 1 H), 9.00 (d, 1 H), 8.00-8.35 (m, 3 H), 6.82-7.56 (m, 2 H), 6.68-6.85 (m, 2 H), 4.82-5.04 (m, 1 H), 3.31-3.76 (m, 1 H), 2.89-3.18 (m, 1 H), 2.74-2.88 (m, 1 H) | 432.2 $[M + H]^+$ | 94.5% |
| 1260 | ($CD_3OD$) δ 8.30 (d, 1 H), 7.66 (s, 1 H), 6.98 (d, 1 H), 6.39-6.91 (m, 3 H), 4.74 (br s, 0.5 H), 4.27 (br d, 0.5 H), 3.73 (br s, 0.5 H), 3.36-3.50 (m, 0.5 H), 2.70-3.17 (m, 2 H), 2.35-2.48 (m, 6 H), 1.64-1.90 (m, 6 H) | 423.2 $[M + H]^+$ | 100% |

TABLE 2-continued

| Ex. # | $^1$H NMR (400 MHz unless otherwise noted) | LCMS: m/z | % ee |
|---|---|---|---|
| 1261 | ($CD_3OD$) δ 8.29 (d, 1 H), 7.67 (s, 1 H), 6.97 (d, 1 H), 6.40-6.91 (m, 3 H), 4.75 (br s, 0.5 H), 4.27 (br d, 0.5 H), 3.74 (br s, 0.5 H), 3.36-3.56 (m, 0.5 H), 2.69-3.18 (m, 2 H), 2.34-2.50 (m, 6 H), 1.63-1.91 (m, 6 H) | 423.2 $[M + H]^+$ | 99.6% |
| 1262 | ($CD_3OD$) δ 8.69 (d, 1 H), 7.57-7.75 (m, 2 H), 6.98 (t, 1 H), 6.40-6.93 (m, 2 H), 4.71-4.81 (m, 0.5 H), 4.31 (br d, 0.5 H), 3.72 (br s, 0.5 H), 3.38-3.55 (m, 0.5 H), 2.73-3.16 (m, 2 H), 2.39 (s, 3 H), 1.61-1.93 (m, 6 H) | 477.2 $[M + H]^+$ | 100% |
| 1263 | ($CD_3OD$) δ 8.69 (d, 1 H), 7.52-7.82 (m, 2 H), 6.98 (t, 1 H), 6.32-6.93 (m, 2 H), 4.78 (br s, 0.5 H), 4.31 (br d, 0.5 H), 3.72 (br s, 0.5 H), 3.46 (br d, 0.5 H), 2.72-3.22 (m, 2 H), 2.39 (s, 3 H), 1.62-1.91 (m, 6 H) | 477.2 $[M + H]^+$ | 100% |
| 1264 | ($CD_3OD$) δ 7.74 (br d, 1 H), 7.56 (s, 1 H), 7.21-7.26 (m, 1 H), 7.11-7.19 (m, 1 H), 6.45-6.87 (m, 2 H), 4.50 (br s, 0.5 H), 4.05-4.31 (m, 0.5 H), 3.72-3.89 (m, 0.5 H), 3.23-3.39 (m, 0.5 H), 2.64-2.98 (m, 2 H), 2.25 (s, 3 H), 1.55-1.79 (m, 6 H) | 477.2 $[M + H]^+$ | 100% |
| 1265 | ($CD_3OD$) δ 7.87 (br d, 1 H), 7.68 (s, 1 H), 7.36 (br d, 1 H), 7.24-7.32 (m, 1 H), 6.55-6.97 (m, 2 H), 4.62 (br s, 0.5 H), 4.17-4.44 (m, 0.5 H), 3.79-4.04 (m, 0.5 H), 3.37-3.56 (m, 0.5 H), 2.78-3.10 (m, 2 H), 2.37 (s, 3 H), 1.66-1.90 (m, 6 H) | 477.2 $[M + H]^+$ | 98.4% |
| 1266 | ($CD_3OD$) δ 7.67 (s, 1 H), 7.62 (br d, 1 H), 7.17-7.22 (m, 1 H), 7.05 (d, 1 H), 6.80 (br d, 2 H), 4.62 (s, 0.5 H), 4.23-4.41 (m, 0.5 H), 3.76-4.00 (m, 0.5 H), 3.39-3.55 (m, 0.5 H), 2.79-3.13 (m, 2 H), 2.40 (s, 3 H), 1.71-1.90 (m, 6 H) | 443.1 $[M + H]^+$ | 100% |
| 1267 | ($CD_3OD$) δ 7.55 (s, 1 H), 7.49 (br d, 1 H), 7.06 (dd, 1 H), 6.92 (d, 1 H), 6,40-6.80 (m, 2 H), 4.50 (s, 0.5 H), 4.16-4.31 (m, 0.5 H), 3.68-3.86 (m, 0.5 H), 3.24-3.41 (m, 0.5 H), 2.67-3.00 (m, 2 H), 2.27 (s, 3 H), 1.59-1.77 (m, 6 H) | 443.1 $[M + H]^+$ | 99.8% |
| 1268 | ($CD_3OD$) δ 7.87 (br d, 1 H), 7.69 (br s, 1 H), 7.33-7.40 (m, 1 H), 7.24-7.33 (m, 1 H), 6.94-7.23 (m, 1 H), 6.74-6.98 (m, 2 H), 4.40 (br s, 1 H), 3.90 (br s, 1 H), 2.68-3.24 (m, 2 H), 1.19-1.46 (m, 4 H) | 509.2 $[M + H]^+$ | 98.1% |
| 1269 | ($CD_3OD$) δ 7.87 (br d, 1 H), 7.69 (br s, 1 H), 7.32-7.42 (m, 1 H), 7.25-7.32 (m, 1 H), 7.08 (br s, 1 H), 6.72-6.96 (m, 2 H), 4.40 (br s, 1 H), 3.90 (br s, 1 H), 2.61-3.20 (m, 2 H), 1.33 (br d, 4 H) | 509.2 $[M + H]^+$ | 95.2% |
| 1270 | ($CD_3OD$) δ 8.15-8.87 (m, 3 H), 7.96 (d, 1 H), 7.59-7.71 (m, 2 H), 7.44 (ddd, 1 H), 6.49-7.14 (m, 4 H), 4.60 (br s, 1 H), 3.33-3.89 (m, 1 H), 3.01-3.13 (m, 1 H), 2.78 (br dd, 1 H) | 452.2 $[M + H]^+$ | 100% |
| 1271 | ($CD_3OD$) δ 8.23-9.01 (m, 3 H), 7.97 (d, 1 H), 7.60-7.71 (m, 2 H), 7.40-7.48 (m, 1 H), 6.47-7.14 (m, 4 H), 4.62 (br s, 1 H), 3.35-3.96 (m, 1 H), 3.04-3.14 (m, 1 H), 2.74-2.83 (m, 1 H) | 452.2 $[M + H]^+$ | 98.8% |
| 1272 | ($CD_3OD$) δ 6.58-7.25 (m, 3 H), 6.36-6.44 (m, 1 H), 6.09 (s, 1 H), 5.85 (ddd, 1 H), 5.70 (d, 1 H), 4.78-5.58 (m, 4 H), 3.06 (br s, 1 H), 1.79-2.37 (m, 1 H), 1.44-1.55 (m, 1 H), 1.19 (br dd, 1 H) | 418.1 $[M + H]^+$ | 97.4% |
| 1273 | ($CD_3OD$) δ 8.21-8.83 (m, 3 H), 7.97 (d, 1 H), 7.67 (s, 1 H), 7.43 (dd, 1 H), 7.29 (d, 1 H), 6.43-7.13 (m, 4 H), 4.61 (br s, 1 H), 3.35-3.95 (m, 1 H), 3.01-3.13 (m, 1 H), 2.77 (br dd, 1 H) | 418.1 $[M + H]^+$ | 98.4% |
| 1274 | ($CD_3OD$) δ 8.33 (br d, 1 H), 7.67 (s, 1 H), 6.41-7.05 (m, 4 H), 4.77 (br s, 0.5 H), 4.30 (br s, 0.5 H), 3.73 (br s, 0.5 H), 3.39 (br s, 0.5 H), 2.71-3.15 (m, 2 H), 2.38 (s, 3 H), 1.64-1.92 (m, 6 H) | 427.2 $[M + H]^+$ | 100% |
| 1275 | ($CD_3OD$) δ 8.34 (d, 1 H), 7.67 (s, 1 H), 6.40-7.07 (m, 4 H), 4.77 (br s, 0.5 H), 4.29 (br d, 0.5 H), 3.72 (br s, 0.5 H), 3.48 (br s, 0.5 H), 2.74-3.17 (m, 2 H), 2.38 (s, 3 H), 1.65-1.87 (m, 6 H) | 427.2 $[M + H]^+$ | 98.1% |
| 1276 | ($CD_3OD$) δ 8.44 (d, 1 H), 7.67 (s, 1 H), 7.29 (d, 1 H), 6.39-6.97 (m, 3 H), 4.77 (br s, 0.5 H), 4.29 (br d, 0.5 H), 3.72 (br s, 0.5 H), 3.37-3.52 (m, 0.5 H), 2.76-3.16 (m, 2 H), 2.39 (s, 3 H), 1.68-1.91 (m, 6 H) | 443.2 $[M + H]^+$ | 100% |
| 1277 | ($CD_3OD$) δ 8.44 (br d, 1 H), 7.67 (br s, 1 H), 7.29 (d, 1 H), 6.40-7.02 (m, 3 H), 4.76 (br s, 0.5 H), 4.29 (br s, 0.5 H), 3.72 (br s, 0.5 H), 3.40 (br s, 0.5 H), 2.70-3.15 (m, 2 H), 2.39 (s, 3 H), 1.63-1.90 (m, 6 H) | 443.2 $[M + H]^+$ | 98.5% |
| 1278 | ($CD_3OD$) δ 7.68 (s, 1 H), 7.47 (br d, 1 H), 7.24 (ddd, 1 H), 6.42-7.00 (m, 3 H), 4.91-5.12 (m, 0.5 H), 4.32 (dt, 0.5 H), 3.38-3.94 (m, 1 H), 2.72-3.15 (m, 2 H), 2.40 (s, 3 H), 1.67-1.91 (m, 6 H) | 427.1 $[M + H]^+$ | 100% |
| 1279 | ($CD_3OD$) δ 7.68 (s, 1 H), 7.47 (br d, 1 H), 7.24 (ddd, 1 H), 6.52-6.89 (m, 3 H), 4.93-5.07 (m, 0.5 H), 4.25-4.38 (m, 0.5 H), 3.46-3.96 (m, 1 H), 2.80-3.15 (m, 2 H), 2.40 (s, 3 H), 1.70-1.89 (m, 6 H) | 427.1 $[M + H]^+$ | 99.9% |
| 1280 | ($CD_3OD$) δ 7.70 (s, 1 H), 7.48 (br d, 1 H), 6.96-7.27 (m, 2 H), 6.67-6.91 (m, 2 H), 6.46-6.64 (m, 1 H), 4.42 (br s, 1 H), 3.87 (br s, 1 H), 2.77-3.15 (m, 2 H), 2.67 (br s, 3 H), 1.26-1.41 (m, 4 H) | 455.2 $[M + H]^+$ | 98.1% |
| 1281 | ($CD_3OD$) δ 7.68 (s, 1 H), 7.48 (br d, 1 H), 6.96-7.27 (m, 2 H), 6.65-6.91 (m, 2 H), 6.43-6.63 (m, 1 H), 4.40 (br s, 1 H), 3.88 (br s, 1 H), 2.82 (br d, 2 H), 2.67 (br s, 3 H), 1.27-1.44 (m, 4 H) | 455.2 $[M + H]^+$ | 100% |

TABLE 2-continued

| Ex. # | $^{1}$H NMR (400 MHz unless otherwise noted) | LCMS: m/z | % ee |
|---|---|---|---|
| 1282 | ($CD_3OD$) δ 8.52-8.62 (m, 1 H), 7.69 (s, 1 H), 7.38-7.51 (m, 1.3 H), 7.08-7.14 (m, 0.2 H), 6.70-7.01 (m, 3.5 H), 4.97 (br dd, 1 H), 3.65-3.83 (m, 0.5 H), 3.35-3.41 (m, 0.5 H), 2.79-3.18 (m, 2 H), 2.59-2.69 (m, 3 H) | 400.2 $[M + H]^+$ | 100% |
| 1283 | ($CD_3OD$) δ 8.52-8.63 (m, 1 H), 7.69 (s, 1 H), 7.37-7.52 (m, 1.3 H), 7.07-7.14 (m, 0.2 H), 6.70-7.02 (m, 3.5 H), 4.97 (br dd, 1 H), 3.67-3.78 (m, 0.5 H), 3.35-3.42 (m, 0.5 H), 2.78-3.18 (m, 2 H), 2.61-2.69 (m, 3 H) | 400.2 $[M + H]^+$ | 100% |
| 1284 | ($CD_3OD$) δ 8.46 (br d, 1 H), 7.54-7.73 (m, 2 H), 7.43-7.49 (m, 0.3 H), 7.14-7.25 (m, 1 H), 6.85-6.94 (m, 1.7 H), 6.51-6.67 (m, 1 H), 4.97 (br s, 1 H), 3.38-3.82 (m, 1 H), 2.81-3.20 (m, 2 H), 1.61 (s, 3 H), 1.39-1.46 (m, 2 H), 1.11 (d, 2 H) | 390.2 $[M + H]^+$ | 100% |
| 1285 | ($CD_3OD$) δ 8.40-8.52 (m, 1 H), 7.54-7.76 (m, 2 H), 7.46 (s, 0.3 H), 7.14-7.26 (m, 1 H), 6.83-6.97 (m, 1.7 H), 6.53-6.66 (m, 1 H), 5.00 (br d, 1 H), 3.40-3.79 (m, 1 H), 2.80-3.19 (m, 2 H), 1.61 (s, 3 H), 1.39-1.46 (m, 2 H), 1.11 (d, 2 H) | 390.2 $[M + H]^+$ | 94.1% |
| 1286 | ($CD_3OD$) δ 8.24-8.88 (m, 3 H), 7.97 (d, 1 H), 7.66 (s, 1 H), 7.44 (dd, 1 H), 6.32-7.19 (m, 5 H), 4.61-4.74 (m, 1 H), 3.39-3.95 (m, 1 H), 3.02-3.12 (m, 1 H), 2.77 (br dd, 1 H), 2.44 (s, 3 H) | 398.2 $[M + H]^+$ | 100% |
| 1287 | ($CD_3OD$) δ 8.20-9.02 (m, 3 H), 7.97 (d, 1 H), 7.66 (s, 1 H), 7.39-7.48 (m, 1 H), 6.38-7.12 (m, 5 H), 4.60-4.78 (m, 1 H), 3.36-3.94 (m, 1 H), 3.01-3.12 (m, 1 H), 2.77 (br dd, 1 H), 2.44 (s, 3 H) | 398.2 $[M + H]^+$ | 98.9% |
| 1288 | ($CD_3OD$) δ 8.21-8.92 (m, 3 H), 7.97 (d, 1 H), 7.66 (s, 1 H), 7.41-7.46 (m, 1 H), 6.47-7.11 (m, 5 H), 4.62 (br s, 1 H), 3.33-3.92 (m, 1 H), 3.02-3.14 (m, 1 H), 2.77 (br dd, 1 H) | 402.2 $[M + H]^+$ | 100% |
| 1289 | ($CD_3OD$) δ 8.20-8.90 (m, 3 H), 7.96 (d, 1 H), 7.66 (s, 1 H), 7.43 (dd, 1 H), 6.48-7.12 (m, 5 H), 4.62 (br s, 1 H), 3.34-3.93 (m, 1 H), 3.01-3.14 (m, 1 H), 2.77 (br dd, 1 H) | 402.2 $[M + H]^+$ | 100% |
| 1290 | ($CD_3OD$) δ 8.69 (d, 1 H), 8.44 (d, 1 H), 8.13 (d, 1 H), 8.00 (td, 1 H), 7.69 (s, 1 H), 7.51-7.61 (m, 2 H), 7.12-7.23 (m, 1 H), 6.84 (t, 1 H), 6.64 (s, 1 H), 6.53 (s, 1 H), 4.44 (dd, 1 H), 3.69-3.85 (m, 1 H), 3.02-3.17 (m, 1 H), 2.84 (dd, 1 H) | 385.1 $[M + H]^+$ | 99.3% |
| 1291 | ($CD_3OD$) δ 8.69 (d, 1 H), 8.44 (d, 1 H), 8.13 (d, 1 H), 7.96-8.05 (m, 1 H), 7.69 (s, 1 H), 7.52-7.63 (m, 2 H), 7.18 (dd, 1 H), 6.85 (t, 1 H), 6.64 (s, 1 H), 6.54 (s, 1 H), 4.44 (dd, 1 H), 3.75-3.87 (m, 1 H), 3.04-3.17 (m, 1 H), 2.85 (dd, 1 H) | 385.1 $[M + H]^+$ | 96.9% |
| 1292 | ($CD_3OD$) δ 9.31 (s, 1 H), 8.80 (d, 1 H), 8.33-8.61 (m, 2 H), 7.64-7.77 (m, 2 H), 7.56 (s, 0.3 H), 7.23-7.37 (m, 1 H), 6.97 (s, 0.7 H), 6.68-6.92 (m, 2 H), 5.10 (br dd, 1 H), 3.73-3.86 (m, 0.7 H), 3.43 (td, 0.3 H), 2.79-3.26 (m, 2 H) | 447.1 $[M + H]^+$ | 100% |
| 1293 | ($CD_3OD$) δ 9.31 (s, 1 H), 8.80 (d, 1 H), 8.32-8.60 (m, 2 H), 7.64-7.76 (m, 2 H), 7.56 (s, 0.3 H), 7.25-7.35 (m, 1 H), 6.97 (s, 0.7 H), 6.68-6.90 (m, 2 H), 5.10 (dd, 1 H), 3.66-3.89 (m, 0.7 H), 3.43 (td, 0.3 H), 2.82-3.25 (m, 2 H) | 447.1 $[M + H]^+$ | 98.5% |
| 1294 | ($CD_3OD$) δ 8.67 (d, 1 H), 8.40-8.52 (m, 1 H), 7.94 (d, 1 H), 7.69-7.83 (m, 2 H), 7.47 (s, 0.4 H), 7.26-7.38 (m, 1 H), 6.99 (s, 0.6 H), 6.77-6.92 (m, 2 H), 4.95-5.03 (m, 1 H), 3.76-3.86 (m, 0.5 H), 3.42-3.51 (m, 0.5 H), 3.02-3.24 (m, 1 H), 2.88 (br d, 1 H) | 465.1 $[M + H]^+$ | 99.9% |
| 1295 | ($CD_3OD$) δ 8.67 (d, 1 H), 8.36-8.53 (m, 1 H), 7.95 (t, 1 H), 7.71-7.80 (m, 2 H), 7.47 (s, 0.3 H), 7.21-7.36 (m, 1 H), 6,99 (s, 0.7 H), 6.77-6.92 (m, 2 H), 4.98 (br d, 1 H), 3.71-3.93 (m, 0.5 H), 3.40-3.55 (m, 0.5 H), 2.99-3.29 (m, 1 H), 2.81-2.96 (m, 1 H) | 465.1 $[M + H]^+$ | 99.5% |
| 1296 | ($CD_3OD$) δ 7.69 (d, 1 H), 7.56-7.65 (m, 1 H), 7.44 (s, 0.4 H), 7.14-7.23 (m, 1 H), 7.05 (d, 1 H), 6.94 (s, 0.6 H), 6.61-6.81 (m, 1 H), 4.92-5.07 (m, 1 H), 3.80-3.92 (m, 0.6 H), 3.35-3.42 (m, 0.4 H), 2.81-3.19 (m, 2 H), 1.60 (s, 3 H), 1.38-1.46 (m, 2 H), 1.10 (d, 2 H) | 424.2 $[M + H]^+$ | 100% |
| 1297 | ($CD_3OD$) δ 7.58 (d, 1 H), 7.44-7.53 (m, 1 H), 7.32 (s, 0.4 H), 7.03-7.11 (m, 1 H), 6.90-6.96 (m, 1 H), 6.83 (s, 0.6 H), 6.50-6.69 (m, 1 H), 4.90 (br dd, 1 H), 3.75 (ddd, 0.6 H), 3.28 (br d, 0.4 H), 2.74 (br d, 2 H), 1.48 (s, 3 H), 1.29 (br d, 2 H), 0.98 (d, 2 H) | 424.1 $[M + H]^+$ | 92.3% |
| 1298 | ($CD_3OD$) δ 8.80-9.04 (m, 1 H), 8.39-8.60 (m, 2 H), 8.29 (d, 1 H), 7.82 (s, 0.3 H), 7.64 (dd, 1 H), 7.26-7.43 (m, 1 H), 7.20 (s, 0.7 H), 7.06 (s, 0.3 H), 6.89-6.97 (m, 1.7 H), 5.25 (br dd, 1 H), 4.01 (s, 3 H), 3.65-3.84 (m, 1 H), 3.38-3.55 (m, 1 H), 2.94-3.19 (m, 1 H) | 477.2 $[M + H]^+$ | 90.8% |
| 1299 | ($CD_3OD$) δ 8.87-9.06 (m, 1 H), 8.41-8.65 (m, 2 H), 8.28 (br d, 1 H), 7.82 (s, 0.3 H), 7.63 (dd, 1 H), 7.38 (d, 1 H), 7.20 (s, 0.7 H), 7.06 (s, 0.3 H), 6.86-6.97 (m, 1.7 H), 5.25 (br dd, 1 H), 4.01 (s, 3 H), 3.75 (br t, 1 H), 3.38-3.54 (m, 1 H), 2.93-3.18 (m, 1 H) | 477.1 $[M + H]^+$ | 94.0% |
| 1300 | ($CD_3OD$) δ 9.48 (d, 1 H), 8.81-8.90 (m, 2 H), 8.63-8.76 (m, 1 H), 7.73-7.84 (m, 1 H), 7.59-7.73 (m, 1 H), 6.80-7.57 (m, 3 H), 4.94-5.13 (m, 1 H), 3.40-3.91 (m, 1 H), 2.81-3.28 (m, 2 H) | 482.2 $[M + H]^+$ | 100% |
| 1301 | ($CD_3OD$) δ 9.48 (s, 1 H), 8.81-9.04 (m, 2 H), 8.63-8.81 (m, 1 H), 7.73-7.91 (m, 1 H), 7.59-7.72 (m, 1 H), 6.79-7.59 (m, 3 H), 5.07 (br dd, 1 H), 3.41-3.96 (m, 1 H), 2.82-3.30 (m, 2 H) | 482.1 $[M + H]^+$ | 99.9% |

TABLE 2-continued

| Ex. # | $^1$H NMR (400 MHz unless otherwise noted) | LCMS: m/z | % ee |
|---|---|---|---|
| 1302 | ($CD_3OD$) δ 9.31 (br s, 1 H), 8.46-8.83 (m, 3 H), 7.71 (s, 3.5 H), 6.91-7.04 (m, 1.5 H), 6.66-6.87 (m, 1 H), 5.12 (dd, 0.7 H), 4.95 (br dd, 0.3 H), 3.70-3.86 (m, 0.7 H), 3.37-3.50 (m, 0.3 H), 2.78-3.26 (m, 2 H) | 481.1 $[M + H]^+$ | 100% |
| 1303 | ($CD_3OD$) δ 9.31 (d, 1 H), 8.48-8.87 (m, 3 H), 7.54-7.74 (m, 3.5 H), 6.92-7.06 (m, 1.5 H), 6.73-6.85 (m, 1 H), 5.12 (dd, 0.7 H), 4.95 (br dd, 0.3 H), 3.75-3.84 (m, 0.7 H), 3.43 (td, 0.3 H), 2.82-3.26 (m, 2 H) | 481.1 $[M + H]^+$ | 99.3% |
| 1304 | ($CD_3OD$) δ 8.61-8.72 (m, 2 H), 8.42-8.49 (m, 1 H), 7.71 (s, 1 H), 7.46-7.66 (m, 2 H), 6.94-7.03 (m, 2 H), 6.77-6.83 (m, 1 H), 5.12 (dd, 0.6 H), 4.95 (br dd, 0.4 H), 3.80 (td, 0.7 H), 3.42 (td, 0.3 H), 3.17-3.26 (m, 1 H), 2.81-3.05 (m, 4 H) | 495.1 $[M + H]^+$ | 100% |
| 1305 | ($CD_3OD$) δ 8.61-8.72 (m, 2 H), 8.41-8.49 (m, 1 H), 7.71 (s, 1 H), 7.45-7.66 (m, 2 H), 6.94-7.02 (m, 2 H), 6.78-6.83 (m, 1 H), 5.12 (br dd, 0.6 H), 4.92-4.97 (m, 0.4 H), 3.75-3.85 (m, 0.7 H), 3.42 (td, 0.3 H), 3.15-3.27 (m, 1 H), 2.82-3.06 (m, 4 H) | 495.1 $[M + H]^+$ | 99.6% |
| 1306 | ($CD_3OD$) δ 9.31 (s, 1 H), 8.75-8.90 (m, 1 H), 8.44-8.63 (m, 1 H), 7.50-7.73 (m, 3.5 H), 7.11-7.25 (m, 1 H), 6.98-7.06 (m, 1.5 H), 6.80 (s, 0.6 H), 6.65 (s, 0.4 H), 5.12 (dd, 0.6 H), 4.95 (br dd, 0.4 H), 3.87-4.00 (m, 0.6 H), 3.40 (td, 0.4 H), 2.97-3.25 (m, 1 H), 2.87 (dd, 1 H) | 447.2 $[M + H]^+$ | 100% |
| 1307 | ($CD_3OD$) δ 9.31 (br s, 1 H), 8.74-8.85 (m, 1 H), 8.55 (br d, 1 H), 7.47-7.73 (m, 3.5 H), 7.11-7.22 (m, 1 H), 6.95-7.07 (m, 1.5 H), 6.80 (s, 0.6 H), 6.64 (s, 0.4 H), 5.11 (br dd, 0.6 H), 4.95 (br dd, 0.4 H), 3.87-3.98 (m, 0.6 H), 3.40 (td, 0.4 H), 2.96-3.26 (m, 1 H), 2.87 (br dd, 1 H) | 447.1 $[M + H]^+$ | 95.4% |
| 1308 | ($CD_3OD$) δ 9.31 (br s, 1 H), 8.80 (br d, 1 H), 8.55 (br d, 1 H), 7.85 (d, 1 H), 7.67 (br d, 1 H), 7.39-7.53 (m, 1.4 H), 7.06-7.18 (m, 1 H), 7.03 (s, 0.6 H), 6.61-6.75 (m, 1.6 H), 6.50 (s, 0.4 H), 5.10 (br dd, 0.6 H), 4.95 (br d, 0.4 H), 3.87-3.99 (m, 0.6 H), 3.37-3.46 (m, 0.4 H), 2.83-3.26 (m, 2 H), 2.49-2.68 (m, 3 H) | 427.2 $[M + H]^+$ | 100% |
| 1309 | ($CD_3OD$) δ 9.31 (s, 1 H), 8.72-8.94 (m, 1 H), 8.54 (br d, 1 H), 7.62-7.81 (m, 2 H), 7.37-7.55 (m, 1.4 H), 7.05-7.17 (m, 1 H), 7.00 (s, 0.6 H), 6.59-6.76 (m, 1.6 H), 6.48 (s, 0.4 H), 5.08 (br dd, 0.5 H), 4.95 (br d, 0.5 H), 3.89-3.98 (m, 0.5 H), 3.41 (td, 0.5 H), 2.83-3.25 (m, 2 H), 2.48-2.70 (m, 3 H) | 427.2 $[M + H]^+$ | 96.9% |
| 1310 | ($CD_3OD$) δ 9.05 (d, 2 H), 8.21-8.40 (m, 1 H), 7.69-7.75 (m, 2 H), 6.76-7.05 (m, 3 H), 6.61-6.69 (m, 1 H), 4.98 (br d, 1 H), 3.79-3.86 (m, 0.5 H), 3.46-3.50 (m, 0.5 H), 2.85-3.21 (m, 2 H), 2.44-2.49 (m, 3 H) | 428.1 $[M + H]^+$ | 100% |
| 1311 | ($CD_3OD$) δ 9.00-9.10 (m, 2 H), 8.21-8.37 (m, 1 H), 7.67-7.75 (m, 2 H), 7.48 (s, 0.3 H), 6.76-7.03 (m, 2.7 H), 6.60-6.71 (m, 1 H), 4.97-5.01 (m, 1 H), 3.79-3.87 (m, 0.5 H), 3.46 (br d, 0.5 H), 2.84-3.26 (m, 2 H), 2.42-2.50 (m, 3 H) | 428.1 $[M + H]^+$ | 98.6% |
| 1312 | ($CD_3OD$) δ 9.03-9.07 (m, 2 H), 8.28-8.41 (m, 1 H), 7.66-7.75 (m, 2 H), 7.38-7.55 (m, 0.3 H), 6.73-7.07 (m, 3.7 H), 4.95-5.04 (m, 1 H), 3.81-3.86 (m, 0.6 H), 3.42-3.51 (m, 0.4 H), 2.83-3.24 (m, 2 H) | 432.2 $[M + H]^+$ | 100% |
| 1313 | ($CD_3OD$) δ 9.05 (d, 2 H), 8.27-8.41 (m, 1 H), 7.67-7.77 (m, 2 H), 7.47 (br s, 0.3 H), 6.78-7.03 (m, 3.7 H), 4.96-5.05 (m, 1 H), 3.79-3.87 (m, 0.6 H), 3.42-3.50 (m, 0.4 H), 2.85-3.27 (m, 2 H) | 432.2 $[M + H]^+$ | 99.6% |
| 1314 | ($CD_3OD$) δ 8.77 (d, 1 H), 8.50-8.64 (m, 1 H), 8.31 (d, 1 H), 8.02-8.16 (m, 1 H), 7.61-7.76 (m, 2 H), 7.52 (s, 0.2 H), 7.37-7.47 (m, 1 H), 6.75-7.17 (m, 3.8 H), 4.93-5.07 (m, 1 H), 3.72-3.86 (m, 0.5 H), 3.42 (td, 0.5 H), 2.80-3.27 (m, 2 H) | 463.2 $[M + H]^+$ | 100% |
| 1315 | ($CD_3OD$) δ 8.77 (d, 1 H), 8.49-8.64 (m, 1 H), 8.31 (d, 1 H), 8.08 (t, 1 H), 7.62-7.75 (m, 2 H), 7.52 (s, 0.2 H), 7.37-7.48 (m, 1 H), 6.77-7.15 (m, 3.8 H), 4.93-5.06 (m, 1 H), 3.71-3.85 (m, 0.5 H), 3.42 (td, 0.5 H), 2.81-3.26 (m, 2 H) | 463.2 $[M + H]^+$ | 99.1% |
| 1316 | ($CD_3OD$) δ 8.50-8.63 (m, 1 H), 8.36-8.45 (m, 1 H), 8.04-8.15 (m, 1 H), 7.70 (s, 1 H), 7.58 (s, 0.2 H), 7.37-7.49 (m, 1 H), 6.67-7.18 (m, 3.8 H), 5.09 (dd, 0.5 H), 4.93 (br d, 0.5 H), 4.00 (s, 3 H), 3.69-3.83 (m, 0.5 H), 3.35-3.45 (m, 0.5 H), 2.74-3.24 (m, 2 H) | 466.2 $[M + H]^+$ | 100% |
| 1317 | ($CD_3OD$) δ 8.51-8.62 (m, 1 H), 8.33-8.43 (m, 1 H), 8.02-8.17 (m, 1 H), 7.70 (s, 1 H), 7.58 (s, 0.2 H), 7.34-7.47 (m, 1 H), 6.70-7.17 (m, 3.8 H), 5.09 (dd, 0.5 H), 4.93 (br d, 0.5 H), 4.00 (s, 3 H), 3.69-3.82 (m, 0.5 H), 3.39 (td, 0.5 H), 2.79-3.23 (m, 2 H) | 466.2 $[M + H]^+$ | 100% |
| 1318 | ($CD_3OD$) δ 7.68 (d, 1 H), 7.35-7.52 (m, 1.5 H), 7.08-7.16 (m, 1 H), 6.95 (s, 0.5 H), 6.43-6.76 (m, 2 H), 4.93-5.03 (m, 1 H), 3.83-3.92 (m, 0.6 H), 3.36-3.42 (m, 0.4 H), 2.82-3.17 (m, 2 H), 2.61-2.69 (m, 3 H), 1.61 (s, 3 H), 1.38-1.44 (m, 2 H), 1.08-1.13 (m, 2 H) | 404.2 $[M + H]^+$ | 100% |
| 1319 | ($CD_3OD$) δ 7.71 (d, 1 H), 7.36 (dd, 1.5 H), 7.07-7.17 (m, 1 H), 6.96 (s, 0.5 H), 6.42-6.78 (m, 2 H), 4.99 (br dd, 1 H), 3.77-3.94 (m, 0.6 H), 3.40 (br d, 0.4 H), 2.81-3.14 (m, 2 H), 2.61-2.69 (m, 3 H), 1.61 (s, 3 H), 1.38-1.46 (m, 2 H), 1.08-1.14 (m, 2 H) | 404.2 $[M + H]^+$ | 99.6% |

TABLE 2-continued

| Ex. # | $^1H$ NMR (400 MHz unless otherwise noted) | LCMS: m/z | % ee |
|---|---|---|---|
| 1320 | ($CD_3OD$) δ 8.19-8.75 (m, 1 H), 7.71 (s, 1 H), 7.24-7.54 (m, 1.4 H), 6.83-6.96 (m, 1.6 H), 6.68-6.77 (m, 1 H), 5.01 (dd, 0.8 H), 4.87 (br s, 0.2 H), 3.35-3.80 (m, 1 H), 2.90-3.23 (m, 1 H), 2.83 (br d, 1 H), 1.54-1.68 (m, 3 H), 1.36-1.48 (m, 2 H), 1.06-1.16 (m, 2 H) | 424.2 $[M + H]^+$ | 100% |
| 1321 | ($CD_3OD$) δ 8.22-8.66 (m, 1 H), 7.71 (s, 1 H), 7.17-7.55 (m, 1.5 H), 6.81-6.98 (m, 1.5 H), 6.67-6.79 (m, 1 H), 5.01 (br dd, 0.8 H), 4.87 (br s, 0.2 H), 3.36-3.80 (m, 1 H), 2.91-3.23 (m, 1 H), 2.83 (br d, 1 H), 1.51-1.66 (m, 3 H), 1.36-1.49 (m, 2 H), 1.04-1.17 (m, 2 H) | 424.2 $[M + H]^+$ | 100% |
| 1322 | ($CD_3OD$) δ 8.09-8.55 (m, 1 H), 7.70 (s, 1 H), 7.37-7.52 (m, 0.3 H), 6.86-7.06 (m, 1.7 H), 6.76-6.84 (m, 1 H), 6.51-6.67 (m, 1 H), 4.98 (dd, 0.8 H), 4.85 (br d, 0.2 H), 3.36-3.84 (m, 1 H), 2.90-3.24 (m, 1 H), 2.73-2.89 (m, 1 H), 2.44-2.50 (m, 3 H), 1.61 (s, 3 H), 1.35-1.49 (m, 2 H), 1.04-1.18 (m, 2 H) | 404.2 $[M + H]^+$ | 100% |
| 1323 | ($CD_3OD$) δ 8.13-8.50 (m, 1 H), 7.70 (s, 1 H), 7.36-7.53 (m, 0.3 H), 6.86-7.10 (m, 1.7 H), 6.74-6.86 (m, 1 H), 6.50-6.68 (m, 1 H), 4.99 (br dd, 1 H), 3.40-3.80 (m, 1 H), 3.15 (br s, 1 H), 2.76-2.90 (m, 1 H), 2.44-2.50 (m, 3 H), 1.61 (s, 3 H), 1.37-1.49 (m, 2 H), 1.03-1.22 (m, 2 H) | 404.2 $[M + H]^+$ | 100% |
| 1324 | ($CD_3OD$) δ 8.44-8.80 (m, 1 H), 7.59-7.77 (m, 2 H), 7.42-7.48 (m, 0.3 H), 6.83-7.12 (m, 1.7 H), 6.73-6.82 (m, 1 H), 5.03 (br dd, 0.8 H), 4.88 (br s, 0.2 H), 3.37-3.80 (m, 1 H), 2.92-3.24 (m, 1 H), 2.83 (br d, 1 H), 1.57-1.65 (m, 3 H), 1.36-1.48 (m, 2 H), 1.03-1.21 (m, 2 H) | 458.2 $[M + H]^+$ | 100% |
| 1325 | ($CD_3OD$) δ 8.71 (br d, 1 H), 7.60-7.75 (m, 2 H), 7.45 (br d, 0.3 H), 6.84-7.10 (m, 1.7 H), 6.69-6.83 (m, 1 H), 5.03 (dd, 0.8 H), 4.86-4.89 (m, 0.2 H), 3.40-3.80 (m, 1 H), 3.15 (br d, 1 H), 2.83 (br d, 1 H), 1.57-1.65 (m, 3 H), 1.38-1.49 (m, 2 H), 1.07-1.15 (m, 2 H) | 458.2 $[M + H]^+$ | 100% |
| 1326 | ($CD_3OD$) δ 8.11-8.93 (m, 3 H), 7.96 (d, 1 H), 7.65 (s, 1 H), 7.43 (dd, 1 H), 6.29-7.25 (m, 5 H), 4.31-4.86 (m, 1 H), 3.95 (s, 3 H), 3.34-3.87 (m, 1 H), 2.98-3.14 (m, 1 H), 2.76 (br dd, 1 H) | 414.2 [M + H]+ | 100% |
| 1327 | ($CD_3OD$) δ 8.05-8.87 (m, 3 H), 7.97 (d, 1 H), 7.65 (s, 1 H), 7.39-7.48 (m, 1 H), 6.23-7.15 (m, 5 H), 4.60 (br s, 1 H), 3.95 (s, 3 H), 3.38-3.80 (m, 1 H), 3.00-3.12 (m, 1 H), 2.76 (br d, 1 H) | 414.2 [M + H]+ | 100% |
| 1328 | ($CD_3OD$) δ 8.61-8.66 (m, 1 H), 8.44 (dd, 1 H), 8.27-8.36 (m, 1 H), 7.70 (br s, 1 H), 7.44-7.57 (m, 1 H), 6.90-7.03 (m, 2 H), 6.73-6.86 (m, 2 H), 5.10 (br dd, 0.6 H), 4.94 (br d, 0.4 H), 3.74-3.84 (m, 0.6 H), 3.38-3.47 (m, 0.4 H), 2.84-3.25 (m, 5 H) | 445.2 $[M + H]^+$ | 100% |
| 1329 | ($CD_3OD$) δ 8.61-8.66 (m, 1 H), 8.44 (dd, 1 H), 8.27-8.36 (m, 1 H), 7.70 (br s, 1 H), 7.44-7.57 (m, 1 H), 6.90-7.03 (m, 2 H), 6.73-6.86 (m, 2 H), 5.10 (br dd, 0.6 H), 4.94 (br d, 0,4 H), 3.74-3.84 (m, 0.6 H), 3.38-3.47 (m, 0.4 H), 2.84-3.25 (m, 5 H) | 445.2 $[M + H]^+$ | 99.7% |
| 1330 | ($CD_3OD$) δ 8.64 (d, 1 H), 8.43-8.48 (m, 1 H), 8.24-8.33 (m, 1 H), 7.69 (s, 1 H), 7.46-7.54 (m, 1 H), 6.95-7.03 (m, 2 H), 6.73-6.81 (m, 1 H), 6.57-6.66 (m, 1 H), 5.07 (dd, 0.6 H), 4.90-4.94 (m, 0.4 H), 3.76-3.86 (m, 0.6 H), 3.40-3.49 (m, 0.4 H), 2.82-3.26 (m, 5 H), 2.41-2.47 (m, 3 H) | 441.2 $[M + H]^+$ | 100% |
| 1331 | ($CD_3OD$) δ 8.64 (br d, 1 H), 8.43-8.48 (m, 1 H), 8.24-8.32 (m, 1 H), 7.70 (s, 1 H), 7.46-7.53 (m, 1 H), 6.95-7.02 (m, 2 H), 6.74-6.82 (m, 1 H), 6.58-6.66 (m, 1 H), 5.08 (br dd, 0.7 H), 4.90-4.95 (m, 0.3 H), 3.77-3.86 (m, 0.6 H), 3.44 (td, 0.4 H), 2.80-3.26 (m, 5 H), 2.40-2.47 (m, 3 H) | 441.2 $[M + H]^+$ | 99.2% |
| 1332 | ($CD_3OD$) δ 9.36 (d, 1 H), 8.66-8.84 (m, 2 H), 8.24-8.43 (m, 1 H), 7.63 (br s, 1 H), 6.84-7.43 (m, 2 H), 6.62-6.82 (m, 2 H), 4.93 (br dd, 1 H), 3.30-3.79 (m, 1 H), 2.66-3.17 (m, 2 H) | 448.1 $[M + H]^+$ | 100% |
| 1333 | ($CD_3OD$) δ 9.36 (d, 1 H), 8.65-8.84 (m, 2 H), 8.21-8.42 (m, 1 H), 7.64 (br s, 1 H), 6.84-7.45 (m, 2 H), 6,60-6.83 (m, 2 H), 4.87-5.03 (m, 1 H), 3.31-3.77 (m, 1 H), 2.66-3.13 (m, 2 H) | 448.1 $[M + H]^+$ | 98.9% |
| 1334 | ($CD_3OD$) δ 8.63-8.67 (m, 1 H), 8.45-8.50 (m, 1 H), 7.47-7.72 (m, 3 H), 7.14-7.22 (m, 1 H), 6.96-7.08 (m, 2 H), 6.81 (s, 0.6 H), 6.66 (s, 0.4 H), 5.12 (dd, 0.5 H), 4.96 (br dd, 0.5 H), 3.88-3.99 (m, 0.6 H), 3.41 (td, 0.4 H), 2.83-3.26 (m, 5 H) | 461.1 $[M + H]^+$ | 100% |
| 1335 | ($CD_3OD$) δ 8.63-8.67 (m, 1 H), 8.47 (br d, 1 H), 7.48-7.73 (m, 3 H), 7.13-7.22 (m, 1 H), 6.95-7.08 (m, 2 H), 6.81 (s, 0.6 H), 6.66 (s, 0.4 H), 5.12 (br dd, 0.5 H), 4.93-4.99 (m, 0.5 H), 3.89-3.98 (m, 0.6 H), 3.36-3.45 (m, 0.4 H), 2.83-3.27 (m, 5 H) | 461.2 $[M + H]^+$ | 99.6% |
| 1336 | ($CD_3OD$) δ 9.03 (t, 2 H), 7.62-7.77 (m, 2 H), 7.37-7.54 (m, 1.5 H), 6.99-7.15 (m, 1.5 H), 6.39-6.76 (m, 2 H), 4.95 (br d, 1 H), 3.79-4.08 (m, 0.8 H), 3.36-3.42 (m, 0.2 H), 2.94-3.26 (m, 1 H), 2.78-2.92 (m, 1 H), 2.42-2.70 (m, 3 H) | 428.2 $[M + H]^+$ | 100% |
| 1337 | ($CD_3OD$) δ 9.03 (t, 2 H), 7.64-7.77 (m, 2 H), 7.36-7.55 (m, 1.5 H), 6.99-7.15 (m, 1.5 H), 6.42-6.74 (m, 2 H), 4.95 (br d, 1 H), 3.80-4.01 (m, 0.8 H), 3.37-3.43 (m, 0.2 H), 2.96-3.26 (m, 1 H), 2.82-2.92 (m, 1 H), 2.43-2.70 (m, 3 H) | 428.2 $[M + H]^+$ | 96.5% |

TABLE 2-continued

| Ex. # | $^1$H NMR (400 MHz unless otherwise noted) | LCMS: m/z | % ee |
|---|---|---|---|
| 1338 | ($CD_3OD$) δ 9.36 (dd, 1 H), 8.65-8.85 (m, 2 H), 7.60 (d, 1 H), 6.83-7.45 (m, 3 H), 6.29-6.70 (m, 2 H), 4.89 (td, 1 H), 3.74-3.92 (m, 0.5 H), 3.24-3.38 (m, 0.5 H), 2.84-3.16 (m, 1 H), 2.69-2.82 (m, 1 H), 2.32-2.66 (m, 3 H) | 428.1 $[M + H]^+$ | 100% |
| 1339 | ($CD_3OD$) δ 9.36 (dd, 1 H), 8.68-8.81 (m, 2 H), 7.59 (d, 1 H), 6.83-7.43 (m, 3 H), 6.32-6.66 (m, 2 H), 4.84-4.95 (m, 1 H), 3.77-3.93 (m, 0.5 H), 3.24-3.37 (m, 0.5 H), 2.83-3.18 (m, 1 H), 2.70-2.83 (m, 1 H), 2.34-2.64 (m, 3 H) | 428.1 $[M + H]^+$ | 98.4% |
| 1340 | ($CD_3OD$) δ 9.31 (s, 1 H), 8.74-8.89 (m, 1 H), 8.34-8.63 (m, 1 H), 7.78-7.92 (m, 1 H), 7.65-7.76 (m, 2 H), 7.56 (br s, 0.5 H), 7.19-7.42 (m, 2 H), 6.80-7.05 (m, 1 H), 6.65 (s, 0.5 H), 4.93-5.16 (m, 1 H), 3.57-4.07 (m, 1 H), 2.96-3.25 (m, 1 H), 2.84-2.92 (m, 1 H) | 481.1 $[M + H]^+$ | 100% |
| 1341 | ($CD_3OD$) δ 9.30 (s, 1 H), 8.73-8.95 (m, 1 H), 8.44-8.66 (m, 1 H), 7.78-7.94 (m, 1 H), 7.62-7.77 (m, 2 H), 7.56 (br s, 0.5 H), 7.18-7.39 (m, 2 H), 6.83-7.05 (m, 1 H), 6.65 (s, 0.5 H), 4.92-5.16 (m, 1 H), 3.98 (br t, 1 H), 2.96-3.24 (m, 1 H), 2.87 (br d, 1 H) | 481.1 $[M + H]^+$ | 97.5% |
| 1342 | ($CD_3OD$) δ 8.64 (td, 1 H), 8.42-8.49 (m, 1 H), 7.79-7.89 (m, 1 H), 7.67-7.75 (m, 1 H), 7.45-7.60 (m, 1.5 H), 7.21-7.39 (m, 2 H), 6.84-7.00 (m, 1 H), 6.66 (s, 0.5 H), 5.12 (dd, 0.5 H), 4.96 (br dd, 0.5 H), 3.94-4.03 (m, 0.5 H), 3.34 (br d, 0.5 H), 2.85-3.29 (m, 5 H) | 495.2 $[M + H]^+$ | 100% |
| 1343 | ($CD_3OD$) δ 8.64 (br t, 1 H), 8.46 (br t, 1 H), 7.80-7.90 (m, 1 H), 7.66-7.77 (m, 1 H), 7.46-7.60 (m, 1.5 H), 7.21-7.38 (m, 2 H), 6.86-7.01 (m, 1 H), 6.67 (s, 0.5 H), 5.12 (br dd, 0.4 H), 4.96 (br dd, 0.6 H), 3.93-4.03 (m, 0.5 H), 3.32-3.36 (m, 0.5 H), 2.85-3.29 (m, 5 H) | 495.2 $[M + H]^+$ | 99.8% |
| 1344 | ($CD_3OD$) δ 8.46 (dd, 1 H), 8.27 (d, 1 H), 7.81-7.94 (m, 1 H), 7.68-7.76 (m, 1 H), 7.63 (ddd, 1.5 H), 7.35-7.40 (m, 0.5 H), 7.23-7.33 (m, 1.5 H), 7.00 (br s, 0.5 H), 6.89 (s, 0.5 H), 6.69 (s, 0.5 H), 4.97-5.10 (m, 1 H), 4.01 (d, 3.5 H), 3.39 (br d, 0.5 H), 3.14-3.27 (m, 0.5 H), 2.96-3.07 (m, 0.5 H), 2.82-2.94 (m, 1 H) | 511.1 $[M + H]^+$ | 96.1% |
| 1345 | ($CD_3OD$) δ 8.45 (dd, 1 H), 8.26 (d, 1 H), 7.81-7.93 (m, 1 H), 7.68-7.76 (m, 1 H), 7.58-7.66 (m, 1.5 H), 7.35-7.40 (m, 0.5 H), 7.22-7.34 (m, 1.5 H), 7.00 (s, 0.5 H), 6.67-6.90 (m, 1 H), 4.96-5.10 (m, 1 H), 4.01 (d, 3.5 H), 3.37-3.45 (m, 0.5 H), 3.12-3.26 (m, 0.5 H), 2.95-3.10 (m, 0.5 H), 2.82-2.95 (m, 1 H) | 511.1 $[M + H]^+$ | 92.3% |
| 1346 | ($CD_3OD$) δ 9.30 (s, 1 H), 8.80 (d, 1 H), 8.32-8.61 (m, 2 H), 7.54-7.74 (m, 3.3 H), 7.13-7.27 (m, 1 H), 6.80-7.03 (m, 1.7 H), 6.54-6.71 (m, 1 H), 4.91-5.11 (m, 1 H), 3.37-3.85 (m, 1 H), 2.82-3.25 (m, 2 H) | 413.2 $[M + H]^+$ | 100% |
| 1347 | ($CD_3OD$) δ 9.30 (s, 1 H), 8.80 (dd, 1 H), 8.34-8.62 (m, 2 H), 7.54-7.72 (m, 3.3 H), 7.12-7.27 (m, 1 H), 6.78-7.03 (m, 1.7 H), 6.49-6.69 (m, 1 H), 5.06 (br dd, 0.5 H), 4.93 (br d, 0.5 H), 3.72-3.87 (m, 0.7 H), 3.43 (td, 0.3 H), 2.81-3.24 (m, 2 H) | 413.1 $[M + H]^+$ | 100% |
| 1348 | $^1$H NMR(METHANOL-$d_4$) δ 8.51-8.62 (m, 1 H), 7.94-8.03 (m, 1 H), 7.70 (s, 1 H), 7.58 (s, 0.2 H), 7.37-7.50 (m, 1 H), 6.71-7.16 (m, 3.8 H), 5.10 (br dd, 0.5 H), 4.93 (br d, 0.5 H), 3.88 (s, 3 H), 3.70-3.83 (m, 0.5 H), 3.37-3.42 (m, 0.5 H), 2.78-3.25 (m, 2 H), 2.61-2.71 (m, 3 H) | 480.2 $[M + H]^+$ | 100% |
| 1349 | ($CD_3OD$) δ 8.46-8.65 (m, 1 H), 7.92-8.07 (m, 1 H), 7.70 (s, 1 H), 7.58 (s, 0.2 H), 7.33-7.50 (m, 1 H), 6.66-7.15 (m, 3.8 H), 5.10 (br dd, 0.5 H), 4.93 (br d, 0.5 H), 3.88 (s, 3 H), 3.68-3.81 (m, 0.5 H), 3.37-3.45 (m, 0.5 H), 2.78-3.26 (m, 2 H), 2.60-2.76 (m, 3 H) | 480.2 $[M + H]^+$ | 100% |
| 1350 | ($CD_3OD$) δ 8.47-8.64 (m, 1 H), 7.70 (s, 1 H), 7.39-7.49 (m, 1.3H), 6.67-7.15 (m, 3.7 H), 4.92-5.00 (m, 1 H), 3.68-3.82 (m, 0.5 H), 3.34-3.43 (m, 0.5 H), 2.77-3.21 (m, 2 H), 1.79-1.97 (m, 6 H) | 446.2 $[M + H]^+$ | 96.2% |
| 1351 | ($CD_3OD$) δ 8.49-8.64 (m, 1 H), 7.70 (s, 1 H), 7.38-7.48 (m, 1.3 H), 6.67-7.15 (m, 3.7 H), 4.92-5.01 (m, 1 H), 3.67-3.83 (m, 0.5 H), 3.35-3.43 (m, 0.5 H), 2.80-3.20 (m, 2 H), 1.81-1.95 (m, 6 H) | 446.2 $[M + H]^+$ | 91.3% |
| 1352 | ($CD_3OD$) δ 8.43-8.63 (m, 1 H), 7.64-7.85 (m, 2 H), 7.36-7.59 (m, 1.3 H), 6.71-7.15 (m, 4.7 H), 4.92-5.09 (m, 1 H), 4.02 (s, 3 H), 3.67-3.86 (m, 0.5 H), 3.39 (td, 0.5 H), 2.76-3.26 (m, 2 H) | 466.2 $[M + H]^+$ | 100% |
| 1353 | ($CD_3OD$) δ 8.59 (br s, 1 H), 7.80 (br s, 2 H), 7.38-7.56 (m, 1 H), 6.74-7.14 (m, 5 H), 5.03 (br d, 1 H), 4.02 (d, 3 H), 3.77 (br t, 0.5 H), 3.39 (br s, 0.5 H), 2.79-3.25 (m, 2 H) | 466.2 $[M + H]^+$ | 100% |
| 1354 | ($CD_3OD$) δ 7.86 (dd, 1 H), 7.64-7.76 (m, 1 H), 7.52 (br s, 0.5 H), 7.25-7.41 (m, 2 H), 6.83-7.01 (m, 1 H), 6.66 (s, 0.5 H), 4.99-5.04 (m, 1 H), 3.59-4.01 (m, 1 H), 2.80-3.19 (m, 2 H), 1.61 (s, 3 H), 1.38-1.46 (m, 2 H), 1.06-1.16 (m, 2 H) | 458.1 $[M + H]^+$ | 100% |
| 1355 | ($CD_3OD$) δ 7.74 (dd, 1 H), 7.52-7.63 (m, 1 H), 7.41 (br s, 0.5 H), 7.11-7.27 (m, 2 H), 6.70-6.85 (m, 1 H), 6.53 (s, 0.5 H), 4.81-4.94 (m, 1 H), 3.24-3.88 (m, 1 H), 2.68-3.05 (m, 2 H), 1.48 (s, 3 H), 1.26-1.33 (m, 2 H), 0.95-1.03 (m, 2 H) | 458.2 $[M + H]^+$ | 98.8% |

TABLE 2-continued

| Ex. # | $^1$H NMR (400 MHz unless otherwise noted) | LCMS: m/z | % ee |
|---|---|---|---|
| 1356 | ($CD_3OD$) δ 8.61-8.66 (m, 1 H), 8.37-8.47 (m, 2 H), 7.71 (s, 1 H), 7.45-7.54 (m, 1.4 H), 7.25-7.32 (m, 1 H), 6.96 (s, 0.6 H), 6.72-6.87 (m, 2 H), 5.10 (dd, 0.6 H), 4.94 (br d, 0.4 H), 3.74-3.84 (m, 0.6 H), 3.43 (td, 0.3 H), 3.14-3.26 (m, 0.7 H), 2.92-3.06 (m, 3 H), 2.80-2.90 (m, 1 H) | 461.1 $[M + H]^+$ | 100% |
| 1357 | ($CD_3OD$) δ 8.64 (br d, 1 H), 8.37-8.47 (m, 2 H), 7.70 (br s, 1 H), 7.45-7.55 (m, 1 H), 7.26-7.32 (m, 1 H), 6.96 (br s, 1 H), 6.72-6.87 (m, 2 H), 5.10 (br dd, 0.6 H), 4.93 (br dd, 0.4 H), 3.75-3.84 (m, 0.6 H), 3.43 (td, 0.4 H), 2.80-3.26 (m, 5 H) | 461.1 $[M + H]^+$ | 99.7% |
| 1358 | ($CD_3OD$) δ 8.60-8.65 (m, 1 H), 8.38-8.45 (m, 1 H), 7.70 (d, 1 H), 7.39-7.51 (m, 2 H), 6.95-7.14 (m, 2 H), 6.60-6.72 (m, 1.6 H), 6.48 (s, 0.4 H), 5.08 (dd, 0.6 H), 4.94 (br s, 0.4 H), 3.88-3.98 (m, 0.6 H), 3.41 (td, 0.4 H), 3.13-3.24 (m, 0.5 H), 2.81-3.04 (m, 4.5 H), 2.65 (s, 1.8 H), 2.47 (s, 1.2 H) | 441.2 $[M + H]^+$ | 100% |
| 1359 | ($CD_3OD$) δ 8.63 (br d, 1 H), 8.43 (br s, 1 H), 7.73 (br s, 1 H), 7.39-7.52 (m, 2 H), 6.96-7.16 (m, 2 H), 6.60-6.75 (m, 1.6 H), 6.49 (s, 0.4 H), 5.09 (br dd, 1 H), 3.88-3.98 (m, 0.6 H), 3.41 (br t, 0.4 H), 3.14-3.25 (m, 0.6 H), 2.81-3.05 (m, 4.4 H), 2.66 (br s, 1.8 H), 2.48 (br s, 1.2 H) | 441.2 $[M + H]^+$ | 99.4% |
| 1360 | ($CD_3OD$) δ 9.35 (s, 1 H), 8.69-8.83 (m, 2 H), 7.69-7.83 (m, 1 H), 7.54-7.66 (m, 1 H), 7.23-7.50 (m, 1 H), 6.84-7.23 (m, 2 H), 6.54-6.81 (m, 1 H), 4.86-4.99 (m, 1 H), 3.82-3.95 (m, 0.5 H), 3.25-3.33 (m, 0.5 H), 2.85-3.16 (m, 1 H), 2.71-2.82 (m, 1 H) | 482.1 $[M + H]^+$ | 100% |
| 1361 | ($CD_3OD$) δ 9.35 (s, 1 H), 8.65-8.83 (m, 2 H), 7.67-7.86 (m, 1 H), 7.53-7.67 (m, 1 H), 7.24-7.51 (m, 1 H), 6.84-7.23 (m, 2 H), 6.49-6.84 (m, 1 H), 4.89-5.00 (m, 1 H), 3.82-3.95 (m, 0.5 H), 3.24-3.32 (m, 0.5 H), 2.86-3.15 (m, 1 H), 2.70-2.84 (m, 1 H) | 482.1 $[M + H]^+$ | 98.6% |
| 1362 | ($CD_3OD$) δ 9.30-9.42 (m, 1 H), 8.74 (br d, 2 H), 8.24-8.41 (m, 1 H), 7.60 (br s, 1 H), 6.83-7.54 (m, 3 H), 6.67-6.83 (m, 1 H), 6.46-6.61 (m, 1 H), 4.90 (br dd, 1 H), 3.62-3.76 (m, 0.5 H), 3.33 (td, 0.5 H), 2.84-3.17 (m, 1 H), 2.76 (br d, 1 H) | 414.2 $[M + H]^+$ | 100% |
| 1363 | ($CD_3OD$) δ 9.33-9.44 (m, 1 H), 8.71-8.80 (m, 2 H), 8.26-8.39 (m, 1 H), 7.60-7.73 (m, 1 H), 6,85-7.54 (m, 3 H), 6.68-6.82 (m, 1 H), 6.47-6.62 (m, 1 H), 4.91 (br dd, 1 H), 3.62-3.76 (m, 0.5 H), 3.26-3.39 (m, 0.5 H), 2.86-3.16 (m, 1 H), 2.69-2.83 (m, 1 H) | 414.2 $[M + H]^+$ | 100% |
| 1364 | ($CD_3OD$) δ 8.63 (br d, 1 H), 8.37-8.48 (m, 2 H), 7.70 (br s, 1 H), 7.45-7.61 (m, 2.4 H), 7.13-7.23 (m, 1 H), 6.96 (s, 0.6 H), 6.80-6.88 (m, 1 H), 6.57-6.65 (m, 1 H), 5.07 (br dd, 1 H), 3.75-3.84 (m, 0.7 H), 3.42 (td, 0.3 H), 3.15-3.24 (m, 0.6 H), 2.82-3.04 (m, 4.4 H) | 427.1 $[M + H]^+$ | 100% |
| 1365 | ($CD_3OD$) δ 8.64 (dd, 1 H), 8.38-8.48 (m, 2 H), 7.70 (br s, 1 H), 7.47-7.62 (m, 2.4 H), 7.15-7.23 (m, 1 H), 6.97 (s, 0.6 H), 6.81-6.89 (m, 1 H), 6.59-6.66 (m, 1 H), 5.07 (dd, 0.6 H), 4.93 (br d, 0.4 H), 3.75-3.85 (m, 0.7 H), 3.43 (td, 0.3 H), 3.15-3.25 (m, 0.7 H), 2.83-3.06 (m, 4.3 H) | 427.1 $[M + H]^+$ | 99.7% |
| 1366 | ($CD_3OD$) δ 7.88 (s, 1 H), 7.54-7.67 (m, 2 H), 7.24-7.49 (m, 1 H), 6.83-7.20 (m, 3 H), 6.48-6.69 (m, 1 H), 4.81-5.03 (m, 1 H), 3.78 (d, 3.6 H), 3.24-3.30 (m, 0.4 H), 2.69-3.09 (m, 2 H), 2.56 (d, 3 H) | 480.2 $[M + H]^+$ | 100% |
| 1367 | ($CD_3OD$) δ 7.87 (s, 1 H), 7.54-7.67 (m, 2 H), 7.24-7.48 (m, 1 H), 6.84-7.20 (m, 3 H), 6.51-6.68 (m, 1 H), 4.81-5.04 (m, 1 H), 3.78 (d, 3.6 H), 3.25-3.31 (m, 0.4 H), 2.70-3.12 (m, 2 H), 2.56 (d, 3 H) | 480.1 $[M + H]^+$ | 99.2% |
| 1368 | ($CD_3OD$) δ 8.43-8.57 (m, 1 H), 7.69 (s, 1 H), 7.29 (d, 1 H), 6.73-7.03 (m, 4 H), 6.28-6.64 (m, 1 H), 4.05-4.12 (m, 1 H), 3.95 (s, 3 H), 3.66-3.77 (m, 0.6 H), 3.20-3.28 (m, 0.3 H), 2.94-3.03 (m, 1 H), 2.72-2.82 (m, 1 H) | 432.1 $[M + H]^+$ | 100% |
| 1369 | ($CD_3OD$) δ 8.42-8.55 (m, 1 H), 7.69 (s, 1 H), 7.29 (d, 1 H), 6.73-7.05 (m, 4 H), 6.32-6.64 (m, 1 H), 4.04-4.14 (m, 1 H), 3.95 (s, 3 H), 3.72 (br t, 0.6 H), 3.25 (br t, 0.4 H), 2.93-3.04 (m, 1 H), 2.71-2.83 (m, 1 H) | 432.1 $[M + H]^+$ | 100% |
| 1370 | ($CD_3OD$) δ 8.68-8.83 (m, 1 H), 7.60-7.71 (m, 2 H), 6.74-7.06 (m, 4 H), 6.31-6.65 (m, 1 H), 4.06-4.13 (m, 1 H), 3.96 (s, 3 H), 3.67-3.76 (m, 0.6 H), 3.19-3.25 (m, 0.4 H), 2.93-3.05 (m, 1 H), 2.70-2.84 (m, 1 H) | 466.1 $[M + H]^+$ | 99.8% |
| 1371 | ($CD_3OD$) δ 8.67-8.82 (m, 1 H), 7.58-7.73 (m, 2 H), 6.72-7.05 (m, 4 H), 6.31-6.65 (m, 1 H), 4.09 (br d, 1 H), 3.96 (s, 3 H), 3.66-3.78 (m, 0.6 H), 3.25 (br d, 0.4 H), 2.99 (br t, 1 H), 2.72-2.85 (m, 1 H) | 466.2 $[M + H]^+$ | 99.4% |
| 1372 | ($CD_3OD$) δ 8.55-8.71 (m, 1 H), 7.69 (s, 1 H), 7.43 (br d, 1 H), 6.72-7.14 (m, 5 H), 6.32-6.66 (m, 1 H), 4.04-4.14 (m, 1 H), 3.95 (s, 3 H), 3.65-3.78 (m, 0.6 H), 3.17-3.27 (m, 0.4 H), 2.92-3.05 (m, 1 H), 2.70-2.83 (m, 1 H) | 448.2 $[M + H]^+$ | 99.7% |
| 1373 | ($CD_3OD$) δ 8.57-8.71 (m, 1 H), 7.69 (s, 1 H), 7.43 (br d, 1 H), 6.73-7.14 (m, 5 H), 6.31-6.63 (m, 1 H), 4.04-4.14 (m, 1 H), 3.95 (s, 3 H), 3.65-3.78 (m, 0.6 H), 3.20-3.27 (m, 0.4 H), 2.93-3.05 (m, 1 H), 2.77 (br t, 1 H) | 448.2 $[M + H]^+$ | 99.0% |

TABLE 2-continued

| Ex. # | $^1$H NMR (400 MHz unless otherwise noted) | LCMS: m/z | % ee |
|---|---|---|---|
| 1374 | ($CD_3OD$) δ 8.91 (br s, 1 H), 8.47-8.66 (m, 1 H), 8.34 (s, 1 H), 7.56-7.82 (m, 2 H), 7.37-7.52 (m, 1 H), 6.72-7.14 (m, 4 H), 5.08 (br dd, 1 H), 3.77 (br t, 0.5 H), 3.36-3.47 (m, 0.5 H), 2.76-3.25 (m, 2 H) | 502.2 $[M + H]^+$ | 100% |
| 1375 | ($CD_3OD$) δ 8.88-8.96 (m, 1 H), 8.51-8.63 (m, 1 H), 8.35 (s, 1 H), 7.55-7.84 (m, 2 H), 7.38-7.52 (m, 1 H), 6.74-7.16 (m, 4 H), 5.10 (br dd, 1 H), 3.71-3.88 (m, 0.5 H), 3.42 (td, 0.5 H), 2.79-3.26 (m, 2 H) | 502.2 $[M + H]^+$ | 100% |
| 1376 | ($CD_3OD$) δ 8.48-8.61 (m, 1 H), 8.33 (d, 1 H), 7.82 (s, 0.3 H), 7.64-7.76 (m, 1.5 H), 7.53 (d, 0.5 H), 7.38-7.47 (m, 1 H), 7.21 (d, 1 H), 6.75-7.13 (m, 3.7 H), 4.94-5.10 (m, 1 H), 3.73-3.83 (m, 0.5 H), 3.35-3.46 (m, 0.5 H), 2.80-3.26 (m, 2 H) | 502.2 $[M + H]^+$ | 100% |
| 1377 | ($CD_3OD$) δ 8.49-8.61 (m, 1 H), 8.33 (d, 1 H), 7.82 (s, 0.3 H), 7.69 (br d, 1.5 H), 7.53 (d, 0.5 H), 7.37-7.47 (m, 1 H), 7.21 (d, 1 H), 6.73-7.15 (m, 3.7 H), 4.92-5.11 (m, 1 H), 3.71-3.86 (m, 0.5 H), 3.35-3.50 (m, 0.5 H), 2.79-3.26 (m, 2 H) | 502.2 $[M + H]^+$ | 99.3% |
| 1378 | ($CD_3OD$) δ 8.29-8.39 (m, 1 H), 7.70 (s, 1 H), 7.45 (s, 0.3 H), 6.65-7.02 (m, 3.7 H), 5.01 (dd, 1 H), 3.74 (ddd, 0.7 H), 3.37-3.46 (m, 0.3 H), 2.80-3.18 (m, 2 H), 1.58-1.63 (m, 3 H), 1.39-1.47 (m, 2 H), 1.08-1.14 (m, 2 H) | 408.2 $[M + H]^+$ | 100% |
| 1379 | ($CD_3OD$) δ 8.30-8.39 (m, 1 H), 7.70 (s, 1 H), 7.45 (s, 0.3 H), 6.68-7.02 (m, 3.7 H), 5.01 (dd, 1 H), 3.64-3.81 (m, 0.7 H), 3.36-3.44 (m, 0.3 H), 2.79-3.18 (m, 2 H), 1.61 (s, 3 H), 1.39-1.47 (m, 2 H), 1.05-1.16 (m, 2 H) | 408.1 $[M + H]^+$ | 99.6% |
| 1380 | ($CD_3OD$) δ 9.03 (d, 2 H), 8.71 (d, 1 H), 7.44-7.74 (m, 3.5 H), 6.81-7.01 (m, 2.5 H), 4.92-5.04 (m, 1 H), 3.80 (ddd, 0.7 H), 3.44 (td, 0.3 H), 3.17-3.27 (m, 0.7 H), 3.00-3.07 (m, 0.3 H), 2.78-2.94 (m, 1 H) | 482.1 $[M + H]^+$ | 100% |
| 1381 | ($CD_3OD$) δ 9.03 (d, 2 H), 8.71 (d, 1 H), 7.43-7.79 (m, 3.5 H), 6.81-7.01 (m, 2.5 H), 4.92-5.06 (m, 1 H), 3.74-3.85 (m, 0.7 H), 3.41-3.49 (m, 0.3 H), 2.98-3.28 (m, 1 H), 2.86 (br d, 1 H) | 482.2 $[M + H]^+$ | 93.5% |
| 1382 | ($CD_3OD$) δ 8.37-8.52 (m, 1 H), 8.07-8.16 (m, 1 H), 7.95 (t, 1 H), 7.78-7.88 (m, 1 H), 6.98-7.68 (m, 4 H), 6.82-6.92 (m, 1 H), 6.60-6.74 (m, 1 H), 4.93-5.10 (m, 1 H), 3.75-3.87 (m, 0.5 H), 3.36-3.52 (m, 0.5 H), 2.98-3.29 (m, 1 H), 2.80-2.92 (m, 1 H), 2.66 (s, 3 H) | 427.2 $[M + H]^+$ | 100% |
| 1383 | ($CD_3OD$) δ 8.38-8.53 (m, 1 H), 8.04-8.16 (m, 1 H), 7.95 (t, 1 H), 7.72 (s, 1 H), 6.95-7.67 (m, 4 H), 6.80-6.96 (m, 1 H), 6.55-6.74 (m, 1 H), 5.02 (dd, 1 H), 3.74-3.92 (m, 0.5 H), 3.38-3.52 (m, 0.5 H), 2.93-3.29 (m, 1 H), 2.76-2.92 (m, 1 H), 2.66 (s, 3 H) | 427.2 $[M + H]^+$ | 100% |
| 1384 | ($CD_3OD$) δ 7.75-7.98 (m, 1 H), 7.62 (br s, 1 H), 6.97-7.39 (m, 3 H), 6.60-6.97 (m, 2 H), 6.33-6.53 (m, 1 H), 4.75 (s, 0.5 H), 4.08 (br s, 0.5 H), 4.02 (s, 3 H), 3.70-3.87 (m, 0.5 H), 3.15 (s, 0.5 H), 2.95-3.08 (m, 1 H), 2.81 (br d, 1 H) | 432.1 $[M + H]^+$ | 99.9% |
| 1385 | ($CD_3OD$) δ 7.70 (s, 1 H), 7.61 (br s, 1 H), 6.95-7.37 (m, 3 H), 6.61-6.95 (m, 2 H), 6.33-6.51 (m, 1 H), 4.85 (br d, 0.5 H), 4.06-4.12 (m, 0.5 H), 4.02 (br d, 3 H), 3.79 (br s, 0.5 H), 3.28 (br s, 0.5 H), 3.00 (br d, 1 H), 2.68-2.87 (m, 1 H) | 432.1 $[M + H]^+$ | 99.6% |
| 1386 | ($CD_3OD$) δ 7.87 (br d, 1 H), 7.71 (br d, 1 H), 6.95-7.53 (m, 3 H), 6.59-6.95 (m, 2 H), 6.29-6.59 (m, 1 H), 4.82 (br d, 0.5 H), 4.07 (br d, 0.5 H), 3.97 (br d, 3 H), 3.78 (br t, 0.5 H), 3.18-3.30 (m, 0.5 H), 3.01 (br d, 1 H), 2.67-2.88 (m, 1 H) | 466.1 $[M + H]^+$ | 99.6% |
| 1387 | ($CD_3OD$) δ 7.88 (br d, 1 H), 7.70 (br s, 1 H), 6.95-7.54 (m, 3 H), 6.59-6.95 (m, 2 H), 6.27-6.58 (m, 1 H), 4.83 (br d, 0.5 H), 4.07 (br d, 0.5 H), 3.97 (br d, 3 H), 3.70-3.86 (m, 0.5 H), 3.29 (br s, 0.5 H), 3.01 (br d, 1 H), 2.66-2.87 (m, 1 H) | 466.1 $[M + H]^+$ | 98.2% |
| 1388 | ($CD_3OD$) δ 7.68 (br d, 1 H), 6.97-7.57 (m, 3 H), 6.58-6.97 (m, 3 H), 6.28-6.44 (m, 1 H), 4.76-4.86 (m, 0.5 H), 4.06 (br d, 0.5 H), 3.97 (br d, 3 H), 3.81 (br t, 0.5 H), 3.37 (br s, 0.5 H), 3.00 (br d, 1 H), 2.82 (br s, 1 H), 2.63-2.77 (m, 3 H) | 412.2 $[M + H]^+$ | 96.9% |
| 1389 | ($CD_3OD$) δ 7.68 (br d, 1 H), 6.96-7.56 (m, 3 H), 6.58-6.96 (m, 3 H), 6.26-6.43 (m, 1 H), 4.82 (br d, 0.5 H), 4.06 (br d, 0.5 H), 3.97 (br d, 3 H), 3.74-3.88 (m, 0.5 H), 3.35-3.42 (m, 0.5 H), 3.00 (br d, 1 H), 2.82 (br s, 1 H), 2.63-2.79 (m, 3 H) | 412.2 $[M + H]^+$ | 99.6% |
| 1390 | ($CD_3OD$) δ 7.66-7.80 (m, 2 H), 7.38-7.60 (m, 1 H), 7.14-7.34 (m, 2.5 H), 6.93 (s, 0.5 H), 6.60-6.79 (m, 1 H), 5.01 (dd, 1 H), 3.81-3.93 (m, 0.6 H), 3.35-3.39 (m, 0.4 H), 2.80-3.17 (m, 2 H), 2.28-2.38 (m, 1 H), 1.26-1.32 (m, 2 H), 1.20-1.25 (m, 2 H) | 426.1 $[M + H]^+$ | 100% |
| 1391 | ($CD_3OD$) δ 7.66-7.80 (m, 2 H), 7.52 (s, 1 H), 7.13-7.37 (m, 2.5 H), 6.93 (s, 0.5 H), 6.61-6.78 (m, 1 H), 5.01 (dd, 1 H), 3.79-3.92 (m, 0,6 H), 3.35-3.40 (m, 0.4 H), 2.81-3.18 (m, 2 H), 2.28-2.38 (m, 1 H), 1.26-1.32 (m, 2 H), 1.23 (br dd, 2 H) | 426.2 $[M + H]^+$ | 92.9% |
| 1392 | ($CD_3OD$) δ 8.84-9.11 (m, 2 H), 7.47-7.73 (m, 3 H), 6.94-7.36 (m, 3 H), 6.59-6.88 (m, 1 H), 4.99 (ddd, 1 H), 3.88-3.99 (m, 0.5 H), 3.34-3.46 (m, 0.5 H), 2.82-3.27 (m, 2 H) | 448.1 $[M + H]^+$ | 100% |

TABLE 2-continued

| Ex. # | $^1$H NMR (400 MHz unless otherwise noted) | LCMS: m/z | % ee |
|---|---|---|---|
| 1393 | ($CD_3OD$) δ 9.03 (dd, 2 H), 7.52-7.76 (m, 3 H), 7.45-7.50 (m, 0.3 H), 6.96-7.21 (m, 2.7 H), 6.58-6.86 (m, 1 H), 4.94-5.05 (m, 1 H), 3.87-3.99 (m, 0.5 H), 3.34-3.44 (m, 0.5 H), 2.83-3.25 (m, 2 H) | 448.1 $[M + H]^+$ | 99.4% |
| 1394 | ($CD_3OD$) δ 8.51-8.68 (m, 2 H), 8.41-8.50 (m, 1 H), 7.70-7.77 (m, 1 H), 7.39-7.59 (m, 2.3 H), 6.77-7.16 (m, 3.7 H), 4.93-5.18 (m, 1 H), 3.72-3.86 (m, 0.5 H), 3.42 (td, 0.5 H), 3.18-3.26 (m, 0.5 H), 2.83-3.06 (m, 4.5 H) | 477.2 $[M + H]^+$ | 100% |
| 1395 | ($CD_3OD$) δ 8.51-8.70 (m, 2 H), 8.37-8.50 (m, 1 H), 7.74 (br s, 1 H), 7.37-7.59 (m, 2.5 H), 6.75-7.16 (m, 3.5 H), 4.93-5.17 (m, 1 H), 3.72-3.88 (m, 0.5 H), 3.37-3.51 (m, 0.5 H), 3.18-3.26 (m, 0.5 H), 2.82-3.06 (m, 4.5 H) | 477.2 $[M + H]^+$ | 99.5% |
| 1396 | ($CD_3OD$) δ 8.07-8.17 (m, 1 H), 7.95 (t, 1 H), 7.72 (d, 1 H), 7.58-7.69 (m, 1 H), 7.03-7.58 (m, 3 H), 6.96-7.03 (m, 1 H), 6.62-6.87 (m, 1 H), 4.93-5.12 (m, 1 H), 3.88-4.01 (m, 0.5 H), 3.41 (td, 0.5 H), 2.95-3.28 (m, 1 H), 2.79-2.94 (m, 1 H), 2.66 (s, 3 H) | 461.1 $[M + H]^+$ | 100% |
| 1397 | ($CD_3OD$) δ 8.08-8.19 (m, 1 H), 7.95 (td, 1 H), 7.72 (d, 1 H), 7.57-7.68 (m, 1 H), 7.04-7.57 (m, 3 H), 6.95-7.04 (m, 1 H), 6.60-6.88 (m, 1 H), 4.95-5.09 (m, 1 H), 3.88-4.01 (m, 0.5 H), 3.38-3.47 (m, 0.5 H), 2.96-3.30 (m, 1 H), 2.82-2.96 (m, 1 H), 2.66 (d, 3 H) | 461.1 $[M + H]^+$ | 98.3% |
| 1398 | ($CD_3OD$) δ 8.11 (dd, 1 H), 7.95 (td, 1 H), 7.71 (d, 1 H), 6.97-7.61 (m, 4 H), 6.65-6.77 (m, 1 H), 6.43-6.65 (m, 1 H), 4.94-5.09 (m, 1 H), 3.89-4.02 (m, 0.5 H), 3.36-3.44 (m, 0.5 H), 2.96-3.28 (m, 1 H), 2.80-2.96 (m, 1 H), 2.45-2.74 (m, 6 H) | 441.2 $[M + H]^+$ | 100% |
| 1399 | ($CD_3OD$) δ 8.11 (dd, 1 H), 7.95 (td, 1 H), 7.71 (d, 1 H), 6.98-7.58 (m, 4 H), 6.66-6.77 (m, 1 H), 6.44-6.66 (m, 1 H), 5.00 (td, 1 H), 3.88-4.02 (m, 0.5 H), 3.36-3.44 (m, 0.5 H), 2.94-3.26 (m, 1 H), 2.81-2.94 (m, 1 H), 2.45-2.76 (m, 6 H) | 441.2 $[M + H]^+$ | 99.6% |
| 1400 | ($CD_3OD$) δ 7.98 (d, 1 H), 7.68-7.88 (m, 2 H), 7.53-7.66 (m, 1 H), 7.22-7.51 (m, 2 H), 6.83-7.22 (m, 2 H), 6.53-6.81 (m, 1 H), 4.83-4.99 (m, 1 H), 3.82-3.94 (m, 0.5 H), 3.24-3.31 (m, 0.5 H), 2.84-3.16 (m, 1 H), 2.71-2.84 (m, 1 H), 2.54 (d, 3 H) | 495.1 $[M + H]^+$ | 100% |
| 1401 | ($CD_3OD$) δ 7.99 (d, 1 H), 7.67-7.88 (m, 2 H), 7.53-7.67 (m, 1 H), 7.23-7.51 (m, 2 H), 6.82-7.23 (m, 2 H), 6.52-6.82 (m, 1 H), 4.83-5.00 (m, 1 H), 3.87 (br t, 0.5 H), 3.24-3.32 (m, 0.5 H), 2.85-3.16 (m, 1 H), 2.68-2.85 (m, 1 H), 2.54 (d, 3 H) | 495.1 $[M + H]^+$ | 88.1% |
| 1402 | ($CD_3OD$) δ 7.76 (br d, 1 H), 7.69 (br d, 1 H), 7.29-7.63 (m, 2 H), 6.94-7.29 (m, 2 H), 6.61-6.94 (m, 2 H), 6.25-6.52 (m, 1 H), 4.83 (br s, 1 H), 4.07 (br d, 0.5 H), 3.96 (br d, 3 H), 3.69-3.86 (m, 0.5 H), 3.00 (br d, 1 H), 2.64-2.90 (m, 1 H) | 448.2 $[M + H]^+$ | 99.9% |
| 1403 | ($CD_3OD$) δ 7.76 (br d, 1 H), 7.70 (br d, 1 H), 7.29-7.59 (m, 2 H), 6.94-7.29 (m, 2 H), 6.61-6.94 (m, 2 H), 6.27-6.53 (m, 1 H), 4.83 (br s, 1 H), 4.07 (br d, 0.5 H), 3.96 (br d, 3 H), 3.78 (br t, 0.5 H), 3.00 (br d, 1 H), 2.69-2.87 (m, 1 H) | 448.2 $[M + H]^+$ | 98.2% |
| 1404 | ($CD_3OD$) δ 8.35 (d, 1 H), 7.43-7.88 (m, 3.5 H), 7.19-7.36 (m, 2 H), 6.99 (s, 0.5 H), 6.72-6.88 (m, 1 H), 6.60-6.71 (m, 1 H), 5.08 (br dd, 0.7 H), 4.96-4.98 (m, 0.3 H), 3.78-3.93 (m, 0.5 H), 3.40-3.53 (m, 0.5 H), 2.96-3.24 (m, 1 H), 2.87 (br d, 1 H) | 470.1 $[M + H]^+$ | 100% |
| 1405 | ($CD_3OD$) δ 8.36 (d, 1 H), 7.96-8.16 (m, 1 H), 7.43-7.89 (m, 2.5 H), 7.19-7.36 (m, 2 H), 7.06 (s, 0.5 H), 6.79-6.93 (m, 1 H), 6.58-6.75 (m, 1 H), 5.13 (br dd, 0.7 H), 4.95-4.97 (m, 0.3 H), 3.75-3.90 (m, 0.7 H), 3.41-3.54 (m, 0.3 H), 3.24 (br d, 0.8 H), 3.04 (br d, 0.2 H), 2.84-2.97 (m, 1 H) | 470.1 $[M + H]^+$ | 100% |
| 1406 | ($CD_3OD$) δ 8.40 (s, 1 H), 8.11 (s, 1 H), 7.66-7.80 (m, 2 H), 7.36-7.60 (m, 1 H), 6.97-7.34 (m, 3 H), 6.61-6.81 (m, 1 H), 4.95-5.15 (m, 1 H), 4.02 (d, 3 H), 3.82-3.97 (m, 0.6 H), 3.36-3.43 (m, 0.4 H), 2.83-3.24 (m, 2 H) | 466.2 $[M + H]^+$ | 100% |
| 1407 | ($CD_3OD$) δ 8.41 (s, 1 H), 8.11 (s, 1 H), 7.67-7.82 (m, 2 H), 7.36-7.61 (m, 1 H), 6.95-7.33 (m, 3 H), 6.61-6.83 (m, 1 H), 4.93-5.15 (m, 1 H), 4.02 (d, 3 H), 3.82-3.95 (m, 0.6 H), 3.36-3.44 (m, 0.4 H), 2.82-3.24 (m, 2 H) | 466.2 $[M + H]^+$ | 99.2% |
| 1408 | ($CD_3OD$) δ 8.45-8.65 (m, 1 H), 7.69 (s, 1 H), 7.43 (br t, 1.3 H), 6.65-7.17 (m, 3.7 H), 4.98 (br dd, 1 H), 3.63-3.83 (m, 0.5 H), 3.34-3.44 (m, 0.5 H), 2.73-3.22 (m, 2 H), 1.45-1.51 (m, 9 H) | 442.1 $[M + H]^+$ | 100 |
| 1409 | ($CD_3OD$) δ 8.43-8.68 (m, 1 H), 7.69 (s, 1 H), 7.43 (br t, 1.3 H), 6.70-7.14 (m, 3.7 H), 4.98 (br dd, 1 H), 3.63-3.81 (m, 0.5 H), 3.34-3.43 (m, 0.5 H), 2.73-3.22 (m, 2 H), 1.43-1.58 (m, 9 H) | 442.2 $[M + H]^+$ | 99.1% |
| 1410 | (DMSO-$d_6$) δ 9.02-9.18 (m, 2 H), 8.56-8.81 (m, 1 H), 8.23 (s, 0.3 H), 7.74-7.85 (m, 1 H), 7.63 (s, 1 H), 7.36-7.49 (m, 1 H), 6.68-6.94 (m, 2.7 H), 4.70-4.92 (m, 1 H), 3.60-3.81 (m, 0.6 H), 2.98-3.09 (m, 1 H), 2.62-2.92 (m, 1.4 H) | 448.1 $[M + H]^+$ | 100% |
| 1411 | (DMSO-$d_6$) δ 8.99-9.17 (m, 2 H), 8.61-8.72 (m, 0.8 H), 8.23 (s, 0.2 H), 7.36-7.87 (m, 3 H), 7.19 (br d, 0.3 H), 6.67-6.95 (m, 2.7 H), 4.85 (br dd, 1 H), 3.66-3.75 (m, 0.5 H), 2.97-3.10 (m, 1 H), 2.73-2.94 (m, 1.5 H) | 448.1 $[M + H]^+$ | 97.3% |
| 1412 | ($CD_3OD$) δ 9.02 (d, 2 H), 8.49-8.62 (m, 1 H), 7.65-7.77 (m, 2 H), 7.38-7.51 (m, 1.3 H), 7.08-7.15 (m, 0.2 H), 6.80-7.02 (m, 3.5 | 464.1 $[M + H]^+$ | 100% |

TABLE 2-continued

| Ex. # | $^{1}$H NMR (400 MHz unless otherwise noted) | LCMS: m/z | % ee |
|---|---|---|---|
| | H), 4.94-5.03 (m, 1 H), 3.79 (ddd, 0.5 H), 3.37-3.49 (m, 0.5 H), 2.83-3.25 (m, 2 H) | | |
| 1413 | ($CD_3OD$) δ 9.03 (d, 2 H), 8.51-8.62 (m, 1 H), 7.64-7.75 (m, 2 H), 7.39-7.49 (m, 1.3 H), 7.09-7.15 (m, 0.2 H), 6.81-7.00 (m, 3.5 H), 4.92-5.04 (m, 1 H), 3.73-3.87 (m, 0.5 H), 3.43 (td, 0.5 H), 2.83-3.26 (m, 2 H) | 464.2 $[M + H]^+$ | 95.7% |
| 1414 | ($CD_3OD$) δ 9.46 (s, 1 H), 8.80-8.89 (m, 2 H), 8.50-8.64 (m, 1 H), 7.71 (s, 1 H), 7.39-7.52 (m, 1.4 H), 7.09-7.14 (m, 0.2 H), 6.80-7.00 (m, 3.4 H), 4.94-5.10 (m, 1 H), 3.72-3.89 (m, 0.5 H), 3.43 (td, 0.5 H), 2.83-3.24 (m, 2 H) | 464.2 $[M + H]^+$ | 100% |
| 1415 | ($CD_3OD$) δ 9.41-9.53 (m, 1 H), 8.80-8.90 (m, 2 H), 8.50-8.66 (m, 1 H), 7.74 (br s, 1 H), 7.40-7.52 (m, 1.4 H), 7.09-7.14 (m, 0.2 H), 6.81-7.00 (m, 3.4 H), 5.03 (br dd, 1 H), 3.70-3.87 (m, 0.5 H), 3.37-3.50 (m, 0.5 H), 2.85-3.24 (m, 2 H) | 464.2 $[M + H]^+$ | 94.7% |
| 1416 | ($CD_3OD$) δ 9.27 (s, 1 H), 8.37-8.92 (m, 3 H), 7.88-8.11 (m, 4 H), 7.55-7.68 (m, 2 H), 7.12-7.43 (m, 2 H), 6.39-6.99 (m, 3 H), 4.49-4.75 (m, 1 H), 3.38-3.86 (m, 1 H), 3.01-3.14 (m, 1 H), 2.77 (br dd, 1 H) | 461.2 $[M + H]^+$ | 100% |
| 1417 | ($CD_3OD$) δ 9.20-9.35 (m, 1 H), 8.24-8.97 (m, 3 H), 7.86-8.13 (m, 4 H), 7.54-7.72 (m, 2 H), 7.33-7.44 (m, 1 H), 7.13-7.26 (m, 1 H), 6.35-7.03 (m, 3 H), 4.43-4.79 (m, 1 H), 3.38-3.97 (m, 1 H), 3.02-3.16 (m, 1 H), 2.78 (br d, 1 H) | 461.2 $[M + H]^+$ | 100% |
| 1418 | ($CD_3OD$) δ 7.67-7.80 (m, 2 H), 7.44 (d, 1 H), 6.94-7.32 (m, 3 H), 6.60-6.80 (m, 1 H), 4.93-5.03 (m, 1 H), 3.81-3.93 (m, 0.6 H), 3.36-3.42 (m, 0.4 H), 2.82-3.19 (m, 2 H), 1.49 (d, 9 H) | 442.2 $[M + H]^+$ | 100% |
| 1419 | ($CD_3OD$) δ 7.55-7.69 (m, 2 H), 7.29-7.47 (m, 1 H), 6.82-7.21 (m, 3 H), 6.48-6.69 (m, 1 H), 4.82-4.91 (m, 1 H), 3.69-3.83 (m, 0.6 H), 3.24-3.28 (m, 0.4 H), 2.70-3.07 (m, 2 H), 1.37 (d, 9 H) | 442.2 $[M + H]^+$ | 99.1% |
| 1420 | ($CD_3OD$) δ 8.61-8.71 (m, 1 H), 8.15-8.26 (m, 1 H), 7.98 (tt, 1 H), 7.53-7.67 (m, 3 H), 7.25-7.48 (m, 1 H), 6.87-7.21 (m, 3 H), 6.50-6.70 (m, 1 H), 4.83-4.95 (m, 1 H), 3.77-3.87 (m, 0.6 H), 3.24-3.30 (m, 0.4 H), 2.73-3.15 (m, 2 H) | 463.1 $[M + H]^+$ | 100% |
| 1421 | ($CD_3OD$) δ 8.61-8.75 (m, 1 H), 8.12-8.29 (m, 1 H), 7.98 (tt, 1 H), 7.53-7.69 (m, 3 H), 7.26-7.49 (m, 1 H), 6.87-7.21 (m, 3 H), 6.48-6.72 (m, 1 H), 4.81-4.93 (m, 1 H), 3.76-3.87 (m, 0.6 H), 3.24-3.30 (m, 0.4 H), 2.72-3.14 (m, 2 H) | 463.1 $[M + H]^+$ | 100% |
| 1422 | ($CD_3OD$) δ 9.32 (s, 1 H), 8.80 (br d, 1 H), 8.50-8.65 (m, 2 H), 7.64-7.77 (m, 2 H), 7.42-7.58 (m, 1.2 H), 6.91-7.17 (m, 2.6 H), 6.77-6.87 (m, 1.2 H), 5.10 (br d, 1 H), 3.79 (br t, 0.5 H), 3.42 (br s, 0.5 H), 2.78-3.23 (m, 2 H) | 463.2 $[M + H]^+$ | 100% |
| 1423 | ($CD_3OD$) δ 9.31 (br s, 1 H), 8.80 (br d, 1 H), 8.47-8.66 (m, 2 H), 7.64-7.76 (m, 2 H), 7.44 (br d, 1.2 H), 6.90-7.16 (m, 3.6 H), 6.76-6.87 (m, 1.2 H), 5.10 (br d, 1 H), 3.72-3.89 (m, 0.5 H), 3.43 (br s, 0.5 H), 2.81-3.24 (m, 2 H) | 463.2 $[M + H]^+$ | 97.7% |
| 1424 | ($CD_3OD$) δ 8.52-8.64 (m, 1 H), 8.45 (d, 1 H), 8.26 (d, 1 H), 7.73 (br s, 1 H), 7.62 (dd, 1 H), 7.40-7.57 (m, 1.3 H), 6.78-7.16 (m, 3.7 H), 4.95-5.10 (m, 1 H), 4.00 (s, 3 H), 3.72-3.87 (m, 0.5 H), 3.43 (td, 0.5 H), 2.75-3.28 (m, 2 H) | 493.1 $[M + H]^+$ | 100% |
| 1425 | ($CD_3OD$) δ 8.51-8.65 (m, 1 H), 8.44 (d, 1 H), 8.25 (d, 1 H), 7.73 (br s, 1 H), 7.52-7.64 (m, 1.3 H), 7.38-7.49 (m, 1 H), 6.78-7.16 (m, 3.7 H), 4.95-5.10 (m, 1 H), 4.00 (s, 3 H), 3.74-3.86 (m, 0.5 H), 3.39-3.48 (m, 0.5 H), 2.81-3.27 (m, 2 H) | 493.2 $[M + H]^+$ | 94.4% |
| 1426 | ($CD_3OD$) δ 8.40-8.63 (m, 2 H), 7.87 (t, 1 H), 7.58-7.75 (m, 2 H), 7.29-7.48 (m, 1.3 H), 6.68-7.14 (m, 3.7 H), 4.94 (br dd, 1 H), 3.68-3.81 (m, 0.5 H), 3.36-3.43 (m, 0.5 H), 2.77-3.22 (m, 2 H) | 481.1 $[M + H]^+$ | 100% |
| 1427 | ($CD_3OD$) δ 8.45-8.70 (m, 2 H), 7.93 (t, 1 H), 7.65-7.79 (m, 2 H), 7.36-7.51 (m, 1.3 H), 6.77-7.16 (m, 3.7 H), 4.94-5.04 (m, 1 H), 3.69-3.86 (m, 0.5 H), 3.42 (td, 0.5 H), 2.81-3.27 (m, 2 H) | 481.2 $[M + H]^+$ | 99.5% |
| 1428 | ($CD_3OD$) δ 8.23-8.38 (m, 1 H), 8.11 (br d, 1 H), 7.95 (br t, 1 H), 7.72 (s, 1 H), 7.54 (br d, 1.3 H), 6.94-7.08 (m, 1.7 H), 6.73-6.86 (m, 1 H), 6.54-6.72 (m, 1 H), 5.02 (br dd, 1 H), 3.82 (br t, 0.6 H), 3.39-3.51 (m, 0.4 H), 2.96-3.28 (m, 1 H), 2.87 (br d, 1 H), 2.66 (s, 3 H), 2.36-2.56 (m, 3 H) | 441.1 $[M + H]^+$ | 100% |
| 1429 | ($CD_3OD$) δ 8.24-8.37 (m, 1 H), 8.11 (br d, 1 H), 7.95 (t, 1 H), 7.73 (s, 1 H), 7.54 (d, 1.3 H), 6.95-7.05 (m, 1.7 H), 6.72-6.85 (m, 1 H), 6.57-6.70 (m, 1 H), 4.93-5.06 (m, 1 H), 3.78-3.87 (m, 0.6 H), 3.45 (td, 0.4H), 2.99-3.27 (m, 1 H), 2.81-2.94 (m, 1 H), 2.66 (s, 3 H), 2.40-2.52 (m, 3 H) | 441.2 $[M + H]^+$ | 99.3% |
| 1430 | ($CD_3OD$) δ 8.38-8.51 (m, 1 H), 8.11 (d, 1 H), 7.95 (t, 1 H), 7.75 (br s, 1 H), 7.54 (d, 1.3 H), 7.26-7.36 (m, 1 H), 7.00 (s, 0.7 H), 6.82-6.92 (m, 1 H), 6.71-6.82 (m, 1 H), 4.92-5.11 (m, 1 H), 3.75-3.87 (m, 0,6 H), 3.40-3.51 (m, 0.4 H), 2.98-3.28 (m, 1 H), 2.79-2.94 (m, 1 H), 2.66 (s, 3 H) | 461.1 $[M + H]^+$ | 100% |

TABLE 2-continued

| Ex. # | $^1$H NMR (400 MHz unless otherwise noted) | LCMS: m/z | % ee |
|---|---|---|---|
| 1431 | ($CD_3OD$) δ 8.27-8.42 (m, 1 H), 7.99 (d, 1 H), 7.83 (t, 1 H), 7.66 (br s, 1 H), 7.42 (d, 1.3 H), 7.13-7.27 (m, 1 H), 6.88 (s, 0.7 H), 6.70-6.81 (m, 1 H), 6.60-6.70 (m, 1 H), 4.82-4.98 (m, 1 H), 3.62-3.76 (m, 0.6 H), 3.27-3.40 (m, 0.4 H), 2.84-3.16 (m, 1 H), 2.68-2.84 (m, 1 H), 2.54 (s, 3 H) | 461.2 $[M + H]^+$ | 98.7% |
| 1432 | ($CD_3OD$) δ 8.51-8.65 (m, 1 H), 8.00 (d, 1 H), 7.77-7.89 (m, 1 H), 7.62 (s, 1 H), 7.47-7.58 (m, 1 H), 7.36-7.47 (m, 1.3 H), 6.80-6.95 (m, 1.7 H), 6.62-6.76 (m, 1 H), 4.83-4.99 (m, 1 H), 3.63-3.75 (m, 0.6 H), 3.26-3.40 (m, 0.4 H), 2.86-3.16 (m, 1 H), 2.70-2.82 (m, 1 H), 2.50-2.58 (m, 3 H) | 495.1 $[M + H]^+$ | 100% |
| 1433 | ($CD_3OD$) δ 8.52-8.66 (m, 1 H), 7.99 (d, 1 H), 7.77-7.90 (m, 1 H), 7.60-7.70 (m, 1 H), 7.49-7.57 (m, 1 H), 7.38-7.46 (m, 1.3 H), 6.81-6.96 (m, 1.7 H), 6.64-6.77 (m, 1 H), 4.82-4.99 (m, 1 H), 3.62-3.75 (m, 0.6 H), 3.27-3.40 (m, 0.4 H), 2.85-3.17 (m, 1 H), 2.69-2.82 (m, 1 H), 2.43-2.60 (m, 3 H) | 495.1 $[M + H]^+$ | 96.5% |
| 1434 | ($CD_3OD$) δ 8.98 (s, 1 H), 8.23-8.78 (m, 2 H), 7.83-8.04 (m, 2 H), 7.56-7.70 (m, 3 H), 7.16-7.22 (m, 1 H), 6.35-6.95 (m, 4 H), 4.46-4.73 (m, 1 H), 3.95 (s, 3 H), 3.46-3.77 (m, 1 H), 3.01-3.15 (m, 1 H), 2.70-2.80 (m, 1 H) | 464.2 $[M + H]^+$ | 100% |
| 1435 | ($CD_3OD$) δ 8.97 (s, 1 H), 8.27-8.77 (m, 2 H), 7.85-8.02 (m, 2 H), 7.55-7.70 (m, 3 H), 7.15-7.22 (m, 1 H), 6.39-7.02 (m, 4 H), 4.47-4.71 (m, 1 H), 3.95 (s, 3 H), 3.36-3.80 (m, 1 H), 3.00-3.14 (m, 1 H), 2.71-2.81 (m, 1 H) | 464.2 $[M + H]^+$ | 99.8% |
| 1436 | ($CD_3OD$) δ 7.66-7.81 (m, 2 H), 7.37-7.60 (m, 1 H), 6.95-7.32 (m, 3 H), 6.60-6.81 (m, 1 H), 4.94-5.02 (m, 1 H), 3.82-3.96 (m, 0.6 H), 3.35-3.40 (m, 0.4 H), 2.82-3.20 (m, 2 H), 1.86-1.97 (m, 6 H) | 446.1 $[M + H]^+$ | 99.9% |
| 1437 | ($CD_3OD$) δ 7.56-7.69 (m, 2 H), 7.26-7.49 (m, 1 H), 6.83-7.20 (m, 3 H), 6.48-6.68 (m, 1 H), 4.82-4.90 (m, 1 H), 3.72-3.84 (m, 0.6 H), 3.23-3.27 (m, 0.4 H), 2.70-3.08 (m, 2 H), 1.75-1.83 (m, 6 H) | 446.1 $[M + H]^+$ | 99.4% |
| 1438 | ($CD_3OD$) δ 7.83 (dd, 1 H), 7.69-7.80 (m, 2 H), 7.38-7.61 (m, 1 H), 6.98-7.34 (m, 4 H), 6.61-6.80 (m, 1 H), 4.95-5.09 (m, 1 H), 4.05 (d, 3 H), 3.91 (ddd, 0.6 H), 3.36-3.41 (m, 0.4 H), 2.83-3.24 (m, 2 H) | 466.1 $[M + H]^+$ | 98.9% |
| 1439 | ($CD_3OD$) δ 7.71 (dd, 1 H), 7.56-7.68 (m, 2 H), 7.26-7.48 (m, 1 H), 6.84-7.22 (m, 4 H), 6.48-6.70 (m, 1 H), 4.83-4.96 (m, 1 H), 3.93 (d, 3 H), 3.79 (ddd, 0.6 H), 3.23-3.30 (m, 0.4 H), 2.71-3.13 (m, 2 H) | 466.1 $[M + H]^+$ | 100% |
| 1440 | ($CD_3OD$) δ 8.93 (d, 1 H), 8.36 (s, 1 H), 7.66-7.82 (m, 3 H), 7.45-7.58 (m, 1 H), 7.16-7.34 (m, 2.5 H), 6.98 (s, 0.5 H), 6.61-6.83 (m, 1 H), 4.96-5.14 (m, 1 H), 3.86-3.98 (m, 0.6 H), 3.36-3.43 (m, 0.4 H), 2.84-3.21 (m, 2 H) | 502.1 $[M + H]^+$ | 100% |
| 1441 | ($CD_3OD$) δ 8.93 (d, 1 H), 8.36 (s, 1 H), 7.66-7.83 (m, 3 H), 7.44-7.58 (m, 1 H), 7.16-7.34 (m, 2.5 H), 6.98 (s, 0.5 H), 6.63-6.80 (m, 1 H), 4,95-5.13 (m, 1 H), 3.86-3.99 (m, 0.6 H), 3.37-3.43 (m, 0.4 H), 2.84-3.22 (m, 2 H) | 502.1 $[M + H]^+$ | 99.6% |
| 1442 | ($CD_3OD$) δ 8.21 (dd, 1 H), 7.53-7.73 (m, 3 H), 7.29-7.45 (m, 1 H), 6.98-7.20 (m, 3.5 H), 6.85 (s, 0.5 H), 6.45-6.67 (m, 1 H), 4.83-4.98 (m, 1 H), 3.74-3.85 (m, 0.6 H), 3.22-3.28 (m, 0.4 H), 2.71-3.11 (m, 2 H) | 502.2 $[M + H]^+$ | 100% |
| 1443 | ($CD_3OD$) δ 8.23 (dd, 1 H), 7.54-7.73 (m, 3 H), 7.30-7.47 (m, 1 H), 7.02-7.20 (m, 3.5 H), 6.86 (s, 0.5 H), 6.49-6.69 (m, 1 H), 4.83-4.97 (m, 1 H), 3.73-3.86 (m, 0.6 H), 3.24-3.29 (m, 0,4 H), 2.72-3.12 (m, 2 H) | 502.1 $[M + H]^+$ | 99.9% |
| 1444 | ($CD_3OD$) δ 9.14 (d, 1 H), 8.47 (s, 1 H), 7.71 (br d, 1 H), 7.50-7.67 (m, 1.5 H), 7.13-7.27 (m, 1 H), 6.94-7.10 (m, 1.5 H), 6.59-6.86 (m, 1 H), 5.11 (br dd, 1 H), 3.83-4.02 (m, 0.5 H), 3.36-3.48 (m, 0.5 H), 2.80-3.25 (m, 2 H) | 504.1 $[M + H]^+$ | 100% |
| 1445 | ($CD_3OD$) δ 9.02 (d, 1 H), 8.36 (s, 1 H), 7.60 (br d, 1 H), 7.36-7.55 (m, 1.5 H), 7.01-7.13 (m, 1 H), 6.84-6.99 (m, 1.5 H), 6.48-6.79 (m, 1 H), 4.99 (br dd, 1 H), 3.74-3.86 (m, 0.5 H), 3.25-3.36 (m, 0.5 H), 2.66-3.15 (m, 2 H) | 504.1 $[M + H]^+$ | 99.6% |
| 1446 | ($CD_3OD$) δ 9.15 (d, 1 H), 8.48 (s, 1 H), 7.72 (d, 1 H), 7.40-7.54 (m, 1.5 H), 7.13 (ddd, 1 H), 7.00 (s, 0.5 H), 6.72 (dd, 1 H), 6.45-6.65 (m, 1 H), 5.07 (dd, 1 H), 3.87-4.01 (m, 0.5 H), 3.36-3.47 (m, 0.5 H), 2.82-3.25 (m, 2 H), 2.51-2.73 (m, 3 H) | 484.1 $[M + H]^+$ | 100% |
| 1447 | ($CD_3OD$) δ 9.15 (d, 1 H), 8.48 (s, 1 H), 7.71 (d, 1 H), 7.40-7.56 (m, 1.5 H), 7.07-7.21 (m, 1 H), 7.00 (s, 0.5 H), 6.66-6.78 (m, 1 H), 6.43-6.65 (m, 1 H), 5.07 (br dd, 1 H), 3.84-4.04 (m, 0.5 H), 3.39-3.47 (m, 0.5 H), 2.80-3.26 (m, 2 H), 2.50-2.74 (m, 3 H) | 484.1 $[M + H]^+$ | 99.7% |
| 1448 | ($CD_3OD$) δ 8.38-8.50 (m, 1 H), 7.70 (s, 1 H), 7.56-7.64 (m, 1 H), 7.41-7.52 (m, 0.3 H), 7.13-7.28 (m, 1 H), 6.92-6.99 (m,0.7 H), 6.79-6.91 (m, 1 H), 6.46-6.71 (m, 1 H), 4.93-5.04 (m, 1 H), 3.65-3.84 (m, 0.7 H), 3.34-3.43 (m, 1 H), 3.28-3.31 (m, 0.3 H), 2.92-3.22 (m, 1 H), 2.83 (br dd, 1 H), 1.45 (d, 6 H) | 378.2 $[M + H]^+$ | 100% |

TABLE 2-continued

| Ex. # | $^1$H NMR (400 MHz unless otherwise noted) | LCMS: m/z | % ee |
|---|---|---|---|
| 1449 | ($CD_3OD$) δ 8.33-8.52 (m, 1 H), 7.71 (s, 1 H), 7.55-7.64 (m, 1 H), 7.45-7.49 (m, 0.3 H), 7.14-7.25 (m, 1 H), 6.92-6.97 (m, 0.7 H), 6.83-6.90 (m, 1 H), 6.53-6.65 (m, 1 H), 4.91 - 5.02 (m, 1 H), 3.75 (ddd, 0.7 H), 3.34-3.44 (m, 1 H), 3.29-3.31 (m, 0.3 H) , 2.90-3.24 (m, 1 H), 2.83 (br dd, 1 H), 1.45 (d, 6 H) | 378.2 $[M + H]^+$ | 100% |
| 1450 | ($CD_3OD$) δ 8.24-8.37 (m, 1 H), 7.68-7.75 (m, 1 H), 7.46 (s, 0.3 H), 6.97-7.03 (m, 1 H), 6.95 (s, 0.7H), 6.76-6.82 (m, 1 H), 6.53-6.66 (m, 1 H), 4.97 (br dd, 1 H), 3.70-3.80 (m, 1 H), 3.34-3.44 (m, 1 H), 2.93-3.21 (m, 1 H), 2.83 (br dd, 1 H), 2.38-2.49 (m, 3 H), 1.45 (d, 6 H) | 392.2 $[M + H]^+$ | 100% |
| 1451 | ($CD_3OD$) δ 8.23-8.37 (m, 1 H), 7.70 (s, 1 H), 7.40-7.50 (m, 0.3 H), 6.97-7.03 (m, 1 H), 6.95 (s, 0.7 H), 6.75-6.83 (m, 1 H), 6.52-6.67 (m, 1 H), 4.97 (br dd, 1 H), 3.68-3.82 (m, 0.7 H), 3.34-3.44 (m, 1 H), 3.29-3.32 (m, 0.3 H), 2.93-3.21 (m, 1 H), 2.77-2.88 (m, 1 H), 2.37-2.50 (m, 3 H), 1.45 (d, 6 H) | 392.2 $[M + H]^+$ | 99.3% |
| 1452 | ($CD_3OD$) δ 8.27-8.43 (m, 1 H), 7.71 (s, 1 H), 7.37 (br d, 0.3 H), 6.90-7.04 (m, 1.7 H), 6.80-6.89 (m, 1 H), 6.68-6.79 (m, 1 H), 5.00 (dd, 1 H), 3.69-3.80 (m, 0.7 H), 3.34-3.44 (m, 1 H), 3.30 (br d, 0.3 H), 2.94-3.22 (m, 1 H), 2.84 (br dd, 1 H), 1.45 (d, 6 H) | 396.2 $[M + H]^+$ | 100% |
| 1453 | ($CD_3OD$) δ 8.26-8.43 (m, 1 H), 7.71 (s, 1 H), 7.36-7.54 (m, 0.3 H), 6.59-7.09 (m, 3.7 H), 4.92-5.04 (m, 1 H), 3.68-3.81 (m, 0.7 H), 3.34-3.45 (m, 1 H), 3.25-3.30 (m, 0.3 H), 2.92-3.23 (m, 1 H), 2.84 (br dd, 1 H), 1.45 (d, 6 H) | 396.1 $[M + H]^+$ | 99.5% |
| 1454 | ($CD_3OD$) δ 8.45 (d, 1 H), 7.68 (s, 1 H), 7.30 (d, 1 H), 6.85 (t, 1 H), 6.65 (s, 1 H), 6.27 (s, 1 H), 4.21 (dd, 1 H), 3.62-3.77 (m, 1 H), 2.95-3.08 (m, 1 H), 2.79 (br dd, 1 H), 2.04-2.13 (m, 1 H), 1.04-1.15 (m, 4 H) | 382.1 $[M + H]^+$ | 100% |
| 1455 | ($CD_3OD$) δ 8.45 (d, 1 H), 7.68 (s, 1 H), 7.31 (d, 1 H), 6.86 (t, 1 H), 6.65 (s, 1 H), 6.27 (br s, 1 H), 4.21 (dd, 1 H), 3.61-3.74 (m, 1 H), 2.97-3.11 (m, 1 H), 2.80 (br dd, 1 H), 1.98-2.16 (m, 1 H), 1.03-1.14 (m, 4 H) | 382.1 $[M + H]^+$ | 99.5% |
| 1456 | (DMSO-$d_6$) δ 12.02-12.24 (m, 1 H), 8.00 (d, 1 H), 7.47-7.71 (m, 2 H), 7.17-7.42 (m, 1.4 H), 6.94-7.02 (m, 1 H), 6.66-6.93 (m, 2.6 H), 4.77-4.96 (m, 1 H), 4.00 (s, 3 H), 3.60-3.86 (m, 0.8 H), 3.37 (br s, 0.2 H), 2.85-3.10 (m, 1 H), 2.69-2.84 (m, 1 H) | 434.2 $[M + H]^+$ | 92.8% |
| 1457 | (DMSO-$d_6$) δ 12.09 (br s, 1 H), 8.00 (d, 1 H), 7.48-7.70 (m, 2 H), 7.19-7.42 (m, 1.4 H), 6.94-7.01 (m, 1 H), 6.70-6.94 (m, 2.6 H), 4.72-4.96 (m, 1 H), 4.00 (s, 3 H), 3.64-3.84 (m, 0.7 H), 3.35-3.40 (m, 0.3 H), 2.84-3.11 (m, 1 H), 2.70-2.84 (m, 1 H) | 434.2 $[M + H]^+$ | 97.8% |
| 1458 | (DMSO-$d_6$) δ 11.87-12.43 (m, 1 H), 8.70 (br d, 1 H), 8.10 (br t, 1 H), 7.83 (dt, 1 H), 7.49-7.67 (m, 2 H), 7.29 (br d, 1 H), 7.15 (br s, 0.3 H), 6.69-6.96 (m, 2.7 H), 4.83 (br dd, 1 H), 3.76 (br s, 0.7 H), 3.36-3.46 (m, 0.3 H), 2.69-3.13 (m, 2 H) | 449.2 $[M + H]^+$ | 100% |
| 1459 | (DMSO-$d_6$) δ 11.96-12.28 (m, 1 H), 8.70 (br d, 1 H), 8.11 (br t, 1 H), 7.83 (dt, 1 H), 7.47-7.69 (m, 2 H), 7.21-7.39 (m, 1 H), 7.14 (s, 0.3 H), 6.69-6.99 (m, 2.7 H), 4.83 (br dd, 1 H), 3.62-3.86 (m, 0.7 H), 3.36-3.44 (m, 0.3 H), 2.71-3.13 (m, 2 H) | 449.1 $[M + H]^+$ | 100% |
| 1460 | (DMSO-$d_6$) δ 12.11 (br s, 1 H), 9.32-9.65 (m, 1 H), 8.83-9.01 (m, 2 H), 7.50-7.72 (m, 2 H), 7.21-7.39 (m, 1 H), 7.12 (s, 0.3 H), 6.68-7.00 (m, 2.7 H), 4.83 (br dd, 1 H), 3.64-3.87 (m, 0.7 H), 3.40 (br t, 0.3 H), 2.72-3.13 (m, 2 H) | 432.1 $[M + H]^+$ | 100% |
| 1461 | (DMSO-$d_6$) δ 12.05-12.26 (m, 1 H), 9.18-9.73 (m, 1 H), 8.94 (br d, 2 H), 7.49-7.70 (m, 2 H), 7.22-7.39 (m, 1 H), 7.12 (s, 0.3 H), 6.71-6.97 (m, 2.7 H), 4.83 (br d, 1 H), 3.78 (br t, 0.7 H), 3.40 (br s, 0.3 H), 2.71-3.15 (m, 2 H) | 432.1 $[M + H]^+$ | 100% |
| 1462 | ($CD_3OD$) δ 7.92-8.21 (m, 1 H), 7.71 (d, 1 H), 7.59 (s, 0.3 H), 7.37-7.53 (m, 1 H), 7.16-7.33 (m, 1 H), 6.98 (s, 0.7 H), 6.55-6.87 (m, 2 H), 5.13 (br dd, 1 H), 3.91 (s, 3 H), 3.41-3.85 (m, 1 H), 2.95-3.26 (m, 1 H), 2.79-2.93 (m, 1 H), 2.64-2.74 (m, 3 H) | 448.1 $[M + H]^+$ | 100% |
| 1463 | ($CD_3OD$) δ 7.91-8.13 (m, 1 H), 7.71 (d, 1 H), 7.59 (s, 0.4 H), 7.42-7.54 (m, 1 H), 7.15-7.37 (m, 1 H), 6.98 (s, 0.6 H), 6.50-6.89 (m, 2 H), 5.07-5.17 (m, 1 H), 3.91 (s, 3 H), 3.45-3.85 (m, 1 H), 2.98-3.23 (m, 1 H), 2.80-2.92 (m, 1 H), 2.66-2.74 (m, 3 H) | 448.1 $[M + H]^+$ | 96.8% |
| 1464 | ($CD_3OD$) δ 8.41-8.63 (m, 1 H), 8.05 (d, 1 H), 7.65-7.96 (m, 2 H), 7.34-7.60 (m, 2.3 H), 6.73-7.15 (m, 3.7 H), 5.03 (br dd, 1 H), 3.71-3.86 (m, 0.5 H), 3.35-3.46 (m, 0.5 H), 2.79-3.24 (m, 2 H), 2.62 (s, 3 H) | 477.2 $[M + H]^+$ | 100% |
| 1465 | ($CD_3OD$) δ 8.49-8.63 (m, 1 H), 8.09 (d, 1 H), 7.80-7.99 (m, 2 H), 7.38-7.60 (m, 2.3 H), 6.74-7.17 (m, 3.7 H), 4.95-5.11 (m, 1 H), 3.78 (ddd, 0.5 H), 3.41 (td, 0.5 H), 2.80-3.27 (m, 2 H), 2.64 (s, 3 H) | 477.1 $[M + H]^+$ | 98.5% |
| 1466 | ($CD_3OD$) δ 8.49-8.63 (m, 1 H), 8.18-8.35 (m, 1 H), 7.39-7.73 (m, 2.3 H), 6.75-7.13 (m, 3.7 H), 5.09 (dd, 1 H), 3.91 (s, 3 H), 3.70-3.81 (m, 0.5 H), 3.39 (td, 0.5 H), 2.79-3.24 (m, 2 H), 2.47-2.60 (m, 3 H) | 480.2 $[M + H]^+$ | 100% |
| 1467 | ($CD_3OD$) δ 8.49-8.63 (m, 1 H), 8.20-8.32 (m, 1 H), 7.35-7.75 (m, 2.3 H), 6.76-7.14 (m, 3.7 H), 5.09 (br dd, 1 H), 3.91 (s, 3 H), | 480.2 $[M + H]^+$ | 99.8% |

TABLE 2-continued

| Ex. # | $^1$H NMR (400 MHz unless otherwise noted) | LCMS: m/z | % ee |
|---|---|---|---|
| | 3.70-3.81 (m, 0.5 H), 3.39 (td, 0.5 H), 2.80-3.24 (m, 2 H), 2.43-2.61 (m, 3 H) | | |
| 1468 | ($CD_3OD$) δ 9.32 (s, 1 H), 8.82 (dd, 1 H), 8.56 (ddt, 1 H), 7.65-7.81 (m, 3 H), 6.99-7.61 (m, 4 H), 6.62-6.84 (m, 1 H), 4.96-5.16 (m, 1 H), 3.88-4.00 (m, 0.6 H), 3.36-3.44 (m, 0.4 H), 2.84-3.26 (m, 2 H) | 463.2 $[M + H]^+$ | 100% |
| 1469 | ($CD_3OD$) δ 9.32 (s, 1 H), 8.76-8.86 (m, 1 H), 8.56 (ddt, 1 H), 7.65-7.80 (m, 3 H), 6.99-7.59 (m, 4 H), 6.62-6.83 (m, 1 H), 4.95-5.14 (m, 1 H), 3.89-3.99 (m, 0.6 H), 3.36-3.44 (m, 0.4 H), 2.85-3.27 (m, 2 H) | 463.1 $[M + H]^+$ | 99.6% |
| 1470 | ($CD_3OD$) δ 8.27-8.44 (m, 1 H), 8.10-8.18 (m, 1 H), 7.96 (t, 1 H), 7.75 (br s, 1 H), 7.54 (d, 1.3 H), 6.90-7.08 (m, 1.7 H), 6.74-6.89 (m, 2 H), 5.05 (br dd, 1 H), 3.75-3.87 (m, 0.5 H), 3.39-3.53 (m, 0.5 H), 2.82-3.29 (m, 2 H), 2.67 (s, 3 H) | 445.2 $[M + H]^+$ | 99.3% |
| 1471 | ($CD_3OD$) δ 8.17-8.29 (m, 1 H), 7.97-8.03 (m, 1 H), 7.84 (t, 1 H), 7.67 (br d, 1 H), 7.42 (d, 1.3 H), 6.81-6.92 (m, 1.7 H), 6.66-6.79 (m, 2 H), 4.94 (br dd, 1 H), 3.64-3.74 (m, 0.5 H), 3.26-3.39 (m, 0.5 H), 2.70-3.17 (m, 2 H), 2.54 (s, 3 H) | 445.1 $[M + H]^+$ | 88.9% |
| 1472 | ($CD_3OD$) δ 9.02 (s, 1 H), 8.35 (s, 1 H), 8.11-8.26 (m, 1 H), 7.34-7.84 (m, 1.3 H), 6.88 (br t, 1.7 H), 6.68 (br s, 1 H), 6.40-6.59 (m, 1 H), 4.94 (br dd, 1 H), 3.68 (br t, 0.7 H), 3.31 (br t, 0.3 H), 2.67-3.16 (m, 2 H), 2.26-2.41 (m, 3 H) | 484.1 $[M + H]^+$ | 100% |
| 1473 | ($CD_3OD$) δ 9.02 (s, 1 H), 8.35 (s, 1 H), 8.11-8.23 (m, 1 H), 7.43-7.64 (m, 1.3 H), 6.82-6.91 (m, 1.7 H), 6.61-6.71 (m, 1 H), 6.42-6.57 (m, 1 H), 4.94 (br dd, 1 H), 3.60-3.75 (m, 0.7 H), 3.25-3.35 (m, 0.3 H), 2.67-3.14 (m, 2 H), 2.26-2.39 (m, 3 H) | 484.1 $[M + H]^+$ | 99.6% |
| 1474 | ($CD_3OD$) δ 8.52 (d, 1 H), 7.71 (s, 1 H), 7.41-7.59 (m, 1.4 H), 7.18-7.32 (m, 2 H), 6.99 (s, 0.6 H), 6.72-6.87 (m, 1 H), 6.61-6.71 (m, 1 H), 5.08 (br dd, 1 H), 3.79-3.94 (m, 0.6 H), 3.40-3.51 (m, 0.4 H), 3.14-3.24 (m, 0.7 H), 3.03 (br t, 0.3 H), 2.87 (br d, 1 H) | 488.1 $[M + H]^+$ | 100% |
| 1475 | ($CD_3OD$) δ 8.52 (d, 1 H), 7.72 (br s, 1 H), 7.42-7.59 (m, 1.3 H), 7.19-7.34 (m, 2 H), 6.99 (s, 0.7 H), 6.72-6.88 (m, 1 H), 6.56-6.71 (m, 1 H), 5.08 (br dd, 0.6 H), 4.97 (br d, 0.4 H), 3.80-3.91 (m, 0.6 H), 3.40-3.54 (m, 0.4 H), 3.13-3.28 (m, 0.8 H), 2.98-3.09 (m, 0.2 H), 2.87 (br d, 1 H) | 488.1 $[M + H]^+$ | 100% |
| 1476 | ($CD_3OD$) δ 8.35-8.54 (m, 2 H), 7.49-7.75 (m, 1 H), 7.25-7.34 (m, 2 H), 6.70-7.00 (m, 3 H), 4.94-5.09 (m, 1 H), 3.73-3.84 (m, 0.6 H), 3.41 (br dd, 0.4 H), 3.15-3.26 (m, 0.7 H), 3.00 (br d, 0.3 H), 2.80-2.90 (m, 1 H) | 504.1 $[M + H]^+$ | 100% |
| 1477 | ($CD_3OD$) δ 8.37-8.53 (m, 2 H), 7.49-7.73 (m, 1 H), 7.25-7.32 (m, 2 H), 6.71-6.98 (m, 3 H), 4.92-5.09 (m, 1 H), 3.72-3.84 (m, 0.7 H), 3.41 (td, 0.3 H), 3.14-3.25 (m, 0.7 H), 2.95-3.07 (m, 0.3 H), 2.81-2.89 (m, 1 H) | 504.1 $[M + H]^+$ | 88.6% |
| 1478 | ($CD_3OD$) δ 8.49 (d, 1 H), 8.23-8.33 (m, 1 H), 7.50-7.75 (m, 1 H), 7.26 (d, 1 H), 6.94-7.01 (m, 2 H), 6.73-6.81 (m, 1 H), 6.58-6.67 (m, 1 H), 4.91-5.06 (m, 1 H), 3.74-3.84 (m, 0.7 H), 3.43 (td, 0.3 H), 3.14-3.25 (m, 0.7 H), 2.96-3.06 (m, 0.3 H), 2.78-2.89 (m, 1 H), 2.39-2.48 (m, 3 H) | 484.2 $[M + H]^+$ | 100% |
| 1479 | ($CD_3OD$) δ 8.50 (d, 1 H), 8.22-8.33 (m, 1 H), 7.53-7.90 (m, 1 H), 7.26 (d, 1 H), 6.94-7.03 (m, 2 H), 6.74-6.82 (m, 1 H), 6.59-6.68 (m, 1 H), 4.91-5.09 (m, 1 H), 3.72-3.84 (m, 0.7 H), 3.43 (td, 0.3 H), 3.16-3.26 (m, 0.7 H), 2.97-3.08 (m, 0.3 H), 2.87 (br dd, 1 H), 2.38-2.48 (m, 3 H) | 484.1 $[M + H]^+$ | 87.8% |
| 1480 | ($CD_3OD$) δ 8.48-8.63 (m, 2 H), 7.70 (s, 1.3 H), 7.44 (br d, 1 H), 7.08-7.30 (m, 1.2 H), 6.73-7.01 (m, 3.5 H), 4.93-5.09 (m, 1 H), 3.71-3.87 (m, 0.7 H), 3.36-3.44 (m, 0.3 H), 3.15-3.26 (m, 0.7 H), 2.97-3.06 (m, 0.3 H), 2.79-2.90 (m, 1 H) | 520.2 $[M + H]^+$ | 100% |
| 1481 | ($CD_3OD$) δ 8.47-8.64 (m, 2 H), 7.53-7.73 (m, 1.3 H), 7.44 (br d, 1 H), 7.09-7.29 (m, 1.2 H), 6.74-7.01 (m, 3.5 H), 4.93-5.10 (m, 1 H), 3.73-3.83 (m, 0.7 H), 3.40 (td, 0.3 H), 3.16-3.25 (m, 0.7 H), 3.01 (br s, 0.3 H), 2.81-2.90 (m, 1 H) | 520.2 $[M + H]^+$ | 89.6% |
| 1482 | ($CD_3OD$) δ 8.49 (d, 1 H), 8.26-8.38 (m, 1 H), 7.46-7.73 (m, 1.3 H), 7.27 (d, 1 H), 6.72-7.01 (m, 3.7 H), 4.92-5.08 (m, 1 H), 3.79 (ddd, 0.7 H), 3.43 (td, 0.3 H), 3.12-3.24 (m, 0.7 H), 2.95-3.06 (m, 0.3 H), 2.79-2.90 (m, 1 H) | 488.2 $[M + H]^+$ | 87.1% |
| 1483 | ($CD_3OD$) δ 8.49 (d, 1 H), 8.27-8.37 (m, 1 H), 7.49-7.71 (m, 1.3 H), 7.26 (d, 1 H), 6.73-7.00 (m, 3.7 H), 4.92-5.08 (m, 1 H), 3.79 (ddd, 0.7 H), 3.43 (td, 0.3 H), 3.12-3.24 (m, 0.7 H), 2.95-3.07 (m, 0.3 H), 2.78-2.90 (m, 1 H) | 488.2 $[M + H]^+$ | 90.0% |
| 1484 | ($CD_3OD$) δ 8.37-8.53 (m, 1 H), 7.71 (s, 1 H), 7.45 (s, 0.3 H), 7.28-7.35 (m, 1 H), 6.94 (s, 0.7 H), 6.81-6.90 (m, 1 H), 6.64-6.79 (m, 1 H), 5.00 (br dd, 1 H), 3.67-3.81 (m, 0.7 H), 3.34-3.45 (m, 1.3 H), 2.93-3.21 (m, 1 H), 2.84 (br dd, 1 H), 1.46 (d, 6 H) | 412.1 $[M + H]^+$ | 100% |
| 1485 | ($CD_3OD$) δ 8.39-8.50 (m, 1 H), 7.71 (s, 1 H), 7.45 (s, 0.3 H), 7.27-7.36 (m, 1 H), 6.94 (s, 0.7 H), 6.83-6.91 (m, 1 H), 6.64-6.79 (m, 1 H), 5.00 (br dd, 1 H), 3.64-3.85 (m, 0.7 H), 3.34-3.45 (m, 1.3 H), 2.92-3.22 (m, 1 H), 2.84 (br dd, 1 H), 1.46 (d, 6 H) | 412.1 $[M + H]^+$ | 96.2% |

TABLE 2-continued

| Ex. # | $^1$H NMR (400 MHz unless otherwise noted) | LCMS: m/z | % ee |
|---|---|---|---|
| 1486 | ($CD_3OD$) δ 8.62-8.75 (m, 1 H), 7.60-7.76 (m, 2 H), 7.41 (s, 0.3 H), 6.89-7.07 (m, 1.7 H), 6.70-6.84 (m, 1 H), 4.95-5.07 (m, 1 H), 3.69-3.79 (m, 1 H), 3.35-3.45 (m, 1 H), 2.91-3.25 (m, 1 H), 2.84 (br d, 1 H), 1.38-1.51 (m, 6 H) | 446.2 $[M + H]^+$ | 100% |
| 1487 | ($CD_3OD$) δ 8.62-8.78 (m, 1 H), 7.60 (s, 2 H), 7.40-7.51 (m, 0.3 H), 6.90-7.06 (m, 1.7 H), 6.69-6.85 (m, 1 H), 4.93-5.06 (m, 1 H), 3.84 (br d, 1 H), 3.35-3.46 (m, 1 H), 2.91-3.24 (m, 1 H), 2.84 (br dd, 1 H), 1.36-1.51 (m, 6 H) | 446.2 $[M + H]^+$ | 99.8% |
| 1488 | ($CD_3OD$) δ 7.70 (d, 1 H), 7.54-7.66 (m, 1 H), 7.38-7.51 (m, 0.4 H), 7.14-7.24 (m, 1 H), 7.01-7.09 (m, 1 H), 6.96 (br s, 0.6 H), 6.79 (s, 0.6 H), 6.65 (s, 0.4 H), 4.92-5.05 (m, 1 H), 3.80-3.97 (m, 0.6 H), 3.34-3.44 (m, 1.4 H), 2.91-3.23 (m, 1 H), 2.74-2.90 (m, 1 H), 1.45 (d, 6 H) | 412.1 $[M + H]^+$ | 100% |
| 1489 | ($CD_3OD$) δ 7.80 (d, 1 H), 7.56-7.68 (m, 1 H), 7.49 (s, 0.4 H), 7.14-7.24 (m, 1 H), 7.02-7.09 (m, 1 H), 6.98 (s, 0.6 H), 6.80 (s, 0.6 H), 6.67 (s, 0.4 H), 4.93-5.06 (m, 1 H), 3.78-3.94 (m, 0.7 H), 3.34-3.44 (m, 1.3 H), 2.91-3.24 (m, 1 H), 2.86 (dd, 1 H), 1.45 (d, 6 H) | 412.1 $[M + H]^+$ | 99.7% |
| 1490 | ($CD_3OD$) δ 7.69 (d, 1 H), 7.37-7.52 (m, 1.4 H), 7.08-7.18 (m, 1 H), 6.97 (br s, 0.6 H), 6.68-6.77 (m, 1 H), 6.41-6.63 (m, 1 H), 4.92-5.01 (m, 1 H), 3.82-3.95 (m, 0.7 H), 3.34-3.42 (m, 1.3 H), 2.92-3.21 (m, 1 H), 2.84 (br d, 1 H), 2.55-2.73 (m, 3 H), 1.45 (d, 6 H) | 392.2 $[M + H]^+$ | 100% |
| 1491 | ($CD_3OD$) δ 7.70 (d, 1 H), 7.37-7.54 (m, 1.4 H), 7.07-7.19 (m, 1 H), 6.97 (s, 0.6 H), 6.68-6.78 (m, 1 H), 6.41-6.65 (m, 1 H), 4.92-5.01 (m, 1 H), 3.81-3.96 (m, 0.7 H), 3.34-3.43 (m, 1.3 H), 2.91-3.20 (m, 1 H), 2.78-2.90 (m, 1 H), 2.56-2.72 (m, 3 H), 1.45 (d, 6 H) | 392.2 $[M + H]^+$ | 99.2% |
| 1492 | ($CD_3OD$) δ 7.65-7.80 (m, 2 H), 7.58 (s, 0.2 H), 7.40-7.50 (m, 1 H), 7.25-7.32 (m, 1.3 H), 7.14-7.24 (m, 1 H), 6.95 (s, 0.5 H), 6.58-6.81 (m, 1 H), 4.92-5.03 (m, 1 H), 3.79-3.95 (m, 0.6 H), 3.34-3.40 (m, 1.4 H), 2.92-3.21 (m, 1 H), 2.84 (br d, 1 H), 1.45 (d, 6 H) | 428.2 $[M + H]^+$ | 100% |
| 1493 | ($CD_3OD$) δ 7.64-7.81 (m, 2 H), 7.58 (s, 0.2 H), 7.39-7.48 (m, 1.3 H), 7.24-7.35 (m, 1 H), 7.12-7.23 (m, 1 H), 6.95 (s, 0.5 H), 6.54-6.80 (m, 1 H), 4.92-5.05 (m, 1 H), 3.77-3.96 (m, 0.6 H), 3.34-3.41 (m, 1.4 H), 2.91-3.22 (m, 1 H), 2.75-2.89 (m, 1 H), 1.45 (d, 6 H) | 428.2 $[M + H]^+$ | 94.2% |
| 1494 | (DMSO-$d_6$) δ 11.64-12.72 (m, 1 H), 8.50-9.07 (m, 1 H), 8.17-8.49 (m, 1 H), 7.61-7.74 (m, 1 H), 7.45-7.61 (m, 2 H), 7.21-7.36 (m, 1 H), 6.52-7.19 (m, 3 H), 4.74-4.96 (m, 1 H), 3.69-3.83 (m, 1 H), 2.97-3.10 (m, 2 H), 2.82-2,90 (m, 3 H), 2.75-2.80 (m, 1 H) | 445.1 $[M + H]^+$ | 100% |
| 1495 | (DMSO-$d_6$) δ 11.80-12.36 (m, 1 H), 8.70 (br s, 1 H), 8.14-8.47 (m, 1 H), 7.41-7.73 (m, 3 H), 7.19-7.37 (m, 1 H), 7.10 (s, 1 H), 6,64-6.95 (m, 3 H), 4,67-4.95 (m, 1 H), 3.58-3.94 (m, 1 H), 2.98-3.14 (m, 1 H), 2.82-2.90 (m, 3 H), 2.69-2.80 (m, 1 H) | 445.1 $[M + H]^+$ | 98.2% |
| 1496 | ($CD_3OD$) δ 8.03-8.27 (m, 1 H), 7.95 (t, 1 H), 7.71 (s, 1 H), 7.32-7.63 (m, 2.3 H), 7.20-7.31 (m, 1 H), 7.00 (s, 0.7 H), 6.71-6.87 (m, 1 H), 6.56-6.71 (m, 1 H), 5.01-5.13 (m, 1 H), 3.79-3.93 (m, 0.7 H), 3.48 (br dd, 0.3 H), 2.98-3.25 (m, 1 H), 2.88 (br dd, 1 H), 2.66 (s, 3 H) | 445.1 $[M + H]^+$ | 100% |
| 1497 | ($CD_3OD$) δ 8.06-8.31 (m, 1 H), 7.96 (t, 1 H), 7.71 (s, 1 H), 7.35-7.64 (m, 2.4 H), 7.18-7.34 (m, 1 H), 7.00 (s, 0.6 H), 6.50-6.91 (m, 2 H), 4.97-5.09 (m, 1 H), 3.43-3.91 (m, 1 H), 2.97-3.25 (m, 1 H), 2.88 (br dd, 1 H), 2.66 (s, 3 H) | 445.2 $[M + H]^+$ | 91.5% |
| 1498 | ($CD_3OD$) δ 9.04 (dd, 2 H), 7.68-7.77 (m, 3 H), 6.97-7.45 (m, 4 H), 6.60-6.80 (m, 1 H), 4.96-5.04 (m, 1 H), 3.88-3.99 (m, 0.6 H), 3.34-3.39 (m, 0.4 H), 2.84-3.23 (m, 2 H) | 464.2 $[M + H]^+$ | 100% |
| 1499 | ($CD_3OD$) δ 9.05 (dd, 2 H), 7.68-7.80 (m, 3 H), 6.98-7.47 (m, 4 H), 6.59-6.82 (m, 1 H), 4.96-5.04 (m, 1 H), 3.87-4.00 (m, 0.6 H), 3.35-3.40 (m, 0.4 H), 2.84-3.27 (m, 2 H) | 464.2 $[M + H]^+$ | 99.7% |
| 1500 | ($CD_3OD$) δ 8.64-8.69 (m, 1 H), 8.47 (d, 1 H), 7.68-7.81 (m, 2 H), 7.35-7.61 (m, 2 H), 6.96-7.32 (m, 3 H), 6.64-6.83 (m, 1 H), 4.96-5.16 (m, 1 H), 3.89-4.01 (m, 0.5 H), 3.36-3.45 (m, 0.5 H), 2.86-3.27 (m, 5 H) | 477.1 $[M + H]^+$ | 100% |
| 1501 | ($CD_3OD$) δ 8.63-8.68 (m, 1 H), 8.47 (br d, 1 H), 7.68-7.81 (m, 2 H), 7.35-7.61 (m, 2 H), 6.97-7.33 (m, 3 H), 6.62-6.85 (m, 1 H), 4.98-5.17 (m, 1 H), 3.88-4.00 (m, 0.5 H), 3.37-3.46 (m, 0.5 H), 2.85-3.26 (m, 5 H) | 477.2 $[M + H]^+$ | 99.4% |
| 1502 | ($CD_3OD$) δ 9.03 (s, 1 H), 8.36 (s, 1 H), 7.58-7.79 (m, 2 H), 7.24-7.51 (m, 1 H), 6.83-7.24 (m, 3 H), 6.49-6.73 (m, 1 H), 4.84-5.05 (m, 1 H), 3.72-3.87 (m, 0.5 H), 3.25-3.32 (m, 0.5 H), 2.84-3.14 (m, 1 H), 2.72-2.84 (m, 1 H) | 520.1 $[M + H]^+$ | 100% |
| 1503 | ($CD_3OD$) δ 9.03 (s, 1 H), 8.36 (s, 1 H), 7.55-7.74 (m, 2 H), 7.31-7.50 (m, 1 H), 6.83-7.28 (m, 3 H), 6.49-6.71 (m, 1 H), 4.85-4.98 (m, 1 H), 3.75-3.85 (m, 0.5 H), 3.24-3.31 (m, 0.5 H), 2.85-3.13 (m, 1 H), 2.69-2.85 (m, 1 H) | 520.1 $[M + H]^+$ | 97.1% |

TABLE 2-continued

| Ex. # | $^1$H NMR (400 MHz unless otherwise noted) | LCMS: m/z | % ee |
|---|---|---|---|
| 1504 | ($CD_3OD$) δ 8.98-9.09 (m, 1 H), 8.25-8.42 (m, 2 H), 7.60 (s, 1 H), 7.45 (s, 0.3 H), 7.14-7.26 (m, 1 H), 6.85 (s, 0.7 H), 6.70-6.81 (m, 1 H), 6.59-6.69 (m, 1 H), 4.83-5.03 (m, 1 H), 3.67 (ddd, 0.7 H), 3.30 (td, 0.3 H), 2.83-3.14 (m, 1 H), 2.66-2.81 (m, 1 H) | 504.1 $[M + H]^+$ | 100% |
| 1505 | ($CD_3OD$) δ 9.09-9.19 (m, 1 H), 8.37-8.51 (m, 2 H), 7.72 (s, 1 H), 7.57 (br s, 0.3 H), 7.26-7.37 (m, 1 H), 6.97 (br s, 0.7 H), 6.81-6.91 (m, 1 H), 6.71-6.80 (m, 1 H), 4.94-5.13 (m, 1 H), 3.73-3.85 (m, 0.7 H), 3.42 (td, 0.3 H), 2.94-3.28 (m, 1 H), 2.77-2.94 (m, 1 H) | 504.1 $[M + H]^+$ | 99.5% |
| 1506 | ($CD_3OD$) δ 8.52 (d, 1 H), 8.38-8.50 (m, 1 H), 7.71 (s, 1 H), 7.48-7.67 (m, 1.3 H), 7.14-7.33 (m, 2 H), 6.93-7.05 (m, 0.7 H), 6.78-6.92 (m, 1 H), 6.57-6.70 (m, 1 H), 4.94-5.09 (m, 1 H), 3.66-3.91 (m, 0.7 H), 3.42-3.54 (m, 0.3 H), 2.94-3.27 (m, 1 H), 2.74-2.91 (m, 1 H) | 470.1 $[M + H]^+$ | 100% |
| 1507 | ($CD_3OD$) δ 8.52 (d, 1 H), 8.39-8.49 (m, 1 H), 7.71 (s, 1 H), 7.53-7.65 (m, 1.3 H), 7.29 (d, 1 H), 7.16-7.25 (m, 1 H), 6.99 (s, 0.7 H), 6.82-6.91 (m, 1 H), 6.59-6.68 (m, 1 H), 4.94-5.08 (m, 1 H), 3.74-3.86 (m, 0.7 H), 3.39-3.47 (m, 0.3 H), 2.97-3.26 (m, 1 H), 2.78-2.91 (m, 1 H) | 470.2 $[M + H]^+$ | 98.9% |
| 1508 | ($CD_3OD$) δ 8.40-8.59 (m, 1 H), 7.72 (d, 1 H), 7.54-7.66 (m, 1 H), 7.44-7.53 (m, 0,4 H), 7.29 (t, 1 H), 7.12-7.24 (m, 1 H), 6.95-7.09 (m, 1.6 H), 6.54-6.87 (m, 1 H), 4.93-5.13 (m, 1 H), 3.80-4.06 (m, 0.5 H), 3.34-3.48 (m, 0.5 H), 2.96-3.28 (m, 1 H), 2.88 (br d, 1 H) | 504.1 $[M + H]^+$ | 100% |
| 1509 | ($CD_3OD$) δ 8.52 (t, 1 H), 7.72 (d, 1 H), 7.55-7.67 (m, 1 H), 7.49 (s, 0.4 H), 7.29 (br s, 1 H), 7.12-7.23 (m, 1 H), 6.95-7.09 (m, 1.6 H), 6.60-6.85 (m, 1 H), 4.93-5.13 (m, 1 H), 3.84-4.00 (m, 0.5 H), 3.35-3.45 (m, 0.5 H), 2.95-3.27 (m, 1 H), 2.82-2.93 (m, 1 H) | 504.1 $[M + H]^+$ | 99.5% |
| 1510 | ($CD_3OD$) δ 8.43-8.61 (m, 1 H), 7.65-7.79 (m, 1 H), 7.36-7.56 (m, 1.5 H), 7.29 (t, 1 H), 7.07-7.20 (m, 1 H), 7.01 (s, 0.5 H), 6.66-6.78 (m, 1 H), 6.40-6.66 (m, 1 H), 4.95-5.12 (m, 1 H), 4.03 (br d, 0.5 H), 3.36-3.45 (m, 0.5 H), 3.09 (s, 1 H), 2.79-2.93 (m, 1 H), 2.42-2.74 (m, 3 H) | 484.2 $[M + H]^+$ | 100% |
| 1511 | ($CD_3OD$) δ 8.39-8.61 (m, 1 H), 7.71 (d, 1 H), 7.38 (s, 1.5 H), 7.29 (t, 1 H), 6.93-7.19 (m, 1.5 H), 6.66-6.78 (m, 1 H), 6.37-6.65 (m, 1 H), 4.97-5.11 (m, 1 H), 3.78-4.16 (m, 0.5 H), 3.37-3.43 (m, 0.5 H), 2.95-3.27 (m, 1 H), 2.80-2.93 (m, 1 H), 2.45-2.73 (m, 3 H) | 484.2 $[M + H]^+$ | 97.6% |
| 1512 | ($CD_3OD$) δ 8.62-8.72 (m, 1 H), 8.50 (d, 1 H), 7.51-7.74 (m, 2 H), 7.27 (d, 1 H), 6.93-7.03 (m, 2 H), 6.76-6.83 (m, 1 H), 4.93-5.09 (m, 1 H), 3.74-3.83 (m, 0.7 H), 3.37-3.46 (m, 0.3 H), 3.20 (br t, 0.7 H), 2.96-3.06 (m, 0.3 H), 2.85 (br d, 1 H) | 538.2 $[M + H]^+$ | 99.0% |
| 1513 | ($CD_3OD$) δ 8.63-8.72 (m, 1 H), 8.50 (d, 1 H), 7.52-7.73 (m, 2 H), 7.27 (d, 1 H), 6.93-7.04 (m, 2 H), 6.75-6.84 (m, 1 H), 4.93-5.11 (m, 1 H), 3.73-3.84 (m, 0.7 H), 3.41 (td, 0.3 H), 3.14-3.27 (m, 0.7 H), 2.95-3.06 (m, 0.3 H), 2.80-2.90 (m, 1 H) | 538.2 $[M + H]^+$ | 91.3% |
| 1514 | ($CD_3OD$) δ 8.37-8.54 (m, 1 H), 7.45-7.86 (m, 2 H), 7.13-7.31 (m, 1 H), 6.48-7.00 (m, 3 H), 4.99 (br dd, 1 H), 3.68-4.01 (m, 1.6 H), 3.39 (td, 0.4 H), 2.72-3.27 (m, 2 H), 2.42-2.61 (m, 4 H), 1.96-2.34 (m, 2 H) | 390.2 $[M + H]^+$ | 99.3% |
| 1515 | ($CD_3OD$) δ 8.34-8.53 (m, 1 H), 7.40-7.73 (m, 2 H), 7.09-7.26 (m, 1 H), 6,48-7.02 (m, 3 H), 4.96 (br dd, 1 H), 3.67-3.99 (m, 1,6 H), 3.34-3.46 (m, 0.4 H), 2.73-3.22 (m, 2 H), 2.37-2.64 (m, 4 H), 1.90-2.29 (m, 2 H) | 390.2 $[M + H]^+$ | 96.0% |
| 1516 | ($CD_3OD$) δ 8.32-8.53 (m, 1 H), 7.69 (s, 1 H), 7.19-7.50 (m, 1 H), 6.60-7.01 (m, 3 H), 4.99 (dd, 1 H), 3.69-3.98 (m, 1.6 H), 3.34-3.44 (m, 0.4 H), 2.72-3.20 (m, 2 H), 2.39-2.62 (m, 4 H), 1.87-2.31 (m, 2 H) | 424.1 $[M + H]^+$ | 100% |
| 1517 | ($CD_3OD$) δ 8.30-8.60 (m, 1 H), 7.69 (s, 1 H), 7.23-7.51 (m, 1 H), 6.62-6.97 (m, 3 H), 4.99 (br dd, 1 H), 3.65-3.98 (m, 1.6 H), 3.36 (br dd, 0.4 H), 2.77-3.21 (m, 2 H), 2.39-2.63 (m, 4 H), 1.93-2.33 (m, 2 H) | 424.1 $[M + H]^+$ | 100% |
| 1518 | ($CD_3OD$) δ 8.57-8.79 (m, 1 H), 7.39-7.78 (m, 2 H), 6.65-7.11 (m, 3 H), 4.92-5.10 (m, 1 H), 3.60-3.95 (m, 2 H), 2.75-3.25 (m, 2 H), 2.43-2.61 (m, 4 H), 1.93-2.33 (m, 2 H) | 458.2 $[M + H]^+$ | 100% |
| 1519 | ($CD_3OD$) δ 8.55-8.78 (m, 1 H), 7.42-7.74 (m, 2 H), 6.56-7.17 (m, 3 H), 4.92-5.09 (m, 1 H), 3.65-3.94 (m, 1.6 H), 3.38 (td, 0.4 H), 2.74-3.25 (m, 2 H), 2.37-2.62 (m, 4 H), 1.92-2.32 (m, 2 H) | 458.1 $[M + H]^+$ | 100% |
| 1520 | ($CD_3OD$) δ 8.49-8.67 (m, 1 H), 7.69 (s, 1 H), 7.38-7.53 (m, 1 H), 6.66-7.16 (m, 4 H), 4.99 (br dd, 1 H), 3.64-3.99 (m, 1.6 H), 3.34-3.43 (m, 0.4 H), 2.75-3.22 (m, 2 H), 2.32-2.61 (m, 4 H), 1.94-2.29 (m, 2 H) | 440.2 $[M + H]^+$ | 100% |
| 1521 | ($CD_3OD$) δ 8.48-8.67 (m, 1 H), 7.69 (s, 1 H), 7.35-7.55 (m, 1 H), 6.64-7.15 (m, 4 H), 4.99 (br dd, 1 H), 3.65-4.01 (m, 1.6 H), 3.37 (br dd, 0.4 H), 2.71-3.25 (m, 2 H), 2.38-2.61 (m, 4 H), 1,92-2.28 (m, 2 H) | 440.2 $[M + H]^+$ | 97.0% |

TABLE 2-continued

| Ex. # | $^1$H NMR (400 MHz unless otherwise noted) | LCMS: m/z | % ee |
|---|---|---|---|
| 1522 | ($DMSO-d_6$) δ 12.13 (br s, 1 H), 9.04-9.71 (m, 1 H), 8.73-9.01 (m, 1 H), 8.33-8.59 (m, 1 H), 7.44-7.80 (m, 3 H), 7.22-7.41 (m, 1 H), 7.06-7.19 (m, 0.3 H), 6.54-6.99 (m, 2.7 H), 4.82 (br dd, 1 H), 3.40-3.88 (m, 1 H), 2.73-3.16 (m, 2 H) | 431.1 $[M + H]^+$ | 100% |
| 1523 | ($DMSO-d_6$) δ 12.10 (br s, 1 H), 9.05-9.83 (m, 1 H), 8.86 (br d, 1 H), 8.22-8.68 (m, 1 H), 7.46-7.81 (m, 3 H), 7.19-7.43 (m, 1 H), 7.10 (s, 0.3 H), 6.60-7.00 (m, 2.7 H), 4.82 (br dd, 1 H), 3.41-3.82 (m, 1 H), 2.77-3.11 (m, 2 H) | 431.1 $[M + H]^+$ | 97.4% |
| 1524 | ($DMSO-d_6$) δ 12.11 (br s, 1 H), 8.52 (d, 1 H), 8.11-8.34 (m, 1 H), 7.48-7.76 (m, 3 H), 7.25-7.38 (m, 1 H), 7.21 (br d, 0.3 H), 6.31-7.10 (m, 2.7 H), 4.87 (br dd, 1 H), 3.96 (s, 3 H), 3.38-3.82 (m, 1 H), 2.72-3.12 (m, 2 H) | 461.1 $[M + H]^+$ | 99.4% |
| 1525 | ($DMSO-d_6$) δ 12.11 (br s, 1 H), 8.52 (d, 1 H), 8.15-8.30 (m, 1 H), 7.49-7.75 (m, 3 H), 7.25-7.35 (m, 1 H), 7.23 (br s, 0.4 H), 6.45-7.02 (m, 2.6 H), 4.68-4.99 (m, 1 H), 3.95 (s, 3 H), 3.38-3.81 (m, 1 H), 2.71-3.13 (m, 2 H) | 461.1 $[M + H]^+$ | 98.2% |
| 1526 | ($CD_3OD$) δ 7.62-7.72 (m, 2 H), 7.40-7.55 (m, 1 H), 7.20-7.29 (m, 1 H), 6.94-7.10 (m, 2 H), 6.60-6.81 (m, 2 H), 4.95-5.12 (m, 1 H), 4.27-4.37 (m, 3 H), 3.77-3.90 (m, 0.7 H), 3.40-3.50 (m, 0.3 H), 2.95-3.22 (m, 1 H), 2.80-2.91 (m, 1 H) | 434.2 $[M + H]^+$ | 100% |
| 1527 | ($CD_3OD$) δ 7.60-7.76 (m, 2 H), 7.39-7.57 (m, 1 H), 7.19-7.29 (m, 1 H), 6.92-7.11 (m, 2 H), 6.59-6.81 (m, 2 H), 5.09 (br dd, 1 H), 4.27-4.36 (m, 3 H), 3.83 (br s, 0.5 H), 3.37-3.51 (m, 0.5 H), 2.94-3.22 (m, 1 H), 2.77-2.92 (m, 1 H) | 434.2 $[M + H]^+$ | 99.4% |
| 1528 | ($CD_3OD$) δ 7.67-7.73 (m, 1 H), 7.41-7.52 (m, 2 H), 7.18-7.28 (m, 1 H), 6.96 (s, 1 H), 6.59-6.81 (m, 2 H), 5.10 (br dd, 0.5 H), 4.94 (br d, 0.5 H), 4.20-4.26 (m, 3 H), 3.84 (ddd, 0.5 H), 3.41 (td, 0.5 H), 3.15-3.25 (m, 1 H), 2.80-3.06 (m, 1 H), 2.32-2.41 (m, 3 H) | 448.1 $[M + H]^+$ | 98.6% |
| 1529 | ($CD_3OD$) δ 7.70 (br d, 1 H), 7.42-7.52 (m, 2 H), 7.24 (ddd, 1 H), 6.96 (s, 1 H), 6.60-6.80 (m, 2 H), 5.10 (dd, 0.7 H), 4.92-4.97 (m, 0.3 H), 4.21-4.24 (m, 3 H), 3.81-3.89 (m, 0.6 H), 3.41 (td, 0.4 H), 3.16-3.25 (m, 1 H), 2.82-3.05 (m, 1 H), 2.32-2.40 (m, 3 H) | 448.2 $[M + H]^+$ | 98.3% |
| 1530 | ($CD_3OD$) δ 8.52-8.63 (m, 1 H), 7.72 (s, 1 H), 7.39-7.58 (m, 1.3 H), 6.75-7.18 (m, 4.7 H), 4.92-5.09 (m, 1 H), 3.92 (s, 3 H), 3.78 (ddd, 0.5 H), 3.36-3.46 (m, 0.5 H), 2.79-3.27 (m, 2 H), 2.40 (s, 3 H) | 480.1 $[M + H]^+$ | 100% |
| 1531 | ($CD_3OD$) δ 8.50-8.64 (m, 1 H), 7.72 (s, 1 H), 7.35-7.59 (m, 1.3 H), 6.74-7.17 (m, 4.7 H), 4.92-5.13 (m, 1 H), 3.92 (s, 3 H), 3.72-3.85 (m, 0.5 H), 3.36-3.45 (m, 0.5 H), 2.80-3.27 (m, 2 H), 2.41 (s, 3 H) | 480.1 $[M + H]^+$ | 99.6% |
| 1532 | ($CD_3OD$) δ 8.52-8.68 (m, 1 H), 7.40-7.79 (m, 3.3 H), 6.76-7.17 (m, 4.7 H), 5.09 (br dd, 1 H), 4.23-4.39 (m, 3 H), 3.74-3.86 (m, 0.5 H), 3.38-3.50 (m, 0.5 H), 2.79-3.26 (m, 2 H) | 466.1 $[M + H]^+$ | 92.4% |
| 1533 | ($CD_3OD$) δ 8.37-8.56 (m, 1 H), 7.28-7.65 (m, 3.3 H), 6.64-7.05 (m, 4.7 H), 4.82-5.04 (m, 1 H), 4.15-4.27 (m, 3 H), 3.58-3.77 (m, 0.5 H), 3.25-3.38 (m, 0.5 H), 2.69-3.16 (m, 2 H) | 466.1 $[M + H]^+$ | 98.1% |
| 1534 | ($CD_3OD$) δ 9.48 (dd, 1 H), 8.82-8.90 (m, 2 H), 7.68-7.81 (m, 2 H), 7.39-7.61 (m, 1 H), 6.99-7.33 (m, 3 H), 6.62-6.84 (m, 1 H), 4.96-5.07 (m, 1 H), 3.89-3.99 (m, 0.6 H), 3.36-3.41 (m, 0.4 H), 2.86-3.26 (m, 2 H) | 464.1 $[M + H]^+$ | 100% |
| 1535 | ($CD_3OD$) δ 9.48 (dd, 1 H), 8.81-8.90 (m, 2 H), 7.69-7.82 (m, 2 H), 7.38-7.61 (m, 1 H), 6.99-7.34 (m, 3 H), 6.61-6.83 (m, 1 H), 4.96-5.08 (m, 1 H), 3.89-4.00 (m, 0.6 H), 3.36-3.42 (m, 0.4 H), 2.85-3.26 (m, 2 H) | 464.1 $[M + H]^+$ | 99.1% |
| 1536 | ($CD_3OD$) δ 7.68-7.79 (m, 2 H), 7.39-7.60 (m, 1 H), 6.97-7.31 (m, 3 H), 6.60-6.79 (m, 2 H), 4.95-5.08 (m, 1 H), 3.91 (d, 3.6 H), 3.35-3.41 (m, 0.4 H), 2.84-3.20 (m, 2 H), 2.40 (d, 3 H) | 480.1 $[M + H]^+$ | 100% |
| 1537 | ($CD_3OD$) δ 7.68-7.79 (m, 2 H), 7.38-7.60 (m, 1 H), 6.96-7.32 (m, 3 H), 6.60-6.79 (m, 2 H), 4.94-5.11 (m, 1 H), 3.91 (d, 3.6 H), 3.34-3.40 (m, 0.4 H), 2.82-3.23 (m, 2 H), 2.40 (d, 3 H) | 480.2 $[M + H]^+$ | 99.0% |
| 1538 | ($CD_3OD$) δ 8.99-9.06 (m, 1 H), 8.53-8.64 (m, 1 H), 8.37 (s, 1 H), 7.63 (br s, 1 H), 7.43-7.57 (m, 1.3 H), 6.82-6.95 (m, 1.7 H), 6.64-6.75 (m, 1 H), 4.83-5.04 (m, 1 H), 3.63-3.73 (m, 0.7 H), 3.31 (td, 0.3 H), 2.84-3.15 (m, 1 H), 2.76 (br d, 1 H) | 538.2 $[M + H]^+$ | 100% |
| 1539 | ($CD_3OD$) δ 8.98-9.07 (m, 1 H), 8.54-8.63 (m, 1 H), 8.33-8.40 (m, 1 H), 7.60 (br s, 1 H), 7.43-7.56 (m, 1.3 H), 6.82-6.94 (m, 1.7 H), 6.66-6.75 (m, 1 H), 4.82-5.04 (m, 1 H), 3.61-3.74 (m, 0.7 H), 3.31 (td, 0.3 H), 2.83-3.15 (m, 1 H), 2.77 (br s, 1 H) | 538.2 $[M + H]^+$ | 98.8% |
| 1540 | ($CD_3OD$) δ 9.15 (s, 1 H), 8.48 (s, 1 H), 8.28-8.39 (m, 1 H), 7.55-7.74 (m, 1.3 H), 6.93-7.03 (m, 1.7 H), 6.80-6.89 (m, 1 H), 6.72-6.79 (m, 1 H), 4.94-5.13 (m, 1 H), 3.80 (ddd, 0.7 H), 3,43 (td, 0.3 H), 2.95-3.25 (m, 1 H), 2.82-2.91 (m, 1 H) | 488.2 $[M + H]^+$ | 99.9% |
| 1541 | ($CD_3OD$) δ 9.03 (s, 1 H), 8.36 (s, 1 H), 8.16-8.27 (m, 1 H), 7.40-7.66 (m, 1.3 H), 6.81-6.92 (m, 1.7 H), 6.68-6.79 (m, 1 H), 6.60-6.68 (m, 1 H), 4.82-5.01 (m, 1 H), 3.63-3.73 (m, 0.7 H), 3.31 (td, 0.3 H), 2.84-3.14 (m, 1 H), 2.74 (br d, 1 H) | 488.1 $[M + H]^+$ | 99.3% |

TABLE 2-continued

| Ex. # | $^1$H NMR (400 MHz unless otherwise noted) | LCMS: m/z | % ee |
|---|---|---|---|
| 1542 | ($CD_3OD$) δ 8.52 (dd, 1 H), 7.79-7.93 (m, 1 H), 7.65-7.77 (m, 1 H), 7.50-7.60 (m, 0.5 H), 7.20-7.41 (m, 3 H), 6.99 (s, 0.5 H), 6.63-6.91 (m, 1 H), 4.93-5.12 (m, 1 H), 3.88-4.07 (m, 0.5 H), 3.34-3.41 (m, 0.5 H), 2.96-3.26 (m, 1 H), 2.81-2.93 (m, 1 H) | 538.1 $[M + H]^+$ | 100% |
| 1543 | ($CD_3OD$) δ 8.46 (s, 1 H), 7.80-7.93 (m, 1 H), 7.65-7.78 (m, 1 H), 7.56 (s, 0.5 H), 7.21-7.41 (m, 3 H), 7.03 (s, 0.5 H), 6.63-6.92 (m, 1 H), 4.93-5.12 (m, 1 H), 4.05 (br d, 0.5 H), 3.37 (br d, 0.5 H), 2.96-3.25 (m, 1 H), 2.82-2.94 (m, 1 H) | 538.1 $[M + H]^+$ | 99.9% |
| 1544 | ($CD_3OD$) δ 8.44-8.56 (m, 1 H), 7.68-7.81 (m, 2 H), 7.59 (s, 0.1 H), 7.14-7.50 (m, 4.3 H), 7.11 (s, 0.1 H), 6.93-7.01 (m, 0.5 H), 6.56-6.83 (m, 1 H), 4.93-5.10 (m, 1 H), 3.83-4.01 (m, 0.5 H), 3.35-3.41 (m, 0.5 H), 2.95-3.27 (m, 1 H), 2.80-2.93 (m, 1 H) | 520.1 $[M + H]^+$ | 100% |
| 1545 | ($CD_3OD$) δ 8.52 (t, 1 H), 7.64-7.82 (m, 2 H), 7.59 (s, 0.2 H), 7.36-7.47 (m, 0.8 H), 7.07-7.34 (m, 3.5 H), 6.99 (s, 0.5 H), 6.59-6.82 (m, 1 H), 4.94-5.10 (m, 1 H), 3.83-3.98 (m, 0.6 H), 3.37 (br s, 0.4 H), 2.95-3.26 (m, 1 H), 2.80-2.93 (m, 1 H) | 520.2 $[M + H]^+$ | 99.7% |
| 1546 | ($CD_3OD$) δ 8.27-8.97 (m, 3 H), 7.94 (d, 1 H), 7.60-7.71 (m, 2 H), 7.46 (br d, 1 H), 6.39-7.18 (m, 3 H), 4.61 (br s, 1 H), 3.55 (s, 3 H), 3.01-3.16 (m, 1 H), 2.78 (br d, 1 H), 2.30 (s, 6 H) | 509.2 $[M + H]^+$ | 100% |
| 1547 | ($CD_3OD$) δ 8.14-9.03 (m, 3 H), 7.94 (d, 1 H), 7.60-7.70 (m, 2 H), 7.46 (d, 1 H), 6.28-7.19 (m, 3 H), 4.61 (br s, 1 H), 3.55 (s, 3 H), 3.02-3.14 (m, 1 H), 2.78 (br d, 1 H), 2.30 (s, 6 H) | 509.2 $[M + H]^+$ | 99.0% |
| 1548 | ($CD_3OD$) δ 8.12-9.00 (m, 3 H), 7.97 (d, 1 H), 7.56-7.83 (m, 2 H), 7.45 (d, 1 H), 6.45-7.19 (m, 3 H), 4.59-4.79 (m, 1 H), 4.54 (s, 2 H), 3.52-4.12 (s, 1 H)3.32-3.48 (m, 3 H)2.98-3.22 (m, 1 H), 2.68-2.89 (m, 1 H) | 496.2 $[M + H]^+$ | 100% |
| 1549 | ($CD_3OD$) δ 8.69-8.94 (m, 3 H), 7.97 (d, 1 H), 7.58-7.78 (m, 2 H), 7.45 (d, 1 H), 6.39-7.14 (m, 3 H), 4.59-4.80 (m, 1 H), 4.55 (s, 2 H), 3.40-4.05 (m, 4 H), 3.01-3.20 (m, 1 H), 2.70-2.90 (m, 1 H) | 496.2 $[M + H]^+$ | 99.4% |
| 1550 | (DMSO-$d_6$) δ 12.06 (br s, 1 H), 9.50 (s, 1 H), 9.04 (br s, 1 H), 8.41-8.78 (m, 2 H), 8.14-8.26 (m, 2 H), 7.88-8.07 (m, 2 H), 7.74 (br d, 1 H), 7.60 (s, 1 H), 7.38-7.45 (m, 1 H), 6.30-7.15 (m, 3 H), 4.48 (br s, 1 H), 3.73 (br s, 1 H), 3.00 (br s, 1 H), 2.65-2.75 (m, 1 H) | 529.1 $[M + H]^+$ | 98.2% |
| 1551 | (DMSO-$d_6$) δ 12.05 (br s, 1 H), 9.50 (s, 1 H), 9.03 (br s, 1 H), 8.39-8.79 (m, 2 H), 8.12-8.26 (m, 2 H), 7.89-8.07 (m, 2 H), 7.74 (br d, 1 H), 7.60 (s, 1 H), 7.34-7.47 (m, 1 H), 6.26-7.21 (m, 3 H), 4.50 (br s, 1 H), 3.75 (s, 1 H), 3.00 (br s, 1 H), 2.71 (br d, 1 H) | 529.1 $[M + H]^+$ | 91.5% |
| 1552 | (DMSO-$d_6$) δ 12.05 (br s, 1 H), 8.93-9.18 (m, 2 H), 8.25-8.53 (m, 2 H), 7.88-8.07 (m, 2 H), 7.67-7.80 (m, 2 H), 7.59 (s, 1 H), 6.32-7.10 (m, 3 H), 4.51 (br s, 1 H), 3.88 (s, 3 H), 3.70 (s, 1 H), 2.99 (br s, 1 H), 2.66-2.73 (m, 1 H) | 532.3 $[M + H]^+$ | 100% |
| 1553 | (DMSO-$d_6$) δ 12.05 (br s, 1 H), 8.88-9.19 (m, 2 H), 8.29 (s, 2 H), 7.90-8.07 (m, 2 H), 7.67-7.80 (m, 2 H), 7.59 (s, 1 H), 6.21-7.14 (m, 3 H), 4.51 (br s, 1 H), 3.88 (s, 3 H), 3.70 (br s, 1 H), 2.99 (br s, 1 H), 2.70 (br d, 1 H) | 532.2 $[M + H]^+$ | 99.8% |
| 1554 | ($CD_3OD$) δ 7.67-7.74 (m, 1 H), 7.41-7.53 (m, 1.3 H), 7.16-7.31 (m, 1 H), 6.95 (s, 0.7 H), 6.79 (d, 0.7 H), 6.59-6.69 (m, 1.3 H), 5.01 (br dd, 1 H), 3.73-3.84 (m, 0.7 H), 3.34-3.44 (m, 1.3 H), 2.91-3.22 (m, 1 H), 2.77-2.89 (m, 1 H), 1.45 (d, 6 H) | 396.2 $[M + H]^+$ | 100% |
| 1555 | ($CD_3OD$) δ 7.67-7.73 (m, 1 H), 7.41-7.52 (m, 1.3 H), 7.19-7.31 (m, 1 H), 6.95 (s, 0.7 H), 6.76-6.82 (m, 0.7 H), 6.59-6.69 (m, 1.3 H), 4.95-5.06 (m, 1 H), 3.73-3.85 (m, 0.7 H), 3.34-3.44 (m, 1.3 H), 2.94-3.22 (m, 1 H), 2.78-2.90 (m, 1 H), 1.46 (d, 6 H) | 396.2 $[M + H]^+$ | 99.5% |
| 1556 | ($CD_3OD$) δ 8.13-8.40 (m, 1 H), 7.35-7.78 (m, 1 H), 6.44-7.12 (m, 4 H), 4.97 (br dd, 1 H), 3.69-3.93 (m, 1.6 H), 3.39 (td, 0.4 H), 2.72-3.21 (m, 2 H), 2.31-2.61 (m, 7 H), 1.97-2.28 (m, 2 H) | 404.2 $[M + H]^+$ | 100% |
| 1557 | ($CD_3OD$) δ 8.14-8.40 (m, 1 H), 7.42-7.85 (m, 1 H), 6.35-7.18 (m, 4 H), 4.96 (br dd, 1 H), 3.68-3.92 (m, 1.6 H), 3.38 (td, 0.4 H), 2.77-3.21 (m, 2 H), 2.32-2.69 (m, 7 H), 1.89-2.31 (m, 2 H) | 404.2 $[M + H]^+$ | 95.9% |
| 1558 | ($CD_3OD$) δ 8.21-8.43 (m, 1 H), 7.69 (s, 1 H), 6.59-7.11 (m, 4 H), 4.99 (br dd, 1 H), 3.66-3.92 (m, 1.6 H), 3.34-3.42 (m, 0.4 H), 2.77-3.21 (m, 2 H), 2.40-2.60 (m, 4 H), 1.95-2.27 (m, 2 H) | 408.2 $[M + H]^+$ | 100% |
| 1559 | ($CD_3OD$) δ 8.24-8.43 (m, 1 H), 7.38-7.83 (m, 1 H), 6.60-7.07 (m, 4 H), 5.00 (br dd, 1 H), 3.71-3.94 (m, 1.6 H), 3.34-3.43 (m, 0.4 H), 2.76-3.22 (m, 2 H), 2.39-2.60 (m, 4 H), 2.00-2.25 (m, 2 H) | 408.2 $[M + H]^+$ | 98.5% |
| 1560 | ($CD_3OD$) δ 7.42-7.71 (m, 2 H), 6.56-7.27 (m, 4 H), 5.00 (br dd, 1 H), 3.76-3.97 (m, 1.6 H), 3.34-3.41 (m, 0.4 H), 2.78-3.21 (m, 2 H), 2.40-2.60 (m, 4 H), 1.95-2.28 (m, 2 H) | 424.2 $[M + H]^+$ | 100% |
| 1561 | ($CD_3OD$) δ 7.41-7.72 (m, 2 H), 6.59-7.23 (m, 4 H), 5.00 (br dd, 1 H), 3.76-3.94 (m, 1.6 H), 3.34-3.43 (m, 0.4 H), 2.77-3.20 (m, 2 H), 2.40-2.57 (m, 4 H), 1.95-2.27 (m, 2 H) | 424.1 $[M + H]^+$ | 98.7% |

TABLE 2-continued

| Ex. # | $^1$H NMR (400 MHz unless otherwise noted) | LCMS: m/z | % ee |
|---|---|---|---|
| 1562 | ($CD_3OD$) δ 7.68 (d, 1 H), 7.35-7.51 (m, 1.4 H), 7.11 (dt, 1 H), 6.95 (s, 0.6 H), 6.39-6.75 (m, 2 H), 4.96 (br dd, 1 H), 3.79-3.99 (m, 1.6 H), 3.34-3.43 (m, 0.4 H), 2.75-3.20 (m, 2 H), 2.38-2.71 (m, 7 H), 1.94-2.32 (m, 2 H) | 404.2 $[M + H]^+$ | 100% |
| 1563 | ($CD_3OD$) δ 7.69 (d, 1 H), 7.36-7.51 (m, 1.4 H), 7.10 (dt, 1 H), 6.95 (s, 0.6 H), 6.31-6.80 (m, 2 H), 4.96 (br dd, 1 H), 3.77-3.98 (m, 1.5 H), 3.32-3.41 (m, 0.5 H), 2.76-3.20 (m, 2 H), 2.39-2.73 (m, 7 H), 1.94-2.29 (m, 2 H) | 404.2 $[M + H]^+$ | 94.5% |
| 1564 | ($CD_3OD$) δ 7.66-7.80 (m, 1 H), 7.41-7.61 (m, 1.3 H), 7.18-7.32 (m, 1 H), 6.98 (s, 0.7 H), 6.70-6.86 (m, 2 H), 6.61-6.70 (m, 1 H), 5.06 (br dd, 0.8 H), 3.92 (s, 3 H), 3.41-3.88 (m, 1.2 H), 3.20 (br d, 1 H), 2.86 (br dd, 1 H), 2.41 (s, 3 H) | 448.1 $[M + H]^+$ | 100% |
| 1565 | ($CD_3OD$) δ 7.71 (s, 1 H), 7.41-7.60 (m, 1.4 H), 7.20-7.31 (m, 1 H), 6.98 (s, 0.6 H), 6.70-6.84 (m, 2 H), 6.60-6.70 (m, 1 H), 5.06 (br dd, 1 H), 3.92 (s, 3 H), 3.42-3.88 (m, 1 H), 2.94-3.27 (m, 1 H), 2.86 (br dd, 1 H), 2.41 (s, (s, 3 H) | 448.1 $[M + H]^+$ | 99.6% |
| 1566 | ($CD_3OD$) δ 8.30 (br s, 1 H), 7.64-7.82 (m, 1 H), 7.58 (br s, 0.3 H), 7.37-7.54 (m, 1 H), 7.13-7.34 (m, 1 H), 6.97 (s, 0.7 H), 6.70-6.85 (m, 1 H), 6.60-6.70 (m, 1 H), 4.97-5.17 (m, 1 H), 3.94 (s, 3 H), 3.39-3.86 (m, 1 H), 2.96-3.25 (m, 1 H), 2.78-2.93 (m, 1 H), 2.47-2.61 (m, 3 H) | 448.2 $[M + H]^+$ | 100% |
| 1567 | ($CD_3OD$) δ 8.30 (s, 1 H), 7.71 (s, 1 H), 7.58 (s, 0.3 H), 7.42-7.54 (m, 1 H), 7.19-7.33 (m, 1 H), 6.97 (s, 0.7 H), 6.70-6.85 (m, 1 H), 6.61-6.70 (m, 1 H), 5.02-5.18 (m, 1 H), 3.94 (s, 3 H), 3.42-3.88 (m, 1 H), 2.94-3.26 (m, 1 H), 2.79-2.93 (m, 1 H), 2.49-2.62 (m, 3 H) | 448.2 $[M + H]^+$ | 100% |
| 1568 | ($CD_3OD$) δ 8.53-8.64 (m, 1 H), 7.72 (s, 1 H), 7.41-7.56 (m, 2 H), 6.73-7.15 (m, 4 H), 4.95-5.17 (m, 1 H), 4.16-4.27 (m, 3 H), 3.75-3.88 (m, 0.5 H), 3.42 (td, 0.5 H), 2.85-3.26 (m, 2 H), 2.29-2.44 (m, 3 H) | 480.2 $[M + H]^+$ | 100% |
| 1569 | ($CD_3OD$) δ 8.54-8.64 (m, 1 H), 7.77 (br d, 1 H), 7.43-7.55 (m, 2 H), 6.78-7.17 (m, 4 H), 4.95-5.16 (m, 1 H), 4.20-4.27 (m, 3 H), 3.74-3.89 (m, 0.5 H), 3.39-3.49 (m, 0.5 H), 2.85-3.25 (m, 2 H), 2.33-2.46 (m, 3 H) | 480.1 $[M + H]^+$ | 97.3% |
| 1570 | ($CD_3OD$) δ 9.11-9.18 (m, 1 H), 8.46-8.62 (m, 2 H), 7.72 (s, 1 H), 7.40-7.62 (m, 1.4 H), 6.91-7.16 (m, 2.6 H), 6.75-6.88 (m, 1 H), 4.95-5.13 (m, 1 H), 3.74-3.84 (m, 0.7 H), 3.39-3.47 (m, 0.3 H), 2.95-3.26 (m, 1 H), 2.80-2.92 (m, 1 H) | 520.1 $[M + H]^+$ | 99.3% |
| 1571 | ($CD_3OD$) δ 8.97-9.07 (m, 1 H), 8.32-8.52 (m, 2 H), 7.60 (s, 1 H), 7.28-7.49 (m, 1.4 H), 6.76-7.06 (m, 2.6 H), 6.62-6.74 (m, 1 H), 4.82-5.03 (m, 1 H), 3.62-3.72 (m, 0.7 H), 3.26-3.35 (m, 0.3 H), 2.83-3.14 (m, 1 H), 2.67-2.81 (m, 1 H) | 520.1 $[M + H]^+$ | 99.5% |
| 1572 | ($CD_3OD$) δ 7.08-7.90 (m, 6 H), 6,53-6.99 (m, 1 H), 4.96-5.06 (m, 1 H), 3.76-3.97 (m, 1.6 H), 3.34 (br s, 0.4 H), 2.77-3.16 (m, 2 H), 2.36-2.63 (m, 4 H), 1.92-2.28 (m, 2 H) | 440.1 $[M + H]^+$ | 97.5% |
| 1573 | ($CD_3OD$) δ 7.08-7.81 (m, 5 H), 6.52-6.99 (m, 2 H), 4.91-5.03 (m, 1 H), 3.75-3.95 (m, 1.6 H), 3.32-3.39 (m, 0.4 H), 2.74-3.19 (m, 2 H), 2.42-2.57 (m, 4 H), 1.94-2.26 (m, 2 H) | 440.1 $[M + H]^+$ | 98.2% |
| 1574 | ($CD_3OD$) δ 7.61-7.75 (m, 1 H), 7.37-7.52 (m, 1 H), 7.17-7.30 (m, 1 H), 6.45-7.13 (m, 3 H), 5.00 (dd, 1 H), 3.73-3.94 (m, 1.6 H), 3.33-3.43 (m, 0.4 H), 2.74-3.21 (m, 2 H), 2.37-2.61 (m, 4 H), 1.94-2.29 (m, 2 H) | 408.1 $[M + H]^+$ | 100% |
| 1575 | ($CD_3OD$) δ 7.62-7.74 (m, 1 H), 7.20-7.52 (m, 2 H), 6.58-6.98 (m, 3 H), 4.91-5.05 (m, 1 H), 3.65-3.98 (m, 1.7 H), 3.35-3.43 (m, 0.3 H), 2.75-3.22 (m, 2 H), 2.41-2.57 (m, 4 H), 1.95-2.28 (m, 2 H) | 408.2 $[M + H]^+$ | 99.7% |
| 1576 | ($CD_3OD$) δ 8.43 (d, 1 H), 7.66 (s, 1 H), 7.57 (d, 1 H), 7.39 (d, 1 H), 7.31 (d, 1 H), 7.14-7.22 (m, 2 H), 7.03-7.11 (m, 1 H), 6.83 (t, 1 H), 6.60 (d, 2 H), 4.54 (dd, 1 H), 3.72 (td, 1 H), 2.98-3.11 (m, 1 H), 2.81 (dd, 1 H) | 357.1 $[M + H]^+$ | 100% |
| 1577 | ($CD_3OD$) δ 8.43 (br d, 1 H), 7.66 (s, 1 H), 7.57 (br d, 1 H), 7.39 (d, 1 H), 7.31 (d, 1 H), 7.13-7.23 (m, 2 H), 7.07 (t, 1 H), 6.83 (br t, 1 H), 6.50-6.66 (m, 2 H), 4.54 (dd, 1 H), 3,61-3.81 (m, 1 H), 2.94-3.12 (m, 1 H), 2.81 (br dd, 1 H) | 357.2 $[M + H]^+$ | 99.5% |
| 1578 | ($CD_3OD$) δ 8.45 (dd, 1 H), 8.26 (dd, 1 H), 7.68-7.81 (m, 2 H), 7.38-7.64 (m, 2 H), 6,99-7.34 (m, 3 H), 6.61-6.83 (m, 1 H), 4.97-5.07 (m, 1 H), 4.00 (d, 3.6 H), 3.37-3.42 (m, 0.4 H), 2.84-3.25 (m, 2 H) | 493.1 $[M + H]^+$ | 100% |
| 1579 | ($CD_3OD$) δ 8.34 (dd, 1 H), 8.15 (dd, 1 H), 7.57-7.68 (m, 2 H), 7.27-7.52 (m, 2 H), 6.86-7.20 (m, 3 H), 6.48-6.70 (m, 1 H), 4.83-4.94 (m, 1 H), 3.78-3.90 (m, 3.6 H), 3.24-3.29 (m, 0.4 H), 2.73-3.10 (m, 2 H) | 493.1 $[M + H]^+$ | 99.7% |
| 1580 | ($CD_3OD$) δ 8.51-8.59 (m, 1 H), 7.79-7.91 (m, 1 H), 7.57-7.70 (m, 3 H), 6.86-7.48 (m, 4 H), 6.46-6.72 (m, 1 H), 4.83-4.93 (m, 1 H), 3.76-3.87 (m, 0.5 H), 3.22-3.31 (m, 0.5 H), 2.73-3.15 (m, 2 H) | 481.1 $[M + H]^+$ | 99.1% |

TABLE 2-continued

| Ex. # | $^1$H NMR (400 MHz unless otherwise noted) | LCMS: m/z | % ee |
|---|---|---|---|
| 1581 | ($CD_3OD$) δ 8.61-8.72 (m, 1 H), 7.91-8.00 (m, 1 H), 7.68-7.82 (m, 3 H), 6.99-7.60 (m, 4 H), 6.56-6.86 (m, 1 H), 4.95-5.02 (m, 1 H), 3.85-4.02 (m, 0.5 H), 3.36-3.45 (m, 0.5 H), 2.83-3.27 (m, 2 H) | 481.1 $[M + H]^+$ | 97.5% |
| 1582 | ($CD_3OD$) δ 8.28 (s, 1 H), 7.68-7.81 (m, 2 H), 7.35-7.60 (m, 1 H), 6.95-7.33 (m, 3 H), 6.57-6.81 (m, 1 H), 4.94-5.14 (m, 1 H), 3.93 (d, 3.5 H), 3.34-3.44 (m, 0.5 H), 2.82-3.25 (m, 2 H), 2.51-2.58 (m, 3 H) | 480.2 $[M + H]^+$ | 98.6% |
| 1583 | ($CD_3OD$) δ 8.15 (s, 1 H), 7.54-7.68 (m, 2 H), 7.23-7.48 (m, 1 H), 6.84-7.19 (m, 3 H), 6.51-6.68 (m, 1 H), 4.82-5.04 (m, 1 H), 3.80 (d, 3.5 H), 3.22-3.31 (m, 0.5 H), 2.72-3.07 (m, 2 H), 2.41 (d, 3 H) | 480.2 $[M + H]^+$ | 98.5% |
| 1584 | ($CD_3OD$) δ 7.67-7.80 (m, 2 H), 7.35-7.59 (m, 2 H), 6.97-7.32 (m, 3 H), 6.65-6.81 (m, 1 H), 4.96-5.13 (m, 1 H), 4.23 (d, 3 H), 3.94 (ddd, 0.6 H), 3.37-3.44 (m, 0.4 H), 2.84-3.23 (m, 2 H), 2.37 (d, 3 H) | 480.1 $[M + H]^+$ | 100% |
| 1585 | ($CD_3OD$) δ 7.56-7.68 (m, 2 H), 7.23-7.47 (m, 2 H), 6.85-7.20 (m, 3 H), 6.54-6.69 (m, 1 H), 4.84-5.01 (m, 1 H), 4.09-4.16 (m, 3 H), 3.82 (ddd, 0.6 H), 3.25-3.33 (m, 0.4 H), 2.72-3.13 (m, 2 H), 2.25 (d, 3 H) | 480.1 $[M + H]^+$ | 96.4% |
| 1586 | ($CD_3OD$) δ 8.39-8.46 (m, 1 H), 7.69 (s, 1 H), 7.37-7.49 (m, 0.3 H), 7.26-7.32 (m, 1 H), 6.92 (br s, 0.7 H), 6.81-6.89 (m, 1 H), 6.68-6.75 (m, 1 H), 4.99 (br dd, 1 H), 3.67-3.82 (m, 1.7 H), 3.35-3.44 (m, 0.3 H), 2.94-3.20 (m, 5 H), 2.82 (br d, 1 H) | 460.1 $[M + H]^+$ | 100% |
| 1587 | ($CD_3OD$) δ 8.39-8.46 (m, 1 H), 7.69 (s, 1 H), 7.44 (s, 0.3 H), 7.26-7.32 (m, 1 H), 6.92 (s, 0.7 H), 6.82-6.88 (m, 1 H), 6.69-6.75 (m, 1 H), 4.99 (dd, 1 H), 3.68-3.81 (m, 1.7 H), 3.38 (td, 0.3 H), 2.97-3.19 (m, 5 H), 2.77-2.87 (m, 1 H) | 460.1 $[M + H]^+$ | 99.0% |
| 1588 | ($CD_3OD$) δ 8.29 (d, 1 H), 7.65 (s, 1 H), 6.97 (d, 1 H), 6.77 (t, 1 H), 6.50 (s, 1 H), 6.24 (br s, 1 H), 4.17 (dd, 1 H), 3.67 (ddd, 1 H), 2.95-3.08 (m, 1 H), 2.77 (dd, 1 H), 2.42 (s, 3 H), 1.99-2.16 (m, 1 H), 1.04-1.13 (m, 4 H) | 362.2 $[M + H]^+$ | 100% |
| 1589 | ($CD_3OD$) δ 8.28 (d, 1 H), 7.65 (s, 1 H), 6.96 (br d, 1 H), 6.76 (t, 1 H), 6.50 (s, 1 H), 6.24 (s, 1 H), 4.17 (dd, 1 H), 3.67 (ddd, 1 H), 2.95-3.06 (m, 1 H), 2.76 (dd, 1 H), 2.41 (s, 3 H), 2.01-2.12 (m, 1 H), 1.00-1.15 (m, 4 H) | 362.2 $[M + H]^+$ | 99.8% |
| 1590 | ($CD_3OD$) δ 8.68 (d, 1 H), 7.60-7.67 (m, 2 H), 6.98 (t, 1 H), 6.68 (s, 1 H), 6.27 (s, 1 H), 4.20 (dd, 1 H), 3.68 (ddd, 1 H), 2.96-3.06 (m, 1 H), 2.78 (dd, 1 H), 2.02-2.11 (m, 1 H), 1.00-1.16 (m, 4 H) | 416.2 $[M + H]^+$ | 98.7% |
| 1591 | ($CD_3OD$) δ 8.68 (d, 1 H), 7.59-7.67 (m, 2 H), 6.98 (t, 1 H), 6.68 (s, 1 H), 6.27 (br s, 1 H), 4.20 (dd, 1 H), 3.64-3.72 (m, 1 H), 2.95-3.06 (m, 1 H), 2.78 (br dd, 1 H), 2.01-2.11 (m, 1 H), 1.00-1.13 (m, 4 H) | 416.2 $[M + H]^+$ | 98.9% |
| 1592 | ($CD_3OD$) δ 8.29-8.53 (m, 3 H), 7.70-7.72 (m, 1 H), 7.64 (s, 1 H), 7.61-7.72 (m, 1 H), 7.56 (d, 1 H), 7.07-7.28 (m, 2 H), 6.83 (td, 1 H), 6.65 (t, 1 H), 6.54 (s, 1 H), 4.96-5.12 (m, 1 H), 3.40-3.56 (m, 1 H), 2.81-3.00 (m, 1 H), 2.70 (dd, 1 H) | 318.2 $[M + H]^+$ | 100% |
| 1593 | ($CD_3OD$) δ 8.32-8.53 (m, 3 H), 7.67 (s, 1 H), 7.56 (d, 1 H), 7.07-7.26 (m, 2 H), 6.83 (t, 1 H), 6.66 (t, 1 H), 6.54 (s, 1 H), 5.04 (br dd, 1 H), 3.39-3.55 (m, 1 H), 2.83-3.00 (m, 1 H), 2.70 (dd, 1 H) | 318.1 $[M + H]^+$ | 99.4% |
| 1594 | ($CD_3OD$) δ 7.92-8.04 (m, 1 H), 7.77-7.88 (m, 1 H), 7.55-7.69 (m, 2 H), 7.25-7.50 (m, 2 H), 6.85-7.22 (m, 3 H), 6.47-6.71 (m, 1 H), 4.85-4.96 (m, 1 H), 3.75-3.88 (m, 0.5 H), 3.24 (br d, 0.5 H), 2.71-3.13 (m, 2 H), 2.54 (br d, 3 H) | 477.2 $[M + H]^+$ | 100% |
| 1595 | ($CD_3OD$) δ 8.07-8.19 (m, 1 H), 7.95 (td, 1 H), 7.68-7.84 (m, 2 H), 7.39-7.61 (m, 2 H), 6.98-7.34 (m, 3 H), 6.60-6.88 (m, 1 H), 4.97-5.08 (m, 1 H), 3.86-3.99 (m, 0.5 H), 3.36-3.42 (m, 0.5 H), 2.85-3.24 (m, 2 H), 2.67 (d, 3 H) | 477.2 $[M + H]^+$ | 98.2% |
| 1596 | ($CD_3OD$) δ 9.01 (s, 1 H), 8.78 (br s, 2 H), 7.85-8.03 (m, 2 H), 7.56-7.75 (m, 3 H), 6.42-7.17 (m, 4 H), 4.65 (br s, 1 H), 3.96 (s, 3 H), 3.44-3.81 (m, 1 H), 3.03-3.16 (m, 1 H), 2.73-2.83 (m, 1 H) | 532.2 $[M + H]^+$ | 100% |
| 1597 | ($CD_3OD$) δ 9.01 (d, 1 H), 8.24-8.89 (m, 2 H), 7.86-8.04 (m, 2 H), 7.56-7.74 (m, 3 H), 6.37-7.09 (m, 4 H), 4.66 (br s, 1 H), 3.96 (s, 3 H), 3.46-3.83 (m, 1 H), 3.04-3.15 (m, 1 H), 2.79 (br d, 1 H) | 532.2 $[M + H]^+$ | 98.4% |
| 1598 | ($CD_3OD$) δ 8.23-8.37 (m, 1 H), 7.35-7.76 (m, 1.4 H), 6.90-7.07 (m, 1.6 H), 6.73-6.86 (m, 1 H), 6.52-6.69 (m, 1 H), 4.98 (dd, 1 H), 3.69-3.90 (m, 1.6 H), 3.36-3.47 (m, 0.4 H), 2.92-3.24 (m, 5 H), 2.84 (br dd, 1 H), 2.37-2.52 (m, 3 H) | 440.1 $[M + H]^+$ | 100% |
| 1599 | ($CD_3OD$) δ 8.22-8.38 (m, 1 H), 7.43-7.78 (m, 1.4 H), 6.91-7.06 (m, 1.6 H), 6.74-6.87 (m, 1 H), 6.53-6.70 (m, 1 H), 4.98 (br dd, 1 H), 3.69-3.87 (m, 1.6 H), 3.37-3.45 (m, 0.4 H), 2.92-3.27 (m, 5 H), 2.84 (br dd, 1 H), 2.37-2.54 (m, 3 H) | 440.1 $[M + H]^+$ | 99.3% |
| 1600 | ($CD_3OD$) δ 8.64-8.76 (m, 1 H), 7.71 (s, 1 H), 7.60-7.68 (m, 1 H), 7.47 (br s, 0.4 H), 6.92-7.06 (m, 1.6 H), 6.73-6.86 (m, 1 H), 4.94-5.10 (m, 1 H), 3.68-3.88 (m, 1.6 H), 3.36-3.46 (m, 0.4 H), 2.93-3.25 (m, 5 H), 2.76-2.91 (m, 1 H) | 494.1 $[M + H]^+$ | 100% |

TABLE 2-continued

| Ex. # | $^1$H NMR (400 MHz unless otherwise noted) | LCMS: m/z | % ee |
|---|---|---|---|
| 1601 | ($CD_3OD$) δ 8.65-8.77 (m, 1 H), 7.72 (s, 1 H), 7.59-7.68 (m, 1 H), 7.47 (s, 0.4 H), 6.92-7.07 (m, 1.6 H), 6.73-6.85 (m, 1 H), 4.93-5.10 (m, 1 H), 3.69-3.87 (m, 1.6 H), 3.37-3.47 (m, 0.4 H), 2.94-3.25 (m, 5 H), 2.79-2.90 (m, 1 H) | 494.1 $[M + H]^+$ | 99.5% |
| 1602 | ($CD_3OD$) δ 8.51-8.70 (m, 1 H), 7.71 (s, 1 H), 7.45 (br d, 1.3 H), 6.73-7.16 (m, 3.7 H), 4.92-5.05 (m, 1 H), 3.68-3.89 (m, 1.5 H), 3.36-3.47 (m, 0.5 H), 2.70-3.23 (m, 6 H) | 476.2 $[M + H]^+$ | 100% |
| 1603 | ($CD_3OD$) δ 8.52-8.66 (m, 1 H), 7.71 (s, 1 H), 7.38-7.51 (m, 1.3 H), 6.72-7.19 (m, 3.7 H), 4.92-5.05 (m, 1 H), 3.69-3.86 (m, 1.5 H), 3.34-3.44 (m, 0.5 H), 2.82-3.22 (m, 6 H) | 476.2 $[M + H]^+$ | 99.5% |
| 1604 | ($CD_3OD$) δ 8.26-8.42 (m, 1 H), 7.71 (s, 1 H), 7.46 (s, 0.5 H), 6.67-7.05 (m, 3.5 H), 5.01 (dd, 1 H), 3.68-3.88 (m, 1.5 H), 3.41 (td, 0.5 H), 2.76-3.24 (m, 6 H) | 444.2 $[M + H]^+$ | 100% |
| 1605 | ($CD_3OD$) δ 8.16-8.30 (m, 1 H), 7.55-7.65 (m, 1 H), 7.34 (s, 0.5 H), 6.57-6.91 (m, 3.5 H), 4.89 (br dd, 1 H), 3.53-3.75 (m, 1.5 H), 3.29 (td, 0.5 H), 2.68-3.09 (m, 6 H) | 444.1 $[M + H]^+$ | 92.0% |
| 1606 | ($CD_3OD$) δ 8.56 (br d, 1 H), 7.65 (s, 1 H), 7.41 (br d, 1 H), 6.68-7.12 (m, 3 H), 6.26 (s, 1 H), 4.13-4.25 (m, 1 H), 3.56-3.75 (m, 1 H), 3.00 (br d, 1 H), 2.78 (dd, 1 H), 1.97-2.13 (m, 1 H), 0.99-1.12 (m, 4 H) | 398.2 $[M + H]^+$ | 93.1% |
| 1607 | ($CD_3OD$) δ 8.57 (d, 1 H), 7.66 (s, 1 H), 7.41 (br d, 1 H), 6.64-7.17 (m, 3 H), 6.27 (s, 1 H), 4.19 (dd, 1 H), 3.67 (ddd, 1 H), 2.94-3.07 (m, 1 H), 2.78 (dd, 1 H), 2.02-2.15 (m, 1 H), 0.96-1.16 (m, 4 H) | 398.2 $[M + H]^+$ | 98.1% |
| 1608 | ($CD_3OD$) δ 7.60-7.82 (m, 3 H), 7.35-7.59 (m, 1 H), 6.97-7.33 (m, 4 H), 6.62-6.85 (m, 1 H), 5.09 (br dd, 1 H), 4.33 (br d, 3 H), 3.86-4.02 (m, 0.6 H), 3.37-3.43 (m, 0.4 H), 2.84-3.25 (m, 2 H) | 466.1 $[M + H]^+$ | 100% |
| 1609 | ($CD_3OD$) δ 7.49-7.70 (m, 3 H), 7.24-7.47 (m, 1 H), 6.85-7.21 (m, 4 H), 6.49-6.70 (m, 1 H), 4.85-5.01 (m, 1 H), 4.21 (br d, 3 H), 3.73-3.89 (m, 0.6 H), 3.25-3.33 (m, 0.4 H), 2.73-3.13 (m, 2 H) | 466.2 $[M + H]^+$ | 95.3% |
| 1610 | ($CD_3OD$) δ 8.68 (d, 2 H), 8.12 (d, 1 H), 8.00 (td, 1 H), 7.84 (s, 1 H), 7.48-7.66 (m, 2 H), 6.76-7.03 (m, 2 H), 6.58 (s, 1 H), 4.48 (dd, 1 H), 3.80 (ddd, 1 H), 3.00-3.21 (m, 1 H), 2.87 (dd, 1 H) | 453.2 $[M + H]^+$ | 98.9% |
| 1611 | ($CD_3OD$) δ 8.57-8.78 (m, 2 H), 8.12 (d, 1 H), 8.00 (td, 1 H), 7.69 (s, 1 H), 7.49-7.64 (m, 2 H), 6.76-7.03 (m, 2 H), 6.55 (br s, 1 H), 4.47 (dd, 1 H), 3.80 (ddd, 1 H), 2.67-3.21 (m, 2 H) | 453.2 $[M + H]^+$ | 99.7% |
| 1612 | ($CD_3OD$) δ 8.69 (d, 1 H), 8.33 (d, 1 H), 8.13 (d, 1 H), 8.01 (td, 1 H), 7.70 (s, 1 H), 7.55 (dd, 1 H), 6.95 (dd, 1 H), 6.77-6.86 (m, 2 H), 6.54 (s, 1 H), 4.47 (dd, 1 H), 3.75-3.86 (m, 1 H), 3.03-3.16 (m, 1 H), 2.86 (br dd, 1 H) | 403.2 $[M + H]^+$ | 100% |
| 1613 | ($CD_3OD$) δ 8.68 (d, 1 H), 8.32 (d, 1 H), 8.12 (d, 1 H), 7.99 (td, 1 H), 7.71 (s, 1 H), 7.51-7.57 (m, 1 H), 6.94 (dd, 1 H), 6.75-6.84 (m, 2 H), 6.53 (s, 1 H), 4.45 (dd, 1 H), 3.75-3.86 (m, 1 H), 3.03-3.15 (m, 1 H), 2.84 (dd, 1 H) | 403.2 $[M + H]^+$ | 99.6% |
| 1614 | ($CD_3OD$) δ 8.12-9.01 (m, 2 H), 8.07 (d, 1 H), 7.86 (d, 1 H), 7.57-7.72 (m, 2 H), 7.42 (dd, 1 H), 6.41-7.07 (m, 3 H), 4.65 (br s, 1 H), 3.79-3.95 (m, 4 H), 3.40-3.78 (m, 1 H), 3.02-3.17 (m, 5 H), 2.77 (br d, 1 H) | 537.3 $[M + H]^+$ | 99.2% |
| 1615 | ($CD_3OD$) δ 8.12-8.93 (m, 2 H), 8.09 (d, 1 H), 7.86 (d, 1 H), 7.57-7.70 (m, 2 H), 7.44 (dd, 1 H), 6.43-7.08 (m, 3 H), 4.65 (br s, 1 H), 3.82-3.90 (m, 4 H), 3.38-3.80 (m, 1 H), 3.03-3.16 (m, 5 H), 2.78 (br d, 1 H) | 537.2 $[M + H]^+$ | 99.7% |
| 1616 | ($CD_3OD$) δ 8.42 (d, 2 H), 8.32 (d, 1 H), 7.65 (s, 1 H), 7.19 (s, 1 H), 6.95 (dd, 1 H), 6.72-6.82 (m, 1 H), 6.62-6.70 (m, 2 H), 5.03-5.13 (m, 1 H), 3.42-3.55 (m, 1 H), 2.83-2.99 (m, 1 H), 2.71 (br dd, 1 H) | 336.1 $[M + H]^+$ | 100% |
| 1617 | ($CD_3OD$) δ 8.41 (d, 2 H), 8.32 (d, 1 H), 7.64 (s, 1 H), 7.18 (s, 1 H), 6,94 (dd, 1 H), 6.75-6.84 (m, 1 H), 6.60-6.73 (m, 2 H), 5.06 (br dd, 1 H), 3.40-3.53 (m, 1 H), 2.82-2.97 (m, 1 H), 2.71 (br dd, 1 H) | 336.2 $[M + H]^+$ | 90.7% |
| 1618 | ($CD_3OD$) δ 8.41 (d, 2 H), 8.28 (br d, 1 H), 7.64 (s, 1 H), 7.20 (s, 1 H), 6.96 (d, 1 H), 6.75 (t, 1 H), 6.65 (t, 1 H), 6.53 (s, 1 H), 5.03 (br dd, 1 H), 3.47 (ddd, 1 H), 2.83-3.04 (m, 1 H), 2.70 (br dd, 1 H), 2.43 (s, 3 H) | 332.2 $[M + H]^+$ | 100% |
| 1619 | ($CD_3OD$) δ 8.28 (d, 2 H), 8.16 (br d, 1 H), 7.52 (s, 1 H), 7.08 (s, 1 H), 6.83 (br d, 1 H), 6.62 (t, 1 H), 6.52 (t, 1 H), 6.41 (s, 1 H), 4.91 (br dd, 1 H), 3.29-3.40 (m, 1 H), 2.72-2.86 (m, 1 H), 2.57 (br dd, 1 H), 2.30 (s, 3 H) | 332.1 $[M + H]^+$ | 97.3% |
| 1620 | (500 MHz, $CD_3OD$) δ 8.88 (s, 1 H), 8.05-8.80 (m, 2 H), 7.85-7.96 (m, 1 H), 7.77 (dd, 1 H), 7.51-7.64 (m, 2 H), 6.23-7.01 (m, 5 H), 4.52 (br s, 1 H), 3.81-3.89 (m, 3 H), 3.28-3.77 (m, 1 H), 2.91-3.04 (m, 1 H), 2.67 (br d, 1 H), 2.34 (s, 3 H) | 478.2 $[M + H]^+$ | 100% |
| 1621 | (500 MHz, $CD_3OD$) δ 9.01 (s, 1 H), 8.27-8.94 (m, 2 H), 8.01 (d, 1 H), 7.89 (dd, 1 H), 7.60-7.77 (m, 2 H), 6.39-7.09 (m, 5 H), 4.64 (br s, 1 H), 3.94-4.09 (m, 3 H), 3.43-3.89 (m, 1 H), 3.02-3.21 (m, 1 H), 2.79 (br d, 1 H), 2.38-2.61 (m, 3 H) | 478.2 $[M + H]^+$ | 98.8% |

TABLE 2-continued

| Ex. # | $^{1}$H NMR (400 MHz unless otherwise noted) | LCMS: m/z | % ee |
|---|---|---|---|
| 1622 | ($CD_3OD$) δ 8.69 (d, 1 H), 8.43 (d, 1 H), 8.13 (d, 1 H), 8.00 (t, 1 H), 7.68 (s, 1 H), 7.54 (dd, 1 H), 7.28 (d, 1 H), 6.83 (t, 1 H), 6.76 (s, 1 H), 6.53 (br s, 1 H), 4.46 (dd, 1 H), 3.79 (td, 1 H), 2.99-3.17 (m, 1 H), 2.84 (br d, 1 H) | 419.1 $[M + H]^+$ | 100% |
| 1623 | ($CD_3OD$) δ 8.68 (d, 1 H), 8.43 (d, 1 H), 8.13 (d, 1 H), 8.00 (t, 1 H), 7.68 (s, 1 H), 7.44-7.57 (m, 1 H), 7.28 (d, 1 H), 6.82 (t, 1 H), 6.76 (s, 1 H), 6.53 (s, 1 H), 4.46 (dd, 1 H), 3.71-3.86 (m, 1 H), 3.02-3.17 (m, 1 H), 2.84 (dd, 1 H) | 419.1 $[M + H]^+$ | 99.0% |
| 1624 | ($CD_3OD$) δ 8.26-8.85 (m, 3 H), 7.97 (d, 1 H), 7.68 (s, 1 H), 7.43-7.52 (m, 1 H), 6.37-7.14 (m, 4 H), 4.63-4.87 (m, 1 H), 3.58 (s, 3 H), 3.03-3.18 (m, 1 H), 2.70-2.85 (m, 1 H), 2.47 (s, 3 H), 2.32 (s, 6 H) | 455.3 $[M + H]^+$ | 97.4% |
| 1625 | ($CD_3OD$) δ 8.24-9.00 (m, 3 H), 7.97 (d, 1 H), 7.68 (s, 1 H), 7.48 (dd, 1 H), 6.28-7.14 (m, 4 H), 4.64-4.88 (m, 1 H), 3.58 (s, 3 H), 3.00-3.16 (m, 1 H), 2.69-2.86 (m, 1 H), 2.46 (s, 3 H), 2.32 (s, 6 H) | 455.3 $[M + H]^+$ | 99.0% |
| 1626 | ($CD_3OD$) δ 8.61-8.82 (m, 1 H), 8.12 (d, 1 H), 7.99 (td, 1 H), 7.72 (dd, 1 H), 7.67 (s, 1 H), 7.54 (ddd, 1 H), 7.20-7.50 (m, 2 H), 7.16 (d, 1 H), 6.73 (s, 1 H), 6.53 (s, 1 H), 4.45 (dd, 1 H), 3.85 (ddd, 1 H), 3.01-3.15 (m, 1 H), 2.85 (dd, 1 H) | 435.1 $[M + H]^+$ | 100% |
| 1627 | ($CD_3OD$) δ 8.69 (br s, 1 H), 8.13 (br d, 1 H), 8.01 (br t, 1 H), 7.64-7.81 (m, 2 H), 7.55 (br s, 1 H), 7.21-7.50 (m, 2 H), 7.17 (br d, 1 H), 6.74 (s, 1 H), 6.54 (br d, 1 H), 4.46 (br dd, 1 H), 3.78-3.97 (m, 1 H), 3.01-3.22 (m, 1 H), 2.76-2.95 (m, 1 H) | 435.2 $[M + H]^+$ | 99.0% |
| 1628 | Data provided above | | |
| 1629 | Data provided above | | |
| 1630 | ($CD_3OD$) δ 8.24-8.97 (m, 3 H), 8.08 (s, 1 H), 7.85-8.03 (m, 2 H), 7.59-7.73 (m, 2 H), 6.41-7.11 (m, 4 H), 4.63 (br s, 1 H), 3.95 (s, 3 H), 3.39-3.83 (m, 1 H), 3.00-3.16 (m, 1 H), 2.77 (br d, 1 H), 2.44 (s, 3 H) | 478.2 $[M + H]^+$ | 100% |
| 1631 | ($CD_3OD$) δ 8.29-8.96 (m, 3 H), 8.11 (s, 1 H), 7.88-8.04 (m, 2 H), 7.63-7.77 (m, 2 H), 6.45-7.12 (m, 4 H), 4.69-4.86 (m, 1 H), 3.97 (s, 3 H), 3.05-3.16 (m, 1 H), 2.80 (br d, 1 H), 2.46 (s, 3 H) | 478.2 $[M + H]^+$ | 98.7% |
| 1632 | ($CD_3OD$) δ 9.03 (s, 1 H), 8.02 (d, 1 H), 7.90 (dd, 2 H), 7.63-7.76 (m, 2 H), 7.24-7.51 (m, 2 H), 6.76 (d, 2 H), 4.56-4.75 (m, 2 H), 3.98 (s, 3 H), 2.98-3.18 (m, 1 H), 2.78 (dd, 1 H) | 532.2 $[M + H]^+$ | 100% |
| 1633 | ($CD_3OD$) δ 9.03 (s, 1 H), 8.03 (d, 1 H), 7.91 (dd, 2 H), 7.63-7.82 (m, 2 H), 7.28-7.50 (m, 2 H), 6.77 (d, 2 H), 4.56-4.73 (m, 2 H), 3.98 (s, 3 H), 3.01-3.19 (m, 1 H), 2.80 (dd, 1 H) | 532.2 $[M + H]^+$ | 100% |
| 1634 | ($CD_3OD$) δ 8.22-9.20 (m, 3 H), 8.01 (d, 1 H), 7.71 (s, 1 H), 7.50 (dd, 1 H), 7.33 (d, 1 H), 6.89 (br t, 3 H), 4.62-4.72 (m, 1 H), 3.92 (s, 2 H), 3.37-3.60 (m, 1 H), 3.00-3.18 (m, 1 H), 2.80 (br dd, 1 H), 2.56 (s, 6 H) | 475.2 $[M + H]^+$ | 98.0% |
| 1635 | ($CD_3OD$) δ 8.23-9.22 (m, 3 H), 8.01 (d, 1 H), 7.71 (s, 1 H), 7.50 (dd, 1 H), 7.33 (d, 1 H), 6.89 (s, 3 H), 4.60-4.73 (m, 1 H), 3.94 (s, 2 H), 3.36-3.58 (m, 1 H), 3.02-3.18 (m, 1 H), 2.72-2.88 (m, 1 H), 2.58 (s, 6 H) | 475.2 $[M + H]^+$ | 100% |
| 1636 | ($CD_3OD$) δ 8.68 (d, 1 H), 8.28 (d, 1 H), 8.13 (d, 1 H), 8.00 (td, 1 H), 7.68 (s, 1 H), 7.54 (ddd, 1 H), 6.97 (d, 1 H), 6.76 (t, 1 H), 6.64 (s, 1 H), 6.52 (s, 1 H), 4.43 (dd, 1 H), 3.71-3.86 (m, 1 H), 3.01-3.15 (m, 1 H), 2.83 (br dd, 1 H), 2.42 (s, 3 H) | 399.2 $[M + H]^+$ | 99.6% |
| 1637 | ($CD_3OD$) δ 8.69 (d, 1 H), 8.29 (br d, 1 H), 8.13 (d, 1 H), 8.00 (td, 1 H), 7.68 (s, 1 H), 7.40-7.59 (m, 1 H), 6.97 (br d, 1 H), 6.77 (t, 1 H), 6.64 (s, 1 H), 6.52 (br s, 1 H), 4.44 (dd, 1 H), 3.69-3.86 (m, 1 H), 3.01-3.18 (m, 1 H), 2.84 (br dd, 1 H), 2.43 (s, 3 H) | 399.2 $[M + H]^+$ | 99.6% |
| 1638 | ($CD_3OD$) δ 8.68 (d, 1 H), 8.13 (d, 1 H), 8.00 (td, 1 H), 7.67 (s, 1 H), 7.52-7.62 (m, 2 H), 7.16 (dd, 1 H), 6.98-7.05 (m, 1 H), 6.76 (s, 1 H), 6.54 (s, 1 H), 4.45 (dd, 1 H), 3.87 (td, 1 H), 3.04-3.15 (m, 1 H), 2.85 (dd, 1 H) | 419.1 $[M + H]^+$ | 100% |
| 1639 | ($CD_3OD$) δ 8.68 (d, 1 H), 8.13 (d, 1 H), 8.00 (td, 1 H), 7.67 (s, 1 H), 7.59 (d, 1 H), 7.54 (dd, 1 H), 7.16 (dd, 1 H), 7.01 (d, 1 H), 6.76 (s, 1 H), 6.54 (s, 1 H), 4.45 (dd, 1 H), 3.82-3.92 (m, 1 H), 3.03-3.15 (m, 1 H), 2.85 (dd, 1 H) | 419.1 $[M + H]^+$ | 95.0% |
| 1640 | ($CD_3OD$) δ 8.68 (br d, 1 H), 8.12 (d, 1 H), 7.99 (td, 1 H), 7.74 (br s, 1 H), 7.54 (ddd, 1 H), 7.45 (d, 1 H), 7.09 (dd, 1 H), 6.87 (s, 1 H), 6.36-6.64 (m, 2 H), 4.43 (dd, 1 H), 3.74-3.99 (m, 1 H), 2.98-3.22 (m, 1 H), 2.85 (br d, 1 H), 2.56-2.67 (m, 3 H) | 399.2 $[M + H]^+$ | 98.5% |
| 1641 | ($CD_3OD$) δ 8.67 (d, 1 H), 8.11 (d, 1 H), 7.99 (td, 1 H), 7.66 (s, 1 H), 7.50-7.58 (m, 1 H), 7.44 (d, 1 H), 7.08 (dd, 1 H), 6.68 (d, 1 H), 6.45-6.61 (m, 2 H), 4.42 (dd, 1 H), 3.85 (td, 1 H), 2.98-3.15 (m, 1 H), 2.83 (br dd, 1 H), 2.60 (s, 3 H) | 399.2 $[M + H]^+$ | 96.8% |
| 1642 | ($CD_3OD$) δ 8.29 (d, 1 H), 7.68 (s, 1 H), 7.39 (d, 1 H), 7.31 (d, 1 H), 7.18 (td, 1 H), 7.03-7.12 (m, 1 H), 6.96 (d, 1 H), 6.76 (t, 1 H), 6.60 (d, 2 H), 4.54 (dd, 1 H), 3.73 (ddd, 1 H), 2.98-3.13 (m, 1 H), 2.82 (dd, 1 H), 2.42 (s, 3 H) | 371.2 $[M + H]^+$ | 99.7% |
| 1643 | ($CD_3OD$) δ 8.28 (d, 1 H), 7.67 (s, 1 H), 7.38 (d, 1 H), 7.31 (d, 1 H), 7.18 (td, 1 H), 7.04-7.11 (m, 1 H), 6.96 (d, 1 H), 6.75 (t, 1 | 371.2 $[M + H]^+$ | 98.0% |

TABLE 2-continued

| Ex. # | $^1$H NMR (400 MHz unless otherwise noted) | LCMS: m/z | % ee |
|---|---|---|---|
| | H), 6.55-6.65 (m, 2 H), 4.54 (dd, 1 H), 3.73 (ddd, 1 H), 2.98-3.13 (m, 1 H), 2.82 (dd, 1 H), 2.42 (s, 3 H) | | |
| 1644 | ($CD_3OD$) δ 9.24 (s, 1 H), 8.75-8.96 (m, 1 H), 8.25-8.45 (s, 1 H), 7.99-8.10 (m, 2 H), 7.84-7.97 (m, 2 H), 7.72 (s, 1 H), 7.31-7.45 (m, 1 H), 6.49-7.09 (m, 4 H), 4.67-4.88 (m, 1 H), 3.37-3.96 (m, 1 H), 3.02-3.19 (m, 1 H), 2.78 (br dd, 1 H) | 479.2 $[M + H]^+$ | 99.3% |
| 1645 | ($CD_3OD$) δ 9.18 (s, 1 H), 8.24-8.59 (m, 4 H), 7.80-8.04 (m, 4 H), 7.25-7.37 (m, 1 H), 6.61-6.96 (m, 4 H), 4.58 (br s, 1 H), 3.30-3.68 (m, 1 H), 2.98-3.16 (m, 1 H), 2.78 (br dd, 1 H) | 479.2 $[M + H]^+$ | 99.1% |
| 1646 | ($CD_3OD$) δ 9.01 (s, 1 H), 8.16-8.90 (m, 2 H), 8.02 (d, 1 H), 7.90 (dd, 1 H), 7.60-7.74 (m, 2 H), 6.49-7.07 (m, 5 H), 4.62 (br s, 1 H), 3.97 (s, 3 H), 3.41-3.86 (m, 1 H), 3.00-3.22 (m, 1 H), 2.80 (br dd, 1 H) | 482.2 $[M + H]^+$ | 94.3% |
| 1647 | ($CD_3OD$) δ 9.02 (s, 1 H), 8.44 (br s, 2 H), 8.02 (dd, 1 H), 7.91 (dd, 1 H), 7.59-7.78 (m, 2 H), 6.49-7.15 (m, 5 H), 4.62 (s, 1 H), 3.98 (s, 3 H), 3.42-3.90 (m, 1 H), 3.02-3.21 (m, 1 H), 2.69-2.89 (m, 1 H) | 482.2 $[M + H]^+$ | 98.6% |
| 1648 | ($CD_3OD$) δ 9.27 (s, 1 H), 8.22-9.01 (m, 3 H), 7.89-8.11 (m, 4 H), 7.67 (s, 1 H), 7.29-7.45 (m, 1 H), 6.35-7.11 (m, 4 H), 4.64-4.79 (m, 1 H), 3.40-3.84 (m, 1 H), 3.02-3.18 (m, 1 H), 2.70-2.86 (m, 1 H), 2.44 (s, 3 H) | 475.2 $[M + H]^+$ | 96.4% |
| 1649 | ($CD_3OD$) δ 9.30 (s, 1 H), 8.23-9.07 (m, 3 H), 7.91-8.12 (m, 4 H), 7.70 (s, 1 H), 7.35-7.45 (m, 1 H), 6.45-7.06 (m, 4 H), 4.66-4.81 (m, 1 H), 3.39-4.00 (m, 1 H), 3.05-3.16 (m, 1 H), 2.80 (br d, 2 H), 2.37-2.52 (m, 3 H) | 475.2 $[M + H]^+$ | 97.5% |
| 1650 | ($CD_3OD$) δ 8.43-8.76 (m, 3 H), 7.98 (d, 1 H), , 7.68-7.69 (m, 1 H), 7.40-7.40 (m, 1 H), 7.33 (d, 1 H), 6.57-7.02 (m, 3 H), 4.94-5.07 (m, 1 H), 4.55 (s, 2 H), 3.40-3.78 (m, 4 H), 3.04-3.18 (m, 1 H), 2.80 (br dd, 1 H) | 462.1 $[M + H]^+$ | 96.2% |
| 1651 | ($CD_3OD$) δ 8.37-8.83 (m, 3 H), 7.91-8.02 (m, 1 H), 7.66-7.79 (m, 1 H), 7.41-7.49 (m, 1 H), 7.32 (d, 1 H), 6.56-6.99 (m, 3 H), 4.93-4.60-4.75 (m, 1 H), 4.54 (s, 2 H), 3.38-3.87 (m, 4 H), 3.03-3.16 (m, 1 H), 2.80 (br dd, 1 H) | 462.1 $[M + H]^+$ | 98.9% |
| 1652 | ($CD_3OD$) δ 8.51 (d, 1 H), 8.02-8.42 (d, 1 H), 7.72 (s, 1 H), 7.52 (s, 0.3 H), 7.29 (d, 1 H), 6.97 (s, 0.7 H), 6.52-6.86 (m, 3 H), 5.02-5.10 (m, 1 H), 3.91-4.01 (m, 3 H), 3.74-3.84 (m, 0.7 H), 3.38-3.46 (m, 0.3 H), 3.14-3.25 (m, 0.7 H), 3.02 (ddd, 0.3 H), 2.77-2.91 (m, 1 H) | 500.1 $[M + H]^+$ | 99.7% |
| 1653 | ($CD_3OD$) δ 8.50 (d, 1 H), 7.92-8.22 (d, 1 H),7.72 (s, 1 H), 7.50 (s, 0.3 H), 7.30 (d, 1 H), 6.97 (s, 0.7 H), 6.48-6.76 (m, 3 H), 4.92-5.15 (m, 1 H), 3.94-4.06 (m, 3 H), 3.71-3.80 (m, 0.7 H), 3.35-3.43 (m, 0.3 H), 3.10-3.24 (m, 0.7 H), 3.03 (ddd, 0.3 H), 2.77-2.91 (m, 1 H) | 500.1 $[M + H]^+$ | 99.4% |
| 1654 | ($CD_3OD$) δ 8.36 (br d, 1 H), 7.71 (br s, 1 H), 7.46 (br s, 0.3 H), 7.18-7.28 (m, 0.2 H), 7.02-7.07 (m, 0.5 H), 6.95-7.02 (m, 1 H), 6.81-6.95 (m, 2 H), 6.63-6.79 (m, 1 H), 5.01 (br dd, 0.4 H), 4.85-4.87 (m, 0.6 H), 3.64-3.81 (m, 0.7 H), 3.37-3.42 (m, 0.3 H), 2.92-3.22 (m, 1 H), 2.85 (br s, 1 H), 2.27-2.38 (m, 1 H), 1.20-1.32 (m, 4 H) | 442.1 $[M + H]^+$ | 97.4% |
| 1655 | ($CD_3OD$) δ 8.28-8.51 (m, 1 H), 7.70 (s, 1 H), 7.46 (br s, 0.3 H), 7.18-7.26 (m, 0.2 H), 7.02-7.09 (m, 0.5 H), 6.95-7.02 (m, 1 H), 6.81-6.95 (m, 2 H), 6.65-6.77 (m, 1 H), 5.01 (br dd, 0.5 H), 4.84-4.87 (m, 0.5 H), 3.66-3.82 (m, 0.7 H), 3.38-3.44 (m, 0.3 H), 2.91-3.23 (m, 1 H), 2.83 (br d, 1 H), 2.28-2.42 (m, 1 H), 1.19-1.32 (m, 4 H) | 442.2 $[M + H]^+$ | 95.2% |
| 1656 | ($CD_3OD$) δ 8.63-8.69 (m, 1 H), 8.28-8.42 (m, 1 H), 7.89-8.00 (m, 1 H), 7.68-7.81 (m, 2 H), 7.20-7.50 (m, 0.7 H), 6.92-7.07 (m, 2 H), 6.74-6.90 (m, 2.3 H), 4.94-5.03 (m, 1 H), 3.81 (ddd, 0.7 H), 3.45 (td, 0.3 H), 2.98-3.29 (m, 1 H), 2.87 (br dd, 1 H) | 497.1 $[M + H]^+$ | 100% |
| 1657 | ($CD_3OD$) δ 8.50-8.59 (m, 1 H), 8.16-8.30 (m, 1 H), 7.83 (t, 1 H), 7.57-7.70 (m, 2 H), 7.05-7.40 (m, 0.7 H), 6.82-6.97 (m, 2 H), 6.60-6.81 (m, 2.3 H), 4.84-4.92 (m, 1 H), 3.63-3.75 (m, 0.7 H), 3.33 (td, 0.3 H), 2.85-3.17 (m, 1 H), 2.76 (br dd, 1 H) | 497.1 $[M + H]^+$ | 99.4% |
| 1658 | ($CD_3OD$) δ 8.30-8.40 (m, 1 H), 7.97-8.05 (m, 1 H), 7.71 (s, 1 H), 7.57 (s, 0.3 H), 7.19-7.25 (m, 0.2 H), 6.70-7.07 (m, 4.5 H), 4.94-5.17 (m, 1 H), 3.90 (s, 3 H), 3.72-3.83 (m, 0.7 H), 3.35-3.46 (m, 0.3 H), 2.96-3.26 (m, 1 H), 2.80-2.91 (m, 1 H), 2.63-2.73 (m, 3 H) | 496.2 $[M + H]^+$ | 98.9% |
| 1659 | ($CD_3OD$) δ 8.28-8.41 (m, 1 H), 7.96-8.06 (m, 1 H), 7.71 (s, 1 H), 7.57 (s, 0.3 H), 7.17-7.27 (m, 0.2 H), 6.68-7.09 (m, 4.5 H), 4.94-5.16 (m, 1 H), 3.90 (s, 3 H), 3.71-3.83 (m, 0.7 H), 3.36-3.47 (m, 0.3 H), 2.95-3.26 (m, 1 H), 2.78-2.92 (m, 1 H), 2.62-2.75 (m, 3 H) | 496.2 $[M + H]^+$ | 99.4% |
| 1660 | ($CD_3OD$) δ 8.89-9.00 (m, 1 H), 8.29-8.43 (m, 2 H), 7.49-7.87 (m, 2.3 H), 7.18-7.30 (m, 0.2 H), 6.66-7.09 (m, 4.5 H), 4.95-5.15 (m, 1 H), 3.73-3.86 (m, 0.7 H), 3.42 (td, 0.3 H), 2.95-3.27 (m, 1 H), 2.87 (br dd, 1 H) | 518.1 $[M + H]^+$ | 100% |

TABLE 2-continued

| Ex. # | $^1$H NMR (400 MHz unless otherwise noted) | LCMS: m/z | % ee |
|---|---|---|---|
| 1661 | ($CD_3OD$) δ 8.77-8.85 (m, 1 H), 8.17-8.28 (m, 2 H), 7.37-7.73 (m, 2.3 H), 7.07-7.14 (m, 0.2 H), 6.55-6.96 (m, 4.5 H), 4.81-5.03 (m, 1 H), 3.61-3.72 (m, 0.7 H), 3.30 (td, 0.3 H), 2.83-3.14 (m, 1 H), 2.74 (br d, 1 H) | 518.2 $[M + H]^+$ | 100% |
| 1662 | ($CD_3OD$) δ 8.21-8.52 (m, 2 H), 7.84 (s, 0.3 H), 7.66-7.76 (m, 1.5 H), 7.48-7.59 (m, 0.5 H), 7.18-7.29 (m, 1.2 H), 6.94-7.08 (m, 2.2 H), 6.81-6.91 (m, 1.3 H), 6.70-6.79 (m, 1 H), 5.06 (dd, 0.8 H), 4.96 (br s, 0.2 H), 3.74-3.87 (m, 0.7 H), 3.43 (td, 0.3 H), 2.95-3.28 (m, 1 H), 2.87 (br d, 1 H) | 518.1 $[M + H]^+$ | 100% |
| 1663 | ($CD_3OD$) δ 8.27-8.48 (m, 2 H), 7.84 (s, 0.3 H), 7.71 (d, 1.4 H), 7.49-7.63 (m, 0.6 H), 7.19-7.28 (m, 1.2 H), 6.93-7.08 (m, 2.1 H), 6.80-6.91 (m, 1.3 H), 6.70-6.79 (m, 1 H), 5.06 (dd, 0.7 H), 4.96 (br s, 0.3 H), 3.74-3.88 (m, 0.7 H), 3.42 (br t, 0.3 H), 2.97-3.27 (m, 1 H), 2.87 (br d, 1 H) | 518.2 $[M + H]^+$ | 99.4% |
| 1664 | ($CD_3OD$) δ 8.30 (d, 3 H), 7.53 (s, 1 H), 7.01-7.20 (m, 2 H), 6.69 (t, 1 H), 6.47-6.61 (m, 2 H), 4.95 (br dd, 1 H), 3.35 (td, 1 H), 2.70-2.87 (m, 1 H), 2.59 (br dd, 1 H) | 352.1 $[M + H]^+$ | 99.0% |
| 1665 | ($CD_3OD$) δ 8.27-8.49 (m, 3 H), 7.64 (s, 1 H), 7.11-7.34 (m, 2 H), 6.81 (t, 1 H), 6.58-6.71 (m, 2 H), 5.06 (br dd, 1 H), 3.37-3.53 (m, 1 H), 2.81-2.99 (m, 1 H), 2.70 (br dd, 1 H) | 352.1 $[M + H]^+$ | 98.5% |
| 1666 | ($CD_3OD$) δ 8.79 (br d, 1 H), 8.22-8.66 (m, 2 H), 7.89 (d, 1 H), 7.63-7.72 (m, 2 H), 7.35 (dd, 1 H), 6.62-7.06 (m, 3 H), 4.61-4.72 (m, 1 H), 3.35-3.88 (m, 1 H), 3.05-3.14 (m, 1 H), 2.79 (br dd, 1 H), 2.41 (s, 3 H) | 466.2 $[M + H]^+$ | 98.8% |
| 1667 | ($CD_3OD$) δ 8.78 (br d, 1 H), 8.21-8.67 (m, 2 H), 7.89 (d, 1 H), 7.63-7.72 (m, 2 H), 7.34 (dd, 1 H), 6.60-7.09 (m, 3 H), 4.61-4.72 (m, 1 H), 3.36-3.85 (m, 1 H), 3.05-3.14 (m, 1 H), 2.79 (dd, 1 H), 2.40 (s, 3 H) | 466.1 $[M + H]^+$ | 98.5% |
| 1668 | ($CD_3OD$) δ 8.32-8.61 (m, 3 H), 7.89 (d, 1 H), 7.67 (s, 1 H), 7.32-7.35 (m, 1 H), 7.00 (d, 1 H), 6.49-6.83 (m, 3 H), 4.61-4.74 (m, 1 H), 3.40-3.75 (m, 1 H), 3.03-3.12 (m, 1 H), 2.78 (br dd, 1 H), 2.45 (s, 3 H), 2.40 (s, 3 H) | 412.2 $[M + H]^+$ | 98.6% |
| 1669 | ($CD_3OD$) δ 8.33-8.68 (m, 3 H), 7.90 (d, 1 H), 7.67 (s, 1 H), 7.34 (d, 1 H), 7.01 (d, 1 H), 6.43-6.89 (m, 3 H), 4.61-4.75 (m, 1 H), 3.35-3.79 (m, 1 H), 3.03-3.12 (m, 1 H), 2.78 (br dd, 1 H), 2.46 (s, 3 H), 2.40 (s, 3 H) | 412.2 $[M + H]^+$ | 96.8% |
| 1670 | ($CD_3OD$) δ 8.20-8.65 (m, 3 H), 7.89 (d, 1 H), 7.68 (s, 1 H), 7.33 (d, 1 H), 6.61-7.01 (m, 4 H), 4.63 (br dd, 1 H), 3.44-3.80 (m, 1 H), 3.04-3.15 (m, 1 H), 2.78 (br dd, 1 H), 2.40 (s, 3 H) | 416.2 $[M + H]^+$ | 98.5% |
| 1671 | ($CD_3OD$) δ 8.20-8.69 (m, 3 H), 7.89 (d, 1 H), 7.62-7.73 (m, 1 H), 7.34 (dd, 1 H), 6.60-7.03 (m, 4 H), 4.56-4.72 (m, 1 H), 3.37-3.80 (m, 1 H), 3.04-3.15 (m, 1 H), 2.79 (br dd, 1 H), 2.40 (s, 3 H) | 416.2 $[M + H]^+$ | 99.6% |
| 1672 | ($CD_3OD$) δ 8.43 (br s, 3 H), 7.87 (br d, 1 H), 7.66 (s, 1 H), 7.16-7.39 (m, 1 H), 6.49-7.03 (m, 4 H), 4.62-4.69 (m, 1 H), 3.40-3.96 (m, 1 H), 2.96-3.18 (m, 1 H), 2.77 (br d, 1 H), 1.89-2.14 (m, 1 H), 0.90-1.12 (m, 2 H), 0.61-0.83 (m, 2 H) | 442.2 $[M + H]^+$ | 96.1% |
| 1673 | ($CD_3OD$) δ 8.43 (s, 3 H), 7.87 (d, 1 H), 7.66 (s, 1 H), 7.21 (dd, 1 H), 6.41-7.08 (m, 4 H), 4.62-4.70 (m, 1 H), 3.42-3.97 (m, 1 H), 2.92-3.16 (m, 1 H), 2.77 (br d, 1 H), 1.83-2.18 (m, 1 H), 0.94-1.10 (m, 2 H), 0.67-0.88 (m, 2 H) | 442.2 $[M + H]^+$ | 99.5% |
| 1674 | (DMSO-$d_6$) δ 12.04 (br s, 1 H), 9.01 (br s, 1 H), 8.17-8.66 (m, 2 H), 7.52-7.87 (m, 3 H), 6.47-7.35 (m, 4 H), 4.33-4.66 (m, 1 H), 3.84 (s, 3 H), 3.16-3.32 (m, 1 H), 2.61-3.08 (m, 2 H) | 482.1 $[M + H]^+$ | 100% |
| 1675 | (DMSO-$d_6$) δ 12.04 (br s, 1 H), 9.01 (br s, 1 H), 8.24-8.62 (m, 2 H), 7.52-8.00 (m, 3 H), 6.34-7.35 (m, 4 H), 4.40-4.63 (m, 1 H), 3.84 (s, 3 H), 3.31-3.33 (m, 1 H), 2.57-3.07 (m, 2 H) | 482.2 $[M + H]^+$ | 100% |
| 1676 | (DMSO-$d_6$) δ 11.93-12.14 (m, 1 H), 8.88 (br s, 1 H), 8.51 (d, 2 H), 7.85 (d, 1 H), 7.39-7.61 (m, 2 H), 7.12-7.31 (m, 2 H), 6.97 (br s, 1 H), 6.49-6.79 (m, 2 H), 4.38-4.63 (m, 1 H), 3.85 (s, 4 H), 2.65-3.06 (m, 2 H) | 464.2 $[M + H]^+$ | 99.0% |
| 1677 | (DMSO-$d_6$) δ 11.89-12.99 (m, 1 H), 8.88 (br s, 1 H), 8.27-8.56 (m, 2 H), 7.62-7.91 (m, 2 H), 7.38-7.57 (m, 1 H), 7.09-7.34 (m, 2 H), 6.98 (br t, 1 H), 6.70 (br s, 2 H), 4.30-4.67 (m, 1 H), 3.85 (s, 4 H), 2,64-3.05 (m, 2 H) | 464.2 $[M + H]^+$ | 99.0% |
| 1678 | ($CD_3OD$) δ 8.28-8.94 (m, 2 H), 7.95 (t, 1 H), 7.62-7.86 (m, 2 H), 7.35-7.60 (m, 0.4 H), 7.10-7.34 (m, 1 H), 6.71-7.09 (m, 2.6 H), 5.01 (br dd, 1 H), 3.73-3.90 (m, 0.6 H), 3.42-3.49 (m, 0.4 H), 2.98-3.29 (m, 1 H), 2.88 (br d, 1 H) | 515.1 $[M + H]^+$ | 100% |
| 1679 | ($CD_3OD$) δ 8.18-8.76 (m, 2 H), 7.75-7.93 (m, 1 H), 7.50-7.74 (m, 2 H), 7.34 (br s, 0.4 H), 7.01-7.22 (m, 1 H), 6.51-7.00 (m, 2.6 H), 4.89 (br dd, 1 H), 3.59-3.81 (m, 0.6 H), 3.30-3.36 (m, 0.4 H), 2.86-3.17 (m, 1 H), 2.67-2.83 (m, 1 H) | 515.1 $[M + H]^+$ | 96.1% |
| 1680 | ($CD_3OD$) δ 9.48 (d, 1 H), 8.70-9.09 (m, 2 H), 8.35-8.63 (m, 1 H), 7.73 (s, 1 H), 7.51 (s, 0.4 H), 7.14-7.34 (m, 1 H), 6.76-7.02 (m, 2.6 H), 5.06 (br dd, 1 H), 3.72-3.92 (m, 0.6 H), 3.42-3.50 (m, 0.4 H), 2.98-3.30 (m, 1 H), 2.77-2.95 (m, 1 H) | 498.1 $[M + H]^+$ | 100% |

TABLE 2-continued

| Ex. # | $^1$H NMR (400 MHz unless otherwise noted) | LCMS: m/z | % ee |
|---|---|---|---|
| 1681 | ($CD_3OD$) δ 9.09-9.84 (m, 1 H), 8.72-9.06 (m, 2 H), 8.29-8.67 (m, 1 H), 7.72 (s, 1 H), 7.51 (br s, 0.4 H), 7.11-7.37 (m, 1 H), 6.58-7.09 (m, 2.6 H), 5.06 (br dd, 1 H), 3.77-3.87 (m, 0.6 H), 3.45 (br dd, 0.4 H), 3.22 (br d, 1 H), 2.88 (br d, 1 H) | 498.1 $[M + H]^+$ | 99.6% |
| 1682 | ($CD_3OD$) δ 8.35-8.54 (m, 2 H), 8.06-8.15 (m, 1 H), 7.73 (s, 1 H), 7.59 (s, 0.3 H), 7.12-7.28 (m, 1 H), 6.73-7.03 (m, 2.7 H), 5.12 (br dd, 1 H), 4.02 (s, 3 H), 3.44-3.83 (m, 1 H), 2.83-3.25 (m, 2 H) | 500.1 $[M + H]^+$ | 100% |
| 1683 | ($CD_3OD$) δ 8.27-8.40 (m, 2 H), 7.96-8.02 (m, 1 H), 7.62 (s, 1 H), 7.47 (s, 0.3 H), 7.05-7.13 (m, 1 H), 6.62-6.86 (m, 2.7 H), 5.00 (br dd, 1 H), 3.90 (s, 3 H), 3.32-3.72 (m, 1 H), 2.70-3.12 (m, 2 H) | 500.2 $[M + H]^+$ | 99.7% |
| 1684 | ($CD_3OD$) δ 8.43-8.53 (m, 1 H), 7.96-8.03 (m, 1 H), 7.71-7.79 (m, 1 H), 7.59 (s, 0.3 H), 7.17-7.25 (m, 1 H), 6.76-6,99 (m, 2.7 H), 5.13 (br dd, 1 H), 3.90 (s, 3 H), 3.43-3.81 (m, 1 H), 2.84-3.24 (m, 2 H), 2.63-2.71 (m, 3 H) | 514.2 $[M + H]^+$ | 99.8% |
| 1685 | ($CD_3OD$) δ 8.32-8.40 (m, 1 H), 7.85-7.93 (m, 1 H), 7.61 (s, 1 H), 7.46 (s, 0.3 H), 7.06-7.13 (m, 1 H), 6.63-6.86 (m, 2.7 H), 5.01 (br dd, 1 H), 3.75-3.83 (m, 3 H), 3.32-3.68 (m, 1 H), 2.74-3.13 (m, 2 H), 2.52-2.61 (m, 3 H) | 514.2 $[M + H]^+$ | 99.2% |
| 1686 | ($CD_3OD$) δ 8.28-8.41 (m, 1 H), 7.71 (br s, 1 H), 7.01-7.48 (m, 1 H), 6.81-7.01 (m, 3 H), 6.61-6.78 (m, 1 H), 4.93-5.03 (m, 1 H), 3.69-3.79 (m, 0.6 H), 3.36-3.45 (m, 0.4 H), 2.93-3.22 (m, 1 H), 2.84 (br dd, 1 H), 1.43-1.58 (m, 9 H) | 458.2 $[M + H]^+$ | 100% |
| 1687 | ($CD_3OD$) δ 8.28-8.41 (m, 1 H), 7.71 (s, 1 H), 7.01-7.46 (m, 1 H), 6.80-7.01 (m, 3 H), 6.64-6.78 (m, 1 H), 4.92-5.03 (m, 1 H), 3.74 (ddd, 0.6 H), 3.40 (td, 0.4 H), 2.93-3.23 (m, 1 H), 2.84 (dd, 1 H), 1.41-1.58 (m, 9 H) | 458.2 $[M + H]^+$ | 99.5% |
| 1688 | ($CD_3OD$) δ 8.76-8.81 (m, 1 H), 8.28-8.41 (m, 2 H), 8.10 (td, 1 H), 7.64-7.74 (m, 2 H), 7.04-7.54 (m, 1 H), 6.72-7.04 (m, 4 H), 4.94-5.07 (m, 1 H), 3.81 (ddd, 0.7 H), 3.45 (td, 0.3 H), 2.96-3.29 (m, 1 H), 2.87 (br d, 1 H) | 479.1 $[M + H]^+$ | 98.7% |
| 1689 | ($CD_3OD$) δ 8.63-8.71 (m, 1 H), 8.16-8.29 (m, 2 H), 7.98 (td, 1 H), 7.51-7.65 (m, 2 H), 6.92-7.43 (m, 1 H), 6.61-6.92 (m, 4 H), 4.81-4.95 (m, 1 H), 3.69 (ddd, 0.7 H), 3.33 (td, 0.3 H), 2.86-3.16 (m, 1 H), 2.66-2.80 (m, 1 H) | 479.1 $[M + H]^+$ | 98.4% |
| 1690 | (DMSO-$d_6$) δ 12.00 (br s, 1 H), 8.68 (s, 2 H), 7.91 (d, 1 H), 7.34-7.65 (m, 3 H), 6.24-7.25 (m, 4 H), 4.33-4.68 (m, 1 H), 3.38-4.08 (m, 3 H), 2.84-3.05 (m, 1 H), 2.69 (br s, 4 H), 2.17 (s, 6 H) | 455.2 $[M + H]^+$ | 100% |
| 1691 | (DMSO-$d_6$) δ 12.00 (br s, 1 H), 8.68 (s, 2 H), 7.91 (br d, 1 H), 7.31-7.61 (m, 3 H), 6.43-7.23 (m, 4 H), 4.31-4.65 (m, 1 H), 3.44 (s, 3 H), 2.94 (br s, 1 H), 2.69 (br s, 4 H), 2.17 (s, 6 H) | 455.2 $[M + H]^+$ | 100% |
| 1692 | ($CD_3OD$) δ 8.54 (br d, 1 H), 8.29 (d, 2 H), 7.41-7.60 (m, 2 H), 7.08 (s, 1 H), 6.74-6.92 (m, 1 H), 6.38-6.66 (m, 2 H), 4.96 (br dd, 1 H), 3.27-3.48 (m, 1 H), 2.70-2.88 (m, 1 H), 2.59 (br dd, 1 H) | 386.1 $[M + H]^+$ | 100% |
| 1693 | ($CD_3OD$) δ 8.54 (br d, 1 H), 8.29 (d, 2 H), 7.40-7.58 (m, 2 H), 7.09 (s, 1 H), 6.82 (br t, 1 H), 6.44-6.62 (m, 2 H), 4.96 (br dd, 1 H), 3.25-3.44 (m, 1 H), 2.70-2.91 (m, 1 H), 2.59 (br dd, 1 H) | 386.1 $[M + H]^+$ | 97.0% |
| 1694 | ($CD_3OD$) δ 8.42 (s, 1 H), 8.37 (br d, 1 H), 7.86 (d, 1 H), 7.65 (s, 1 H), 7.19 (d, 1 H), 6.99 (br d, 1 H), 6.79 (br t, 1 H), 6.53 (br s, 1 H), 4.60 (br s, 1 H), 3.37-3.91 (m, 1 H), 2.98-3.11 (m, 1 H), 2.70-2.89 (m, 1 H), 2.44 (s, 3 H), 1.93-2.06 (m, 1 H), 0.95-1.06 (m, 2 H), 0.70-0.82 (m, 2 H) | 438.2 $[M + H]^+$ | 100% |
| 1695 | ($CD_3OD$) δ 8.42 (s, 1 H), 8.37 (br s, 1 H), 7.87 (d, 1 H), 7.65 (s, 1 H), 7.20 (dd, 1 H), 6.99 (d, 1 H), 6.79 (t, 1 H), 6.53 (br s, 1 H), 4.60 (s, 1 H), 3.48 (s, 1 H), 2.97-3.13 (m, 1 H), 2.63-2.85 (m, 1 H), 2.44 (s, 3 H), 1.89-2.12 (m, 1 H), 0.97-1.14 (m, 2 H), 0.73-0.86 (m, 2 H) | 438.2 $[M + H]^+$ | 98.7% |
| 1696 | (DMSO-$d_6$) δ 12.02 (br s, 1 H), 8.19-8.77 (m, 3 H), 7.85 (dd, 1 H), 7.56 (d, 1 H), 7.04-7.33 (m, 2 H), 6.50-6,95 (m, 3 H), 4.26-4.74 (m, 1 H), 3.84 (d, 4 H), 2.61-3.08 (m, 2 H) | 432.2 $[M + H]^+$ | 100% |
| 1697 | (DMSO-$d_6$) δ 11.94-12.13 (m, 1 H), 8.20-8.75 (m, 3 H), 7.85 (d, 1 H), 7.57 (s, 1 H), 7.06-7.31 (m, 2 H), 6.47-6.91 (m, 3 H), 4.29-4.72 (m, 1 H), 3.84 (s, 3 H), 3.25-3.33 (m, 1 H), 2.62-3.05 (m, 2 H) | 432.2 $[M + H]^+$ | 100% |
| 1698 | (DMSO-$d_6$) δ 12.02 (br s, 1 H), 8.74 (br d, 1 H), 8.51 (s, 2 H), 7.85 (d, 1 H), 7.18-7.65 (m, 3 H), 6.30-7.02 (m, 3 H), 4.36-4.68 (m, 1 H), 3.85 (s, 3 H), 3.30 (br s, 1 H), 2.59-3.06 (m, 2 H) | 448.1 $[M + H]^+$ | 97.5% |
| 1699 | (DMSO-$d_6$) δ 12.02 (br s, 1 H), 8.73 (br s, 1 H), 8.51 (s, 2 H), 7.85 (d, 1 H), 7.18-7.65 (m, 3 H), 6.40-6.95 (m, 3 H), 4.30-4.67 (m, 1 H), 3.85 (s, 3 H), 3.29-3.32 (m, 1 H), 2.57-3.07 (m, 2 H) | 448.1 $[M + H]^+$ | 93.6% |
| 1700 | ($CD_3OD$) δ 8.34-8.55 (m, 2 H), 8.15 (dd, 1 H), 7.79 (d, 1 H), 7.63 (s, 1 H), 7.56 (d, 1 H), 7.12-7.20 (m, 1 H), 6.75-6.91 (m, 2 H), 6.52 (s, 1 H), 4.69 (dd, 1 H), 3.62 (ddd, 1 H), 2.90-3.06 (m, 1 H), 2.75 (dd, 1 H) | 318.2 $[M + H]^+$ | 100% |

TABLE 2-continued

| Ex. # | $^1H$ NMR (400 MHz unless otherwise noted) | LCMS: m/z | % ee |
|---|---|---|---|
| 1701 | ($CD_3OD$) δ 8.25-8.53 (m, 2 H), 8.04 (dd, 1 H), 7.67 (d, 1 H), 7.51 (s, 1 H), 7.38-7.47 (m, 1 H), 7.06 (s, 1 H), 6.70 (s, 2 H), 6.40 (s, 1 H), 4.57 (dd, 1 H), 3.50 (ddd, 1 H), 2.78-2.93 (m, 1 H), 2.63 (dd, 1 H) | 318.2 $[M + H]^+$ | 100% |
| 1702 | ($CD_3OD$) δ 8.39-8.84 (m, 1 H), 7.67-7.93 (m, 2 H), 7.53 (s, 0.4 H), 7.14-7.37 (m, 1 H), 6.56-7.14 (m, 3.6 H), 5.06 (br dd, 1 H), 4.04 (s, 3 H), 3.79 (ddd, 0.6 H), 3.39-3.46 (m, 0.4 H), 3.21 (br t, 1 H), 2.75-2.94 (m, 1 H) | 500.1 $[M + H]^+$ | 100% |
| 1703 | ($CD_3OD$) δ 8.15-9.00 (m, 1 H), 7.68-7.98 (m, 2 H), 7.53 (br s, 0.4 H), 7.11-7.31 (m, 1 H), 6.59-7.09 (m, 3,6 H), 5.06 (br dd, 1 H), 4.05 (s, 3 H), 3.79 (br dd, 0.6 H), 3.42 (br s, 0.4 H), 3.21 (br s,1 H), 2.86 (br d, 1 H) | 500.1 $[M + H]^+$ | 99.7% |
| 1704 | ($CD_3OD$) δ 8.22-8.82 (m, 2 H), 7.38-8.13 (m, 2.4 H), 7.11-7.37 (m, 2 H), 6.65-7.09 (m, 2.6 H), 5.07 (dd, 1 H), 3.76-3.84 (m, 0.6 H), 3.39-3.47 (m, 0.4 H), 3.22 (br s, 1 H), 2.78-2.94 (m, 1 H) | 536.1 $[M + H]^+$ | 100% |
| 1705 | ($CD_3OD$) δ 8.18-8.80 (m, 2 H), 7.41-8.03 (m, 2.4 H), 7.11-7.36 (m, 2 H), 6.65-7.07 (m, 2.6 H), 5.07 (br dd, 1 H), 3.76-3.85 (m, 0.6 H), 3.43 (td, 0.4 H), 2.96-3.29 (m, 1 H), 2.87 (br d, 1 H) | 536.1 $[M + H]^+$ | 100% |
| 1706 | ($CD_3OD$) δ 8.38-8.57 (m, 2 H), 7.72 (s, 1 H), 7.41-7.59 (m, 0.3 H), 7.12-7.33 (m, 2 H), 6.85-7.02 (m, 1.7 H), 6.73-6.83 (m, 1 H), 4.94-5.13 (m, 1 H), 3.73-3.88 (m, 0.6 H), 3.44 (td, 0.4 H), 2.96-3.25 (m, 1 H), 2.79-2.92 (m, 1 H) | 554.2 $[M + H]^+$ | 100% |
| 1707 | ($CD_3OD$) δ 8.42-8.56 (m, 2 H), 7.72 (s, 1 H), 7.53 (s, 0.3 H), 7.16-7.34 (m, 2 H), 6.86-7.03 (m, 1.7 H), 6.73-6.85 (m, 1 H), 4.95-5.12 (m, 1 H), 3.75-3.86 (m, 0.6 H), 3.44 (td, 0.4 H), 2.97-3.27 (m, 1 H), 2.79-2.93 (m, 1 H) | 554.2 $[M + H]^+$ | 100% |
| 1708 | ($CD_3OD$) δ 8.51 (d, 1 H), 8.25-8.42 (m, 1 H), 7.72 (s, 1 H), 7.40-7.59 (m, 0.3 H), 7.29 (d, 1 H), 7.17-7.25 (m, 0.2 H), 6.93-7.09 (m, 2.2 H), 6.80-6.91 (m, 1.3 H), 6.70-6.80 (m, 1 H), 4.95-5.12 (m, 1 H), 3.74-3.87 (m, 0.6 H), 3.43 (td, 0.4 H), 2.95-3.27 (m, 1 H), 2.87 (br d, 1 H) | 536.1 $[M + H]^+$ | 100% |
| 1709 | ($CD_3OD$) δ 8.39 (d, 1 H), 8.16-8.30 (m, 1 H), 7.60 (s, 1 H), 7.30-7.44 (m, 0.3 H), 7.17 (d, 1 H), 7.06-7.13 (m, 0.2 H), 6.80-6.97 (m, 2.2 H), 6.68-6.79 (m, 1.3 H), 6.57-6.68 (m, 1 H), 4.94 (br dd, 1 H), 3.63-3.73 (m, 0.6 H), 3.31 (td, 0.4 H), 2.85-3.15 (m, 1 H), 2.75 (br d, 1 H) | 536.1 $[M + H]^+$ | 99.6% |
| 1710 | ($CD_3OD$) δ 8.30 (d, 1 H), 7.68 (s, 1 H), 6.92-7.19 (m, 1.7 H), 6.67-6.91 (m, 1.3 H), 6.58 (s, 1 H), 6.39 (s, 1 H), 4.32 (dd, 1 H), 3.62-3.89 (m, 1 H), 2.98-3.16 (m, 1 H), 2.83 (br dd, 1 H), 2.44 (s, 3 H) | 372.1 $[M + H]^+$ | 100% |
| 1711 | ($CD_3OD$) δ 8.31 (d, 1 H), 7.68 (s, 1 H), 6.94-7.22 (m, 1.7 H), 6.70-6.92 (m, 1.3 H), 6.58 (s, 1 H), 6.39 (br s, 1 H), 4.32 (dd, 1 H), 3.78 (ddd, 1 H), 2.98-3.18 (m, 1 H), 2.84 (br dd, 1 H), 2.45 (s, 3 H) | 372.2 $[M + H]^+$ | 99.7% |
| 1712 | ($CD_3OD$) δ 8.29-8.96 (m, 3 H), 7.89 (d, 1 H), 7.68 (s, 1 H), 7.45 (br d, 1 H), 7.33 (d, 1 H), 6.63-7.16 (m, 4 H), 4.58-4.74 (m, 1 H), 3.39-3.82 (m, 1 H), 2.75-3.11 (m, 2 H), 2.40 (s, 3 H) | 448.2 $[M + H]^+$ | 100% |
| 1713 | ($CD_3OD$) δ 8.25-8.92 (m, 3 H), 7.89 (d, 1 H), 7.68 (s, 1 H), 7.45 (br d, 1 H), 7.34 (dd, 1 H), 6.60-7.15 (m, 4 H), 4.59-4.74 (m, 1 H), 3.35-3.79 (m, 1 H), 2.76-3.15 (m, 2 H), 2.40 (s, 3 H) | 448.1 $[M + H]^+$ | 99.5% |
| 1714 | ($CD_3OD$) δ 8.28-8.72 (m, 3 H), 7.89 (d, 1 H), 7.68 (s, 1 H), 7.28-7.35 (m, 2 H), 6.47-6.93 (m, 3 H), 4.62 (br s, 1 H), 3.38-3.84 (m, 1 H), 2.76-3.13 (m, 2 H), 2.39 (s, 3 H) | 432.1 $[M + H]^+$ | 100% |
| 1715 | ($CD_3OD$) δ 8.24-8.77 (m, 3 H), 7.89 (d, 1 H), 7.68 (s, 1 H), 7.28-7.36 (m, 2 H), 6.50-6.94 (m, 3 H), 4.58-4.72 (m, 1 H), 3.37 (br s, 1 H), 2.75-3.12 (m, 2 H), 2.39 (s, 3 H) | 432.1 $[M + H]^+$ | 99.7% |
| 1716 | ($CD_3OD$) δ 8.77 (br d, 1 H), 8.43 (s, 2 H), 7.86 (d, 1 H), 7.57-7.73 (m, 2 H), 7.21 (d, 1 H), 7.00 (br t, 1 H), 6.49-6.90 (m, 2 H), 4.57-4.68 (m, 1,6 H), 3.40-3.72 (m, 0.4 H), 2.98-3.15 (m, 1 H), 2.77 (br dd, 1 H), 1.91-2.12 (m, 1 H), 0.96-1.10 (m, 2 H), 0.67-0.85 (m, 2 H) | 492.2 $[M + H]^+$ | 98.0% |
| 1717 | ($CD_3OD$) δ 8.77 (br d, 1 H), 8.42 (s, 2 H), 7.86 (d, 1 H), 7.52-7.73 (m, 2 H), 7.21 (dd, 1 H), 7.00 (t, 1 H), 6.47-6.92 (m, 2 H), 4.59 (s, 1.5 H), 3.40-3.69 (m, 0.5 H), 2.97-3.17 (m, 1 H), 2.77 (br dd, 1 H), 1.92-2.09 (m, 1 H), 0.96-1.09 (m, 2 H), 0.71-0.83 (m, 2 H) | 492.2 $[M + H]^+$ | 98.1% |
| 1718 | ($DMSO-d_6$) δ 11.99 (br s, 1 H), 8.51 (d, 2 H), 7.86 (d, 1 H), 7.45-7.62 (m, 2 H), 7.08-7.29 (m, 2 H), 6.24-6.94 (m, 3 H), 4.35-4.71 (m, 1 H), 3.42-4.33 (m, 4 H), 2.86-3.01 (m, 1 H), 2.56-2.78 (m, 4 H) | 428.2 $[M + H]^+$ | 99.9% |
| 1719 | ($DMSO-d_6$) δ 11.99 (br s, 1 H), 8.51 (d, 2 H), 7.87 (d, 1 H), 7.55 (br s, 2 H), 7.10-7.32 (m, 2 H), 6.33-6.92 (m, 3 H), 4.51 (br d, 1 H), 3.53-4.28 (m, 4 H), 2.85-3.00 (m, 1 H), 2.69 (br s, 4 H) | 428.2 $[M + H]^+$ | 99.8% |
| 1720 | ($DMSO-d_6$) δ 12.02 (br s, 1 H), 8.08-8.84 (m, 2 H), 7.86 (br d, 1 H), 7.46-7.66 (m, 2 H), 7.24 (br d, 2 H), 6.34-7.02 (m, 3 H), 4.28-4.74 (m, 1 H), 3.54-4.26 (m, 4 H), 2.89-3.05 (m, 1 H), 2.69 (br d, 1 H) | 432.2 $[M + H]^+$ | 99.7% |

TABLE 2-continued

| Ex. # | $^1$H NMR (400 MHz unless otherwise noted) | LCMS: m/z | % ee |
|---|---|---|---|
| 1721 | (DMSO-$d_6$) δ 11.84-12.18 (m, 1 H), 8.15-8.69 (m, 2 H), 7.86 (d, 1 H), 7.44-7.65 (m, 2 H), 7.15-7.38 (m, 2 H), 6.27-6.95 (m, 3 H), 4.49 (br d, 1 H), 3.85 (s, 4 H), 2.86-3.05 (m, 1 H), 2.63-2.76 (m, 1 H) | 432.1 $[M + H]^+$ | 98.5% |
| 1722 | ($CD_3OD$) δ 8.32-8.38 (m, 1 H), 8.02-8.13 (m, 1 H), 7.84 (s, 0.3 H), 7.71 (d, 1.5 H), 7.53 (d, 0.5 H), 7.21-7.27 (m, 1 H), 6.97 (s, 0.7 H), 6.75-6.84 (m, 1 H), 6.56-6.71 (m, 2 H), 4.97-5.08 (m, 1 H), 3.94-4.01 (m, 3 H), 3.74-3.84 (m, 0.5 H), 3.39-3.53 (m, 0.5 H), 3.13-3.26 (m, 0.8 H), 2.95-3.08 (m, 0.2 H), 2.81-2.91 (m, 1 H) | 482.1 $[M + H]^+$ | 99.6% |
| 1723 | ($CD_3OD$) δ 8.19-8.27 (m, 1 H), 7.89-8.03 (m, 1 H), 7.72 (s, 0.3 H), 7.54-7.63 (m, 1.5 H), 7.37-7.45 (m, 0.5 H), 7.08-7.14 (m, 1 H), 6.85 (s, 0.7 H), 6.63-6.72 (m, 1 H), 6.43-6.59 (m, 2 H), 4.84-4.94 (m, 1 H), 3.81-3.89 (m, 3 H), 3.61-3.73 (m, 0.6 H), 3.27-3.36 (m, 0.4 H), 3.02-3.15 (m, 0.7 H), 2.84-2.96 (m, 0.3 H), 2.69-2.81 (m, 1 H) | 482.2 $[M + H]^+$ | 98.7% |
| 1724 | ($CD_3OD$) δ 8.32-8.65 (m, 1 H), 7.70 (s, 1 H), 7.46 (br s, 0.3 H), 7.22 (br d, 1 H), 6.86-6.97 (m, 1.7 H), 6.69-6.79 (m, 1 H), 4.94-5.07 (m, 1 H), 3.74 (ddd, 0.6 H), 3.36-3.47 (m, 0.4 H), 2.83 (br d, 2 H), 2.29-2.38 (m, 1 H), 1.20-1.33 (m, 4 H) | 460.2 $[M + H]^+$ | 100% |
| 1725 | ($CD_3OD$) δ 8.38-8.56 (m, 1 H), 7.70 (s, 1 H), 7.47 (s, 0.3 H), 7.16-7.27 (m, 1 H), 6.83-6.99 (m, 1.7 H), 6.66-6.79 (m, 1 H), 5.02 (br dd, 1 H), 3.74 (ddd, 0.6 H), 3.35-3.45 (m, 0.4 H), 2.80-3.21 (m, 2 H), 2.26-2.39 (m, 1 H), 1.19-1.33 (m, 4 H) | 460.2 $[M + H]^+$ | 100% |
| 1726 | ($CD_3OD$) δ 8.39-8.57 (m, 1 H), 7.71 (s, 1 H), 7.41 (s, 0.3 H), 7.17-7.25 (m, 1 H), 6.88-6.98 (m, 1.7 H), 6.70-6.82 (m, 1 H), 4.99 (br dd, 1 H), 3.77 (ddd, 0.6 H), 3.40 (br d, 0.4 H), 2.85 (br dd, 2 H), 1.83-1.97 (m, 6 H) | 480.1 $[M + H]^+$ | 100% |
| 1727 | ($CD_3OD$) δ 8.39-8.56 (m, 1 H), 7.71 (s, 1 H), 7.41 (s, 0.3 H), 7.17-7.25 (m, 1 H), 6.88-6.98 (m, 1.7 H), 6.70-6.80 (m, 1 H), 4.94-5.03 (m, 1 H), 3.77 (ddd, 0.6 H), 3.40 (td, 0.4 H), 2.81-3.21 (m, 2 H), 1.78-2.01 (m, 6 H) | 480.2 $[M + H]^+$ | 99.4% |
| 1728 | ($CD_3OD$) δ 8.17-8.54 (m, 1 H), 7.72 (br s, 1 H), 7.42 (br s, 0.3 H), 7.18-7.25 (m, 0.2 H), 6.91-7.10 (m, 2 H), 6.80-6.90 (m, 1.3 H), 6.56-6.79 (m, 1.2 H), 4.98 (br dd, 1 H), 3.68-3.83 (m, 0.7 H), 3.37-3.46 (m, 0.3 H), 3.09-3.23 (m, 0.8 H), 2.99 (br d, 0.2 H), 2.85 (br d, 1 H), 1.75-2.00 (m, 6 H) | 462.1 $[M + H]^+$ | 100% |
| 1729 | ($CD_3OD$) δ 8.27-8.41 (m, 1 H), 7.71 (s, 1 H), 7.42 (s, 0.3 H), 7.18-7.26 (m, 0.2 H), 6.92-7.09 (m, 2.2 H), 6.82-6.90 (m, 1.3 H), 6.64-6.79 (m, 1 H), 4.98 (br dd, 1 H), 3.64-3.88 (m, 0.7 H), 3.38-3.44 (m, 0.3 H), 3.13-3.23 (m, 0.7 H), 2.94-3.06 (m, 0.3 H), 2.85 (dd, 1 H), 1.78-2.00 (m, 6 H) | 462.2 $[M + H]^+$ | 100% |
| 1730 | ($CD_3OD$) δ 8.62 (br d, 3 H), 7.96 (d, 1 H), 7.67 (br s, 1 H), 7.31-7.51 (m, 2 H), 6.49-7.20 (m, 5 H), 4.94-5.29 (m, 1 H), 3.33-3.92 (m, 1 H), 2.97-3.14 (m, 1 H), 2.78 (br d, 1 H) | 434.1 $[M + H]^+$ | 99.5% |
| 1731 | ($CD_3OD$) δ 8.62 (br d, 3 H), 7.96 (d, 1 H), 7.66 (s, 1 H), 7.36-7.51 (m, 2 H), 6.63-7.16 (m, 5 H), 4.93-5.21 (m, 1 H), 3.57 (br s, 1 H), 3.00-3.16 (m, 1 H), 2.77 (br dd, 1 H) | 434.1 $[M + H]^+$ | 99.8% |
| 1732 | ($CD_3OD$) δ 8.59 (d, 1 H), 7.69 (s, 1 H), 7.44 (br d, 1 H), 7.12 (d, 0.5 H), 6.90-7.05 (m, 2 H), 6.85 (d, 0.5 H), 6.76 (s, 1 H), 6.41 (br s, 1 H), 4.34 (dd, 1 H), 3.77 (ddd, 1 H), 2.99-3.17 (m, 1 H), 2.84 (br dd, 1 H) | 408.1 $[M + H]^+$ | 97.2% |
| 1733 | ($CD_3OD$) δ 8.59 (d, 1 H), 7.69 (s, 1 H), 7.44 (d, 1 H), 7.12 (d, 0.5 H), 6.90-7.04 (m, 2 H), 6.85 (d, 0.5 H), 6.76 (s, 1 H), 6.41 (s, 1 H), 4.35 (dd, 1 H), 3.77 (ddd, 1 H), 2.98-3.19 (m, 1 H), 2.84 (dd, 1 H) | 408.1 $[M + H]^+$ | 97.1% |
| 1734 | ($CD_3OD$) δ 8.70 (d, 1 H), 7.54-7.84 (m, 2 H), 6.93-7.21 (m, 1.7 H), 6.69-6.90 (m, 1.3 H), 6.42 (s, 1 H), 4.36 (dd, 1 H), 3.78 (ddd, 1 H), 3.07 (br d, 1 H), 2.85 (dd, 1 H) | 426.1 $[M + H]^+$ | 98.6% |
| 1735 | ($CD_3OD$) δ 8.58 (d, 1 H), 7.32-7.74 (m, 2 H), 6.81-7.05 (m, 1.7 H), 6.56-6.78 (m, 1.3 H), 6.30 (s, 1 H), 4.24 (dd, 1 H), 3.66 (ddd, 1 H), 2.96 (br s, 1 H), 2.73 (dd, 1 H) | 426.1 $[M + H]^+$ | 97.4% |
| 1736 | ($CD_3OD$) δ 8.35 (d, 1 H), 7.69 (s, 1 H), 7.12 (s, 0.3 H), 6.78-7.03 (m, 2.7 H), 6.72 (s, 1 H), 6.39 (s, 1 H), 4.34 (dd, 1 H), 3.78 (ddd, 1 H), 2.98-3.18 (m, 1 H), 2.84 (dd, 1 H) | 376.1 $[M + H]^+$ | 98.9% |
| 1737 | ($CD_3OD$) δ 8.35 (d, 1 H), 7.70 (s, 1 H), 7.12 (s, 0.3 H), 6.76-7.06 (m, 2.7 H), 6.72 (s, 1 H), 6.40 (s, 1 H), 4.34 (dd, 1 H), 3.78 (ddd, 1 H), 2.99-3.21 (m, 1 H), 2.84 (dd, 1 H) | 376.1 $[M + H]^+$ | 100% |
| 1738 | ($CD_3OD$) δ 8.45 (d, 1 H), 7.69 (s, 1 H), 7.31 (d, 1 H), 7.12 (s, 0.3 H), 6.99 (s, 0.5 H), 6.81-6.91 (m, 1.2 H), 6.71 (s, 1 H), 6.39 (br s, 1 H), 4.34 (dd, 1 H), 3.78 (ddd, 1 H), 2.98-3.15 (m, 1 H), 2.84 (br dd, 1 H) | 392.1 $[M + H]^+$ | 98.2% |
| 1739 | ($CD_3OD$) δ 8.45 (d, 1 H), 7.70 (s, 1 H), 7.30 (d, 1 H), 7.12 (s, 0.3 H), 6.99 (s, 0.5 H), 6.78-6.91 (m, 1.2 H), 6.71 (s, 1 H), 6.39 (s, 1 H), 4.34 (dd, 1 H), 3.78 (ddd, 1 H), 2.96-3.19 (m, 1 H), 2.84 (dd, 1 H) | 392.1 $[M + H]^+$ | 99.6% |

TABLE 2-continued

| Ex. # | $^1$H NMR (400 MHz unless otherwise noted) | LCMS: m/z | % ee |
|---|---|---|---|
| 1740 | ($CD_3OD$) δ 7.66 (s, 1 H), 7.45 (d, 1 H), 6.82-7.15 (m, 2 H), 6.70 (d, 1 H), 6.50 (s, 1 H), 6.38 (s, 1 H), 4.31 (dd, 1 H), 3.78 (ddd, 1 H), 2.98-3.12 (m, 1 H), 2.82 (dd, 1 H), 2.62 (s, 3 H) | 372.1 $[M + H]^+$ | 98.9% |
| 1741 | ($CD_3OD$) δ 7.66 (s, 1 H), 7.44 (br d, 1 H), 6.82-7.16 (m, 2 H), 6.68 (br d, 1 H), 6.50 (s, 1 H), 6.38 (s, 1 H), 4.30 (dd, 1 H), 3.72-3.84 (m, 1 H), 3.03 (br d, 1 H), 2.81 (br dd, 1 H), 2.61 (s, 3 H) | 372.2 $[M + H]^+$ | 98.5% |
| 1742 | ($CD_3OD$) δ 8.30-8.76 (m, 3 H), 7.86 (d, 1 H), 7.66 (s, 1 H), 7.43 (br d, 1 H), 6.51-7.24 (m, 5 H), 4.62 (br d, 1 H), 3.39-3.70 (m, 1 H), 3.01-3.11 (m, 1 H), 2.77 (br dd, 1 H), 1.92-2.07 (m, 1 H), 0.97-1.07 (m, 2 H), 0.69-0.83 (m, 2 H) | 474.2 $[M + H]^+$ | 92.4% |
| 1743 | ($CD_3OD$) δ 8.30-8.76 (m, 3 H), 7.86 (d, 1 H), 7.66 (s, 1 H), 7.43 (br d, 1 H), 6.48-7.24 (m, 5 H), 4.62 (br s, 1 H), 3.39-3.75 (m, 1 H), 2.98-3.14 (m, 1 H), 2.77 (br dd, 1 H), 1.93-2.08 (m, 1 H), 0.94-1.08 (m, 2 H), 0.70-0.82 (m, 2 H) | 474.2 $[M + H]^+$ | 93.8% |
| 1744 | ($CD_3OD$) δ 8.62-9.24 (m, 1 H), 8.40 (s, 1 H), 7.88 (d, 1 H), 7.55-7.68 (m, 2 H), 7.13-7.24 (m, 2 H), 7.05 (d, 1 H), 6.45-6.94 (m, 2 H), 4.63 (br s, 1 H), 3.35-3.64 (m, 1 H), 2.98-3.11 (m, 1 H), 2.75 (dd, 1 H), 1.94-2.06 (m, 1 H), 0.97-1.07 (m, 2 H), 0.71-0.80 (m, 2 H) | 458.2 $[M + H]^+$ | 100% |
| 1745 | ($CD_3OD$) δ 8.52-9.28 (m, 1 H), 8.41 (s, 1 H), 7.88 (d, 1 H), 7.56-7.68 (m, 2 H), 6.98-7.25 (m, 3 H), 6.49-6.92 (m, 2 H), 4.61-4.72 (m, 1 H), 3.36-3.68 (m, 1 H), 2.96-3.12 (m, 1 H), 2.75 (dd, 1 H), 1.94-2.06 (m, 1 H), 0.96-1.08 (m, 2 H), 0.73-0.83 (m, 2 H) | 458.2 $[M + H]^+$ | 99.0% |
| 1746 | ($CD_3OD$) δ 8.77 (br d, 1 H), 8.35 (br s, 1 H), 7.92 (d, 1 H), 7.84 (d, 1 H), 7.57-7.71 (m, 2 H), 7.38 (dd, 1 H), 7.00 (t, 1 H), 6.59-6.92 (m, 2 H), 4.64 (br s, 1 H), 3,42-3.78 (m, 1 H), 3.02-3.16 (m, 1 H), 2.95 (s, 6 H), 2.71-2.83 (m, 1 H) | 495.2 $[M + H]^+$ | 100% |
| 1747 | ($CD_3OD$) δ 8.78 (br s, 1 H), 8.37 (br s, 1 H), 7.92 (d, 1 H), 7.84 (d, 1 H), 7.55-7.72 (m, 2 H), 7.39 (dd, 1 H), 7.00 (br t, 1 H), 6.56-6.92 (m, 2 H), 4.65 (br s, 1 H), 3.56 (br s, 1 H), 3.03-3.18 (m, 1 H), 2.95 (s, 6 H), 2.77 (br d, 1 H) | 495.2 $[M + H]^+$ | 99.8% |
| 1748 | ($CD_3OD$) δ 9.00 (s, 2 H), 8.15 (br d, 1 H), 7.99 (d, 1 H), 7.88 (d, 1 H), 7.61-7.69 (m, 2 H), 6.65-7.16 (m, 3 H), 6.58 (d, 2 H), 4.59 (br d, 1 H), 3.96 (s, 7 H), 3.07 (br d, 1 H), 2.72-2.83 (m, 1 H) | 494.3 $[M + H]^+$ | 98.4% |
| 1749 | ($CD_3OD$) δ 8.95 (br d, 2 H), 8.13 (br s, 1 H), 7.96 (br d, 1 H), 7.73-7.90 (m, 1 H), 7.57-7.72 (m, 2 H), 6.61-7.20 (m, 3 H), 6.54 (br d, 2 H), 4.59 (br s, 1 H), 3.41-3.98 (m, 7 H), 2.92-3.18 (m, 1 H), 2.76 (br d, 1 H) | 494.2 $[M + H]^+$ | 99.2% |
| 1750 | ($CD_3OD$) δ 8.37 (br d, 2 H), 7.92 (d, 1 H), 7.85 (d, 1 H), 7.65 (s, 1 H), 7.38 (dd, 1 H), 6.99 (d, 1 H), 6.38-6.91 (m, 3 H), 4.63-4.71 (m, 1 H), 3.58 (br s, 1 H), 3.00-3.16 (m, 1 H), 2.95 (s, 6 H), 2.76 (br d, 1 H), 2.44 (s, 3 H) | 441.2 $[M + H]^+$ | 100% |
| 1751 | ($CD_3OD$) δ 8.37 (br d, 2 H), 7.91 (d, 1 H), 7.84 (d, 1 H), 7.65 (s, 1 H), 7.38 (dd, 1 H), 6.99 (d, 1 H), 6.43-6.91 (m, 3 H), 4.61-4.70 (m, 1 H), 3.56 (br s, 1 H), 3.00-3.14 (m, 1 H), 2.95 (s, 6 H), 2.76 (br d, 1 H), 2.44 (s, 3 H) | 441.2 $[M + H]^+$ | 100% |
| 1752 | ($CD_3OD$) δ 8.64 (s, 2 H), 8.40 (d, 1 H), 7.44-7.72 (m, 2 H), 7.07-7.30 (m, 2 H), 6.80 (td, 1 H), 6.54 (s, 1 H), 5.15 (dd, 1 H), 3.42-3.60 (m, 1 H), 2.58-3.02 (m, 2 H) | 386.1 $[M + H]^+$ | 100% |
| 1753 | ($CD_3OD$) δ 8.63 (s, 2 H), 8.39 (dd, 1 H), 7.63 (s, 1 H), 7.53 (d, 1 H), 7.23 (s, 1 H), 7.14 (ddd, 1 H), 6.80 (td, 1 H), 6.45-6.61 (m, 1 H), 5.14 (dd, 1 H), 3.50 (td, 1 H), 2.71-2.99 (m, 2 H) | 386.2 $[M + H]^+$ | 99.5% |
| 1754 | ($CD_3OD$) δ 8.65 (s, 2 H), 8.26 (d, 1 H), 7.65 (s, 1 H), 7.24 (s, 1 H), 6.95 (d, 1 H), 6.74 (t, 1 H), 6.54 (s, 1 H), 5.16 (dd, 1 H), 3.52 (td, 1 H), 2.68-2.98 (m, 2 H), 2.41 (s, 3 H) | 400.2 $[M + H]^+$ | 100% |
| 1755 | ($CD_3OD$) δ 8.65 (s, 2 H), 8.26 (d, 1 H), 7.64 (s, 1 H), 7.24 (s, 1 H), 6.95 (d, 1 H), 6.74 (t, 1 H), 6.54 (s, 1 H), 5.15 (dd, 1 H), 3.52 (td, 1 H), 2.67-3.00 (m, 2 H), 2.41 (s, 3 H) | 400.2 $[M + H]^+$ | 99.5% |
| 1756 | Data provided above | | |
| 1757 | Data provided above | | |
| 1758 | ($CD_3OD$) δ 8.30-8.40 (m, 1 H), 7.59 (s, 1 H), 7.29 (s, 0.3 H), 7.05-7.13 (m, 1 H), 6.76-6.85 (m, 1.7 H), 6.56-6.68 (m, 1 H), 4.89 (br dd, 1 H), 3.63 (ddd, 0.6 H), 3.28 (td, 0.4 H), 2.69-3.08 (m, 2 H), 1.32-1.42 (m, 9 H) | 476.2 $[M + H]^+$ | 99.8% |
| 1759 | ($CD_3OD$) δ 8.30-8.40 (m, 1 H), 7.59 (s, 1 H), 7.29 (s, 0.3 H), 7.05-7.12 (m, 1 H), 6.75-6.84 (m, 1.7 H), 6.57-6.69 (m, 1 H), 4.88 (br dd, 1 H), 3.58-3.67 (m, 0.6 H), 3.28 (td, 0.4 H), 2.70-3.08 (m, 2 H), 1.33-1.41 (m, 9 H) | 476.1 $[M + H]^+$ | 99.4% |
| 1760 | ($CD_3OD$) δ 8.78 (d, 1 H), 8.42-8.53 (m, 1 H), 8.32 (d, 1 H), 8.09 (t, 1 H), 7.65-7.76 (m, 2 H), 7.51 (s, 0.3 H), 7.17-7.25 (m, 1 H), 6.86-7.00 (m, 1.7 H), 6.75-6.82 (m, 1 H), 4.94-5.09 (m, 1 H), 3.77-3.85 (m, 0.6 H), 3.45 (td, 0.4 H), 2.84-3.24 (m, 2 H) | 497.1 $[M + H]^+$ | 100% |
| 1761 | ($CD_3OD$) δ 8.78 (d, 1 H), 8.42-8.56 (m, 1 H), 8.32 (d, 1 H), 8.09 (td, 1 H), 7.63-7.76 (m, 2 H), 7.51 (s, 0.3 H), 7.15-7.26 (m, 1 H), 6.86-7.01 (m, 1.7 H), 6.77-6.84 (m, 1 H), 4.94-5.09 (m, 1 H), 3.77-3.85 (m, 0.6 H), 3.40-3.49 (m, 0.4 H), 2.85-3.27 (m, 2 H) | 497.1 $[M + H]^+$ | 99.5% |

TABLE 2-continued

| Ex. # | $^1$H NMR (400 MHz unless otherwise noted) | LCMS: m/z | % ee |
|---|---|---|---|
| 1762 | ($CD_3OD$) δ 8.56 (br d, 1 H), 8.41 (d, 2 H), 7.64 (s, 1 H), 7.40 (br d, 1 H), 7.21 (s, 1 H), 6.81-7.13 (m, 2 H), 6.71 (s, 1 H), 6.66 (t, 1 H), 5.06 (dd, 1 H), 3.40-3.51 (m, 1 H), 2.84-2.97 (m, 1 H), 2.70 (br dd, 1 H) | 368.1 $[M + H]^+$ | 100% |
| 1763 | ($CD_3OD$) δ 8.56 (d, 1 H), 8.41 (d, 2 H), 7.64 (s, 1 H), 7.40 (br d, 1 H), 7.21 (s, 1 H), 6.81-7.12 (m, 2 H), 6.71 (s, 1 H), 6.66 (t, 1 H), 5.06 (dd, 1 H), 3.40-3.52 (m, 1 H), 2.84-2.99 (m, 1 H), 2.70 (dd, 1 H) | 368.2 $[M + H]^+$ | 98.2% |
| 1764 | ($CD_3OD$) δ 8.39 (d, 2 H), 7.82 (d, 1 H), 7.61 (s, 1 H), 7.09-7.34 (m, 3 H), 6.75 (s, 1 H), 6.64 (t, 1 H), 5.08 (dd, 1 H), 3.61 (td, 1 H), 2.83-2.97 (m, 1 H), 2.71 (dd, 1 H) | 386.1 $[M + H]^+$ | 99.3% |
| 1765 | ($CD_3OD$) δ 8.39 (d, 2 H), 7.82 (d, 1 H), 7.61 (s, 1 H), 7.08-7.38 (m, 3 H), 6.75 (s, 1 H), 6.64 (t, 1 H), 5.08 (br dd, 1 H), 3.54-3.68 (m, 1 H), 2.83-2.97 (m, 1 H), 2.71 (br dd, 1 H) | 386.1 $[M + H]^+$ | 98.4% |
| 1766 | ($CD_3OD$) δ 8.60 (d, 1 H), 7.70 (s, 1 H), 7.45 (br d, 1 H), 6.83-7.15 (m, 2 H), 6.76 (s, 1 H), 6.43 (s, 1 H), 4.36 (dd, 1 H), 3.73-3.84 (m, 1 H), 3.02-3.16 (m, 1 H), 2.85 (dd, 1 H) | 426.1 $[M + H]^+$ | 99.8% |
| 1767 | ($CD_3OD$) δ 8.60 (br d, 1 H), 7.70 (s, 1 H), 7.45 (br d, 1 H), 6.83-7.15 (m, 2 H), 6.76 (s, 1 H), 6.43 (br s, 1 H), 4.36 (dd, 1 H), 3.79 (td, 1 H), 3.02-3.15 (m, 1 H), 2.85 (br dd, 1 H) | 426.1 $[M + H]^+$ | 99.6% |
| 1768 | ($CD_3OD$) δ 8.22-8.77 (m, 3 H), 7.86 (d, 1 H), 7.66 (s, 1 H), 7.29 (d, 1 H), 7.20 (dd, 1 H), 6.54-7.03 (m, 3 H), 4.60 (br s, 1 H), 3.61 (q, 1 H), 3.00-3.17 (m, 1 H), 2.66-2.83 (m, 1 H), 1.97-2.06 (m, 1 H), 0.98-1.07 (m, 2 H), 0.73-0.81 (m, 2 H) | 458.2 $[M + H]^+$ | 98.1% |
| 1769 | ($CD_3OD$) δ 8.25-8.68 (m, 3 H), 7.86 (d, 1 H), 7.67 (s, 1 H), 7.29 (d, 1 H), 7.19 (br d, 1 H), 6.40-6.97 (m, 3 H), 4.61 (br s, 1 H), 3.44-3.80 (m, 1 H), 3.01-3.18 (m, 1 H), 2.77 (br d, 1 H), 1.95-2.05 (m, 1 H), 0.97-1.07 (m, 2 H), 0.71-0.80 (m, 2 H) | 458.1 $[M + H]^+$ | 97.8% |
| 1770 | ($CD_3OD$) δ 8.03-8.83 (m, 2 H), 7.80-7.95 (m, 2 H), 7.66 (s, 1 H), 7.33-7.49 (m, 2 H), 6.59-7.17 (m, 4 H), 4.64 (br s, 1 H), 3.40-3.81 (m, 1 H), 3.01-3.17 (m, 1 H), 2.95 (s, 6 H), 2.77 (br d, 1 H) | 477.2 $[M + H]^+$ | 99.4% |
| 1771 | ($CD_3OD$) δ 8.00-8.80 (m, 2 H), 7.77-7.97 (m, 2 H), 7.66 (s, 1 H), 7.31-7.47 (m, 2 H), 6.55-7.18 (m, 4 H), 4.64 (br s, 1 H), 3.43-3.92 (m, 1 H), 3.01-3.13 (m, 1 H), 2.95 (s, 6 H), 2.77 (br d, 1 H) | 477.2 $[M + H]^+$ | 99.4% |
| 1772 | ($CD_3OD$) δ 8.41 (br d, 2 H), 7.92 (d, 1 H), 7.85 (d, 1 H), 7.66 (s, 1 H), 7.38 (dd, 1 H), 6.97 (dd, 1 H), 6.55-6.91 (m, 3 H), 4.63 (br s, 1 H), 3.45-3.80 (m, 1 H), 3.02-3.16 (m, 1 H), 2.95 (s, 6 H), 2.77 (br dd, 1 H) | 445.2 $[M + H]^+$ | 100% |
| 1773 | ($CD_3OD$) δ 8.41 (br d, 2 H), 7.91 (d, 1 H), 7.84 (d, 1 H), 7.65 (s, 1 H), 7.37 (dd, 1 H), 6.96 (dd, 1 H), 6.56-6.89 (m, 3 H), 4.63 (br s, 1 H), 3.43-3.78 (m, 1 H), 3.02-3.13 (m, 1 H), 2.94 (s, 6 H), 2.76 (br dd, 1 H) | 445.2 $[M + H]^+$ | 99.8% |
| 1774 | ($CD_3OD$) δ 8.57-8.74 (m, 3 H), 7.55-7.71 (m, 2 H), 7.24 (s, 1 H), 6.95 (t, 1 H), 6.71 (s, 1 H), 5.20 (dd, 1 H), 3.45-3.63 (m, 1 H), 2.67-3.00 (m, 2 H) | 454.1 $[M + H]^+$ | 99.4% |
| 1775 | ($CD_3OD$) δ 8.56-8.75 (m, 3 H), 7.54-7.69 (m, 2 H), 7.24 (s, 1 H), 6.95 (t, 1 H), 6.71 (s, 1 H), 5.20 (dd, 1 H), 3.44-3.58 (m, 1 H), 2.69-2.98 (m, 2 H) | 454.1 $[M + H]^+$ | 98.1% |
| 1776 | ($CD_3OD$) δ 8.49-8.69 (m, 3 H), 7.65 (s, 1 H), 7.39 (br d, 1 H), 7.25 (s, 1 H), 7.09 (s, 0.2 H), 6.78-7.00 (m, 1.8 H), 6.72 (s, 1 H), 5.18 (dd, 1 H), 3.51 (td, 1 H), 2.69-2.96 (m, 2 H) | 436.1 $[M + H]^+$ | 100% |
| 1777 | ($CD_3OD$) δ 8.47-8.71 (m, 3 H), 7.65 (s, 1 H), 7.39 (br d, 1 H), 7.25 (s, 1 H), 7.09 (s, 0.2 H), 6.78-6.99 (m, 1.8 H), 6.72 (s, 1 H), 5.18 (dd, 1 H), 3.51 (td, 1 H), 2.68-2.98 (m, 2 H) | 436.1 $[M + H]^+$ | 100% |
| 1778 | ($CD_3OD$) δ 8.67 (s, 2 H), 8.32 (d, 1 H), 7.66 (s, 1 H), 7.24 (s, 1 H), 6.94 (dd, 1 H), 6.81 (td, 1 H), 6.70 (s, 1 H), 5.20 (dd, 1 H), 3.48-3.63 (m, 1 H), 2.69-3.03 (m, 2 H) | 404.1 $[M + H]^+$ | 99.5% |
| 1779 | ($CD_3OD$) δ 8.64 (s, 2 H), 8.28 (d, 1 H), 7.65 (s, 1 H), 7.22 (s, 1 H), 6.91 (dd, 1 H), 6.73-6.82 (m, 1 H), 6.67 (s, 1 H), 5.17 (dd, 1 H), 3.51 (td, 1 H), 2.67-2.98 (m, 2 H) | 404.2 $[M + H]^+$ | 99.3% |
| 1780 | ($CD_3OD$) δ 8.65 (s, 2 H), 8.40 (d, 1 H), 7.65 (s, 1 H), 7.17-7.34 (m, 2 H), 6.80 (t, 1 H), 6.66 (s, 1 H), 5.18 (dd, 1 H), 3.51 (td, 1 H), 2.72-2.97 (m, 2 H) | 420.1 $[M + H]^+$ | 99.0% |
| 1781 | ($CD_3OD$) δ 8.66 (s, 2 H), 8.40 (br d, 1 H), 7.65 (s, 1 H), 7.13-7.33 (m, 2 H), 6.81 (t, 1 H), 6.66 (s, 1 H), 5.19 (dd, 1 H), 3.42-3.59 (m, 1 H), 2.66-2.98 (m, 2 H) | 420.1 $[M + H]^+$ | 99.4% |
| 1782 | ($CD_3OD$) δ 8.91-8.95 (m, 1 H), 8.44-8.53 (m, 1 H), 8.34-8.39 (m, 1 H), 7.78-7.82 (m, 1.2 H), 7.51-7.67 (m, 1 H), 7.16-7.26 (m, 1 H), 6.88-6.99 (m, 1.8 H), 6.76-6.83 (m, 1 H), 5.12 (dd, 1 H), 3.75-3.83 (m, 0.6 H), 3.40-3.48 (m, 0.4 H), 2.84-3.22 (m, 2 H) | 536.1 $[M + H]^+$ | 100% |
| 1783 | (CD3OD) δ 8.89-8.96 (m, 1 H), 8.43-8.52 (m, 1 H), 8.36 (s, 1 H), 7.72-7.82 (m, 1.2 H), 7.51-7.67 (m, 1 H), 7.17-7.28 (m, 1 H), 6.87-7.00 (m, 1.8 H), 6.74-6.83 (m, 1 H), 4.97-5.16 (m, 1 H), 3.75-3.83 (m, 0.6 H), 3.43 (td, 0.4 H), 2.85-3.22 (m, 2 H) | 536.2 $[M + H]^+$ | 100% |

TABLE 2-continued

| Ex. # | $^1$H NMR (400 MHz unless otherwise noted) | LCMS: m/z | % ee |
|---|---|---|---|
| 1784 | ($CD_3OD$) δ 8.38-8.98 (m, 3 H), 7.91 (d, 1 H), 7.63-7.72 (m, 2 H), 7.42 (dd, 1 H), 7.02 (br t, 1 H), 6.58-6.92 (m, 2 H), 4.89-4.96 (m, 1 H), 3.69 (t, 2 H), 3.35-3.51 (m, 4 H), 3.04-3.19 (m, 1 H), 2.95 (t, 2 H), 2.73-2.84 (m, 1 H) | 510.2 $[M + H]^+$ | 99.5% |
| 1785 | ($CD_3OD$) δ 8.28-8.95 (m, 3 H), 7.91 (d, 1 H), 7.63-7.73 (m, 2 H), 7.43 (dd, 1 H), 6.58-7.10 (m, 3 H), 4.90-5.03 (m, 1 H), 3.69 (t, 2 H), 3.37 (s, 4 H), 3.04-3.16 (m, 1 H), 2.95 (t, 2 H), 2.80 (br dd, 1 H) | 510.2 $[M + H]^+$ | 100% |
| 1786 | ($CD_3OD$) δ 8.05-8.86 (m, 2 H), 7.76 (d, 1 H), 7.54 (s, 1 H), 7.33 (d, 1 H), 7.18 (dd, 1 H), 7.11 (ddd, 1 H), 6.42-6.87 (m, 3 H), 4.49-4.58 (m, 1 H), 3.24 (br s, 1 H), 2.89-3.01 (m, 1 H), 2.65 (br dd, 1 H), 2.26 (s, 3 H) | 416.2 $[M + H]^+$ | 99.5% |
| 1787 | ($CD_3OD$) δ 8.22-8.92 (m, 2 H), 7.90 (d, 1 H), 7.66 (s, 1 H), 7.47 (dd, 1 H), 7.33 (dd, 1 H), 7.25 (ddd, 1 H), 6.55-6.96 (m, 3 H), 4.62 (br s, 1 H), 3.35-3.77 (m, 1 H), 3.03-3.12 (m, 1 H), 2.78 (dd, 1 H), 2.40 (s, 3 H) | 416.2 $[M + H]^+$ | 99.5% |
| 1788 | ($CD_3OD$) δ 8.42 (s, 2 H), 8.14 (br d, 1 H), 7.86 (d, 1 H), 7.64 (s, 1 H), 7.20 (dd, 1 H), 6.39-6.93 (m, 4 H), 4.60-4.70 (m, 1 H), 3.95 (s, 3 H), 3.37-3.74 (m, 1 H), 2.98-3.11 (m, 1 H), 2.75 (br dd, 1 H), 1.94-2.07 (m, 1 H), 0.94-1.08 (m, 2 H), 0.71-0.85 (m, 2 H) | 454.2 $[M + H]^+$ | 97.5% |
| 1789 | ($CD_3OD$) δ 8.42 (s, 2 H), 8.14 (br d, 1 H), 7.86 (d, 1 H), 7.64 (s, 1 H), 7.20 (d, 1 H), 6.37-7.01 (m, 4 H), 4.59-4.71 (m, 1 H), 3,95 (s, 3 H), 3.49 (br s, 1 H), 3.00-3.10 (m, 1 H), 2.70-2.81 (m, 1 H), 1.95-2.08 (m, 1 H), 0.94-1.08 (m, 2 H), 0.72-0.83 (m, 2 H) | 454.2 $[M + H]^+$ | 97.8% |
| 1790 | ($CD_3OD$) δ 8.42 (s, 2 H), 7.87 (d, 1 H), 7.64 (s, 1 H), 7.46 (d, 1 H), 7.14-7.30 (m, 2 H), 6.38-7.05 (m, 3 H), 4.59-4.71 (m, 1 H), 3.45-3.98 (m, 1 H), 2.96-3.15 (m, 1 H), 2.76 (br d, 1 H), 1.96-2.09 (m, 1 H), 0.95-1.07 (m, 2 H), 0.72-0.84 (m, 2 H) | 442.2 $[M + H]^+$ | 99.7% |
| 1791 | ($CD_3OD$) δ 8.42 (s, 2 H), 7.87 (d, 1 H), 7.65 (s, 1 H), 7.45 (d, 1 H), 7.13-7.31 (m, 2 H), 6.44-7.01 (m, 3 H), 4.60-4.70 (m, 1 H), 3.47-3.92 (m, 1 H), 2.96-3.11 (m, 1 H), 2.76 (br dd, 1 H), 1.91-2.08 (m, 1 H), 0.97-1.11 (m, 2 H), 0.68-0.84 (m, 2 H) | 442.2 $[M + H]^+$ | 99.7% |
| 1792 | ($CD_3OD$) δ 8.51 (br d, 2 H), 7.77-7.94 (m, 2 H), 7.67 (s, 1 H), 7.37 (dd, 1 H), 7.29 (d, 1 H), 6.36-6.96 (m, 3 H), 4.63 (br s, 1 H), 3.38-3.72 (m, 1 H), 3.00-3.14 (m, 1 H), 2.94 (s, 6 H), 2.71-2.82 (m, 1 H) | 461.2 $[M + H]^+$ | 100% |
| 1793 | ($CD_3OD$) δ 8.51 (br d, 2 H), 7.80-7.95 (m, 2 H), 7.66 (s, 1 H), 7.37 (dd, 1 H), 7.29 (d, 1 H), 6.49-6.98 (m, 3 H), 4.65 (br s, 1 H), 3.43-3.83 (m, 1 H), 3.01-3.15 (m, 1 H), 2.94 (s, 6 H), 2.77 (br dd, 1 H) | 461.2 $[M + H]^+$ | 99.4% |
| 1794 | ($CD_3OD$) δ 8.49-9.39 (m, 1 H), 7.80-7.94 (m, 2 H), 7.63 (s, 1 H), 7.47 (d, 1 H), 7.36 (dd, 1 H), 7.13 (dd, 1 H), 6.34-6.91 (m, 3 H), 4.62-4.71 (m, 1 H), 3,49 (br s, 1 H), 3.00-3.10 (m, 1 H), 2.94 (s, 6 H), 2.69-2.78 (m, 4 H) | 441.2 $[M + H]^+$ | 99.9% |
| 1795 | ($CD_3OD$) δ 8.23-9.44 (m, 1 H), 7.78-7.95 (m, 2 H), 7.64 (s, 1 H), 7.47 (d, 1 H), 7.37 (dd, 1 H), 7.13 (dd, 1 H), 6.33-6.97 (m, 3 H), 4.63-4.73 (m, 1 H), 3.39-3.86 (m, 1 H), 2.99-3.14 (m, 1 H), 2.95 (s, 6 H), 2.70-2.78 (m, 4 H) | 441.3 $[M + H]^+$ | 99.7% |
| 1796 | ($CD_3OD$) δ 8.24-8.53 (m, 3 H), 7.79 (d, 1 H), 7.56 (s, 1 H), 7.30 (dd, 1 H), 6.87 (dd, 1 H), 6.40-6.82 (m, 3 H), 4.82 (br s, 1 H), 3.57 (t, 2 H), 3.24 (s, 4 H), 2.91-3.04 (m, 1 H), 2.83 (t, 2 H), 2.67 (br dd, 1 H) | 460.2 $[M + H]^+$ | 100% |
| 1797 | ($CD_3OD$) δ 8.25-8.55 (m, 3 H), 7.80 (d, 1 H), 7.56 (s, 1 H), 7.30 (dd, 1 H), 6.87 (dd, 1 H), 6.49-6.80 (m, 3 H), 4.81 (br s, 1 H), 3.57 (1, 2 H), 3.22-3.33 (m, 4 H), 2.88-3.05 (m, 1 H), 2.83 (t, 2 H), 2.67 (br dd, 1 H) | 460.2 $[M + H]^+$ | 99.2% |
| 1798 | ($CD_3OD$) δ 8.17 (d, 1 H), 7.55 (s, 1 H), 6.86 (d, 1 H), 6.66 (t, 1 H), 6.42 (s, 1 H), 6.17 (s, 1 H), 4.10 (dd, 1 H), 3.60 (ddd, 1 H), 2.83-3.00 (m, 1 H), 2.69 (dd, 1 H), 2.31 (s, 3 H), 1.28 (s, 9 H) | 378.2 $[M + H]^+$ | 99.8% |
| 1799 | ($CD_3OD$) δ 8.17 (br d, 1 H), 7.55 (s, 1 H), 6.86 (br d, 1 H), 6.66 (1, 1 H), 6.42 (s, 1 H), 6.17 (s, 1 H), 4.10 (br dd, 1 H), 3.51-3.70 (m, 1 H), 2.84-2.99 (m, 1 H), 2.69 (br dd, 1 H), 2.31 (s, 3 H), 1.28 (s, 9 H) | 378.2 $[M + H]^+$ | 99.7% |
| 1800 | ($CD_3OD$) δ 8.63 (s, 2 H), 7.51-7.65 (m, 2 H), 7.24 (s, 1 H), 7.13 (dd, 1 H), 6.98 (dd, 1 H), 6.69 (s, 1 H), 5.19 (dd, 1 H), 3.62 (td, 1 H), 2.71-2.97 (m, 2 H) | 420.1 $[M + H]^+$ | 99.5% |
| 1801 | ($CD_3OD$) δ 8.64 (s, 2 H), 7.50-7.67 (m, 2 H), 7.24 (s, 1 H), 7.14 (dd, 1 H), 6.98 (dd, 1 H), 6.69 (s, 1 H), 5.19 (dd, 1 H), 3.55-3.71 (m, 1 H), 2.72-2.95 (m, 2 H) | 420.1 $[M + H]^+$ | 99.8% |
| 1802 | ($CD_3OD$) δ 8.63 (s, 2 H), 7.61 (s, 1 H), 7.42 (d, 1 H), 7.24 (s, 1 H), 7.07 (dd, 1 H), 6.66 (d, 1 H), 6.51 (s, 1 H), 5.17 (dd, 1 H), 3.63 (td, 1 H), 2.70-2.95 (m, 2 H), 2.64 (s, 3 H) | 400.2 $[M + H]^+$ | 99.6% |
| 1803 | ($CD_3OD$) δ 8.64 (s, 2 H), 7.61 (s, 1 H), 7.43 (d, 1 H), 7.24 (s, 1 H), 7.08 (dd, 1 H), 6.67 (d, 1 H), 6.51 (s, 1 H), 5.17 (dd, 1 H), 3.63 (td, 1 H), 2.71-2.94 (m, 2 H), 2.64 (s, 3 H) | 400.2 $[M + H]^+$ | 99.2% |

TABLE 2-continued

| Ex. # | $^1$H NMR (400 MHz unless otherwise noted) | LCMS: m/z | % ee |
|---|---|---|---|
| 1804 | ($CD_3OD$) δ 8.46 (d, 1 H), 8.31 (d, 1 H), 8.16 (dd, 1 H), 7.80 (d, 1 H), 7.64 (s, 1 H), 6.98 (d, 1 H), 6.82 (br s, 1 H), 6.77 (t, 1 H), 6.53 (s, 1 H), 4.70 (br dd, 1 H), 3.57-3.72 (m, 1 H), 2.91-3.06 (m, 1 H), 2.76 (dd, 1 H), 2.43 (s, 3 H) | 332.2 $[M + H]^+$ | 100% |
| 1805 | ($CD_3OD$) δ 8.46 (d, 1 H), 8.31 (d, 1 H), 8.13-8.22 (m, 1 H), 7.80 (d, 1 H), 7.64 (s, 1 H), 6.98 (d, 1 H), 6.82 (s, 1 H), 6.77 (t, 1 H), 6.53 (s, 1 H), 4.70 (br dd, 1 H), 3.63 (ddd, 1 H), 2.88-3.06 (m, 1 H), 2.76 (dd, 1 H), 2.43 (s, 3 H) | 332.2 $[M + H]^+$ | 97.6% |
| 1806 | ($CD_3OD$) δ 8.46 (d, 1 H), 7.69 (s, 1 H), 7.60 (d, 1 H), 7.21 (ddd, 1 H), 6.88 (td, 1 H), 6.59 (s, 1 H), 6.40 (s, 1 H), 4.34 (dd, 1 H), 3.79 (ddd, 1 H), 3.02-3.14 (m, 1 H), 2.84 (dd, 1 H) | 376.1 $[M + H]^+$ | 99.6% |
| 1807 | ($CD_3OD$) δ 8.46 (d, 1 H), 7.69 (s, 1 H), 7.60 (d, 1 H), 7.15-7.27 (m, 1 H), 6.81-6.93 (m, 1 H), 6.59 (s, 1 H), 6.40 (s, 1 H), 4.34 (dd, 1 H), 3.79 (ddd, 1 H), 3.00-3.14 (m, 1 H), 2.84 (dd, 1 H) | 376.1 $[M + H]^+$ | 99.9% |
| 1808 | ($CD_3OD$) δ 8.31 (d, 1 H), 7.70 (s, 1 H), 7.00 (d, 1 H), 6.80 (t, 1 H), 6.59 (s, 1 H), 6.41 (s, 1 H), 4.34 (dd, 1 H), 3.79 (ddd, 1 H), 3.00-3.16 (m, 1 H), 2.85 (dd, 1 H), 2.45 (s, 3 H) | 390.2 $[M + H]^+$ | 100% |
| 1809 | ($CD_3OD$) δ 8.31 (d, 1 H), 7.70 (s, 1 H), 7.00 (d, 1 H), 6.80 (t, 1 H), 6.59 (s, 1 H), 6.41 (s, 1 H), 4.34 (dd, 1 H), 3.79 (ddd, 1 H), 3.00-3.16 (m, 1 H), 2.85 (dd, 1 H), 2.45 (s, 3 H) | 390.1 $[M + H]^+$ | 100% |
| 1810 | ($CD_3OD$) δ 8.63 (s, 2 H), 7.80 (d, 1 H), 7.62 (s, 1 H), 7.18-7.30 (m, 3 H), 6.77 (s, 1 H), 5.21 (dd, 1 H), 3.65 (td, 1 H), 2.83-2.96 (m, 1 H), 2.70-2.81 (m, 1 H) | 454.2 $[M + H]^+$ | 98.9% |
| 1811 | ($CD_3OD$) δ 8.53 (s, 2 H), 7.70 (d, 1 H), 7.52 (s, 1 H), 7.06-7.23 (m, 3 H), 6.67 (s, 1 H), 5.11 (dd, 1 H), 3.48-3.63 (m, 1 H), 2.57-2.89 (m, 2 H) | 454.1 $[M + H]^+$ | 99.7% |
| 1812 | ($CD_3OD$) δ 8.54 (s, 2 H), 7.47-7.66 (m, 2 H), 7.26-7.44 (m, 1 H), 7.02-7.16 (m, 3 H), 6.56 (s, 1 H), 5.10 (dd, 1 H), 3.52 (td, 1 H), 2.58-2.87 (m, 2 H) | 436.1 $[M + H]^+$ | 99.8% |
| 1813 | ($CD_3OD$) δ 8.53 (s, 2 H), 7.49-7.63 (m, 2 H), 7.26-7.44 (m, 1 H), 6.97-7.15 (m, 3 H), 6.56 (s, 1 H), 5.10 (dd, 1 H), 3.43-3.59 (m, 1 H), 2.59-2.86 (m, 2 H) | 436.1 $[M + H]^+$ | 99.8% |
| 1814 | ($CD_3OD$) δ 8.45 (d, 1 H), 8.13 (br d, 1 H), 7.49-7.71 (m, 3 H), 7.12-7.24 (m, 1 H), 7.05 (d, 1 H), 6.83 (t, 1 H), 6.77 (br s, 1 H), 6.66 (dd, 1 H), 6.50 (s, 1 H), 4.56 (br dd, 1 H), 3.51-3.63 (m, 1 H), 2.87-3.06 (m, 1 H), 2.68 (br d, 1 H) | 317.2 $[M + H]^+$ | 100% |
| 1815 | ($CD_3OD$) δ 8.45 (br d, 1 H), 8.13 (br d, 1 H), 7.47-7.69 (m, 3 H), 7.12-7.25 (m, 1 H), 7.05 (d, 1 H), 6.71-6.89 (m, 2 H), 6.66 (dd, 1 H), 6.50 (s, 1 H), 4.56 (br dd, 1 H), 3.51-3.64 (m, 1 H), 2.89-3.04 (m, 1 H), 2.68 (br d, 1 H) | 317.2 $[M + H]^+$ | 100% |
| 1816 | ($CD_3OD$) δ 8.58 (br d, 1 H), 8.47 (d, 1 H), 8.16 (dd, 1 H), 7.80 (d, 1 H), 7.67 (br s, 1 H), 7.42 (br d, 1 H), 6.79-7.15 (m, 3 H), 6.70 (s, 1 H), 4.71 (dd, 1 H), 3.61 (ddd, 1 H), 2.91-3.04 (m, 1 H), 2.77 (br d, 1 H) | 368.1 $[M + H]^+$ | 100% |
| 1817 | ($CD_3OD$) δ 8.59 (d, 1 H), 8.47 (d, 1 H), 8.17 (dd, 1 H), 7.80-7.86 (m, 2 H), 7.42 (br d, 1 H), 6.79-7.16 (m, 3 H), 6.71 (s, 1 H), 4.71 (dd, 1 H), 3.61 (ddd, 1 H), 2.93-3.05 (m, 1 H), 2.78 (br dd, 1 H) | 368.1 $[M + H]^+$ | 98.2% |
| 1818 | ($CD_3OD$) δ 8.69 (d, 1 H), 8.47 (d, 1 H), 8.17 (dd, 1 H), 7.81 (d, 1 H), 7.57-7.72 (m, 2 H), 6.97 (t, 1 H), 6.86 (br s, 1 H), 6.69 (s, 1 H), 4.72 (br dd, 1 H), 3.61 (ddd, 1 H), 2.92-3.06 (m, 1 H), 2.77 (br dd, 1 H) | 386.2 $[M + H]^+$ | 100% |
| 1819 | ($CD_3OD$) δ 8.69 (d, 1 H), 8.47 (d, 1 H), 8.17 (dd, 1 H), 7.81 (d, 1 H), 7.57-7.72 (m, 2 H), 6.97 (t, 1 H), 6.86 (br s, 1 H), 6.69 (s, 1 H), 4.72 (br dd, 1 H), 3.61 (ddd, 1 H), 2.92-3.05 (m, 1 H), 2.77 (br dd, 1 H) | 386.2 $[M + H]^+$ | 99.6% |
| 1820 | ($CD_3OD$) δ 8.71 (d, 1 H), 7.71 (s, 1 H), 7.64 (d, 1 H), 7.01 (t, 1 H), 6.77 (s, 1 H), 6.43 (s, 1 H), 4.38 (dd, 1 H), 3.80 (td, 1 H), 3.03-3.15 (m, 1 H), 2.86 (dd, 1 H) | 444.1 $[M + H]^+$ | 95.6% |
| 1821 | ($CD_3OD$) δ 8.71 (d, 1 H), 7.70 (s, 1 H), 7.64 (d, 1 H), 7.00 (t, 1 H), 6.77 (s, 1 H), 6.43 (br s, 1 H), 4.38 (dd, 1 H), 3.72-3.86 (m, 1 H), 3.02-3.16 (m, 1 H), 2.86 (br dd, 1 H) | 444.1 $[M + H]^+$ | 93.2% |
| 1822 | ($CD_3OD$) δ 8.24 (d, 1 H), 7.58 (s, 1 H), 6.86 (dd, 1 H), 6.73 (td, 1 H), 6.61 (s, 1 H), 6.29 (s, 1 H), 4.24 (dd, 1 H), 3.68 (ddd, 1 H), 2.91-3.03 (m, 1 H), 2.73 (dd, 1 H) | 394.1 $[M + H]^+$ | 99.7% |
| 1823 | ($CD_3OD$) δ 8.23 (d, 1 H), 7.58 (s, 1 H), 6.86 (dd, 1 H), 6.73 (td, 1 H), 6.61 (s, 1 H), 6.29 (s, 1 H), 4.24 (dd, 1 H), 3.68 (ddd, 1 H), 2.90-3.03 (m, 1 H), 2.73 (dd, 1 H) | 394.1 $[M + H]^+$ | 99.8% |
| 1824 | ($CD_3OD$) δ 8.57 (d, 1 H), 7.67 (s, 1 H), 7.43 (br d, 1 H), 6.67-7.18 (m, 3 H), 6.31 (s, 1 H), 4.24 (dd, 1 H), 3.72 (ddd, 1 H), 2.95-3.14 (m, 1 H), 2.83 (dd, 1 H), 1.41 (s, 9 H) | 414.2 $[M + H]^+$ | 98.4% |
| 1825 | ($CD_3OD$) δ 8.57 (d, 1 H), 7.67 (s, 1 H), 7.43 (br d, 1 H), 6.62-7.19 (m, 3 H), 6.31 (br s, 1 H), 4.24 (dd, 1 H), 3.72 (ddd, 1 H), 2.97-3.11 (m, 1 H), 2.83 (br dd, 1 H), 1.41 (s, 9 H) | 414.2 $[M + H]^+$ | 99.8% |
| 1826 | ($CD_3OD$) δ 8.27 (d, 1 H), 8.06 (s, 2 H), 7.61 (s, 1 H), 7.05 (s, 1 H), 6.95 (d, 1 H), 6.74 (t, 1 H), 6.49 (s, 1 H), 4.81 (br dd, 1 H), 3.43 (ddd, 1 H), 2.84-2.95 (m, 1 H), 2.59-2.68 (m, 1 H), 2.42 (s, 3 H) | 347.2 $[M + H]^+$ | 97.1% |

TABLE 2-continued

| Ex. # | $^1$H NMR (400 MHz unless otherwise noted) | LCMS: m/z | % ee |
|---|---|---|---|
| 1827 | ($CD_3OD$) δ 8.16 (d, 1 H), 7.91-7.99 (m, 2 H), 7.50 (s, 1 H), 6.93 (s, 1 H), 6.80-6.86 (m, 1 H), 6.62 (t, 1 H), 6.37 (s, 1 H), 4.65-4.70 (m, 1 H), 3.27-3.36 (m, 1 H), 2.72-2.83 (m, 1 H), 2.52 (dd, 1 H), 2.30 (s, 3 H) | 347.2 $[M + H]^+$ | 93.3% |
| 1828 | ($CD_3OD$) δ 8.59 (d, 1 H), 8.40 (s, 1 H), 7.81 (s, 1 H), 7.69 (s, 1 H), 7.42 (d, 1 H), 6.81-7.14 (m, 2 H), 6.75 (d, 2 H), 4.72 (br dd, 1 H), 3.61 (ddd, 1 H), 2.91-3.05 (m, 1 H), 2.79 (dd, 1 H) | 402.1 $[M + H]^+$ | 100% |
| 1829 | ($CD_3OD$) δ 8.59 (d, 1 H), 8.41 (s, 1 H), 7.81 (s, 1 H), 7.69 (s, 1 H), 7.43 (d, 1 H), 6.81-7.15 (m, 2 H), 6.75 (d, 2 H), 4.73 (dd, 1 H), 3.61 (ddd, 1 H), 2.92-3.04 (m, 1 H), 2.79 (dd, 1 H) | 402.1 $[M + H]^+$ | 99.9% |
| 1830 | ($CD_3OD$) δ 8.41 (d, 1 H), 7.66 (s, 1 H), 7.26 (d, 1 H), 6.82 (t, 1 H), 6.65 (s, 1 H), 6.30 (s, 1 H), 4.23 (dd, 1 H), 3.60-3.76 (m, 2 H), 2.95-3.09 (m, 1 H), 2.79 (br dd, 1 H), 2.33-2.48 (m, 4 H), 1.95-2.17 (m, 2 H) | 396.1 $[M + H]^+$ | 99.7% |
| 1831 | ($CD_3OD$) δ 8.36-8.51 (m, 1 H), 7.68 (s, 1 H), 7.28 (d, 1 H), 6.84 (t, 1 H), 6.67 (s, 1 H), 6.31 (s, 1 H), 4.25 (dd, 1 H), 3.60-3.76 (m, 2 H), 2.98-3.09 (m, 1 H), 2.77-2.86 (m, 1 H), 2.33-2.49 (m, 4 H), 1.97-2.20 (m, 2 H) | 396.1 $[M + H]^+$ | 98.9% |
| 1832 | ($CD_3OD$) δ 8.44 (d, 1 H), 7.68 (s, 1 H), 7.30 (d, 1 H), 6.86 (t, 1 H), 6.67 (s, 1 H), 6.30 (br s, 1 H), 4.24 (dd, 1 H), 3.71 (ddd, 1 H), 2.97-3.11 (m, 1 H), 2.82 (br dd, 1 H), 1.41 (s, 9 H) | 398.2 $[M + H]^+$ | 100% |
| 1833 | ($CD_3OD$) δ 8.44 (d, 1 H), 7.68 (s, 1 H), 7.30 (d, 1 H), 6.85 (t, 1 H), 6.67 (s, 1 H), 6.30 (br s, 1 H), 4.24 (dd, 1 H), 3.71 (ddd, 1 H), 2.96-3.10 (m, 1 H), 2.76-2.90 (m, 1 H), 1.41 (s, 9 H) | 398.2 $[M + H]^+$ | 100% |
| 1834 | ($CD_3OD$) δ 8.66 (d, 1 H), 8.06 (s, 2 H), 7.63 (s, 1 H), 7.59 (d, 1 H), 7.05 (s, 1 H), 6.94 (t, 1 H), 6.66 (s, 1 H), 4.84 (br d, 1 H), 3.42 (ddd, 1 H), 2.86-2.96 (m, 1 H), 2.61-2.69 (m, 1 H) | 401.1 $[M + H]^+$ | 89.0% |
| 1835 | ($CD_3OD$) δ 8.54 (d, 1 H), 7.94 (s, 2 H), 7.52 (s, 1 H), 7.43-7.50 (m, 1 H), 6.94 (s, 1 H), 6.82 (t, 1 H), 6.54 (s, 1 H), 4.72 (br d, 1 H), 3.30 (ddd, 1 H), 2.73-2.84 (m, 1 H), 2.53 (dd, 1 H) | 401.2 $[M + H]^+$ | 97.7% |
| 1836 | ($CD_3OD$) δ 8.31 (d, 1 H), 8.06 (s, 2 H), 7.62 (s, 1 H), 7.03 (s, 1 H), 6.92 (dd, 1 H), 6.78 (td, 1 H), 6.62 (s, 1 H), 4.78-4.84 (m, 1 H), 3.42 (ddd, 1 H), 2.83-2.97 (m, 1 H), 2.65 (dd, 1 H) | 351.1 $[M + H]^+$ | 98.8% |
| 1837 | ($CD_3OD$) δ 8.19 (d, 1 H), 7.94 (s, 2 H), 7.50 (s, 1 H), 6.91 (s, 1 H), 6.80 (dd, 1 H), 6.67 (td, 1 H), 6.50 (s, 1 H), 4.70 (br d, 1 H), 3.30 (ddd, 1 H), 2.70-2.88 (m, 1 H), 2.53 (dd, 1 H) | 351.2 $[M + H]^+$ | 90.6% |
| 1838 | ($CD_3OD$) δ 8.18-8.32 (m, 1 H), 7.68 (s, 1 H), 7.45 (br s, 0.3 H), 6.93 (s, 0.7 H), 6.58-6.84 (m, 3 H), 4.97 (br dd, 1 H), 3.65-3.78 (m, 0.7 H), 3.34-3.42 (m, 0.3 H), 3.06-3.18 (m, 0.7 H), 2.91-3.03 (m, 0.3 H), 2.81 (br dd, 1 H), 2.26-2.36 (m, 1 H), 2.01-2.14 (m, 1 H), 1.19-1.30 (m, 4 H), 0.97-1.08 (m, 2 H), 0.72-0.83 (m, 2 H) | 416.2 $[M + H]^+$ | 96.5% |
| 1839 | ($CD_3OD$) δ 8.20-8.35 (m, 1 H), 7.68 (s, 1 H), 7.45 (br s, 0.3 H), 6.93 (s, 0.7 H), 6.65-6.84 (m, 3 H), 4.97 (br dd, 1 H), 3.66-3.77 (m, 0.6 H), 3.33-3.44 (m, 0.4 H), 3.06-3.18 (m, 0.6 H), 2.91-3.03 (m, 0.4 H), 2.76-2.87 (m, 1 H), 2.24-2.44 (m, 1 H), 2.09 (td, 1 H), 1.20-1.30 (m, 4 H), 0.94-1.09 (m, 2 H), 0.69-0.86 (m, 2 H) | 416.2 $[M + H]^+$ | 91.5% |
| 1840 | ($CD_3OD$) δ 8.19-8.32 (m, 1 H), 7.69 (s, 1 H), 6.93-7.48 (m, 1 H), 6.66-6.85 (m, 3 H), 4.93-5.00 (m, 1 H), 3.75 (ddd, 0.7 H), 3.40 (td, 0.3 H), 3.09-3.21 (m, 0.7 H), 2.92-3.02 (m, 0.3 H), 2.83 (br dd, 1 H), 2.00-2.17 (m, 1 H), 1.42-1.53 (m, 9 H), 0.96-1.07 (m, 2 H), 0.71-0.82 (m, 2 H) | 432.2 $[M + H]^+$ | 100% |
| 1841 | ($CD_3OD$) δ 8.18-8.33 (m, 1 H), 7.69 (s, 1 H), 7.41 (br s, 0.3 H), 6.95 (s, 0.7 H), 6.63-6.84 (m, 3 H), 4.96 (dd, 1 H), 3.75 (ddd, 0.7 H), 3.35-3.45 (m, 0.3 H), 3.09-3.20 (m, 0.7 H), 2.92-3.03 (m, 0.3 H), 2.83 (br dd, 1 H), 2.01-2.15 (m, 1 H), 1.43-1,53 (m, 9 H), 0.98-1.07 (m, 2 H), 0.73-0.81 (m, 2 H) | 432.2 $[M + H]^+$ | 95.1% |
| 1842 | Data provided above | | |
| 1843 | Data provided above | | |
| 1844 | ($CD_3OD$) δ 8.31 (d, 1 H), 7.52-7.79 (m, 2 H), 7.23 (t, 2 H), 7.00 (d, 1 H), 6.79 (t, 1 H), 6.62 (s, 1 H), 6.42 (s, 1 H), 4.36 (dd, 1 H), 3.81 (ddd, 1 H), 3.02-3.17 (m, 1 H), 2.86 (br dd, 1 H), 2.45 (s, 3 H) | 434.1 $[M + H]^+$ | 99.7% |
| 1845 | ($CD_3OD$) δ 8.31 (d, 1 H), 7.54-7.78 (m, 2 H), 7.22 (t, 2 H), 6.99 (d, 1 H), 6.79 (t, 1 H), 6.61 (s, 1 H), 6.42 (s, 1 H), 4.36 (dd, 1 H), 3.80 (ddd, 1 H), 3.00-3.18 (m, 1 H), 2.85 (dd, 1 H), 2.45 (s, 3 H) | 434.2 $[M + H]^+$ | 99.7% |
| 1846 | ($CD_3OD$) δ 8.70 (br d, 1 H), 7.48-7.85 (m, 3 H), 7.22 (t, 2 H), 6.99 (t, 1 H), 6.79 (s, 1 H), 6.43 (br s, 1 H), 4.40 (dd, 1 H), 3.65-3.95 (m, 1 H), 2.99-3.19 (m, 1 H), 2.87 (br dd, 1 H) | 488.1 $[M + H]^+$ | 97.8% |
| 1847 | ($CD_3OD$) δ 8.70 (d, 1 H), 7.47-7.87 (m, 3 H), 7.22 (t, 2 H), 6.99 (t, 1 H), 6.79 (s, 1 H), 6.44 (s, 1 H), 4.40 (dd, 1 H), 3.67-3.99 (m, 1 H), 3.00-3.20 (m, 1 H), 2.87 (br dd, 1 H) | 488.1 $[M + H]^+$ | 99.4% |
| 1848 | ($CD_3OD$) δ 8.46 (br d, 1 H), 7.77 (br s, 1 H), 7.32 (d, 1 H), 6.87 (t, 1 H), 6.72 (s, 1 H), 6.42 (s, 1 H), 4.36 (dd, 1 H), 3.69-3.86 (m, 1 H), 3.01-3.16 (m, 1 H), 2.86 (br d, 1 H) | 410.1 $[M + H]^+$ | 99.8% |
| 1849 | ($CD_3OD$) δ 8.34 (d, 1 H), 7.65 (s, 1 H), 7.20 (d, 1 H), 6.75 (t, 1 H), 6.60 (s, 1 H), 6.31 (s, 1 H), 4.24 (dd, 1 H), 3.67 (ddd, 1 H), 2.90-3.02 (m, 1 H), 2.74 (dd, 1 H) | 410.1 $[M + H]^+$ | 99.6% |

TABLE 2-continued

| Ex. # | $^1$H NMR (400 MHz unless otherwise noted) | LCMS: m/z | % ee |
|---|---|---|---|
| 1850 | ($CD_3OD$) δ 7.60 (s, 1 H), 7.36 (d, 1 H), 7.02 (dd, 1 H), 6.62 (d, 1 H), 6.41 (s, 1 H), 6.29 (s, 1 H), 4.23 (dd, 1 H), 3.69 (ddd, 1 H), 2.90-3.02 (m, 1 H), 2.74 (dd, 1 H), 2.52 (s, 3 H) | 390.1 $[M + H]^+$ | 99.4% |
| 1851 | ($CD_3OD$) δ 7.73 (s, 1 H), 7.48 (d, 1 H), 7.13 (dd, 1 H), 6.73 (d, 1 H), 6.53 (s, 1 H), 6.41 (s, 1 H), 4.35 (dd, 1 H), 3.80 (ddd, 1 H), 3.02-3.14 (m, 1 H), 2.85 (dd, 1 H), 2.63 (s, 3 H) | 390.1 $[M + H]^+$ | 93.6% |
| 1852 | ($CD_3OD$) δ 8.43 (d, 1 H), 7.94 (s, 2 H), 7.51 (s, 1 H), 7.28 (br d, 1 H), 6.83-6.99 (m, 1.8 H), 6.77 (t, 1 H), 6.70 (s, 0.2 H), 6.55 (s, 1 H), 4.70 (br d, 1 H), 3.25-3.34 (m, 1 H), 2.72-2.84 (m, 1 H), 2.53 (dd, 1 H) | 383.2 $[M + H]^+$ | 100% |
| 1853 | ($CD_3OD$) δ 8.43 (d, 1 H), 7.94 (s, 2 H), 7.51 (s, 1 H), 7.27 (br d, 1 H), 6.92-6.99 (m, 1.2 H), 6.84 (s, 0.6 H), 6.77 (t, 1 H), 6.70 (s, 0.2 H), 6.55 (s, 1 H), 4.70 (br d, 1 H), 3.26-3.34 (m, 1 H), 2.73-2.83 (m, 1 H), 2.52 (dd, 1 H) | 383.2 $[M + H]^+$ | 99.3% |
| 1854 | ($CD_3OD$) δ 8.63 (br d, 1 H), 8.17-8.32 (m, 1 H), 7.92 (br t, 1 H), 7.68-7.80 (m, 2 H), 7.47 (br s, 0.3 H), 6.99 (s, 0.7 H), 6.71-6.82 (m, 3 H), 4.93-4.99 (m, 1 H), 3.77-3.87 (m, 0.7 H), 3.45 (td, 0.3 H), 3.17-3.26 (m, 0.7 H), 2.98-3.07 (m, 0.3 H), 2.85 (br d, 1 H), 2.02-2.15 (m, 1 H), 0.95-1.07 (m, 2 H), 0.70-0.81 (m, 2 H) | 471.2 $[M + H]^+$ | 98.6% |
| 1855 | ($CD_3OD$) δ 8.62 (d, 1 H), 8.19-8.31 (m, 1 H), 7.91 (t, 1 H), 7.69-7.77 (m, 2 H), 7.47 (s, 0.3 H), 6.99 (s, 0.7 H), 6.71-6.82 (m, 3 H), 4.93-4.99 (m, 1 H), 3.77-3.86 (m, 0.7 H), 3.45 (td, 0.3 H), 3.17-3.26 (m, 0.7 H), 2.97-3.06 (m, 0.3 H), 2.86 (br dd, 1 H), 2.01-2.14 (m, 1 H), 0.96-1.07 (m, 2 H), 0.72-0.81 (m, 2 H) | 471.2 $[M + H]^+$ | 97.9% |
| 1856 | ($CD_3OD$) δ 9.44 (s, 1 H), 8.79-8.86 (m, 2 H), 8.19-8.30 (m, 1 H), 7.70 (s, 1 H), 7.50 (br s, 0.3 H), 6.98 (s, 0.7 H), 6.67-6.85 (m, 3 H), 5.01-4.89 (br dd, 1 H), 3.77-3.86 (m, 0.6 H), 3.45 (td, 0.4 H), 3.14-3.27 (m, 0.7 H), 2.97-3.07 (m, 0.3 H), 2.80-2.91 (m, 1 H), 2.00-2.15 (m, 1 H), 0.96-1.08 (m, 2 H), 0.71-0.82 (m, 2 H) | 454.2 $[M + H]^+$ | 99.9% |
| 1857 | ($CD_3OD$) δ 9.45 (s, 1 H), 8.83 (br d, 2 H), 8.17-8.34 (m, 1 H), 7.70 (s, 1 H), 7.50 (s, 0.3 H), 6.99 (s, 0.7 H), 6.72-6.82 (m, 3 H), 4.93-5.05 (m, 1 H), 3.78-3.86 (m, 0.7 H), 3.45 (td, 0.3 H), 3.15-3.26 (m, 0.7 H), 2.97-3.06 (m, 0.3 H), 2.86 (br dd, 1 H), 1.99-2.15 (m, 1 H), 0.97-1.08 (m, 2 H), 0.72-0.82 (m, 2 H) | 454.2 $[M + H]^+$ | 99.3% |
| 1858 | ($CD_3OD$) δ 8.13-8.23 (m, 1 H), 7.58 (s, 1 H), 7.35 (s, 0.3 H), 6.91-6.97 (m, 1 H), 6.82 (s, 0.7 H), 6.65-6.76 (m, 1 H), 6.49-6.61 (m, 1 H), 4.82-4.87 (m, 1 H), 3.60-3.69 (m, 0.6 H), 3.24-3.34 (m, 0.4 H), 2.83-3.13 (m, 2 H), 2.71 (br dd, 1 H), 2.48-2.55 (m, 3 H), 1.18-1.26 (m, 6 H) | 392.2 $[M + H]^+$ | 100% |
| 1859 | ($CD_3OD$) δ 8.14-8.23 (m, 1 H), 7.58 (s, 1 H), 7.35 (s, 0.3 H), 6.91-6.98 (m, 1 H), 6.82 (s, 0.7 H), 6.68-6.76 (m, 1 H), 6.48-6.61 (m, 1 H), 4.81-4.88 (m, 1 H), 3.60-3.70 (m, 0.6 H), 3.24-3.34 (m, 0.4 H), 2.81-3.14 (m, 2 H), 2.65-2.77 (m, 1 H), 2.48-2.58 (m, 3 H), 1.18-1.26 (m, 6 H) | 392.2 $[M + H]^+$ | 99.7% |
| 1860 | ($CD_3OD$) δ 8.46 (d, 1 H), 8.03 (dd, 2 H), 7.69 (s, 1 H), 7.60 (d, 1 H), 7.30 (t, 2 H), 7.16-7.24 (m, 1 H), 6.86 (t, 1 H), 6.60 (s, 1 H), 6.45 (s, 1 H), 4.37 (dd, 1 H), 3.73-3.83 (m, 1 H), 3.02-3.21 (m, 1 H), 2.85 (dd, 1 H) | 402.2 $[M + H]^+$ | 100% |
| 1861 | ($CD_3OD$) δ 8.46 (br d, 1 H), 7.97-8.09 (m, 2 H), 7.67-7.73 (m, 1 H), 7.60 (br d, 1 H), 7.27-7.34 (m, 2 H), 7.16-7.24 (m, 1 H), 6.83-6.92 (m, 1 H), 6.60 (s, 1 H), 6.45 (s, 1 H), 4.32-4.45 (m, 1 H), 3.73-3.86 (m, 1 H), 3.04-3.18 (m, 1 H), 2.78-2.92 (m, 1 H) | 402.2 $[M + H]^+$ | 95.2% |
| 1862 | ($CD_3OD$) δ 8.58 (br d, 1 H), 7.50-7.82 (m, 2 H), 7.42 (br d, 1 H), 7.20 (t, 2 H), 6.83-7.14 (m, 2 H), 6.79 (s, 1 H), 6.44 (br s, 1 H), 4.38 (br dd, 1 H), 3.70-3.90 (m, 1 H), 3.01-3.17 (m, 1 H), 2.86 (br d, 1 H) | 470.1 $[M + H]^+$ | 99.7% |
| 1863 | ($CD_3OD$) δ 8.59 (d, 1 H), 7.55-7.79 (m, 2 H), 7.44 (br d, 1 H), 7.22 (t, 2 H), 6.84-7.15 (m, 2 H), 6.79 (s, 1 H), 6.44 (s, 1 H), 4.38 (dd, 1 H), 3.80 (ddd, 1 H), 3.01-3.20 (m, 1 H), 2.86 (dd, ] H) | 470.2 $[M + H]^+$ | 99.5% |
| 1864 | ($CD_3OD$) δ 8.35 (d, 1 H), 7.52-7.80 (m, 2 H), 7.22 (t, 2 H), 6.97 (dd, 1 H), 6.84 (td, 1 H), 6.74 (s, 1 H), 6.42 (br s, 1 H), 4.38 (dd, 1 H), 3.81 (ddd, 1 H), 3.01-3.18 (m, 1 H), 2.86 (dd, 1 H) | 438.1 $[M + H]^+$ | 99.4% |
| 1865 | ($CD_3OD$) δ 8.23 (d, 1 H), 7.36-7.70 (m, 2 H), 7.10 (t, 2 H), 6.85 (dd, 1 H), 6.72 (td, 1 H), 6.62 (s, 1 H), 6.30 (br s, 1 H), 4.26 (dd, 1 H), 3.69 (ddd, 1 H), 2.88-3.06 (m, 1 H), 2.74 (br dd, 1 H) | 438.2 $[M + H]^+$ | 99.3% |
| 1866 | ($CD_3OD$) δ 8.35 (br s, 1 H), 7.30-7.91 (m, 3 H), 6.94-7.19 (m, 1 H), 6.27-6.87 (m, 3 H), 4.56-4.75 (m, 1 H), 4.26-4.43 (m, 0.5 H), 3.64 (br s, 0.5 H), 2.53-3.10 (m, 2 H), 1.31 (br s, 9 H) | 391.2 $[M + H]^+$ | 100% |
| 1867 | ($CD_3OD$) δ 8.31 (br s, 1 H), 7.33-7.96 (m, 3 H), 7.04 (br t, 1 H), 6.21-6.89 (m, 3 H), 4.70-4.81 (m, 1 H), 4.14-4.47 (m, 0.5 H), 3.63 (br s, 0.5 H), 2.47-3.08 (m, 2 H), 1.29 (br s, 9 H) | 391.2 $[M + H]^+$ | 99.5% |
| 1868 | ($CD_3OD$) δ 8.32-8.56 (m, 2 H), 8.11 (s, 1 H), 7.79 (br s, 1 H), 7.58 (s, 0.3 H), 7.41-7.51 (m, 1 H), 6.96 (s, 0.7 H), 6.60-6.86 (m, 2 H), 5.10 (br dd, 1 H), 4.00 (s, 3 H), 3.68-3.81 (m, 0.7 H), 3.37-3.45 (m, 0.3 H), 3.12-3.23 (m, 0.7 H), 2.94-3.05 (m, 0.3 H), 2.85 (br d, 1 H) | 494.1 $[M + H]^+$ | 100% |

TABLE 2-continued

| Ex. # | $^1$H NMR (400 MHz unless otherwise noted) | LCMS: m/z | % ee |
|---|---|---|---|
| 1869 | ($CD_3OD$) δ 8.29-8.57 (m, 2 H), 8.11 (s, 1 H), 7.83 (br d, 1 H), 7.59 (s, 0.3 H), 7.43-7.50 (m, 1 H), 6.97 (s, 0.7 H), 6.65-6.85 (m, 2 H), 5.11 (br dd, 1 H), 4.01 (s, 3 H), 3.68-3.84 (m, 0.7 H), 3.41 (br d, 0.3 H), 2.95-3.24 (m, 1 H), 2.86 (br d, 1 H) | 494.1 $[M + H]^+$ | 99.4% |
| 1870 | ($CD_3OD$) δ 8.69 (d, 1 H), 8.14 (br d, 1 H), 7.71 (s, 1 H), 7.54-7.66 (m, 2 H), 7.06 (d, 1 H), 6.96 (t, 1 H), 6.86 (s, 1 H), 6.60-6.74 (m, 2 H), 4.57 (br dd, 1 H), 3.46-3.62 (m, 1 H), 2.90-3.03 (m, 1 H), 2.70 (br dd, 1 H) | 385.1 $[M + H]^+$ | 98.2% |
| 1871 | ($CD_3OD$) δ 8.69 (d, 1 H), 8.09-8.23 (m, 1 H), 7.77 (s, 1 H), 7.55-7.69 (m, 2 H), 7.06 (d, 1 H), 6.96 (t, 1 H), 6.89 (s, 1 H), 6.62-6.75 (m, 2 H), 4.57 (br dd, 1 H), 3.49-3.61 (m, 1 H), 2.91-3.05 (m, 1 H), 2.70 (br dd, 1 H) | 385.2 $[M + H]^+$ | 95.9% |
| 1872 | ($CD_3OD$) δ 8.41 (d, 1 H), 8.06 (s, 2 H), 7.63 (s, 1 H), 7.26 (d, 1 H), 7.03 (s, 1 H), 6.80 (t, 1 H), 6.61 (s, 1 H), 4.83 (br d, 1 H), 3.39-3.46 (m, 1 H), 2.84-2.95 (m, 1 H), 2.65 (br dd, 1 H) | 367.1 $[M + H]^+$ | 99.7% |
| 1873 | ($CD_3OD$) δ 8.41 (d, 1 H), 8.06 (s, 2 H), 7.62 (s, 1 H), 7.26 (d, 1 H), 7.03 (s, 1 H), 6.80 (t, 1 H), 6.61 (s, 1 H), 4.83 (br d, 1 H), 3.39-3.46 (m, 1 H), 2.85-2.95 (m, 1 H), 2.65 (dd, 1 H) | 367.1 $[M + H]^+$ | 98.5% |
| 1874 | ($CD_3OD$) δ 8.16-8.43 (m, 1 H), 7.68 (s, 1 H), 7.44 (s, 0.5 H), 6.76-7.09 (m, 2.5 H), 6.41-6.71 (m, 1 H), 4.97 (br dd, 1 H), 3.66-3.78 (m, 0.5 H), 3.38 (td, 0.5 H), 2.89-3.21 (m, 1 H), 2.71-2.88 (m, 3 H), 2.19-2.40 (m, 1 H), 1.13-1.34 (m, 7 H) | 404.2 $[M + H]^+$ | 100% |
| 1875 | ($CD_3OD$) δ 8.19-8.36 (m, 1 H), 7.68 (s, 1 H), 7.44 (br s, 0.5 H), 6.75-7.05 (m, 2.5 H), 6.50-6.68 (m, 1 H), 4.97 (br dd, 1 H), 3.65-3.84 (m, 0.5 H), 3.32-3.44 (m, 0.5 H), 2.90-3.22 (m, 1 H), 2.69-2.87 (m, 3 H), 2.18-2.39 (m, 1 H), 1.13-1.42 (m, 7 H) | 404.2 $[M + H]^+$ | 94.8% |
| 1876 | ($CD_3OD$) δ 8.39 (s, 1 H), 8.20-8.30 (m, 1 H), 8.07-8.12 (m, 1 H), 7.69 (s, 1 H), 7.57 (s, 0.3 H), 6.97 (s, 0.7 H), 6.70-6.83 (m, 3 H), 5.07 (br dd, 1 H), 4.00 (s, 3 H), 3.74-3.82 (m, 0.7 H), 3.42 (td, 0.3 H), 3.13-3.23 (m, 0.7 H), 2.95-3.03 (m, 0.3 H), 2.80-2.87 (m, 1 H), 2.01-2.15 (m, 1 H), 0.97-1.07 (m, 2 H), 0.73-0.81 (m, 2 H) | 556.2 $[M + H]^+$ | 100% |
| 1877 | ($CD_3OD$) δ 8.38 (s, 1 H), 8.20-8.29 (m, 1 H), 8.06-8.12 (m, 1 H), 7.69 (s, 1 H), 7.58 (s, 0.3 H), 6.96 (s, 0.7 H), 6.69-6.83 (m, 3 H), 5.07 (dd, 1 H), 4.00 (s, 3 H), 3.74-3.82 (m, 0.7 H), 3.42 (td, 0.3 H), 3.12-3.22 (m, 0.7 H), 2.93-3.04 (m, 0.3 H), 2.77-2.89 (m, 1 H), 2.01-2.15 (m, 1 H), 0.96-1.07 (m, 2 H), 0.72-0.81 (m, 2 H) | 556.1 $[M + H]^+$ | 95.1% |
| 1878 | ($CD_3OD$) δ 8.91 (s, 1 H), 8.34 (s, 1 H), 8.21-8.30 (m, 1 H), 7.92-8.00 (m, 1 H), 7.61-7.81 (m, 1 H), 7.50 (s, 0.2 H), 7.02 (s, 0.8 H), 6.74-6.84 (m, 3 H), 5.10 (br dd, 1 H), 3.74-3.83 (m, 0.7 H), 3.39-3.48 (m, 0.3 H), 3.17-3.24 (m, 0.7 H), 2.97-3.05 (m, 0.3 H), 2.83-2.92 (m, 1 H), 2.01-2.15 (m, 1 H), 0.98-1.06 (m, 2 H), 0.74-0.81 (m, 2 H) | 492.2 $[M + H]^+$ | 98.9% |
| 1879 | ($CD_3OD$) δ 8.92 (s, 1 H), 8.35 (s, 1 H), 8.21-8.30 (m, 1 H), 7.89-7.99 (m, 1 H), 7.61-7.82 (m, 1 H), 7.50 (s, 0.2 H), 7.02 (s, 0.8 H), 6.75-6.84 (m, 3 H), 5.10 (br dd, 1 H), 3.72-3.85 (m, 0.7 H), 3.39-3.47 (m, 0.3 H), 3.17-3.24 (m, 0.7 H), 3.00 (br dd, 0.3 H), 2,82-2.92 (m, 1 H), 2.03-2.15 (m, 1 H), 0.98-1.07 (m, 2 H), 0.74-0.81 (m, 2 H) | 492.2 $[M + H]^+$ | 98.2% |
| 1880 | ($CD_3OD$) δ 8.49 (d, 1 H), 8.19-8.33 (m, 1 H), 7.70 (s, 1 H), 7.52 (s, 0.3 H), 7.26 (d, 1 H), 6.98 (s, 0.7 H), 6,70-6.83 (m, 3 H), 4.92-5.05 (m, 1 H), 3.73-3.87 (m, 0.7 H), 3.43 (td, 0.3 H), 3.15-3.24 (m, 0.7 H), 2.97-3.06 (m, 0.3 H), 2.85 (br dd, 1 H), 2.01-2.15 (m, 1 H), 0.96-1.07 (m, 2 H), 0.71-0.82 (m, 2 H) | 510.2 $[M + H]^+$ | 100% |
| 1881 | (CD3OD) δ 8.49 (d, 1 H), 8.16-8.32 (m, 1 H), 7.70 (s, 1 H), 7.52 (s, 0.3 H), 7.26 (br s, 1 H), 6.98 (s, 0.7 H), 6.67-6.85 (m, 3 H), 4.92-5.06 (m, 1 H), 3.70-3.89 (m, 0.7 H), 3.43 (td, 0.3 H), 3.14-3.25 (m, 0.7 H), 2.96-3.06 (m, 0.3 H), 2.85 (br dd, 1 H), 2.00-2.15 (m, 1 H), 0.95-1.10 (m, 2 H) , 0.74 -0.79 (dt, 2 H) | 510.2 $[M + H]^+$ | 99.5% |
| 1882 | ($CD_3OD$) δ 8.08-8.25 (m, 1 H), 7.58 (s, 1 H), 7.34 (s, 0.3 H), 6.91-6.98 (m, 1 H), 6.69-6.83 (m, 1.7 H), 6.46-6.60 (m, 1 H), 4.87 (br dd, 1 H), 3.58-3.67 (m, 0.7 H), 3.26-3.34 (m, 0.3 H), 2.81-3.09 (m, 2 H), 2.71 (br dd, 1 H), 2.17-2.26 (m, 1 H), 1.08-1.26 (m, 10 H) | 418.2 $[M + H]^+$ | 100% |
| 1883 | ($CD_3OD$) δ 8.08-8.25 (m, 1 H), 7.58 (s, 1 H), 7.34 (s, 0.3 H), 6.91-6.98 (m, 1 H), 6.69-6.83 (m, 1.7 H), 6.46-6.60 (m, 1 H), 4.87 (br dd, 1 H), 3.58-3.67 (m, 0.6 H), 3.26-3.34 (m, 0.4 H), 2.81-3.09 (m, 2 H), 2.71 (br dd, 1 H), 2.17-2.26 (m, 1 H), 1.08-1.26 (m, 10 H) | 418.2 $[M + H]^+$ | 99.4% |
| 1884 | ($CD_3OD$) δ 8.07-8.23 (m, 1 H), 7.59 (s, 1 H), 7.29 (s, 0.3 H), 6.88-6.99 (m, 1 H), 6.84 (s, 0.7 H), 6.68-6.76 (m, 1 H), 6.48-6.62 (m, 1 H), 4.83-4.88 (m, 1 H), 3.66 (ddd, 0.6 H), 3.30 (td, 0.4 H), 2.83-3.12 (m, 2 H), 2.73 (br dd, 1 H), 1.73-1.84 (m, 6 H), 1.18-1.26 (m, 6 H) | 438.2 $[M + H]^+$ | 100% |

TABLE 2-continued

| Ex. # | $^1$H NMR (400 MHz unless otherwise noted) | LCMS: m/z | % ee |
|---|---|---|---|
| 1885 | ($CD_3OD$) δ 8.12-8.23 (m, 1 H), 7.59 (s, 1 H), 7.29 (s, 0.3 H), 6.91-6.99 (m, 1 H), 6.84 (s, 0.7 H), 6.68-6.76 (m, 1 H), 6.46-6.63 (m, 1 H), 4.82-4.88 (m, 1 H), 3.62-3.71 (m, 0.6 H), 3.26-3.35 (m, 0.4 H), 2.83-3.13 (m, 2 H), 2.73 (br dd, 1 H), 1.73-1.86 (m, 6 H), 1.19-1.26 (m, 6 H) | 438.2 $[M + H]^+$ | 99.1% |
| 1886 | ($CD_3OD$) δ 8.37-8.44 (m, 1 H), 8.24-8.35 (m, 1 H), 8.06-8.16 (m, 1 H), 7.71 (s, 1 H), 7.57 (br s, 0.3 H), 7.02-7.11 (m, 1 H), 6.80-6.99 (m, 1.7 H), 6.62-6.74 (m, 1 H), 4.99-5.13 (m, 1 H), 4.02 (s, 3 H), 3.75-3.85 (m, 0.7 H), 3.38-3.50 (m, 0.3 H), 2.99-3.25 (m, 2 H), 2.81-2.92 (m, 1 H), 1.31-1.37 (m, 6 H) | 458.2 $[M + H]^+$ | 98.8% |
| 1887 | ($CD_3OD$) δ 8.40 (s, 1 H), 8.23-8.35 (m, 1 H), 8.07-8.13 (m, 1 H), 7.71 (s, 1 H), 7.57 (s, 0.3 H), 7.02-7.10 (m, 1 H), 6.81-6.99 (m, 1.7 H), 6.62-6.74 (m, 1 H), 5.01-5.13 (m, 1 H), 4.01 (s, 3 H), 3.75-3.86 (m, 0.7 H), 3.38-3.50 (m, 0.3 H), 2.97-3.24 (m, 2 H), 2.81-2.90 (m, 1 H), 1.29-1.37 (m, 6 H) | 458.2 $[M + H]^+$ | 95.4% |
| 1888 | ($CD_3OD$) δ 8.34-8.60 (m, 1 H), 7.62-7.91 (m, 2 H), 7.33-7.60 (m, 1,3 H), 6.89-7.17 (m, 1.7 H), 6.50-6.88 (m, 2 H), 5.03 (br dd, 1 H), 4.03 (s, 3 H), 3.71-3.81 (m, 0.6 H), 3.36-3.44 (m, 0.4 H), 3.12-3.24 (m, 0.5 H), 2.94-3.05 (m, 0.5 H), 2.84 (br d, 1 H) | 494.1 $[M + H]^+$ | 98.5% |
| 1889 | ($CD_3OD$) δ 8.34-8.56 (m, 1 H), 7.63-7.89 (m, 2 H), 7.26-7.61 (m, 1.3 H), 6.87-7.12 (m, 1.6 H), 6.59-6.84 (m, 2 H), 5.04 (br dd, 1 H), 4.03 (s, 3 H), 3.72-3.81 (m, 0.5 H), 3.34-3.44 (m, 0.5 H), 3.10-3.25 (m, 0.7 H), 2.93-3.07 (m, 0.3 H), 2.78-2.89 (m, 1 H) | 494.1 $[M + H]^+$ | 98.0% |
| 1890 | ($CD_3OD$) δ 8.32 (d, 1 H), 7.97-8.09 (m, 2 H), 7.69 (s, 1 H), 7.24-7.35 (m, 2 H), 6.99 (d, 1 H), 6.79 (t, 1 H), 6.59 (s, 1 H), 6.45 (s, 1 H), 4.37 (dd, 1 H), 3.79 (ddd, 1 H), 3.03-3.17 (m, 1 H), 2.85 (dd, 1 H), 2.45 (s, 3 H) | 416.2 $[M + H]^+$ | 99.4% |
| 1891 | ($CD_3OD$) δ 8.20 (d, 1 H), 7.85-8.00 (m, 2 H), 7.57 (s, 1 H), 7.12-7.25 (m, 2 H), 6.87 (d, 1 H), 6.67 (t, 1 H), 6.47 (s, 1 H), 6.33 (s, 1 H), 4.25 (dd, 1 H), 3.60-3.74 (m, 1 H), 2.90-3.04 (m, 1 H), 2.66-2.79 (m, 1 H), 2.33 (s, 3 H) | 416.2 $[M + H]^+$ | 98.3% |
| 1892 | ($CD_3OD$) δ 8.71 (d, 1 H), 7.97-8.09 (m, 2 H), 7.70 (s, 1 H), 7.63 (d, 1 H), 7.25-7.35 (m, 2 H), 6.99 (t, 1 H), 6.78 (s, 1 H), 6.48 (s, 1 H), 4.41 (dd, 1 H), 3.71-3.87 (m, 1 H), 3.03-3.19 (m, 1 H), 2.87 (dd, 1 H) | 470.1 $[M + H]^+$ | 99.9% |
| 1893 | ($CD_3OD$) δ 8.70 (d, 1 H), 7.98-8.08 (m, 2 H), 7.71 (s, 1 H), 7.63 (d, 1 H), 7.23-7.34 (m, 2 H), 6.99 (t, 1 H), 6.78 (s, 1 H), 6.48 (s, 1 H), 4.41 (dd, 1 H), 3.79 (ddd, 1 H), 3.05-3.18 (m, 1 H), 2.87 (dd, 1 H) | 470.1 $[M + H]^+$ | 98.5% |
| 1894 | ($CD_3OD$) δ 8.75 (d, 1 H), 8.17-8.35 (m, 2 H), 8.06 (td, 1 H), 7.58-7.75 (m, 2 H), 7.48 (s, 0.5 H), 6.92-7.05 (m, 1.5 H), 6.55-6.86 (m, 2 H), 4.99 (br dd, 1 H), 3.81 (ddd, 0.5 H), 3.44 (td, 0.5 H), 2.91-3.25 (m, 1 H), 2.72-2.88 (m, 3 H), 1.22-1.35 (m, 3 H) | 441.2 $[M + H]^+$ | 99.0% |
| 1895 | ($CD_3OD$) δ 8.76 (d, 1 H), 8.19-8.35 (m, 2 H), 8.06 (td, 1 H), 7.58-7.76 (m, 2 H), 7.48 (s, 0.5 H), 6.92-7.07 (m, 1.5 H), 6.73-6.85 (m, 1 H), 6.59-6.70 (m, 1 H), 5.00 (br dd, 1 H), 3.81 (ddd, 0.5 H), 3.44 (td, 0.5 H), 2.93-3.25 (m, 1 H), 2.71-2.89 (m, 3 H), 1.23-1.33 (m, 3 H) | 441.2 $[M + H]^+$ | 99.7% |
| 1896 | ($CD_3OD$) δ 8.77 (d, 1 H), 8.19-8.33 (m, 2 H), 8.08 (td, 1 H), 7.62-7.72 (m, 2 H), 7.50 (s, 0.3 H), 6.99 (s, 0.7 H), 6.71-6.84 (m, 3 H), 4.92-5.04 (m, 1 H), 3.82 (ddd, 0.7 H), 3.45 (td, 0.3 H), 3.16-3.25 (m, 0.7 H), 2.97-3.06 (m, 0.3 H), 2.86 (br dd, 1 H), 2.02-2.15 (m, 1 H), 0.97-1.08 (m, 2 H), 0.72-0.82 (m, 2 H) | 453.2 $[M + H]^+$ | 100% |
| 1897 | ($CD_3OD$) δ 8.76 (d, 1 H), 8.19-8.32 (m, 2 H), 8.07 (td, 1 H), 7.62-7.74 (m, 2 H), 7.50 (s, 0.3 H), 6.99 (s, 0.7 H), 6.71-6.82 (m, 3 H), 4.92-5.04 (m, 1 H), 3.77-3.86 (m, 0.7 H), 3.44 (td, 0.3 H), 3.16-3.25 (m, 0.7 H), 2.97-3.06 (m, 0.3 H), 2.81-2.90 (m, 1 H), 2.02-2.15 (m, 1 H), 0.97-1.07 (m, 2 H), 0.73-0.82 (m, 2 H) | 453.2 $[M + H]^+$ | 99.7% |
| 1898 | ($CD_3OD$) δ 8.19-8.38 (m, 1 H), 7.97-8.06 (m, 1 H), 7.71 (s, 1 H), 7.57 (s, 0.3), 6.99 (s, 0.7), 6.73-6.85 (m, 3 H), 5.07-5.12 (m, 1 H), 3.88-3.94 (m, 3 H), 3.76-3.85 (m, 0.7H), 3.46-3.51 (m, 0.3H), 3.14-3.26 (m, 1 H), 2.81-2.92 (m, 1 H), 2.62-2.76 (m, 3 H), 2.01-2.21 (m, 1 H), 0.99-1.10 (m, 2 H), 0.75-0.86 (m, 2 H) | 470.2 $[M + H]^+$ | 95.8% |
| 1899 | ($CD_3OD$) δ 8.08-8.24 (m, 1 H), 7.84-7.94 (m, 1 H), 7.60 (br s, 1 H), 7.45 (br s, 0.3 H), 6.87 (br s, 0.7 H), 6.57-6.76 (m, 3 H), 4.82-5.07 (m, 1 H), 3.75-3.84 (m, 3 H), 3.60-3.74 (m, 0.7 H), 3.27-3.40 (m, 0.3 H), 3.02-3.14 (m, 0.7 H), 2.83-2.97 (m, 0.3 H), 2.68-2.81 (m, 1 H), 2.50-2.62 (m, 3 H), 1.91-2.07 (m, 1 H), 0.85-1.01 (m, 2 H), 0.62-0.72 (m, 2 H) | 470.2 $[M + H]^+$ | 95.0% |
| 1900 | ($CD_3OD$) δ 8.21-8.33 (m, 1 H), 7.83 (d, 1 H), 7.72 (s, 1 H), 7.54 (s, 0.3 H), 6.95-7.05 (m, 1.7 H), 6.70-6.85 (m, 3 H), 4.99-5.08 (m, 1 H), 4.05 (s, 3 H), 3.75-3.87 (m, 0.7 H), 3.44 (td, 0.3 H), 3.14-3.26 (m, 0.7 H), 2.97-3.07 (m, 0.3 H), 2.81-2.91 (m, 1 H), 2.02-2.18 (m, 1 H), 0.98-1.11 (m, 2 H), 0.74-0.85 (m, 2 H) | 456.2 $[M + H]^+$ | 98.4% |
| 1901 | ($CD_3OD$) δ 8.21-8.35 (m, 1 H), 7.83 (d, 1 H), 7.72 (s, 1 H), 7.55 (br s, 0.3 H), 6.97-7.03 (m, 1.7 H), 6.71-6.86 (m, 3 H), 5.04-5.09 (m, 1 H), 4.05 (s, 3 H), 3.75-3.88 (m, 0.7 H), 3.45-3.51 (m, 0.3 | 456.2 $[M + H]^+$ | 99.4% |

TABLE 2-continued

| Ex. # | $^1$H NMR (400 MHz unless otherwise noted) | LCMS: m/z | % ee |
|---|---|---|---|
| | H), 3.15-3.26 (m, 0.7 H), 2.97-3.07 (m, 0.3 H), 2.87 (br dd, 1 H), 2.02-2.19 (m, 1 H), 0.98-1.10 (m, 2 H), 0.71-0.86 (m, 2 H) | | |
| 1902 | ($CD_3OD$) δ 8.22-8.40 (m, 1 H), 7.71 (s, 1 H), 7.34-7.48 (m, 0.3 H), 7.03-7.11 (m, 1 H), 6.80-7.00 (m, 1.7 H), 6.59-6.75 (m, 1 H), 4.95-5.01 (m, 1 H), 3.70-3.82 (m, 0.6 H), 3.38-3.47 (m, 0.4 H), 2.92-3.25 (m, 2 H), 2.84 (br d, 1 H), 1.44-1.54 (m, 9 H), 1.30-1.40 (m, 6 H) | 434.2 $[M + H]^+$ | 100% |
| 1903 | ($CD_3OD$) δ 8.24-8.36 (m, 1 H), 7.71 (s, 1 H), 7.41 (s, 0.3 H), 7.04-7.11 (m, 1 H), 6.80-6.99 (m, 1.7 H), 6.58-6.74 (m, 1 H), 4.98 (br dd, 1 H), 3.72-3.82 (m, 0.6 H), 3.42 (td, 0.4 H), 2.97-3.26 (m, 2 H), 2.84 (br d, 1 H), 1.45-1.53 (m, 9 H), 1.31-1.38 (m, 6 H) | 434.2 $[M + H]^+$ | 99.4% |
| 1904 | (DMSO-$d_6$) δ 7.97 (br s, 1 H), 7.41-7.55 (m, 2 H), 7.24-7.33 (m, 1 H), 6.83-6.95 (m, 2 H), 6.67 (br s, 0.3 H), 6.14-6.32 (m, 1.7 H), 5.86-6.07 (m, 2 H), 4.15-4.25 (m, 1 H), 2.96-3.06 (m, 0.6 H), 2.60-2.72 (m, 0.4 H), 2.03-2.43 (m, 3 H), 0.49-0.57 (m, 6 H) | 455.2 $[M + H]^+$ | 99.7% |
| 1905 | (DMSO-$d_6$) δ 7.97 (br d, 1 H), 7.42-7.55 (m, 2 H), 7.28 (td, 1 H), 6.81-6.94 (m, 2 H), 6.68 (br s, 0.3 H), 6.16-6.29 (m, 1.7 H), 5.87-6.06 (m, 2 H), 4.22 (br s, 1 H), 2.99-3.08 (m, 0.6 H), 2.62-2.72 (m, 0.4 H), 2.03-2.42 (m, 3 H), 0.47-0.57 (m, 6 H) | 455.2 $[M + H]^+$ | 98.6% |
| 1906 | ($CD_3OD$) δ 8.65 (d, 1 H), 8.21-8.38 (m, 1 H), 7.94 (t, 1 H), 7.68-7.79 (m, 2 H), 7.45 (br s, 0.3 H), 6.97-7.10 (m, 1.7 H), 6.68-6.88 (m, 2 H), 4.93-5.02 (m, 1 H), 3.76-3.87 (m, 0.6 H), 3.43-3.52 (m, 0.4 H), 3.01-3.28 (m, 2 H), 2.87 (br d, 1 H), 1.31-1.38 (m, 6 H) | 473.2 $[M + H]^+$ | 100% |
| 1907 | ($CD_3OD$) δ 8.65 (d, 1 H), 8.23-8.36 (m, 1 H), 7.94 (t, 1 H), 7.68-7.79 (m, 2 H), 7.45 (br s, 0.3 H), 6.97-7.11 (m, 1.7 H), 6.68-6.89 (m, 2 H), 4.93-5.01 (m, 1 H), 3.79-3.89 (m, 0.6 H), 3.43-3.52 (m, 0.4 H), 3.00-3.27 (m, 2 H), 2.82-2.92 (m, 1 H), 1.31-1.37 (m, 6 H) | 473.2 $[M + H]^+$ | 99.7% |
| 1908 | ($CD_3OD$) δ 8.36-8.57 (m, 1 H), 7.69 (s, 1 H), 7.35-7.56 (m, 1.3 H), 6.90 (s, 0.7 H), 6.74-6.82 (m, 1 H), 6.59-6.71 (m, 1 H), 4.99 (br dd, 1 H), 3.66-3.76 (m, 0.6 H), 3.34-3.40 (m, 0.4 H), 3.07-3.18 (m, 0.7 H), 2.91-3.01 (m, 0.3 H), 2.76-2.86 (m, 1 H), 2.24-2.38 (m, 1 H), 1.19-1.31 (m, 4 H) | 454.1 $[M + H]^+$ | 99.3% |
| 1909 | ($CD_3OD$) δ 8.38-8.53 (m, 1 H), 7.69 (s, 1 H), 7.34-7.59 (m, 1.3 H), 6.90 (s, 0.7 H), 6.75-6.82 (m, 1 H), 6.60-6.72 (m, 1 H), 4.99 (br dd, 1 H), 3.67-3.75 (m, 0.6 H), 3.35-3.40 (m, 0.4 H), 3.08-3.17 (m, 0.7 H), 2.92-3.01 (m, 0.3 H), 2.81 (br d, 1 H), 2.26-2.39 (m, 1 H), 1.19-1.29 (m, 4 H) | 454.1 $[M + H]^+$ | 93.7% |
| 1910 | ($CD_3OD$) δ 8.78 (br d, 1 H), 8.40-8.52 (m, 1 H), 8.31 (d, 1 H), 8.08 (t, 1 H), 7.62-7.76 (m, 2 H), 7.39-7.55 (m, 1.4 H), 6.97 (s, 0.6 H), 6.67-6.84 (m, 2 H), 4.94-5.07 (m, 1 H), 3.74-3.83 (m, 0.7 H), 3.38-3.46 (m, 0.3 H), 3.16-3.25 (m, 0.7 H), 2.96-3.06 (m, 0.3 H), 2.81-2.89 (m, 1 H) | 491.1 $[M + H]^+$ | 99.9% |
| 1911 | ($CD_3OD$) δ 8.77 (dd, 1 H), 8.39-8.52 (m, 1 H), 8.25-8.35 (m, 1 H), 8.08 (td, 1 H), 7.60-7.74 (m, 2 H), 7.40-7.53 (m, 1.3 H), 6.97 (s, 0.7 H), 6.66-6.86 (m, 2 H), 5.02 (br dd, 1 H), 3.74-3.83 (m, 0.5 H), 3.42 (td, 0.5 H), 3.16-3.25 (m, 0.7 H), 2.97-3.06 (m, 0.3 H), 2.80-2.92 (m, 1 H) | 491.1 $[M + H]^+$ | 98.6% |
| 1912 | ($CD_3OD$) δ 8.47 (d, 1 H), 7.86-7.97 (m, 2 H), 7.58 (s, 1 H), 7.31 (br d, 1 H), 7.13-7.22 (m, 2 H), 7.00 (s, 0.2, 6.78-6.88 (m, 1.5, 6.73 (s, 0.3, 6.66 (s, 1 H), 6.35 (s, 1 H), 4.27 (dd, 1 H), 3.67 (ddd, 1 H), 2.91-3.07 (m, 1 H), 2.74 (dd, 1 H) | 452.2 $[M + H]^+$ | 99.3% |
| 1913 | ($CD_3OD$) δ 8.60 (br d, 1 H), 7.97-8.10 (m, 2 H), 7.70 (s, 1 H), 7.44 (br d, 1 H), 7.25-7.34 (m, 2 H), 7.12 (s, 0.2, 6.90-7.01 (m, 1.5, 6.85 (s, 0.3) 6.78 (s, 1 H), 6.47 (s, 1 H), 4.39 (br dd, 1 H), 3.74-3.83 (m, 1 H), 3.06-3.16 (m, 1 H), 2.86 (br dd, 1 H) | 452.2 $[M + H]^+$ | 98.8% |
| 1914 | ($CD_3OD$) δ 8.36-8.49 (m, 2 H), 7.76 (dd, 1 H), 7.64 (s, 1 H), 7.56 (d, 1 H), 7.10-7.24 (m, 2 H), 6.91 (s, 1 H), 6.83 (td, 1 H), 6.53 (s, 1 H), 4.71 (br dd, 1 H), 3.61 (ddd, 1 H), 2.89-3.02 (m, 1 H), 2.73 (dd, 1 H) | 385.2 $[M + H]^+$ | 100% |
| 1915 | ($CD_3OD$) δ 8.26-8.36 (m, 2 H), 7.64 (dd, 1 H), 7.52 (s, 1 H), 7.44 (d, 1 H), 6.97-7.10 (m, 2 H), 6.79 (s, 1 H), 6.71 (td, 1 H), 6.41 (s, 1 H), 4.59 (br dd, 1 H), 3.40-3.55 (m, 1 H), 2.75-2.91 (m, 1 H), 2.61 (dd, 1 H) | 385.1 $[M + H]^+$ | 99.2% |
| 1916 | ($CD_3OD$) δ 8.46 (br d, 1 H), 8.30 (s, 1 H), 7.65 (dd, 1 H), 7.53 (s, 1 H), 7.29 (br d, 1 H), 6.68-7.08 (m, 4 H), 6.58 (s, 1 H), 4.61 (br dd, 1 H), 3.42-3.54 (m, 1 H), 2.77-2.91 (m, 1 H), 2.62 (br dd, 1 H) | 435.1 $[M + H]^+$ | 100% |
| 1917 | ($CD_3OD$) δ 8.58 (br d, 1 H), 8.42 (s, 1 H), 7.72-7.85 (m, 1 H), 7.66 (s, 1 H), 7.42 (br d, 1 H), 6.79-7.22 (m, 4 H), 6.70 (s, 1 H), 4.73 (br dd, 1 H), 3.53-3.65 (m, 1 H), 2.91-3.04 (m, 1 H), 2.69-2.82 (m, 1 H) | 435.1 $[M + H]^+$ | 100% |
| 1918 | ($CD_3OD$) δ 8.18-8.44 (m, 1 H), 7.52-7.98 (m, 2 H), 6.98 (br d, 1 H), 6.43-6.89 (m, 3 H), 4.40-4.57 (m, 0.5 H), 3.57-3.84 (m, 0.5 H), 2.90-3.18 (m, 1 H), 2.61-2.88 (m, 1 H), 2.43 (s, 3 H), 2.08-2.31 (m, 1 H), 0.93-1.36 (m, 5 H) | 389.2 $[M + H]^+$ | 98.5% |

TABLE 2-continued

| Ex. # | $^1$H NMR (400 MHz unless otherwise noted) | LCMS: m/z | % ee |
|---|---|---|---|
| 1919 | ($CD_3OD$) δ 8.24-8.44 (m, 1 H), 7.53-7.95 (m, 2 H), 7.00 (br d, 1 H), 6.41-6.93 (m, 3 H), 4.39-4.55 (m, 0.5 H), 3.64-3.85 (m, 0.5 H), 2.93-3.11 (m, 1 H), 2.82 (br d, 1 H), 2.45 (s, 3 H), 2.19 (br d, 1 H), 0.95-1.39 (m, 5 H) | 389.2 $[M + H]^+$ | 97.4% |
| 1920 | ($CD_3OD$) δ 8.19 (br s, 1 H), 7.35-7.98 (m, 2 H), 6.13-7.14 (m, 4 H), 4.42-4.67 (m, 1 H), 3.23-3.81 (m, 1 H), 2.57-3.08 (m, 2 H), 2.32 (s, 3 H), 1.32 (br s, 9 H) | 405.2 $[M + H]^+$ | 99.7% |
| 1921 | ($CD_3OD$) δ 8.31 (br d, 1 H), 7.39-8.06 (m, 2 H), 6.28-7.19 (m, 4 H), 4.53-4.70 (m, 1 H), 3.35-3.96 (m, 1 H), 2.65-3.17 (m, 2 H), 2.45 (br s, 3 H), 1.42 (br s, 9 H) | 405.2 $[M + H]^+$ | 99.6% |
| 1922 | ($CD_3OD$) δ 8.23-8.33 (m, 1 H), 7.69 (s, 1 H), 7.40 (s, 0.5 H), 6.88-7.04 (m, 1.5 H), 6.81 (q, 1 H), 6.52-6.69 (m, 1 H), 4.92-4.99 (m, 1 H), 3.76 (ddd, 0.5 H), 3.36-3.44 (m, 0.5 H), 2.77-3.21 (m, 4 H), 1.83-1.93 (m, 6 H), 1.27-1.35 (m, 3 H) | 424.2 $[M + H]^+$ | 99.1% |
| 1923 | ($CD_3OD$) δ 8.17-8.38 (m, 1 H), 7.69 (s, 1 H), 7.40 (s, 0.5 H), 6.89-7.09 (m, 1.5 H), 6.75-6.87 (m, 1 H), 6.50-6.69 (m, 1 H), 4.96 (br d, 1 H), 3.76 (ddd, 0.5 H), 3.39 (br dd, 0.5 H), 2.74-3.20 (m, 4 H), 1.77-1.98 (m, 6 H), 1.27-1.34 (m, 3 H) | 424.2 $[M + H]^+$ | 98.6% |
| 1924 | ($CD_3OD$) δ 8.21-8.42 (m, 2 H), 7.98-8.14 (m, 1 H), 7.48-7.76 (m, 1.5 H), 6.90-7.08 (m, 1.5 H), 6.76-6.86 (m, 1 H), 6.55-6.68 (m, 1 H), 5.06 (br dd, 1 H), 4.00 (s, 3 H), 3.72-3.83 (m, 0.5 H), 3.41 (td, 0.5 H), 2.75-3.22 (m, 4 H), 1.23-1.36 (m, 3 H) | 444.2 $[M + H]^+$ | 96.6% |
| 1925 | ($CD_3OD$) δ 8.21-8.44 (m, 2 H), 8.02-8.16 (m, 1 H), 7.69 (s, 1.5 H), 6.91-7.10 (m, 1.5 H), 6.73-6.87 (m, 1 H), 6.46-6.72 (m, 1 H), 5.07 (br dd, 1 H), 4.00 (s, 3 H), 3.71-3.83 (m, 0.5 H), 3.38-3.45 (m, 0.5 H), 2.79-3.21 (m, 4 H), 1.24-1.36 (m, 3 H) | 444.2 $[M + H]^+$ | 95.6% |
| 1926 | (500 MHz, $CD_3OD$) δ 8.18-8.35 (m, 1 H), 7.77-7.87 (m, 1 H), 7.71 (s, 1 H), 7.53 (s, 0.5 H), 6.94-7.07 (m, 2.5 H), 6.75-6.87 (m, 1 H), 6.56-6.73 (m, 1 H), 5.03 (br dd, 1 H), 4.03 (s, 3 H), 3.71-3.86 (m, 0.5 H), 3.43 (td, 0.5 H), 2.91-3.26 (m, 1 H), 2.72-2.88 (m, 3 H), 1.15-1.42 (m, 3 H) | 444.2 $[M + H]^+$ | 99.2% |
| 1927 | ($CD_3OD$) δ 8.02-8.26 (m, 1 H), 7.68 (d, 1 H), 7.59 (s, 1 H), 7.40 (s, 0.5 H), 6.77-6.98 (m, 2.5 H), 6.61-6.74 (m, 1 H), 6.46-6.57 (m, 1 H), 4.91 (br dd, 1 H), 3.90 (s, 3 H), 3.60-3.76 (m, 0.5 H), 3.31 (td, 0.5 H), 2.82-3.13 (m, 1 H), 2.60-2.78 (m, 3 H), 1.04-1.26 (m, 3 H) | 444.2 $[M + H]^+$ | 99.3% |
| 1928 | ($CD_3OD$) δ 9.08-9.19 (m, 1 H), 8.48 (s, 1 H), 8.21-8.33 (m, 1 H), 7.72 (s, 1 H), 7.50-7.62 (m, 0.3 H), 6.92-7.08 (m, 0.7 H), 6.72-6.85 (m, 3 H), 4.94-5.12 (m, 1 H), 3.77-3.88 (m, 0.7 H), 3.41-3.51 (m, 0.3 H), 3.14-3.24 (m, 0.7 H), 2.96-3.08 (m, 0.3 H), 2.80-2.92 (m, 1 H), 1.99-2.21 (m, 1 H), 0.96-1.12 (m, 2 H), 0.72-0.87 (m, 2 H) | 510.2 $[M + H]^+$ | 99.6% |
| 1929 | ($CD_3OD$) δ 9.09-9.16 (m, 1 H), 8.48 (s, 1 H), 8.22-8.32 (m, 1 H), 7.72 (s, 1 H), 7.58 (s, 0.3 H), 6.99 (s, 0.7 H), 6.72-6.86 (m, 3 H), 5.07 (dd, 1 H), 3.77-3.87 (m, 0.7 H), 3.41-3.49 (m, 0.3 H), 3.15-3.23 (m, 0.7 H), 2.97-3.06 (m, 0.3 H), 2.82-2.91 (m, 1 H), 2.03-2.17 (m, 1 H), 1.00-1.09 (m, 2 H), 0.75-0.84 (m, 2 H) | 510.2 $[M + H]^+$ | 99.1% |
| 1930 | ($CD_3OD$) δ 8.08-8.29 (m, 2 H), 7.72 (s, 0.3 H), 7.59 (d, 1.5 H), 7.42 (s, 0.5 H), 7.11 (d, 1 H), 6.88 (s, 0.7 H), 6.59-6.75 (m, 3 H), 4.92 (dd, 1 H), 3.63-3.77 (m, 0.7 H), 3.33 (td, 0.3 H), 3.03-3.14 (m, 0.7 H), 2.85-2.96 (m, 0.3 H), 2.75 (br dd, 1 H), 1.90-2.05 (m, 1 H), 0.85-0.98 (m, 2 H), 0.61-0.71 (m, 2 H) | 492.2 $[M + H]^+$ | 99.3% |
| 1931 | ($CD_3OD$) δ 8.09-8.25 (m, 2 H), 7.72 (s, 0.3 H), 7.55-7.62 (m, 1.5 H), 7.42 (s, 0.5 H), 7.11 (d, 1 H), 6.88 (s, 0.7 H), 6.60-6.73 (m, 3 H), 4.92 (dd, 1 H), 3.64-3.75 (m, 0.7 H), 3.29-3.38 (m, 0.3 H), 3.04-3.13 (m, 0.7 H), 2.85-2.96 (m, 0.3 H), 2.70-2.80 (m, 1 H), 1.88-2.08 (m, 1 H), 0.87-0.98 (m, 2 H), 0.63-0.72 (m, 2 H) | 492.2 $[M + H]^+$ | 99.1% |
| 1932 | ($CD_3OD$) δ 8.18-8.28 (m, 1 H), 7.69 (s, 1 H), 7.52 (s, 0.3 H), 6.96 (s, 0.7 H), 6.69-6.80 (m, 4 H), 5.00 (br dd, 1 H), 3.88 (s, 3 H), 3,74-3.82 (m, 0.7 H), 3.41 (td, 0.3 H), 3.12-3.23 (m, 0.7 H), 2.95-3.03 (m, 0.3 H), 2.79-2.87 (m, 1 H), 2.37 (s, 3 H), 2.00-2.13 (m, 1 H), 0.95-1.05 (m, 2 H), 0.70-0.80 (m, 2 H) | 470.2 $[M + H]^+$ | 99.8% |
| 1933 | ($CD_3OD$) δ 8.18-8.29 (m, 1 H), 7.69 (s, 1 H), 7.52 (s, 0.3 H), 6.97 (s, 0.7 H), 6.68-6.81 (m, 4 H), 5.00 (br dd, 1 H), 3.88 (s, 3 H), 3.75-3.83 (m, 0.7 H), 3.41 (td, 0.3 H), 3.11-3.23 (m, 0.7 H), 2.94-3.04 (m, 0.3 H), 2.78-2.88 (m, 1 H), 2.37 (s, 3 H), 1.99-2.14 (m, 1 H), 0.94-1.07 (m, 2 H), 0.68-0.83 (m, 2 H) | 470.2 $[M + H]^+$ | 99.6% |
| 1934 | ($CD_3OD$) δ 9.31-9.40 (m, 1 H), 8.73 (br d, 2 H), 8.12-8.22 (m, 1 H), 7.60 (s, 1 H), 7.36 (s, 0.3 H), 6.85-6.98 (m, 1.7 H), 6.58-6.76 (m, 2 H), 4.84-4.94 (m, 1 H), 3.65-3.79 (m, 0.7 H), 3.32-3.42 (m, 0.3 H), 2.87-3.13 (m, 2 H), 2.76 (br dd, 1 H), 1.19-1.25 (m, 6 H) | 456.2 $[M + H]^+$ | 100% |
| 1935 | ($CD_3OD$) δ 9.29-9.41 (m, 1 H), 8.71-8.77 (m, 2 H), 8.12-8.23 (m, 1 H), 7.60 (s, 1 H), 7.37 (s, 0.3 H), 6.86-6.98 (m, 1.7 H), 6.58-6.76 (m, 2 H), 4.91 (br dd, 1 H), 3.67-3.78 (m, 0.7 H), 3.31-3.42 (m, 0.3 H), 2.88-3.13 (m, 2 H), 2.70-2.81 (m, 1 H), 1.20-1.26 (m, 6 H) | 456.2 $[M + H]^+$ | 99.7% |

TABLE 2-continued

| Ex. # | $^1$H NMR (400 MHz unless otherwise noted) | LCMS: m/z | % ee |
| --- | --- | --- | --- |
| 1936 | ($CD_3OD$) δ 8.77-8.84 (m, 1 H), 8.10-8.25 (m, 2 H), 7.39-7.69 (m, 2.5 H), 6.85-6.97 (m, 1.5 H), 6.51-6.75 (m, 2 H), 4.96 (br dd, 1 H), 3.65-3.76 (m, 0.7 H), 3.33 (td, 0.3 H), 2.86-3.13 (m, 2 H), 2.69-2.79 (m, 1 H), 1.18-1.25 (m, 6 H) | 494.2 $[M + H]^+$ | 100% |
| 1937 | ($CD_3OD$) δ 8.90-8.95 (m, 1 H), 8.24-8.38 (m, 2 H), 7.50-7.84 (m, 2.5 H), 6.97-7.09 (m, 1.5 H), 6.65-6.88 (m, 2 H), 5.08 (br dd, 1 H), 3.76-3.87 (m, 0.7 H), 3.45 (td, 0.3 H), 2.98-3.25 (m, 2 H), 2.82-2.92 (m, 1 H), 1.31-1.37 (m, 6 H) | 494.2 $[M + H]^+$ | 99.8% |
| 1938 | ($CD_3OD$) δ 8.31-8.54 (m, 1 H), 7.70 (s, 1 H), 7.29-7.50 (m, 1.4 H), 6.93 (br s, 0.6 H), 6.58-6.84 (m, 2 H), 4.97 (br dd, 1 H), 3.69-3.78 (m, 0.6 H), 3.35-3.41 (m, 0.4 H), 2.94-3.20 (m, 1 H), 2.78-2.88 (m, 1 H), 1.85-1.93 (m, 6 H) | 474.1 $[M + H]^+$ | 96.1% |
| 1939 | ($CD_3OD$) δ 8.31-8.62 (m, 1 H), 7.70 (s, 1 H), 7.29-7.56 (m, 1.3 H), 6.93 (br s, 0.7 H), 6.52-6.85 (m, 2 H), 4.97 (br dd, 1 H), 3.35-3.79 (m, 1 H), 2.93-3.20 (m, 1 H), 2.83 (br d, 1 H), 1.78-1.97 (m, 6 H) | 474.1 $[M + H]^+$ | 91.2% |
| 1940 | ($CD_3OD$) δ 8.42 (s, 1 H), 8.31 (d, 1 H), 7.77 (dd, 1 H), 7.64 (s, 1 H), 7.14 (d, 1 H), 6.86-7.01 (m, 2 H), 6.76 (1, 1 H), 6.53 (s, 1 H), 4.72 (br dd, 1 H), 3.55-3.68 (m, 1 H), 2.88-3.02 (m, 1 H), 2.74 (dd, 1 H), 2.43 (s, 3 H) | 399.2 $[M + H]^+$ | 99.9% |
| 1941 | ($CD_3OD$) δ 8.42 (s, 1 H), 8.31 (d, 1 H), 7.77 (dd, 1 H), 7.64 (s, 1 H), 7.14 (d, 1 H), 6.87-7.01 (m, 2 H), 6.76 (t, 1 H), 6.53 (s, 1 H), 4.72 (br dd, 1 H), 3.55-3.68 (m, 1 H), 2.89-3.03 (m, 1 H), 2.74 (dd, 1 H), 2.43 (s, 3 H) | 399.2 $[M + H]^+$ | 98,8% |
| 1942 | ($CD_3OD$) δ 8.41 (s, 1 H), 8.32 (d, 1 H), 7.76 (dd, 1 H), 7.70 (s, 1 H), 7.13 (d, 1 H), 6.88-6.99 (m, 2 H), 6.80 (td, 1 H), 6.65 (s, 1 H), 4.71 (br dd, 1 H), 3.59 (ddd, 1 H), 2.85-3.02 (m, 1 H), 2.73 (dd, 1 H) | 403.1 $[M + H]^+$ | 99.1% |
| 1943 | ($CD_3OD$) δ 8.40 (s, 1 H), 8.32 (d, 1 H), 7.76 (dd, 1 H), 7.63 (s, 1 H), 7.13 (d, 1 H), 6.86-6.97 (m, 2 H), 6.79 (td, 1 H), 6.65 (s, 1 H), 4.72 (br dd, 1 H), 3.59 (ddd, 1 H), 2.85-3.01 (m, 1 H), 2.73 (dd, 1 H) | 403.2 $[M + H]^+$ | 97.4% |
| 1944 | ($CD_3OD$) δ 8.29 (d, 1 H), 8.14 (s, 1 H), 7.67 (s, 1 H), 6.31-7.05 (m, 4 H), 4.36 (br s, 1 H), 3.71 (br s, 1 H), 2.96-3.14 (m, 1 H), 2.78 (br dd, 1 H), 2.44 (s, 3 H), 2.19-2.38 (m, 1 H), 0.83-1.07 (m, 4 H) | 389.2 $[M + H]^+$ | 94.8% |
| 1945 | ($CD_3OD$) δ 8.31 (d, 1 H), 8.15 (s, 1 H), 7.68 (s, 1 H), 6.55-7.05 (m, 4 H), 4.39 (br s, 1 H), 3.52-3.85 (m, 1 H), 3.06 (br s, 1 H), 2.80 (br dd, 1 H), 2.46 (s, 3 H), 2.24-2.41 (m, 1 H), 0.92-1.03 (m, 4 H) | 389.2 $[M + H]^+$ | 98.3% |
| 1946 | ($CD_3OD$) δ 9.09-9.17 (m, 1 H), 8.48 (s, 1 H), 8.23-8.37 (m, 1 H), 7.71 (s, 1 H), 7.56 (s, 0.3 H), 7.03-7.11 (m, 1 H), 6.81-6.99 (m, 1.7 H), 6.64-6.74 (m, 1 H), 4.99-5.13 (m, 1 H), 3.77-3.87 (m, 0.7 H), 3.41-3.52 (m, 0.3 H), 2.98-3.25 (m, 2 H), 2.83-2.92 (m, 1 H), 1.32-1.38 (m, 6 H) | 512.2 $[M + H]^+$ | 99.4% |
| 1947 | ($CD_3OD$) δ 9.07-9.17 (m, 1 H), 8.48 (s, 1 H), 8.24-8.35 (m, 1 H), 7.72 (s, 1 H), 7.56 (s, 0.3 H), 7.03-7.11 (m, 1 H), 6.81-6.99 (m, 1.7 H), 6.63-6.74 (m, 1 H), 5.07 (br dd, 1 H), 3.76-3.87 (m, 0.7 H), 3.45 (td, 0.3 H), 3.20 (td, 2 H), 2.80-2.92 (m, 1 H), 1.31-1.38 (m, 6 H) | 512.2 $[M + H]^+$ | 99.4% |
| 1948 | ($CD_3OD$) δ 8.11-8.22 (m, 1 H), 7.83-7.89 (m, 1 H), 7.59 (s, 1 H), 7.44 (s, 0.3 H), 6.90-6.96 (m, 1 H), 6.67-6.87 (m, 1.7 H), 6.53-6.61 (m, 1 H), 4.84-5.04 (m, 1 H), 3.77 (s, 3 H), 3.64-3.73 (m, 0.7 H), 3.32 (td, 0.3 H), 2.84-3.13 (m, 2 H), 2.68-2.79 (m, 1 H), 2.51-2.59 (m, 3 H), 1.18-1.25 (m, 6 H) | 472.2 $[M + H]^+$ | 98.0% |
| 1949 | ($CD_3OD$) δ 8.11-8.22 (m, 1 H), 7.83-7.90 (m, 1 H), 7.59 (s, 1 H), 7.43 (s, 0.3 H), 6.90-6.98 (m, 1 H), 6.66-6.86 (m, 1.7 H), 6.52-6.61 (m, 1 H), 4.98 (br dd, 1 H), 3.77 (s, 3 H), 3.63-3.72 (m, 0.7 H), 3.26-3.37 (m, 0.3 H), 2.84-3.14 (m, 2 H), 2.67-2.78 (m, 1 H), 2.52-2.59 (m, 3 H), 1.18-1,25 (m, 6 H) | 472.2 $[M + H]^+$ | 94.1% |
| 1950 | ($CD_3OD$) δ 8.23-8.36 (m, 1 H), 7.82 (d, 1 H), 7.71 (s, 1 H), 7.48-7.56 (m, 0.3 H), 7.03-7.09 (m, 1 H), 6.79-7.01 (m, 2.7 H), 6.64-6.74 (m, 1 H), 5.04 (br dd, 1 H), 4.04 (s, 3 H), 3.81 (ddd, 0.7 H), 3.45 (td, 0.3 H), 2.98-3.25 (m, 2 H), 2.82-2.91 (m, 1 H), 1.28-1.38 (m, 6 H) | 458.2 $[M + H]^+$ | 99.7% |
| 1951 | ($CD_3OD$) δ 8.24-8.36 (m, 1 H), 7.83 (d, 1 H), 7.71 (s, 1 H), 7.52 (s, 0.3 H), 7.03-7.10 (m, 1 H), 6.80-7.02 (m, 2.7 H), 6.64-6.75 (m, 1 H), 4.97-5.10 (m, 1 H), 4.04 (s, 3 H), 3.74-3.89 (m, 0.7 H), 3.41-3.51 (m, 0.3 H), 2.98-3.27 (m, 2 H), 2.81-2.91 (m, 1 H), 1.30-1.38 (m, 6 H) | 458.2 $[M + H]^+$ | 99.7% |
| 1952 | ($CD_3OD$) δ 8.36 (d, 1 H), 7.97-8.09 (m, 2 H), 7.70 (s, 1 H), 7.30 (t, 2 H), 6.93-7.01 (m, 1 H), 6.80-6.87 (m, 1 H), 6.73 (s, 1 H), 6.46 (br s, 1 H), 4.39 (dd, 1 H), 3.73-3.86 (m, 1 H), 3.03-3.19 (m, 1 H), 2.86 (br dd, 1 H) | 420.1 $[M + H]^+$ | 99.1% |

TABLE 2-continued

| Ex. # | $^1$H NMR (400 MHz unless otherwise noted) | LCMS: m/z | % ee |
|---|---|---|---|
| 1953 | ($CD_3OD$) δ 8.31-8.41 (m, 1 H), 7.98-8.09 (m, 2 H), 7.67-7.75 (m, 1 H), 7.24-7.37 (m, 2 H), 6.92-7.03 (m, 1 H), 6.80-6.88 (m, 1 H), 6.73 (s, 1 H), 6.38-6.53 (m, 1 H), 4.34-4.45 (m, 1 H), 3.72-3.87 (m, 1 H), 3.04-3.18 (m, 1 H), 2.81-2.94 (m, 1 H) | 420.1 $[M + H]^+$ | 99.4% |
| 1954 | ($CD_3OD$) δ 8.34 (d, 1 H), 7.57-7.75 (m, 2 H), 6.94 (dd, 1 H), 6.78-6.90 (m, 2 H), 6.62-6.76 (m, 2 H), 6.21 (dd, 1 H), 4.52-4.59 (m, 1 H), 3.56 (ddd, 1 H), 2.89-3.02 (m, 1 H), 2.62-2.77 (m, 1 H) | 353.1 $[M + H]^+$ | 99.8% |
| 1955 | ($CD_3OD$) δ 8.34 (d, 1 H), 7.59-7.72 (m, 2 H), 6.94 (dd, 1 H), 6.77-6.89 (m, 2 H), 6.60-6.76 (m, 2 H), 6.21 (dd, 1 H), 4.58 (br s, 1 H), 3.49-3.64 (m, 1 H), 2.84-3.03 (m, 1 H), 2.70 (br dd, 1 H) | 353.1 $[M + H]^+$ | 99.6% |
| 1956 | ($CD_3OD$) δ 8.22-8.50 (m, 1 H), 7.54-8.13 (m, 2 H), 7.48 (d, 1 H), 7.02-7.34 (m, 1 H), 6.76 (br d, 1.6 H), 6.33-6.65 (m, 1.4 H), 4.60-4.71 (m, 0.5 H), 4.34 (br s, 0.5 H), 3.66 (br s, 0.5 H), 3.27-3.37 (m, 0.5 H), 2.80-3.07 (m, 1 H), 2.73 (br d, 1 H), 1.58-2.02 (m, 6 H) | 395.2 $[M + H]^+$ | 99.1% |
| 1957 | ($CD_3OD$) δ 8.35 (br s, 1 H), 7.91 (br s, 0.4 H), 7.54-7.73 (m, 1.6 H), 7.49 (d, 1 H), 7.02-7.20 (m, 1 H), 6.76 (br s, 1.6 H), 6.31-6.63 (m, 1.4 H), 4.57-4.70 (m, 0.5 H), 4.19-4.42 (m, 0.5 H), 3.66 (br s, 0.6 H), 3.27-3.34 (m, 0.4 H), 2.99 (br s, 1 H), 2.73 (br d, 1 H), 1.72 (br d, 6 H) | 395.2 $[M + H]^+$ | 99.3% |
| 1958 | ($CD_3OD$) δ 8.20 (br s, 1 H), 7.90 (br s, 0.5 H), 7.48-7.72 (m, 1.5 H), 6.89 (br d, 1 H), 6.61-6.83 (m, 1.6 H), 6.32-6.59 (m, 1.4 H), 4.58-4.71 (m, 0.5 H), 4.35 (br s, 0.5 H), 3.66 (br s, 0.5 H), 3.25-3.36 (m, 0.5 H), 2.82-3.11 (m, 1 H), 2.72 (br s, 1 H), 2.34 (s, 3 H), 1.57-1.87 (m, 6 H) | 409.2 $[M + H]^+$ | 99.6% |
| 1959 | ($CD_3OD$) δ 8.06-8.33 (m, 1 H), 7.91 (br s, 0.5 H), 7.50-7.72 (m, 1.5 H), 6.89 (br d, 1 H), 6.63-6.83 (m, 1.5 H), 6.34-6.61 (m, 1.5 H), 4.56-4.69 (m, 0.5 H), 4.25-4.42 (m, 0.5 H), 3.52-3.73 (m, 0.5 H), 3.27 (br d, 0.5 H), 2.80-3.08 (m, 1 H), 2.73 (br d, 1 H), 2.34 (s, 3 H), 1.55-1.83 (m, 6 H) | 409.2 $[M + H]^+$ | 99.4% |
| 1960 | ($CD_3OD$) δ 8.28 (br s, 2 H), 7.73-8.16 (m, 2 H), 7.70 (s, 1 H), 7.00 (br d, 1 H), 6.70-6.96 (m, 2 H), 6.63 (br s, 1 H), 4.62 (br s, 1 H), 3.98 (s, 3 H), 3.80 (br s, 0.5 H), 3.37-3.54 (m, 0.5 H), 2.78-3.22 (m, 2 H), 2.45 (s, 3 H) | 429.2 $[M + H]^+$ | 98.3% |
| 1961 | ($CD_3OD$) δ 8.04-8.35 (m, 2 H), 7.64-8.02 (m, 2 H), 7.59 (s, 1 H), 6.89 (br d, 1 H), 6.56-6.83 (m, 2 H), 6.51 (br s, 1 H), 4.49 (br s, 1 H), 3.86 (s, 3 H), 3.68 (br s, 0.5 H), 3.25-3.43 (m, 0.5 H), 2.58-3.12 (m, 2 H), 2.34 (s, 3 H) | 429.2 $[M + H]^+$ | 89.5% |
| 1962 | ($CD_3OD$) δ 8.23 (br s, 1 H), 7.67-8.02 (m, 2 H), 7.64 (s, 1 H), 6.89 (br d, 1 H), 6.57-6.84 (m, 2 H), 6.50 (br s, 1 H), 4.60-4.69 (m, 1 H), 3.74 (br s, 3 H), 3.24-3.68 (m, 1 H), 2.63-3.12 (m, 2 H), 2.52 (br d, 3 H), 2.34 (s, 3 H) | 443.2 $[M + H]^+$ | 100% |
| 1963 | ($CD_3OD$) δ 8.23 (br s, 1 H), 7.82 (br s, 2 H), 7.65 (br s, 1 H), 6.89 (br d, 1 H), 6.58-6.84 (m, 2 H), 6.51 (br s, 1 H), 4.56-4.68 (m, 1 H), 3.74 (br s, 3 H), 3.25-3.69 (m, 1 H), 2.69-3.08 (m, 2 H), 2.39-2.63 (m, 3 H), 2.34 (s, 3 H) | 443.2 $[M + H]^+$ | 99.0% |
| 1964 | ($CD_3OD$) δ 8.68-8.76 (m, 1 H), 8.33 (br s, 1 H), 8.23 (br d, 1.5 H), 7.87-8.10 (m, 1.5 H), 7.71 (br s, 1 H), 7.52-7.63 (m, 1 H), 7.01 (br d, 1 H), 6.57-6.97 (m, 3 H), 4.70-4.82 (m, 1 H), 3.41-3.95 (m, 1 H), 2.96-3.28 (m, 1 H), 2.86 (br s, 1 H), 2.47 (s, 3 H) | 426.2 $[M + H]^+$ | 100% |
| 1965 | ($CD_3OD$) δ 8.73 (d, 1 H), 8.33 (br s, 1 H), 8.24 (br s, 1.5 H), 7.87-8.10 (m, 1.5 H), 7.70 (br s, 1 H), 7.59 (dd, 1 H), 7.01 (br d, 1 H), 6.55-6.97 (m, 3 H), 4.63-4.80 (m, 1 H), 3.43-3.91 (m, 1 H), 2.95-3.28 (m, 1 H), 2.86 (br s, 1 H), 2.47 (s, 3 H) | 426.2 $[M + H]^+$ | 99.9% |
| 1966 | ($CD_3OD$) δ 8.69 (br d, 1 H), 8.29-8.54 (m, 2 H), 8.02 (td, 1 H), 7.66-7.83 (m, 1.3 H), 7.48-7.66 (m, 2 H), 7.08-7.32 (m, 1 H), 6.75-7.06 (m, 1.7 H), 6.50-6.72 (m, 1 H), 5.13 (dd, 1 H), 3.66-3.88 (m, 0.6 H), 3.45 (td, 0.4 H), 2.95-3.28 (m, 1 H), 2.83 (dd, 1 H) | 429.1 $[M + H]^+$ | 100% |
| 1967 | ($CD_3OD$) δ 8.70 (br d, 1 H), 8.25-8.53 (m, 2 H), 8.02 (td, 1 H), 7.47-7.87 (m, 3.3 H), 7.11-7.32 (m, 1 H), 6.77-7.04 (m, 1.7 H), 6.51-6.72 (m, 1 H), 5.13 (dd, 1 H), 3.65-3.89 (m, 0.7 H), 3.45 (td, 0.3 H), 2.97-3.27 (m, 1 H), 2.84 (dd, 1 H) | 429.1 $[M + H]^+$ | 99.8% |
| 1968 | ($CD_3OD$) δ 8.70 (br d, 1 H), 8.25-8.45 (m, 2 H), 7.92-8.11 (m, 1 H), 7.65-7.82 (m, 1.4 H), 7.57 (dd, 1 H), 6.90-7.04 (m, 1.6 H), 6.70-6.90 (m, 2 H), 5.17 (dd, 1 H), 3.77 (ddd, 0.6 H), 3.44 (td, 0.4 H), 2.96-3.27 (m, 1 H), 2.84 (dd, 1 H) | 447.1 $[M + H]^+$ | 100% |
| 1969 | ($CD_3OD$) δ 8.58 (br d, 1 H), 8.08-8.35 (m, 2 H), 7.79-8.00 (m, 1 H), 7.64 (br s, 1.4 H), 7.45 (dd, 1 H), 6.44-7.08 (m, 3.6 H), 5.06 (br dd, 1 H), 3.57-3.76 (m, 0.6 H), 3.32 (td, 0.4 H), 2.85-3.16 (m, 1 H), 2.73 (br dd, 1 H) | 447.1 $[M + H]^+$ | 99.8% |
| 1970 | ($CD_3OD$) δ 8.46-9.12 (m, 1 H), 8.19-8.43 (m, 2 H), 8.01 (td, 1 H), 7.64-7.87 (m, 1.3 H), 7.56 (dd, 1 H), 6.98 (q, 1.7 H), 6.71-6.84 (m, 1 H), 6.52-6.69 (m, 1 H), 5.13 (dd, 1 H), 3.69-3.85 (m, 0.7 H), 3.40-3.51 (m, 0.3 H), 2.96-3.27 (m, 1 H), 2.84 (dd, 1 H), 2.29-2.56 (m, 3 H) | 443.1 $[M + H]^+$ | 100% |

TABLE 2-continued

| Ex. # | $^1$H NMR (400 MHz unless otherwise noted) | LCMS: m/z | % ee |
|---|---|---|---|
| 1971 | ($CD_3OD$) δ 8.51-9.00 (m, 1 H), 8.19-8.48 (m, 2 H), 7.92-8.15 (m, 1 H), 7.47-7.86 (m, 2.3 H), 6.92-7.11 (m, 1.7 H), 6.71-6.89 (m, 1 H), 6.51-6.69 (m, 1 H), 5.13 (br dd, 1 H), 3.71-3.85 (m, 0.7 H), 3.41-3.50 (m, 0.3 H), 2.96-3.27 (m, 1 H), 2.84 (br dd, 1 H), 2.39-2.53 (m, 3 H) | 443.2 $[M + H]^+$ | 100% |
| 1972 | ($CD_3OD$) δ 9.46-9.54 (m, 2 H), 9.41 (s, 1 H), 8.26-8.36 (m, 1 H), 7.72-7.79 (m, 1 H), 7.56 (s, 0.3 H), 6.98-7.05 (m, 1.7 H), 6.77-6.85 (m, 1 H), 6.59-6.69 (m, 1 H), 5.11 (br d, 1 H), 3.80-3.87 (m, 0.7 H), 3.50 (br d, 0.3 H), 3.16-3.24 (m, 0.7 H), 3.00-3.05 (m, 0.3 H), 2.84-2.92 (m, 1 H), 2.43-2.49 (m, 3 H) | 428.2 $[M + H]^+$ | 99.9% |
| 1973 | ($CD_3OD$) δ 9.46-9.52 (m, 2 H), 9.40 (s, 1 H), 8.26-8.35 (m, 1 H), 7.72 (s, 1 H), 7.55 (br s, 0.3 H), 7.01 (br t, 1.7 H), 6.77-6.84 (m, 1 H), 6.60-6.68 (m, 1 H), 5.09 (br d, 1 H), 3.83 (ddd, 0.7 H), 3.46-3.52 (m, 0.3 H), 3.15-3.27 (m, 0.7 H), 2.98-3.08 (m, 0.3 H), 2.83-2.93 (m, 1 H), 2.42-2.49 (m, 3 H) | 428.1 $[M + H]^+$ | 98.8% |
| 1974 | ($CD_3OD$) δ 9.47-9.53 (m, 2 H), 9.40 (s, 1 H), 8.31-8.39 (m, 1 H), 7.72 (s, 1 H), 7.51-7.60 (m, 0.3 H), 6.95-7.02 (m, 1.7 H), 6.81-6.90 (m, 1 H), 6.75-6.80 (m, 1 H), 5.11 (m, 1 H), 3.75-3.90 (m, 0.7 H), 3.39-3.51 (m, 0.3 H), 3.16-3.26 (m, 0.7 H), 2.99-3.05 (m, 0.3 H), 2.83-2.94 (m, 1 H) | 432.2 $[M + H]^+$ | 99.7% |
| 1975 | ($CD_3OD$) δ 9.44-9.55 (m, 2 H), 9.40 (s, 1 H), 8.30-8.40 (m, 1 H), 7.72 (s, 1 H), 7.56 (s, 0.3 H), 6.94-7.04 (m, 1.7 H), 6.82-6.90 (m, 1 H), 6.76-6.81 (m, 1 H), 5.11 (br d, 1 H), 3.78-3.87 (m, 0.7 H), 3.46 (br d, 0.3 H), 3.17-3.27 (m, 0.7 H), 2.97-3.05 (m, 0.3 H), 2.90 (br s, 1 H) | 432.1 $[M + H]^+$ | 98.9% |
| 1976 | ($CD_3OD$) δ 8.34 (d, 1 H), 8.07-8.18 (m, 1 H), 7.63 (s, 1 H), 7.54-7.61 (m, 1 H), 7.05 (d, 1 H), 6.94 (dd, 1 H), 6.76-6.85 (m, 2 H), 6.67 (dd, 1 H), 6.63 (s, 1 H), 4.57 (dd, 1 H), 3.52-3.64 (m, 1 H), 2.88-3.05 (m, 1 H), 2.69 (dd, 1 H) | 335.1 $[M + H]^+$ | 99.7% |
| 1977 | ($CD_3OD$) δ 8.34 (d, 1 H), 8.10-8.17 (m, 1 H), 7.62 (s, 1 H), 7.55-7.61 (m, 1 H), 7.05 (d, 1 H), 6.94 (dd, 1 H), 6.76-6.86 (m, 2 H), 6.67 (dd, 1 H), 6.63 (s, 1 H), 4.52-4.60 (m, 1 H), 3.51-3.63 (m, 1 H), 2.88-3.03 (m, 1 H), 2.69 (dd, 1 H) | 335.2 $[M + H]^+$ | 98.6% |
| 1978 | ($CD_3OD$) δ 8.58 (br d, 1 H), 8.13 (dd, 1 H), 7.54-7.66 (m, 2 H), 7.41 (br d, 1 H), 6.74-7.13 (m, 4 H), 6.62-6.72 (m, 2 H), 4.56 (br d, 1 H), 3.49-3.61 (m, 1 H), 2.90-3.03 (m, 1 H), 2.69 (br dd, 1 H) | 367.2 $[M + H]^+$ | 98.9% |
| 1979 | ($CD_3OD$) δ 8.58 (br d, 1 H), 8.13 (dd, 1 H), 7.54-7.67 (m, 2 H), 7.41 (br d, 1 H), 6.75-7.12 (m, 4 H), 6.63-6.71 (m, 2 H), 4.55 (br s, 1 H), 3.56 (ddd, 1 H), 2.89-3.03 (m, 1 H), 2.69 (br dd, 1 H) | 367.1 $[M + H]^+$ | 96.6% |
| 1980 | ($CD_3OD$) δ 9.04 (br d, 2 H), 8.22-8.38 (m, 1 H), 7.66-7.79 (m, 2 H), 7.46 (br s, 0.3 H), 6.95-7.13 (m, 1.7 H), 6.69-6.89 (m, 2 H), 5.00-5.02 (m, 1 H), 3.76-3.90 (m, 0.6 H), 3.44-3.51 (m, 0.4 H), 2.97-3.27 (m, 2 H), 2.88 (br d, 1 H), 1.30-1.42 (m, 6 H) | 456.2 $[M + H]^+$ | 99.6% |
| 1981 | ($CD_3OD$) δ 9.02-9.08 (m, 2 H), 8.23-8.36 (m, 1 H), 7.68-7.75 (m, 2 H), 7.41-7.49 (m, 0.3 H), 6.97-7.11 (m, 1.7 H), 6.69-6.88 (m, 2 H), 4.99-5.03 (m, 1 H), 3.79-3.88 (m, 0.6 H), 3.43-3.53 (m, 0.4 H), 2.99-3.27 (m, 2 H), 2.88 (br d, 1 H), 1.31-1.38 (m, 6 H) | 456.2 $[M + H]^+$ | 99.0% |
| 1982 | ($CD_3OD$) δ 8.22-8.39 (m, 2 H), 7.49-7.86 (m, 2.3 H), 7.23 (d, 1 H), 6.95-7.11 (m, 1.7 H), 6.64-6.89 (m, 2 H), 5.04 (br dd, 1 H), 3.77-3.88 (m, 0.6 H), 3.42-3.52 (m, 0.4 H), 3.21 (tt, 2 H), 2.83-2.93 (m, 1 H), 1.30-1.39 (m, 6 H) | 494.2 $[M + H]^+$ | 100% |
| 1983 | ($CD_3OD$) δ 8.22-8.37 (m, 2 H), 7.47-7.86 (m, 2.3 H), 7.24 (d, 1 H), 6.96-7.11 (m, 1.7 H), 6.63-6.90 (m, 2 H), 5.04 (br dd, 1 H), 3.77-3.89 (m, 0.6 H), 3.41-3.52 (m, 0.4 H), 2.99-3.27 (m, 2 H), 2.83-2.92 (m, 1 H), 1.31-1.38 (m, 6 H) | 494.2 $[M + H]^+$ | 100% |
| 1984 | ($CD_3OD$) δ 8.52 (d, 1 H), 8.21-8.37 (m, 2 H), 7.63 (s, 0.3 H), 7.29 (d, 1 H), 7.10 (br t, 1.7 H), 6.78-6.91 (m, 2 H), 5.13 (br dd, 1 H), 3.77-3.86 (m, 0.6 H), 3.42-3.53 (m, 0.4 H), 3.03-3.29 (m, 2 H), 2.95 (br d, 1 H), 1.32-1.38 (m, 6 H) | 512.2 $[M + H]^+$ | 100% |
| 1985 | ($CD_3OD$) δ 8.40 (d, 1 H), 8.12-8.26 (m, 1 H), 7.60 (br s, 1 H), 7.40 (br s, 0.3 H), 7.17 (d, 1 H), 6.84-7.00 (m, 1.7 H), 6.54-6.77 (m, 2 H), 4.90-4.95 (m, 1 H), 3.65-3.75 (m, 0.6 H), 3.29-3.39 (m, 0.4 H), 2.90-3.14 (m, 2 H), 2.70-2.81 (m, 1 H), 1.20-1.26 (m, 6 H) | 512.2 $[M + H]^+$ | 99.7% |
| 1986 | ($CD_3OD$) δ 8.34 (d, 1 H), 8.14 (s, 1 H), 7.67 (s, 1 H), 6.42-7.07 (m, 4 H), 4.18-4.57 (m, 1 H), 3.70 (br s, 1 H), 2.93-3.18 (m, 1 H), 2.79 (br dd, 1 H), 2.20-2.45 (m, 1 H), 0.83-1.13 (m, 4 H) | 393.2 $[M + H]^+$ | 99.2% |
| 1987 | ($CD_3OD$) δ 8.34 (d, 1 H), 8.14 (s, 1 H), 7.67 (s, 1 H), 6.46-7.05 (m, 4 H), 4.38 (br s, 1 H), 3.54-3.84 (m, 1 H), 3.01-3.15 (m, 1 H), 2.72-2.86 (m, 1 H), 2.35 (br s, 1 H), 0.91-1.00 (m, 4 H) | 393.2 $[M + H]^+$ | 98.0% |
| 1988 | ($CD_3OD$) δ 8.23-8.32 (m, 1 H), 8.08-8.12 (m, 1 H), 7.65-7.73 (m, 1.3 H), 7.37-7.43 (m, 1 H), 6.81-7.14 (m, 1.7 H), 6.71-6.80 (m, 1 H), 6.49-6.64 (m, 1 H), 5.04 (dd, 1 H), 3.69 (ddd, 0.7 H), 3.33-3.40 (m, 0.3 H), 3.07-3.18 (m, 0.7 H), 2.90-3.00 (m, 0.3 H), 2.78 (dd, 1 H), 2.36-2.47 (m, 3 H) | 349.2 $[M + H]^+$ | 100% |
| 1989 | ($CD_3OD$) δ 8.25-8.31 (m, 1 H), 8.09-8.12 (m, 1 H), 7.68 (s, 1 H), 7.38-7.44 (m, 1 H), 6.93-7.00 (m, 2 H), 6.73-6.81 (m, 1 H), 6.47- | 349.1 $[M + H]^+$ | 99.4% |

TABLE 2-continued

| Ex. # | $^1$H NMR (400 MHz unless otherwise noted) | LCMS: m/z | % ee |
|---|---|---|---|
| | 6.63 (m, 1 H), 4.94-5.08 (m, 1 H), 3.69 (ddd, 0.7 H), 3.35-3.41 (m, 0.3 H), 3.08-3.18 (m, 0.7 H), 2.90-2.98 (m, 0.3 H), 2.78 (dd, 1 H), 2.38-2.47 (m, 3 H) | | |
| 1990 | ($CD_3OD$) δ 8.39-8.52 (m, 1 H), 7.65-7.80 (m, 1.3 H), 7.53-7.64 (m, 1 H), 7.14-7.27 (m, 1 H), 6.79-6.99 (m, 1,7 H), 6.51-6.67 (m, 1 H), 5.14 (br dd, 0.5 H), 4.79-4.87 (m, 0.5 H), 3.62-3.78 (m, 0.5 H), 3.36-3.48 (m, 0.5 H), 2.91-3.22 (m, 1 H), 2.80 (br d, 1 H), 2.48-2.63 (m, 1 H), 1.12-1.43 (m, 4 H) | 392.1 $[M + H]^+$ | 100% |
| 1991 | ($CD_3OD$) δ 8.37-8.50 (m, 1 H), 7.65-7.78 (m, 1.3 H), 7.53-7.64 (m, 1 H), 7.12-7.27 (m, 1 H), 6.79-6.98 (m, 1,7 H), 6.51-6.68 (m, 1 H), 5.14 (dd, 0.5 H), 4.79-4.86 (m, 0.5 H), 3.64-3.78 (m, 0.5 H), 3.36-3.47 (m, 0.5 H), 2.92-3.21 (m, 1 H), 2.80 (br dd, 1 H), 2.49-2.63 (m, 1 H), 1.16-1.40 (m, 4 H) | 392.1 $[M + H]^+$ | 96.4% |
| 1992 | ($CD_3OD$) δ 8.28-8.40 (m, 1 H), 7.66-7.78 (m, 1.3 H), 6.89-7.03 (m, 1.7 H), 6.79-6.89 (m, 1 H), 6.69-6.77 (m, 1 H), 5.17 (dd, 0.5 H), 4.85 (br d, 0.5 H), 3.66-3.78 (m, 0.5 H), 3.36-3.46 (m, 0.5 H), 2.92-3.21 (m, 1 H), 2.81 (dd, 1 H), 2.51-2.62 (m, 1 H), 1.17-1.40 (m, 4 H) | 410.1 $[M + H]^+$ | 99.6% |
| 1993 | ($CD_3OD$) δ 8.26-8.42 (m, 1 H), 7.66-7.77 (m, 1.3 H), 6.89-7.04 (m, 1.7 H), 6.78-6.89 (m, 1 H), 6.67-6.77 (m, 1 H), 5.17 (dd, 0.5 H), 4.85 (br d, 0.5 H), 3.71 (ddd, 0.5 H), 3.36-3.49 (m, 0.5 H), 2.92-3.20 (m, 1 H), 2.81 (dd, 1 H), 2.49-2.63 (m, 1 H), 1.17-1.41 (m, 4 H) | 410.1 $[M + H]^+$ | 88.5% |
| 1994 | ($CD_3OD$) δ 8.20-8.43 (m, 1 H), 7.63-7.84 (m, 2 H), 6.65-7.03 (m, 5 H), 5.22 (dd, 1 H), 3.99 (s, 3 H), 3.65-3.79 (m, 0.6 H), 3.42 (td, 0.4 H), 2.92-3.24 (m, 1 H), 2.82 (br dd, 1 H) | 450.1 $[M + H]^+$ | 99.2% |
| 1995 | ($CD_3OD$) δ 8.17-8.41 (m, 1 H), 7.51-7.84 (m, 2 H), 6.60-7.02 (m, 5 H), 5.22 (dd, 1 H), 3.98 (s, 3 H), 3.65-3.78 (m, 0.6 H), 3.37-3.50 (m, 0.4 H), 2.94-3.25 (m, 1 H), 2.73-2.89 (m, 1 H) | 450.1 $[M + H]^+$ | 99.1% |
| 1996 | ($CD_3OD$) δ 8.24-8.37 (m, 1 H), 7.64-7.78 (m, 1.3 H), 6.90-7.05 (m, 1.7 H), 6.74-6.84 (m, 1 H), 6.51-6.65 (m, 1 H), 5.14 (dd, 0.5 H), 4.80-4.87 (m, 0.5 H), 3.72 (ddd, 0.5 H), 3.42 (td, 0.5 H), 2.93-3.21 (m, 1 H), 2.80 (dd, 1 H), 2.52-2.63 (m, 1 H), 2.40-2.50 (m, 3 H), 1.16-1.41 (m, 4 H) | 406.2 $[M + H]^+$ | 100% |
| 1997 | ($CD_3OD$) δ 8.25-8.37 (m, 1 H), 7.65-7.77 (m, 1.3 H), 6.89-7.05 (m, 1.7 H), 6.73-6.84 (m, 1 H), 6.54-6.66 (m, 1 H), 5.14 (dd, 0.5 H), 4.79-4.86 (m, 0.5 H), 3.65-3.78 (m, 0.5 H), 3.37-3.48 (m, 0.5 H), 2.93-3.22 (m, 1 H), 2.80 (dd, 1 H), 2.51-2.63 (m, 1 H), 2.39-2.50 (m, 3 H), 1.16-1.42 (m, 4 H) | 406.2 $[M + H]^+$ | 99.6% |
| 1998 | ($CD_3OD$) δ 8.18-8.39 (m, 1 H), 7.59-7.82 (m, 2.5 H), 6.85-7.02 (m, 2.5 H), 6.69-6.81 (m, 1 H), 6.50-6.66 (m, 1 H), 5.18 (dd, 1 H), 3.98 (s, 3 H), 3.65-3.84 (m, 0.7 H), 3.43 (td, 0.3 H), 2.92-3.24 (m, 1 H), 2.81 (br dd, 1 H), 2.34-2.48 (m, 3 H) | 446.2 $[M + H]^+$ | 99.1% |
| 1999 | ($CD_3OD$) δ 8.15-8.36 (m, 1 H), 7.54-7.80 (m, 2.5 H), 6.86-7.04 (m, 2.5 H), 6.70-6.82 (m, 1 H), 6.45-6.67 (m, 1 H), 5.18 (dd, 1 H), 3.98 (s, 3 H), 3.67-3.80 (m, 0.6 H), 3.43 (td, 0.4 H), 2.94-3.24 (m, 1 H), 2.81 (br dd, 1 H), 2.32-2.50 (m, 3 H) | 446.2 $[M + H]^+$ | 98.8% |
| 2000 | ($CD_3OD$) δ 8.37-8.51 (m, 1 H), 8.01-8.27 (m, 2.5 H), 7.68 (d, 1 H), 7.46-7.64 (m, 3 H), 7.06-7.31 (m, 1 H), 6.98 (s, 0.5 H), 6.74-6.91 (m, 1 H), 6.47-6.71 (m, 1 H), 5.49 (dd, 0.5 H), 4.90-4.95 (m, 0.5 H), 3.64-3.81 (m, 0.7 H), 3.36-3.56 (m, 0.3 H), 3.10 (s, 1 H), 2.82 (br d, 1 H) | 401.1 $[M + H]^+$ | 100% |
| 2001 | ($CD_3OD$) δ 8.38-8.50 (m, 1 H), 8.05-8.27 (m, 2.5 H), 7.69 (s, 1 H), 7.49-7.66 (m, 3 H), 7.08-7.27 (m, 1 H), 6.99 (s, 0.5 H), 6.73-6.92 (m, 1 H), 6.44-6.71 (m, 1 H), 5.35-5.59 (m, 0.5 H), 4.93 (s, 0.5 H), 3.64-3.85 (m, 0.5 H), 3.32-3.51 (m, 0.5 H), 2.98-3.20 (m, 1 H), 2.72-2.87 (m, 1 H) | 401.1 $[M + H]^+$ | 99.4% |
| 2002 | ($CD_3OD$) δ 8.18-8.46 (m, 1.4 H), 7.94-8.16 (m, 2 H), 7.69 (s, 1 H), 7.58 (dq, 2 H), 6.89-7.08 (m, 1.6 H), 6.62-6.88 (m, 2 H), 5.53 (br dd, 0.5 H), 4.93-5.05 (m, 0.5 H), 3.73 (td, 0.6 H), 3.38-3.52 (m, 0.4 H), 2.95-3.25 (m, 1 H), 2.82 (br d, 1 H) | 419.1 $[M + H]^+$ | 100% |
| 2003 | ($CD_3OD$) δ 8.20-8.44 (m, 1.5 H), 8.00-8.19 (m, 2 H), 7.69 (s, 1 H), 7.46-7.63 (m, 2 H), 6.88-7.09 (m, 1.5 H), 6.58-6.87 (m, 2 H), 5.53 (br dd, 0.5 H), 4.94-4.99 (m, 0.5 H), 3.66-3.76 (m, 0.6 H), 3.40-3.49 (m, 0.4 H), 2.94-3.25 (m, 1 H), 2.77-2.88 (m, 1 H) | 419.1 $[M + H]^+$ | 99.6% |
| 2004 | ($CD_3OD$) δ 8.28-8.55 (m, 1 H), 7.42-7.92 (m, 3.4 H), 7.14-7.26 (m, 1 H), 7.05-7.10 (m, 1 H), 6.96 (br s, 0.6 H), 6.81-6.89 (m, 1 H), 6.47-6.76 (m, 1 H), 5.04 (br dd, 1 H), 4.22-4.41 (m, 3 H), 3.39-3.86 (m, 1 H), 2.95-3.26 (m, 1 H), 2.75-2.93 (m, 1 H) | 416.2 $[M + H]^+$ | 98.4% |
| 2005 | ($CD_3OD$) δ 8.33-8.55 (m, 1 H), 7.48-7.78 (m, 3.3 H), 7.14-7.24 (m, 1 H), 7.05-7.10 (m, 1 H), 6.96 (s, 0.7 H), 6.78-6.89 (m, 1 H), 6.55-6.68 (m, 1 H), 5.04 (dd, 1 H), 4.23-4.37 (m, 3 H), 3.74-3.85 (m, 0.6 H), 3.37-3.45 (m, 0.4 H), 2.94-3.24 (m, 1 H), 2.78-2.90 (m, 1 H) | 416.2 $[M + H]^+$ | 97.6% |
| 2006 | ($CD_3OD$) δ 8.22-8.37 (m, 1 H), 7.64-7.75 (m, 1 H), 7.51 (s, 0.3 H), 6.95-7.22 (m, 1.7 H), 6.63-6.92 (m, 3 H), 5.02 (br dd, 1 H), 3.88-3.96 (m, 3 H), 3.75-3.86 (m, 0.6 H), 3.40-3.48 (m, 0.4 H), | 472.2 $[M + H]^+$ | 100% |

TABLE 2-continued

| Ex. # | $^1$H NMR (400 MHz unless otherwise noted) | LCMS: m/z | % ee |
|---|---|---|---|
| | 2.98-3.27 (m, 2 H), 2.86 (br d, 1 H), 2.41 (s, 3 H), 1.30-1.39 (m, 6 H) | | |
| 2007 | ($CD_3OD$) δ 8.24-8.36 (m, 1 H), 7.63-7.74 (m, 1 H), 7.51 (s, 0.3 H), 6.96-7.22 (m, 1.7 H), 6.60-6.92 (m, 3 H), 4.99-5.07 (m, 1 H), 3.88-3.96 (m, 3 H), 3.75-3.85 (m, 0.6 H), 3.40-3.49 (m, 0.4 H), 2.97-3.27 (m, 2 H), 2.86 (br d, 1 H), 2.41 (s, 3 H), 1.31-1.39 (m, 6 H) | 472.2 $[M + H]^+$ | 100% |
| 2008 | ($CD_3OD$) δ 8.46 (d, 1 H), 7.99-8.06 (m, 2 H), 7.70 (s, 1 H), 7.26-7.34 (m, 3 H), 6.85 (t, 1 H), 6.72 (s, 1 H), 6.42-6.49 (m, 1 H), 4.39 (dd, 1 H), 3.79 (ddd, 1 H), 3.05-3.16 (m, 1 H), 2.81-2.92 (m, 1 H) | 436.1 $[M + H]^+$ | 99.1% |
| 2009 | ($CD_3OD$) δ 8.45 (d, 1 H), 7.96-8.12 (m, 2 H), 7.70 (s, 1 H), 7.16-7.40 (m, 3 H), 6.85 (t, 1 H), 6.72 (s, 1 H), 6.45 (br s, 1 H), 4.39 (dd, 1 H), 3.71-3.84 (m, 1 H), 3.04-3.16 (m, 1 H), 2.80-2.91 (m, 1 H) | 436.1 $[M + H]^+$ | 99.3% |
| 2010 | ($CD_3OD$) δ 7.97-8.14 (m, 2 H), 7.68 (s, 1 H), 7.47 (d, 1 H), 7.30 (t, 2 H), 7.12 (dd, 1 H), 6.71 (d, 1 H), 6.53 (s, 1 H), 6.46 (s, 1 H), 4.36 (dd, 1 H), 3.82 (td, 1 H), 3.04-3.15 (m, 1 H), 2.81-2.91 (m, 1 H), 2.63 (s, 3 H) | 416.2 $[M + H]^+$ | 100% |
| 2011 | ($CD_3OD$) δ 7.99-8.08 (m, 2 H), 7.68 (s, 1 H), 7.47 (d, 1 H), 7.25-7.34 (m, 2 H), 7.12 (dd, 1 H), 6.71 (d, 1 H), 6.53 (s, 1 H), 6.46 (s, 1 H), 4.36 (dd, 1 H), 3.76-3.88 (m, 1 H), 3.03-3.17 (m, 1 H), 2.86 (dd, 1 H), 2.63 (s, 3 H) | 416.2 $[M + H]^+$ | 99.6% |
| 2012 | ($CD_3OD$) δ 8.69 (d, 1 H), 8.43 (s, 1 H), 7.78 (dd, 1 H), 7.57-7.70 (m, 2 H), 7.16 (d, 1 H), 6.91-7.01 (m, 2 H), 6.70 (s, 1 H), 4.74 (br dd, 1 H), 3.53-3.67 (m, 1 H), 2.89-3.03 (m, 1 H), 2.75 (dd, 1 H) | 453.1 $[M + H]^+$ | 100% |
| 2013 | ($CD_3OD$) δ 8.57 (d, 1 H), 8.31 (s, 1 H), 7.66 (dd, 1 H), 7.44-7.57 (m, 2 H), 7.04 (d, 1 H), 6.85 (br t, 2 H), 6.58 (s, 1 H), 4.62 (br dd, 1 H), 3.43-3.54 (m, 1 H), 2.76-2.91 (m, 1 H), 2.63 (dd, 1 H) | 453.2 $[M + H]^+$ | 79.7% |
| 2014 | ($CD_3OD$) δ 8.69 (d, 1 H), 8.13 (s, 1 H), 7.53-7.75 (m, 2 H), 6.45-7.12 (m, 3 H), 4.39 (br s, 1 H), 3.37-3.87 (m, 1 H), 3.05 (br s, 1 H), 2.71-2.86 (m, 1 H), 2.36 (br s, 1 H), 0.89-1.03 (m, 4 H) | 443.2 $[M + H]^+$ | 99.9% |
| 2015 | ($CD_3OD$) δ 8.68 (d, 1 H), 8.13 (s, 1 H), 7.55-7.74 (m, 2 H), 6.51-7.06 (m, 3 H), 4.41 (br s, 1 H), 3.39-3.85 (m, 1 H), 3.05 (br s, 1 H), 2.79 (br dd, 1 H), 2.36 (br s, 1 H), 0.74-1.15 (m, 4 H) | 443.2 $[M + H]^+$ | 98.8% |
| 2016 | ($CD_3OD$) δ 8.31-8.53 (m, 1 H), 7.54-7.89 (m, 3 H), 7.09-7.29 (m, 1 H), 6.75-7.02 (m, 3 H), 6.48-6.69 (m, 1 H), 5.18 (br d, 1 H), 3.98 (s, 3 H), 3.72 (br t, 0.5 H), 3.40 (br d, 0.5 H), 2.72-3.25 (m, 2 H) | 432.1 $[M + H]^+$ | 100% |
| 2017 | ($CD_3OD$) δ 8.29-8.53 (m, 1 H), 7.50-7.83 (m, 3 H), 7.09-7.26 (m, 1 H), 6.77-6.97 (m, 3 H), 6.50-6.67 (m, 1 H), 5.18 (br dd, 1 H), 3.98 (s, 3 H), 3.59-3.83 (m, 0.5 H), 3.42 (td, 0.5 H), 2.93-3.23 (m, 1 H), 2.81 (br dd, 1 H) | 432.1 $[M + H]^+$ | 98.0% |
| 2018 | ($CD_3OD$) δ 8.28-8.41 (m, 2 H), 8.08 (s, 1 H), 7.84 (s, 0.3 H), 7.65-7.76 (m, 1 H), 6.91-7.03 (m, 1.7 H), 6.72-6.90 (m, 2 H), 5.29 (dd, 0.6 H), 4.93-4.99 (m, 0.4 H), 4.00 (s, 3 H), 3.68-3.80 (m, 0.6 H), 3.45 (td, 0.4 H), 2.95-3.23 (m, 1 H), 2.77-2.90 (m, 1 H) | 450.2 $[M + H]^+$ | 100% |
| 2019 | ($CD_3OD$) δ 8.28-8.40 (m, 2 H), 8.08 (s, 1 H), 7.84 (s, 0.3 H), 7.71 (s, 1 H), 6.89-7.03 (m, 1.7 H), 6.69-6.88 (m, 2 H), 5.29 (dd, 0.6 H), 4.93-4.98 (m, 0.4 H), 4.00 (d, 3 H), 3.68-3.81 (m, 0.6 H), 3.45 (td, 0.4 H), 2.96-3.24 (m, 1 H), 2.84 (br d, 1 H) | 450.1 $[M + H]^+$ | 99.8% |
| 2020 | ($CD_3OD$) δ 8.19-8.44 (m, 1 H), 7.83-7.97 (m, 1 H), 7.63-7.82 (m, 2 H), 7.43-7.62 (m, 2.2 H), 6.93-7.13 (m, 1.8 H), 6.72-6.89 (m, 1 H), 6.42-6.71 (m, 1 H), 5.00 (br d, 1 H), 3.70-3.90 (m, 0.5 H), 3.39-3.49 (m, 0.5 H), 2.96-3.29 (m, 1 H), 2.78-2.91 (m, 1 H), 2.37-2.55 (m, 3 H) | 399.2 $[M + H]^+$ | 100% |
| 2021 | ($CD_3OD$) δ 8.20-8.39 (m, 1 H), 7.82-7.96 (m, 1 H), 7.62-7.79 (m, 2 H), 7.40-7.61 (m, 2.2 H), 6.91-7.11 (m, 1.8 H), 6.71-6.85 (m, 1 H), 6.41-6.70 (m, 1 H), 4.98-5.03 (m, 1 H), 3.67-3.87 (m, 0.5 H), 3.36-3.47 (m, 0.5 H), 2.97-3.26 (m, 1 H), 2.73-2.90 (m, 1 H), 2.31-2.55 (m, 3 H) | 399.2 $[M + H]^+$ | 98.2% |
| 2022 | (DMSO-$d_6$) δ 12.00-12.33 (m, 1 H), 8.59-9.05 (m, 1 H), 7.93-8.32 (m, 2.5 H), 7.44-7.77 (m, 4 H), 7.05-7.35 (m, 1 H), 6.85-7.04 (m, 1 H), 6.57-6.81 (m, 1.5 H), 5.40-5.56 (m, 0.6 H), 4.76-4.91 (m, 0.4 H), 3.62-3.78 (m, 0.6 H), 3.24-3.30 (m, 0.4 H), 2.73-3.11 (m, 2 H) | 451.2 $[M + H]^+$ | 100% |
| 2023 | (DMSO-$d_6$) δ 11.96-12.33 (m, 1 H), 8.65-8.97 (m, 1 H), 7.94-8.37 (m, 2.5 H), 7.44-7.71 (m, 4 H), 7.09-7.44 (m, 1 H), 6.87-7.04 (m, 1 H), 6.64-6.84 (m, 1.5 H), 5.33-5.63 (m, 0.6 H), 4.84 (br dd, 0.4 H), 3.51-3.78 (m, 0.5 H), 3.22-3.31 (m, 0.5 H), 2.72-3.12 (m, 2 H) | 451.1 $[M + H]^+$ | 99.8% |

TABLE 2-continued

| Ex. # | $^1$H NMR (400 MHz unless otherwise noted) | LCMS: m/z | % ee |
|---|---|---|---|
| 2024 | ($CD_3OD$) δ 8.21-8.40 (m, 1 H), 7.64 (d, 1 H), 6.92-7.01 (m, 1 H), 6.88 (s, 0.6 H), 6.71-6.81 (m, 1 H), 6.48-6.67 (m, 1.4 H), 4.76 (br dd, 0.3 H), 4.51 (br dd, 0.7 H), 3.62-3.71 (m, 0.5 H), 3.22 (td, 0.5 H), 2.90-3.00 (m, 0.5 H), 2.65-2.85 (m, 1.5 H), 2.06-2.44 (m, 4 H), 0.78-1.13 (m, 4 H) | 322.1 $[M + H]^+$ | 99.6% |
| 2025 | ($CD_3OD$) δ 8.23-8.37 (m, 1 H), 7.64 (d, 1 H), 6.92-7.00 (m, 1 H), 6.88 (s, 0.6 H), 6.70-6.79 (m, 1 H), 6.47-6.64 (m, 1.4 H), 4.76 (br dd, 0.3 H), 4.51 (br dd, 0.7 H), 3.66 (ddd, 0.5 H), 3.22 (td, 0.5 H), 2.89-3.01 (m, 0.5 H), 2.64-2.85 (m, 1.5 H), 2.03-2.44 (m, 4 H), 0.76-1.13 (m, 4 H) | 322.2 $[M + H]^+$ | 99.6% |
| 2026 | ($CD_3OD$) δ 8.28 (br d, 1 H), 7.61-7.69 (m, 1 H), 6.88-7.06 (m, 1.8 H), 6.71-6.80 (m, 1 H), 6.47-6.58 (m, 1.2 H), 4.84 (br d, 0.3 H), 4.33 (br dd, 0.7 H), 3.70 (ddd, 0.7 H), 3.35-3.43 (m, 0.3 H), 3.09 (td, 0.8 H), 2.69-2.96 (m, 2.2 H), 2.42 (s, 3 H), 1.99-2.12 (m, 1 H), 1.81 (br dd, 1 H) | 358.2 $[M + H]^+$ | 100% |
| 2027 | ($CD_3OD$) δ 8.23-8.40 (m, 1 H), 7.66 (d, 1 H), 6.96 (br dd, 1 H), 6.68-6.88 (m, 1.5 H), 6.32-6.60 (m, 1.5 H), 4.75 (br dd, 0.5 H), 4.31 (br dd, 0.5 H), 3.65-3.81 (m, 0.5 H), 3.48 (td, 0.5 H), 2.95-3.25 (m, 1.5 H), 2.67-2.87 (m, 1.5 H), 2.41 (s, 3 H), 2.06-2.21 (m, 1 H), 1.70-1.95 (m, 1 H) | 358.2 $[M + H]^+$ | 100% |
| 2028 | ($CD_3OD$) δ 8.25-8.32 (m, 1 H), 7.59-7.71 (m, 1 H), 6.91-7.02 (m, 2 H), 6.76 (t, 1 H), 6.47-6.57 (m, 1 H), 4.83 (br d, 0.2 H), 4.33 (dd, 0.8 H), 3.70 (ddd, 0.8 H), 3.34-3.42 (m, 0.2 H), 3.09 (ddd, 0.8 H), 2.69-2.94 (m, 2.2 H), 2.42 (s, 3 H), 2.05 (dtd, 1 H), 1.76-1.88 (m, 1 H) | 358.2 $[M + H]^+$ | 100% |
| 2029 | ($CD_3OD$) δ 8.24-8.43 (m, 1 H), 7.66 (d, 1 H), 6.97 (br dd, 1 H), 6.68-6.87 (m, 1.5 H), 6.35-6.55 (m, 1.5 H), 4.75 (br dd, 1 H), 4.31 (dd, 0.5 H), 3.66-3.77 (m, 0.5 H), 3.43-3.53 (m, 0.5 H), 3.20 (td, 0.5 H), 2.95-3.14 (m, 1 H), 2.71-2.85 (m, 1 H), 2.41 (s, 3 H), 2.04-2.18 (m, 1 H), 1.74-1.91 (m, 1 H) | 358.2 $[M + H]^+$ | 98.5% |
| 2030 | ($CD_3OD$) δ 8.32 (d, 1 H), 7.66 (s, 1 H), 6.90-7.01 (m, 1.7 H), 6.81 (td, 1 H), 6.50-6.69 (m, 1.3 H), 4.85 (br d, 0.4 H), 4.36 (dd, 0.6 H), 3.69 (ddd, 0.8 H), 3.36-3.41 (m, 0.2 H), 3.04-3.15 (m, 0.8 H), 2.69-2.96 (m, 2.2 H), 1.99-2.11 (m, 1 H), 1.73-1.91 (m, 1 H) | 362.2 $[M + H]^+$ | 100% |
| 2031 | ($CD_3OD$) δ 8.28-8.44 (m, 1 H), 7.67 (d, 1 H), 6.89-7.00 (m, 1 H), 6.39-6.89 (m, 3 H), 4.76 (br dd, 0.7 H), 4.34 (br dd, 0.3 H), 3.66-3.77 (m, 0.5 H), 3.41-3.51 (m, 0.5 H), 3.09-3.22 (m, 1 H), 2.95-3.08 (m, 0.5 H), 2.69-2.88 (m, 1.5 H), 2.06-2.19 (m, 1 H), 1.76-1.96 (m, 1 H) | 362.1 $[M + H]^+$ | 90.8% |
| 2032 | ($CD_3OD$) δ 8.72 (d, 1 H), 7.85-8.47 (m, 4 H), 7.68 (s, 1 H), 7.49-7.61 (m, 1 H), 6.65-7.04 (m, 4 H), 4.61-4.76 (m, 1 H), 3.41-3.90 (m, 1 H), 2.94-3.24 (m, 1 H), 2.70-2.93 (m, 1 H) | 430.1 $[M + H]^+$ | 100% |
| 2033 | ($CD_3OD$) δ 8.71 (dt, 1 H), 7.85-8.50 (m, 4 H), 7.68 (br s, 1 H), 7.57 (dd, 1 H), 6.67-7.02 (m, 4 H), 4.61-4.74 (m, 1 H), 3.38-3.90 (m, 1 H), 2.95-3.25 (m, 1 H), 2.85 (br d, 1 H) | 430.1 $[M + H]^+$ | 99.6% |
| 2034 | ($CD_3OD$) δ 8.50-8.80 (m, 2 H), 7.81-8.36 (m, 3 H), 7.69 (br s, 1 H), 7.53-7.61 (m, 1 H), 7.44 (br d, 1 H), 6.52-7.28 (m, 4 H), 4.62-4.79 (m, 1 H), 3.40-3.88 (m, 1 H), 2.68-3.27 (m, 2 H) | 462.2 $[M + H]^+$ | 100% |
| 2035 | ($CD_3OD$) δ 8.42-8.80 (m, 2 H), 7.87-8.32 (m, 3 H), 7.68 (br s, 1 H), 7.57 (br dd, 1 H), 7.44 (br d, 1 H), 6.69-7.15 (m, 4 H), 4.62-4.78 (m, 1 H), 3.42-3.90 (m, 1 H), 2.74-3.25 (m, 2 H) | 462.1 $[M + H]^+$ | 99.7% |
| 2036 | ($CD_3OD$) δ 8.50-8.86 (m, 2 H), 7.83-8.32 (m, 3 H), 7.46-7.77 (m, 3 H), 6.64-7.16 (m, 3 H), 4.62-4.79 (m, 1 H), 3.43-3.91 (m, 1 H), 2.70-3.25 (m, 2 H) | 480.1 $[M + H]^+$ | 99.9% |
| 2037 | ($CD_3OD$) δ 8.57-8.85 (m, 2 H), 7.88-8.30 (m, 3 H), 7.50-7.72 (m, 3 H), 6.69-7.10 (m, 3 H), 4.62-4.79 (m, 1 H), 3.42-3.88 (m, 1 H), 2.78-3.25 (m, 2 H) | 480.2 $[M + H]^+$ | 99.8% |
| 2038 | ($CD_3OD$) δ 8.58 (d, 1 H), 8.13 (s, 1 H), 7.68 (s, 1 H), 7.42 (br d, 1 H), 6.65-7.14 (m, 4 H), 4.38 (br s, 1 H), 3.69 (br s, 1 H), 2.94-3.15 (m, 1 H), 2.79 (br dd, 1 H), 2.36 (br s, 1 H), 0.90-0.99 (m, 4 H) | 425.2 $[M + H]^+$ | 99.0% |
| 2039 | ($CD_3OD$) δ 8.58 (d, 1 H), 8.13 (s, 1 H), 7.67 (s, 1 H), 7.42 (br d, 1 H), 6.64-7.15 (m, 4 H), 4.37 (br s, 1 H), 3.70 (br s, 1 H), 2.96-3.19 (m, 1 H), 2.79 (br dd, 1 H), 2.09-2.46 (m, 1 H), 0.90-1.00 (m, 4 H) | 425.2 $[M + H]^+$ | 100% |
| 2040 | ($CD_3OD$) δ 8.43 (d, 1 H), 8.13 (s, 1 H), 7.68 (s, 1 H), 7.29 (d, 1 H), 6.42-6.94 (m, 3 H), 4.39 (br s, 1 H), 3.38-3.93 (m, 1 H), 2.95-3.16 (m, 1 H), 2.72-2.87 (m, 1 H), 2.36 (br s, 1 H), 0.89-1.03 (m, 4 H) | 409.1 $[M + H]^+$ | 99.5% |
| 2041 | ($CD_3OD$) δ 8.43 (d, 1 H), 8.13 (s, 1 H), 7.67 (s, 1 H), 7.29 (d, 1 H), 6.35-7.00 (m, 3 H), 4.39 (br s, 1 H), 3.36-3.80 (m, 1 H), 3.05 (br s, 1 H), 2.79 (br dd, 1 H), 2.21-2.47 (m, 1 H), 0.92-1.04 (m, 4 H) | 409.2 $[M + H]^+$ | 99.1% |
| 2042 | ($CD_3OD$) δ 8.03 (s, 1 H), 7.40-7.60 (m, 2 H), 6.43-7.08 (m, 4 H), 4.28 (br s, 1 H), 3.76 (br s, 1 H), 2.89 (br d, 1 H), 2.68 (br dd, 1 H), 2.25 (br s, 1 H), 0.85 (br d, 4 H) | 409.2 $[M + H]^+$ | 99.6% |

TABLE 2-continued

| Ex. # | $^{1}$H NMR (400 MHz unless otherwise noted) | LCMS: m/z | % ee |
|---|---|---|---|
| 2043 | ($CD_3OD$) δ 8.03 (s, 1 H), 7.37-7.60 (m, 2 H), 6.47-7.13 (m, 4 H), 4.29 (br s, 1 H), 3.27-3.87 (m, 1 H), 2.82-2.99 (m, 1 H), 2.68 (dd, 1 H), 2.25 (br s, 1 H), 0.86 (br d, 4 H) | 409.2 $[M + H]^+$ | 99.8% |
| 2044 | ($CD_3OD$) δ 8.30-8.38 (m, 1 H), 8.24 (s, 1 H), 7.96 (s, 1 H), 7.72 (s, 0.4 H), 7.55-7.60 (m, 1 H), 7.44-7.51 (m, 1 H), 7.04-7.14 (m, 1 H), 6.83 (s, 0.6 H), 6.75 (br dd, 1 H), 6.43-6.55 (m, 1 H), 5.13 (dd, 0.6 H), 4.80-4.85 (m, 0.4 H), 3.88 (s, 3 H), 3.57-3.68 (m, 0.6 H), 3.32 (td, 0.4 H), 2.84-3.12 (m, 1 H), 2.71 (br d, 1 H) | 432.1 $[M + H]^+$ | 100% |
| 2045 | ($CD_3OD$) δ 8.28-8.39 (m, 1 H), 8.25 (s, 1 H), 7.96 (s, 1 H), 7.68-7.75 (m, 0.4 H), 7.54-7.61 (m, 1 H), 7.41-7.52 (m, 1 H), 7.02-7.14 (m, 1 H), 6.83 (s, 0.6 H), 6.69-6.79 (m, 1 H), 6.42-6.57 (m, 1 H), 5.13 (dd, 0.6 H), 4.80-4.86 (m, 0.4 H), 3.88 (s, 3 H), 3.57-3.68 (m, 0.6 H), 3.26-3.41 (m, 0.4 H), 2.84-3.11 (m, 1 H), 2.71 (br d, 1 H) | 432.1 $[M + H]^+$ | 100% |
| 2046 | ($CD_3OD$) δ 8.12-8.27 (m, 2 H), 7.96 (s, 1 H), 7.72 (s, 0.4 H), 7.52-7.61 (m, 1 H), 6.79-6.93 (m, 1.6 H), 6.59-6.72 (m, 1 H), 6.44-6.54 (m, 1 H), 5.07-5.35 (m, 0.6 H), 4.80-4.86 (m, 0.4 H), 3.88 (s, 3 H), 3.58-3.68 (m, 0.6 H), 3.33 (td, 0.4 H), 2.84-3.13 (m, 1 H), 2.71 (br d, 1 H), 2.28-2.37 (m, 3 H) | 446.2 $[M + H]^+$ | 100% |
| 2047 | ($CD_3OD$) δ 8.11-8.28 (m, 2 H), 7.96 (s, 1 H), 7.72 (s, 0.4 H), 7.52-7.62 (m, 1 H), 6.78-6.92 (m, 1.6 H), 6.60-6.73 (m, 1 H), 6.44-6.55 (m, 1 H), 5.08-5.35 (m, 0.6 H), 4.80-4.87 (m, 0.4 H), 3.88 (s, 3 H), 3.57-3.68 (m, 0.6 H), 3.28-3.38 (m, 0.4 H), 2.83-3.12 (m, 1 H), 2.62-2.77 (m, 1 H), 2.28-2.36 (m, 3 H) | 446.2 $[M + H]^+$ | 99.2% |
| 2048 | ($CD_3OD$) δ 8.25-8.47 (m, 1 H), 7.76 (d, 1 H), 7.56-7.69 (m, 2.4 H), 7.42-7.53 (m, 2 H), 7.36-7.42 (m, 1 H), 7.00-7.16 (m, 1 H), 6.89 (s, 0.6 H), 6.67-6.82 (m, 1 H), 6.40-6.58 (m, 1 H), 4.85-4.92 (m, 1 H), 3.58-3.75 (m, 0.5 H), 3.23-3.37 (m, 0.5 H), 2.85-3.17 (m, 1 H), 2.73 (br dd, 1 H) | 385.1 $[M + H]^+$ | 98.2% |
| 2049 | ($CD_3OD$) δ 8.20-8.44 (m, 1 H), 7.76 (d, 1 H), 7.55-7.69 (m, 2.3 H), 7.42-7.52 (m, 2 H), 7.35-7.42 (m, 1 H), 7.03-7.17 (m, 1 H), 6.90 (s, 0.7 H), 6.67-6.83 (m, 1 H), 6.39-6.60 (m, 1 H), 4.88 (br dd, 1 H), 3.59-3.74 (m, 0.6 H), 3.25-3.35 (m, 0.4 H), 2.87-3.16 (m, 1 H), 2.74 (br dd, 1 H) | 385.2 $[M + H]^+$ | 97.7% |
| 2050 | ($CD_3OD$) δ 8.25-8.42 (m, 1 H), 7.84-7.91 (m, 1 H), 7.65-7.83 (m, 2.4 H), 7.45-7.62 (m, 2 H), 6.92-7.04 (m, 1.6 H), 6.81-6.91 (m, 1 H), 6.67-6.81 (m, 1 H), 4.98-5.06 (m, 1 H), 3.70-3.89 (m, 0.7 H), 3.41 (td, 0.3 H), 2.98-3.28 (m, 1 H), 2.85 (br dd, 1 H) | 403.1 $[M + H]^+$ | 100% |
| 2051 | ($CD_3OD$) δ 8.27-8.45 (m, 1 H), 7.86-7.95 (m, 1 H), 7.71-7.84 (m, 2.3 H), 7.47-7.66 (m, 2 H), 6.93-7.08 (m, 1.7 H), 6.83-6.91 (m, 1 H), 6.70-6.82 (m, 1 H), 4.99-5.09 (m, 1 H), 3.73-3.87 (m, 0.6 H), 3.38-3.48 (m, 0.4 H), 3.00-3.31 (m, 1 H), 2.88 (dd, 1 H) | 403.2 $[M + H]^+$ | 99.2% |
| 2052 | (DMSO-$d_6$) δ 11.98-12.19 (m, 1 H), 8.66-8.95 (m, 1 H), 7.81-8.06 (m, 2 H), 7.61-7.71 (m, 1 H), 7.56-7.61 (m, 1 H), 7.47-7.55 (m, 2 H), 7.08-7.45 (m, 1 H), 6.88-7.05 (m, 1 H), 6.58-6.83 (m, 2 H), 4.84 (br dd, 1 H), 3.55-3.80 (m, 0.6 H), 3.15-3.30 (m, 0.4 H), 2.85-3.11 (m, 1 H), 2.65-2.83 (m, 1 H) | 435.2 $[M + H]^+$ | 99.2% |
| 2053 | (DMSO-$d_6$) δ 11.86-12.54 (m, 1 H), 8.57-9.00 (m, 1 H), 7.84-7.99 (m, 2 H), 7.63-7.70 (m, 1 H), 7.55-7.62 (m, 1 H), 7.46-7.54 (m, 2.3 H), 7.46 (br s, 1 H), 6.89-7.03 (m, 1 H), 6.62-6.86 (m, 1.7 H), 4.84 (br dd, 1 H), 3.64-3.75 (m, 0.5 H), 3.20-3.27 (m, 0.5 H), 2.84-3.12 (m, 1 H), 2.77 (br d, 1 H) | 435.2 $[M + H]^+$ | 98.8% |
| 2054 | (DMSO-$d_6$) δ 11.83-12.41 (m, 1 H), 8.74-9.12 (m, 1 H), 7.83-8.06 (m, 2 H), 7.69-7.82 (m, 1 H), 7.62-7.68 (m, 1 H), 7.46-7.61 (m, 2.5 H), 6.93-7.09 (m, 1 H), 6.57-6.85 (m, 1.5 H), 4.86 (br dd, 1 H), 3.59-3.83 (m, 0.6 H), 3.16-3.28 (m, 0.4 H), 2.85-3.11 (m, 1 H), 2.71-2.83 (m, 1 H) | 453.1 $[M + H]^+$ | 99.4% |
| 2055 | (DMSO-$d_6$) δ 11.98-12.28 (m, 1 H), 8.81-9.08 (m, 1 H), 7.81-8.03 (m, 2 H), 7.69-7.79 (m, 1 H), 7.62-7.69 (m, 1 H), 7.45-7.61 (m, 2.5 H), 6.95-7.10 (m, 1 H), 6.58-6.85 (m, 1.5 H), 4.86 (br dd, 1 H), 3.63-3.79 (m, 0.6 H), 3.20-3.30 (m, 0.4 H), 2.84-3.11 (m, 1 H), 2.72-2.83 (m, 1 H) | 453.2 $[M + H]^+$ | 99.0% |
| 2056 | ($CD_3OD$) δ 8.28 (d, 1 H), 7.70 (s, 1 H), 6.69-6.86 (m, 3 H), 6.42 (s, 1 H), 4.35 (dd, 1 H), 3.73-3.87 (m, 1 H), 3.00-3.16 (m, 1 H), 2.85 (dd, 1 H), 2.00-2.17 (m, 1 H), 0.93-1.09 (m, 2 H), 0.67-0.84 (m, 2 H) | 416.2 $[M + H]^+$ | 99.5% |
| 2057 | ($CD_3OD$) δ 8.29 (d, 1 H), 7.70 (s, 1 H), 6.72-6.89 (m, 3 H), 6.41 (s, 1 H), 4.35 (dd, 1 H), 3.73-3.87 (m, 1 H), 3.01-3.16 (m, 1 H), 2.85 (dd, 1 H), 2.02-2.16 (m, 1 H), 0.96-1.09 (m, 2 H), 0.71-0.85 (m, 2 H) | 416.2 $[M + H]^+$ | 99.8% |
| 2058 | ($CD_3OD$) δ 8.28 (d, 1 H), 7.67 (s, 1 H), 6.65-6.87 (m, 3 H), 6.27 (s, 1 H), 4.19 (dd, 1 H), 3.62-3.79 (m, 1 H), 2.93-3.10 (m, 1 H), 2.80 (dd, 1 H), 2.00-2.18 (m, 2 H), 1.01-1.14 (m, 6 H), 0.75-0.82 (m, 2 H) | 388.2 $[M + H]^+$ | 99.8% |

TABLE 2-continued

| Ex. # | $^1$H NMR (400 MHz unless otherwise noted) | LCMS: m/z | % ee |
|---|---|---|---|
| 2059 | ($CD_3OD$) δ 8.28 (d, 1 H), 7.67 (s, 1 H), 6.64-6.86 (m, 3 H), 6.27 (s, 1 H), 4.19 (dd, 1 H), 3.62-3.75 (m, 1 H), 2.94-3.10 (m, 1 H), 2.80 (dd, 1 H), 2.03-2.15 (m, 2 H), 0.98-1.14 (m, 6 H), 0.71-0.82 (m, 2 H) | 388.2 $[M + H]^+$ | 99.7% |
| 2060 | ($CD_3OD$) δ 8.16-8.34 (m, 1 H), 7.70 (s, 1 H), 7.42 (s, 0.3 H), 6.95 (s, 0.7 H), , 6.60-6.85 (m, 3 H), 4.97 (br d, 1 H), 3.76 (ddd, 0.7 H), 3.40 (td, 0.3 H), 3.08-3.23 (m, 0.7 H), 2.94-3.04 (m, 0.3 H), 2.84 (br dd, 1 H), 2.02-2.15 (m, 1 H), 1.80-1.97 (m, 6 H), 0.92-1.11 (m, 2 H), 0.71-0.83 (m, 2 H) | 436.2 $[M + H]^+$ | 99.9% |
| 2061 | ($CD_3OD$) δ 8.15-8.35 (m, 1 H), 7.70 (s, 1 H), 7.42 (s, 0.3 H), 6.95 (s, 0.7 H), 6.66-6.87 (m, 3 H), 4.95-5.01 (m, 1 H), 3.70-3.84 (m, 0.7 H), 3.35-3.44 (m, 0.3 H), 3.10-3.22 (m, 0.7 H), 2.93-3.05 (m, 0.3 H), 2.78-2.89 (m, 1 H), 2.03-2.15 (m, 1 H), 1.80-1.97 (m, 6 H), 0.96-1.09 (m, 2 H), 0.73-0.83 (m, 2 H) | 436.2 $[M + H]^+$ | 99.1% |
| 2062 | ($CD_3OD$) δ 8.44 (d, 1 H), 7.54-7.79 (m, 2 H), 7.15-7.38 (m, 3 H), 6.69-6.93 (m, 2 H), 6.42 (s, 1 H), 4.38 (dd, 1 H), 3.80 (ddd, 1 H), 3.00-3.20 (m, 1 H), 2.86 (dd, 1 H) | 454.1 $[M + H]^+$ | 100% |
| 2063 | ($CD_3OD$) δ 8.32 (d, 1 H), 7.42-7.68 (m, 2 H), 7.00-7.24 (m, 3 H), 6.53-6.82 (m, 2 H), 6.30 (s, 1 H), 4.26 (dd, 1 H), 3.68 (ddd, 1 H), 2.90-3.06 (m, 1 H), 2.73 (dd, 1 H) | 454.1 $[M + H]^+$ | 96.6% |
| 2064 | ($CD_3OD$) δ 8.37 (br s, 1 H), 8.01 (br s, 0.5 H), 7.64-7.84 (m, 1.5 H), 6.99 (br t, 1 H), 6.87 (br s, 1.6 H), 6.57-6.81 (m, 1.4 H), 4.73-4.83 (m, 0.4 H), 4.49 (br s, 0.6 H), 3.78 (br s, 0.6 H), 3.36-3.46 (m, 0.4 H), 3.12 (br s, 1 H), 2.84 (br s, 1 H), 1.73-1.95 (m, 6 H) | 413.2 $[M + H]^+$ | 100% |
| 2065 | ($CD_3OD$) δ 8.36 (br s, 1 H), 8.01 (br s, 0.4 H), 7.62-7.88 (m, 1.6 H), 6.93-7.05 (m, 1 H), 6.86 (br s, 1.5 H), 6.52-6.80 (m, 1.5 H), 4.69-4.81 (m, 0.4 H), 4.46 (br s, 0.6 H), 3.78 (br s, 0.6 H), 3.37 (br s, 0.4 H), 2.94-3.19 (m, 1 H), 2.83 (br s, 1 H), 1.84 (br d, 6 H) | 413.2 $[M + H]^+$ | 100% |
| 2066 | ($CD_3OD$) δ 8.38 (br s, 1 H), 7.74-8.15 (m, 2 H), 7.70 (s, 1 H), 6.94-7.07 (m, 1 H), 6.59-6.93 (m, 3 H), 4.66-4.87 (m, 1 H), 3.86 (br s, 3 H), 3.50 (s, 1 H), 2.78-3.23 (m, 2 H), 2.44-2.77 (m, 3 H) | 447.2 $[M + H]^+$ | 100% |
| 2067 | ($CD_3OD$) δ 8.39 (br s, 1 H), 7.75-8.16 (m, 2 H), 7.70 (s, 1 H), 6.99 (br t, 1 H), 6.57-6.94 (m, 3 H), 4.65-4.84 (m, 1 H), 3.86 (br s, 3 H), 3.50 (s, 1 H), 2.79-3.26 (m, 2 H), 2.66 (br s, 3 H) | 447.2 $[M + H]^+$ | 100% |
| 2068 | ($CD_3OD$) δ 8.62 (br s, 1 H), 7.76-8.15 (m, 2 H), 7.70 (s, 1 H), 7.46 (br d, 1 H), 6.63-7.18 (m, 4 H), 4.65-4.84 (m, 1 H), 3.86 (br s, 3 H), 3.38-3.82 (m, 1 H), 2.78-3.24 (m, 2 H), 2.42-2.76 (m, 3 H) | 479.2 $[M + H]^+$ | 99.7% |
| 2069 | ($CD_3OD$) δ 8.62 (br s, 1 H), 7.75-8.13 (m, 2 H), 7.70 (s, 1 H), 7.45 (br d, 1 H), 6.67-7.18 (m, 4 H), 4.82 (br s, 1 H), 3.86 (br s, 3 H), 3.37-3.82 (m, 1 H), 2.79-3.25 (m, 2 H), 2.43-2.78 (m, 3 H) | 479.2 $[M + H]^+$ | 98.9% |
| 2070 | ($CD_3OD$) δ 8.16 (s, 1 H), 7.43-7.68 (m, 2 H), 6.47-7.17 (m, 4 H), 4.38 (br s, 1 H), 3.58-3.99 (m, 1 H), 2.78-3.11 (m, 2 H), 2.66 (s, 3 H), 2.32 (br s, 1 H), 0.97 (br d, 4 H) | 389.2 $[M + H]^+$ | 100% |
| 2071 | ($CD_3OD$) δ 8.16 (s, 1 H), 7.39-7.76 (m, 2 H), 6.22-7.18 (m, 4 H), 4.39 (br s, 1 H), 3.53-4.00 (m, 1 H), 2.76-3.14 (m, 2 H), 2.66 (s, 3 H), 2.32 (br s, 1 H), 0.97 (br d, 4 H) | 389.2 $[M + H]^+$ | 95.0% |
| 2072 | ($CD_3OD$) δ 8.24 (br d, 1 H), 7.66-8.14 (m, 2 H), 7.57 (s, 1 H), 6.50-6.90 (m, 4 H), 4.37-4.63 (m, 1 H), 3.83 (s, 3 H), 3.51-3.73 (m, 0.7 H), 3.27-3.46 (m, 0.3 H), 2.86-3.11 (m, 1 H), 2.72 (br d, 1 H), 2.25-2.37 (m, 1 H), 0.80-0.95 (m, 4 H) | 473.2 $[M + H]^+$ | 99.0% |
| 2073 | ($CD_3OD$) δ 8.23 (br s, 1 H), 7.65-8.14 (m, 2 H), 7.57 (s, 1 H), 6.48-6.91 (m, 4 H), 4.37-4.64 (m, 1 H), 3.82 (br s, 3 H), 3.49-3.71 (m, 0.7 H), 3.26-3.42 (m, 0.3 H), 2.88-3.08 (m, 1 H), 2.71 (br d, 1 H), 2.31 (quin, 1 H), 0.78-0.95 (m, 4 H) | 473.2 $[M + H]^+$ | 98.8% |
| 2074 | ($CD_3OD$) δ 8.33 (br d, 1 H), 7.78-8.25 (m, 2 H), 7.69 (s, 1 H), 6.50-7.06 (m, 4 H), 4.48-4.76 (m, 1 H), 3.94 (br s, 3 H), 3.65-3.84 (m, 0.6 H), 3.41-3.59 (m, 0.4 H), 3.00-3.20 (m, 1 H), 2.73-2.93 (m, 1 H), 2.38-2.54 (m, 4 H), 0.86-1.14 (m, 4 H) | 469.2 $[M + H]^+$ | 99.5% |
| 2075 | ($CD_3OD$) δ 8.15-8.31 (m, 1 H), 7.68-8.13 (m, 2 H), 7.57 (s, 1 H), 6.41-6.90 (m, 4 H), 4.42-4.70 (m, 1 H), 3.81 (br s, 3 H), 3.51-3.71 (m, 0.6 H), 3.25-3.38 (m, 0.4 H), 2.86-3.10 (m, 1 H), 2.60-2.81 (m, 1 H), 2.26-2.38 (m, 4 H), 0.80-0.94 (m, 4 H) | 469.2 $[M + H]^+$ | 99.5% |
| 2076 | ($CD_3OD$) δ 8.47-8.63 (m, 1 H), 8.10 (s, 1 H), 7.65-7.77 (m, 1 H), 7.34-7.49 (m, 2 H), 6.67-7.15 (m, 4 H), 5.07 (dd, 1 H), 3.68 (ddd, 0.7 H), 3.33-3.38 (m, 0.3 H), 3.06-3.19 (m, 0.7 H), 2.89-3.01 (m, 0.3 H), 2.79 (dd, 1 H) | 385.1 $[M + H]^+$ | 100% |
| 2077 | ($CD_3OD$) δ 8.50-8.60 (m, 1 H), 8.10 (s, 1 H), 7.64-7.78 (m, 1 H), 7.33-7.49 (m, 2 H), 6.68-7.16 (m, 4 H), 5.08 (dd, 1 H), 3.68 (ddd, 0.7 H), 3.33-3.38 (m, 0.3 H), 3.07-3.19 (m, 0.7 H), 2.91-3.01 (m, 0.3 H), 2.79 (dd, 1 H) | 385.1 $[M + H]^+$ | 98.1% |

TABLE 2-continued

| Ex. # | $^1$H NMR (400 MHz unless otherwise noted) | LCMS: m/z | % ee |
|---|---|---|---|
| 2078 | ($CD_3OD$) δ 8.61-8.73 (m, 1 H), 8.11 (s, 1 H), 7.68-7.79 (m, 1 H), 7.56-7.65 (m, 1 H), 7.34-7.46 (m, 1 H), 6.92-7.04 (m, 2 H), 6.64-6.82 (m, 1 H), 5.10 (dd, 1 H), 3.68 (ddd, 0.7 H), 3.33-3.38 (m, 0.3 H), 3.09-3.19 (m, 0.7 H), 2.91-3.01 (m, 0.3 H), 2.79 (dd, 1 H) | 403.1 $[M + H]^+$ | 99.9% |
| 2079 | ($CD_3OD$) δ 8.62-8.73 (m, 1 H), 8.11 (s, 1 H), 7.67-7.78 (m, 1 H), 7.55-7.66 (m, 1 H), 7.35-7.46 (m, 1 H), 6.90-7.04 (m, 2 H), 6.64-6.80 (m, 1 H), 5.10 (dd, 1 H), 3.68 (ddd, 0.6 H), 3.33-3.38 (m, 0.4 H), 3.09-3.19 (m, 0.7 H), 2.92-3.01 (m, 0.3 H), 2.79 (dd, 1 H) | 403.1 $[M + H]^+$ | 98.8% |
| 2080 | ($CD_3OD$) δ 8.27-8.42 (m, 1 H), 7.60-7.68 (m, 1 H), 6.74-6.99 (m, 2.7 H), 6.50-6.68 (m, 1 H), 6.11 (s, 0.3 H), 4.78 (br dd, 0.3 H), 4.01 (br dd, 0.7 H), 3.85 (t, 0.3 H), 3.45-3.62 (m, 1.4 H), 3.12 (td, 0.3 H), 2.47-2.86 (m, 2 H), 1.80-2.42 (m, 6 H) | 340.2 $[M + H]^+$ | 99.7% |
| 2081 | ($CD_3OD$) δ 8.27-8.41 (m, 1 H), 7.61-7.67 (m, 1 H), 6.89-6.99 (m, 1 H), 6.74-6.87 (m, 1.7 H), 6.51-6.65 (m, 1 H), 6.11 (s, 0.3 H), 4.78 (br dd, 0.3 H), 4.02 (dd, 0.7 H), 3.86 (quin, 0.3 H), 3.47-3.60 (m, 1.4 H), 3.07-3.17 (m, 0.3 H), 2.47-2.86 (m, 2 H), 1.80-2.42 (m, 6 H) | 340.2 $[M + H]^+$ | 99.5% |
| 2082 | ($CD_3OD$) δ 8.18 (d, 1 H), 7.55 (s, 1 H), 6.94 (d, 1 H), 6.72 (t, 1 H), 6.49 (s, 1 H), 6.18 (s, 1 H), 4.10 (dd, 1 H), 3.59 (ddd, 1 H), 2.86-3.12 (m, 2 H), 2.67 (dd, 1 H), 2.32 (s, 3 H), 1.22 (dd, 6 H) | 364.2 $[M + H]^+$ | 99.3% |
| 2083 | ($CD_3OD$) δ 8.18 (d, 1 H), 7.55 (s, 1 H), 6.93 (d, 1 H), 6.61-6.78 (m, 1 H), 6.49 (s, 1 H), 6.18 (s, 1 H), 4.10 (dd, 1 H), 3.59 (ddd, 1 H), 2.87-3.12 (m, 2 H), 2.67 (dd, 1 H), 2.32 (s, 3 H), 1.17-1.25 (m, 6 H) | 364.2 $[M + H]^+$ | 99.3% |
| 2084 | ($CD_3OD$) δ 8.31 (d, 1 H), 7.69 (s, 1 H), 6.83-7.15 (m, 3 H), 6.66 (s, 1 H), 6.39 (s, 1 H), 4.33 (dd, 1 H), 3.79 (ddd, 1 H), 3.03-3.25 (m, 2 H), 2.84 (dd, 1 H), 1.35 (dd, 6 H) | 400.2 $[M + H]^+$ | 99.9% |
| 2085 | ($CD_3OD$) δ 8.31 (d, 1 H), 7.69 (s, 1 H), 6.83-7.15 (m, 3 H), 6.62-6.70 (m, 1 H), 6.39 (s, 1 H), 4.33 (dd, 1 H), 3.73-3.86 (m, 1 H), 3.02-3.24 (m, 2 H), 2.84 (dd, 1 H), 1.35 (dd, 6 H) | 400.2 $[M + H]^+$ | 99.8% |
| 2086 | ($CD_3OD$) δ 8.03 (dd, 2 H), 7.68 (s, 1 H), 7.59 (dd, 1 H), 7.28 (t, 2 H), 7.17 (dd, 1 H), 7.03 (dd, 1 H), 6.71 (s, 1 H), 6.47 (s, 1 H), 4.38 (dd, 1 H), 3.76-3.91 (m, 1 H), 3.02-3.17 (m, 1 H), 2.87 (dd, 1 H) | 436.1 $[M + H]^+$ | 100% |
| 2087 | ($CD_3OD$) δ 8.03 (dd, 2 H), 7.68 (s, 1 H), 7.60 (d, 1 H), 7.29 (t, 2 H), 7.17 (dd, 1 H), 7.03 (d, 1 H), 6.71 (s, 1 H), 6.47 (s, 1 H), 4.38 (dd, 1 H), 3.77-3.91 (m, 1 H), 3.04-3.16 (m, 1 H), 2.79-2.94 (m, 1 H) | 436.1 $[M + H]^+$ | 99.3% |
| 2088 | ($CD_3OD$) δ 7.59-7.69 (m, 3 H), 7.15-7.26 (m, 3 H), 7.04 (dd, 1 H), 6.74 (s, 1 H), 6.43 (s, 1 H), 4.38 (dd, 1 H), 3.87 (ddd, 1 H), 3.01-3.19 (m, 1 H), 2.86 (dd, 1 H) | 454.1 $[M + H]^+$ | 100% |
| 2089 | ($CD_3OD$) δ 7.57-7.71 (m, 3 H), 7.14-7.26 (m, 3 H), 7.03 (dd, 1 H), 6.73 (s, 1 H), 6.43 (s, 1 H), 4.38 (dd, 1 H), 3.87 (ddd, 1 H), 3.01-3.18 (m, 1 H), 2.86 (dd, 1 H) | 454.1 $[M + H]^+$ | 98.4% |
| 2090 | ($CD_3OD$) δ 7.46-7.59 (m, 2 H), 7.35 (d, 1 H), 6.96-7.13 (m, 3 H), 6.59 (d, 1 H), 6.25-6.47 (m, 2 H), 4.24 (dd, 1 H), 3.72 (ddd, 1 H), 2.88-3.05 (m, 1 H), 2.73 (dd, 1 H), 2.51 (s, 3 H) | 434.2 $[M + H]^+$ | 100% |
| 2091 | ($CD_3OD$) δ 7.57-7.69 (m, 2 H), 7.47 (d, 1 H), 7.08-7.25 (m, 3 H), 6.71 (d, 1 H), 6.38-6.56 (m, 2 H), 4.36 (dd, 1 H), 3.84 (ddd, 1 H), 3.01-3.16 (m, 1 H), 2.85 (dd, 1 H), 2.63 (s, 3 H) | 434.2 $[M + H]^+$ | 100% |
| 2092 | ($CD_3OD$) δ 7.75 (d, 1 H), 7.58-7.71 (m, 2 H), 7.50 (s, 0.3 H), 7.36 (s, 0.5 H), 7.17-7.31 (m, 4.2 H), 6.70 (s, 1 H), 6.42 (br s, 1 H), 4.38 (dd, 1 H), 3.78-3.91 (m, 1 H), 3.01-3.18 (m, 1 H), 2.86 (br dd, 1 H) | 470.2 $[M + H]^+$ | 100% |
| 2093 | ($CD_3OD$) δ 7.74 (d, 1 H), 7.58-7.71 (m, 2 H), 7.49 (s, 0.3 H), 7.36 (s, 0.5 H), 7.16-7.31 (m, 4.2 H), 6.70 (s, 1 H), 6.42 (s, 1 H), 4.38 (dd, 1 H), 3.75-3.94 (m, 1 H), 3.01-3.18 (m, 1 H), 2.86 (dd, 1 H) | 470.2 $[M + H]^+$ | 100% |
| 2094 | ($CD_3OD$) δ 8.26-8.35 (m, 2 H), 7.65 (dd, 1 H), 7.53 (s, 1 H), 7.15 (d, 1 H), 7.02 (d, 1 H), 6.80 (s, 1 H), 6.70 (t, 1 H), 6.53 (s, 1 H), 4.61 (br dd, 1 H), 3.40-3.56 (m, 1 H), 2.76-2.91 (m, 1 H), 2.62 (br dd, 1 H) | 419.1 $[M + H]^+$ | 99.5% |
| 2095 | ($CD_3OD$) δ 8.44 (br d, 2 H), 7.78 (dd, 1 H), 7.66 (s, 1 H), 7.28 (d, 1 H), 7.15 (d, 1 H), 6.92 (s, 1 H), 6.82 (t, 1 H), 6.65 (s, 1 H), 4.73 (br dd, 1 H), 3.53-3.66 (m, 1 H), 2.89-3.03 (m, 1 H), 2.75 (br dd, 1 H) | 419.1 $[M + H]^+$ | 98.6% |
| 2096 | ($CD_3OD$) δ 8.39 (s, 1 H), 7.76 (dd, 1 H), 7.62 (s, 1 H), 7.44 (d, 1 H), 7.20 (d, 1 H), 7.10 (dd, 1 H), 6.80 (s, 1 H), 6.69 (d, 1 H), 6.48 (s, 1 H), 4.83 (br dd, 1 H), 3.60-3.73 (m, 1 H), 2.88-3.01 (m, 1 H), 2.74 (dd, 1 H), 2.69 (s, 3 H) | 399.2 $[M + H]^+$ | 97.4% |
| 2097 | ($CD_3OD$) δ 8.28 (s, 1 H), 7.64 (dd, 1 H), 7.50 (s, 1 H), 7.33 (d, 1 H), 7.09 (d, 1 H), 6.98 (dd, 1 H), 6.68 (s, 1 H), 6.58 (d, 1 H), 6.36 (s, 1 H), 4.72 (br dd, 1 H), 3.50-3.62 (m, 1 H), 2.77-2.89 (m, 1 H), 2.62 (dd, 1 H), 2.57 (s, 3 H) | 399.2 $[M + H]^+$ | 96.1% |

TABLE 2-continued

| Ex. # | $^1$H NMR (400 MHz unless otherwise noted) | LCMS: m/z | % ee |
|---|---|---|---|
| 2098 | ($CD_3OD$) δ 8.20-8.54 (m, 1 H), 7.54-7.99 (m, 2 H), 6.91-7.05 (m, 1 H), 6.46-6.89 (m, 3 H), 4.34-4.81 (m, 1 H), 3.42-3.93 (m, 1 H), 2.69-3.21 (m, 2 H), 2.18 (br d, 1 H), 1.14 (br s, 4 H) | 393.2 $[M + H]^+$ | 99.4% |
| 2099 | ($CD_3OD$) δ 8.20-8.54 (m, 1 H), 7.67 (s, 2 H), 6.91-7.07 (m, 1 H), 6.39-6.90 (m, 3 H), 4.42-4.79 (m, 1 H), 3.38-4.00 (m, 1 H), 2.61-3.15 (m, 2 H), 2.18 (br d, 1 H), 1.14 (br s, 4 H) | 393.2 $[M + H]^+$ | 98.4% |
| 2100 | ($CD_3OD$) δ 8.36 (br s, 1 H), 7.58-8.04 (m, 2 H), 6.55-7.10 (m, 4 H), 4.58-4.84 (m, 1 H), 3.35-3.87 (m, 1 H), 2.68-3.21 (m, 2 H), 1.26-1.55 (m, 9 H) | 409.2 $[M + H]^+$ | 100% |
| 2101 | ($CD_3OD$) δ 8.23 (br s, 1 H), 7.37-7.93 (m, 2 H), 6.38-7.02 (m, 4 H), 4.46-4.74 (m, 1 H), 3.24-3.81 (m, 1 H), 2.53-3.10 (m, 2 H), 1.08-1.49 (m, 9 H) | 409.2 $[M + H]^+$ | 99.6% |
| 2102 | ($CD_3OD$) δ 8.58 (br d, 1 H), 7.50-7.95 (m, 2 H), 7.43 (br d, 1 H), 6.48-7.17 (m, 4 H), 4.38-4.83 (m, 1 H), 3.34-3.88 (m, 1 H), 2.69-3.12 (m, 2 H), 2.18 (br s, 1 H), 1.14 (br s, 4 H) | 425.2 $[M + H]^+$ | 100% |
| 2103 | ($CD_3OD$) δ 8.41-8.77 (m, 1 H), 7.55-7.99 (m, 2 H), 7.43 (br d, 1 H), 6.39-7.20 (m, 4 H), 4.40-4.82 (m, 1 H), 3.43-3.88 (m, 1 H), 2.67-3.12 (m, 2 H), 2.18 (br d, 1 H), 1.14 (br s, 4 H) | 425.2 $[M + H]^+$ | 99.2% |
| 2104 | ($CD_3OD$) δ 8.48-8.75 (m, 1 H), 7.34-8.01 (m, 3 H), 6.57-7.20 (m, 4 H), 4.60-4.85 (m, 1 H), 3.34-3.86 (m, 1 H), 2.68-3.20 (m, 2 H), 1.25-1.60 (m, 9 H) | 441.2 $[M + H]^+$ | 100% |
| 2105 | ($CD_3OD$) δ 8.60 (br d, 1 H), 7.57-8.02 (m, 2 H), 7.45 (br d, 1 H), 6.58-7.18 (m, 4 H), 4.62-4.84 (m, 1 H), 3.34-3.88 (m, 1 H), 2.68-3.25 (m, 2 H), 1.25-1.58 (m, 9 H) | 441.2 $[M + H]^+$ | 99.5% |
| 2106 | ($CD_3OD$) δ 8.42-8.92 (m, 1 H), 8.02 (br s, 0.4 H), 7.65-7.86 (m, 1.6 H), 7.46 (br d, 1 H), 7.14 (s, 0.2 H), 6.55-7.05 (m, 3.8 H), 4.73-4.83 (m, 0.3 H), 4.47 (br s, 0.7 H), 3.77 (br s, 0.6 H), 3.38-3.47 (m, 0.4 H), 2.96-3.22 (m, 1 H), 2.85 (br s, 1 H), 1.70-1.95 (m, 6 H) | 445.2 $[M + H]^+$ | 100% |
| 2107 | ($CD_3OD$) δ 8.48-8.79 (m, 1 H), 8.01 (br s, 0.4 H), 7.70 (br s, 1.6 H), 7.46 (br d, 1 H), 7.13 (s, 0.2 H), 6.58-7.07 (m, 3.8 H), 4.82 (br s, 0.5 H), 4.47 (br s, 0.5 H), 3.77 (br s, 0.6 H), 3.38-3.47 (m, 0.4 H), 2.94-3.21 (m, 1 H), 2.86 (br d, 1 H), 1.69-1.99 (m, 6 H) | 445.2 $[M + H]^+$ | 99.1% |
| 2108 | ($CD_3OD$) δ 8.70 (br s, 1 H), 7.58-8.11 (m, 4 H), 6.71-7.04 (m, 4 H), 4.67-4.83 (m, 1 H), 3.99 (s, 3 H), 3.39-3.86 (m, 1 H), 2.78-3.23 (m, 2 H) | 483.1 $[M + H]^+$ | 100% |
| 2109 | ($CD_3OD$) δ 8.70 (br s, 1 H), 7.59-8.08 (m, 4 H), 6.77-7.05 (m, 4 H), 4.69-4.83 (m, 1 H), 3.99 (s, 3 H), 3.44-3.89 (m, 1 H), 2.81-3.24 (m, 2 H) | 483.2 $[M + H]^+$ | 98.5% |
| 2110 | ($CD_3OD$) δ 8.74 (br s, 1 H), 7.97 (br s, 2 H), 7.57-7.75 (m, 2 H), 6.61-7.12 (m, 3 H), 4.64-4.85 (m, 1 H), 3.87 (br s, 3 H), 3.35-3.81 (m, 1 H), 2.79-3.23 (m, 2 H), 2.67 (br s, 3 H) | 497.2 $[M + H]^+$ | 99.8% |
| 2111 | ($CD_3OD$) δ 8.60 (br s, 1 H), 7.63-8.03 (m, 2 H), 7.44-7.62 (m, 2 H), 6.51-6.95 (m, 3 H), 4.52-4.73 (m, 1 H), 3.69-3.82 (m, 3 H), 3.26-3.66 (m, 1 H), 2.62-3.12 (m, 2 H), 2.31-2.61 (m, 3 H) | 497.2 $[M + H]^+$ | 99.5% |
| 2112 | ($CD_3OD$) δ 8.13 (s, 1 H), 7.62-7.76 (m, 2 H), 7.34-7.56 (m, 1 H), 7.15-7.29 (m, 2 H), 6.47-6.95 (m, 2 H), 4.37 (br s, 1 H), 3.83 (br s, 1 H), 3.01 (br s, 1 H), 2.78 (dd, 1 H), 2.30 (br d, 1 H), 0.96 (br d, 4 H) | 425.2 $[M + H]^+$ | 100% |
| 2113 | ($CD_3OD$) δ 8.14 (s, 1 H), 7.62-7.77 (m, 2 H), 7.34-7.56 (m, 1 H), 7.13-7.31 (m, 2 H), 6.45-6.95 (m, 2 H), 4.39 (br s, 1 H), 3.56-3.98 (m, 1 H), 3.01 (br s, 1 H), 2.78 (dd, 1 H), 2.31 (br s, 1 H), 0.96 (br d, 4 H) | 425.2 $[M + H]^+$ | 100% |
| 2114 | ($CD_3OD$) δ 8.60 (br d, 1 H), 7.86-8.45 (m, 2 H), 7.74 (s, 1 H), 7.43 (br d, 1 H), 7.14 (s, 0.3 H), 6.70-7.03 (m, 3.7 H), 4.45-4.86 (m, 1 H), 3.86-4.07 (m, 3 H), 3.39-3.83 (m, 1 H), 2.99-3.22 (m, 1 H), 2.84 (br d, 1 H), 2.35-2.52 (m, 1 H), 0.88-1.10 (m, 4 H) | 505.2 $[M + H]^+$ | 99.6% |
| 2115 | ($CD_3OD$) δ 8.59 (br d, 1 H), 7.88-8.43 (m, 2 H), 7.81 (br s, 1 H), 7.42 (br d, 1 H), 7.13 (s, 0.3 H), 6.76-7.02 (m, 3.7 H), 4.41-4.81 (m, 1 H), 3.93 (br s, 3 H), 3.39-3.81 (m, 1 H), 2.99-3.22 (m, 1 H), 2.72-2.93 (m, 1 H), 2.36-2.50 (m, 1 H), 0.91-1.07 (m, 4 H) | 505.2 $[M + H]^+$ | 99.4% |
| 2116 | ($CD_3OD$) δ 8.72 (br d, 1 H), 7.78-8.30 (m, 2 H), 7.70 (s, 1 H), 7.63 (br d, 1 H), 6.99 (t, 1 H), 6.70-6.94 (m, 2 H), 4.43-4.77 (m, 1 H), 3.94 (br s, 3 H), 3.40-3.84 (m, 1 H), 2.99-3.23 (m, 1 H), 2.75-2.92 (m, 1 H), 2.38-2.50 (m, 1 H), 0.94-1.06 (m, 4 H) | 523.2 $[M + H]^+$ | 99.3% |
| 2117 | ($CD_3OD$) δ 8.71 (br d, 1 H), 7.77-8.34 (m, 2 H), 7.70 (s, 1 H), 7.63 (br d, 1 H), 6.98 (t, 1 H), 6.72-6.94 (m, 2 H), 4.44-4.79 (m, 1 H), 3.87-4.00 (m, 3 H), 3.38-3.82 (m, 1 H), 2.97-3.23 (m, 1 H), 2.84 (br d, 1 H), 2.33-2.52 (m, 1 H), 0.91-1.08 (m, 4 H) | 523.2 $[M + H]^+$ | 99.1% |
| 2118 | ($CD_3OD$) δ 8.68 (d, 1 H), 8.35 (d, 1 H), 7.85-8.22 (m, 2 H), 7.45-7.76 (m, 2 H), 6.59-7.28 (m, 4 H), 4.44-4.81 (m, 1 H), 3.45-3.89 (m, 1 H), 2.96-3.28 (m, 1 H), 2.83 (br d, 1 H), 2.33-2.57 (m, 1 H), 0.94-1.16 (m, 4 H) | 470.2 $[M + H]^+$ | 100% |
| 2119 | ($CD_3OD$) δ 8.68 (d, 1 H), 8.35 (d, 1 H), 7.83-8.25 (m, 2 H), 7.44-7.75 (m, 2 H), 6.62-7.25 (m, 4 H), 4.30-4.60 (m, 1 H), 3.46-3.87 (m, 1 H), 2.94-3.28 (m, 1 H), 2.83 (br d, 1 H), 2.43 (br s, 1 H), 0.97-1.19 (m, 4 H) | 470.2 $[M + H]^+$ | 99.7% |

TABLE 2-continued

| Ex. # | $^1$H NMR (400 MHz unless otherwise noted) | LCMS: m/z | % ee |
|---|---|---|---|
| 2120 | ($CD_3OD$) δ 8.67 (d, 1 H), 8.31 (d, 1 H), 7.83-8.21 (m, 2 H), 7.44-7.72 (m, 2 H), 6.55-7.06 (m, 4 H), 4.39-4.59 (m, 1 H), 3.50-3.90 (m, 1 H), 2.94-3.26 (m, 1 H), 2.73-2.90 (m, 1 H), 2.46 (s, 4 H), 0.93-1.19 (m, 4 H) | 466.2 $[M + H]^+$ | 100% |
| 2121 | ($CD_3OD$) δ 8.67 (d, 1 H), 8.31 (d, 1 H), 7.84-8.19 (m, 2 H), 7.38-7.73 (m, 2 H), 6.43-7.05 (m, 4 H), 4.42-4.58 (m, 1 H), 3.48-3.91 (m, 1 H), 2.95-3.26 (m, 1 H), 2.75-2.90 (m, 1 H), 2.46 (s, 4 H), 0.90-1.20 (m, 4 H) | 466.2 $[M + H]^+$ | 99.7% |
| 2122 | ($CD_3OD$) δ 8.68 (d, 1 H), 8.59 (br d, 1 H), 7.81-8.22 (m, 2 H), 7.68 (br s, 1 H), 7.48-7.59 (m, 1 H), 7.43 (br d, 1 H), 6.60-7.20 (m, 4 H), 4.38-4.60 (m, 1 H), 3.49-3.88 (m, 1 H), 2.98-3.27 (m, 1 H), 2.83 (br d, 1 H), 2.36-2.52 (m, 1 H), 0.92-1.19 (m, 4 H) | 502.2 $[M + H]^+$ | 100% |
| 2123 | ($CD_3OD$) δ 8.67 (d, 1 H), 8.59 (br d, 1 H), 7.85-8.24 (m, 2 H), 7.68 (br s, 1 H), 7.48-7.58 (m, 1 H), 7.43 (br d, 1 H), 6.68-7.17 (m, 4 H), 4.28-4.59 (m, 1 H), 3.46-3.90 (m, 1 H), 2.96-3.28 (m, 1 H), 2.83 (br d, 1 H), 2.43 (br d, 1 H), 0.94-1.18 (m, 4 H) | 502.2 $[M + H]^+$ | 99.6% |
| 2124 | ($CD_3OD$) δ 8.55-8.80 (m, 2 H), 7.83-8.27 (m, 2 H), 7.59-7.78 (m, 2 H), 7.54 (br dd, 1 H), 6.98 (br t, 3 H), 4.59 (s, 1 H), 3.50-3.89 (m, 1 H), 3.01-3.25 (m, 1 H), 2.76-2.92 (m, 1 H), 2.35-2.54 (m, 1 H), 0.96-1.16 (m, 4 H) | 520.2 $[M + H]^+$ | 98.7% |
| 2125 | ($CD_3OD$) δ 8.63-8.76 (m, 2 H), 7.81-8.28 (m, 2 H), 7.45-7.76 (m, 3 H), 6.57-7.30 (m, 3 H), 4.42-4.68 (m, 1 H), 3.50-3.92 (m, 1 H), 2.95-3.26 (m, 1 H), 2.83 (br dd, 1 H), 2.37-2.53 (m, 1 H), 0.98-1.16 (m, 4 H) | 520.2 $[M + H]^+$ | 91.1% |
| 2126 | ($CD_3OD$) δ 8.31 (s, 1 H), 8.13 (br s, 1 H), 7.58 (br s, 1.7 H), 6.93-7.10 (m, 2.3 H), 6.40-6.87 (m, 4 H), 4.56 (br s, 1 H), 3.58 (br s, 1 H), 2.65-3.09 (m, 2 H), 2.44 (br s, 3 H) | 331.2 $[M + H]^+$ | 97.8% |
| 2127 | ($CD_3OD$) δ 8.31 (d, 1 H), 8.13 (br d, 1 H), 7.62 (s, 1 H), 7.58 (t, 1 H), 7.05 (d, 1 H), 6.97 (d, 1 H), 6.72-6.85 (m, 2 H), 6.63-6.70 (m, 1 H), 6.50 (s, 1 H), 4.57 (br dd, 1 H), 3.53-3.66 (m, 1 H), 2.87-3.05 (m, 1 H), 2.60-2.75 (m, 1 H), 2.42 (s, 3 H) | 331.2 $[M + H]^+$ | 95.2% |
| 2128 | ($CD_3OD$) δ 8.03 (dd, 2 H), 7.85 (d, 1 H), 7.69 (s, 1 H), 7.23-7.36 (m, 4 H), 6.74 (s, 1 H), 6.46 (br s, 1 H), 4.38 (dd, 1 H), 3.79 (td, 1 H), 3.01-3.21 (m, 1 H), 2.87 (br dd, 1 H) | 470.2 $[M + H]^+$ | 99.7% |
| 2129 | ($CD_3OD$) δ 8.03 (dd, 2 H), 7.85 (d, 1 H), 7.69 (s, 1 H), 7.23-7.36 (m, 4 H), 6.74 (s, 1 H), 6.46 (br s, 1 H), 4.38 (dd, 1 H), 3.79 (td, 1 H), 3.01-3.21 (m, 1 H), 2.87 (br dd, 1 H) | 470.2 $[M + H]^+$ | 94.3% |
| 2130 | ($CD_3OD$) δ 8.02 (dd, 2 H), 7.74 (d, 1 H), 7.68 (s, 1 H), 7.49 (s, 0.3 H), 7.36 (s, 0.5 H), 7.25-7.33 (m, 3 H), 7.16-7.23 (m, 1.2 H), 6.70 (s, 1 H), 6.46 (s, 1 H), 4.39 (dd, 1 H), 3.77-3.89 (m, 1 H), 3.04-3.17 (m, 1 H), 2.81-2.92 (m, 1 H) | 452.2 $[M + H]^+$ | 99.5% |
| 2131 | ($CD_3OD$) δ 8.01 (br t, 2 H), 7.74 (br d, 1 H), 7.68 (s, 1 H), 7.49 (s, 0.3 H), 7.35 (s, 0.5 H), 7.28 (q, 3 H), 7.13-7.23 (m, 1.2 H), 6.69 (s, 1 H), 6.45 (br s, 1 H), 4.38 (br dd, 1 H), 3.83 (br t, 1 H), 3.02-3.17 (m, 1 H), 2.86 (br d, 1 H) | 452.1 $[M + H]^+$ | 98.6% |
| 2132 | ($CD_3OD$) δ 7.86 (d, 1 H), 7.53-7.75 (m, 2 H), 7.11-7.41 (m, 4 H), 6.77 (s, 1 H), 6.42 (br s, 1 H), 4.39 (dd, 1 H), 3.73-3.93 (m, 1 H), 3.01-3.17 (m, 1 H), 2.86 (dd, 1 H) | 488.2 $[M + H]^+$ | 100% |
| 2133 | ($CD_3OD$) δ 7.86 (d, 1 H), 7.55-7.76 (m, 2 H), 7.11-7.44 (m, 4 H), 6.77 (s, 1 H), 6.42 (br s, 1 H), 4.39 (dd, 1 H), 3.83 (td, 1 H), 3.00-3.20 (m, 1 H), 2.86 (dd, 1 H) | 488.2 [M + H]+ | 97.1% |
| 2134 | ($CD_3OD$) δ 8.43 (d, 1 H), 7.50-7.75 (m, 3 H), 7.01-7.27 (m, 1 H), 6.76-6.94 (m, 2 H), 6.69 (s, 1 H), 6.50 (s, 1 H), 6.18 (dd, 1 H), 4.55 (dd, 1 H), 3.54 (ddd, 1 H), 2.83-3.01 (m, 1 H), 2.67 (br dd, 1 H) | 335.1 $[M + H]^+$ | 98.8% |
| 2135 | ($CD_3OD$) δ 8.43 (d, 1 H), 7.40-7.75 (m, 3 H), 7.06-7.27 (m, 1 H), 6.75-6.91 (m, 2 H), 6.69 (s, 1 H), 6.50 (s, 1 H), 6.18 (dd, 1 H), 4.55 (dd, 1 H), 3.54 (ddd, 1 H), 2.84-3.00 (m, 1 H), 2.67 (br dd, 1 H) | 335.2 $[M + H]^+$ | 98.9% |
| 2136 | ($CD_3OD$) δ 8.40 (s, 1 H), 7.76 (dd, 1 H), 7.63 (s, 1 H), 7.56 (dd, 1 H), 7.19 (d, 1 H), 7.15 (dd, 1 H), 7.00 (dd, 1 H), 6.85 (s, 1 H), 6.65 (s, 1 H), 4.81 (br dd, 1 H), 3.68 (ddd, 1 H), 2.87-3.04 (m, 1 H), 2.75 (dd, 1 H) | 419.1 $[M + H]^+$ | 100% |
| 2137 | ($CD_3OD$) δ 8.28 (s, 1 H), 7.65 (dd, 1 H), 7.52 (s, 1 H), 7.46 (dd, 1 H), 7.08 (d, 1 H), 7.04 (dd, 1 H), 6.90 (dd, 1 H), 6.73 (s, 1 H), 6.54 (s, 1 H), 4.69 (br dd, 1 H), 3.56 (ddd, 1 H), 2.76-2.91 (m, 1 H), 2.63 (dd, 1 H) | 419.1 $[M + H]^+$ | 100% |
| 2138 | ($CD_3OD$) δ 8.40 (s, 1 H), 7.76 (dd, 1 H), 7.67-7.73 (m, 1 H), 7.64 (s, 1 H), 7.30-7.60 (m, 1 H), 7.25 (dd, 1 H), 7.13-7.21 (m, 2 H), 6.82 (s, 1 H), 6.62 (s, 1 H), 4.83 (br dd, 1 H), 3.60-3.71 (m, 1 H), 2.89-3.02 (m, 1 H), 2.75 (dd, 1 H) | 435.1 $[M + H]^+$ | 100% |
| 2139 | ($CD_3OD$) δ 8.40 (s, 1 H), 7.76 (dd, 1 H), 7.71 (d, 1 H), 7.63 (s, 1 H), 7.30-7.59 (m, 1 H), 7.22-7.28 (m, 1 H), 7.14-7.21 (m, 2 H), 6.81 (s, 1 H), 6.62 (s, 1 H), 4.84 (br dd, 1 H), 3.59-3.72 (m, 1 H), 2.89-3.02 (m, 1 H), 2.75 (dd, 1 H) | 435.1 $[M + H]^+$ | 100% |
| 2140 | ($CD_3OD$) δ 8.52-8.94 (m, 1 H), 7.47-8.03 (m, 3 H), 6.91-7.19 (m, 1 H), 6.51-6.88 (m, 2 H), 4.65-4.80 (m, 0.5 H), 4.32-4.56 (m, | 443.2 $[M + H]^+$ | 100% |

TABLE 2-continued

| Ex. # | $^1$H NMR (400 MHz unless otherwise noted) | LCMS: m/z | % ee |
|---|---|---|---|
| | 0.5 H), 3.51-3.88 (m, 1 H), 2.69-3.10 (m, 2 H), 2.18 (br d, 1 H), 1.02-1.27 (m, 4 H) | | |
| 2141 | ($CD_3OD$) δ 8.57-8.90 (m, 1 H), 7.44-8.06 (m, 3 H), 6.99 (br s, 1 H), 6.42-6.92 (m, 2 H), 4.64-4.82 (m, 0.5 H), 4.38-4.57 (m, 0.5 H), 3.42-3.89 (m, 1 H), 2.69-3.19 (m, 2 H), 2.18 (br s, 1 H), 0.98-1.23 (m, 4 H) | 443.2 $[M + H]^+$ | 99.6% |
| 2142 | ($CD_3OD$) δ 8.47-8.79 (m, 1 H), 7.43-7.82 (m, 3 H), 6.89 (br t, 1 H), 6.46-6.80 (m, 2 H), 4.53-4.74 (m, 1 H), 3.24-3.72 (m, 1 H), 2.61-3.06 (m, 2 H), 1.17-1.38 (m, 9 H) | 459.2 [M + H]+ | 100% |
| 2143 | ($CD_3OD$) δ 8.71 (br s, 1 H), 7.51-7.94 (m, 3 H), 6.52-7.18 (m, 3 H), 4.66-4.88 (m, 1 H), 3.37-3.91 (m, 1 H), 2.69-3.23 (m, 2 H), 1.26-1.58 (m, 9 H) | 459.2 $[M + H]^+$ | 99.5% |
| 2144 | ($CD_3OD$) δ 8.74 (br d, 1 H), 7.75-8.05 (m, 1 H), 7.60-7.73 (m, 2 H), 7.01 (br s, 1 H), 6.60-6.94 (m, 2 H), 4.82 (br s, 0.3 H), 4.48 (br s, 0.7 H), 3.78 (br s, 0.5 H), 3.36-3.48 (m, 0.5 H), 3.15 (br s, 1 H), 2.86 (br d, 1 H), 1.73-1.91 (m, 6 H) | 463.2 $[M + H]^+$ | 100% |
| 2145 | ($CD_3OD$) δ 8.72 (br s, 1 H), 7.75-8.09 (m, 1 H), 7.60-7.74 (m, 2 H), 7.01 (br s, 1 H), 6.56-6.95 (m, 2 H), 4.75-4.84 (m, 0.5 H), 4.48 (br s, 0.5 H), 3.78 (br s, 0.6 H), 3.36-3.47 (m, 0.4 H), 2.95-3.23 (m, 1 H), 2.84 (br s, 1 H), 1.69-1.92 (m, 6 H) | 463.2 $[M + H]^+$ | 98.5% |
| 2146 | ($CD_3OD$) δ 8.29 (d, 1 H), 7.74 (s, 1 H), 7.05 (d, 1 H), 6.84 (t, 1 H), 6.66 (s, 1 H), 6.40 (s, 1 H), 4.33 (dd, 1 H), 3.79 (ddd, 1 H), 2.99-3.25 (m, 2 H), 2.84 (br dd, 1 H), 1.33 (dd, 6 H) | 418.2 $[M + H]^+$ | 100% |
| 2147 | ($CD_3OD$) δ 8.31 (d, 1 H), 7.69 (s, 1 H), 7.07 (d, 1 H), 6.86 (1, 1 H), 6.67 (s, 1 H), 6.40 (s, 1 H), 4.35 (dd, 1 H), 3.81 (ddd, 1 H), 3.05-3.26 (m, 2 H), 2.85 (dd, 1 H), 1.35 (dd, 6 H) | 418.2 $[M + H]^+$ | 99.6% |
| 2148 | ($CD_3OD$) δ 8.42 (s, 1 H), 8.25-8.35 (m, 1 H), 7.73-7.82 (m, 1 H), 7.65 (s, 1 H), 7.11-7.18 (m, 1 H), 7.04 (d, 1 H), 6.92 (s, 1 H), 6.81 (t, 1 H), 6.60 (s, 1 H), 4.68-4.75 (m, 1 H), 3.56-3.70 (m, 1 H), 3.18 (dt, 1 H), 2.89-3.03 (m, 1 H), 2.74 (br dd, 1 H), 1.33 (dd, 6 H) | 427.2 $[M + H]^+$ | 98.7% |
| 2149 | ($CD_3OD$) δ 8.27-8.36 (m, 1 H), 8.13-8.23 (m, 1 H), 7.62-7.70 (m, 1 H), 7.46-7.57 (m, 1 H), 7.03 (d, 1 H), 6.92 (d, 1 H), 6.80 (s, 1 H), 6.70 (t, 1 H), 6.48 (s, 1 H), 4.60 (br dd, 1 H), 3.45-3.57 (m, 1 H), 3.07 (dt, 1 H), 2.77-2.91 (m, 1 H), 2.56-2.69 (m, 1 H), 1.21 (dd, 6 H) | 427.2 $[M + H]^+$ | 99.6% |
| 2150 | ($CD_3OD$) δ 7.96 (d, 1 H), 7.56 (s, 1 H), 6.63-7.05 (m, 2 H), 6.39-6.54 (m, 2 H), 6.25 (s, 1 H), 4.19 (dd, 1 H), 3.84 (s, 3 H), 3.54-3.72 (m, 1 H), 2.84-3.04 (m, 1 H), 2.71 (dd, 1 H) | 388.2 $[M + H]^+$ | 99.7% |
| 2151 | ($CD_3OD$) δ 8.07 (d, 1 H), 7.66 (s, 1 H), 7.10 (s, 0.2 H), 6.97 (s, 0.5 H), 6.73-6.87 (m, 1.3 H), 6.48-6.65 (m, 2 H), 6.35 (s, 1 H), 4.30 (dd, 1 H), 3.94 (s, 3 H), 3.66-3.79 (m, 1 H), 2.97-3.13 (m, 1 H), 2.81 (dd, 1 H) | 388.2 $[M + H]^+$ | 99.1% |
| 2152 | ($CD_3OD$) δ 8.36 (d, 1 H), 7.69 (s, 1 H), 7.10-7.26 (m, 0.5 H), 6.92-7.07 (m, 2 H), 6.80-6.90 (m, 1.5 H), 6.70 (s, 1 H), 6.39 (s, 1 H), 4.34 (dd, 1 H), 3.77 (ddd, 1 H), 2.98-3.20 (m, 1 H), 2.84 (dd, 1 H) | 424.1 $[M + H]^+$ | 99.7% |
| 2153 | ($CD_3OD$) δ 8.36 (d, 1 H), 7.69 (s, 1 H), 7.08-7.27 (m, 0.5 H), 6.93-7.07 (m, 2 H), 6.79-6.93 (m, 1.5 H), 6.70 (s, 1 H), 6.39 (s, 1 H), 4.34 (dd, 1 H), 3.77 (ddd, 1 H), 2.98-3.16 (m, 1 H), 2.84 (dd, 1 H) | 424.1 $[M + H]^+$ | 98.1% |
| 2154 | ($CD_3OD$) δ 8.24 (br d, 1 H), 7.59 (br s, 1 H), 7.10 (s, 0.2 H), 6.82-6.97 (m, 1.5 H), 6.68-6.81 (m, 1.3 H), 6.58 (s, 1 H), 6.29 (br s, 1 H), 4.23 (dd, 1 H), 3.55-3.76 (m, 1 H), 2.86-3.06 (m, 1 H), 2.74 (br d, 1 H) | 442.1 $[M + H]^+$ | 99.6% |
| 2155 | ($CD_3OD$) δ 8.24 (d, 1 H), 7.58 (s, 1 H), 7.10 (s, 0.3 H), 6.80-6.96 (m, 1.5 H), 6.70-6.78 (m, 1.2 H), 6.58 (s, 1 H), 6.29 (s, 1 H), 4.24 (dd, 1 H), 3.66 (ddd, 1 H), 2.88-3.05 (m, 1 H), 2.73 (dd, 1 H) | 442.1 $[M + H]^+$ | 99.1% |
| 2156 | ($CD_3OD$) δ 9.23 (s, 1 H), 8.67 (br d, 2 H), 8.24 (br d, 1 H), 7.68 (s, 1 H), 6.92 (br d, 1 H), 6.67-6.78 (m, 1 H), 6.42-6.63 (m, 2 H), 4.41 (br dd, 1 H), 3.70-3.87 (m, 1 H), 2.96-3.14 (m, 1 H), 2.77-2.88 (m, 1 H), 2.38 (s, 3 H) | 400.2 $[M + H]^+$ | 99.4% |
| 2157 | ($CD_3OD$) δ 9.28 (d, 1 H), 8.66-8.77 (m, 2 H), 8.29 (d, 1 H), 7.68 (s, 1 H), 6.97 (d, 1 H), 6.76 (t, 1 H), 6.63 (s, 1 H), 6.51 (s, 1 H), 4.43 (dd, 1 H), 3.81 (ddd, 1 H), 3.03-3.15 (m, 1 H), 2.84 (dd, 1 H), 2.43 (s, 3 H) | 400.2 $[M + H]^+$ | 99.4% |
| 2158 | ($CD_3OD$) δ 9.24 (s, 1 H), 8.68 (br dd, 2 H), 8.30 (br d, 1 H), 7.68 (s, 1 H), 6.91 (br dd, 1 H), 6.69-6.84 (m, 2 H), 6.49 (br s, 1 H), 4.43 (br dd, 1 H), 3.73-3.86 (m, 1 H), 3.00-3.17 (m, 1 H), 2.84 (br dd, 1 H) | 404.2 $[M + H]^+$ | 99.9% |
| 2159 | ($CD_3OD$) δ 9.23 (s, 1 H), 8.62-8.71 (m, 2 H), 8.28 (d, 1 H), 7.68 (s, 1 H), 6.90 (dd, 1 H), 6.69-6.82 (m, 2 H), 6.49 (s, 1 H), 4.42 (br dd, 1 H), 3.73-3.86 (m, 1 H), 3.00-3.14 (m, 1 H), 2.83 (br dd, 1 H) | 404.2 $[M + H]^+$ | 99.0% |
| 2160 | ($CD_3OD$) δ 9.27 (s, 1 H), 8.70 (br dd, 2 H), 8.42 (br d, 1 H), 7.69 (s, 1 H), 7.27 (br d, 1 H), 6.82 (t, 1 H), 6.75 (s, 1 H), 6.51 (s, 1 | 420.1 $[M + H]^+$ | 100% |

TABLE 2-continued

| Ex. # | $^1$H NMR (400 MHz unless otherwise noted) | LCMS: m/z | % ee |
|---|---|---|---|
| | H), 4.45 (br dd, 1 H), 3.75-3.86 (m, 1 H), 3.03-3.15 (m, 1 H), 2.85 (br dd, 1 H) | | |
| 2161 | ($CD_3OD$) δ 9.26 (s, 1 H), 8.65-8.77 (m, 2 H), 8.40 (d, 1 H), 7.69 (s, 1 H), 7.25 (d, 1 H), 6.80 (t, 1 H), 6.74 (s, 1 H), 6.50 (s, 1 H), 4.44 (dd, 1 H), 3.69-3.89 (m, 1 H), 3.00-3.20 (m, 1 H), 2.84 (br dd, 1 H) | 420.1 [M + H]$^+$ | 98.8% |
| 2162 | ($CD_3OD$) δ 9.27 (d, 1 H), 8.94 (d, 1 H), 8.67 (d, 1 H), 8.09 (dd, 1 H), 7.69 (s, 1 H), 7.61 (d, 1 H), 6.96 (t, 1 H), 6.82 (s, 1 H), 6.55 (s, 1 H), 4.49 (dd, 1 H), 3.82 (ddd, 1 H), 3.04-3.18 (m, 1 H), 2.86 (dd, 1 H) | 454.2 [M + H]$^+$ | 99.5% |
| 2163 | ($CD_3OD$) δ 9.27 (d, 1 H), 8.94 (d, 1 H), 8.68 (d, 1 H), 8.10 (dd, 1 H), 7.69 (s, 1 H), 7.61 (d, 1 H), 6.97 (t, 1 H), 6.82 (s, 1 H), 6.55 (br s, 1 H), 4.49 (dd, 1 H), 3.72-3.92 (m, 1 H), 3.01-3.19 (m, 1 H), 2.86 (br dd, 1 H) | 454.2 [M + H]$^+$ | 96.9% |
| 2164 | ($CD_3OD$) δ 8.07 (d, 1 H), 7.67 (s, 1 H), 6.79 (t, 1 H), 6.53-6.64 (m, 2 H), 6.36 (s, 1 H), 4.31 (dd, 1 H), 3.94 (s, 3 H), 3.75 (td, 1 H), 2.99-3.14 (m, 1 H), 2.82 (br dd, 1 H) | 406.1 [M + H]$^+$ | 100% |
| 2165 | ($CD_3OD$) δ 8.07 (d, 1 H), 7.67 (s, 1 H), 6.79 (t, 1 H), 6.50-6.65 (m, 2 H), 6.36 (br s, 1 H), 4.31 (dd, 1 H), 3.95 (s, 3 H), 3.69-3.83 (m, 1 H), 2.99-3.12 (m, 1 H), 2.76-2.87 (m, 1 H) | 406.1 [M + H]$^+$ | 99.6% |
| 2166 | ($CD_3OD$) δ 8.16 (d, 1 H), 7.57 (s, 1 H), 6.59-7.03 (m, 4 H), 6.28 (s, 1 H), 4.21 (dd, 1 H), 3.67 (ddd, 1 H), 2.83-3.03 (m, 1 H), 2.72 (dd, 1 H), 1.78-2.10 (m, 1 H), 0.88-0.96 (m, 2 H), 0.62-0.71 (m, 2 H) | 398.2 [M + H]$^+$ | 90.7% |
| 2167 | ($CD_3OD$) δ 8.17 (d, 1 H), 7.58 (s, 1 H), 6.56-7.04 (m, 4 H), 6.28 (s, 1 H), 4.21 (dd, 1 H), 3.67 (td, 1 H), 2.85-3.06 (m, 1 H), 2.72 (dd, 1 H), 1.87-2.06 (m, 1 H), 0.86-1.01 (m, 2 H), 0.63-0.73 (m, 2 H) | 398.2 [M + H]$^+$ | 100% |
| 2168 | ($CD_3OD$) δ 8.31 (br d, 1 H), 7.66 (s, 1 H), 7.06 (d, 1 H), 6.84 (t, 1 H), 6.59 (s, 1 H), 6.14-6.33 (m, 1 H), 4.19 (dd, 1 H), 3.70 (td, 1 H), 3.20 (dt, 1 H), 2.95-3.10 (m, 1 H), 2.73-2.87 (m, 1 H), 2.02-2.15 (m, 1 H), 1.34 (dd, 6 H), 1.04-1.15 (m, 4 H) | 390.2 [M + H]$^+$ | 98.6% |
| 2169 | ($CD_3OD$) δ 8.19 (d, 1 H), 7.54 (s, 1 H), 6.94 (d, 1 H), 6.72 (t, 1 H), 6.47 (s, 1 H), 6.14 (br s, 1 H), 4.07 (dd, 1 H), 3.58 (td, 1 H), 3.08 (dt, 1 H), 2.85-2.96 (m, 1 H), 2.67 (br dd, 1 H), 1.92-2.05 (m, 1 H), 1.22 (dd, 6 H), 0.92-1.03 (m, 4 H) | 390.2 [M + H]$^+$ | 97.5% |
| 2170 | ($CD_3OD$) δ 8.30 (s, 1 H), 8.16 (d, 1 H), 7.65 (dd, 1 H), 7.54 (s, 1 H), 7.03 (d, 1 H), 6.81 (s, 1 H), 6.59-6.70 (m, 2 H), 6.57 (s, 1 H), 4.60 (br dd, 1 H), 3.44-3.58 (m, 1 H), 2.78-2.91 (m, 1 H), 2.62 (dd, 1 H), 1.89-2.02 (m, 1 H), 0.86-0.96 (m, 2 H), 0.59-0.69 (m, 2 H) | 425.2 [M + H]$^+$ | 80.9% |
| 2171 | ($CD_3OD$) δ 8.30 (s, 1 H), 8.16 (d, 1 H), 7.65 (dd, 1 H), 7.54 (s, 1 H), 7.03 (d, 1 H), 6.82 (s, 1 H), 6.60-6.70 (m, 2 H), 6.57 (s, 1 H), 4.60 (br dd, 1 H), 3.44-3.57 (m, 1 H), 2.79-2.90 (m, 1 H), 2.62 (dd, 1 H), 1.91-2.01 (m, 1 H), 0.85-0.96 (m, 2 H), 0.61-0.69 (m, 2 H) | 425.2 [M + H]$^+$ | 96.3% |
| 2172 | ($CD_3OD$) δ 8.40 (d, 2 H), 8.25 (d, 1 H), 7.64 (s, 1 H), 7.22 (s, 1 H), 6.70-6.81 (m, 2 H), 6.69 (s, 1 H), 6.64 (t, 1 H), 5.03 (dd, 1 H), 3.48 (ddd, 1 H), 2.85-2.98 (m, 1 H), 2.70 (dd, 1 H), 2.01-2.13 (m, 1 H), 0.97-1.07 (m, 2 H), 0.71-0.81 (m, 2 H) | 358.2 [M + H]$^+$ | 100% |
| 2173 | ($CD_3OD$) δ 8.41 (d, 2 H), 8.25 (d, 1 H), 7.64 (s, 1 H), 7.22 (s, 1 H), 6.71-6.80 (m, 2 H), 6.69 (s, 1 H), 6.65 (t, 1 H), 5.04 (dd, 1 H), 3.48 (ddd, 1 H), 2.84-3.00 (m, 1 H), 2.70 (dd, 1 H), 2.00-2.13 (m, 1 H), 0.97-1.07 (m, 2 H), 0.70-0.81 (m, 2 H) | 358.2 [M + H]$^+$ | 100% |
| 2174 | ($CD_3OD$) δ 8.56 (s, 2 H), 8.14 (d, 1 H), 7.55 (s, 1 H), 7.16 (s, 1 H), 6.52-6.74 (m, 3 H), 5.06 (dd, 1 H), 3.42 (td, 1 H), 2.74-2.87 (m, 1 H), 2.60-2.69 (m, 1 H), 1.89-2.06 (m, 1 H), 0.84-0.95 (m, 2 H), 0.59-0.71 (m, 2 H) | 426.2 [M + H]$^+$ | 100% |
| 2175 | ($CD_3OD$) δ 8.56 (s, 2 H), 8.14 (d, 1 H), 7.55 (s, 1 H), 7.16 (s, 1 H), 6.54-6.73 (m, 3 H), 5.07 (dd, 1 H), 3.42 (td, 1 H), 2.72-2.90 (m, 1 H), 2.57-2.71 (m, 1 H), 1.86-2.06 (m, 1 H), 0.85-0.97 (m, 2 H), 0.59-0.73 (m, 2 H) | 426.2 [M + H]$^+$ | 99.7% |
| 2176 | ($CD_3OD$) δ 9.28 (d, 1 H), 8.67-8.75 (m, 2 H), 8.28 (d, 1 H), 7.68 (s, 1 H), 7.03 (d, 1 H), 6.81 (1, 1 H), 6.72 (s, 1 H), 6.51 (s, 1 H), 4.43 (dd, 1 H), 3.82 (td, 1 H), 3.04-3.23 (m, 2 H), 2.85 (dd, 1 H), 1.29-1.35 (m, 6 H) | 428.2 [M + H]$^+$ | 100% |
| 2177 | ($CD_3OD$) δ 9.29 (d, 1 H), 8.68-8.75 (m, 2 H), 8.29 (d, 1 H), 7.68 (s, 1 H), 7.04 (d, 1 H), 6.82 (t, 1 H), 6.72 (s, 1 H), 6.51 (s, 1 H), 4.44 (dd, 1 H), 3.77-3.88 (m, 1 H), 3.04-3.25 (m, 2 H), 2.85 (dd, 1 H), 1.29-1.35 (m, 6 H) | 428.2 [M + H]$^+$ | 99.0% |
| 2178 | ($CD_3OD$) δ 9.27 (d, 1 H), 8.94 (d, 1 H), 8.32 (br d, 1 H), 8.10 (dd, 1 H), 7.69 (br s, 1 H), 6.95 (dd, 1 H), 6.73-6.86 (m, 2 H), 6.52 (s, 1 H), 4.47 (dd, 1 H), 3.72-3.89 (m, 1 H), 2.98-3.17 (m, 1 H), 2.86 (br d, 1 H) | 404.2 [M + H]$^+$ | 100% |

TABLE 2-continued

| Ex. # | $^1$H NMR (400 MHz unless otherwise noted) | LCMS: m/z | % ee |
|---|---|---|---|
| 2179 | ($CD_3OD$) δ 9.28 (d, 1 H), 8.95 (d, 1 H), 8.33 (br d, 1 H), 8.10 (dd, 1 H), 7.69 (br s, 1 H), 6.95 (dd, 1 H), 6.73-6.87 (m, 2 H), 6.53 (s, 1 H), 4.47 (br dd, 1 H), 3.69-3.91 (m, 1 H), 3.01-3.16 (m, 1 H), 2.78-2.93 (m, 1 H) | 404.2 $[M + H]^+$ | 94.6% |
| 2180 | ($CD_3OD$) δ 9.28 (d, 1 H), 8.95 (d, 1 H), 8.29 (d, 1 H), 8.11 (dd, 1 H), 7.68 (s, 1 H), 7.04 (d, 1 H), 6.82 (t, 1 H), 6.72 (s, 1 H), 6.52 (br s, 1 H), 4.46 (dd, 1 H), 3.83 (ddd, 1 H), 3.02-3.24 (m, 2 H), 2.86 (br dd, 1 H), 1.32 (dd, 6 H) | 428.2 $[M + H]^+$ | 100% |
| 2181 | ($CD_3OD$) δ 9.27 (s, 1 H), 8.94 (d, 1 H), 8.28 (d, 1 H), 8.10 (d, 1 H), 7.68 (s, 1 H), 7.04 (d, 1 H), 6.82 (t, 1 H), 6.72 (s, 1 H), 6.52 (br s, 1 H), 4.46 (dd, 1 H), 3.75-3.93 (m, 1 H), 3.00-3.23 (m, 2 H), 2.86 (br dd, 1 H), 1.28-1.34 (m, 6 H) | 428.2 $[M + H]^+$ | 97.8% |
| 2182 | ($CD_3OD$) δ 9.27 (s, 1 H), 8.94 (d, 1 H), 8.42 (d, 1 H), 8.10 (dd, 1 H), 7.69 (s, 1 H), 7.27 (d, 1 H), 6.82 (t, 1 H), 6.76 (s, 1 H), 6.53 (br s, 1 H), 4,47 (dd, 1 H), 3.81 (td, 1 H), 3.01-3.16 (m, 1 H), 2.86 (br dd, 1 H) | 420.1 $[M + H]^+$ | 100% |
| 2183 | ($CD_3OD$) δ 9.26 (s, 1 H), 8.94 (d, 1 H), 8.42 (d, 1 H), 8.09 (d, 1 H), 7.69 (s, 1 H), 7.27 (d, 1 H), 6.82 (t, 1 H), 6.75 (s, 1 H), 6.52 (s, 1 H), 4.47 (dd, 1 H), 3.70-3.89 (m, 1 H), 3.00-3.16 (m, 1 H), 2.85 (br dd, 1 H) | 420.1 $[M + H]^+$ | 96.9% |
| 2184 | ($CD_3OD$) δ 8.68 (s, 2 H), 8.29 (d, 1 H), 7.66 (s, 1 H), 7.26 (s, 1 H), 7.05 (d, 1 H), 6.82 (t, 1 H), 6.63 (s, 1 H), 5.18 (dd, 1 H), 3.47-3.60 (m, 1 H), 3.19 (dt, 1 H), 2.86-2.99 (m, 1 H), 2.70-2.81 (m, 1 H), 1.34 (dd, 6 H) | 428.2 $[M + H]^+$ | 100% |
| 2185 | ($CD_3OD$) δ 8.66 (s, 2 H), 8.27 (d, 1 H), 7.67 (s, 1 H), 7.25 (s, 1 H), 7.03 (d, 1 H), 6.80 (t, 1 H), 6.61 (s, 1 H), 5.17 (dd, 1 H), 3.46-3.59 (m, 1 H), 3.17 (dt, 1 H), 2.85-2.98 (m, 1 H), 2.69-2.79 (m, 1 H), 1.32 (dd, 6 H) | 428.2 $[M + H]^+$ | 100% |
| 2186 | ($CD_3OD$) δ 8.29 (d, 1 H), 7.67 (s, 1 H), 6.74-6.85 (m, 2 H), 6.69 (s, 1 H), 6.31 (s, 1 H), 4.22 (dd, 1 H), 3.64-3.78 (m, 1 H), 2.97-3.10 (m, 1 H), 2.79 (dd, 1 H), 2.45 (s, 3 H), 2.04-2.15 (m, 1 H), 1.00-1.07 (m, 2 H), 0.75-0.83 (m, 2 H) | 362.2 $[M + H]^+$ | 99.7% |
| 2187 | ($CD_3OD$) δ 8.29 (d, 1 H), 7.67 (s, 1 H), 6.75-6.85 (m, 2 H), 6.69 (s, 1 H), 6.31 (s, 1 H), 4.22 (dd, 1 H), 3.71 (ddd, 1 H), 2.95-3.12 (m, 1 H), 2.79 (dd, 1 H), 2.45 (s, 3 H), 1.99-2.21 (m, 1 H), 0.99-1.08 (m, 2 H), 0.73-0.82 (m, 2 H) | 362.2 $[M + H]^+$ | 91.9% |
| 2188 | ($CD_3OD$) δ 8.31 (d, 1 H), 7.67 (s, 1 H), 6.99 (d, 1 H), 6.79 (t, 1 H), 6.52 (s, 1 H), 6.24 (s, 1 H), 4.18 (dd, 1 H), 3.64-3.76 (m, 1 H), 2.96-3.08 (m, 1 H), 2.79 (dd, 1 H), 2.44 (s, 3 H), 1.50 (s, 3 H), 1.23-1.31 (m, 2 H), 0.91-0.97 (m, 2 H) | 376.2 $[M + H]^+$ | 99.8% |
| 2189 | ($CD_3OD$) δ 8.31 (d, 1 H), 7.67 (s, 1 H), 6.99 (d, 1 H), 6.79 (t, 1 H), 6.52 (s, 1 H), 6.24 (s, 1 H), 4.18 (dd, 1 H), 3.62-3.76 (m, 1 H), 2.94-3.09 (m, 1 H), 2.79 (dd, 1 H), 2.44 (s, 3 H), 1.50 (s, 3 H), 1.24-1.31 (m, 2 H), 0.90-0.99 (m, 2 H) | 376.2 $[M + H]^+$ | 99.8% |
| 2190 | ($CD_3OD$) δ 8.32 (d, 1 H), 7.51-7.58 (m, 1 H), 7.46 (d, 1 H), 7.02-7.11 (m, 1 H), 6.70-6.78 (m, 1 H), 6.45 (s, 1 H), 6.25 (s, 1 H), 4.18 (dd, 1 H), 3.64 (ddd, 1 H), 2.85-3.00 (m, 1 H), 2.70 (dd, 1 H), 1.92-2.06 (m, 3 H) | 372.1 $[M + H]^+$ | 100% |
| 2191 | ($CD_3OD$) δ 8.32 (d, 1 H), 7.56 (s, 1 H), 7.47 (d, 1 H), 6.99-7.13 (m, 1 H), 6.74 (t, 1 H), 6.45 (s, 1 H), 6.25 (s, 1 H), 4.18 (dd, 1 H), 3.64 (ddd, 1 H), 2.87-3.00 (m, 1 H), 2.70 (dd, 1 H), 1.99 (t, 3 H) | 372.1 $[M + H]^+$ | 99.9% |
| 2192 | ($CD_3OD$) δ 8.31 (d, 1 H), 7.69 (s, 1 H), 7.00 (d, 1 H), 6.80 (t, 1 H), 6.59 (s, 1 H), 6.38 (s, 1 H), 4.31 (dd, 1 H), 3.73-3.84 (m, 1 H), 3.00-3.15 (m, 1 H), 2.84 (dd, 1 H), 2.45 (s, 3 H), 2.12 (1, 3 H) | 386.2 $[M + H]^+$ | 100% |
| 2193 | ($CD_3OD$) δ 8.31 (d, 1 H), 7.69 (s, 1 H), 7.00 (d, 1 H), 6.80 (t, 1 H), 6.59 (s, 1 H), 6.38 (br s, 1 H), 4.31 (dd, 1 H), 3.78 (ddd, 1 H), 2.95-3.13 (m, 1 H), 2.83 (br dd, 1 H), 2.45 (s, 3 H), 2.12 (t, 3 H) | 386.2 $[M + H]^+$ | 100% |
| 2194 | ($CD_3OD$) δ 8.70 (d, 1 H), 7.70 (s, 1 H), 7.64 (d, 1 H), 6.96-7.03 (m, 1 H), 6.71-6.80 (m, 1 H), 6.41 (s, 1 H), 4.35 (dd, 1 H), 3.71-3.85 (m, 1 H), 3.02-3.13 (m, 1 H), 2.85 (dd, 1 H), 2.03-2.19 (m, 3 H) | 440.2 $[M + H]^+$ | 99.9% |
| 2195 | ($CD_3OD$) δ 8.69 (d, 1 H), 7.69 (s, 1 H), 7.63 (d, 1 H), 6.99 (t, 1 H), 6.76 (s, 1 H), 6.40 (br s, 1 H), 4.34 (dd, 1 H), 3.70-3.84 (m, 1 H), 3.01-3.14 (m, 1 H), 2.85 (br dd, 1 H), 2.11 (t, 3 H) | 440.2 $[M + H]^+$ | 99.4% |
| 2196 | ($CD_3OD$) δ 8.35 (d, 1 H), 7.69 (s, 1 H), 6.97 (dd, 1 H), 6.80-6.87 (m, 1 H), 6.69-6.74 (m, 1 H), 6.38 (s, 1 H), 4.27-4.38 (m, 1 H), 3.71-3.85 (m, 1 H), 3.01-3.12 (m, 1 H), 2.84 (dd, 1 H), 2.12 (t, 3 H) | 390.2 $[M + H]^+$ | 99.4% |
| 2197 | ($CD_3OD$) δ 8.35 (d, 1 H), 7.69 (s, 1 H), 6.97 (dd, 1 H), 6.84 (td, 1 H), 6.72 (s, 1 H), 6.38 (s, 1 H), 4.27-4.39 (m, 1 H), 3.78 (ddd, 1 H), 3.01-3.14 (m, 1 H), 2.84 (dd, 1 H), 2.12 (t, 3 H) | 390.2 $[M + H]^+$ | 99.8% |
| 2198 | ($CD_3OD$) δ 9.29 (dd, 1 H), 8.25-8.52 (m, 2 H), 7.89 (dd, 1 H), 7.70 (s, 1 H), 7.29 (d, 1 H), 6.73-6.95 (m, 2 H), 6.57 (br s, 1 H), 4.50 (dd, 1 H), 3.74-3.95 (m, 1 H), 3.12 (br d, 1 H), 2.88 (br dd, 1 H) | 420.1 $[M + H]^+$ | 100% |

TABLE 2-continued

| Ex. # | $^1$H NMR (400 MHz unless otherwise noted) | LCMS: m/z | % ee |
|---|---|---|---|
| 2199 | ($CD_3OD$) δ 9.19-9.41 (m, 1 H), 8.25-8.55 (m, 2 H), 7.89 (dd, 1 H), 7.71 (s, 1 H), 7.29 (d, 1 H), 6.73-6.91 (m, 2 H), 6.57 (s, 1 H), 4.50 (dd, 1 H), 3.68-4.01 (m, 1 H), 3.03-3.23 (m, 1 H), 2.87 (dd, 1 H) | 420.1 $[M + H]^+$ | 98.6% |
| 2200 | ($CD_3OD$) δ 8.65 (s, 2 H), 8.04 (d, 1 H), 7.63 (s, 1 H), 7.21 (s, 1 H), 6.75 (t, 1 H), 6.48-6.63 (m, 2 H), 5.15 (dd, 1 H), 3.93 (s, 3 H), 3.41-3.57 (m, 1 H), 2.84-2.95 (m, 1 H), 2.66-2.80 (m, 1 H) | 416.2 $[M + H]^+$ | 100% |
| 2201 | ($CD_3OD$) δ 8.65 (s, 2 H), 8.04 (d, 1 H), 7.64 (s, 1 H), 7.21 (s, 1 H), 6.75 (t, 1 H), 6.45-6.61 (m, 2 H), 5.15 (dd, 1 H), 3.93 (s, 3 H), 3.41-3.57 (m, 1 H), 2.82-2.97 (m, 1 H), 2.69-2.78 (m, 1 H) | 416.2 $[M + H]^+$ | 98.9% |
| 2202 | ($CD_3OD$) δ 8.59 (d, 1 H), 7.69 (s, 1 H), 7.44 (br d, 1 H), 6.83-7.14 (m, 2 H), 6.76 (s, 1 H), 6.40 (s, 1 H), 4.33 (dd, 1 H), 3.77 (ddd, 1 H), 3.00-3.14 (m, 1 H), 2.84 (dd, 1 H), 2.12 (t, 3 H) | 422.2 $[M + H]^+$ | 96.6% |
| 2203 | ($CD_3OD$) δ 8.59 (d, 1 H), 7.69 (s, 1 H), 7.44 (br d, 1 H), 6.82-7.15 (m, 2 H), 6.76 (s, 1 H), 6.40 (s, 1 H), 4.33 (dd, 1 H), 3.77 (ddd, 1 H), 2.99-3.13 (m, 1 H), 2.84 (br dd, 1 H), 2.12 (t, 3 H) | 422.2 $[M + H]^+$ | 99.9% |
| 2204 | ($CD_3OD$) δ 8.28 (d, 1 H), 7.69 (s, 1 H), 6.67-6.87 (m, 3 H), 6.39 (br s, 1 H), 4.32 (dd, 1 H), 3.79 (ddd, 1 H), 3.00-3.13 (m, 1 H), 2.84 (br dd, 1 H), 2.02-2.18 (m, 4 H), 0.97-1.08 (m, 2 H), 0.71-0.82 (m, 2 H) | 412.2 $[M + H]^+$ | 99.7% |
| 2205 | ($CD_3OD$) δ 8.28 (br d, 1 H), 7.69 (br s, 1 H), 6.73-6.84 (m, 3 H), 6.39 (br s, 1 H), 4.32 (dd, 1 H), 3.72-3.88 (m, 1 H), 3.00-3.15 (m, 1 H), 2.77-2.92 (m, 1 H), 2.06-2.17 (m, 4 H), 1.00-1.08 (m, 2 H), 0.75-0.81 (m, 2 H) | 412.2 $[M + H]^+$ | 99.9% |
| 2206 | ($CD_3OD$) δ 8.54 (dd, 1 H), 8.22-8.42 (m, 2 H), 7.69 (s, 1 H), 7.45 (dd, 1 H), 6.99 (d, 1 H), 6.78 (t, 1 H), 6.59 (s, 1 H), 6.46 (br s, 1 H), 4.39 (dd, 1 H), 3.71-3.92 (m, 1 H), 3.05-3.19 (m, 1 H), 2.88 (s, 4 H), 2.44 (s, 3 H) | 413.2 $[M + H]^+$ | 99.6% |
| 2207 | ($CD_3OD$) δ 8.47-8.62 (m, 1 H), 8.32 (t, 2 H), 7.76 (s, 1 H), 7.45 (dd, 1 H), 6.99 (d, 1 H), 6.78 (t, 1 H), 6.60 (s, 1 H), 6.47 (s, 1 H), 4.40 (dd, 1 H), 3.73-3.90 (m, 1 H), 3.02-3.20 (m, 1 H), 2.81-2.93 (m, 4 H), 2.44 (s, 3 H) | 413.2 $[M + H]^+$ | 99.1% |
| 2208 | ($CD_3OD$) δ 8.71 (br d, 1 H), 8.55 (d, 1 H), 8.33 (d, 1 H), 7.57-7.78 (m, 2 H), 7.45 (dd, 1 H), 6.99 (t, 1 H), 6.78 (s, 1 H), 6.49 (br s, 1 H), 4.43 (dd, 1 H), 3.74-3.90 (m, 1 H), 3.05-3.19 (m, 1 H), 2.80-2.94 (m, 4 H) | 467.2 $[M + H]^+$ | 100% |
| 2209 | ($CD_3OD$) δ 8.71 (br d, 1 H), 8.55 (dd, 1 H), 8.33 (dd, 1 H), 7.56-7.80 (m, 2 H), 7.46 (dd, 1 H), 6.99 (br t, 1 H), 6.78 (s, 1 H), 6.49 (br s, 1 H), 4.43 (dd, 1 H), 3.82 (br d, 1 H), 3.02-3.20 (m, 1 H), 2.89 (s, 4 H) | 467.2 $[M + H]^+$ | 99.5% |
| 2210 | ($CD_3OD$) δ 8.13-8.89 (m, 3 H), 7.71 (s, 1 H), 7.37-7.54 (m, 2 H), 6.72-7.18 (m, 3 H), 6.48 (s, 1 H), 4.41 (dd, 1 H), 3.67-3.94 (m, 1 H), 3.05-3.19 (m, 1 H), 2.74-3.01 (m, 4 H) | 449.2 $[M + H]^+$ | 99.9% |
| 2211 | ($CD_3OD$) δ 8.48-8.70 (m, 2 H), 8.33 (dd, 1 H), 7.70 (s, 1 H), 7.36-7.60 (m, 2 H), 6.73-7.17 (m, 3 H), 6.48 (s, 1 H), 4.41 (dd, 1 H), 3.81 (ddd, 1 H), 3.03-3.18 (m, 1 H), 2.77-2.97 (m, 4 H) | 449.2 $[M + H]^+$ | 99.6% |
| 2212 | ($CD_3OD$) δ 8.54 (dd, 1 H), 8.22-8.42 (m, 2 H), 7.69 (s, 1 H), 7.45 (dd, 1 H), 6.99 (d, 1 H), 6.78 (t, 1 H), 6.59 (s, 1 H), 6.46 (br s, 1 H), 4.39 (dd, 1 H), 3.71-3.92 (m, 1 H), 3.05-3.19 (m, 1 H), 2.88 (s, 4 H), 2.44 (s, 3 H) | 413.2 $[M + H]^+$ | 99.6% |
| 2213 | ($CD_3OD$) δ 8.41 (dd, 1 H), 8.10-8.30 (m, 2 H), 7.58 (s, 1 H), 7.32 (dd, 1 H), 6.53-6.90 (m, 3 H), 6.34 (s, 1 H), 4.28 (dd, 1 H), 3.69 (ddd, 1 H), 2.90-3.07 (m, 1 H), 2.65-2.87 (m, 4 H) | 417.2 $[M + H]^+$ | 98.9% |
| 2214 | ($CD_3OD$) δ 8.25-8.34 (m, 1 H), 7.69 (br d, 1 H), 6.92-7.01 (m, 2 H), 6.82-6.91 (m, 1 H), 6.77 (dt, 1 H), 6.34-6.72 (m, 1 H), 4.44 (dd, 1 H), 4.10 (s, 3 H), 3.62-3.77 (m, 0.6 H), 3.10-3.28 (m, 1 H), 2.92-3.05 (m, 0.4 H), 2.68-2.87 (m, 1 H), 2.34-2.48 (m, 3 H) | 413.1 $[M + H]^+$ | 100% |
| 2215 | ($CD_3OD$) δ 8.23-8.38 (m, 1 H), 7.70 (br s, 1 H), 6.92-7.02 (m, 2 H), 6.82-6.91 (m, 1 H), 6.77 (dt, 1 H), 6.35-6.72 (m, 1 H), 4.44 (br dd, 1 H), 4.10 (s, 3 H), 3.58-3.77 (m, 0.6 H), 3.11-3.30 (m, 1 H), 2.93-3.03 (m, 0.4 H), 2.67-2.87 (m, 1 H), 2.35-2.49 (m, 3 H) | 413.1 $[M + H]^+$ | 100% |
| 2216 | ($CD_3OD$) δ 8.46 (br s, 1 H), 7.70 (s, 2 H), 7.32 (d, 1 H), 6.59-6.92 (m, 3 H), 4.42-4.80 (m, 1 H), 3.75 (br s, 1 H), 2.96-3.22 (m, 1 H), 2.84 (br d, 1 H), 1.66 (br s, 6 H) | 427.1 $[M + H]^+$ | 100% |
| 2217 | ($CD_3OD$) δ 8.46 (br s, 1 H), 7.59-8.02 (m, 2 H), 7.31 (br s, 1 H), 6.61-6.93 (m, 3 H), 4.35-4.65 (m, 1 H), 3.75 (br s, 1 H), 3.14 (br s, 1 H), 2.82 (br s, 1 H), 1.64 (br s, 6 H) | 427.1 [M + H] | 99.4% |
| 2218 | ($CD_3OD$) δ 8.44-8.54 (m, 1 H), 7.70 (s, 1 H), 7.48 (s, 0.3 H), 7.16-7.25 (m, 1 H), 6.87-6.98 (m, 1.7 H), 6.66-6.81 (m, 1 H), 4.91-5.05 (m, 1 H), 3.75 (ddd, 0.6 H), 3.36-3.45 (m, 0.4 H), 2.81-3.20 (m, 2 H), 2.62-2.69 (m, 3 H) | 434.1 $[M + H]^+$ | 100% |
| 2219 | ($CD_3OD$) δ 8.28-8.42 (m, 1 H), 7.58 (s, 1 H), 7.36 (s, 0.3 H), 6.98-7.14 (m, 1 H), 6.72-6.88 (m, 1.7 H), 6.58-6.68 (m, 1 H), 4.87 (br dd, 1 H), 3.63 (ddd, 0.6 H), 3.27 (td, 0.4 H), 2.67-3.09 (m, 2 H), 2.48-2.57 (m, 3 H) | 434.1 $[M + H]^+$ | 99.8% |
| 2220 | ($CD_3OD$) δ 7.73 (d, 1 H), 7.66 (s, 1 H), 7.32-7.50 (m, 0.7 H), 7.23-7.30 (m, 1 H), 7.16-7.22 (m, 1.3 H), 6.78-7.12 (m, 1 H), | 408.1 $[M + H]^+$ | 99.5% |

TABLE 2-continued

| Ex. # | $^1$H NMR (400 MHz unless otherwise noted) | LCMS: m/z | % ee |
|---|---|---|---|
| | 6.66 (s, 1 H), 6.37 (br s, 1 H), 4.33 (dd, 1 H), 3.70-3.89 (m, 1 H), 2.99-3.10 (m, 1 H), 2.76-2.88 (m, 1 H) | | |
| 2221 | ($CD_3OD$) δ 7.72 (d, 1 H), 7.66 (s, 1 H), 7.31-7.50 (m, 0.8 H), 7.23-7.30 (m, 1 H), 7.18 (t, 1.2 H), 6.81-7.12 (m, 1 H), 6.66 (s, 1 H), 6.38 (s, 1 H), 4.33 (dd, 1 H), 3.79 (ddd, 1 H), 2.97-3.11 (m, 1 H), 2.82 (dd, 1 H) | 408.2 $[M + H]^+$ | 98.7% |
| 2222 | ($CD_3OD$) δ 8.27-8.39 (m, 1 H), 7.65 (s, 1 H), 6.88-7.02 (m, 1.8 H), 6.81 (td, 1 H), 6.53-6.69 (m, 1.2 H), 4.85 (br s, 0.3 H), 4.36 (dd, 0.7 H), 3.70 (ddd, 0.8 H), 3.36-3.41 (m, 0.2 H), 3.10 (ddd, 0.8 H), 2.69-2.95 (m, 2.2 H), 2.01-2.11 (m, 1 H), 1.75-1.88 (m, 1 H) | 362.1 $[M + H]^+$ | 97.2% |
| 2223 | ($CD_3OD$) δ 8.23-8.44 (m, 1 H), 7.67 (d, 1 H), 6.71-7.01 (m, 2.5 H), 6.33-6.67 (m, 1.5 H), 4.76 (dd, 0.5 H), 4.33 (dd, 0.5 H), 3.70 (ddd, 0.5 H), 3.39-3.52 (m, 0.5 H), 2.95-3.22 (m, 1.5 H), 2.66-2.88 (m, 1.5 H), 2.05-2.19 (m, 1 H), 1.76-1.93 (m, 1 H) | 362.1 $[M + H]^+$ | 90.7% |
| 2224 | ($CD_3OD$) δ 8.34 (br s, 1 H), 7.95-8.23 (m, 2 H), 7.34-7.74 (m, 2 H), 6.49-6.80 (m, 4 H), 4.54 (br s, 1 H), 3.41-3.62 (m, 1 H), 2.78-2.94 (m, 1 H), 2.67 (br dd, 1 H), 1.86-2.04 (m, 1 H), 0.89 (br d, 2 H), 0.63 (br d, 2 H) | 358.2 $[M + H]^+$ | 100% |
| 2225 | ($CD_3OD$) δ 8.33 (br s, 1 H), 7.96-8.22 (m, 2 H), 7.35-7.76 (m, 2 H), 6.50-6.80 (m, 4 H), 4.55 (br s, 1 H), 3.42-3.61 (m, 1 H), 2.81-2.96 (m, 1 H), 2.56-2.79 (m, 1 H), 1.82-2.03 (m, 1 H), 0.88 (br d, 2 H), 0.63 (br d, 2 H) | 358.2 $[M + H]^+$ | 98.3% |
| 2226 | ($CD_3OD$) δ 8.15 (d, 1 H), 7.55 (s, 1 H), 6.61-6.72 (m, 2 H), 6.55 (s, 1 H), 6.13 (s, 1 H), 4.06 (dd, 1 H), 3.59 (ddd, 1 H), 2.84-2.97 (m, 1 H), 2.68 (dd, 1 H), 1.91-2.02 (m, 1 H), 1.38 (s, 3 H), 1.12-1.18 (m, 2 H), 0.87-0.95 (m, 2 H), 0.78-0.85 (m, 2 H), 0.61-0.70 (m, 2 H) | 402.2 $[M + H]^+$ | 99.7% |
| 2227 | ($CD_3OD$) δ 8.16 (d, 1 H), 7.55 (s, 1 H), 6.62-6.73 (m, 2 H), 6.56 (s, 1 H), 6.13 (br s, 1 H), 4.07 (dd, 1 H), 3.59 (ddd, 1 H), 2.84-2.96 (m, 1 H), 2.68 (br dd, 1 H), 1.92-2.03 (m, 1 H), 1.38 (s, 3 H), 1.12-1.19 (m, 2 H), 0.89-0.95 (m, 2 H), 0.80-0.85 (m, 2 H), 0.62-0.70 (m, 2 H) | 402.2 $[M + H]^+$ | 99.6% |
| 2228 | ($CD_3OD$) δ 8.18 (d, 1 H), 7.54 (s, 1 H), 6.94 (d, 1 H), 6.72 (t, 1 H), 6.47 (s, 1 H), 6.12 (br s, 1 H), 4.06 (dd, 1 H), 3.59 (ddd, 1 H), 3.02-3.13 (m, 1 H), 2.83-2.97 (m, 1 H), 2.68 (dd, 1 H), 1.38 (s, 3 H), 1.22 (dd, 6 H), 1.12-1.17 (m, 2 H), 0.78-0.86 (m, 2 H) | 404.3 $[M + H]^+$ | 99.8% |
| 2229 | ($CD_3OD$) δ 8.18 (d, 1 H), 7.54 (s, 1 H), 6.94 (d, 1 H), 6.72 (t, 1 H), 6.47 (s, 1 H), 6.12 (s, 1 H), 4.06 (dd, 1 H), 3.53-3.67 (m, 1 H), 3.01-3.14 (m, 1 H), 2.83-2.96 (m, 1 H), 2.68 (dd, 1 H), 1.38 (s, 3 H), 1.22 (dd, 6 H), 1.12-1.18 (m, 2 H), 0.77-0.86 (m, 2 H) | 404.3 $[M + H]^+$ | 99.3% |
| 2230 | ($CD_3OD$) δ 8.31 (d, 1 H), 7.62-7.73 (m, 1 H), 7.07 (d, 1 H), 6.81-6.90 (m, 1 H), 6.66 (s, 1 H), 6.38 (s, 1 H), 4.32 (dd, 1 H), 3.79 (ddd, 1 H), 3.20 (dt, 1 H), 3.01-3.12 (m, 1 H), 2.84 (dd, 1 H), 2.12 (t, 3 H), 1.32-1.37 (m, 6 H) | 414.2 $[M + H]^+$ | 100% |
| 2231 | ($CD_3OD$) δ 8.31 (d, 1 H), 7.68 (s, 1 H), 7.07 (d, 1 H), 6.85 (t, 1 H), 6.66 (s, 1 H), 6.32-6.44 (m, 1 H), 4.32 (dd, 1 H), 3.79 (ddd, 1 H), 3.20 (dt, 1 H), 3.01-3.12 (m, 1 H), 2.84 (br dd, 1 H), 2.12 (t, 3 H), 1.35 (dd, 6 H) | 414.2 $[M + H]^+$ | 99.4% |
| 2232 | ($CD_3OD$) δ 8.33 (d, 1 H), 7.58 (s, 1 H), 7.18 (d, 1 H), 6.74 (t, 1 H), 6.59 (s, 1 H), 6.27 (s, 1 H), 4.21 (dd, 1 H), 3.65 (ddd, 1 H), 2.89-3.01 (m, 1 H), 2.72 (dd, 1 H), 2.00 (t, 3 H) | 406.1 $[M + H]^+$ | 100% |
| 2233 | ($CD_3OD$) δ 8.33 (d, 1 H), 7.57 (s, 1 H), 7.19 (d, 1 H), 6.74 (t, 1 H), 6.59 (s, 1 H), 6.26 (br s, 1 H), 4.21 (dd, 1 H), 3.65 (ddd, 1 H), 2.89-3.00 (m, 1 H), 2.72 (br dd, 1 H), 2.00 (t, 3 H) | 406.1 $[M + H]^+$ | 99.9% |
| 2234 | ($CD_3OD$) δ 8.54 (dd, 1 H), 8.24-8.43 (m, 2 H), 7.72 (s, 1 H), 7.45 (dd, 1 H), 7.06 (d, 1 H), 6.84 (t, 1 H), 6.68 (s, 1 H), 6.46 (s, 1 H), 4.40 (dd, 1 H), 3.74-3.92 (m, 1 H), 3.03-3.28 (m, 2 H), 2.78-2.95 (m, 4 H), 1.34 (dd, 6 H) | 441.2 $[M + H]^+$ | 100% |
| 2235 | ($CD_3OD$) δ 8.54 (dd, 1 H), 8.24-8.41 (m, 2 H), 7.70 (s, 1 H), 7.45 (dd, 1 H), 7.05 (d, 1 H), 6.83 (t, 1 H), 6.68 (s, 1 H), 6.46 (s, 1 H), 4.40 (dd, 1 H), 3.71-3.91 (m, 1 H), 3.01-3.28 (m, 2 H), 2.88 (s, 4 H), 1.33 (dd, 6 H) | 441.2 $[M + H]^+$ | 99.8% |
| 2236 | ($CD_3OD$) δ 8.26-8.61 (m, 3 H), 7.70 (s, 1 H), 7.45 (dd, 1 H), 7.29 (d, 1 H), 6.66-6.90 (m, 2 H), 6.46 (s, 1 H), 4.41 (dd, 1 H), 3.81 (br dd, 1 H), 3.02-3.20 (m, 1 H), 2.76-3.00 (m, 4 H) | 433.1 $[M + H]^+$ | 100% |
| 2237 | ($CD_3OD$) δ 8.11-8.50 (m, 3 H), 7.58 (s, 1 H), 7.11-7.41 (m, 2 H), 6.54-6.79 (m, 2 H), 6.34 (s, 1 H), 4.29 (dd, 1 H), 3.54-3.81 (m, 1 H), 2.99 (br s, 1 H), 2.61-2.85 (m, 4 H) | 433.2 $[M + H]^+$ | 99.6% |
| 2238 | ($CD_3OD$) δ 8.42 (d, 1 H), 7.60 (s, 1 H), 7.51 (d, 1 H), 7.06-7.23 (m, 5 H), 6.74-6.84 (m, 2 H), 6.35 (s, 1 H), 6.00 (s, 1 H), 3.84-3.92 (m, 1 H), 3.53-3.68 (m, 1 H), 2.87-2.98 (m, 1 H), 2.67 (br dd, 1 H) | 316.1 $[M + H]^+$ | 100% |
| 2239 | ($CD_3OD$) δ 8.42 (d, 1 H), 7.85 (s, 1 H), 7.52 (d, 1 H), 7.06-7.25 (m, 5 H), 6.74-6.87 (m, 2 H), 6.37 (s, 1 H), 6.04 (s, 1 H), 3.78-3.97 (m, 1 H), 3.50-3.69 (m, 1 H), 2.94 (ddd, 1 H), 2.69 (br dd, 1 H) | 316.1 $[M + H]^+$ | 99.4% |

TABLE 2-continued

| Ex. # | $^1$H NMR (400 MHz unless otherwise noted) | LCMS: m/z | % ee |
|---|---|---|---|
| 2240 | ($CD_3OD$) δ 9.33-9.50 (m, 1 H), 8.70-8.89 (m, 2 H), 7.93-8.51 (m, 2 H), 7.64-7.88 (m, 1 H), 6.59-7.13 (m, 4 H), 4.64 (br s, 1 H), 3.46-3.93 (m, 1 H), 2.97-3.22 (m, 1 H), 2.89 (br d, 1 H), 2.48 (s, 3 H) | 427.2 $[M + H]^+$ | 100% |
| 2241 | ($CD_3OD$) δ 9.42 (s, 1 H), 8.72-8.86 (m, 2 H), 7.92-8.49 (m, 2 H), 7.70 (br s, 1 H), 6.64-7.07 (m, 4 H), 4.79 (br s, 0.5 H), 4.56-4.63 (m, 0.5 H), 3.43-3.93 (m, 1 H), 2.96-3.29 (m, 1 H), 2.77-2.93 (m, 1 H), 2.48 (s, 3 H) | 427.2 $[M + H]^+$ | 100% |
| 2242 | ($CD_3OD$) δ 9.42 (s, 1 H), 8.73-8.82 (m, 2 H), 8.51-8.72 (m, 1 H), 7.92-8.33 (m, 1 H), 7.71 (br s, 1 H), 7.46 (br d, 1 H), 6.69-7.20 (m, 4 H), 4.60-4.83 (m, 1 H), 3.42-3.93 (m, 1 H), 2.99-3.25 (m, 1 H), 2.89 (br s, 1 H) | 463.1 $[M + H]^+$ | 100% |
| 2243 | ($CD_3OD$) δ 9.42 (s, 1 H), 8.72-8.85 (m, 2 H), 8.54-8.71 (m, 1 H), 7.91-8.30 (m, 1 H), 7.71 (br s, 1 H), 7.46 (br d, 1 H), 6.72-7.19 (m, 4 H), 4.65-4.80 (m, 1 H), 3.44-3.92 (m, 1 H), 3.04 (br s, 1 H), 2.86 (br s, 1 H) | 463.2 $[M + H]^+$ | 96.3% |
| 2244 | ($CD_3OD$) δ 9.42 (s, 1 H), 8.78 (s, 3 H), 7.91-8.27 (m, 1 H), 7.59-7.79 (m, 2 H), 6.71-7.18 (m, 3 H), 4.65-4.80 (m, 1 H), 3.42-3.92 (m, 1 H), 2.97-3.22 (m, 1 H), 2.88 (br s, 1 H) | 481.2 $[M + H]^+$ | 99.6% |
| 2245 | ($CD_3OD$) δ 9.42 (s, 1 H), 8.78 (s, 3 H), 7.93-8.30 (m, 1 H), 7.57-7.80 (m, 2 H), 6.72-7.17 (m, 3 H), 4.82 (br s, 1 H), 3.43-3.93 (m, 1 H), 2.98-3.28 (m, 1 H), 2.88 (br s, 1 H) | 481.2 $[M + H]^+$ | 95.9% |
| 2246 | ($CD_3OD$) δ 8.44 (s, 1 H), 8.08 (d, 1 H), 7.95 (s, 1 H), 7.79 (dd, 1 H), 7.15 (d, 1 H), 7.00 (s, 1 H), 6.78 (t, 1 H), 6.45-6.66 (m, 2 H), 4.70 (br dd, 1 H), 3.95 (s, 3 H), 3.55-3.67 (m, 1 H), 2.89-3.05 (m, 1 H), 2.65-2.84 (m, 1 H) | 415.2 $[M + H]^+$ | 100% |
| 2247 | ($CD_3OD$) δ 8.43 (s, 1 H), 8.08 (d, 1 H), 7.69-7.91 (m, 2 H), 7.14 (d, 1 H), 6.96 (s, 1 H), 6.77 (t, 1 H), 6.57 (t, 2 H), 4.70 (br dd, 1 H), 3.95 (s, 3 H), 3.52-3.69 (m, 1 H), 2.89-3.05 (m, 1 H), 2.65-2.83 (m, 1 H) | 415.2 $[M + H]^+$ | 96.9% |
| 2248 | ($CD_3OD$) δ 8.49 (d, 1 H), 7.68 (s, 1 H), 7.14-7.27 (m, 1 H), 6.91 (t, 1 H), 6.70 (s, 1 H), 6.31 (s, 1 H), 4.24 (dd, 1 H), 3.70 (ddd, 1 H), 2.99-3.11 (m, 1 H), 2.80 (dd, 1 H), 2.44 (s, 3 H) | 406.1 $[M + H]^+$ | 100% |
| 2249 | ($CD_3OD$) δ 8.49 (d, 1 H), 7,68 (s, 1 H), 7.21 (br d, 1 H), 6.91 (t, 1 H), 6.70 (s, 1 H), 6.31 (br s, 1 H), 4.24 (dd, 1 H), 3.64-3.78 (m, 1 H), 2.97-3.11 (m, 1 H), 2.80 (br dd, 1 H), 2.44 (s, 3 H) | 406.1 $[M + H]^+$ | 96.1% |
| 2250 | ($CD_3OD$) δ 8.37 (d, 1 H), 7.58 (s, 1 H), 7.09 (d, 1 H), 6.72-7.01 (m, 2 H), 6.62 (s, 1 H), 6.28 (s, 1 H), 4.23 (dd, 1 H), 3.66 (ddd, 1 H), 2.85-3.03 (m, 1 H), 2.73 (dd, 1 H) | 442.1 $[M + H]^+$ | 99.6% |
| 2251 | ($CD_3OD$) δ 8.37 (d, 1 H), 7.57 (s, 1 H), 7.09 (br d, 1 H), 6.73-7.00 (m, 2 H), 6.62 (s, 1 H), 6.28 (br s, 1 H), 4.23 (dd, 1 H), 3.60-3.73 (m, 1 H), 2.88-3.02 (m, 1 H), 2.73 (br dd, 1 H) | 442.1 $[M + H]^+$ | 98.9% |
| 2252 | ($CD_3OD$) δ 8.38 (d, 1 H), 7.61 (s, 1 H), 7.10 (d, 1 H), 6.80 (t, 1 H), 6.63 (s, 1 H), 6.30 (s, 1 H), 4.25 (dd, 1 H), 3.67 (ddd, 1 H), 2.91-3.03 (m, 1 H), 2.74 (dd, 1 H) | 460.1 $[M + H]^+$ | 99.6% |
| 2253 | ($CD_3OD$) δ 8.50 (d, 1 H), 7.71 (s, 1 H), 7.22 (d, 1 H), 6.93 (t, 1 H), 6.75 (s, 1 H), 6.42 (s, 1 H), 4.37 (dd, 1 H), 3.80 (td, 1 H), 3.03-3.14 (m, 1 H), 2.86 (dd, 1 H) | 460.1 $[M + H]^+$ | 96.9% |
| 2254 | ($CD_3OD$) δ 8.07-8.59 (m, 3 H), 7.65 (s, 1 H), 6.95-7.28 (m, 2 H), 6.77-6.95 (m, 2 H), 6.55-6.72 (m, 2 H), 5.06 (dd, 1 H), 3.38-3.57 (m, 1 H), 2.82-2.99 (m, 1 H), 2.70 (br dd, 1 H) | 384.2 $[M + H]^+$ | 99.5% |
| 2255 | ($CD_3OD$) δ 8.22-8.50 (m, 3 H), 7.65 (s, 1 H), 6.96-7.28 (m, 2 H), 6.76-6.96 (m, 2 H), 6.58-6.71 (m, 2 H), 5.06 (dd, 1 H), 3.46 (ddd, 1 H), 2.82-2.98 (m, 1 H), 2.70 (br dd, 1 H) | 384.2 $[M + H]^+$ | 98.7% |
| 2256 | ($CD_3OD$) δ 8.68 (s, 2 H), 8.33 (d, 1 H), 7.67 (s, 1 H), 6.96-7.32 (m, 2 H), 6.79-6.96 (m, 2 H), 6.68 (s, 1 H), 5.20 (dd, 1 H), 3.53 (td, 1 H), 2.64-3.05 (m, 2 H) | 452.1 $[M + H]^+$ | 99.2% |
| 2257 | ($CD_3OD$) δ 8.68 (s, 2 H), 8.33 (d, 1 H), 7.67 (s, 1 H), 6.98-7.30 (m, 2 H), 6.78-6.97 (m, 2 H), 6.68 (s, 1 H), 5.20 (dd, 1 H), 3.40-3.64 (m, 1 H), 2.51-3.02 (m, 2 H) | 452.1 $[M + H]^+$ | 98.2% |
| 2258 | ($CD_3OD$) δ 8.33 (d, 1 H), 7.56 (s, 1 H), 7.18 (d, 1 H), 6.73 (t, 1 H), 6.52 (s, 1 H), 6.12 (s, 1 H), 4.08 (dd, 1 H), 3.57 (ddd, 1 H), 2.84-2.97 (m, 1 H), 2.68 (dd, 1 H), 1.38 (s, 3 H), 1.11-1.18 (m, 2 H), 0.78-0.86 (m, 2 H) | 396.2 $[M + H]^+$ | 100% |
| 2259 | ($CD_3OD$) δ 8.33 (d, 1 H), 7.55 (s, 1 H), 7.18 (d, 1 H), 6.73 (t, 1 H), 6.52 (s, 1 H), 6.12 (s, 1 H), 4.08 (dd, 1 H), 3.57 (ddd, 1 H), 2.84-2.95 (m, 1 H), 2.68 (dd, 1 H), 1.38 (s, 3 H), 1.10-1.17 (m, 2 H), 0.79-0.85 (m, 2 H) | 396.2 $[M + H]^+$ | 99.4% |
| 2260 | ($CD_3OD$) δ 9.16 (d, 1 H), 8.69 (dd, 1 H), 8.40 (br d, 1 H), 8.31 (br d, 1 H), 7.70 (s, 1 H), 7.61 (dd, 1 H), 7.06 (br d, 1 H), 6.84 (t, 1 H), 6.69 (s, 1 H), 6.42-6.53 (m, 1 H), 4.41 (dd, 1 H), 3.76-3.90 (m, 1 H), 3.04-3.25 (m, 2 H), 2.87 (br dd, 1 H), 1.33 (t, 6 H) | 427.2 $[M + H]^+$ | 99.0% |
| 2261 | ($CD_3OD$) δ 9.16 (d, 1 H), 8.64-8.74 (m, 1 H), 8.40 (br d, 1 H), 8.31 (d, 1 H), 7.72 (s, 1 H), 7.61 (dd, 1 H), 7.06 (d, 1 H), 6.84 (t, 1 H), 6.69 (s, 1 H), 6.49 (s, 1 H), 4.42 (dd, 1 H), 3.74-3.91 (m, 1 H), 3.01-3.25 (m, 2 H), 2.87 (br dd, 1 H), 1.33 (t, 6 H) | 427.2 $[M + H]^+$ | 97.3% |

TABLE 2-continued

| Ex. # | $^1H$ NMR (400 MHz unless otherwise noted) | LCMS: m/z | % ee |
|---|---|---|---|
| 2262 | ($CD_3OD$) δ 9.15 (s, 1 H), 8.69 (br d, 1 H), 8.45 (br d, 1 H), 8.39 (br dd, 1 H), 7.71 (s, 1 H), 7.56-7.64 (m, 1 H), 7.29 (dd, 1 H), 6.79-6.88 (m, 1 H), 6.73 (s, 1 H), 6.49 (s, 1 H), 4.43 (dd, 1 H), 3.81 (ddd, 1 H), 3.05-3.18 (m, 1 H), 2.87 (dd, 1 H) | 419.1 $[M + H]^+$ | 100% |
| 2263 | ($CD_3OD$) δ 9.15 (d, 1 H), 8.69 (dd, 1 H), 8.45 (d, 1 H), 8.39 (dt, 1 H), 7.70 (s, 1 H), 7.61 (dd, 1 H), 7.30 (d, 1 H), 6.85 (t, 1 H), 6.73 (s, 1 H), 6.49 (s, 1 H), 4.43 (dd, 1 H), 3.74-3.86 (m, 1 H), 3.05-3.18 (m, 1 H), 2.87 (dd, 1 H) | 419.1 $[M + H]^+$ | 99.7% |
| 2264 | ($CD_3OD$) δ 8.48-8.57 (m, 1 H), 8.28 (s, 2 H), 7.73 (s, 1 H), 7.43-7.56 (m, 1 H), 7.00 (d, 1 H), 6.79 (t, 1 H), 6.62 (s, 1 H), 6.47 (S, 1 H), 4.40 (dd, 1 H), 3.66-3.95 (m, 1 H), 3.01-3.20 (m, 1 H), 2.79-2.95 (m, 1 H), 2.45 (s, 3 H) | 417.2 $[M + H]^+$ | 100% |
| 2265 | ($CD_3OD$) δ 8.45-8.61 (m, 1 H), 8.24-8.41 (m, 2 H), 7.75 (br s, 1 H), 7.44-7.56 (m, 1 H), 6.99 (d, 1 H), 6.79 (t, 1 H), 6.62 (s, 1 H), 6.47 (s, 1 H), 4.40 (dd, 1 H), 3.70-3.90 (m, 1 H), 3.04-3.22 (m, 1 H), 2.87 (br dd, 1 H), 2.44 (s, 3 H) | 417.2 $[M + H]^+$ | 99.3% |
| 2266 | ($CD_3OD$) δ 8.51 (br d, 1 H), 8.41 (d, 1 H), 7.82 (br d, 1 H), 7.67 (s, 1 H), 7.55 (d, 1 H), 7.42 (dd, 1 H), 7.15 (t, 1 H), 6.76-6.87 (m, 1 H), 6.62 (s, 1 H), 6.54 (s, 1 H), 4.44 (dd, 1 H), 3.77 (ddd, 1 H), 3.01-3.15 (m, 1 H), 2.82 (dd, 1 H), 2.68 (s, 3 H) | 399.2 $[M + H]^+$ | 99.7% |
| 2267 | ($CD_3OD$) δ 8.52 (br d, 1 H), 8.42 (br d, 1 H), 7.83 (br d, 1 H), 7.67 (s, 1 H), 7.56 (br d, 1 H), 7.43 (dd, 1 H), 7.16 (br t, 1 H), 6.78-6.88 (m, 1 H), 6.63 (s, 1 H), 6.54 (s, 1 H), 4.44 (dd, 1 H), 3.78 (ddd, 1 H), 3.02-3.15 (m, 1 H), 2.78-2.85 (m, 1 H), 2.68 (s, 3 H) | 399.2 $[M + H]^+$ | 99.0% |
| 2268 | ($CD_3OD$) δ 8.54 (d, 1 H), 8.29 (d, 1 H), 7.86 (d, 1 H), 7.67 (s, 1 H), 7.45 (dd, 1 H), 6.97 (d, 1 H), 6.76 (t, 1 H), 6.53-6.67 (m, 2 H), 4.45 (dd, 1 H), 3.79 (ddd, 1 H), 3.04-3.15 (m, 1 H), 2.83 (br dd, 1 H), 2.70 (s, 3 H), 2.43 (s, 3 H) | 413.2 $[M + H]^+$ | 99.9% |
| 2269 | ($CD_3OD$) δ 8.53 (d, 1 H), 8.29 (d, 1 H), 7.85 (d, 1 H), 7.67 (s, 1 H), 7.45 (dd, 1 H), 6.97 (d, 1 H), 6.76 (t, 1 H), 6.65 (s, 1 H), 6.55 (br s, 1 H), 4.45 (dd, 1 H), 3.74-3.84 (m, 1 H), 3.02-3.16 (m, 1 H), 2.83 (br dd, 1 H), 2.70 (s, 3 H), 2.43 (s, 3 H) | 413.2 $[M + H]^+$ | 98.8% |
| 2270 | ($CD_3OD$) δ 8.44-8.47 (m, 1 H), 8.41 (d, 2 H), 7.65 (s, 1 H), 7.13-7.22 (m, 2 H), 6.86 (t, 1 H), 6.61-6.70 (m, 2 H), 5.07 (dd, 1 H), 3.39-3.51 (m, 1 H), 2.85-2.96 (m, 1 H), 2.71 (dd, 1 H) | 402.2 $[M + H]^+$ | 99.6% |
| 2271 | ($CD_3OD$) δ 8.46 (d, 1 H), 8.41 (d, 2 H), 7.65 (s, 1 H), 7.15-7.21 (m, 2 H), 6.87 (t, 1 H), 6.64-6.69 (m, 2 H), 5.07 (dd, 1 H), 3.41-3.51 (m, 1 H), 2.85-2.97 (m, 1 H), 2.71 (dd, 1 H) | 402.1 $[M + H]^+$ | 98.9% |
| 2272 | ($CD_3OD$) δ 8.28-8.49 (m, 2 H), 7.77 (dd, 1 H), 7.65 (s, 1 H), 6.98-7.23 (m, 2 H), 6.73-6.98 (m, 3 H), 6.64 (s, 1 H), 4.73 (br dd, 1 H), 3.52-3.72 (m, 1 H), 2.88-3.04 (m, 1 H), 2.74 (br dd, 1 H) | 415.2 $[M + H]^+$ | 99.1% |
| 2273 | ($CD_3OD$) δ 8.22-8.53 (m, 2 H), 7.77 (dd, 1 H), 7.65 (s, 1 H), 7.00-7.25 (m, 2 H), 6.79-6.97 (m, 3 H), 6.64 (s, 1 H), 4.73 (br dd, 1 H), 3.61 (ddd, 1 H), 2.87-3.03 (m, 1 H), 2.74 (dd, 1 H) | 415.2 $[M + H]^+$ | 92.9% |
| 2274 | ($CD_3OD$) δ 8.49-8.57 (m, 1 H), 8.37 (d, 1 H), 7.68 (s, 1 H), 7.45-7.54 (m, 2 H), 7.12 (dd, 1 H), 6.72 (d, 1 H), 6.43-6.59 (m, 2 H), 4.40 (dd, 1 H), 3.78-3.94 (m, 1 H), 3.05-3.16 (m, 1 H), 2.87 (br dd, 1 H), 2.64 (s, 3 H) | 417.2 $[M + H]^+$ | 100% |
| 2275 | ($CD_3OD$) δ 8.52 (ddd, 1 H), 8.37 (d, 1 H), 7.68 (s, 1 H), 7.42-7.54 (m, 2 H), 7.12 (dd, 1 H), 6.72 (d, 1 H), 6.43-6.59 (m, 2 H), 4.40 (dd, 1 H), 3.87 (ddd, 1 H), 3.03-3.19 (m, 1 H), 2.86 (br dd, 1 H), 2.64 (s, 3 H) | 417.2 $[M + H]^+$ | 98.4% |
| 2276 | ($CD_3OD$) δ 8.68 (d, 1 H), 8.51-8.55 (m, 1 H), 7.85 (d, 1 H), 7.69 (s, 1 H), 7.60 (d, 1 H), 7.45 (dd, 1 H), 6.96 (t, 1 H), 6.84 (s, 1 H), 6.58 (s, 1 H), 4.49 (dd, 1 H), 3.80 (ddd, 1 H), 3.04-3.16 (m, 1 H), 2.84 (dd, 1 H), 2.70 (s, 3 H) | 467.2 $[M + H]^+$ | 100% |
| 2277 | ($CD_3OD$) δ 8.68 (d, 1 H), 8.53 (d, 1 H), 7.85 (d, 1 H), 7.68 (s, 1 H), 7.61 (d, 1 H), 7.45 (dd, 1 H), 6.96 (1, 1 H), 6.84 (s, 1 H), 6.58 (s, 1 H), 4.49 (dd, 1 H), 3.74-3.85 (m, 1 H), 3.05-3.16 (m, 1 H), 2.84 (br dd, 1 H), 2.70 (s, 3 H) | 467.2 $[M + H]^+$ | 98.7% |
| 2278 | ($CD_3OD$) δ 8.51-8.62 (m, 2 H), 7.86 (d, 1 H), 7.68 (s, 1 H), 7.39-7.49 (m, 2 H), 6.81-7.12 (m, 3 H), 6.58 (br s, 1 H), 4.47 (dd, 1 H), 3.78 (ddd, 1 H), 3.04-3.15 (m, 1 H), 2.84 (br dd, 1 H), 2.70 (s, 3 H) | 449.2 $[M + H]^+$ | 98.6% |
| 2279 | ($CD_3OD$) δ 8.50-8.63 (m, 2 H), 7.86 (d, 1 H), 7.68 (s, 1 H), 7.39-7.49 (m, 2 H), 6.79-7.15 (m, 3 H), 6.58 (s, 1 H), 4.47 (dd, 1 H), 3.78 (ddd, 1 H), 3.05-3.15 (m, 1 H), 2.84 (dd, 1 H), 2.70 (s, 3 H) | 449.2 $[M + H]^+$ | 96.9% |
| 2280 | ($CD_3OD$) δ 8.54 (dd, 1 H), 8.34 (d, 1 H), 7.86 (d, 1 H), 7.70 (s, 1 H), 7.46 (dd, 1 H), 6.95 (dd, 1 H), 6.76-6.88 (m, 2 H), 6.56 (s, 1 H), 4.48 (dd, 1 H), 3.75-3.85 (m, 1 H), 3.05-3.15 (m, 1 H), 2.84 (br dd, 1 H), 2.71 (s, 3 H) | 471.2 $[M + H]^+$ | 98.2% |
| 2281 | ($CD_3OD$) δ 8.53 (d, 1 H), 8.33 (d, 1 H), 7.86 (d, 1 H), 7.70 (s, 1 H), 7.45 (dd, 1 H), 6.95 (dd, 1 H), 6.76-6.85 (m, 2 H), 6.56 (s, 1 H), 4.47 (dd, 1 H), 3.75-3.85 (m, 1 H), 3.05-3.16 (m, 1 H), 2.84 (dd, 1 H), 2.70 (s, 3 H) | 417.2 $[M + H]^+$ | 99.6% |

TABLE 2-continued

| Ex. # | $^1$H NMR (400 MHz unless otherwise noted) | LCMS: m/z | % ee |
|---|---|---|---|
| 2282 | ($CD_3OD$) δ 8.53 (d, 1 H), 8.26 (d, 1 H), 7.85 (d, 1 H), 7.68 (s, 1 H), 7.44 (dd, 1 H), 6.71-6.84 (m, 3 H), 6.56 (s, 1 H), 4.46 (dd, 1 H), 3.73-3.87 (m, 1 H), 3.03-3.18 (m, 1 H), 2.83 (dd, 1 H), 2.70 (s, 3 H), 2.03-2.13 (m, 1 H), 0.96-1.05 (m, 2 H), 0.71-0.80 (m, 2 H) | 439.2 $[M + H]^+$ | 100% |
| 2283 | ($CD_3OD$) δ 8.54 (d, 1 H), 8.26 (d, 1 H), 7.85 (d, 1 H), 7.76 (s, 1 H), 7.45 (dd, 1 H), 6.72-6.85 (m, 3 H), 6.58 (s, 1 H), 4.46 (dd, 1 H), 3.80 (ddd, 1 H), 3.00-3.16 (m, 1 H), 2.84 (dd, 1 H), 2.70 (s, 3 H), 2.04-2.14 (m, 1 H), 0.97-1.06 (m, 2 H), 0.72-0.80 (m, 2 H) | 439.2 $[M + H]^+$ | 92.5% |
| 2284 | ($CD_3OD$) δ 8.53 (br d, 1 H), 8.23-8.31 (m, 1 H), 7.64-7.88 (m, 2 H), 7.36-7.49 (m, 1 H), 6.98-7.07 (m, 1 H), 6.72-6.84 (m, 2 H), 6.55 (s, 1 H), 4.45 (br dd, 1 H), 3.80 (td, 1 H), 3.04-3.22 (m, 2 H), 2.83 (br dd, 1 H), 2.63-2.72 (m, 3 H), 1.23-1.36 (m, 6 H) | 441.2 $[M + H]^+$ | 100% |
| 2285 | ($CD_3OD$) δ 8.53 (d, 1 H), 8.28 (d, 1 H), 7.84 (d, 1 H), 7.67 (s, 1 H), 7.44 (dd, 1 H), 7.02 (d, 1 H), 6.73-6.83 (m, 2 H), 6.55 (s, 1 H), 4.45 (dd, 1 H), 3.80 (ddd, 1 H), 3.04-3.22 (m, 2 H), 2.83 (dd, 1 H), 2.69 (s, 3 H), 1.31 (t, 6 H) | 441.2 $[M + H]^+$ | 98.4% |
| 2286 | $^1$H (METHANOL-$d_4$) δ 8.52 (d, 1 H), 8.42 (d, 1 H), 7.84 (br d, 1 H), 7.68 (s, 1 H), 7.43 (dd, 1 H), 7.26 (d, 1 H), 6.74-6.85 (m, 2 H), 6.55 (s, 1 H), 4.47 (dd, 1 H), 3.79 (ddd, 1 H), 3.04-3.14 (m, 1 H), 2.83 (dd, 1 H), 2.69 (s, 3 H) | 433.1 $[M + H]^+$ | 100% |
| 2287 | ($CD_3OD$) δ 8.51 (br d, 1 H), 8.40 (d, 1 H), 7.82 (br d, 1 H), 7.68 (s, 1 H), 7.42 (dd, 1 H), 7.24 (d, 1 H), 6.74-6.83 (m, 2 H), 6.55 (s, 1 H), 4.47 (br dd, 1 H), 3.73-3.84 (m, 1 H), 3.01-3.15 (m, 1 H), 2.63-2.73 (m, 1 H), 2.68 (s, 3 H) | 433.1 $[M + H]^+$ | 99.1% |
| 2288 | ($CD_3OD$) δ 8.54-8.60 (m, 1 H), 8.31-8.37 (m, 1 H), 7.86 (ddd, 1 H), 7.68-7.71 (m, 1 H), 7.63 (dt, 1 H), 6.96 (dd, 1 H), 6.80-6.86 (m, 1 H), 6.78-6.80 (m, 1 H), 6.54 (s, 1 H), 4.47 (dd, 1 H), 3.78-3.86 (m, 1 H), 3.06-3.16 (m, 1 H), 2.86 (br dd, 1 H) | 421.1 $[M + H]^+$ | 100% |
| 2289 | ($CD_3OD$) δ 8.57 (d, 1 H), 8.30-8.39 (m, 1 H), 7.80-7.92 (m, 1 H), 7.72 (s, 1 H), 7.64 (dt, 1 H), 6.96 (dd, 1 H), 6.81-6,86 (m, 1 H), 6.78-6.80 (m, 1 H), 6.54 (s, 1 H), 4.47 (dd, 1 H), 3.77-3.88 (m, 1 H), 3.06-3.17 (m, 1 H), 2.86 (dd, 1 H) | 421.1 $[M + H]^+$ | 99.0% |
| 2290 | ($CD_3OD$) δ 8.10-8.24 (m, 1 H), 7.60 (s, 1 H), 7.40 (s, 0.3 H), 6.81-6.96 (m, 1.7 H), 6.61-6.71 (m, 2 H), 6.42-6.58 (m, 1 H), 4.89 (br dd, 1 H), 3.62-3.73 (m, 0.7 H), 3.31 (td, 0.3 H), 2.84-3.14 (m, 1 H), 2.73 (br dd, 1 H), 2.25-2.38 (m, 6 H) | 430.2 $[M + H]^+$ | 100% |
| 2291 | ($CD_3OD$) δ 8.10-8.24 (m, 1 H), 7.61 (s, 1 H), 7.41 (s, 0.3 H), 6.82-6.92 (m, 1.7 H), 6.60-6.72 (m, 2 H), 6.44-6.57 (m, 1 H), 4.89 (br dd, 1 H), 3.62-3.72 (m, 0.7 H), 3.31 (td, 0.3 H), 2.84-3.15 (m, 1 H), 2.69-2.78 (m, 1 H), 2.26-2.37 (m, 6 H) | 430.2 $[M + H]^+$ | 98.8% |
| 2292 | ($CD_3OD$) δ 8.11-8.25 (m, 1 H), 7.64 (d, 1 H), 7.57 (s, 1 H), 7.33-7.43 (m, 0.3 H), 6.83-6.93 (m, 1.7 H), 6.62-6.72 (m, 1 H), 6.47-6.58 (m, 1 H), 4.82-4.95 (m, 1H), 3.60-3.79 (m, 0.7 H), 3.27-3.39 (m, 0.3 H), 3.04-3.15 (m, 0.7 H), 2.86-2.96 (m, 0.3 H), 2.68-2.80 (m, 1 H), 2.28-2.37 (m, 6 H) | 430.2 $[M + H]^+$ | 100% |
| 2293 | ($CD_3OD$) δ 8.12-8.24 (m, 1 H), 7.59 (d, 2 H), 7.38 (s, 0.3 H), 6.83-6.93 (m, 1.7 H), 6.62-6.72 (m, 1 H), 6.45 (s, 1 H), 4.82-4.94 (m, 1 H), 3.62-3.75 (m, 0.7 H), 3.27-3.39 (m, 0.3 H), 3.03-3.14 (m, 0.7 H), 2.84-2.97 (m, 0.3 H), 2.68-2.77 (m, 1 H), 2.27-2.40 (m, 6 H) | 430.2 $[M + H]^+$ | 96.9% |
| 2294 | ($CD_3OD$) δ 8.13-8.27 (m, 1 H), 7.60 (s, 1 H), 7.41 (s, 0.3 H), 6.79-6.93 (m, 1.7 H), 6.59-6.78 (m, 3 H), 4.83-4.97 (m, 1 H), 3.61-3.73 (m, 0.7 H), 3.29 (td, 0.3 H), 2.82-3.13 (m, 1 H), 2.74 (br dd, 1 H), 2.29 (s, 3 H) | 434.1 $[M + H]^+$ | 99.2% |
| 2295 | ($CD_3OD$) δ 8.15-8.28 (m, 1 H), 7.63 (s, 1 H), 7.42 (s, 0.3 H), 6.79-6.90 (m, 1.7 H), 6.59-6.77 (m, 3 H), 4.92 (br dd, 1 H), 3.60-3.72 (m, 0.7 H), 3.29 (td, 0.3 H), 2.83-3.15 (m, 1 H), 2.68-2.79 (m, 1 H), 2.29 (s, 3 H) | 434.2 $[M + H]^+$ | 96.8% |
| 2296 | ($CD_3OD$) δ 8.15-8.30 (m, 1 H), 7.54-7.65 (m, 2 H), 7.36 (s, 0.3 H), 6.80-6.92 (m, 1.7 H), 6.61-6.78 (m, 2 H), 4.83-4.96 (m, 1 H), 3.61-3.75 (m, 0.7 H), 3.30 (td, 0.3 H), 3.02-3.15 (m, 0.7 H), 2.86-2.95 (m, 0.3 H), 2.69 (d, 1 H), 2.28-2.34 (m, 3 H) | 434.2 $[M + H]^+$ | 100% |
| 2297 | ($CD_3OD$) δ 8.17-8.28 (m, 1 H), 7.53-7.67 (m, 2 H), 7.40 (s, 0.3 H), 6.80-6.91 (m, 1.7 H), 6.61-6.77 (m, 2 H), 4.84-4.96 (m, 1 H), 3.68 (ddd, 0.7 H), 3.30 (td, 0.3 H), 3.02-3.14 (m, 0.7 H), 2.84-2.96 (m, 0.3 H), 2.68-2.80 (m, 1 H), 2.26-2.37 (m, 3 H) | 434.2 $[M + H]^+$ | 98.2% |
| 2298 | ($CD_3OD$) δ 8.39 (d, 2 H), 8.04 (d, 1 H), 7.61 (s, 1 H), 7.15 (s, 1 H), 6.73 (t, 1 H), 6.63 (t, 1 H), 6.46-6.57 (m, 2 H), 5.01 (dd, 1 H), 3.93 (s, 3 H), 3.36-3.49 (m, 1 H), 2.78-2.95 (m, 1 H), 2.68 (dd, 1 H) | 348.1 $[M + H]^+$ | 99.8% |
| 2299 | ($CD_3OD$) δ 8.40 (d, 2 H), 8.05 (d, 1 H), 7.63 (s, 1 H), 7.17 (s, 1 H), 6.75 (t, 1 H), 6.64 (t, 1 H), 6.51-6.58 (m, 2 H), 5.03 (dd, 1 H), 3.94 (s, 3 H), 3.37-3.49 (m, 1 H), 2.83-2.95 (m, 1 H), 2.69 (dd, 1 H) | 348.1 $[M + H]^+$ | 98.7% |
| 2300 | ($CD_3OD$) δ 8.43 (d, 1 H), 7.65 (s, 1 H), 7.57 (d, 1 H), 7.12-7.22 (m, 1 H), 6.85 (td, 1 H), 6.52 (s, 1 H), 6.27 (s, 1 H), 4.20 (dd, 1 | 350.2 $[M + H]^+$ | 99.9% |

TABLE 2-continued

| Ex. # | $^{1}H$ NMR (400 MHz unless otherwise noted) | LCMS: m/z | % ee |
|---|---|---|---|
| | H), 3.68 (ddd, 1 H), 2.94-3.15 (m, 2 H), 2.78 (dd, 1 H), 1.35 (d, 6 H) | | |
| 2301 | ($CD_3OD$) δ 8.43 (d, 1 H), 7.65 (s, 1 H), 7.57 (d, 1 H), 7.14-7.25 (m, 1 H), 6.85 (td, 1 H), 6.52 (s, 1 H), 6.27 (s, 1 H), 4.20 (dd, 1 H), 3.68 (ddd, 1 H), 2.95-3.19 (m, 2 H), 2.78 (dd, 1 H), 1.35 (d, 6 H) | 350.2 $[M + H]^+$ | 99.6% |
| 2302 | ($CD_3OD$) δ 8.28 (d, 1 H), 7.66 (s, 1 H), 6.97 (d, 1 H), 6.77 (t, 1 H), 6.52 (s, 1 H), 6.28 (s, 1 H), 4.20 (dd, 1 H), 3.69 (ddd, 1 H), 2.94-3.19 (m, 2 H), 2.78 (dd, 1 H), 2.42 (s, 3 H), 1.35 (dd, 6 H) | 364.2 $[M + H]^+$ | 98.6% |
| 2303 | ($CD_3OD$) δ 8.28 (d, 1 H), 7.65 (s, 1 H), 6.98 (d, 1 H), 6.77 (t, 1 H), 6.52 (s, 1 H), 6.27 (br s, 1 H), 4.20 (dd, 1 H), 3.69 (ddd, 1 H), 2.95-3.18 (m, 2 H), 2.79 (br dd, 1 H), 2.43 (s, 3 H), 1.35 (dd, 6 H) | 364.2 $[M + H]^+$ | 99.6% |
| 2304 | ($CD_3OD$) δ 8.70 (d, 1 H), 7.70 (s, 1 H), 7.64 (d, 1 H), 7.00 (t, 1 H), 6.73 (s, 1 H), 6.33 (s, 1 H), 4.26 (dd, 1 H), 3.72 (ddd, 1 H), 2.98-3.19 (m, 2 H), 2.82 (dd, 1 H), 1.37 (d, 6 H) | 418.2 $[M + H]^+$ | 99.9% |
| 2305 | ($CD_3OD$) δ 8.67 (d, 1 H), 7.66 (s, 1 H), 7.62 (d, 1 H), 6.98 (t, 1 H), 6.71 (s, 1 H), 6.31 (s, 1 H), 4.24 (dd, 1 H), 3.64-3.77 (m, 1 H), 2.95-3.17 (m, 2 H), 2.80 (dd, 1 H), 1.35 (d, 6 H) | 418.2 $[M + H]^+$ | 98.9% |
| 2306 | ($CD_3OD$) δ 8.51 (br d, 1 H), 7.83 (br d, 1 H), 7.67 (s, 1 H), 7.57 (br d, 1 H), 7.42 (dd, 1 H), 7.14 (dd, 1 H), 6.99 (br d, 1 H), 6.76 (s, 1 H), 6.56 (s, 1 H), 4.47 (dd, 1 H), 3.79-3.95 (m, 1 H), 3.03-3.17 (m, 1 H), 2.83 (dd, 1 H), 2.68 (s, 3 H) | 433.2 $[M + H]^+$ | 100% |
| 2307 | ($CD_3OD$) δ 8.51 (br d, 1 H), 7.83 (br d, 1 H), 7.66 (s, 1 H), 7.57 (dd, 1 H), 7.42 (td, 1 H), 7.10-7.17 (m, 1 H), 6.99 (dd, 1 H), 6.76 (s, 1 H), 6.56 (s, 1 H), 4.47 (dd, 1 H), 3.79-3.92 (m, 1 H), 3.02-3.14 (m, 1 H), 2.83 (dd, 1 H), 2.68 (s, 3 H) | 433.2 $[M + H]^+$ | 99.4% |
| 2308 | ($CD_3OD$) δ 8.47-8.54 (m, 1 H), 7.77-7.88 (m, 1 H), 7.66 (s, 1 H), 7.37-7.49 (m, 2 H), 7.01-7.14 (m, 1 H), 6.52-6.71 (m, 3 H), 4.45 (br dd, 1 H), 3.79-3.93 (m, 1 H), 2.99-3.16 (m, 1 H), 2.83 (br dd, 1 H), 2.56-2.72 (m, 6 H) | 413.2 $[M + H]^+$ | 100% |
| 2309 | ($CD_3OD$) δ 8.52 (d, 1 H), 7.84 (br d, 1 H), 7.66 (s, 1 H), 7.39-7.48 (m, 2 H), 7.09 (dd, 1 H), 6.68 (br d, 1 H), 6.53-6.61 (m, 2 H), 4.45 (dd, 1 H), 3.85 (ddd, 1 H), 3.03-3.15 (m, 1 H), 2.83 (dd, 1 H), 2.58-2.71 (m, 6 H) | 413.2 $[M + H]^+$ | 99.4% |
| 2310 | ($CD_3OD$) δ 8.27 (d, 1 H), 7.58 (s, 1 H), 7.15-7.23 (m, 2 H), 7.09 (d, 2 H), 6.93 (d, 1 H), 6.69-6.80 (m, 2 H), 6.34 (s, 1 H), 5.99 (s, 1 H), 3.88 (br dd, 1 H), 3.60-3.70 (m, 1 H), 2.87-2.98 (m, 1 H), 2.66 (br dd, 1 H), 2.38 (s, 3 H) | 330.2 $[M + H]^+$ | 99.5% |
| 2311 | ($CD_3OD$) δ 8.28 (d, 1 H), 7.60 (s, 1 H), 7.17-7.24 (m, 2 H), 7.09 (d, 2 H), 6.94 (d, 1 H), 6.75 (dt, 2 H), 6.35 (s, 1 H), 6.00 (s, 1 H), 3.89 (br dd, 1 H), 3.60-3.71 (m, 1 H), 2.86-2.99 (m, 1 H), 2.67 (br dd, 1 H), 2.39 (s, 3 H) | 330.2 $[M + H]^+$ | 99.1% |
| 2312 | ($CD_3OD$) δ 8.31 (d, 1 H), 7.60 (s, 1 H), 7.17-7.24 (m, 2 H), 7.09 (d, 2 H), 6.91 (dd, 1 H), 6.74-6.81 (m, 2 H), 6.47 (s, 1 H), 6.02 (s, 1 H), 3.89 (br dd, 1 H), 3.59-3.69 (m, 1 H), 2.93 (tt, 1 H), 2.68 (br dd, 1 H) | 334.2 $[M + H]^+$ | 100% |
| 2313 | ($CD_3OD$) δ 8.31 (d, 1 H), 7.61 (s, 1 H), 7.17-7.24 (m, 2 H), 7.09 (d, 2 H), 6.91 (dd, 1 H), 6.74-6.82 (m, 2 H), 6.47 (s, 1 H), 6.02 (s, 1 H), 3.89 (br dd, 1 H), 3.59-3.68 (m, 1 H), 2.93 (ddd, 1 H), 2.68 (br dd, 1 H) | 334.2 $[M + H]^+$ | 99.7% |
| 2314 | ($CD_3OD$) δ 8.37 (d, 1 H), 7.55 (s, 1 H), 7.09 (br d, 1 H), 6.79 (t, 1 H), 6.56 (s, 1 H), 6.15 (br s, 1 H), 4.09 (dd, 1 H), 3.51-3.63 (m, 1 H), 2.85-2.96 (m, 1 H), 2.68 (br dd, 1 H), 1.92-2.02 (m, 1 H), 0.89-1.07 (m, 4 H) | 432.2 $[M + H]^+$ | 100% |
| 2315 | ($CD_3OD$) δ 8.37 (d, 1 H), 7.56 (s, 1 H), 7.09 (d, 1 H), 6.79 (t, 1 H), 6.56 (s, 1 H), 6.15 (s, 1 H), 4.06-4.13 (m, 1 H), 3.57 (ddd, 1 H), 2.85-2.97 (m, 1 H), 2.63-2.73 (m, 1 H), 1.93-1.99 (m, 1 H), 0.91-1.03 (m, 4 H) | 432.2 $[M + H]^+$ | 97.1% |
| 2316 | ($CD_3OD$) δ 8.56 (s, 2 H), 8.30-8.38 (m, 1 H), 7.56 (s, 1 H), 7.13 (s, 1 H), 7.03-7.09 (m, 1 H), 6.76 (t, 1 H), 6.59 (s, 1 H), 5.09 (dd, 1 H), 3.35-3.48 (m, 1 H), 2.74-2.87 (m, 1 H), 2.65 (dd, 1 H) | 470.1 $[M + H]^+$ | 99.9% |
| 2317 | ($CD_3OD$) δ 8.56 (s, 2 H), 8.34 (d, 1 H), 7.55 (s, 1 H), 7.13 (s, 1 H), 7.06 (br d, 1 H), 6.76 (t, 1 H), 6.59 (s, 1 H), 5.09 (dd, 1 H), 3.42 (td, 1 H), 2.76-2.86 (m, 1 H), 2.62-2.68 (m, 1 H) | 470.1 $[M + H]^+$ | 96.0% |
| 2318 | ($CD_3OD$) δ 8.34 (s, 1 H), 8.23 (br d, 1 H), 7.97-8.12 (m, 1 H), 7.69 (d, 1 H), 7.57 (br s, 1 H), 6.78-7.14 (m, 2 H), 6.68-6.75 (m, 2 H), 6.52 (s, 1 H), 4.59 (br dd, 1 H), 3.42-3.56 (m, 1 H), 2.78-2.92 (m, 1 H), 2.67 (br s, 1 H) | 384.1 $[M + H]^+$ | 99.8% |
| 2319 | ($CD_3OD$) δ 8.34 (d, 1 H), 8.23 (d, 1 H), 8.05 (dd, 1 H), 7.68 (d, 1 H), 7.53 (s, 1 H), 6.79-7.18 (m, 2 H), 6.66-6.76 (m, 2 H), 6.51 (s, 1 H), 4.59 (br dd, 1 H), 3.49 (br dd, 1 H), 2.86 (br s, 1 H), 2.67 (br d, 1 H) | 384.1 $[M + H]^+$ | 96.2% |
| 2320 | ($CD_3OD$) δ 8.57 (br d, 1 H), 7.66 (s, 1 H), 7.42 (br d, 1 H), 6.80-7.14 (m, 2 H), 6.70 (s, 1 H), 6.30 (br s, 1 H), 4.22 (dd, 1 H), 3.61-3.78 (m, 1 H), 2.91-3.18 (m, 2 H), 2.80 (br dd, 1 H), 1.35 (d, 6 H) | 400.2 $[M + H]^+$ | 99.9% |

TABLE 2-continued

| Ex. # | $^1$H NMR (400 MHz unless otherwise noted) | LCMS: m/z | % ee |
|---|---|---|---|
| 2321 | ($CD_3OD$) δ 8.57 (d, 1 H), 7.66 (s, 1 H), 7.42 (br d, 1 H), 6.80-7.14 (m, 2 H), 6.70 (s, 1 H), 6.30 (s, 1 H), 4.22 (dd, 1 H), 3.69 (ddd, 1 H), 2.97-3.18 (m, 2 H), 2.80 (dd, 1 H), 1.35 (dd, 6 H) | 400.2 $[M + H]^+$ | 99.0% |
| 2322 | ($CD_3OD$) δ 8.32 (d, 1 H), 7.66 (s, 1 H), 6.73-7.04 (m, 2 H), 6.66 (s, 1 H), 6.29 (s, 1 H), 4.22 (dd, 1 H), 3.61-3.79 (m, 1 H), 2.94-3.17 (m, 2 H), 2.79 (br dd, 1 H), 1.35 (d, 6 H) | 368.2 $[M + H]^+$ | 99.9% |
| 2323 | ($CD_3OD$) δ 8.32 (d, 1 H), 7.66 (s, 1 H), 6.77-7.01 (m, 2 H), 6.66 (s, 1 H), 6.29 (s, 1 H), 4.22 (dd, 1 H), 3.70 (td, 1 H), 2.94-3.18 (m, 2 H), 2.79 (br dd, 1 H), 1.35 (d, 6 H) | 368.2 $[M + H]^+$ | 99.3% |
| 2324 | ($CD_3OD$) δ 8.43 (d, 1 H), 7.66 (s, 1 H), 7.29 (d, 1 H), 6.84 (1, 1 H), 6.65 (s, 1 H), 6.28 (br s, 1 H), 4.22 (dd, 1 H), 3.56-3.80 (m, 1 H), 2.93-3.17 (m, 2 H), 2.79 (br dd, 1 H), 1.35 (d, 6 H) | 384.2 $[M + H]^+$ | 100% |
| 2325 | ($CD_3OD$) δ 8.43 (d, 1 H), 7.66 (s, 1 H), 7.29 (d, 1 H), 6.84 (t, 1 H), 6.65 (s, 1 H), 6.28 (br s, 1 H), 4.22 (dd, 1 H), 3.69 (ddd, 1 H), 2.92-3.20 (m, 2 H), 2.79 (br dd, 1 H), 1.35 (d, 6 H) | 384.2 $[M + H]^+$ | 99.2% |
| 2326 | ($CD_3OD$) δ 7.68 (s, 1 H), 7.58-7.65 (m, 1 H), 7.20 (dd, 1 H), 7.06 (d, 1 H), 6.71 (s, 1 H), 6.40 (br s, 1 H), 4.29-4.40 (m, 1 H), 3.76-3.90 (m, 1 H), 2.99-3.15 (m, 1 H), 2.85 (dd, 1 H), 2.12 (t, 3 H) | 406.1 $[M + H]^+$ | 100% |
| 2327 | ($CD_3OD$) δ 7.56 (s, 1 H), 7.49 (dd, 1 H), 7.07 (dd, 1 H), 6.93 (dd, 1 H), 6.58 (s, 1 H), 6.28 (s, 1 H), 4.20 (br d, 1 H), 3.70 (br s, 1 H), 2.88-3.01 (m, 1 H), 2.73 (dd, 1 H), 2.00 (t, 3 H) | 406.1 $[M + H]^+$ | 99.4% |
| 2328 | ($CD_3OD$) δ 7.68 (s, 1 H), 7.48 (d, 1 H), 7.13 (dd, 1 H), 6.73 (d, 1 H), 6.51 (s, 1 H), 6.38 (br s, 1 H), 4.22-4.40 (m, 1 H), 3.71-3.87 (m, 1 H), 2.96-3.13 (m, 1 H), 2.84 (dd, 1 H), 2.65 (s, 3 H), 2.12 (t, 3 H) | 386.2 $[M + H]^+$ | 100% |
| 2329 | ($CD_3OD$) δ 7.56 (s, 1 H), 7.35 (d, 1 H), 7.01 (dd, 1 H), 6.61 (d, 1 H), 6.39 (s, 1 H), 6.26 (s, 1 H), 4.19 (dd, 1 H), 3.67 (td, 1 H), 2.88-3.02 (m, 1 H), 2.72 (dd, 1 H), 2.52 (s, 3 H), 2.00 (t, 3 H) | 386.2 $[M + H]^+$ | 97.7% |
| 2330 | ($CD_3OD$) δ 8.41 (dd, 1 H), 8.25 (dd, 1 H), 7.41-7.61 (m, 2 H), 7.32 (dd, 1 H), 7.05 (dd, 1 H), 6.91 (dd, 1 H), 6.57 (s, 1 H), 6.36 (s, 1 H), 4.28 (dd, 1 H), 3.62-3.81 (m, 1 H), 2.91-3.08 (m, 1 H), 2.68-2.85 (m, 4 H) | 433.1 $[M + H]^+$ | 100% |
| 2331 | ($CD_3OD$) δ 8.41 (dd, 1 H), 8.25 (dd, 1 H), 7.43-7.66 (m, 2 H), 7.32 (dd, 1 H), 7.05 (dd, 1 H), 6.91 (dd, 1 H), 6.57 (s, 1 H), 6.36 (s, 1 H), 4.28 (dd, 1 H), 3.63-3.80 (m, 1 H), 2.88-3.07 (m, 1 H), 2.68-2.84 (m, 4 H) | 433.1 $[M + H]^+$ | 98.2% |
| 2332 | ($CD_3OD$) δ 8.42 (dd, 1 H), 8.23 (dd, 1 H), 7.56 (s, 1 H), 7.24-7.40 (m, 2 H), 6.99 (dd, 1 H), 6.58 (d, 1 H), 6.30-6.45 (m, 2 H), 4.26 (dd, 1 H), 3,64-3.83 (m, 1 H), 2.88-3.07 (m, 1 H), 2.68-2.83 (m, 4 H), 2.50 (s, 3 H) | 413.2 $[M + H]^+$ | 99.9% |
| 2333 | ($CD_3OD$) δ 8.40 (dd, 1 H), 8.21 (dd, 1 H), 7.57 (s, 1 H), 7.23-7.41 (m, 2 H), 6.97 (dd, 1 H), 6.57 (d, 1 H), 6.26-6.46 (m, 2 H), 4.26 (dd, 1 H), 3.62-3.82 (m, 1 H), 2.89-3.04 (m, 1 H), 2.68-2.82 (m, 4 H), 2.49 (s, 3 H) | 413.2 $[M + H]^+$ | 99.2% |
| 2334 | ($CD_3OD$) δ 8.37-8.46 (m, 1 H), 8.23-8.27 (m, 1 H), 8.19 (d, 1 H), 7.58 (s, 1 H), 7.34-7.44 (m, 1 H), 6.94 (d, 1 H), 6.72 (t, 1 H), 6.58 (s, 1 H), 6.35 (s, 1 H), 4.28 (dd, 1 H), 3.64-3.77 (m, 1 H), 2.93-3.14 (m, 2 H), 2.75 (dd, 1 H), 1.22 (dd, 6 H) | 445.2 $[M + H]^+$ | 100% |
| 2335 | ($CD_3OD$) δ 8.36-8.44 (m, 1 H), 8.24 (br d, 1 H), 8.18 (d, 1 H), 7.58 (s, 1 H), 7.38 (br t, 1 H), 6.93 (br d, 1 H), 6.67-6.76 (m, 1 H), 6.58 (s, 1 H), 6.34 (s, 1 H), 4.28 (dd, 1 H), 3.63-3.78 (m, 1 H), 2.92-3.15 (m, 2 H), 2.75 (dd, 1 H), 1.21 (t, 6 H) | 445.2 $[M + H]^+$ | 98.9% |
| 2336 | ($CD_3OD$) δ 8.52 (d, 1 H), 7.81-7.88 (m, 2 H), 7.69 (s, 1 H), 7.44 (dd, 1 H), 7.20-7.35 (m, 2 H), 6.80 (s, 1 H), 6.57 (s, 1 H), 4.46 (dd, 1 H), 3.83 (td, 1 H), 3.04-3.15 (m, 1 H), 2.84 (dd, 1 H), 2.69 (s, 3 H) | 467.1 $[M + H]^+$ | 100% |
| 2337 | ($CD_3OD$) δ 8.53 (d, 1 H), 7.82-7.91 (m, 3 H), 7.46 (dd, 1 H), 7.23-7.35 (m, 2 H), 6.83 (s, 1 H), 6.61 (s, 1 H), 4.48 (dd, 1 H), 3.77-3.87 (m, 1 H), 3.06-3.17 (m, 1 H), 2.84-2.90 (m, 1 H), 2.71 (s, 3 H) | 467.2 $[M + H]^+$ | 99.2% |
| 2338 | ($CD_3OD$) δ 8.43 (d, 1 H), 8.30 (d, 1 H), 7.66-7.76 (m, 1 H), 7.57 (s, 1 H), 7.41-7.52 (m, 2 H), 7.05 (dd, 1 H), 6.71 (td, 1 H), 6.51 (s, 1 H), 6.40 (s, 1 H), 4.31 (dd, 1 H), 3.62-3.74 (m, 1 H), 2.91-3.05 (m, 1 H), 2.72 (dd, 1 H) | 403.2 $[M + H]^+$ | 100% |
| 2339 | ($CD_3OD$) δ 8.43 (d, 1 H), 8.31 (d, 1 H), 7.72 (t, 1 H), 7.57 (s, 1 H), 7.42-7.53 (m, 2 H), 7.01-7.11 (m, 1 H), 6.71 (t, 1 H), 6.52 (s, 1 H), 6.40 (s, 1 H), 4.32 (dd, 1 H), 3.62-3.74 (m, 1 H), 2.91-3.05 (m, 1 H), 2.72 (dd, 1 H) | 403.2 $[M + H]^+$ | 94.1% |
| 2340 | ($CD_3OD$) δ 8.44 (d, 1 H), 8.17 (d, 1 H), 7.65-7.81 (m, 1 H), 7.54-7.60 (m, 1 H), 7.50 (dt, 1 H), 6.82-6.88 (m, 1 H), 6.64 (t, 1 H), 6.53 (s, 1 H), 6.41 (s, 1 H), 4.32 (dd, 1 H), 3.64-3.78 (m, 1 H), 2.92-3.05 (m, 1 H), 2.73 (dd, 1 H), 2.31 (s, 3 H) | 417.2 $[M + H]^+$ | 99.9% |
| 2341 | ($CD_3OD$) δ 8.44 (d, 1 H), 8.17 (d, 1 H), 7.72 (t, 1 H), 7.57 (s, 1 H), 7.50 (dt, 1 H), 6.85 (d, 1 H), 6.64 (t, 1 H), 6.53 (s, 1 H), 6.41 (s, 1 H), 4.33 (dd, 1 H), 3.70 (td, 1 H), 2.93-3.05 (m, 1 H), 2.73 (dd, 1 H), 2.31 (s, 3 H) | 417.1 $[M + H]^+$ | 99.3% |

TABLE 2-continued

| Ex. # | $^1$H NMR (400 MHz unless otherwise noted) | LCMS: m/z | % ee |
|---|---|---|---|
| 2342 | ($CD_3OD$) δ 8.44 (d, 1 H), 7.80-7.95 (m, 2 H), 7.68 (s, 1 H), 7.58 (d, 1 H), 7.40 (d, 1 H), 7.18 (dd, 1 H), 6.84 (td, 1 H), 6.62 (s, 1 H), 6.53 (s, 1 H), 4.44 (dd, 1 H), 3.64-3.84 (m, 1 H), 3.00-3.18 (m, 1 H), 2.83 (br dd, 1 H), 2.62 (s, 3 H) | 399.1 $[M + H]^+$ | 100% |
| 2343 | ($CD_3OD$) δ 8.43 (d, 1 H), 7.79-7.97 (m, 2 H), 7.67 (s, 1 H), 7.57 (d, 1 H), 7.39 (d, 1 H), 7.12-7.22 (m, 1 H), 6.83 (td, 1 H), 6.62 (s, 1 H), 6.53 (s, 1 H), 4.43 (dd, 1 H), 3.77 (ddd, 1 H), 3.03-3.17 (m, 1 H), 2.75-2.88 (m, 1 H), 2.61 (s, 3 H) | 399.1 $[M + H]^+$ | 98.3% |
| 2344 | ($CD_3OD$) δ 8.29 (d, 1 H), 7.79-7.98 (m, 2 H), 7.68 (s, 1 H), 7.40 (d, 1 H), 6.97 (d, 1 H), 6.76 (t, 1 H), 6.63 (s, 1 H), 6.53 (s, 1 H), 4.44 (dd, 1 H), 3.69-3.85 (m, 1 H), 3.00-3.18 (m, 1 H), 2.75-2.88 (m, 1 H), 2.62 (s, 3 H), 2.43 (s, 3 H) | 413.2 $[M + H]^+$ | 99.5% |
| 2345 | ($CD_3OD$) δ 8.27 (d, 1 H), 7.77-7.93 (m, 2 H), 7.68 (s, 1 H), 7.37 (d, 1 H), 6.94 (d, 1 H), 6.73 (t, 1 H), 6.62 (s, 1 H), 6.52 (s, 1 H), 4.43 (dd, 1 H), 3.67-3.84 (m, 1 H), 3.02-3.15 (m, 1 H), 2.82 (br dd, 1 H), 2.60 (s, 3 H), 2.40 (s, 3 H) | 413.2 $[M + H]^+$ | 99.6% |
| 2346 | ($CD_3OD$) δ 8.57 (d, 1 H), 7.80-7.97 (m, 2 H), 7.72 (s, 1 H), 7.29-7.49 (m, 2 H), 6.76-7.15 (m, 3 H), 6.56 (s, 1 H), 4.46 (dd, 1 H), 3.68-3.89 (m, 1 H), 3.02-3.19 (m, 1 H), 2.76-2.91 (m, 1 H), 2.62 (s, 3 H) | 449.1 $[M + H]^+$ | 99.6% |
| 2347 | ($CD_3OD$) δ 8.57 (br d, 1 H), 7.79-7.96 (m, 2 H), 7.69 (s, 1 H), 7.35-7.51 (m, 2 H), 6.75-7.16 (m, 3 H), 6.56 (br s, 1 H), 4.46 (dd, 1 H), 3.66-3.90 (m, 1 H), 3.00-3.20 (m, 1 H), 2.74-2.92 (m, 1 H), 2.62 (s, 3 H) | 449.1 $[M + H]^+$ | 99.5% |
| 2348 | ($CD_3OD$) δ 8.48 (d, 1 H), 8.43 (s, 1 H), 7.74-7.81 (m, 1 H), 7.65 (s, 1 H), 7.12-7.22 (m, 2 H), 6.85-6.97 (m, 2 H), 6.67 (s, 1 H), 4.74 (br dd, 1 H), 3.61 (ddd, 1 H), 2.91-3.01 (m, 1 H), 2.71-2.80 (m, 1 H) | 469.1 $[M + H]^+$ | 98.0% |
| 2349 | ($CD_3OD$) δ 8.36 (d, 1 H), 8.28-8.33 (m, 1 H), 7.66 (dd, 1 H), 7.56 (s, 1 H), 7.00-7.10 (m, 2 H), 6.73-6.85 (m, 2 H), 6.55 (s, 1 H), 4.62 (br dd, 1 H), 3.42-3.55 (m, 1 H), 2.78-2.91 (m, 1 H), 2.63 (dd, 1 H) | 469.1 $[M + H]^+$ | 98.5% |
| 2350 | ($CD_3OD$) δ 8.40 (ddd, 1 H), 8.33 (d, 1 H), 8.25 (d, 1 H), 7.59 (s, 1 H), 7.34-7.45 (m, 1 H), 7.18 (d, 1 H), 6.73 (t, 1 H), 6.62 (s, 1 H), 6.35 (s, 1 H), 4.30 (dd, 1 H), 3.61-3.76 (m, 1 H), 2.92-3.07 (m, 1 H), 2.75 (dd, 1 H) | 437.1 $[M + H]^+$ | 100% |
| 2351 | ($CD_3OD$) δ 8.37-8.44 (m, 1 H), 8.34 (d, 1 H), 8.25 (br d, 1 H), 7.59 (s, 1 H), 7.31-7.44 (m, 1 H), 7.19 (d, 1 H), 6.73 (t, 1 H), 6.62 (s, 1 H), 6.35 (s, 1 H), 4.30 (dd, 1 H), 3.59-3.76 (m, 1 H), 2.91-3.07 (m, 1 H), 2.75 (br dd, 1 H) | 437.1 $[M + H]^+$ | 100% |
| 2352 | ($CD_3OD$) δ 8.52 (br d, 1 H), 7.84 (br d, 1 H), 7.67-7.75 (m, 2 H), 7.13-7.51 (m, 4 H), 6.73 (s, 1 H), 6.56 (s, 1 H), 4.47 (dd, 1 H), 3.78-3.90 (m, 1 H), 3.03-3.16 (m, 1 H), 2.84 (dd, 1 H), 2.68 (s, 3 H) | 449.2 $[M + H]^+$ | 100% |
| 2353 | ($CD_3OD$) δ 8.52 (d, 1 H), 7.84 (br d, 1 H), 7.65-7.75 (m, 2 H), 7.13-7.49 (m, 4 H), 6.73 (s, 1 H), 6.56 (s, 1 H), 4.47 (dd, 1 H), 3.79-3.90 (m, 1 H), 3.02-3.15 (m, 1 H), 2.84 (dd, 1 H), 2.68 (s, 3 H) | 449.1 $[M + H]^+$ | 99.8% |
| 2354 | ($CD_3OD$) δ 8.45 (d, 1 H), 8.17 (d, 1 H), 7.73 (t, 1 H), 7.58 (s, 1 H), 7.51 (dt, 1 H), 6.92 (d, 1 H), 6.70 (t, 1 H), 6.63 (s, 1 H), 6.41 (s, 1 H), 4.33 (dd, 1 H), 3.64-3.78 (m, 1 H), 2.94-3.11 (m, 2 H), 2.74 (dd, 1 H), 1.21 (t, 6 H) | 445.2 $[M + H]^+$ | 99.7% |
| 2355 | ($CD_3OD$) δ 8.44 (br d, 1 H), 8.17 (d, 1 H), 7.73 (t, 1 H), 7.58 (s, 1 H), 7.50 (dt, 1 H), 6.92 (d, 1 H), 6.67-6.74 (m, 1 H), 6.63 (s, 1 H), 6.41 (s, 1 H), 4.33 (br dd, 1 H), 3.65-3.77 (m, 1 H), 2.94-3.10 (m, 2 H), 2.74 (br dd, 1 H), 1.20 (1, 6 H) | 445.2 $[M + H]^+$ | 98.6% |
| 2356 | ($CD_3OD$) δ 8.68 (d, 1 H), 7.77-7.99 (m, 2 H), 7.69 (s, 1 H), 7.60 (d, 1 H), 7.40 (d, 1 H), 6.96 (t, 1 H), 6.82 (s, 1 H), 6.56 (s, 1 H), 4.47 (dd, 1 H), 3.66-3.91 (m, 1 H), 3.02-3.17 (m, 1 H), 2.85 (dd, 1 H), 2.62 (s, 3 H) | 467.2 $[M + H]^+$ | 100% |
| 2357 | ($CD_3OD$) δ 8.68 (d, 1 H), 7.78-7.97 (m, 2 H), 7.69 (s, 1 H), 7.60 (d, 1 H), 7.40 (d, 1 H), 6.96 (t, 1 H), 6.82 (s, 1 H), 6.56 (s, 1 H), 4.47 (dd, 1 H), 3.79 (td, 1 H), 3.05-3.20 (m, 1 H), 2.77-2.92 (m, 1 H), 2.61 (s, 3 H) | 467.1 $[M + H]^+$ | 97.8% |
| 2358 | ($CD_3OD$) δ 8.25 (d, 1 H), 7.78-7.98 (m, 2 H), 7.68 (s, 1 H), 7.38 (d, 1 H), 6.68-6.87 (m, 3 H), 6.41-6.63 (m, 1 H), 4.44 (dd, 1 H), 3.79 (td, 1 H), 2.99-3.20 (m, 1 H), 2.76-2.93 (m, 1 H), 2.61 (s, 3 H), 2.00-2.16 (m, 1 H), 0.72-1.04 (m, 4 H) | 439.2 $[M + H]^+$ | 100% |
| 2359 | ($CD_3OD$) δ 8.26 (d, 1 H), 7.80-8.04 (m, 2 H), 7.68 (s, 1 H), 7.39 (d, 1 H), 6.67-6.97 (m, 3 H), 6.39-6.64 (m, 1 H), 4.44 (dd, 1 H), 3.66-3.91 (m, 1 H), 3.03-3.21 (m, 1 H), 2.76-2.97 (m, 1 H), 2.61 (s, 3 H), 1.97-2.28 (m, 1 H), 0.70-1.07 (m, 4 H) | 439.2 $[M + H]^+$ | 99.7% |
| 2360 | ($CD_3OD$) δ 8.29 (d, 1 H), 8.11 (q, 1 H), 8.00 (dd, 1 H), 7.68 (s, 1 H), 7.21 (dd, 1 H), 6.97 (d, 1 H), 6.76 (1, 1 H), 6.63 (s, 1 H), 6.50 (s, 1 H), 4.42 (dd, 1 H), 3.79 (ddd, 1 H), 3.00-3.16 (m, 1 H), 2.84 (dd, 1 H), 2.43 (s, 3 H) | 417.2 $[M + H]^+$ | 100% |

TABLE 2-continued

| Ex. # | $^1H$ NMR (400 MHz unless otherwise noted) | LCMS: m/z | % ee |
|---|---|---|---|
| 2361 | ($CD_3OD$) δ 8.29 (d, 1 H), 8.11 (q, 1 H), 8.00 (dd, 1 H), 7.68 (s, 1 H), 7.21 (dd, 1 H), 6.97 (d, 1 H), 6.77 (t, 1 H), 6.63 (s, 1 H), 6.50 (s, 1 H), 4.42 (dd, 1 H), 3.79 (ddd, 1 H), 2.96-3.16 (m, 1 H), 2.84 (dd, 1 H), 2.43 (s, 3 H) | 417.2 $[M + H]^+$ | 99.8% |
| 2362 | ($CD_3OD$) δ 8.69 (d, 1 H), 8.11 (q, 1 H), 8.00 (dd, 1 H), 7.69 (s, 1 H), 7.61 (d, 1 H), 7.22 (dd, 1 H), 6.97 (t, 1 H), 6.82 (s, 1 H), 6.53 (br s, 1 H), 4.46 (dd, 1 H), 3.80 (ddd, 1 H), 3.00-3.19 (m, 1 H), 2.85 (br dd, 1 H) | 471.2 $[M + H]^+$ | 99.9% |
| 2363 | ($CD_3OD$) δ 8.68 (br d, 1 H), 8.07-8.16 (m, 1 H), 8.00 (br d, 1 H), 7.69 (s, 1 H), 7.61 (br d, 1 H), 7.22 (br d, 1 H), 6.97 (br t, 1 H), 6.82 (s, 1 H), 6.53 (br s, 1 H), 4.46 (dd, 1 H), 3.73-3.87 (m, 1 H), 3.00-3.16 (m, 1 H), 2.85 (br dd, 1 H) | 471.2 $[M + H]^+$ | 97.4% |
| 2364 | ($CD_3OD$) δ 8.71 (d, 1 H), 8.35-8.51 (m, 2 H), 7.90 (td, 1 H), 7.71 (s, 1 H), 7.51-7.66 (m, 1.3 H), 7.15-7.27 (m, 1 H), 6.99 (s, 0.7 H), 6.82-6.92 (m, 1 H), 6.58-6.70 (m, 1 H), 5.02 (br dd, 1 H), 3.75-3.87 (m, 0.7 H), 3.44 (td, 0.3 H), 3.15-3.26 (m, 0.7 H), 2.97-3.07 (m, 0.3 H), 2.86 (br dd, 1 H) | 431.0 $[M + H]^+$ | 100% |
| 2365 | ($CD_3OD$) δ 8.71 (d, 1 H), 8.35-8.50 (m, 2 H), 7.90 (td, 1 H), 7.74-7.77 (m, 1 H), 7.52-7.66 (m, 1.3 H), 7.15-7.26 (m, 1 H), 6.99 (s, 0.7 H), 6.81-6.92 (m, 1 H), 6.60-6.70 (m, 1 H), 5.03 (dd, 1 H), 3.74-3.86 (m, 0.7 H), 3.44 (td, 0.3 H), 3.16-3.28 (m, 0.7 H), 2.98-3.08 (m, 0.3 H), 2.82-2.90 (m, 1 H) | 431.0 $[M + H]^+$ | 100% |
| 2366 | ($CD_3OD$) δ 8.45 (br s, 1.4 H), 8.02 (br s, 0.6 H), 7.65 (s, 1 H), 7.58 (br d, 1 H), 7.15-7.25 (m, 1 H), 6.91-7.13 (m, 1.3 H), 6.73-6.90 (m, 1.3 H), 6.61 (br s, 0.7 H), 6.07-6.47 (m, 0.7 H), 4.67-4.84 (m, 0.6 H), 4.06 (br s, 0.4 H), 3.66 (br s, 0.5 H), 3.14-3.30 (m, 0.5 H), 2.93 (br s, 1 H), 2.70 (br d, 1 H) | 384.1 $[M + H]^+$ | 100% |
| 2367 | ($CD_3OD$) δ 8.46 (br s, 1.4 H), 8.03 (br s, 0.6 H), 7.65 (s, 1 H), 7.58 (br d, 1 H), 7.16-7.23 (m, 1 H), 6.92-7.12 (m, 1.3 H), 6.77-6.91 (m, 1.4 H), 6.61 (br s, 0.6 H), 6.17-6.44 (m, 0.7 H), 4.64-4.85 (m, 0.6 H), 4.06 (br s, 0.4 H), 3.66 (br s, 0.4 H), 3.16-3.31 (m, 0.6 H), 2.96 (br d, 1 H), 2.70 (br d, 1 H) | 384.1 $[M + H]^+$ | 99.8% |
| 2368 | ($CD_3OD$) δ 8.36-8.64 (m, 1 H), 7.77-8.34 (m, 1 H), 7.47-7.74 (m, 2 H), 7.02-7.42 (m, 2 H), 6.76-6.99 (m, 1.5 H), 6.09-6.70 (m, 1.5 H), 5.11 (q, 2 H), 4.06 (br d, 1 H), 3.70 (br s, 1 H), 2.90-3.04 (m, 1 H), 2.73 (dd, 1 H) | 466.0 $[M + H]^+$ | 100% |
| 2369 | ($CD_3OD$) δ 8.37-8.62 (m, 1 H), 7.79-8.35 (m, 1 H), 7.49-7.76 (m, 2 H), 7.01-7.43 (m, 2 H), 6.80-6.99 (m, 1.4 H), 6.13-6.70 (m, 1.6 H), 5.11 (q, 2 H), 4.05 (br s, 1 H), 3.70 (br s, 1 H), 2.90-3.04 (m, 1 H), 2.73 (br dd, 1 H) | 466.0 $[M + H]^+$ | 100% |
| 2370 | ($CD_3OD$) δ 8.26-8.62 (m, 1 H), 7.47-7.74 (m, 2.3 H), 7.09-7.43 (m, 1.7 H), 6.79-6.99 (m, 1.6 H), 5.98-6.71 (m, 2.4 H), 4.13 (br dd, 1 H), 3.56-3.79 (m, 0.6 H), 2.86-3.28 (m, 1.4 H), 2.74 (br d, 1 H) | 399.0 $[M + H]^+$ | 99.2% |
| 2371 | ($CD_3OD$) δ 8.34-8.60 (m, 1 H), 7.50-7.75 (m, 2.2 H), 7.13-7.49 (m, 1.8 H), 6.77-7.03 (m, 1.5 H), 5.99-6.69 (m, 2.5 H), 4.13 (br dd, 1 H), 3.57-3.76 (m, 0.6 H), 2.87-3.29 (m, 1.4 H), 2.74 (br d, 1 H) | 399.0 $[M + H]^+$ | 99.4% |
| 2372 | ($CD_3OD$) δ 8.35-8.53 (m, 1 H), 7.48-7.75 (m, 2 H), 7.08-7.28 (m, 1 H), 6.73-7.03 (m, 2 H), 6.28-6.70 (m, 1 H), 4.44 (dd, 1 H), 4.00-4.23 (m, 3 H), 3.68 (ddd, 1 H), 2.91-3.29 (m, 1 H), 2.67-2.87 (m, 1 H) | 417.2 $[M + H]^+$ | 100% |
| 2373 | ($CD_3OD$) δ 8.37-8.51 (m, 1 H), 7.46-7.75 (m, 2 H), 7.10-7.26 (m, 1 H), 6.75-7.00 (m, 2 H), 6.31-6.70 (m, 1 H), 4.44 (dd, 1 H), 4.04-4.24 (m, 3 H), 3.68 (ddd, 1 H), 2.89-3.29 (m, 1 H), 2.71-2.87 (m, 1 H) | 417.2 $[M + H]^+$ | 100% |
| 2374 | ($CD_3OD$) δ 8.34 (d, 1 H), 7.56 (s, 1 H), 7.49 (br d, 1 H), 7.04-7.17 (m, 1 H), 6.75 (td, 1.6 H), 6.25-6.56 (m, 1.4 H), 4.80-4.85 (m, 1 H), 4.02-4.21 (m, 1 H), 3.56-3.76 (m, 1 H), 2.61-3.10 (m, 2 H), 1.46 (br d, 3 H) | 413.20 $[M + H]^+$ | 100% |
| 2375 | ($CD_3OD$) δ 8.46 (d, 1 H), 7.68 (s, 1 H), 7.61 (br d, 1 H), 7.15-7.28 (m, 1 H), 6.87 (td, 1.6 H), 6.35-6.71 (m, 1.4 H), 4.92-4.96 (m, 1 H), 4.21 (br d, 1 H), 3.64-3.86 (m, 1 H), 2.72-3.20 (m, 2 H), 1.59 (br d, 3 H) | 413.20 $[M + H]^+$ | 96.6% |
| 2376 | ($CD_3OD$) δ 8.46 (d, 1 H), 7.68 (s, 1 H), 7.61 (br d, 1 H), 7.15-7.28 (m, 1 H), 6.87 (td, 1.6 H), 6.30-6.69 (m, 1.4 H), 4.93-4.96 (m, 1 H), 4.22 (br d, 1 H), 3.78 (br s, 1 H), 2.77-3.20 (m, 2 H), 1.48-1.65 (m, 3 H) | 413.10 $[M + H]^+$ | 100% |
| 2377 | ($CD_3OD$) δ 8.34 (d, 1 H), 7.56 (s, 1 H), 7.49 (br d, 1 H), 7.05-7.13 (m, 1 H), 6.75 (td, 1.6 H), 6.25-6.55 (m, 1.4 H), 4.80-4.85 (m, 1 H), 3.99-4.19 (m, 1 H), 3.66 (br s, 1 H), 2.59-3.09 (m, 2 H), 1.47 (br d, 3 H) | 413.0 $[M + H]^+$ | 97.3% |
| 2378 | ($CD_3OD$) δ 8.37-8.44 (m, 1 H), 7.68 (s, 1 H), 7.19-7.45 (m, 1 H), 6.78-6.97 (m, 2 H), 6.61-6.75 (m, 1 H), 4.93 (br d, 1 H), 3.63-3.80 (m, 0.7 H), 3.35-3.44 (m, 0.3 H), 2.91-3.20 (m, 1 H), 2.81 (br d, 1 H), 1.67 (s, 6 H) | 428.1 $[M + H]^+$ | 100% |

TABLE 2-continued

| Ex. # | $^1$H NMR (400 MHz unless otherwise noted) | LCMS: m/z | % ee |
|---|---|---|---|
| 2379 | ($CD_3OD$) δ 8.37-8.44 (m, 1 H), 7.68 (s, 1 H), 7.22-7.42 (m, 1 H), 6.78-6.94 (m, 2 H), 6.60-6.73 (m, 1 H), 4.93 (br d, 1 H), 3.61-3.78 (m, 0.6 H), 3.32-3.42 (m, 0.4 H), 2.91-3.19 (m, 1 H), 2.80 (dd, 1 H), 1.67 (s, 6 H) | 428.1 $[M + H]^+$ | 100% |
| 2380 | ($CD_3OD$) δ 8.39 (s, 1 H), 8.17-8.28 (m, 1 H), 8.10 (s, 1 H), 7.68 (s, 1 H), 7.42-7.61 (m, 1 H), 7.02-7.12 (m, 1 H), 6.93 (br s, 1 H), 6.44-6.60 (m, 1 H), 5.05 (br dd, 1 H), 4.00 (s, 3 H), 3.67-3.84 (m, 1 H), 2.91-3.22 (m, 1 H), 2.82 (br d, 1 H), 2.23-2.36 (m, 3 H) | 430.2 $[M + H]^+$ | 100% |
| 2381 | ($CD_3OD$) δ 8.39 (s, 1 H), 8.15-8.28 (m, 1 H), 8.10 (s, 1 H), 7.68 (s, 1 H), 7.42-7.58 (m, 1 H), 7.01-7.11 (m, 1 H), 6.93 (s, 1 H), 6.44-6.61 (m, 1 H), 5.05 (br dd, 1 H), 4.00 (s, 3 H), 3.70-3.83 (m, 0.7 H), 3.39-3.44 (m, 0.3 H), 2.92-3.22 (m, 1 H), 2.70-2.88 (m, 1 H), 2.21-2.34 (m, 3 H) | 430.2 $[M + H]^+$ | 99.8% |
| 2382 | ($CD_3OD$) δ 8.35 (br s, 1 H), 7.93 (br s, 1 H), 7.67 (s, 2 H), 6.91-7.04 (m, 1 H), 6.60-6.90 (m, 3 H), 4.41-4.83 (m, 1 H), 3.36-3.87 (m, 1 H), 2.68-3.19 (m, 2 H), 1.64 (br s, 6 H) | 411.2 $[M + H]^+$ | 100% |
| 2383 | ($CD_3OD$) δ 8.35 (br s, 1 H), 7.93 (br s, 1 H), 7.68 (s, 2 H), 6.92-7.08 (m, 1 H), 6.57-6.91 (m, 3 H), 4.42-4.83 (m, 1 H), 3.36-3.90 (m, 1 H), 2.73-3.24 (m, 2 H), 1.64 (br s, 6 H) | 411.2 $[M + H]^+$ | 99.1% |
| 2384 | ($CD_3OD$) δ 8.79 (br d, 1 H), 8.24-8.38 (m, 2 H), 8.10 (t, 1 H), 7.64-7.73 (m, 2 H), 7.51 (s, 0.3 H), 7.32-7.39 (m, 1 H), 6.96 (s, 0.7 H), 6.67-6.77 (m, 1 H), 6.44-6.53 (m, 1 H), 5.00 (br dd, 1 H), 3.75-3.86 (m, 0.7 H), 3.43 (br dd, 0.3 H), 2.97-3.26 (m, 1 H), 2.80-2.90 (m, 1 H), 2.34-2.42 (m, 3 H) | 427.2 $[M + H]^+$ | 97.4% |
| 2385 | ($CD_3OD$) δ 8.79 (br d, 1 H), 8.24-8.38 (m, 2 H), 8.10 (t, 1 H), 7.64-7.74 (m, 2 H), 7.51 (s, 0.3 H), 7.32-7.41 (m, 1 H), 6.96 (s, 0.7 H), 6.67-6.76 (m, 1 H), 6.44-6.55 (m, 1 H), 5.00 (br dd, 1 H), 3.75-3.86 (m, 0.7 H), 3.39-3.46 (m, 0.3 H), 2.98-3.27 (m, 1 H), 2.81-2.91 (m, 1 H), 2.33-2.41 (m, 3 H) | 427.2 $[M + H]^+$ | 99.6% |
| 2386 | ($CD_3OD$) δ 8.34-8.71 (m, 1 H), 7.66-7.80 (m, 1 H), 7.55-7.66 (m, 1 H), 7.50 (d, 1 H), 7.17-7.27 (m, 1 H), 7.01 (s, 0.6 H), 6.83-6.93 (m, 1 H), 6.62-6.80 (m, 1 H), 6.27-6.58 (m, 1 H), 6.14 (br s, 0.4 H), 3.92 (br dd, 1 H), 3.57-3.82 (m, 1.6 H), 3.36-3.47 (m, 0.4 H), 2.87-3.10 (m, 1 H), 2.67-2.86 (m, 1 H), 1.10 (br s, 1 H), 0.64-0.98 (m, 3 H) | 374.2 $[M + H]^+$ | 99.9% |
| 2387 | ($CD_3OD$) δ 8.40-8.62 (m, 1 H), 7.66-7.74 (m, 1 H), 7.54-7.66 (m, 1 H), 7.50 (d, 1 H), 7.21 (t, 1 H), 7.01 (s, 0.6 H), 6.83-6.94 (m, 1 H), 6.60-6.80 (m, 1 H), 6.29-6.60 (m, 1 H), 6.14 (s, 0,4 H), 3.85-4.00 (m, 1 H), 3.57-3.80 (m, 1.6 H), 3.35-3.46 (m, 0.4 H), 2.87-3.10 (m, 1 H), 2.69-2.85 (m, 1 H), 1.10 (br d, 1 H), 0.63-0.97 (m, 3 H) | 374.2 $[M + H]^+$ | 100% |
| 2388 | ($CD_3OD$) δ 8.31-8.40 (m, 1 H), 7.79-7.91 (m, 3 H), 7.53-7.78 (m, 2 H), 7.06-7.19 (m, 1 H), 6.83-7.05 (m, 3 H), 6.44-6.81 (m, 1.6 H), 5.88 (s, 0.4 H), 3.38-3.84 (m, 2 H), 2.57-3.16 (m, 2 H) | 429.2 $[M + H]^+$ | 91.1% |
| 2389 | ($CD_3OD$) δ 8.31-8.40 (m, 1 H), 7.79-7.92 (m, 3 H), 7.54-7.78 (m, 2 H), 7.07-7.19 (m, 1 H), 6.84-7.05 (m, 3 H), 6.44-6.80 (m, 1.6 H), 5.88 (s, 0.4 H), 3.40-3.83 (m, 2 H), 2.58-3.15 (m, 2 H) | 429.2 $[M + H]^+$ | 94.3% |
| 2390 | ($CD_3OD$) δ 8.31-8.51 (m, 1 H), 7.70 (s, 1 H), 6.69-7.19 (m, 3 H), 6.32-6.61 (m, 2 H), 4.15 (br d, 1 H), 3.85 (s, 3 H), 3.63-3.78 (m, 1 H), 2.69-3.10 (m, 2 H), 2.28 (br s, 3 H) | 380.2 $[M + H]^+$ | 100% |
| 2391 | ($CD_3OD$) δ 8.28-8.57 (m, 1 H), 7.70 (s, 1 H), 6.70-7.06 (m, 3 H), 6.29-6.63 (m, 2 H), 4.15 (br d, 1 H), 3.61-3.91 (m, 4 H), 2.67-3.10 (m, 2 H), 2.16-2.32 (m, 3 H) | 380.2 $[M + H]^+$ | 99.7% |
| 2392 | ($CD_3OD$) δ 7.94-8.01 (m, 1 H), 7.58 (d, 1 H), 6.16-6.86 (m, 4 H), 4.74-4.76 (m, 0.4 H), 4.22 (dd, 0.6 H), 3.79-3.89 (m, 6 H), 3.55 (ddd, 0.5 H), 2.80-3.18 (m, 1.5 H), 2.57-2.76 (m, 1 H), 2.25 (s, 3 H) | 393.2 $[M + H]^+$ | 100% |
| 2393 | ($CD_3OD$) δ 8.04-8.14 (m, 1 H), 7.70 (d, 1 H), 6.27-6.98 (m, 4 H), 4.86-4.88 (m, 0.4 H), 4.34 (dd, 0.6 H), 3.90-4.00 (m, 6 H), 3.61-3.74 (m, 0.5 H), 2.92-3.29 (m, 1.5 H), 2.70-2.89 (m, 1 H), 2.37 (s, 3 H) | 393.2 $[M + H]^+$ | 99.0% |
| 2394 | ($CD_3OD$) δ 7.98 (d, 1 H), 7.83 (dd, 1 H), 7.69 (d, 1 H), 7.46 (dd, 1.5 H), 7.11 (ddd, 1 H), 6.98 (s, 0.5 H), 6.70 (dd, 1 H), 6.42-6.64 (m, 1 H), 4.91-5.11 (m, 1 H), 4.10 (s, 3 H), 3.85-3.98 (m, 0.6 H), 3.35-3.43 (m, 0.4 H), 2.78-3.24 (m, 2 H), 2.49-2.71 (m, 3 H) | 430.2 $[M + H]^+$ | 100% |
| 2395 | ($CD_3OD$) δ 7.98 (d, 1 H), 7.83 (d, 1 H), 7.69 (d, 1 H), 7.46 (dd, 1.4 H), 7.11 (ddd, 1 H), 6.98 (s, 0.6 H), 6.70 (dd, 1 H), 6.41-6.65 (m, 1 H), 4.92-5.11 (m, 1 H), 4.10 (s, 3 H), 3.85-3.99 (m, 0.5 H), 3.34-3.45 (m, 0.5 H), 2.79-3.23 (m, 2 H), 2.43-2.71 (m, 3 H) | 430.2 $[M + H]^+$ | 93.5% |
| 2396 | ($CD_3OD$) δ 7.69 (d, 1 H), 7.51-7.63 (m, 1 H), 7.11-7.20 (m, 1 H), 6.90-7.05 (m, 2 H), 6.78-6.87 (m, 1 H), 6.45-6.73 (m, 1 H), 4.36 (dd, 1 H), 4.12 (d, 3 H), 3.69-3.81 (m, 0.5 H), 3.08-3.25 (m, 1 H), 2.92-3.03 (m, 0.5 H), 2.71-2.88 (m, 1 H) | 433.1 $[M + H]^+$ | 100% |

TABLE 2-continued

| Ex. # | $^1$H NMR (400 MHz unless otherwise noted) | LCMS: m/z | % ee |
|---|---|---|---|
| 2397 | ($CD_3OD$) δ 7.69 (d, 1 H), 7.50-7.62 (m, 1 H), 7.11-7.19 (m, 1 H), 6.90-7.04 (m, 2 H), 6.77-6.87 (m, 1 H), 6.43-6.73 (m, 1 H), 4.36 (br dd, 1 H), 4.12 (d, 3 H), 3.71-3.81 (m, 0.5 H), 3.09-3.24 (m, 1 H), 2.91-3.03 (m, 0.5 H), 2.71-2.87 (m, 1 H) | 433.1 $[M + H]^+$ | 96.7% |
| 2398 | ($CD_3OD$) δ 8.30-8.38 (m, 1 H), 7.61-7.74 (m, 1 H), 6.89-7.00 (m, 2 H), 6,79-6.87 (m, 1 H), 6.76 (s, 0,6 H), 6.54 (s, 0.4 H), 4.48 (dd, 1 H), 4.06-4.23 (m, 3 H), 3.68 (ddd, 0.6 H), 3.11-3.29 (m, 1 H), 2.92-3.04 (m, 0,4 H), 2.72-2.88 (m, 1 H) | 435.1 $[M + H]^+$ | 100% |
| 2399 | ($CD_3OD$) δ 8.26-8.40 (m, 1 H), 7.70 (d, 1 H), 6.89-7.03 (m, 2 H), 6.79-6.88 (m, 1 H), 6.76 (s, 0.6 H), 6.54 (s, 0.4 H), 4.48 (dd, 1 H), 4.12-4.17 (m, 3 H), 3.68 (ddd, 0.6 H), 3.11-3.28 (m, 1 H), 2.93-3.04 (m, 0.4 H), 2.72-2.88 (m, 1 H) | 435.1 $[M + H]^+$ | 100% |
| 2400 | ($CD_3OD$) δ 8.35-8.62 (m, 2 H), 7.69 (s, 1 H), 7.00-7.47 (m, 2 H), 6.47-6.90 (m, 3 H), 4.34 (br d, 1 H), 3.73 (br s, 1 H), 2.94-3.25 (m, 1 H), 2.81 (br d, 1 H) | 403.1 $[M + H]^+$ | 97.1% |
| 2401 | ($CD_3OD$) δ 8.39-8.57 (m, 2 H), 7.69 (s, 1 H), 6.97-7.40 (m, 2 H), 6.44-6.88 (m, 3 H), 4.34 (br d, 1 H), 3.73 (br t, 1 H), 2.92-3.25 (m, 1 H), 2.81 (br d, 1 H) | 403.1 $[M + H]^+$ | 97.0% |
| 2402 | ($CDCl_3$) δ 8.04-8.19 (m, 1 H), 7.56 (d, 1 H), 7.33 (dd, 1 H), 6.88-7.01 (m, 2 H), 6.55-6.86 (m, 1 H), 6.29-6.54 (m, 1 H), 4.69-4.98 (m, 1 H), 3.23-3.85 (m, 1 H), 2.91-3.22 (m, 1 H), 2.74 (br d, 1 H), 2.28 (s, 3 H) | 413.2 $[M + H]^+$ | 100% |
| 2403 | ($CDCl_3$) δ 8.03-8.22 (m, 1 H), 7.58 (d, 1 H), 7.28-7.38 (m, 1 H), 6.85-7.03 (m, 2 H), 6.22-6.85 (m, 2 H), 4.63-5.07 (m, 1 H), 4.09-4.20 (m, 3 H), 3.26-3.83 (m, 1 H), 2.89-3.25 (m, 1 H), 2.69-2.86 (m, 1 H), 2.29 (s, 3 H) | 413.2 $[M + H]^+$ | 99.2% |
| 2404 | ($CD_3OD$) δ 8.51 (br s, 1 H), 7.56-7.75 (m, 2 H), 7.44 (s, 0.3 H), 7.12-7.30 (m, 1 H), 6.88 (s, 0.7 H), 6.52-6.72 (m, 1 H), 4.97 (br dd, 1 H), 3.34-3.78 (m, 1 H), 2.70-3.20 (m, 2 H), 2.30 (br d, 1 H), 1.18-1.30 (m, 4 H) | 394.1 $[M + H]^+$ | 100% |
| 2405 | ($CD_3OD$) δ 8.51 (br s, 1 H), 7.56-7.72 (m, 2 H), 7.44 (s, 0.3 H), 7.22 (br t, 1 H), 6.88 (s, 0.7 H), 6.53-6.75 (m, 1 H), 4.97 (br dd, 1 H), 3.34-3.79 (m, 1 H), 2.74-3.19 (m, 2 H), 2.20-2.41 (m, 1 H), 1.18-1.30 (m, 4 H) | 394.2 $[M + H]^+$ | 100% |
| 2406 | ($CD_3OD$) δ 8.63 (d, 1 H), 8.05 (br s, 1 H), 7.69 (s, 1 H), 6.96-7.31 (m, 2 H), 6.56-6.93 (m, 2 H), 4.76-4.81 (m, 0.3 H), 4.36 (br d, 0.7 H), 3.60-3.88 (m, 0.7 H), 3.39 (br s, 0.3 H), 2.72-3.25 (m, 2 H), 1.48-1.75 (m, 6 H) | 511.1 $[M + H]^+$ | 99.2% |
| 2407 | ($CD_3OD$) δ 8.63 (d, 1 H), 8.05 (br s, 1 H), 7.68 (s, 1 H), 6.95-7.30 (m, 2 H), 6.54-6.94 (m, 2 H), 4.84 (br s, 0.3 H), 4.36 (br d, 0.7 H), 3.73 (br t, 0.7 H), 3.39 (br s, 0.3 H), 2.70-3.23 (m, 2 H), 1.49-1.76 (m, 6 H) | 511.2 $[M + H]^+$ | 99.4% |
| 2408 | ($CD_3OD$) δ 7.86 (dd, 1 H), 7.53-7.77 (m, 1.5 H), 7.23-7.42 (m, 2 H), 6.81-7.04 (m, 1 H), 6.67 (s, 0.5 H), 4.96-5.02 (m, 1 H), 3.82-4.00 (m, 0.5 H), 2.93-3.32 (m, 1.5 H), 2.85 (dd, 1 H), 1.49 (d, 9 H) | 460.2 $[M + H]^+$ | 100% |
| 2409 | ($CD_3OD$) δ 7.75 (dd, 1 H), 7.36-7.65 (m, 1.5 H), 7.09-7.31 (m, 2 H), 6.71-6.91 (m, 1 H), 6.55 (s, 0.5 H), 4.85-4.92 (m, 1 H), 3.71-3.88 (m, 0.5 H), 2.82-3.20 (m, 1.5 H), 2.73 (dd, 1 H), 1.37 (d, 9 H) | 460.2 $[M + H]^+$ | 99.6% |
| 2410 | ($CD_3OD$) δ 8.64 (br s, 1 H), 7.86-8.18 (m, 1 H), 7.69 (br s, 1 H), 6.51-7.21 (m, 4 H), 4.47 (br d, 0.4 H), 4.11 (br d, 3 H), 3.67 (br s, 0.6 H), 2.64-3.25 (m, 3 H) | 467.2 $[M + H]^+$ | 100% |
| 2411 | ($CD_3OD$) δ 8.60-8.68 (m, 1 H), 7.89-8.21 (m, 1 H), 7.70 (d, 1 H), 6.63-7.13 (m, 4 H), 4.47 (dd, 0.4 H), 4.04-4.18 (m, 3 H), 3.67 (ddd, 0.6 H), 2.68-3.28 (m, 3 H) | 467.2 $[M + H]^+$ | 100% |
| 2412 | ($CD_3OD$) δ 7.71 (d, 1 H), 7.54-7.66 (m, 1 H), 7.14-7.23 (m, 1 H), 7.05 (d, 1 H), 6.96 (br s, 1 H), 6,46-6.86 (m, 1 H), 4.96 (br d, 0.5 H), 4.41 (dd, 0.5 H), 4.18 (d, 3 H), 3.73-3.85 (m, 0.5 H), 2.76-3.26 (m, 2.5 H) | 451.1 $[M + H]^+$ | 100% |
| 2413 | ($CD_3OD$) δ 7.57-7.63 (m, 1 H), 7.42-7.53 (m, 1 H), 7.02-7.11 (m, 1 H), 6.94 (d, 1 H), 6.84 (br s, 1 H), 6.36-6.71 (m, 1 H), 4.84 (br d, 0.5 H), 4.29 (br dd, 0.5 H), 4.06 (d, 3 H), 3.62-3.72 (m, 0.5 H), 2.64-3.12 (m, 2.5 H) | 451.1 $[M + H]^+$ | 98.4% |
| 2414 | ($CD_3OD$) δ 8.85-8.98 (m, 1 H), 8.77 (d, 1 H), 8.30 (d, 1 H), 8.08 (t, 1 H), 7.63-7.83 (m, 3 H), 7.29-7.53 (m, 1.4 H), 6.79-6.99 (m, 1.6 H), 4.93-5.04 (m, 1 H), 3.38-3.86 (m, 1 H), 2.95-3.26 (m, 1 H), 2.85 (br d, 1 H) | 481.2 $[M + H]^+$ | 100% |
| 2415 | ($CD_3OD$) δ 8.84-8.99 (m, 1 H), 8.77 (d, 1 H), 8.30 (d, 1 H), 8.08 (t, 1 H), 7.63-7.82 (m, 3 H), 7.31-7.52 (m, 1.4 H), 6.78-6.98 (m, 1.6 H), 4.95-5.06 (m, 1 H), 3.42-3.85 (m, 1 H), 2.93-3.26 (m, 1 H), 2.85 (br d, 1 H) | 481.1 $[M + H]^+$ | 99.8% |
| 2416 | ($CD_3OD$) δ 8.87-8.95 (m, 1 H), 8.35-8.43 (m, 1 H), 8.05-8.13 (m, 1 H), 7.67-7.81 (m, 2 H), 7.58 (s, 0.3 H), 7.31-7.38 (m, 1 H), 6.95 (s, 0.7 H), 6.76-6.84 (m, 1 H), 5.10 (dd, 1 H), 4.00 (s, 3 H), 3.37-3.81 (m, 1 H), 2.95-3.21 (m, 1 H), 2.78-2.87 (m, 1 H) | 484.2 $[M + H]^+$ | 100% |

TABLE 2-continued

| Ex. # | $^1$H NMR (400 MHz unless otherwise noted) | LCMS: m/z | % ee |
|---|---|---|---|
| 2417 | ($CD_3OD$) δ 8.85-8.99 (m, 1 H), 8.38 (s, 1 H), 8.04-8.14 (m, 1 H), 7.63-7.82 (m, 2 H), 7.58 (s, 0.3 H), 7.29-7.39 (m, 1 H), 6.94 (s, 0.7 H), 6.74-6.85 (m, 1 H), 5.10 (br dd, 1 H), 4.00 (s, 3 H), 3.37-3.84 (m, 1 H), 2.93-3.22 (m, 1 H), 2.75-2.91 (m, 1 H) | 484.2 $[M + H]^+$ | 98.9% |
| 2418 | ($CD_3OD$) δ 7.64-8.07 (m, 2 H), 7.20-7.47 (m, 2 H), 6.41-7.09 (m, 2 H), 4.20 (dd, 1 H), 3.90 (d, 3 H), 3.62-3.78 (m, 0.5 H), 3.22 (td, 4.5 Hz, 0.5 H), 2.90-3.15 (m, 1 H), 2.65-2.89 (m, 1 H), 1.92-2.10 (m, 1 H), 0.77-1.11 (m, 4 H) | 457.2 $[M + H]^+$ | 95.3% |
| 2419 | ($CD_3OD$) δ 7.59-7.99 (m, 2 H), 7.15-7.54 (m, 2 H), 6.44-7.04 (m, 2 H), 4.03-4.29 (m, 1 H), 3.89 (d, 3 H), 3.67-3.76 (m, 0.5 H), 3.22 (td, 4.6 Hz, 0.5 H), 2.89-3.13 (m, 1 H), 2.60-2.89 (m, 1 H), 1.91-2.13 (m, 1 H), 0.83-1.03 (m, 4 H) | 457.2 $[M + H]^+$ | 81.0% |
| 2420 | ($CD_3OD$) δ 8.86-8.96 (m, 1 H), 7.72-7.81 (m, 1 H), 7.69 (s, 1 H), 7.29-7.45 (m, 1.3 H), 6.68-7.02 (m, 1.7 H), 4.93-5.01 (m, 1 H), 3.35-3.80 (m, 1 H), 2.94-3.20 (m, 1 H), 2.82 (br dd, 1 H), 1.84-1.93 (m, 6 H) | 464.2 $[M + H]^+$ | 99.5% |
| 2421 | ($CD_3OD$) δ 8.86-8.96 (m, 1 H), 7.72-7.81 (m, 1 H), 7.69 (s, 1 H), 7.31-7.44 (m, 1.3 H), 6.64-7.04 (m, 1.7 H), 4.97 (br dd, 1 H), 3.35-3.81 (m, 1 H), 2.93-3.20 (m, 1 H), 2.82 (br dd, 1 H), 1.78-1.97 (m, 6 H) | 464.2 $[M + H]^+$ | 98.2% |
| 2422 | ($CD_3OD$) δ 7.86 (br d, 1 H), 7.66 (s, 1 H), 7.31-7.37 (m, 1 H), 7.22-7.30 (m, 1 H), 6.84 (br s, 2 H), 4.78 (br s, 1 H), 4.36 (br s, 1 H), 3.87 (br s, 0.5 H), 3.34-3.52 (m, 0.5 H), 3.05 (br s, 1 H), 2.79 (dd, 3.6 Hz, 1 H), 2.34 (s, 3 H), 1.56 (br s, 3 H) | 461.2 $[M + H]^+$ | 99.2% |
| 2423 | ($CD_3OD$) δ 7.85 (br d, 1 H), 7.65 (s, 1 H), 7.31-7.40 (m, 1 H), 7.22-7.30 (m, 1 H), 6.83 (br s, 2 H), 4.68-4.77 (m, 1 H), 4.35 (br s, 1 H), 3.87 (br s, 0.5 H), 3.48 (br s, 0.5 H), 2.91-3.15 (m, 1 H), 2.68-2.87 (m, 1 H), 2.34 (s, 3 H), 1.56 (br s, 3 H) | 461.2 $[M + H]^+$ | 99.7% |
| 2424 | ($CD_3OD$) δ 8.63 (d, 2 H), 8.00 (d, 1 H), 7.56-7.67 (m, 2 H), 7.40-7.45 (m, 1 H), 7.19 (t, 1 H), 7.02-7.09 (m, 2 H), 6.63 (br s, 2 H), 4.63 (br s, 1 H), 3.48 (br s, 1 H), 3.00-3.10 (m, 1 H), 2.75 (dd, 1 H) | 418.1 [M + H]+ | 96.8% |
| 2425 | ($CD_3OD$) δ 8.63 (d, 2 H), 8.00 (d, 1 H), 7.55-7.67 (m, 2 H), 7.39-7.47 (m, 1 H), 7.18 (t, 1 H), 7.02-7.11 (m, 2 H), 6.64 (br s, 2 H), 4.64 (br s, 1 H), 3.48 (br s, 1 H), 3.00-3.10 (m, 1 H), 2.75 (dd, 1 H) | 418.2 [M + H]+ | 98.7% |
| 2426 | ($CD_3OD$) δ 9.02 (s, 1 H), 8.36 (s, 2 H), 7.35-7.74 (m, 2.3 H), 7.02-7.18 (m, 1 H), 6.65-6.93 (m, 1.7 H), 6.41-6.58 (m, 1 H), 4.94 (br dd, 1 H), 3.59-3.78 (m, 0.6 H), 3.25-3.40 (m, 0.4 H), 2.83-3.13 (m, 1 H), 2.77 (br s, 1 H) | 470.1 $[M + H]^+$ | 100% |
| 2427 | ($CD_3OD$) δ 9.14 (s, 1 H), 8.37-8.53 (m, 2 H), 7.54-7.77 (m, 2.3 H), 7.15-7.30 (m, 1 H), 6.80-7.03 (m, 1.7 H), 6.53-6.71 (m, 1 H), 4.92-5.13 (m, 1 H), 3.73-3.86 (m, 0.6 H), 3.38-3.52 (m, 0.4 H), 2.94-3.26 (m, 1 H), 2.86 (br d, 1 H) | 470.1 $[M + H]^+$ | 99.1% |
| 2428 | ($CD_3OD$) δ 9.13 (s, 1 H), 8.47 (s, 1 H), 7.80-7.98 (m, 1 H), 7.76 (d, 1 H), 7.57 (s, 0.5 H), 7.22-7.44 (m, 2 H), 6.99 (s, 0.5 H), 6.65-6.92 (m, 1 H), 4.96-5.17 (m, 1 H), 3.92-4.04 (m, 0.5 H), 3.36 (br d, 0.5 H), 2.86-3.26 (m, 2 H) | 538.1 $[M + H]^+$ | 100% |
| 2429 | ($CD_3OD$) δ 9.01 (s, 1 H), 8.34 (s, 1 H), 7.68-7.81 (m, 1 H), 7.62 (br d, 1 H), 7.45 (s, 0.5 H), 7.07-7.29 (m, 2 H), 6.87 (s, 0.5 H), 6.51-6.78 (m, 1 H), 4.84-5.07 (m, 1 H), 3.79-3.91 (m, 0.5 H), 3.24 (br d, 0.5 H), 2.70-3.13 (m, 2 H) | 538.1 $[M + H]^+$ | 99.4% |
| 2430 | ($CD_3OD$) δ 7.20-7.90 (m, 4.5 H), 6.52-7.03 (m, 1.5 H), 4.92-5.05 (m, 1 H), 3.78-3.98 (m, 1,5 H), 2.80-3.28 (m, 2.5 H), 2.39-2.61 (m, 4 H), 1.98-2.29 (m, 2 H) | 458.1 $[M + H]^+$ | 100% |
| 2431 | ($CD_3OD$) δ 7.21-7.88 (m, 4.5 H), 6.56-7.03 (m, 1.5 H), 4.92-5.04 (m, 1 H), 3.72-3.99 (m, 1.5 H), 2.80-3.25 (m, 2.5 H), 2.40-2.57 (m, 4 H), 1.96-2.27 (m, 2 H) | 458.2 $[M + H]^+$ | 94.4% |
| 2432 | ($CD_3OD$) δ 8.33 (d, 1 H), 7.66 (s, 1 H), 6.95 (dd, 1 H), 6.82 (td, 1 H), 6.64 (s, 1 H), 6.25 (s, 1 H), 4.19 (dd, 1 H), 3.67 (ddd, 1 H), 2.96-3.08 (m, 1 H), 2.78 (br dd, 1 H), 1.99-2.11 (m, 1 H), 0.98-1.16 (m, 4 H) | 366.2 $[M + H]^+$ | 98.2% |
| 2433 | ($CD_3OD$) δ 8.33 (d, 1 H), 7.67 (s, 1 H), 6.93-7.03 (m, 1 H), 6.82 (td, 1 H), 6.64 (s, 1 H), 6.25 (s, 1 H), 4.19 (dd, 1 H), 3.67 (ddd, 1 H), 2.90-3.08 (m, 1 H), 2.78 (dd, 1 H), 1.97-2.16 (m, 1 H), 0.89-1.18 (m, 4 H) | 366.2 $[M + H]^+$ | 98.8% |
| 2434 | ($CD_3OD$) δ 8.25-8.90 (m, 3 H), 8.08 (s, 1 H), 7.87-8.01 (m, 2 H), 7.57-7.78 (m, 2 H), 6.48-7.07 (m, 4 H), 4.93-5.08 (m, 1 H), 3.95 (s, 3 H), 3.41-3.84 (m, 1 H), 2.72-3.15 (m, 2 H) | 482.2 $[M + H]^+$ | 97.7% |
| 2435 | ($CD_3OD$) δ 8.26-8.89 (m, 3 H), 7.80-8.13 (m, 3 H), 7.55-7.76 (m, 2 H), 6.54-7.03 (m, 4 H), 4.92-5.07 (m, 1 H), 3.82-4.08 (m, 3 H), 3.40-3.81 (m, 1 H), 2.72-3.13 (m, 2 H) | 482.2 $[M + H]^+$ | 98.3% |
| 2436 | ($CD_3OD$) δ 8.62 (s, 1.6 H), 8.17-8.52 (m, 1.4 H), 7.92 (s, 1 H), 7.69 (s, 1 H), 7.44 (d, 1 H), 7.01 (br d, 1 H), 6.81 (br t, 1 H), 6.45-6.65 (m, 1 H), 6.43-7.20 (m, 1 H), 4.63 (br s, 1 H), 4.54 (s, 2 H), 3.52-3.93 (m, 1 H), 3.44 (s, 3 H), 3.00-3.15 (m, 1 H), 2.72-2.85 (m, 1 H), 2.46 (s, 3 H) | 444.2 $[M + H]^+$ | 100% |

TABLE 2-continued

| Ex. # | $^1$H NMR (400 MHz unless otherwise noted) | LCMS: m/z | % ee |
|---|---|---|---|
| 2437 | ($CD_3OD$) δ 8.22-8.88 (m, 3 H), 7.97 (d, 1 H), 7.76 (br d, 1 H), 7.44 (dd, 1 H), 6.35-7.08 (m, 4 H), 4.58-4.75 (m, 1 H), 4.49-4.57 (m, 2 H), 3.50-3.89 (m, 1 H), 3.44 (s, 3 H), 3.00-3.17 (m, 1 H), 2.71-2.86 (m, 1 H), 2.46 (s, 3 H) | 442.2 $[M + H]^+$ | 90.1% |
| 2438 | ($CD_3OD$) δ 8.88 (s, 2 H), 8.11 (s, 1 H), 7.85-8.04 (m, 3 H), 7.59-7.77 (m, 2 H), 7.21-7.53 (m, 2 H), 6.30-7.08 (m, 2 H), 4.65-4.80 (m, 1 H), 3.97 (s, 3 H), 3.37-3.51 (m, 1 H), 3.03-3.16 (m, 1 H), 2.78 (br dd, 1 H) | 532.2 $[M + H]^+$ | 100% |
| 2439 | ($CD_3OD$) δ 8.88 (s, 2 H), 8.12 (s, 1 H), 7.85-8.03 (m, 3 H), 7.61-7.75 (m, 2 H), 7.28-7.52 (m, 2 H), 6.39-7.11 (m, 2 H), 4.66-4.78 (m, 1 H), 3.97 (s, 3 H), 3.36-3.52 (m, 1 H), 3.04-3.16 (m, 1 H), 2.78 (br dd, 1 H) | 532.2 $[M + H]^+$ | 99.6% |
| 2440 | ($CD_3OD$) δ 8.68 (d, 1 H), 8.13 (d, 1 H), 8.01 (td, 1 H), 7.84 (d, 1 H), 7.69 (s, 1 H), 7.55 (ddd, 1 H), 7.17-7.37 (m, 2 H), 6.80 (s, 1 H), 6.55 (s, 1 H), 4.45 (dd, 1 H), 3.74-3.94 (m, 1 H), 3.00-3.16 (m, 1 H), 2.86 (dd, 1 H) | 453.1 $[M + H]^+$ | 100% |
| 2441 | ($CD_3OD$) δ 8.67 (d, 1 H), 8.12 (d, 1 H), 8.00 (td, 1 H), 7.83 (d, 1 H), 7.67 (s, 1 H), 7.54 (ddd, 1 H), 7.12-7.34 (m, 2 H), 6.78 (s, 1 H), 6.53 (s, 1 H), 4.44 (dd, 1 H), 3.66-3.94 (m, 1 H), 2.96-3.22 (m, 1 H), 2.85 (dd, 1 H) | 453.1 $[M + H]^+$ | 98.3% |
| 2442 | ($CD_3OD$) δ 8.29 (d, 1 H), 7.67 (s, 1 H), 6.96 (d, 1 H), 6.77 (1, 1 H), 6.54 (s, 1 H), 6.30 (s, 1 H), 4.21 (dd, 1 H), 3.59-3.85 (m, 1 H), 2.95-3.14 (m, 1 H), 2.78 (dd, 1 H), 2.42 (d, 3 H), 2.40 (d, 3 H) | 336.2 $[M + H]^+$ | 100% |
| 2443 | ($CD_3OD$) δ 8.31 (br d, 1 H), 7.67 (s, 1 H), 7.00 (d, 1 H), 6.80 (t, 1 H), 6.54 (s, 1 H), 6.30 (s, 1 H), 4.22 (dd, 1 H), 3.70 (ddd, 1 H), 2.96-3.12 (m, 1 H), 2.79 (br dd, 1 H), 2.75 (s, 3 H), 2.43 (s, 3 H) | 336.2 $[M + H]^+$ | 99.7% |
| 2444 | ($CD_3OD$) δ 8.22-8.57 (m, 2 H), 8.12 (s, 0.8 H), 7.47-7.84 (m, 1 H), 7.18-7.29 (m, 0.2 H), 6.91-7.15 (m, 2 H), 6.66-6.91 (m, 2 H), 5.10 (br dd, 1 H), 4.02 (s, 3 H), 3.68-3.87 (m, 0.6 H), 3.36-3.48 (m, 0.4 H), 2.94-3.25 (m, 1 H), 2.77-2.92 (m, 1 H) | 482.2 $[M + H]^+$ | 100% |
| 2445 | ($CD_3OD$) δ 8.24-8.57 (m, 2 H), 8.12 (s, 0.8 H), 7.56-7.78 (m, 1 H), 7.17-7.30 (m, 0.2 H), 6.91-7.14 (m, 2 H), 6.66-6.90 (m, 2 H), 5.10 (dd, 1 H), 4.02 (s, 3 H), 3.67-3.89 (m, 0.6 H), 3.37-3.48 (m, 0.4 H), 2.95-3.27 (m, 1 H), 2.75-2.95 (m, 1 H) | 482.1 $[M + H]^+$ | 98.6% |
| 2446 | ($CD_3OD$) δ 8.90-8.96 (m, 1 H), 8.37 (s, 1 H), 8.03-8.11 (m, 1 H), 7.82 (s, 0.2 H), 7.69 (d, 1.5 H), 7.51-7.57 (m, 0.5 H), 6.77-6.96 (m, 1.8 H), 6.57-6.69 (m, 2 H), 5.06 (br dd, 1 H), 3.94-3.98 (m, 3 H), 3.78 (br s, 0.6 H), 3.37-3.50 (m, 0.4 H), 2.84-3.21 (m, 2 H) | 482.2 $[M + H]^+$ | 97.1% |
| 2447 | ($CD_3OD$) δ 8.94 (s, 1 H), 8.37 (s, 1 H), 8.00-8.14 (m, 1 H), 7.82 (s, 0.2 H), 7.65-7.73 (m, 1.5 H), 7.54 (br d, 0.5 H), 6.76-6.99 (m, 1.8 H), 6.57-6.72 (m, 2 H), 5.06 (br dd, 1 H), 3.93-3.99 (m, 3 H), 3.77 (br d, 0.6 H), 3.35-3.50 (m, 0.4 H), 2.85-3.16 (m, 2 H) | 482.1 $[M + H]^+$ | 99.0% |
| 2448 | ($CD_3OD$) δ 9.31-9.40 (m, 1 H), 8.68-8.79 (m, 2 H), 8.16-8.32 (m, 1 H), 7.06-7.67 (m, 1.5 H), 6.61-6.96 (m, 4.5 H), 4.83-4.97 (m, 1 H), 3.69 (ddd, 0.7 H), 3.34 (td, 0.3 H), 2.86-3.15 (m, 1 H), 2.69-2.81 (m, 1 H) | 480.1 $[M + H]^+$ | 96.6% |
| 2449 | ($CD_3OD$) δ 9.31-9.40 (m, 1 H), 8.68-8.79 (m, 2 H), 8.16-8.31 (m, 1 H), 7.08-7.65 (m, 1,5 H), 6.61-6.96 (m, 4.5 H), 4.83-4.98 (m, 1 H), 3.69 (ddd, 0.7 H), 3.34 (td, 0.3 H), 2.87-3.16 (m, 1 H), 2.75 (br d, 1 H) | 480.2 $[M + H]^+$ | 94.9% |
| 2450 | (DMSO-$d_6$) δ 11.99 (br s, 1 H), 8.21-8.74 (m, 3 H), 7.85 (d, 1 H), 7.55 (s, 1 H), 7.24 (dd, 1 H), 6.33-7.07 (m, 4 H), 4.34-4.66 (m, 1 H), 3.84 (s, 3 H), 3.25-3.31 (m, 1 H), 2.85-3.06 (m, 1 H), 2.67 (br s, 1 H), 2.40 (s, 3 H) | 428.1 $[M + H]^+$ | 100% |
| 2451 | (DMSO-$d_6$) δ 11.88-12.17 (m, 1 H), 8.20-8.87 (m, 3 H), 7.85 (d, 1 H), 7.55 (s, 1 H), 7.17-7.33 (m, 1 H), 6.37-7.09 (m, 4 H), 4.34-4.69 (m, 1 H), 3.84 (s, 3 H), 3.33 (br s, 1 H), 2.86-3.05 (m, 1 H), 2.63-2.73 (m, 1 H), 2.34-2.44 (m, 3 H) | 428.2 $[M + H]^+$ | 100% |
| 2452 | ($CD_3OD$) δ 9.31 (s, 2 H), 8.67 (d, 1 H), 7.84-8.15 (m, 5 H), 7.65 (s, 1 H), 7.25-7.51 (m, 3 H), 6.66 (br s, 2 H), 4.66 (br s, 1 H), 3.36-3.64 (m, 1 H), 3.08 (br s, 1 H), 2.77 (dd, 1 H) | 529.2 $[M + H]^+$ | 100% |
| 2453 | ($CD_3OD$) δ 9.31 (s, 2 H), 8.67 (d, 1 H), 7.87-8.12 (m, 5 H), 7.65 (s, 1 H), 7.15-7.52 (m, 3 H), 6.68 (br s, 2 H), 4.67 (br s, 1 H), 3.48 (br s, 1 H), 2.98-3.20 (m, 1 H), 2.77 (dd, 1 H) | 529.2 $[M + H]^+$ | 100% |
| 2454 | ($CD_3OD$) δ 8.39 (d, 2 H), 7.48-7.70 (m, 2 H), 7.07-7.25 (m, 2 H), 6.99 (d, 1 H), 6.56-6.72 (m, 2 H), 5.06 (br dd, 1 H), 3.50-3.65 (m, 1 H), 2.82-2.98 (m, 1 H), 2.70 (dd, 1 H) | 352.1 $[M + H]^+$ | 100% |
| 2455 | ($CD_3OD$) δ 8.27 (d, 2 H), 7.36-7.56 (m, 2 H), 6.95-7.16 (m, 2 H), 6.86 (d, 1 H), 6.46-6.62 (m, 2 H), 4.93-4.98 (m, 1 H), 3.38-3.50 (m, 1 H), 2.70-2.86 (m, 1 H), 2.58 (dd, 1 H) | 352.1 $[M + H]^+$ | 99.2% |
| 2456 | ($CD_3OD$) δ 8.33 (d, 1 H), 7.56 (s, 1 H), 7.19 (d, 1 H), 6.74 (t, 1 H), 6.55 (s, 1 H), 6.18 (s, 1 H), 4.12 (dd, 1 H), 3.58 (ddd, 1 H), 2.84-3.00 (m, 1 H), 2.61-2.76 (m, 1 H), 2.33 (s, 3 H) | 356.1 $[M + H]^+$ | 100% |
| 2457 | ($CD_3OD$) δ 8.33 (d, 1 H), 7.56 (s, 1 H), 7.19 (d, 1 H), 6,74 (t, 1 H), 6.55 (s, 1 H), 6.19 (s, 1 H), 4.12 (dd, 1 H), 3.58 (ddd, 1 H), 2.86-2.98 (m, 1 H), 2.67 (br dd, 1 H), 2.33 (s, 3 H) | 356.1 $[M + H]^+$ | 93.9% |

TABLE 2-continued

| Ex. # | $^1$H NMR (400 MHz unless otherwise noted) | LCMS: m/z | % ee |
|---|---|---|---|
| 2458 | ($CD_3OD$) δ 9.05-9.25 (m, 1 H), 8.48 (s, 1 H), 8.29-8.42 (m, 1 H), 7.71 (s, 1 H), 7.56 (s, 0.3 H), 7.17-7.28 (m, 0.3 H), 6.94-7.08 (m, 2.2 H), 6.81-6.91 (m, 1.2 H), 6.69-6.79 (m, 1 H), 5.08 (dd, 0.7 H), 4.95 (br d, 0.3 H), 3.72-3.88 (m, 0.7 H), 3.43 (td, 0.3 H), 3.12-3.26 (m, 0.7 H), 2.95-3.08 (m, 0.3 H), 2.78-2.92 (m, 1 H) | 536.1 $[M + H]^+$ | 100% |
| 2459 | ($CD_3OD$) δ 9.05-9.26 (m, 1 H), 8.48 (s, 1 H), 8.29-8.42 (m, 1 H), 7.72 (s, 1 H), 7.56 (s, 0.3 H), 7.18-7.26 (m, 0.3 H), 6.94-7.08 (m, 2.2 H), 6.81-6.92 (m, 1.2 H), 6.69-6.79 (m, 1 H), 5.08 (dd, 0.7 H), 4.95 (br d, 0.3 H), 3.71-3.86 (m, 0.7 H), 3.43 (td, 0.3 H), 3.13-3.26 (m, 0.7 H), 2.96-3.09 (m, 0.3 H), 2.79-2.92 (m, 1 H) | 536.2 $[M + H]^+$ | 99.9% |
| 2460 | ($CD_3OD$) δ 8.45 (d, 1 H), 7.43-7.85 (m, 2 H), 7.15-7.28 (m, 1 H), 6.78-7.13 (m, 2 H), 6.58 (s, 1 H), 6.38 (s, 1 H), 4.32 (dd, 1 H), 3.77 (ddd, 1 H), 2.97-3.18 (m, 1 H), 2.83 (br dd, 1 H) | 358.1 $[M + H]^+$ | 99.3% |
| 2461 | ($CD_3OD$) δ 8.44 (d, 1 H), 7.44-7.84 (m, 2 H), 7.20 (dd, 1 H), 6.78-7.13 (m, 2 H), 6.57 (s, 1 H), 6.37 (s, 1 H), 4.31 (dd, 1 H), 3.76 (ddd, 1 H), 2.95-3.16 (m, 1 H), 2.82 (br dd, 1 H) | 358.2 $[M + H]^+$ | 99.4% |
| 2462 | ($CD_3OD$) δ 8.07-9.10 (m, 2 H), 7.85 (d, 1 H), 7.75 (d, 1 H), 7.40-7.66 (m, 2 H), 7.27-7.35 (m, 1 H), 7.16-7.23 (m, 2 H), 6.62 (br s, 2 H), 4.61-4.73 (m, 1 H), 3.36-3.98 (m, 1 H), 2.98-3.10 (m, 1 H), 2.75 (dd, 1 H), 1.96-2.05 (m, 1 H), 0.98-1.06 (m, 2 H), 0.74-0.80 (m, 2 H) | 474.2 [M + H]+ | 100% |
| 2463 | ($CD_3OD$) δ 8.41 (s, 2 H), 7.85 (d, 1 H), 7.74 (d, 1 H), 7.43-7.68 (m, 2 H), 7.26-7.34 (m, 1 H), 7.16-7.24 (m, 2 H), 6.62 (br s, 2 H), 4.60-4.72 (m, 1 H), 3.32-3.77 (m, 1 H), 2.99-3.10 (m, 1 H), 2.75 (dd, 1 H), 1.97-2.04 (m, 1 H), 0.99-1.05 (m, 2 H), 0.74-0.80 (m, 2 H) | 474.2 [M + H]+ | 99.4% |
| 2464 | (DMSO-$d_6$) δ 12.02 (br s, 1 H), 8.50 (d, 2 H), 7.88 (d, 1 H), 7.69 (br d, 1 H), 7.56 (s, 1 H), 7.07-7.33 (m, 3 H), 6.70 (br d, 2 H), 4.33-4.72 (m, 1 H), 3.84 (s, 4 H), 2.93 (br d, 1 H), 2.56-2.75 (m, 1 H) | 448.1 $[M + H]^+$ | 99.8% |
| 2465 | (DMSO-$d_6$) δ 12.02 (br s, 1 H), 8.51 (s, 2 H), 7.88 (d, 1 H), 7.69 (br d, 1 H), 7.56 (s, 1 H), 7.09-7.36 (m, 3 H), 6.33-6.93 (m, 2 H), 4.50 (br d, 1 H), 3.84 (s, 4 H), 2.95 (br s, 1 H), 2.57-2.78 (m, 1 H) | 448.1 $[M + H]^+$ | 99.5% |
| 2466 | ($CD_3OD$) δ 8.59 (d, 1 H), 7.68 (s, 1 H), 7.35-7.50 (m, 1 H), 6.81-7.15 (m, 2 H), 6.71 (s, 1 H), 6.33 (s, 1 H), 4.24 (dd, 1 H), 3.69 (ddd, 1 H), 2.98-3.11 (m, 1 H), 2.79 (dd, 1 H), 2.45 (s, 3 H) | 372.2 $[M + H]^+$ | 99.6% |
| 2467 | ($CD_3OD$) δ 8.47 (d, 1 H), 7.58 (s, 1 H), 7.32 (d, 1 H), 6.70-7.05 (m, 2 H), 6.60 (s, 1 H), 6.21 (s, 1 H), 4.12 (dd, 1 H), 3.49-3.65 (m, 1 H), 2.85-3.00 (m, 1 H), 2.62-2.74 (m, 1 H), 2.33 (s, 3 H) | 372.1 $[M + H]^+$ | 98.4% |
| 2468 | ($CD_3OD$) δ 9.05 (d, 2 H), 8.43-8.56 (m, 1 H), 7.69-7.75 (m, 2 H), 7.47 (br s, 0.3 H), 7.18-7.26 (m, 1 H), 6.79-7.01 (m, 2.7 H), 5.00 (td, 1 H), 3.78-3.85 (m, 0.6 H), 3.46 (td, 0.4 H), 2.86-3.26 (m, 2 H) | 498.1 $[M + H]^+$ | 100% |
| 2469 | ($CD_3OD$) δ 9.05 (d, 2 H), 8.42-8.53 (m, 1 H), 7.69-7.75 (m, 2 H), 7.47 (s, 0.3 H), 7.18-7.26 (m, 1 H), 6.80-7.01 (m, 2.7 H), 5.00 (td, 1 H), 3.82 (ddd, 0.6 H), 3.46 (td, 0.4 H), 2.85-3.26 (m, 2 H) | 498.1 $[M + H]^+$ | 100% |
| 2470 | ($CD_3OD$) δ 7.99-8.70 (m, 3 H), 7.76 (d, 1 H), 7.54 (s, 1 H), 7.20 (d, 1 H), 6.34-6.87 (m, 4 H), 4.44-4.59 (m, 1 H), 3.84 (s, 3 H), 3.27-3.59 (m, 1 H), 2.62-3.00 (m, 2 H), 2.27 (s, 3 H) | 428.2 $[M + H]^+$ | 100% |
| 2471 | ($CD_3OD$) δ 7.89-8.57 (m, 3 H), 7.74 (br d, 1 H), 7.54 (br s, 1 H), 7.17 (br d, 1 H), 6.29-6.79 (m, 4 H), 4.45-4.60 (m, 1 H), 3.82 (s, 3 H), 3.24-3.59 (m, 1 H), 2.60-3.01 (m, 2 H), 2.25 (br s, 3 H) | 428.2 $[M + H]^+$ | 100% |
| 2472 | ($CD_3OD$) δ 8.21-9.59 (m, 1 H), 7.79-7.95 (m, 3 H), 7.63 (s, 1 H), 7.24-7.45 (m, 3 H), 6.67 (br s, 2 H), 4.64 (br d, 1 H), 3.48 (br s, 1 H), 3.00-3.11 (m, 1 H), 2.95 (s, 6 H), 2.75 (dd, 1 H) | 495.2 $[M + H]^+$ | 99.7% |
| 2473 | ($CD_3OD$) δ 8.91 (br s, 1 H), 7.75-8.01 (m, 3 H), 7.64 (s, 1 H), 7.21-7.46 (m, 3 H), 6.47-6.98 (m, 2 H), 4.64 (br d, 1 H), 3.38-3.82 (m, 1 H), 2.99-3.11 (m, 1 H), 2.95 (s, 6 H), 2.75 (dd, 1 H) | 495.2 $[M + H]^+$ | 99.1% |
| 2474 | ($CD_3OD$) δ 8.26-9.27 (m, 1 H), 7.80-7.96 (m, 2 H), 7.55-7.69 (m, 2 H), 7.36 (dd, 1 H), 7.18 (dd, 1 H), 7.05 (d, 1 H), 6.50-6.96 (m, 2 H), 4.64 (br s, 1 H), 3.42-3.97 (m, 1 H), 3.00-3.15 (m, 1 H), 2.94 (s, 6 H), 2.75 (dd, 1 H) | 461.2 $[M + H]^+$ | 99.5% |
| 2475 | ($CD_3OD$) δ 8.11-9.10 (m, 1 H), 7.77-7.94 (m, 2 H), 7.53-7.70 (m, 2 H), 7.37 (dd, 1 H), 7.11-7.24 (m, 1 H), 7.06 (br d, 1 H), 6.47-6.92 (m, 2 H), 4.64 (br s, 1 H), 3.48 (br s, 1 H), 2.99-3.17 (m, 1 H), 2.95 (s, 6 H), 2.75 (br dd, 1 H) | 461.2 $[M + H]^+$ | 99.5% |
| 2476 | ($CD_3OD$) δ 8.77 (br s, 1 H), 8.54 (s, 2 H), 7.91 (d, 1 H), 7.59-7.72 (m, 2 H), 7.39 (d, 1 H), 6.44-7.13 (m, 3 H), 4.59 (br s, 1 H), 3.48 (br s, 1 H), 3.03-3.12 (m, 1 H), 2.85-2.91 (m, 2 H), 2.78 (br d, 1 H), 2.63-2.70 (m, 2 H), 2.34 (s, 6 H) | 523.2 [M + H]+ | 97.7% |
| 2477 | ($CD_3OD$) δ 8.78 (br s, 1 H), 8.54 (s, 2 H), 7.91 (d, 1 H), 7.56-7.73 (m, 2 H), 7.39 (d, 1 H), 6.41-7.16 (m, 3 H), 4.59 (br s, 1 H), 3.38-3.76 (m, 1 H), 3.02-3.12 (m, 1 H), 2.84-2.90 (m, 2 H), 2.74-2.81 (m, 1 H), 2.62-2.69 (m, 2 H), 2.33 (s, 6 H) | 523.3 [M + H]+ | 98.2% |

TABLE 2-continued

| Ex. # | $^1$H NMR (400 MHz unless otherwise noted) | LCMS: m/z | % ee |
|---|---|---|---|
| 2478 | ($CD_3OD$) δ 8.27-8.76 (m, 3 H), 7.84 (s, 1 H), 7.67 (s, 1 H), 7.42 (dd, 1 H), 6.99-7.06 (m, 1 H), 6.48-6.90 (m, 3 H), 4.96 (br s, 1 H), 3.69 (t, 2 H), 3.34-3.42 (m, 4 H), 3.02-3.14 (m, 1 H), 2.95 (t, 2 H), 2.73-2.84 (m, 1 H), 2.42-2.50 (m, 3 H) | 456.2 $[M + H]^+$ | 100% |
| 2479 | ($CD_3OD$) δ 8.30 (s, 3 H), 7.85-7.95 (m, 1 H), 7.60-7.73 (m, 1 H), 7.42 (dd, 1 H), 6.97-7.06 (m, 1 H), 6.46-6.91 (m, 3 H), 4.94-5.08 (m, 1 H), 3.69 (t, 2 H), 3.37 (s, 4 H), 3.02-3.13 (m, 1 H), 2.89-2.99 (m, 2 H), 2.70-2.83 (m, 1 H), 2.50 (s, 3 H) | 456.2 $[M + H]^+$ | 91.8% |
| 2480 | ($CD_3OD$) δ 8.30 (d, 1 H), 7.67 (s, 1 H), 6.98 (d, 1 H), 6.78 (t, 1 H), 6.54 (s, 1 H), 6.31 (s, 1 H), 4.23 (dd, 1 H), 3.61-3.78 (m, 2 H), 2.98-3.12 (m, 1 H), 2.80 (br dd, 1 H), 2.33-2.52 (m, 7 H), 1.98-2.22 (m, 2 H) | 376.2 $[M + H]^+$ | 99.8% |
| 2481 | ($CD_3OD$) δ 8.30 (br d, 1 H), 7.69 (s, 1 H), 6.98 (br d, 1 H), 6.78 (t, 1 H), 6.54 (s, 1 H), 6.31 (s, 1 H), 4.23 (dd, 1 H), 3.61-3.77 (m, 2 H), 2.97-3.10 (m, 1 H), 2.80 (br dd, 1 H), 2.38-2.46 (m, 7 H), 2.00-2.18 (m, 2 H) | 376.2 $[M + H]^+$ | 99.8% |
| 2482 | ($CD_3OD$) δ 8.57 (d, 1 H), 7.46-7.69 (m, 2 H), 6.88 (t, 1 H), 6.61 (s, 1 H), 6.22 (s, 1 H), 4.15 (dd, 1 H), 3.51-3.67 (m, 2 H), 2.87-3.00 (m, 1 H), 2.70 (dd, 1 H), 2.23-2.35 (m, 4 H), 1.86-2.09 (m, 2 H) | 430.2 $[M + H]^+$ | 100% |
| 2483 | ($CD_3OD$) δ 8.57 (d, 1 H), 7.47-7.59 (m, 2 H), 6.83-6.92 (m, 1 H), 6.61 (s, 1 H), 6.22 (s, 1 H), 4.15 (dd, 1 H), 3.50-3.63 (m, 2 H), 2.87-2.96 (m, 1 H), 2.66-2.73 (m, 1 H), 2.25-2.35 (m, 4 H), 1.88-2.05 (m, 2 H) | 430.1 $[M + H]^+$ | 100% |
| 2484 | ($CD_3OD$) δ 8.46 (d, 1 H), 7.56 (s, 1 H), 7.32 (d, 1 H), 6.69-7.02 (m, 2 H), 6.16-6.64 (m, 2 H), 4.13 (dd, 1 H), 3.45-3.66 (m, 2 H), 2.85-2.98 (m, 1 H), 2.70 (dd, 1 H), 2.22-2.37 (m, 4 H), 1.85-2.08 (m, 2 H) | 412.1 $[M + H]^+$ | 99.9% |
| 2485 | ($CD_3OD$) δ 8.49 (br d, 1 H), 7.59 (s, 1 H), 7.35 (br d, 1 H), 6.74-7.04 (m, 2 H), 6.64 (s, 1 H), 6.24 (s, 1 H), 4.16 (dd, 1 H), 3.50-3.71 (m, 2 H), 2.89-3.01 (m, 1 H), 2.73 (br dd, 1 H), 2.24-2.40 (m, 4 H), 1.92-2.11 (m, 2 H) | 412.2 $[M + H]^+$ | 99.6% |
| 2486 | ($CD_3OD$) δ 7.67-7.79 (m, 2 H), 7.15-7.51 (m, 3 H), 6.69 (s, 1 H), 6.41 (s, 1 H), 4.37 (dd, 1 H), 3.73-3.87 (m, 1 H), 3.01-3.14 (m, 1 H), 2.86 (dd, 1 H) | 426.1 $[M + H]^+$ | 100% |
| 2487 | ($CD_3OD$) δ 7.64-7.80 (m, 2 H), 7.15-7.51 (m, 3 H), 6.69 (s, 1 H), 6.41 (s, 1 H), 4.37 (dd, 1 H), 3.74-3.87 (m, 1 H), 3.02-3.14 (m, 1 H), 2.86 (dd, 1 H) | 426.1 $[M + H]^+$ | 99.0% |
| 2488 | ($CD_3OD$) δ 8.58-8.75 (m, 1 H), 8.39 (s, 1 H), 8.10 (s, 1 H), 7.45-7.75 (m, 2.4 H), 7.17-7.37 (m, 1 H), 6.92 (s, 0.6 H), 6.55-6.75 (m, 1 H), 5.09 (br d, 1 H), 4.00 (s, 3 H), 3.68-3.83 (m, 0.7 H), 3.34-3.44 (m, 0.3 H), 3.07-3.23 (m, 1 H), 2.71-2.91 (m, 1 H) | 494.1 $[M + H]^+$ | 100% |
| 2489 | ($CD_3OD$) δ 8.59-8.75 (m, 1 H), 8.40 (s, 1 H), 8.10 (s, 1 H), 7.70 (s, 1 H), 7.47-7.62 (m, 1.4 H), 7.23-7.39 (m, 1 H), 6.93 (s, 0.6 H), 6.57-6.75 (m, 1 H), 5.08 (dd, 1 H), 4.02 (s, 3 H), 3.71-3.86 (m, 0.7 H), 3.33-3.46 (m, 0.3 H), 2.93-3.24 (m, 1 H), 2.58-2.89 (m, 1 H) | 494.1 $[M + H]^+$ | 99.4% |
| 2490 | ($CD_3OD$) δ 7.86 (d, 1 H), 7.73 (s, 1 H), 7.25-7.40 (m, 2 H), 6.74 (s, 1 H), 6.40 (s, 1 H), 4.37 (dd, 1 H), 3.73 (td, 1 H), 3.02-3.14 (m, 1 H), 2.86 (dd, 1 H) | 444.1 $[M + H]^+$ | 100% |
| 2491 | ($CD_3OD$) δ 7.86 (d, 1 H), 7.71 (s, 1 H), 7.22-7.42 (m, 2 H), 6.73 (s, 1 H), 6.40 (s, 1 H), 4.37 (dd, 1 H), 3.65-3.79 (m, 1 H), 3.00-3.13 (m, 1 H), 2.86 (dd, 1 H) | 444.1 $[M + H]^+$ | 98.2% |
| 2492 | ($CD_3OD$) δ 7.69 (s, 1 H), 7.62 (dd, 1 H), 7.20 (dd, 1 H), 7.06 (dd, 1 H), 6.71 (s, 1 H), 6.42 (s, 1 H), 4.37 (dd, 1 H), 3.83 (ddd, 1 H), 3.00-3.16 (m, 1 H), 2.86 (dd, 1 H) | 410.1 $[M + H]^+$ | 95.7% |
| 2493 | ($CD_3OD$) δ 7.57 (s, 1 H), 7.50 (dd, 1 H), 7.08 (dd, 1 H), 6.94 (dd, 1 H), 6.59 (s, 1 H), 6.30 (s, 1 H), 4.25 (dd, 1 H), 3.71 (ddd, 1 H), 2.89-3.04 (m, 1 H), 2.74 (dd, 1 H) | 410.1 $[M + H]^+$ | 84.1% |
| 2494 | ($CD_3OD$) δ 8.20-8.33 (m, 1 H), 7.70 (s, 1 H), 7.49 (br s, 0.3 H), 6.96 (s, 0.7 H), 6.70-6.85 (m, 3 H), 4.93-5.01 (m, 1 H), 3.77 (ddd, 0.7 H), 3.41 (td, 0.3 H), 2.93-3.21 (m, 1 H), 2.77-2.89 (m, 1 H), 2.60-2.70 (m, 3 H), 1.90-2.32 (m, 1 H), 0.96-1.10 (m, 2 H), 0.69-0.85 (m, 2 H) | 390.2 $[M + H]^+$ | 100% |
| 2495 | ($CD_3OD$) δ 8.21-8.33 (m, 1 H), 7.70 (s, 1 H), 7.45-7.53 (m, 0.3 H), 6.96 (s, 0.7 H), 6.69-6.86 (m, 3 H), 4.98 (br d, 1 H), 3.77 (ddd, 0.6 H), 3.39-3.46 (m, 0.4 H), 2.93-3.21 (m, 1 H), 2.79-2.90 (m, 1 H), 2.63-2.68 (m, 3 H), 2.04-2.17 (m, 1 H), 0.99-1.13 (m, 2 H), 0.75-0.87 (m, 2 H) | 390.2 $[M + H]^+$ | 100% |
| 2496 | ($CD_3OD$) δ 8.32-8.71 (m, 1 H), 7.49-8.01 (m, 3 H), 7.13-7.29 (m, 1 H), 6.37-6.98 (m, 3 H), 4.68-4.79 (m, 0.5 H), 4.38-4.57 (m, 0.5 H), 3.62-3.84 (m, 0.5 H), 2.93-3.14 (m, 1 H), 2.64-2.92 (m, 1 H), 2.20 (br d, 1 H), 0.92-1.40 (m, 4.5 H) | 375.2 $[M + H]^+$ | 100% |
| 2497 | ($CD_3OD$) δ 8.35-8.60 (m, 1 H), 7.49-8.04 (m, 3 H), 7.13-7.30 (m, 1 H), 6.36-7.03 (m, 3 H), 4.70-4.80 (m, 0.5 H), 4.37-4.56 (m, 0.5 H), 3.62-3.89 (m, 0.5 H), 2.93-3.15 (m, 1 H), 2.65-2.92 (m, 1 H), 2.21 (br d, 1 H), 0.94-1.39 (m, 4.5 H) | 375.2 $[M + H]^+$ | 99.3% |

TABLE 2-continued

| Ex. # | $^1$H NMR (400 MHz unless otherwise noted) | LCMS: m/z | % ee |
|---|---|---|---|
| 2498 | ($CD_3OD$) δ 8.33 (br s, 1 H), 7.79-8.17 (m, 1 H), 7.74 (s, 1 H), 7.67 (s, 1 H), 6.96-7.05 (m, 1 H), 6.83-6.96 (m, 2 H), 6.79 (br t, 1 H), 6.65 (br s, 1 H), 4.80-4.82 (m, 1 H), 3.92-4.12 (m, 3 H), 3.71-3.86 (m, 0.5 H), 3.45-3.54 (m, 0.5 H), 3.01-3.21 (m, 1 H), 2.72-2.92 (m, 1 H), 2.45 (s, 3 H) | 429.2 $[M + H]^+$ | 100% |
| 2499 | ($CD_3OD$) δ 8.24-8.43 (m, 1 H), 7.79-8.16 (m, 1 H), 7.61-7.78 (m, 2 H), 6.99 (br d, 1 H), 6.85-6.95 (m, 2 H), 6.73-6.82 (m, 1 H), 6.51-6.68 (m, 1 H), 4.77 (br dd, 1 H), 4.00 (s, 3 H), 3.66-3.88 (m, 0.6 H), 3.34-3.61 (m, 0.5 H), 2.97-3.20 (m, 0.5 H), 2.71-2.91 (m, 1 H), 2.45 (s, 3 H) | 429.2 $[M + H]^+$ | 100% |
| 2500 | (500 MHz, $CD_3OD$) δ 8.15-8.36 (m, 1 H), 7.54-7.78 (m, 1.5 H), 6.86-7.06 (m, 1.5 H), 6.70-6.85 (m, 1 H), 6.37-6.66 (m, 1 H), 5.09 (dd, 1 H), 3.63-3.79 (m, 0.5 H), 3.34-3.47 (m, 0.5 H), 2.91-3.20 (m, 1 H), 2.73-2.85 (m, 4 H), 2.35-2.49 (m, 3 H) | 380.2 $[M + H]^+$ | 100% |
| 2501 | (500 MHz, $CD_3OD$) δ 8.12-8.41 (m, 1 H), 7.68 (d, 1.5 H), 6.88-7.07 (m, 1.5 H), 6.69-6.81 (m, 1 H), 6.47-6.64 (m, 1 H), 5.09 (dd, 1 H), 3.61-3.78 (m, 0.5 H), 3.32-3.47 (m, 0.5 H), 2.90-3.21 (m, 1 H), 2.73-2.87 (m, 4 H), 2.34-2.45 (m, 3 H) | 380.1 $[M + H]^+$ | 99.4% |
| 2502 | ($CD_3OD$) δ 8.18-8.40 (m, 1.4 H), 8.01-8.17 (m, 2 H), 7.69 (s, 1 H), 7.44-7.64 (m, 2 H), 6.90-7.06 (m, 1.6 H), 6.70-6.84 (m, 1 H), 6.48-6.67 (m, 1 H), 5.49 (dd, 0.5 H), 4.90 (br s, 0.5 H), 3.61-3.86 (m, 0.7 H), 3.44 (td, 0.3 H), 2.98-3.25 (m, 1 H), 2.74-2.88 (m, 1 H), 2.29-2.51 (m, 3 H) | 415.1 $[M + H]^+$ | 100% |
| 2503 | ($CD_3OD$) δ 8.21-8.40 (m, 1.4 H), 8.07-8.19 (m, 2 H), 7.71 (s, 1 H), 7.51-7.66 (m, 2 H), 6.94-7.06 (m, 1.6 H), 6.72-6.85 (m, 1 H), 6.49-6.69 (m, 1 H), 5.44-5.60 (m, 0.5 H), 4.93-4.98 (m, 0.5 H), 3.67-3.86 (m, 0.7 H), 3.41-3.55 (m, 0.3 H), 3.12 (s, 1 H), 2.76-2.91 (m, 1 H), 2.35-2.53 (m, 3 H) | 415.2 $[M + H]^+$ | 99.6% |
| 2504 | ($CD_3OD$) δ 8.17-8.39 (m, 1 H), 7.71-8.05 (m, 1 H), 7.48-7.69 (m, 2 H), 6.52-6.99 (m, 5 H), 4.82-4.97 (m, 1 H), 3.83-4.06 (m, 3 H), 3.56-3.78 (m, 0.6 H), 3.34-3.49 (m, 0.4 H), 2.86-3.12 (m, 1 H), 2.59-2.82 (m, 1 H) | 433.2 $[M + H]^+$ | 100% |
| 2505 | ($CD_3OD$) δ 8.28-8.53 (m, 1 H), 7.84-8.15 (m, 1 H), 7.61-7.82 (m, 2 H), 6.69-7.10 (m, 5 H), 4.95-5.05 (m, 1 H), 4.02 (s, 3 H), 3.70-3.91 (m, 0.5 H), 3.45-3.59 (m, 0.5 H), 3.00-3.24 (m, 1 H), 2.73-2.94 (m, 1 H) | 433.2 $[M + H]^+$ | 96.1% |
| 2506 | ($CD_3OD$) δ 8.73 (br s, 1 H), 8.29 (br s, 1 H), 7.78-8.13 (m, 2 H), 7.58-7.77 (m, 2 H), 6.63-7.12 (m, 3 H), 4.51-4.84 (m, 1 H), 3.99 (s, 3 H), 3.37-3.88 (m, 1 H), 2.71-3.24 (m, 2 H) | 483.2 $[M + H]^+$ | 100% |
| 2507 | ($CD_3OD$) δ 8.73 (br s, 1 H), 8.29 (br s, 1 H), 7.77-8.12 (m, 2 H), 7.58-7.77 (m, 2 H), 6.62-7.10 (m, 3 H), 4.63 (br s, 1 H), 3.98 (s, 3 H), 3.80 (br s, 1 H), 2.78-3.26 (m, 2 H) | 483.2 $[M + H]^+$ | 99.1% |
| 2508 | ($CD_3OD$) δ 8.36 (d, 1 H), 7.67 (s, 1 H), 6.77-7.26 (m, 3 H), 6.64 (s, 1 H), 6.26 (s, 1 H), 4.20 (dd, 1 H), 3.59-3.80 (m, 1 H), 2.95-3.10 (m, 1 H), 2.80 (br dd, 1 H), 2.00-2.18 (m, 1 H), 0.94-1.22 (m, 4 H) | 414.2 $[M + H]^+$ | 100% |
| 2509 | ($CD_3OD$) δ 8.24 (d, 1 H), 7.57 (s, 1 H), 6.64-7.16 (m, 3 H), 6.52 (s, 1 H), 6.14 (s, 1 H), 4.08 (dd, 1 H), 3.47-3.67 (m, 1 H), 2.82-3.01 (m, 1 H), 2.68 (br dd, 1 H), 1.90-2.02 (m, 1 H), 0.86-1.08 (m, 4 H) | 414.2 $[M + H]^+$ | 99.1% |
| 2510 | ($CD_3OD$) δ 9.26 (s, 1 H), 8.60-8.77 (m, 3 H), 7.69 (s, 1 H), 7.59 (br d, 1 H), 6.95 (br t, 1 H), 6.81 (s, 1 H), 6.53 (s, 1 H), 4.46 (br dd, 1 H), 3.73-3.91 (m, 1 H), 3.03-3.18 (m, 1 H), 2.85 (br dd, 1 H) | 454.1 $[M + H]^+$ | 98.7% |
| 2511 | ($CD_3OD$) δ 9.27 (d, 1 H), 8.57-8.79 (m, 3 H), 7.69 (s, 1 H), 7.60 (br d, 1 H), 6.96 (t, 1 H), 6.81 (s, 1 H), 6.54 (s, 1 H), 4.46 (dd, 1 H), 3.71-3.88 (m, 1 H), 2.99-3.21 (m, 1 H), 2.86 (br dd, 1 H) | 454.2 $[M + H]^+$ | 95.4% |
| 2512 | ($CD_3OD$) δ 9.17 (dd, 1 H), 8.10-8.36 (m, 2 H), 7.77 (dd, 1 H), 7.58 (s, 1 H), 6.93 (d, 1 H), 6.56-6.82 (m, 2 H), 6.44 (s, 1 H), 4.37 (dd, 1 H), 3.63-3.86 (m, 1 H), 2.91-3.15 (m, 2 H), 2.75 (br dd, 1 H), 1.21 (t, 6 H) | 428.2 $[M + H]^+$ | 100% |
| 2513 | ($CD_3OD$) δ 9.17 (dd, 1 H), 8.08-8.35 (m, 2 H), 7.77 (dd, 1 H), 7.58 (s, 1 H), 6.92 (d, 1 H), 6.59-6.84 (m, 2 H), 6.44 (s, 1 H), 4.37 (dd, 1 H), 3.63-3.85 (m, 1 H), 2.91-3.14 (m, 2 H), 2.75 (br dd, 1 H), 1.21 (t, 6 H) | 428.2 $[M + H]^+$ | 99.3% |
| 2514 | ($CD_3OD$) δ 8.31-8.38 (m, 1 H), 7.67 (s, 1 H), 6.97 (dd, 1 H), 6.84 (td, 1 H), 6.65 (s, 1 H), 6.25 (s, 1 H), 4.20 (dd, 1 H), 3.62-3.76 (m, 1 H), 2.95-3.09 (m, 1 H), 2.80 (br dd, 1 H), 1.50 (s, 3 H), 1.21-1.29 (m, 2 H), 0.91-0.96 (m, 2 H) | 380.2 $[M + H]^+$ | 100% |
| 2515 | ($CD_3OD$) δ 8.35 (d, 1 H), 7.67 (s, 1 H), 6.97 (dd, 1 H), 6.84 (td, 1 H), 6.58-6.71 (m, 1 H), 6.25 (s, 1 H), 4.20 (dd, 1 H), 3.59-3.80 (m, 1 H), 2.95-3.11 (m, 1 H), 2.80 (dd, 1 H), 1.50 (s, 3 H), 1.21-1.34 (m, 2 H), 0.84-0.98 (m, 2 H) | 380.2 $[M + H]^+$ | 100% |
| 2516 | ($CD_3OD$) δ 9.42 (d, 1 H), 8.78 (s, 2 H), 8.32-8.65 (m, 1 H), 7.65-8.28 (m, 2 H), 6.67-7.17 (m, 4 H), 4.64 (br s, 1 H), 3.83 (br s, 0.5 H), 3.45-3.63 (m, 0.5 H), 2.99-3.30 (m, 1 H), 2.76-2.96 (m, 1 H) | 431.2 $[M + H]^+$ | 100% |

TABLE 2-continued

| Ex. # | $^1H$ NMR (400 MHz unless otherwise noted) | LCMS: m/z | % ee |
|---|---|---|---|
| 2517 | ($CD_3OD$) δ 9.42 (s, 1 H), 8.78 (s, 2 H), 8.31-8.65 (m, 1 H), 7.61-8.28 (m, 2 H), 6.69-7.11 (m, 4 H), 4.82 (br s, 1 H), 3.82 (br s, 0.5 H), 3.40-3.63 (m, 0.5 H), 2.98-3.30 (m, 1 H), 2.78-2.96 (m, 1 H) | 431.2 $[M + H]^+$ | 99.1% |
| 2518 | ($CD_3OD$) δ 8.29 (d, 1 H), 7.66 (s, 1 H), 7.05 (d, 1 H), 6.83 (t, 1 H), 6.60 (s, 1 H), 6.30 (s, 1 H), 4.23 (dd, 1 H), 3.71 (ddd, 1 H), 3.49-3.62 (m, 1 H), 3.18 (dt, 1 H), 2.93-3.09 (m, 5 H), 2.80 (br dd, 1 H), 1.32 (dd, 6 H) | 440.2 $[M + H]^+$ | 99.6% |
| 2519 | ($CD_3OD$) δ 8.29 (d, 1 H), 7.66 (s, 1 H), 7.05 (d, 1 H), 6.83 (t, 1 H), 6.60 (s, 1 H), 6.29 (br s, 1 H), 4.23 (dd, 1 H), 3.71 (ddd, 1 H), 3.49-3.62 (m, 1 H), 3.18 (dt, 1 H), 2.90-3.09 (m, 5 H), 2.79 (br dd, 1 H), 1.33 (dd, 6 H) | 440.2 $[M + H]^+$ | 98.9% |
| 2520 | ($CD_3OD$) δ 9.28 (d, 1 H), 8.68-8.75 (m, 2 H), 7.64-7.76 (m, 2 H), 7.14-7.51 (m, 3 H), 6.74 (s, 1 H), 6.52 (br s, 1 H), 4.45 (dd, 1 H), 3.80-3.95 (m, 1 H), 3.03-3.20 (m, 1 H), 2.86 (br dd, 1 H) | 436.2 $[M + H]^+$ | 100% |
| 2521 | ($CD_3OD$) δ 9.26 (d, 1 H), 8.67-8.74 (m, 2 H), 7.63-7.76 (m, 2 H), 7.13-7.49 (m, 3 H), 6.73 (s, 1 H), 6.51 (s, 1 H), 4.45 (dd, 1 H), 3.77-3.96 (m, 1 H), 2.99-3.15 (m, 1 H), 2.85 (br dd, 1 H) | 436.1 $[M + H]^+$ | 99.4% |
| 2522 | ($CD_3OD$) δ 7.53-7.70 (m, 2 H), 7.02-7.40 (m, 3 H), 6.56 (s, 1 H), 6.27 (s, 1 H), 4.13-4.29 (m, 1 H), 3.60-3.76 (m, 1 H), 2.86-3.00 (m, 1 H), 2.73 (dd, 1 H), 2.00 (t, 3 H) | 422.2 $[M + H]^+$ | 100% |
| 2523 | ($CD_3OD$) δ 7.63 (d, 1 H), 7.57 (s, 1 H), 7.05-7.39 (m, 3 H), 6.55 (s, 1 H), 6.26 (s, 1 H), 4.21 (dd, 1 H), 3.67 (td, 1 H), 2.89-3.02 (m, 1 H), 2.73 (dd, 1 H), 2.00 (t, 3 H) | 422.2 $[M + H]^+$ | 96.4% |
| 2524 | ($CD_3OD$) δ 8.30-8.65 (m, 1 H), 8.03 (d, 0.3 H), 7.41-7.84 (m, 3.7 H), 7.17-7.32 (m, 2.5 H), 6.54-6.97 (m, 2.5 H), 4.36-4.78 (m, 1 H), 3.38-3.86 (m, 1 H), 2.97-3.28 (m, 1 H), 2.76-2.91 (m, 1 H) | 448.2 $[M + H]^+$ | N/A |

Cell Based Phenylalanine Flux Assay

Cells expressing R408W PAH were made by transducing A375 cells with lentivirus encoding human PAH with the R408W mutation in pLVX-Puro, then selecting with puroinycin until stable cell lines were generated. A375 R408W cells were seeded into 96 well plates in DMEM+ 10% FBS at a density of 40.000 cells/well one hour prior to compound addition. Compounds were resuspended in DMSO, and 2-fold serial dilutions were performed to generate a 10-point dose curve. Compounds were added to plated cells in a total volume of 100 μl, and a final DMSO concentration of 0.5%. Each compound was tested in duplicate. Following compound addition, cells were placed in a 5% $CO_2$, 37° C. tissue culture incubator for 24 hrs. After the incubation period. 20 μM sepiapterin and 800 μM 13C9, 15N-Phenylalanine were added. After 4 hours, cell media was removed. An aliquot of 10 μl of cell media was combined with 200 μl of extraction buffer (80% acetonitrile/ 20% $H_2O$) for each well. Determination of $^{13}C$-Tyrosine concentration was assessed by liquid chromatography mass spectrometry.

Specific compounds disclosed herein were tested in the foregoing assay and they were determined to have an $AC_{50}$ according to the following scores: (A) less than or equal to 0.500 μM (B) greater than 0.500 and less than 1.000 μM, (C) greater than or equal to 1.000 and less than 5.000 μM, (D) greater than or equal to 5.000 μM, (E) no fit, and (NT) not tested, as shown below. Where a compound was tested multiple times, the average value of the tests is reported.

| Ex. # | $AC_{50}$ |
|---|---|
| 600 | B |
| 601 | D |
| 602 | A |
| 603 | C |
| 604 | D |
| 605 | B |
| 606 | A |

-continued

| Ex. # | $AC_{50}$ |
|---|---|
| 607 | D |
| 608 | C |
| 609 | D |
| 610 | A |
| 611 | C |
| 612 | A |
| 613 | C |
| 614 | A |
| 615 | C |
| 616 | B |
| 617 | D |
| 618 | A |
| 619 | C |
| 620 | C |
| 621 | D |
| 622 | B |
| 623 | C |
| 624 | C |
| 625 | C |
| 626 | C |
| 627 | E |
| 628 | A |
| 629 | C |
| 630 | A |
| 631 | C |
| 632 | A |
| 633 | D |
| 634 | A |
| 635 | C |
| 636 | A |
| 637 | C |
| 638 | A |
| 639 | C |
| 640 | B |
| 641 | D |
| 642 | B |
| 643 | D |
| 644 | A |
| 645 | C |
| 646 | C |
| 647 | D |
| 648 | A |
| 649 | D |

-continued

| Ex. # | $AC_{50}$ |
|---|---|
| 650 | C |
| 65] | C |
| 652 | A |
| 653 | D |
| 654 | A |
| 655 | C |
| 656 | A |
| 657 | D |
| 658 | C |
| 659 | C |
| 660 | B |
| 661 | D |
| 662 | A |
| 663 | C |
| 664 | D |
| 665 | A |
| 666 | B |
| 667 | D |
| 668 | D |
| 669 | A |
| 670 | A |
| 671 | D |
| 672 | D |
| 673 | B |
| 674 | C |
| 675 | D |
| 676 | A |
| 677 | D |
| 678 | C |
| 679 | D |
| 680 | A |
| 681 | D |
| 682 | B |
| 683 | D |
| 684 | B |
| 685 | D |
| 686 | A |
| 687 | C |
| 688 | A |
| 689 | D |
| 690 | A |
| 691 | D |
| 692 | A |
| 693 | D |
| 694 | A |
| 695 | D |
| 696 | A |
| 697 | D |
| 698 | C |
| 699 | A |
| 700 | A |
| 701 | C |
| 702 | A |
| 703 | C |
| 704 | A |
| 705 | C |
| 706 | A |
| 707 | E |
| 708 | A |
| 709 | E |
| 710 | A |
| 711 | D |
| 712 | A |
| 713 | D |
| 714 | A |
| 715 | D |
| 716 | A |
| 717 | B |
| 718 | A |
| 719 | D |
| 720 | A |
| 721 | D |
| 722 | A |
| 723 | C |
| 724 | A |
| 725 | D |
| 726 | B |

-continued

| Ex. # | $AC_{50}$ |
|---|---|
| 727 | C |
| 728 | A |
| 729 | D |
| 730 | A |
| 731 | D |
| 732 | D |
| 733 | A |
| 734 | D |
| 735 | A |
| 736 | A |
| 737 | C |
| 738 | A |
| 739 | C |
| 740 | D |
| 741 | A |
| 742 | D |
| 743 | A |
| 744 | A |
| 745 | C |
| 746 | A |
| 747 | D |
| 748 | A |
| 749 | D |
| 750 | A |
| 751 | D |
| 752 | A |
| 753 | C |
| 754 | A |
| 755 | D |
| 756 | A |
| 757 | C |
| 758 | A |
| 759 | C |
| 760 | C |
| 761 | C |
| 762 | A |
| 763 | C |
| 764 | B |
| 765 | C |
| 766 | A |
| 767 | D |
| 768 | A |
| 769 | D |
| 770 | A |
| 771 | C |
| 772 | A |
| 773 | B |
| 774 | A |
| 775 | D |
| 776 | A |
| 777 | D |
| 778 | D |
| 779 | B |
| 780 | A |
| 781 | C |
| 782 | A |
| 783 | C |
| 784 | A |
| 785 | C |
| 786 | A |
| 787 | C |
| 788 | A |
| 789 | C |
| 790 | D |
| 791 | A |
| 792 | A |
| 793 | B |
| 794 | A |
| 795 | C |
| 796 | A |
| 797 | D |
| 798 | A |
| 799 | D |
| 800 | B |
| 801 | D |
| 802 | A |
| 803 | D |

-continued

| Ex. # | $AC_{50}$ |
|---|---|
| 804 | A |
| 805 | C |
| 806 | B |
| 807 | D |
| 808 | D |
| 809 | B |
| 810 | A |
| 811 | C |
| 812 | B |
| 813 | D |
| 814 | A |
| 815 | D |
| 816 | D |
| 817 | A |
| 818 | D |
| 819 | A |
| 820 | A |
| 821 | D |
| 822 | A |
| 823 | C |
| 824 | D |
| 825 | A |
| 826 | A |
| 827 | D |
| 828 | A |
| 829 | D |
| 830 | A |
| 831 | C |
| 832 | A |
| 833 | D |
| 834 | B |
| 835 | D |
| 836 | A |
| 837 | D |
| 838 | A |
| 839 | C |
| 840 | B |
| 841 | C |
| 842 | A |
| 843 | C |
| 844 | A |
| 845 | D |
| 846 | A |
| 847 | D |
| 848 | A |
| 849 | E |
| 850 | A |
| 851 | D |
| 852 | B |
| 853 | E |
| 854 | A |
| 855 | D |
| 856 | A |
| 857 | F |
| 858 | A |
| 859 | E |
| 860 | A |
| 861 | E |
| 862 | A |
| 863 | E |
| 864 | A |
| 865 | E |
| 866 | E |
| 867 | A |
| 868 | D |
| 869 | B |
| 870 | D |
| 871 | A |
| 872 | D |
| 873 | B |
| 874 | D |
| 875 | A |
| 876 | D |
| 877 | A |
| 878 | D |
| 879 | A |
| 880 | D |

-continued

| Ex. # | $AC_{50}$ |
|---|---|
| 881 | A |
| 882 | D |
| 883 | A |
| 884 | B |
| 885 | E |
| 886 | A |
| 887 | D |
| 888 | D |
| 889 | B |
| 890 | D |
| 891 | A |
| 892 | A |
| 893 | E |
| 894 | A |
| 895 | D |
| 896 | A |
| 897 | D |
| 898 | A |
| 899 | E |
| 900 | A |
| 901 | D |
| 902 | A |
| 903 | C |
| 904 | D |
| 905 | A |
| 906 | A |
| 907 | D |
| 908 | C |
| 909 | A |
| 910 | B |
| 911 | D |
| 912 | A |
| 913 | D |
| 914 | B |
| 915 | D |
| 916 | A |
| 917 | E |
| 918 | A |
| 919 | D |
| 920 | E |
| 921 | A |
| 922 | A |
| 923 | D |
| 924 | A |
| 925 | D |
| 926 | A |
| 927 | D |
| 928 | A |
| 929 | D |
| 930 | D |
| 931 | A |
| 932 | A |
| 933 | D |
| 934 | B |
| 935 | D |
| 936 | A |
| 937 | D |
| 938 | A |
| 939 | D |
| 940 | B |
| 941 | D |
| 942 | A |
| 943 | D |
| 944 | B |
| 945 | D |
| 946 | A |
| 947 | D |
| 948 | A |
| 949 | C |
| 950 | A |
| 951 | C |
| 952 | B |
| 953 | C |
| 954 | A |
| 955 | D |
| 956 | D |
| 957 | A |

-continued

| Ex. # | AC50 |
|---|---|
| 958 | A |
| 959 | C |
| 960 | B |
| 961 | C |
| 962 | A |
| 963 | D |
| 964 | A |
| 965 | D |
| 966 | B |
| 967 | D |
| 968 | C |
| 969 | A |
| 970 | D |
| 971 | B |
| 972 | A |
| 973 | D |
| 974 | C |
| 975 | A |
| 976 | A |
| 977 | D |
| 978 | C |
| 979 | A |
| 980 | A |
| 981 | C |
| 982 | A |
| 983 | D |
| 984 | B |
| 985 | C |
| 986 | C |
| 987 | B |
| 988 | A |
| 989 | C |
| 990 | B |
| 991 | E |
| 992 | B |
| 993 | E |
| 994 | A |
| 995 | E |
| 996 | A |
| 997 | A |
| 998 | E |
| 999 | E |
| 1000 | B |
| 1001 | E |
| 1002 | E |
| 1003 | B |
| 1004 | E |
| 1005 | A |
| 1006 | E |
| 1007 | B |
| 1008 | E |
| 1009 | B |
| 1010 | B |
| 1011 | E |
| 1012 | B |
| 1013 | D |
| 1014 | A |
| 1015 | D |
| 1016 | A |
| 1017 | D |
| 1018 | A |
| 1019 | D |
| 1020 | A |
| 1021 | C |
| 1022 | A |
| 1023 | D |
| 1024 | A |
| 1025 | C |
| 1026 | C |
| 1027 | A |
| 1028 | A |
| 1029 | C |
| 1030 | A |
| 1031 | D |
| 1032 | B |
| 1033 | C |
| 1034 | B |

-continued

| Ex. # | AC50 |
|---|---|
| 1035 | D |
| 1036 | B |
| 1037 | D |
| 1038 | A |
| 1039 | D |
| 1040 | B |
| 1041 | D |
| 1042 | A |
| 1043 | D |
| 1044 | A |
| 1045 | E |
| 1046 | D |
| 1047 | A |
| 1048 | E |
| 1049 | B |
| 1050 | A |
| 1051 | D |
| 1052 | A |
| 1053 | C |
| 1054 | A |
| 1055 | C |
| 1056 | A |
| 1057 | D |
| 1058 | B |
| 1059 | D |
| 1060 | A |
| 1061 | E |
| 1062 | A |
| 1063 | E |
| 1064 | B |
| 1065 | C |
| 1066 | A |
| 1067 | D |
| 1068 | A |
| 1069 | C |
| 1070 | A |
| 1071 | D |
| 1072 | B |
| 1073 | C |
| 1074 | B |
| 1075 | E |
| 1076 | A |
| 1077 | E |
| 1078 | A |
| 1079 | F |
| 1080 | E |
| 1081 | A |
| 1082 | A |
| 1083 | E |
| 1084 | A |
| 1085 | C |
| 1086 | A |
| 1087 | E |
| 1088 | B |
| 1089 | D |
| 1090 | B |
| 1091 | D |
| 1092 | B |
| 1093 | C |
| 1094 | A |
| 1095 | D |
| 1096 | D |
| 1097 | B |
| 1098 | D |
| 1099 | B |
| 1100 | B |
| 1101 | D |
| 1102 | B |
| 1103 | D |
| 1104 | A |
| 1105 | C |
| 1106 | A |
| 1107 | C |
| 1108 | D |
| 1109 | A |
| 1110 | B |
| 1111 | D |

-continued

| Ex. # | $AC_{50}$ |
|---|---|
| 1112 | A |
| 1113 | C |
| 1114 | B |
| 1115 | E |
| 1116 | A |
| 1117 | D |
| 1118 | A |
| 1119 | D |
| 1120 | A |
| 1121 | C |
| 1122 | C |
| 1123 | A |
| 1124 | B |
| 1125 | C |
| 1126 | A |
| 1127 | C |
| 1128 | B |
| 1129 | C |
| 1130 | B |
| 1131 | C |
| 1132 | A |
| 1133 | C |
| 1134 | A |
| 1135 | C |
| 1136 | C |
| 1137 | B |
| 1138 | A |
| 1139 | C |
| 1140 | B |
| 1141 | E |
| 1142 | A |
| 1143 | E |
| 1144 | B |
| 1145 | E |
| 1146 | A |
| 1147 | E |
| 1148 | B |
| 1149 | C |
| 1150 | A |
| 1151 | E |
| 1152 | A |
| 1153 | E |
| 1154 | A |
| 1155 | E |
| 1156 | A |
| 1157 | E |
| 1158 | B |
| 1159 | E |
| 1160 | C |
| 1161 | B |
| 1162 | A |
| 1163 | E |
| 1164 | A |
| 1165 | C |
| 1166 | B |
| 1167 | E |
| 1168 | B |
| 1169 | D |
| 1170 | D |
| 1171 | B |
| 1172 | A |
| 1173 | E |
| 1174 | B |
| 1175 | C |
| 1176 | A |
| 1177 | E |
| 1178 | A |
| 1179 | E |
| 1180 | B |
| 1181 | E |
| 1182 | C |
| 1183 | B |
| 1184 | B |
| 1185 | C |
| 1186 | B |
| 1187 | C |
| 1188 | B |

-continued

| Ex. # | $AC_{50}$ |
|---|---|
| 1189 | C |
| 1190 | B |
| 1191 | C |
| 1192 | A |
| 1193 | C |
| 1194 | C |
| 1195 | B |
| 1196 | A |
| 1197 | C |
| 1198 | B |
| 1199 | C |
| 1200 | B |
| 1201 | B |
| 1202 | A |
| 1203 | C |
| 1204 | A |
| 1205 | D |
| 1206 | B |
| 1207 | D |
| 1208 | A |
| 1209 | D |
| 1210 | B |
| 1211 | E |
| 1212 | B |
| 1213 | E |
| 1214 | A |
| 1215 | D |
| 1216 | E |
| 1217 | A |
| 1218 | E |
| 1219 | B |
| 1220 | A |
| 1221 | C |
| 1222 | A |
| 1223 | C |
| 1224 | B |
| 1225 | C |
| 1226 | A |
| 1227 | B |
| 1228 | E |
| 1229 | B |
| 1230 | A |
| 1231 | C |
| 1232 | A |
| 1233 | C |
| 1234 | A |
| 1235 | C |
| 1236 | A |
| 1237 | C |
| 1238 | A |
| 1239 | C |
| 1240 | A |
| 1241 | C |
| 1242 | C |
| 1243 | C |
| 1244 | C |
| 1245 | B |
| 1246 | B |
| 1247 | C |
| 1248 | C |
| 1249 | A |
| 1250 | A |
| 1251 | B |
| 1252 | A |
| 1253 | C |
| 1254 | C |
| 1255 | A |
| 1256 | A |
| 1257 | C |
| 1258 | B |
| 1259 | C |
| 1260 | A |
| 1261 | E |
| 1262 | A |
| 1263 | E |
| 1264 | E |
| 1265 | A |

-continued

| Ex. # | $AC_{50}$ |
|---|---|
| 1266 | A |
| 1267 | E |
| 1268 | A |
| 1269 | E |
| 1270 | A |
| 1271 | E |
| 1272 | A |
| 1273 | F |
| 1274 | A |
| 1275 | A |
| 1276 | A |
| 1277 | A |
| 1278 | A |
| 1279 | E |
| 1280 | A |
| 1281 | C |
| 1282 | E |
| 1283 | B |
| 1284 | A |
| 1285 | C |
| 1286 | A |
| 1287 | B |
| 1288 | B |
| 1289 | A |
| 1290 | C |
| 1291 | B |
| 1292 | A |
| 1293 | C |
| 1294 | C |
| 1295 | A |
| 1296 | A |
| 1297 | C |
| 1298 | C |
| 1299 | A |
| 1300 | A |
| 1301 | D |
| 1302 | A |
| 1303 | C |
| 1304 | A |
| 1305 | C |
| 1306 | A |
| 1307 | C |
| 1308 | A |
| 1309 | C |
| 1310 | C |
| 1311 | B |
| 1312 | C |
| 1313 | B |
| 1314 | A |
| 1315 | C |
| 1316 | A |
| 1317 | C |
| 1318 | C |
| 1319 | A |
| 1320 | C |
| 1321 | A |
| 1322 | C |
| 1323 | A |
| 1324 | C |
| 1325 | A |
| 1326 | A |
| 1327 | E |
| 1328 | A |
| 1329 | D |
| 1330 | A |
| 1331 | C |
| 1332 | A |
| 1333 | C |
| 1334 | A |
| 1335 | D |
| 1336 | C |
| 1337 | B |
| 1338 | D |
| 1339 | A |
| 1340 | B |
| 1341 | C |
| 1342 | B |

-continued

| Ex. # | $AC_{50}$ |
|---|---|
| 1343 | C |
| 1344 | C |
| 1345 | C |
| 1346 | B |
| 1347 | C |
| 1348 | A |
| 1349 | D |
| 1350 | A |
| 1351 | D |
| 1352 | A |
| 1353 | D |
| 1354 | B |
| 1355 | C |
| 1356 | A |
| 1357 | D |
| 1358 | A |
| 1359 | C |
| 1360 | D |
| 1361 | B |
| 1362 | B |
| 1363 | D |
| 1364 | A |
| 1365 | D |
| 1366 | A |
| 1367 | C |
| 1368 | A |
| 1369 | C |
| 1370 | A |
| 1371 | E |
| 1372 | A |
| 1373 | C |
| 1374 | A |
| 1375 | D |
| 1376 | D |
| 1377 | A |
| 1378 | A |
| 1379 | D |
| 1380 | C |
| 1381 | B |
| 1382 | A |
| 1383 | D |
| 1384 | A |
| 1385 | E |
| 1386 | B |
| 1387 | E |
| 1388 | A |
| 1389 | D |
| 1390 | B |
| 1391 | C |
| 1392 | C |
| 1393 | A |
| 1394 | A |
| 1395 | D |
| 1396 | A |
| 1397 | C |
| 1398 | A |
| 1399 | C |
| 1400 | A |
| 1401 | C |
| 1402 | B |
| 1403 | E |
| 1404 | C |
| 1405 | A |
| 1406 | A |
| 1407 | D |
| 1408 | C |
| 1409 | A |
| 1410 | C |
| 1411 | A |
| 1412 | E |
| 1413 | B |
| 1414 | A |
| 1415 | C |
| 1416 | A |
| 1417 | C |
| 1418 | C |
| 1419 | B |

-continued

| Ex. # | $AC_{50}$ |
|---|---|
| 1420 | D |
| 1421 | A |
| 1422 | A |
| 1423 | D |
| 1424 | A |
| 1425 | C |
| 1426 | A |
| 1427 | D |
| 1428 | D |
| 1429 | A |
| 1430 | D |
| 1431 | A |
| 1432 | C |
| 1433 | A |
| 1434 | B |
| 1435 | C |
| 1436 | B |
| 1437 | C |
| 1438 | B |
| 1439 | D |
| 1440 | B |
| 1441 | D |
| 1442 | A |
| 1443 | C |
| 1444 | A |
| 1445 | C |
| 1446 | B |
| 1447 | D |
| 1448 | B |
| 1449 | C |
| 1450 | A |
| 1451 | D |
| 1452 | A |
| 1453 | D |
| 1454 | D |
| 1455 | A |
| 1456 | A |
| 1457 | C |
| 1458 | C |
| 1459 | A |
| 1460 | E |
| 1461 | B |
| 1462 | A |
| 1463 | C |
| 1464 | C |
| 1465 | A |
| 1466 | A |
| 1467 | C |
| 1468 | A |
| 1469 | D |
| 1470 | A |
| 1471 | C |
| 1472 | B |
| 1473 | C |
| 1474 | A |
| 1475 | C |
| 1476 | A |
| 1477 | C |
| 1478 | A |
| 1479 | C |
| 1480 | A |
| 1481 | C |
| 1482 | A |
| 1483 | C |
| 1484 | A |
| 1485 | C |
| 1486 | A |
| 1487 | D |
| 1488 | A |
| 1489 | C |
| 1490 | B |
| 1491 | C |
| 1492 | B |
| 1493 | C |
| 1494 | A |
| 1495 | D |
| 1496 | A |

-continued

| Ex. # | $AC_{50}$ |
|---|---|
| 1497 | C |
| 1498 | E |
| 1499 | B |
| 1500 | A |
| 1501 | D |
| 1502 | B |
| 1503 | D |
| 1504 | A |
| 1505 | D |
| 1506 | A |
| 1507 | D |
| 1508 | A |
| 1509 | D |
| 1510 | B |
| 1511 | C |
| 1512 | A |
| 1513 | C |
| 1514 | A |
| 1515 | D |
| 1516 | E |
| 1517 | A |
| 1518 | E |
| 1519 | A |
| 1520 | A |
| 1521 | C |
| 1522 | A |
| 1523 | D |
| 1524 | D |
| 1525 | B |
| 1526 | B |
| 1527 | D |
| 1528 | A |
| 1529 | C |
| 1530 | D |
| 1531 | A |
| 1532 | A |
| 1533 | D |
| 1534 | C |
| 1535 | B |
| 1536 | D |
| 1537 | B |
| 1538 | B |
| 1539 | D |
| 1540 | B |
| 1541 | C |
| 1542 | B |
| 1543 | C |
| 1544 | A |
| 1545 | C |
| 1546 | B |
| 1547 | D |
| 1548 | B |
| 1549 | C |
| 1550 | A |
| 1551 | C |
| 1552 | A |
| 1553 | E |
| 1554 | D |
| 1555 | C |
| 1556 | A |
| 1557 | C |
| 1558 | C |
| 1559 | A |
| 1560 | D |
| 1561 | A |
| 1562 | B |
| 1563 | C |
| 1564 | D |
| 1565 | A |
| 1566 | B |
| 1567 | C |
| 1568 | A |
| 1569 | D |
| 1570 | A |
| 1571 | C |
| 1572 | C |
| 1573 | B |

-continued

| Ex. # | $AC_{50}$ |
|---|---|
| 1574 | C |
| 1575 | A |
| 1576 | E |
| 1577 | B |
| 1578 | B |
| 1579 | D |
| 1580 | A |
| 1581 | D |
| 1582 | B |
| 1583 | D |
| 1584 | B |
| 1585 | D |
| 1586 | C |
| 1587 | A |
| 1588 | D |
| 1589 | B |
| 1590 | E |
| 1591 | B |
| 1592 | B |
| 1593 | C |
| 1594 | A |
| 1595 | D |
| 1596 | A |
| 1597 | D |
| 1598 | B |
| 1599 | D |
| 1600 | B |
| 1601 | E |
| 1602 | B |
| 1603 | E |
| 1604 | B |
| 1605 | D |
| 1606 | E |
| 1607 | B |
| 1608 | B |
| 1609 | D |
| 1610 | B |
| 1611 | E |
| 1612 | D |
| 1613 | A |
| 1614 | B |
| 1615 | E |
| 1616 | A |
| 1617 | D |
| 1618 | A |
| 1619 | C |
| 1620 | D |
| 1621 | A |
| 1622 | C |
| 1623 | A |
| 1624 | B |
| 1625 | D |
| 1626 | B |
| 1627 | D |
| 1628 | B |
| 1629 | E |
| 1630 | B |
| 1631 | E |
| 1632 | B |
| 1633 | E |
| 1634 | B |
| 1635 | E |
| 1636 | E |
| 1637 | A |
| 1638 | E |
| 1639 | B |
| 1640 | B |
| 1641 | D |
| 1642 | D |
| 1643 | B |
| 1644 | A |
| 1645 | D |
| 1646 | B |
| 1647 | D |
| 1648 | B |
| 1649 | D |
| 1650 | B |

-continued

| Ex. # | $AC_{50}$ |
|---|---|
| 1651 | E |
| 1652 | B |
| 1653 | D |
| 1654 | B |
| 1655 | F |
| 1656 | D |
| 1657 | B |
| 1658 | B |
| 1659 | E |
| 1660 | B |
| 1661 | E |
| 1662 | B |
| 1663 | D |
| 1664 | A |
| 1665 | C |
| 1666 | B |
| 1667 | D |
| 1668 | B |
| 1669 | D |
| 1670 | B |
| 1671 | E |
| 1672 | A |
| 1673 | D |
| 1674 | B |
| 1675 | E |
| 1676 | B |
| 1677 | D |
| 1678 | D |
| 1679 | A |
| 1680 | B |
| 1681 | F |
| 1682 | A |
| 1683 | F |
| 1684 | A |
| 1685 | F |
| 1686 | E |
| 1687 | B |
| 1688 | E |
| 1689 | A |
| 1690 | B |
| 1691 | D |
| 1692 | A |
| 1693 | C |
| 1694 | A |
| 1695 | D |
| 1696 | B |
| 1697 | E |
| 1698 | A |
| 1699 | D |
| 1700 | C |
| 1701 | B |
| 1702 | A |
| 1703 | E |
| 1704 | A |
| 1705 | E |
| 1706 | A |
| 1707 | D |
| 1708 | B |
| 1709 | D |
| 1710 | D |
| 1711 | B |
| 1712 | B |
| 1713 | D |
| 1714 | A |
| 1715 | E |
| 1716 | A |
| 1717 | D |
| 1718 | B |
| 1719 | C |
| 1720 | B |
| 1721 | E |
| 1722 | D |
| 1723 | B |
| 1724 | A |
| 1725 | E |
| 1726 | B |
| 1727 | E |

-continued

| Ex. # | AC50 |
|---|---|
| 1728 | B |
| 1729 | D |
| 1730 | A |
| 1731 | D |
| 1732 | E |
| 1733 | A |
| 1734 | E |
| 1735 | A |
| 1736 | E |
| 1737 | B |
| 1738 | E |
| 1739 | A |
| 1740 | D |
| 1741 | B |
| 1742 | A |
| 1743 | C |
| 1744 | C |
| 1745 | D |
| 1746 | A |
| 1747 | D |
| 1748 | B |
| 1749 | E |
| 1750 | B |
| 1751 | D |
| 1752 | A |
| 1753 | E |
| 1754 | A |
| 1755 | D |
| 1756 | D |
| 1757 | A |
| 1758 | E |
| 1759 | B |
| 1760 | A |
| 1761 | E |
| 1762 | A |
| 1763 | C |
| 1764 | C |
| 1765 | B |
| 1766 | B |
| 1767 | A |
| 1768 | A |
| 1769 | C |
| 1770 | B |
| 1771 | D |
| 1772 | B |
| 1773 | D |
| 1774 | A |
| 1775 | D |
| 1776 | A |
| 1777 | D |
| 1778 | A |
| 1779 | E |
| 1780 | A |
| 1781 | D |
| 1782 | B |
| 1783 | E |
| 1784 | B |
| 1785 | E |
| 1786 | B |
| 1787 | C |
| 1788 | B |
| 1789 | D |
| 1790 | B |
| 1791 | D |
| 1792 | A |
| 1793 | E |
| 1794 | B |
| 1795 | D |
| 1796 | B |
| 1797 | E |
| 1798 | D |
| 1799 | B |
| 1800 | A |
| 1801 | E |
| 1802 | B |
| 1803 | D |
| 1804 | C |

-continued

| Ex. # | AC50 |
|---|---|
| 1805 | A |
| 1806 | E |
| 1807 | B |
| 1808 | E |
| 1809 | A |
| 1810 | B |
| 1811 | E |
| 1812 | B |
| 1813 | E |
| 1814 | A |
| 1815 | D |
| 1816 | D |
| 1817 | A |
| 1818 | D |
| 1819 | A |
| 1820 | D |
| 1821 | A |
| 1822 | D |
| 1823 | B |
| 1824 | F |
| 1825 | B |
| 1826 | E |
| 1827 | B |
| 1828 | C |
| 1829 | A |
| 1830 | D |
| 1831 | B |
| 1832 | E |
| 1833 | B |
| 1834 | E |
| 1835 | B |
| 1836 | E |
| 1837 | B |
| 1838 | A |
| 1839 | D |
| 1840 | A |
| 1841 | D |
| 1842 | D |
| 1843 | A |
| 1844 | D |
| 1845 | A |
| 1846 | E |
| 1847 | A |
| 1848 | D |
| 1849 | A |
| 1850 | B |
| 1851 | C |
| 1852 | B |
| 1853 | C |
| 1854 | D |
| 1855 | A |
| 1856 | E |
| 1857 | B |
| 1858 | A |
| 1859 | E |
| 1860 | E |
| 1861 | A |
| 1862 | D |
| 1863 | A |
| 1864 | E |
| 1865 | A |
| 1866 | A |
| 1867 | E |
| 1868 | A |
| 1869 | D |
| 1870 | A |
| 1871 | D |
| 1872 | D |
| 1873 | B |
| 1874 | D |
| 1875 | A |
| 1876 | B |
| 1877 | D |
| 1878 | B |
| 1879 | E |
| 1880 | A |
| 1881 | D |

-continued

| Ex. # | $AC_{50}$ |
|---|---|
| 1882 | A |
| 1883 | F |
| 1884 | A |
| 1885 | D |
| 1886 | A |
| 1887 | D |
| 1888 | D |
| 1889 | A |
| 1890 | E |
| 1891 | A |
| 1892 | E |
| 1893 | A |
| 1894 | D |
| 1895 | A |
| 1896 | D |
| 1897 | B |
| 1898 | A |
| 1899 | C |
| 1900 | A |
| 1901 | D |
| 1902 | A |
| 1903 | E |
| 1904 | D |
| 1905 | A |
| 1906 | A |
| 1907 | D |
| 1908 | A |
| 1909 | C |
| 1910 | D |
| 1911 | A |
| 1912 | D |
| 1913 | A |
| 1914 | A |
| 1915 | D |
| 1916 | A |
| 1917 | D |
| 1918 | B |
| 1919 | E |
| 1920 | A |
| 1921 | E |
| 1922 | A |
| 1923 | D |
| 1924 | A |
| 1925 | D |
| 1926 | D |
| 1927 | A |
| 1928 | B |
| 1929 | E |
| 1930 | A |
| 1931 | D |
| 1932 | D |
| 1933 | B |
| 1934 | A |
| 1935 | E |
| 1936 | A |
| 1937 | C |
| 1938 | A |
| 1939 | C |
| 1940 | D |
| 1941 | A |
| 1942 | E |
| 1943 | A |
| 1944 | A |
| 1945 | C |
| 1946 | A |
| 1947 | E |
| 1948 | A |
| 1949 | C |
| 1950 | D |
| 1951 | A |
| 1952 | D |
| 1953 | A |
| 1954 | C |
| 1955 | A |
| 1956 | E |
| 1957 | B |
| 1958 | E |

-continued

| Ex. # | $AC_{50}$ |
|---|---|
| 1959 | A |
| 1960 | B |
| 1961 | D |
| 1962 | B |
| 1963 | D |
| 1964 | B |
| 1965 | D |
| 1966 | A |
| 1967 | D |
| 1968 | A |
| 1969 | D |
| 1970 | A |
| 1971 | D |
| 1972 | B |
| 1973 | D |
| 1974 | B |
| 1975 | D |
| 1976 | D |
| 1977 | B |
| 1978 | D |
| 1979 | A |
| 1980 | E |
| 1981 | B |
| 1982 | D |
| 1983 | A |
| 1984 | A |
| 1985 | D |
| 1986 | A |
| 1987 | C |
| 1988 | E |
| 1989 | B |
| 1990 | E |
| 1991 | B |
| 1992 | D |
| 1993 | A |
| 1994 | D |
| 1995 | A |
| 1996 | C |
| 1997 | B |
| 1998 | A |
| 1999 | D |
| 2000 | C |
| 2001 | D |
| 2002 | B |
| 2003 | D |
| 2004 | B |
| 2005 | D |
| 2006 | E |
| 2007 | A |
| 2008 | E |
| 2009 | A |
| 2010 | A |
| 2011 | D |
| 2012 | E |
| 2013 | A |
| 2014 | A |
| 2015 | C |
| 2016 | A |
| 2017 | D |
| 2018 | A |
| 2019 | D |
| 2020 | A |
| 2021 | D |
| 2022 | B |
| 2023 | D |
| 2024 | A |
| 2025 | E |
| 2026 | E |
| 2027 | B |
| 2028 | A |
| 2029 | D |
| 2030 | A |
| 2031 | C |
| 2032 | A |
| 2033 | D |
| 2034 | B |
| 2035 | D |

-continued

| Ex. # | $AC_{50}$ |
|---|---|
| 2036 | A |
| 2037 | D |
| 2038 | C |
| 2039 | A |
| 2040 | A |
| 2041 | C |
| 2042 | B |
| 2043 | C |
| 2044 | D |
| 2045 | B |
| 2046 | D |
| 2047 | B |
| 2048 | B |
| 2049 | D |
| 2050 | A |
| 2051 | D |
| 2052 | B |
| 2053 | D |
| 2054 | B |
| 2055 | D |
| 2056 | D |
| 2057 | A |
| 2058 | E |
| 2059 | B |
| 2060 | D |
| 2061 | B |
| 2062 | D |
| 2063 | A |
| 2064 | A |
| 2065 | E |
| 2066 | B |
| 2067 | D |
| 2068 | B |
| 2069 | D |
| 2070 | A |
| 2071 | D |
| 2072 | D |
| 2073 | B |
| 2074 | A |
| 2075 | C |
| 2076 | B |
| 2077 | D |
| 2078 | B |
| 2079 | E |
| 2080 | A |
| 2081 | D |
| 2082 | E |
| 2083 | A |
| 2084 | D |
| 2085 | A |
| 2086 | A |
| 2087 | D |
| 2088 | D |
| 2089 | A |
| 2090 | D |
| 2091 | A |
| 2092 | D |
| 2093 | A |
| 2094 | E |
| 2095 | A |
| 2096 | D |
| 2097 | B |
| 2098 | A |
| 2099 | E |
| 2100 | A |
| 2101 | E |
| 2102 | A |
| 2103 | E |
| 2104 | A |
| 2105 | E |
| 2106 | A |
| 2107 | E |
| 2108 | E |
| 2109 | B |
| 2110 | A |
| 2111 | E |
| 2112 | B |
| 2113 | D |
| 2114 | B |
| 2115 | C |
| 2116 | A |
| 2117 | C |
| 2118 | A |
| 2119 | C |
| 2120 | A |
| 2121 | C |
| 2122 | A |
| 2123 | C |
| 2124 | A |
| 2125 | C |
| 2126 | D |
| 2127 | A |
| 2128 | E |
| 2129 | A |
| 2130 | D |
| 2131 | A |
| 2132 | C |
| 2133 | A |
| 2134 | C |
| 2135 | A |
| 2136 | A |
| 2137 | D |
| 2138 | A |
| 2139 | E |
| 2140 | A |
| 2141 | E |
| 2142 | A |
| 2143 | E |
| 2144 | A |
| 2145 | E |
| 2146 | E |
| 2147 | A |
| 2148 | A |
| 2149 | D |
| 2150 | D |
| 2151 | A |
| 2152 | E |
| 2153 | A |
| 2154 | D |
| 2155 | A |
| 2156 | E |
| 2157 | B |
| 2158 | E |
| 2159 | B |
| 2160 | D |
| 2161 | A |
| 2162 | B |
| 2163 | D |
| 2164 | A |
| 2165 | D |
| 2166 | D |
| 2167 | A |
| 2168 | C |
| 2169 | A |
| 2170 | A |
| 2171 | D |
| 2172 | A |
| 2173 | C |
| 2174 | A |
| 2175 | D |
| 2176 | D |
| 2177 | B |
| 2178 | B |
| 2179 | D |
| 2180 | B |
| 2181 | D |
| 2182 | B |
| 2183 | D |
| 2184 | E |
| 2185 | A |
| 2186 | E |
| 2187 | A |
| 2188 | D |
| 2189 | B |

-continued

| Ex. # | AC50 |
|---|---|
| 2190 | E |
| 2191 | B |
| 2192 | E |
| 2193 | A |
| 2194 | E |
| 2195 | A |
| 2196 | E |
| 2197 | B |
| 2198 | B |
| 2199 | E |
| 2200 | A |
| 2201 | D |
| 2202 | D |
| 2203 | A |
| 2204 | E |
| 2205 | A |
| 2206 | B |
| 2207 | D |
| 2208 | B |
| 2209 | E |
| 2210 | C |
| 2211 | E |
| 2212 | A |
| 2213 | D |
| 2214 | A |
| 2215 | E |
| 2216 | B |
| 2217 | E |
| 2218 | C |
| 2219 | D |
| 2220 | D |
| 2221 | C |
| 2222 | E |
| 2223 | C |
| 2224 | C |
| 2225 | A |
| 2226 | D |
| 2227 | B |
| 2228 | D |
| 2229 | A |
| 2230 | D |
| 2231 | A |
| 2232 | D |
| 2233 | A |
| 2234 | B |
| 2235 | D |
| 2236 | A |
| 2237 | D |
| 2238 | C |
| 2239 | A |
| 2240 | B |
| 2241 | D |
| 2242 | B |
| 2243 | D |
| 2244 | B |
| 2245 | D |
| 2246 | D |
| 2247 | A |
| 2248 | E |
| 2249 | A |
| 2250 | E |
| 2251 | A |
| 2252 | B |
| 2253 | A |
| 2254 | A |
| 2255 | C |
| 2256 | A |
| 2257 | D |
| 2258 | D |
| 2259 | B |
| 2260 | D |
| 2261 | B |
| 2262 | B |
| 2263 | D |
| 2264 | B |
| 2265 | D |
| 2266 | D |

-continued

| Ex. # | AC50 |
|---|---|
| 2267 | A |
| 2268 | D |
| 2269 | A |
| 2270 | A |
| 2271 | D |
| 2272 | A |
| 2273 | D |
| 2274 | B |
| 2275 | D |
| 2276 | A |
| 2277 | D |
| 2278 | D |
| 2279 | A |
| 2280 | A |
| 2281 | D |
| 2282 | D |
| 2283 | A |
| 2284 | D |
| 2285 | A |
| 2286 | D |
| 2287 | A |
| 2288 | E |
| 2289 | A |
| 2290 | E |
| 2291 | C |
| 2292 | A |
| 2293 | D |
| 2294 | D |
| 2295 | B |
| 2296 | A |
| 2297 | D |
| 2298 | C |
| 2299 | A |
| 2300 | E |
| 2301 | B |
| 2302 | E |
| 2303 | A |
| 2304 | E |
| 2305 | B |
| 2306 | D |
| 2307 | A |
| 2308 | D |
| 2309 | B |
| 2310 | C |
| 2311 | A |
| 2312 | C |
| 2313 | A |
| 2314 | A |
| 2315 | E |
| 2316 | A |
| 2317 | E |
| 2318 | D |
| 2319 | A |
| 2320 | E |
| 2321 | A |
| 2322 | D |
| 2323 | B |
| 2324 | D |
| 2325 | A |
| 2326 | E |
| 2327 | C |
| 2328 | D |
| 2329 | C |
| 2330 | B |
| 2331 | D |
| 2332 | B |
| 2333 | D |
| 2334 | D |
| 2335 | B |
| 2336 | B |
| 2337 | E |
| 2338 | B |
| 2339 | D |
| 2340 | D |
| 2341 | B |
| 2342 | C |
| 2343 | D |

-continued

| Ex. # | $AC_{50}$ |
|---|---|
| 2344 | D |
| 2345 | B |
| 2346 | D |
| 2347 | B |
| 2348 | B |
| 2349 | E |
| 2350 | B |
| 2351 | E |
| 2352 | B |
| 2353 | E |
| 2354 | D |
| 2355 | B |
| 2356 | E |
| 2357 | B |
| 2358 | D |
| 2359 | B |
| 2360 | D |
| 2361 | A |
| 2362 | E |
| 2363 | B |
| 2364 | D |
| 2365 | C |
| 2366 | C |
| 2367 | E |
| 2368 | C |
| 2369 | D |
| 2370 | C |
| 2371 | E |
| 2372 | C |
| 2373 | E |
| 2374 | E |
| 2375 | E |
| 2376 | C |
| 2377 | C |
| 2378 | C |
| 2379 | E |
| 2380 | C |
| 2381 | D |
| 2382 | C |
| 2383 | E |
| 2384 | C |
| 2385 | D |
| 2386 | C |
| 2387 | E |
| 2388 | C |
| 2389 | E |
| 2390 | C |
| 2391 | E |
| 2392 | E |
| 2393 | C |
| 2394 | D |
| 2395 | C |
| 2396 | C |
| 2397 | E |
| 2398 | C |
| 2399 | C |
| 2400 | A |
| 2401 | C |
| 2402 | E |
| 2403 | C |
| 2404 | C |
| 2405 | D |
| 2406 | A |
| 2407 | E |
| 2408 | E |
| 2409 | C |
| 2410 | B |
| 2411 | E |
| 2412 | C |
| 2413 | E |
| 2414 | C |
| 2415 | C |
| 2416 | C |
| 2417 | C |
| 2418 | E |
| 2419 | C |
| 2420 | C |

-continued

| Ex. # | $AC_{50}$ |
|---|---|
| 2421 | C |
| 2422 | C |
| 2423 | E |
| 2424 | C |
| 2425 | E |
| 2426 | C |
| 2427 | D |
| 2428 | C |
| 2429 | C |
| 2430 | C |
| 2431 | C |
| 2432 | E |
| 2433 | C |
| 2434 | C |
| 2435 | D |
| 2436 | C |
| 2437 | D |
| 2438 | C |
| 2439 | E |
| 2440 | C |
| 2441 | E |
| 2442 | E |
| 2443 | C |
| 2444 | E |
| 2445 | C |
| 2446 | C |
| 2447 | D |
| 2448 | C |
| 2449 | D |
| 2450 | C |
| 2451 | D |
| 2452 | C |
| 2453 | E |
| 2454 | C |
| 2455 | C |
| 2456 | C |
| 2457 | E |
| 2458 | C |
| 2459 | E |
| 2460 | E |
| 2461 | C |
| 2462 | C |
| 2463 | E |
| 2464 | C |
| 2465 | D |
| 2466 | E |
| 2467 | C |
| 2468 | E |
| 2469 | C |
| 2470 | C |
| 2471 | D |
| 2472 | C |
| 2473 | E |
| 2474 | C |
| 2475 | D |
| 2476 | C |
| 2477 | E |
| 2478 | C |
| 2479 | E |
| 2480 | D |
| 2481 | C |
| 2482 | C |
| 2483 | E |
| 2484 | E |
| 2485 | C |
| 2486 | E |
| 2487 | C |
| 2488 | C |
| 2489 | E |
| 2490 | E |
| 2491 | C |
| 2492 | E |
| 2493 | C |
| 2494 | C |
| 2495 | E |
| 2496 | C |
| 2497 | E |

-continued

| Ex. # | $AC_{50}$ |
|---|---|
| 2498 | E |
| 2499 | C |
| 2500 | E |
| 2501 | C |
| 2502 | C |
| 2503 | D |
| 2504 | D |
| 2505 | C |
| 2506 | C |
| 2507 | E |
| 2508 | E |
| 2509 | C |
| 2510 | C |
| 2511 | D |
| 2512 | C |

-continued

| Ex. # | $AC_{50}$ |
|---|---|
| 2513 | E |
| 2514 | E |
| 2515 | C |
| 2516 | C |
| 2517 | D |
| 2518 | E |
| 2519 | C |
| 2520 | E |
| 2521 | C |
| 2522 | E |
| 2523 | C |
| 2524 | B |

Additionally, the following compounds were tested with an $AC_{50}$ of C, D, or E:

| Compound(s) | $AC_{50}$ |
|---|---|
| 4S and 4R enantiomers of 1-[4-{pyrazolo[1,5-a]pyridin-2-yl}-1H,4H,5H,6H,7H-imidazo[4,5-c]pyridin-5-yl]-3-(1,3-thiazol-2-yl)propan-1-one | C, E |
| 4S and 4R enantiomers of 3-(5-methyl-1,3,4-thiadiazol-2-yl)-1-[4-{pyrazolo[1,5-a]pyridin-2-yl}-1H,4H,5H,6H,7H-imidazo[4,5-c]pyridin-5-yl]propan-1-one | D, E |
| 4S and 4R enantiomers of 5-[4-{pyrazolo[1,5-a]pyridin-2-yl}-1H,4H,5H,6H,7H-imidazo[4,5-c]pyridine-5-carbonyl]-1,3-oxazole | C, C |
| 4S and 4R enantiomers of 2-methyl-5-[4-{pyrazolo[1,5-a]pyridin-2-yl}-1H,4H,5H,6H,7H-imidazo[4,5-c]pyridine-5-carbonyl]-1,3,4-oxadiazole | C, D |
| 4S and 4R enantiomers of 2-{4-methyl-5-[4-{pyrazolo[1,5-a]pyridin-2-yl}-1H,4H,5H,6H,7H-imidazo[4,5-c]pyridine-5-carbonyl]-1,3-oxazol-2-yl}propan-2-ol | C, E |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1,3-oxazol-2-yl}pyridine | C, D |
| 4S and 4R enantiomers of 2-{4-methyl-5-[4-{pyrazolo[1,5-a]pyridin-2-yl}-1H,4H,5H,6H,7H-imidazo[4,5-c]pyridine-5-carbonyl]-1,3-oxazol-2-yl}pyridine | C, D |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1,3-oxazol-2-yl}propan-2-ol | C, E |
| 4S and 4R enantiomers of dimethyl({3-[4-{pyrazolo[1,5-a]pyridin-2-yl}-1H,4H,5H,6H,7H-imidazo[4,5-c]pyridine-5-carbonyl]pyrazolo[1,5-a]pyridin-6-yl}methyl)amine | C, E |
| 4S and 4R enantiomers of 5-[6-(methoxymethyl)pyrazolo[1,5-a]pyridine-3-carbonyl]-4-{pyrazolo[1,5-a]pyridin-2-yl}-1H,4H,5H,6H,7H-imidazo[4,5-c]pyridine | C, E |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1,3,4-oxadiazol-2-yl}propan-2-ol | C, E |
| 4S and 4R enantiomers of 1-[4-{pyrazolo[1,5-a]pyridin-2-yl}-1H,4H,5H,6H,7H-imidazo[4,5-c]pyridin-5-yl]-2-{pyrazolo[1,5-a]pyridin-3-yl}ethan-1-one | C, D |
| 4S and 4R enantiomers of 5-cyclopropanecarbonyl-4-{pyrazolo[1,5-a]pyridin-2-yl}-1H,4H,5H,6H,7H-imidazo[4,5-c]pyridine | C, E |
| 4S and 4R enantiomers of 1-[4-{pyrazolo[1,5-a]pyridin-2-yl}-3H,4H,5H,6H,7H-imidazo[4,5-c]pyridin-5-yl]-2-(1,3,4-thiadiazol-2-yl)ethan-1-one | C, E |
| 4S and 4R enantiomers of 1-methyl-4-{5-[4-{pyrazolo[1,5-a]pyridin-2-yl}-1H,4H,5H,6H,7H-imidazo[4,5-c]pyridine-5-carbonyl]-1,3,4-oxadiazol-2-yl}piperazine | D, E |
| 4S and 4R enantiomers of 4-{5-[4-{pyrazolo[1,5-a]pyridin-2-yl}-1H,4H,5H,6H,7H-imidazo[4,5-c]pyridine-5-carbonyl]-1,3,4-oxadiazol-2-yl}morpholine | C, E |
| 4S and 4R enantiomers of 2-{4-cyclopropyl-5-[4-{pyrazolo[1,5-a]pyridin-2-yl}-1H,4H,5H,6H,7H,8H-imidazo[4,5-c]azepine-5-carbonyl]-1,3-oxazol-2-yl}pyridine | C, E |
| 4S and 4R enantiomers of 2-{5-[4-{pyrazolo[1,5-a]pyridin-2-yl}-1H,4H,5H,6H,7H,8H-imidazo[4,5-c]azepine-5-carbonyl]-1,3,4-oxadiazol-2-yl}pyridine | D, E |
| 4S and 4R enantiomers of 5-[(1R)-2,2-difluorocyclopropanecarbonyl]-4-{pyrazolo[1,5-a]pyridin-2-yl}-1H,4H,5H,6H,7H-imidazo[4,5-c]pyridine | C, E |
| 4S and 4R enantiomers of 5-[(1S)-2,2-difluorocyclopropanecarbonyl]-4-{pyrazolo[1,5-a]pyridin-2-yl}-1H,4H,5H,6H,7H-imidazo[4,5-c]pyridine | C, E |
| 4S and 4R enantiomers of 4-fluoro-1-{5-[4-{pyrazolo[1,5-a]pyridin-2-yl}-1H,4H,5H,6H,7H-imidazo[4,5-c]pyridine-5-carbonyl]-1,3,4-oxadiazol-2-yl}piperidine | C, E |
| 4S and 4R enantiomers of N,N-dimethyl-5-[4-{pyrazolo[1,5-a]pyridin-2-yl}-1H,4H,5H,6H,7H-imidazo[4,5-c]pyridine-5-carbonyl]-1,3,4-oxadiazol-2-amine | C, E |
| 4S and 4R enantiomers of 2-(3-fluoroazetidin-1-yl)-5-[4-{pyrazolo[1,5-a]pyridin-2-yl}-1H,4H,5H,6H,7H-imidazo[4,5-c]pyridine-5-carbonyl]-1,3,4-oxadiazole | C, E |
| 4S and 4R enantiomers of N-cyclopropyl-5-[4-{pyrazolo[1,5-a]pyridin-2-yl}-1H,4H,5H,6H,7H-imidazo[4,5-c]pyridine-5-carbonyl]-1,3,4-oxadiazol-2-amine | C, E |
| 4S and 4R enantiomers of 2-(methoxymethyl)-5-[4-{pyrazolo[1,5-a]pyridin-2-yl}-1H,4H,5H,6H,7H-imidazo[4,5-c]pyridine-5-carbonyl]-1,3-thiazole | C, D |
| 4S and 4R enantiomers of 2-(methoxymethyl)-5-[4-{pyrazolo[1,S-a]pyridin-2-yl}-1H,4H,5H,6H,7H-imidazo[4,5-c]pyridine-5-carbonyl]-1,3-oxazole | C, E |
| 4'S and 4'R enantiomers of 5'-(4-methyl-1,3-oxazole-5-carbonyl)-4'-{pyrazolo[1,5-a]pyridin-2-yl}-1',4',5',6'-tetrahydrospiro[cyclopropane-1,7'-imidazo[4,5-c]pyridine] | C, E |
| 4S and 4R enantiomers of N-(2-methoxyethyl)-5-[4-{pyrazolo[1,5-a]pyridin-2-yl}-1H,4H,5H,6H,7H-imidazo[4,5-c]pyridine-5-carbonyl]-1,3,4-oxadiazol-2-amine | D, D |

-continued

| Compound(s) | $AC_{50}$ |
| --- | --- |
| 4S and 4R enantiomers of dimethyl({5-[4-{pyrazolo[1,5-a]pyridin-2-yl}-1H,4H,5H,6H,7H-imidazo[4,5-c]pyridine-5-carbonyl]-1,3,4-oxadiazol-2-yl}methyl)amine | D. E |
| 4S and 4R enantiomers of 3-(difluoromethyl)-1-methyl-5-[4-{pyrazolo[1,5-a]pyridin-2-yl}-1H,4H,5H,6H,7H-imidazo[4,5-c]pyridine-5-carbonyl]-1H-pyrazole | C, D |
| 4S and 4R enantiomers of 2-(methoxymethyl)-5-[4-{pyrazolo[1,5-a]pyridin-2-yl}-1H,4H,5H,6H,7H-imidazo[4,5-c]pyridine-5-carbonyl]-1,3,4-oxadiazole | C, E |
| 4S and 4R enantiomers of 5-(difluoromethyl)-1-methyl-4-[4-{pyrazolo[1,5-a]pyridin-2-yl}-1H,4H,5H,6H,7H-imidazo[4,5-c]pyridine-5-carbonyl]-1H-pyrazole | C, C |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1,3,4-oxadiazol-2-yl}-5-(trifluoromethyl)pyridine | C, D |
| 4S and 4R enantiomers of 2-(1H-pyrazol-4-yl)-5-[4-{pyrazolo[1,5-a]pyridin-2-yl}-1H,4H,5H,6H,7H-imidazo[4,5-c]pyridine-5-carbonyl]-1,3,4-oxadiazole | C, E |
| 4S and 4R enantiomers of 2-{3-[4-{pyrazolo[1,5-a]pyridin-2-yl}-1H,4H,5H,6H,7H-imidazo[4,5-c]pyridine-5-carbonylJazetidin-1-yl}pyridine | C, E |
| 4S and 4R enantiomers of 1-methyl-5-[4-{pyrazolo[1,5-a]pyridin-2-yl}-1H,4H,5H,6H,7H-imidazo[4,5-c]pyridine-5-carbonyl]-1H-1,2,4-triazole | C, E |
| 4S and 4R enantiomers of 2-(2-fluoropropan-2-yl)-5-[4-{pyrazolo[1,5-a]pyridin-2-yl}-1H,4H,5H,6H,7H-imidazo[4,5-c]pyridine-5-carbonyl]-1,3,4-oxadiazole | C, C |
| 4S and 4R enantiomers of methyl 3-[4-{pyrazolo[1,5-a]pyridin-2-yl}-1H,4H,5H,6H,7H-imidazo[4,5-c]pyridine-5-carbonyl]azetidine-1-carboxylate | D, E |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1H-pyrazol-1-yl}pyridine | C.E |
| 4S and 4R enantiomers of 2-[1-(2,2-difluoroethyl)-1H-pyrazol-4-yl]-5-[4-{pyrazolo[1,5-a]pyridin-2-yl}-1H,4H,5H,6H,7H-imidazo[4,5-c]pyridine-5-carbonyl]-1,3,4-oxadiazole | C, E |
| 4S and 4R enantiomers of 2-(3,3-difluorocyclobutyl)-5-[4-{pyrazolo[1,5-a]pyridin-2-yl}-1H,4H,5H,6H,7H-imidazo[4,5-c]pyridine-5-carbonyl]-1,3,4-oxadiazole | C, E |
| 4S and 4R enantiomers of 3-[4-{pyrazolo[1,5-a]pyridin-2-yl}-1H,4H,5H,6H,7H-imidazo[4,5-clpyridine-5-carbonyl]-1-(2,2,2-trifluoroethyl)azetidine | D, E |
| 4S and 4R enantiomers of 2-{5-chloro-4-[4-{pyrazolo[1,5-a]pyridin-2-yl}-1H,4H,5H,6H,7H-imidazo[4,5-c]pyridine-5-carbonyl]-1H-pyrazol-1-yl}pyridine | C, D |
| 4S and 4R enantiomers of 2-(1H-pyrazol-3-yl)-5-[4-{pyrazolo[1,5-a]pyridin-2-yl}-1H,4H,5H,6H,7H-imidazo[4,5-c]pyridine-5-carbonyl]-1,3,4-oxadiazole | C, D |
| 4S and 4R enantiomers of 5-[4-{pyrazolo[1,5-a]pyridin-2-yl}-1H,4H,5H,6H,7H-imidazo[4,5-c]pyridine-5-carbonyl]-1,3-oxazole-4-carboxamide | C, E |
| 4S and 4R enantiomers of (IR)-1-{4-methyl-5-[4-{pyrazolo[1,5-a]pyridin-2-yl}-1H,4H,5H,6H,7H-imidazo[4,5-c]pyridine-5-carbonyl]-1,3-oxazol-2-yl}ethan-1-ol | C, E |
| 4S and 4R enantiomers of 5-[4-{3-bromopyrazolo[1,5-a]pyridin-2-yl}-1H,4H,5H,6H,7H-imidazo[4,5-c]pyridine-5-carbonyl]-1,3-oxazole-4-carbonitrile | C, C |
| 4S and 4R enantiomers of (1S)-1-{4-methyl-5-[4-{pyrazolo[1,5-a]pyridin-2-yl}-1H,4H,5H,6H,7H-imidazo[4,5-c]pyridine-5-carbonyl]-1,3-oxazol-2-yl}ethan-1-ol | C, E |
| 4S and 4R enantiomers of 2-[4-{3-bromopyrazolo[1,5-a]pyridin-2-yl}-1H,4H,5H,6H,7H-imidazo[4,5-c]pyridine-5-carbonyl]-5-(1-methyl-1H-pyrazol-4-yl)-1,3,4-oxadiazole | C, E |
| 4S and 4R enantiomers of 5-chloro-4-[4-{pyrazolo[1,5-a]pyridin-2-yl}-1H,4H,5H,6H,7H-imidazo[4,5-c]pyridine-5-carbonyl]-1H-pyrazole | C, C |
| 4S and 4R enantiomers of 5-[4-{pyrazolo[1,5-alpyridin-2-yl}-1H,4H,5H,6H,7H-imidazo[4,5-clpyridine-5-carbonyl]-1H-pyrazole | D, E |
| 4S and 4R enantiomers of 4-[4-{pyrazolo[1,5-a]pyridin-2-yl}-1H,4H,5H,6H,7H-imidazo[4,5-c]pyridine-5-carbonyl]-1H-pyrazole | D, E |
| 4S and 4R enantiomers of 1-methyl-3-[4-{pyrazolo[1,5-a]pyridin-2-yl}-1H,4H,5H,6H,7H-imidazo[4,5-c]pyridine-5-carbonyl]-1H-pyrazole | D, E |
| 4S and 4R enantiomers of 1-methyl-5-[4-{pyrazolo[1,5-a]pyridin-2-yl}-1H,4H,5H,6H,7H-imidazo[4,5-c]pyridine-5-carbonyl]-1H-pyrazol-3-amine | D, E |
| 4S and 4R enantiomers of 5-chloro-4-[4-{pyrazolo[1,5-a]pyridin-2-yl}-1H,4H,5H,6H,7H-imidazo[4,5-c]pyridine-5-carbonyl]-1-(2,2,2-trifluorocthyl)-1H-pyrazole | C, E |
| 4S and 4R enantiomers of (1S)-1-{5-[4-{4-chloropyrazolo[1,5-a]pyridin-2-yl}-1H,4H,5H,6H,7H-imidazo[4,5-c]pyridine-5-carbonyl]-4-(difluoromethyl)-1,3-oxazol-2-yl}ethan-1-ol | C, E |
| 4S and 4R enantiomers of 4-ethyl-3-[4-{pyrazolo[1,5-a]pyridin-2-yl}-1H,4H,5H,6H,7H-imidazo[4,5-c]pyridine-5-carbonyl]-4H-1,2,4-triazole | C, E |
| 4S and 4R enantiomers of 2-{5-[4-{4-chloropyrazolo[1,5-a]pyridin-2-yl}-1H,4H,5H,6H,7H-imidazo[4,5-c]pyridine-5-carbonyl]-4-(trifluoromethyl)-1,3-oxazol-2-yl}propan-2-ol | E, E |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1,2-oxazol-3-yl}propan-2-ol | C, E |
| 4S and 4R enantiomers of 2-{3-[4-{pyrazolo[1,5-a]pyridin-2-yl}-1H,4H,5H,6H,7H-imidazo[4,5-c]pyridine-5-carbonyl]-1,2-oxazol-5-yl}propan-2-ol | D, E |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1,2,4-oxadiazol-3-yl}propan-2-ol | D, E |
| 4S and 4R enantiomers of (1S)-1-{5-[4-{4-fluoropyrazolo[1,5-a]pyridin-2-yl}-1H,4H,5H,6H,7H-imidazo[4,5-c]pyridine-5-carbonyl]-4-methyl-1,3-oxazol-2-yl}ethan-1-ol | C, E |
| 4S and 4R enantiomers of 2-{3-[4-{pyrazolo[1,5-a]pyridin-2-yl}-1H,4H,5H,6H,7H-imidazo[4,5-c]pyridine-5-carbonyl]-1,2,4-oxadiazol-5-yl}propan-2-ol | D, E |
| 4S and 4R enantiomers of (1S)-1-[4-(difluoromethyl)-5-[4-{4-methylpyrazolo[1,5-a]pyridin-2-yl}-1H,4H,5H,6H,7H-imidazo[4,5-c]pyridine-5-carbonyl]-1,3-oxazol-2-ylJethan-1-ol | C, E |
| 4S and 4R enantiomers of 4-(difluoromethyl)-5-[4-{4-methylpyrazolo[1,5-a]pyridin-2-yl}-1H,4H,5H,6H,7H-imidazo[4,5-c]pyridine-5-carbonyl]-1,3-oxazole | C. E |
| 4S and 4R enantiomers of 5-[4-{4-chloropyrazolo[1,5-alpyridin-2-yl}-1H,4H,5H,6H,7H-imidazo[4,5-c]pyridine-5-carbonyl]-4-(difluoromethyl)-1,3-oxazole | C, E |

-continued

| Compound(s) | $AC_{50}$ |
|---|---|
| 4S and 4R enantiomers of 5-[4-{4-chloropyrazolo[1,5-a]pyridin-2-yl}-1H,4H,5H,6H,7H-imidazo[4,5-c]pyridine-5-carbonyl]-4-(trifluoromethyl)-1,3-oxazole | E. E |
| 4S and 4R enantiomers of 4-(difluoromethyl)-5-[4-{4-methoxypyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of 2-4-(difluoromethyl)-5-[4-{4-methoxypyrazolo[1,5-a]pyridin-2-yl}-1H,4H,5H,6H,7H-imidazo[4,5-c]pyridine-5-carbonyl]-1,3-oxazol-2-yl]propan-2-ol | D, E |
| 4S and 4R enantiomers of 5-[4-{4-methylpyrazolo[1,5-a]pyridin-2-yl}-1H,4H,5H,6H,7H-imidazo[4,5-c]pyridine-5-carbonyl]-4-(trifluoromethyl)-1,3-oxazole | E, E |
| 4S and 4R enantiomers of 1-(difluoromethyl)-5-[4-{4-methylpyrazolo[1,5-a]pyridin-2-yl}-1H,4H,5H,6H,7H-imidazo[4,5-c]pyridine-5-carbonyl]-1H-pyrazole | C, E |
| 4S and 4R enantiomers of 2-[4-{4-methoxypyrazolo[1,5-a]pyridin-2-yl}-1H,4H,5H,6H,7H-imidazo[4,5-c]pyridine-5-carbonyl]-5-(1-methyl-1H-pyrazol-4-yl)-1,3,4-oxadiazole | C, E |
| 4S and 4R enantiomers of 2-[4-{4-methoxypyrazolo[1,5-a]pyridin-2-yl}-1H,4H,5H,6H,7H-imidazo[4,5-c]pyridine-5-carbonyl]-5-(1-methyl-1H-pyrazol-3-yl)-1,3,4-oxadiazole | C, D |
| 4S and 4R enantiomers of 2-{5-[4-{4-methylpyrazolo[1,5-a]pyridin-2-yl}-1H,4H,5H,6H,7H-imidazo[4,5-c]pyridine-5-carbonyl]-1,3-oxazol-2-yl}propan-2-ol | C, E |
| 4S and 4R enantiomers of 2-(5-[4-{4-methylpyrazolo[1,5-a]pyridin-2-yl}-1H,4H,5H,6H,7H-imidazo[4,5-c]pyridine-5-carbonyl]-4-(trifluoromethyl)-1,3-oxazol-2-yl}propan-2-ol | E, E |
| 4S and 4R enantiomers of 2-{5-[4-{3-methylpyrazolo[1,5-a]pyridin-2-yl}-1H,4H,5H,6H,7H-imidazo[4,5-c]pyridine-5-carbonyl]-1,3,4-oxadiazol-2-yl}pyridine | C, E |
| 4S and 4R enantiomers of 2-(1-methyl-1H-pyrazol-4-yl)-5-[4-{3-methylpyrazolo[1,5-alpyridin-2-yl}-1H,4H,5H,6H,7H-imidazo[4,5-c]pyridine-5-carbonyl]-1,3,4-oxadiazole | C, E |
| 4S and 4R enantiomers of 2-(1-methyl-1H-pyrazol-3-yl)-5-[4-{3-methylpyrazolo[1,5-alpyridin-2-yl}-1H,4H,5H,6H,7H-imidazo[4,5-c]pyridine-5-carbonyl]-1,3,4-oxadiazole | C, D |
| 4S and 4R enantiomers of 4-(difluoromethyl)-5-[4-{6-methylpyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of 2-[4-{4-fluoropyrazolo[1,5-a]pyridin-2-yl}-1H,4H,5H,6H,7H-imidazo[4,5-c]pyridinc-5-carbonyl]-5-(1-methyl-1H-imidazol-5-yl)-1,3,4-oxadiazole | C, E |
| 4S and 4R enantiomers of 2-[4-(difluoromethyl)-5-[4-{5-methylpyrazolo[1,5-a]pyridin-2-yl}-1H,4H,5H,6H,7H-imidazo[4,5-c]pyridine-5-carbonyl]-1,3-oxazol-2-yl]propan-2-ol | E, E |
| 4S and 4R enantiomers of 2-(1-methyl-1H-imidazol-5-yl)-5-[4-{4-methylpyrazolo[1,5-alpyridin-2-yl}-1H,4H,5H,6H,7H-imidazo[4,5-c]pyridine-5-carbonyl]-1,3,4-oxadiazole | C, E |
| 4S and 4R enantiomers of 2-(1-methyl-1H-pyrazol-4-yl)-5-[4-{5-methylpyrazolo[1,5-alpyridin-2-yl}-1H,4H,5H,6H,7H-imidazo[4,5-c]pyridine-5-carbonyl]-1,3,4-oxadiazole | C, D |
| 4S and 4R enantiomers of 2-(5-[4-{4-fluoropyrazolo[1,5-a]pyridin-2-yl}-1H,4H,5H,6H,7H-imidazo[4,5-c]pyridine-5-carbonyl]-1,3,4-oxadiazol-2-yl}propan-2-ol | C, E |
| 4S and 4R enantiomers of 2-(1-methyl-1H-pyrazol-3-yl)-5-[4-{5-methylpyrazolo[1,5-alpyridin-2-yl}-1H,4H,5H,6H,7H-imidazo[4,5-c]pyridine-5-carbonyl]-1,3,4-oxadiazole | C, D |
| 4S and 4R enantiomers of 5-[4-{4-methylpyrazolo[1,5-a]pyridin-2-yl}-1H,4H,5H,6H,7H-imidazo[4,5-c]pyridine-5-carbonyl]-1-(trifluoromethyl)-1H-pyrazole | E, E |
| 4S and 4R enantiomers of 2-{5-[4-{4-methylpyrazolo[1,5-a]pyridin-2-yl}-1H,4H,5H,6H,7H-imidazo[4,5-c]pyridine-5-carbonyl]-1,3,4-oxadiazol-2-yl}propan-2-ol | C, E |
| 4S and 4R enantiomers of 5-[4-{4-methoxypyrazolo[1,5-a]pyridin-2-yl}-1H,4H,5H,6H,7H-imidazo[4,5-c]pyridine-5-carbonyl]-1-(trifluoromethyl)-1H-pyrazole | E, E |
| 4S and 4R enantiomers of 2-[4-(difluoromethyl)-5-[4-{4-methylpyrazolo[1,5-a]pyridin-2-yl}-1H,4H,5H,6H,7H-imidazo[4,5-c]pyridine-5-carbonyl]-1,3-oxazol-2-yl]pyridine | C, E |
| 4S and 4R enantiomers of 4-{5-[4-{4-fluoropyrazolo[1,5-a]pyridin-2-yl}-1H,4H,5H,6H,7H-imidazo[4,5-c]pyridine-5-carbonyl]-1,3,4-oxadiazol-2-yl}morpholine | C, E |
| 4S and 4R enantiomers of 1-methyl-5-[4-{4-methylpyrazolo[1,5-a]pyridin-2-yl}-1H,4H,5H,6H,7H-imidazo[4,5-c]pyridine-5-carbonyl]-1H-pyrazole | E, E |
| 4S and 4R enantiomers of 5-[4-{4-methylpyrazolo[1,5-a]pyridin-2-yl}-1H,4H,5H,6H,7H-imidazo[4,5-c]pyridine-5-carbonyl]-1-(propan-2-yl)-1H-pyrazole | E, E |
| 4S and 4R enantiomers of 1-cyclopropyl-5-[4-{4-methoxypyrazolo[1,5-a]pyridin-2-yl}-1H,4H,5H,6H,7H-imidazo[4,5-c]pyridine-5-carbonyl]-1H-pyrazole | E, E |
| 4S and 4R enantiomers of 4-(difluoromethyl)-2-(1-methyl-1H-pyrazol-3-yl)-5-14-{pyrazolo[1,5-a]pyridin-2-yl}-1H,4H,5H,6H,7H-imidazo[4,5-c]pyridine-5-carbonyl]-1,3-oxazole | D, E |
| 4S and 4R enantiomers of 4-(difluoromethyl)-5-[4-{4-fluoropyrazolo[1,5-a]pyridin-2-yl}-1H,4H,5H,6H,7H-imidazo[4,5-c]pyridine-5-carbonyl]-2-(1-methyl-1H-pyrazol-3-yl)-1,3-oxazole | D, E |
| 4S and 4R enantiomers of 4-(difluoromethyl)-2-(1-methyl-1H-pyrazol-3-yl)-5-[4-{4-methylpyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of 4-{5-[4-{4-methylpyrazolo[1,5-a]pyridin-2-yl}-1H,4H,5H,6H,7H-imidazo[4,5-c]pyridine-5-carbonyl]-1,3,4-oxadiazol-2-yl}morpholine | C, D |
| 4S and 4R enantiomers of 5-[4-{4-fluoropyrazolo[1,5-a]pyridin-2-yl}-1H,4H,5H,6H,7H-imidazo[4,5-c]pyridine-5-carbonyl]-1,3-dimethyl-1H-1,2,4-triazole | C, E |
| 4S and 4R enantiomers of 4-(difluoromethyl)-2-(1-methyl-1H-pyrazol-4-yl)-5-[4-(pyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of 5-[4-{4-methoxypyrazolo[1,5-a]pyridin-2-yl}-1H,4H,5H,6H,7H-imidazo[4,5-c]pyridine-5-carbonyl]-1-methyl-1H-1,2,4-triazole | E, E |
| 4S and 4R enantiomers of 5-[4-{4-methoxypyrazolo[1,5-a]pyridin-2-yl}-1H,4H,5H,6H,7H-imidazo[4,5-c]pyridine-5-carbonyl]-1-(propan-2-yl)-1H-pyrazole | E, E |
| 4S and 4R enantiomers of 3-tert-butyl-1-methyl-5-[4-{pyrazolo[1,5-a]pyridin-2-yl}-1H,4H,5H,6H,7H-imidazo[4,5-c]pyridine-5-carbonyl]-1H-pyrazole | C, C |

-continued

| Compound(s) | $AC_{50}$ |
|---|---|
| 4S and 4R enantiomers of 3-tert-butyl-5-[4-{4-fluoropyrazolo[1,5-a]pyridin-2-yl}-1H,4H,5H,6H,7H-imidazo[4,5-c]pyridine-5-carbonyl]-1-methyl-1H-pyrazole | C, D |
| 4S and 4R enantiomers of 3-tert-butyl-1-methyl-5-[4-{4-methylpyrazolo[1,5-a]pyridin-2-yl}-1H,4H,5H,6H,7H-imidazo[4,5-c]pyridine-5-carbonyl]-1H-pyrazole | C, D |
| 4S and 4R enantiomers of 1-{5-[4-{4-fluoropyrazolo[1,5-a]pyridin-2-yl}-1H,4H,5H,6H,7H-imidazo[4,5-c]pyridine-5-carbonyl]-1,3,4-oxadiazol-2-yl}-4-methylpiperazine | C, E |
| 4S and 4R enantiomers of 1,3-dimethyl-5-[4-{pyrazolo[1,5-a]pyridin-2-yl}-1H,4H,5H,6H,7H-imidazo[4,5-c]pyridine-5-carbonyl]-1H-1,2,4-triazole | C, E |
| 4S and 4R enantiomers of 5-[4-{4-methoxypyrazolo[1,5-a]pyridin-2-yl}-1H,4H,5H,6H,7H-imidazo[4,5-c]pyridine-5-carbonyl]-1-methyl-1H-pyrazole | E, E |
| 4S and 4R enantiomers of 3-tert-butyl-5-[4-{4-methoxypyrazolo[1,5-a]pyridin-2-yl}-LH,4H,5H,6H,7H-imidazo[4,5-c]pyridine-5-carbonyl]-1-methyl-1H-pyrazole | C, D |
| 4S and 4R enantiomers of 4-(difluoromethyl)-2-(1-methyl-1H-imidazol-4-yl)-5-[4-(pyrazolo[1,5-a]pyridin-2-yl}-1H,4H,5H,6H,7H-imidazo[4,5-c]pyridine-5-carbonyl]-1,3-oxazole | E, E |
| 4S and 4R enantiomers of 2-{3-[4-{4-fluoropyrazolo[1,5-a]pyridin-2-yl}-1H,4H,5H,6H,7H-imidazo[4,5-c]pyridine-5-carbonyl]-1H-pyrazol-1-yl}pyridine | C, C |
| 4S and 4R enantiomers of 2-(3-[4-{4-methylpyrazolo[1,5-a]pyridin-2-yl}-1H,4H,5H,6H,7H-imidazo[4,5-c]pyridine-5-carbonyl]-1H-pyrazol-1-yl}pyridine | C, D |
| 4S and 4R enantiomers of 1-methyl-4-{5-[4-{4-methylpyrazolo[1,5-a]pyridin-2-yl}-1H,4H,5H,6H,7H-imidazo[4,5-c]pyridine-5-carbonyl]-1,3,4-oxadiazol-2-yl}piperazine | C, E |
| 4S and 4R enantiomers of 2-(1-methyl-1H-imidazol-5-yl)-5-14-[4-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 2-(1-methyl-1H-imidazol-5-yl)-5-[4-{7-methylpyrazolo[1,5-alpyridin-2-yl}-1H,4H,5H,6H,7H-imidazo[4,5-c]pyridine-5-carbonyl]-1,3,4-oxadiazole | C, E |
| 4S and 4R enantiomers of 2-{5-[-4-{7-methylpyrazolo[1,5-a]pyridin-2-yl}-1H,4H,5H,6H,7H-imidazo[4,5-c]pyridine-5-carbonyl]-1,3,4-oxadiazol-2-yl}propan-2-ol | C, E |
| 4S and 4R enantiomers of 2-{5-[4-[4-(trifluoromethyl)pyrazolo[1,5-a]pyridin-2-yl]-1H,4H,5H,6H,7H-imidazo[4,5-c]pyridine-5-carbonyl]-1,3,4-oxadiazol-2-yl}propan-2-ol | C, E |
| 4S and 4R enantiomers of 2-methyl-5-[4-{7-methylpyrazolo[1,5-a]pyridin-2-yl}-1H,4H,5H,6H,7H-imidazo[4,5-c]pyridine-5-carbonyl]-1,3,4-oxadiazole | C, D |
| 4S and 4R enantiomers of 2-[4-{4-fluoropyrazolo[1,5-a]pyridin-2-yl}-1H,4H,5H,6H,7H-imidazo[4,5-c]pyridine-5-carbonyl]-5-methyl-1,3,4-oxadiazole | C, D |
| 4S and 4R enantiomers of 2-(1-methyl-1H-imidazol-5-yl)-5-[4-[7-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 1-(difluoromethyl)-5-[4-{5-methylpyrazolo[1,5-a]pyridin-2-yl}-1H,4H,5H,6H,7H-imidazo[4,5-c]pyridine-5-carbonyl]-1H-pyrazole | C, E |
| 4S and 4R enantiomers of 2-methyl-5-[4-{5-methylpyrazolo[1,5-a]pyridin-2-yl}-1H,4H,5H,6H,7H-imidazo[4,5-c]pyridine-5-carbonyl]-1,3,4-oxadiazole | D, E |
| 4S and 4R enantiomers of 2-(2-fluoropropan-2-yl)-5-[4-{5-methylpyrazolo[1,5-a]pyridin-2-yl}-1H,4H,5H,6H,7H-imidazo[4,5-c]pyridine-5-carbonyl]-1,3,4-oxadiazole | C, D |
| 4S and 4R enantiomers of 2-{5-[4-{5-methylpyrazolo[1,5-a]pyridin-2-yl}-1H,4H,5H,6H,7H-imidazo[4,5-c]pyridine-5-carbonyl]-1,3,4-oxadiazol-2-yl}propan-2-ol | C, D |
| 4S and 4R enantiomers of 3-(difluoromethyl)-5-[4-{5-fluoropyrazolo[1,5-a]pyridin-2-yl}-1H,4H,5H,6H,7H-imidazo[4,5-c]pyridine-5-carbonyl]-1-methyl-1H-1,2,4-triazole | C, E |
| 4S and 4R enantiomers of 3-cyclopropyl-5-[4-{4-fluoropyrazolo[1,5-a]pyridin-2-yl}-1H,4H,5H,6H,7H-imidazo[4,5-c]pyridine-5-carbonyl]-1-methyl-1H-1,2,4-triazole | C, E |
| 4S and 4R enantiomers of 3-(difluoromethyl)-1-methyl-5-[4-{7-methylpyrazolo[1,5-alpyridin-2-yl}-1H,4H,5H,6H,7H-imidazo[4,5-c]pyridine-5-carbonyl]-1H-1,2,4-triazole | C, E |
| 4S and 4R enantiomers of 1-methyl-5-[4-{7-methylpyrazolo[1,5-a]pyridin-2-yl}-1H,4H,5H,6H,7H-imidazo[4,5-c]pyridine-5-carbonyl]-1H-1,2,4-triazole | C, D |
| 4S and 4R enantiomers of 1-methyl-5-[4-{7-methylpyrazolo[1,5-a]pyridin-2-yl}-1H,4H,5H,6H,7H-imidazo[4,5-c]pyridine-5-carbonyl]-3-(trifluoromethyl)-1H-1,2,4-triazole | C, D |
| 4S and 4R enantiomers of 3-(difluoromethyl)-5-[4-{6-fluoropyrazolo[1,5-a]pyridin-2-yl}-1H,4H,5H,6H,7H-imidazo[4,5-c]pyridine-5-carbonyl]-1-methyl-1H-1,2,4-triazole | C, E |
| 4S and 4R enantiomers of 2-tert-butyl-5-[4-{5-methylpyrazolo[1,5-a]pyridin-2-yl}-1H,4H,5H,6H,7H-imidazo[4,5-c]pyridine-5-carbonyl]-1,3,4-oxadiazole | C, C |
| 4S and 4R enantiomers of 2-[4-{5-fluoropyrazolo[1,5-a]pyridin-2-yl}-1H,4H,5H,6H,7H-imidazo[4,5-c]pyridine-5-carbonyl]-5-(1-methyl-1H-pyrazol-4-yl)-1,3,4-oxadiazole | C, C |
| 4S and 4R enantiomers of 4-(2,2-difluoroethyl)-5-[4-{pyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of 3-cyclopropyl-1-methyl-5-[4-{7-methylpyrazolo[1,5-a]pyridin-2-yl}-1H,4H,5H,6H,7H-imidazo[4,5-c]pyridine-5-carbonyl]-1H-1,2,4-triazole | C, E |
| 4S and 4R enantiomers of 1,3-dimethyl-5-[4-{7-methylpyrazolo[1,5-a]pyridin-2-yl}-1H,4H,5H,6H,7H-imidazo[4,5-c]pyridine-5-carbonyl]-1H-1,2,4-triazole | C, E |
| 4S and 4R enantiomers of 2-{5-[4-{5-fluoropyrazolo[1,5-a]pyridin-2-yl}-1H,4H,5H,6H,7H-imidazo[4,5-c]pyridine-5-carbonyl]-1,3,4-oxadiazol-2-yl}pyridine | C, D |
| 4S and 4R enantiomers of 2-[4-{5-fluoropyrazolo[1,5-a]pyridin-2-yl}-1H,4H,5H,6H,7H-imidazo[4,5-c]pyridine-5-carbonyl]-5-(1-methyl-1H-pyrazol-3-yl)-1,3,4-oxadiazole | C, D |
| 4S and 4R enantiomers of 2-[4-{7-chloropyrazolo[1,5-alpyridin-2-yl}-1H,4H,5H,6H,7H-imidazo[4,5-c]pyridine-5-carbonyl]-5-(1-methyl-1H-imidazol-5-yl)-1,3,4-oxadiazole | C, E |
| 4S and 4R enantiomers of 2-{5-[4-{7-chloropyrazolo[1,5-alpyridin-2-yl}-1H,4H,5H,6H,7H-imidazo[4,5-c]pyridine-5-carbonyl]-1,3,4-oxadiazol-2-yl}propan-2-ol | C, E |
| 4S and 4R enantiomers of 2-[4-{6-fluoropyrazolo[1,5-a]pyridin-2-yl}-1H,4H,5H,6H,7H-imidazo[4,5-c]pyridine-5-carbonyl]-5-methyl-1,3,4-oxadiazole | C, E |

-continued

| Compound(s) | $AC_{50}$ |
|---|---|
| 4S and 4R enantiomers of 2-{5-[4-{5-fluoropyrazolo[1,5-a]pyridin-2-yl}-1H,4H,5H,6H,7H-imidazo[4,5-c]pyridine-5-carbonyl]-1,3,4-oxadiazol-2-yl}propan-2-ol | D, E |
| 4S and 4R enantiomers of 2-tert-butyl-5-[4-{5-fluoropyrazolo[1,5-a]pyridin-2-yl}-1H,4H,5H,6H,7H-imidazo[4,5-c]pyridine-5-carbonyl]-1,3,4-oxadiazole | C, D |
| 4S and 4R enantiomers of 4-(difluoromethyl)-5-[4-[5-(trifluoromethyl)pyrazolo[1,5-a]pyridin-2-yl]-1H,4H,5H,6H,7H-imidazo[4,5-c]pyridine-5-carbonyl]-1,3-oxazole | C, E |
| 4S and 4R enantiomers of 2-{5-[4-[7-(trifluoromethyl)pyrazolo[1,5-a]pyridin-2-yl]-1H,4H,5H,6H,7H-imidazo[4,5-c]pyridine-5-carbonyl]-1,3,4-oxadiazol-2-yl}propan-2-ol | C, C |
| 4S and 4R enantiomers of 2-{5-[4-{6-fluoropyrazolo[1,5-a]pyridin-2-yl}-1H,4H,5H,6H,7H-imidazo[4,5-c]pyridine-5-carbonyl]-1,3,4-oxadiazol-2-yl}propan-2-ol | C, E |
| 4S and 4R enantiomers of 2-[4-{5-fluoropyrazolo[1,5-a]pyridin-2-yl}-1H,4H,5H,6H,7H-imidazo[4,5-c]pyridine-5-carbonyl]-5-methyl-1,3,4-oxadiazole | C, C |
| 4S and 4R enantiomers of 2-(2-fluoropropan-2-yl)-5-[4-{5-fluoropyrazolo[1,5-a]pyridin-2-yl}-1H,4H,5H,6H,7H-imidazo[4,5-c]pyridine-5-carbonyl]-1,3,4-oxadiazole | C, C |
| 4S and 4R enantiomers of 2-{5-[4-[5-(trifluoromethyl)pyrazolo[1,5-a]pyridin-2-yl]-1H,4H,5H,6H,7H-imidazo[4,5-c]pyridine-5-carbonyl]-1,3,4-oxadiazol-2-yl}pyridine | C, C |
| 4S and 4R enantiomers of 2-[4-{7-chloropyrazolo[1,5-a]pyridin-2-yl}-1H,4H,5H,6H,7H-imidazo[4,5-c]pyridine-5-carbonyl]-5-methyl-1,3,4-oxadiazole | C, C |
| 4S and 4R enantiomers of 2-methyl-5-[4-[7-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, C |
| 4S and 4R enantiomers of 5-[4-{7-chloropyrazolo[1,5-a]pyridin-2-yl}-1H,4H,5H,6H,7H-imidazo[4,5-c]pyridine-5-carbonyl]-1-methyl-1H-1,2,4-triazole | C, C |
| 4S and 4R enantiomers of 2-methyl-5-[4-[6-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 2-cyclopropyl-5-[4-[6-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 2-{5-[4-[6-(trifluoromethyl)pyrazolo[1,5-a]pyridin-2-yl]-1H,4H,5H,6H,7H-imidazo[4,5-c]pyridine-5-carbonyl]-1,3,4-oxadiazol-2-yl}propan-2-ol | C, E |
| 4S and 4R enantiomers of 2-tert-butyl-5-[4-[6-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 2-cyclopropyl-5-[4-{5-methylpyrazolo[1,5-a]pyridin-2-yl}-1H,4H,5H,6H,7H-imidazo[4,5-c]pyridine-5-carbonyl]-1,3,4-oxadiazole | C, C |
| 4S and 4R enantiomers of 2-(1-methyl-1H-pyrazol-4-yl)-5-[4-[5-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, D |
| 4S and 4R enantiomers of 2-cyclopropyl-5-[4-[5-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 2-cyclopropyl-5-[4-{3-methylpyrazolo[1,5-a]pyridin-2-yl}-1H,4H,5H,6H,7H-imidazo[4,5-c]pyridine-5-carbonyl]-1,3,4-oxadiazole | C, C |
| 4S and 4R enantiomers of 5-[4-{7-chloropyrazolo[1,5-a]pyridin-2-yl}-1H,4H,5H,6H,7H-imidazo[4,5-c]pyridine-5-carbonyl]-3-cyclopropyl-1-methyl-1H-1,2,4-triazole | C, E |
| 4S and 4R enantiomers of 5-[4-{7-chloropyrazolo[1,5-a]pyridin-2-yl}-1H,4H,5H,6H,7H-imidazo[4,5-c]pyridine-5-carbonyl]-1,3-dimethyl-1H-1,2,4-triazole | D, E |
| 4S and 4R enantiomers of 3-(difluoromethyl)-1-methyl-5-[4-[7-(trifluoromethyl)pyrazolo[1,5-a]pyridin-2-yl]-1H,4H,5H,6H,7H-imidazo[4,5-c]pyridine-5-carbonyl]-1H-1,2,4-triazole | C, E |
| 4S and 4R enantiomers of 1,3-dimethyl-5-[4-[7-(trifluoromethyl)pyrazolo[1,5-a]pyridin-2-yl]-1H,4H,5H,6H,7H-imidazo[4,5-c]pyridine-5-carbonyl]-1H-1,2,4-triazole | C, D |
| 4S and 4R enantiomers of 2-(1-methyl-1H-pyrazol-3-yl)-5-[4-15-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, D |
| 4S and 4R enantiomers of 2-methyl-5-[4-[5-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 5-[4-{7-methylpyrazolo[1,5-a]pyridin-2-yl}-1H,4H,5H,6H,7H-imidazo[4,5-c]pyridine-5-carbonyl]-1,3-oxazole | C, C |
| 4S and 4R enantiomers of 2-{5-[4-{7-methylpyrazolo[1,5-a]pyridin-2-yl}-1H,4H,5H,6H,7H-imidazo[4,5-c]pyridine-5-carbonyl]-1,3-oxazol-2-yl}propan-2-ol | C, E |
| 4S and 4R enantiomers of 5-[4-[7-(trifluoromethyl)pyrazolo[1,5-a]pyridin-2-yl]-1H,4H,5H,6H,7H-imidazo[4,5-c]pyridine-5-carbonyl]-1,3-oxazole | C, D |
| 4S and 4R enantiomers of 5-[4-{3-methylpyrazolo[1,5-a]pyridin-2-yl}-1H,4H,5H,6H,7H-imidazo[4,5-c]pyridine-5-carbonyl]-1,3-oxazole | C, C |
| 4S and 4R enantiomers of 2-methyl-5-[4-{3-methylpyrazolo[1,5-a]pyridin-2-yl}-1H,4H,5H,6H,7H-imidazo[4,5-c]pyridine-5-carbonyl]-1,3,4-oxadiazole | C, C |
| 4S and 4R enantiomers of 2-(2-fluoropropan-2-yl)-5-[4-{3-methylpyrazolo[1,5-a]pyridin-2-yl}-1H,4H,5H,6H,7H-imidazo[4,5-c]pyridine-5-carbonyl]-1,3,4-oxadiazole | C, E |
| 4S and 4R enantiomers of 5-[4-{5-fluoropyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of 5-[4-[6-(trifluoromethyl)pyrazolo[1,5-a]pyridin-2-yl]-1H,4H,5H,6H,7H-imidazo[4,5-c]pyridine-5-carbonyl]-1,3-oxazole | C, E |
| 4S and 4R enantiomers of 2-(2-fluoropropan-2-yl)-5-[4-[5-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 2-{5-[4-[5-(trifluoromethyl)pyrazolo[1,5-a]pyridin-2-yl]-1H,4H,5H,6H,7H-imidazo[4,5-c]pyridine-5-carbonyl]-1,3,4-oxadiazol-2-yl}propan-2-ol | D, E |
| 4S and 4R enantiomers of 2-tert-butyl-5-[4-[5-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 2-{4-methyl-5-[4-{7-methylpyrazolo[1,5-a]pyridin-2-yl}-1H,4H,5H,6H,7H-imidazo[4,5-c]pyridine-5-carbonyl]-1,3-oxazol-2-yl}propan-2-ol | C, E |

-continued

| Compound(s) | $AC_{50}$ |
|---|---|
| 4S and 4R enantiomers of (1S)-1-{4-methyl-5-[4-{7-methylpyrazolo[1,5-a]pyridin-2-yl}-1H,4H,5H,6H,7H-imidazo[4,5-c]pyridine-5-carbonyl]-1,3-oxazol-2-yl}ethan-1-ol | C, E |
| 4S and 4R enantiomers of (1R)-1-(4-methyl-5-[4-{7-methylpyrazolo[1,5-a]pyridin-2-yl}-1H,4H,5H,6H,7H-imidazo[4,5-c]pyridine-5-carbonyl]-1,3-oxazol-2-yl}ethan-1-ol | C, E |
| 4S and 4R enantiomers of 2-[4-{4-methoxypyrazolo[1,5-a]pyridin-2-yl}-1H,4H,5H,6H,7H-imidazo[4,5-c]pyridine-5-carbonyl]-5-methyl-1,3,4-oxadiazole | C, D |
| 4S and 4R enantiomers of 2-{5-[4-{3-methylpyrazolo[1,5-a]pyridin-2-yl}-1H,4H,5H,6H,7H-imidazo[4,5-c]pyridine-5-carbonyl]-1,3,4-oxadiazol-2-yl}propan-2-ol | D, E |
| 4S and 4R enantiomers of 2-tert-butyl-5-[4-{3-methylpyrazolo[1,5-a]pyridin-2-yl}-1H,4H,5H,6H,7H-imidazo[4,5-c]pyridine-5-carbonyl]-1,3,4-oxadiazole | C, E |
| 4S and 4R enantiomers of 2-methyl-5-[4-{6-methylpyrazolo[1,5-a]pyridin-2-yl}-1H,4H,5H,6H,7H-imidazo[4,5-c]pyridine-5-carbonyl]-1,3,4-oxadiazole | C, E |
| 4S and 4R enantiomers of 2-{5-[4-{6-methylpyrazolo[1,5-a]pyridin-2-yl}-1H,4H,5H,6H,7H-imidazo[4,5-c]pyridine-5-carbonyl]-1,3,4-oxadiazol-2-yl}propan-2-ol | C. E |
| 4S and 4R enantiomers of 5-[4-{7-chloropyrazolo[1,5-alpyridin-2-yl}-1H,4H,5H,6H,7H-imidazo[4,5-c]pyridine-5-carbonyl]-1,3-oxazole | C, E |
| 4S and 4R enantiomers of 2-{5-[4-{4-methoxypyrazolo[1,5-a]pyridin-2-yl}-1H,4H,5H,6H,7H-imidazo[4,5-c]pyridine-5-carbonyl]-1,3,4-oxadiazol-2-yl}propan-2-ol | D, E |
| 4S and 4R enantiomers of 5-[4-[5-(trifluoromethyl)pyrazolo[1,5-a]pyridin-2-yl]-1H,4H,5H,6H,7H-imidazo[4,5-c]pyridine-5-carbonyl]-1,3-oxazole | C, D |
| 4S and 4R enantiomers of 5-[4-{6-fluoropyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of (1R)-1-{5-[4-{7-chloropyrazolo[1,5-a]pyridin-2-yl}-1H,4H,5H,6H,7H-imidazo[4,5-c]pyridine-5-carbonyl]-4-methyl-1,3-oxazol-2-yl}ethan-1-ol | C, D |
| 4S and 4R enantiomers of 2-{5-[4-[7-(trifluoromethyl)pyrazolo[1,5-a]pyridin-2-yl]-1H,4H,5H,6H,7H-imidazo[4,5-c]pyridine-5-carbonyl]-1,3-oxazol-2-yl}propan-2-ol | C, E |
| 4S and 4R enantiomers of 2-{4-methyl-5-[4-[7-(trifluoromethyl)pyrazolo[1,5-a]pyridin-2-yl]-1H,4H,5H,6H,7H-imidazo[4,5-c]pyridine-5-carbonyl]-1,3-oxazol-2-yl}propan-2-ol | C, C |
| 4S and 4R enantiomers of (IR)-1-{4-methyl-5-[4-[7-(trifluoromethyl)pyrazolo[1,5-a]pyridin-2-yl]-1H,4H,5H,6H,7H-imidazo[4,5-c]pyridine-5-carbonyl]-1,3-oxazol-2-yl}ethan-1-ol | C, E |
| 4S and 4R enantiomers of 2-{5-[4-{7-chloropyrazolo[1,5-a]pyridin-2-yl}-1H,4H,5H,6H,7H-imidazo[4,5-c]pyridine-5-carbonyl]-1,3-oxazol-2-yl}propan-2-ol | C, E |
| 4S and 4R enantiomers of 2-(1,5-dimethyl-1H-pyrazol-4-yl)-5-[4-{3-methylpyrazolo[1,5-alpyridin-2-yl}-1H,4H,5H,6H,7H-imidazo[4,5-c]pyridine-5-carbonyl]-1,3,4-oxadiazole | C, C |
| 4S and 4R enantiomers of (1S)-1-{5-[4-{pyrazolo[1,5-a]pyridin-2-yl}-1H,4H,5H,6H,7H-imidazo[4,5-c]pyridine-5-carbonyl]-1,3,4-oxadiazol-2-yl}ethan-1-ol | C, E |
| 4S and 4R enantiomers of 1-methyl-3-(trifluoromethyl)-5-[4-[7-(trifluoromethyl)pyrazolo[1,5-a]pyridin-2-yl]-1H,4H,5H,6H,7H-imidazo[4,5-c]pyridine-5-carbonyl]-1H-1,2,4-triazole | C, E |
| 4S and 4R enantiomers of (IR)-1-{5-[4-{pyrazolo[1,5-a]pyridin-2-yl}-1H,4H,5H,6H,7H-imidazo[4,5-c]pyridine-5-carbonyl]-1,3,4-oxadiazol-2-yl}ethan-1-ol | C, E |
| 4S and 4R enantiomers of 2-[4-{7-fluoropyrazolo[1,5-a]pyridin-2-yl}-1H,4H,5H,6H,7H-imidazo[4,5-c]pyridine-5-carbonyl]-5-methyl-1,3,4-oxadiazole | C, C |
| 4S and 4R enantiomers of 2-cyclopropyl-5-[4-{pyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 4-{7-methylpyrazolo[1,5-a]pyridin-2-yl}-5-{pyrazolo[1,5-alpyridine-3-carbonyl}-1H,4H,5H,6H,7H-imidazo[4,5-c]pyridine | C, E |
| 4S and 4R enantiomers of 5-{pyrazolo[1,5-a]pyridine-3-carbonyl}-4-[7-(trifluoromethyl)pyrazolo[1,5-a]pyridin-2-yl]-1H,4H,5H,6H,7H-imidazo[4,5-c]pyridine | C, E |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1,3,4-oxadiazol-2-yl}pyrimidine | C, E |
| 4S and 4R enantiomers of 2-[4-[7-(difluoromethyl)pyrazolo[1,5-a]pyridin-2-yl]-1H,4H,5H,6H,7H-imidazo[4,5-c]pyridine-5-carbonyl]-5-methyl-1,3,4-oxadiazole | C, C |
| 4S and 4R enantiomers of 2-{5-[4-[7-(trifluoromethyl)pyrazolo[1,5-a]pyridin-2-yl]-1H,4H,5H,6H,7H-imidazo[4,5-c]pyridine-5-carbonyl]-1,3,4-oxadiazol-2-yl}pyrimidine | C, D |
| 4S and 4R enantiomers of 1-methyl-4-{3-[4-{pyrazolo[1,5-a]pyridin-2-yl}-1H,4H,5H,6H,7H-imidazo[4,5-c]pyridine-5-carbonyl]pyrazolo[1,5-a]pyridin-6-yl}-1H-pyrazole | C, C |
| 4S and 4R enantiomers of 4-{3-[4-{pyrazolo[1,5-a]pyridin-2-yl}-1H,4H,5H,6H,7H-imidazo[4,5-c]pyridine-5-carbonyl]pyrazolo[1,5-a]pyridin-6-yl}morpholine | C, D |
| 4S and 4R enantiomers of 2-[4-[4-(difluoromethyl)pyrazolo[1,5-a]pyridin-2-yl]-1H,4H,5H,6H,7H-imidazo[4,5-c]pyridine-5-carbonyl]-5-(propan-2-yl)-1,3,4-oxadiazole | D, E |
| 4S and 4R enantiomers of 2-{5-[4-[7-(difluoromethyl)pyrazolo[1,5-a]pyridin-2-yl]-1H,4H,5H,6H,7H-imidazo[4,5-c]pyridine-5-carbonyl]-1,3,4-oxadiazol-2-yl}propan-2-ol | C, E |
| 4S and 4R enantiomers of 2-{5-[4-[4-(difluoromethyl)pyrazolo[1,5-a]pyridin-2-yl]-1H,4H,5H,6H,7H-imidazo[4,5-c]pyridine-5-carbonyl]-1,3,4-oxadiazol-2-yl}propan-2-ol | C, E |
| 4S and 4R enantiomers of 2-{5-[4-{7-fluoropyrazolo[1,5-a]pyridin-2-yl}-1H,4H,5H,6H,7H-imidazo[4,5-c]pyridine-5-carbonyl]-1,3,4-oxadiazol-2-yl}pyrimidine | C, E |
| 4S and 4R enantiomers of 2-(propan-2-yl)-5-[4-[7-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, C |
| 4S and 4R enantiomers of 2-cyclopropyl-5-[4-{7-fluoropyrazolo[1,5-alpyridin-2-yl}-1H,4H,5H,6H,7H-imidazo[4,5-c]pyridin-5-yl]-1,3,4-oxadiazole | C, E |
| 4S and 4R enantiomers of 2-[4-[4-(difluoromethyl)pyrazolo[1,5-a]pyridin-2-yl]-1H,4H,5H,6H,7H-imidazo[4,5-c]pyridine-5-carbonyl]-5-(1-methyl-1H-imidazol-4-yl)-1,3,4-oxadiazole | C, E |
| 4S and 4R enantiomers of 2-[4-{7-fluoropyrazolo[1,5-a]pyridin-2-yl}-1H,4H,5H,6H,7H-imidazo[4,5-c]pyridine-5-carbonyl]-5-[1-(trifluoromethyl)-1H-pyrazol-4-yl]-1,3,4-oxadiazole | C, D |

-continued

| Compound(s) | $AC_{50}$ |
|---|---|
| 4S and 4R enantiomers of 2-(3,3-difluorocyclobutyl)-5-[4-[7-(trifluoromethyl)pyrazolo[1,5-a]pyridin-2-yl]-1H,4H,5H,6H,7H-imidazo[4,5-c]pyridine-5-carbonyl]-1,3,4-oxadiazole | C, E |
| 4S and 4R enantiomers of 2-(3,3-difluorocyclobutyl)-5-[4-[7-(difluoromethyl)pyrazolo[1,5-a]pyridin-2-yl]-1H,4H,5H,6H,7H-imidazo[4,5-c]pyridine-5-carbonyl]-1,3,4-oxadiazole | C, D |
| 4S and 4R enantiomers of 2-cyclopropyl-5-[4-{7-methylpyrazolo[1,5-a]pyridin-2-yl}-1H,4H,5H,6H,7H-imidazo[4,5-c]pyridin-5-yl]-1,3,4-oxadiazole | C, D |
| 4S and 4R enantiomers of 2-methyl-5-[4-{pyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-[4-[4-(difluoromethyl)pyrazolo[1,5-a]pyridin-2-yl]-1H,4H,5H,6H,7H-imidazo[4,5-c]pyridine-5-carbonyl]-5-(1-methyl-1H-imidazol-5-yl)-1,3,4-oxadiazole | C, E |
| 4S and 4R enantiomers of 2-[4-[7-(difluoromethyl)pyrazolo[1,5-a]pyridin-2-yl]-1H,4H,5H,6H,7H-imidazo[4,5-c]pyridine-5-carbonyl]-5-(1-methyl-1H-imidazol-5-yl)-1,3,4-oxadiazole | C, D |
| 4S and 4R enantiomers of 2-[4-{7-chloropyrazolo[1,5-a]pyridin-2-yl}-1H,4H,5H,6H,7H-imidazo[4,5-c]pyridine-5-carbonyl]-5-(3,3-difluorocyclobutyl)-1,3,4-oxadiazole | C, D |
| 4S and 4R enantiomers of 2-(3,3-difluorocyclobutyl)-5-[4-{7-methylpyrazolo[1,5-a]pyridin-2-yl}-1H,4H,5H,6H,7H-imidazo[4,5-c]pyridine-5-carbonyl]-1,3,4-oxadiazole | C, D |
| 4S and 4R enantiomers of 2-cyclopropyl-5-[4-[7-(trifluoromethyl)pyrazolo[1,5-a]pyridin-2-yl]-1H,4H,5H,6H,7H-imidazo[4,5-c]pyridin-5-yl]-1,3,4-oxadiazole | C, E |
| 4S and 4R enantiomers of 2-cyclopropyl-5-[4-[7-(difluoromethyl)pyrazolo[1,5-a]pyridin-2-yl]-1H,4H,5H,6H,7H-imidazo[4,5-c]pyridin-5-yl]-1,3,4-oxadiazole | C, E |
| 4S and 4R enantiomers of 2-[4-[7-(difluoromethyl)pyrazolo[1,5-a]pyridin-2-yl]-1H,4H,5H,6H,7H-imidazo[4,5-c]pyridine-5-carbonyl]-5-(1-methyl-1H-imidazol-4-yl)-1,3,4-oxadiazole | C, E |
| 4S and 4R enantiomers of 2-(3,3-difluorocyclobutyl)-5-[4-{7-fluoropyrazolo[1,5-a]pyridin-2-yl}-1H,4H,5H,6H,7H-imidazo[4,5-c]pyridine-5-carbonyl]-1,3,4-oxadiazole | C, E |
| 4S and 4R enantiomers of 2-[4-{7-chloropyrazolo[1,5-a]pyridin-2-yl}-1H,4H,5H,6H,7H-imidazo[4,5-c]pyridin-5-yl]-5-cyclopropyl-1,3,4-oxadiazole | C, E |
| 4S and 4R enantiomers of N,N-dimethyl-5-[4-{pyrazolo[1,5-a]pyridin-2-yl}-1H,4H,5H,6H,7H-imidazo[4,5-c]pyridin-5-yl]-1,3,4-oxadiazole-2-carboxamide | C, E |
| 4S and 4R enantiomers of 2-{5-[4-[4-(difluoromethyl)pyrazolo[1,5-a]pyridin-2-yl]-3H,4H,5H,6H,7H-imidazo[4,5-c]pyridin-5-yl]-1,3,4-oxadiazol-2-yl}pyridine | C, E |
| 4S and 4R enantiomers of 2-(1-methyl-1H-pyrazol-4-yl)-5-[4-{pyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-[4-{4-fluoropyrazolo[1,5-a]pyridin-2-yl}-1H,4H,5H,6H,7H-imidazo[4,5-c]pyridin-5-yl]-1,3-benzoxazole | C, E |
| 4S and 4R enantiomers of ({3-[4-{4-fluoropyrazolo[1,5-a]pyridin-2-yl}-1H,4H,5H,6H,7H-imidazo[4,5-c]pyridine-5-carbonyl]pyrazolo[1,5-a]pyridin-6-yl}methyl)dimethylamine | C, E |
| 4S and 4R enantiomers of 2-{5-[4-{7-fluoropyrazolo[1,5-a]pyridin-2-yl}-1H,4H,5H,6H,7H-imidazo[4,5-c]pyridin-5-yl]-1,3,4-oxadiazol-2-yl}pyridine | C, B |
| 4S and 4R enantiomers of 5-[4-{4-fluoropyrazolo[1,5-a]pyridin-2-yl}-1H,4H,5H,6H,7H-imidazo[4,5-c]pyridin-5-yl]-N,N-dimethyl-1,3,4-oxadiazole-2-carboxamide | C, E |
| 4S and 4R enantiomers of N,N-dimethyl-5-[4-{4-methylpyrazolo[1,5-a]pyridin-2-yl}-1H,4H,5H,6H,7H-imidazo[4,5-c]pyridin-5-yl]-1,3,4-oxadiazole-2-carboxamide | C, E |
| 4S and 4R enantiomers of dimethyl({3-[4-[7-(trifluoromethyl)pyrazolo[1,5-a]pyridin-2-yl]-1H,4H,5H,6H,7H-imidazo[4,5-c]pyridine-5-carbonyl]pyrazolo[1,5-a]pyridin-6-yl}methyl)amine | C, E |
| 4S and 4R enantiomers of 5-[6-(methoxymethyl)pyrazolo[1,5-a]pyridine-3-carbonyl]-4-[7-(trifluoromethyl)pyrazolo[1,5-a]pyridin-2-yl]-1H,4H,5H,6H,7H-imidazo[4,5-c]pyridine | C, E |
| 4S and 4R enantiomers of 2-[4-[4-(difluoromethoxy)pyrazolo[1,5-a]pyridin-2-yl]-1H,4H,5H,6H,7H-imidazo[4,5-c]pyridine-5-carbonyl]-5-(1-methyl-1H-pyrazol-3-yl)-1,3,4-oxadiazole | C, D |
| 4S and 4R enantiomers of ({3-[4-[4-(difluoromethyl)pyrazolo[1,5-a]pyridin-2-yl]-1H,4H,5H,6H,7H-imidazo[4,5-c]pyridine-5-carbonyl]pyrazolo[1,5-a]pyridin-6-yl}methyl)dimethylamine | C, E |
| 4S and 4R enantiomers of ({3-[4-{7-fluoropyrazolo[1,5-a]pyridin-2-yl}-1H,4H,5H,6H,7H-imidazo[4,5-c]pyridine-5-carbonyl]pyrazolo[1,5-a]pyridin-6-yl}methyl)dimethylamine | C, E |
| 4S and 4R enantiomers of 2-[4-{4-fluoropyrazolo[1,5-a]pyridin-2-yl}-1H,4H,5H,6H,7H-imidazo[4,5-c]pyridin-5-yl]-5-methyl-1,3,4-oxadiazole | C, E |
| 4S and 4R enantiomers of 2-[4-{4-fluoropyrazolo[1,5-a]pyridin-2-yl}-1H,4H,5H,6H,7H-imidazo[4,5-c]pyridin-5-yl]-5-(1-methyl-1H-pyrazol-4-yl)-1,3,4-oxadiazole | C, E |
| 4S and 4R enantiomers of 4-{3-[4-{4-fluoropyrazolo[1,5-a]pyridin-2-yl}-1H,4H,5H,6H,7H-imidazo[4,5-c]pyridine-5-carbonyl]pyrazolo[1,5-a]pyridin-6-yl}morpholine | C, E |
| 4S and 4R enantiomers of 4-{3-[4-{4-methylpyrazolo[1,5-a]pyridin-2-yl}-1H,4H,5H,6H,7H-imidazo[4,5-c]pyridine-5-carbonyl]pyrazolo[1,5-a]pyridin-6-yl}morpholine | C, E |
| 4S and 4R enantiomers of 3-fluoro-2-{5-[4-{4-methoxypyrazolo[1,5-a]pyridin-2-yl}-1H,4H,5H,6H,7H-imidazo[4,5-c]pyridine-5-carbonyl]-1,3,4-oxadiazol-2-yl}pyridine | C, E |
| 4S and 4R enantiomers of 2-{5-[4-{4-methoxypyrazolo[1,5-a]pyridin-2-yl}-1H,4H,5H,6H,7H-imidazo[4,5-c]pyridine-5-carbonyl]-1,3,4-oxadiazol-2-yl}pyrimidine | D, E |
| 4S and 4R enantiomers of 4-[4-(difluoromethyl)pyrazolo[1,5-a]pyridin-2-yl]-5-[6-(methoxymethyl)pyrazolo[1,5-a]pyridine-3-carbonyl]-1H,4H,5H,6H,7H-imidazo[4,5-c]pyridine | C, E |
| 4S and 4R enantiomers of 4-{3-[4-[7-(trifluoromethyl)pyrazolo[1,5-a]pyridin-2-yl]-1H,4H,5H,6H,7H-imidazo[4,5-c]pyridine-5-carbonyl]pyrazolo[1,5-a]pyridin-6-yl}morpholine | C, E |
| 4S and 4R enantiomers of 2-{5-[4-{4-methoxypyrazolo[1,5-a]pyridin-2-yl}-1H,4H,5H,6H,7H-imidazo[4,5-c]pyridine-5-carbonyl]-1,3,4-oxadiazol-2-yl}pyrazine | C, E |

-continued

| Compound(s) | $AC_{50}$ |
|---|---|
| 4S and 4R enantiomers of 2-{5-[4-[4-(difluoromethoxy)pyrazolo[1,5-a]pyridin-2-yl]-1H,4H,5H,6H,7H-imidazo[4,5-c]pyridine-5-carbonyl]-1,3,4-oxadiazol-2-yl}pyrimidine | C, E |
| 4S and 4R enantiomers of 4-{7-chloropyrazolo[1,5-a]pyridin-2-yl}-5-[6-(methoxymethyl)pyrazolo[1,5-a]pyridine-3-carbonyl]-1H,4H,5H,6H,7H-imidazo[4,5-c]pyridine | C, D |
| 4S and 4R enantiomers of 5-{6-methoxypyrazolo[1,5-a]pyridine-3-carbonyl}-4-[7-(trifluoromethyl)pyrazolo[1,5-a]pyridin-2-yl]-1H,4H,5H,6H,7H-imidazo[4,5-c]pyridine | C, E |
| 4S and 4R enantiomers of ({3-[4-{7-chloropyrazolo[1,5-a]pyridin-2-yl}-1H,4H,5H,6H,7H-imidazo[4,5-c]pyridine-5-carbonyl]pyrazolo[1,5-a]pyridin-6-yl}methyl)dimethylamine | C, E |
| 4S and 4R enantiomers of ({3-[4-[7-(difluoromethyl)pyrazolo[1,5-a]pyridin-2-yl]-1H,4H,5H,6H,7H-imidazo[4,5-c]pyridine-5-carbonyl]pyrazolo[1,5-a]pyridin-6-yl}methyl)dimethylamine | C, D |
| 4S and 4R enantiomers of 4-{3-[4-{4-methoxypyrazolo[1,5-alpyridin-2-yl}-1H,4H,5H,6H,7H-imidazo[4,5-c]pyridine-5-carbonyl]pyrazolo[1,5-a]pyridin-6-yl}morpholine | D, E |
| 4S and 4R enantiomers of 4-{5-[4-{pyrazolo[1,5-a]pyridin-2-yl}-1H,4H,5H,6H,7H-imidazo[4,5-c]pyridin-5-yl]-1,3,4-oxadiazol-2-yl}morpholine | D, E |
| 4S and 4R enantiomers of 4-{5-[4-{4-fluoropyrazolo[1,5-a]pyridin-2-yl}-1H,4H,5H,6H,7H-imidazo[4,5-c]pyridin-5-yl]-1,3,4-oxadiazol-2-yl}morpholine | C, E |
| 4S and 4R enantiomers of 4-{5-[4-{4-methylpyrazolo[1,5-a]pyridin-2-yl}-1H,4H,5H,6H,7H-imidazo[4,5-c]pyridin-5-yl]-1,3,4-oxadiazol-2-yl}morpholine | C, E |
| 4S and 4R enantiomers of 2-(1-methyl-1H-pyrazol-4-yl)-5-[4-{4-methylpyrazolo[1,5-alpyridin-2-yl}-1H,4H,5H,6H,7H-imidazo[4,5-c]pyridin-5-yl]-1,3,4-oxadiazole | C, E |
| 4S and 4R enantiomers of 4-{7-fluoropyrazolo[1,5-a]pyridin-2-yl}-5-[6-(methoxymethyl)pyrazolo[1,5-a]pyridine-3-carbonyl]-1H,4H,5H,6H,7H-imidazo[4,5-c]pyridine | C, E |
| 4S and 4R enantiomers of 2-methyl-5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazole | C, E |
| 4S and 4R enantiomers of 2-[4-[4-(trifluoromethyl)pyrazolo[1,5-a]pyridin-2-yl]-1H,4H,5H,6H,7H-imidazo[4,5-c]pyridin-5-yl]-1,3-benzoxazole | D, E |
| 4S and 4R enantiomers of 2-[4-{7-fluoropyrazolo[1,5-a]pyridin-2-yl}-1H,4H,5H,6H,7H-imidazo[4,5-c]pyridin-5-yl]pyrimidine | C, D |
| 4S and 4R enantiomers of 2-[5-{6-methylpyrazolo[1,5-a]pyridine-3-carbonyl}-1H,4H,5H,6H,7H-imidazo[4,5-c]pyridin-4-yl]-7-(trifluoromethyl)pyrazolo[1,5-a]pyridine | C, E |
| 4S and 4R enantiomers of 7-(difluoromethyl)-2-[5-{6-methylpyrazolo[1,5-a]pyridine-3-carbonyl}-1H,4H,5H,6H,7H-imidazo[4,5-c]pyridin-4-yl]pyrazolo[1,5-a]pyridine | C, E |
| 4S and 4R enantiomers of 5-{6-cyclopropylpyrazolo[1,5-a]pyridine-3-carbonyl}-4-17-(trifluoromethyl)pyrazolo[1,5-a]pyridin-2-yl]-1H,4H,5H,6H,7H-imidazo[4,5-c]pyridine | C, E |
| 4S and 4R enantiomers of 4-{4-methoxypyrazolo[1,5-a]pyridin-2-yl}-5-{6-methoxypyrazolo[1,5-alpyridine-3-carbonyl}-1H,4H,5H,6H,7H-imidazo[4,5-c]pyridine | C, D |
| 4S and 4R enantiomers of 2-[4-{4-methoxypyrazolo[1,5-a]pyridin-2-yl}-1H,4H,5H,6H,7H-imidazo[4,5-c]pyridine-5-carbonyl]-5-[1-(trifluoromethyl)-1H-pyrazol-4-yl]-1,3,4-oxadiazole | C, E |
| 4S and 4R enantiomers of 2-[4-[4-(difluoromethoxy)pyrazolo[1,5-a]pyridin-2-yl]-1H,4H,5H,6H,7H-imidazo[4,5-c]pyridine-5-carbonyl]-5-methyl-1,3,4-oxadiazole | C, E |
| 4S and 4R enantiomers of 4-[7-(difluoromethyl)pyrazolo[1,5-a]pyridin-2-yl]-5-[6-(methoxymethyl)pyrazolo[1,5-a]pyridine-3-carbonyl]-1H,4H,5H,6H,7H-imidazo[4,5-c]pyridine | C, E |
| 4S and 4R enantiomers of 5-[6-(methoxymethyl)pyrazolo[1,5-a]pyridine-3-carbonyl]-4-{7-methylpyrazolo[1,5-a]pyridin-2-yl}-1H,4H,5H,6H,7H-imidazo[4,5-c]pyridine | C, E |
| 4S and 4R enantiomers of 5-[4-[4-(difluoromethyl)pyrazolo[1,5-a]pyridin-2-yl]-1H,4H,5H,6H,7H-imidazo[4,5-c]pyridin-5-yl]-N,N-dimethyl-1,3,4-oxadiazole-2-carboxamide | C, E |
| 4S and 4R enantiomers of N,N-dimethyl-5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazole-2-carboxamide | C, E |
| 4S and 4R enantiomers of 2-[4-{7-methylpyrazolo[1,5-a]pyridin-2-yl}-1H,4H,5H,6H,7H-imidazo[4,5-c]pyridin-5-yl]pyrimidine | C, E |
| 4S and 4R enantiomers of 2-[4-{7-chloropyrazolo[1,5-a]pyridin-2-yl}-1H,4H,5H,6H,7H-imidazo[4,5-c]pyridin-5-yl]-5-methyl-1,3,4-oxadiazole | C, E |
| 4S and 4R enantiomers of 2-[4-{7-fluoropyrazolo[1,5-a]pyridin-2-yl}-1H,4H,5H,6H,7H-imidazo[4,5-c]pyridin-5-yl]-5-methyl-1,3,4-oxadiazole | D, E |
| 4S and 4R enantiomers of 5-{6-cyclopropylpyrazolo[1,5-a]pyridine-3-carbonyl}-4-{7-methylpyrazolo[1,5-a]pyridin-2-yl}-1H,4H,5H,6H,7H-imidazo[4,5-c]pyridine | C, D |
| 4S and 4R enantiomers of 4-[7-(difluoromethyl)pyrazolo[1,5-a]pyridin-2-yl]-5-{6-methoxypyrazolo[1,5-a]pyridine-3-carbonyl}-1H,4H,5H,6H,7H-imidazo[4,5-c]pyridine | C, D |
| 4S and 4R enantiomers of 2-[4-[4-(trifluoromethoxy)pyrazolo[1,5-a]pyridin-2-yl]-1H,4H,5H,6H,7H-imidazo[4,5-c]pyridine-5-carbonyl]-5-[1-(trifluoromethyl)-1H-pyrazol-4-yl]-1,3,4-oxadiazole | C, E |
| 4S and 4R enantiomers of 7-(difluoromethyl)-2-[5-{pyrazolo[1,5-a]pyridine-3-carbonyl}-1H,4H,5H,6H,7H-imidazo[4,5-c]pyridin-4-yl]pyrazolo[1,5-a]pyridine | C, E |
| 4S and 4R enantiomers of 5-[6-(methoxymethyl)pyrazolo[1,5-alpyridine-3-carbonyl]-4-{4-methoxypyrazolo[1,5-a]pyridin-2-yl}-1H,4H,5H,6H,7H-imidazo[4,5-c]pyridine | C, E |
| 4S and 4R enantiomers of ({3-[4-{4-methoxypyrazolo[1,5-a]pyridin-2-yl}-1H,4H,5H,6H,7H-imidazo[4,5-c]pyridine-5-carbonyl]pyrazolo[1,5-a]pyridin-6-yl}methyl)dimethylamine | C, E |
| 4S and 4R enantiomers of 2-[4-[4-(difluoromethyl)pyrazolo[1,5-a]pyridin-2-yl]-1H,4H,5H,6H,7H-imidazo[4,5-c]pyridin-5-yl]-1,3-benzoxazole | D, D |
| 4S and 4R enantiomers of 4-{5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazol-2-yl}morpholine | D, E |

-continued

| Compound(s) | $AC_{50}$ |
|---|---|
| 4S and 4R enantiomers of 2-(1-methyl-1H-pyrazol-4-yl)-5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazole | C, E |
| 4S and 4R enantiomers of 2-methyl-5-[4-{7-methylpyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-methyl-5-[4-[7-(trifluoromethyl)pyrazolo[1,5-a]pyridin-2-yl]-1H,4H,5H,6H,7H-imidazo[4,5-c]pyridin-5-yl]-1,3,4-oxadiazole | C, E |
| 4S and 4R enantiomers of 2-{5-[4-{4-methoxypyrazolo[1,5-a]pyridin-2-yl}-1H,4H,5H,6H,7H-imidazo[4,5-c]pyridin-5-yl]-1,3,4-oxadiazol-2-yl}pyridine | C, E |
| 4S and 4R enantiomers of 4-{3-[4-{4-methoxypyrazolo[1,5-a]pyridin-2-yl}-1H,4H,5H,6H,7H-imidazo[4,5-c]pyridine-5-carbonyl]pyrazolo[1,5-a]pyridin-6-yl}-1-methyl-1H-pyrazole | C, D |
| 4S and 4R enantiomers of 2-[4-[7-(difluoromethyl)pyrazolo[1,5-a]pyridin-2-yl]-1H,4H,5H,6H,7H-imidazo[4,5-c]pyridin-5-yl]pyrimidine | C, C |
| 4S and 4R enantiomers of 2-(difluoromethyl)-5-[4-[7-(trifluoromethyl)pyrazolo[1,5-a]pyridin-2-yl]-1H,4H,5H,6H,7H-imidazo[4,5-c]pyridin-5-yl]-1,3,4-oxadiazole | C, E |
| 4S and 4R enantiomers of 2-cyclopropyl-5-[4-{4-methoxypyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 7-methyl-2-[5-{6-methylpyrazolo[1,5-a]pyridine-3-carbonyl}-1H,4H,5H,6H,7H-imidazo[4,5-c]pyridin-4-yl]pyrazolo[1,5-a]pyridine | C, D |
| 4S and 4R enantiomers of 3-14-{4-methoxypyrazolo[1,5-a]pyridin-2-yl}-1H,4H,5H,6H,7H-imidazo[4,5-c]pyridine-5-carbonyl]-N,N-dimethylpyrazolo[1,5-a]pyridin-6-amine | C, D |
| 4S and 4R enantiomers of 5-[6-(2-methoxyethyl)pyrazolo[1,5-a]pyridine-3-carbonyl]-4-[7-(trifluoromethyl)pyrazolo[1,5-a]pyridin-2-yl]-1H,4H,5H,6H,7H-imidazo[4,5-c]pyridine | C, E |
| 4S and 4R enantiomers of 4-{5-[4-[4-(difluoromethyl)pyrazolo[1,5-a]pyridin-2-yl]-1H,4H,5H,6H,7H-imidazo[4,5-c]pyridin-5-yl]-1,3,4-oxadiazol-2-yl}morpholine | D, E |
| 4S and 4R enantiomers of 2-(difluoromethyl)-5-[4-{7-fluoropyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-[4-{7-chloropyrazolo[1,5-a]pyridin-2-yl}-1H,4H,5H,6H,7H-imidazo[4,5-c]pyridin-5-yl]-5-(difluoromethyl)-1,3,4-oxadiazole | C, E |
| 4S and 4R enantiomers of 7-chloro-2-[5-{6-methylpyrazolo[1,5-a]pyridine-3-carbonyl}-1H,4H,5H,6H,7H-imidazo[4,5-c]pyridin-4-yl]pyrazolo[1,5-a]pyridine | C, D |
| 4S and 4R enantiomers of 2-tert-butyl-5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazole | C, E |
| 4S and 4R enantiomers of 2-[4-{7-methylpyrazolo[1,5-a]pyridin-2-yl}-1H,4H,5H,6H,7H-imidazo[4,5-c]pyridin-5-yl]pyrimidin-5-amine | C, E |
| 4S and 4R enantiomers of 5-[6-(2-methoxyethyl)pyrazolo[1,5-a]pyridine-3-carbonyl]-4-{pyrazolo[1,5-a]pyridin-2-yl}-1H,4H,5H,6H,7H-imidazo[4,5-c]pyridine | D, E |
| 4S and 4R enantiomers of 2-[4-[7-(difluoromethyl)pyrazolo[1,5-a]pyridin-2-yl]-1H,4H,5H,6H,7H-imidazo[4,5-c]pyridin-5-yl]-5-methyl-1,3,4-oxadiazole | D, E |
| 4S and 4R enantiomers of 3-[4-{7-fluoropyrazolo[1,5-a]pyridin-2-yl}-1H,4H,5H,6H,7H-imidazo[4,5-c]pyridine-5-carbonyl]-N,N-dimethylpyrazolo[1,5-a]pyridin-6-amine | C, E |
| 4S and 4R enantiomers of (2-{3-[4-{4-fluoropyrazolo[1,5-a]pyridin-2-yl}-1H,4H,5H,6H,7H-imidazo[4,5-c]pyridine-5-carbonyl]pyrazolo[1,5-a]pyridin-6-yl}ethyl)dimethylamine | C, E |
| 4S and 4R enantiomers of dimethyl(2-{3-[4-{4-methylpyrazolo[1,5-a]pyridin-2-yl}-1H,4H,5H,6H,7H-imidazo[4,5-c]pyridine-5-carbonyl]pyrazolo[1,5-a]pyridin-6-yl}ethyl)amine | C, E |
| 4S and 4R enantiomers of 2-cyclobutyl-5-[4-{pyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-cyclobutyl-5-[4-{4-fluoropyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-tert-butyl-5-[4-{pyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 6-[4-{pyrazolo[1,5-a]pyridin-2-yl}-1H,4H,5H,6H,7H-imidazo[4,5-c]pyridin-5-yl]pyridin-3-amine | D, E |
| 4S and 4R enantiomers of 3-[4-[7-(difluoromethyl)pyrazolo[1,5-a]pyridin-2-yl]-1H,4H,5H,6H,7H-imidazo[4,5-c]pyridine-5-carbonyl]-N,N-dimethylpyrazolo[1,5-a]pyridin-6-amine | C, E |
| 4S and 4R enantiomers of 2-cyclobutyl-5-[4-[7-(trifluoromethyl)pyrazolo[1,5-a]pyridin-2-yl]-1H,4H,5H,6H,7H-imidazo[4,5-c]pyridin-5-yl]-1,3,4-oxadiazole | C, E |
| 4S and 4R enantiomers of 2-tert-butyl-5-[4-{4-fluoropyrazolo[1,5-a]pyridin-2-yl}-1H,4H,5H,6H,7H-imidazo[4,5-c]pyridin-5-yl]-1,3,4-oxadiazole | D, E |
| 4S and 4R enantiomers of 2-[4-{pyrazolo[1,5-a]pyridin-2-yl}-1H,4H,5H,6H,7H-imidazo[4,5-c]pyridin-5-yl]pyrimidin-5-amine | D, E |
| 4S and 4R enantiomers of 2-[4-[7-(trifluoromethyl)pyrazolo[1,5-a]pyridin-2-yl]-1H,4H,5H,6H,7H-imidazo[4,5-c]pyridin-5-yl]pyrimidin-5-amine | D, E |
| 4S and 4R enantiomers of 2-[4-[7-(difluoromethyl)pyrazolo[1,5-a]pyridin-2-yl]-1H,4H,5H,6H,7H-imidazo[4,5-c]pyridin-5-yl]pyrimidin-5-amine | D, E |
| 4S and 4R enantiomers of 2-[4-{4-fluoropyrazolo[1,5-a]pyridin-2-yl}-1H,4H,5H,6H,7H-imidazo[4,5-c]pyridine-5-carbonyl]-5-(1H-pyrazol-4-yl)-1,3,4-oxadiazole | C, E |
| 4S and 4R enantiomers of 2-[4-{pyrazolo[1,5-a]pyridin-2-yl}-1H,4H,5H,6H,7H-imidazo[4,5-c]pyridine-5-carbonyl]-1,3-thiazole | C, E |
| 4S and 4R enantiomers of 6-[4-[4-(difluoromethyl)pyrazolo[1,5-a]pyridin-2-yl]-1H,4H,5H,6H,7H-imidazo[4,5-c]pyridin-5-yl]pyridin-3-amine | C, E |
| 4S and 4R enantiomers of 2-[4-[4-(difluoromethyl)pyrazolo[1,5-a]pyridin-2-yl]-1H,4H,5H,6H,7H-imidazo[4,5-c]pyridin-5-yl]-5-(1-methyl-1H-pyrazol-4-yl)-1,3,4-oxadiazole | D, E |

-continued

| Compound(s) | $AC_{50}$ |
|---|---|
| 4S and 4R enantiomers of dimethyl(2-{3-[4-{pyrazolo[1,5-a]pyridin-2-yl}-1H,4H,5H,6H,7H-imidazo[4,5-c]pyridine-5-carbonyl]pyrazolo[1,5-a]pyridin-6-yl}ethyl)amine | D, E |
| 4S and 4R enantiomers of dimethyl(2-{3-[4-[7-(trifluoromethyl)pyrazolo[1,5-a]pyridin-2-yl]-1H,4H,5H,6H,7H-imidazo[4,5-c]pyridine-5-carbonyl]pyrazolo[1,5-a]pyridin-6-yl}ethyl)amine | C, D |
| 4S and 4R enantiomers of 2-[4-{7-chloropyrazolo[1,5-a]pyridin-2-yl}-1H,4H,5H,6H,7H-imidazo[4,5-c]pyridin-5-yl]-5-cyclobutyl-1,3,4-oxadiazole | C, E |
| 4S and 4R enantiomers of 2-tert-butyl-5-[4-{7-chloropyrazolo[1,5-a]pyridin-2-yl}-1H,4H,5H,6H,7H-imidazo[4,5-c]pyridin-5-yl]-1,3,4-oxadiazole | D, E |
| 4S and 4R enantiomers of 2-cyclobutyl-5-[4-{7-methylpyrazolo[1,5-a]pyridin-2-yl}-1H,4H,5H,6H,7H-imidazo[4,5-c]pyridin-5-yl]-1,3,4-oxadiazole | C, D |
| 4S and 4R enantiomers of 2-cyclobutyl-5-[4-[7-(difluoromethyl)pyrazolo[1,5-a]pyridin-2-yl]-1H,4H,5H,6H,7H-imidazo[4,5-c]pyridin-5-yl]-1,3,4-oxadiazole | C, D |
| 4S and 4R enantiomers of 2-tert-butyl-5-[4-{7-methylpyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-tert-butyl-5-[4-[7-(trifluoromethyl)pyrazolo[1,5-a]pyridin-2-yl]-1H,4H,5H,6H,7H-imidazo[4,5-c]pyridin-5-yl]-1,3,4-oxadiazole | D, E |
| 4S and 4R enantiomers of 2-[4-{7-fluoropyrazolo[1,5-a]pyridin-2-yl}-1H,4H,5H,6H,7H-imidazo[4,5-c]pyridin-5-yl]-5-(trifluoromethyl)-1,3,4-oxadiazole | C, E |
| 4S and 4R enantiomers of 2-tert-butyl-5-[4-[7-(difluoromethyl)pyrazolo[1,5-a]pyridin-2-yl]-1H,4H,5H,6H,7H-imidazo[4,5-c]pyridin-5-yl]-1,3,4-oxadiazole | D, E |
| 4S and 4R enantiomers of 2-[4-{4-methylpyrazolo[1,5-a]pyridin-2-yl}-1H,4H,5H,6H,7H-imidazo[4,5-c]pyridine-5-carbonyl]-5-(1H-pyrazol-4-yl)-1,3,4-oxadiazole | C, D |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1,3-oxazol-2-yl}pyrimidine | C, E |
| 4S and 4R enantiomers of 2-{5-[4-{4-methylpyrazolo[1,5-a]pyridin-2-yl}-1H,4H,5H,6H,7H-imidazo[4,5-c]pyridine-5-carbonyl]-1,3-oxazol-2-yl}pyrimidine | C, E |
| 4S and 4R enantiomers of 2-[4-{7-chloropyrazolo[1,5-a]pyridin-2-yl}-1H,4H,5H,6H,7H-imidazo[4,5-c]pyridin-5-yl]pyrimidin-5-amine | C, E |
| 4S and 4R enantiomers of 2-(1-methyl-1H-pyrazol-4-yl)-5-[4-(pyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of 2-(1-methyl-1H-pyrazol-3-yl)-5-[4-{pyrazolo[1,5-a]pyridin-2-yl}-1H,4H,5H,6H,7H-imidazo[4,5-c]pyridine-5-carbonyl]-1,3-oxazole | C, D |
| 4S and 4R enantiomers of 2-(1,5-dimethyl-1H-pyrazol-4-yl)-5-[4-{pyrazolo[1,5-a]pyridin-2-yl}-1H,4H,5H,6H,7H-imidazo[4,5-c]pyridine-5-carbonyl]-1,3-oxazole | C, D |
| 4S and 4R enantiomers of 2-{5-14-{4-cyclopropylpyrazolo[1,5-a]pyridin-2-yl}-1H,4H,5H,6H,7H-imidazo[4,5-c]pyridine-5-carbonyl]-1,3,4-oxadiazol-2-yl}pyrimidine | D, E |
| 4S and 4R enantiomers of 2-methyl-5-[4-{pyrazolo[1,5-a]pyridin-2-yl}-1H,4H,5H,6H,7H-imidazo[4,5-c]pyridine-5-carbonyl]-1,3,4-thiadiazole | C, E |
| 4S and 4R enantiomers of 2-[4-{4-fluoropyrazolo[1,5-a]pyridin-2-yl}-1H,4H,5H,6H,7H-imidazo[4,5-c]pyridine-5-carbonyl]-5-methyl-1,3,4-thiadiazole | C, E |
| 4S and 4R enantiomers of 2-[4-{pyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of 2-[4-{4-fluoropyrazolo[1,5-a]pyridin-2-yl}-1H,4H,5H,6H,7H-imidazo[4,5-c]pyridine-5-carbonyl]-1,3-oxazole | C, E |
| 4S and 4R enantiomers of 2-[4-[4-(trifluoromethyl)pyrazolo[1,5-a]pyridin-2-yl]-1H,4H,5H,6H,7H-imidazo[4,5-c]pyridine-5-carbonyl]-1,3-benzothiazole | C, E |
| 4S and 4R enantiomers of 5-cyclopropanecarbonyl-4-{4-fluoropyrazolo[1,5-a]pyridin-2-yl}-1H,4H,5H,6H,7H-imidazo[4,5-c]pyridine | D, E |
| 4S and 4R enantiomers of 2-fluoro-6-[4-{4-methylpyrazolo[1,5-a]pyridin-2-yl}-1H,4H,5H,6H,7H-imidazo[4,5-c]pyridin-5-yl]pyridine | C, E |
| 4S and 4R enantiomers of 2-{5-[4-{4-fluoropyrazolo[1,5-a]pyridin-2-yl}-1H,4H,5H,6H,7H-imidazo[4,5-c]pyridine-5-carbonyl]-1,3-oxazol-2-yl}pyrimidine | D, D |
| 4S and 4R enantiomers of 2-{5-[4-[4-(difluoromethyl)pyrazolo[1,5-a]pyridin-2-yl]-1H,4H,5H,6H,7H-imidazo[4,5-c]pyridine-5-carbonyl]-1,3-oxazol-2-yl}pyrimidine | D, E |
| 4S and 4R enantiomers of 2-{5-[4-[4-(trifluoromethyl)pyrazolo[1,5-a]pyridin-2-yl]-1H,4H,5H,6H,7H-imidazo[4,5-c]pyridine-5-carbonyl]-1,3-oxazol-2-yl}pyrimidine | C, E |
| 4S and 4R enantiomers of 4-cyclopropyl-5-[4-[7-(trifluoromethyl)pyrazolo[1,5-a]pyridin-2-yl]-1H,4H,5H,6H,7H-imidazo[4,5-c]pyridine-5-carbonyl]-1,3-oxazole | C, D |
| 4S and 4R enantiomers of 4-cyclopropyl-2-(1-methyl-1H-pyrazol-4-yl)-5-[4-{pyrazolo[1,5-alpyridin-2-yl}-1H,4H,5H,6H,7H-imidazo[4,5-c]pyridine-5-carbonyl]-1,3-oxazole | C, D |
| 4S and 4R enantiomers of 5-cyclobutanecarbonyl-4-{pyrazolo[1,5-a]pyridin-2-yl}-1H,4H,5H,6H,7H-imidazo[4,5-c]pyridine | D, E |
| 4S and 4R enantiomers of 5-cyclobutanecarbonyl-4-(4-methylpyrazolo[1,5-a]pyridin-2-yl}-1H,4H,5H,6H,7H-imidazo[4,5-c]pyridine | D, E |
| 4S and 4R enantiomers of 5-[4-[4-(difluoromethyl)pyrazolo[1,5-a]pyridin-2-yl]-1H,4H,5H,6H,7H-imidazo[4,5-c]pyridine-5-carbonyl]-2-(1-methyl-1H-pyrazol-3-yl)-1,3-oxazole | C, E |
| 4S and 4R enantiomers of 5-(trifluoromethyl)-2-[4-[7-(trifluoromethyl)pyrazolo[1,5-alpyridin-2-yl]-1H,4H,5H,6H,7H-imidazo[4,5-c]pyridin-5-yl]pyridine | C, E |
| 4S and 4R enantiomers of 5-[4-{4-fluoropyrazolo[1,5-a]pyridin-2-yl}-1H,4H,5H,6H,7H-imidazo[4,5-c]pyridine-5-carbonyl]-2-(1-methyl-1H-pyrazol-4-yl)-1,3-oxazole | C, D |
| 4S and 4R enantiomers of 5-[4-[4-(difluoromethyl)pyrazolo[1,5-a]pyridin-2-yl]-1H,4H,5H,6H,7H-imidazo[4,5-c]pyridine-5-carbonyl]-2-(1-methyl-1H-pyrazol-4-yl)-1,3-oxazole | C, E |
| 4S and 4R enantiomers of 2-[4-[4-(difluoromethoxy)pyrazolo[1,5-a]pyridin-2-yl]-1H,4H,5H,6H,7H-imidazo[4,5-c]pyridin-5-yl]-5-methyl-1,3,4-oxadiazole | C, E |

-continued

| Compound(s) | $AC_{50}$ |
|---|---|
| 4S and 4R enantiomers of 2-{5-[4-{pyrazolo[1,5-a]pyridin-2-yl}-1H,4H,5H,6H,7H-imidazo[4,5-c]pyridin-5-yl]-1,3,4-oxadiazol-2-yl}pyrazine | C, E |
| 4S and 4R enantiomers of 2-{5-[4-[4-(difluoromethyl)pyrazolo[1,5-a]pyridin-2-yl]-1H,4H,5H,6H,7H-imidazo[4,5-c]pyridin-5-yl]-1,3,4-oxadiazol-2-yl}pyrazine | C, E |
| 4S and 4R enantiomers of 4-{5-[4-{pyrazolo[1,5-alpyridin-2-yl}-1H,4H,5H,6H,7H-imidazo[4,5-c]pyridin-5-yl]-1,3,4-oxadiazol-2-yl}pyrimidine | C, D |
| 4S and 4R enantiomers of 4-{5-[4-{4-methylpyrazolo[1,5-a]pyridin-2-yl}-1H,4H,5H,6H,7H-imidazo[4,5-c]pyridin-5-yl]-1,3,4-oxadiazol-2-yl}pyrimidine | C, D |
| 4S and 4R enantiomers of 2-(1-methylcyclopropyl)-5-[4-{pyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-{5-[4-{pyrazolo[1,5-a]pyridin-2-yl}-1H,4H,5H,6H,7H-imidazo[4,5-c]pyridin-5-yl]-1,3,4-oxadiazol-2-yl}pyrimidine | C, E |
| 4S and 4R enantiomers of 2-{5-[4-{4-methylpyrazolo[1,5-a]pyridin-2-yl}-1H,4H,5H,6H,7H-imidazo[4,5-c]pyridin-5-yl]-1,3,4-oxadiazol-2-yl}pyrimidine | C, E |
| 4S and 4R enantiomers of 2-{5-[4-{4-cyclopropylpyrazolo[1,5-a]pyridin-2-yl}-1H,4H,5H,6H,7H-imidazo[4,5-c]pyridin-5-yl]-1,3,4-oxadiazol-2-yl}pyrazine | C, E |
| 4S and 4R enantiomers of 4-{5-[4-[4-(difluoromethyl)pyrazolo[1,5-a]pyridin-2-yl]-1H,4H,5H,6H,7H-imidazo[4,5-c]pyridin-5-yl]-1,3,4-oxadiazol-2-yl}pyrimidine | E, E |
| 4S and 4R enantiomers of 4-{5-[4-{4-cyclopropylpyrazolo[1,5-a]pyridin-2-yl}-1H,4H,5H,6H,7H-imidazo[4,5-c]pyridin-5-yl]-1,3,4-oxadiazol-2-yl}pyrimidine | C, D |
| 4S and 4R enantiomers of 3-{5-[4-{pyrazolo[1,5-a]pyridin-2-yl}-1H,4H,5H,6H,7H-imidazo[4,5-c]pyridin-5-yl]-1,3,4-oxadiazol-2-yl}pyridazine | C, E |
| 4S and 4R enantiomers of 3-(5-[4-{4-methylpyrazolo[1,5-a]pyridin-2-yl}-1H,4H,5H,6H,7H-imidazo[4,5-c]pyridin-5-yl]-1,3,4-oxadiazol-2-yl}pyridazine | C, E |
| 4S and 4R enantiomers of 3-{5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazol-2-yl}pyridazine | C, E |
| 4S and 4R enantiomers of 3-{5-[4-[4-(difluoromethyl)pyrazolo[1,5-a]pyridin-2-yl]-1H,4H,5H,6H,7H-imidazo[4,5-c]pyridin-5-yl]-1,3,4-oxadiazol-2-yl}pyridazine | C, E |
| 4S and 4R enantiomers of 3-{5-[4-{pyrazolo[1,5-a]pyridin-2-yl}-1H,4H,5H,6H,7H-imidazo[4,5-c]pyridin-5-yl]-1,3,4-oxadiazol-2-yl}pyridine | C, D |
| 4S and 4R enantiomers of 2-[4-{4-methoxypyrazolo[1,5-a]pyridin-2-yl}-1H,4H,5H,6H,7H-imidazo[4,5-c]pyridin-5-yl]-5-methyl-1,3,4-oxadiazole | C, E |
| 4S and 4R enantiomers of 2-(1-methylcyclopropyl)-5-[4-[4-(trifluoromethyl)pyrazolo[1,5-alpyridin-2-yl]-1H,4H,5H,6H,7H-imidazo[4,5-c]pyridin-5-yl]-1,3,4-oxadiazole | C, E |
| 4S and 4R enantiomers of 2-(2-fluoropropan-2-yl)-5-[4-{4-methylpyrazolo[1,5-a]pyridin-2-yl}-1H,4H,5H,6H,7H-imidazo[4,5-c]pyridin-5-yl]-1,3,4-oxadiazole | D, E |
| 4S and 4R enantiomers of 2-(2-fluoropropan-2-yl)-5-[4-[4-(trifluoromethyl)pyrazolo[1,5-alpyridin-2-yl]-1H,4H,5H,6H,7H-imidazo[4,5-c]pyridin-5-yl]-1,3,4-oxadiazole | D, E |
| 4S and 4R enantiomers of 2-[4-[4-(difluoromethyl)pyrazolo[1,5-a]pyridin-2-yl]-1H,4H,5H,6H,7H-imidazo[4,5-c]pyridin-5-yl]-5-(2-fluoropropan-2-yl)-1,3,4-oxadiazole | D, E |
| 4S and 4R enantiomers of 2-(3,3-difluorocyclobutyl)-5-[4-{pyrazolo{1,5-a]pyridin-2-yl}-1H,4H,5H,6H,7H-imidazo[4,5-c]pyridin-5-yl]-1,3,4-oxadiazole | D, E |
| 4S and 4R enantiomers of 2-(3,3-difluorocyclobutyl)-5-[4-{4-methylpyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-{5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazol-2-yl}pyrimidine | C, E |
| 4S and 4R enantiomers of 2-{5-[4-[4-(difluoromethyl)pyrazolo[1,5-a]pyridin-2-yl]-1H,4H,5H,6H,7H-imidazo[4,5-c]pyridin-5-yl]-1,3,4-oxadiazol-2-yl}pyrimidine | C, E |
| 4S and 4R enantiomers of 2-{5-[4-{4-fluoropyrazolo[1,5-a]pyridin-2-yl}-1H,4H,5H,6H,7H-imidazo[4,5-c]pyridin-5-yl]-1,3,4-oxadiazol-2-yl}pyrimidine | C, E |
| 4S and 4R enantiomers of 3-{5-[4-{4-fluoropyrazolo[1,5-a]pyridin-2-yl}-1H,4H,5H,6H,7H-imidazo[4,5-c]pyridin-5-yl]-1,3,4-oxadiazol-2-yl}pyridazine | C, E |
| 4S and 4R enantiomers of 3-{5-[4-{4-cyclopropylpyrazolo[1,5-a]pyridin-2-yl}-1H,4H,5H,6H,7H-imidazo[4,5-c]pyridin-5-yl]-1,3,4-oxadiazol-2-yl}pyridazine | C, B |
| 4S and 4R enantiomers of 4-[4-{4-fluoropyrazolo[1,5-a]pyridin-2-yl}-1H,4H,5H,6H,7H-imidazo[4,5-c]pyridin-5-yl]-1-methyl-1H-pyrazole | C, E |
| 4S and 4R enantiomers of 2-[4-[4-(propan-2-yl)pyrazolo[1,5-a]pyridin-2-yl]-1H,4H,5H,6H,7H-imidazo[4,5-c]pyridin-5-yl]pyrimidine | E, E |
| 4S and 4R enantiomers of 2-[4-[4-(difluoromethyl)pyrazolo[1,5-a]pyridin-2-yl]-1H,4H,5H,6H,7H-imidazo[4,5-c]pyridin-5-yl]-5-(1-methylcyclopropyl)-1,3,4-oxadiazole | C, E |
| 4S and 4R enantiomers of 2-(2-fluoropropan-2-yl)-5-[4-{pyrazolo[1,5-a]pyridin-2-yl}-1H,4H,5H,6H,7H-imidazo[4,5-c]pyridin-5-yl]-1,3,4-oxadiazole | D, E |
| 4S and 4R enantiomers of 2-(3,3-difluorocyclobutyl)-5-[4-[4-(trifluoromethyl)pyrazolo[1,5-alpyridin-2-yl]-1H,4H,5H,6H,7H-imidazo[4,5-c]pyridin-5-yl]-1,3,4-oxadiazole | C, E |
| 4S and 4R enantiomers of 2-(3,3-difluorocyclobutyl)-5-[4-[4-(difluoromethyl)pyrazolo[1,5-alpyridin-2-yl]-1H,4H,5H,6H,7H-imidazo[4,5-c]pyridin-5-yl]-1,3,4-oxadiazole | C, E |
| 4S and 4R enantiomers of 2-(3,3-difluorocyclobutyl)-5-[4-{4-fluoropyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 2-[4-{4-cyclopropylpyrazolo[1,5-a]pyridin-2-yl}-1H,4H,5H,6H,7H-imidazo[4,5-c]pyridin-5-yl]-5-(3,3-difluorocyclobutyl)-1,3,4-oxadiazole | C, E |
| 4S and 4R enantiomers of 2-{5-[4-{4-cyclopropylpyrazolo[1,5-a]pyridin-2-yl}-1H,4H,5H,6H,7H-imidazo[4,5-c]pyridin-5-yl]-1,3,4-oxadiazol-2-yl}pyrimidine | C, E |
| 4S and 4R enantiomers of 2-{5-[4-[4-(propan-2-yl)pyrazolo[1,5-a]pyridin-2-yl]-1H,4H,5H,6H,7H-imidazo[4,5-c]pyridin-5-yl]-1,3,4-oxadiazol-2-yl}pyrimidine | C, E |
| 4S and 4R enantiomers of 2-{5-[4-{4-chloropyrazolo[1,5-a]pyridin-2-yl}-1H,4H,5H,6H,7H-imidazo[4,5-c]pyridin-5-yl]-1,3,4-oxadiazol-2-yl}pyrimidine | C, E |

-continued

| Compound(s) | $AC_{50}$ |
|---|---|
| 4S and 4R enantiomers of 2-{5-[4-{7-chloropyrazolo[1,5-a]pyridin-2-yl}-1H,4H,5H,6H,7H-imidazo[4,5-c]pyridin-5-yl]-1,3,4-oxadiazol-2-yl}pyrazine | C, E |
| 4S and 4R enantiomers of 2-{5-[4-{7-methylpyrazolo[1,5-a]pyridin-2-yl}-1H,4H,5H,6H,7H-imidazo[4,5-c]pyridin-5-yl]-1,3,4-oxadiazol-2-yl}pyrazine | C, D |
| 4S and 4R enantiomers of 3-{5-[4-{4-methylpyrazolo[1,5-a]pyridin-2-yl}-1H,4H,5H,6H,7H-imidazo[4,5-c]pyridin-5-yl]-1,3,4-oxadiazol-2-yl}pyridine | C, D |
| 4S and 4R enantiomers of 3-(5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazol-2-yl}pyridine | C, E |
| 4S and 4R enantiomers of 2-methyl-3-{5-[4-{pyrazolo[1,5-a]pyridin-2-yl}-1H,4H,5H,6H,7H-imidazo[4,5-c]pyridin-5-yl]-1,3,4-oxadiazol-2-yl}pyridine | C, E |
| 4S and 4R enantiomers of 2-{5-[4-{pyrazolo[1,5-a]pyridin-2-yl}-1H,4H,5H,6H,7H-imidazo[4,5-c]pyridine-5-carbonyl]-1,3-oxazol-2-yl}pyrazine | C, D |
| 4S and 4R enantiomers of 1-methyl-4-[4-{pyrazolo[1,5-a]pyridin-2-yl}-1H,4H,5H,6H,7H-imidazo[4,5-c]pyridin-5-yl]-1H-pyrazole | D, E |
| 4S and 4R enantiomers of 2-[4-{4-chloropyrazolo[1,5-a]pyridin-2-yl}-1H,4H,5H,6H,7H-imidazo[4,5-c]pyridin-5-yl]-5-(3,3-difluorocyclobutyl)-1,3,4-oxadiazole | C, E |
| 4S and 4R enantiomers of 2-{5-[4-[7-(trifluoromethyl)pyrazolo[1,5-a]pyridin-2-yl]-1H,4H,5H,6H,7H-imidazo[4,5-c]pyridin-5-yl]-1,3,4-oxadiazol-2-yl}pyrazine | C, E |
| 4S and 4R enantiomers of 3-{5-[4-[4-(difluoromethyl)pyrazolo[1,5-a]pyridin-2-yl]-1H,4H,5H,6H,7H-imidazo[4,5-c]pyridin-5-yl]-1,3,4-oxadiazol-2-yl}pyridine | C, D |
| 4S and 4R enantiomers of 3-{5-[4-{4-fluoropyrazolo[1,5-a]pyridin-2-yl}-1H,4H,5H,6H,7H-imidazo[4,5-c]pyridin-5-yl]-1,3,4-oxadiazol-2-yl}pyridine | C, D |
| 4S and 4R enantiomers of 3-{5-[4-{4-cyclopropylpyrazolo[1,5-a]pyridin-2-yl}-1H,4H,5H,6H,7H-imidazo[4,5-c]pyridin-5-yl]-1,3,4-oxadiazol-2-yl}-2-methylpyridine | C, C |
| 4S and 4R enantiomers of 1-methyl-4-[4-{4-methylpyrazolo[1,5-a]pyridin-2-yl}-1H,4H,5H,6H,7H-imidazo[4,5-c]pyridin-5-yl]-1H-pyrazole | C, E |
| 4S and 4R enantiomers of 2-(2-fluoropropan-2-yl)-5-[4-{4-fluoropyrazolo[1,5-a]pyridin-2-yl}-1H,4H,5H,6H,7H-imidazo[4,5-c]pyridin-5-yl]-1,3,4-oxadiazole | C, E |
| 4S and 4R enantiomers of 3-{5-[4-{4-cyclopropylpyrazolo[1,5-a]pyridin-2-yl}-1H,4H,5H,6H,7H-imidazo[4,5-c]pyridin-5-yl]-1,3,4-oxadiazol-2-yl}pyridine | C, D |
| 4S and 4R enantiomers of 2-fluoro-3-{5-[4-{pyrazolo[1,5-a]pyridin-2-yl}-1H,4H,5H,6H,7H-imidazo[4,5-c]pyridin-5-yl]-1,3,4-oxadiazol-2-yl}pyridine | C, D |
| 4S and 4R enantiomers of 2-(3-methyl-1H-pyrazol-4-yl)-5-[4-{4-methylpyrazolo[1,5-alpyridin-2-yl}-1H,4H,5H,6H,7H-imidazo[4,5-c]pyridine-5-carbonyl]-1,3,4-oxadiazole | C, E |
| 4S and 4R enantiomers of 2-[4-{4-fluoropyrazolo[1,5-a]pyridin-2-yl}-1H,4H,5H,6H,7H-imidazo[4,5-c]pyridine-5-carbonyl]-5-(3-methyl-1H-pyrazol-4-yl)-1,3,4-oxadiazole | C, E |
| 4S and 4R enantiomers of 2-fluoro-3-{5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazol-2-yl}pyridine | C, E |
| 4S and 4R enantiomers of 3-{5-[4-[4-(difluoromethyl)pyrazolo[1,5-a]pyridin-2-yl]-1H,4H,5H,6H,7H-imidazo[4,5-c]pyridin-5-yl]-1,3,4-oxadiazol-2-yl}-2-fluoropyridine | C, D |
| 4S and 4R enantiomers of 2-[4-{4-cyclopropylpyrazolo[1,5-a]pyridin-2-yl}-1H,4H,5H,6H,7H-imidazo[4,5-c]pyridin-5-yl]-5-(2-fluoropropan-2-yl)-1,3,4-oxadiazole | D, E |
| 4S and 4R enantiomers of 2-(2-fluoropropan-2-yl)-5-[4-[4-(propan-2-yl)pyrazolo[1,5-alpyridin-2-yl]-1H,4H,5H,6H,7H-imidazo[4,5-c]pyridin-5-yl]-1,3,4-oxadiazole | C, E |
| 4S and 4R enantiomers of 2-[4-{4-chloropyrazolo[1,5-a]pyridin-2-yl}-1H,4H,5H,6H,7H-imidazo[4,5-c]pyridin-5-yl]-5-(2-fluoropropan-2-yl)-1,3,4-oxadiazole | D, E |
| 4S and 4R enantiomers of 3-{5-[4-{4-cyclopropylpyrazolo[1,5-a]pyridin-2-yl}-1H,4H,5H,6H,7H-imidazo[4,5-c]pyridin-5-yl]-1,3,4-oxadiazol-2-yl}-2-fluoropyridine | C, D |
| 4S and 4R enantiomers of 2-[4-[4-(propan-2-yl)pyrazolo[1,5-a]pyridin-2-yl]-1H,4H,5H,6H,7H-imidazo[4,5-c]pyridin-5-yl]pyrazine | D. E |
| 4S and 4R enantiomers of 2-[4-{4-cyclopropylpyrazolo[1,5-a]pyridin-2-yl}-1H,4H,5H,6H,7H-imidazo[4,5-c]pyridin-5-yl]-5-(propan-2-yl)-1,3,4-oxadiazole | D, E |
| 4S and 4R enantiomers of 2-(propan-2-yl)-5-[4-[4-(propan-2-yl)pyrazolo[1,5-a]pyridin-2-yl]-1H,4H,5H,6H,7H-imidazo[4,5-c]pyridin-5-yl]-1,3,4-oxadiazole | D, E |
| 4S and 4R enantiomers of 2-(1,1-difluoroethyl)-5-[4-[7-(trifluoromethyl)pyrazolo[1,5-alpyridin-2-yl]-1H,4H,5H,6H,7H-imidazo[4,5-c]pyridin-5-yl]-1,3,4-oxadiazole | C, E |
| 4S and 4R enantiomers of 3-fluoro-2-{5-[4-[4-(trifluoromethyl)pyrazolo[1,5-a]pyridin-2-yl]-1H,4H,5H,6H,7H-imidazo[4,5-c]pyridin-5-yl]-1,3,4-oxadiazol-2-yl}pyridine | C, E |
| 4S and 4R enantiomers of 2-{5-[4-[4-(difluoromethyl)pyrazolo[1,5-a]pyridin-2-yl]-1H,4H,5H,6H,7H-imidazo[4,5-c]pyridin-5-yl]-1,3,4-oxadiazol-2-yl}-3-fluoropyridine | C, E |
| 4S and 4R enantiomers of 2-(5-[4-{4-cyclopropylpyrazolo[1,5-a]pyridin-2-yl}-1H,4H,5H,6H,7H-imidazo[4,5-c]pyridin-5-yl]-1,3,4-oxadiazol-2-yl}-3-fluoropyridine | C, D |
| 4S and 4R enantiomers of 2-fluoro-6-{5-[4-{pyrazolo[1,5-a]pyridin-2-yl}-1H,4H,5H,6H,7H-imidazo[4,5-c]pyridin-5-yl]-1,3,4-oxadiazol-2-yl}pyridine | C, E |
| 4S and 4R enantiomers of 5-fluoro-2-{5-[4-{pyrazolo[1,5-a]pyridin-2-yl}-1H,4H,5H,6H,7H-imidazo[4,5-c]pyridin-5-yl]-1,3,4-oxadiazol-2-yl}pyridine | C, D |
| 2-[2-(3-fluoroazetidin-1-yl)ethyl]-5-(4-{pyrazolo[1,5-a]pyridin-2-yl}-1H,4H,5H,6H,7H-imidazo[4,5-c]pyridine-5-carbonyl)-1,3,4-oxadiazole | D |

Having now fully described the methods, compounds, and compositions of matter provided herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications and publications cited herein are fully incorporated by reference herein in their entirety.

What is claimed is:

1. A compound of Formula I:

I

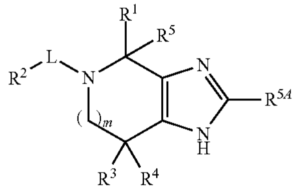

or a pharmaceutically acceptable salt thereof, wherein:

m is 1 or 2;

$R^1$ is

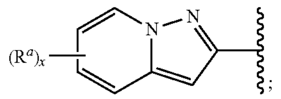

x is 0 to 5;

each $R^a$ independently is halo, $C_{1-6}$alkyl, $C_{3-6}$cycloalkyl, $C_{1-6}$haloalkyl, $C_{1-6}$alkoxy or $C_{1-6}$haloalkoxy;

$R^2$ is $C_{1-4}$alkyl, optionally substituted $C_{3-8}$cycloalkyl, optionally substituted heterocyclyl, optionally substituted aryl,

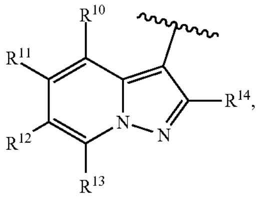

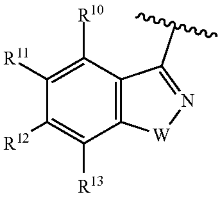

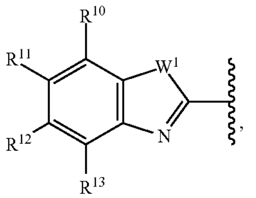

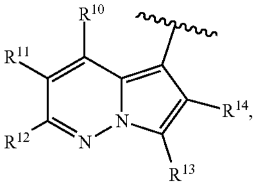

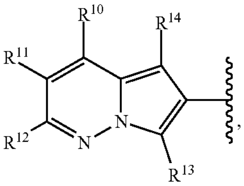

or

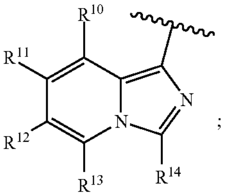

$R^3$ is H or $C_{1-6}$alkyl;

$R^4$ is H or $C_{1-6}$alkyl;

or $R^3$ and $R^4$, together with the atom to which they are attached, form a $C_{3-6}$cycloalkyl;

$R^5$ is H or D;

$R^{5A}$ is H or D;

L is a bond, carbonyl, optionally substituted $C_{1-6}$alkylene, optionally substituted $C_{1-6}$alkylenecarbonyl, optionally substituted $C_{2-6}$alkenylenecarbonyl, optionally substituted $C_{1-6}$haloalkylenecarbonyl, or optionally substituted —C(O)NR$^b$($C_{1-6}$alkylene)-, wherein the carbon atom of the carbonyl group is connected to N in Formula I;

$R^b$ is H or $C_{1-6}$alkyl;

W is S or NR$^{15}$;

$W^1$ is S, O, or NR$^{15}$;

$R^{10}$, $R^{11}$, $R^{12}$, $R^{13}$, and $R^{14}$ are independently H, $C_{1-6}$alkyl, $C_{1-6}$haloalkyl, $C_{1-6}$alkoxy, $C_{1-6}$alkoxy(alkylene), $C_{1-6}$hydroxyalkyl, $C_{1-6}$haloalkoxy, $C_{1-6}$haloalkoxy(alkylene), $C_{2-6}$alkenyl, CN, halo, $(CR^vR^x)_pNR^yR^z$, C(O)NR$^{y2}$R$^{z2}$, optionally substituted $C_{3-8}$cycloalkyl, optionally substituted heterocyclyl, optionally substituted heterocyclyl(alkylene), optionally substituted aryl, or optionally substituted heteroaryl;

$R^v$ and $R^x$ are independently H or $C_{1-6}$alkyl;

$R^y$ and $R^z$ are independently H, $C_{1-6}$alkyl, $C_{3-6}$cycloalkyl, $C_{1-6}$hydroxyalkyl, $C_{1-6}$haloalkyl, $C_{1-6}$alkoxy(alkylene), or C(O)O$C_{1-6}$alkyl;

$R^{y2}$ and $R^{z2}$ are independently H, $C_{1-6}$alkyl, or $C_{3-6}$cycloalkyl;

p is 0, 1, 2, or 3; and $R^{15}$ is H or $C_{1-6}$alkyl.

2. The compound of claim 1, wherein the compound is of Formula I-A-1:

I-A-1

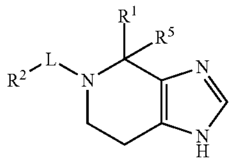

or a pharmaceutically acceptable salt thereof.

3. The compound of claim 1, wherein the compound is of Formula I-B-1:

I-B-1

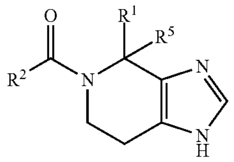

or a pharmaceutically acceptable salt thereof.

4. The compound of claim 1, wherein the compound is of Formula I-C-1:

I-C-1

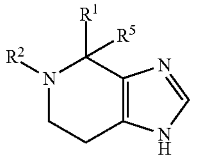

or a pharmaceutically acceptable salt thereof.

5. The compound of claim 2, or a pharmaceutically acceptable salt thereof, wherein L is a bond, —C(O)—, —$C(O)CH_2$—, or —$C(O)CF_2$—.

6. The compound of claim 5, or a pharmaceutically acceptable salt thereof, wherein $R^1$ is

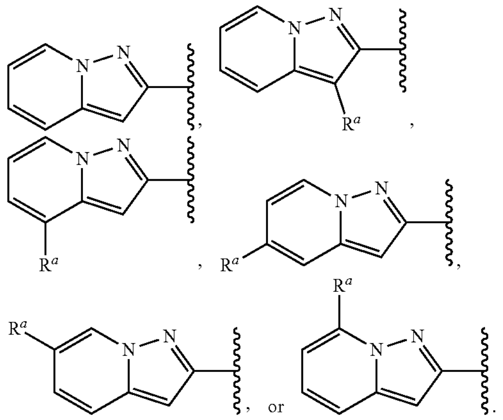

, , , , or .

7. The compound of claim 6, or a pharmaceutically acceptable salt thereof, wherein $R^a$ is F, Br, Cl, methyl, ethyl, isopropyl, methoxy, ethoxy, $CF_3$, $CHF_2$, $OCF_3$, $OCHF_2$, or cyclopropyl.

8. The compound of claim 7, or a pharmaceutically acceptable salt thereof, wherein $R^5$ is H.

9. The compound of claim 8, or a pharmaceutically acceptable salt thereof, wherein $R^2$ is optionally substituted $C_{3-8}$cycloalkyl, optionally substituted heterocyclyl, or optionally substituted aryl.

10. The compound of claim 9, or a pharmaceutically acceptable salt thereof, wherein $R^2$ is $C_{3-8}$cycloalkyl, optionally substituted with one or more of halo, $C_{1-6}$alkyl, $C_{1-6}$haloalkyl, or OH.

11. The compound of claim 10, or a pharmaceutically acceptable salt thereof, wherein $R^2$ is unsubstituted cyclopropyl, unsubstituted cyclobutyl, unsubstituted cyclopentyl, unsubstituted cyclohexyl,

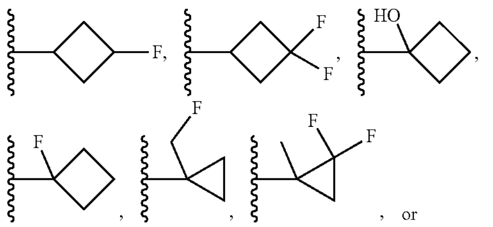

, , , , , or

-continued

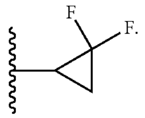

12. The compound of claim 9, or a pharmaceutically acceptable salt thereof, wherein $R^2$ is aryl, optionally substituted with one or more of halo or $C_{1-6}$alkoxy.

13. The compound of claim 8, or a pharmaceutically acceptable salt thereof, wherein $R^2$ is:

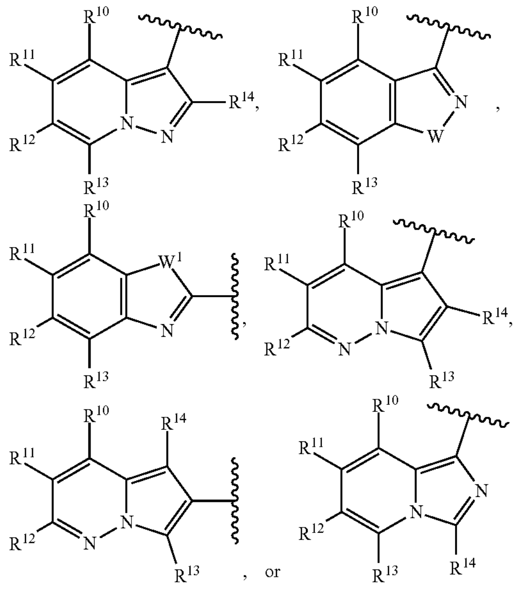

, , , , or

14. The compound of claim 13, or a pharmaceutically acceptable salt thereof, wherein $R^{10}$, $R^{11}$, $R^{12}$, $R^{13}$, and $R^{14}$ are each H.

15. The compound of claim 13, or a pharmaceutically acceptable salt thereof, wherein $R^2$ is:

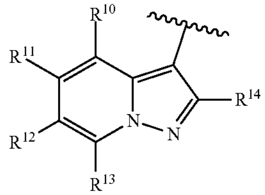

wherein:

$R^{10}$, $R^{11}$, $R^{12}$, $R^{13}$ and $R^{14}$ are independently H, $C_{1-6}$alkyl, $C_{3-6}$cycloalkyl, $C_{1-6}$alkoxy, $C_{1-6}$alkoxy(alkylene), optionally substituted heterocyclyl, optionally substituted heterocyclyl(alkylene), optionally substituted heteroaryl, or $(CR^vR^x)_pNR^yR^z$;

$R^v$ and $R^x$ are, independently, H or $C_{1-6}$alkyl;

$R^y$ and $R^z$ are, independently, H, $C_{1-6}$alkyl, $C_{3-6}$cycloalkyl, or $C(O)OC_{1-6}$alkyl; and p is 0, 1, 2, or 3.

16. The compound of claim 15, or a pharmaceutically acceptable salt thereof, wherein the optionally substituted heteroaryl is substituted with one or more of halo, $C_{1-6}$haloalkyl, or $C_{1-6}$alkyl.

17. The compound of claim 15, or a pharmaceutically acceptable salt thereof, wherein $R^{10}$, $R^{11}$, $R^{13}$, and $R^{14}$ are each hydrogen.

18. The compound of claim 8, wherein the compound is an S-enantiomer, or a pharmaceutically acceptable salt thereof.

19. A pharmaceutical composition comprising a compound of claim 1, or a pharmaceutically acceptable salt thereof, and a pharmaceutically acceptable excipient.

20. A method for stabilizing a mutant PAH protein, comprising contacting the protein with a compound of claim 1, or a pharmaceutically acceptable salt thereof.

21. The method of claim 20, wherein the mutant PAH protein contains at least one R408W, R261Q, R243Q, Y414C, L48S, A403V, I65T, R241C, L348V, R408Q, or V388M mutation.

22. The method of claim 20, wherein the mutant PAH protein contains at least one R408W, Y414C, I65T, F39L, R408Q, L348V, R261Q, A300S, or L48S mutation.

23. The method of claim 20, wherein the mutant PAH protein contains at least one R408W mutation.

24. A method for reducing blood phenylalanine concentration in a subject suffering from phenylketonuria comprising administering a compound of claim 1, or a pharmaceutically acceptable salt thereof.

25. The method of claim 24, wherein the blood phenylalanine concentration is reduced to a concentration less than or equal to about 600 μM.

26. The method of claim 25, wherein the blood phenylalanine concentration is reduced to a concentration less than or equal to about 360 μM.

27. The method of claim 24, wherein the subject has a blood phenylalanine concentration greater than about 600 μM prior to administration of the compound.

28. The method of claim 24, wherein the subject has a blood phenylalanine concentration greater than about 1200 μM prior to administration of the compound.

29. A compound, or a pharmaceutically acceptable salt thereof, wherein the compound is selected from the following:

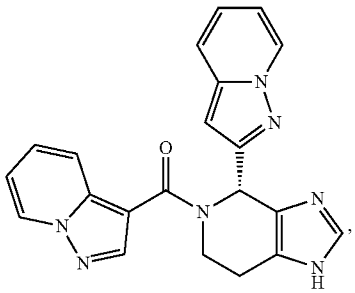 [SMILES: O=C(c1cnn2ccccc12)N1CCc2[nH]cnc2[C@H]1c1cc2ccccn2n1]

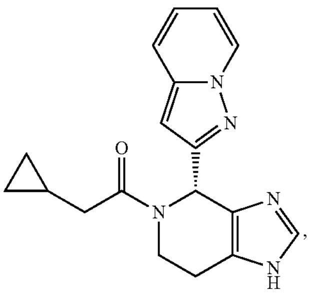 [SMILES: O=C(CC1CC1)N1CCc2[nH]cnc2[C@H]1c1cc2ccccn2n1]

-continued

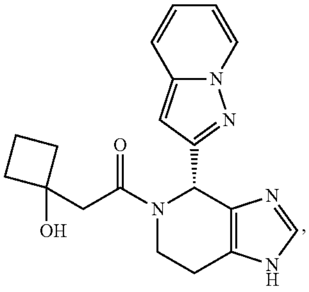 [SMILES: O=C(CC1(O)CCC1)N1CCc2[nH]cnc2[C@H]1c1cc2ccccn2n1]

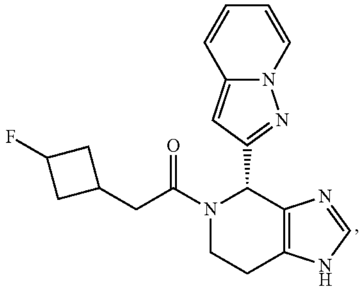 [SMILES: O=C(CC1CC(F)C1)N1CCc2[nH]cnc2[C@H]1c1cc2ccccn2n1]

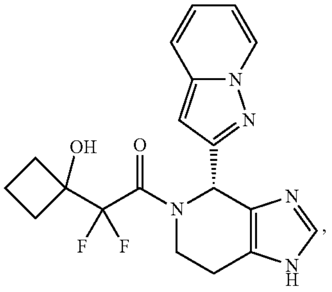 [SMILES: O=C(N1CCc2[nH]cnc2[C@H]1c1cc2ccccn2n1)C(F)(F)C1(O)CCC1]

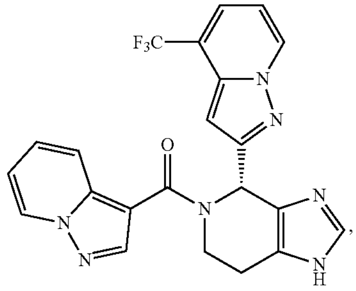 [SMILES: O=C(c1cnn2ccccc12)N1CCc2[nH]cnc2[C@H]1c1cc2c(C(F)(F)F)cccn2n1]

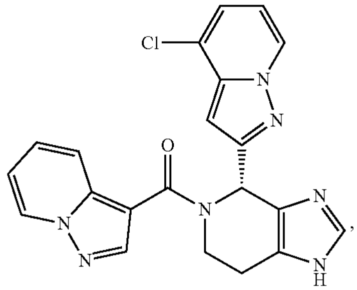 [SMILES: O=C(c1cnn2ccccc12)N1CCc2[nH]cnc2[C@H]1c1cc2c(Cl)cccn2n1]

-continued
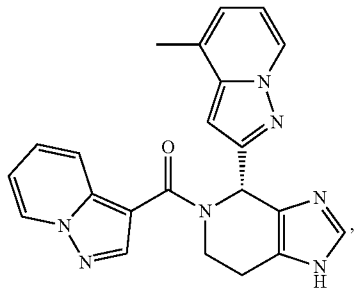 [SMILES: Cc1cccn2nc([C@@H]3c4nc[nH]c4CCN3C(=O)c3cnn4ccccc34)cc12]
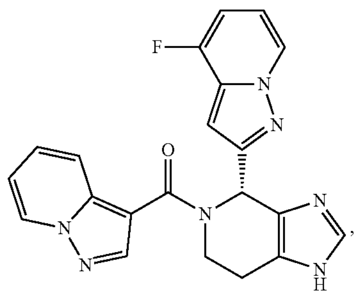 [SMILES: O=C(c1cnn2ccccc12)N1CCc2[nH]cnc2[C@H]1c1cc2c(F)cccn2n1]
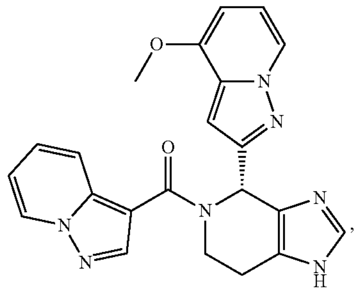 [SMILES: COc1cccn2nc([C@@H]3c4nc[nH]c4CCN3C(=O)c3cnn4ccccc34)cc12]
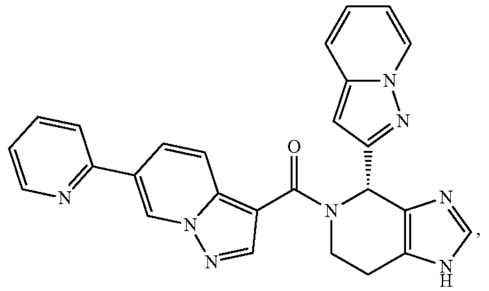 [SMILES: O=C(c1cnn2cc(-c3ccccn3)ccc12)N1CCc2[nH]cnc2[C@H]1c1cc2ccccn2n1]
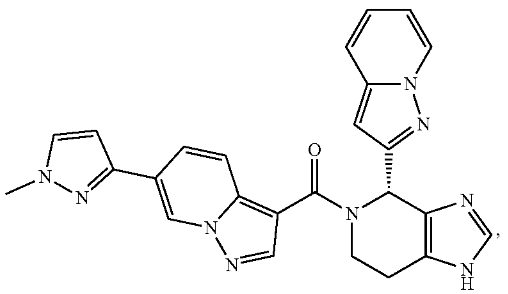 [SMILES: Cn1ccc(-c2ccc3c(C(=O)N4CCc5[nH]cnc5[C@H]4c4cc5ccccn5n4)cnn3c2)n1]
-continued
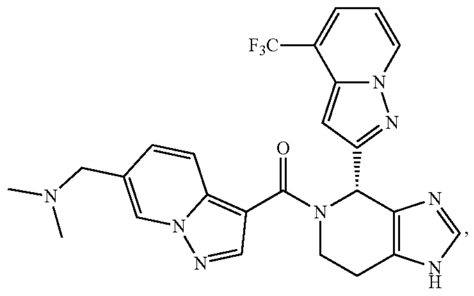 [SMILES: CN(C)Cc1ccc2c(C(=O)N3CCc4[nH]cnc4[C@H]3c3cc4c(C(F)(F)F)cccn4n3)cnn2c1]
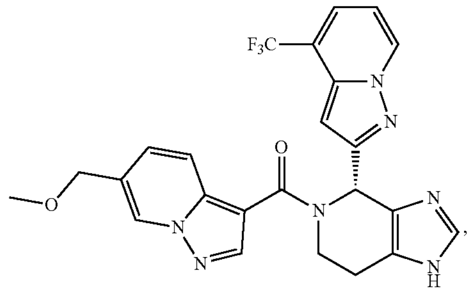 [SMILES: COCc1ccc2c(C(=O)N3CCc4[nH]cnc4[C@H]3c3cc4c(C(F)(F)F)cccn4n3)cnn2c1]
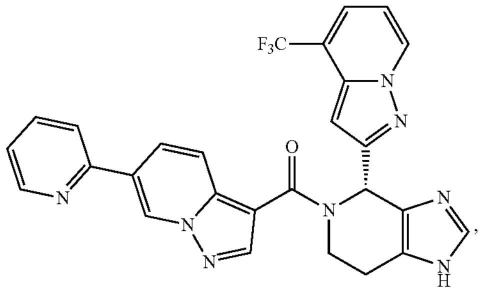 [SMILES: O=C(c1cnn2cc(-c3ccccn3)ccc12)N1CCc2[nH]cnc2[C@H]1c1cc2c(C(F)(F)F)cccn2n1]
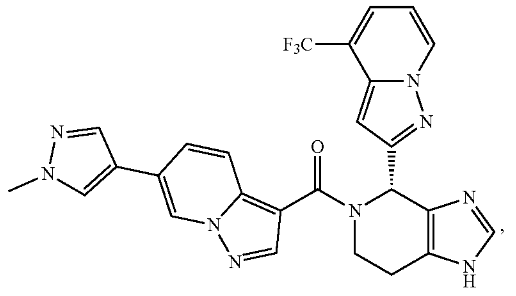 [SMILES: Cn1cc(-c2ccc3c(C(=O)N4CCc5[nH]cnc5[C@H]4c4cc5c(C(F)(F)F)cccn5n4)cnn3c2)cn1]
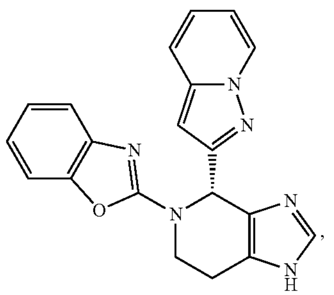 [SMILES: c1ccc2oc(N3CCc4[nH]cnc4[C@H]3c3cc4ccccn4n3)nc2c1]

-continued
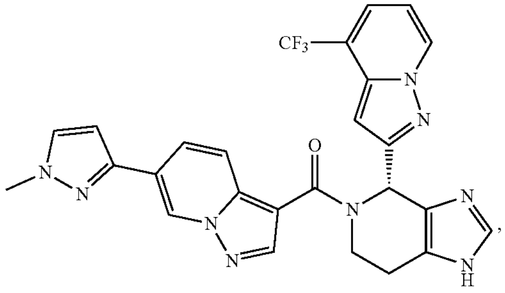 [SMILES: Cn1ccc(-c2ccc3c(C(=O)N4CCc5[nH]cnc5[C@H]4c4cc5c(C(F)(F)F)cccn5n4)cnn3c2)n1],
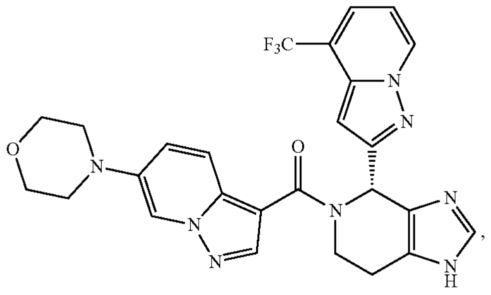 [SMILES: O=C(c1cnn2cc(N3CCOCC3)ccc12)N1CCc2[nH]cnc2[C@H]1c1cc2c(C(F)(F)F)cccn2n1],
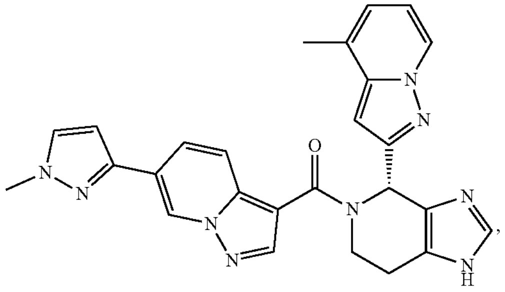 [SMILES: Cc1cccn2nc([C@@H]3c4nc[nH]c4CCN3C(=O)c3cnn4cc(-c5ccn(C)n5)ccc34)cc12],
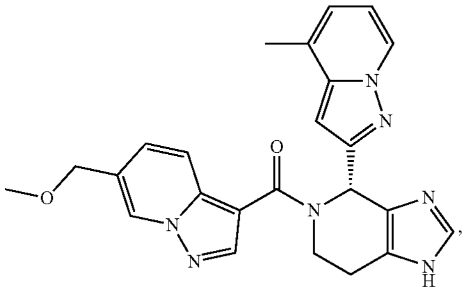 [SMILES: COCc1ccc2c(C(=O)N3CCc4[nH]cnc4[C@H]3c3cc4c(C)cccn4n3)cnn2c1],
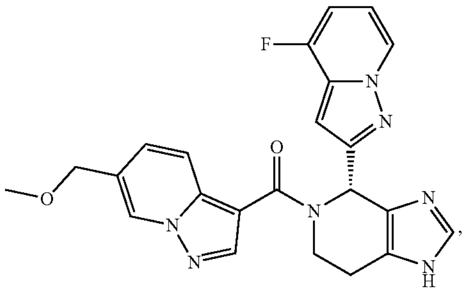 [SMILES: COCc1ccc2c(C(=O)N3CCc4[nH]cnc4[C@H]3c3cc4c(F)cccn4n3)cnn2c1],
-continued
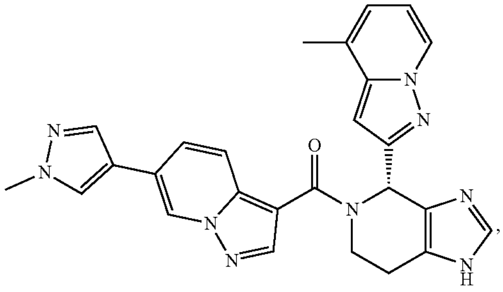 [SMILES: Cc1cccn2nc([C@@H]3c4nc[nH]c4CCN3C(=O)c3cnn4cc(-c5cnn(C)c5)ccc34)cc12],
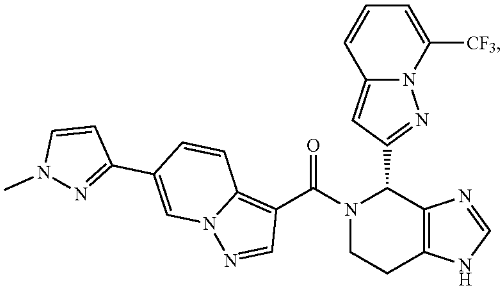 [SMILES: Cn1ccc(-c2ccc3c(C(=O)N4CCc5[nH]cnc5[C@H]4c4cc5cccc(C(F)(F)F)n5n4)cnn3c2)n1],
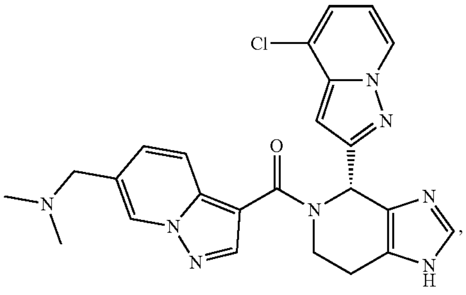 [SMILES: CN(C)Cc1ccc2c(C(=O)N3CCc4[nH]cnc4[C@H]3c3cc4c(Cl)cccn4n3)cnn2c1],
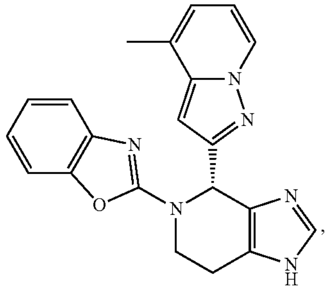 [SMILES: Cc1cccn2nc([C@@H]3c4nc[nH]c4CCN3c3nc4ccccc4o3)cc12],
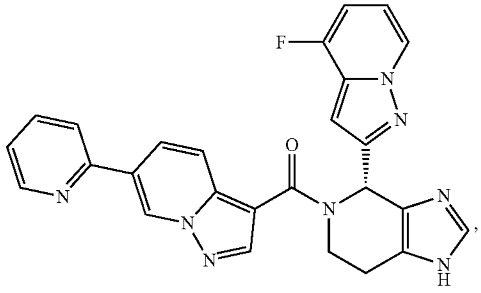 [SMILES: O=C(c1cnn2cc(-c3ccccn3)ccc12)N1CCc2[nH]cnc2[C@H]1c1cc2c(F)cccn2n1], -continued
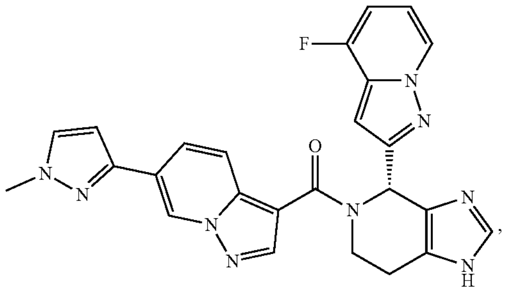 [SMILES: Cn1ccc(-c2ccc3c(C(=O)N4CCc5[nH]cnc5[C@H]4c4cc5c(F)cccn5n4)cnn3c2)n1]
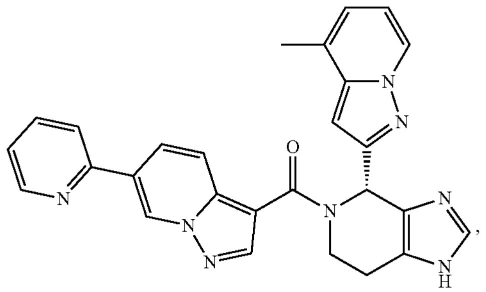 [SMILES: Cc1cccn2nc([C@@H]3c4nc[nH]c4CCN3C(=O)c3cnn4cc(-c5ccccn5)ccc34)cc12]
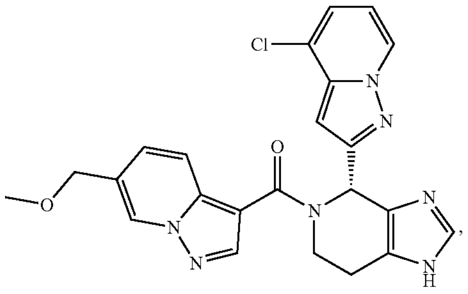 [SMILES: COCc1ccc2c(C(=O)N3CCc4[nH]cnc4[C@H]3c3cc4c(Cl)cccn4n3)cnn2c1]
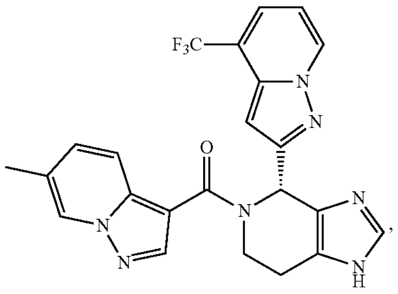 [SMILES: Cc1ccc2c(C(=O)N3CCc4[nH]cnc4[C@H]3c3cc4c(C(F)(F)F)cccn4n3)cnn2c1]
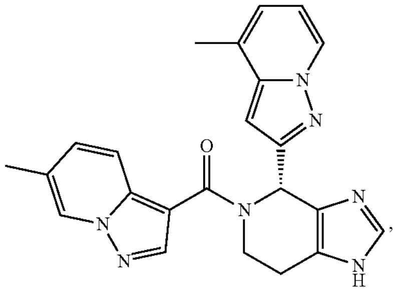 [SMILES: Cc1ccc2c(C(=O)N3CCc4[nH]cnc4[C@H]3c3cc4c(C)cccn4n3)cnn2c1]
-continued
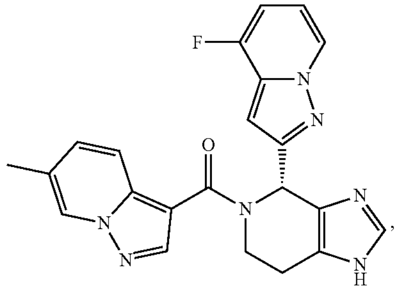 [SMILES: Cc1ccc2c(C(=O)N3CCc4[nH]cnc4[C@H]3c3cc4c(F)cccn4n3)cnn2c1]
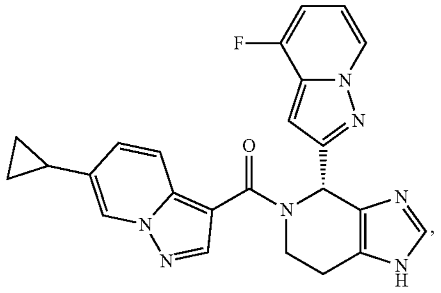 [SMILES: O=C(c1cnn2cc(C3CC3)ccc12)N1CCc2[nH]cnc2[C@H]1c1cc2c(F)cccn2n1]
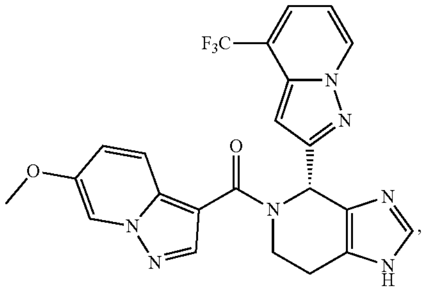 [SMILES: COc1ccc2c(C(=O)N3CCc4[nH]cnc4[C@H]3c3cc4c(C(F)(F)F)cccn4n3)cnn2c1]
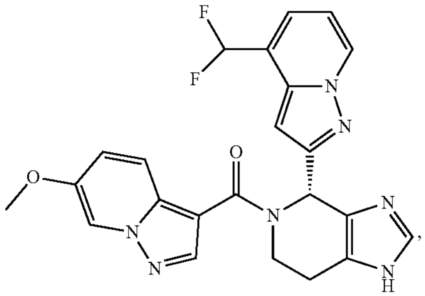 [SMILES: COc1ccc2c(C(=O)N3CCc4[nH]cnc4[C@H]3c3cc4c(C(F)F)cccn4n3)cnn2c1]
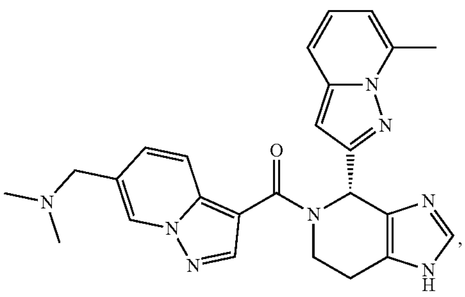 [SMILES: Cc1cccc2cc([C@@H]3c4nc[nH]c4CCN3C(=O)c3cnn4cc(CN(C)C)ccc34)nn12]

-continued
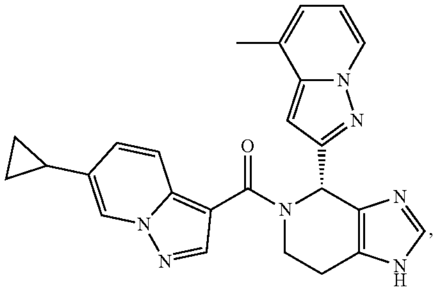 [SMILES: Cc1cccn2nc([C@@H]3c4nc[nH]c4CCN3C(=O)c3cnn4cc(C5CC5)ccc34)cc12]
,
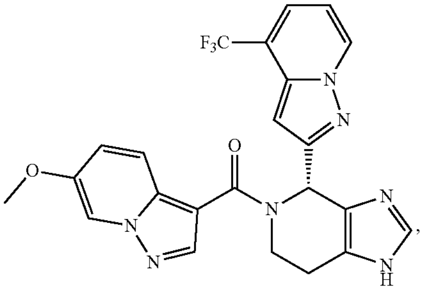 [SMILES: COc1ccc2c(C(=O)N3CCc4[nH]cnc4[C@H]3c3cc4c(C(F)(F)F)cccn4n3)cnn2c1]
,
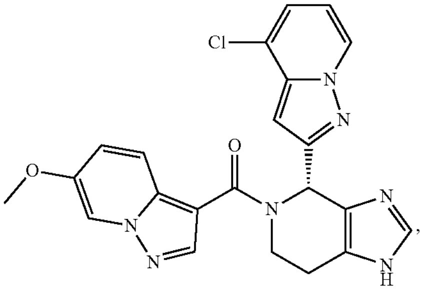 [SMILES: COc1ccc2c(C(=O)N3CCc4[nH]cnc4[C@H]3c3cc4c(Cl)cccn4n3)cnn2c1]
,
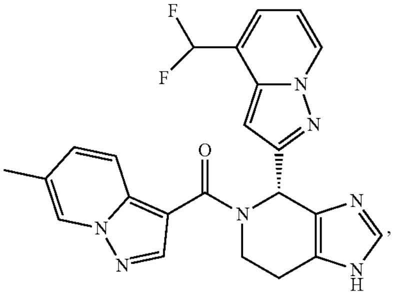 [SMILES: Cc1ccc2c(C(=O)N3CCc4[nH]cnc4[C@H]3c3cc4c(C(F)F)cccn4n3)cnn2c1]
,
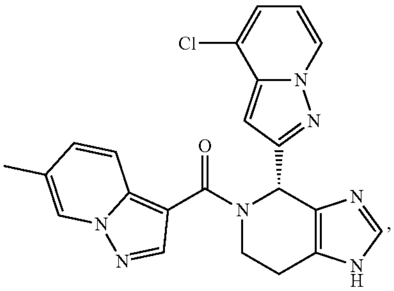 [SMILES: Cc1ccc2c(C(=O)N3CCc4[nH]cnc4[C@H]3c3cc4c(Cl)cccn4n3)cnn2c1]
,
-continued
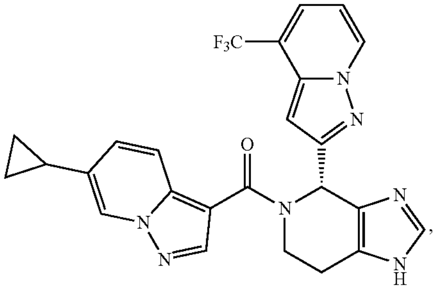 [SMILES: O=C(c1cnn2cc(C3CC3)ccc12)N1CCc2[nH]cnc2[C@H]1c1cc2c(C(F)(F)F)cccn2n1]
,
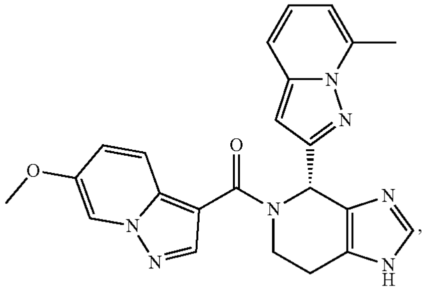 [SMILES: COc1ccc2c(C(=O)N3CCc4[nH]cnc4[C@H]3c3cc4cccc(C)n4n3)cnn2c1]
,
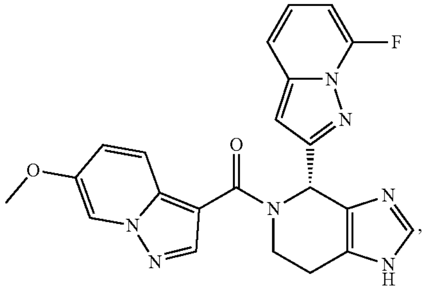
,
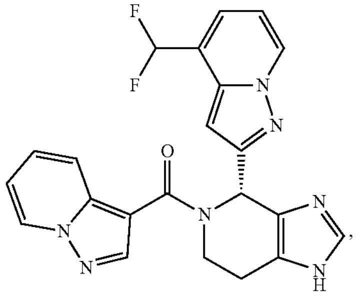 [SMILES: O=C(c1cnn2ccccc12)N1CCc2[nH]cnc2[C@H]1c1cc2c(C(F)F)cccn2n1]
,
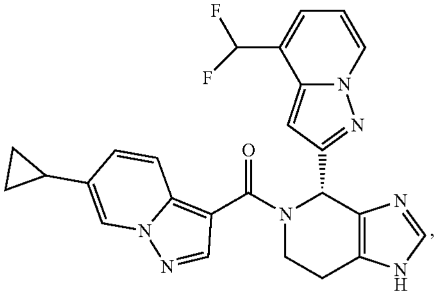 [SMILES: O=C(c1cnn2cc(C3CC3)ccc12)N1CCc2[nH]cnc2[C@H]1c1cc2c(C(F)F)cccn2n1]
, -continued
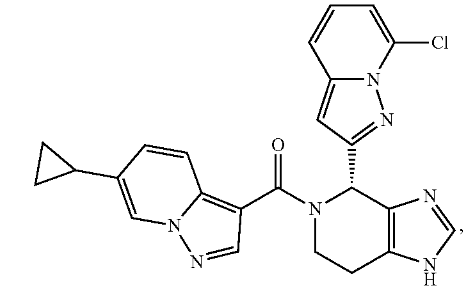 [SMILES: O=C(c1cnn2cc(C3CC3)ccc12)N1CCc2[nH]cnc2[C@H]1c1cc2cccc(Cl)n2n1],
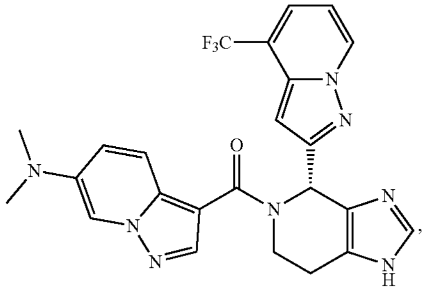 [SMILES: CN(C)c1ccc2c(C(=O)N3CCc4[nH]cnc4[C@H]3c3cc4c(C(F)(F)F)cccn4n3)cnn2c1],
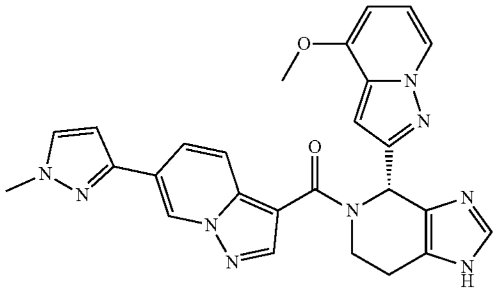,
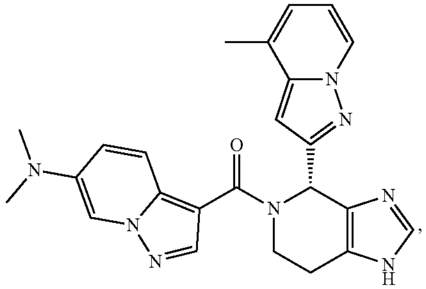 [SMILES: Cc1cccn2nc([C@@H]3c4nc[nH]c4CCN3C(=O)c3cnn4cc(N(C)C)ccc34)cc12],
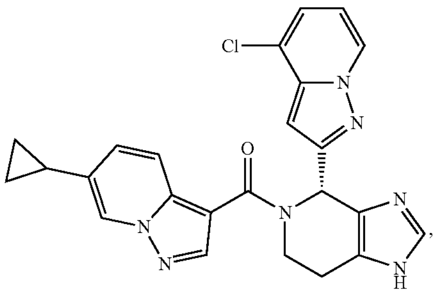 [SMILES: O=C(c1cnn2cc(C3CC3)ccc12)N1CCc2[nH]cnc2[C@H]1c1cc2c(Cl)cccn2n1],
-continued
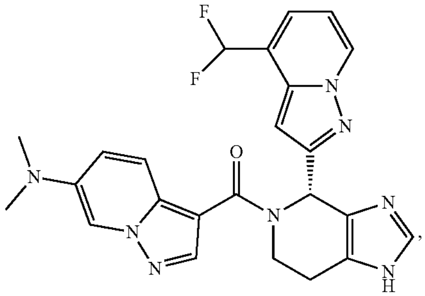 [SMILES: CN(C)c1ccc2c(C(=O)N3CCc4[nH]cnc4[C@H]3c3cc4c(C(F)F)cccn4n3)cnn2c1],
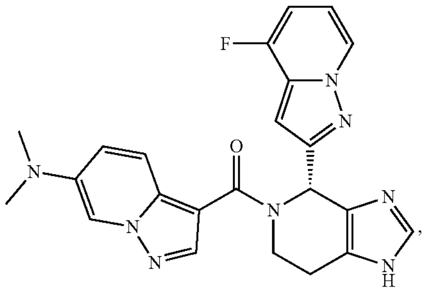 [SMILES: CN(C)c1ccc2c(C(=O)N3CCc4[nH]cnc4[C@H]3c3cc4c(F)cccn4n3)cnn2c1],
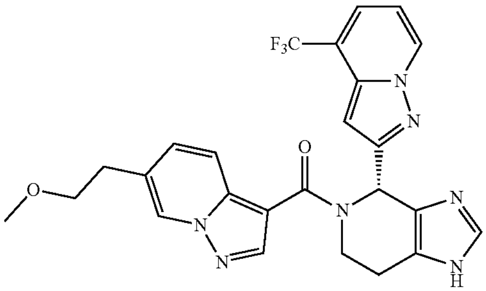,
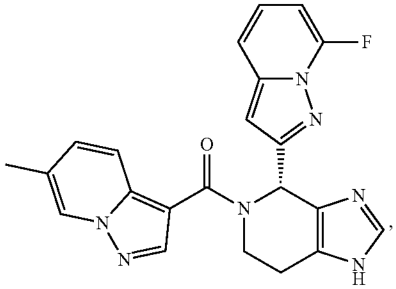 [SMILES: Cc1ccc2c(C(=O)N3CCc4[nH]cnc4[C@H]3c3cc4cccc(F)n4n3)cnn2c1],
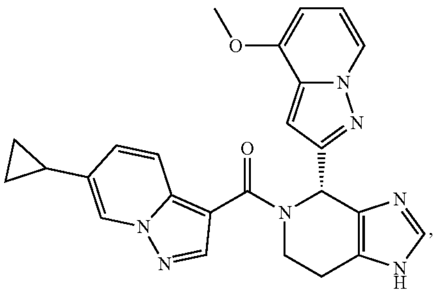 [SMILES: COc1cccn2nc([C@@H]3c4nc[nH]c4CCN3C(=O)c3cnn4cc(C5CC5)ccc34)cc12], -continued
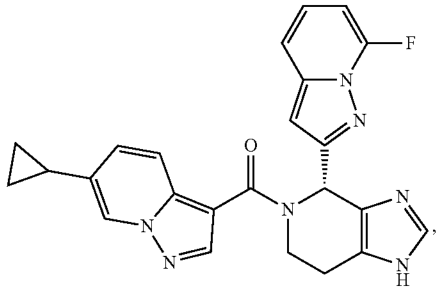 [SMILES: O=C(c1cnn2cc(C3CC3)ccc12)N1CCc2[nH]cnc2[C@H]1c1cc2cccc(F)n2n1]
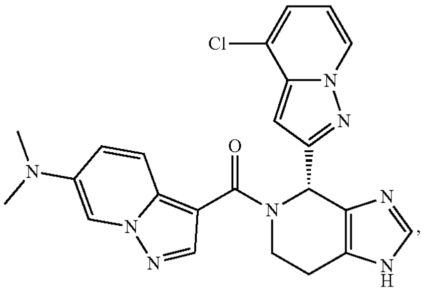 [SMILES: CN(C)c1ccc2c(C(=O)N3CCc4[nH]cnc4[C@H]3c3cc4c(Cl)cccn4n3)cnn2c1]
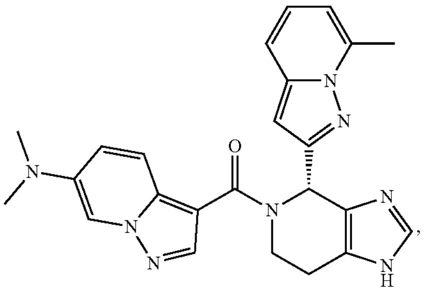 [SMILES: Cc1cccc2cc([C@@H]3c4nc[nH]c4CCN3C(=O)c3cnn4cc(N(C)C)ccc34)nn12]
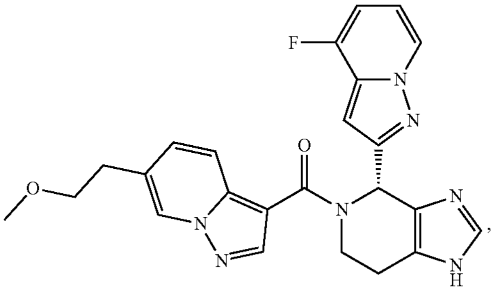 [SMILES: COCCc1ccc2c(C(=O)N3CCc4[nH]cnc4[C@H]3c3cc4c(F)cccn4n3)cnn2c1]
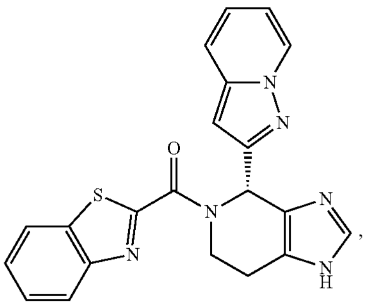 [SMILES: O=C(c1nc2ccccc2s1)N1CCc2[nH]cnc2[C@H]1c1cc2ccccn2n1]
-continued
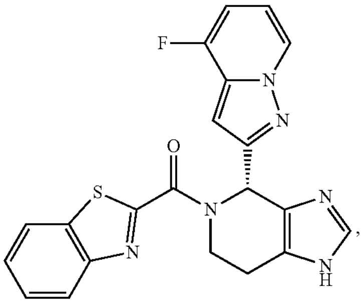 [SMILES: O=C(c1nc2ccccc2s1)N1CCc2[nH]cnc2[C@H]1c1cc2c(F)cccn2n1]
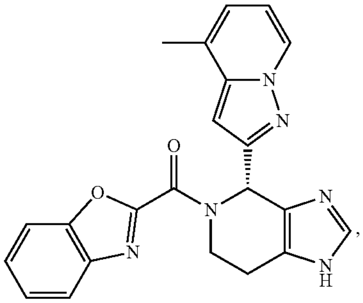 [SMILES: Cc1cccn2nc([C@@H]3c4nc[nH]c4CCN3C(=O)c3nc4ccccc4o3)cc12]
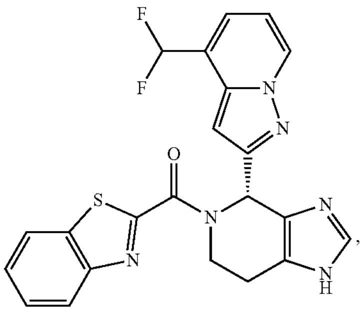 [SMILES: O=C(c1nc2ccccc2s1)N1CCc2[nH]cnc2[C@H]1c1cc2c(C(F)F)cccn2n1]
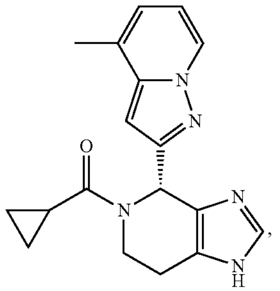 [SMILES: Cc1cccn2nc([C@@H]3c4nc[nH]c4CCN3C(=O)C3CC3)cc12]
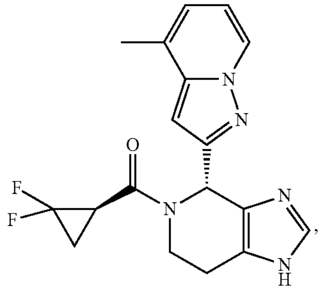 [SMILES: Cc1cccn2nc([C@@H]3c4nc[nH]c4CCN3C(=O)[C@H]3CC3(F)F)cc12]

-continued
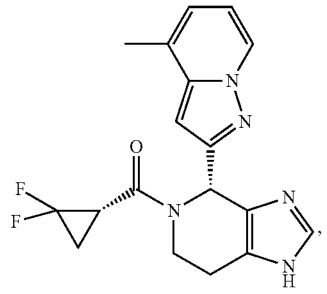 [SMILES: Cc1cccn2nc([C@@H]3c4nc[nH]c4CCN3C(=O)[C@@H]3CC3(F)F)cc12]
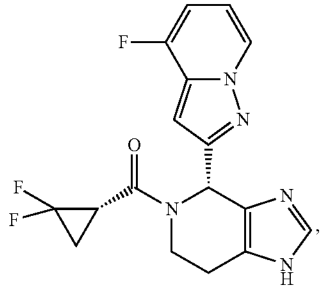 [SMILES: O=C([C@@H]1CC1(F)F)N1CCc2[nH]cnc2[C@H]1c1cc2c(F)cccn2n1]
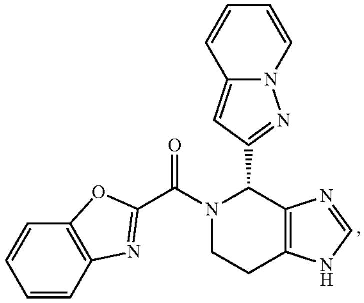 [SMILES: O=C(c1nc2ccccc2o1)N1CCc2[nH]cnc2[C@H]1c1cc2ccccn2n1]
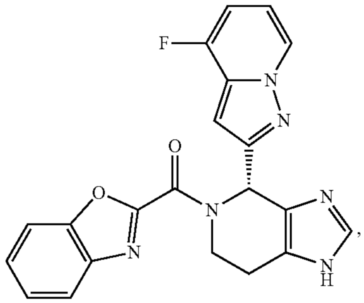 [SMILES: O=C(c1nc2ccccc2o1)N1CCc2[nH]cnc2[C@H]1c1cc2c(F)cccn2n1]
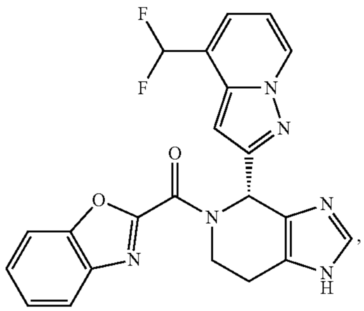
-continued
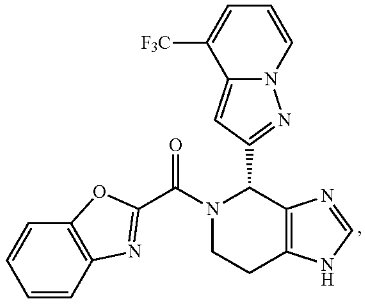 [SMILES: O=C(c1nc2ccccc2o1)N1CCc2[nH]cnc2[C@H]1c1cc2c(C(F)(F)F)cccn2n1]
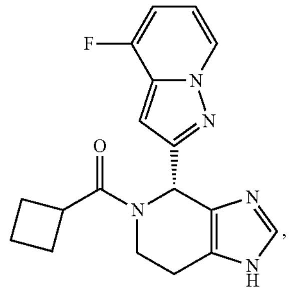 [SMILES: O=C(C1CCC1)N1CCc2[nH]cnc2[C@H]1c1cc2c(F)cccn2n1]
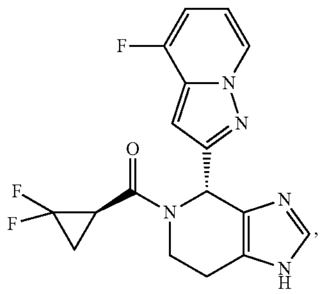 [SMILES: O=C([C@H]1CC1(F)F)N1CCc2[nH]cnc2[C@H]1c1cc2c(F)cccn2n1]
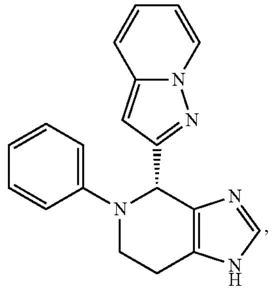 [SMILES: c1ccc(N2CCc3[nH]cnc3[C@H]2c2cc3ccccn3n2)cc1]
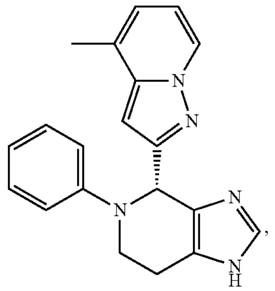 [SMILES: Cc1cccn2nc([C@@H]3c4nc[nH]c4CCN3c3ccccc3)cc12]

-continued
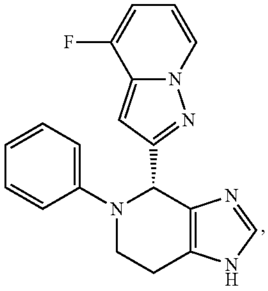 [SMILES: Fc1cccn2nc([C@@H]3c4nc[nH]c4CCN3c3ccccc3)cc12]
,
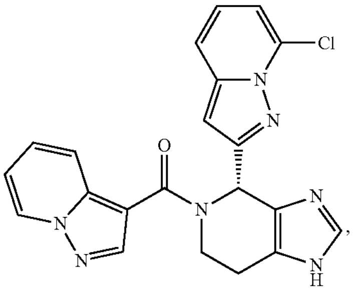 [SMILES: O=C(c1cnn2ccccc12)N1CCc2[nH]cnc2[C@H]1c1cc2cccc(Cl)n2n1]
,
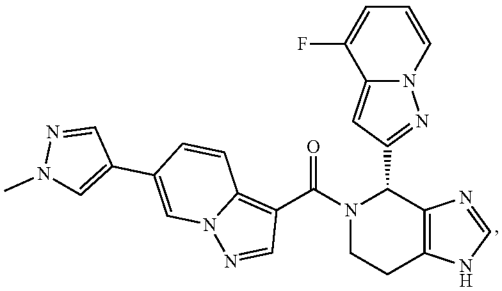 [SMILES: Cn1cc(-c2ccc3c(C(=O)N4CCc5[nH]cnc5[C@H]4c4cc5c(F)cccn5n4)cnn3c2)cn1]
,
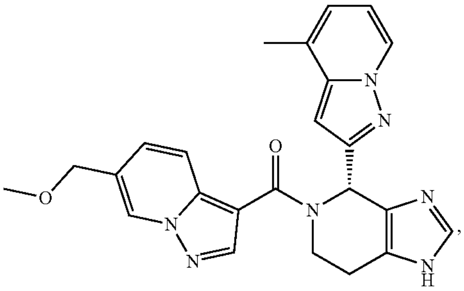 [SMILES: COCc1ccc2c(C(=O)N3CCc4[nH]cnc4[C@H]3c3cc4c(C)cccn4n3)cnn2c1]
,
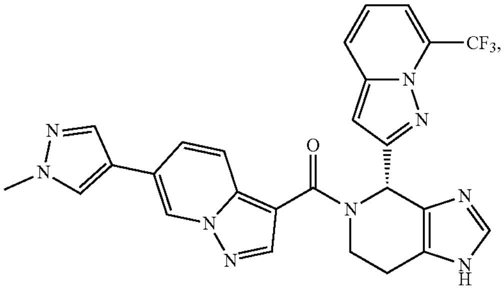 [SMILES: Cn1cc(-c2ccc3c(C(=O)N4CCc5[nH]cnc5[C@H]4c4cc5cccc(C(F)(F)F)n5n4)cnn3c2)cn1]
,
-continued
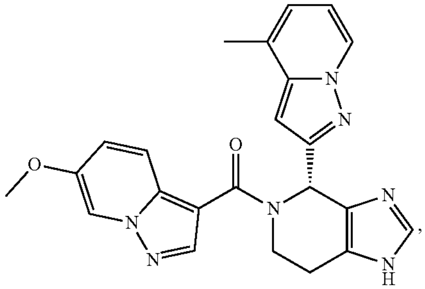 [SMILES: COc1ccc2c(C(=O)N3CCc4[nH]cnc4[C@H]3c3cc4c(C)cccn4n3)cnn2c1]
,
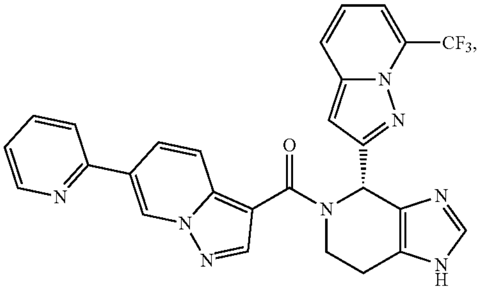 [SMILES: O=C(c1cnn2cc(-c3ccccn3)ccc12)N1CCc2[nH]cnc2[C@H]1c1cc2cccc(C(F)(F)F)n2n1]
,
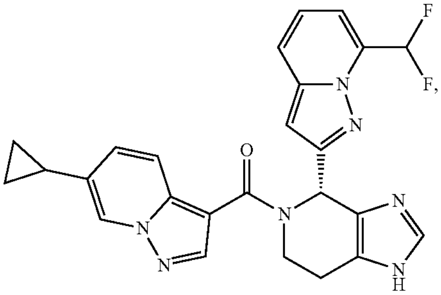 [SMILES: O=C(c1cnn2cc(C3CC3)ccc12)N1CCc2[nH]cnc2[C@H]1c1cc2cccc(C(F)F)n2n1]
,
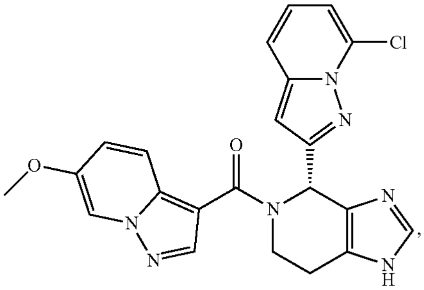 [SMILES: COc1ccc2c(C(=O)N3CCc4[nH]cnc4[C@H]3c3cc4cccc(Cl)n4n3)cnn2c1]
,
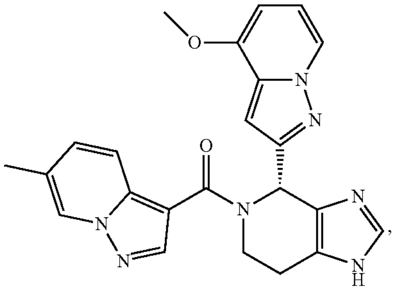 [SMILES: COc1cccn2nc([C@@H]3c4nc[nH]c4CCN3C(=O)c3cnn4cc(C)ccc34)cc12]
, -continued

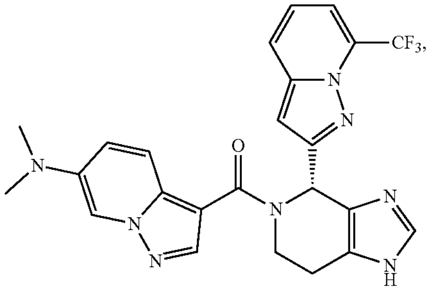 [SMILES: CN(C)c1ccc2c(C(=O)N3CCc4[nH]cnc4[C@H]3c3cc4cccc(C(F)(F)F)n4n3)cnn2c1]

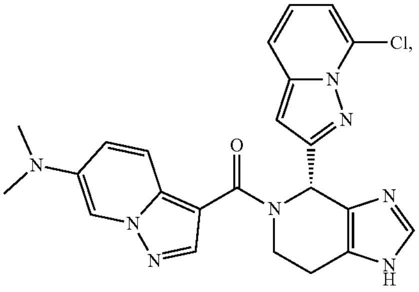 [SMILES: CN(C)c1ccc2c(C(=O)N3CCc4[nH]cnc4[C@H]3c3cc4cccc(Cl)n4n3)cnn2c1]

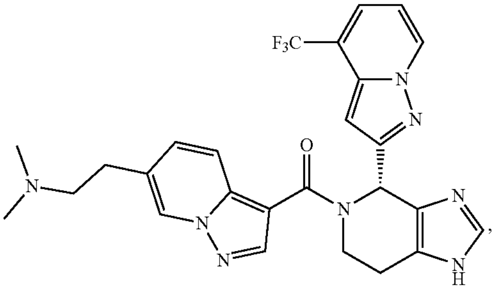 [SMILES: CN(C)CCc1ccc2c(C(=O)N3CCc4[nH]cnc4[C@H]3c3cc4c(C(F)(F)F)cccn4n3)cnn2c1]

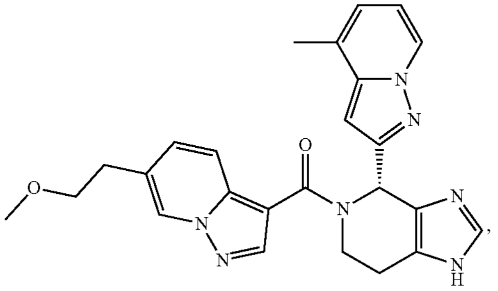 [SMILES: COCCc1ccc2c(C(=O)N3CCc4[nH]cnc4[C@H]3c3cc4c(C)cccn4n3)cnn2c1]

-continued

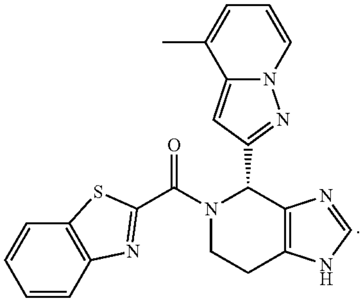

30. A pharmaceutical composition comprising a compound of claim 29, or a pharmaceutically acceptable salt thereof, and a pharmaceutically acceptable excipient.

31. A method for stabilizing a mutant PAH protein, comprising contacting the protein with a compound of claim 29, or a pharmaceutically acceptable salt thereof.

32. The method of claim 31, wherein the mutant PAH protein contains at least one R408W, R261Q, R243Q, Y414C, L48S, A403V, I65T, R241C, L348V, R408Q, or V388M mutation.

33. The method of claim 31, wherein the mutant PAH protein contains at least one R408W, Y414C, I65T, F39L, R408Q, L348V, R261Q, A300S, or L48S mutation.

34. The method of claim 31, wherein the mutant PAH protein contains at least one R408W mutation.

35. A method for reducing blood phenylalanine concentration in a subject suffering from phenylketonuria comprising administering a compound of claim 29, or a pharmaceutically acceptable salt thereof.

36. The method of claim 35, wherein the blood phenylalanine concentration is reduced to a concentration less than or equal to about 600 μM.

37. The method of claim 36, wherein the blood phenylalanine concentration is reduced to a concentration less than or equal to about 360 μM.

38. The method of claim 35, wherein the subject has a blood phenylalanine concentration greater than about 600 μM prior to administration of the compound.

39. The method of claim 35, wherein the subject has a blood phenylalanine concentration greater than about 1200 μM prior to administration of the compound.

* * * * *